US012679815B2

(12) United States Patent
Plaunt et al.

(10) Patent No.: US 12,679,815 B2
(45) Date of Patent: Jul. 14, 2026

(54) LINEAR DIPEPTIDYL PEPTIDASE 1 INHIBITORS AND USES THEREOF

(71) Applicant: Insmed Incorporated, Bridgewater, NJ (US)

(72) Inventors: Adam J. Plaunt, Bridgewater, NJ (US); Gianpaolo Gobbo, Bridgewater, NJ (US); Byungchan Kim, Bridgewater, NJ (US); Yingxin Shi, Bridgewater, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 0 days.

(21) Appl. No.: 19/323,862

(22) Filed: Sep. 9, 2025

(65) Prior Publication Data

US 2026/0008758 A1 Jan. 8, 2026

Related U.S. Application Data

(63) Continuation of application No. PCT/CN2025/075611, filed on Jan. 30, 2025.

(30) Foreign Application Priority Data

Jan. 31, 2024 (WO) ................ PCT/CN2024/074986
Oct. 14, 2024 (WO) ................ PCT/CN2024/124776
Dec. 6, 2024 (WO) ................ PCT/CN2024/137503

(51) Int. Cl.

| | |
|---|---|
| ***C07D 263/58*** | (2006.01) |
| ***A61K 31/397*** | (2006.01) |
| ***A61K 31/423*** | (2006.01) |
| ***A61K 31/427*** | (2006.01) |
| ***A61K 31/4439*** | (2006.01) |
| ***C07D 413/12*** | (2006.01) |
| ***C07D 417/12*** | (2006.01) |
| ***C07D 491/107*** | (2006.01) |

(52) U.S. Cl.

CPC .......... *C07D 263/58* (2013.01); *A61K 31/397* (2013.01); *A61K 31/423* (2013.01); *A61K 31/427* (2013.01); *A61K 31/4439* (2013.01); *C07D 413/12* (2013.01); *C07D 417/12* (2013.01); *C07D 491/107* (2013.01)

(58) Field of Classification Search

CPC .................................................... C07D 263/58
See application file for complete search history.

(56) References Cited

U.S. PATENT DOCUMENTS

| | | | |
|---|---|---|---|
| 8,552,034 | B2 | 10/2013 | Verwijs et al. |
| 8,871,783 | B2 | 10/2014 | Anderskewitz et al. |
| 8,877,775 | B2 | 11/2014 | Anderskewitz et al. |
| 8,889,708 | B2 | 11/2014 | Grauert et al. |
| 8,987,249 | B2 | 3/2015 | Anderskewitz et al. |
| 8,999,975 | B2 | 4/2015 | Grundl et al. |
| 9,073,869 | B2 | 7/2015 | Anderskewitz et al. |
| 9,440,960 | B2 | 9/2016 | Grauert et al. |
| 9,522,894 | B2 | 12/2016 | Lonn et al. |
| 9,540,373 | B2 | 1/2017 | Vintonyak et al. |
| 9,713,606 | B2 | 7/2017 | Anderskewitz et al. |
| 9,815,805 | B2 | 11/2017 | Lonn et al. |
| 9,856,228 | B2 | 1/2018 | Lauritzen et al. |
| 9,879,026 | B2 | 1/2018 | Vintonyak et al. |
| 10,238,633 | B2 | 3/2019 | Anderskewitz et al. |
| 10,287,258 | B2 | 5/2019 | Lonn et al. |
| RE47,636 | E | 10/2019 | Vintonyak et al. |
| 10,479,781 | B2 | 11/2019 | Lauritzen et al. |

(Continued)

FOREIGN PATENT DOCUMENTS

| | | | |
|---|---|---|---|
| CN | 101945851 | A | 1/2011 |
| CN | 102574830 | A | 7/2012 |

(Continued)

OTHER PUBLICATIONS

Lew "Substrate analogues incorporating b-amino acids: potential application for peptidase inhibition." FASEB Journal, 2001, 15(9), 1664-1666.*
International Application No. PCT/US2025/033193, International Search Report and Written Opinion mailed Oct. 9, 2025, Applicant: Insmed Incorporated, 14 pages.
International Application No. PCT/US2025/033193, Invitation to Pay Additional Fees mailed Aug. 11, 2025, Applicant: Insmed Incorporated, 3 pages.
Adkison, A. M. et al. (2002), "Dipeptidyl peptidase I activates neutrophil-derived serine proteases and regulates the development of acute experimental arthritis," J. Clin. Invest. 109(3):363-371.

(Continued)

*Primary Examiner* — David K O'Dell
(74) *Attorney, Agent, or Firm* — Cooley LLP

(57) ABSTRACT

Provided herein are compounds of Formula (I), or pharmaceutically acceptable salts or deuterated forms thereof, wherein $R^1$, $R^2$, $R^3$, $R^4$, L, n, m, $R^a$, $R^b$, $R^c$, and $R^d$ are defined herein. Also provided herein are pharmaceutical compositions comprising a compound of Formula (I) or pharmaceutically acceptable salt or deuterated form thereof, and methods of using a compound of Formula (I) or pharmaceutically acceptable salt or deuterated form thereof, e.g., in the treatment of a disease that is treatable by administration of a DPP1 inhibitor.

(I)

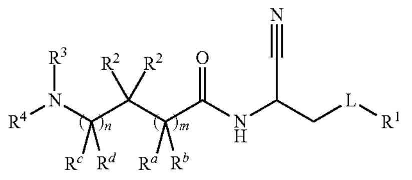

30 Claims, No Drawings

(56) References Cited

U.S. PATENT DOCUMENTS

| | | | |
|---|---|---|---|
| 10,669,245 | B2 | 6/2020 | Lonn et al. |
| 11,117,874 | B2 | 9/2021 | Lonn et al. |
| 11,655,221 | B2 | 5/2023 | Lönn et al. |
| 11,655,222 | B2 | 5/2023 | Lönn et al. |
| 11,655,223 | B2 | 5/2023 | Lönn et al. |
| 11,655,224 | B2 | 5/2023 | Lönn et al. |
| 11,667,615 | B2 | 6/2023 | Lönn et al. |
| 11,673,871 | B2 | 6/2023 | Lönn et al. |
| 11,673,872 | B2 | 6/2023 | Lönn et al. |
| 11,680,049 | B2 | 6/2023 | Lönn et al. |
| 11,773,069 | B2 | 10/2023 | Lönn et al. |
| 11,807,635 | B2 | 11/2023 | Li et al. |
| 11,814,359 | B2 | 11/2023 | Lönn et al. |
| 11,998,553 | B2 | 6/2024 | Zhang |
| 12,054,465 | B2 | 8/2024 | Lönn |
| 12,059,424 | B2 | 8/2024 | Wikström et al. |
| 12,201,638 | B2 | 1/2025 | Wikström et al. |
| 12,479,837 | B2 | 11/2025 | Plaunt et al. |
| 2004/0063935 | A1 | 4/2004 | Yasuda et al. |
| 2008/0221093 | A1 | 9/2008 | Gege et al. |
| 2009/0306042 | A1 | 12/2009 | Furber et al. |
| 2011/0201581 | A1 | 8/2011 | Furber et al. |
| 2011/0236367 | A1 | 9/2011 | Olsen et al. |
| 2012/0315271 | A1 | 12/2012 | Shelton et al. |
| 2012/0329775 | A1 | 12/2012 | Ford et al. |
| 2014/0275159 | A1 | 9/2014 | Anderskewitz et al. |
| 2015/0025058 | A1 | 1/2015 | Deutsch et al. |
| 2015/0105375 | A1 | 4/2015 | Anderskewitz et al. |
| 2015/0210655 | A1 | 7/2015 | Lonn et al. |
| 2015/0224199 | A1 | 8/2015 | De Weer et al. |
| 2015/0346203 | A1 | 12/2015 | Xu et al. |
| 2016/0061824 | A1 | 3/2016 | Hahn et al. |
| 2016/0324854 | A1 | 11/2016 | Finnie et al. |
| 2017/0027907 | A1 | 2/2017 | Legangneux et al. |
| 2017/0057938 | A1 | 3/2017 | Lonn et al. |
| 2018/0028541 | A1 | 2/2018 | Lonn et al. |
| 2018/0044328 | A1 | 2/2018 | Lauritzen et al. |
| 2018/0169017 | A1 | 6/2018 | Desai et al. |
| 2018/0251436 | A1 | 9/2018 | Lonn et al. |
| 2019/0091236 | A1 | 3/2019 | Lonn et al. |
| 2019/0167636 | A1 | 6/2019 | Anderskewitz et al. |
| 2019/0247400 | A1 | 8/2019 | Dipetrillo et al. |
| 2020/0017455 | A1 | 1/2020 | Lonn et al. |
| 2020/0138780 | A1 | 5/2020 | Anderskewitz et al. |
| 2020/0179398 | A1 | 6/2020 | Lonn et al. |
| 2020/0247765 | A1 | 8/2020 | Lonn et al. |
| 2020/0256866 | A1 | 8/2020 | Tirouvanziam |
| 2020/0390781 | A1 | 12/2020 | Dipetrillo et al. |
| 2021/0186931 | A1 | 6/2021 | Davidson et al. |
| 2021/0186984 | A1 | 6/2021 | Dipetrillo et al. |
| 2021/0238152 | A1 | 8/2021 | Lönn et al. |
| 2021/0252015 | A1 | 8/2021 | Zhang |
| 2021/0322438 | A1 | 10/2021 | Zhang |
| 2021/0369732 | A1 | 12/2021 | Wikström et al. |
| 2022/0133737 | A1 | 5/2022 | Lonn et al. |
| 2023/0025351 | A1 | 1/2023 | Lönn et al. |
| 2023/0028726 | A1 | 1/2023 | Lönn et al. |
| 2023/0033573 | A1 | 2/2023 | Lönn et al. |
| 2023/0062646 | A1 | 3/2023 | Lönn et al. |
| 2023/0069044 | A1 | 3/2023 | Lönn et al. |
| 2023/0085620 | A1 | 3/2023 | Lönn et al. |
| 2023/0115170 | A1 | 4/2023 | Lönn et al. |
| 2023/0116721 | A1 | 4/2023 | Lönn et al. |
| 2023/0144871 | A1 | 5/2023 | Martin et al. |
| 2023/0250071 | A1 | 8/2023 | Lönn et al. |
| 2023/0278969 | A1 | 9/2023 | Lönn et al. |
| 2024/0041896 | A1 | 2/2024 | Lonn et al. |
| 2024/0059681 | A1 | 2/2024 | Li et al. |
| 2024/0083888 | A1 | 3/2024 | Hao et al. |
| 2024/0132455 | A1 | 4/2024 | Lönn et al. |
| 2024/0150335 | A1 | 5/2024 | Wu et al. |
| 2024/0226112 | A1 | 7/2024 | Usansky et al. |
| 2024/0252512 | A1 | 8/2024 | Wikström et al. |
| 2024/0336582 | A1 | 10/2024 | Lönn et al. |
| 2025/0101011 | A1 | 3/2025 | Ye et al. |
| 2025/0223284 | A1 | 7/2025 | Plaunt et al. |
| 2026/0008760 | A1 | 1/2026 | Plaunt et al. |
| 2026/0055093 | A1 | 2/2026 | Plaunt et al. |
| 2026/0062420 | A1 | 3/2026 | Plaunt et al. |

FOREIGN PATENT DOCUMENTS

| | | | |
|---|---|---|---|
| CN | 105026395 | A | 11/2015 |
| CN | 105612149 | A | 5/2016 |
| CN | 112920124 | A | 6/2021 |
| CN | 114106005 | A | 3/2022 |
| CN | 114591315 | A | 6/2022 |
| CN | 115925696 | A | 4/2023 |
| CN | 116332937 | A | 6/2023 |
| CN | 117510493 | A | 2/2024 |
| EP | 1317555 | B1 | 11/2007 |
| EP | 2840083 | A1 | 2/2015 |
| EP | 2970283 | B1 | 11/2020 |
| JP | 2006527704 | A | 12/2006 |
| JP | 2008501692 | A | 1/2008 |
| JP | 2008504307 | A | 2/2008 |
| JP | 2010540526 | A | 12/2010 |
| JP | 2011506421 | A | 3/2011 |
| JP | 2011522011 | A | 7/2011 |
| JP | 2012522764 | A | 9/2012 |
| JP | 2012526093 | A | 10/2012 |
| JP | 2016515576 | A | 5/2016 |
| JP | 2017503832 | A | 2/2017 |
| JP | 2019070029 | A | 5/2019 |
| JP | 2021046423 | A | 3/2021 |
| JP | 2022096662 | A | 6/2022 |
| TW | 201041889 | A | 12/2010 |
| WO | WO-9917777 | A1 | 4/1999 |
| WO | WO-0116108 | A2 | 3/2001 |
| WO | WO-0196285 | A1 | 12/2001 |
| WO | WO-02051831 | A1 | 7/2002 |
| WO | WO-03048123 | A1 | 6/2003 |
| WO | WO-2004076434 | A1 | 9/2004 |
| WO | WO-2004087153 | A2 | 10/2004 |
| WO | WO-2004106289 | A1 | 12/2004 |
| WO | WO-2004110988 | A1 | 12/2004 |
| WO | WO-2005106012 | A2 | 11/2005 |
| WO | WO-2005107762 | A2 | 11/2005 |
| WO | WO-2005120465 | A2 | 12/2005 |
| WO | WO-2006000228 | A2 | 1/2006 |
| WO | WO-2006020145 | A2 | 2/2006 |
| WO | WO-2007005668 | A2 | 1/2007 |
| WO | WO-2008109180 | A2 | 9/2008 |
| WO | WO-2008109181 | A2 | 9/2008 |
| WO | WO-2009026701 | A1 | 3/2009 |
| WO | WO-2009042187 | A1 | 4/2009 |
| WO | WO-2009074829 | A1 | 6/2009 |
| WO | WO-2009147238 | A1 | 12/2009 |
| WO | WO-2010077680 | A2 | 7/2010 |
| WO | WO-2010114405 | A2 | 10/2010 |
| WO | WO-2010128324 | A1 | 11/2010 |
| WO | WO-2010142985 | A1 | 12/2010 |
| WO | WO-2011154677 | A1 | 12/2011 |
| WO | WO-2012064715 | A1 | 5/2012 |
| WO | WO-2012119941 | A1 | 9/2012 |
| WO | WO-2013041497 | A1 | 3/2013 |
| WO | WO-2014043068 | A1 | 3/2014 |
| WO | WO-2014091443 | A1 | 6/2014 |
| WO | WO-2014140075 | A1 | 9/2014 |
| WO | WO-2014140081 | A1 | 9/2014 |
| WO | WO-2014140091 | A1 | 9/2014 |
| WO | WO-2014151784 | A1 | 9/2014 |
| WO | WO-2014165303 | A1 | 10/2014 |
| WO | WO-2015032942 | A1 | 3/2015 |
| WO | WO-2015032943 | A1 | 3/2015 |
| WO | WO-2015032945 | A1 | 3/2015 |
| WO | WO-2015052264 | A1 | 4/2015 |
| WO | WO-2015110826 | A1 | 7/2015 |
| WO | WO-2015175939 | A1 | 11/2015 |
| WO | WO-2016016242 | A1 | 2/2016 |
| WO | WO-2016038007 | A1 | 3/2016 |
| WO | WO-2016075240 | A1 | 5/2016 |
| WO | WO-2016139351 | A1 | 9/2016 |
| WO | WO-2017004500 | A1 | 1/2017 |

(56) References Cited

FOREIGN PATENT DOCUMENTS

| | | | |
|---|---|---|---|
| WO | WO-2018022978 | A1 | 2/2018 |
| WO | WO-2019157050 | A1 | 8/2019 |
| WO | WO-2019166626 | A1 | 9/2019 |
| WO | WO-2020018547 | A1 | 1/2020 |
| WO | WO-2020018551 | A1 | 1/2020 |
| WO | WO-2020247665 | A1 | 12/2020 |
| WO | WO-2022042591 | A1 | 3/2022 |
| WO | WO-2022117059 | A1 | 6/2022 |
| WO | WO-2022140516 | A1 | 6/2022 |
| WO | WO-2022166721 | A1 | 8/2022 |
| WO | WO-2022232420 | A1 | 11/2022 |
| WO | WO-2022232573 | A1 | 11/2022 |
| WO | WO-2023076615 | A1 | 5/2023 |
| WO | WO-2023134656 | A1 | 7/2023 |
| WO | WO-2023160541 | A1 | 8/2023 |
| WO | WO-2023160542 | A1 | 8/2023 |
| WO | WO-2023160579 | A1 | 8/2023 |
| WO | WO-2023236877 | A1 | 12/2023 |
| WO | WO-2023236879 | A1 | 12/2023 |
| WO | WO-2023243601 | A1 | 12/2023 |
| WO | WO-2024008680 | A1 | 1/2024 |
| WO | WO-2024026433 | A2 | 2/2024 |
| WO | WO-2024088307 | A1 | 5/2024 |
| WO | WO-2024094208 | A1 | 5/2024 |
| WO | WO-2024148308 | A1 | 7/2024 |
| WO | WO-2024173556 | A2 | 8/2024 |
| WO | WO-2024192416 | A1 | 9/2024 |
| WO | WO-2025056038 | A1 | 3/2025 |
| WO | WO-2025059526 | A1 | 3/2025 |
| WO | WO-2025162472 | A1 | 8/2025 |
| WO | WO-2025165806 | A1 | 8/2025 |
| WO | WO-2025214073 | A1 | 10/2025 |

OTHER PUBLICATIONS

Alpsoy, E. (Apr. 2005), "Behcet's Disease: Treatment of Mucocutaneous Lesions," Clinical and Experimental Rheumatology, vol. 23, No. 4, pp. 532-539.

Avci, D. (Feb. 2019), "Dipeptidyl Peptidase-4 Inhibitors and Inflammation: Dpp-4 Inhibitors Improve Mean Pleatelet vol. and Gamma Glutamyl Transferase Level," Journal of Biosciences and Medicines, vol. 7, No. 2, pp. 42-53.

Bae, S. et al. (Jul. 2012), "Elevated interleukin-32 expression in granulomatosis with polyangiitis," Rheumatology 2012;51:1979-1988, doi:10.1093/rheumatology/kes163, Advance Access publication.

Banerjee, A. et al., "Development of potent and selective Cathepsin C inhibitors free of aortic binding liability by application of a conformational restriction strategy," Bioorg. Med. Chem. Lett., vol. 47, 128202, Jun. 2021, 7 pages.

Birring, S. S. et al. (2003), "Development of a symptom specific health status measure for patients with chronic cough: Leicester Cough Questionnaire (LCQ)," Thorax; 58:339-343.

Bondebjerg, J. et al. (2005), "Novel semicarbazide-derived inhibitors of human dipeptidyl peptidase I (hDPPI)," Bioorg Med Chem; 13:4408-4424.

Bondejberg, J. et al. (2006), "Dipeptidyl Nitriles as Human Dipeptidyl Peptidase 1 Inhibitors," Bioorg Med Chem Lett;16:3614-3617.

Bragg, R. A. et al. (Sep. 2015), "Aortic Binding of AZD5248: Mechanistic Insight and Reactivity Assays to Support Lead Optimization," Chem Res Toxicol. Oct. 19, 2015;28(10):1991-1999.

Canonica, G. W. et al. (May 2020), "Chronic rhinosinusitis with nasal polyps impact in severe asthma patients: Evidences from the Severe Asthma Network Italy (SANI) registry," Respiratory Medicine, vol. 166, 105947, pp. 1-5.

Cartin-Ceba, R. et al. (Nov. 2012), "Rituximab for Remission Induction and Maintenance in Refractory Granulomatosis With Polyangiitis (Wegener's)," Arthritis & Rheumatism, vol. 64, No. 11, pp. 3770-3778.

Chalmers, J. D. et al. (2017), "Neutrophil Elastase Activity Is Associated with Exacerbations and Lung Function Decline in Bronchiectasis," Am J Respir Crit Care Med, 195(10):1384-1393.

Chalmers, J. D. et al. (Mar. 2014), "The Bronchiectasis Severity Index. An International Derivation and Validation Study," Am. J. Respir. Crit. Care Med., 189(5):576-585.

Chalmers, J. D. et al. (Nov. 2020), "Phase 2 Trial of the DPP-1 Inhibitor Brensocatib in Bronchiectasis," N Engl J Med ;383(22):2127-2137.

Clinical Trials Identifier: NCT03218917, ClinicalTrials.gov submitted on Aug. 15, 2017, 5 pages.

Clinical Trials Identifier: NCT03218917, ClinicalTrials.gov submitted on Aug. 20, 2018, 17 pages.

Clinical Trials Identifier: NCT03218917, ClinicalTrials.gov submitted on Dec. 11, 2020, 10 pages.

Clinical Trials Identifier: NCT03218917, ClinicalTrials.gov submitted on Dec. 17, 2018, 17 pages.

Clinical Trials Identifier: NCT03218917, ClinicalTrials.gov submitted on Dec. 17, 2019, 10 pages.

Clinical Trials Identifier: NCT03218917, ClinicalTrials.gov submitted on Dec. 4, 2019, 10 pages.

Clinical Trials Identifier: NCT03218917, ClinicalTrials.gov submitted on Dec. 8, 2018, 17 pages.

Clinical Trials Identifier: NCT03218917, ClinicalTrials.gov submitted on Feb. 11, 2019, 17 pages.

Clinical Trials Identifier: NCT03218917, ClinicalTrials.gov submitted on Feb. 12, 2019, 17 pages.

Clinical Trials Identifier: NCT03218917, ClinicalTrials.gov submitted on Feb. 5, 2018, 5 pages.

Clinical Trials Identifier: NCT03218917, ClinicalTrials.gov submitted on Jan. 14, 2019, 17 pages.

Clinical Trials Identifier: NCT03218917, ClinicalTrials.gov submitted on Jan. 28, 2019, 17 pages.

Clinical Trials Identifier: NCT03218917, ClinicalTrials.gov submitted on Jan. 3, 2019, 17 pages.

Clinical Trials Identifier: NCT03218917, ClinicalTrials.gov submitted on Jan. 31, 2019, 17 pages.

Clinical Trials Identifier: NCT03218917, ClinicalTrials.gov submitted on Jul. 12, 2017, 7 pages.

Clinical Trials Identifier: NCT03218917, ClinicalTrials.gov submitted on Jul. 30, 2018, 5 pages.

Clinical Trials Identifier: NCT03218917, ClinicalTrials.gov submitted on Mar. 28, 2019, 16 pages.

Clinical Trials Identifier: NCT03218917, ClinicalTrials.gov submitted on May 28, 2019, 10 pages.

Clinical Trials Identifier: NCT03218917, ClinicalTrials.gov submitted on Nov. 13, 2018, 17 pages.

Clinical Trials Identifier: NCT03218917, ClinicalTrials.gov submitted on Nov. 28, 2018, 17 pages.

Clinical Trials Identifier: NCT03218917, ClinicalTrials.gov submitted on Nov. 6, 2018, 17 pages.

Clinical Trials Identifier: NCT03218917, ClinicalTrials.gov submitted on Oct. 16, 2018, 17 pages.

Clinical Trials Identifier: NCT03218917, ClinicalTrials.gov submitted on Sep. 12, 2018, 17 pages.

Clinical Trials Identifier: NCT03218917, ClinicalTrials.gov submitted on Sep. 24, 2018, 17 pages.

Clinical Trials Identifier: NCT04594369. ClinicalTrials.gov submitted on Apr. 12, 2022, 33 pages.

Clinical Trials Identifier: NCT04594369. ClinicalTrials.gov submitted on Apr. 22, 2021, 14 pages.

Clinical Trials Identifier: NCT04594369. ClinicalTrials.gov submitted on Apr. 22, 2022, 32 pages.

Clinical Trials Identifier: NCT04594369. ClinicalTrials.gov submitted on Apr. 5, 2022, 32 pages.

Clinical Trials Identifier: NCT04594369. ClinicalTrials.gov submitted on Apr. 9, 2021, 13 pages.

Clinical Trials Identifier: NCT04594369. ClinicalTrials.gov submitted on Aug. 1, 2022, 32 pages.

Clinical Trials Identifier: NCT04594369. ClinicalTrials.gov submitted on Aug. 18, 2022, 32 pages.

Clinical Trials Identifier: NCT04594369. ClinicalTrials.gov submitted on Aug. 23, 2021, 24 pages.

Clinical Trials Identifier: NCT04594369. ClinicalTrials.gov submitted on Aug. 30, 2022, 32 pages.

(56) References Cited

OTHER PUBLICATIONS

Clinical Trials Identifier: NCT04594369. ClinicalTrials.gov submitted on Aug. 9, 2021, 23 pages.
Clinical Trials Identifier: NCT04594369. ClinicalTrials.gov submitted on Dec. 1, 2020, 6 pages.
Clinical Trials Identifier: NCT04594369. ClinicalTrials.gov submitted on Dec. 10, 2020, 6 pages.
Clinical Trials Identifier: NCT04594369. ClinicalTrials.gov submitted on Dec. 3, 2021, 28 pages.
Clinical Trials Identifier: NCT04594369. ClinicalTrials.gov submitted on Jul. 11, 2022, 32 pages.
Clinical Trials Identifier: NCT04594369. ClinicalTrials.gov submitted on Jul. 23, 2021, 21 pages.
Clinical Trials Identifier: NCT04594369. ClinicalTrials.gov submitted on Jul. 27, 2022, 32 pages.
Clinical Trials Identifier: NCT04594369. ClinicalTrials.gov submitted on Jul. 9, 2021, 21 pages.
Clinical Trials Identifier: NCT04594369. ClinicalTrials.gov submitted on Jun. 20, 2022, 32 pages.
Clinical Trials Identifier: NCT04594369. ClinicalTrials.gov submitted on Jun. 21, 2021, 19 pages.
Clinical Trials Identifier: NCT04594369. ClinicalTrials.gov submitted on Jun. 24, 2021, 19 pages.
Clinical Trials Identifier: NCT04594369. ClinicalTrials.gov submitted on Jun. 30, 2021, 20 pages.
Clinical Trials Identifier: NCT04594369. ClinicalTrials.gov submitted on Jun. 7, 2021, 19 pages.
Clinical Trials Identifier: NCT04594369. ClinicalTrials.gov submitted on Jun. 7, 2022, 32 pages.
Clinical Trials Identifier: NCT04594369. ClinicalTrials.gov submitted on Mar. 11, 2021, 9 pages.
Clinical Trials Identifier: NCT04594369. ClinicalTrials.gov submitted on Mar. 25, 2021, 11 pages.
Clinical Trials Identifier: NCT04594369. ClinicalTrials.gov submitted on Mar. 25, 2022, 34 pages.
Clinical Trials Identifier: NCT04594369. ClinicalTrials.gov submitted on Mar. 4, 2022, 32 pages.
Clinical Trials Identifier: NCT04594369. ClinicalTrials.gov submitted on May 13, 2022, 33 pages.
Clinical Trials Identifier: NCT04594369. ClinicalTrials.gov submitted on May 25, 2022, 31 pages.
Clinical Trials Identifier: NCT04594369. ClinicalTrials.gov submitted on Nov. 10, 2021, 29 pages.
Clinical Trials Identifier: NCT04594369. ClinicalTrials.gov submitted on Nov. 15, 2022, 30 pages.
Clinical Trials Identifier: NCT04594369. ClinicalTrials.gov submitted on Nov. 19, 2020, 6 pages.
Clinical Trials Identifier: NCT04594369. ClinicalTrials.gov submitted on Nov. 23, 2022, 30 pages.
Clinical Trials Identifier: NCT04594369. ClinicalTrials.gov submitted on Oct. 10, 2022, 31 pages.
Clinical Trials Identifier: NCT04594369. ClinicalTrials.gov submitted on Oct. 14, 2020, 6 pages.
Clinical Trials Identifier: NCT04594369. ClinicalTrials.gov submitted on Oct. 27, 2022, 31 pages.
Clinical Trials Identifier: NCT04594369. ClinicalTrials.gov submitted on Oct. 28, 2021, 29 pages.
Clinical Trials Identifier: NCT04594369. ClinicalTrials.gov submitted on Oct. 29, 2021, 29 pages.
Clinical Trials Identifier: NCT04594369. ClinicalTrials.gov submitted on Oct. 8, 2021, 28 pages.
Clinical Trials Identifier: NCT04594369. ClinicalTrials.gov submitted on Sep. 12, 2022, 31 pages.
Clinical Trials Identifier: NCT04594369. ClinicalTrials.gov submitted on Sep. 27, 2022, 31 pages.
Clinical Trials Identifier: NCT04594369. ClinicalTrials.gov submitted on Sep. 7, 2021, 25 pages.
Clinical Trials Identifier: NCT04817332. ClinicalTrials.gov submitted on Aug. 12, 2021, 8 pages.
Clinical Trials Identifier: NCT04817332. ClinicalTrials.gov submitted on Mar. 25, 2021, 8 pages.
Clinical Trials Identifier: NCT05090904. ClinicalTrials.gov submitted on Apr. 14, 2022, 6 pages.
Clinical Trials Identifier: NCT05090904. ClinicalTrials.gov submitted on Apr. 5, 2022, 6 pages.
Clinical Trials Identifier: NCT05090904. ClinicalTrials.gov submitted on Aug. 23, 2022, 7 pages.
Clinical Trials Identifier: NCT05090904. ClinicalTrials.gov submitted on Dec. 3, 2021, 6 pages.
Clinical Trials Identifier: NCT05090904. ClinicalTrials.gov submitted on Jul. 27, 2022, 7 pages.
Clinical Trials Identifier: NCT05090904. ClinicalTrials.gov submitted on Jul. 29, 2022, 7 pages.
Clinical Trials Identifier: NCT05090904. ClinicalTrials.gov submitted on Jul. 4, 2022, 7 pages.
Clinical Trials Identifier: NCT05090904. ClinicalTrials.gov submitted on Jun. 22, 2022, 7 pages.
Clinical Trials Identifier: NCT05090904. ClinicalTrials.gov submitted on Jun. 7, 2022, 7 pages.
Clinical Trials Identifier: NCT05090904. ClinicalTrials.gov submitted on Mar. 8, 2022, 6 pages.
Clinical Trials Identifier: NCT05090904. ClinicalTrials.gov submitted on May 13, 2022, 7 pages.
Clinical Trials Identifier: NCT05090904. ClinicalTrials.gov submitted on May 25, 2022, 7 pages.
Clinical Trials Identifier: NCT05090904. ClinicalTrials.gov submitted on Nov. 10, 2022, 7 pages.
Clinical Trials Identifier: NCT05090904. ClinicalTrials.gov submitted on Oct. 12, 2022, 7 pages.
Clinical Trials Identifier: NCT05090904. ClinicalTrials.gov submitted on Oct. 14, 2021, 5 pages.
Clinical Trials Identifier: NCT05090904. ClinicalTrials.gov submitted on Oct. 29, 2021, 5 pages.
Clinical Trials Identifier: NCT05090904. ClinicalTrials.gov submitted on Sep. 9, 2022, 7 pages.
Clinical Trials Identifier: NCT05344508. ClinicalTrials.gov submitted on Apr. 18, 2022, 3 pages.
Clinical Trials Identifier: NCT05344508. ClinicalTrials.gov submitted on Aug. 3, 2022, 3 pages.
Clinical Trials Identifier: NCT05344508. ClinicalTrials.gov submitted on Oct. 6, 2022, 3 pages.
Clinical Trials Identifier: NCT05355935. ClinicalTrials.gov submitted on Apr. 26, 2022, 6 pages.
Clinical Trials Identifier: NCT05355935. ClinicalTrials.gov submitted on Aug. 16, 2022, 6 pages.
Clinical Trials Identifier: NCT05355935. ClinicalTrials.gov submitted on Jul. 27, 2022, 6 pages.
Clinical Trials Identifier: NCT05355935. ClinicalTrials.gov submitted on Jul. 5, 2022, 6 pages.
Clinical Trials Identifier: NCT05355935. ClinicalTrials.gov submitted on Jun. 7, 2022, 6 pages.
Clinical Trials Identifier: NCT05355935. ClinicalTrials.gov submitted on May 16, 2022, 6 pages.
Clinical Trials Identifier: NCT05355935. ClinicalTrials.gov submitted on Oct. 19, 2022, 5 pages.
Clinical Trials Identifier: NCT05355935. ClinicalTrials.gov submitted on Sep. 9, 2022, 6 pages.
Clinical Trials Identifier: NCT05517525. ClinicalTrials.gov submitted on Aug. 24, 2022, 5 pages.
Clinical Trials Identifier: NCT05517525. ClinicalTrials.gov submitted on Nov. 7, 2022, 4 pages.
Clinical Trials Identifier: NCT05517525. ClinicalTrials.gov submitted on Oct. 17, 2022, 4 pages.
Clinical Trials Identifier: NCT05517525. ClinicalTrials.gov submitted on Sep. 21, 2022, 5 pages.
Dadoniene, J. et al. (2017), "Clinical characteristics and long-term survival differences of the ANCA-associated vasculitis group: a cross-sectional study of 27 patients," ACTA Medica Lituanica, vol. 24, No. 2, pp. 107-112.
Doyle, K. et al. (Oct. 2016), "Discovery of second generation reversible covalent DPP1 inhibitors leading to an Oxazepane

(56) References Cited

OTHER PUBLICATIONS

Amidoacetonitrile based clinical candidate (AZD7986)," Journal of Medicinal Chemistry, 59(20):9457-9472.
Everts-Graber, J. et al. (2019), "Proteomic analysis of neutrophils in ANCA-associated vasculitis reveals a dysregulation in proteinase 3-associated proteins such as annexin-A1 involved in apoptotic cell clearance," Kidney International 96, 397-408; https://doi.org/10.1016/j.kint.2019.02.017.
Extended European Search Report for European Application No. 17195612.1, mailed Mar. 21, 2018, 5 pages.
Extended European Search Report for European Application No. 17835331.4, mailed Feb. 11, 2020, 8 pages.
Extended European Search Report for European Application No. 19751012.6, mailed Oct. 4, 2021, 7 pages.
Extended European Search Report for European Application No. 19837016.5, mailed Mar. 18, 2022, 10 pages.
Extended European Search Report for European Application No. 19838400.0, mailed Mar. 24, 2022, 9 pages.
Extended European Search Report for European Application No. 20173862.2, mailed Sep. 11, 2020, 7 pages.
Extended European Search Report for European Application No. 22796849.2 mailed Feb. 7, 2025, 10 pages.
Extended European search report for European Application No. 25150988.1 mailed May 27, 2025, 7 pages.
Falk, R. J. et al. (Jun. 1990) "Anti-neutrophil cytoplasmic autoantibodies induce neutrophils to degranulate and produce oxygen radicals in vitro," Proc. Natl. Acad. Sci. USA, vol. 87, pp. 4115-4119.
Floris, A. et al. (Apr. 2016), "Using the Birmingham vasculitis activity score as a screening tool in patients with suspected vasculitis," i174, Poster Viewing III, Retrieved from the Internet: URL: https://academic.oup.com/rheumatology/article-abstract/55/suppl_1/1174/1795586, Retrieved from the Internet on Apr. 23, 2018, 1 page.
Furber, M. et al. (2014), "Cathepsin C Inhibitors: Property Optimization and Identification of a Clinical Candidate," Journal of Medicinal Chemistry, vol. 57, pp. 2357-2367.
Gardiner, P. et al. (2016), "Neutrophil maturation rate determines the effects of dipeptidyl peptidase 1 inhibition on neutrophil serine protease activity," Br J Pharmacol; 173:2390-401.
Geetha, D. et al. (2015), "Current therapy of granulomatosis with polyangiitis and microscopic polyangiitis: the role of rituximab," J Nephrol 28:17-27.
Gerald, L. B. et al. (Apr. 2009), "Changes in environmental tobacco smoke exposure and asthma morbidity among urban school children," Chest, vol. 135, No. 4, pp. 911-916.
Goeminne, P. C. et al. (Feb. 2014), "Mortality in non-cystic fibrosis bronchiectasis: A prospective cohort analysis," Respir. Med., 108(2):287-296.
Golchert, D. et al. (Sep. 2013), "Evaluation of some compression aids in tableting of roller compacted swellable core drug layer," Int J Pharm., 453(2):322-328.
Guarino, C. et al. (2017), "Prolonged pharmacological inhibition of cathepsin C results in elimination of neutrophil serine proteases," Biochem Pharmacol; 131:52-67.
Guay, D. et al. (2009), "Design and synthesis of dipeptidyl nitriles as potent, selective, and reversible inhibitors of cathepsin C," Bioorg Med Chem Lett; 19:5392-5396.
Guay, D. et al. (2010), "Therapeutic Utility and Medicinal chemistry of Cathepsin C Inhibitors," Curr Top Med Chem; 10:708-716.
Guillevin, L. et al. (Mar. 1999), "Microscopic Polyangiitis," Arthritis & Rheumatism, vol. 42, No. 3, pp. 421-430.
Huang, L. L. et al., "3D-QSAR, molecular docking and molecular dynamics simulations of oxazepane amidoacetonitrile derivatives as novel DPPI inhibitors," Journal of Molecular Structure, vol. 1168, May 2018, pp. 223-233.
Insmed, (Feb. 2020), "Insmed Announces Positive Top-Line Results from Phase 2 WILLOW Study ofINS1007 in Patients with Non-Cystic Fibrosis Bronchiectasis," 5 pages.
Insmed, "Insmed Announces Worldwide License Agreement with AstraZeneca for Oral DPP1 Inhibitor," Oct. 2016, 3 pages.
Insmed, "Insmed Reports Third Quarter 2016 Financial Results and Provides Business Update," Nov. 2016, 11 pages.
International Preliminary Report on Patentability for International Application No. PCT/EP2019/055138 dated Sep. 10, 2020, 8 pages.
International Preliminary Report on Patentability for International Application No. PCT/US2021/064810, dated Jul. 6, 2023, 6 pages.
International Preliminary Report on Patentability for International Application No. PCT/US2022/027026, dated Nov. 9, 2023, 8 pages.
International Preliminary Report on Patentability for International Application No. PCT/US2023/062731 mailed Aug. 29, 2024, 6 pages.
International Preliminary Report on Patentability for International Application No. PCT/US2024/010555 mailed Jul. 17, 2025, 10 pages.
International Preliminary Report on Patentability for International Application No. PCT/US2024/015802 mailed Aug. 28, 2025, 8 pages.
International Search Report and Written Opinion for International Application No. PCT/CN2024/118880 mailed Nov. 21, 2024, 14 pages.
International Search Report and Written Opinion for International Application No. PCT/CN2025/082555 mailed May 30, 2025, 16 pages.
International Search Report and Written Opinion for International Application No. PCT/EP2019/055138, mailed Jul. 19, 2019, 11 pages.
International Search Report and Written Opinion for International Application No. PCT/GB2015/050155, mailed Mar. 6, 2015, 7 pages.
International Search Report and Written Opinion for International Application No. PCT/US2017/044343, mailed Oct. 12, 2017, 7 pages.
International Search Report and Written Opinion for International Application No. PCT/US2019/016844, mailed May 31, 2019, 10 pages.
International Search Report and Written Opinion for International Application No. PCT/US2019/042021, mailed Sep. 4, 2019, 7 pages.
International Search Report and Written Opinion for International Application No. PCT/US2019/042026, mailed Sep. 4, 2019, 7 pages.
International Search Report and Written Opinion for International Application No. PCT/US2021/064810, mailed Mar. 16, 2022, 8 pages.
International Search Report and Written Opinion for International Application No. PCT/US2022/026769, mailed Sep. 9, 2022, 15 pages.
International Search Report and Written Opinion for International Application No. PCT/US2022/027026, mailed Sep. 14, 2022, 11 pages.
International Search Report and Written Opinion for International Application No. PCT/US2022/048249, mailed Feb. 1, 2023, 8 pages.
International Search Report and Written Opinion for International Application No. PCT/US2023/062731, dated May 30, 2023, 32 pages.
International search report and Written Opinion for International Application No. PCT/US2024/015802 mailed Jul. 9, 2024, 12 pages.
International Search Report and Written Opinion for PCT Application No. PCT/CN2025/075611 mailed May 8, 2025, 17 pages.
International Search Report and Written Opinion for PCT Application No. PCT/CN2025/075960 mailed Apr. 23, 2025, 13 pages.
International Search Report and Written Opinion for PCT Application No. PCT/CN2025/088450 mailed Jul. 2, 2025, 13 pages.
International Search Report and Written Opinion for PCT Application No. PCT/US2023/071162 dated Feb. 21, 2024, 12 pages.
International Search Report and Written Opinion for PCT Application No. PCT/US2024/010555 dated Apr. 29, 2024, 13 pages.
International Search Report and Written Opinion for PCT Application No. PCT/US2024/020305 mailed Jul. 1, 2024, 12 pages.
International Search Report and Written Opinion for PCT Application No. PCT/US2024/046701 mailed Dec. 23, 2024, 11 pages.

(56) References Cited

OTHER PUBLICATIONS

International Search Report and Written Opinion for PCT Application No. PCT/US2025/013490 mailed Jun. 4, 2025, 12 pages.
International Search Report and Written Opinion for PCT Application No. PCT/US2025/024417 mailed Aug. 14, 2025, 13 pages.
Invitation to Pay Additional Fees for International Application No. PCT/US2022/026769, mailed Jun. 27, 2022, 3 pages.
Invitation to Pay Additional Fees for International Application No. PCT/US2022/027026, mailed Jul. 8, 2022, 2 pages.
Invitation to pay additional fees for International Application No. PCT/US2023/071162, dated Nov. 14, 2023, 2 pages.
Invitation to pay additional fees for International Application No. PCT/US2024/010555 dated Mar. 12, 2024, 2 pages.
Invitation to pay additional fees for International Application No. PCT/US2024/015802 dated Apr. 15, 2024, 2 pages.
Invitation to pay additional fees for International Application No. PCT/US2024/020305, dated May 15, 2024, 2 pages.
Invitation to pay additional fees for International Application No. PCT/US2024/046701, mailed Oct. 31, 2024, 2 pages.
Invitation to Pay Additional fees for International Application No. PCT/US2025/013490, mailed Mar. 25, 2025, 2 pages.
Invitation to Pay Additional Fees for PCT Application No. PCT/US2025/024417 mailed Jun. 16, 2025, 2 pages.
Jarrot, P-A et al. (Jul. 2016), "Review Pathogenesis of ANCA-associated vasculitis: An update," Autoimmunity Reviews, vol. 15, Issue 7, pp. 704-713.
Jenne, D. E. (Aug. 1990), "Wegener's autoantigen decoded," Nature, vol. 346, p. 520, 1 page.
Jennette, J. C. (2011), "Nomenclature and classification of vasculitis: lessons learned from granulomatosis with polyangiitis (Wegener's granulomatosis)," Clinical and Experimental Immunology, 164 (Suppl. 1), pp. 7-10.
Jones, B. E. et al. (2017), "Gene-Specific DNA Methylation Changes Predict Remission in Patients with ANCA-Associated Vasculitis," J Am Soc Nephrol 28: 1175-1187. doi: 10.1681/ASN.2016050548.
Kallenberg, C. G. M. et al. (Dec. 2006), "Mechanisms of Disease: pathogenesis and treatment of ANCA-associated vasculitides," Nature Clinical Practice Rheumatology, vol. 2, No. 12, pp. 661-670.
Karthik, V. V. (Jun. 2016), "Excipients Used in the Formulation of Tablets," Research and Reviews: Journal of chemistry, 5(2):143-154.
Kelly, M. G. et al. (Sep. 2003), "Bronchiectasis in secondary care: A comprehensive profile of a neglected disease," Eur. J. Intern. Med., 14(8):488-492.
Keogh, K. A. et al. (2006), "Rituximab for Refractory Wegener's Granulomatosis. Report of a Prospective, Open-Label Pilot Trial," Am J Respir Crit Care Med vol. 173. pp 180-187.
Kettritz, R. (Jun. 2008), "Autoimmunity in kidney diseases," The Scandinavian Journal of Clinical & Laboratory Investigation, vol. 68, No. S241, 99-103.
Knopf, A. et al. (2015), "Clinical aspects of granulomatosis with polyangiitis affecting the head and neck," Eur Arch Otorhinolaryngol 272:185-193.
Kono, H., et al. (Oct. 2012), "The IL-1-dependent sterile inflammatory response has a substantial caspase-1-independent component that requires cathepsin C," The Journal of Immunology, vol. 189, No. 7, pp. 3734-3740.
Korkmaz, B. et al. (2013), "Neutrophil proteinase 3 and dipeptidyl peptidase I (cathepsin C)as pharmacological targets in granulomatosis with polyangiitis (Wegener granulomatosis)," Semin Immunopathol, 35:411-421.
Korkmaz, B. et al. (2018) "Therapeutic targeting of cathepsin C: from pathophysiology to treatment," Pharmacol Ther; 190:202-236.
Korkmaz, B. et al. (2019), "Structure-based design and in vivo anti-arthritic activity evaluation of a potent dipeptidyl cyclopropyl nitrile inhibitor of cathepsin C," Biochem Pharmacol ;164:349-367.
Korkmaz, B. et al. (2020), "Lung Protection by Cathepsin C Inhibition: A New Hope for COVID-19 and ARDS?" J Med Chem ;63:13258-13265. doi:10.1021/acs.jmedchem.0c00776.
Korkmaz, B. et al. (Dec. 2021), "Cathepsin C inhibition as a potential treatment strategy in cancer," Biochemical Pharmacology, 194:114803, 15 pages.
Korkmaz, B. et al. (Nov. 2010), "Neutrophil Elastase, Proteinase 3, and Cathepsin G as Therapeutic Targets in Human Diseases," Pharmacological Reviews, vol. 62, No. 4, pp. 726-759.
Laine, D. I. et al. (2010), "Discovery of novel cyanamide-based inhibitors of cathepsin C," ACS Med Chem Lett.;2(2):142-147.
Laine, D. I. et al. (2010), "Inhibitors of Cathepsin C (DPPI)," Expert Rev. Ther Pat; 20: 497-506.
Li, J. et al. (2014), "Lubricants in Pharmaceutical Solid Dosage Forms", Lubricants, 2(1):21-43.
Lins, L. et al. (2016), "SF-36 total score as a single measure of health-related quality of life: Scoping review," SAGE Open Medicine, vol. 4:1-12.
Ludvigsson, J. W. et al. (2018), "Degradation caused by incompatibility between sodium stearyl fumarate (PRUV) and AZD7986 in the drug product," Journal of Pharmaceutical and Biomedical Analysis, 158:82-87.
Luqmani, R. A. et al. (1994), "Birmingham Vasculitis Activity Score (BVAS) in Systemic Necrotizing Vasculitis," Q. J. Med; 87:671-678.
Mayo Clinic, "Periodontitis," Oct. 19, 2021, 4 pages.
Mcshane, P. J. et al. (2013), "Non-cystic fibrosis bronchiectasis," Am J Respir Crit Care Med; 188(6):647-656. doi: 10.1164/rccm.201303-0411CI.
Methot, N. et al. (2008), "In Vivo Inhibition of Serine Protease Processing Requires a High Fractional Inhibition of Cathepsin C," Mol. Pharm; 73(6):1857-1865.
Methot, N. et al. (Jul. 2007), "Inhibition of the activation of multiple serine proteases with a cathepsin C inhibitor requires sustained exposure to prevent proenzyme processing," J. Biol. Chem., 282(29):20836-20846.
Miller, B. E. et al. (2017), "Epithelial desquamation observed in a Phase I study of an oral cathepsin C inhibitor (GSK2793660)," Br J Clin Pharmacol;83(12):2813-2820. doi:10.1111/bcp.13398.
Miller, M. R. et al. (2005), "Standardisation of spirometry," Eur. Respir. J; 26:319-338.
Mukhtyar, C. et al. (2009), "Modification and validation of the Birmingham Vasculitis Activity Score (version 3)," Ann Rheum Dis;68:1827-1832.
Murray, M. P. et al. (2009), "Sputum colour: a useful clinical tool in non-cystic fibrosis bronchiectasis," Eur Respir J; 34: 361-364.
Murray, M. P. et al. (2009), "Validation of the Leicester Cough Questionnaire in non- cystic fibrosis bronchiectasis," Eur Respir J; 34: 125-131.
National Center for Biotechnology Information (2025). PubChem Substance Record for SID 103924055, BDBM50011502, Source: BindingDB. Retrieved Apr. 7, 2025 from https://pubchem.ncbi.nlm.nih.gov/substance/103924055, 6 pages.
National Center for Biotechnology Information (2025). PubChem Substance Record for SID 311692964, SCHEMBL16932317, Source: SureChEMBL. Retrieved May 21, 2024 from https://pubchem.ncbi.nlm.nih.gov/substance/311692964, 7 pages.
National Center for Biotechnology Information (2025). PubChem Substance Record for SID 461766587, SID 461766587, Source: Patentscope (WIPO). Retrieved May 8, 2024 from https://pubchem.ncbi.nlm.nih.gov/substance/461766587, 6 pages.
Ochsenkuhn, T. et al. (Jan. 2018), "Ustekinumab as rescue treatment in therapy-refractory or -intolerant ulcerative colitis," Abstract P759, Abstracts of the 13th Congress of ECCO, Journal of Crohn's and Colitis, vol. 12, Supplement 1, p. S495, 1 page.
Pagnoux, C. et al. (2015), "Treatment of granulomatosis with polyangiitis (Wegener's)," Expert Review of Clinical Immunology, 11:3, 339-348.
Pagnoux, C. et al. (2016), "Optimal therapy and prospects for new medicines in eosinophilic granulomatosis with polyangiitis (Churg-Strauss syndrome)," Expert Review of Clinical Immunology, vol. 12, No. 10, pp. 1059-1067.
Palmer, R. et al. (2018), "Dipeptidyl Peptidase 1 Inhibitor AZD7986 Induces a Sustained, Exposure-Dependent Reduction in Neutrophil Elastase Activity in Healthy Subjects," Clin Pharmacol Ther; 104(6):1155-1164. doi:10.1002/cpt.1053.

(56) References Cited

OTHER PUBLICATIONS

Pham, C. T. (Jul. 2006), "Neutrophil serine proteases: specific regulators of inflammation," Nat. Rev. Immunol;6:541-550.
Popa, E. R. et al. (1999), "Differential B- and T-cell activation in Wegener's granulomatosis," J Allergy Clin Immunol ;103:885-894.
Pubchem, CID 134527801, "(2S)-2-[[Hydroxy-[(2S)-1,4-oxazepan-2-yl]methyl]amino]-3-[4-(3-methyl-2-oxo-1,3-benzoxazol-5-yl)phenyl]propanenitrile," Jun. 23, 2018, Retrieved from the Internet: URL: https://pubchem.ncbi.nlm.nih.gov/compound/134527801, 6 pages.
PubChem CID 169550959, Jan. 2024, 9 pages.
PubChem CID 61118902, Oct. 2012, 7 pages.
PubChem CID 63873324, Oct. 2012, 8 pages.
Rawn, S. et al. (2014), "Purpura, petechiae, and bullae as first signs of juvenile granulomatosis with polyangiitis," Eur J Pediatr 173:1685-1689.
Registry RN 2781135-46-2, Jun. 2022, 8 pages.
Rehm, S. R. T. et al. (2019), "Premedication with a cathepsin C inhibitor alleviates early primary graft dysfunction in mouse recipients after lung transplantation," Sci Rep;9(1):9925-9933.
Rosati, M. G. et al. (Jan.-Feb. 2016), "Relationships among allergic rhinitis, asthma, and chronic rhinosinusitis," American Journal of Rhinology and Allergy, vol. 30, No. 1, pp. 44-47.
Schirmer, J. H. et al. (2016), "Clinical presentation and long-term outcome of 144 patients with microscopic polyangiitis in a monocentric German cohort," Rheumatology ;55:71-79.
Schreiber, A. et al. (Mar. 2012), "Neutrophil serine proteases promote IL-1B generation and injury in necrotizing crescentic glomerulonephritis," Journal of the American Society of Nephrology, vol. 23, No. 3, pp. 470-482.
Selga, D. et al. (2006), "Polyarteritis nodosa when applying the Chapel Hill nomenclature—a descriptive study on ten patients," Rheumatology;45:1276-1281.
Shapiro, S. C. et al. (2016), "Inflammatory bowel disease mimicking granulomatosis with polyangiitis: a case report," Journal of Medical Case Reports 10:214, 5 pages.
Stenton, "The MRC breathlessness scale" Occupational Med., May 2008, 58:226-227.
Stockley, R. et al., (Feb. 2013), "Phase II study of a neutrophil elastase inhibitor (AZD9668) in patients with bronchiectasis," Respiratory Medicine, vol. 107, No. 4, pp. 524-533.
Stone, J. H. et al., (Apr. 2001), "A Disease-Specific Activity Index for Wegener's Granulomatosis," Arthritis & Rheumatism, vol. 44, No. 4, pp. 912-920.
Suka, M. et al. (2012), "Improvement in health-related quality of life in MPO-ANCA-associated vasculitis patients treated with cyclophosphamide plus prednisolone: an analysis of 18 months of follow-up data from the JMAAV study," Mod Rheumatol 22:877-884.
Suppiah, R. et al., (2011), "A cross-sectional study of the Birmingham Vasculitis Activity Score version 3 in systemic vasculitis," Rheumatology;50:899-905.
Trouvin, A.-P. et al. (2014), "Usefulness of monitoring of B cell depletion in rituximab-treated rheumatoid arthritis patients in order to predict clinical relapse: a prospective observational study," Clinical and Experimental Immunology, vol. 180, pp. 11-18.
U.S. National Library of Medicine, "History of Changes for Study: NCT02653872," Jul. 14, 2017, [Online], Retrieved from the Internet: URL:https://classic.clinicaltrials.gov/ct2/history/NCT02653872?V_6=View#StudyPageT op; 17 pages.
U.S. National Library of Medicine, "Randomized, Double-Blind, Placebo-Controlled, Parallel-Group, Multi-Center Study of Efficacy, Safety & Tolerability, and Pharmacokinetics of INS1007 Administered Daily for 24 Weeks in Non-Cystic Fibrosis Bronchiectasis—The Willow Study," Study NCT03218917 [online], Retrieved from the Internet: https://clinicaltrials.gov/ct2/history/NCT03218917?V_1=View#StudyPage Top , Jul. 2017, 8 pages.
Von Vietinghoff, S. et al., (2005), "Membrane proteinase 3 and Wegener's granulomatosis," Clinical Nephrology, vol. 64, No. 4, pp. 453-459.
Wang, J. et al. (2010), "Lubrication in tablet formulations," European Journal of Pharmaceutics and Biopharmaceutics, 75:1-15.
Wickremasinghe, M. et al. (2005), "Non-tuberculous mycobacteria in patients with bronchiectasis," Thorax, 60(12):1045-1051.
Yates, M. et al. (2016), "EULAR/ERA-EDTA recommendations for the management of ANCA-associated vasculitis," Ann Rheum Dis 75:1583-1594.
Zhang, J. et al. (2019), "INS1007, a Reversible Dipeptidyl Peptidase 1 Inhibitor, Ameliorates Interferon-alpha-Accelerated Lupus Nephritis in Mice," Abstract Review, 17th International Congress of Immunology. Abstract: A-1059-0027-00953, 1 page.
Zhang, J. et al. (2019), "The Reversible Dipeptidyl Peptidase 1 Inhibitor, INS1007, Decreases Surface Proteinase 3 Expression and Neutrophil Serine Protease Activities in Human Neutrophils," Rheumatology. 58(Supplement 2), p. ii24.
Atzrodt, J. et al. (Oct. 2007), "The renaissance of H/D exchange," Angew Chem Int Ed Engl., 46(41):7744-7765.
Birmingham Vasculitis Activity Score (Dec. 2009), Version 3, Annals of the Rheumatic Diseases, 1 page.
Economidou, M. et al. (Sep. 2023), "Palladium Extraction Following Metal-Catalyzed Reactions: Recent Advances and Applications in the Pharmaceutical Industry," Organic Process Research & Development, vol. 27, Issue 96, pp. 1585-1615.
Hulikal, V. (2010), "Deuterium Labeled Compounds in Drug Discovery Process," Bioorganics and Applied Materials Pvt Ltd., Abstract, 1 page.
International Application No. PCT/IB2025/060616, International Search Report and Written Opinion mailed Jan. 19, 2026; Applicant: Insmed Incorporated; 13 pages.
International Application No. PCT/US2025/055533, Invitation to Pay Additional Fees mailed Mar. 2, 2026; Applicant: Insmed Incorporated; 12 pages.

* cited by examiner

LINEAR DIPEPTIDYL PEPTIDASE 1 INHIBITORS AND USES THEREOF

CROSS-REFERENCE TO RELATED APPLICATIONS

This application is a continuation of International Patent Application No. PCT/CN2025/075611, filed Jan. 30, 2025, which claims priority to International Patent Application No. PCT/CN2024/074986 filed on Jan. 31, 2024, International Patent Application No. PCT/CN2024/124776 filed on Oct. 14, 2024, and International Patent Application No. PCT/CN2024/137503 filed on Dec. 6, 2024. The contents of each are hereby incorporated by reference in their entirety for all purposes.

BACKGROUND

Dipeptidyl peptidase 1 (DPP1; EC 3.4.14.1), also known as cathepsin C, is a lysosomal cysteine protease belonging to the papain family having a molecular weight of 200 kDa. DPP1 was first discovered by Gutman and Fruton in 1948 (*J Biol Chem,* 174, 851-858); however, the cDNA of the human enzyme was first described in 1995 (Paris et al. 1995, FEBS Lett, 369, 326-330). DPP1 is the only member of the papain family that is functional as a tetramer, consisting of four identical subunits. Each subunit is composed of an N-terminal fragment, a heavy chain and a light chain (Dolenc et al. 1995, *J Biol Chem,* 270, 21626-21631).

DPP1 is constitutively expressed in many tissues with highest levels in lung, kidney, liver and spleen. DPP1 catalyzes the removal of dipeptides from the N-terminal end of polypeptide substrates with broad specificity. Recent data suggest that besides being an important enzyme in lysosomal protein degradation, DPP1 also functions as a key enzyme in the activation of granule serine proteases in cytotoxic T-lymphocytes and natural killer cells (granzymes A and B), mast cells (chymase and tryptase) and neutrophils (cathepsin G, neutrophil elastase and proteinase-3).

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the MC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion.

Neutrophils play a critical role in host defense against invading pathogens. Neutrophils are produced in the bone marrow and are fully mature when released into the circulation to take up their role as the first line of cellular defense. Pro-inflammatory mediators and chemotactic attractants activate neutrophils and draw them to the site of infection, where they act to engulf bacteria by phagocytosis, assaulting them with an arsenal of anti-bacterial compounds that use both oxidative and non-oxidative methods of attack. The powerful serine protease, neutrophil elastase, is one of those anti-bacterial compounds that are clearly involved in destroying bacteria. Neutrophil elastase is released into the phagolysome surrounding the microorganism, which it proceeds to destroy. Neutrophil elastase is able to attack the outer membrane protein, OmpA, in gram-negative bacteria, helping to directly kill the pathogen by degrading its membrane, as well as enabling other anti-bacterial compounds to gain access to the pathogen. In addition, neutrophil elastase may help process other antibacterial compounds, converting them from inactive pro-peptides into their active states, such as for cathelicidin.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defense against infection by degrading phagocyte surface receptors and opsonins. Its negative role has been reported in a number of diseases characterized by tissue destruction and inflammation.

As such, there is a need in the art to provide novel DPP1 inhibitors in order to treat the aforementioned diseases, and others associated with DPP1 and neutrophil elastase.

SUMMARY

In embodiment, the present disclosure provides a compound of Formula (I)

(I)

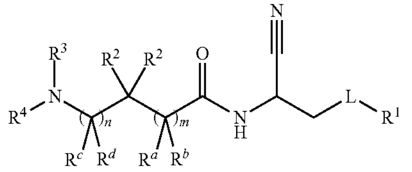

or a pharmaceutically acceptable salt, a stereoisomer or a deuterated form thereof, wherein $R^1$ is carbocyclyl, aryl, heterocyclyl or heteroaryl, wherein $R^1$ is optionally substituted with 1-5 groups independently selected from $R^5$ or $R^6$;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-NH($C_{1-6}$ alkyl$)_2$, $C_{1-6}$ alkylene-N($C_{1-6}$ alkyl$)_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl$)_2$, COOH, $C(=)OC_{1-6}$ alkyl, $C(=O)OC_{1-6}$ alkyl, $C(=O)N_{1-6}$ alkyl, C(=O)N($C_{1-6}$ alkyl$)_2$, or $NHC(=O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$ each of $R^a$, $R^b$, $R^c$ and $R^d$ is independently selected from H, alkyl, halogen or haloalkyl;

each of n and m is independently 0, 1, 2, or 3;

provided that the compound is not

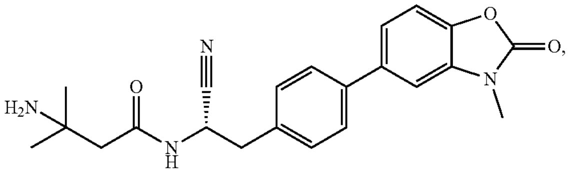

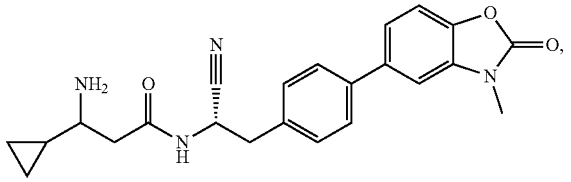

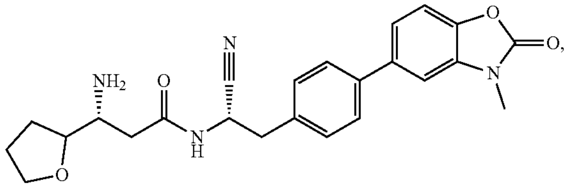

-continued

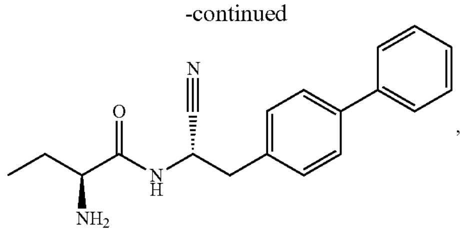
,

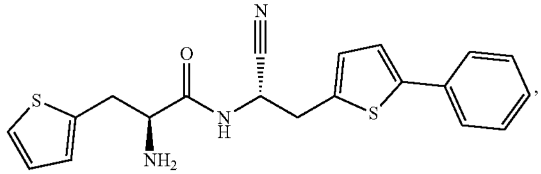
,

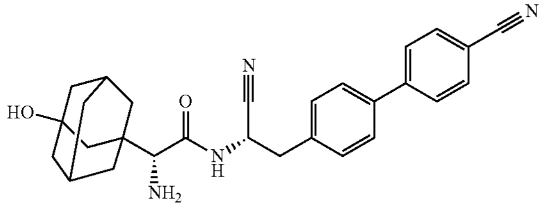
or

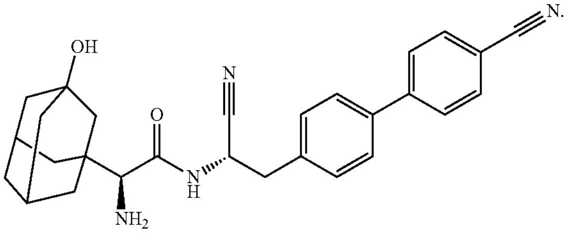

In embodiments, the present disclosure provides a compound of Formula (II):

(II)

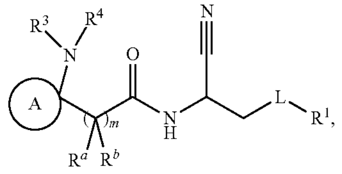

or a pharmaceutically acceptable salt, a stereoisomer, or a deuterated form thereof, wherein:

$R^1$ is carbocyclyl, aryl, heterocyclyl or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

Ring A is a carbocyclyl, aryl or heterocyclyl wherein Ring A is optionally substituted with 1-5 $R^5$;

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O)alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2—C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycyl, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$ each of $R^a$ and $R^b$ is independently selected from H, alkyl, halogen or haloalkyl; and m is independently 0, 1, 2, or 3;

provided that the compound is not

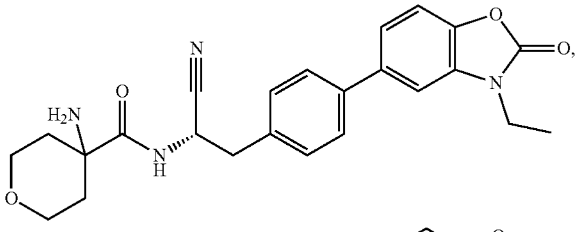

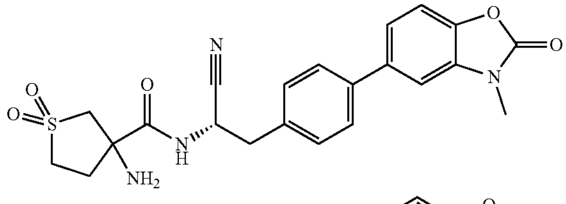

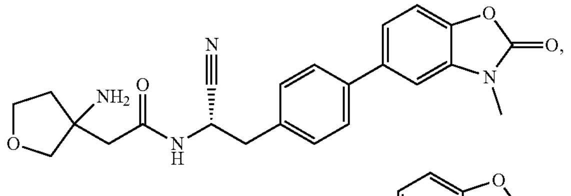

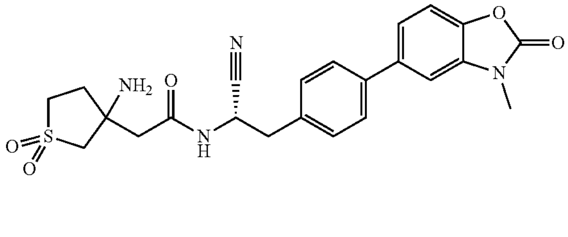

-continued

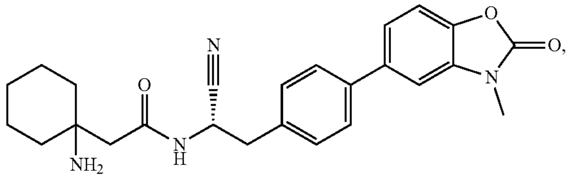

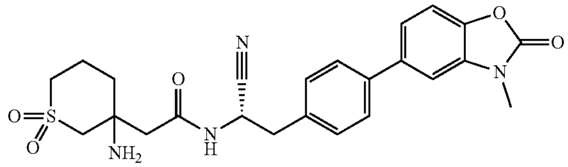

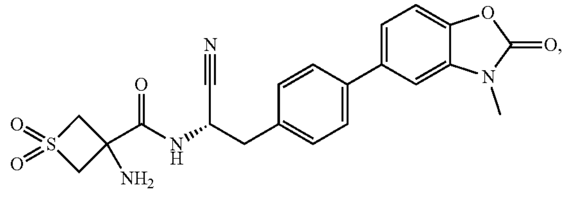

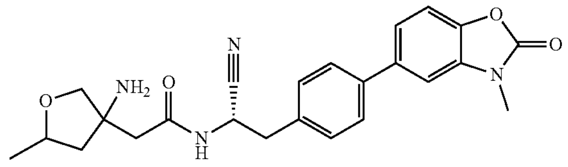

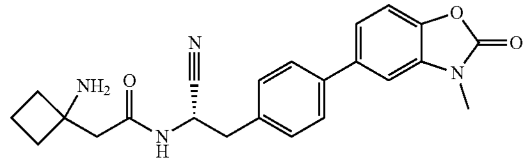

or

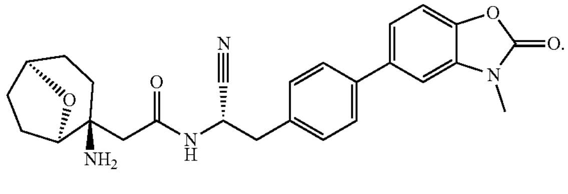

In embodiments, the present disclosure provides a compound of Formula (III):

(III)

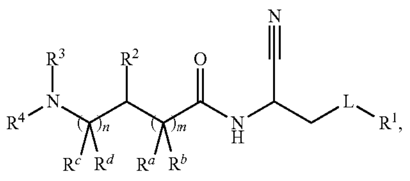

or a pharmaceutically acceptable salt, a stereoisomer or a deuterated form thereof, wherein $R^1$, $R^2$, $R^3$, $R^4$, $R^a$, $R^b$, $R^c$, $R^d$, L, m and n are defined anywhere herein.

In embodiments, the present disclosure provides a compound of Formula (IV):

(IV)

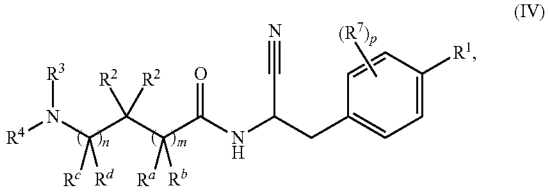

or a pharmaceutically acceptable salt, a stereoisomer or a deuterated form thereof, wherein $R^1$, $R^2$, $R^3$, $R^4$, $R^a$, $R^b$, $R^c$, $R^d$, $R^7$, p, m and n are defined anywhere herein.

In embodiments, the present disclosure provides a compound of Formula (V):

(V)

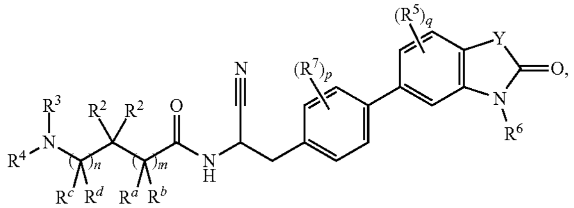

or a pharmaceutically acceptable salt, a stereoisomer or a deuterated form thereof, wherein Y, $R^1$, $R^2$, $R^3$, $R^4$, $R^a$, $R^b$, $R^c$, $R^d$, $R^5$, $R^6$, $R^7$, p, q, m and n are defined anywhere herein.

In embodiments, the present disclosure provides a compound of Formula (VI):

(VI)

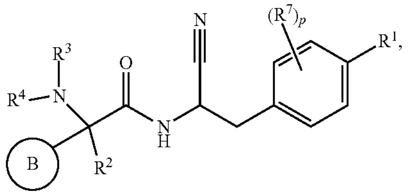

or a pharmaceutically acceptable salt, a stereoisomer or a deuterated form thereof, wherein ring B, $R^1$, $R^2$, $R^3$, $R^4$, $R^7$ and p are defined anywhere herein.

In embodiments, the present disclosure provides a compound of Formula (VII):

(VII)

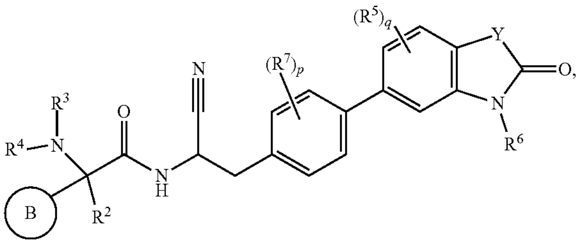

or a pharmaceutically acceptable salt, a stereoisomer or a deuterated form thereof, wherein Y, ring B, $R^2$, $R^3$, $R^4$, $R^5$, $R^6$, $R^7$, p, q are defined anywhere herein.

In embodiments, the present disclosure provides a compound of Formula (VIII):

(VIII)

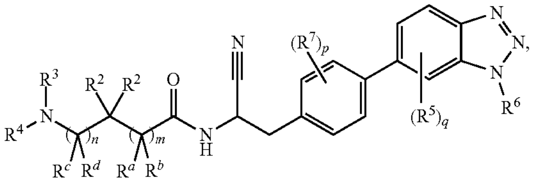

or a pharmaceutically acceptable salt, a stereoisomer or a deuterated form thereof, wherein $R^2$, $R^3$, $R^4$, $R^a$, $R^b$, $R^c$, $R^d$, $R^5$, $R^6$, $R^7$, m, n, p and q are defined anywhere herein.

In embodiments, the present disclosure provides a compound of Formula (IX):

(IX)

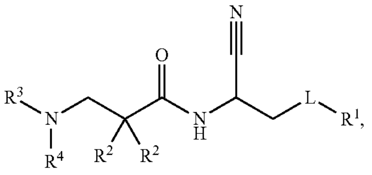

or a pharmaceutically acceptable salt, a stereoisomer or a deuterated form thereof, wherein L, $R^1$, $R^2$, $R^3$ and $R^4$ are defined anywhere herein.

In embodiments, the present disclosure provides a compound of Formula (IX-A):

(IX-A)

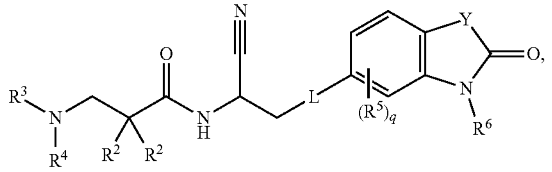

or a pharmaceutically acceptable salt, a stereoisomer or a deuterated form thereof, wherein Y, L, $R^2$, $R^3$, $R^4$, $R^5$, $R^6$, $R^7$ and q are defined anywhere herein.

In embodiments, the present disclosure provides a compound of Formula (IX-B):

(IX-B)

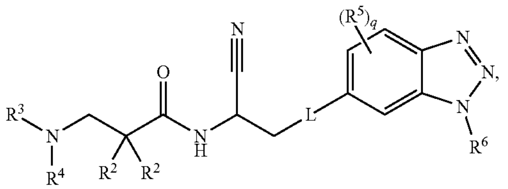

or a pharmaceutically acceptable salt, a stereoisomer or a deuterated form thereof, wherein L, $R^2$, $R^3$, $R^4$, $R^5$, $R^6$, and q are defined anywhere herein.

In embodiments, the present disclosure provides a compound of Formula (IX-C):

(IX-C)

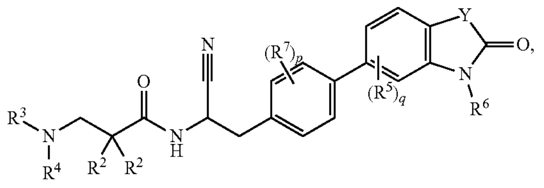

or a pharmaceutically acceptable salt, a stereoisomer or a deuterated form thereof, wherein Y, $R^2$, $R^3$, $R^4$, $R^5$, $R^6$, $R^7$, p and q are defined anywhere herein.

In embodiments, the present disclosure provides a compound of Formula (IX-D):

(IX-D)

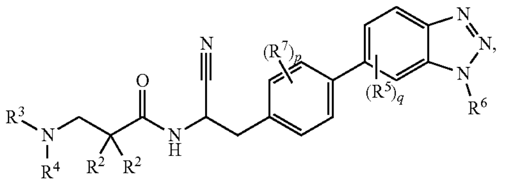

or a pharmaceutically acceptable salt, a stereoisomer or a deuterated form thereof, wherein $R^2$, $R^3$, $R^4$, $R^5$, $R^6$, $R^7$, p and q are defined anywhere herein.

In embodiments, the present disclosure provides a compound of Formula (X):

(X)

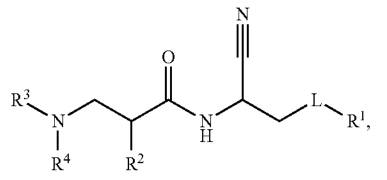

or a pharmaceutically acceptable salt, a stereoisomer or a deuterated form thereof, wherein L, $R^1$, $R^2$, $R^3$ and $R^4$ are defined anywhere herein.

In embodiments, the present disclosure provides a compound of Formula (X-A):

(X-A)

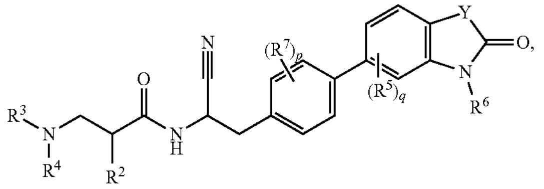

or a pharmaceutically acceptable salt, a stereoisomer or a deuterated form thereof, wherein Y, $R^2$, $R^3$, $R^4$, $R^5$, $R^6$, $R^7$, p and q are defined anywhere herein.

In embodiments, the present disclosure provides a compound of Formula (X-B):

(X-B)

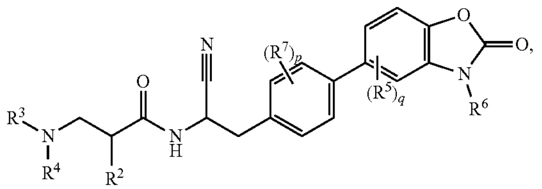

or a pharmaceutically acceptable salt, a stereoisomer or a deuterated form thereof, wherein $R^2$, $R^3$, $R^4$, $R^5$, $R^6$, $R^7$, p and q are defined anywhere herein.

In embodiments, the present disclosure provides a compound of Formula (X-C):

(X-C)

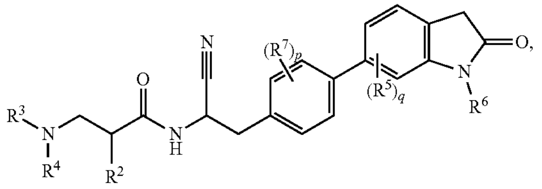

or a pharmaceutically acceptable salt, a stereoisomer or a deuterated form thereof, wherein $R^2$, $R^3$, $R^4$, $R^5$, $R^6$, $R^7$, p and q are defined anywhere herein.

In embodiments, the present disclosure provides a compound of Formula (X-D):

(X-D)

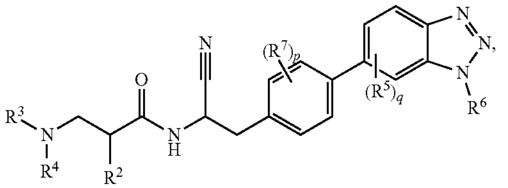

or a pharmaceutically acceptable salt, a stereoisomer or a deuterated form thereof, wherein $R^2$, $R^3$, $R^4$, $R^5$, $R^6$, $R^7$, p and q are defined anywhere herein.

In embodiments, the present disclosure provides a compound of Formula (XI):

(XI)

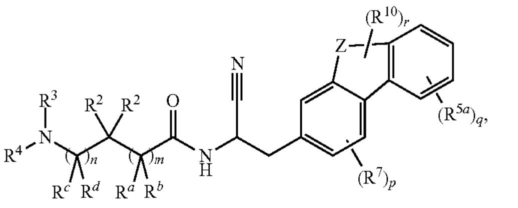

or a pharmaceutically acceptable salt, a stereoisomer or a deuterated form thereof, wherein $R^2$, $R^3$, $R^4$, $R^a$, $R^b$, $R^c$, $R^d$, $R^{5a}$, $R^7$, $R^{10}$, p, q, r, m and n are defined anywhere herein.

In embodiments, the present disclosure provides a compound of Formula (XI-A):

(XI-A)

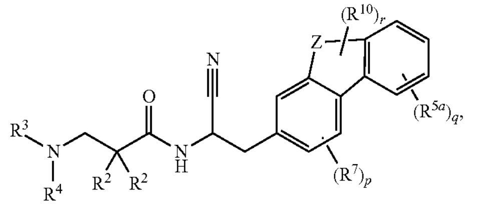

or a pharmaceutically acceptable salt, a stereoisomer or a deuterated form thereof, wherein $R^2$, $R^3$, $R^4$, $R^{5a}$, $R^7$, $R^{10}$, p, q, r are defined anywhere herein.

In embodiments, the present disclosure provides a compound of Formula (XII):

(XII)

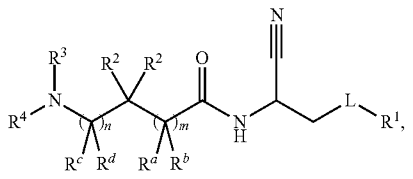

or a pharmaceutically acceptable salt, a stereoisomer or a deuterated form thereof, wherein L, $R^1$, $R^2$, $R^3$, $R^4$, $R^a$, $R^b$, $R^c$, $R^d$, $R^5$, $R^6$, $R^7$, p, q, m and n are defined anywhere herein.

In embodiments, the present disclosure provides a compound of Formula (XII-A):

(XII-A)

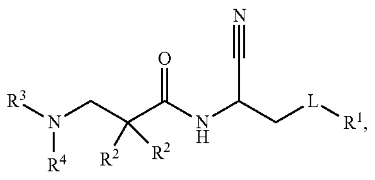

or a pharmaceutically acceptable salt, a stereoisomer or a deuterated form thereof, wherein L, $R^1$, $R^2$, $R^3$, $R^4$, $R^a$, $R^b$, $R^c$, $R^d$, $R^5$, $R^6$, $R^7$, p, q, m and n are defined herein.

$R^1$, $R^2$, $R^3$, $R^4$, $R^5$, $R^6$, $R^7$, $R^8$, $R^9$, $R^{10}$, $R^a$, $R^b$, $R^c$, $R^d$, L, m, n, p, q, r, Z, Ring A and Ring B of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) are described herein.

In embodiments, the present disclosure provides compounds of Table A or a pharmaceutically acceptable salt, a stereoisomer, or a deuterated form thereof.

In embodiments, the present disclosure provides a pharmaceutical composition comprising a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof), and a pharmaceutically acceptable adjuvant, diluent or carrier.

In embodiments, the present disclosure provides a method for treating an obstructive disease of the airway in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating cystic fibrosis in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating chronic rhinosinusitis in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or Table A, or a pharmaceutically acceptable salt, a stereoisomer, or a deuterated form thereof).

In embodiments, the present disclosure provides a method for treating hidradenitis suppurativa in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating cancer in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating lupus nephritis in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating rheumatoid arthritis in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating osteoarthritis (OA) in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, C or a pharmaceutically acceptable salt, a stereoisomer, or a deuterated form thereof).

In embodiments, the present disclosure provides a method for treating inflammatory bowel disease in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating an anti-neutrophil cytoplasmic antibody associated vasculitis in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating an ischemia/reperfusion (IR) injury in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating liver injury (e.g., drug-induced acute liver injury) in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

In embodiments, the present disclosure provides a method for treating a disease in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof), wherein the disease is giant cell arteritis, polyarteritis nodosa, anti-GBM disease (Goodpasture's), systemic scleroderma, diabetic nephropathy, diabetic neuropathy, diabetic retinopathy, diabetic ulcers, Duchenne muscular dystrophy, bronchiolitis obliterans, atopic dermatitis, pyoderma gangrenosum, sweet's syndrome, dermatomyositis/polymyositis, neutrophilic dermatoses, thrombosis (e.g., deep vein thrombosis (DVT)), bronchopulmonary dysplasia, amyotrophic lateral sclerosis, sickle cell anemia, psoriasis, or a ventilator-induced lung injury.

In embodiments, the present disclosure provides a method for treating heart failure in a patient in need thereof, comprising administering to the patient an effective amount of a compound disclosed herein (e.g., a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof).

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

Listed below are definitions of various terms used in the specification and claims to describe the present disclosure.

Unless defined otherwise, all technical and scientific terms used in this disclosure have the same meanings as commonly understood by one of ordinary skill in the art to which this disclosure belongs.

The term "about" when immediately preceding a numerical value means a range encompassing said numerical value plus or minus an acceptable amount of variation in the art (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms below, as used herein, have the following meanings, unless indicated otherwise:

"Cyano" refers to the —CN radical.

"Hydroxy" or "hydroxyl" refers to the —OH radical.

"Oxo" refers to the =O substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkenyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkynyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the Formula —$OR_a$ where $R_a$ is an alkyl, alkenyl or alkynyl radical as defined above containing one to twelve carbon atoms. Unless stated otherwise specifically in the specification, an alkoxy group can be optionally substituted.

"Alkylamino" refers to a radical of the Formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Aryl" refers to a hydrocarbon ring system radical comprising hydrogen, 6 to 18 carbon ring atoms and at least one aromatic ring. For purposes of this disclosure, the aryl radical can be a monocyclic, bicyclic, tricyclic or tetracyclic ring system, which can include fused, bridged, or spiro ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In embodiments where "L" is aryl, the aryl radical is a diradical. Unless stated otherwise specifically in the specification, the term "aryl" is meant to include aryl radicals that are optionally substituted.

"Aralkyl" or "arylalkyl" refers to a radical of the Formula —$R_b$—$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon and hydrogen. Carbocyclic rings can comprise from 3 to 20 carbon atoms in the ring. Carbocyclic rings include cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiro ring systems, having from three to twenty carbon atoms, e.g., having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiro ring systems, having from three to twenty carbon atoms, e.g., having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiro ring systems, having from three to twenty carbon atoms, e.g., having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the Formula $-R_b-R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl" "heterocyclic ring" or "heterocycle" refers to a stable 3- to 20-membered non-aromatic, saturated or partially unsaturated ring radical which consists of two to nineteen carbon ring atoms and from one to six heteroatoms as ring atoms selected from nitrogen, oxygen or sulfur, at least one non-aromatic, saturated or partially unsaturated ring containing at least one heteroatom as a ring atom. Unless stated otherwise specifically in the specification, the heterocyclyl radical can be a monocyclic, bicyclic, tricyclic or tetracyclic ring system, which can include fused, bridged, or spiro ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In embodiments where "L" is heterocyclyl, the heterocyclyl radical is a diradical. Unless stated otherwise specifically in the specification, a heterocyclyl group can be optionally substituted.

"Heterocyclylalkyl" refers to a radical of the Formula $-R_b-R_e$ where $R_b$ is an alkylene group as defined above and $R_e$ is a heterocyclyl radical as defined above. Unless stated otherwise specifically in the specification, a heterocycloalkyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical comprising one to nineteen carbon ring atoms, one to six heteroatoms as ring atoms selected from nitrogen, oxygen and sulfur, and at least one aromatic ring and at least one heteroatom as a ring atom. For purposes of this disclosure, the heteroaryl radical can be a monocyclic, bicyclic, tricyclic or tetracyclic ring system, which can include fused, bridged, or spiro ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, thiophene (i.e. thienyl), 2-oxo-2,3-dihydrobenzo[d]oxazolyl (e.g., 2-oxo-2,3-dihydrobenzo[d]oxazol-5-yl), and 2-oxoindolinyl (e.g., 2-oxoindolin-6-yl). In embodiments where "L" is heteroaryl, the heteroaryl radical is a diradical. Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the Formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Thioalkyl" refers to a radical of the Formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" can occur as valency allows and to produce a stable compound.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC$(═O)$R_h$, —$NR_gC$(═O)$NR_gR_h$, —$NR_gC$(═O)$OR_h$, —$NR_gSO_2R_h$, —OC(═O)$NR_gR_h$, —$OR_g$, —$SR_g$, —$SOR_g$, —$SO_2R_g$, —$OSO_2R_g$, —$SO_2OR_g$, ═$NSO_2R_g$, and —$SO_2NR_gR_h$. "Substituted also means any of the above groups in which one or more hydrogen atoms are replaced with —C(═O)$R_g$, —C(═O)$OR_g$, —C(═O)$NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further includes any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. "Substituted" can occur as valency allows and to produce a stable compound As used herein, the symbol " 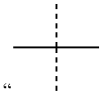 " or "  "

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, " 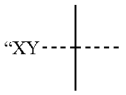

" or " 

"

indicates that the chemical entity "XY" is bonded to another chemical entity via the point of attachment bond. Furthermore, the specific point of attachment to the non-depicted chemical entity can be specified by inference.

In this specification, unless stated otherwise, the term "pharmaceutically acceptable" is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

The term "pharmaceutically acceptable salt" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The compounds of the disclosure, or their pharmaceutically acceptable salts can contain one or more asymmetric centers and can thus give rise to enantiomers, diastereomers, and other stereoisomeric forms that can be defined, in terms of absolute stereochemistry, as (R)– or (S)– or, as (D)– or (L)– for amino acids. The present disclosure is meant to include all such possible isomers, as well as their racemic and optically pure forms whether or not they are specifically depicted herein. Optically active (+) and (–), (R)– and (S)–, or (D)– and (L)– isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

The term "treating" as used herein with regard to a patient, refers to an approach for obtaining beneficial or desired results including but not limited to a therapeutic benefit and/or a prophylactic benefit. Therapeutic benefit refers to any therapeutically relevant improvement in or effect on one or more diseases, conditions, or symptoms under treatment. The term "treating" in one embodiment, includes: (1) preventing or delaying the appearance of clinical symptoms of the state, disorder or condition developing in the patient that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); (3) relieving the condition (for example, by causing regression, or reducing the severity of the state, disorder or condition or at least one of its clinical or subclinical symptoms).

An "effective amount" means the amount compound or pharmaceutical Formulation, that when administered to a patient for treating a state, disorder or condition is sufficient to effect such treatment.

The terms "subject," "individual," and "patient" are used interchangeably herein to refer to a vertebrate, such as a mammal. The mammal may be, for example, a mouse, a rat, a rabbit, a cat, a dog, a pig, a sheep, a horse, a non-human primate (e.g., cynomolgus monkey, chimpanzee), or a human.

Compounds

In various embodiments of the present disclosure, a DPP1 inhibitor is provided, and the DPP1 inhibitor is a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof.

Formulae

In embodiment, the present disclosure provides a compound of Formula (I)

(I)

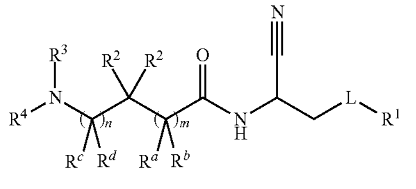

or a pharmaceutically acceptable salt, a stereoisomer or a deuterated form thereof, wherein $R^1$ is carbocyclyl, aryl, heterocyclyl or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, N($C_{1-6}$ alkyl)$_2$, COOH, C(=O)$C_{1-6}$ alkyl, C(=O)$OC_{1-6}$ alkyl, C(=O)$NHC_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycyl, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=)$OC_{1-6}$ alkyl, C(=O)$OC_{1-6}$ alkyl, C(=O)$N_{1-6}$ alkyl, C(=O)N($C_{1-6}$ alkyl)$_2$, or NHC(=O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$;

each of $R^a$, $R^b$, $R^c$ and $R^d$ is independently selected from H, alkyl, halogen or haloalkyl; each of n and m is independently 0, 1, 2, or 3.

In embodiments of the compounds of Formula (I), or a pharmaceutically acceptable salt, a stereoisomer, or a deuterated form thereof, the compound is not

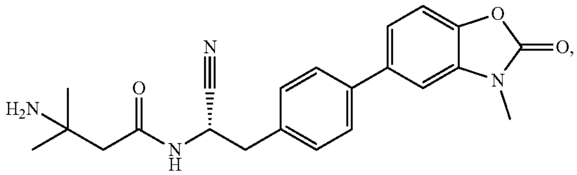
,

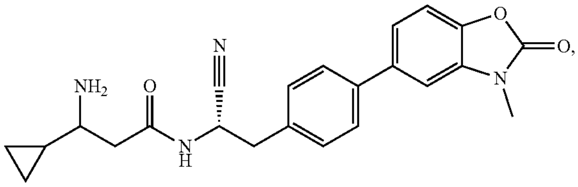
,

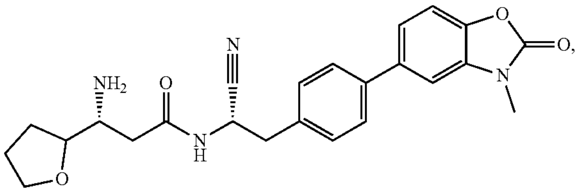
,

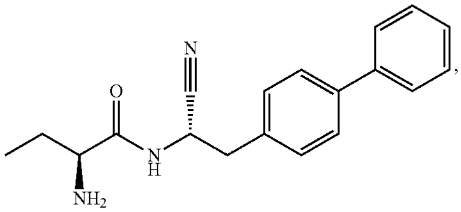
,

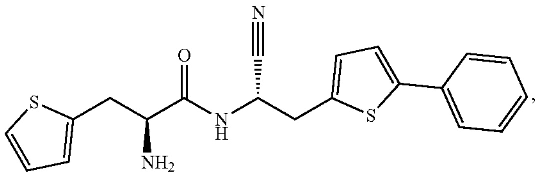
,

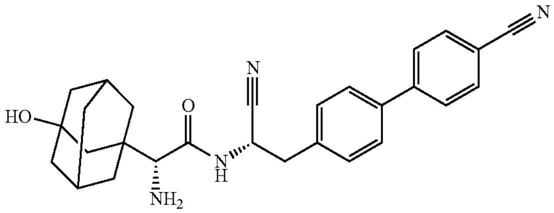
or

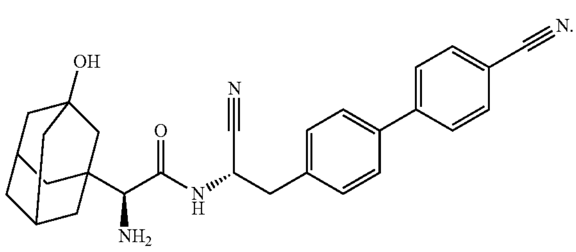
.

In embodiments, the present disclosure provides a compound of Formula (II):

(II)

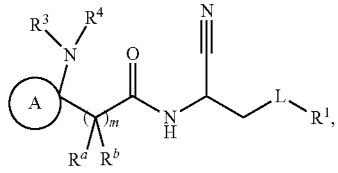
, or a pharmaceutically acceptable salt, a stereoisomer, or a deuterated form thereof, wherein:

$R^1$ is carbocyclyl, aryl, heterocyclyl or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

Ring A is a carbocyclyl, aryl or heterocyclyl wherein Ring A is optionally substituted with 1-5 $R^5$;

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}\ alkyl)_2$, COOH, $C(═O)C_{1-6}$ alkyl, $C(═O)OC_{1-6}$ alkyl, $C(═O)NHC_{1-6}$ alkyl, $C(═O)N(C_{1-6}\ alkyl)_2$, $NHC(═O)C_{1-6}$ alkyl, $S(═O)_2—C_{1-6}$ alkyl, $C_{1-6}$ alkylene-cycloalkyl, $S(═O)_2$-cycloalkyl, $C_{1-6}$ alkylene-heterocyclyl, $S(═O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-$NH(C_{1-6}\ alkyl)_2$, $C_{1-6}$ alkylene-$N(C_{1-6}\ alkyl)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(═O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}\ alkyl)_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}\ alkyl)_2$, COOH, $C(═)OC_{1-6}$ alkyl, $C(═O)OC_{1-6}$ alkyl, $C(═O)N_{1-6}$ alkyl, $C(═O)N(C_{1-6}\ alkyl)_2$, or $NHC(═O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$;

each of $R^a$ and $R^b$ is independently selected from H, alkyl, halogen or haloalkyl; and m is independently 0, 1, 2, or 3.

In embodiments of the compounds of Formula (II), or a pharmaceutically acceptable salt, a stereoisomer, or a deuterated form thereof, the compound is not

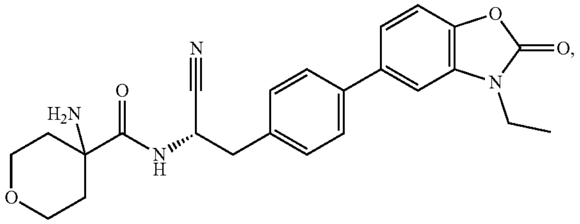,

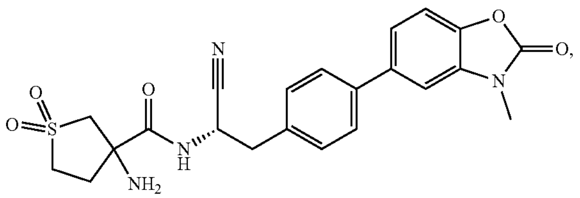,

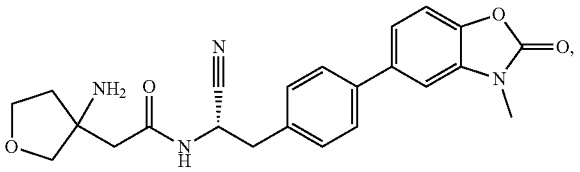,

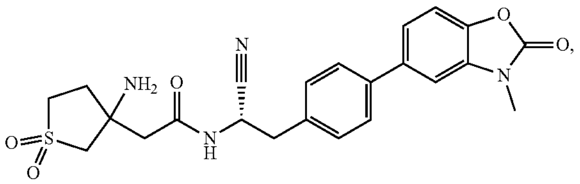,

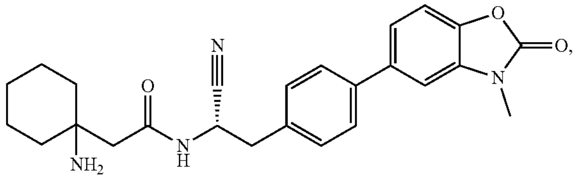,

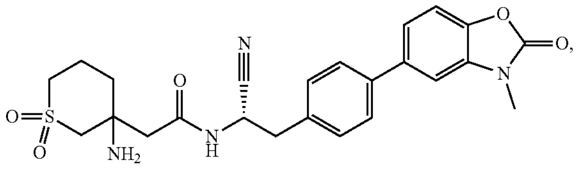,

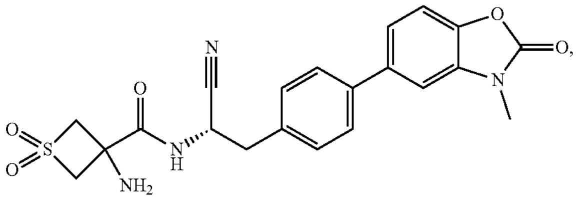,

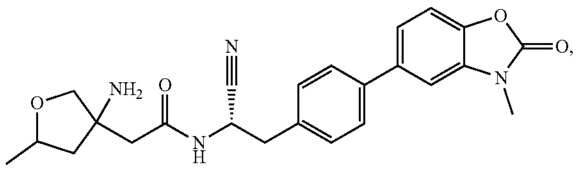,

-continued

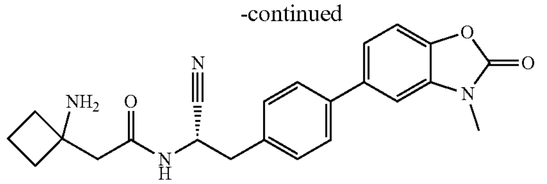

or

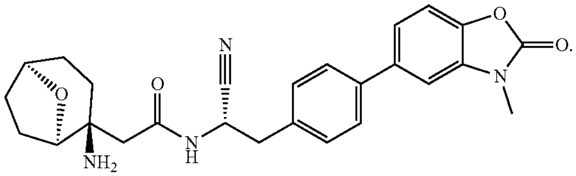.

In embodiments of the compounds of Formula (III), or a pharmaceutically acceptable salt, a stereoisomer or a deuterated form thereof, m is 0, 1 or 2. In embodiments, m is 0. In embodiments, m is 1. In embodiments, m is 2. In embodiments, $R^a$ and $R^b$ are each independently selected from H, $C_{1-6}$ alkyl, halogen or $C_{1-6}$ haloalkyl. In embodiments, $R^a$ and $R^b$ are independently selected from H, $CH_3$, $CH_2CH_3$, $CH(CH_3)_2$, $CH_2C_1$ or $CHF_2$. In embodiments, $R^a$ and $R^b$ are each H. In embodiments, $R^a$ is H and $R^b$ is $CH_3$, $CH_2CH_3$, $CH(CH_3)_2$, $CH_2C_1$ or $CHF_2$. In embodiments, $R^a$ is H and $R^b$ is $CH_3$.

In embodiments, the present disclosure provides a compound of Formula (III):

(III)

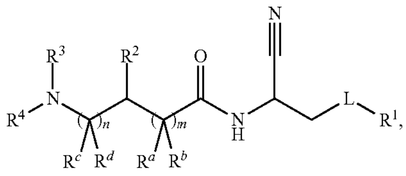, or a pharmaceutically acceptable salt, a stereoisomer or a deuterated form thereof, wherein $R^1$ is carbocyclyl, aryl, heterocyclyl or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$;

each of $R^a$, $R^b$, $R^c$ and $R^d$ is independently selected from H, alkyl, halogen or haloalkyl; and each of n and m is independently 0, 1, 2, or 3.

In embodiments of the compounds of Formula (III), or a pharmaceutically acceptable salt, a stereoisomer, or deuterated form thereof, the compound is not

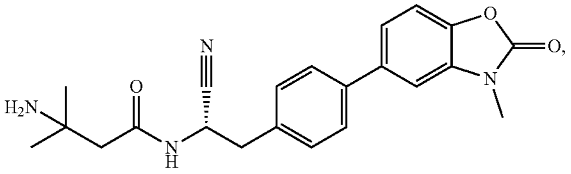

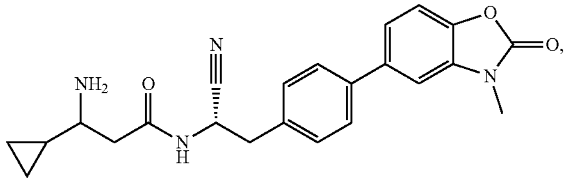

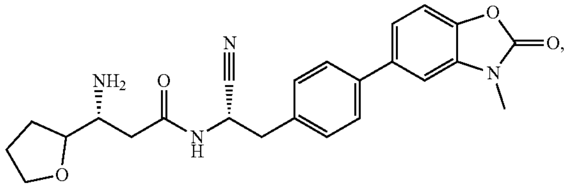

-continued

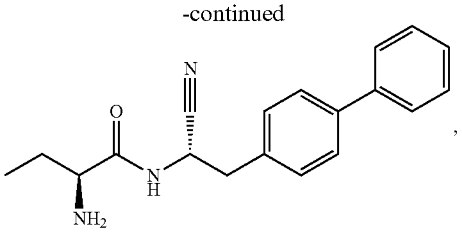

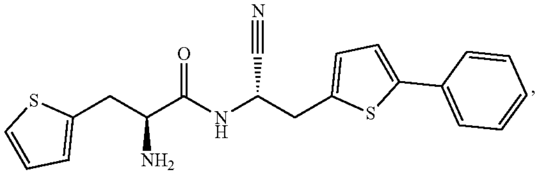

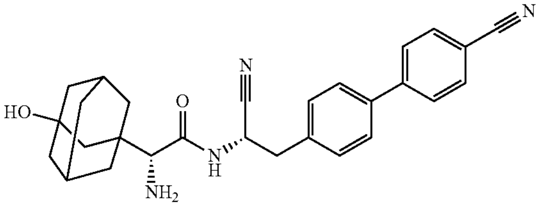

or

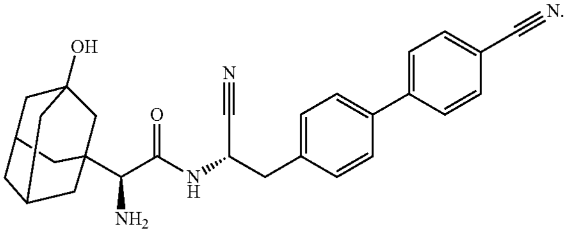

In embodiments, the present disclosure provides a compound of Formula (IV):

(IV)

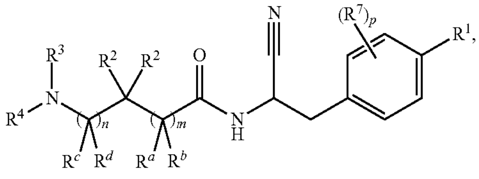

or a pharmaceutically acceptable salt, a stereoisomer or a deuterated form thereof, wherein $R^1$ is carbocyclyl, aryl, heterocyclyl or heteroaryl, wherein $R^1$ is optionally substituted with 1-5 groups independently selected from $R^5$ or $R^6$ each $R^2$ is independently H, halogen, OH, CN, Oalkyl, $NH_2$, N(alkyl), SH, C(=O)alkyl, $C(=O)NH_2$, alkyl, haloalkyl, alkylene-OH, alkylene-CH(COOH)($NH_2$), alkenyl, alkynyl, S(alkyl), S(=O)alkyl, $S(=O)_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O)alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}$ alkyl$)_2$, COOH, C(=O)$C_{1-6}$ alkyl, C(=O)$OC_{1-6}$ alkyl, C(=O)$NHC_{1-6}$ alkyl, C(=O)N($C_{1-6}$ alkyl$)_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl$)_2$, $C_{1-6}$ alkylene-N($C_{1-6}$ alkyl$)_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl$)_2$, COOH, C(=)$OC_{1-6}$ alkyl, C(=O)$OC_{1-6}$ alkyl, C(=O)$N_{1-6}$ alkyl, C(=O)N($C_{1-6}$ alkyl$)_2$, or NHC(=O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$;

each of $R^a$, $R^b$, $R^c$ and $R^d$ is independently selected from H, alkyl, halogen or haloalkyl; and each of n and m is independently 0, 1, 2, or 3.

In embodiments of the compounds of Formula (IV), or a pharmaceutically acceptable salt, a stereoisomer or a deuterated form thereof, the compound is not

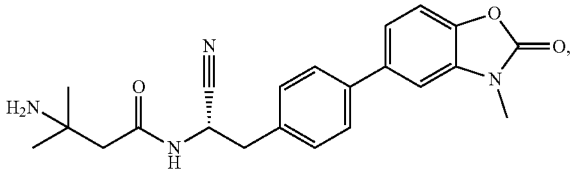

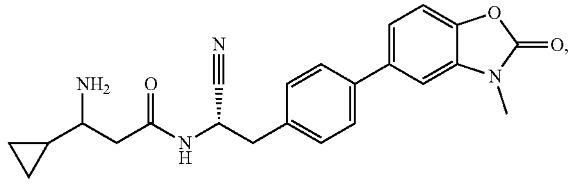

-continued

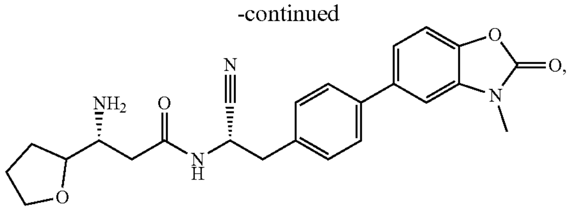

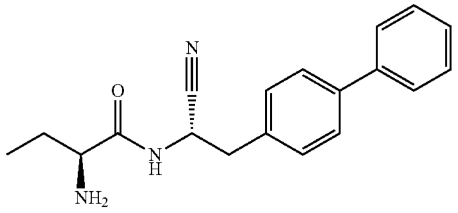

or

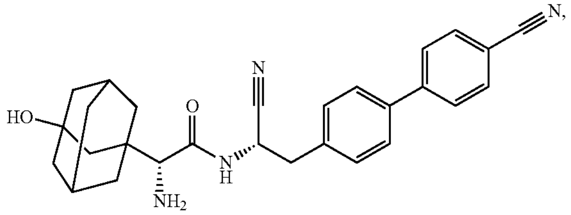

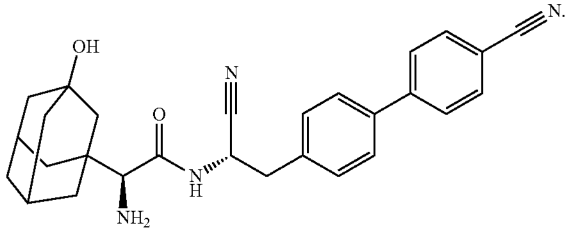

In embodiments, the present disclosure provides a compound of Formula (V):

(V)

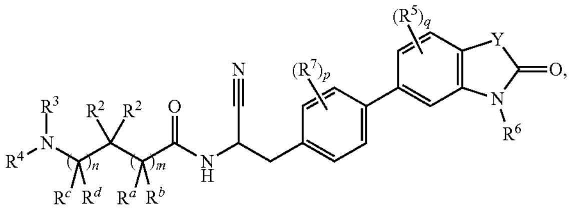

or a pharmaceutically acceptable salt, a stereoisomer or a deuterated form thereof, wherein p is 0, 1, 2, 3 or 4;

q is 0, 1, 2 or 3;

each Y is independently $NR^6$, O, $CR^8R^9$, S, S(O) or S(O)$_2$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, C(═O)$C_{1-6}$ alkyl, C(═O)$OC_{1-6}$ alkyl, C(═O)$NHC_{1-6}$ alkyl, C(═O)$N(C_{1-6}$ alkyl$)_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$;

$R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl;

or $R^8$ and $R^9$ form ═O;

each of $R^a$, $R^b$, $R^c$ and $R^d$ is independently selected from H, alkyl, halogen or haloalkyl; and each of n and m is independently 0, 1, 2, or 3.

In embodiments of the compounds of Formula (V), or a pharmaceutically acceptable salt, a stereoisomer or a deuterated form thereof, the compound is not

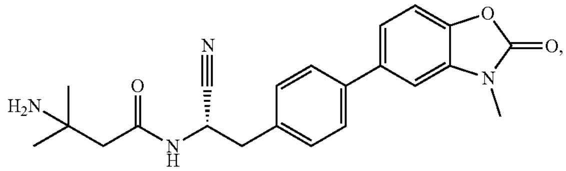

-continued

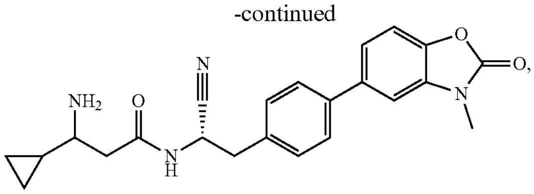

or

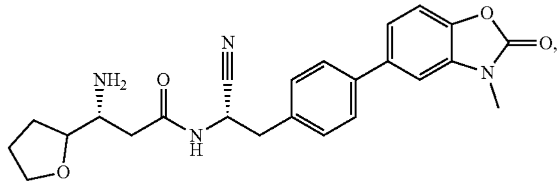

In embodiments, the present disclosure provides a compound of Formula (VI)

(VI)

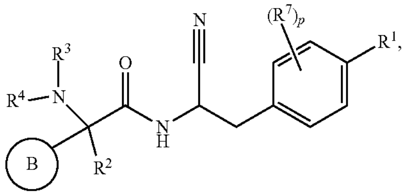

or a pharmaceutically acceptable salt, a stereoisomer or a deuterated form thereof, wherein $R^1$ is carbocyclyl, aryl, heterocyclyl or heteroaryl, wherein $R^1$ is optionally substituted with 1-5 groups independently selected from $R^5$ or $R^6$ Ring B is carbocyclyl, aryl, heterocyclyl or heteroaryl, wherein Ring B is optionally substituted with 1-4 $R^{2a}$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

p is 0, 1, 2 or 3;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl is optionally substituted with 1-4 groups selected from $R^5$ or $R^6$.

In embodiments of compounds of Formula (VI), the compound is not

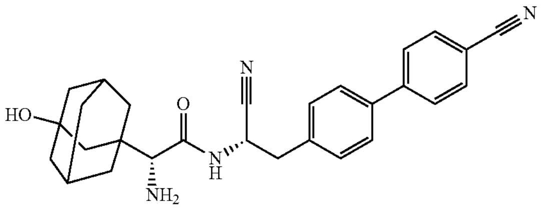

or

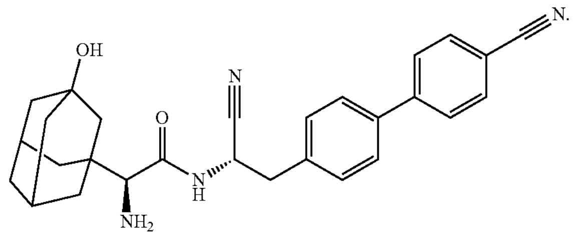

In embodiments of compounds of Formula (VI) or a pharmaceutically acceptable salt, a stereoisomer or a deuterated form thereof, each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, $C_{3-8}$ cycloalkyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, In embodiments of compounds of Formula (VI) or a pharmaceutically acceptable salt, a stereoisomer or a deuterated form thereof, $R^1$ is aryl or heteroaryl, each of which is optionally substituted with 1-5 groups independently selected from $R^5$ or $R^6$. In embodiments, one $R^7$ and one $R^5$ together form a heterocyclyl. In embodiments,

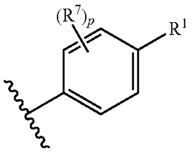

is

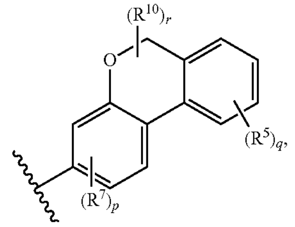

wherein p is 0, 1, 2 or 3, q is 0, 1, 2 or 3, r is 0 or 1, $R^5$ and $R^7$ are independently selected from H, alkyl, halogen, Oalkyl, haloalkyl, OH, oxo, CN, cycloalkyl or heterocyclyl, and $R^{10}$ is alkyl, halogen, Oalkyl, haloalkyl, OH or CN. In embodiments,

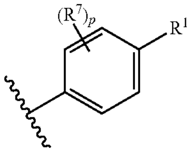

is

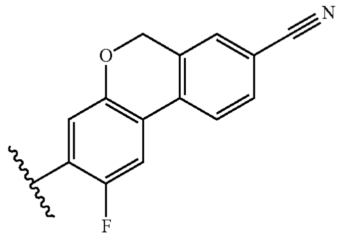

or

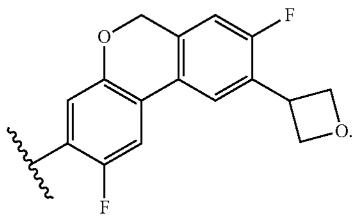

In embodiments, $R^1$ is

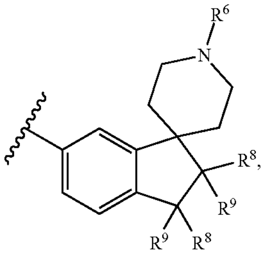

wherein $R^6$ is selected from H, $C_{1-6}$ alkyl or $COC_{1-6}$ alkyl, $R^8$ and $R^9$ are each independently selected from H, halogen, $C_{1-6}$ alkyl or $OC_{1-6}$ alkyl. In embodiments, $R^8$ and $R^9$ are each H. In embodiments, $R^1$ is

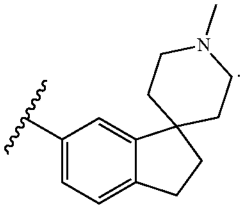 [SMILES: *c1ccc2c(c1)C1(CC2)CCN(C)CC1]

In embodiments, $R^1$ is

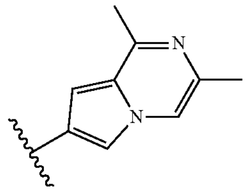

or

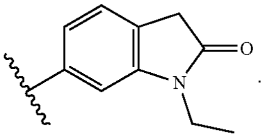

.

In embodiments, $R^2$ is H.

In embodiments, the present disclosure provides a compound of Formula (VII):

(VII)

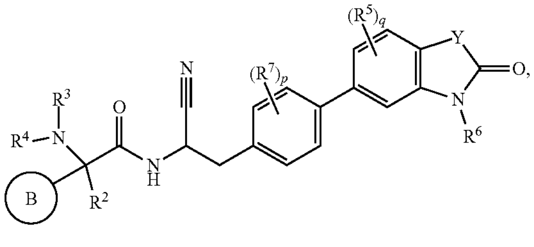

or a pharmaceutically acceptable salt, a stereoisomer or a deuterated form thereof, wherein Ring B is a 3-6 membered carbocyclyl or heterocyclyl;

each Y is independently $NR^6$, O, $CR^8R^9$, S, S(O) or $S(O)_2$;

p is 0, 1, 2, 3 or 4;

q is 0, 1, 2 or 3;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl;

$R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl;

or $R^8$ and $R^9$ form ═O.

In embodiments of compounds of Formula (VI) or (VII), or a pharmaceutically acceptable salt, a stereoisomer, or a deuterated form thereof, Ring B is $C_{3-6}$ cycloalkyl. In embodiments of compounds of Formula (VI) or (VII), or a pharmaceutically acceptable salt, a stereoisomer, or a deuterated form thereof, Ring B is $C_{4-6}$ cycloalkyl. In embodiments of compounds of Formula (VI) or (VII), or a pharmaceutically acceptable salt, a stereoisomer, or a deuterated form thereof, Ring B is

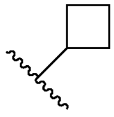

or

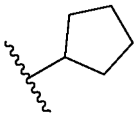

.

In embodiments of compounds of Formula (VI) or (VII), or a pharmaceutically acceptable salt, a stereoisomer, or a deuterated form thereof, Ring B is $C_{3-6}$ cycloalkyl, and $R^2$ is $C_{1-6}$ alkyl. In embodiments of compounds of Formula (VI) or (VII), or a pharmaceutically acceptable salt, a stereoisomer, or a deuterated form thereof, Ring B is

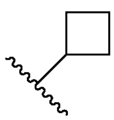

or

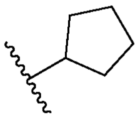

, and $R^2$ is $C_{1-6}$ alkyl. In embodiments of compounds of Formula (VI) or (VII), or a pharmaceutically acceptable salt, a stereoisomer, or a deuterated form thereof, Ring B is

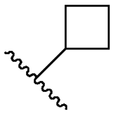 or 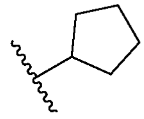, and $R^2$ is $CH_3$. In embodiments, each of $R^3$ and $R^4$ is independently selected from H and alkyl. In embodiments, each of $R^3$ and $R^4$ is H. In embodiments, $R^5$ is independently selected from H, halogen, or $C_{1-6}$ alkyl. In embodiments, $R^6$ is $C_{1-6}$ alkyl, $C_{1-6}$ alkylene-$NH_2$, $C_{1-6}$ alkylene-N($C_{1-6}$ alkyl)$_2$, —$COC_{1-6}$ alkyl, wherein the alkyl, $NH_2$, and N($C_{1-6}$ alkyl)$_2$, is optionally substituted with 1-3 groups selected from halogen, CN, OH, $C_{1-6}$ alkyl, $OC_{1-6}$ alkyl, $NH_2$, NH($C_{1-6}$ alkyl), or N($C_{1-6}$ alkyl)$_2$. In embodiments, $R^6$ is

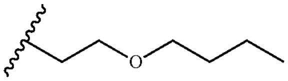, 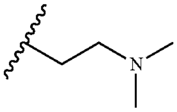, or

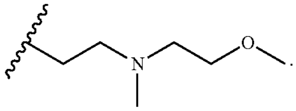.

In embodiments, p is 0, 1 or 2. In embodiments, p is 0 or 1. In embodiments, p is 0. In embodiments, $R^7$ is halogen. In embodiments, $R^7$ is fluoro. In embodiments, p is 1 and $R^7$ is fluoro. In embodiments, Y is O or $CH_2$. In embodiments, Y is O.

In embodiments, the present disclosure provides a compound of Formula (VIII):

(VIII)

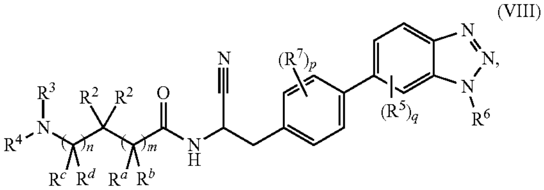

or a pharmaceutically acceptable salt, a stereoisomer or a deuterated form thereof, wherein p is 0, 1, 2, 3 or 4;

q is 0, 1, 2 or 3;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O)alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=O)$C_{1-6}$ alkyl, C(=O)$OC_{1-6}$ alkyl, C(=O)$NHC_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=)$OC_{1-6}$ alkyl, C(=O)$OC_{1-6}$ alkyl, C(=O)$N_{1-6}$ alkyl, C(=O)N($C_{1-6}$ alkyl)$_2$, or NHC(=O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$ each of $R^a$, $R^b$, $R^c$ and $R^d$ is independently selected from H, alkyl, halogen or haloalkyl; and each of n and m is independently 0, 1, 2, or 3.

In embodiments, the present disclosure provides a compound of Formula (IX):

(IX)

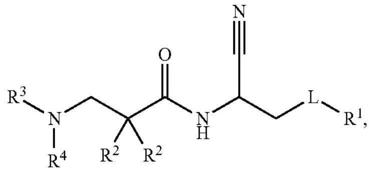

or a pharmaceutically acceptable salt, a stereoisomer or a deuterated form thereof, wherein, $R^1$ is carbocyclyl, aryl, heterocyclyl or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, N($C_{1-6}$ alkyl)$_2$, COOH, C(=O)$C_{1-6}$ alkyl, C(=O)$OC_{1-6}$ alkyl, C(=O)$NHC_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH; and each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=)$OC_{1-6}$ alkyl, C(=O)$OC_{1-6}$ alkyl, C(=O)$N_{1-6}$ alkyl, C(=O)N($C_{1-6}$ alkyl)$_2$, or NHC(=O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$.

In embodiments, the present disclosure provides a compound of Formula (IX-A):

(IX-A)

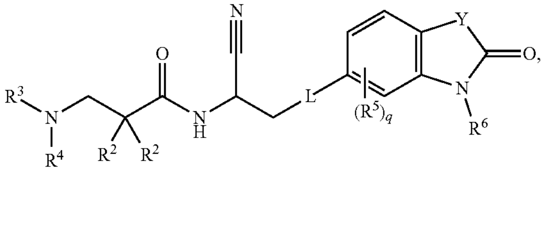

or a pharmaceutically acceptable salt, a stereoisomer or a deuterated form thereof, wherein q is 0, 1, 2 or 3;

each Y is independently $NR^6$, O, $CR^8R^9$, S, S(O) or S(O)$_2$;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=O)$C_{1-6}$ alkyl, C(=O)$OC_{1-6}$ alkyl, C(=O)$NHC_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=)$OC_{1-6}$ alkyl, C(=O)$OC_{1-6}$ alkyl, C(=O)$N_{1-6}$ alkyl, C(=O)N($C_{1-6}$ alkyl)$_2$, or NHC(=O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$ $R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl; and or $R^8$ and $R^9$ form =O.

In embodiments, the present disclosure provides a compound of Formula (IX-B):

(IX-B)

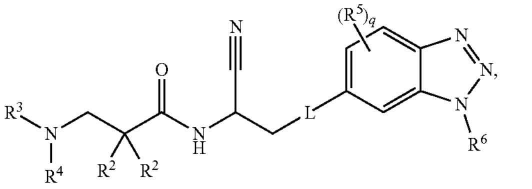

or a pharmaceutically acceptable salt, a stereoisomer or a deuterated form thereof, wherein, q is 0, 1, 2 or 3;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl; and or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$.

In embodiments, the present disclosure provides a compound of Formula (IX-C):

(IX-C)

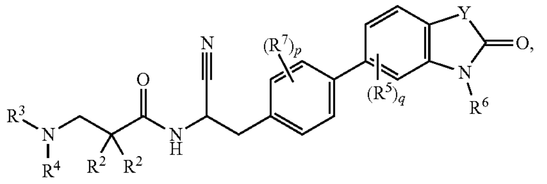

or a pharmaceutically acceptable salt, a stereoisomer or a deuterated form thereof, wherein q is 0, 1, 2 or 3;

each Y is independently $NR^6$, O, $CR^8R^9$, S, S(O) or S(O)$_2$;

p is 0, 1, 2, 3 or 4;

q is 0, 1, 2 or 3;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$;

$R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl; and or $R^8$ and $R^9$ form =O.

In embodiments, the present disclosure provides a compound of Formula (IX-D):

(IX-D)

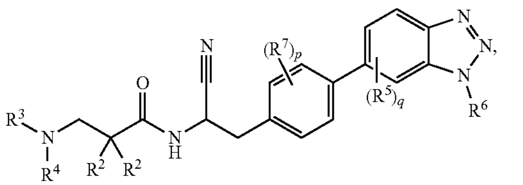

or a pharmaceutically acceptable salt, a stereoisomer or a deuterated form thereof, wherein p is 0, 1, 2, 3 or 4;

q is 0, 1, 2 or 3;

each $R^2$ is independently H, halogen, OH, CN, Oalkyl, $NH_2$, N(alkyl), SH, C(=O)alkyl, $C(=O)NH_2$, alkyl, haloalkyl, alkylene-OH, alkylene-CH(COOH)($NH_2$), alkenyl, alkynyl, S(alkyl), S(=O)alkyl, $S(=O)_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (=O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl; and or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$.

In embodiments, the present disclosure provides a compound of Formula (X):

(X)

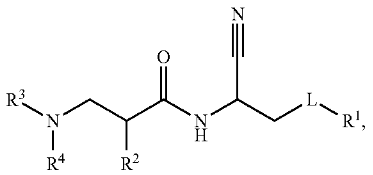

or a pharmaceutically acceptable salt, a stereoisomer or a deuterated form thereof, wherein L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, $C(=O)NH_2$, alkyl, haloalkyl, alkylene-OH, alkylene-CH(COOH)($NH_2$), alkenyl, alkynyl, S(alkyl), S(=O)alkyl, $S(=O)_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2-C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl$)(C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH; and each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$.

In embodiments of the compounds of Formula (X), or a pharmaceutically acceptable salt, a stereoisomer or a deuterated form thereof, L is

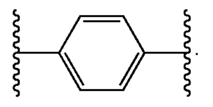

In embodiments, L is

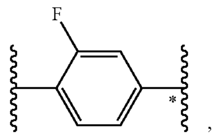 [SMILES: *c1ccc(*)c(F)c1]

Wherein the asterisk represents the point of attachment to $R^1$. In embodiments, $R^1$ is

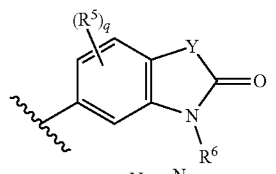

or

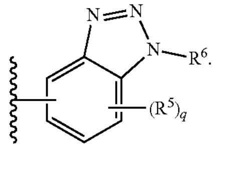

In embodiments, $R^1$ is

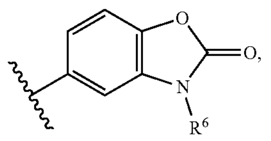

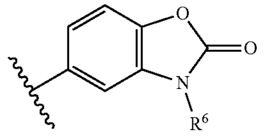

or

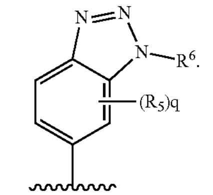

In embodiments, $R^1$ is

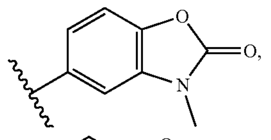

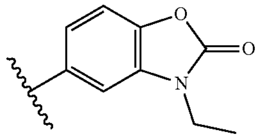

or

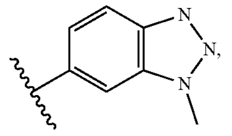

In embodiments, $R^3$ and $R^4$ are each $C_{1-6}$ alkyl. In embodiments, $R^3$ and $R^4$ are each $CH_3$. In embodiments, $R^2$ is OH or $OC_{1-6}$ alkyl. In embodiments, $R^2$ is OH, $OCH_3$ or $OCH_2CH_3$. In embodiments, $R^2$ is OH or $OCH_3$. In embodiments, $R^2$ is OH. In embodiments, $R^2$ is $OCH_3$. In embodiments, p is 0, 1 or 2. In embodiments, p is 0. In embodiments p is 1. In embodiments, $R^7$ is halogen or $C_{1-6}$ alkyl. In embodiments, $R^7$ is halogen. In embodiments, $R^7$ is F. In embodiments, q is 0, 1, 2 or 3. In embodiments, q is 0. In embodiments, q is 1. In embodiments, q is 2. In embodiments, q is 3. In embodiments, $R^5$ is halogen, $C_{1-6}$ alkyl, $OC_{1-6}$ alkyl, CN or heterocyclyl. In embodiments, $R^5$ is $CH_3$, F or CN. In embodiments, $R^6$ is $C_{1-6}$ alkyl, $C_{1-6}$ alkylene-O—$C_{1-6}$ alkyl, $C_{1-6}$ alkylene-$N(C_{1-6}$ alkyl$)_2$, $C_{1-6}$ alkylene-$N(C_{1-6}$ alkylene-O—$C_{1-6}$ alkyl$)(C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

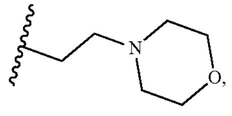

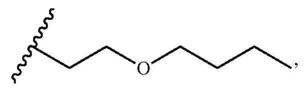

-continued

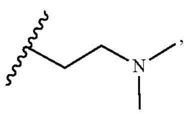

or

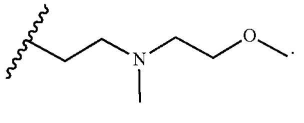

In embodiments, $R^6$ is $CH_3$ or $CH_2CH_3$. In embodiments, $R^6$ is $CH_3$. In embodiments, $R^6$ is $CH_2CH_3$.

In embodiments of the compounds of Formula (X), or a pharmaceutically acceptable salt, a stereoisomer or a deuterated form thereof, -L-$R^1$ is

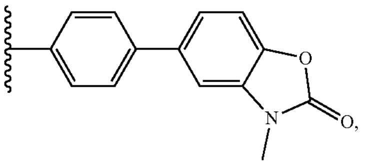

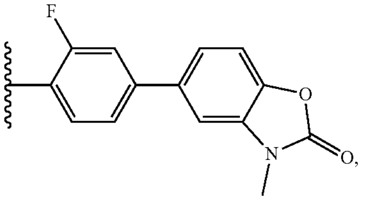

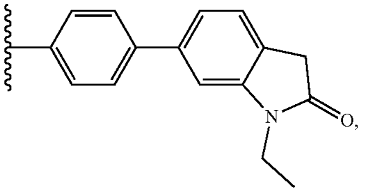

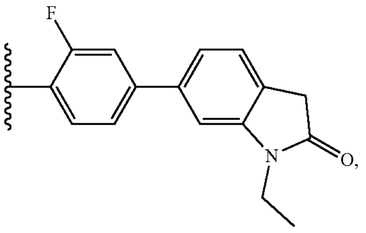

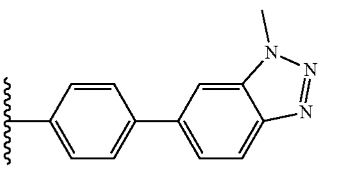

or

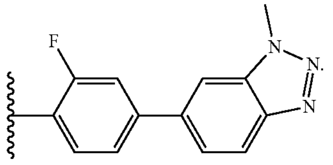

In embodiments, the present disclosure provides a compound of Formula (X-A):

(X-A)

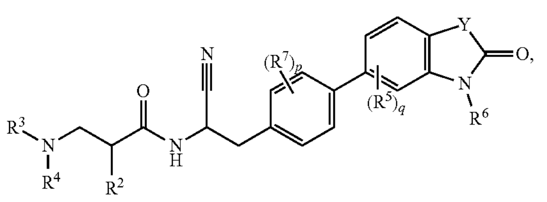

or a pharmaceutically acceptable salt, a stereoisomer or a deuterated form thereof, wherein q is 0, 1, 2 or 3;

each Y is independently $NR^6$, O, $CR^8R^9$, S, S(O) or $S(O)_2$;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(=O)$C_{1-6}$ alkyl, C(=O) $OC_{1-6}$ alkyl, C(=O)$NHC_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl;

$R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl; and or $R^8$ and $R^9$ form =O.

In embodiments of the compounds of Formula (X-A), or a pharmaceutically acceptable salt, a stereoisomer or a deuterated form thereof, Y is NH, O, S, $CH_2$, ClF, or $CF_2$. In embodiments, Y is O or $CH_2$. In embodiments, Y is O. In embodiments, Y is $CH_2$. In embodiments, $R^3$ and $R^4$ are each $C_{1-6}$ alkyl. In embodiments, $R^3$ and $R^4$ are each $CH_3$. In embodiments, $R^2$ is OH or $OC_{1-6}$ alkyl. In embodiments, $R^2$ is OH, $OCH_3$ or $OCH_2CH_3$. In embodiments, $R^2$ is OH or $OCH_3$ In embodiments, $R^2$ is OH. In embodiments, $R^2$ is $OCH_3$. In embodiments, p is 0, 1 or 2. In embodiments, p is 0. In embodiments p is 1. In embodiments, $R^7$ is halogen or $C_{1-6}$ alkyl. In embodiments, $R^7$ is halogen. In embodiments, $R^7$ is F. In embodiments, q is 0, 1, 2 or 3. In embodiments, q is 0. In embodiments, q is 1. In embodiments, q is 2. In embodiments, q is 3. In embodiments, $R^5$ is halogen, $C_{1-6}$ alkyl, $OC_{1-6}$ alkyl, CN or heterocyclyl. In embodiments, $R^5$ is $CH_3$, F or CN. In embodiments, $R^6$ is $C_{1-6}$ alkyl, $C_{1-6}$ alkylene-O—$C_{1-6}$ alkyl, $C_{1-6}$ alkylene-$N(C_{1-6}$ alkyl$)_2$, $C_{1-6}$ alkylene-$N(C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

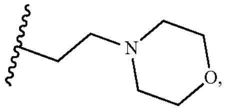

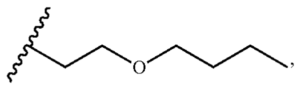

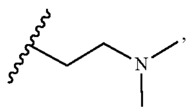

or

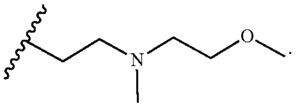

In embodiments, $R^6$ is $CH_3$ or $CH_2CH_3$. In embodiments, $R^6$ is $CH_3$. In embodiments, $R^6$ is $CH_2CH_3$.

In embodiments, the present disclosure provides a compound of Formula (X-B):

(X-B)

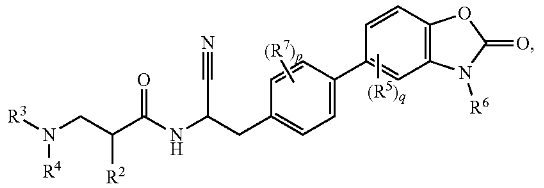

or a pharmaceutically acceptable salt, a stereoisomer or a deuterated form thereof, wherein q is 0, 1, 2 or 3;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, $C(=O)NH_2$, alkyl, haloalkyl, alkylene-OH, alkylene-CH(COOH)($NH_2$), alkenyl, alkynyl, S(alkyl), S(=O)alkyl, $S(=O)_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O)alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), $NH(alkyl)_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH; and each $R^7$ is independently selected from =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=)OC_{1-6}$ alkyl, $C(=O)OC_{1-6}$ alkyl, $C(=O)N_{1-6}$ alkyl, $C(=O)N(C_{1-6}$ alkyl$)_2$, or $NHC(=O)C_{1-6}$ alkyl.

In embodiments, the present disclosure provides a compound of Formula (X-C):

(X-C)

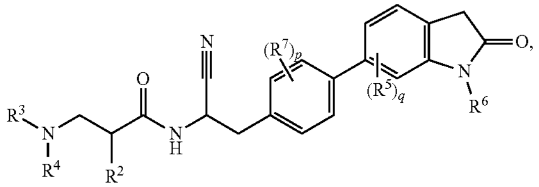

or a pharmaceutically acceptable salt, a stereoisomer or a deuterated form thereof, wherein, q is 0, 1, 2 or 3;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, $C(=O)NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, O$C_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, NH$C_{1-6}$ alkyl, N($C_{1-6}$ alkyl)$_2$, COOH, C(=O)$C_{1-6}$ alkyl, C(=O)O$C_{1-6}$ alkyl, C(=O)NH$C_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, O$C_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, O$C_{1-6}$ alkyl, $NH_2$, NH($C_{1-6}$ alkyl), N($C_{1-6}$ alkyl)$_2$, cycloalkyl, aryl, heterocyclyl, heteroaryl or COOH; and each $R^7$ is independently selected from =O, halogen, $C_{1-6}$ alkyl, O$C_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH$C_{1-6}$ alkyl, N($C_{1-6}$ alkyl)$_2$, COOH, C(=)O$C_{1-6}$ alkyl, C(=O)O$C_{1-6}$ alkyl, C(=O)$N_{1-6}$ alkyl, C(=O)N($C_{1-6}$ alkyl)$_2$, or NHC(=O)$C_{1-6}$ alkyl.

In embodiments, the present disclosure provides a compound of Formula (X-D):

(X-D)

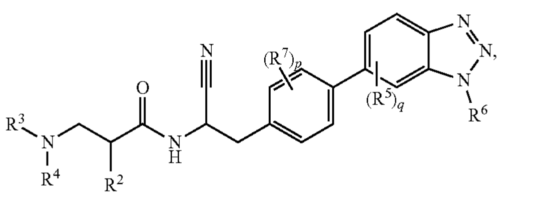

or a pharmaceutically acceptable salt, a stereoisomer or a deuterated form thereof, wherein q is 0, 1, 2 or 3;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(=O) alkyl, C(=O)cycloalkyl, C=(O)aryl or C(=O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(=O)OH, $NH_2$, NH(alkyl), NH(alkyl)$_2$, cycloalkyl or heterocyclyl;

each $R^5$ is independently selected from halogen, $C_{1-6}$ alkyl, O$C_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, NH$C_{1-6}$ alkyl, N($C_{1-6}$ alkyl)$_2$, COOH, C(=O)$C_{1-6}$ alkyl, C(=O)O$C_{1-6}$ alkyl, C(=O)NH$C_{1-6}$ alkyl, C(=O)N($C_{1-6}$ alkyl)$_2$, NHC(=O)$C_{1-6}$ alkyl, S(=O)$_2$—$C_{1-6}$ alkyl, $C_{1-6}$ alkylene-cycloalkyl, S(=O)$_2$-cycloalkyl, $C_{1-6}$ alkylene-heterocyclyl, S(=O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, O$C_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(=O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, O$C_{1-6}$ alkyl, $NH_2$, NH($C_{1-6}$ alkyl), N($C_{1-6}$ alkyl)$_2$, cycloalkyl, aryl, heterocyclyl, heteroaryl or COOH; and each $R^7$ is independently selected from =O, halogen, $C_{1-6}$ alkyl, O$C_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH$C_{1-6}$ alkyl, N($C_{1-6}$ alkyl)$_2$, COOH, C(=)O$C_{1-6}$ alkyl, C(=O)O$C_{1-6}$ alkyl, C(=O)$N_{1-6}$ alkyl, C(=O)N($C_{1-6}$ alkyl)$_2$, or NHC(=O)$C_{1-6}$ alkyl.

In embodiments of the compounds of Formula (X-B), (X-C) or (X-D) or a pharmaceutically acceptable salt, a stereoisomer or a deuterated form thereof, $R^3$ and $R^4$ are each $C_{1-6}$ alkyl. In embodiments, $R^3$ and $R^4$ are each $CH_3$. In embodiments, $R^2$ is OH or O$C_{1-6}$ alkyl. In embodiments, $R^2$ is OH, $OCH_3$ or $OCH_2CH_3$. In embodiments, $R^2$ is OH or $OCH_3$ In embodiments, $R^2$ is OH. In embodiments, $R^2$ is $OCH_3$. In embodiments, p is 0, 1 or 2. In embodiments, p is 0. In embodiments p is 1. In embodiments, $R^7$ is halogen or $C_{1-6}$ alkyl. In embodiments, $R^7$ is halogen. In embodiments, $R^7$ is F. In embodiments, q is 0, 1, 2 or 3. In embodiments, q is 0. In embodiments, q is 1. In embodiments, q is 2. In embodiments, q is 3. In embodiments, $R^5$ is halogen, $C_{1-6}$ alkyl, O$C_{1-6}$ alkyl, CN or heterocyclyl. In embodiments, $R^5$ is $CH_3$, F or CN. In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl)$_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

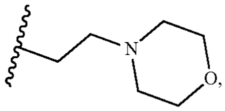,
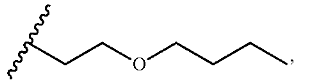,
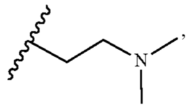, or
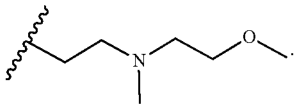.

In embodiments, $R^6$ is $CH_3$ or $CH_2CH_3$. In embodiments, $R^6$ is $CH_3$. In embodiments, $R^6$ is $CH_2CH_3$.

In embodiments, the present disclosure provides a compound of Formula (XI):

(XI)

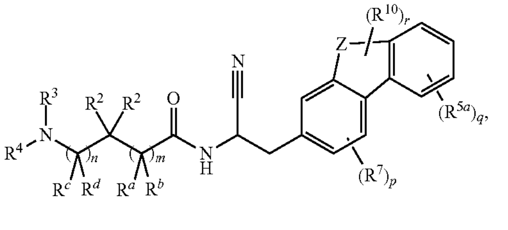

or a pharmaceutically acceptable salt, a stereoisomer or a deuterated form thereof, wherein, Z is O, $CH_2O$, $OCH_2$, $CH_2$ or $CH_2CH_2$;

p is 0, 1, 2, 3 or 4;

q is 0, 1, 2 or 3;

r is 0, 1 or 2;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^{5a}$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

or two $R^{5a}$ together with the atoms they are attached to form a ring structure;

$R^{10}$ is alkyl, halogen, Oalkyl, haloalkyl, OH or CN;

each of $R^a$, $R^b$, $R^c$ and $R^d$ is independently selected from H, alkyl, halogen or haloalkyl; and each of n and m is independently 0, 1, 2 or 3.

In embodiments, the present disclosure provides a compound of Formula (XI-A):

(XI-A)

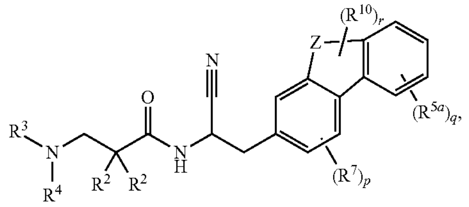

or a pharmaceutically acceptable salt, a stereoisomer or a deuterated form thereof, wherein, Z is O, $CH_2O$, $OCH_2$, $CH_2$ or $CH_2CH_2$;

p is 0, 1, 2, 3 or 4;

q is 0, 1, 2 or 3;

r is 0, 1 or 2;

L is arylene, heterocyclylene, heteroarylene or cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^{5a}$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

or two $R^{5a}$ together with the atoms they are attached to form a ring structure; each of $R^a$, $R^b$, $R^c$ and $R^d$ is independently selected from H, alkyl, halogen or haloalkyl;

$R^{10}$ is alkyl, halogen, Oalkyl, haloalkyl, OH or CN; and each of n and m is independently 0, 1, 2 or 3.

In embodiments of the compounds of Formula (XI) or (XI-A) or a pharmaceutically acceptable salt, a stereoisomer, or a deuterated form thereof,

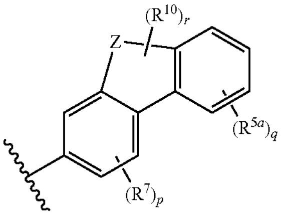

is

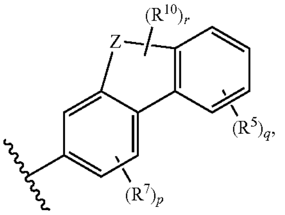

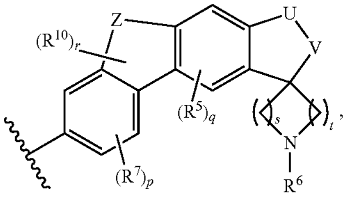

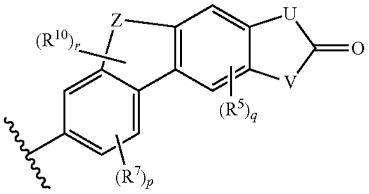

or

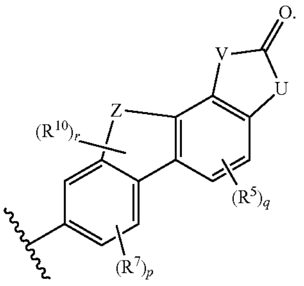

In embodiments,

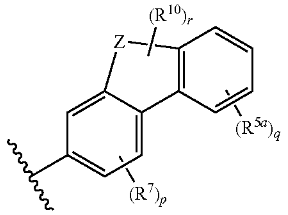

is

-continued

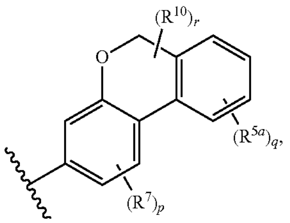

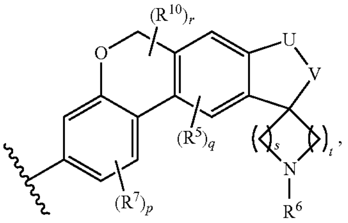

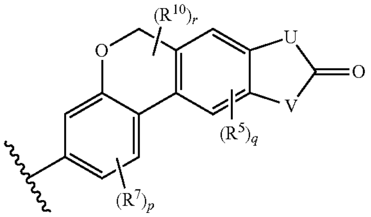

or

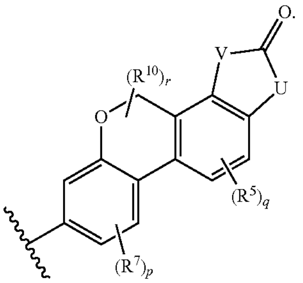

In embodiments,

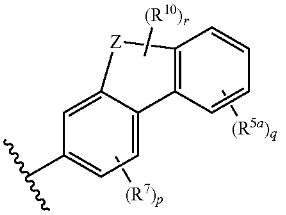

is

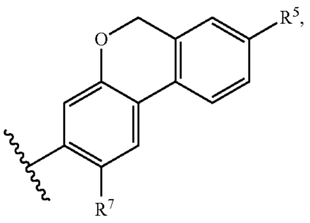

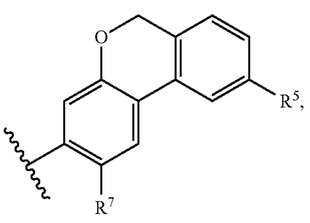

-continued

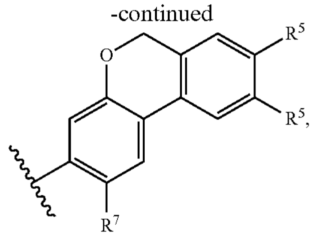

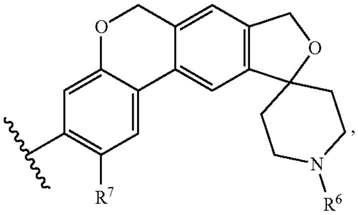

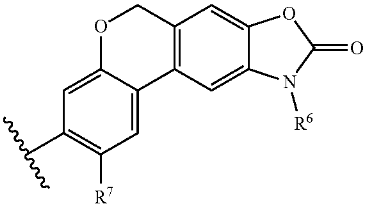

or

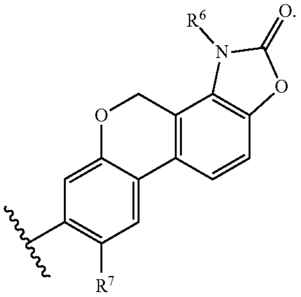

In embodiments, Z is $CH_2O$ or $OCH_2$.

In embodiments, U and V are each independently $CH_2$, O or $N(R^6)$. U and V are each independently $CH_2$, O or $N(CH_3)$. In embodiments, U is $CH_2$, and V is O. In embodiments, U is O, and V is $N(CH_3)$.

In embodiments, r is 0 or 1. In embodiments, r is 0. In embodiments r is 1.

In embodiments, p is 0, 1, 2. In embodiments, p is 0. In embodiments q is 1. In embodiments, p is 2.

In embodiments, q is 0, 1 or 2. In embodiments, q is 0. In embodiments q is 1. In embodiments, q is 2.

In embodiments, $R^5$ is halogen, $C_{1-6}$ alkyl, $OC_{1-6}$ alkyl, $C_{3-6}$ cycloalkyl, CN, $C_{1-6}$ alkylene-heterocyclyl or heterocyclyl. In embodiments, $R^5$ is F, CN or

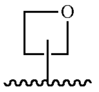

.

In embodiments, $R^5$ is F, CN or

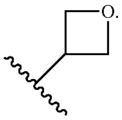

In embodiments, $R^6$ is H, $C_{1-6}$ alkyl, $C_{3-6}$ cycloalkyl, heterocyclyl or $C_{1-6}$ alkylene-heterocyclyl. In embodiments, $R^6$ is H, $C_{1-6}$ alkyl, or heterocyclyl. In embodiments, $R^6$ is H, CN or

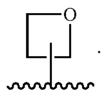

.

In embodiments, $R^6$ is H, CN or

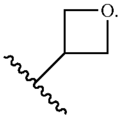

In embodiments, $R^7$ is halogen CN, or $C_{1-6}$ alkyl or $OC_{1-6}$ alkyl. In embodiments, $R^7$ is F.

In embodiments, $R^{10}$ is $C_{1-6}$ alkyl, halogen or CN. In embodiments, $R^{10}$ is $CH_3$, F or CN.

In embodiments of the compounds of Formula (XI) or (XI-A) or a pharmaceutically acceptable salt, a stereoisomer, or a deuterated form thereof,

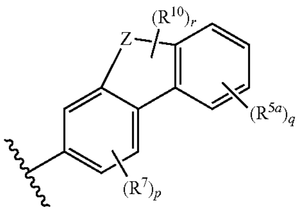

is

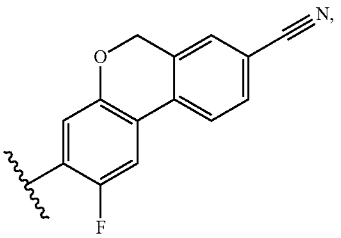

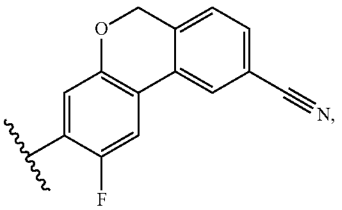

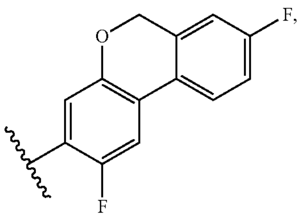

-continued

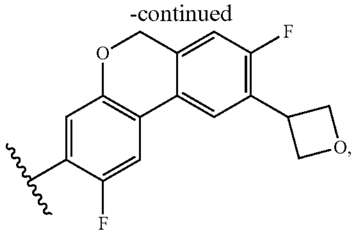

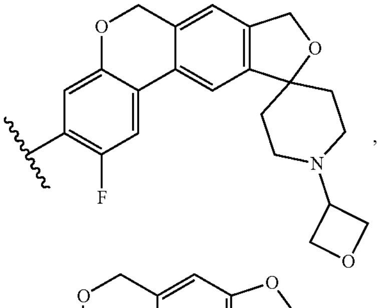

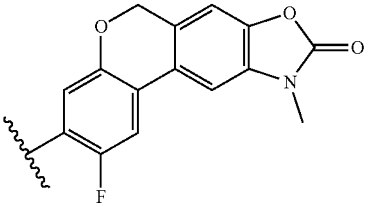

or

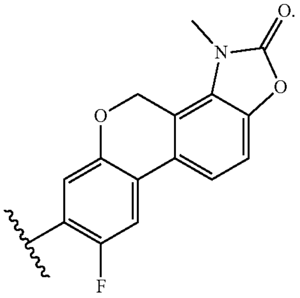

In embodiments, the present disclosure provides a compound of Formula (XII):

(XII)

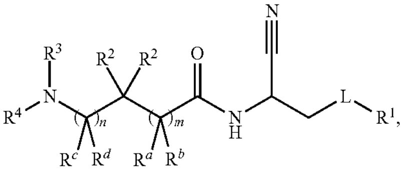

or a pharmaceutically acceptable salt, a stereoisomer or a deuterated form thereof, wherein, $R^1$ is carbocyclyl, aryl, heterocyclyl or heteroaryl, wherein $R^1$ is optionally substituted with 1-5 groups independently selected from $R^5$ or $R^6$;

L is polycyclic arylene, polycyclic heterocyclylene, polycyclic heteroarylene or polycyclic cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$ each of $R^a$, $R^b$, $R^c$ and $R^d$ is independently selected from H, alkyl, halogen or haloalkyl; and each of n and m is independently 0, 1, 2 or 3.

In embodiments, the present disclosure provides a compound of Formula (XII-A):

(XII-A)

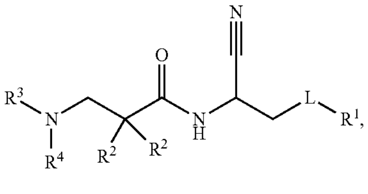

or a pharmaceutically acceptable salt, a stereoisomer or a deuterated form thereof, wherein, $R^1$ is carbocyclyl, aryl, heterocyclyl or heteroaryl, wherein $R^1$ is optionally substituted with 1-5 groups independently selected from $R^5$ or $R^6$ L is polycyclic arylene, polycyclic heterocyclylene, polycyclic heteroarylene or polycyclic cycloalkylene, wherein L is optionally substituted by 1-4 $R^7$;

each $R^2$ is independently H, halogen, OH, CN, Oalkyl, $NH_2$, N(alkyl), SH, C(═O)alkyl, C(═O)$NH_2$, alkyl, haloalkyl, alkylene-OH, alkylene-CH(COOH)($NH_2$), alkenyl, alkynyl, S(alkyl), S(═O)alkyl, S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, or two $R^2$ together form (═O);

each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O) alkyl, C(═O)cycloalkyl, C═(O)aryl or C(═O)heteroaryl, wherein $R^3$ and $R^4$ are optionally substituted with 1-4 $R^{3a}$;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently selected from alkyl, halogen, haloalkyl, Oalkyl, OH, CN, C(═O)OH, $NH_2$, NH(alkyl), NH(alkyl)$_2$, cycloalkyl or heterocyclyl;

each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, oxo, OH, $NH_2$, $NHC_{1-6}$ alkyl, N($C_{1-6}$ alkyl)$_2$, COOH, C(═O)$C_{1-6}$ alkyl, C(═O)$OC_{1-6}$ alkyl, C(═O)$NHC_{1-6}$ alkyl, C(═O)N($C_{1-6}$ alkyl)$_2$, NHC(═O)$C_{1-6}$ alkyl, S(═O)$_2$—$C_{1-6}$ alkyl, $C_{1-6}$ alkylene-cycloalkyl, S(═O)$_2$-cycloalkyl, $C_{1-6}$ alkylene-heterocyclyl, S(═O)$_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

each $R^7$ is independently selected from ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, N($C_{1-6}$ alkyl)$_2$, COOH, C(═)$OC_{1-6}$ alkyl, C(═O)$OC_{1-6}$ alkyl, C(═O)$N_{1-6}$ alkyl, C(═O)N($C_{1-6}$ alkyl)$_2$, or NHC(═O)$C_{1-6}$ alkyl;

or one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$;

each of $R^a$, $R^b$, $R^c$ and $R^d$ is independently selected from H, alkyl, halogen or haloalkyl; and each of n and m is independently 0, 1, 2, or 3.

The compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) is not

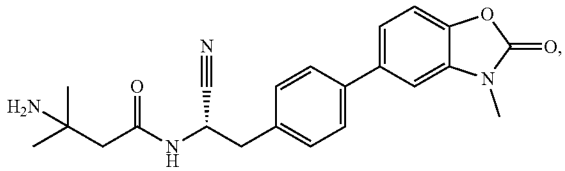
,

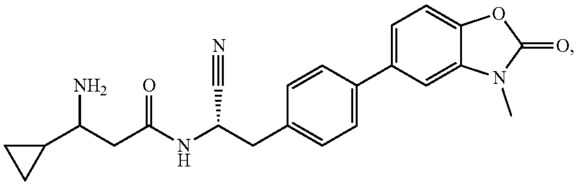
,

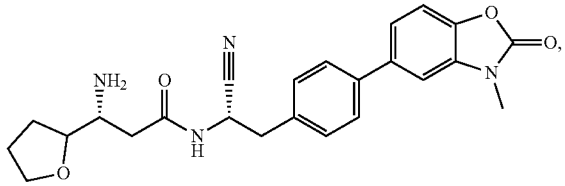
,

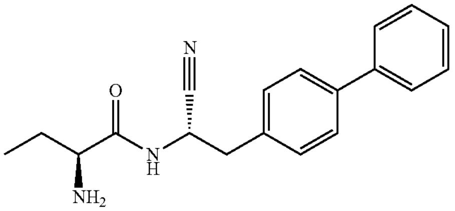
,

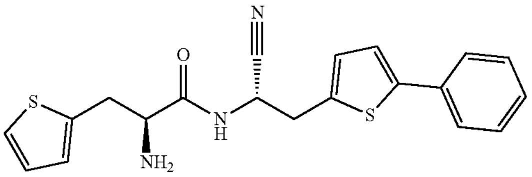
,

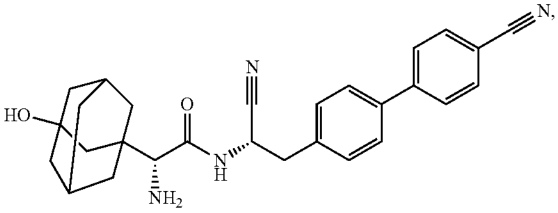
,

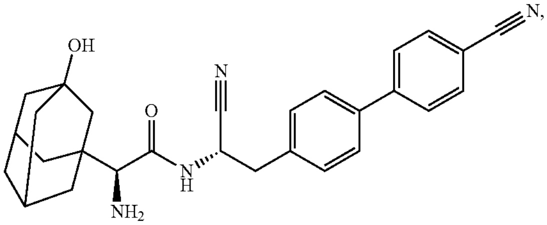
,

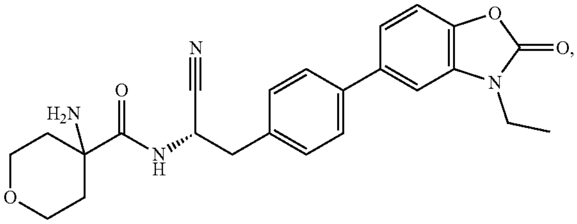
,

-continued

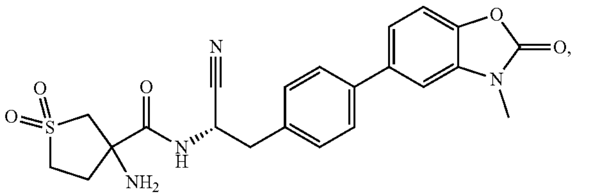

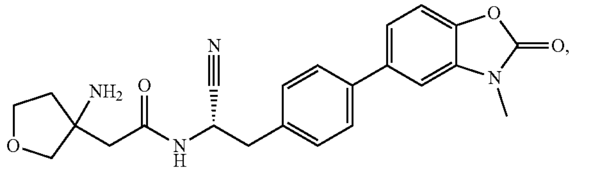

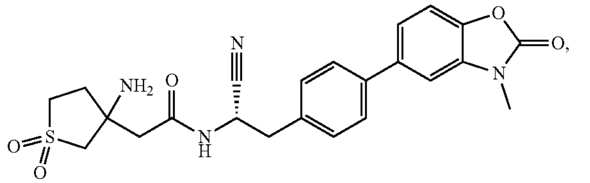

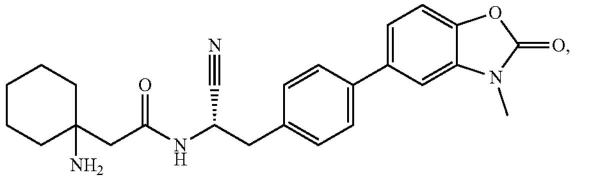

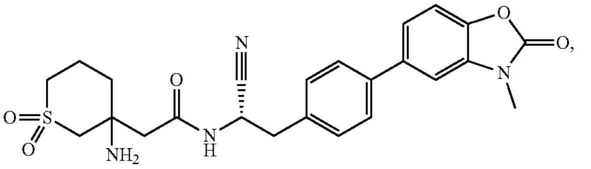

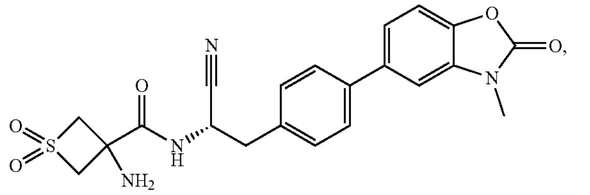

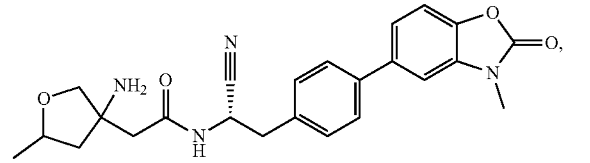

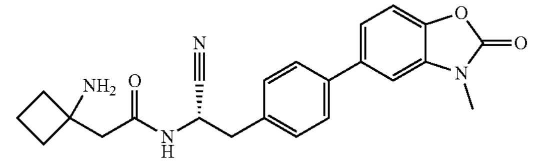

or

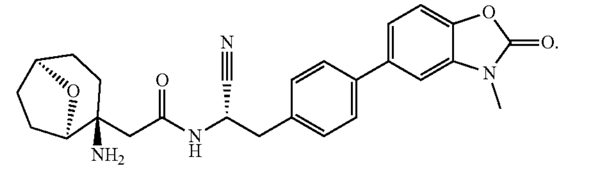

$R^1$, $R^2$, $R^3$, $R^4$, $R^5$, $R^6$, $R^7$, $R^8$, $R^9$, $R^{10}$, $R^a$, $R^b$, $R^c$, $R^d$, L, m, n, p, q, r, Z, Ring A and Ring B of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) are described herein.

$R^2$, $R^{2a}$

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is independently H, halogen, OH, CN, Oalkyl, $NH_2$, N(alkyl), SH, C(=O)alkyl, C(=O)$NH_2$, alkyl, haloalkyl, alkylene-OH, alkylene-CH(COOH)($NH_2$), alkenyl, alkynyl, S(alkyl), S(=O)alkyl, S(=O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is H, halogen, OH, CN, $OC_{1-6}$ alkyl, $NH_2$, SH, $C_{1-6}$ alkyl, $C_{1-6}$ haloalkyl, $C_{1-6}$ alkylene-OH, $C_{1-6}$ alkylene-CH(COOH)($NH_2$), $C_{2-6}$ alkenyl, cycloalkyl, heterocyclyl, aryl, heteroaryl, $C_{1-6}$ alkylene-aryl, $C_{1-6}$ alkylene-heteroaryl, or $C_{1-6}$ alkylene-cycloalkyl, wherein $R^2$ is optionally substituted with 1-4 $R^{2a}$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is H, halogen, OH, CN, $OC_{1-6}$ alkyl, $NH_2$, SH, $C_{1-6}$ alkyl, $C_{1-6}$ haloalkyl, $C_{1-6}$ alkylene-OH, $C_{1-6}$ alkylene-CH(COOH)($NH_2$), $C_{2-6}$ alkenyl, $C_{3-6}$ cycloalkyl, 3-6 membered heterocyclyl, 6-12 membered aryl, 5-6 membered heteroaryl, $C_{1-6}$ alkylene-aryl, $C_{1-6}$ alkylene-heteroaryl, or $C_{1-6}$ alkylene-cycloalkyl, wherein $R^2$ is optionally substituted with 1-4 $R^{2a}$.

In embodiments, the $C_{1-6}$ alkylene-heteroaryl is $CH_2$-heteroaryl. In embodiments, the $C_{1-6}$ alkylene-heteroaryl is $CH_2$-5-6 membered heteroaryl. In embodiments, the $C_{1-6}$ alkylene-heteroaryl is $CH_2$-5-6 membered heteroaryl comprising 1-3 heteroatoms selected from 0, S or N. In embodiments, the heteroaryl is 5-6 membered heteroaryl comprising 1-3 hetero atoms selected from 0, S or N. In embodiments, the 5-6 membered heteroaryl is furanyl, thiazolyl, isothiazolyl, thiophenyl, oxazolyl, isoxazolyl, pyrazolyl, imidazolyl, pyridinyl, pyrimidinyl, pyrazinyl, or pyrazinyl.

In embodiments, the $C_{1-6}$ alkylene-cycloalkyl is $C_{1-3}$ alkylene-cycloalkyl. In embodiments, the cycloalkyl is $C_{3-6}$ cycloalkyl. In embodiments, the cycloalkyl is cyclopropyl. In embodiments, the cycloalkyl is cyclobutyl. In embodiments, the cycloalkyl is cyclopentyl. In embodiments, the cycloalkyl is cyclohexyl.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is independently H, F, Cl, Br, OH, CN, $OC_{1-6}$ alkyl, SH, $NH_2$, $C_{1-6}$ alkyl, $C_{2-6}$ alkenyl, $C_{1-3}$ haloalkyl, CH(COOH)$NH_2$, $C_{1-4}$ alkylene-OH,

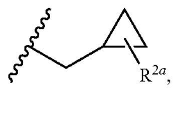, 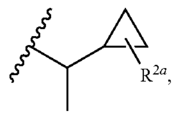,

-continued
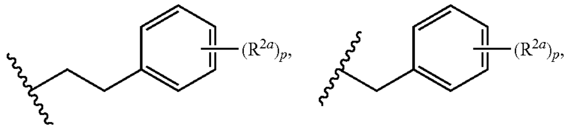
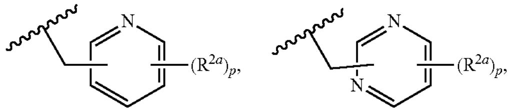
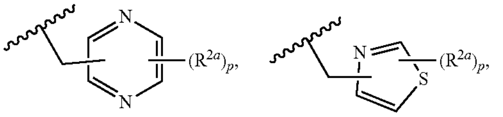
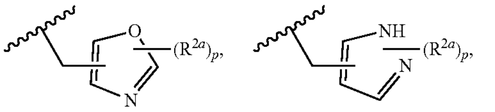
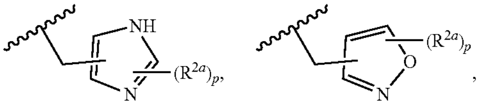
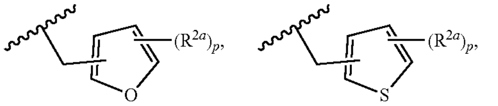
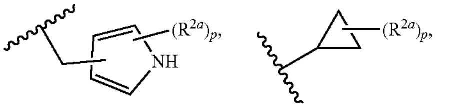
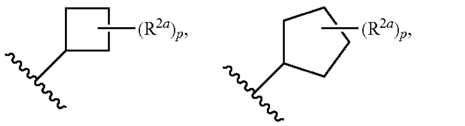
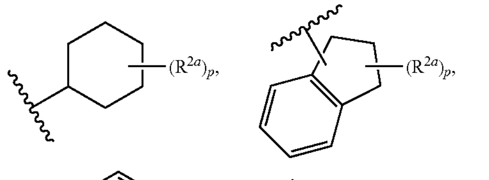
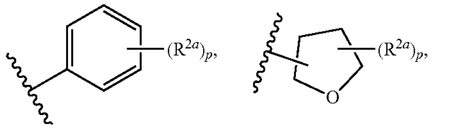
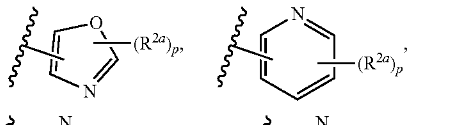
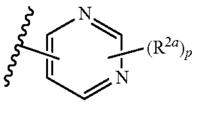
or
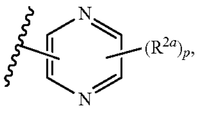
wherein p is 0, 1, 2, 3 or 4.
In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is independently H, F, Cl, Br, OH, CN, $OC_{1-6}$ alkyl, SH, $NH_2$, $C_{1-6}$ alkyl, $C_{2-6}$ alkenyl, $C_{1-3}$ haloalkyl, $CH(COOH)NH_2$, $C_{1-6}$ alkylene-OH,
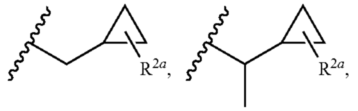
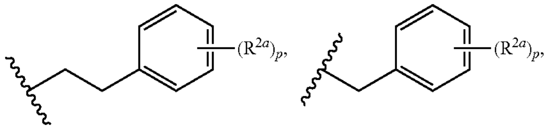
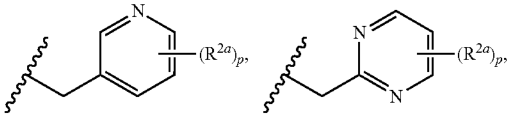
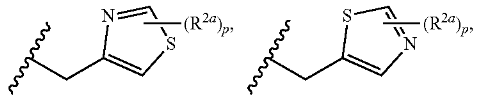
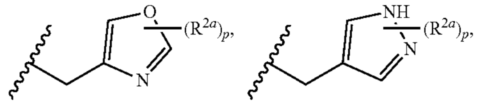
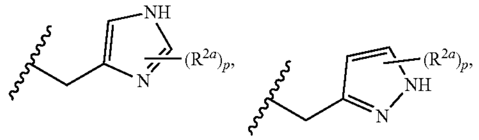
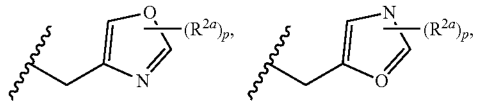
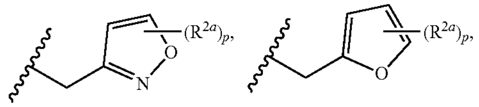
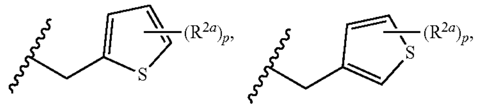
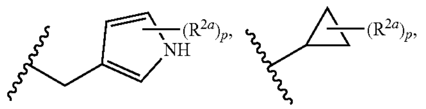
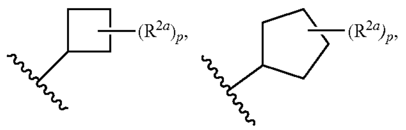
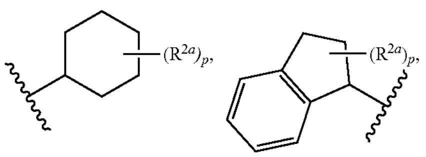
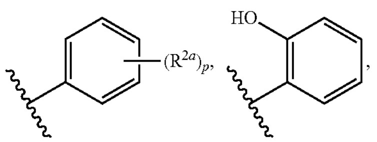
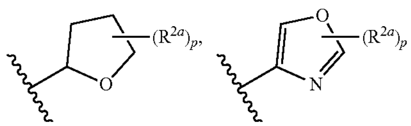
or -continued

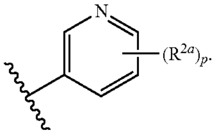

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is independently H, F, Cl, Br, OH, CN, $OCH_3$, $OCH_2CH_3$, $OCH_2CH_2CH_3$, SH, $NH_2$, $CH_3$, $CH_2CH_3$, $CH_2(CH_3)_2$,

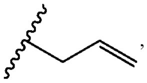 [SMILES: *CC=C], $CH_2F$, $CHF_2$, $CH_2Cl$, $CH(COOH)NH_2$, $CH_2CH_2CH_2F$,

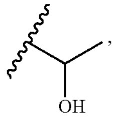, 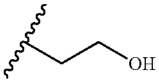, 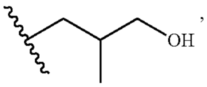,

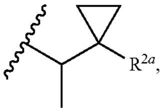, 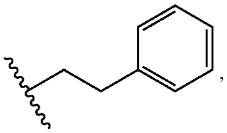,

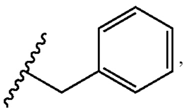, 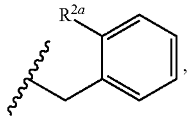,

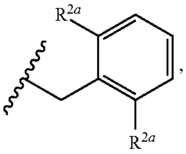, 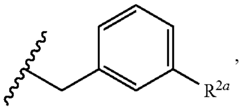,

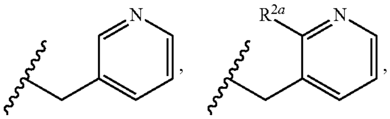

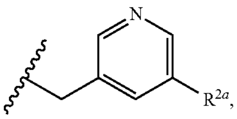, 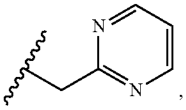,

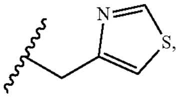, 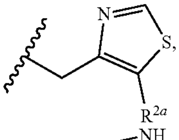, 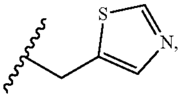

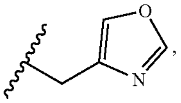, 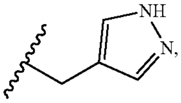, 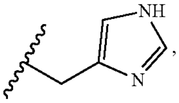,

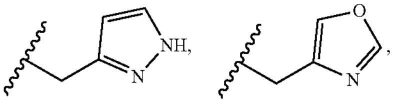

-continued

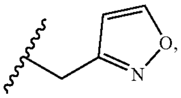, 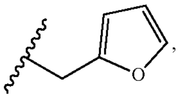, 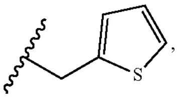,

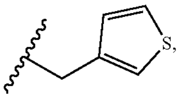, 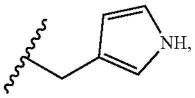

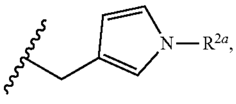, 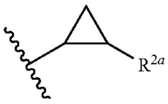, 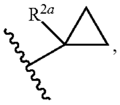,

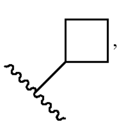, 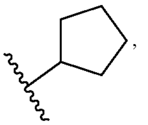, 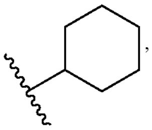,

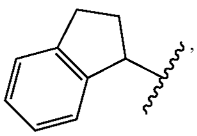, 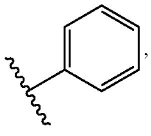,

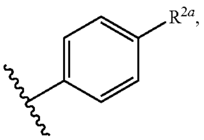, 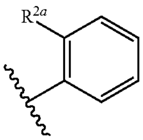, 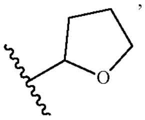,

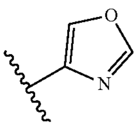 or 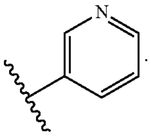.

In embodiments of compound of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^{2a}$ is halogen, OH, $C_{1-6}$ alkyl, $NH_2$, $NH(C_{1-6}$ alkyl) or $N(C_{1-6}$ alkyl). In embodiments, $R^{2a}$ is F, Cl, $CH_3$, OH or $NH_2$.

In embodiments of compound of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is OH or Oalkyl. In embodiments, $R^2$ is OH or $OC_{1-6}$ alkyl. In embodiments, $R^2$ is OH or $OC_{1-4}$ alkyl. In embodiments, $R^2$ is OH, $OCH_3$, $OCH_2CH_3$, or $OCH_2CH_2CH_3$.

In embodiments of compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is $C_{1-6}$ alkyl. In embodiments, $R^2$ is $CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is independently H, F, Cl, Br, OH, CN, $OCH_3$, $OCH_2CH_3$, $OCH_2CH_2CH_3$, SH, $NH_2$, $CH_3$, $CH_2CH_3$, $CH_2(CH_3)_2$,

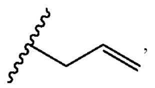 [SMILES: *CC=C]

$CH_2F$, $CHF_2$, $CH_2Cl$, $CH(COOH)NH_2$, $CH_2CH_2CH_2F$,

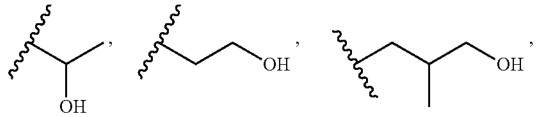

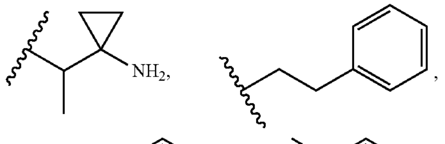

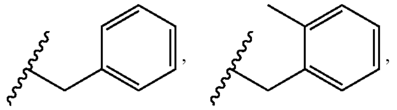

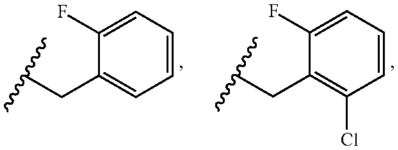

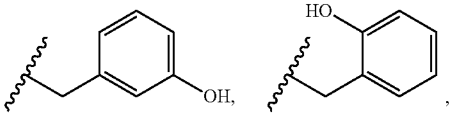

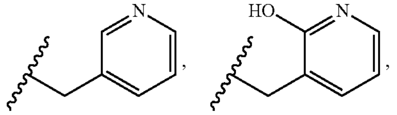

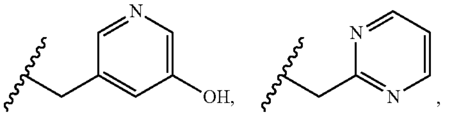

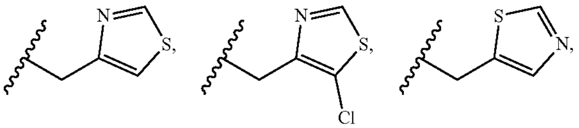

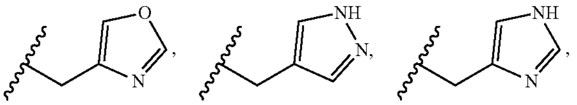

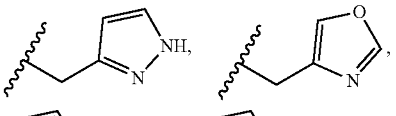

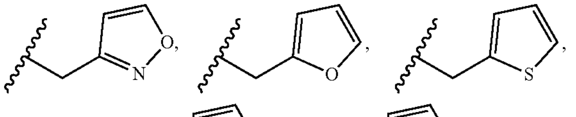

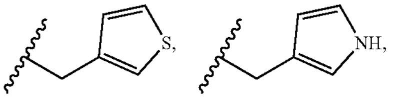

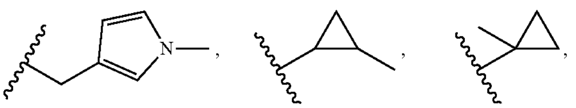

-continued

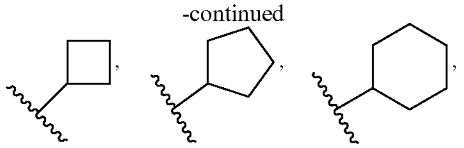

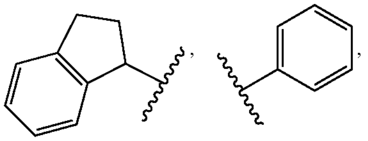

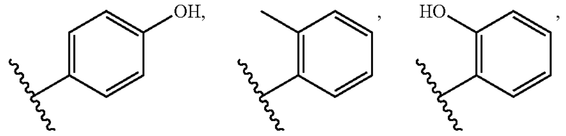

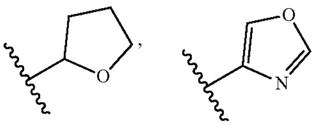 or 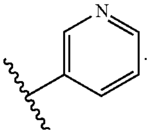

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is OH, $OCH_3$, $CH_3$, $CH_2CH_3$, $CH(CH_3)_2$,

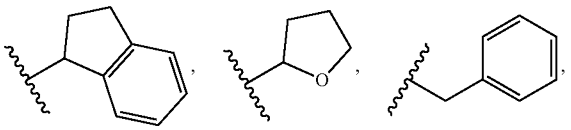

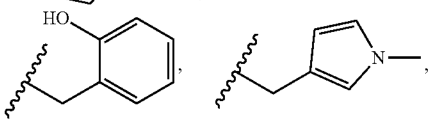

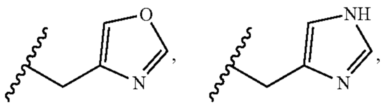

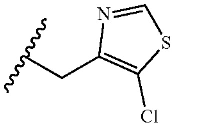 or 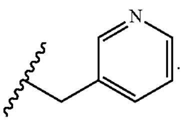

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is OH or $OCH_3$.

In embodiments, the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is OH.

In embodiments, the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^2$ is $OCH_3$.

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, one $R^2$ is H, and the other $R^2$ is H, F, OH, CN, $OCH_3$, $OCH_2CH_3$, $OCH_2CH_2CH_3$, SH, $NH_2$, $CH_3$, $CH_2CH_3$, $CH_2(CH_3)_2$,

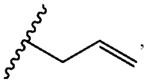 [SMILES: *CC=C], $CH_2F$, $CHF_2$, $CH_2Cl$, —CH(COOH)$NH_2$, $CH_2CH_2CH_2F$,

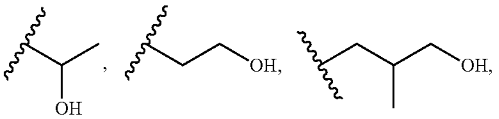

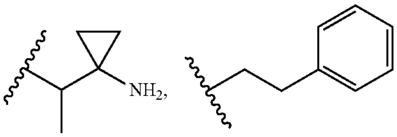

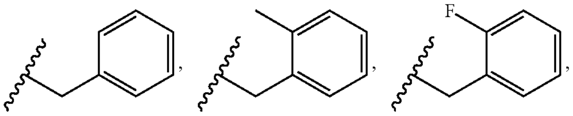

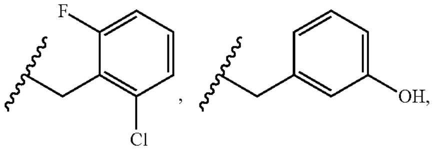

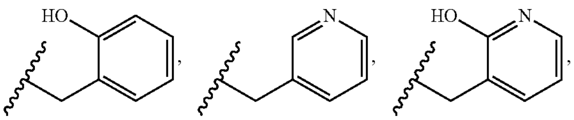

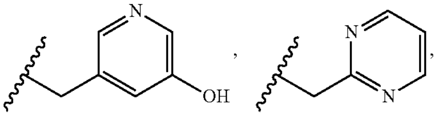

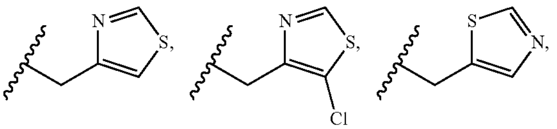

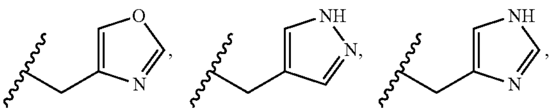

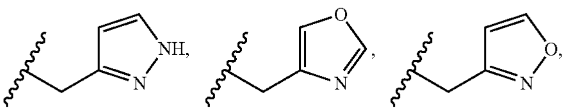

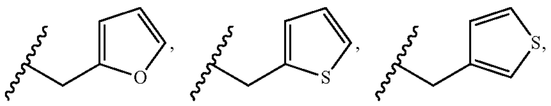

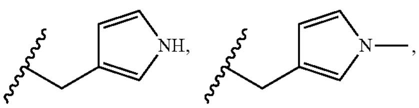

-continued

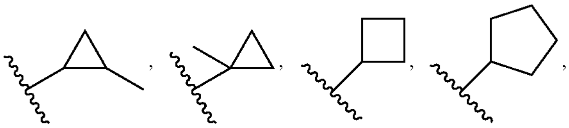

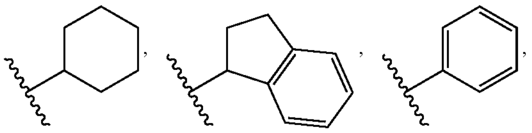

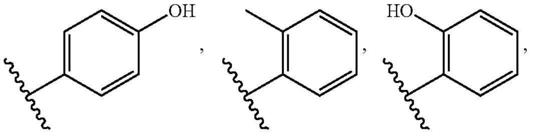

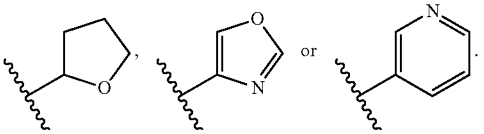

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, one $R^2$ is H, and the other $R^2$ is OH, $OCH_3$, $CH_3$, $CH_2CH_3$, $CH(CH_3)_2$,

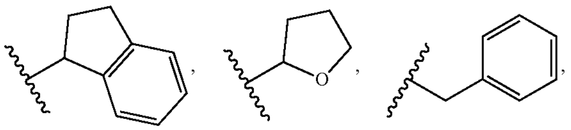

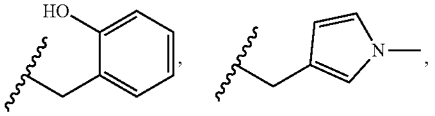

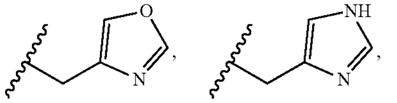

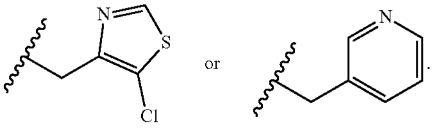

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, one $R^2$ is H, and the other $R^2$ is OH or $OCH_3$. In embodiments, one $R^2$ is H, and the other $R^2$ is OH. In embodiments, one $R^2$ is H, and the other $R^2$ is $OCH_3$.

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, one $R^2$ is $CH_3$, and the other $R^2$ is H, F, OH, CN, $OCH_3$, $OCH_2CH_3$, $OCH_2CH_2CH_3$, SH, $NH_2$, $CH_3$, $CH_2CH_3$, $CH_2(CH_3)_2$,

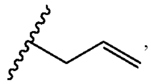 [SMILES: *CC=C]

$CH_2F$, $CHF_2$, $CH_2Cl$, $—CH(COOH)NH_2$, $CH_2CH_2CH_2F$,

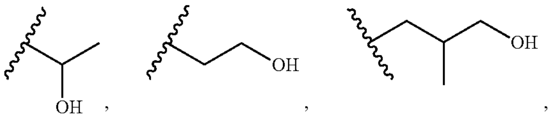

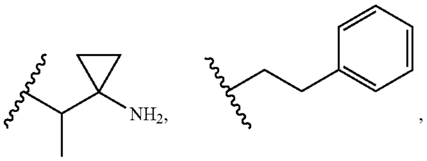

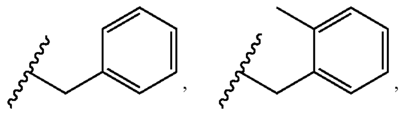

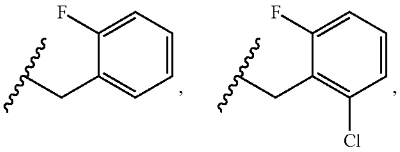

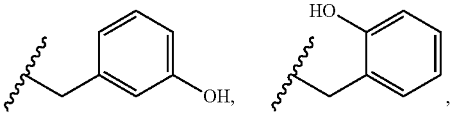

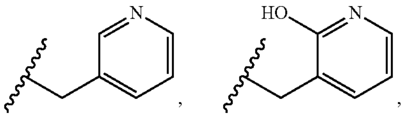

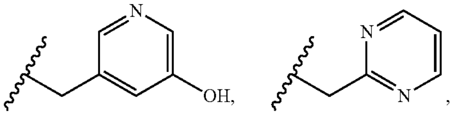

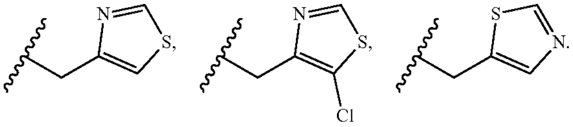

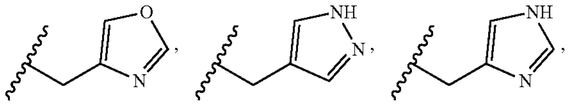

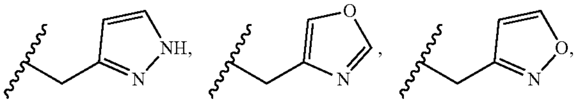

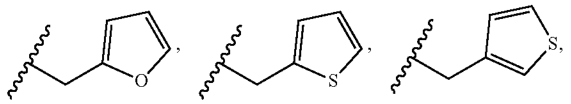

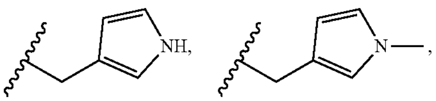

-continued

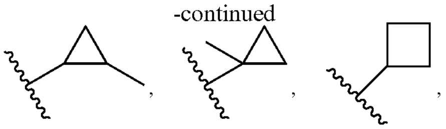

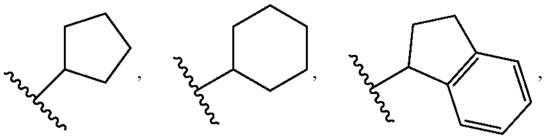

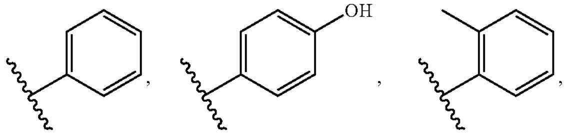

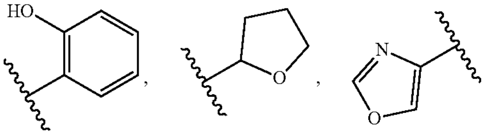 or

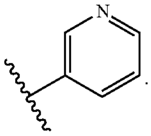

In embodiments, the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, $R^2$ is $C_{1-6}$ alkyl, and the other $R^2$ is cycloalkyl. In embodiments, one $R^2$ is $C_{1-6}$ alkyl, and the other $R^2$ is $C_{3-6}$ cycloalkyl. In embodiments, $R^2$ is $CH_3$, and the other $R^2$ is

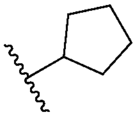 or 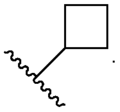

In embodiments, one $R^2$ is $CH_3$, and the other $R^2$ is

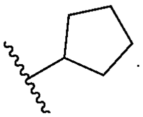 [SMILES: *C1CCCC1]

In embodiments, one $R^2$ is $CH_3$, and the other $R^2$ is

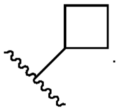

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, one $R^2$ is $CH_3$, and the other $R^2$ is OH or $OCH_3$. In embodiments, one $R^2$ is $CH_3$, and the other $R^2$ is OH. In embodiments, one $R^2$ is $CH_3$, and the other $R^2$ is $OCH_3$.

In embodiments of the compounds of Formula (I), (II), (IV), (V), (VIII), (IX), (IX-A), (IX-B), (IX-C), (IX-D), (X), (XI), (XI-A), (XII) or (XII-A), or a pharmaceutically acceptable salt, a stereoisomer, or a deuterated form thereof, two $R^2$ together form (=O).

Ring A

In embodiments of compounds of Formula (II), or a pharmaceutically acceptable salt, a stereoisomer, or a deuterated form thereof, Ring A is cycloalkyl, aryl or heterocyclyl wherein Ring A is optionally substituted with 1-5 $R^5$. In embodiments, Ring A is $C_{3-8}$ cycloalkyl, 6-12 membered aryl or 3-8 membered heterocyclyl, wherein Ring A is optionally substituted with 1-5 $R^5$. In embodiments, the 3-8 membered heterocyclyl comprises 1-3 heteroatoms selected from O, S or N. In embodiments, the 3-8 membered heterocyclyl comprises 1 or 2 heteroatoms selected from O, S or N. In embodiments, the 3-8 membered heterocyclyl comprises 1 heteroatom selected from O, S or N.

In embodiments of compounds of Formula (II), or a pharmaceutically acceptable salt, a stereoisomer, or a deuterated form thereof, Ring A is

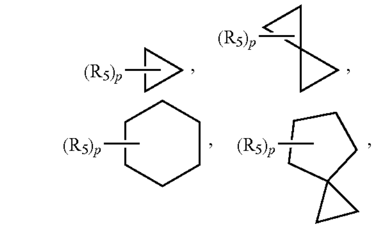
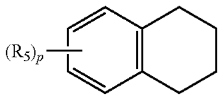
or
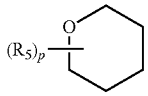
, wherein p is 0, 1, 2, or 3, and

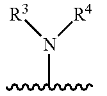
and
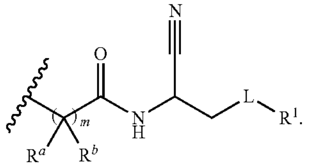

are attached to any ring atoms of ring A.

In embodiments of compounds of Formula (II), or a pharmaceutically acceptable salt, a stereoisomer, or a deuterated form thereof, Ring A is

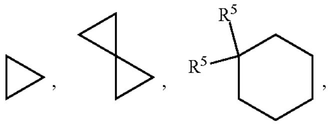
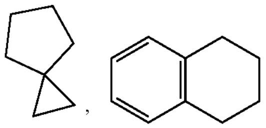
or
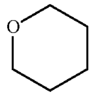
, wherein

-continued

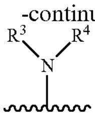
and
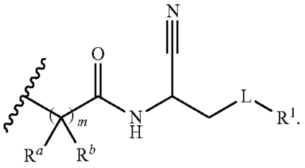

are attached to any ring atoms of ring A.

In embodiments, p is 0, 1 or 2. In embodiments, p is 0. In embodiments, p is 1. In embodiments, p is 2.

In embodiments, $R^5$ is halogen, CN, $C_{1-6}$ alkyl, halo$C_{1-6}$ alkyl, or $OC_{1-6}$ alkyl. In embodiments, $R^5$ is F.

In embodiments of compounds of Formula (II), or a pharmaceutically acceptable salt, a stereoisomer, or a deuterated form thereof, Ring A is

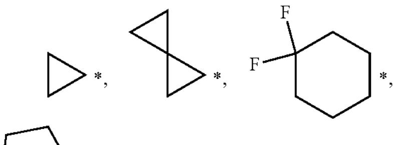
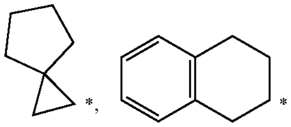
or
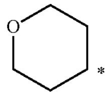

wherein the asterisk represents the site of attachment to

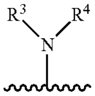
and
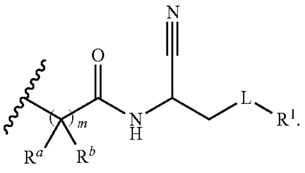

In embodiments of compounds of Formula (II), or a pharmaceutically acceptable salt, a stereoisomer, or a deuterated form thereof, Ring A is

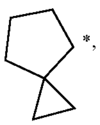

wherein the asterisk represents the site of attachment to

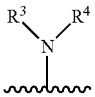
and

-continued

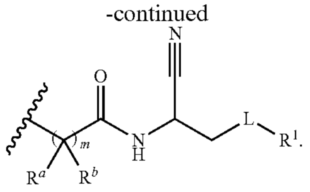

Ring B

In embodiments of compounds of Formula (VI), (VII) or a pharmaceutically acceptable salt, a stereoisomer or a deuterated form thereof, Ring B is carbocyclyl, aryl, heterocyclyl or heteroaryl, wherein Ring B is optionally substituted with 1-4 $R^{2a}$. In embodiments, Ring B is carbocyclyl, aryl, heterocyclyl or heteroaryl. In embodiments, Ring B is $C_{3-6}$ cycloalkyl, $C_{6-12}$ aryl, 5-6 membered heterocyclyl or 5-6 heteroaryl, wherein Ring B is optionally substituted with 1-4 $R^{2a}$. In embodiments, the heterocyclyl and heteroaryl comprise 1-3 heteroatom selected from O, S or N. In embodiments, the heterocyclyl and heteroaryl comprise 1-2 heteroatom selected from O or N.

In embodiments of compounds of Formula (VI), (VII), or a pharmaceutically acceptable salt, a stereoisomer or a deuterated form thereof, Ring B is

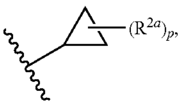 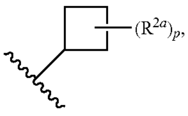 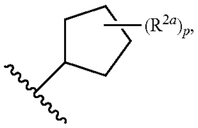 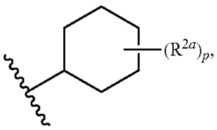 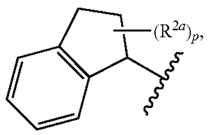 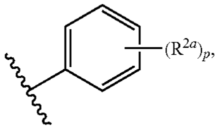 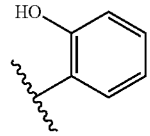 , 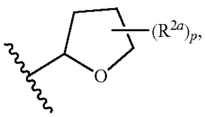 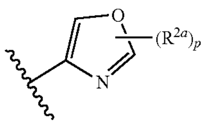 or 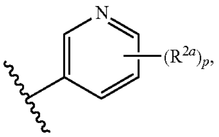 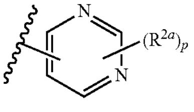 or 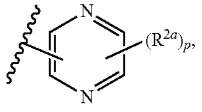

wherein p is 0, 1, 2, 3 or 4.

In embodiments, Ring B is

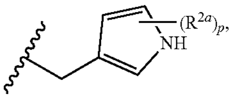 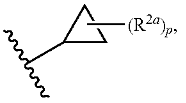

-continued

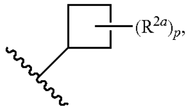 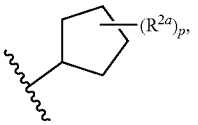 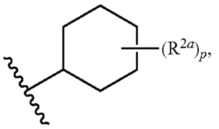 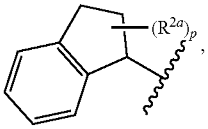 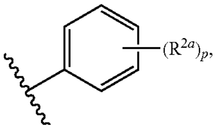 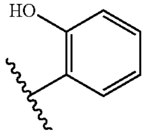 , 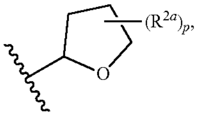 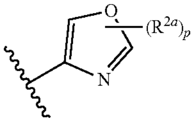 or 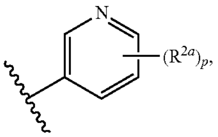

wherein p is 0, 1, 2, 3 or 4. In embodiments, $R^{2a}$ is halogen, $C_{1-6}$ alkyl, $NH_2$, $NH(C_{1-6}$ alkyl) or $N(C_{1-6}$ alkyl). In embodiments, $R^{2a}$ is F, Cl, $CH_3$, OH or $NH_2$.

In embodiments, Ring B is

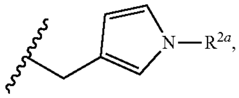 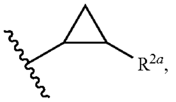 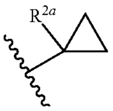 , 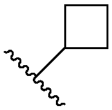 , 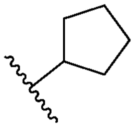 , 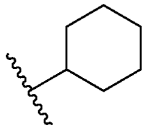 , 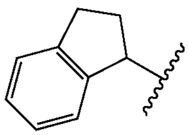 , 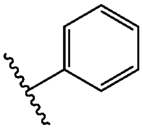 , 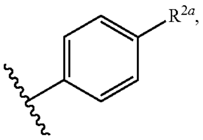 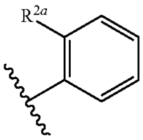 , 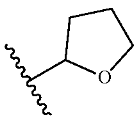 , 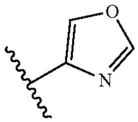 or 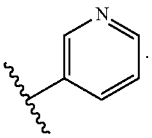 .

In embodiments, Ring B is

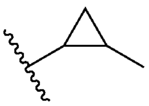 , 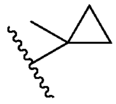 ,

-continued

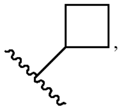, 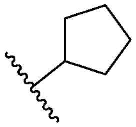,

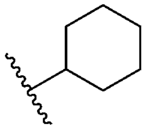, 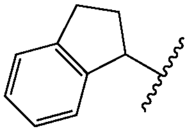, 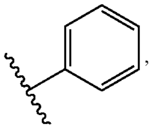,

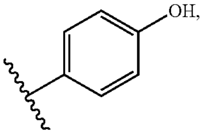 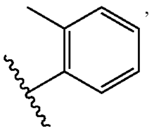,

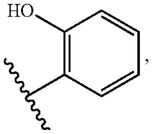, 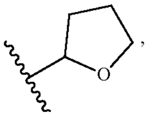,

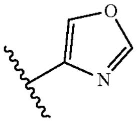 or 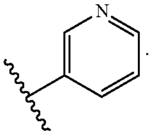.

In embodiments of compounds of Formula (VI) or (VII), or a pharmaceutically acceptable salt, a stereoisomer, or a deuterated form thereof, Ring B is $C_{3-6}$ cycloalkyl optionally substituted with 1-4 $R^{2a}$. In embodiments, Ring B is $C_{4-6}$ cycloalkyl optionally substituted with 1-4 $R^{2a}$. In embodiments, Ring B is $C_{4-5}$ cycloalkyl optionally substituted with 1-4 $R^{2a}$.

In embodiments of compounds of Formula (VI) or (VII), or a pharmaceutically acceptable salt, a stereoisomer, or a deuterated form thereof, $R^{2a}$ is halogen, $C_{1-6}$ alkyl, $NH_2$, OH, $NH(C_{1-6}$ alkyl) or $N(C_{1-6}$ alkyl). In embodiments, $R^{2a}$ is F, Cl, $CH_3$, OH or $NH_2$.

In embodiments of compounds of Formula (VI) or (VII), or a pharmaceutically acceptable salt, a stereoisomer, or a deuterated form thereof, Ring B is

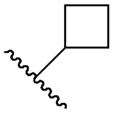 or 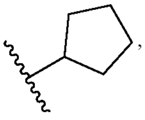,

In embodiments of compounds of Formula (VI) or (VII), or a pharmaceutically acceptable salt, a stereoisomer, or a deuterated form thereof, Ring B is $C_{3-6}$ cycloalkyl, and $R^2$ is $C_{1-6}$ alkyl.

In embodiments of compounds of Formula (VI) or (VII), or a pharmaceutically acceptable salt, a stereoisomer, or a deuterated form thereof, Ring B is

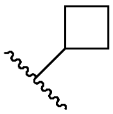 or 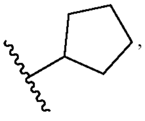, and $R^2$ is $C_{1-6}$ alkyl.

In embodiments of compounds of Formula (VI) or (VII), or a pharmaceutically acceptable salt, a stereoisomer, or a deuterated form thereof, Ring B is

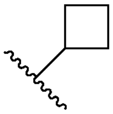 or 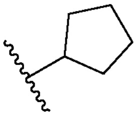, and $R^2$ is $CH_3$.

In embodiments of compounds of Formula (VI) or (VII), or a pharmaceutically acceptable salt, a stereoisomer, or a deuterated form thereof, Ring B is

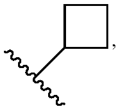 [SMILES: *C1CCC1], and $R^2$ is $CH_3$.

In embodiments of compounds of Formula (VI) or (VII), or a pharmaceutically acceptable salt, a stereoisomer, or a deuterated form thereof, Ring B is

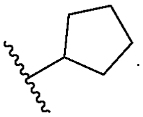 [SMILES: *C1CCCC1].

and $R^2$ is $CH_3$.

$R^3$, $R^4$

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from H, alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ are not H at the same time.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from alkyl, cycloalkyl, aryl, heterocyclyl, heteroaryl, alkylene-OH, alkylene-O-alkyl, alkylene-carbocyclyl, alkylene-heterocyclyl, alkylene-aryl, alkylene-heteroaryl, C(═O)alkyl, C(═O)cycloalkyl, C═(O)aryl or C(═O)heteroaryl, wherein $R^3$ and $R^4$ are optionally substituted with 1-4 $R^{3a}$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from H, $C_{1-6}$ alkyl, $C_{1-6}$ alkylene-OH, $C_{1-6}$ alkylene-O—$C_{1-6}$ alkyl, $C_{1-6}$ alkylene-heteroaryl, or C(═O)heteroaryl, wherein the $C_{1-6}$ alkyl, alkylene-heteroaryl, and C(═O)heteroaryl are optionally substituted with 1-4 $R^{3a}$. In embodiments, each of $R^3$ and $R^4$ is independently selected from H, $C_{1-6}$ alkyl, $C_{1-6}$ alkylene-OH, $C_{1-6}$ alkylene-O—$C_{1-6}$ alkyl, $C_{1-6}$ alkylene-heteroaryl, or C(═O)heteroaryl.

In embodiments, the C(═O)heteroaryl is C(═O)-5-6 membered heteroaryl. In embodiments, the C(═O)heteroaryl is C(═O)-5-6 membered heteroaryl, wherein the heteroaryl comprises 1-3 heteroatoms selected from O, S or N. In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, In embodiments, $R^{3a}$ is $C_{1-6}$ alkyl, halogen, CN or $OC_{1-6}$ alkyl. In embodiments $R^{3a}$ is $C_{1-6}$ alkyl. In embodiments, $R^{3a}$ is $CH_3$.

In embodiments, the alkylene-heteroaryl is $C_{1-6}$ alkylene-heteroaryl. In embodiments, the alkylene-heteroaryl is $C_{1-3}$ alkylene-heteroaryl. In embodiments, the heteroaryl is thiophenyl, oxazolyl, isoxazolyl, thiazolyl, isothiazolyl, pyrazolyl, pyrrolyl, or furanyl.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from H, $C_{1-6}$ alkyl, $C_{1-6}$ alkylene-OH, $C_{1-6}$ alkylene-O—$C_{1-6}$ alkyl,

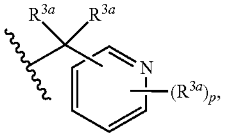 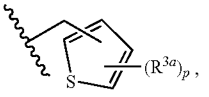

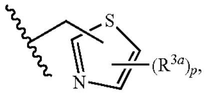 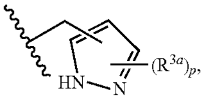

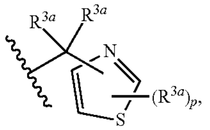 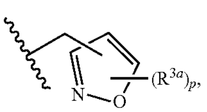

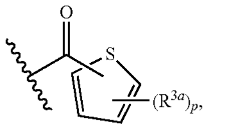 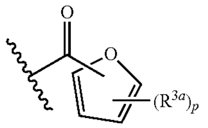 or

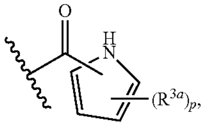

wherein p is 0, 1, 2 or 3. In embodiments, p is 0, 1 or 2. In embodiments p is 0. In embodiments, p is 1. In embodiments p is 2. In embodiments, $R^{3a}$ is $C_{1-6}$ alkyl, halogen, CN or $OC_{1-6}$ alkyl. In embodiments $R^{3a}$ is $C_{1-6}$ alkyl. In embodiments, $R^{3a}$ is $CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ is independently selected from H, $C_{1-6}$ alkyl, $C_{1-6}$ alkylene-OH, $C_{1-6}$ alkylene-O—$C_{1-6}$ alkyl,

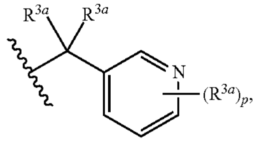

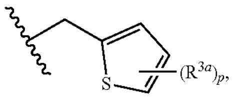

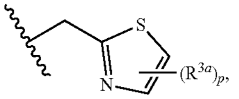

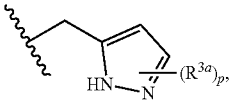

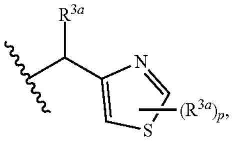

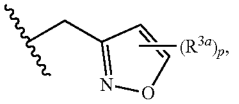

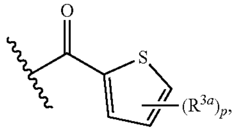 or

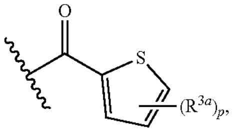

wherein p is 0, 1, 2 or 3. In embodiments, p is 0, 1 or 2. In embodiments p is 0. In embodiments, p is 1. In embodiments p is 2. In embodiments, $R^{3a}$ is $C_{1-6}$ alkyl, halogen, CN or $OC_{1-6}$ alkyl. In embodiments $R^{3a}$ is $C_{1-6}$ alkyl. In embodiments, $R^{3a}$ is $CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ is independently selected from H, $CH_3$, $CH_2CH_3$, $CH_2CH_2CH_3$,

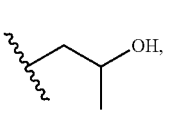 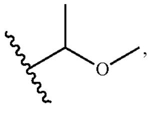 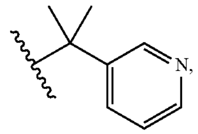

-continued

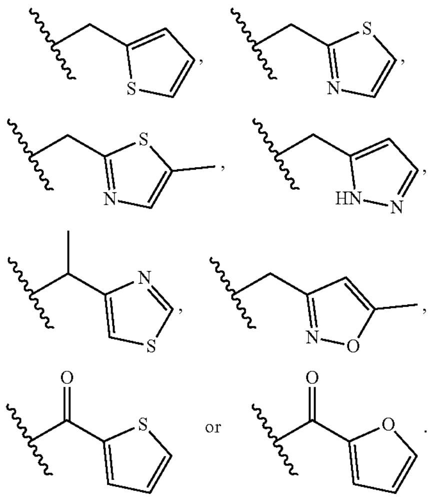

or

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ is independently selected from $CH_3$, $CH_2CH_3$, $CH_2CH_2CH_3$,

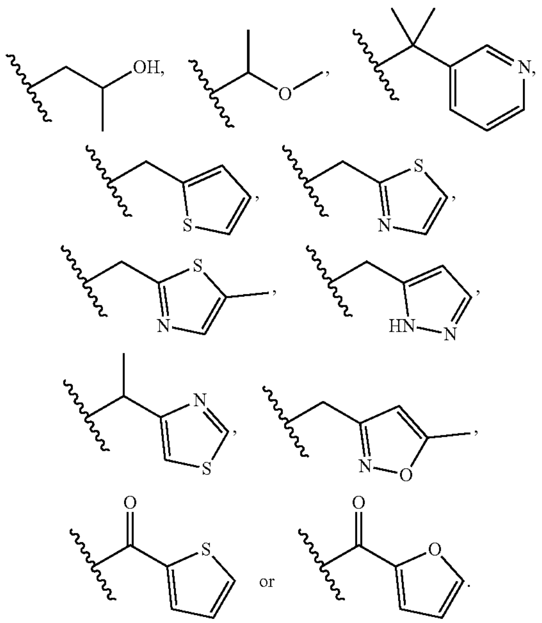

or

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ are each H.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ is H and $R^4$ is $CH_3$, $CH_2CH_3$, $CH_2CH_2CH_3$,

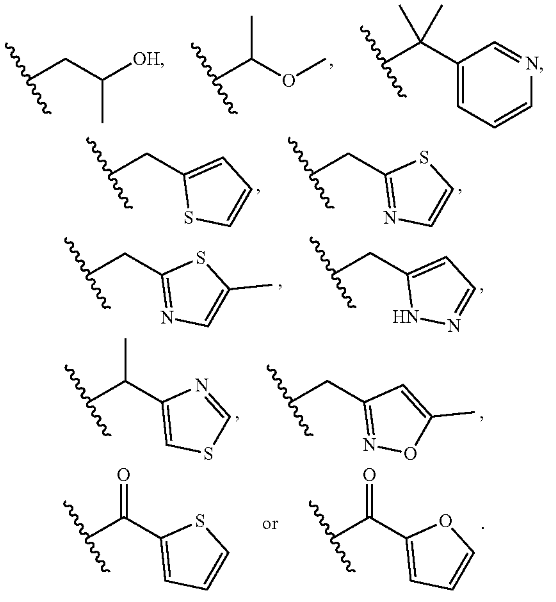

or

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from H or $C_{1-6}$ alkyl. In embodiments, each of $R^3$ and $R^4$ is independently selected from H, $CH_3$, $CH_2CH_3$ or $CH_2CH_2CH_3$. In embodiments, $R^3$ is H and $R^4$ is $CH_3$, $CH_2CH_3$ or $CH_2CH_2CH_3$. In embodiments, $R^3$ is H and $R^4$ is $CH_3$. In embodiments, $R^3$ is H and $R^4$ is $CH_2CH_3$. In embodiments, $R^3$ is H and $R^4$ is $CH_2CH_2CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is independently selected from $C_{1-6}$ alkyl optionally substituted with 1-4 $R^{3a}$. In embodiments, each of $R^3$ and $R^4$ is independently selected from $C_{1-6}$ alkyl. In embodiments, each of $R^3$ and $R^4$ is independently $CH_3$, $CH_2CH_3$ or $CH_2CH_2CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is $CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, each of $R^3$ and $R^4$ is $CH_2CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ is $CH_3$ and $R^4$ is $CH_2CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII)

or (XII-A) or a pharmaceutically acceptable salt, a stereoisomer, or a deuterated form thereof, $R^3$ is $CH_3$ and $R^4$ is $CH_2CH_2CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ with the nitrogen they are connected to are taken together to form a heterocyclyl optionally substituted with 1-4 $R^{3a}$. In embodiments, $R^3$ and $R^4$ with the nitrogen they are connected to are taken together to form a 3-8 membered heterocyclyl substituted with 1-4 $R^{3a}$. In embodiments, $R^3$ and $R^4$ with the nitrogen they are connected to are taken together to form a 4-6 membered heterocyclyl substituted with 1-4 $R^{3a}$. In embodiments, $R^3$ and $R^4$ with the nitrogen they are connected to are taken together to form a 4-6 membered heterocyclyl.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ with the nitrogen they are connected to are taken together to form a heterocyclyl selected from

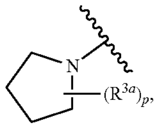 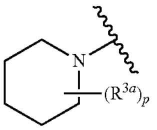 or 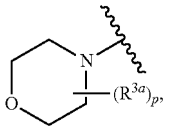

wherein p is 0, 1, 2 or 3. In embodiments, p is 0. In embodiments, p is 1. In embodiments, $R^{3a}$ is $C_{1-6}$ alkyl, halogen, CN or $OC_{1-6}$ alkyl. In embodiments $R^{3a}$ is $C_{1-6}$ alkyl. In embodiments, $R^{3a}$ is $CH_3$.

In embodiments of the compounds of Formula (I), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A) or a pharmaceutically acceptable salt, a stereoisomer, or a deuterated form thereof, $R^3$ and $R^4$ with the nitrogen they are connected to are taken together to form a heterocyclyl selected from,

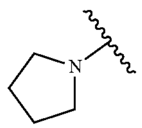, 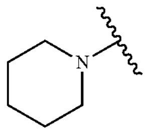 or 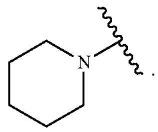.

$R^a$, $R^b$, $R^e$, $R^d$, m and n

In embodiments of compounds of Formula (I), (III), (IV), (V), (VIII), (XI) or (XII), or a pharmaceutically acceptable salt, a stereoisomer, or a deuterated form thereof, each of $R^a$, $R^b$, $R^c$ and $R^d$ is independently selected from H, alkyl, halogen or haloalkyl.

In embodiments of compounds of Formula (I), (III), (IV), (V), (VIII), (XI) or (XII), or a pharmaceutically acceptable salt, a stereoisomer, or a deuterated form thereof, each of $R^a$, $R^b$, $R^c$ and $R^d$ is selected from H, $C_{1-6}$ alkyl, halogen or $C_{1-6}$ haloalkyl.

In embodiments of compounds of Formula (I), (III), (IV), (V), (VIII), (XI) or (XII), or a pharmaceutically acceptable salt, a stereoisomer, or a deuterated form thereof, each of $R^a$, $R^b$, $R^c$ and $R^d$ is H, $CH_3$, $CH_2CH_3$, $CH(CH_3)_2$, $CH_2Cl$, $CHCl_2$, $CH_2F$, $CHF_2$ or $CF_3$. In embodiments, each of $R^a$, $R^b$, $R^c$ and $R^d$ is H, $CH_3$, $CH_2CH_3$, $CH(CH_3)_2$, $CH_2C_1$ or $CHF_2$.

In embodiments of compounds of Formula (I), (III), (IV), (V), (VIII), (XI) or (XII), or a pharmaceutically acceptable salt, a stereoisomer, or a deuterated form thereof, each of $R^a$, $R^b$, $R^c$ and $R^d$ is H.

In embodiments of compounds of Formula (I), (III), (IV), (V), (VIII), (XI) or (XII), or a pharmaceutically acceptable salt, a stereoisomer, or a deuterated form thereof, one of $R^a$, $R^b$, $R^c$ and $R^d$ is $CH_3$, $CH_2CH_3$, $CH(CH_3)_2$, $CH_2C_1$ or $CHF_2$, and all the remaining $R^a$, $R^b$, $R^c$ and $R^d$ is H.

In embodiments of compounds of Formula (I), (III), (IV), (V), (VIII), (XI) or (XII), or a pharmaceutically acceptable salt, a stereoisomer, or a deuterated form thereof, wherein $R^c$ is $CH_3$, $CH_2CH_3$, $CH(CH_3)_2$, $CH_2C_1$ or $CHF_2$, and each of $R^a$, $R^b$ and $R^d$ is H.

In embodiments of compounds of Formula (I), (II), (III), (IV), (V), (VIII), (XI) or (XII), or a pharmaceutically acceptable salt, a stereoisomer, or a deuterated form thereof, m is 0, 1 or 2.

In embodiments of compounds of Formula (I), (II), (III), (IV), (V), (VIII), (XI) or (XII), or a pharmaceutically acceptable salt, a stereoisomer, or a deuterated form thereof, m is 0.

In embodiments of compounds of Formula (I), (II), (III), (IV), (V), (VIII), (XI) or (XII), or a pharmaceutically acceptable salt, a stereoisomer, or a deuterated form thereof, m is 1.

In embodiments of compounds of Formula (I), (II), (III), (IV), (V), (VIII), (XI) or (XII), or a pharmaceutically acceptable salt, a stereoisomer, or a deuterated form thereof, m is 2.

In embodiments of compounds of Formula (I), (III), (IV), (V), (VIII), (XI) or (XII), or a pharmaceutically acceptable salt, a stereoisomer, or a deuterated form thereof, n is 0, 1 or 2.

In embodiments of compounds of Formula (I), (III), (IV), (V), (VIII), (XI) or (XII), or a pharmaceutically acceptable salt, a stereoisomer, or a deuterated form thereof, n is 0.

In embodiments of compounds of Formula (I), (III), (IV), (V), (VIII), (XI) or (XII), or a pharmaceutically acceptable salt, a stereoisomer, or a deuterated form thereof, n is 1.

In embodiments of compounds of Formula (I), (III), (IV), (V), (VIII), (XI) or (XII), or a pharmaceutically acceptable salt, a stereoisomer, or a deuterated form thereof, n is 2.

In embodiments of compounds of Formula (I), (III), (IV), (V), (VIII), (XI) or (XII), or a pharmaceutically acceptable salt, a stereoisomer, or a deuterated form thereof, m is 0 and n is 0, 1, or 2.

In embodiments of compounds of Formula (I), (III), (IV), (V), (VIII), (XI) or (XII), or a pharmaceutically acceptable salt, a stereoisomer, or a deuterated form thereof, m is 0 and n is 0.

In embodiments of compounds of Formula (I), (III), (IV), (V), (VIII), (XI) or (XII), or a pharmaceutically acceptable salt, a stereoisomer, or a deuterated form thereof, m is 0 and n is 1.

In embodiments of compounds of Formula (I), (III), (IV), (V), (VIII), (XI) or (XII), or a pharmaceutically acceptable salt, a stereoisomer, or a deuterated form thereof, m is 0 and n is 2.

In embodiments of compounds of Formula (I), (III), (IV), (V), (VIII), (XI) or (XII), or a pharmaceutically acceptable salt, a stereoisomer, or a deuterated form thereof, m is 1 and n is 0 or 1.

In embodiments of compounds of Formula (I), (III), (IV), (V), (VIII), (XI) or (XII), or a pharmaceutically acceptable salt, a stereoisomer, or a deuterated form thereof, m is 1 and n is 0.

In embodiments of compounds of Formula (I), (III), (IV), (V), (VIII), (XI) or (XII), or a pharmaceutically acceptable salt, a stereoisomer, or a deuterated form thereof, m is 1 and n is 1.

In embodiments of compounds of Formula (I), (III), (IV), (V), (VIII), (XI) or (XII), or a pharmaceutically acceptable salt, a stereoisomer, or a deuterated form thereof, m is 2 and n is 0.

L, $R^7$,p

In embodiments of compounds of Formula (I), (II), (III), (IX), (IX-A),(IX-B), (X), (XII) or (XII-A), or a pharmaceutically acceptable salt, a stereoisomer, or a deuterated form thereof, L is alkylene, cycloalkylene, arylene, heterocyclylene or heteroarylene, wherein L is optionally substituted by 1-4 $R^7$. In embodiments L is arylene, heterocyclylene or heteroarylene, wherein L is optionally substituted by 1-4 $R^7$. In embodiments L is arylene, or heteroarylene, wherein L is optionally substituted by 1-4 $R^7$.

In embodiments of compounds of Formula (I), (II), (III), (IX), (IX-A),(IX-B), (X), (XII) or (XII-A), or a pharmaceutically acceptable salt, a stereoisomer, or a deuterated form thereof, L is arylene optionally substituted by 1-4 $R^7$. In embodiments, L is monocyclic arylene optionally substituted by 1-4 $R^7$.

In embodiments of compounds of Formula (I), (II), (III), (IX), (IX-A),(IX-B) or (X), or a pharmaceutically acceptable salt, a stereoisomer, or a deuterated form thereof, L is monocyclic arylene. In embodiments, L is

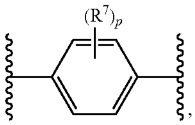

wherein p is 0, 1, 2, 3 or 4.

In embodiments of Formula (I), (II), (III), (IX), (IX-A), (IX-B), (X), (XII) or (XII-A), or a pharmaceutically acceptable salt, a stereoisomer, p is 0, 1, 2 or 3. In embodiments, p is 0. In embodiments, p is 1. In embodiments, p is 2. In embodiments, p is 3.

In embodiments of Formula (I), (II), (III), (IX), (IX-A), (IX-B), (X), (XII) or (XII-A), or a pharmaceutically acceptable salt, a stereoisomer, or a deuterated form thereof, each $R^7$ is independently selected from =O, halogen, $C_{1-6}$ alkyl, $OC_{1-6}$ alkyl, $C_{1-6}$ haloalkyl, S—$C_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, C(=)$OC_{1-6}$ alkyl, C(=O)$OC_{1-6}$ alkyl, C(=O)$N_{1-6}$ alkyl, C(=O)N($C_{1-6}$ alkyl$)_2$, or NHC(=O)$C_{1-6}$ alkyl.

In embodiments of Formula (I), (II), (III), (IX), (IX-A), (IX-B), (X), (XII) or (XII-A), or a pharmaceutically acceptable salt, a stereoisomer, or a deuterated form thereof, each $R^7$ is independently halogen, $C_{1-6}$ alkyl or $OC_{1-6}$ alkyl. $R^7$ is independently halogen. In embodiments, $R^7$ is F, Cl, Br or I. In embodiments, $R^7$ is $CH_3$, Cl, F or $OCH_3$. In embodiments, $R^7$ is F.

In embodiments of compounds of Formula (I), (II), (III), (IX), (IX-A),(IX-B) or (X), or a pharmaceutically acceptable salt, a stereoisomer, or a deuterated form thereof, L is

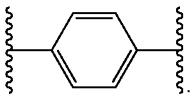 [SMILES: *c1ccc(*)cc1]

In embodiments of compounds of Formula (I), (II), (III), (IX), (IX-A),(IX-B) or (X), or a pharmaceutically acceptable salt, a stereoisomer, or a deuterated form thereof, L is

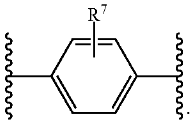

In embodiments, L is

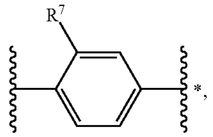

wherein the asterisk represents the point of attachment to $R^1$, and $R^1$ is

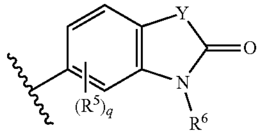

or

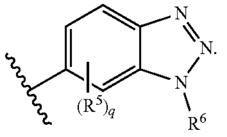

In embodiments of compounds of Formula (I), (II), (III), (IX), (IX-A),(IX-B) or (X), or a pharmaceutically acceptable salt, a stereoisomer, or a deuterated form thereof, L is

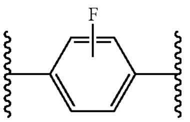

or

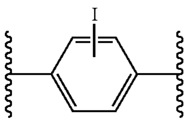

In embodiments of compounds of Formula (I), (II), (III), (IX), (IX-A),(IX-B) or (X), or a pharmaceutically acceptable salt, a stereoisomer, or a deuterated form thereof, L is

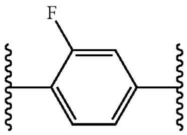

or

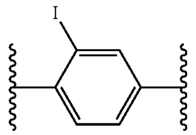

In embodiments of compounds of Formula (I), (II), (III), (IX), (IX-A),(IX-B) or (X), or a pharmaceutically acceptable salt, a stereoisomer, or a deuterated form thereof, L is

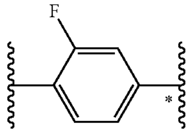 or 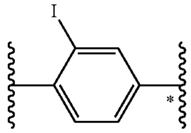, wherein the asterisk represents the point of attachment to $R^1$, and $R^1$ is

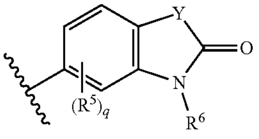 or 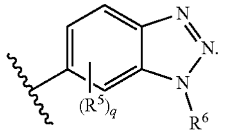

In a preferred embodiment of a compound of Formula (I), (II), (III), (IX), (IX-A),(IX-B) or (X), or a pharmaceutically acceptable salt, a stereoisomer, or a deuterated form thereof, L is

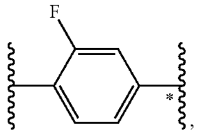 [SMILES: *c1ccc(*)c(F)c1], wherein the asterisk represents the point of attachment to $R^1$, and $R^1$ is

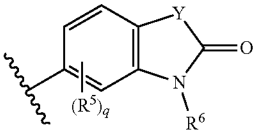 or 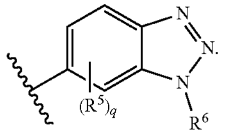

In an embodiment of a compound of Formula (IV), (V), (VI), (VII), (VIII), (IX-C), (IX-D), (X-A), (X-B), (X-C), (X-D), or a pharmaceutically acceptable salt, a stereoisomer, or a deuterated form thereof,

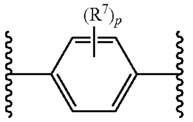 is 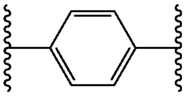.

In embodiments of a compound of Formula (IV), (V), (VI), (VII), (VIII), (IX-C), (IX-D), (X-A), (X-B), (X-C), (X-D), or a pharmaceutically acceptable salt, a stereoisomer, or a deuterated form thereof,

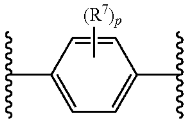 is 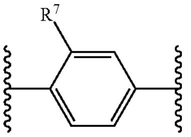.

In embodiments,

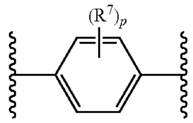 is 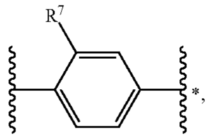, wherein the asterisk represents the point of attachment to $R^1$, and $R^1$ is

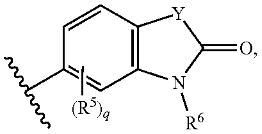 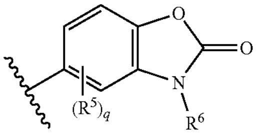

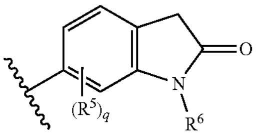 or 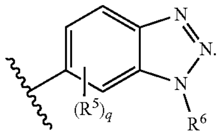

In embodiments, $R^7$ is halogen. In embodiments, $R^7$ is I or F.

In a preferred embodiment of a compound of Formula (IV), (V), (VI), (VII), (VIII), (IX-C), (IX-D), (X-A), (X-B), (X-C), (X-D), or a pharmaceutically acceptable salt, a stereoisomer, or a deuterated form thereof,

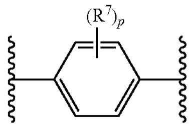 is 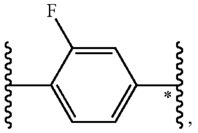, wherein the asterisk represents the point of attachment to $R^1$, and $R^1$ is

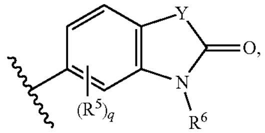 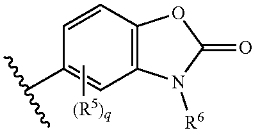

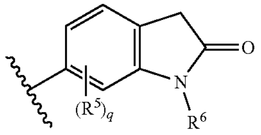 or 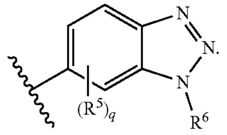

In embodiments of compounds of Formula (I), (II), (III), (IX), (X), (XII) or (XII-A), or a pharmaceutically acceptable salt, a stereoisomer, or a deuterated form thereof, L is heteroarylene optionally substituted by 1-4 $R^7$. In embodiments, L is a monocyclic heteroarylene. In embodiments, the monocyclic heteroarylene is a 5-membered, 6-membered, 7-membered, 8 membered, or 9-membered heteroarylene optionally substituted with 1-4 $R^7$, or 2-3 $R^7$. In a further embodiment, the monocyclic heteroarylene is a 5-membered heteroarylene optionally substituted with 1-3 $R^7$. In embodiments, the monocyclic heteroarylene contains 1-3 heteroatoms selected from N, S, or O. In a further embodiment, the monocyclic heteroarylene contains 1 or 2 heteroatoms selected from N, S, or O. In embodiments, the monocyclic heteroarylene is

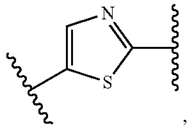 [SMILES: *c1cnc(*)s1]

, which is optionally substituted with 1 $R^7$. In embodiments, the monocyclic heteroarylene is not substituted.

In embodiments, L is

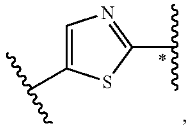 [SMILES: *c1cnc(*)s1]

, wherein the asterisk represents the point of attachment to $R^1$, and $R^1$ is

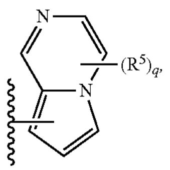

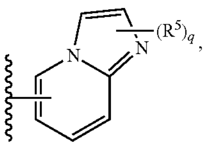

,

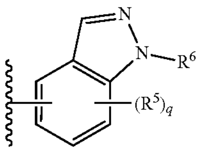

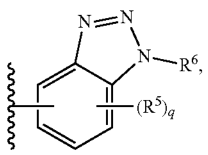

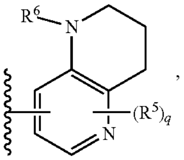

,

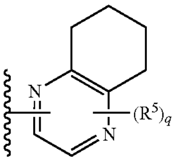

or

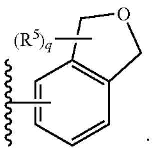

.

In embodiments, L is

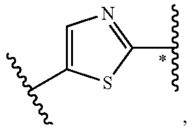 [SMILES: *c1cnc(*)s1]

, wherein the asterisk represents the point of attachment to $R^1$, and $R^1$ is

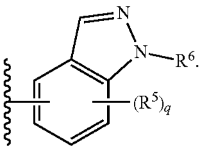

In embodiments, L is

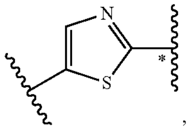 [SMILES: *c1cnc(*)s1]

, wherein the asterisk represents the point of attachment to $R^1$, and $R^1$ is

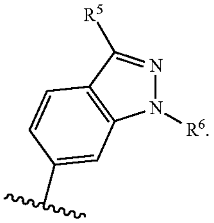

In embodiments, L is

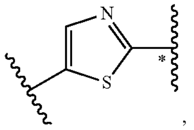 [SMILES: *c1cnc(*)s1]

, wherein the asterisk represents the point of attachment to $R^1$, and $R^1$ is

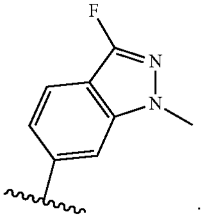 [SMILES: *c1ccc2c(F)nn(C)c2c1]

.

In embodiments of the compounds of (I), (II), (III), (IX), (IX-A),(IX-B), (X), (XII) or (XII-A), or a pharmaceutically acceptable salt, a stereoisomer, or a deuterated form thereof, L is polycyclic heteroarylene optionally substituted with by 1-4 $R^7$. In embodiments, L is a polycyclic heteroarylene comprising 8-12 ring atoms optionally substituted with 1-4 $R^7$. In embodiments, L is 8-12 membered bicyclic heteroarylene optionally substituted with 1-4 $R^7$. In embodiments, L is 8-10 membered bicyclic heteroarylene optionally substituted with 1-4 $R^7$. In embodiments, L is 8-membered bicyclic heteroarylene optionally substituted with 1-4 $R^7$. In embodiments, L is 9-membered bicyclic heteroarylene. In embodiments, L is 10-membered bicyclic heteroarylene optionally substituted with 1-4 $R^7$.

In embodiments of the compounds of Formula (I), (II), (III), (IX), (IX-A),(IX-B), (X), (XII), or a pharmaceutically acceptable salt, a stereoisomer, or a deuterated form thereof, L is 8-10 membered fused bicyclic heteroarylene comprising 1-3 heteroatoms selected from O, S or N. In embodiments, L is 9-membered fused bicyclic heteroarylene comprising 1-3 heteroatoms selected from O, S or N. In embodiments, L is 8-membered fused bicyclic heteroarylene comprising 1-3 heteroatoms selected from O, S or N. In embodiments, L is a 5,5-, 5,6-, 6,5-, or 6,6-fused bicyclic heteroarylene comprising 1-3 heteroatoms selected from O, S or N. In embodiments, L is a 5,5, -fused bicyclic heteroarylene comprising 1-3 heteroatoms selected from O, S or N. In embodiments, L is 5,6- or 6,5-, fused bicyclic heteroarylene comprising 1-3 heteroatoms selected from O, S or N.

In embodiments of the compounds of Formula (I), (II), (III), (IX), (IX-A),(IX-B), (X), (XII), or a pharmaceutically acceptable salt, a stereoisomer, or a deuterated form thereof, L is a 5,5, -fused bicyclic heteroarylene comprising 1-3 heteroatoms selected from O, S or N. In embodiments,

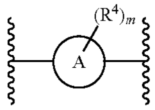 is 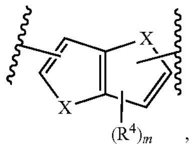 , wherein each X is independently selected from O, S, NH or N($C_{1-6}$ alkyl). In embodiments, X is O or S. In embodiments,

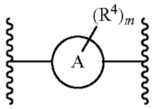 is 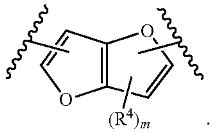 .

In embodiments, L is

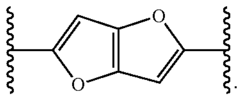 [SMILES: *c1cc2oc(*)cc2o1]

In embodiments of the compounds of Formula (I), (II), (III), (IX), (IX-A),(IX-B), (X), (XII), or a pharmaceutically acceptable salt, a stereoisomer, or a deuterated form thereof, L is a 5,6- or 6,5-,fused bicyclic heteroarylene comprising 1-3 heteroatoms selected from O, S or N. In embodiments, L is

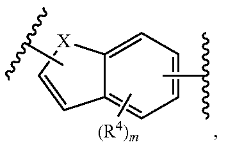 , wherein X is selected from O, S, NH or N($C_{1-6}$ alkyl).

In embodiments, X is O or S. In embodiments, L is

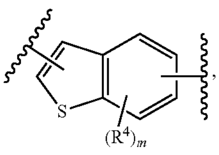 , 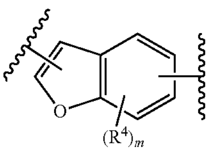 or

-continued

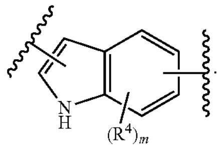

In embodiments, L is

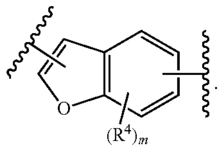

In embodiments, L is

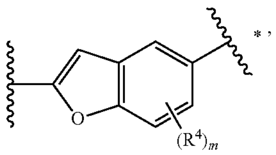

wherein the asterisk (*) represents the point of attachment to $R^1$.

In embodiments of the compounds of Formula (I), (II), (III), (IX), (IX-A),(IX-B), (X), (XII), or a pharmaceutically acceptable salt, a stereoisomer, or a deuterated form thereof, L is

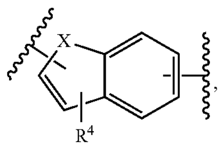

wherein X is selected from O, S, NH or N($C_{1-6}$ alkyl), wherein $R^4$ is attached to any ring atoms of ring A. In embodiments, X is O or S. In embodiments X is O. In embodiments, L is

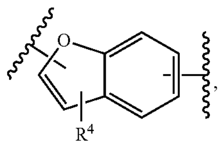

wherein $R^4$ is attached to any ring atoms of ring A. In embodiments, $R^4$ is $C_{1-6}$ alkyl or halogen. In embodiments, $R^4$ is halogen. In embodiments, $R^4$ is F, Cl or Br. In embodiments, $R^4$ is F. In embodiments, L is

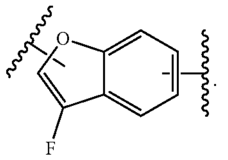

In embodiments, L is

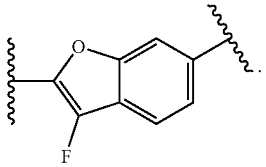 [SMILES: *c1ccc2c(F)c(*)oc2c1]

In embodiments, L is

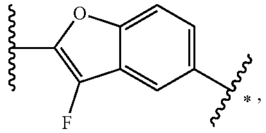 [SMILES: *c1ccc2oc(*)c(F)c2c1]

wherein the asterisk (*) represents the point of attachment to $R^1$, and $R^1$ is

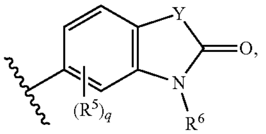

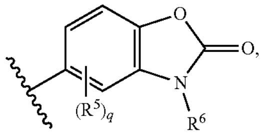

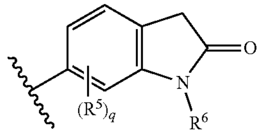

or

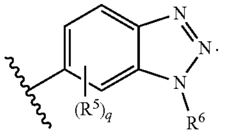

$R^1$, $R^8$, $R^9$

In embodiments of compounds of Formula (I), (II), (III), (IV), (VI), (IX), (X), (XII), (XII-A)(XII-A), or a pharmaceutically acceptable salt, a stereoisomer, or a deuterated form thereof, $R^1$ is 6-18 membered aryl optionally substituted with 1-3 groups independently selected from $R^5$ or $R^6$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is a monocyclic aryl optionally substituted with 1-3 groups independently selected from $R^5$ or $R^6$. In embodiments, $R^1$ is

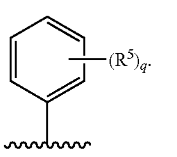

In embodiments, $R^1$ is

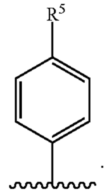

In embodiments, p is 0, 1, 2 or 3, In embodiments, p is 0. In embodiments, p is 1. In embodiments, p is 2. In embodiments, $R^5$ is halogen, $C_{1-6}$ alkyl, $OC_{1-6}$ alkyl, $C_{3-6}$ cycloalkyl, CN, OH, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocyclyl or heterocyclyl. In embodiments, $R^5$ is halogen, $C_{1-6}$ alkyl, $OC_{1-6}$ alkyl, CN, $C_{1-6}$ alkylene-heterocyclyl or $S(=O)_2$-heterocyclyl. In embodiments, $R^5$ is CN,

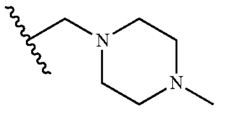

or

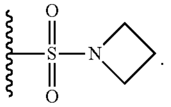

In embodiments of compounds of Formula (I), (II), (III), (IV), (VI) or a pharmaceutically acceptable salt, a stereoisomer, or a deuterated form thereof, $R^1$ is

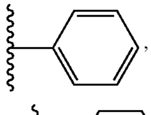

,

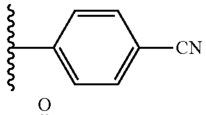

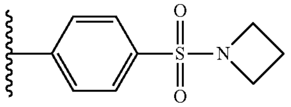

or

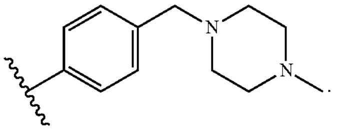

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is 5-20 membered heteroaryl containing 1-3 heteroatoms selected from N, S or O, wherein the heteroaryl is optionally substituted with 1-5 groups independently selected from $R^5$ or $R^6$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is selected from:

- 5-12 membered monocyclic heteroaryl containing 1-3 heteroatoms selected from N, S or O, wherein the monocyclic heteroaryl is optionally substituted with 1-3 groups independently selected from $R^5$ or $R^6$,
- 7-14 membered bicyclic heteroaryl containing 1-3 heteroatoms selected from N, S or O, wherein the bicyclic heteroaryl is optionally substituted with 1-4 groups independently selected from $R^5$ or $R^6$, or
- 7-20 membered tricyclic heteroaryl containing 1-3 heteroatoms selected from N, S or O, wherein the tricyclic heteroaryl is optionally substituted with 1-5 groups independently selected from $R^5$ or $R^6$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is 7-14 membered bicyclic heteroaryl containing 1-3 heteroatoms selected from N, S or O, wherein the heteroaryl is optionally substituted with 1-4 groups independently selected from $R^5$ or $R^6$. In embodiments, $R^1$ is 8-12 membered bicyclic heteroaryl containing 1-3 heteroatoms selected from N, S or O, wherein the heteroaryl is optionally substituted with 1-4 groups independently selected from $R^5$ or $R^6$. In embodiments, $R^1$ is 8-10 membered bicyclic heteroaryl containing 1-3 heteroatoms selected from N, S or O, wherein the heteroaryl is optionally substituted with 1-4 groups independently selected from $R^5$ or $R^6$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is a fused bicyclic 8-10 membered heteroaryl containing 1-4 heteroatoms selected from N, S or O, wherein the heteroaryl is optionally substituted with 1-5 groups independently selected from $R^5$ or $R^6$. In embodiments, $R^1$ is a fused bicyclic 9-10 membered heteroaryl containing 1-4 heteroatoms selected from N, S or O, wherein the heteroaryl is optionally substituted with 1-5 groups independently selected from $R^5$ or $R^6$. In embodiments, $R^1$ is a fused bicyclic 9-membered heteroaryl containing 1-4 heteroatoms selected from N, S or O, wherein the heteroaryl is optionally substituted with 1-5 groups independently selected from $R^5$ or $R^6$. In embodiments, $R^1$ is a fused bicyclic 10-membered heteroaryl containing 1-4 heteroatoms selected from N, S or O, wherein the heteroaryl is optionally substituted with 1-5 groups independently selected from $R^5$ or $R^6$.

In embodiments, $R^1$ is a 5,5-, 5,6-, 6,5-, or 6,6-fused bicyclic heteroaryl, optionally substituted with 1, 2, 3, or 4 groups selected from $R^5$ or $R^6$. In embodiments, $R^1$ is a 5,5-, 5,6-6,5-, or 6,6-fused bicyclic heteroaryl, comprising one aromatic ring, wherein $R^1$ is optionally substituted with 1, 2, 3, or 4 groups selected from $R^5$ or $R^6$. In embodiments, $R^1$ is a 5,5-, 5,6-, 6,5-, or 6,6-fused bicyclic heteroaryl, comprising two aromatic rings, wherein $R^1$ is optionally substituted with 1, 2, 3, or 4 groups selected from $R^5$ or $R^6$.

In embodiments, $R^1$ is a 5,6-fused bicyclic heteroaryl, comprising two aromatic rings, wherein $R^1$ is optionally substituted with 1, 2, 3, or 4 groups selected from $R^5$ or $R^6$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$

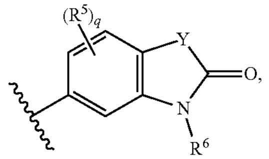

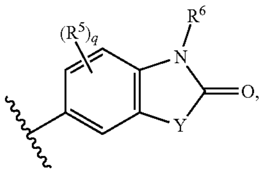

or

-continued

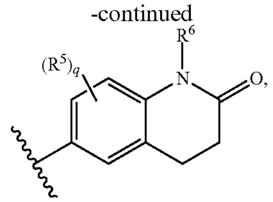

wherein q is 0, 1, 2 or 3.

each Y is independently $NR^6$, O, $CR^8R^9$, S, S(O) or $S(O)_2$, each $R^5$ is independently selected from halogen, $C_{1-6}$ alkyl, $OC_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, NHC$(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly or heterocyclyl; wherein the alkyl, alkenyl, alkynyl, cycloalkyl and heterocyclyl groups within $R^5$ are optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl$)(C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

$R^8$ and $R^9$ are each independently selected from H, halogen, $C_{1-6}$ alkyl, $OC_{1-6}$ alkyl, $C_{1-6}$ haloalkyl or $C_{3-6}$ cycloalkyl;

alternatively, $R^8$ and $R^9$ form =O.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

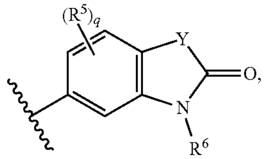

q is 0, 1, 2 or 3.

each Y is independently $NR^6$, O, $CR^8R^9$, S, S(O) or $S(O)_2$, each $R^5$ is independently selected from halogen, $C_{1-6}$ alkyl, $OC_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, NHC$(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly or heterocyclyl; wherein the alkyl, alkenyl, alkynyl, cycloalkyl and heterocyclyl groups within $R^5$ are optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, C(═O)$C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH; and $R^8$ and $R^9$ are each independently selected from H, halogen, $C_{1-6}$ alkyl, $OC_{1-6}$ alkyl, $C_{1-6}$ haloalkyl or $C_{3-6}$ cycloalkyl;

alternatively, $R^8$ and $R^9$ form ═O.

In embodiments, $R^8$ and $R^9$ are each independently selected from H, halogen or $C_{1-6}$ alkyl. In embodiments, $R^8$ and $R^9$ are each H.

In embodiments, Y is O, S, $NR^6$ or $CR^8R^9$. In embodiments, Y is NH, O, S, $CH_2$, CHF, or $CF_2$. In embodiments, Y is O or $CH_2$. In embodiments, Y is O. In embodiments, Y is $CH_2$.

In embodiments, q is 0 or 1. In embodiments, q is 0. In embodiments, q is 1.

In embodiments, $R^5$ is $C_{1-6}$ alkyl, halogen, $C_{1-6}$ haloalkyl, CN, or heterocyclyl. In embodiments, $R^5$ is $CH_3$, F or CN.

In embodiments, $R^6$ is H, $C_{1-6}$ alkyl, $C_{1-6}$ alkylene-$NH_2$, $C_{1-6}$ alkylene-O—$C_{1-6}$ alkyl, $C_1$-6 alkylene-NH($C_{1-6}$ alkyl), $C_{1-6}$ alkylene-N($C_{1-6}$ alkyl)$_2$, $C_{1-6}$ alkylene-NH($C_{1-6}$ alkylene-O—$C_1$-6 alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl or heterocyclyl. In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl)$_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl.

In embodiments, $R^6$ is $C_{1-6}$ alkyl. In embodiments, $R^6$ is $CH_3$, $CH_2CH_3$,

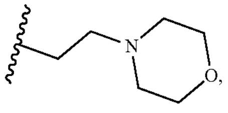
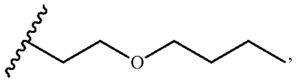
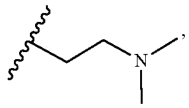
or
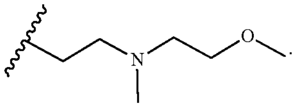

In embodiments, $R^6$ is $CH_3$ or $CH_2CH_3$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

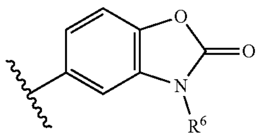
or
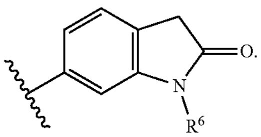

In embodiments, $R^6$ is H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl or heterocyclyl. In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl)$_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

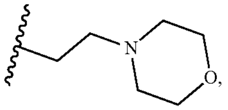
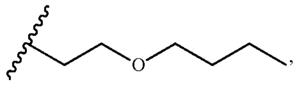
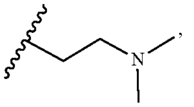
or
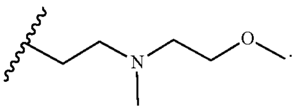

In embodiments, $R^6$ is $CH_3$ or $CH_2CH_3$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

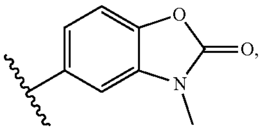
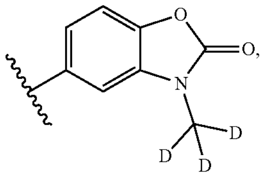
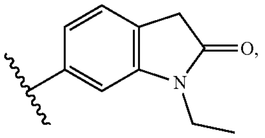
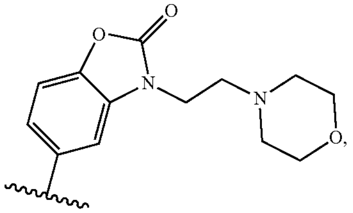
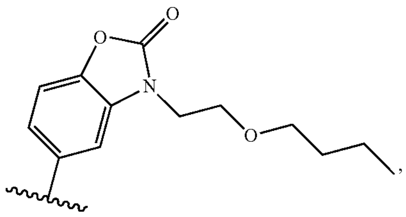
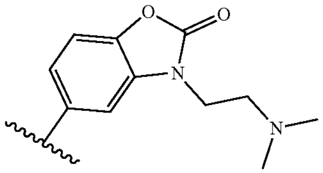
or

-continued

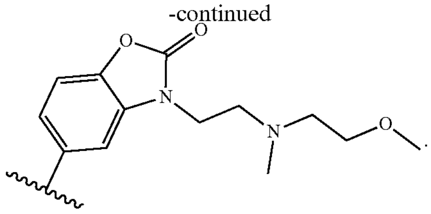

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

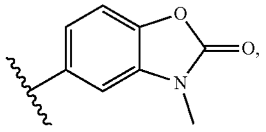 [SMILES: *c1ccc2oc(=O)n(C)c2c1]

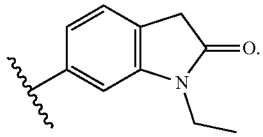 [SMILES: *c1ccc2c(c1)N(CC)C(=O)C2]

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

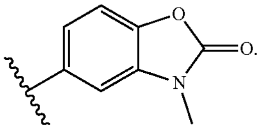

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

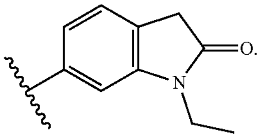

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

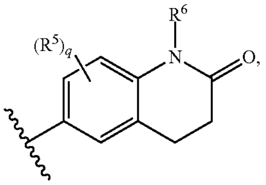

wherein q is 0, 1, 2 or 3.

each $R^5$ is independently selected from halogen, $C_{1-6}$ alkyl, $OC_{1-6}$ alkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly or heterocyclyl; wherein the alkyl, alkenyl, alkynyl, cycloalkyl and heterocyclyl groups within $R^5$ are optionally substituted with 1-3 groups selected from halogen, CN, OH, $NH_2$, $C_{1-6}$ alkyl, $OC_{1-6}$ alkyl, COOH, cycloalkyl or heterocyclyl; and each $R^6$ is independently selected from H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl)$_2$, $C_{1-6}$ alkylene-N($C_{1-6}$ alkyl)$_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl, $C(=O)C_{1-6}$ alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH.

In embodiments, q is not 0, and $R^5$ is $C_{1-6}$ alkyl, halogen, $C_{1-6}$ haloalkyl, CN, or heterocyclyl.

In embodiments, q is 0.

In embodiments, $R^6$ is H, $C_{1-6}$ alkyl, $C_{1-6}$ alkylene-$NH_2$, $C_{1-6}$ alkylene-O—$C_{1-6}$ alkyl, $C_1$-6 alkylene-NH($C_{1-6}$ alkyl), $C_{1-6}$ alkylene-N($C_{1-6}$ alkyl)$_2$, $C_{1-6}$ alkylene-NH($C_{1-6}$ alkylene-O—$C_1$-6 alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl or heterocyclyl. In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl)$_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, or $CH_2CH_3$. In embodiments, $R^6$ is $CH_3$.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

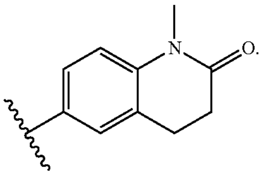 [SMILES: *c1ccc2c(c1)CCC(=O)N2C]

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

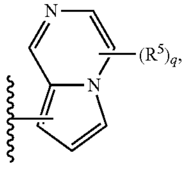

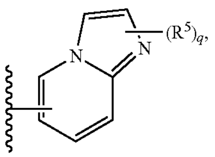

-continued

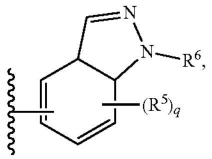
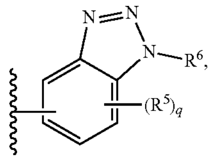
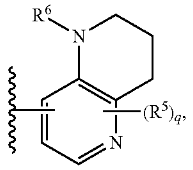
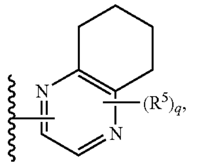
or
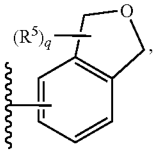

wherein q is 0, 1, 2, or 3, each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl; and each $R^6$ is independently selected from H, $C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_1$-6 alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH.

In embodiments of compounds of Formula (I), (II), (III), (IV), (VI), (IX), (X), (XII) or (XII-A), $R^1$

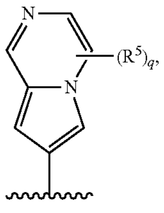
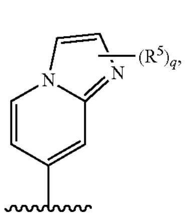
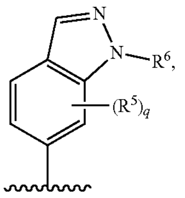
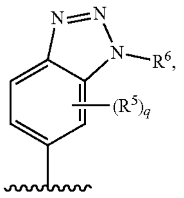

-continued

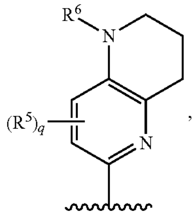
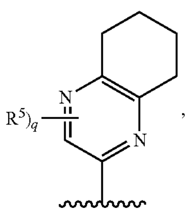
or
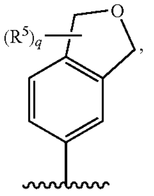

wherein q is 0, 1, 2, or 3, each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl; and each $R^6$ is independently selected from H, $C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_1$-6 alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH.

In embodiments of compounds of Formula (I), (II), (III), (IV), (VI), (IX), (X), (XII) or (XII-A), $R^1$ is

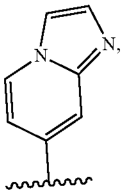
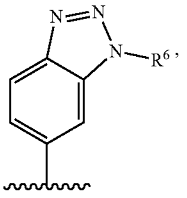
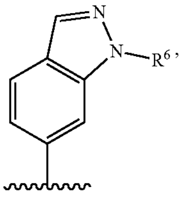
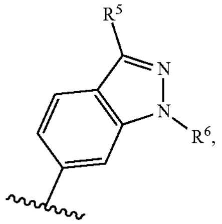
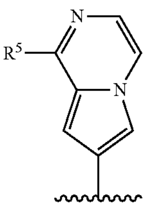
,
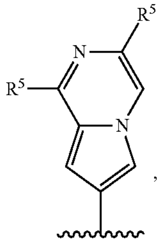
,

-continued

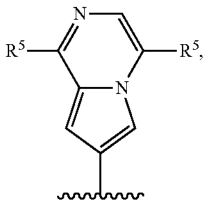
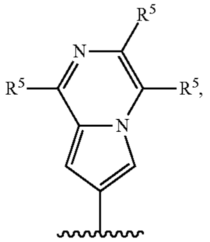

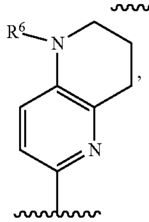
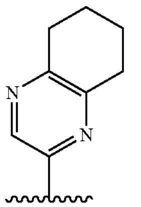

or

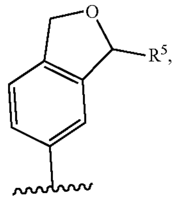

wherein each $R^5$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2-C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl; and each $R^6$ is independently selected from H, $C_{1-6}$ alkyl, $C_{1-6}$ alkylene-$NH_2$, $C_{1-6}$ alkylene-$NH(C_{1-6}$ alkyl$)_2$, $C_{1-6}$ alkylene-$N(C_{1-6}$ alkyl$)_2$, $C_{1-6}$ alkylene-$NH(C_{1-6}$ alkylene-O—$C_{1-6}$ alkyl), $C_{1-6}$ alkylene-$N(C_{1-6}$ alkylene-O—$C_{1-6}$ alkyl)($C_{1-6}$ alkyl), $C_{1-6}$ alkylene-heterocyclyl, $C(=O)C_1$-6 alkyl, $C_{2-6}$ alkenyl, $C_{2-6}$ alkynyl, $C_{3-6}$ cycloalkyl, heterocyclylene-heterocyclyl or heterocyclyl; wherein the $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH.

In embodiments, q is 0. In embodiments, q is 1. In embodiments q is 2. In embodiments, q is 3.

In embodiments, $R^5$ is halogen, $C_{1-6}$ alkyl, $OC_{1-6}$ alkyl, $C_{1-6}$ haloalkyl, CN, $C_{1-6}$ alkylene-heterocyclyl, heterocyclylene-heterocyclyl or heterocyclyl. In embodiments, $R^5$ is halogen, $C_{1-6}$ alkyl heterocyclylene-heterocyclyl. $R^5$ is $CH_3$, F or

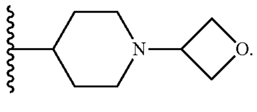

In embodiments, $R^6$ is H, $C_{1-6}$ alkyl, heterocyclyl or heterocyclylene-heterocyclyl, alkylene-heterocyclyl, $C(=O)C_{1-6}$ alkyl or $C_{3-6}$ cycloalkyl. In embodiments, $R^6$ is H, $C_{1-6}$ alkyl, heterocyclyl or heterocyclylene-heterocyclyl. In embodiments, $R^6$ is H, $CH_3$,

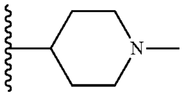

or

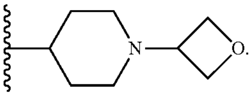 [SMILES: *C1CCN(C2COC2)CC1]

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

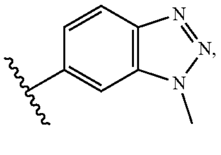
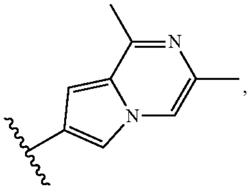
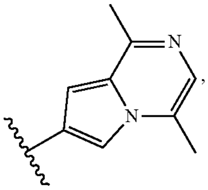
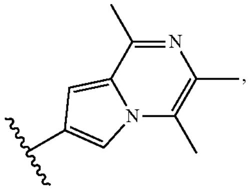
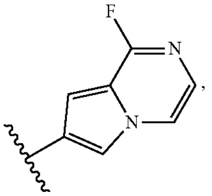
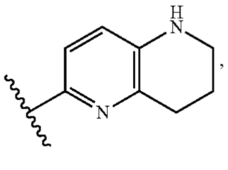
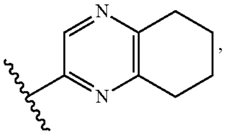
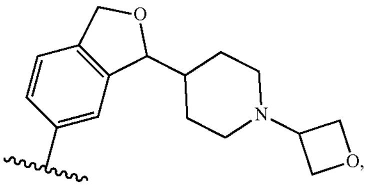
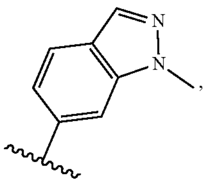
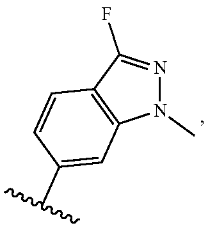

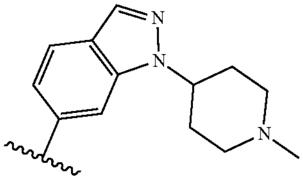

or

-continued

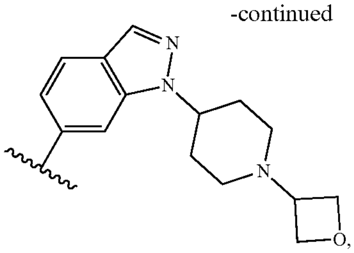

,

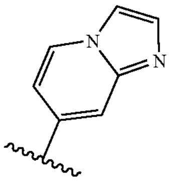

.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

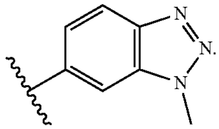 [SMILES: *c1ccc2nnn(C)c2c1]

.

In embodiments of compounds of Formula (I), (II), (III), (IV), (VI), (IX), (X), (XII) or a pharmaceutically acceptable salt, a stereoisomer, or a deuterated form thereof, $R^1$ is 7-20 membered tricyclic heteroaryl containing heteroatoms selected from N, S or O, wherein the tricyclic heteroaryl is optionally substituted with 1-5 $R^5$ or $R^6$ groups. In embodiments, $R^1$ is 7-20 membered spiro tricyclic heteroaryl containing heteroatoms selected from N, S or O, wherein the tricyclic heteroaryl is optionally substituted with 1-5 $R^5$ or $R^6$ groups.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

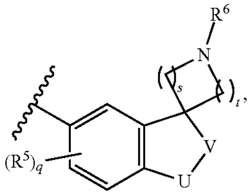

, wherein q is 0, 1, 2 or 3;

r and s are each independently 0, 1, 2, or 3; provided that s and t are not 0 at the same time, U and V are each independently $CR^8R^9$,O or $NR^6$.

$R^5$ is independently selected from halogen, $C_{1-6}$ alkyl, $OC_{1-6}$ alkyl, $C_{3-6}$ cycloalkyl, CN, OH, $C_{1-6}$ alkylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{3-6}$ cycloalkyl, $C_{1-6}$ alkylene-heterocyclyl, heterocyclylene-heterocyclyl or heterocyclyl; wherein $R^6$ is optionally substituted with 1-3 groups optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

$R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl;

or $R^8$ and $R^9$ form =O.

In embodiments, $R^1$

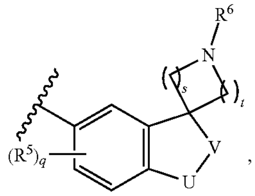

,

In embodiments, U and V are each independently $CH_2$, C(=O), 0 or $NR^6$. In embodiments, U and V are each independently $CH_2$, C(=O), O or $NCH_3$. In embodiments, U is $CH_2$, C(=O) or $NCH_3$, and V is C(=O) or O. In embodiment, U is $NCH_3$ and V is C(=O). In embodiments, U is C(=O) and V is O. In embodiments, U is $CH_2$ and V is O. In embodiments, s and t are each independently 1, 2 or 3. In embodiments, r is 1, 2 or 3, and s is 1 or 2. In embodiments, r is 1 and s is 1. In embodiments, r is 2, and t is 2. In embodiments, r is 3 and t is 1. In embodiments, q is 0 or 1. In embodiments, q is 0. In embodiments, $R^5$ is halogen, $C_{1-6}$ alkyl, $OC_{1-6}$ alkyl or heterocyclyl, In embodiments, $R^6$ is H, $C_{1-6}$ alkyl or heterocyclyl. In embodiments, $R^6$ is H, $C_{1-6}$ alkyl or 3-6 membered-heterocyclyl. In embodiments, $R^6$ is H, $CH_3$ or oxetanyl. In embodiments, $R^6$ is H, $CH_3$ or

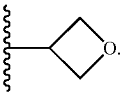

.

n embodiments, $R^6$ is $CH_3$ or

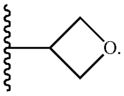 [SMILES: *C1COC1]

.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

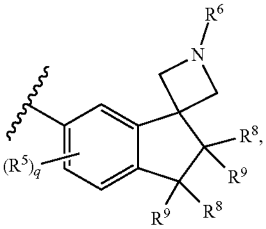

,

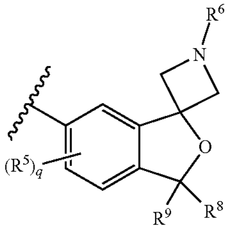

,

-continued

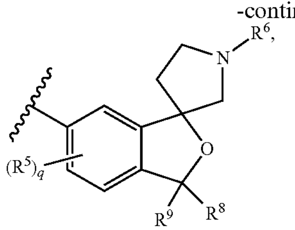 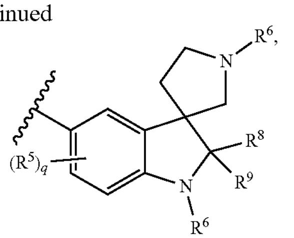

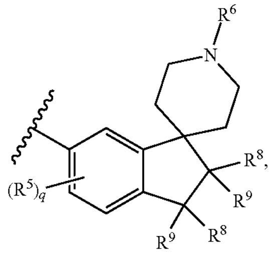 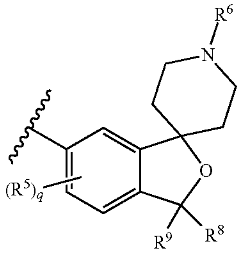 ,

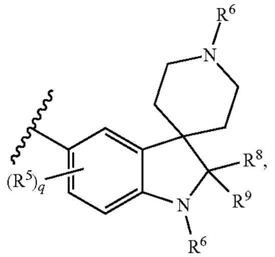 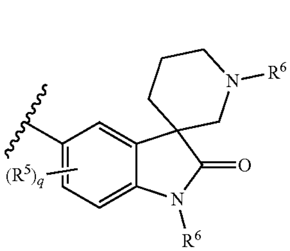 ,

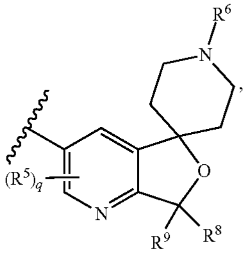 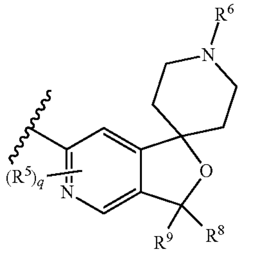 or

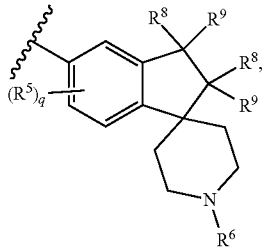

wherein

- $R^5$ is independently selected from halogen, $C_{1-6}$ alkyl, $OC_{1-6}$ alkyl, $C_{3-6}$ cycloalkyl, CN, OH, $C_{1-6}$ alkylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;
- each $R^6$ is independently selected from H, $C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{3-6}$ cycloalkyl, $C_{1-6}$ alkylene-heterocyclyl, heterocyclylene-heterocyclyl or heterocyclyl; wherein $R^6$ is optionally substituted with 1-3 groups optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;
- $R^8$ and $R^9$ are each independently selected from H, halogen, $C_{1-6}$ alkyl, $OC_{1-6}$ alkyl, $C_{1-6}$ haloalkyl, $C_{3-6}$ cycloalkyl or heterocyclyl;
- or $R^8$ and $R^9$ form =O.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

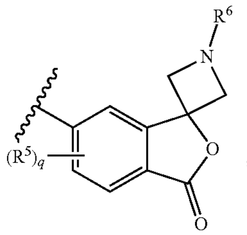 , 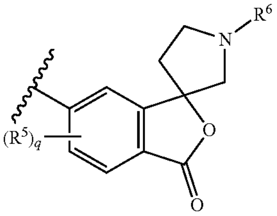 ,

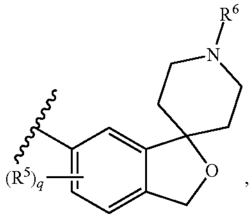 , 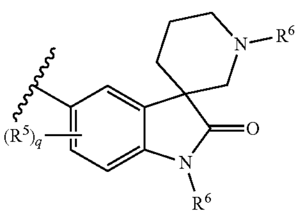 or

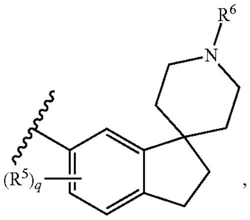 , wherein

- q is 0, 12 or 3;
- $R^5$ is independently selected from halogen, $C_{1-6}$ alkyl, $OC_{1-6}$ alkyl, $C_{3-6}$ cycloalkyl, CN, OH, $C_{1-6}$ alkylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;
- each $R^6$ is independently selected from H, $C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{3-6}$ cycloalkyl, $C_{1-6}$ alkylene-heterocyclyl, heterocyclylene-heterocyclyl or heterocyclyl; wherein $R^6$ is optionally substituted with 1-3 groups optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH.

In embodiments, q is 0 or 1. In embodiments, q is 0. In embodiments, q is 1.

In embodiments, $R^5$ is halogen, $C_{1-6}$ alkyl, CN, $OC_{1-6}$ alkyl or heterocyclyl. In embodiments, $R^5$ is F, $CH_3$ or CN. In embodiments, $R^6$ is H, $C_{1-6}$ alkyl or heterocyclyl. In embodiments, $R^6$ is H, $C_{1-6}$ alkyl or 3-6 membered-heterocyclyl. In embodiments, $R^6$ is H, $CH_3$ or oxetanyl. In embodiments, $R^6$ is H, $CH_3$ or

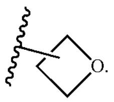

In embodiments, $R^6$ is $CH_3$ or

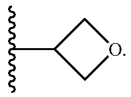

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

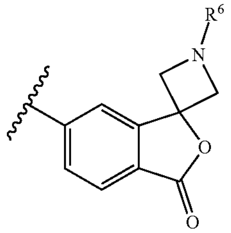,
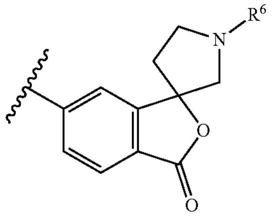,
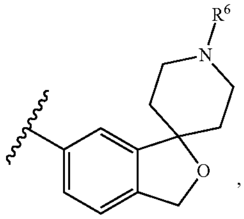,
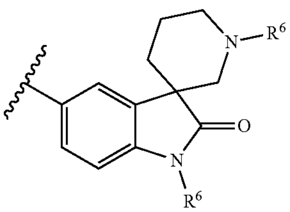 or
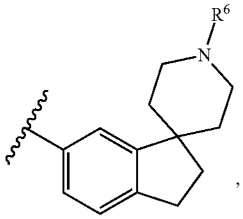,

In embodiments, is $R^6$ is H, $C_{1-6}$ alkyl, $C_{3-6}$ cycloalkyl, heterocyclyl or $C_{1-6}$ alkylene-heterocyclyl. In embodiments, $R^6$ is H, $CH_3$ or

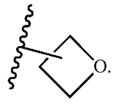

In embodiments, $R^6$ is H, $CH_3$ or

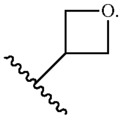

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

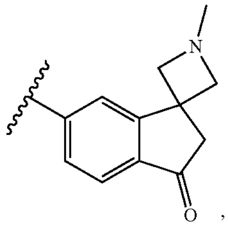,
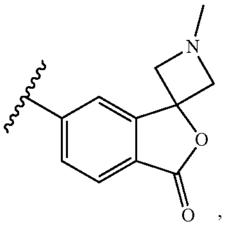,
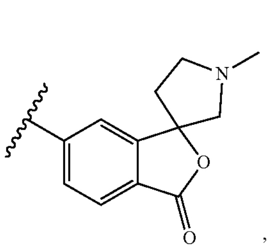,
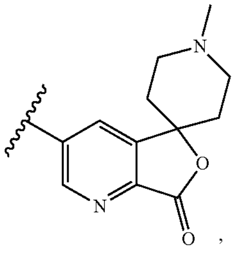,
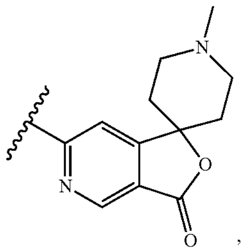,
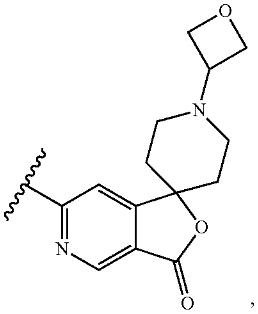,
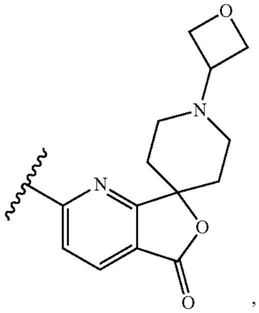,
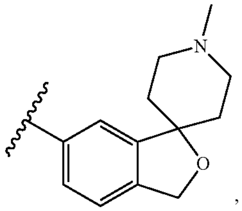,
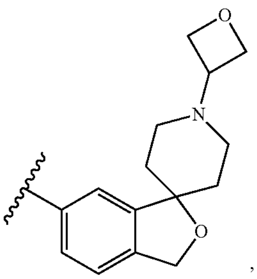,
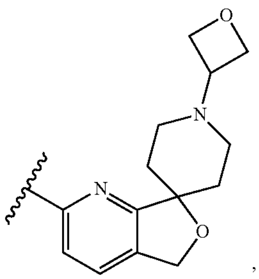,
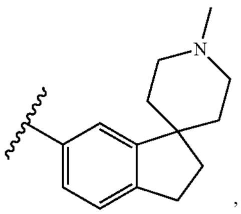,
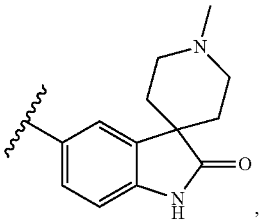, -continued

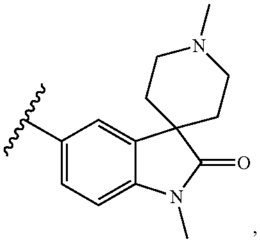

,

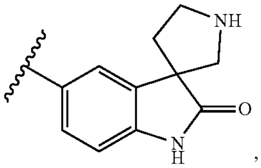

,

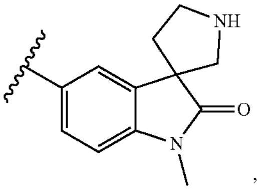

,

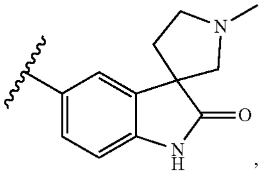

,

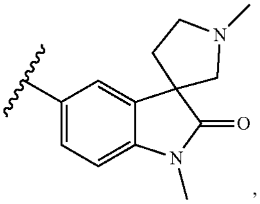

,

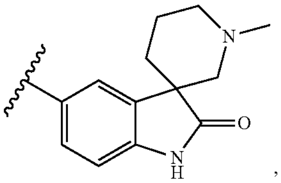

,

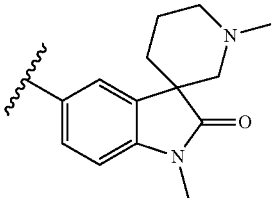

or

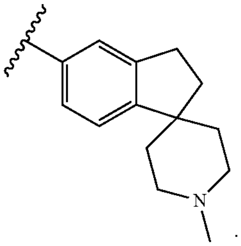

.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

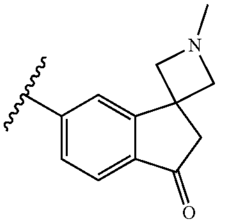

,

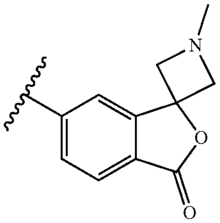

,

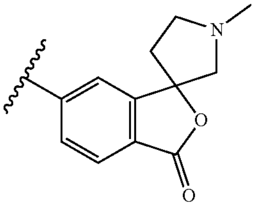

,

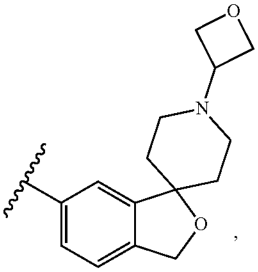

,

-continued

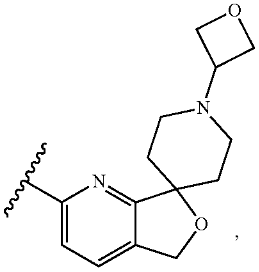

,

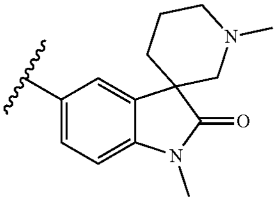

or

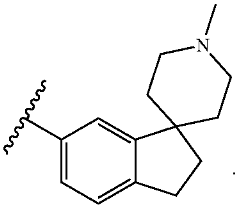

.

In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

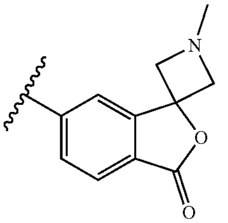

,

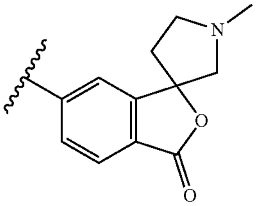

,

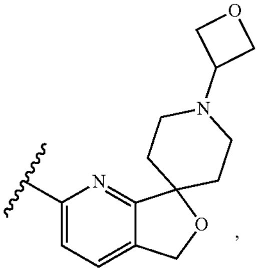

,

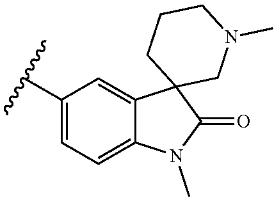

or

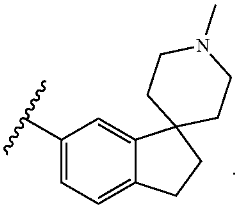 [SMILES: *c1ccc2c(c1)C1(CC2)CCN(C)CC1]

.

embodiments of compounds of Formula (I), (II), (III), (IV), (VI), (IX), (X), (XII) or (XII-A), or a pharmaceutically acceptable salt, a stereoisomer, or a deuterated form thereof, $R^1$ is

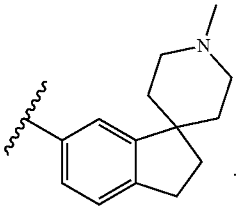
In embodiments of compounds of Formula (I), (II), (III), (IV), (VI), (IX), (X), (XII) or (XII-A), or a pharmaceutically acceptable salt, a stereoisomer, or a deuterated form thereof, $R^1$ is
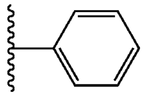
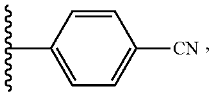
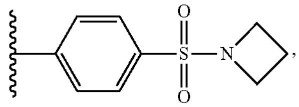
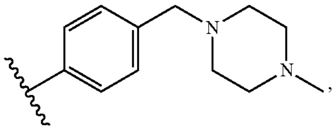
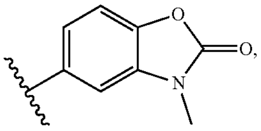
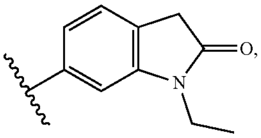
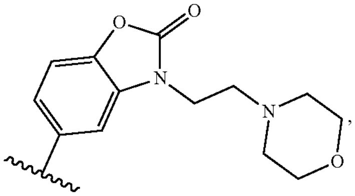
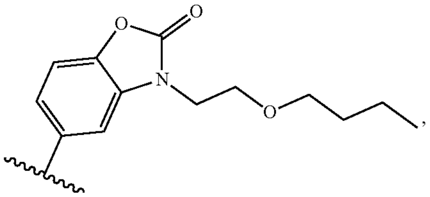
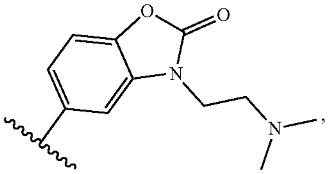
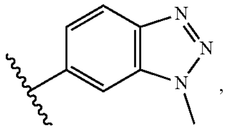
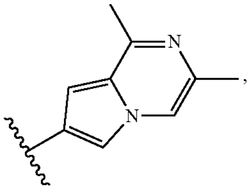
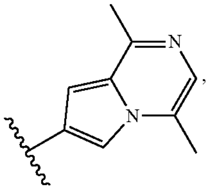
-continued
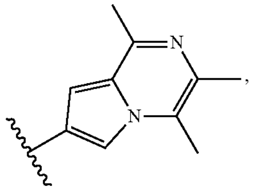
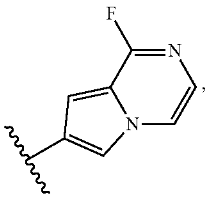
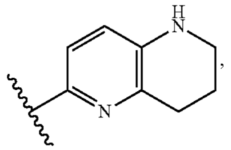
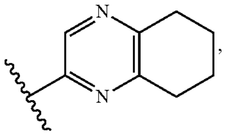
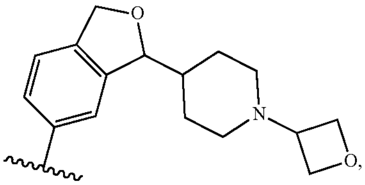
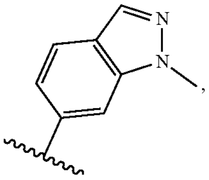
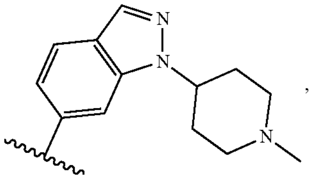
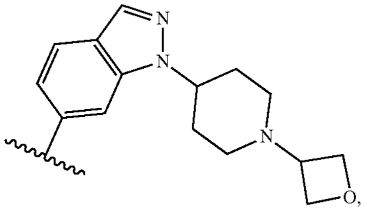
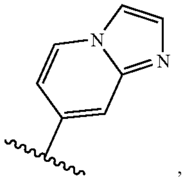
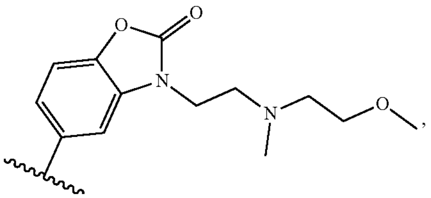
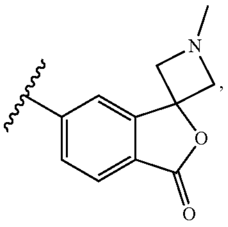
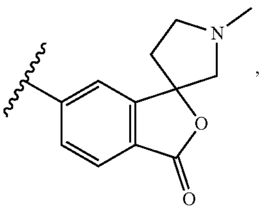
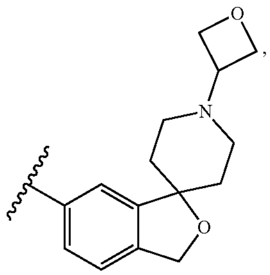

-continued

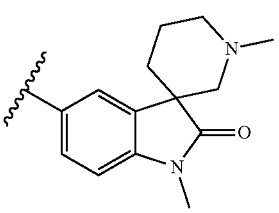

or

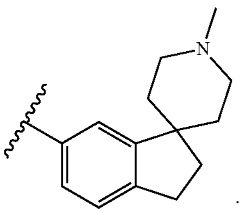

.

In embodiments of the compounds of Formula (I), (II), (III), (IX) or (X) or a pharmaceutically acceptable salt, a stereoisomer or a deuterated form thereof, -L-$R^1$ is

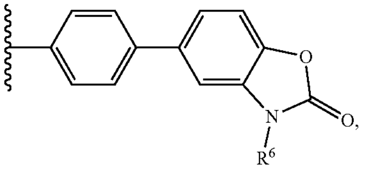

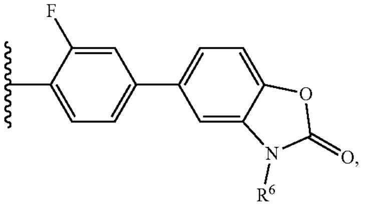

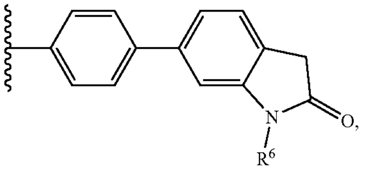

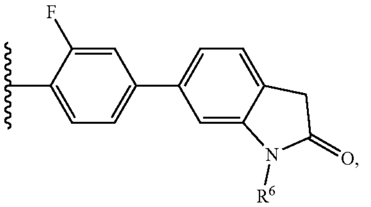

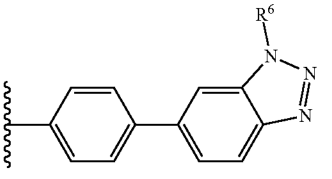

or

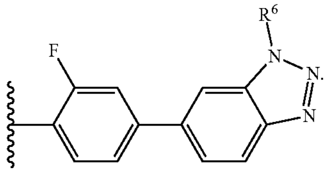

In embodiments, In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl)$_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

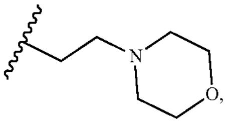

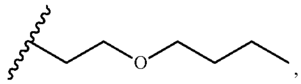

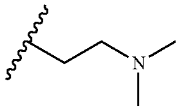

or

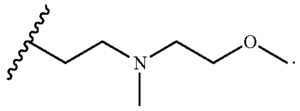

In embodiments, $R^6$ is $CH_3$ or $CH_2CH_3$. In embodiments, $R^6$ is $CH_3$. In embodiments, $R^6$ is $CH_2CH_3$.

In embodiments of the compounds of Formula (I), (II), (III), (IX) or (X) or a pharmaceutically acceptable salt, a stereoisomer or a deuterated form thereof, -L-$R^1$ is

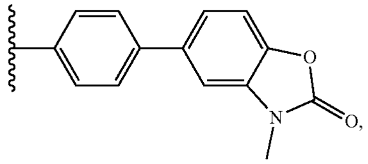

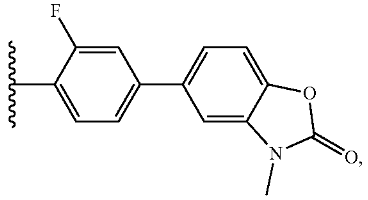

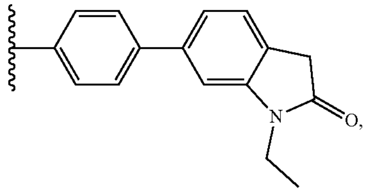

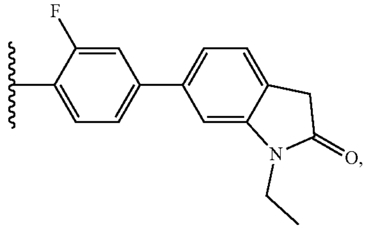

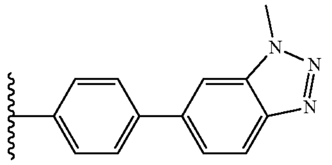

or

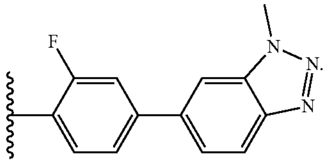

In embodiments of Formula In embodiments of compounds of Formula (I), (II), (III), (IV), (VI), (IX), (X), (XII), or (XII-A), or a pharmaceutically acceptable salt, a stereoisomer, or a deuterated form thereof, or a pharmaceutically acceptable salt, a stereoisomer, or a deuterated form thereof, one $R^7$ and one $R^5$ together form a carbocyclyl, aryl, heterocyclyl or heteroaryl ring, wherein the carbocyclyl, aryl, heterocyclyl and heteroaryl are optionally substituted with 1-4 groups selected from $R^5$ or $R^6$.

In embodiments, the ring formed by one $R^7$ and one $R^5$ is optionally substituted with 1-4 groups selected from alkyl, halogen, Oalkyl, haloalkyl, OH or CN. In embodiments, the ring formed by one $R^7$ and one $R^5$ is optionally substituted with 1-4 groups selected from $C_{1-6}$ alkyl, halogen, $OC_{1-6}$ alkyl, haloalkyl, OH, CN, or heterocyclyl. In embodiments, the ring formed by one $R^7$ and one $R^5$ is optionally substituted with 1-4 groups selected from $CH_3$, F, CN or

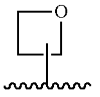

.

In embodiments, the ring formed by one $R^7$ and one $R^5$ is optionally substituted with 1-4 groups selected from $CH_3$, F, CN or

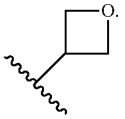

In embodiments, one $R^7$ and one $R^5$ together with the atoms they are attached to form a bicyclic ring wherein the ring is cycloalkyl, cycloalkenyl, aryl, heterocyclyl or heteroaryl. In embodiments, one $R^7$ and one $R^5$ together with the atoms they are attached to form a tricyclic ring wherein the ring is cycloalkyl, cycloalkenyl, aryl, heterocyclyl or heteroaryl. In embodiments, one $R^7$ and one $R^5$ together with the atoms they are attached to form a tetracyclic ring wherein the ring is cycloalkyl, cycloalkenyl, aryl, heterocyclyl or heteroaryl. In embodiments, one $R^7$ and one $R^5$ together with the atoms they are attached to form a 5-20 membered heteroaryl ring. In embodiments, one $R^7$ and one $R^5$ together with the atoms they are attached to form a bicyclic 5-20 membered heteroaryl ring. In embodiments, one $R^7$ and one $R^5$ together with the atoms they are attached to form a tricyclic 5-20 membered heteroaryl ring. In embodiments, one $R^7$ and one $R^5$ together with the atoms they are attached to form a tetracyclic 5-20 membered heteroaryl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a cycloalkyl ring. In embodiments, one $R^7$ and one $R^5$ together with the atoms they are attached to form a bicyclic cycloalkyl ring. In embodiments, one $R^7$ and one $R^5$ together with the atoms they are attached to form a tricyclic cycloalkyl ring. In embodiments, one $R^7$ and one $R^5$ together with the atoms they are attached to form a tetracyclic cycloalkyl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a cycloalkenyl ring. In embodiments, one $R^7$ and one $R^5$ together with the atoms they are attached to form a bicyclic cycloalkenyl ring. In embodiments, one $R^7$ and one $R^5$ together with the atoms they are attached to form a tricyclic cycloalkenyl ring. In embodiments, one $R^7$ and one $R^5$ together with the atoms they are attached to form a tetracyclic cycloalkenyl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a aryl ring. In embodiments, one $R^7$ and one $R^5$ together with the atoms they are attached to form a bicyclic aryl ring. In embodiments, one $R^7$ and one $R^5$ together with the atoms they are attached to form a tricyclic aryl ring. In embodiments, one $R^7$ and one $R^5$ together with the atoms they are attached to form a tetracyclic aryl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a heterocyclyl ring. In embodiments, one $R^7$ and one $R^5$ together with the atoms they are attached to form a bicyclic heterocyclyl ring. In embodiments, one $R^7$ and one $R^5$ together with the atoms they are attached to form a tricyclic c heterocyclyl ring. In embodiments, one $R^7$ and one $R^5$ together with the atoms they are attached to form a tetracyclic c heterocyclyl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a heteroaryl ring. In embodiments, one $R^7$ and one $R^5$ together with the atoms they are attached to form a bicyclic heteroaryl ring. In embodiments, one $R^7$ and one $R^5$ together with the atoms they are attached to form a tricyclic heteroaryl ring. In embodiments, one $R^7$ and one $R^5$ together with the atoms they are attached to form a tetracyclic heteroaryl ring.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form heteroaryl ring. In embodiments, one $R^7$ and one $R^5$ together with the atoms they are attached to form fused heteroaryl ring. In embodiments, one $R^7$ and one $R^5$ together with the atoms they are attached to form a fuse bicyclic heteroaryl, optionally substituted with 1, 2, 3, or 4 groups selected from $R^5$ or $R^6$. In embodiments, one $R^7$ and one $R^5$ together with the atoms they are attached to form a fuse bicyclic 8-10 membered heteroaryl ring, optionally substituted with 1, 2, 3, or 4 groups selected from $R^5$ or $R^6$. In embodiments, one $R^7$ and one $R^5$ together with the atoms they are attached to form a 5,5-, 5,6-, 6,5-, or 6,6-fused bicyclic heteroaryl, optionally substituted with 1, 2, 3, or 4 groups selected from $R^5$ or $R^6$. In embodiments, one $R^7$ and one $R^5$ together with the atoms they are attached to form a 5,5-, 5,6-, 6,5-, or 6,6-fused bicyclic heteroaryl, comprising one aromatic ring, wherein the fused bicyclic ring is optionally substituted with 1, 2, 3, or 4 groups selected from $R^5$ or $R^6$.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a fuse tricyclic heteroaryl ring, optionally substituted with 1, 2, 3, or 4 groups selected from $R^5$ or $R^6$. In embodiments, one $R^7$ and one $R^5$ together with the atoms they are attached to form a 5,6,5-, 6,6,5-, 6,6,6-fused tricyclic heteroaryl, optionally substituted with 1, 2, 3, or 4 groups selected from $R^5$ or $R^6$.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form a fuse tetracyclic heteroaryl, optionally substituted with 1, 2, 3, or 4 groups selected from $R^5$ or $R^6$. In embodiments, one $R^7$ and one $R^5$ together with the atoms they are attached to form a 6,5,6,6-6,5,6,5-, 6,6,6,6-fused tetracyclic heteroaryl, optionally substituted with 1, 2, 3, or 4 groups selected from $R^5$ or $R^6$. In embodiments, one $R^7$ and one $R^5$ together with the atoms they are attached to form a 6,5,6,6-, fused tetracyclic heteroaryl, comprising one aromatic ring, wherein the fused tetracyclic ring is optionally substituted with 1, 2, 3, or 4 groups selected from $R^5$ or $R^6$.

In embodiments of the compounds of Formula (I), (II), (III), (IV), (VI), (IX), (X), (XII), or (XII-A), or a pharmaceutically acceptable salt, a stereoisomer, or a deuterated form thereof, one $R^7$ and one $R^5$ together with the atoms they are attached to form

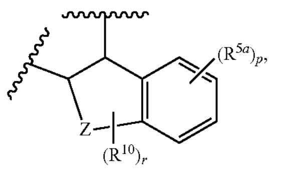

wherein r is 0, 1 or 2;

p is 0, 1, 2 or 3;

Z is O, $CH_2O$, $OCH_2$, $CH_2$ or $CH_2CH_2$;

each $R^{5a}$ is independently selected from halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

or two $R^{5a}$ together with the atoms they are attached to form a ring structure; each of $R^a$, $R^b$, $R^c$ and $R^d$ is independently selected from H, alkyl, halogen or haloalkyl;

$R^{10}$ is alkyl, halogen, Oalkyl, haloalkyl, OH or CN.

In embodiments, two $R^{5a}$ together with the atoms they are attached to form a monocyclic ring structure. In embodiments, two $R^{5a}$ together with the atoms they are attached to form a bicyclic ring structure. In embodiments, two $R^{5a}$ together with the atoms they are attached to form a monocyclic heterocyclyl. In embodiments, two $R^{5a}$ together with the atoms they are attached to form a bicyclic heterocyclyl. In embodiments, two $R^{5a}$ together with the atoms they are attached to form a monocyclic heterocycloalkenyl. In embodiments, two $R^{5a}$ together with the atoms they are attached to form a bicyclic heterocycloalkenyl. In embodiments, two $R^{5a}$ together with the atoms they are attached to form a monocyclic heterocyclyl. In embodiments, two $R^{5a}$ together with the atoms they are attached to form a bicyclic heterocycloalkyl. In embodiments, two $R^{5a}$ together with the atoms they are attached to form a monocyclic heteroaryl. In embodiments, two $R^{5a}$ together with the atoms they are attached to form a bicyclic heteroaryl.

In embodiments, two $R^{5a}$ together with the atoms they are attached to form a ring structure selected from In embodiments, two $R^{5a}$ together with the atoms they are attached to form a ring structure selected from

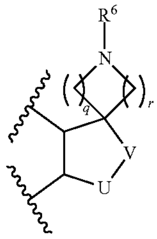

or

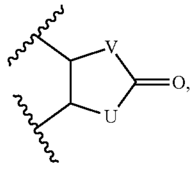

wherein each of q and r is 0, 1, 2 or 3, provided that q and r is not 0 at the same time; U and V are each independently $CH_2$, C(=O), O or $NR^6$. n embodiments, U is $CH_2$. In embodiments, V is O. In embodiments, V is $NR^6$. In embodiments, U is O. In embodiments U is O and V is $NR^6$. In embodiments, U is $CH_2$ and V is O. In embodiments, q is 2. In embodiments, r is 2. In embodiments, q is 2 and r is 2. In embodiments, $R^6$ is $C_{1-6}$ alkyl or 3-6 membered-heterocyclyl. In embodiments, $R^6$ is $CH_3$ or oxetanyl. In embodiments, $R^6$ is $CH_3$ or

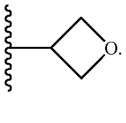 [SMILES: *C1COC1]

In embodiments of compounds of Formula (I), (II), (III), (V), (XII) or (XII-A), or a pharmaceutically acceptable salt, a stereoisomer, or a deuterated form thereof,

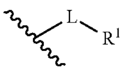

is

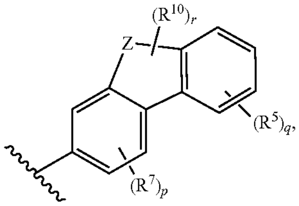

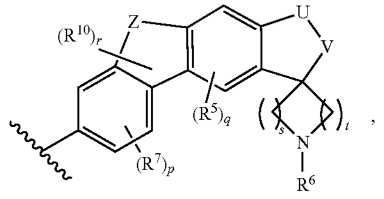

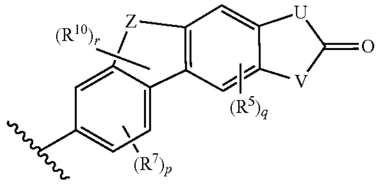

or

-continued

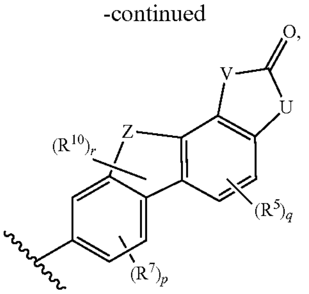

wherein p is 0, 1, 2 or 3;

q is 0, 1, 2 or 3;

r is 0 or 1;

each of s and t is 0, 1, 2 or 3, provided that s and t are not 0 at the same time;

Z is O, $CH_2O$, $OCH_2$, $CH_2$ or $CH_2CH_2$;

U and V are each independently $CR^8R^9$, O or $NR^6$;

each $R^5$ is independently selected from halogen, $C_{1-6}$ alkyl, $OC_{1-6}$ alkyl, $C_{3-6}$ cycloalkyl, CN, OH, $C_{1-6}$ alkylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{3-6}$ cycloalkyl, $C_{1-6}$ alkylene-heterocyclyl, heterocyclylene-heterocyclyl or heterocyclyl; wherein $R^6$ is optionally substituted with 1-3 groups optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

$R^8$ and $R^9$ are each independently selected from H, halogen, $C_{1-6}$ alkyl, O $C_{1-6}$ alkyl, $C_{1-6}$ haloalkyl, $C_{3-6}$ cycloalkyl or heterocyclyl;

or $R^8$ and $R^9$ form =O; and $R^{10}$ is $C_{1-6}$ alkyl, halogen, $OC_{1-6}$ alkyl, haloalkyl, OH or CN.

In embodiments, Z is $CH_2O$ or $OCH_2$.

In embodiments, U and V are each independently $CH_2$, O or N($R^6$). U and V are each independently $CH_2$, O or N($CH_3$). In embodiments, U is $CH_2$, and V is O. In embodiments, U is O, and V is N($CH_3$).

In embodiments of compounds of Formula (I), (II), (III), (IV), (VI) or a pharmaceutically acceptable salt, a stereoisomer, or a deuterated form thereof,

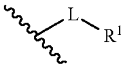 is 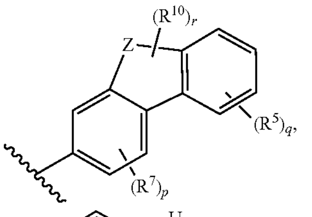

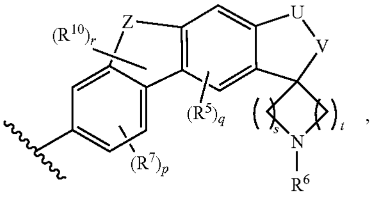

-continued

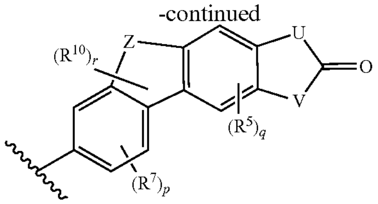 or

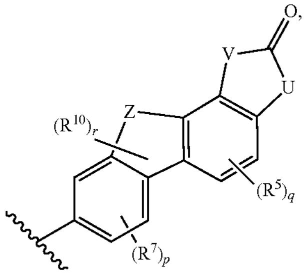

wherein p is 0, 1, 2 or 3;

q is 0, 1, 2 or 3;

r is 0 or 1;

each of s and t is 0, 1, 2 or 3, provided that s and t are not 0 at the same time;

U and V are each independently $CR^8R^9$,O or $NR^6$;

each $R^5$ is independently selected from halogen, $C_{1-6}$ alkyl, $OC_{1-6}$ alkyl, $C_{3-6}$ cycloalkyl, CN, OH, $C_{1-6}$ alkylene-heterocyclyl or heterocyclyl; wherein $R^5$ is optionally substituted with 1-3 groups selected from halogen, CN, OH, $NH_2$, $C_{1-6}$ alkyl, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl)$_2$, $C_{3-6}$ cycloalkyl, $C_{1-6}$ alkylene-heterocyclyl, heterocyclylene-heterocyclyl or heterocyclyl; wherein $R^6$ is optionally substituted with 1-3 groups optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

$R^8$ and $R^9$ are each independently selected from H, halogen, $C_{1-6}$ alkyl, O $C_{1-6}$ alkyl, $C_{1-6}$ haloalkyl, $C_{3-6}$ cycloalkyl or heterocyclyl;

or $R^8$ and $R^9$ form =O; and $R^{10}$ is $C_{1-6}$ alkyl, halogen, $OC_{1-6}$ alkyl, haloalkyl, OH or CN.

In embodiments, U and V are each independently $CH_2$, O or N($R^6$). U and V are each independently $CH_2$, O or N($CH_3$). In embodiments, U is $CH_2$, and V is O. In embodiments, U is O, and V is N($CH_3$).

In embodiments of compounds of Formula (I), (II), (III), (IV), (VI) or a pharmaceutically acceptable salt, a stereoisomer, or a deuterated form thereof,

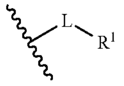 is 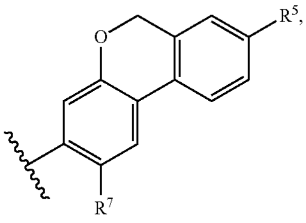

-continued

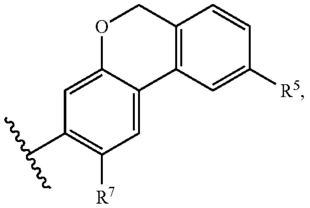

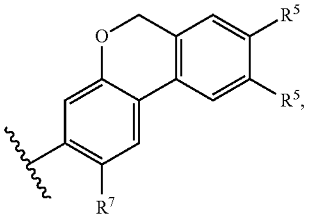

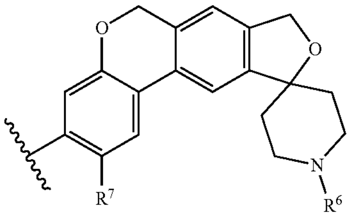

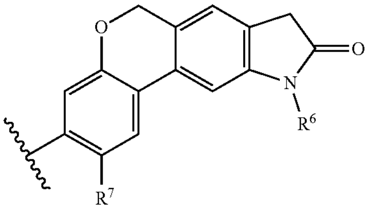

or

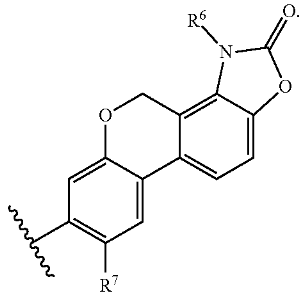

In embodiments, r is 0 or 1. In embodiments, r is 0. In embodiments r is 1.

In embodiments, p is 0, 1, 2. In embodiments, p is 0. In embodiments q is 1. In embodiments, p is 2.

In embodiments, q is 0, 1 or 2. In embodiments, q is 0. In embodiments q is 1. In embodiments, q is 2.

In embodiments, $R^5$ is halogen, $C_{1-6}$ alkyl, $OC_{1-6}$ alkyl, $C_{3-6}$ cycloalkyl, alkylene-heterocyclyl or heterocyclyl. In embodiments, $R^5$ is F, CN or

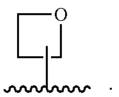

In embodiments, $R^5$ is F, CN or

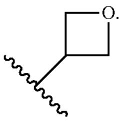

In embodiments, $R^6$ is H, $C_{1-6}$ alkyl, $C_{3-6}$ cycloalkyl, heterocyclyl or $C_{1-6}$ alkylene-heterocyclyl. In embodiments, $R^6$ is H, $C_{1-6}$ alkyl, or heterocyclyl. In embodiments, $R^6$ is H, CN or

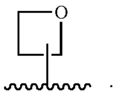

In embodiments, $R^6$ is H, CN or

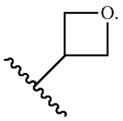

In embodiments, $R^7$ is halogen CN, or $C_{1-6}$ alkyl or $OC_{1-6}$ alkyl. In embodiments, $R^7$ is F.

In embodiments, $R^{10}$ is $C_{1-6}$ alkyl, halogen or CN. In embodiments, $R^{10}$ is $CH_3$, F or CN.

In embodiments of compounds of Formula (I), (II), (III), (IV), (VI) or a pharmaceutically acceptable salt, a stereoisomer, or a deuterated form thereof,

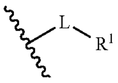

is

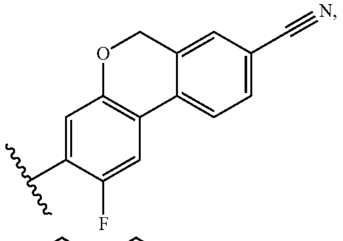

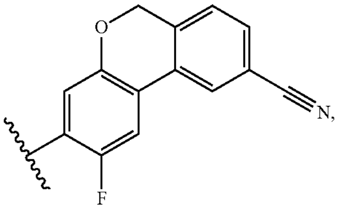

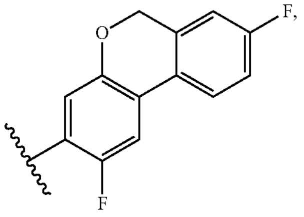

-continued

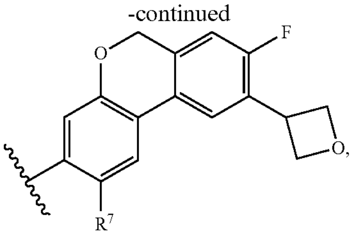

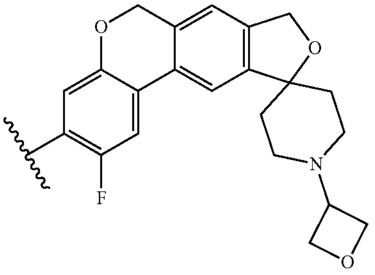

,

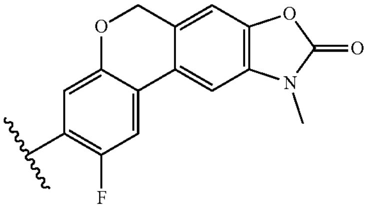

or

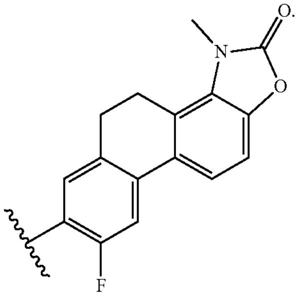

In embodiments of compounds of Formula (I), (II), (III), (IV), (VI) or a pharmaceutically acceptable salt, a stereoisomer, or a deuterated form thereof,

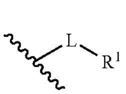

is

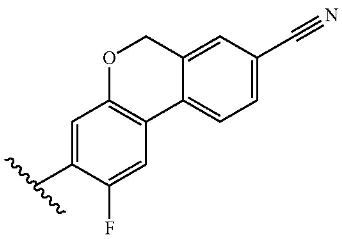

or

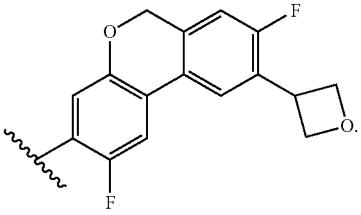

Y, $R^5$, $R^6$

In embodiments of compounds of Formula (V), (VII), (XI-A), (IX-C) or a pharmaceutically acceptable salt, a stereoisomer, or a deuterated form thereof, Y is $NR^6$, O, $CR^8R^9$, S, S(O) or $S(O)_2$. In embodiments, Y is O, S, $NR^6$ or $CR^8R^9$. In embodiments, $R^8$ and $R^9$ are each independently selected from H, halogen or $C_{1-6}$ alkyl. In embodiments, $R^8$ and $R^9$ are each H or $CH_3$. In embodiments, $R^8$ and $R^9$ are each H. In embodiments, Y is NH, O, S, $CH_2$, CHF, or $CF_2$. In embodiments, Y is O or $CH_2$. In embodiments, Y is O. In embodiments, Y is $CH_2$.

In embodiments of compounds of Formula (V), (VII), (VIII), (XI-A), (IX-C), (IX-D), (X-A), (X-B), (X-C) or (X-D), or a pharmaceutically acceptable salt, a stereoisomer, or a deuterated form thereof, p is 0, 1 or 2. In embodiments, p is 0. In embodiments p is 1.

In embodiments of compounds of Formula (V), (VII), (VIII), (XI-A), (IX-C), (IX-D), (X-A), (X-B), (X-C) or (X-D), or a pharmaceutically acceptable salt, a stereoisomer, or a deuterated form thereof, $R^7$ is halogen or $C_{1-6}$ alkyl. In embodiments, $R^7$ is F or $CH_3$. In embodiments, $R^7$ is F.

In embodiments of compounds of Formula (V), (VII), (VIII), (XI-A), (IX-C), (IX-D), (X-A), (X-B), (X-C) or (X-D), or a pharmaceutically acceptable salt, a stereoisomer, or a deuterated form thereof, q is 0, 1, 2 or 3. In embodiments, q is 0. In embodiments, q is 1. In embodiments, q is 2. In embodiments, q is 3.

In embodiments of compounds of Formula (V), (VII), (VIII), (XI-A), (IX-C), (IX-D), (X-A), (X-B), (X-C) or (X-D), or a pharmaceutically acceptable salt, a stereoisomer, or a deuterated form thereof, $R^5$ is halogen, $C_{1-6}$ alkyl, $OC_{1-6}$ alkyl, $C_{1-6}$ haloalkyl, $C_{2-6}$ alkenyl, $C_{2-6}$ alkynyl, $C_{3-6}$ cycloalkyl, CN, OH, $NH_2$, $NHC_{1-6}$ alkyl, $N(C_{1-6}$ alkyl$)_2$, COOH, $C(=O)C_{1-6}$ alkyl, $C(=O)OC_{1-6}$ alkyl, $C(=O)NHC_{1-6}$ alkyl, $C(=O)N(C_{1-6}$ alkyl$)_2$, $NHC(=O)C_{1-6}$ alkyl, $S(=O)_2$—$C_{1-6}$ alkyl, $C_{1-6}$ alkylene-cycloalkyl, $S(=O)_2$-cycloalkyl, $C_{1-6}$ alkylene-heterocyclyl, $S(=O)_2$-heterocycly, heterocyclylene-heterocyclyl or heterocyclyl. In embodiments, $R^5$ is halogen, $C_{1-6}$ alkyl, $OC_{1-6}$ alkyl, CN or heterocyclyl, $C_{1-6}$ alkylene-heterocyclyl or $S(=O)_2$-heterocyclyl. In embodiments, $R^5$ is

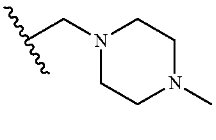

,

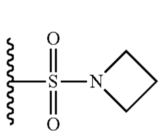

, $CH_3$, F or CN. In embodiments, $R^5$ is $CH_3$, F or CN.

In embodiments, provided herein is a compound of In embodiments of compounds of Formula (V), (VII), (VIII), (XI-A), (IX-C), (IX-D), (X-A), (X-B), (X-C) or (X-D), or a pharmaceutically acceptable salt, a stereoisomer, or a deuterated form thereof, $R^6$ is H, $C_{1-6}$ alkyl, $C_{1-6}$ alkylene-O—$C_{1-6}$ alkyl, $C_{1-6}$ alkylene-$NH_2$, $C_{1-6}$ alkylene-NH($C_{1-6}$ alkyl), $C_{1-6}$ alkylene-N($C_{1-6}$ alkyl$)_2$, $C_{1-6}$ alkylene-NH($C_{1-6}$ alkylene-O—$C_{1-6}$ alkyl), $C_{1-6}$ alkylene-N($C_{1-6}$ alkylene-O—$C_{1-6}$ alkyl)($C_{1-6}$ alkyl), $C_{1-6}$ alkylene-heterocyclyl or heterocyclyl. In embodiments, $R^6$ is $C_{1-6}$ alkyl, $C_{1-6}$ alkylene-O—$C_{1-6}$ alkyl, $C_{1-6}$ alkylene-N($C_{1-6}$ alkyl$)_2$, $C_{1-6}$ alkylene-N($C_{1-6}$ alkylene-O—$C_{1-6}$ alkyl)($C_{1-6}$ alkyl) or $C_{1-6}$ alkylene-heterocyclyl. In embodiments, $R^6$ is $C_{1-6}$ alkyl. In embodiments, $R^6$ is $CH_3$, $CH_2CH_3$,

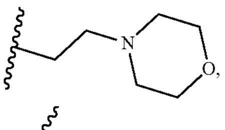
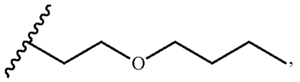
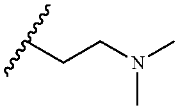
or
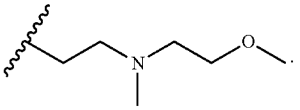

In embodiments, $R^6$ is $CH_3$ or $CH_2CH_3$. In embodiments, $R^6$ is $CH_3$. In embodiments, $R^6$ is $CH_3$ or $CH_2CH_3$.

In embodiments, provided herein is a pharmaceutically acceptable salt of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A). Further embodiments of the disclosure relate to a deuterated compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or a pharmaceutically acceptable salt thereof. Further embodiments of the disclosure relate to a stereoisomer of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or a pharmaceutically acceptable salt thereof.

In embodiments, provided herein is a compound in Table A, or a pharmaceutically acceptable salt thereof, racemic form thereof, or stereoisomer thereof.

In embodiments, provided herein is a compound in Table A, or a pharmaceutically acceptable salt thereof, or stereoisomer thereof.

In embodiments, provided herein is a compound in Table A, or a pharmaceutically acceptable salt thereof.

In one embodiment, provided herein is a compound set forth in Table A.

In some embodiments, provided herein is a pharmaceutically acceptable salt of a compound in Table A.

TABLE A

Exemplary compounds of the disclosure.

| Compound No. | Structure |
|---|---|
| 101 | 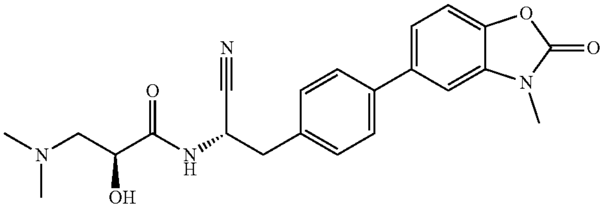 [SMILES: CN(C)C[C@H](O)C(=O)N[C@H](C#N)Cc1ccc(-c2ccc3oc(=O)n(C)c3c2)cc1] |
| 102 | 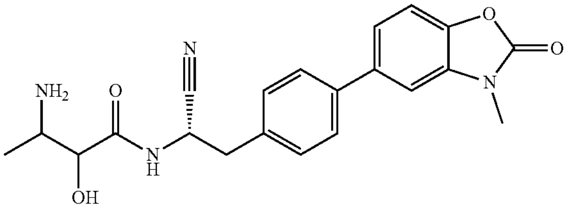 [SMILES: CC(N)C(O)C(=O)N[C@H](C#N)Cc1ccc(-c2ccc3oc(=O)n(C)c3c2)cc1] |
| 103 | 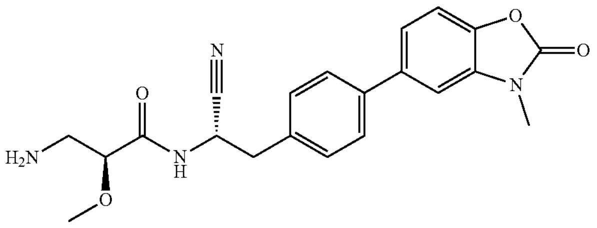 [SMILES: CO[C@@H](CN)C(=O)N[C@H](C#N)Cc1ccc(-c2ccc3oc(=O)n(C)c3c2)cc1] |
| 104 | 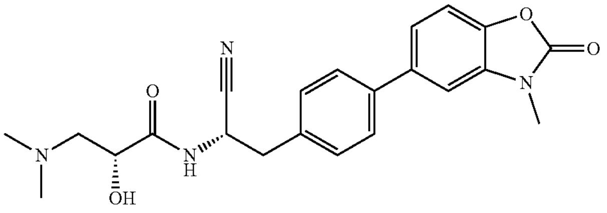 [SMILES: CN(C)C[C@@H](O)C(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 105 | 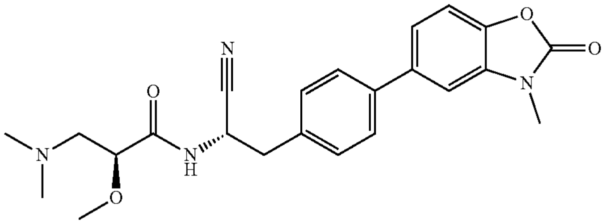 |
| 106 | 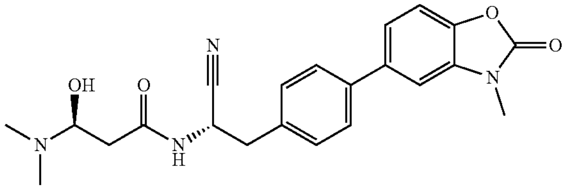 [SMILES: CN(C)[C@@H](O)CC(=O)N[C@H](C#N)Cc1ccc(-c2ccc3oc(=O)n(C)c3c2)cc1] |
| 107 | 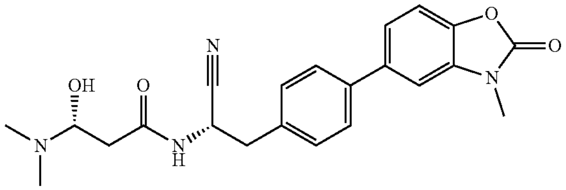 [SMILES: CN(C)[C@H](O)CC(=O)N[C@H](C#N)Cc1ccc(-c2ccc3oc(=O)n(C)c3c2)cc1] |
| 108 | 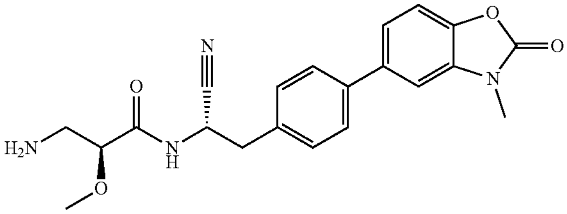 [SMILES: CO[C@@H](CN)C(=O)N[C@H](C#N)Cc1ccc(-c2ccc3oc(=O)n(C)c3c2)cc1] |
| 109 | 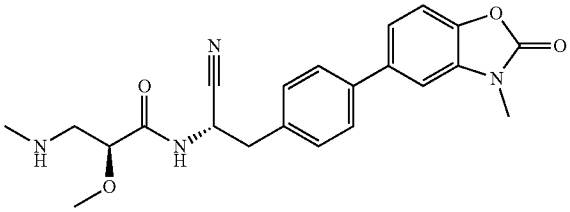 |
| 110 | 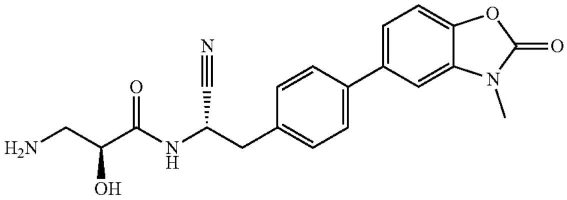 [SMILES: Cn1c(=O)oc2ccc(-c3ccc(C[C@@H](C#N)NC(=O)[C@@H](O)CN)cc3)cc21] |
| 111 | 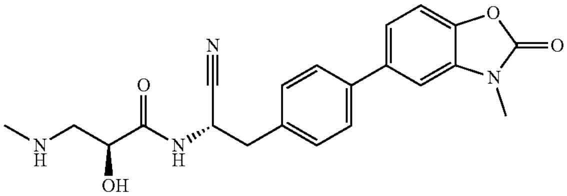 [SMILES: CNC[C@H](O)C(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 112 | 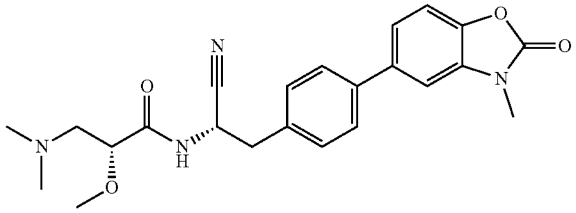 [SMILES: CO[C@H](CN(C)C)C(=O)N[C@H](C#N)Cc1ccc(-c2ccc3oc(=O)n(C)c3c2)cc1] |
| 113 | 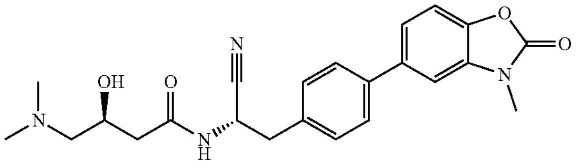 [SMILES: CN(C)C[C@@H](O)CC(=O)N[C@H](C#N)Cc1ccc(-c2ccc3oc(=O)n(C)c3c2)cc1] |
| 114 | 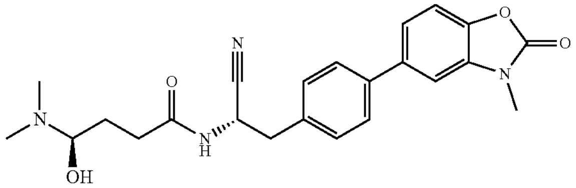 [SMILES: CN(C)[C@H](O)CCC(=O)N[C@H](C#N)Cc1ccc(-c2ccc3oc(=O)n(C)c3c2)cc1] |
| 115 | 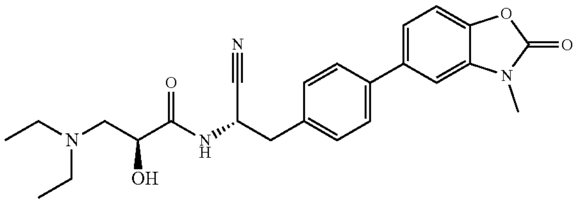 [SMILES: CCN(CC)C[C@H](O)C(=O)N[C@H](C#N)Cc1ccc(-c2ccc3oc(=O)n(C)c3c2)cc1] |
| 116 | 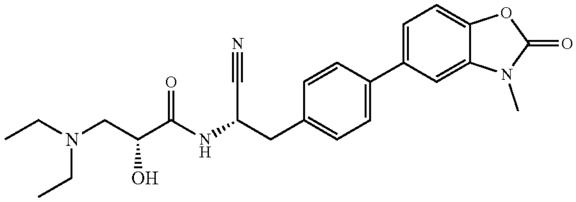 [SMILES: CCN(CC)C[C@@H](O)C(=O)N[C@H](C#N)Cc1ccc(-c2ccc3oc(=O)n(C)c3c2)cc1] |
| 117 | 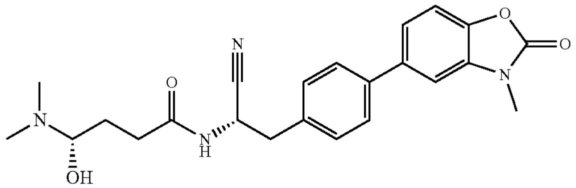 [SMILES: CN(C)[C@@H](O)CCC(=O)N[C@H](C#N)Cc1ccc(-c2ccc3oc(=O)n(C)c3c2)cc1] |
| 118 | 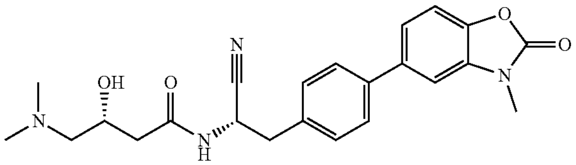 [SMILES: CN(C)C[C@H](O)CC(=O)N[C@H](C#N)Cc1ccc(-c2ccc3oc(=O)n(C)c3c2)cc1] |

TABLE A-continued
| Compound No. | Structure |
| --- | --- |
| Exemplary compounds of the disclosure. | |
| 119 | 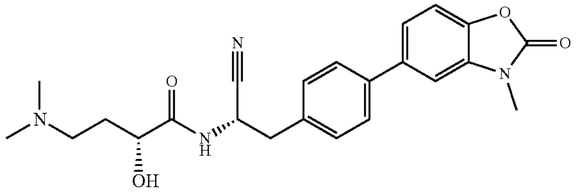 [SMILES: CN(C)CC[C@@H](O)C(=O)N[C@H](C#N)Cc1ccc(-c2ccc3oc(=O)n(C)c3c2)cc1] |
| 120 | 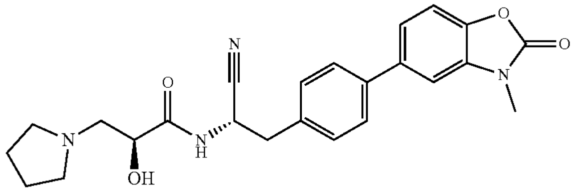 [SMILES: Cn1c(=O)oc2ccc(-c3ccc(C[C@@H](C#N)NC(=O)[C@@H](O)CN4CCCC4)cc3)cc21] |
| 121 | 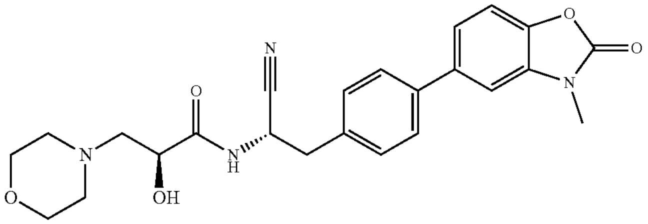 [SMILES: Cn1c(=O)oc2ccc(-c3ccc(C[C@@H](C#N)NC(=O)[C@@H](O)CN4CCOCC4)cc3)cc21] |
| 122 | 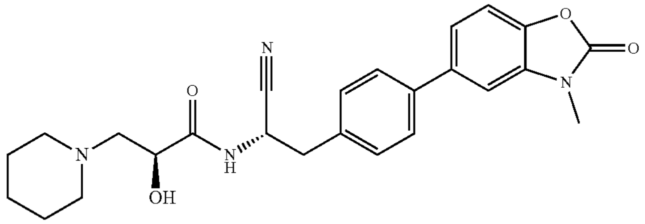 [SMILES: Cn1c(=O)oc2ccc(-c3ccc(C[C@@H](C#N)NC(=O)[C@@H](O)CN4CCCCC4)cc3)cc21] |
| 123 | 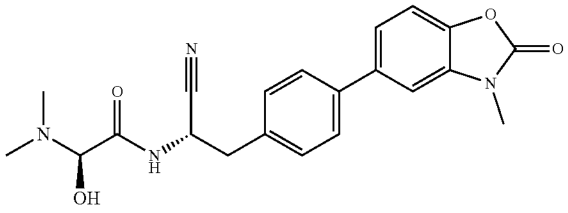 [SMILES: CN(C)[C@H](O)C(=O)N[C@H](C#N)Cc1ccc(-c2ccc3oc(=O)n(C)c3c2)cc1] |
| 124 | 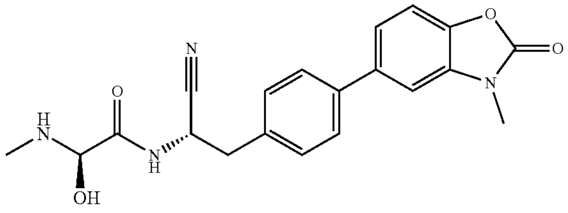 [SMILES: CN[C@H](O)C(=O)N[C@H](C#N)Cc1ccc(-c2ccc3oc(=O)n(C)c3c2)cc1] |
| 125 | 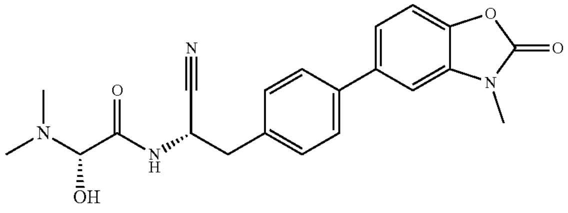 [SMILES: CN(C)[C@@H](O)C(=O)N[C@H](C#N)Cc1ccc(-c2ccc3oc(=O)n(C)c3c2)cc1]

TABLE A-continued
| Exemplary compounds of the disclosure. | |
|---|---|
| Compound No. | Structure |
| 126 | 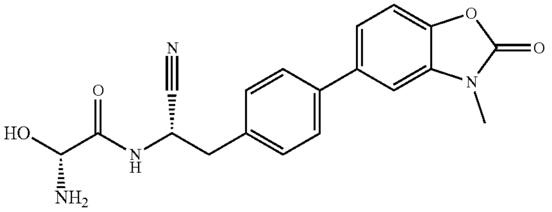 [SMILES: Cn1c(=O)oc2ccc(-c3ccc(C[C@@H](C#N)NC(=O)[C@H](N)O)cc3)cc21] |
| 127 | 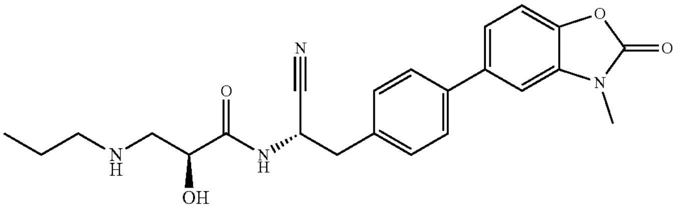 [SMILES: CCCNC[C@H](O)C(=O)N[C@H](C#N)Cc1ccc(-c2ccc3oc(=O)n(C)c3c2)cc1] |
| 128 | 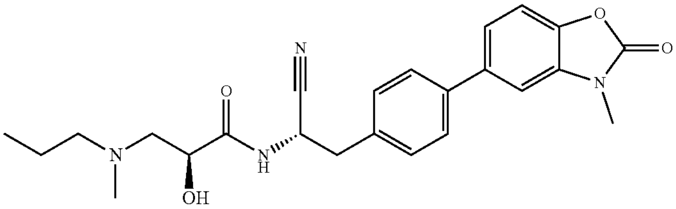 [SMILES: CCCN(C)C[C@H](O)C(=O)N[C@H](C#N)Cc1ccc(-c2ccc3oc(=O)n(C)c3c2)cc1] |
| 129 | 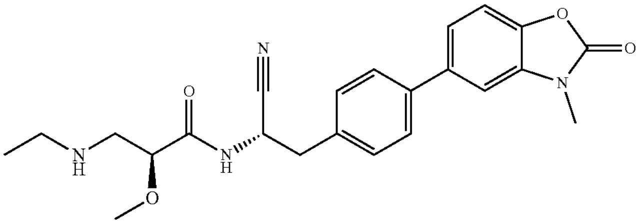 [SMILES: CCNC[C@H](OC)C(=O)N[C@H](C#N)Cc1ccc(-c2ccc3oc(=O)n(C)c3c2)cc1] |
| 130 | 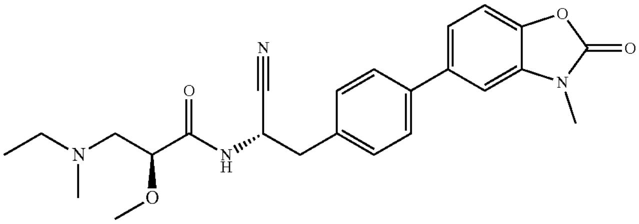 [SMILES: CCN(C)C[C@H](OC)C(=O)N[C@H](C#N)Cc1ccc(-c2ccc3oc(=O)n(C)c3c2)cc1] |
| 131 | 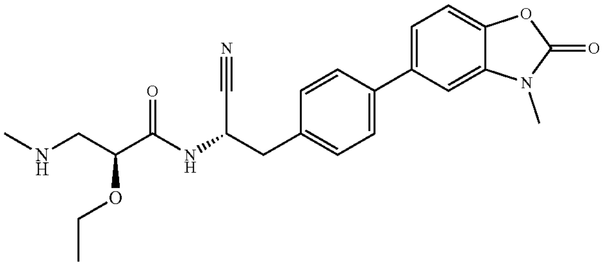 [SMILES: CCO[C@@H](CNC)C(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 132 | 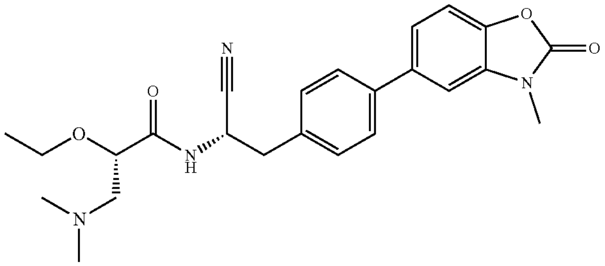 [SMILES: CCO[C@@H](CN(C)C)C(=O)N[C@H](C#N)Cc1ccc(-c2ccc3oc(=O)n(C)c3c2)cc1] |
| 133 | 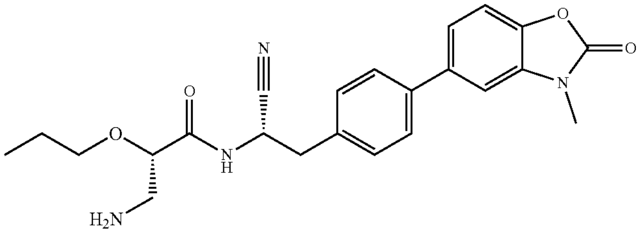 [SMILES: CCCO[C@@H](CN)C(=O)N[C@H](C#N)Cc1ccc(-c2ccc3oc(=O)n(C)c3c2)cc1] |
| 134 | 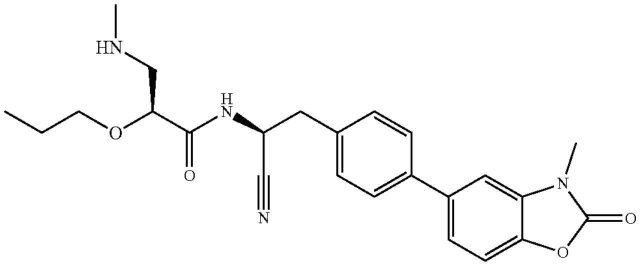 [SMILES: CCCO[C@@H](CNC)C(=O)N[C@H](C#N)Cc1ccc(-c2ccc3oc(=O)n(C)c3c2)cc1] |
| 135 | 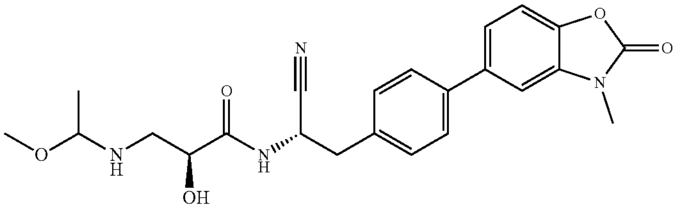 [SMILES: COC(C)NC[C@H](O)C(=O)N[C@H](C#N)Cc1ccc(-c2ccc3oc(=O)n(C)c3c2)cc1] |
| 136 | 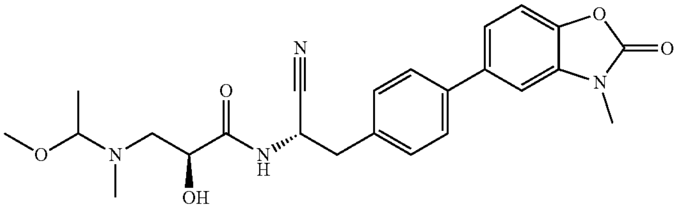 [SMILES: COC(C)N(C)C[C@H](O)C(=O)N[C@H](C#N)Cc1ccc(-c2ccc3oc(=O)n(C)c3c2)cc1] |
| 137 | 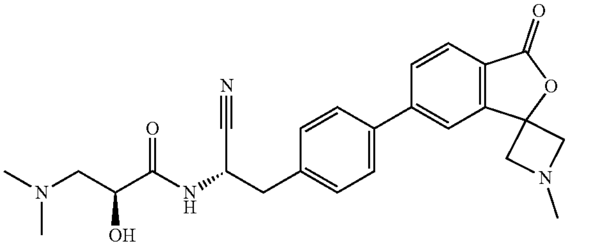 [SMILES: CN(C)C[C@H](O)C(=O)N[C@H](C#N)Cc1ccc(-c2ccc3c(c2)C2(CN(C)C2)OC3=O)cc1] |

TABLE A-continued
| Exemplary compounds of the disclosure. | |
|---|---|
| Compound No. | Structure |
| 138 | 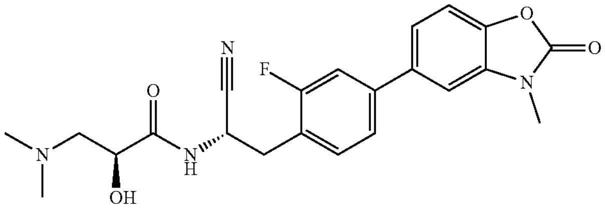 |
| 139 | 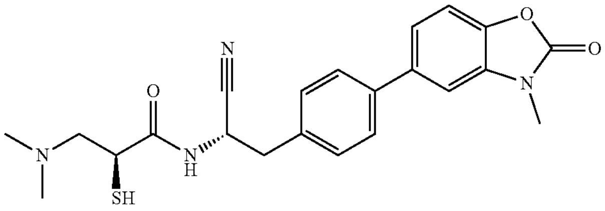 |
| 140 | 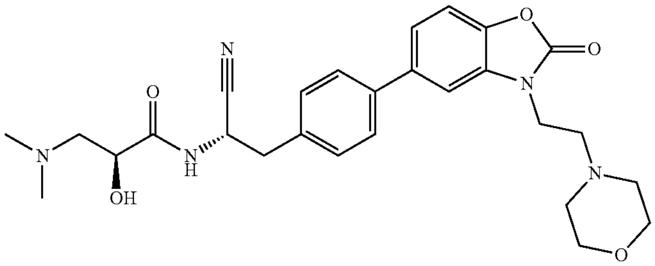 [SMILES: CN(C)C[C@H](O)C(=O)N[C@H](C#N)Cc1ccc(-c2ccc3oc(=O)n(CCN4CCOCC4)c3c2)cc1] |
| 141 | 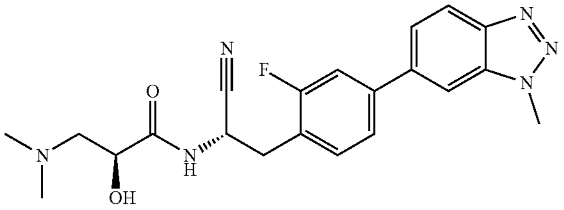 |
| 142 | 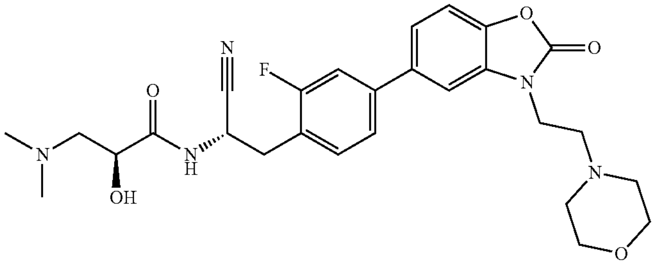 [SMILES: CN(C)C[C@H](O)C(=O)N[C@H](C#N)Cc1ccc(-c2ccc3oc(=O)n(CCN4CCOCC4)c3c2)cc1F] |
| 143 | 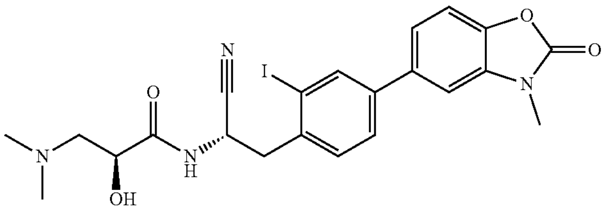 [SMILES: CN(C)C[C@H](O)C(=O)N[C@H](C#N)Cc1ccc(-c2ccc3oc(=O)n(C)c3c2)cc1I] |

TABLE A-continued
| Exemplary compounds of the disclosure. | |
|---|---|
| Compound No. | Structure |
| 144 | 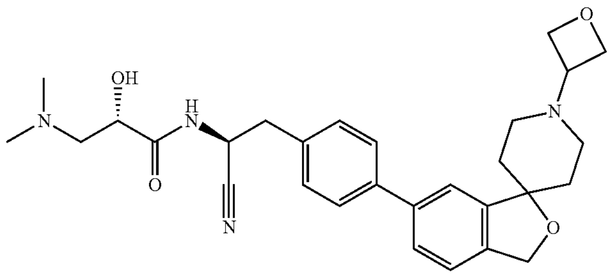 [SMILES: CN(C)C[C@H](O)C(=O)N[C@H](C#N)Cc1ccc(-c2ccc3c(c2)C2(CCN(C4COC4)CC2)OC3)cc1] |
| 145 | 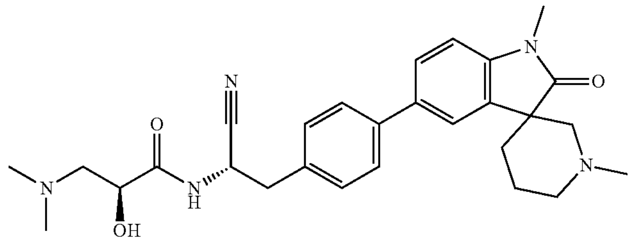 |
| 146 | 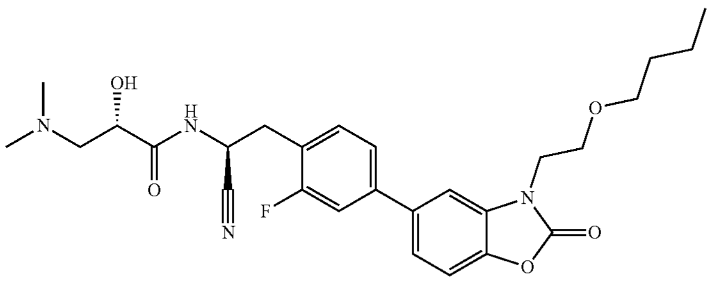 [SMILES: CCCCOCCn1c(=O)oc2ccc(-c3ccc(C[C@@H](C#N)NC(=O)[C@@H](O)CN(C)C)c(F)c3)cc21] |
| 147 | 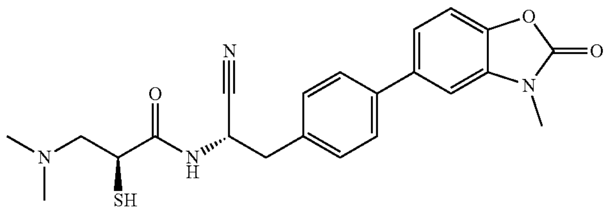 |
| 148 | 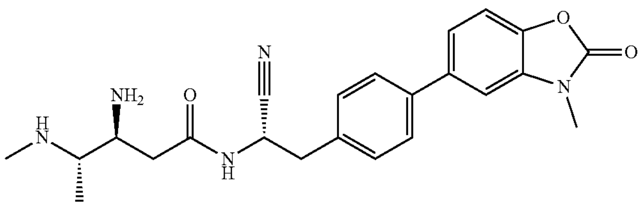 [SMILES: CN[C@@H](C)[C@@H](N)CC(=O)N[C@H](C#N)Cc1ccc(-c2ccc3oc(=O)n(C)c3c2)cc1] |
| 149 | 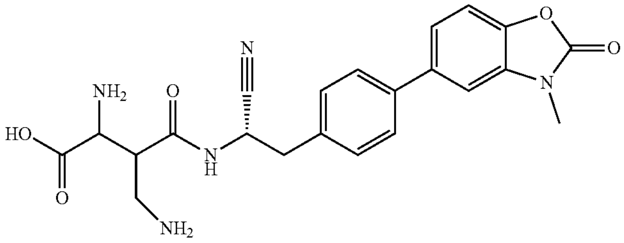 [SMILES: Cn1c(=O)oc2ccc(-c3ccc(C[C@@H](C#N)NC(=O)C(CN)C(N)C(=O)O)cc3)cc21] |

TABLE A-continued
| Exemplary compounds of the disclosure. | |
|---|---|
| Compound No. | Structure |
| 150 | 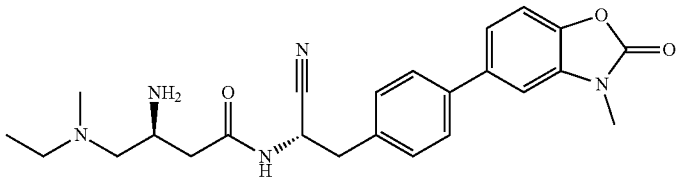 [SMILES: CCN(C)C[C@@H](N)CC(=O)N[C@H](C#N)Cc1ccc(-c2ccc3oc(=O)n(C)c3c2)cc1] |
| 151 | 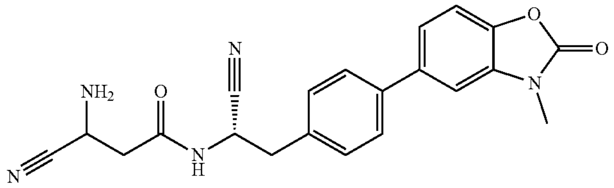 [SMILES: Cn1c(=O)oc2ccc(-c3ccc(C[C@@H](C#N)NC(=O)CC(N)C#N)cc3)cc21] |
| 152 | 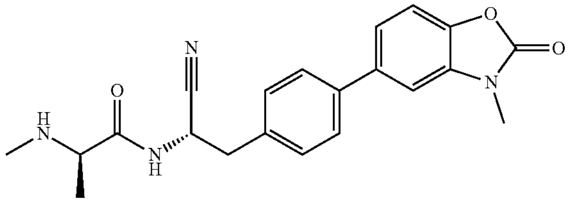 [SMILES: CN[C@H](C)C(=O)N[C@H](C#N)Cc1ccc(-c2ccc3oc(=O)n(C)c3c2)cc1] |
| 153 | 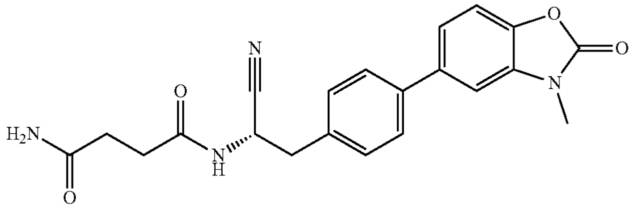 [SMILES: Cn1c(=O)oc2ccc(-c3ccc(C[C@@H](C#N)NC(=O)CCC(N)=O)cc3)cc21] |
| 154 | 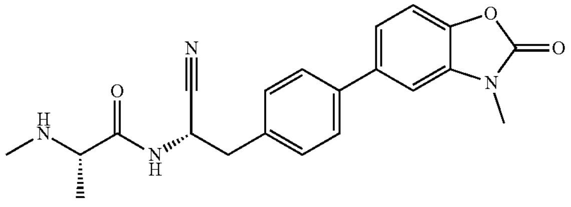 [SMILES: CN[C@@H](C)C(=O)N[C@H](C#N)Cc1ccc(-c2ccc3oc(=O)n(C)c3c2)cc1] |
| 155 | 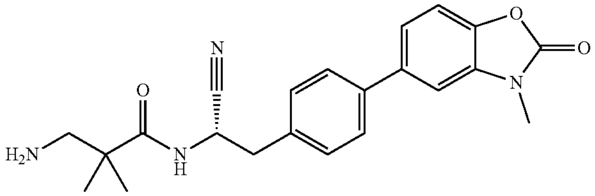 [SMILES: Cn1c(=O)oc2ccc(-c3ccc(C[C@@H](C#N)NC(=O)C(C)(C)CN)cc3)cc21] |
| 156 | 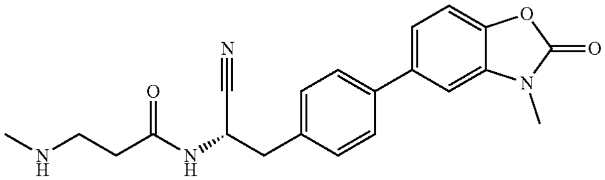 [SMILES: CNCCC(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 157 | 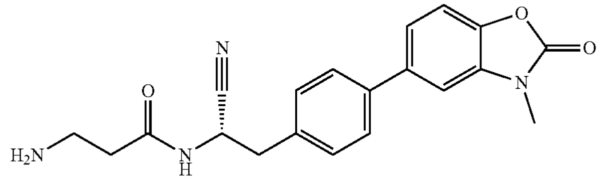 [SMILES: Cn1c(=O)oc2ccc(-c3ccc(C[C@@H](C#N)NC(=O)CCN)cc3)cc21] |
| 158 | 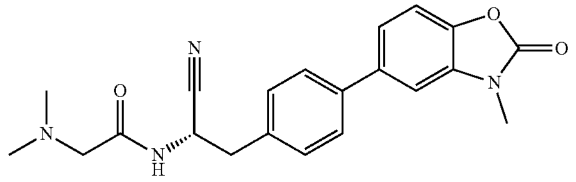 [SMILES: CN(C)CC(=O)N[C@H](C#N)Cc1ccc(-c2ccc3oc(=O)n(C)c3c2)cc1] |
| 159 | 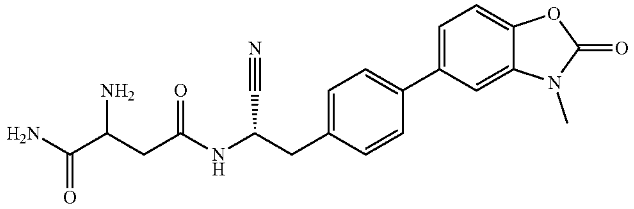 [SMILES: Cn1c(=O)oc2ccc(-c3ccc(C[C@@H](C#N)NC(=O)CC(N)C(N)=O)cc3)cc21] |
| 160 | 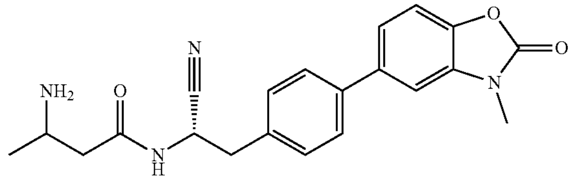 [SMILES: CC(N)CC(=O)N[C@H](C#N)Cc1ccc(-c2ccc3oc(=O)n(C)c3c2)cc1] |
| 161 | 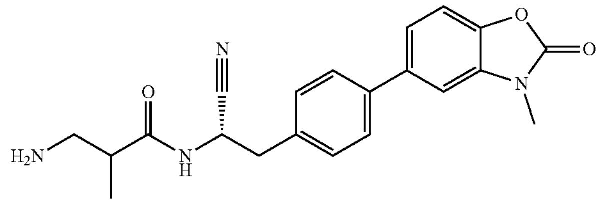 [SMILES: CC(CN)C(=O)N[C@H](C#N)Cc1ccc(-c2ccc3oc(=O)n(C)c3c2)cc1] |
| 162 | 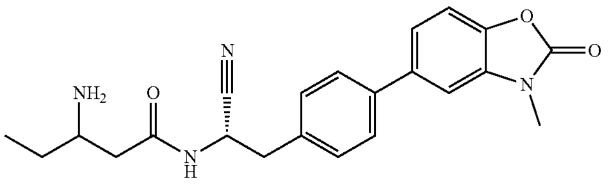 [SMILES: CCC(N)CC(=O)N[C@H](C#N)Cc1ccc(-c2ccc3oc(=O)n(C)c3c2)cc1] |
| 163 | 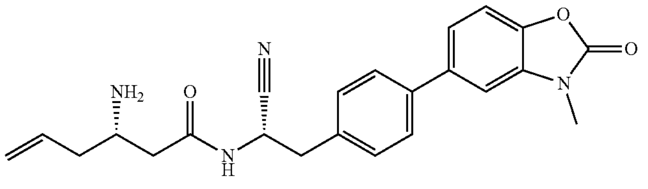 [SMILES: C=CC[C@H](N)CC(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 164 | 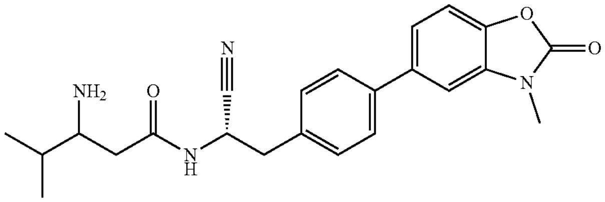 [SMILES: CC(C)C(N)CC(=O)N[C@H](C#N)Cc1ccc(-c2ccc3oc(=O)n(C)c3c2)cc1] |
| 165 | 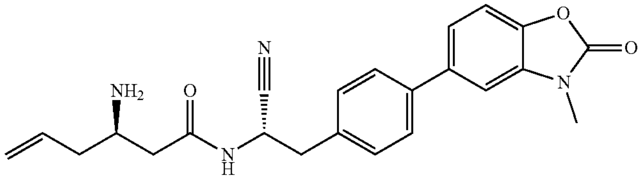 [SMILES: C=CC[C@@H](N)CC(=O)N[C@H](C#N)Cc1ccc(-c2ccc3oc(=O)n(C)c3c2)cc1] |
| 166 | 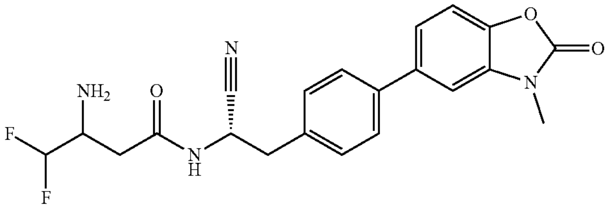 [SMILES: Cn1c(=O)oc2ccc(-c3ccc(C[C@@H](C#N)NC(=O)CC(N)C(F)F)cc3)cc21] |
| 167 | 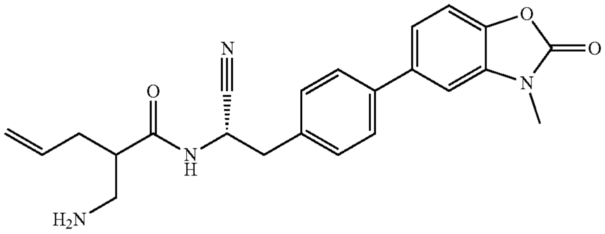 [SMILES: C=CCC(CN)C(=O)N[C@H](C#N)Cc1ccc(-c2ccc3oc(=O)n(C)c3c2)cc1] |
| 168 | 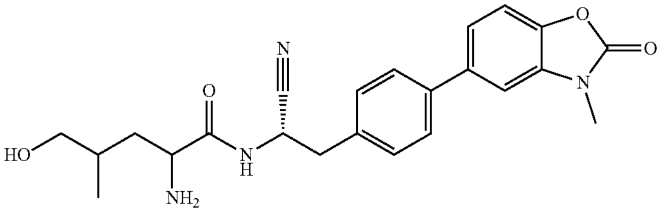 [SMILES: CC(CO)CC(N)C(=O)N[C@H](C#N)Cc1ccc(-c2ccc3oc(=O)n(C)c3c2)cc1] |
| 169 | 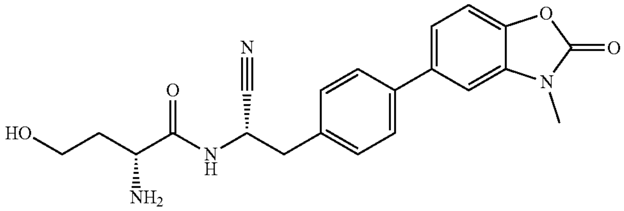 [SMILES: Cn1c(=O)oc2ccc(-c3ccc(C[C@@H](C#N)NC(=O)[C@H](N)CCO)cc3)cc21] |
| 170 | 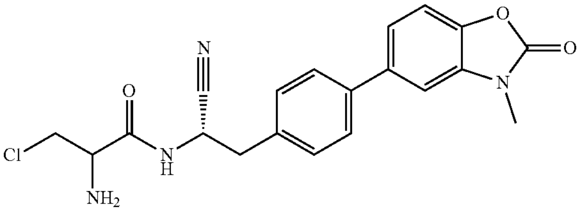 [SMILES: Cn1c(=O)oc2ccc(-c3ccc(C[C@@H](C#N)NC(=O)C(N)CCl)cc3)cc21] |

TABLE A-continued
| Exemplary compounds of the disclosure. | |
|---|---|
| Compound No. | Structure |
| 171 | 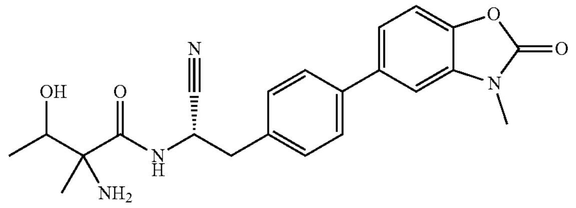 [SMILES: CC(O)C(C)(N)C(=O)N[C@H](C#N)Cc1ccc(-c2ccc3oc(=O)n(C)c3c2)cc1] |
| 171A | 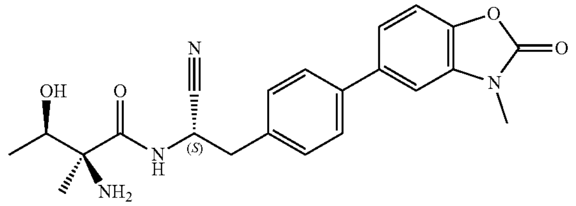 |
| 171B | 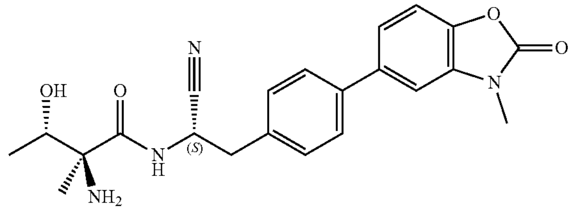 |
| 171C | 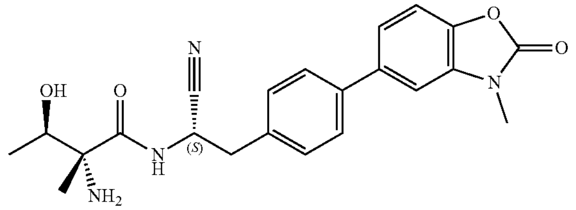 |
| 171D | 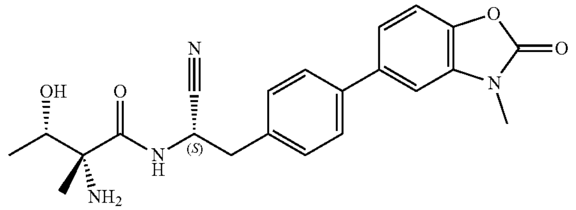 |
| 172 | 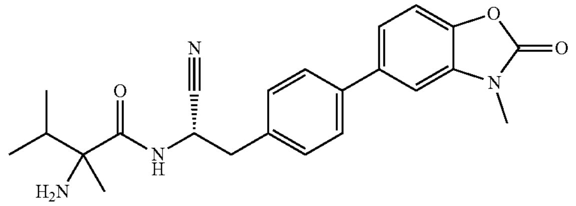 [SMILES: CC(C)C(C)(N)C(=O)N[C@H](C#N)Cc1ccc(-c2ccc3oc(=O)n(C)c3c2)cc1] |
| 173 | 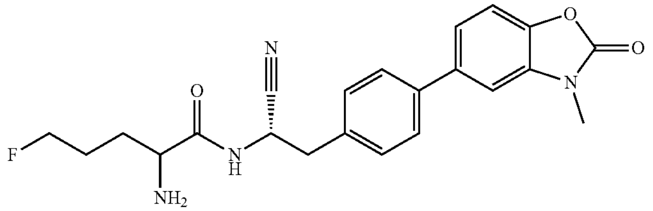 [SMILES: Cn1c(=O)oc2ccc(-c3ccc(C[C@@H](C#N)NC(=O)C(N)CCCF)cc3)cc21] |

TABLE A-continued
| Exemplary compounds of the disclosure. | |
|---|---|
| Compound No. | Structure |
| 174 | 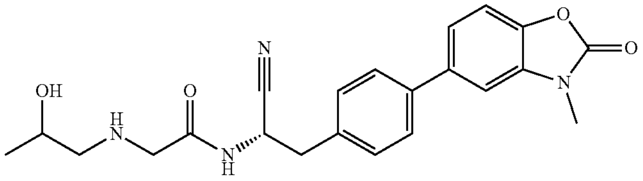 [SMILES: CC(O)CNCC(=O)N[C@H](C#N)Cc1ccc(-c2ccc3oc(=O)n(C)c3c2)cc1] |
| 176 | 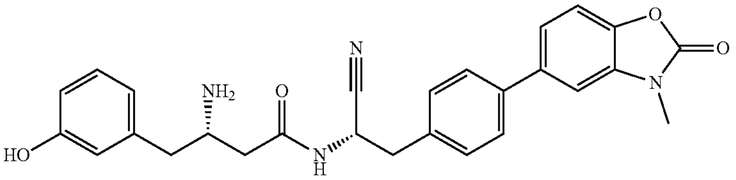 [SMILES: Cn1c(=O)oc2ccc(-c3ccc(C[C@@H](C#N)NC(=O)C[C@@H](N)Cc4cccc(O)c4)cc3)cc21] |
| 177 | 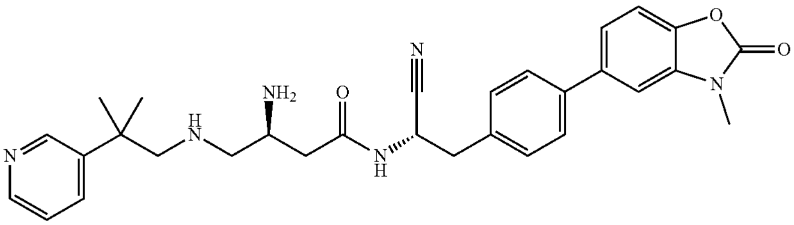 [SMILES: Cn1c(=O)oc2ccc(-c3ccc(C[C@@H](C#N)NC(=O)C[C@H](N)CNCC(C)(C)c4cccnc4)cc3)cc21] |
| 178 | 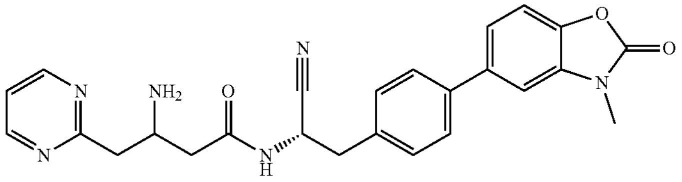 [SMILES: Cn1c(=O)oc2ccc(-c3ccc(C[C@@H](C#N)NC(=O)CC(N)Cc4ncccn4)cc3)cc21] |
| 179 | 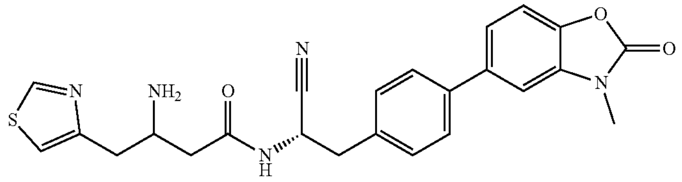 [SMILES: Cn1c(=O)oc2ccc(-c3ccc(C[C@@H](C#N)NC(=O)CC(N)Cc4cscn4)cc3)cc21] |
| 180 | 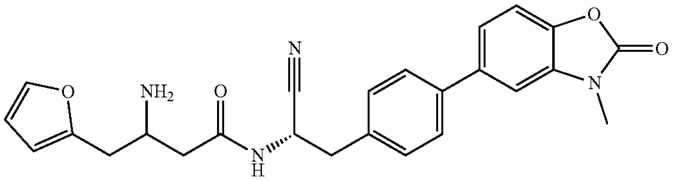 |
| 181 | 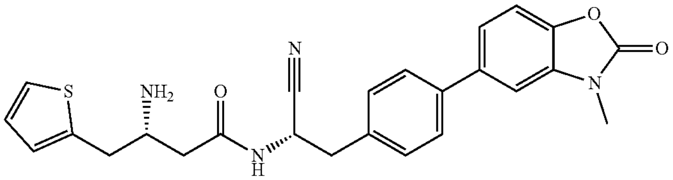 [SMILES: Cn1c(=O)oc2ccc(-c3ccc(C[C@@H](C#N)NC(=O)CC(N)Cc4ccco4)cc3)cc21] |
| 182 | 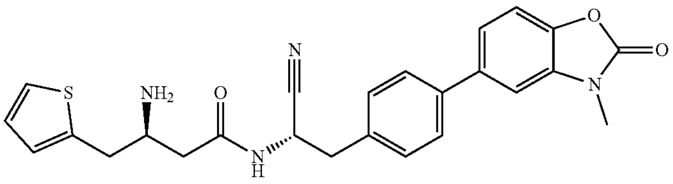 [SMILES: Cn1c(=O)oc2ccc(-c3ccc(C[C@@H](C#N)NC(=O)C[C@H](N)Cc4cccs4)cc3)cc21] |

TABLE A-continued
| Exemplary compounds of the disclosure. | |
|---|---|
| Compound No. | Structure |
| 183 | 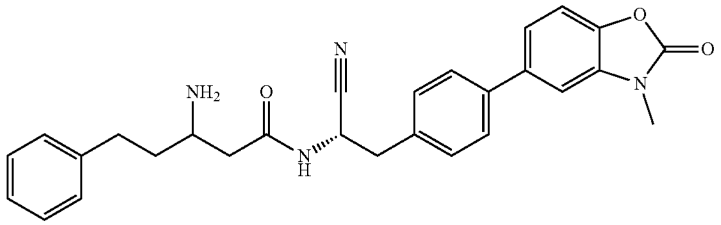 [SMILES: Cn1c(=O)oc2ccc(-c3ccc(C[C@@H](C#N)NC(=O)CC(N)CCc4ccccc4)cc3)cc21] |
| 184 | 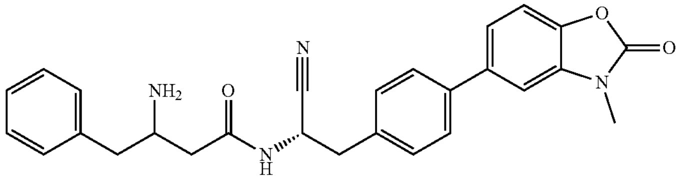 [SMILES: Cn1c(=O)oc2ccc(-c3ccc(C[C@@H](C#N)NC(=O)CC(N)Cc4ccccc4)cc3)cc21] |
| 185 | 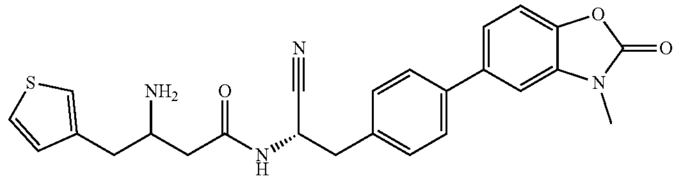 [SMILES: Cn1c(=O)oc2ccc(-c3ccc(C[C@@H](C#N)NC(=O)CC(N)Cc4ccsc4)cc3)cc21] |
| 186 | 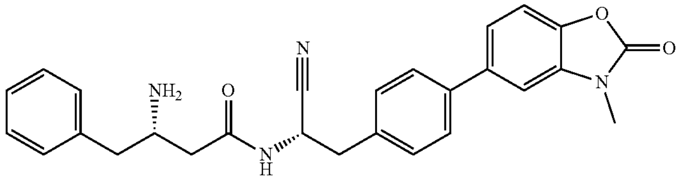 |
| 187 | 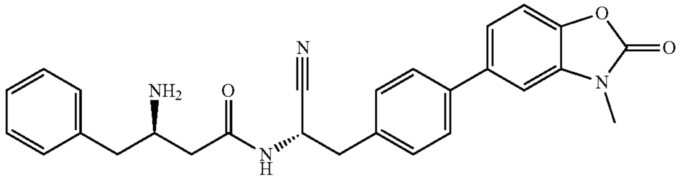 [SMILES: Cn1c(=O)oc2ccc(-c3ccc(C[C@@H](C#N)NC(=O)C[C@H](N)Cc4ccccc4)cc3)cc21] |
| 188 | 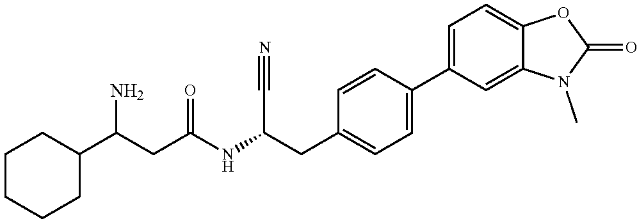 [SMILES: Cn1c(=O)oc2ccc(-c3ccc(C[C@@H](C#N)NC(=O)CC(N)C4CCCCC4)cc3)cc21] |
| 189 | 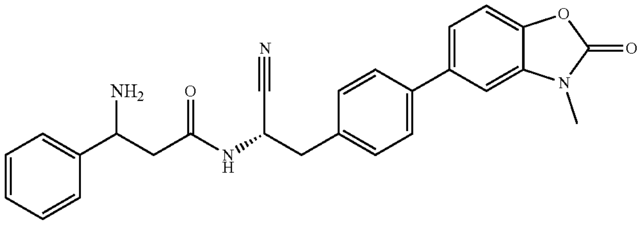 [SMILES: Cn1c(=O)oc2ccc(-c3ccc(C[C@@H](C#N)NC(=O)CC(N)c4ccccc4)cc3)cc21] |

TABLE A-continued
| Exemplary compounds of the disclosure. | |
|---|---|
| Compound No. | Structure |
| 190 | 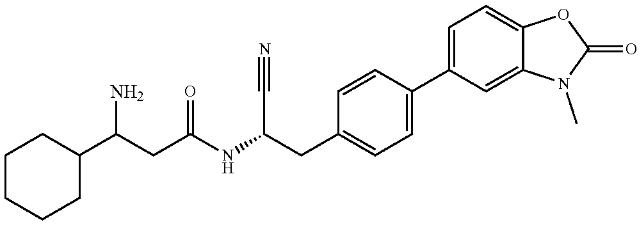 [SMILES: Cn1c(=O)oc2ccc(-c3ccc(C[C@@H](C#N)NC(=O)CC(N)C4CCCCC4)cc3)cc21] |
| 191 | 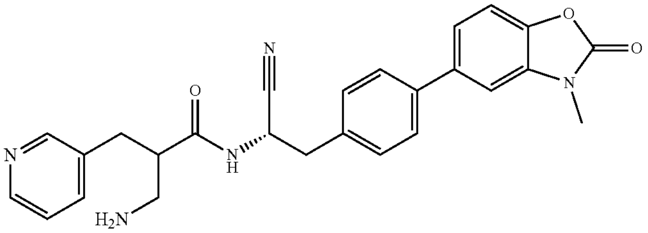 [SMILES: Cn1c(=O)oc2ccc(-c3ccc(C[C@@H](C#N)NC(=O)C(CN)Cc4cccnc4)cc3)cc21] |
| 192 | 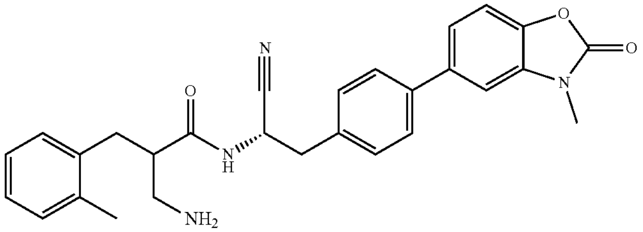 [SMILES: Cc1ccccc1CC(CN)C(=O)N[C@H](C#N)Cc1ccc(-c2ccc3oc(=O)n(C)c3c2)cc1] |
| 193 | 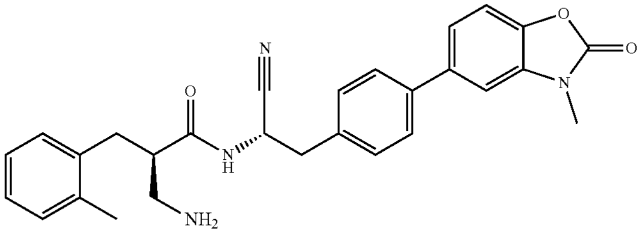 [SMILES: Cc1ccccc1C[C@H](CN)C(=O)N[C@H](C#N)Cc1ccc(-c2ccc3oc(=O)n(C)c3c2)cc1] |
| 194 | 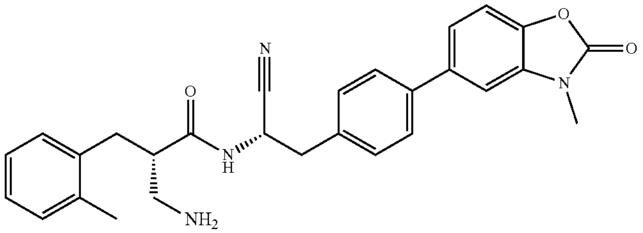 |
| 195 | 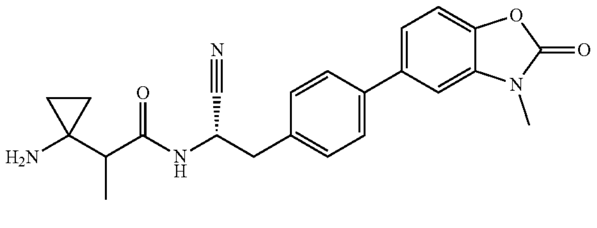 [SMILES: CC(C(=O)N[C@H](C#N)Cc1ccc(-c2ccc3oc(=O)n(C)c3c2)cc1)C1(N)CC1] |

TABLE A-continued
| Exemplary compounds of the disclosure. | |
|---|---|
| Compound No. | Structure |
| 196 | 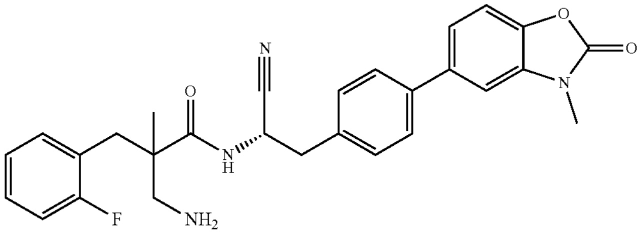 [SMILES: Cn1c(=O)oc2ccc(-c3ccc(C[C@@H](C#N)NC(=O)C(C)(CN)Cc4ccccc4F)cc3)cc21] |
| 197 | 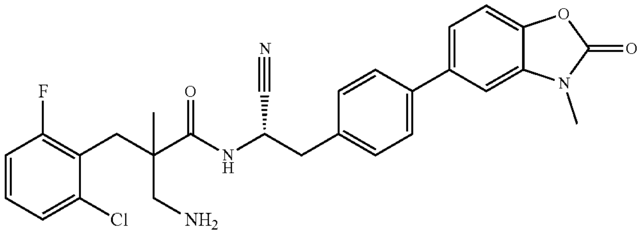 [SMILES: Cn1c(=O)oc2ccc(-c3ccc(C[C@@H](C#N)NC(=O)C(C)(CN)Cc4c(F)cccc4Cl)cc3)cc21] |
| 198 | 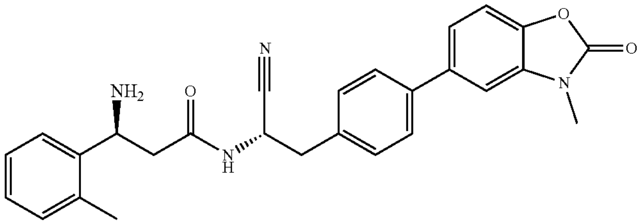 [SMILES: Cc1ccccc1[C@@H](N)CC(=O)N[C@H](C#N)Cc1ccc(-c2ccc3oc(=O)n(C)c3c2)cc1] |
| 199 | 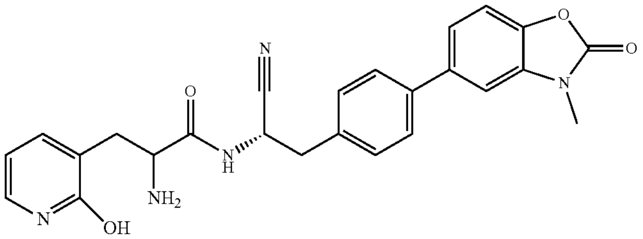 [SMILES: Cn1c(=O)oc2ccc(-c3ccc(C[C@@H](C#N)NC(=O)C(N)Cc4cccnc4O)cc3)cc21] |
| 200 | 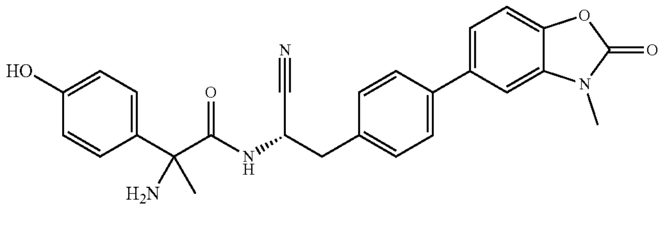 [SMILES: Cn1c(=O)oc2ccc(-c3ccc(C[C@@H](C#N)NC(=O)C(C)(N)c4ccc(O)cc4)cc3)cc21] |
| 201 | 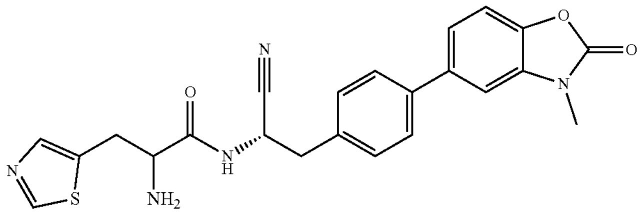 [SMILES: Cn1c(=O)oc2ccc(-c3ccc(C[C@@H](C#N)NC(=O)C(N)Cc4cncs4)cc3)cc21] |

TABLE A-continued
| Exemplary compounds of the disclosure. | |
| --- | --- |
| Compound No. | Structure |
| 202 | 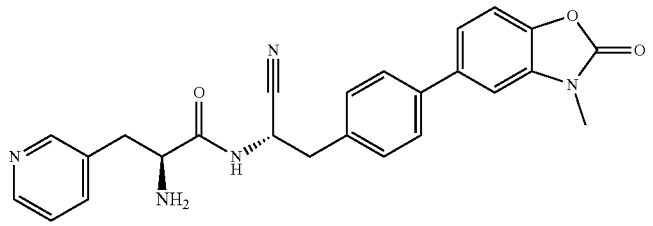 [SMILES: Cn1c(=O)oc2ccc(-c3ccc(C[C@@H](C#N)NC(=O)[C@@H](N)Cc4cccnc4)cc3)cc21] |
| 203 | 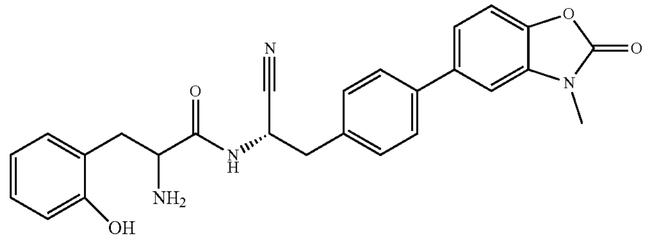 [SMILES: Cn1c(=O)oc2ccc(-c3ccc(C[C@@H](C#N)NC(=O)C(N)Cc4ccccc4O)cc3)cc21] |
| 204 | 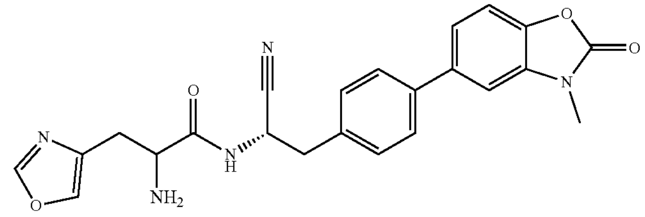 [SMILES: Cn1c(=O)oc2ccc(-c3ccc(C[C@@H](C#N)NC(=O)C(N)Cc4cocn4)cc3)cc21] |
| 205 | 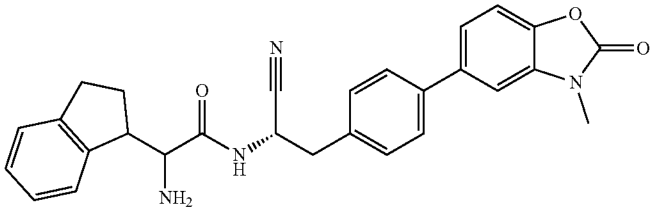 [SMILES: Cn1c(=O)oc2ccc(-c3ccc(C[C@@H](C#N)NC(=O)C(N)C4CCc5ccccc54)cc3)cc21] |
| 206 | 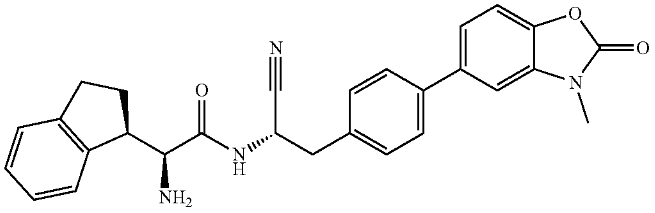 [SMILES: Cn1c(=O)oc2ccc(-c3ccc(C[C@@H](C#N)NC(=O)[C@@H](N)[C@@H]4CCc5ccccc54)cc3)cc21] |
| 207 | 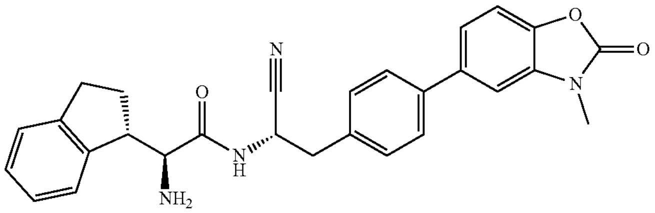 [SMILES: Cn1c(=O)oc2ccc(-c3ccc(C[C@@H](C#N)NC(=O)[C@@H](N)[C@H]4CCc5ccccc54)cc3)cc21] |

TABLE A-continued
| Exemplary compounds of the disclosure. | |
|---|---|
| Compound No. | Structure |
| 208 | 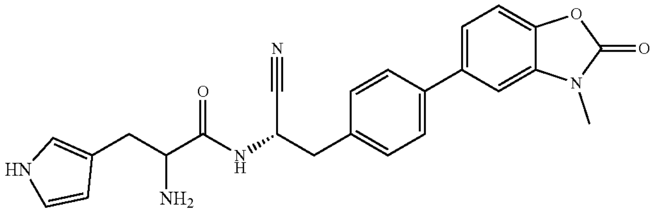 |
| 209 | 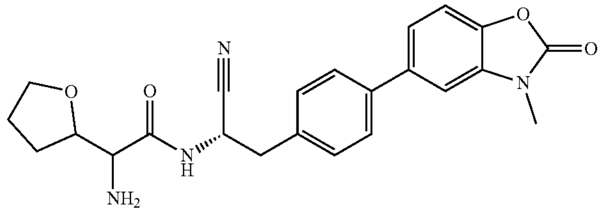 |
| 210 | 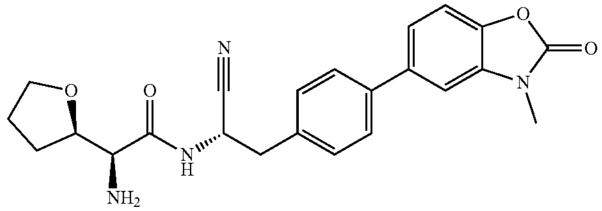 [SMILES: Cn1c(=O)oc2ccc(-c3ccc(C[C@@H](C#N)NC(=O)[C@@H](N)[C@H]4CCCO4)cc3)cc21] |
| 211 | 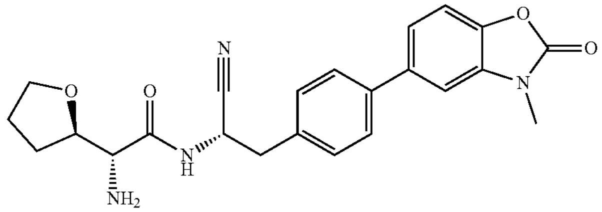 |
| 212 | 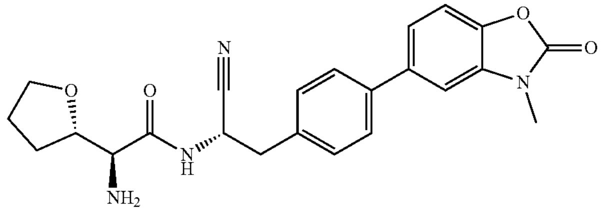 |
| 213 | 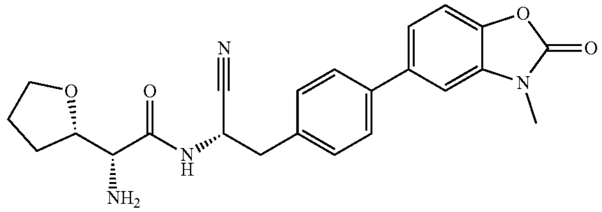 [SMILES: Cn1c(=O)oc2ccc(-c3ccc(C[C@@H](C#N)NC(=O)[C@H](N)[C@@H]4CCCO4)cc3)cc21] |
| 214 | 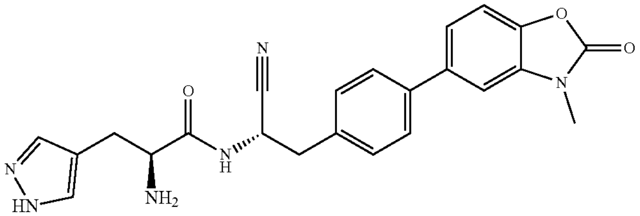 [SMILES: Cn1c(=O)oc2ccc(-c3ccc(C[C@@H](C#N)NC(=O)[C@@H](N)Cc4cn[nH]c4)cc3)cc21] |

TABLE A-continued
| Exemplary compounds of the disclosure. | |
|---|---|
| Compound No. | Structure |
| 215 | 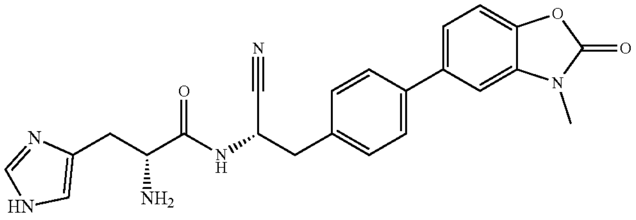 [SMILES: Cn1c(=O)oc2ccc(-c3ccc(C[C@@H](C#N)NC(=O)[C@H](N)Cc4c[nH]cn4)cc3)cc21] |
| 216 | 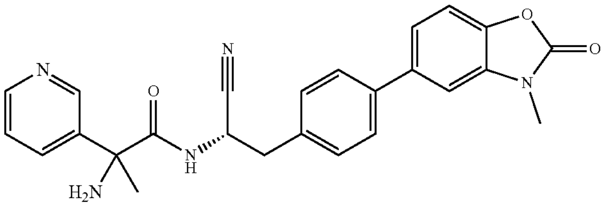 [SMILES: Cn1c(=O)oc2ccc(-c3ccc(C[C@@H](C#N)NC(=O)C(C)(N)c4cccnc4)cc3)cc21] |
| 217 | 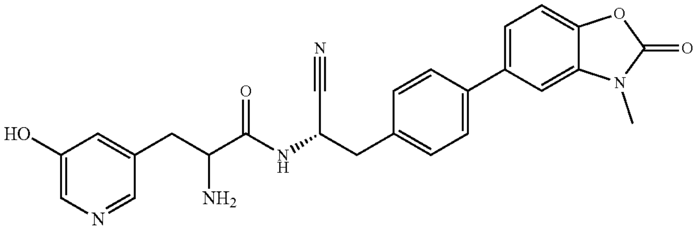 [SMILES: Cn1c(=O)oc2ccc(-c3ccc(C[C@@H](C#N)NC(=O)C(N)Cc4cncc(O)c4)cc3)cc21] |
| 218 | 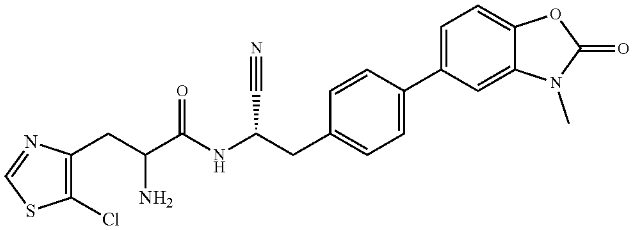 [SMILES: Cn1c(=O)oc2ccc(-c3ccc(C[C@@H](C#N)NC(=O)C(N)Cc4ncsc4Cl)cc3)cc21] |
| 219 | 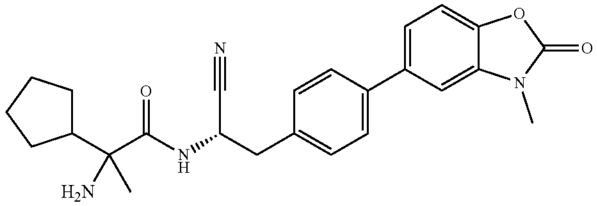 [SMILES: Cn1c(=O)oc2ccc(-c3ccc(C[C@@H](C#N)NC(=O)C(C)(N)C4CCCC4)cc3)cc21] |
| 219A | 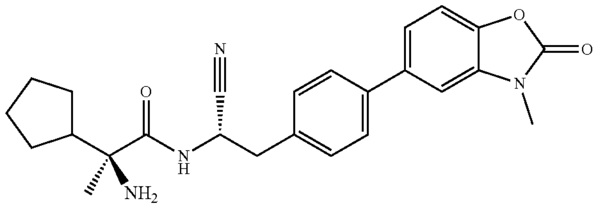 [SMILES: Cn1c(=O)oc2ccc(-c3ccc(C[C@@H](C#N)NC(=O)[C@@](C)(N)C4CCCC4)cc3)cc21] |

TABLE A-continued
| Exemplary compounds of the disclosure. | |
|---|---|
| Compound No. | Structure |
| 219B | 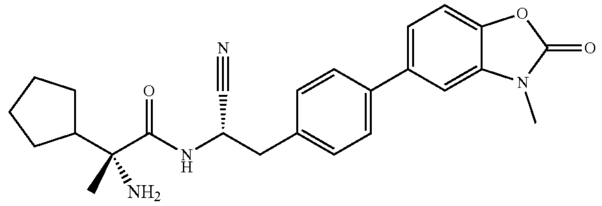 [SMILES: Cn1c(=O)oc2ccc(-c3ccc(C[C@@H](C#N)NC(=O)[C@](C)(N)C4CCCC4)cc3)cc21] |
| 220 | 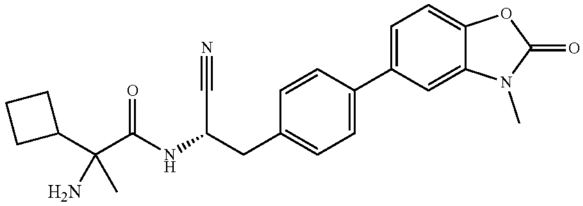 [SMILES: Cn1c(=O)oc2ccc(-c3ccc(C[C@@H](C#N)NC(=O)C(C)(N)C4CCC4)cc3)cc21] |
| 221 | 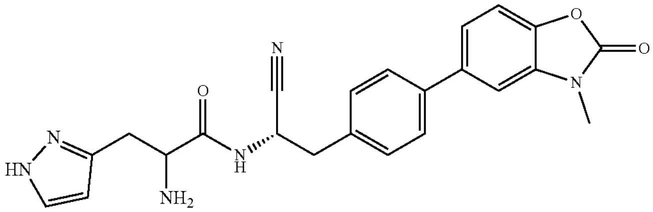 [SMILES: Cn1c(=O)oc2ccc(-c3ccc(C[C@@H](C#N)NC(=O)C(N)Cc4cc[nH]n4)cc3)cc21] |
| 222 | 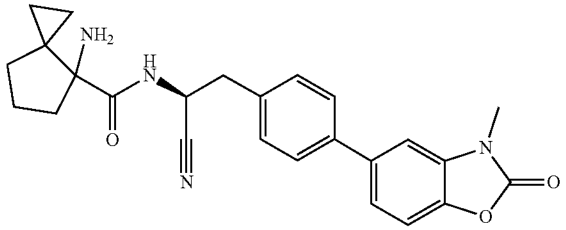 [SMILES: Cn1c(=O)oc2ccc(-c3ccc(C[C@@H](C#N)NC(=O)C4(N)CCCC45CC5)cc3)cc21] |
| 223 | 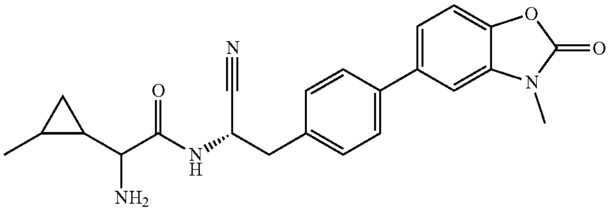 [SMILES: CC1CC1C(N)C(=O)N[C@H](C#N)Cc1ccc(-c2ccc3oc(=O)n(C)c3c2)cc1] |
| 224 | 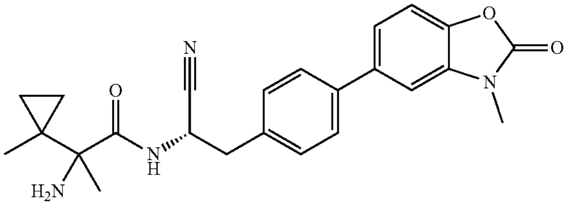 [SMILES: Cn1c(=O)oc2ccc(-c3ccc(C[C@@H](C#N)NC(=O)C(C)(N)C4(C)CC4)cc3)cc21] |
| 225 | 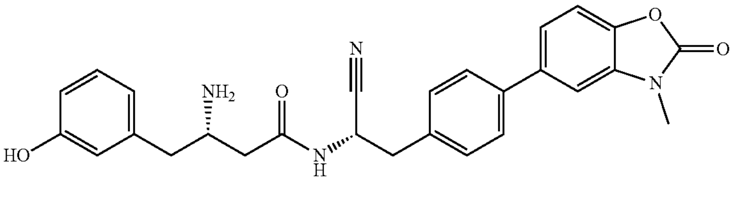 [SMILES: Cn1c(=O)oc2ccc(-c3ccc(C[C@@H](C#N)NC(=O)C[C@@H](N)Cc4cccc(O)c4)cc3)cc21] |

TABLE A-continued
| Exemplary compounds of the disclosure. | |
|---|---|
| Compound No. | Structure |
| 226 | 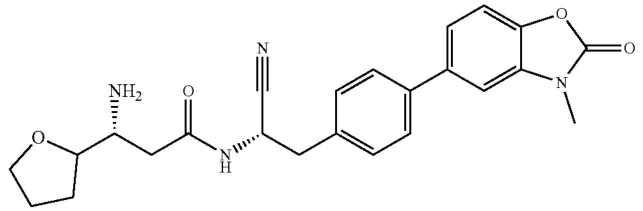 [SMILES: Cn1c(=O)oc2ccc(-c3ccc(C[C@@H](C#N)NC(=O)C[C@@H](N)C4CCCO4)cc3)cc21] |
| 227 | 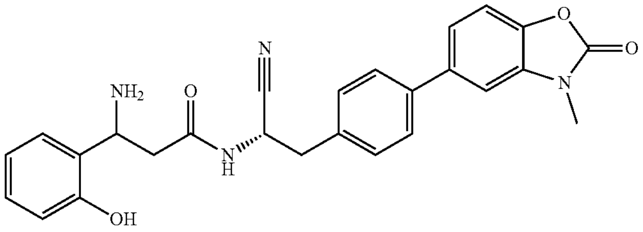 [SMILES: Cn1c(=O)oc2ccc(-c3ccc(C[C@@H](C#N)NC(=O)CC(N)c4ccccc4O)cc3)cc21] |
| 227A | 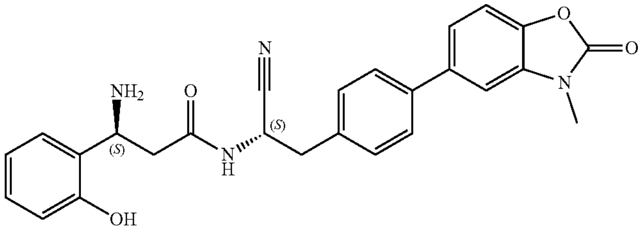 |
| 227B | 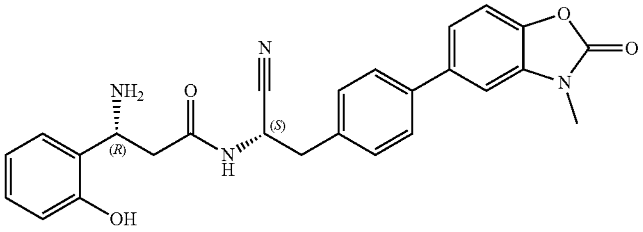 |
| 228 | 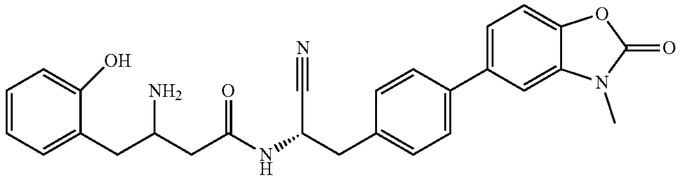 [SMILES: Cn1c(=O)oc2ccc(-c3ccc(C[C@@H](C#N)NC(=O)CC(N)Cc4ccccc4O)cc3)cc21] |
| 229 | 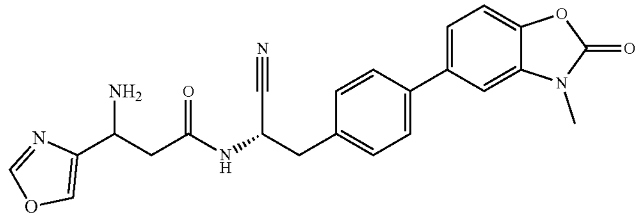 [SMILES: Cn1c(=O)oc2ccc(-c3ccc(C[C@@H](C#N)NC(=O)CC(N)c4cocn4)cc3)cc21] |
| 230 | 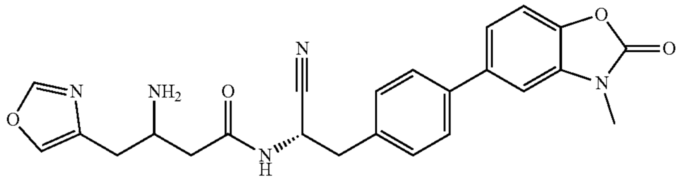 |

TABLE A-continued
| Exemplary compounds of the disclosure. | |
|---|---|
| Compound No. | Structure |
| 231 | 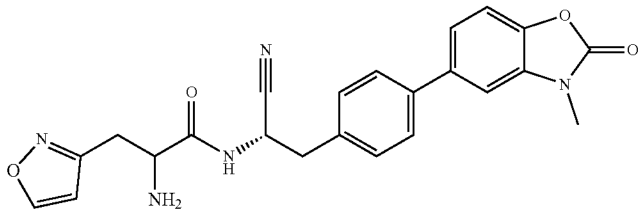 [SMILES: Cn1c(=O)oc2ccc(-c3ccc(C[C@@H](C#N)NC(=O)C(N)Cc4ccon4)cc3)cc21] |
| 232 | 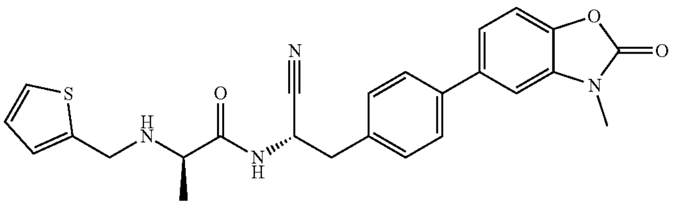 [SMILES: C[C@@H](NCc1cccs1)C(=O)N[C@H](C#N)Cc1ccc(-c2ccc3oc(=O)n(C)c3c2)cc1] |
| 233 | 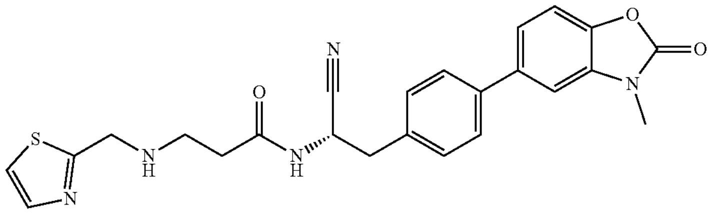 [SMILES: Cn1c(=O)oc2ccc(-c3ccc(C[C@@H](C#N)NC(=O)CCNCc4nccs4)cc3)cc21] |
| 234 | 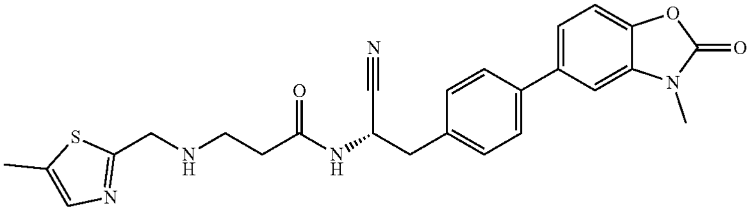 [SMILES: Cc1cnc(CNCCC(=O)N[C@H](C#N)Cc2ccc(-c3ccc4oc(=O)n(C)c4c3)cc2)s1] |
| 235 | 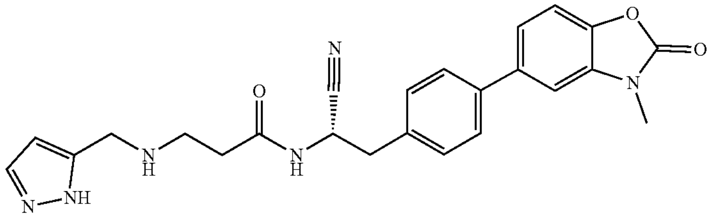 [SMILES: Cn1c(=O)oc2ccc(-c3ccc(C[C@@H](C#N)NC(=O)CCNCc4ccn[nH]4)cc3)cc21] |
| 236 | 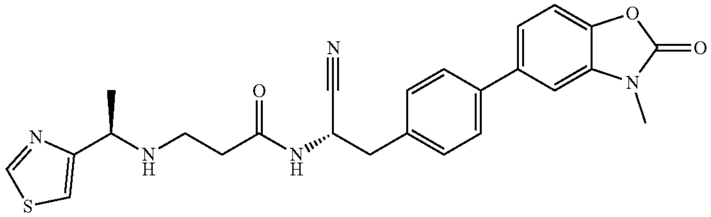 [SMILES: C[C@@H](NCCC(=O)N[C@H](C#N)Cc1ccc(-c2ccc3oc(=O)n(C)c3c2)cc1)c1cscn1] |
| 237 | 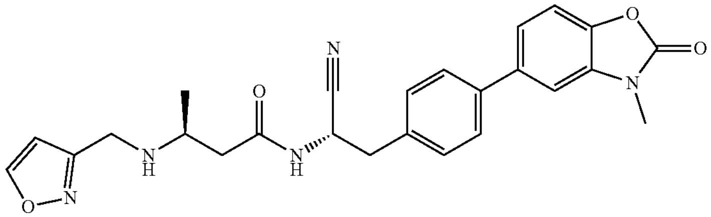 [SMILES: C[C@@H](CC(=O)N[C@H](C#N)Cc1ccc(-c2ccc3oc(=O)n(C)c3c2)cc1)NCc1ccon1] |

TABLE A-continued
| Exemplary compounds of the disclosure. | |
|---|---|
| Compound No. | Structure |
| 238 | 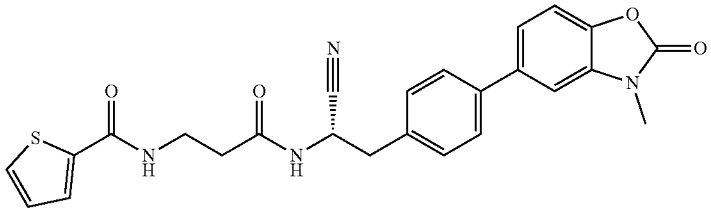 [SMILES: Cn1c(=O)oc2ccc(-c3ccc(C[C@@H](C#N)NC(=O)CCNC(=O)c4cccs4)cc3)cc21] |
| 239 | 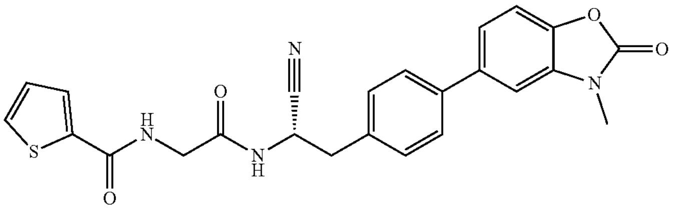 [SMILES: Cn1c(=O)oc2ccc(-c3ccc(C[C@@H](C#N)NC(=O)CNC(=O)c4cccs4)cc3)cc21] |
| 240 | 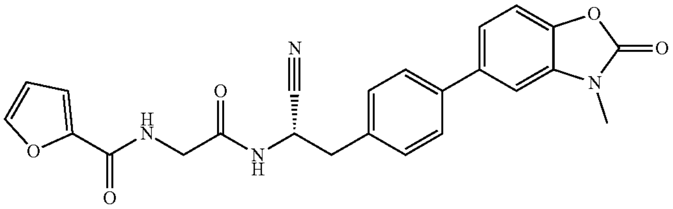 [SMILES: Cn1c(=O)oc2ccc(-c3ccc(C[C@@H](C#N)NC(=O)CNC(=O)c4ccco4)cc3)cc21] |
| 241 | 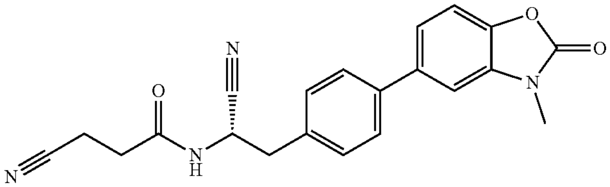 [SMILES: Cn1c(=O)oc2ccc(-c3ccc(C[C@@H](C#N)NC(=O)CCC#N)cc3)cc21] |
| 242 | 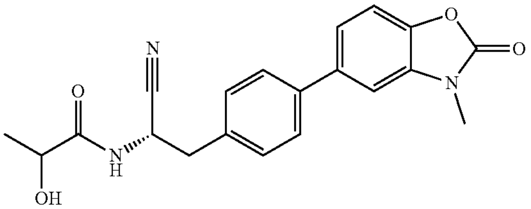 [SMILES: CC(O)C(=O)N[C@H](C#N)Cc1ccc(-c2ccc3oc(=O)n(C)c3c2)cc1] |
| 243 | 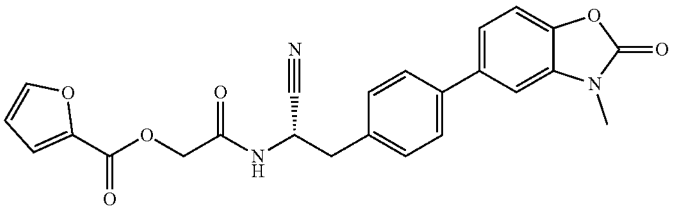 |
| 244 | 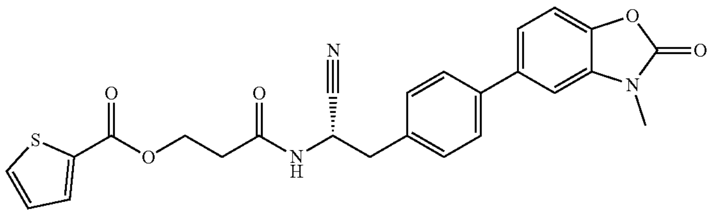 [SMILES: Cn1c(=O)oc2ccc(-c3ccc(C[C@@H](C#N)NC(=O)CCOC(=O)c4cccs4)cc3)cc21] |

TABLE A-continued
| Exemplary compounds of the disclosure. | |
|---|---|
| Compound No. | Structure |
| 245 | 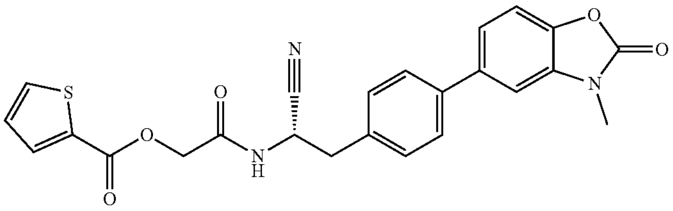 [SMILES: Cn1c(=O)oc2ccc(-c3ccc(C[C@@H](C#N)NC(=O)COC(=O)c4cccs4)cc3)cc21] |
| 246 | 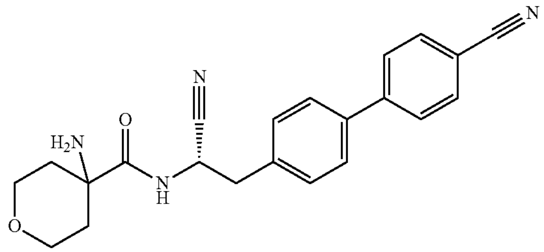 [SMILES: N#Cc1ccc(-c2ccc(C[C@@H](C#N)NC(=O)C3(N)CCOCC3)cc2)cc1] |
| 247 | 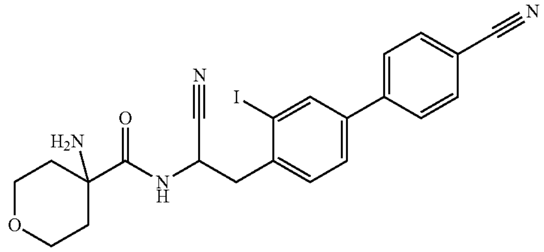 [SMILES: N#Cc1ccc(-c2ccc(CC(C#N)NC(=O)C3(N)CCOCC3)c(I)c2)cc1] |
| 248 | 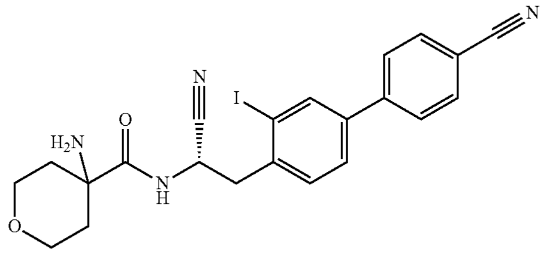 [SMILES: N#Cc1ccc(-c2ccc(C[C@@H](C#N)NC(=O)C3(N)CCOCC3)c(I)c2)cc1] |
| 249 | 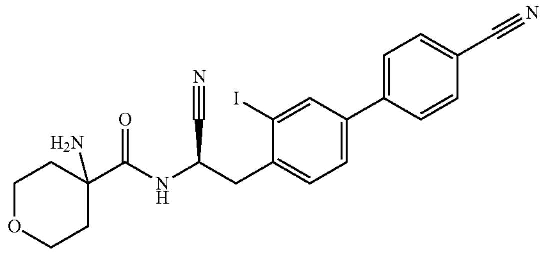 [SMILES: N#Cc1ccc(-c2ccc(C[C@H](C#N)NC(=O)C3(N)CCOCC3)c(I)c2)cc1] |
| 250 | 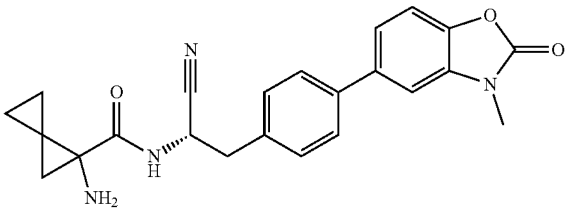 [SMILES: Cn1c(=O)oc2ccc(-c3ccc(C[C@@H](C#N)NC(=O)C4(N)CC45CC5)cc3)cc21] |

TABLE A-continued
| Exemplary compounds of the disclosure. | |
|---|---|
| Compound No. | Structure |
| 251 | 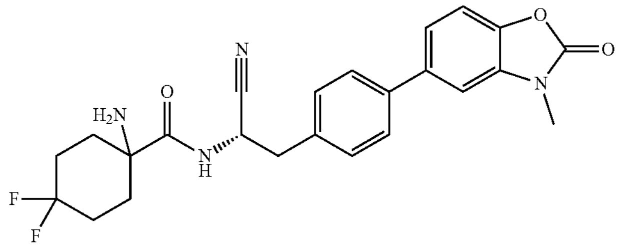 [SMILES: Cn1c(=O)oc2ccc(-c3ccc(C[C@@H](C#N)NC(=O)C4(N)CCC(F)(F)CC4)cc3)cc21] |
| 252 | 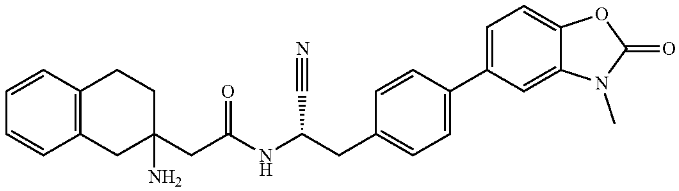 [SMILES: Cn1c(=O)oc2ccc(-c3ccc(C[C@@H](C#N)NC(=O)CC4(N)CCc5ccccc5C4)cc3)cc21] |
| 253 | 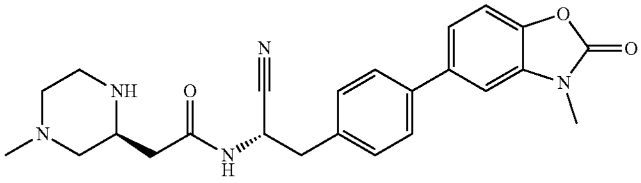 [SMILES: CN1CCN[C@@H](CC(=O)N[C@H](C#N)Cc2ccc(-c3ccc4oc(=O)n(C)c4c3)cc2)C1] |
| 254 | 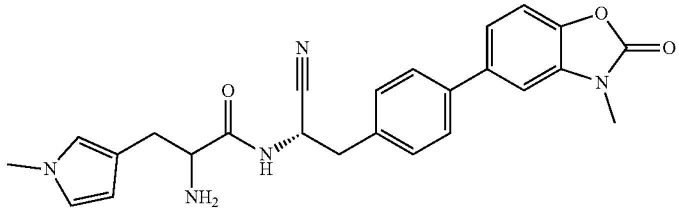 [SMILES: Cn1ccc(CC(N)C(=O)N[C@H](C#N)Cc2ccc(-c3ccc4oc(=O)n(C)c4c3)cc2)c1] |
| 255 | 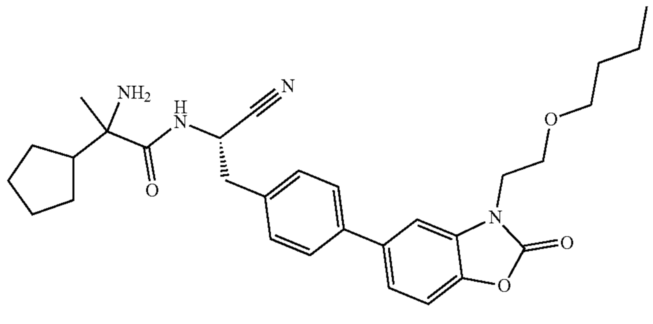 [SMILES: CCCCOCCn1c(=O)oc2ccc(-c3ccc(C[C@@H](C#N)NC(=O)C(C)(N)C4CCCC4)cc3)cc21] |
| 256 | 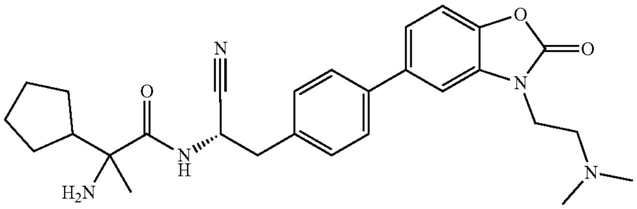 [SMILES: CN(C)CCn1c(=O)oc2ccc(-c3ccc(C[C@@H](C#N)NC(=O)C(C)(N)C4CCCC4)cc3)cc21] |

TABLE A-continued
| Exemplary compounds of the disclosure. | |
|---|---|
| Compound No. | Structure |
| 257 | 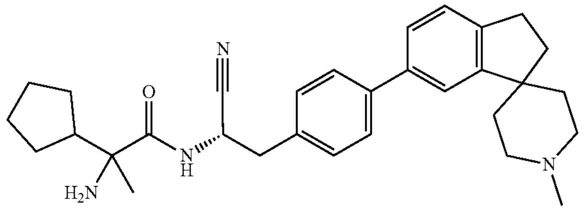 [SMILES: CN1CCC2(CCc3ccc(-c4ccc(C[C@@H](C#N)NC(=O)C(C)(N)C5CCCC5)cc4)cc32)CC1] |
| 258 | 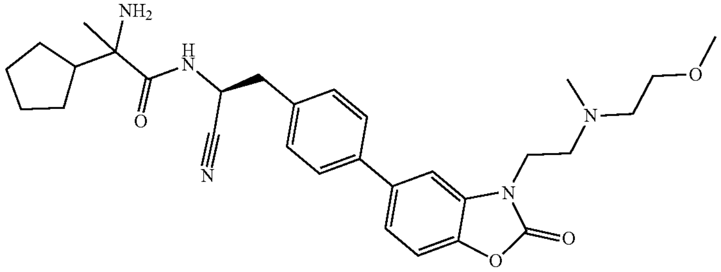 [SMILES: COCCN(C)CCn1c(=O)oc2ccc(-c3ccc(C[C@@H](C#N)NC(=O)C(C)(N)C4CCCC4)cc3)cc21] |
| 259 | 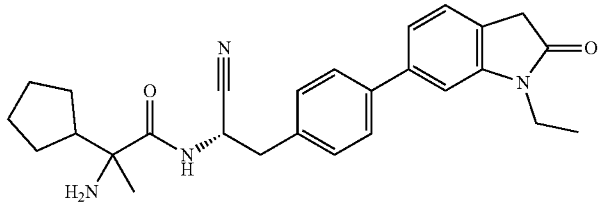 [SMILES: CCN1C(=O)Cc2ccc(-c3ccc(C[C@@H](C#N)NC(=O)C(C)(N)C4CCCC4)cc3)cc21] |
| 260 | 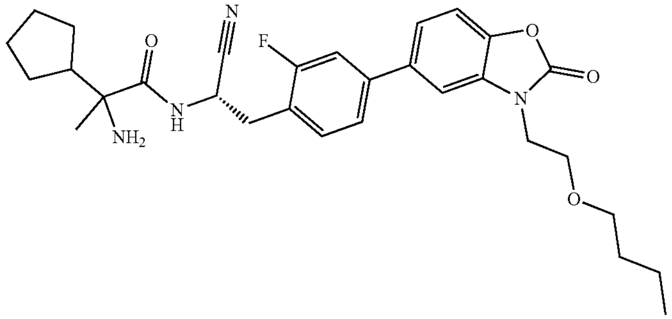 [SMILES: CCCCOCCn1c(=O)oc2ccc(-c3ccc(C[C@@H](C#N)NC(=O)C(C)(N)C4CCCC4)c(F)c3)cc21] |
| 261 | 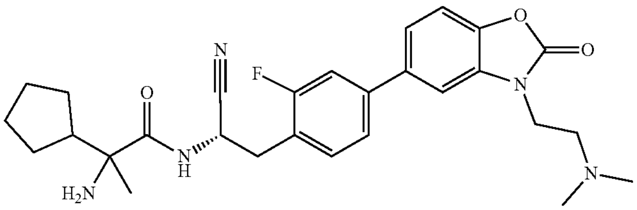 [SMILES: CN(C)CCn1c(=O)oc2ccc(-c3ccc(C[C@@H](C#N)NC(=O)C(C)(N)C4CCCC4)c(F)c3)cc21] |
| 262 | 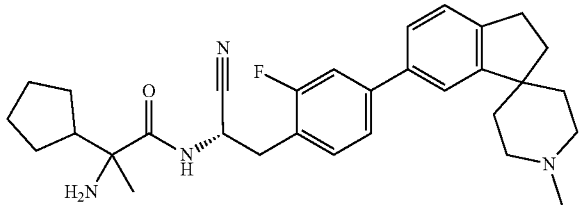 [SMILES: CN1CCC2(CCc3ccc(-c4ccc(C[C@@H](C#N)NC(=O)C(C)(N)C5CCCC5)c(F)c4)cc32)CC1] |

TABLE A-continued
| Exemplary compounds of the disclosure. | |
|---|---|
| Compound No. | Structure |
| 263 | 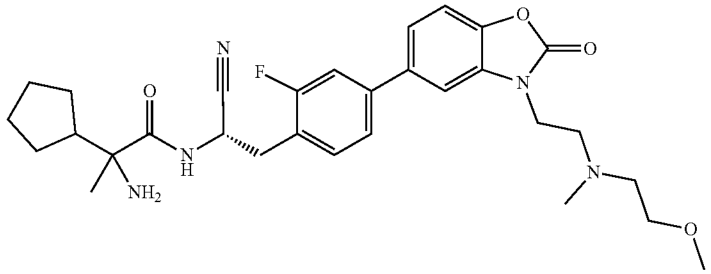 [SMILES: COCCN(C)CCn1c(=O)oc2ccc(-c3ccc(C[C@@H](C#N)NC(=O)C(C)(N)C4CCCC4)c(F)c3)cc21] |
| 264 | 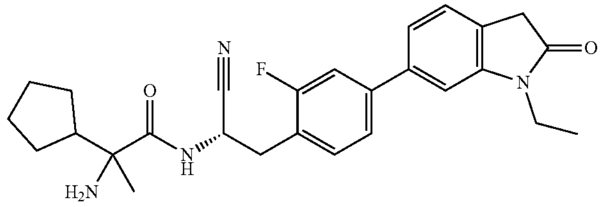 |
| 264A | 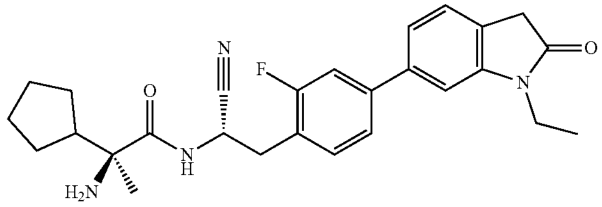 [SMILES: CCN1C(=O)Cc2ccc(-c3ccc(C[C@@H](C#N)NC(=O)[C@@](C)(N)C4CCCC4)c(F)c3)cc21] |
| 264B | 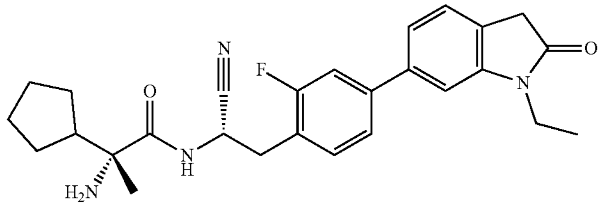 [SMILES: CCN1C(=O)Cc2ccc(-c3ccc(C[C@@H](C#N)NC(=O)[C@](C)(N)C4CCCC4)c(F)c3)cc21] |
| 265 | 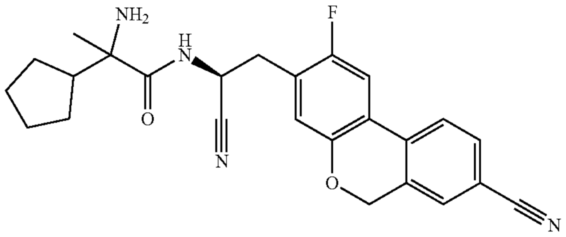 [SMILES: CC(N)(C(=O)N[C@H](C#N)Cc1cc2c(cc1F)-c1ccc(C#N)cc1CO2)C1CCCC1] |
| 266 | 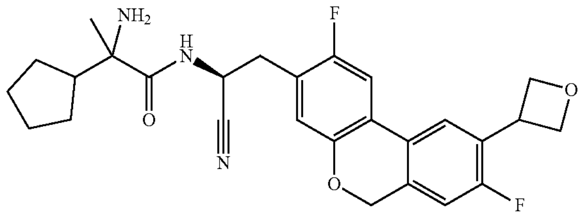 [SMILES: CC(N)(C(=O)N[C@H](C#N)Cc1cc2c(cc1F)-c1cc(C3COC3)c(F)cc1CO2)C1CCCC1] |

TABLE A-continued
| Exemplary compounds of the disclosure. | |
|---|---|
| Compound No. | Structure |
| 267 | 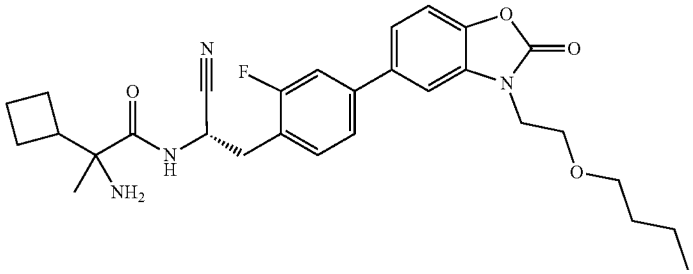 [SMILES: CCCCOCCn1c(=O)oc2ccc(-c3ccc(C[C@@H](C#N)NC(=O)C(C)(N)C4CCC4)c(F)c3)cc21] |
| 268 | 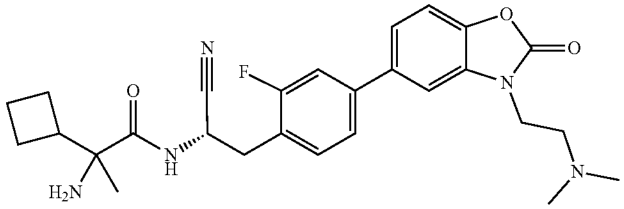 [SMILES: CN(C)CCn1c(=O)oc2ccc(-c3ccc(C[C@@H](C#N)NC(=O)C(C)(N)C4CCC4)c(F)c3)cc21] |
| 269 | 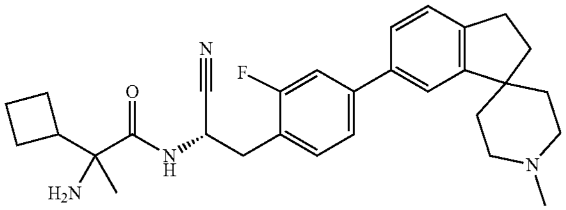 [SMILES: CN1CCC2(CCc3ccc(-c4ccc(C[C@@H](C#N)NC(=O)C(C)(N)C5CCC5)c(F)c4)cc32)CC1] |
| 270 | 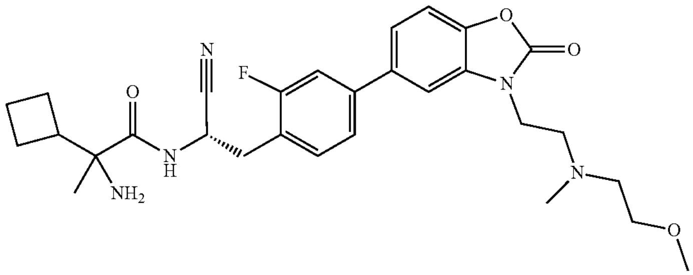 [SMILES: COCCN(C)CCn1c(=O)oc2ccc(-c3ccc(C[C@@H](C#N)NC(=O)C(C)(N)C4CCC4)c(F)c3)cc21] |
| 271 | 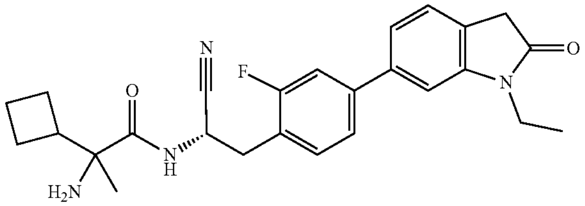 [SMILES: CCN1C(=O)Cc2ccc(-c3ccc(C[C@@H](C#N)NC(=O)C(C)(N)C4CCC4)c(F)c3)cc21] |
| 272 | 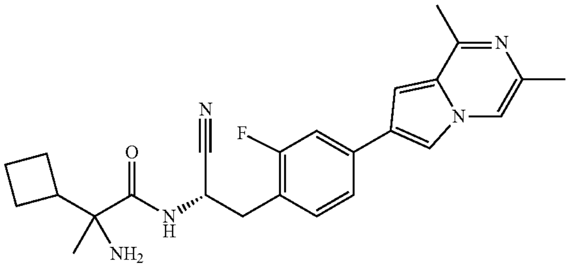 [SMILES: Cc1cn2cc(-c3ccc(C[C@@H](C#N)NC(=O)C(C)(N)C4CCC4)c(F)c3)cc2c(C)n1] |

TABLE A-continued
| Exemplary compounds of the disclosure. | |
|---|---|
| Compound No. | Structure |
| 272A | 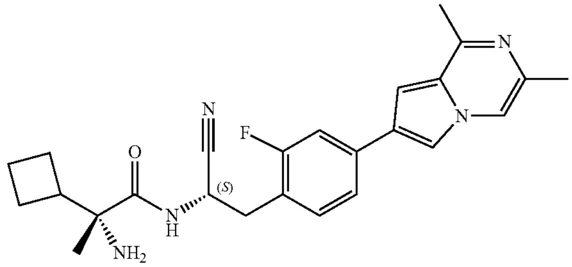 |
| 272B | 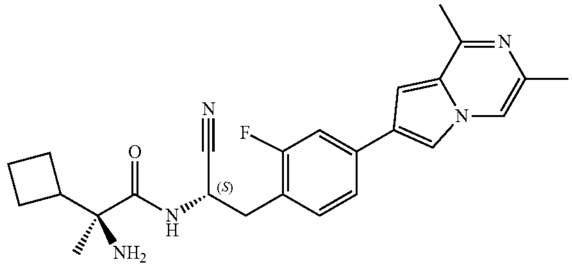 |
| 273 | 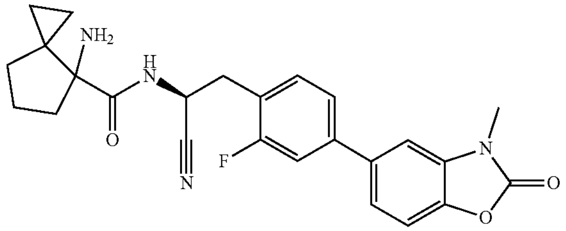 [SMILES: Cn1c(=O)oc2ccc(-c3ccc(C[C@@H](C#N)NC(=O)C4(N)CCCC45CC5)c(F)c3)cc21] |
| 274 | 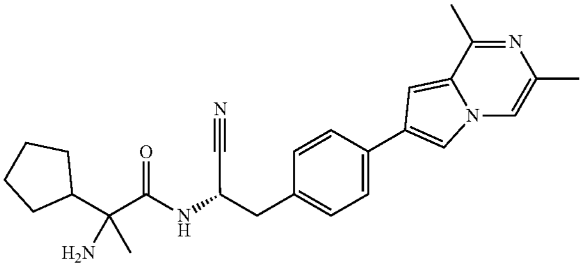 [SMILES: Cc1cn2cc(-c3ccc(C[C@@H](C#N)NC(=O)C(C)(N)C4CCCC4)cc3)cc2c(C)n1] |
| 275 | 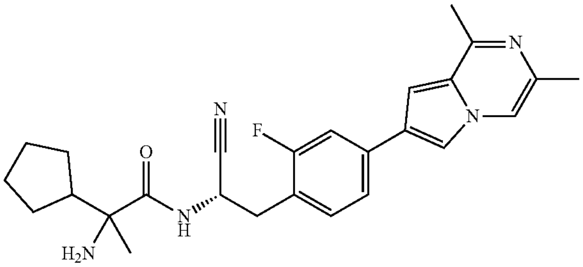 [SMILES: Cc1cn2cc(-c3ccc(C[C@@H](C#N)NC(=O)C(C)(N)C4CCCC4)c(F)c3)cc2c(C)n1] |

TABLE A-continued
| Exemplary compounds of the disclosure. | |
|---|---|
| Compound No. | Structure |
| 276 | 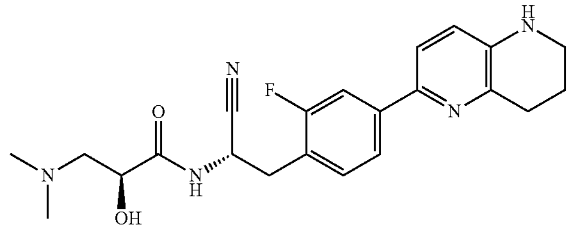 [SMILES: CN(C)C[C@H](O)C(=O)N[C@H](C#N)Cc1ccc(-c2ccc3c(n2)CCCN3)cc1F] |
| 277 | 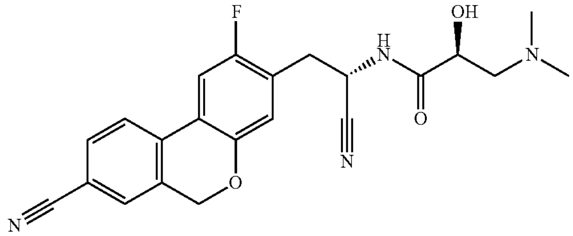 [SMILES: CN(C)C[C@H](O)C(=O)N[C@H](C#N)Cc1cc2c(cc1F)-c1ccc(C#N)cc1CO2] |
| 277A | 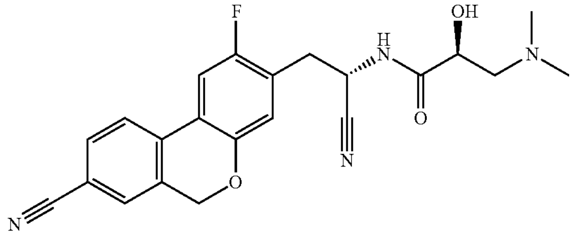 [SMILES: CN(C)C[C@H](O)C(=O)N[C@H](C#N)Cc1cc2c(cc1F)-c1ccc(C#N)cc1CO2] |
| 277B | 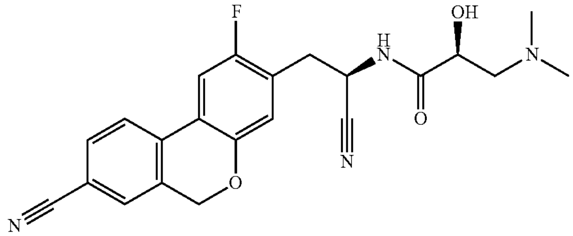 [SMILES: CN(C)C[C@H](O)C(=O)N[C@@H](C#N)Cc1cc2c(cc1F)-c1ccc(C#N)cc1CO2] |
| 278 | 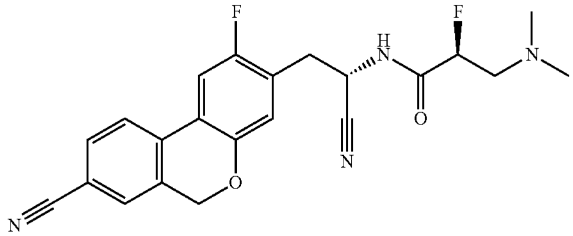 [SMILES: CN(C)C[C@H](F)C(=O)N[C@H](C#N)Cc1cc2c(cc1F)-c1ccc(C#N)cc1CO2] |
| 279 | 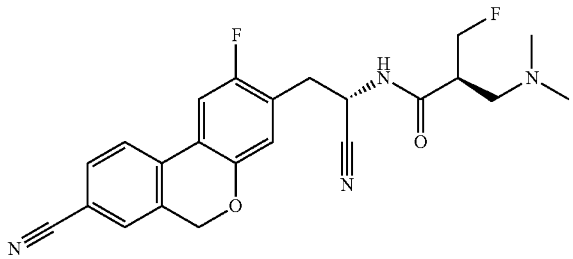 [SMILES: CN(C)C[C@H](CF)C(=O)N[C@H](C#N)Cc1cc2c(cc1F)-c1ccc(C#N)cc1CO2] |

TABLE A-continued
| Exemplary compounds of the disclosure. | |
|---|---|
| Compound No. | Structure |
| 280 | 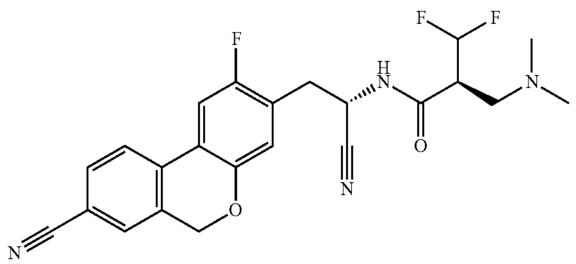 [SMILES: CN(C)C[C@@H](C(=O)N[C@H](C#N)Cc1cc2c(cc1F)-c1ccc(C#N)cc1CO2)C(F)F] |
| 281 | 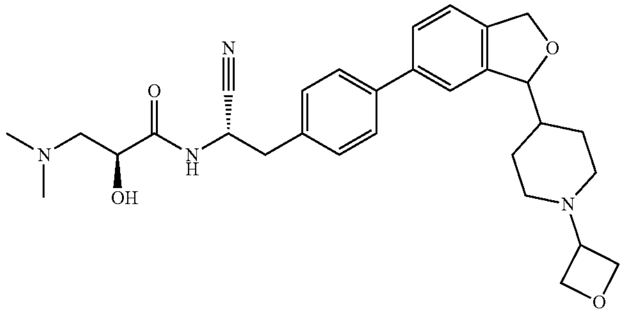 [SMILES: CN(C)C[C@H](O)C(=O)N[C@H](C#N)Cc1ccc(-c2ccc3c(c2)C(C2CCN(C4COC4)CC2)OC3)cc1] |
| 282 | 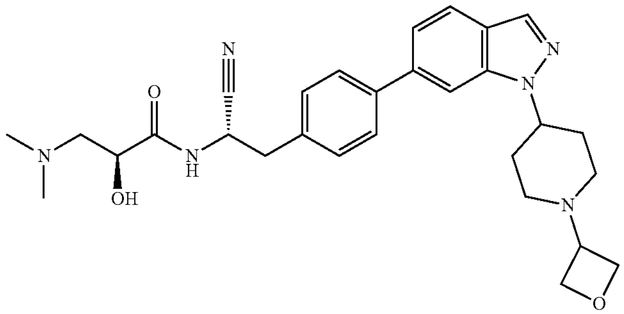 [SMILES: CN(C)C[C@H](O)C(=O)N[C@H](C#N)Cc1ccc(-c2ccc3cnn(C4CCN(C5COC5)CC4)c3c2)cc1] |
| 283 | 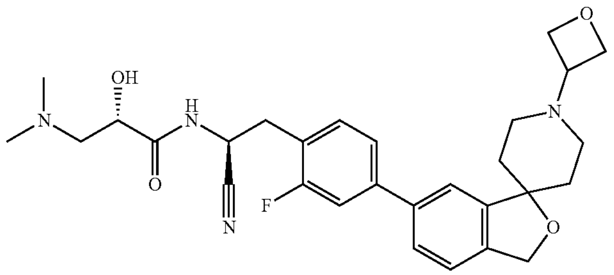 [SMILES: CN(C)C[C@H](O)C(=O)N[C@H](C#N)Cc1ccc(-c2ccc3c(c2)C2(CCN(C4COC4)CC2)OC3)cc1F] |
| 284 | 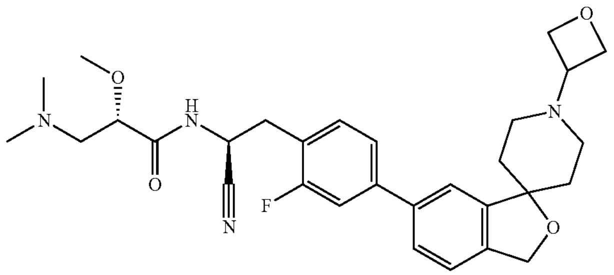 [SMILES: CO[C@@H](CN(C)C)C(=O)N[C@H](C#N)Cc1ccc(-c2ccc3c(c2)C2(CCN(C4COC4)CC2)OC3)cc1F] |

TABLE A-continued
| Exemplary compounds of the disclosure. | |
|---|---|
| Compound No. | Structure |
| 285 | 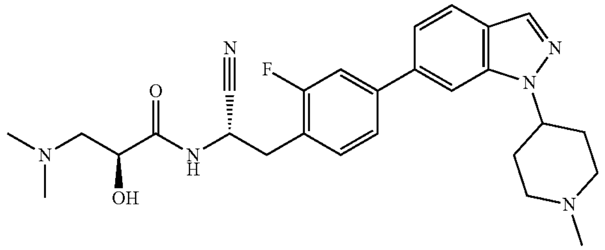 [SMILES: CN(C)C[C@H](O)C(=O)N[C@H](C#N)Cc1ccc(-c2ccc3cnn(C4CCN(C)CC4)c3c2)cc1F] |
| 286 | 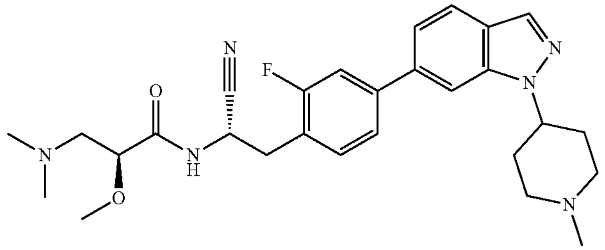 [SMILES: CO[C@@H](CN(C)C)C(=O)N[C@H](C#N)Cc1ccc(-c2ccc3cnn(C4CCN(C)CC4)c3c2)cc1F] |
| 287 | 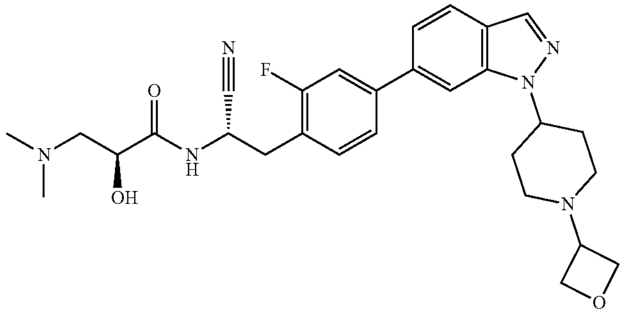 [SMILES: CN(C)C[C@H](O)C(=O)N[C@H](C#N)Cc1ccc(-c2ccc3cnn(C4CCN(C5COC5)CC4)c3c2)cc1F] |
| 288 | 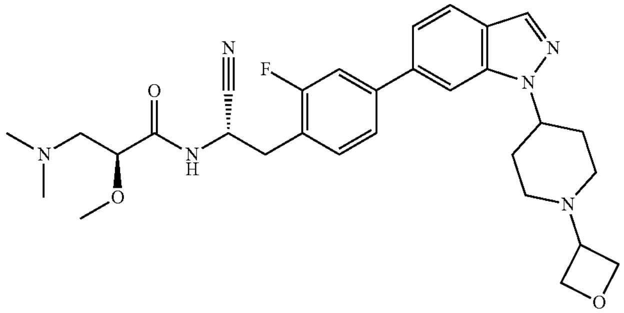 [SMILES: CO[C@@H](CN(C)C)C(=O)N[C@H](C#N)Cc1ccc(-c2ccc3cnn(C4CCN(C5COC5)CC4)c3c2)cc1F] |
| 289 | 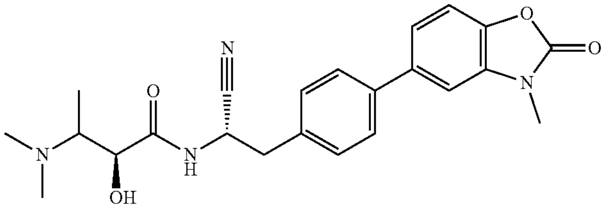 [SMILES: CC([C@H](O)C(=O)N[C@H](C#N)Cc1ccc(-c2ccc3oc(=O)n(C)c3c2)cc1)N(C)C] |

TABLE A-continued
| Exemplary compounds of the disclosure. | |
|---|---|
| Compound No. | Structure |
| 289A | 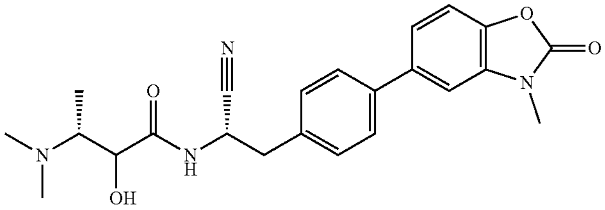 [SMILES: C[C@H](C(O)C(=O)N[C@H](C#N)Cc1ccc(-c2ccc3oc(=O)n(C)c3c2)cc1)N(C)C] |
| 292 | 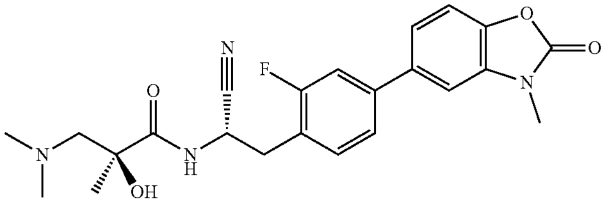 [SMILES: CN(C)C[C@](C)(O)C(=O)N[C@H](C#N)Cc1ccc(-c2ccc3oc(=O)n(C)c3c2)cc1F] |
| 293 | 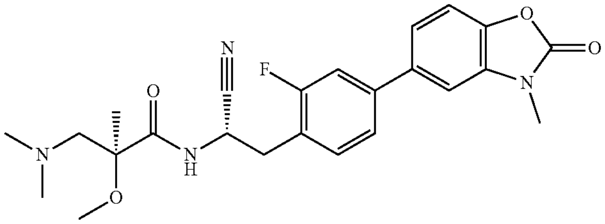 [SMILES: CO[C@@](C)(CN(C)C)C(=O)N[C@H](C#N)Cc1ccc(-c2ccc3oc(=O)n(C)c3c2)cc1F] |
| 294 | 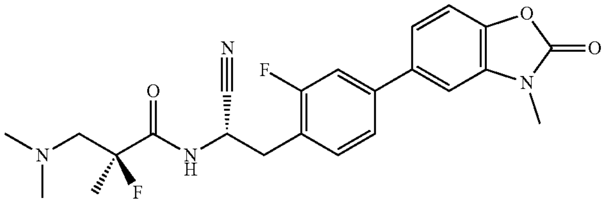 [SMILES: CN(C)C[C@](C)(F)C(=O)N[C@H](C#N)Cc1ccc(-c2ccc3oc(=O)n(C)c3c2)cc1F] |
| 102A | 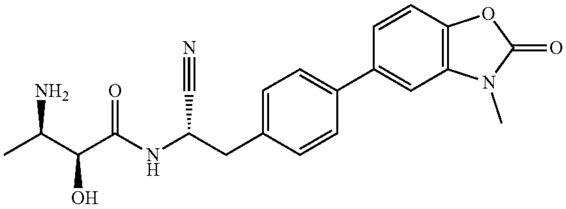 [SMILES: C[C@@H](N)[C@H](O)C(=O)N[C@H](C#N)Cc1ccc(-c2ccc3oc(=O)n(C)c3c2)cc1] |
| 102B | 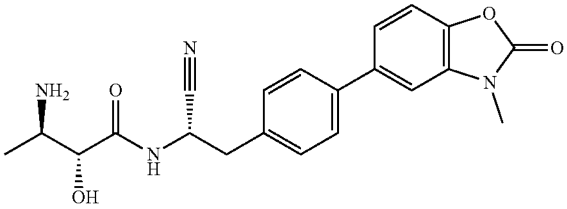 [SMILES: C[C@@H](N)[C@@H](O)C(=O)N[C@H](C#N)Cc1ccc(-c2ccc3oc(=O)n(C)c3c2)cc1] |
| 102C | 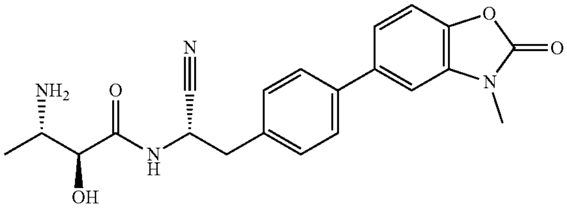 [SMILES: C[C@H](N)[C@H](O)C(=O)N[C@H](C#N)Cc1ccc(-c2ccc3oc(=O)n(C)c3c2)cc1] |

TABLE A-continued
| Exemplary compounds of the disclosure. | |
|---|---|
| Compound No. | Structure |
| 258A | 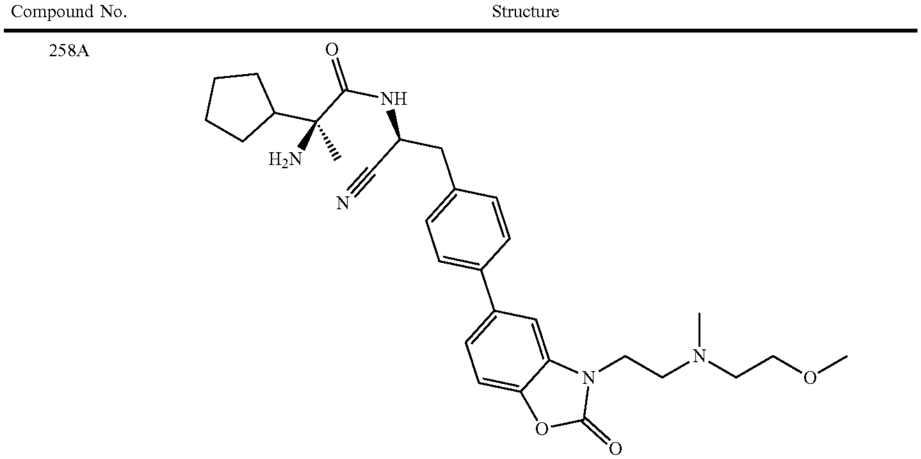 |
| 258B | 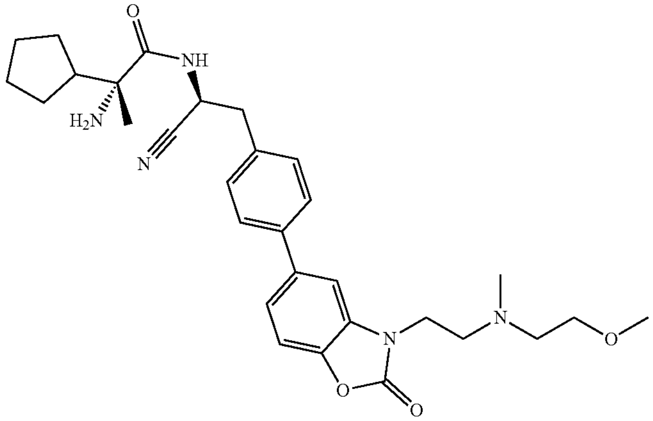 [SMILES: COCCN(C)CCn1c(=O)oc2ccc(-c3ccc(C[C@@H](C#N)NC(=O)[C@](C)(N)C4CCCC4)cc3)cc21] |
| 259A | 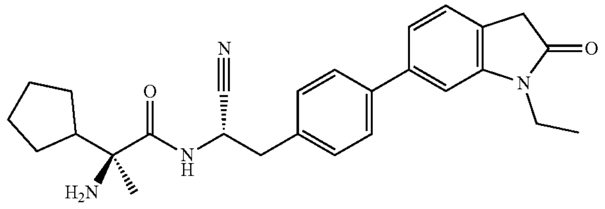 [SMILES: CCN1C(=O)Cc2ccc(-c3ccc(C[C@@H](C#N)NC(=O)[C@@](C)(N)C4CCCC4)cc3)cc21] |
| 259B | 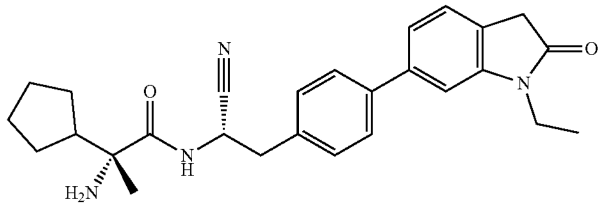 [SMILES: CCN1C(=O)Cc2ccc(-c3ccc(C[C@@H](C#N)NC(=O)[C@](C)(N)C4CCCC4)cc3)cc21] |
| 272A | 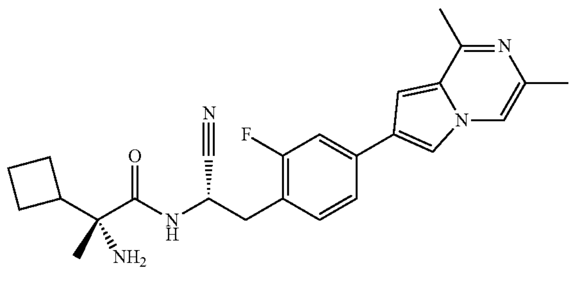 [SMILES: Cc1cn2cc(-c3ccc(C[C@@H](C#N)NC(=O)[C@](C)(N)C4CCC4)c(F)c3)cc2c(C)n1] |

TABLE A-continued
| Exemplary compounds of the disclosure. | |
|---|---|
| Compound No. | Structure |
| 272B | 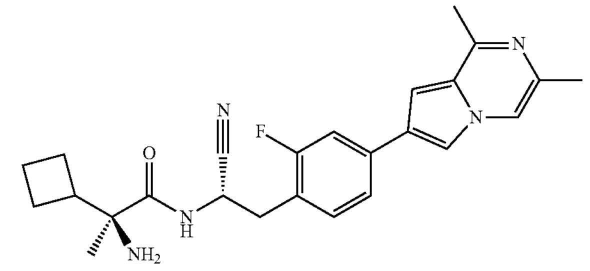 [SMILES: Cc1cn2cc(-c3ccc(C[C@@H](C#N)NC(=O)[C@@](C)(N)C4CCC4)c(F)c3)cc2c(C)n1] |
| 270A | 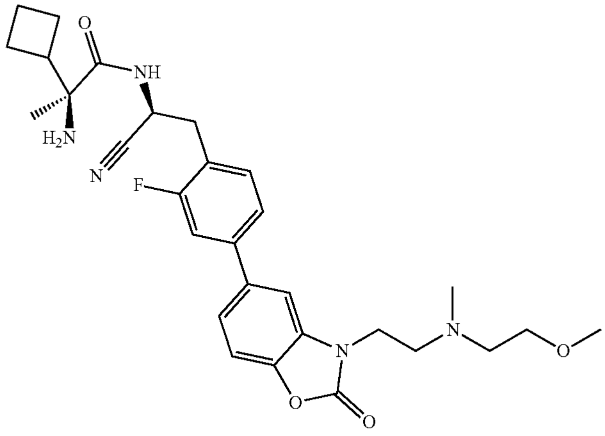 [SMILES: COCCN(C)CCn1c(=O)oc2ccc(-c3ccc(C[C@@H](C#N)NC(=O)[C@@](C)(N)C4CCC4)c(F)c3)cc21] |
| 270B | 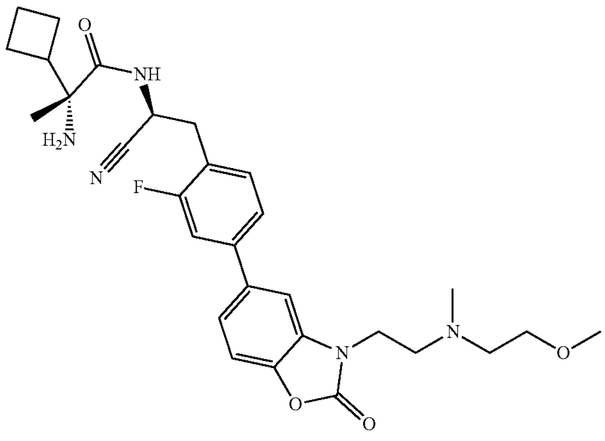 [SMILES: COCCN(C)CCn1c(=O)oc2ccc(-c3ccc(C[C@@H](C#N)NC(=O)[C@](C)(N)C4CCC4)c(F)c3)cc21] |
| 273A | 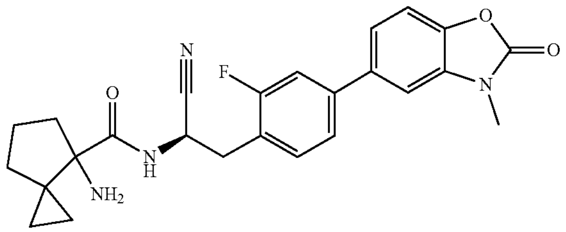 [SMILES: Cn1c(=O)oc2ccc(-c3ccc(C[C@H](C#N)NC(=O)C4(N)CCCC45CC5)c(F)c3)cc21] |

TABLE A-continued
| Exemplary compounds of the disclosure. | |
|---|---|
| Compound No. | Structure |
| 273B | 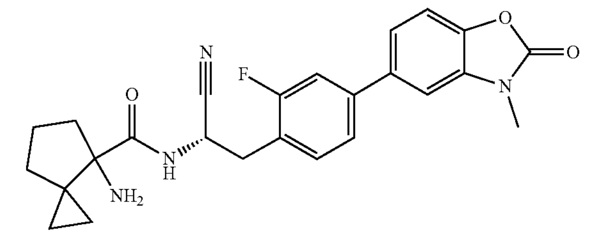 [SMILES: Cn1c(=O)oc2ccc(-c3ccc(C[C@@H](C#N)NC(=O)C4(N)CCCC45CC5)c(F)c3)cc21] |
| 274 | 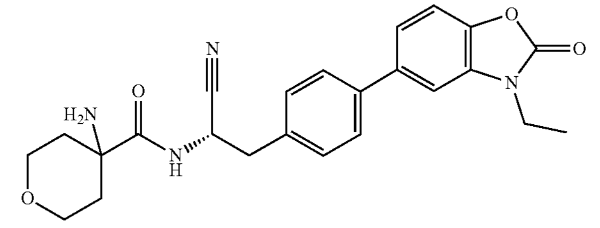 [SMILES: CCn1c(=O)oc2ccc(-c3ccc(C[C@@H](C#N)NC(=O)C4(N)CCOCC4)cc3)cc21] |
| 295 | 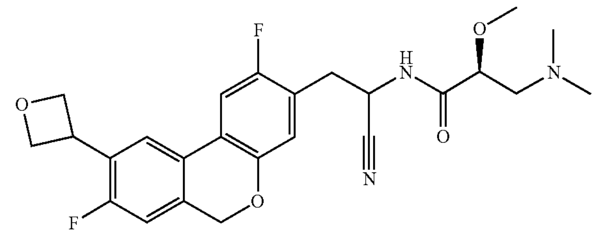 [SMILES: CO[C@@H](CN(C)C)C(=O)NC(C#N)Cc1cc2c(cc1F)-c1cc(C3COC3)c(F)cc1CO2] |
| 296 | 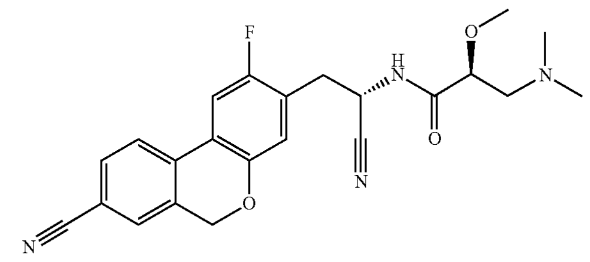 [SMILES: CO[C@@H](CN(C)C)C(=O)N[C@H](C#N)Cc1cc2c(cc1F)-c1ccc(C#N)cc1CO2] |
| 297 | 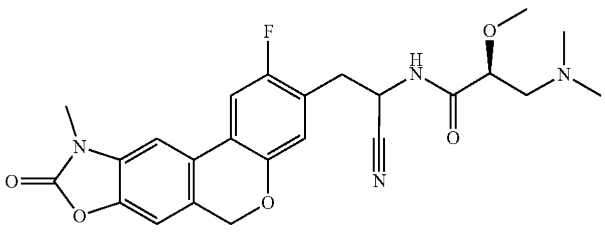 [SMILES: CO[C@@H](CN(C)C)C(=O)NC(C#N)Cc1cc2c(cc1F)-c1cc3c(cc1CO2)oc(=O)n3C] |
| 298 | 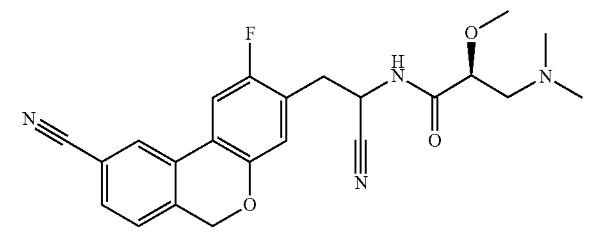 [SMILES: CO[C@@H](CN(C)C)C(=O)NC(C#N)Cc1cc2c(cc1F)-c1cc(C#N)ccc1CO2] |

TABLE A-continued
| Exemplary compounds of the disclosure. | |
|---|---|
| Compound No. | Structure |
| 299 | 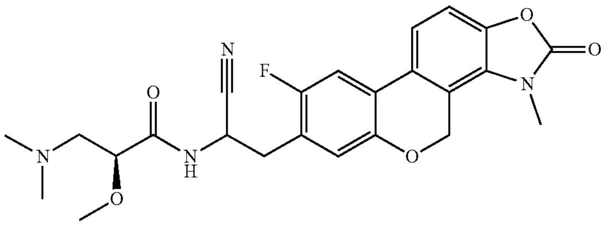 [SMILES: CO[C@@H](CN(C)C)C(=O)NC(C#N)Cc1cc2c(cc1F)-c1ccc3oc(=O)n(C)c3c1CO2] |
| 300 | 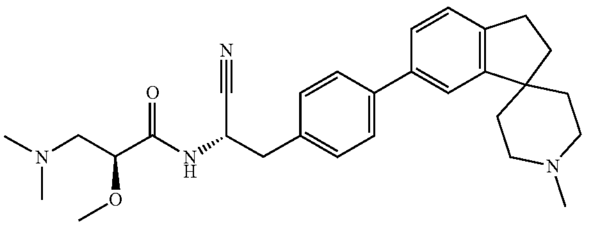 [SMILES: CO[C@@H](CN(C)C)C(=O)N[C@H](C#N)Cc1ccc(-c2ccc3c(c2)C2(CC3)CCN(C)CC2)cc1] |
| 301 | 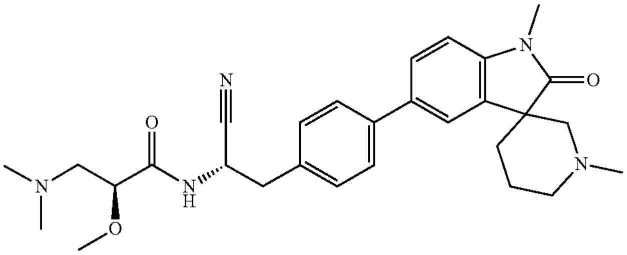 |
| 302 | 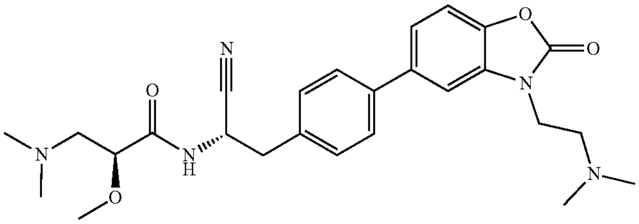 |
| 303 | 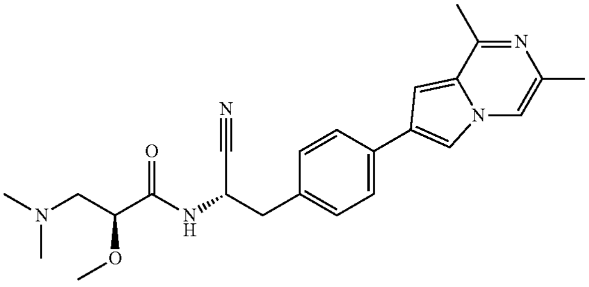 |
| 304 | 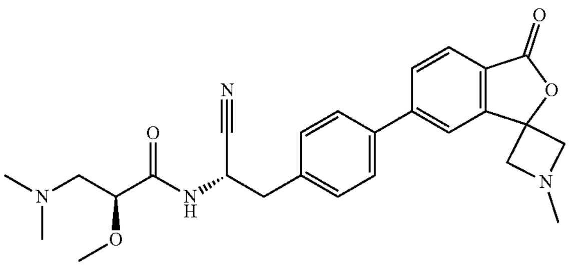 [SMILES: CO[C@@H](CN(C)C)C(=O)N[C@H](C#N)Cc1ccc(-c2ccc3c(c2)C2(CN(C)C2)OC3=O)cc1] |

TABLE A-continued
| Exemplary compounds of the disclosure. | |
|---|---|
| Compound No. | Structure |
| 305 | 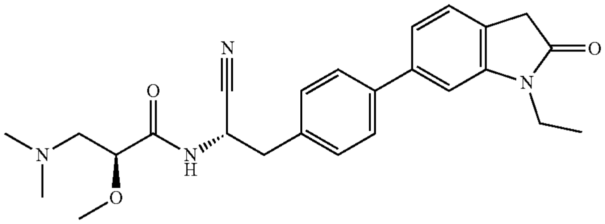 [SMILES: CCN1C(=O)Cc2ccc(-c3ccc(C[C@@H](C#N)NC(=O)[C@H](CN(C)C)OC)cc3)cc21] |
| 306 | 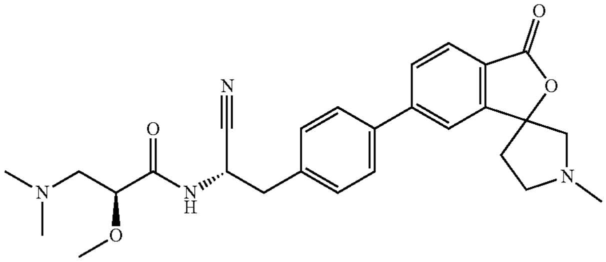 |
| 307 | 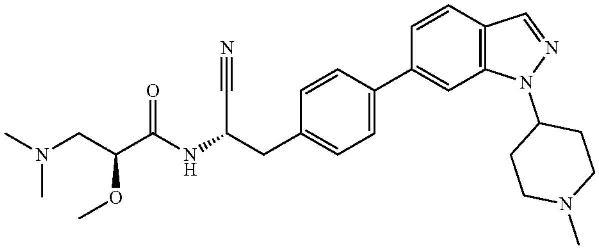 [SMILES: CO[C@@H](CN(C)C)C(=O)N[C@H](C#N)Cc1ccc(-c2ccc3cnn(C4CCN(C)CC4)c3c2)cc1] |
| 308 | 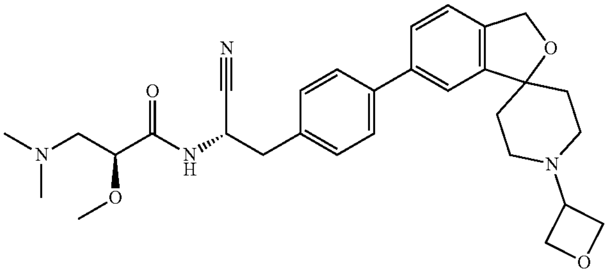 [SMILES: CO[C@@H](CN(C)C)C(=O)N[C@H](C#N)Cc1ccc(-c2ccc3c(c2)C2(CCN(C4COC4)CC2)OC3)cc1] |
| 309 | 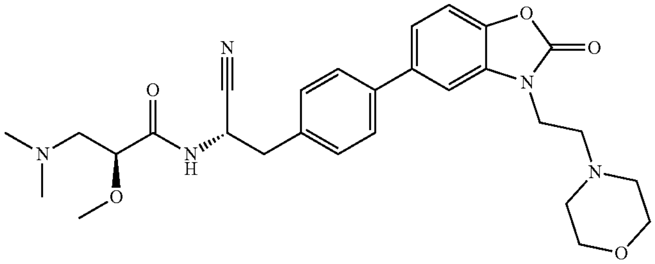 [SMILES: CO[C@@H](CN(C)C)C(=O)N[C@H](C#N)Cc1ccc(-c2ccc3oc(=O)n(CCN4CCOCC4)c3c2)cc1] |
| 310 | 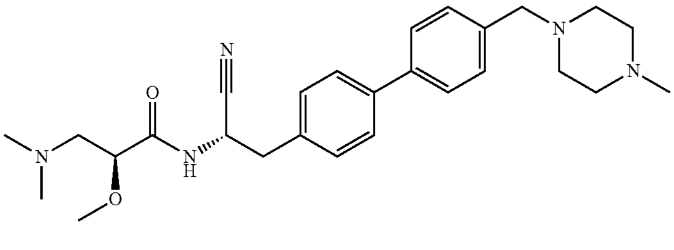 |

TABLE A-continued
| Exemplary compounds of the disclosure. | |
|---|---|
| Compound No. | Structure |
| 311 | 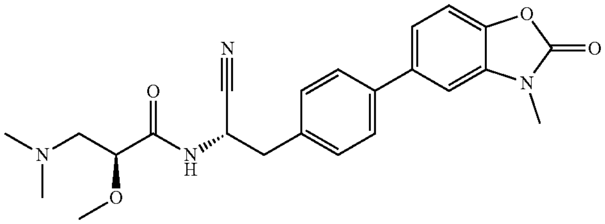 [SMILES: CO[C@@H](CN(C)C)C(=O)N[C@H](C#N)Cc1ccc(-c2ccc3oc(=O)n(C)c3c2)cc1] |
| 312 | 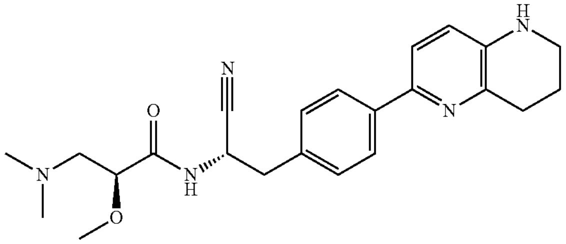 [SMILES: CO[C@@H](CN(C)C)C(=O)N[C@H](C#N)Cc1ccc(-c2ccc3c(n2)CCCN3)cc1] |
| 313 | 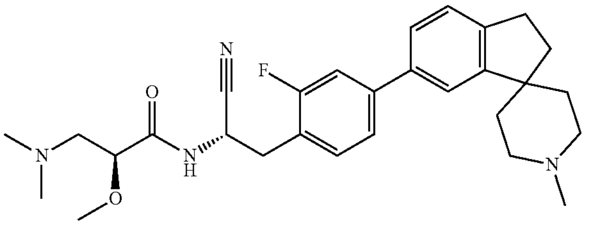 [SMILES: CO[C@@H](CN(C)C)C(=O)N[C@H](C#N)Cc1ccc(-c2ccc3c(c2)C2(CC3)CCN(C)CC2)cc1F] |
| 314 | 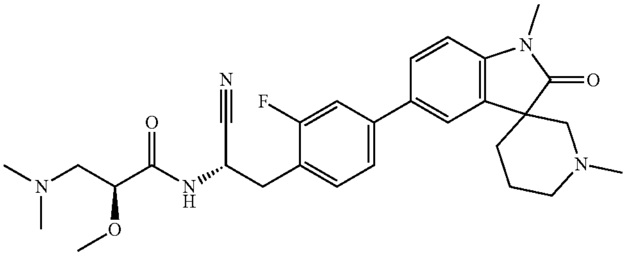 |
| 315 | 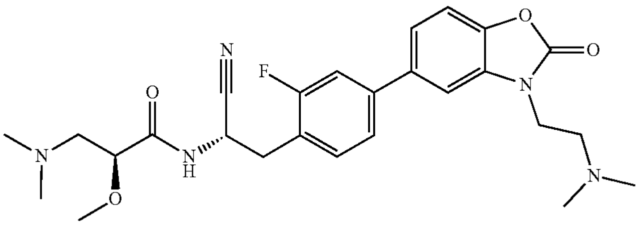 |
| 316 | 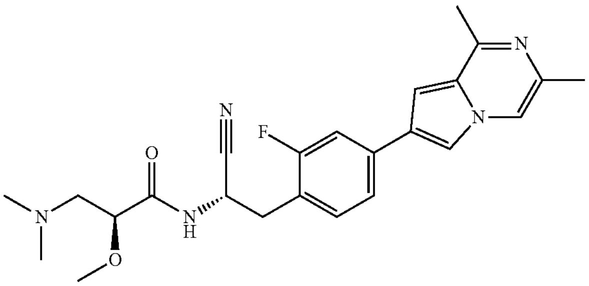 |

TABLE A-continued
| Exemplary compounds of the disclosure. | |
|---|---|
| Compound No. | Structure |
| 317 | 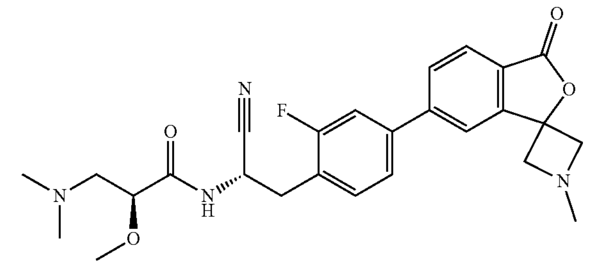 [SMILES: CO[C@@H](CN(C)C)C(=O)N[C@H](C#N)Cc1ccc(-c2ccc3c(c2)C2(CN(C)C2)OC3=O)cc1F] |
| 318 | 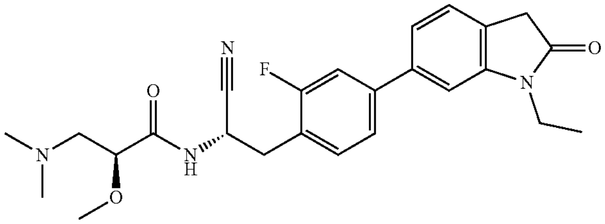 [SMILES: CCN1C(=O)Cc2ccc(-c3ccc(C[C@@H](C#N)NC(=O)[C@H](CN(C)C)OC)c(F)c3)cc21] |
| 319 | 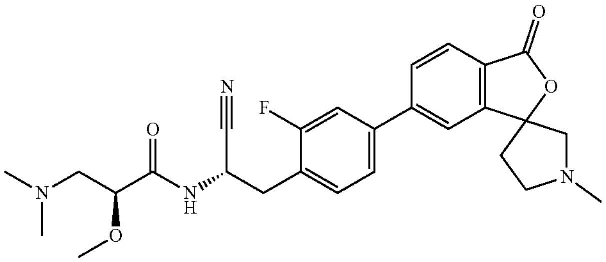 |
| 320 | 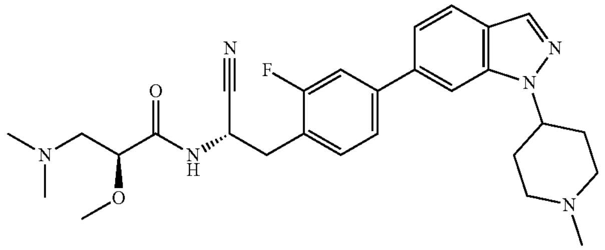 [SMILES: CO[C@@H](CN(C)C)C(=O)N[C@H](C#N)Cc1ccc(-c2ccc3cnn(C4CCN(C)CC4)c3c2)cc1F] |
| 321 | 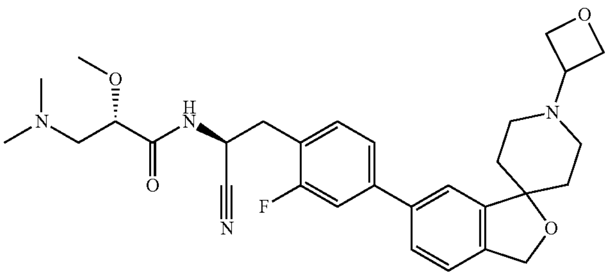 [SMILES: CO[C@@H](CN(C)C)C(=O)N[C@H](C#N)Cc1ccc(-c2ccc3c(c2)C2(CCN(C4COC4)CC2)OC3)cc1F] |

TABLE A-continued
| Exemplary compounds of the disclosure. | |
|---|---|
| Compound No. | Structure |
| 322 | 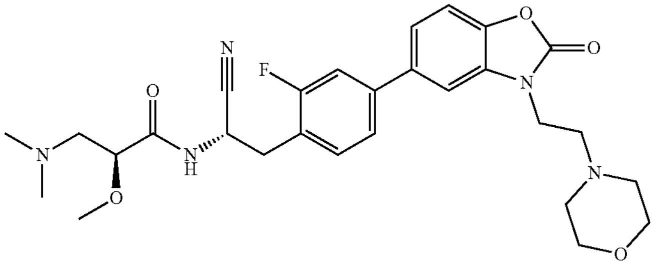 |
| 323 | 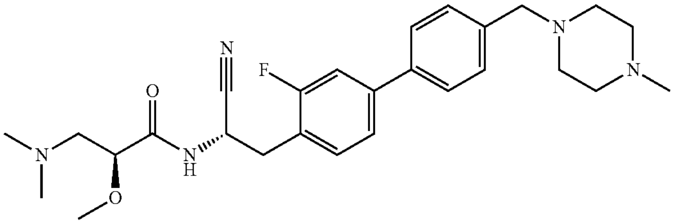 |
| 324 | 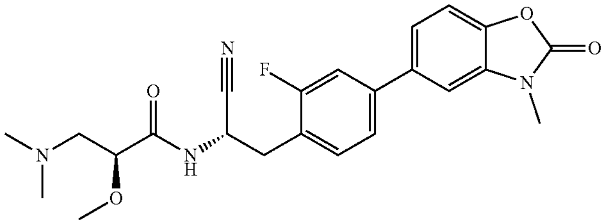 [SMILES: CO[C@@H](CN(C)C)C(=O)N[C@H](C#N)Cc1ccc(-c2ccc3oc(=O)n(C)c3c2)cc1F] |
| 325 | 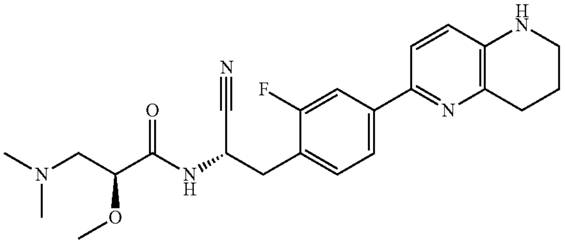 [SMILES: CO[C@@H](CN(C)C)C(=O)N[C@H](C#N)Cc1ccc(-c2ccc3c(n2)CCCN3)cc1F] |
| 326 | 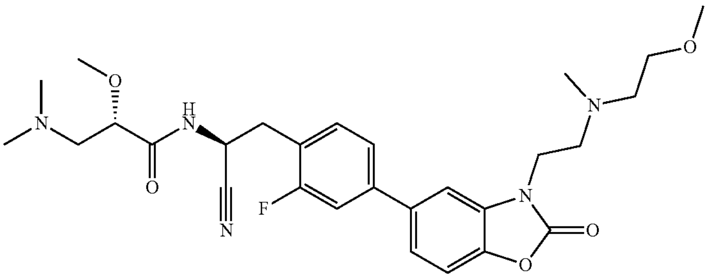 |
| 327 | 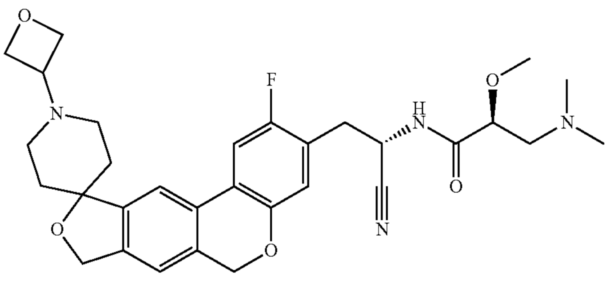 [SMILES: CO[C@@H](CN(C)C)C(=O)N[C@H](C#N)Cc1cc2c(cc1F)-c1cc3c(cc1CO2)COC31CCN(C2COC2)CC1] |

TABLE A-continued
| Exemplary compounds of the disclosure. | |
|---|---|
| Compound No. | Structure |
| 328 | 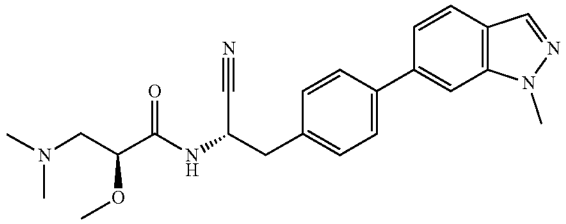 [SMILES: CO[C@@H](CN(C)C)C(=O)N[C@H](C#N)Cc1ccc(-c2ccc3cnn(C)c3c2)cc1] |
| 329 | 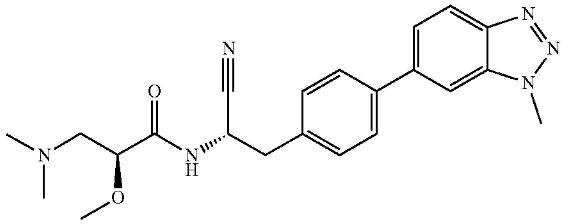 [SMILES: CO[C@@H](CN(C)C)C(=O)N[C@H](C#N)Cc1ccc(-c2ccc3nnn(C)c3c2)cc1] |
| 330 | 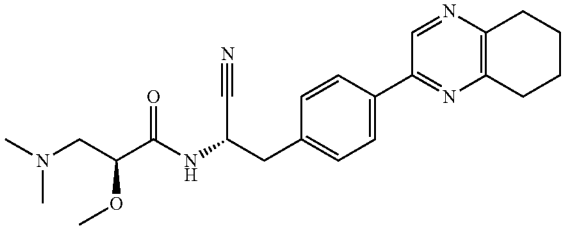 [SMILES: CO[C@@H](CN(C)C)C(=O)N[C@H](C#N)Cc1ccc(-c2cnc3c(n2)CCCC3)cc1] |
| 331 | 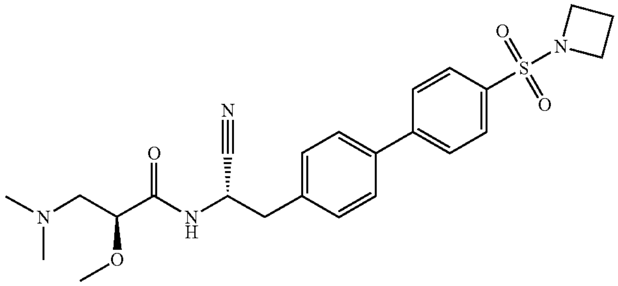 [SMILES: CO[C@@H](CN(C)C)C(=O)N[C@H](C#N)Cc1ccc(-c2ccc(S(=O)(=O)N3CCC3)cc2)cc1] |
| 332 | 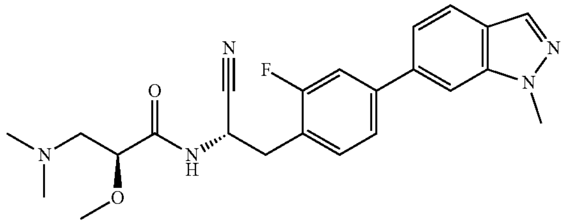 [SMILES: CO[C@@H](CN(C)C)C(=O)N[C@H](C#N)Cc1ccc(-c2ccc3cnn(C)c3c2)cc1F] |
| 333 | 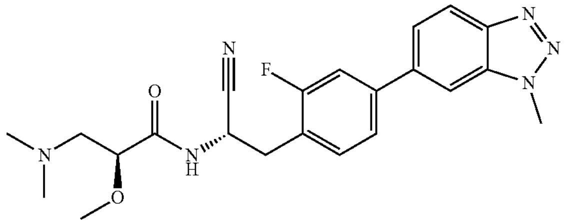 [SMILES: CO[C@@H](CN(C)C)C(=O)N[C@H](C#N)Cc1ccc(-c2ccc3nnn(C)c3c2)cc1F] |

TABLE A-continued
| Exemplary compounds of the disclosure. | |
|---|---|
| Compound No. | Structure |
| 334 | 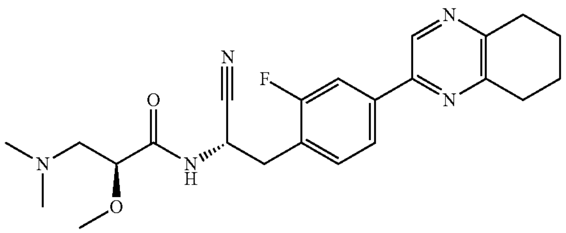 [SMILES: CO[C@@H](CN(C)C)C(=O)N[C@H](C#N)Cc1ccc(-c2cnc3c(n2)CCCC3)cc1F] |
| 335 | 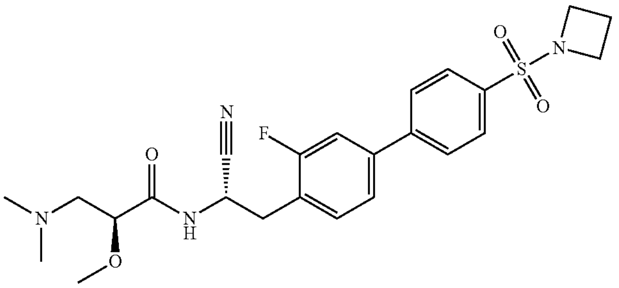 [SMILES: CO[C@@H](CN(C)C)C(=O)N[C@H](C#N)Cc1ccc(-c2ccc(S(=O)(=O)N3CCC3)cc2)cc1F] |
| 336 | 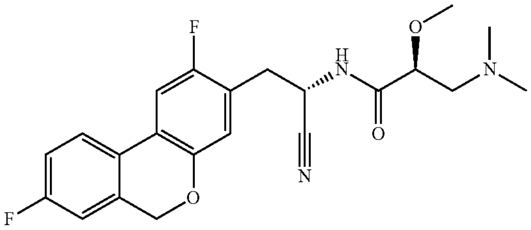 [SMILES: CO[C@@H](CN(C)C)C(=O)N[C@H](C#N)Cc1cc2c(cc1F)-c1ccc(F)cc1CO2] |
| 337 | 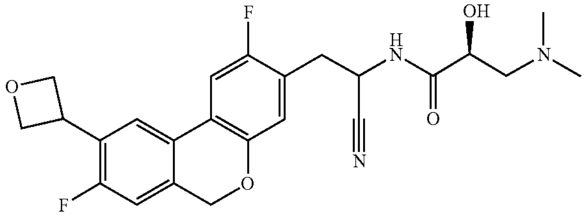 [SMILES: CN(C)C[C@H](O)C(=O)NC(C#N)Cc1cc2c(cc1F)-c1cc(C3COC3)c(F)cc1CO2] |
| 338 | 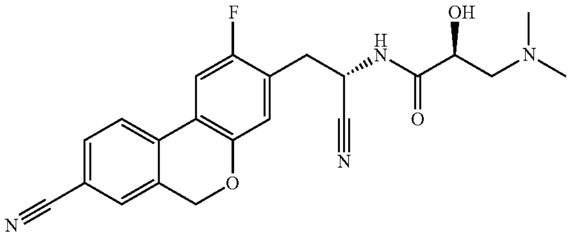 [SMILES: CN(C)C[C@H](O)C(=O)N[C@H](C#N)Cc1cc2c(cc1F)-c1ccc(C#N)cc1CO2] |
| 339 | 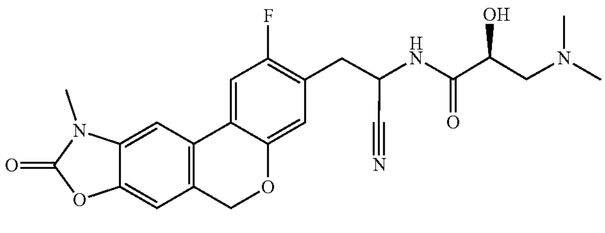 [SMILES: CN(C)C[C@H](O)C(=O)NC(C#N)Cc1cc2c(cc1F)-c1cc3c(cc1CO2)oc(=O)n3C] |

TABLE A-continued
| Exemplary compounds of the disclosure. | |
|---|---|
| Compound No. | Structure |
| 340 | 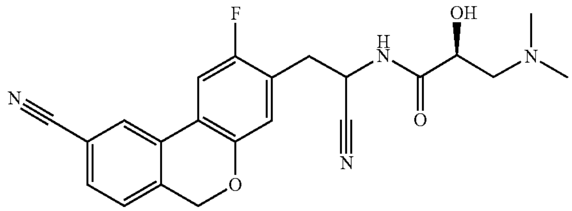 [SMILES: CN(C)C[C@H](O)C(=O)NC(C#N)Cc1cc2c(cc1F)-c1cc(C#N)ccc1CO2] |
| 341 | 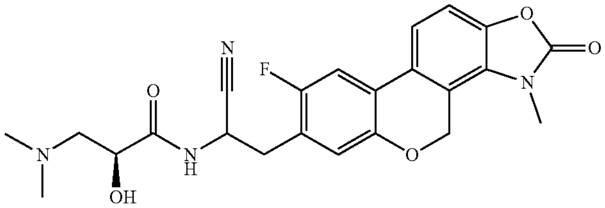 [SMILES: CN(C)C[C@H](O)C(=O)NC(C#N)Cc1cc2c(cc1F)-c1ccc3oc(=O)n(C)c3c1CO2] |
| 342 | 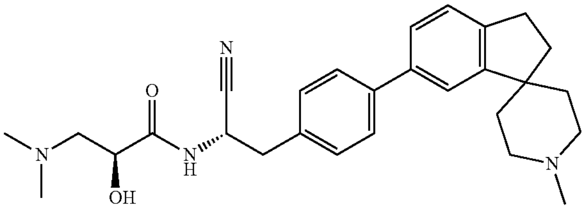 [SMILES: CN(C)C[C@H](O)C(=O)N[C@H](C#N)Cc1ccc(-c2ccc3c(c2)C2(CC3)CCN(C)CC2)cc1] |
| 343 | 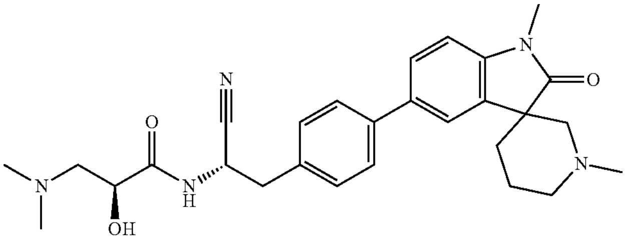 |
| 344 | 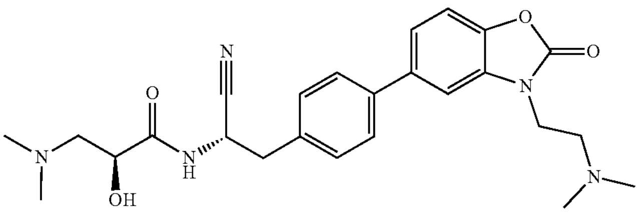 |
| 345 | 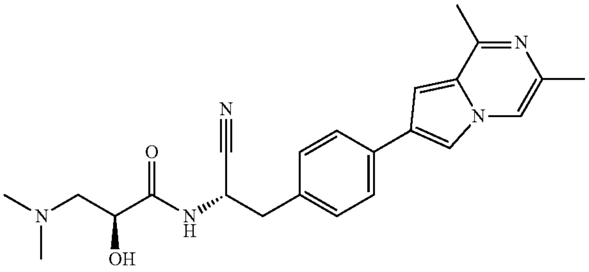 |

TABLE A-continued
| Exemplary compounds of the disclosure. | |
|---|---|
| Compound No. | Structure |
| 346 | 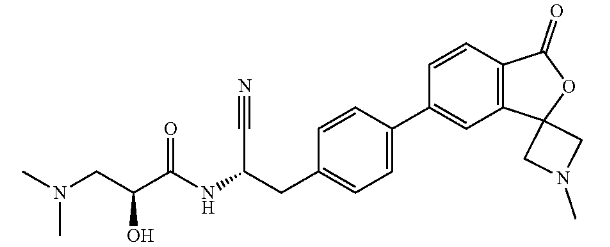 [SMILES: CN(C)C[C@H](O)C(=O)N[C@H](C#N)Cc1ccc(-c2ccc3c(c2)C2(CN(C)C2)OC3=O)cc1] |
| 347 | 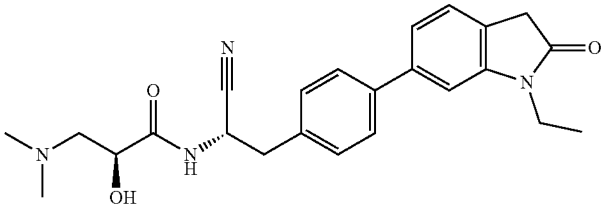 [SMILES: CCN1C(=O)Cc2ccc(-c3ccc(C[C@@H](C#N)NC(=O)[C@@H](O)CN(C)C)cc3)cc21] |
| 348 | 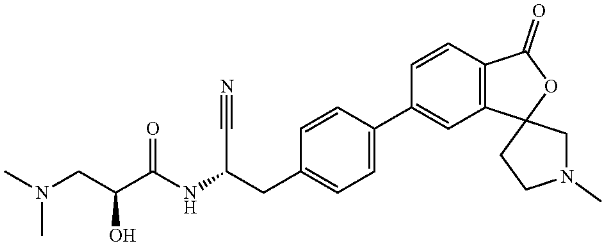 |
| 349 | 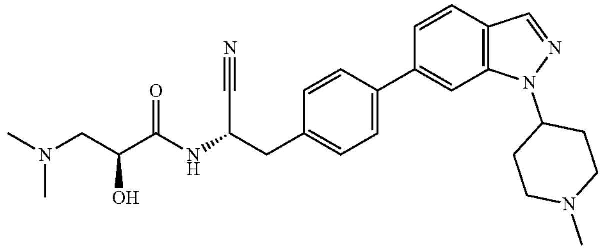 [SMILES: CN(C)C[C@H](O)C(=O)N[C@H](C#N)Cc1ccc(-c2ccc3cnn(C4CCN(C)CC4)c3c2)cc1] |
| 350 | 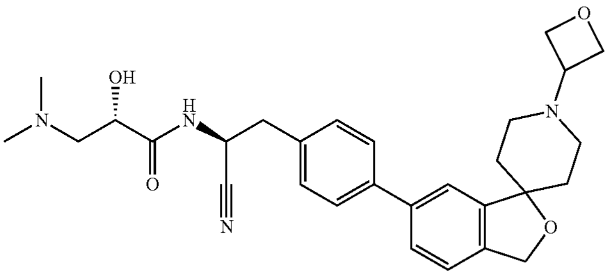 [SMILES: CN(C)C[C@H](O)C(=O)N[C@H](C#N)Cc1ccc(-c2ccc3c(c2)C2(CCN(C4COC4)CC2)OC3)cc1] |
| 351 | 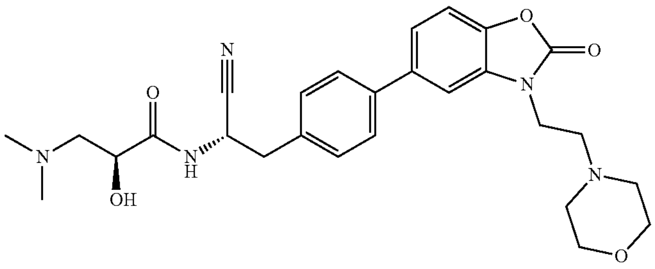 [SMILES: CN(C)C[C@H](O)C(=O)N[C@H](C#N)Cc1ccc(-c2ccc3oc(=O)n(CCN4CCOCC4)c3c2)cc1] |

TABLE A-continued
| Exemplary compounds of the disclosure. | |
|---|---|
| Compound No. | Structure |
| 352 | 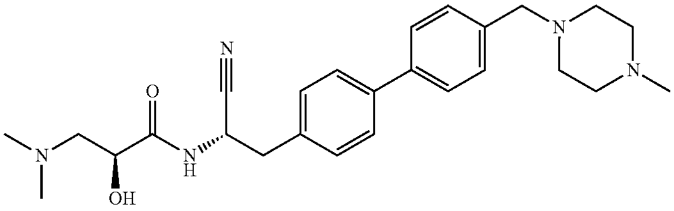 |
| 353 | 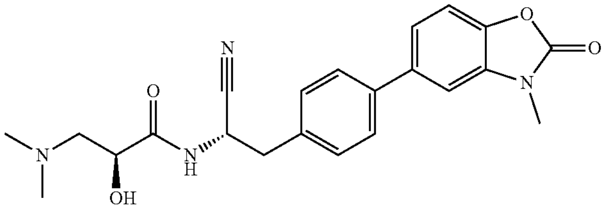 |
| 354 | 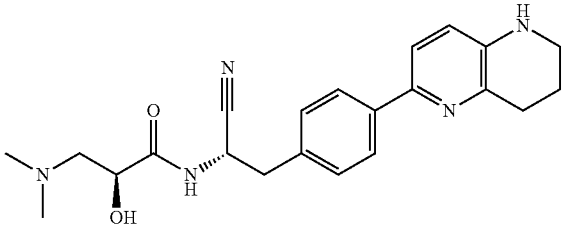 [SMILES: CN(C)C[C@H](O)C(=O)N[C@H](C#N)Cc1ccc(-c2ccc3c(n2)CCCN3)cc1] |
| 355 | 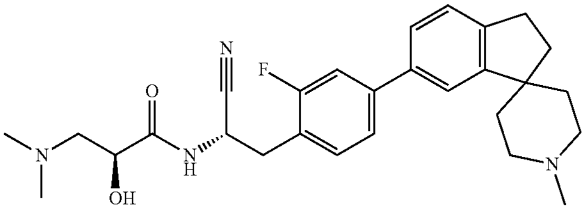 [SMILES: CN(C)C[C@H](O)C(=O)N[C@H](C#N)Cc1ccc(-c2ccc3c(c2)C2(CC3)CCN(C)CC2)cc1F] |
| 356 | 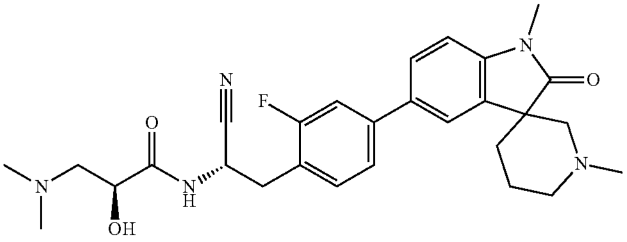 |
| 357 | 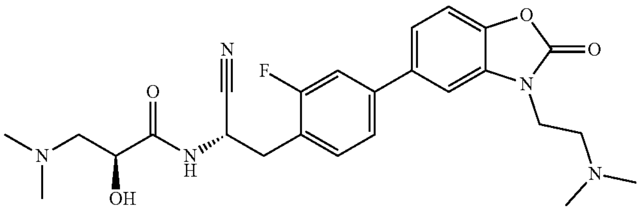 |

TABLE A-continued
| Exemplary compounds of the disclosure. | |
|---|---|
| Compound No. | Structure |
| 358 | 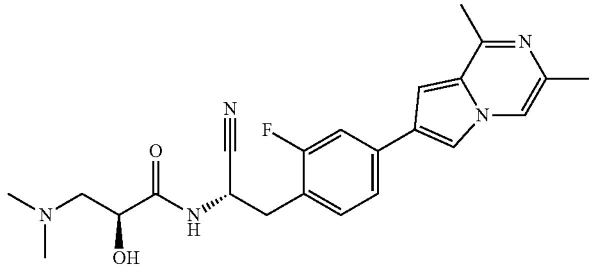 |
| 359 | 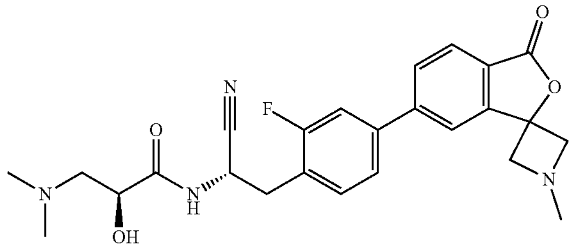 [SMILES: CN(C)C[C@H](O)C(=O)N[C@H](C#N)Cc1ccc(-c2ccc3c(c2)C2(CN(C)C2)OC3=O)cc1F] |
| 360 | 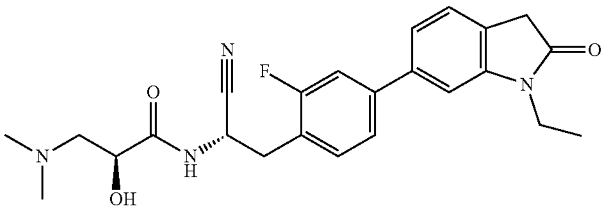 [SMILES: CCN1C(=O)Cc2ccc(-c3ccc(C[C@@H](C#N)NC(=O)[C@@H](O)CN(C)C)c(F)c3)cc21] |
| 361 | 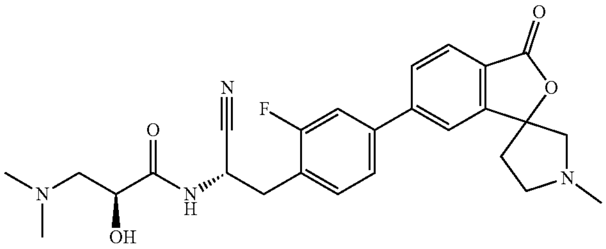 |
| 362 | 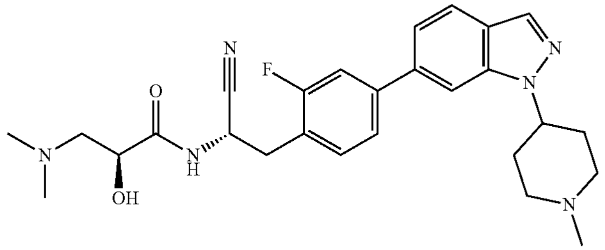 [SMILES: CN(C)C[C@H](O)C(=O)N[C@H](C#N)Cc1ccc(-c2ccc3cnn(C4CCN(C)CC4)c3c2)cc1F] |
| 363 | 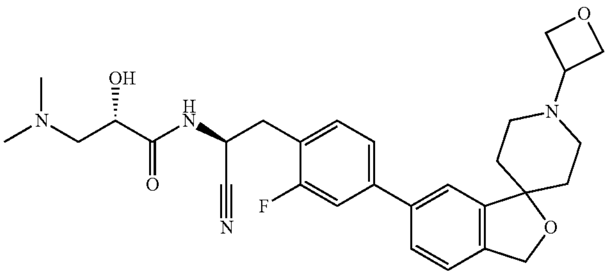 [SMILES: CN(C)C[C@H](O)C(=O)N[C@H](C#N)Cc1ccc(-c2ccc3c(c2)C2(CCN(C4COC4)CC2)OC3)cc1F] |

TABLE A-continued
Exemplary compounds of the disclosure.
| Compound No. | Structure |
| --- | --- |
| 364 | 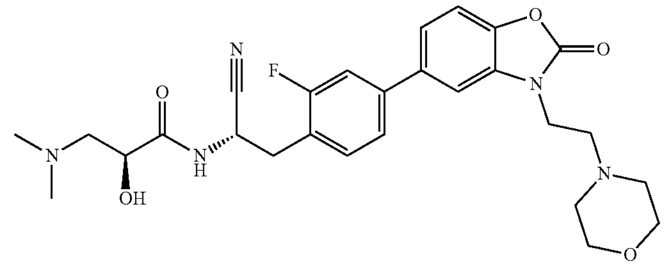 [SMILES: CN(C)C[C@H](O)C(=O)N[C@H](C#N)Cc1ccc(-c2ccc3oc(=O)n(CCN4CCOCC4)c3c2)cc1F] |
| 365 | 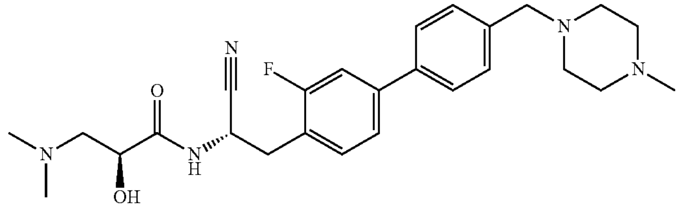 |
| 366 | 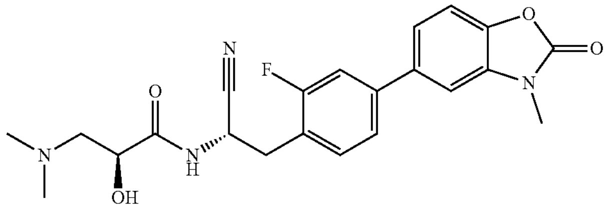 |
| 367 | 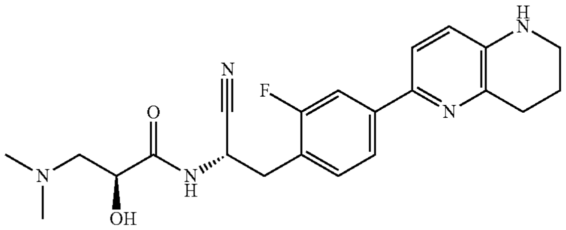 [SMILES: CN(C)C[C@H](O)C(=O)N[C@H](C#N)Cc1ccc(-c2ccc3c(n2)CCCN3)cc1F] |
| 368 | 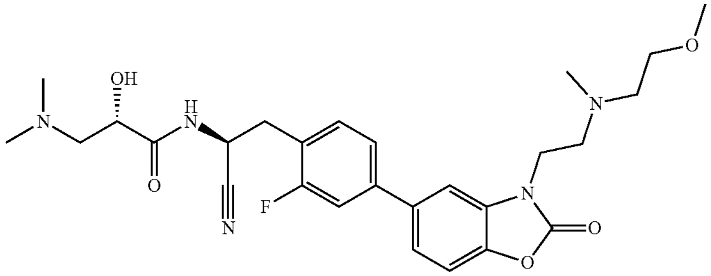 |
| 369 | 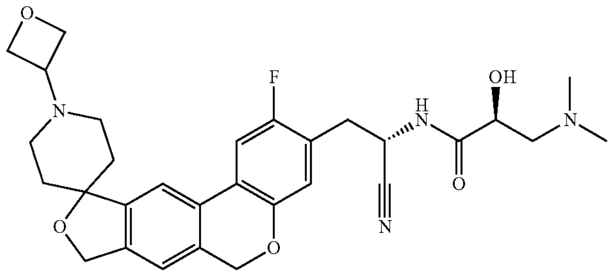 [SMILES: CN(C)C[C@H](O)C(=O)N[C@H](C#N)Cc1cc2c(cc1F)-c1cc3c(cc1CO2)COC31CCN(C2COC2)CC1] |

TABLE A-continued
| Exemplary compounds of the disclosure. | |
|---|---|
| Compound No. | Structure |
| 370 | 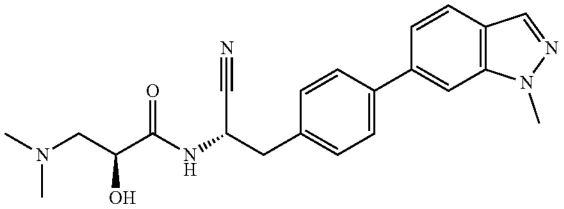 [SMILES: CN(C)C[C@H](O)C(=O)N[C@H](C#N)Cc1ccc(-c2ccc3cnn(C)c3c2)cc1] |
| 371 | 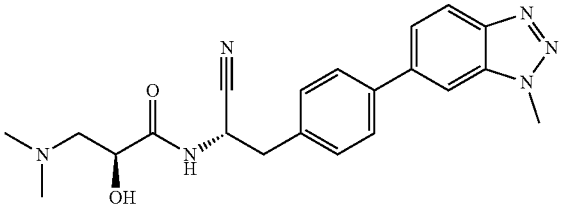 [SMILES: CN(C)C[C@H](O)C(=O)N[C@H](C#N)Cc1ccc(-c2ccc3nnn(C)c3c2)cc1] |
| 372 | 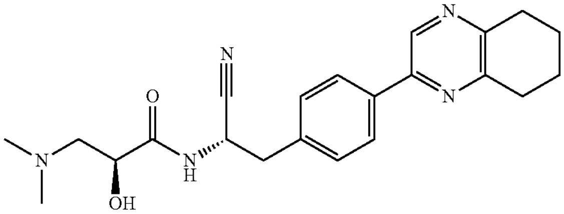 [SMILES: CN(C)C[C@H](O)C(=O)N[C@H](C#N)Cc1ccc(-c2cnc3c(n2)CCCC3)cc1] |
| 373 | 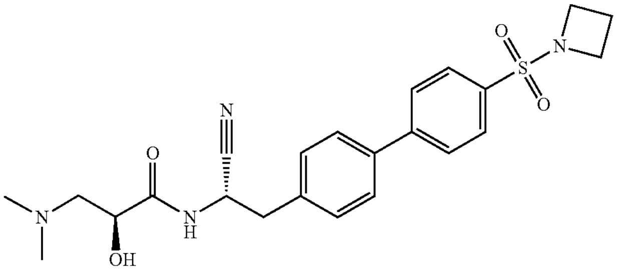 [SMILES: CN(C)C[C@H](O)C(=O)N[C@H](C#N)Cc1ccc(-c2ccc(S(=O)(=O)N3CCC3)cc2)cc1] |
| 374 | 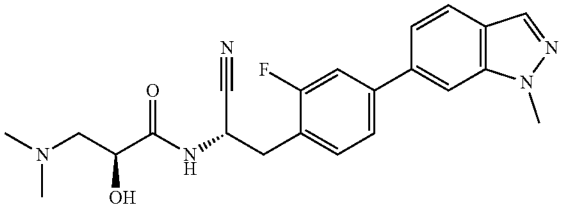 [SMILES: CN(C)C[C@H](O)C(=O)N[C@H](C#N)Cc1ccc(-c2ccc3cnn(C)c3c2)cc1F] |
| 375 | 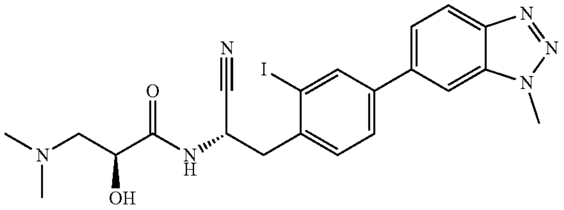 [SMILES: CN(C)C[C@H](O)C(=O)N[C@H](C#N)Cc1ccc(-c2ccc3nnn(C)c3c2)cc1I] |

TABLE A-continued
| Exemplary compounds of the disclosure. | |
|---|---|
| Compound No. | Structure |
| 376 | 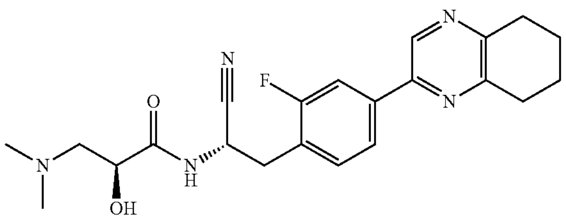 [SMILES: CN(C)C[C@H](O)C(=O)N[C@H](C#N)Cc1ccc(-c2cnc3c(n2)CCCC3)cc1F] |
| 377 | 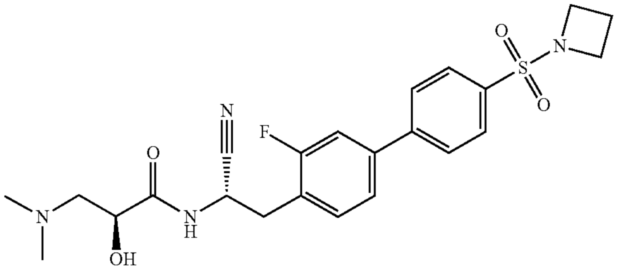 [SMILES: CN(C)C[C@H](O)C(=O)N[C@H](C#N)Cc1ccc(-c2ccc(S(=O)(=O)N3CCC3)cc2)cc1F] |
| 378 | 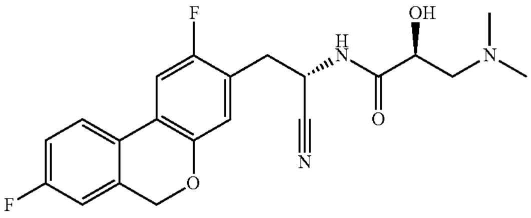 [SMILES: CN(C)C[C@H](O)C(=O)N[C@H](C#N)Cc1cc2c(cc1F)-c1ccc(F)cc1CO2] |
| 379 | 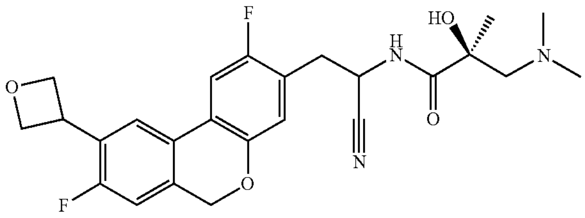 [SMILES: CN(C)C[C@](C)(O)C(=O)NC(C#N)Cc1cc2c(cc1F)-c1cc(C3COC3)c(F)cc1CO2] |
| 380 | 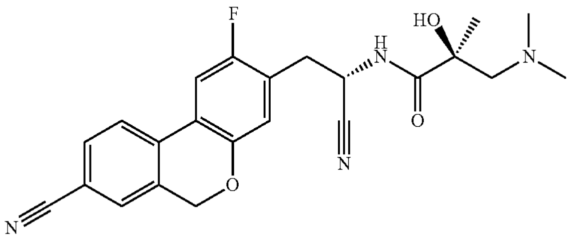 [SMILES: CN(C)C[C@](C)(O)C(=O)N[C@H](C#N)Cc1cc2c(cc1F)-c1ccc(C#N)cc1CO2] |
| 381 | 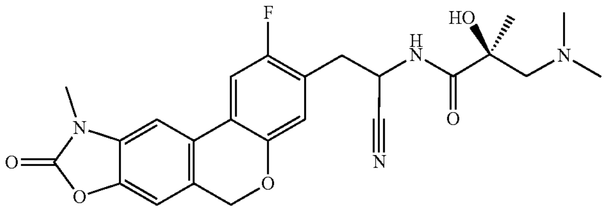 [SMILES: CN(C)C[C@](C)(O)C(=O)NC(C#N)Cc1cc2c(cc1F)-c1cc3c(cc1CO2)oc(=O)n3C] |

TABLE A-continued
| Exemplary compounds of the disclosure. | |
|---|---|
| Compound No. | Structure |
| 382 | 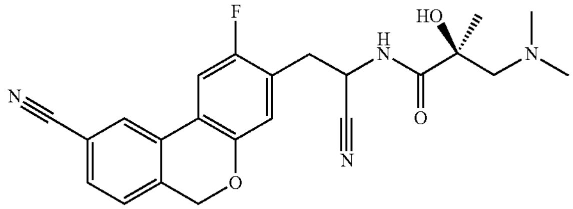 [SMILES: CN(C)C[C@](C)(O)C(=O)NC(C#N)Cc1cc2c(cc1F)-c1cc(C#N)ccc1CO2] |
| 383 | 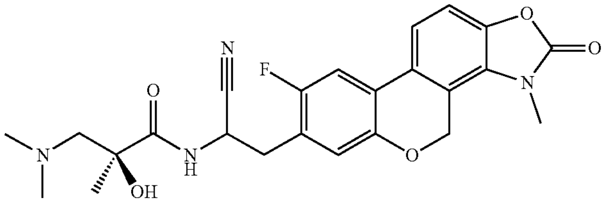 [SMILES: CN(C)C[C@](C)(O)C(=O)NC(C#N)Cc1cc2c(cc1F)-c1ccc3oc(=O)n(C)c3c1CO2] |
| 384 | 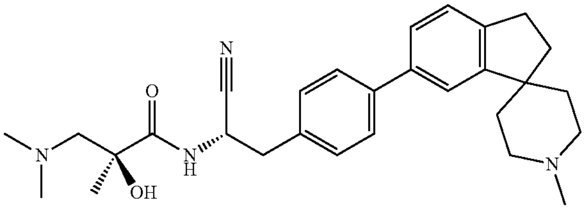 [SMILES: CN(C)C[C@](C)(O)C(=O)N[C@H](C#N)Cc1ccc(-c2ccc3c(c2)C2(CC3)CCN(C)CC2)cc1] |
| 385 | 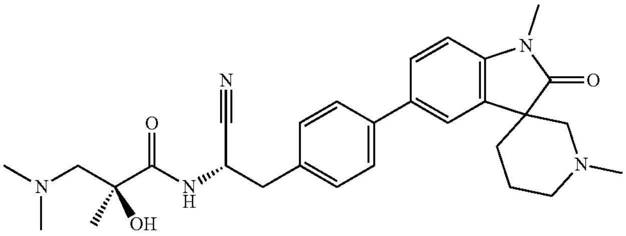 |
| 386 | 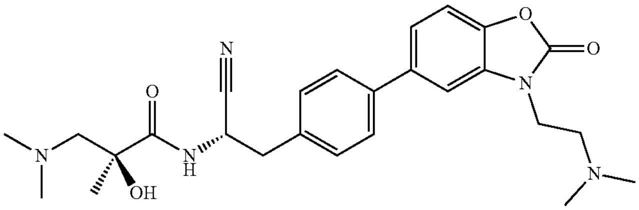 |
| 387 | 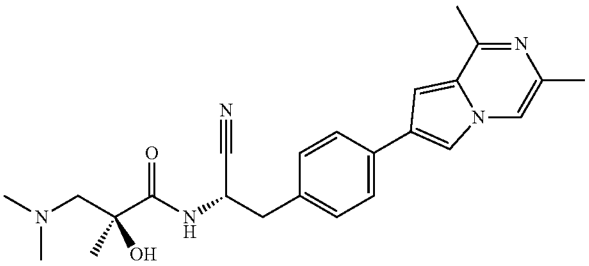 |

TABLE A-continued
| Exemplary compounds of the disclosure. | |
|---|---|
| Compound No. | Structure |
| 388 | 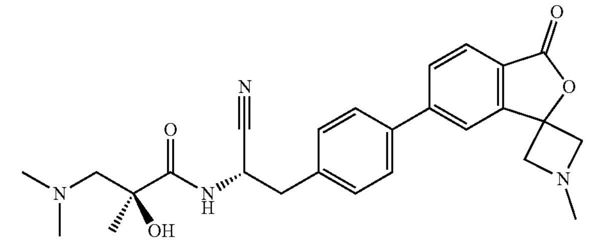 [SMILES: CN(C)C[C@](C)(O)C(=O)N[C@H](C#N)Cc1ccc(-c2ccc3c(c2)C2(CN(C)C2)OC3=O)cc1] |
| 389 | 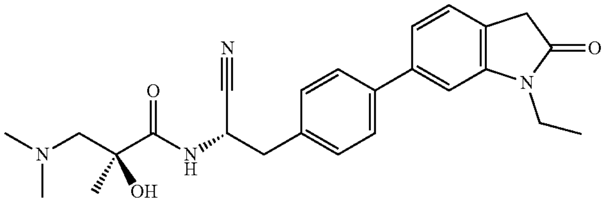 [SMILES: CCN1C(=O)Cc2ccc(-c3ccc(C[C@@H](C#N)NC(=O)[C@@](C)(O)CN(C)C)cc3)cc21] |
| 390 | 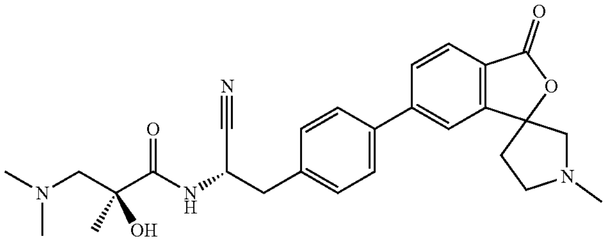 |
| 391 | 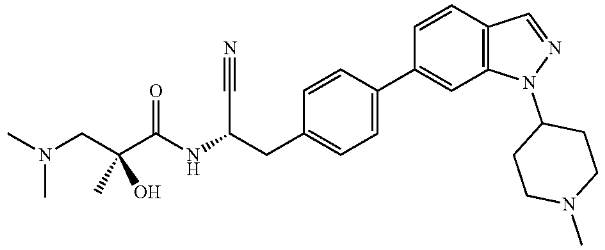 [SMILES: CN(C)C[C@](C)(O)C(=O)N[C@H](C#N)Cc1ccc(-c2ccc3cnn(C4CCN(C)CC4)c3c2)cc1] |
| 392 | 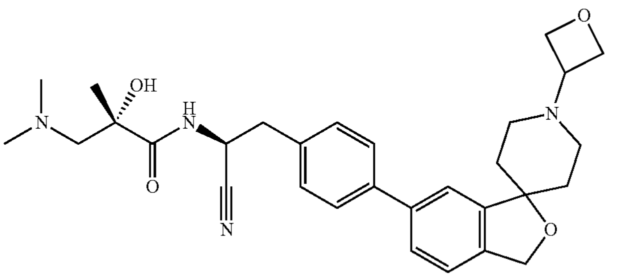 [SMILES: CN(C)C[C@](C)(O)C(=O)N[C@H](C#N)Cc1ccc(-c2ccc3c(c2)C2(CCN(C4COC4)CC2)OC3)cc1] |
| 393 | 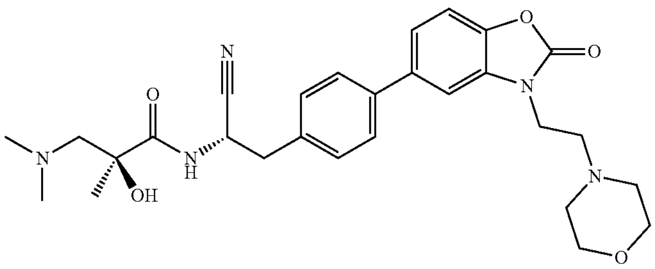 [SMILES: CN(C)C[C@](C)(O)C(=O)N[C@H](C#N)Cc1ccc(-c2ccc3oc(=O)n(CCN4CCOCC4)c3c2)cc1] |

TABLE A-continued
| Exemplary compounds of the disclosure. | |
| --- | --- |
| Compound No. | Structure |
| 394 | 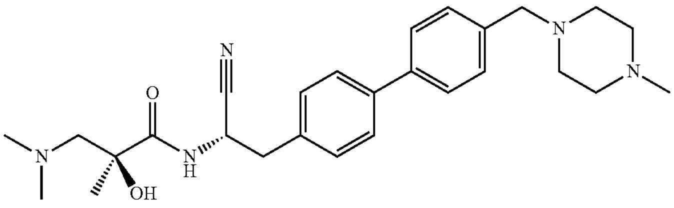 |
| 395 | 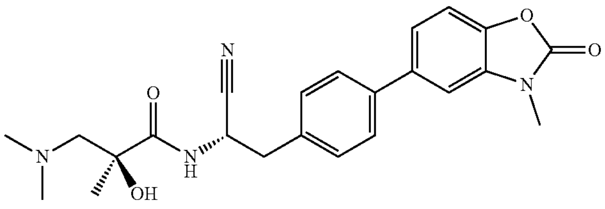 [SMILES: CN(C)C[C@](C)(O)C(=O)N[C@H](C#N)Cc1ccc(-c2ccc3oc(=O)n(C)c3c2)cc1] |
| 396 | 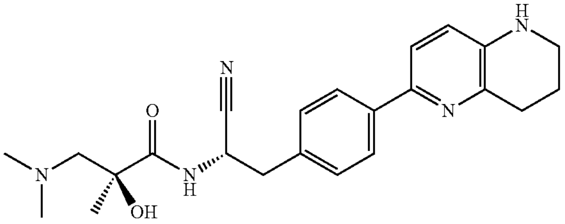 [SMILES: CN(C)C[C@](C)(O)C(=O)N[C@H](C#N)Cc1ccc(-c2ccc3c(n2)CCCN3)cc1] |
| 397 | 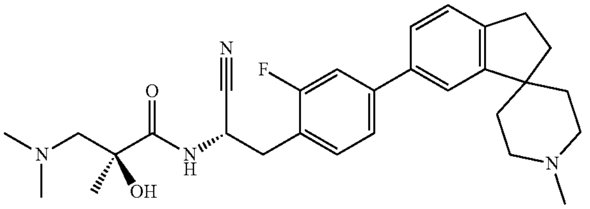 [SMILES: CN(C)C[C@](C)(O)C(=O)N[C@H](C#N)Cc1ccc(-c2ccc3c(c2)C2(CC3)CCN(C)CC2)cc1F] |
| 398 | 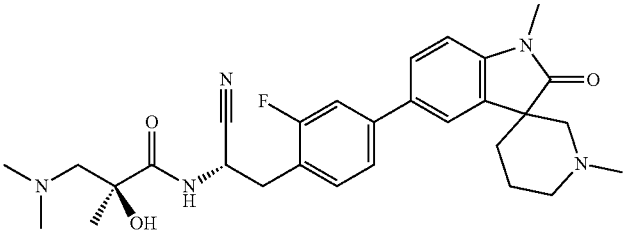 |
| 399 | 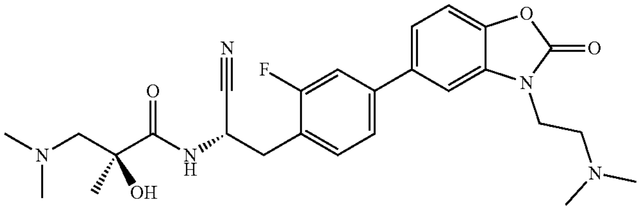 |

TABLE A-continued
Exemplary compounds of the disclosure.
| Compound No. | Structure |
| --- | --- |
| 400 | 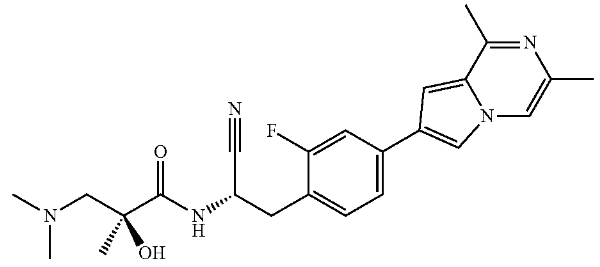 |
| 401 | 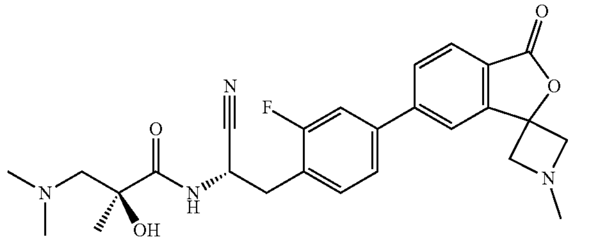 [SMILES: CN(C)C[C@](C)(O)C(=O)N[C@H](C#N)Cc1ccc(-c2ccc3c(c2)C2(CN(C)C2)OC3=O)cc1F] |
| 402 | 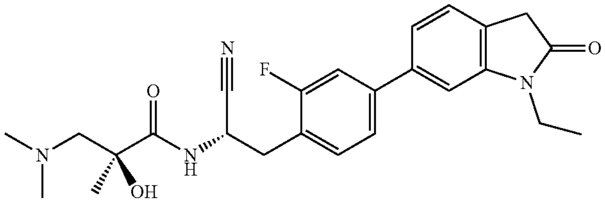 |
| 403 | 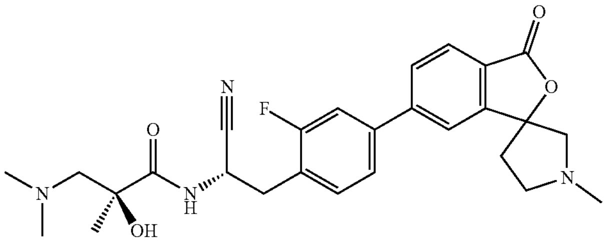 |
| 404 | 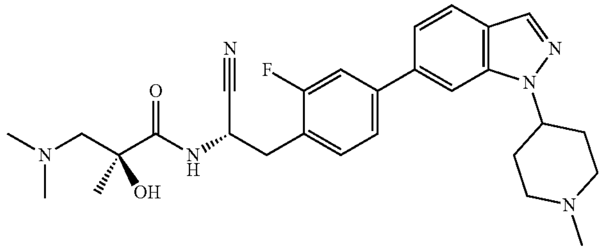 [SMILES: CN(C)C[C@](C)(O)C(=O)N[C@H](C#N)Cc1ccc(-c2ccc3cnn(C4CCN(C)CC4)c3c2)cc1F] |
| 405 | 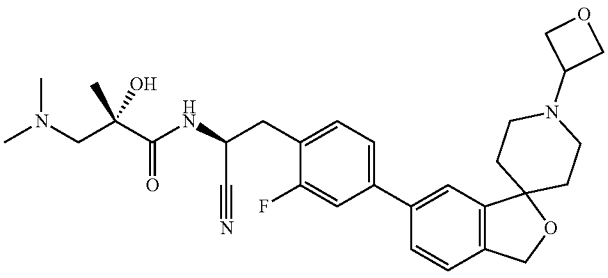 [SMILES: CN(C)C[C@](C)(O)C(=O)N[C@H](C#N)Cc1ccc(-c2ccc3c(c2)C2(CCN(C4COC4)CC2)OC3)cc1F] |

TABLE A-continued
| Exemplary compounds of the disclosure. | |
|---|---|
| Compound No. | Structure |
| 406 | 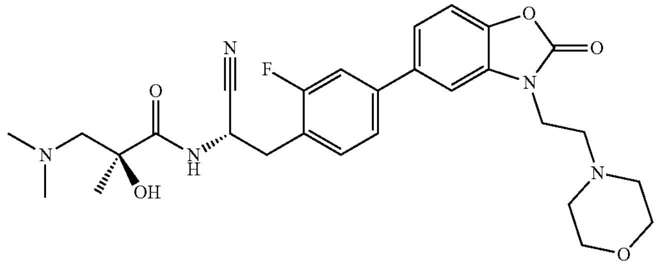 [SMILES: CN(C)C[C@](C)(O)C(=O)N[C@H](C#N)Cc1ccc(-c2ccc3oc(=O)n(CCN4CCOCC4)c3c2)cc1F] |
| 407 | 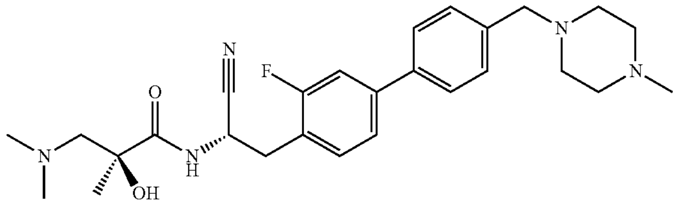 |
| 408 | 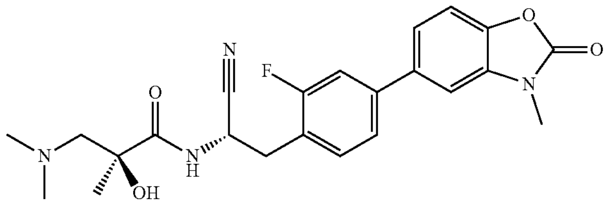 [SMILES: CN(C)C[C@](C)(O)C(=O)N[C@H](C#N)Cc1ccc(-c2ccc3oc(=O)n(C)c3c2)cc1F] |
| 409 | 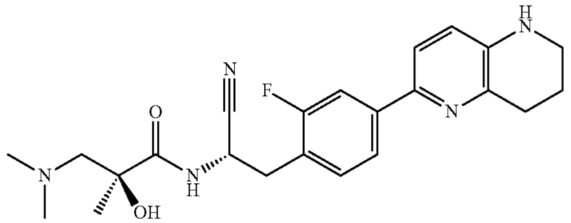 [SMILES: CN(C)C[C@](C)(O)C(=O)N[C@H](C#N)Cc1ccc(-c2ccc3c(n2)CCCN3)cc1F] |
| 410 | 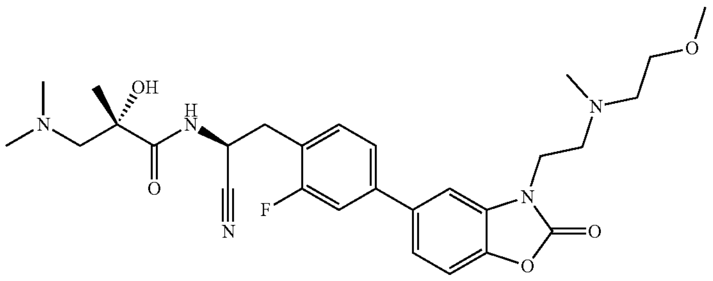 |
| 411 | 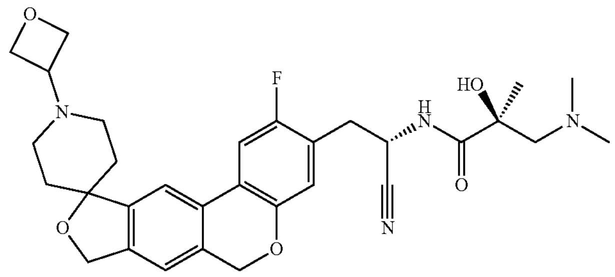 [SMILES: CN(C)C[C@](C)(O)C(=O)N[C@H](C#N)Cc1cc2c(cc1F)-c1cc3c(cc1CO2)COC31CCN(C2COC2)CC1] |

TABLE A-continued
| Exemplary compounds of the disclosure. | |
|---|---|
| Compound No. | Structure |
| 412 | 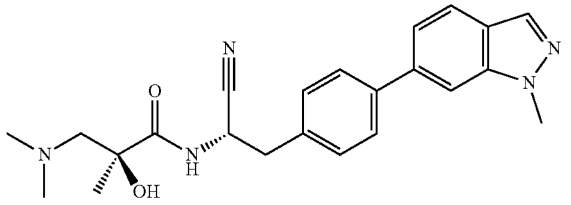 [SMILES: CN(C)C[C@](C)(O)C(=O)N[C@H](C#N)Cc1ccc(-c2ccc3cnn(C)c3c2)cc1] |
| 413 | 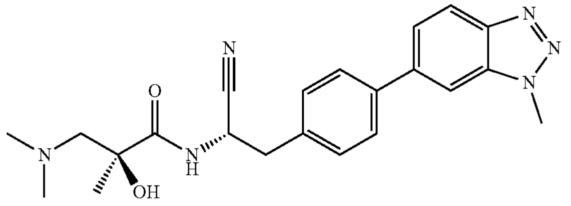 [SMILES: CN(C)C[C@](C)(O)C(=O)N[C@H](C#N)Cc1ccc(-c2ccc3nnn(C)c3c2)cc1] |
| 414 | 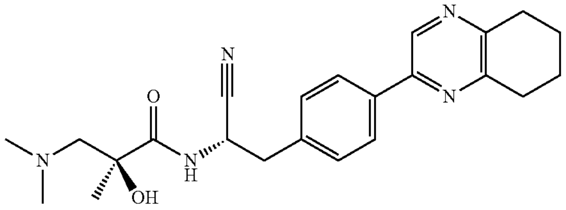 [SMILES: CN(C)C[C@](C)(O)C(=O)N[C@H](C#N)Cc1ccc(-c2cnc3c(n2)CCCC3)cc1] |
| 415 | 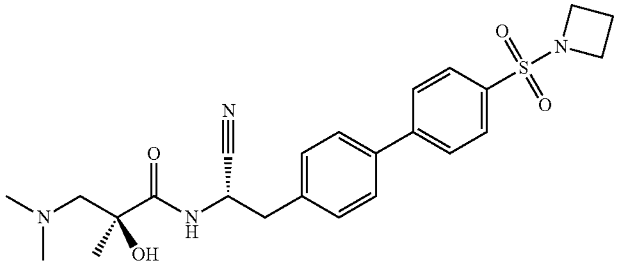 [SMILES: CN(C)C[C@](C)(O)C(=O)N[C@H](C#N)Cc1ccc(-c2ccc(S(=O)(=O)N3CCC3)cc2)cc1] |
| 416 | 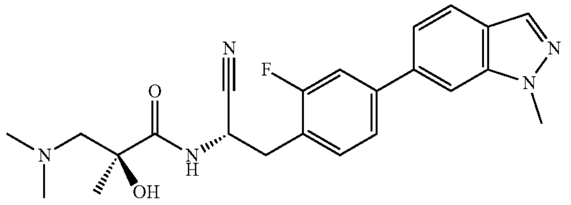 [SMILES: CN(C)C[C@](C)(O)C(=O)N[C@H](C#N)Cc1ccc(-c2ccc3cnn(C)c3c2)cc1F] |
| 417 | 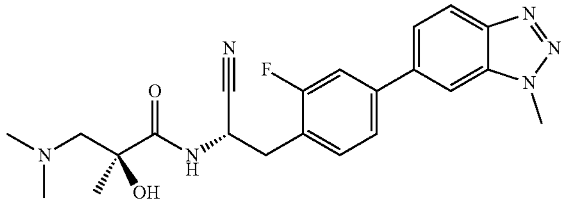 [SMILES: CN(C)C[C@](C)(O)C(=O)N[C@H](C#N)Cc1ccc(-c2ccc3nnn(C)c3c2)cc1F] |
| 418 | 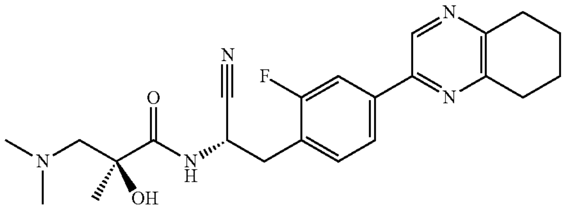 [SMILES: CN(C)C[C@](C)(O)C(=O)N[C@H](C#N)Cc1ccc(-c2cnc3c(n2)CCCC3)cc1F] |

TABLE A-continued
| Exemplary compounds of the disclosure. | |
|---|---|
| Compound No. | Structure |
| 419 | 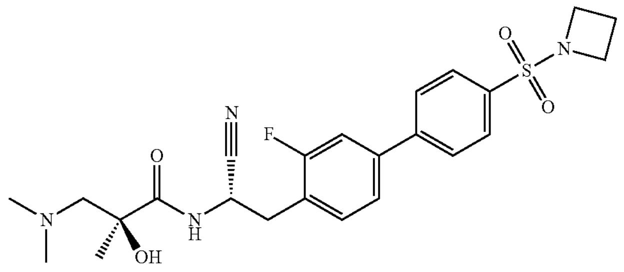 [SMILES: CN(C)C[C@](C)(O)C(=O)N[C@H](C#N)Cc1ccc(-c2ccc(S(=O)(=O)N3CCC3)cc2)cc1F] |
| 420 | 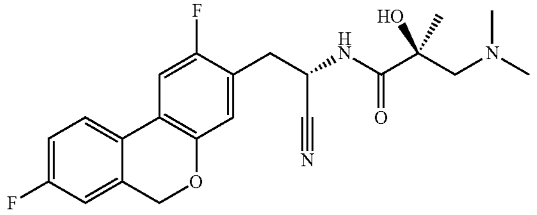 [SMILES: CN(C)C[C@](C)(O)C(=O)N[C@H](C#N)Cc1cc2c(cc1F)-c1ccc(F)cc1CO2] |
| 421 | 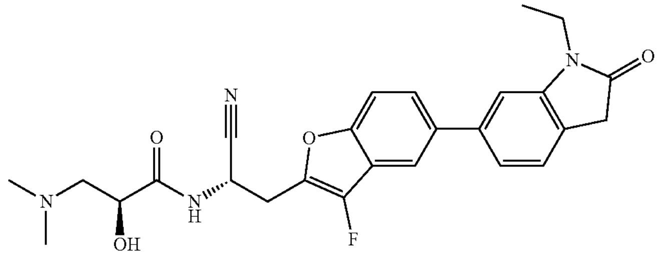 [SMILES: CCN1C(=O)Cc2ccc(-c3ccc4oc(C[C@@H](C#N)NC(=O)[C@@H](O)CN(C)C)c(F)c4c3)cc21] |
| 422 | 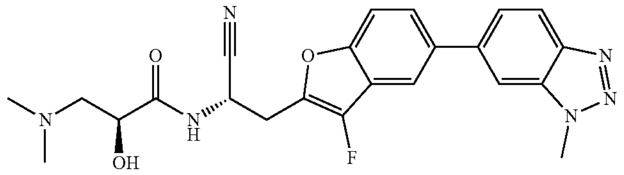 [SMILES: CN(C)C[C@H](O)C(=O)N[C@H](C#N)Cc1oc2ccc(-c3ccc4nnn(C)c4c3)cc2c1F] |
| 423 | 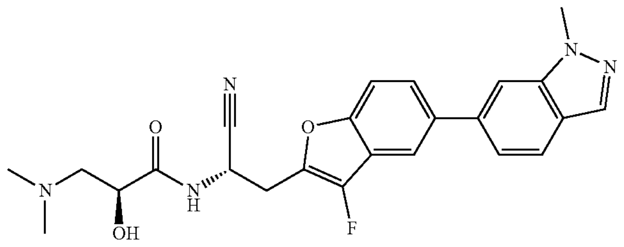 [SMILES: CN(C)C[C@H](O)C(=O)N[C@H](C#N)Cc1oc2ccc(-c3ccc4cnn(C)c4c3)cc2c1F] |
| 424 | 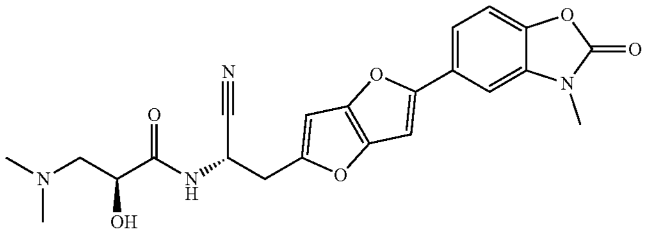 [SMILES: CN(C)C[C@H](O)C(=O)N[C@H](C#N)Cc1cc2oc(-c3ccc4oc(=O)n(C)c4c3)cc2o1] |

TABLE A-continued
Exemplary compounds of the disclosure.
| Compound No. | Structure |
| --- | --- |
| 425 | 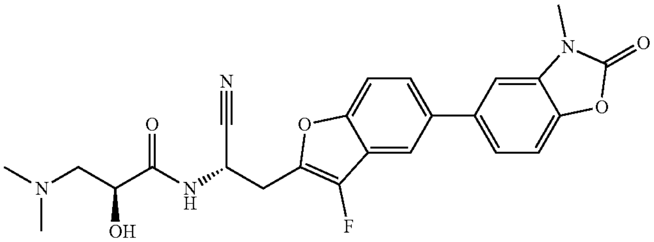 [SMILES: CN(C)C[C@H](O)C(=O)N[C@H](C#N)Cc1oc2ccc(-c3ccc4oc(=O)n(C)c4c3)cc2c1F] |
| 426 | 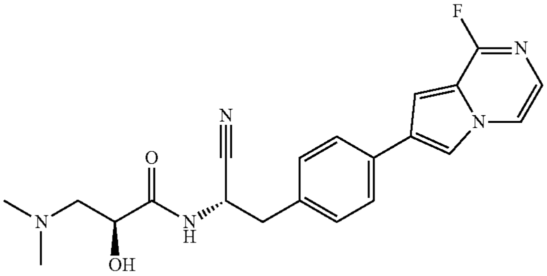 [SMILES: CN(C)C[C@H](O)C(=O)N[C@H](C#N)Cc1ccc(-c2cc3c(F)nccn3c2)cc1] |
| 427 | 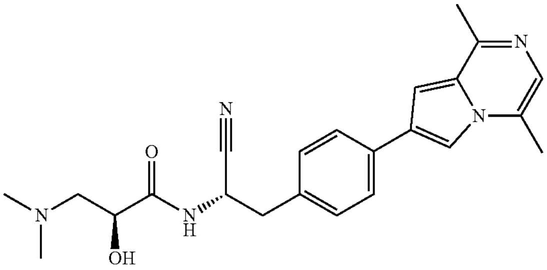 |
| 428 | 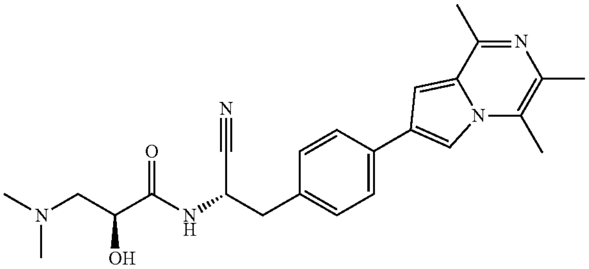 |
| 429 | 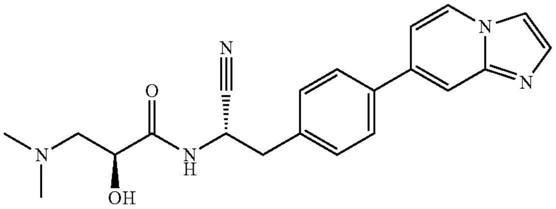 [SMILES: CN(C)C[C@H](O)C(=O)N[C@H](C#N)Cc1ccc(-c2ccn3ccnc3c2)cc1] |
| 430 | 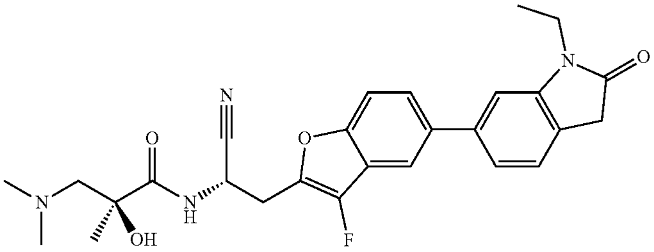 [SMILES: CCN1C(=O)Cc2ccc(-c3ccc4oc(C[C@@H](C#N)NC(=O)[C@@](C)(O)CN(C)C)c(F)c4c3)cc21] |

TABLE A-continued
| Exemplary compounds of the disclosure. | |
|---|---|
| Compound No. | Structure |
| 431 | 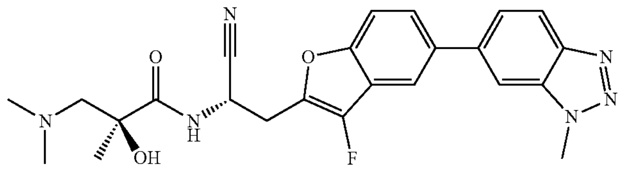 [SMILES: CN(C)C[C@](C)(O)C(=O)N[C@H](C#N)Cc1oc2ccc(-c3ccc4nnn(C)c4c3)cc2c1F] |
| 432 | 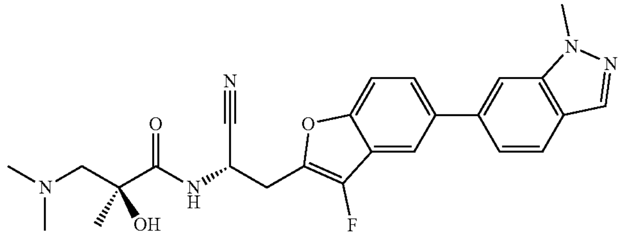 [SMILES: CN(C)C[C@](C)(O)C(=O)N[C@H](C#N)Cc1oc2ccc(-c3ccc4cnn(C)c4c3)cc2c1F] |
| 433 | 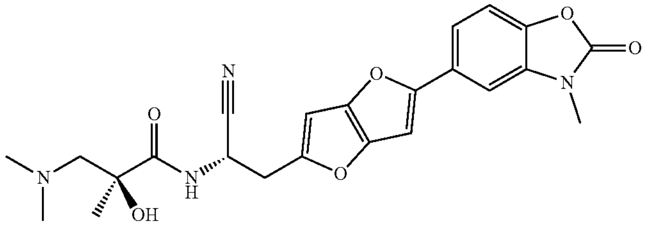 [SMILES: CN(C)C[C@](C)(O)C(=O)N[C@H](C#N)Cc1cc2oc(-c3ccc4oc(=O)n(C)c4c3)cc2o1] |
| 434 | 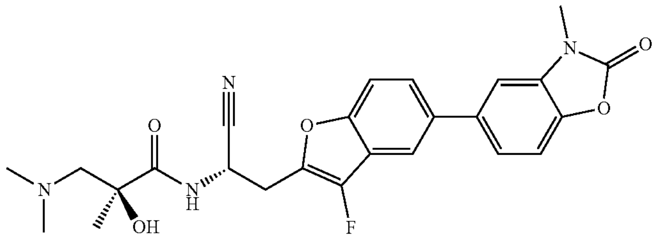 [SMILES: CN(C)C[C@](C)(O)C(=O)N[C@H](C#N)Cc1oc2ccc(-c3ccc4oc(=O)n(C)c4c3)cc2c1F] |
| 435 | 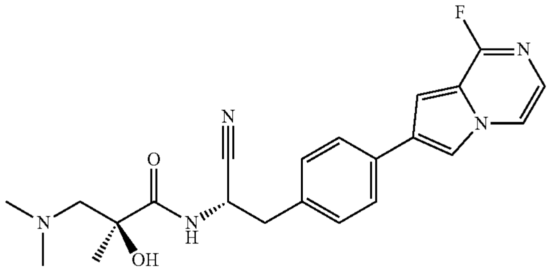 [SMILES: CN(C)C[C@](C)(O)C(=O)N[C@H](C#N)Cc1ccc(-c2cc3c(F)nccn3c2)cc1] |
| 436 | 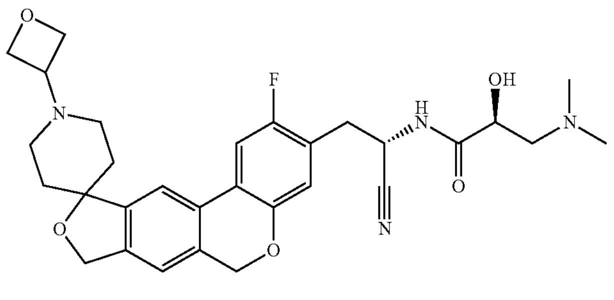 [SMILES: CN(C)C[C@H](O)C(=O)N[C@H](C#N)Cc1cc2c(cc1F)-c1cc3c(cc1CO2)COC31CCN(C2COC2)CC1] |

TABLE A-continued
| Exemplary compounds of the disclosure. | |
|---|---|
| Compound No. | Structure |
| 437 | 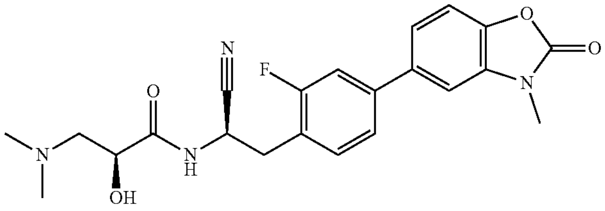 [SMILES: CN(C)C[C@H](O)C(=O)N[C@@H](C#N)Cc1ccc(-c2ccc3oc(=O)n(C)c3c2)cc1F] |
| 438 | 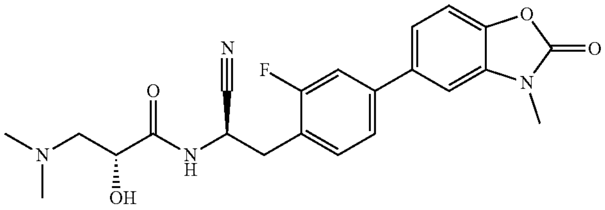 [SMILES: CN(C)C[C@@H](O)C(=O)N[C@@H](C#N)Cc1ccc(-c2ccc3oc(=O)n(C)c3c2)cc1F] |
| 439 | 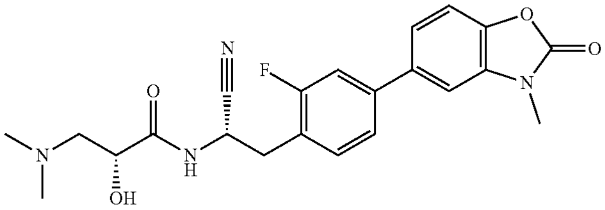 [SMILES: CN(C)C[C@@H](O)C(=O)N[C@H](C#N)Cc1ccc(-c2ccc3oc(=O)n(C)c3c2)cc1F] |
| 440 | 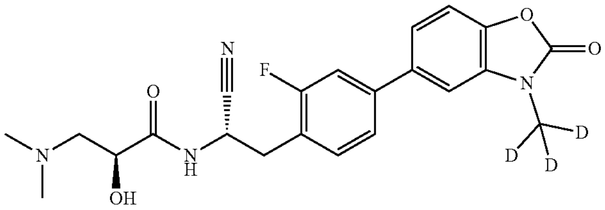 [SMILES: [2H]C([2H])([2H])n1c(=O)oc2ccc(-c3ccc(C[C@@H](C#N)NC(=O)[C@@H](O)CN(C)C)c(F)c3)cc21] |
| 441 | 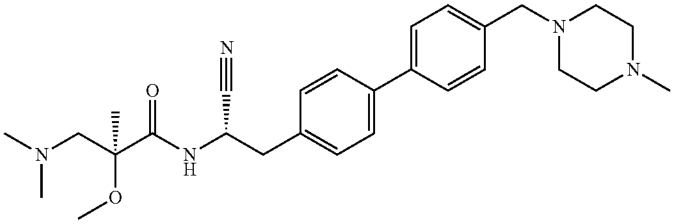 |
| 442 | 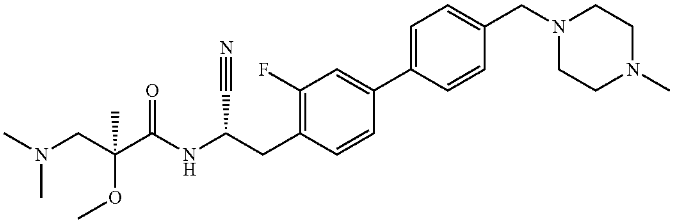 |

TABLE A-continued

| Exemplary compounds of the disclosure. | |
|---|---|
| Compound No. | Structure |
| 443 | 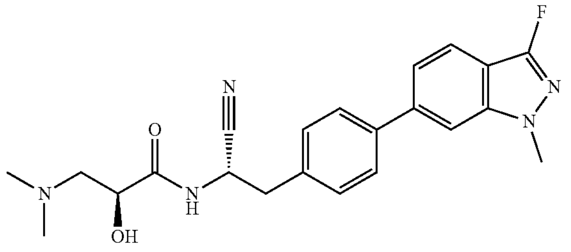 [SMILES: CN(C)C[C@H](O)C(=O)N[C@H](C#N)Cc1ccc(-c2ccc3c(F)nn(C)c3c2)cc1] |
| 444 | 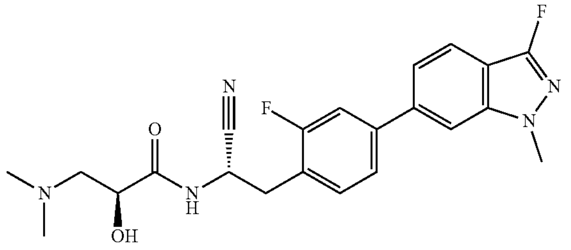 [SMILES: CN(C)C[C@H](O)C(=O)N[C@H](C#N)Cc1ccc(-c2ccc3c(F)nn(C)c3c2)cc1F] |
| 445 | 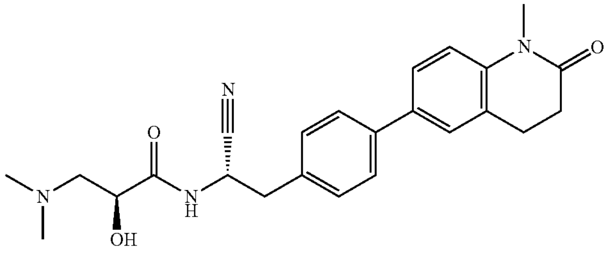 [SMILES: CN(C)C[C@H](O)C(=O)N[C@H](C#N)Cc1ccc(-c2ccc3c(c2)CCC(=O)N3C)cc1] |
| 446 | 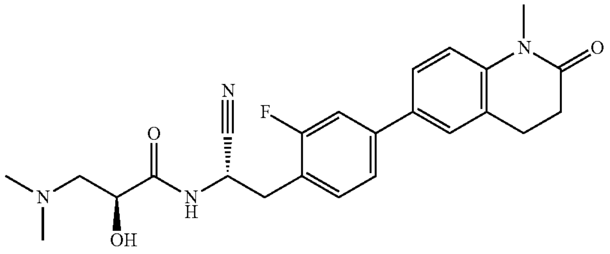 [SMILES: CN(C)C[C@H](O)C(=O)N[C@H](C#N)Cc1ccc(-c2ccc3c(c2)CCC(=O)N3C)cc1F] |
| 447 | 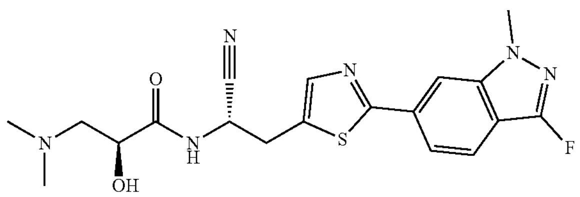 [SMILES: CN(C)C[C@H](O)C(=O)N[C@H](C#N)Cc1cnc(-c2ccc3c(F)nn(C)c3c2)s1] |

Compositions

The compounds of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A or pharmaceutically acceptable salts thereof, or deuterated versions of the foregoing, may be used on their own but will generally be administered in the form of a pharmaceutical composition in which the Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A compound/salt (active ingredient) is in association with pharmaceutically acceptable adjuvant(s), diluents(s) or carrier(s). Conventional procedures for the selection and preparation of suitable pharmaceutical Formulations are described in, for example, "Pharmaceuticals—The Science of Dosage Form Designs", M. E. Aulton, Churchill Livingstone, 2nd Ed. 2002.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

In embodiments, the present disclosure provides pharmaceutical composition(s) comprising a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A or a pharmaceutically acceptable salt thereof, as hereinbefore defined in association with pharmaceutically acceptable adjuvant(s), diluent(s) or carrier(s).

The disclosure further provides a process for the preparation of a pharmaceutical composition of the disclosure which comprises mixing a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A or a pharmaceutically acceptable salt thereof, as hereinbefore defined with a pharmaceutically acceptable adjuvant(s), diluents(s) or carrier (s).

The pharmaceutical compositions may be administered topically (e.g., to the skin or to the lung and/or airways) in the form, e.g., of creams, solutions, suspensions, heptafluoroalkane (HFA) aerosols and dry powder; or systemically, e.g., by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration the compound of the disclosure may be admixed with adjuvant(s), diluent(s) or carrier(s), for example, lactose, saccharose, sorbitol, mannitol; starch, for example, potato starch, corn starch or amylopectin; cellulose derivative; binder, for example, gelatin or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatin, talcum and titanium dioxide.

For the preparation of soft gelatin capsules, the compound of the disclosure may be admixed with, for example, a vegetable oil or polyethylene glycol. Hard gelatin capsules may contain granules of the compound using pharmaceutical excipients like the abovementioned excipients for tablets. Additionally, liquid or semisolid Formulations of the compound of the disclosure may be filled into hard gelatin capsules.

Liquid preparations for oral application may be in the form of syrups, solutions or suspensions. Solutions, for example may contain the compound of the disclosure, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making Formulations for oral use.

Therapeutic Use

In embodiments, the compounds of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A and their pharmaceutically acceptable salts, are DPP1 inhibitors, and thus may be used in any disease area where DPP1 plays a role. As such, in one aspect of the disclosure, a method of treatment is provided. The method of treatment, in one embodiment, comprises, administering to a subject in need thereof, a composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A or a pharmaceutically acceptable salt of (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A. In embodiments, the composition is administered to the patient for an administration period.

In embodiments, a compound or composition of the present disclosure is administered to a patient in a method for treating a obstructive disease of the airway; chronic rhinosinusitis (CRS); hidradenitis suppurativa (HS); cancer (e.g., cancer metastasis); granulomatosis with polyangiitis (GPA); microscopic polyangiitis (MPA); giant cell arteritis; polyarteritis nodosa; anti-GBM disease (Goodpasture's); rheumatoid arthritis; lupus nephritis; systemic lupus erythematosus; systemic scleroderma; inflammatory bowel disease (IBD)(e.g., ulcerative colitis; Crohn's disease); diabetic nephropathy; diabetic neuropathy; diabetic retinopathy; diabetic ulcers; Duchenne muscular dystrophy; bronchiolitis obliterans; long covid)—prophylaxis of ILD; atopic dermatitis; pyoderma gangrenosum; sweet's syndrome; dermatomyositis/polymyositis; neutrophilic dermatoses; uveitis; Behcet's disease; thrombosis (e.g., deep vein thrombosis (DVT)); bronchopulmonary dysplasia; amyotrophic lateral sclerosis; sickle cell anemia; psoriasis; ventilator-induced lung injury.

In embodiments, a compound or composition of the present disclosure is administered to a patient in a method for treating an obstructive disease of the airway. The obstructive disease of the airway, in one embodiment, is asthma (e.g., neutrophilic, bronchial, allergic, intrinsic, extrinsic, exercise-induced, drug-induced (including aspirin and NSAID-induced and dust-induced asthma, both intermittent and persistent and of all severities) airway hyperresponsiveness, chronic obstructive pulmonary disease (COPD), bronchitis (e.g., infectious bronchitis, eosinophilic bronchitis), emphysema, cystic fibrosis (CF), bronchiectasis (e.g., non-CF bronchiectasis (NCFBE) and bronchiectasis associated with CF), cystic fibrosis; sarcoidosis; alpha-1 antitrypsin (A1AT) deficiency, farmer's lung and related diseases, hypersensitivity pneumonitis, interstitial lung disease, pulmonary fibrosis ((PF), also known as lung fibrosis (PF); including idiopathic pulmonary fibrosis, cryptogenic fibrosing alveolitis, idiopathic interstitial pneumonias, fibrosis complicating anti-neoplastic therapy and chronic infection, including tuberculosis and aspergillosis and other fungal infections), complications of lung transplantation, vasculitic and thrombotic disorders of the lung vasculature, pulmonary hypertension (e.g., pulmonary arterial hypertension), antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus (e.g., respiratory syncytial virus, influenza, coronavirus (including SARS) and adenovirus), acute lung injury, acute respiratory distress syndrome (ARDS), as well as exacerbations of each of the foregoing respiratory tract disease states.

In embodiments, a compound or composition of the present disclosure is administered to a patient in a method for treating asthma. In embodiments, the asthma is neutrophilic asthma.

In embodiments, a compound or composition of the present disclosure is administered to a patient in a method for treating pulmonary hypertension. In some embodiment, pulmonary hypertension is pulmonary arterial hypertension. In some embodiments, pulmonary hypertension is pulmonary hypertension due to left heart disease. In some embodiments, pulmonary hypertension is pulmonary hypertension associated with chronic lung disease.

Cystic fibrosis (CF) is caused by abnormalities in the CF transmembrane conductance regulator protein, causing chronic lung infections (particularly with *Pseudomonas aeruginosa*) and excessive inflammation, and leading to bronchiectasis, declining lung function, respiratory insufficiency and quality of life. The inflammatory process is dominated by neutrophils that produce NE, as well as other destructive NSPs including CatG and PR3, that directly act upon extracellular matrix proteins and play a role in the host response to inflammation and infection (Dittrich et al., *Eur Respir J.* 2018; 51(3)). The methods provided herein employ reversible inhibitors of DPP1. Without wishing to be bound by theory, it is thought that the compounds of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof, administered via the methods provided herein have beneficial effects via inhibiting the activation of NSPs and decreasing inflammation, which in turn leads to a decrease in pulmonary exacerbations, a decrease in the rate of pulmonary exacerbations, and/or an improvement in lung function (e.g., forced expiratory volume in 1 second [$FEV_1$]) in CF patients.

In one embodiment, a method is provided for treating CF comprising administering to a CF patient in need of treatment, a composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof.

In one CF treatment method, a composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof, is administered to a CF patient in need of treatment for an administration period. The method comprises improving the lung function of the patient during the administration period, as compared to the lung function of the patient prior to the administration period. The improvement in lung function in one embodiment, is measured by spirometry.

Improving the lung function of the patient, in one embodiment, comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value prior to the administration period. Increasing, in one embodiment, is by about 5%, by about 10%, by about 15%, by about 20%, by about 25%, by about 30%, by about 35%, by about 40%, by about 45% or by about 50% of the respective value. Increasing, in one embodiment, is by at least about 5%, by at least about 10%, by at least about 15%, by at least about 20%, by at least about 25%, by at least about 30%, by at least about 35%, by at least about 40%, by at least about 45% or by at least about 50%. In yet another embodiment, the increasing is by about 5% to about 50%, by about 5% to about 40%, by about 5% to about 30% or by about 5% to about 20%. In even another embodiment, increasing is by about 10% to about 50%, by about 15% to about 50%, by about 20% to about 50%, or by about 25% to about 50%.

In one embodiment of a method provided herein, a composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof, is administered to a bronchiectasis patient in need of treatment for an administration period. Bronchiectasis is considered a pathological endpoint that results from many disease processes and is a persistent or progressive condition characterized by dilated thick-walled bronchi. The symptoms vary from intermittent episodes of expectoration and infection localized to the region of the lung that is affected to persistent daily expectoration often of large volumes of purulent sputum. Bronchiectasis may be associated with other non-specific respiratory symptoms. The underlying pathological process of bronchiectasis, without wishing to be bound by theory, has been reported as damage to the airways which results from an event or series of events where inflammation is central to the process (Guideline for non-CF Bronchiectasis, Thorax, July 2010, V. 65(Suppl 1), incorporated by reference herein in its entirety for all purposes).

Bronchiectasis is considered a pathological endpoint that results from many disease processes and is a persistent or progressive condition characterized by dilated thick-walled bronchi. The symptoms vary from intermittent episodes of expectoration and infection localized to the region of the lung that is affected to persistent daily expectoration often of large volumes of purulent sputum. Bronchiectasis may be associated with other non-specific respiratory symptoms. The underlying pathological process of bronchiectasis, without wishing to be bound by theory, has been reported as damage to the airways which results from an event or series of events where inflammation is central to the process (Guideline for non-CF Bronchiectasis, Thorax, July 2010, V. 65(Suppl 1), incorporated by reference herein in its entirety for all purposes).

The methods provided herein employ reversible inhibitors of DPP1. Without wishing to be bound by theory, it is thought that the compounds of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof, administered via the methods provided herein have beneficial effects via decreasing inflammation and mucus hypersecretion, which in some embodiments, leads to a decrease in pulmonary exacerbations, a decrease in the rate of pulmonary exacerbations, and/or an improvement in lung function (cough, sputum production, and forced expiratory volume in 1 second [$FEV_1$]) in bronchiectasis patients. Without wishing to be bound by theory, it is thought that the methods provided herein modify bronchiectasis progression by reducing the accelerated rate of lung function decline or lung tissue destruction.

In one embodiment, the bronchiectasis is non-CF bronchiectasis.

In one embodiment, the method for treating bronchiectasis comprises improving lung function of the patient during the administration period, as compared to the lung function of the patient prior to the administration period.

A pulmonary exacerbation, in one embodiment, is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis. In a further embodiment, the three or more symptoms result in a physician's decision to prescribe an antibiotic(s) to the patient exhibiting the symptoms.

In one embodiment of a method for treating bronchiectasis, the method comprises decreasing the rate of pulmonary exacerbation in the subject, compared to the rate of pulmonary exacerbation experienced by the subject prior to the administration period of the composition, or compared to a control subject with bronchiectasis that is not subject to the method of treatment. In a further embodiment, the bronchiectasis is non-CF bronchiectasis.

In another aspect, a method for treating chronic rhinosinusitis (CRS) in a subject in need thereof is provided. The method comprises in one embodiment, administering to the subject for an administration period, a pharmaceutical composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof.

The chronic rhinosinusitis is chronic rhinosinusitis without nasal polyps (CRSsNP), or chronic rhinosinusitis with nasal polyps (CRSwNP). In some embodiments, the chronic rhinosinusitis is chronic rhinosinusitis without nasal polyps (CRSsNP). In some embodiments, the chronic rhinosinusitis is chronic rhinosinusitis with nasal polyps (CRSwNP). In some embodiments, the chronic rhinosinusitis is refractory chronic rhinosinusitis. In some embodiments, the refractory chronic rhinosinusitis is refractory chronic rhinosinusitis without nasal polyps (CRSsNP). In some embodiments, the refractory chronic rhinosinusitis is refractory chronic rhinosinusitis with nasal polyps (CRSwNP).

In some embodiments, the subject exhibits one or more symptoms of CRS. In some embodiments, the one or more symptoms of CRS are: (a) nasal congestion; (b) nasal obstruction; (c) nasal discharge; (d) post-nasal drip; (e) facial pressure; (f) facial pain; (g) facial fullness; (h) reduced smell; (i) depression; (j) mucosal edema; (k) mucopurulent discharge; (1) obstruction of the middle meatus; (m) mucosal changes within the ostiomeatal complex and sinuses; (n) rhinorrhea; or (o) any combinations thereof. In some embodiments, obstruction of the middle meatus is mucosal obstruction, edematous obstruction, or a combination thereof.

In some embodiments, the administration of the pharmaceutical composition reduces, diminishes the severity of, delays the onset of, or eliminates one or more symptoms of CRS. In some embodiments, the one or more symptoms of CRS are: (a) nasal congestion; (b) nasal obstruction; (c) nasal discharge; (d) post-nasal drip; (e) facial pressure; (f) facial pain; (g) facial fullness; (h) reduced smell; (i) depression; (j) mucosal edema; (k) mucopurulent discharge; (1) obstruction of the middle meatus; (m) mucosal changes within the ostiomeatal complex and sinuses; (n) rhinorrhea; (o) or any combinations thereof. In some embodiments, the administration of the pharmaceutical composition enhances sinus drainage.

In some embodiments, the methods comprise reducing a composite severity score of one or more symptoms of CRS. As used herein, the "composite severity score" is a quantitative measure of all the symptoms of CRS exhibited by the subject. In some embodiments, the composite severity score is a sum total of all the daily symptoms exhibited by the subject. In some embodiments, the composite severity score is reduced during or subsequent to the administration period, as compared to the composite severity score measured prior to the administration period. In some embodiments, the one or more symptoms of CRS exhibited by the subject may be any symptoms described herein or known in the art to be associated with CRS. In some embodiments, the one or more symptoms of CRS are: nasal congestion, reduced smell, rhinorrhea, or any combination thereof. In some embodiments, the rhinorrhea is anterior rhinorrhea. In some embodiments, the rhinorrhea is posterior rhinorrhea.

In some embodiments, the methods comprise decreasing the Sino-Nasal Outcome Test-22 (SNOT-22) score of the subject during the administration period or subsequent to the administration period, compared to the SNOT-22 score of the subject prior to the administration period. As used herein, "SNOT-22" is a patient-reported measure of outcome developed for use in CRS with or without nasal polyps and contains 22 individual questions. The questions cover a broad range of health and health-related quality of life problems including physical problems, functional limitations and emotional consequences. The theoretical range of the SNOT-22 score is 0-110, with lower scores implying a better health-related quality of life. Further details of SNOT-22 are provided in Hopkins, et al., *Clin. Otolaryngol.* 2009, 34, 447-454, and Kennedy, et al., *Ann Allergy Asthma Immunol.* 2013 October; 111(4): 246-251, the contents of which are incorporated herein by reference in its entirety.

Hidradenitis suppurativa (HS) is a chronic relapsing inflammatory disorder. The symptoms include skin lesions that are often associated hair follicles, and may be painful, inflamed and/or swollen. In some cases, when the skin lesions heal, they can recur, and may lead to tunnels under the skin and progressive scarring. Since HS is a chronic condition, it can persist for many years and also, worsen over time, with serious effects on quality of life, psychological and emotional well-being. In fact, HS patients have increased rates of anxiety and depression with a risk of suicide two and a half times that of the general population.

HS patients are categorized according to disease severity, termed Hurley staging, as mild (Stage I), moderate (Stage II), or severe (Stage III). Although more than 200,000 cases of HS are diagnosed in the U.S. per year, this disease can be difficult to diagnose and requires specialized care. HS may be mistaken for an infection, an ingrown hair or other conditions. Moreover, current treatment options are limited and lack efficacy.

In one aspect, a method of treating HS in a subject in need thereof is provided. The method comprises in one embodiment, administering to the subject for an administration period, a pharmaceutical composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof. In a further embodiment, the method of treating HS comprises reducing neutrophilic inflammation in the subject.

The HS in one embodiment, is Hurley Stage I HS, Hurley Stage II HS or Hurley Stage III HS. In some embodiments, the HS is Hurley Stage I HS. In some embodiments, the HS is Hurley Stage II HS. In some embodiments, the HS is Hurley Stage III HS.

The disclosure provides methods of treating cancer in a subject in need thereof, comprising, administering to the subject, a pharmaceutical composition comprising an effective amount of any one of the compounds disclosed herein. The disclosure provides methods of treating cancer-induced pain in a subject having cancer, comprising, administering to the subject for an administration period, a pharmaceutical composition comprising an effective amount of any one of the compounds disclosed herein. In some embodiments, the cancer-induced pain is cancer-induced bone pain. The disclosure also provides methods of treating cancer-induced bone pain in a subject having cancer, comprising, administering to the subject for an administration period, a pharmaceutical composition comprising an effective amount of any one of the compounds disclosed herein.

In some embodiments, the cancer comprises a primary solid tumor. In some embodiments, the cancer is bladder cancer, lung cancer, brain cancer, ovarian cancer, pancreatic cancer, colorectal cancer, prostate cancer, liver cancer, hepatocellular carcinoma, kidney cancer, stomach cancer, skin cancer, fibroid cancer, lymphoma, virus-induced cancer, oropharyngeal cancer, testicular cancer, thymus cancer, thyroid cancer, melanoma, or bone cancer.

In some embodiments, the cancer is bladder cancer. In some embodiments, the cancer is lung cancer. In some embodiments, the cancer is brain cancer. In some embodiments, the cancer is ovarian cancer. In some embodiments, the cancer is pancreatic cancer. In some embodiments, the cancer is colorectal cancer. In some embodiments, the cancer is prostate cancer. In some embodiments, the cancer is liver cancer. In some embodiments, the cancer is hepatocellular carcinoma. In some embodiments, the cancer is kidney cancer. In some embodiments, the cancer is stomach cancer. In some embodiments, the cancer is skin cancer. In some embodiments, the cancer is fibroid cancer. In some embodiments, the cancer is lymphoma. In some embodiments, the cancer is virus-induced cancer. In some embodiments, the cancer is oropharyngeal cancer. In some embodiments, the cancer is testicular cancer. In some embodiments, the cancer is thymus cancer. In some embodiments, the cancer is thyroid cancer. In some embodiments, the cancer is melanoma. In some embodiments, the cancer is bone cancer. In some embodiments, the fibroid cancer is leiomyosarcoma.

In some embodiments, the breast cancer comprises ductal carcinoma, lobular carcinoma, medullary carcinoma, colloid carcinoma, tubular carcinoma, or inflammatory breast cancer. In some embodiments, the breast cancer comprises ductal carcinoma. In some embodiments, the breast cancer comprises lobular carcinoma. In some embodiments, the breast cancer comprises medullary carcinoma. In some embodiments, the breast cancer comprises colloid carcinoma. In some embodiments, the breast cancer comprises tubular carcinoma. In some embodiments, the breast cancer comprises inflammatory breast cancer.

In some embodiments, the breast cancer is triple-negative breast cancer. In some embodiments, the breast cancer does not respond to hormonal therapy or therapeutics that target the HER2 protein receptors.

In some embodiments, the lymphoma is Hodgkin's lymphoma, non-Hodgkin's lymphoma, diffuse large B-cell lymphoma, B-cell immunoblastic lymphoma, Natural Killer cell lymphoma, T-cell lymphoma, Burkitt lymphoma or Kaposi's Sarcoma. In some embodiments, the lymphoma is Hodgkin's lymphoma. In some embodiments, the lymphoma is non-Hodgkin's lymphoma. In some embodiments, the lymphoma is diffuse large B-cell lymphoma. In some embodiments, the lymphoma is B-cell immunoblastic lymphoma. In some embodiments, the lymphoma is Natural Killer cell lymphoma. In some embodiments, the lymphoma is T-cell lymphoma. In some embodiments, the lymphoma is Burkitt lymphoma. In some embodiments, the lymphoma is Kaposi's Sarcoma.

In some embodiments, the brain cancer is astrocytoma, anaplastic astrocytoma, glioblastoma multiforme, oligodendroglioma, ependymoma, meningioma, schwannoma, or medulloblastoma. In some embodiments, the brain cancer is astrocytoma. In some embodiments, the brain cancer is anaplastic astrocytoma. In some embodiments, the brain cancer is glioblastoma multiforme. In some embodiments, the brain cancer is oligodendroglioma. In some embodiments, the brain cancer is ependymoma. In some embodiments, the brain cancer is meningioma. In some embodiments, the brain cancer is schwannoma. In some embodiments, the brain cancer is medulloblastoma.

In some embodiments, the cancer is liquid tumor. In some embodiments, the liquid tumor is acute myeloid leukemia (AML), acute lymphoblastic leukemia, acute lymphocytic leukemia, acute promyelocytic leukemia, chronic myeloid leukemia, hairy cell leukemia, a myeloproliferative disorder, Natural Killer cell leukemia, blastic plasmacytoid dendritic cell neoplasm, chronic myelogenous leukemia (CML), mastocytosis, chronic lymphocytic leukemia (CLL), multiple myeloma (MM), or myelodysplastic syndrome (MDS). In some embodiments, the liquid tumor is acute myeloid leukemia (AML). In some embodiments, the liquid tumor is acute lymphoblastic leukemia. In some embodiments, the liquid tumor is acute lymphocytic leukemia. In some embodiments, the liquid tumor is acute promyelocytic leukemia. In some embodiments, the liquid tumor is chronic myeloid leukemia. In some embodiments, the liquid tumor is hairy cell leukemia. In some embodiments, the liquid tumor is a myeloproliferative disorder. In some embodiments, the liquid tumor is Natural Killer cell leukemia. In some embodiments, the liquid tumor is blastic plasmacytoid dendritic cell neoplasm. In some embodiments, the liquid tumor is chronic myelogenous leukemia (CML). In some embodiments, the liquid tumor is mastocytosis. In some embodiments, the liquid tumor is chronic lymphocytic leukemia (CLL). In some embodiments, the liquid tumor is multiple myeloma (MM). In some embodiments, the liquid tumor is myelodysplastic syndrome (MDS).

In some embodiments, the cancer is a pediatric cancer. In some embodiments, the pediatric cancer is neuroblastoma, Wilms tumor, rhabdomyosarcoma, retinoblastoma, osteosarcoma or Ewing sarcoma. In some embodiments, the pediatric cancer is neuroblastoma. In some embodiments, the pediatric cancer is Wilms tumor. In some embodiments, the pediatric cancer is rhabdomyosarcoma. In some embodiments, the pediatric cancer is retinoblastoma. In some embodiments, the pediatric cancer is osteosarcoma. In some embodiments, the pediatric cancer is Ewing sarcoma.

In some embodiments, the cancer is metastatic cancer. In some embodiments, the subject is at a risk for developing metastatic cancer. In some embodiments, the metastatic cancer comprises metastasis of breast cancer to the brain, bone, pancreas, lymph nodes, and/or liver. In some embodiments, the metastatic cancer comprises metastasis of bone cancer to the lung. In some embodiments, the metastatic cancer comprises metastasis of colorectal cancer to the peritoneum, the pancreas, the stomach, the lung, the liver, the kidney, and/or the spleen. In some embodiments, the metastatic cancer comprises metastasis of stomach cancer to the mesentery, the spleen, the pancreas, the lung, the liver, the adrenal gland, and/or the ovary. In some embodiments, the metastatic cancer comprises metastasis of leukemia to the lymph nodes, the lung, the liver, the hind limb, the brain, the kidney, and/or the spleen. In some embodiments, the metastatic cancer comprises metastasis of liver cancer to the intestine, the spleen, the pancreas, the stomach, the lung, and/or the kidney. In some embodiments, the metastatic cancer comprises metastasis of lymphoma to the kidney, the ovary, the liver, the bladder, and/or the spleen.

In some embodiments, the metastatic cancer comprises metastasis of hematopoietic cancer to the intestine, the lung, the liver, the spleen, the kidney, and/or the stomach. In some embodiments, the metastatic cancer comprises metastasis of melanoma to lymph nodes and/or the lung. In some embodiments, the metastatic cancer comprises metastasis of pancreatic cancer to the mesentery, the ovary, the kidney, the spleen, the lymph nodes, the stomach, and/or the liver. In some embodiments, the metastatic cancer comprises metastasis of prostate cancer to the lung, the pancreas, the kidney, the spleen, the intestine, the liver, the bone, and/or the lymph nodes. In some embodiments, the metastatic cancer comprises metastasis of ovarian cancer to the diaphragm, the liver, the intestine, the stomach, the lung, the pancreas, the spleen, the kidney, the lymph nodes, and/or the uterus. In some embodiments, the metastatic cancer comprises metastasis of myeloma to the bone.

In some embodiments, the metastatic cancer comprises metastasis of lung cancer to the bone, the brain, the lymph nodes, the liver, the ovary, and/or the intestine. In some embodiments, the metastatic cancer comprises metastasis of kidney cancer to the liver, the lung, the pancreas, the stomach, the brain, and/or the spleen. In some embodiments, the metastatic cancer comprises metastasis of bladder cancer to the bone, the liver and/or the lung. In some embodiments, the metastatic cancer comprises metastasis of thyroid cancer to the bone, the liver and/or the lung.

In some embodiments, the methods disclosed herein comprise treating cancer-induced bone pain (CIBP) in a subject having metastasis of a cancer to the bone. In some embodiments, the subject has metastasis of prostate cancer, breast cancer, lung cancer, or myeloma to the bone. In some embodiments, the subject is identified as having metastasis to the bone by the use of any one of the following methods: plain film radiography, computed tomography, technetium 99m bone scan, magnetic resonance imaging, fluorodeoxyglucose positron emission tomography, fluorine positron emission tomography, and/or choline positron emission tomography, but is not yet feeling cancer-induced bone pain. In some embodiments, the subject is suffering from cancer-induced bone pain, which is indicative of metastasis of a previously treated or untreated primary tumor to the bone. In some embodiments, the cancer has metastasized to vertebrae, pelvis, long bones, or ribs.

In some embodiments, administration of the composition diminishes the severity of, delays the onset of, or eliminates a symptom of cancer. In some embodiments, the symptom of cancer is cancer-induced bone pain (CIBP). In some embodiments, the CIBP is neuropathic pain. In some embodiments, the CIBP is inflammatory pain. In some embodiments, the CIBP is spontaneous pain. In some embodiments, the symptom of cancer is nociceptive hypersensitivity. In some embodiments, the symptom of cancer is allodynia. In some embodiments, the allodynia is tactile allodynia. In some embodiments, the tactile allodynia is static mechanical allodynia. In some embodiments, the tactile allodynia is dynamic mechanical allodynia. In some embodiments, the subject has bone cancer or metastasis to the bone.

In yet another embodiment of the present disclosure, a method for treating lupus nephritis (LN) in a subject in need thereof is provided. The method comprises administering to the subject for an administration period, a pharmaceutical composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof.

Rheumatoid arthritis (RA) is characterized by inflammation and thickening of the joint capsule, together with an effect on the underlying bone and cartilage. Currently, the cause of RA is unknown and no satisfactory cure for RA is available. While a number of therapeutic agents have been developed and utilized to alleviate pain and inflammation associated with the disease, such as disease-modifying anti-rheumatic drugs (DMARDs) and non-steroidal anti-inflammatory agents (NSAIDs), they often produce intolerable side effects. To addresses this and other needs, the present disclosure, in one embodiment, provides a method for treating RA using reversible inhibitors of DPP1 of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof. In one embodiment, a method of for treating RA in a subject in need thereof is provided, and comprises administering to the subject for an administration period, a pharmaceutical composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof. In a further embodiment, the method comprises reducing neutrophilic inflammation in the subject.

Osteoarthritis (OA) is typically not autoimmune in origin and is typically a gradual, degenerative joint disease due to age-related chronic use or injury of the joints leading to cartilage breakdown, bone changes and local non-resolving synovial inflammation. In embodiments, the present disclosure provides a method for treating osteoarthritis (OA) in a patient in need thereof, comprising administering to the patient an effective amount of a compound disclosed herein (e.g., a compound of Formula ((I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof). In embodiments, the treating of osteoarthritis (OA) comprises improving weight loss and/or inflamed paw volume of the patient during the administration period, as compared to the weight loss and/or inflamed paw volume of the patient prior reducing weight loss and/or inflamed paw volume of the patient during the administration period, as compared to the weight loss and/or inflamed paw volume of the patient prior to the administration period.

Inflammatory bowel disease (IBD) is a group of inflammatory conditions that affect the colon and small intestine. The most common IBDs are Crohn's disease and ulcerative colitis. The present disclosure, in one embodiment, addresses the need for novel IBD therapies. Specifically, in one embodiment, a method for treating an inflammatory bowel disease (IBD) in a subject in need thereof is provided. The method comprises administering to the subject for an administration period, a pharmaceutical composition comprising an effective amount of a compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof.

In a further embodiment, the IBD is Crohn's disease or ulcerative colitis. In even a further embodiment, the method comprises reducing neutrophilic inflammation in the subject.

In embodiments, a compound or composition of the present disclosure is administered to a patient in a method for treating heart failure. In some embodiment, heart failure is heart failure with reduced ejection fraction. In some embodiments, heart failure is heart failure with preserved ejection fraction.

In yet another embodiment of the disclosure, a method for treating ischemia/reperfusion (IR) injury is provide, comprising administering to a patient in need of treatment, a compound or composition of the present disclosure to the patient in need of treatment. The IR injury, in one embodiment, is due to Heart transplantation (HTX). As such, in one embodiment, the patient is a heart transplant recipient. In a further embodiment, the patient is administered a compound or composition of the present disclosure during heart transplantation or subsequent to heart transplantation. In one embodiment of this method, the patient is administered one of the compounds set forth in Table A. In a further embodiment, the compound is compound 101, 105, 130, 138, 140 or 142. In even a further embodiment, the compound is compound 138 as set forth in Table A. In yet even a further embodiment, the compound is present in an oral composition and is administered once daily to the patient in need of treatment.

Treating the IR injury in one embodiment, comprises improving left-ventricular (LV) graft function. Graft function can be measured, in one embodiment, by measuring LV systolic function, e.g., by measuring left-ventricular systolic pressure (LVSP), developed pressure, maximal slope of systolic pressure increment ($dP/dt_{max}$), and/or rate pressure product (mmHg*bpm).

In one embodiment, treating IR injury comprises increasing the patient's LVSP (mmHg) during or subsequent to the administration period, as compared to the patient's LVSP (mmHg) prior to the administration period. In one embodiment, treating IR injury comprises increasing the patient's developed pressure (mmHg) during or subsequent to the administration period, as compared to the patient's developed pressure (mmHg) prior to the administration period. In yet another embodiment, treating IR injury in a patient in need of treatment comprises increasing the maximal slope of systolic pressure increment ($dP/dt_{max}$) for the patient during or subsequent to the administration period, as compared to the maximal slope of systolic pressure increment ($dP/dt_{max}$) for the patient prior to the administration period. In even yet another embodiment, treating IR injury in a patient in need of treatment comprises increasing the patient's rate pressure product during or subsequent to the administration period, as compared to the patient's rate pressure product prior to the administration period.

In one embodiments of the disclosure, a method for treating sepsis is provided, comprising administering to a patient in need of treatment, a compound or composition of the present disclosure to the patient in need of treatment. In one embodiment, sepsis is a consequence of the patient's response to overwhelming bacterial infection. In one embodiment, treatment of sepsis prevents organ dysfunction and death of the patient.

In one embodiments of the disclosure, a method for treating liver injury is provided, comprising administering to a patient in need of treatment, a compound or composition of the present disclosure to the patient in need of treatment. In one embodiment, the liver injury is drug-induced acute liver injury (ALI). In one embodiment, the liver injury is acetaminophen (APAP)-induced acute liver injury. In one embodiment, the liver injury is caused by acetaminophen (APAP) overdose. In embodiment, the liver injury is caused by nonsteroidal anti-inflammatory drugs (NSAIDs), such as ibuprofen, diclofenac, and naproxen. In one embodiment, the treatment of ALI is a prophylactic treatment.

In embodiments, the treatment of liver injury (such as drug-induced acute liver injury) comprises improving the patient's liver function test (LFT) results during or subsequent to the administration period, as compared to the patient's LFT results prior to the administration period. In embodiments, LFTs include testing the levels of liver function biomarkers such as alanine aminotransferase (ALT), aspartate aminotransferase (AST), alkaline phosphatase (ALP), gamma-glutamyl transferase (GGT), and bilirubin levels in blood samples. In embodiments, the treatment of liver injury (such as drug-induced acute liver injury) comprises reducing the patient's levels of one or more liver function biomarkers in blood samples during or subsequent to the administration period, as compared to the patient's LFT results prior to the administration period.

The length of the administration period in any given case may depend on the nature and severity of the condition being treated and/or prevented and be determined by the physician. In one embodiment, the administration period starts at about the time of condition/disease diagnosis and continues for the lifetime of the patient.

In some embodiments, the administration period is about 30 days, about 35 days, about 40 days, about 45 days, about 50 days, about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 30 months, about 36 months, about 4 years, about 5 years, about 10 years, about 15 years or about 20 years. In some embodiments, the compounds or compositions disclosed herein may be administered for a period of about 24 weeks. In some embodiments, the compounds or compositions disclosed herein may be administered for a period of about 52 weeks. In yet another embodiment, the administration period is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 4 years, at least about 5 years, at least about 10 years, at least about 15 years or at least about 20 years.

In some embodiments, the administration period for the methods provided herein is at least about 30 days, at least about 35 days, at least about 40 days, at least about 45 days, at least about 50 days, at least about 2 months, at least about 3 months, at least about 4 months or at least about 6 months, at least about 7 months, at least about 8 months, at least about 9 months, at least about 10 months, at least about 11 months, at least about 1 year, at least about 2 years, at least about 3 years, at least about 4 years, at least about 5 years. The administration period for the methods provided herein, in another embodiment, is from about 30 days to about 180 days. In another embodiment, the administration period is from about 30 days to about 36 months, or from about 30 days to about 30 months, or from about 30 days to about 24 months, or from about 30 days to about 18 months, or from about 30 days to about 12 months, or from about 30 days to about 6 months, or from about 6 months to about 30 months, or from about 6 months to about 24 months, or from about 6 months to about 18 months, or from about 12 months to about 36 months, or from about 12 months to about 24 months.

In one embodiment, the administration period is from about 1 year to about 30 years. For example, the administration period, in one embodiment, is from about 1 year to about 25 years, 1 year to about 20 years, from about 1 year to about 15 years, from about 1 year to about 10 years, from about 1 year to about 5 years, from about 1 year to about 3 years, from about 1 year to about 2 years, from about 2 years to about 15 years, from about 2 year to about 10 years, from about 2 years to about 8 years, from about 2 year to about 5 years, from about 2 years to about 4 years, or from about 2 years to about 3 years.

The dosage administered will vary with the compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof employed, the mode of administration, and the treatment outcome desired. For example, in one embodiment, the daily dosage of the compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof if inhaled, may be in the range from 0.05 micrograms per kilogram body weight (g/kg) to 100 micrograms per kilogram body weight (g/kg). Alternatively, in one embodiment, if the compound of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof is administered orally, then the daily dosage of the compound of the disclosure may be in the range from 0.01 micrograms per kilogram body weight (g/kg) to 100 milligrams per kilogram body weight (mg/kg).

The compounds of Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof may be used on their own but will generally be administered in the form of a pharmaceutical composition in which the Formula (I), (II), (III), (IV), (V), (VI), (VII), (VIII), (IX), (IX-A), (IX-B), (IX-C), (IX-D), (X), (X-A), (X-B), (X-C), (X-D), (XI), (XI-A), (XII) or (XII-A), or Table A, or a pharmaceutically acceptable salt, a stereoisomer, or a deuterated form thereof is in association with pharmaceutically acceptable adjuvant (s), diluents(s) or carrier(s). Conventional procedures for the selection and preparation of suitable pharmaceutical Formulations are described in, for example, "Pharmaceuticals—The Science of Dosage Form Designs", M. E. Aulton, Churchill Livingstone, 2nd Ed. 2002.

EXAMPLES

The present disclosure is further illustrated by reference to the following Examples. However, it should be noted that these Examples, like the embodiments described above, are illustrative and are not to be construed as restricting the scope of the disclosure in any way.

In embodiments, compounds of the present disclosure can be synthesized using the following methods. General reaction conditions are given, and reaction products can be purified by generally known methods including silica gel chromatography using various organic solvents such as hexane, dichloromethane, ethyl acetate, methanol and the like or preparative reverse phase high pressure liquid chromatography.

In the following examples, the term "assumed", where present, refers to the particular stereochemistry of the respective product. Further characterization will confirm the absolute stereochemistry of the products.

Example 1. Synthesis of Compound 105: (2S)—N-[(1S)-1-cyano-2-[4-(3-methyl-2-oxo-1,3-benzoxazol-5-yl)phenyl]ethyl]-3-(dimethylamino)-2-methoxypropanamide

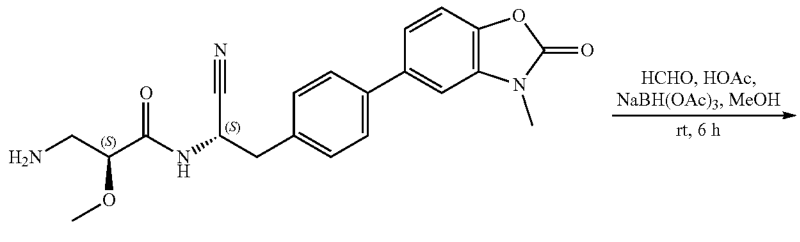

compound 103

-continued

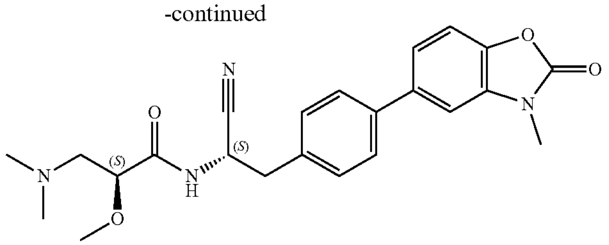

compound 105

To a stirred solution of (2S)-3-amino-N-[(1S)-1-cyano-2-[4-(3-methyl-2-oxo-1,3-benzoxazol-5-yl)phenyl]ethyl]-2-methoxypropanamide (100 mg, 0.25 mmol, 1.0 equiv) in MeOH (2 mL) were added HCHO (380 mg, 3.81 mmol, 15.0 equiv, 30% in water) and HOAc (15 mg, 0.25 mmol, 1.0 equiv) dropwise at room temperature under nitrogen atmosphere. The resulting mixture was stirred for 0.5 h at room temperature under nitrogen atmosphere. To the above mixture was added $NaBH(OAc)_3$ (214 mg, 1.01 mmol, 4.0 equiv) in portions at 0° C. The resulting mixture was stirred for additional 3 h at room temperature. The reaction solution was purified by reversed-phase flash chromatography with the following conditions: column, $C_{18}$ silica gel-120 g; mobile phase, MeCN in Water (0.1% $NH_3{\cdot}H_2O$), 10% to 70% gradient in 10 min; detector, UV 254 nm. This resulted in (2S)—N-[(1S)-1-cyano-2-[4-(3-methyl-2-oxo-1,3-benzoxazol-5-yl)phenyl]ethyl]-3-(dimethylamino)-2-methoxypropanamide (30 mg, 28%).

LCMS (ES, m z): $[M+H]^+$: 423.2

$^1$H NMR (300 MHz, DMSO-$d_6$) δ 8.84 (d, J=8.3 Hz, 1H), 7.66 (d, J=8.2 Hz, 2H), 7.57 (t, J=1.2 Hz, 1H), 7.44-7.39 (m, 4H), 5.16-5.02 (m, 1H), 3.71 (dd, J=6.9, 4.7 Hz, 1H), 3.42 (s, 3H), 3.30-3.09 (m, 5H), 2.37-2.18 (m, 2H), 2.09 (s, 6H).

Example 2. Synthesis of Compound 109: (S)—N—((S)-1-cyano-2-(4-(3-methyl-2-oxo-2,3-dihydrobenzo[d]oxazol-5-yl phenyl ethyl)-2-methoxy-3-(methylamino)propenamide compund 109

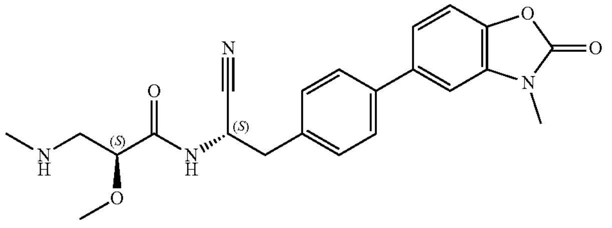

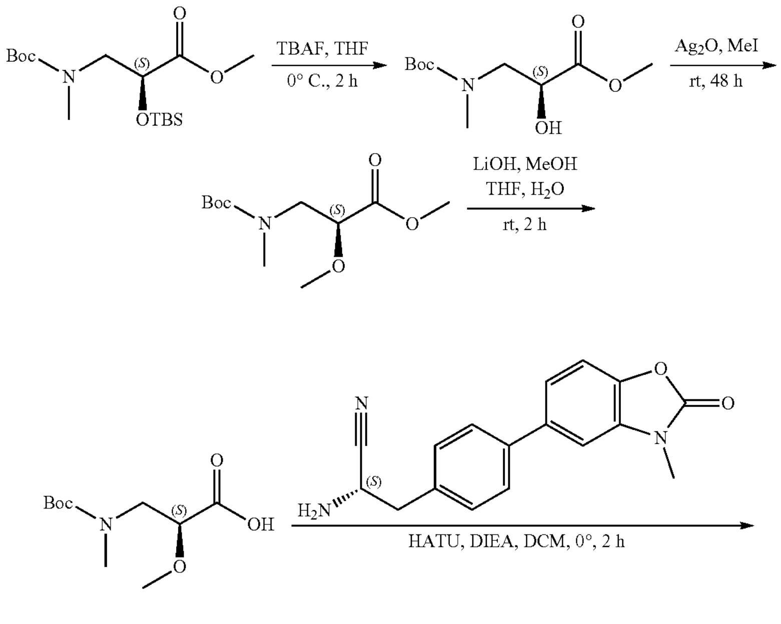

-continued

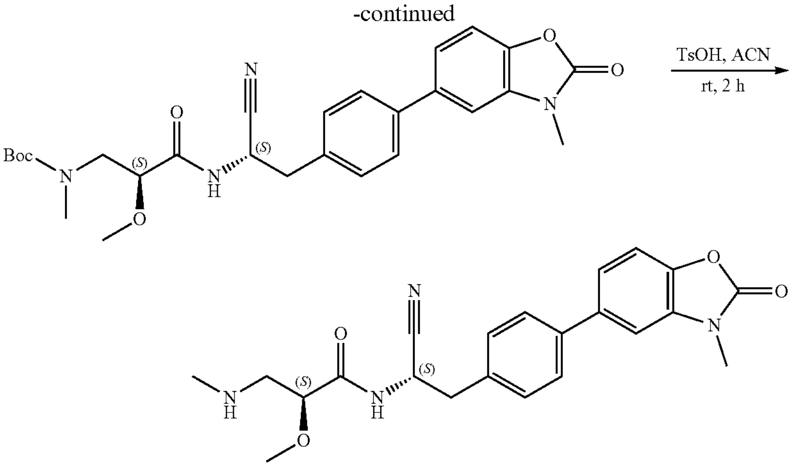

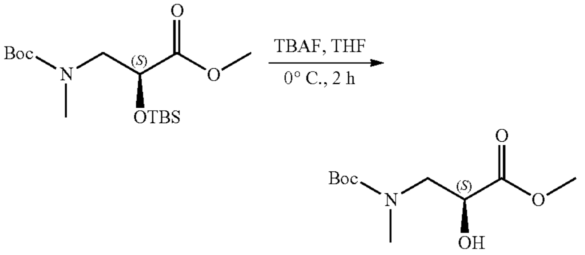

Synthesis of methyl (S)-3-((tert-butoxycarbonyl)(methyl)amino)-2-hydroxypropanoate To a stirred solution methyl (2S)-3-[(tert-butoxycarbonyl)(methyl)amino]-2-[(tert-butyldimethylsilyl) oxy]propanoate (1.7 g, 4.89 mmol, 1.0 equiv) in THE (17 mL) was added TBAF (1.28 g, 4.89 mmol, 1.0 equiv) at 0° C. The resulting mixture was stirred for 2 h at room temperature. The resulting mixture was diluted with water (40 mL). The resulting mixture was extracted with EtOAc (3×40 mL). The combined organic layer were washed with water (2×20 mL), dried over anhydrous $Na_2SO_4$. After filtration, the filtrate was concentrated under reduced pressure. The residue was purified by silica gel column chromatography, eluted with PE/EA (3:1) to afford methyl (S)-3-((tert-butoxycarbonyl)(methyl)amino)-2-hydroxypropanoate (850 mg, 74.5%). LCMS (ES) $[M+H]^+$ m/z: 234.

Synthesis of methyl (2S)-3-[(tert-butoxycarbonyl)(methyl)amino]-2-methoxypropanoate

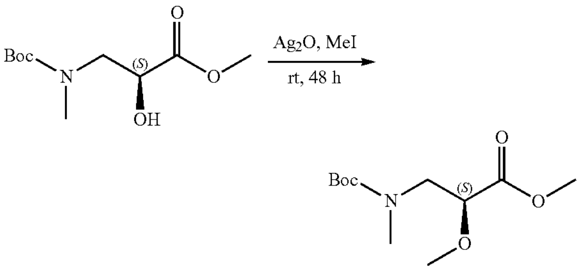

To a stirred solution of methyl (S)-3-((tert-butoxycarbonyl)(methyl)amino)-2-hydroxypropanoate (850 mg, 3.64 mmol, 1.0 equiv) and $Ag_2O$ (1.68 g, 7.29 mmol, 2 equiv) in DCM (10 mL) was added MeI (775 mg, 5.47 mmol, 1.5 equiv) dropwise at 0° C. The resulting mixture was stirred for 48 h at room temperature. The resulting mixture was filtered; the filter cake was washed with $CH_2Cl_2$ (2×4 mL). The filtrate was concentrated under reduced pressure. The residue was purified by silica gel column chromatography, eluted with PE/EA (4:1) to afford methyl (2S)-3-[(tert-butoxycarbonyl)(methyl)amino]-2-methoxypropanoate (600 mg, 66.6%). LCMS (ES) $[M+H]^+$ m/z: 248.

Synthesis of (2S)-3-[(tert-butoxycarbonyl)(methyl)amino]-2-methoxypropanoic acid

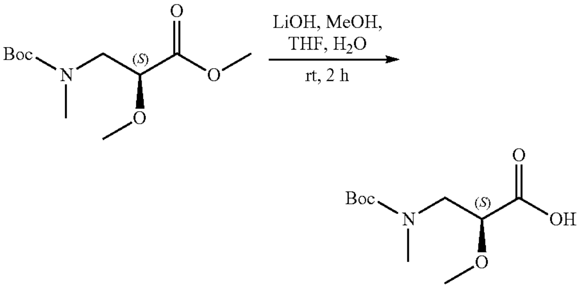

To a stirred solution of methyl (2S)-3-[(tert-butoxycarbonyl)(methyl)amino]-2-methoxypropanoate (600 mg, 2.43 mmol, 1.0 equiv) in mixed solvent, MeOH (4 mL), THF (4 mL), and $H_2O$ (2 mL) was added LiOH (58 mg, 2.43 mmol, 1.0 equiv). The resulting mixture was stirred for 2 h at room temperature. The reaction mixture was diluted with water (10 mL), extracted with (2×10 mL) of EA. The aqueous phase was acidified to pH 6 with citric acid, extracted with EtOAc (3×10 mL). The combined organic layer was washed with water (2×10 mL), dried over anhydrous $Na_2SO_4$. After filtration, the filtrate was concentrated under reduced pressure. This resulted in (2S)-3-[(tert-butoxycarbonyl)(methyl)amino]-2-methoxypropanoic acid (350 mg, 61.8%) which was used to the next step without further purification. LCMS (ES) $[M+H]^+$ m/z: 234.

Synthesis of tert-butyl N-[(2S)-2-{[(1S)-1-cyano-2-[4-(3-methyl-2-oxo-1,3-benzoxazol-5-yl) phenyl]ethyl]carbamoyl}-2-methoxyethyl]—N-methylcarbamate

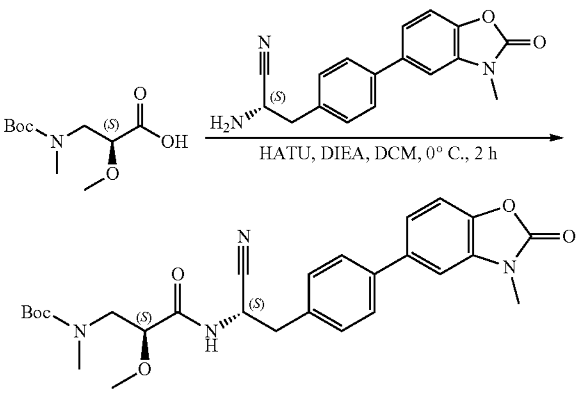

To a stirred solution of (2S)-3-[(tert-butoxycarbonyl)(methyl)amino]-2-methoxypropanoic acid (110 mg, 0.47 mmol, 1.0 equiv), (2S)-2-amino-3-[4-(3-methyl-2-oxo-1,3-benzoxazol-5-yl)phenyl]propanenitrile (110 mg, 0.38 mmol, 0.8 equiv) and DIEA (182 mg, 1.42 mmol, 3.0 equiv) in DCM (2 mL) was added HATU (215 mg, 0.57 mmol, 1.2 equiv) in portions at 0° C. The resulting mixture was stirred for 2 h at 0° C. Concentrated to remove the solvent, the residue was purified by silica gel column chromatography, eluted with PE/EA (1:1) to afford tert-butyl N-[(2S)-2-{[(1S)-1-cyano-2-[4-(3-methyl-2-oxo-1,3-benzoxazol-5-yl) phenyl]ethyl]carbamoyl}-2-methoxyethyl]—N-methylcarbamate (130 mg, 54.2%). LCMS (ES) $[M+H]^+$ m/z: 509.

Synthesis of (2S)—N-[(1S)-1-cyano-2-[4-(3-methyl-2-oxo-1,3-benzoxazol-5-yl) phenyl]ethyl]-2-methoxy-3-(methylamino) procainamide

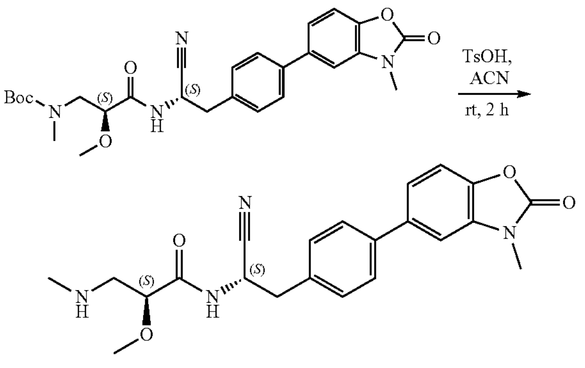

A solution of tert-butyl N-[(2S)-2-{[(1S)-1-cyano-2-[4-(3-methyl-2-oxo-1,3-benzoxazol-5-yl) phenyl]ethyl]carbamoyl}-2-methoxyethyl]—N-methylcarbamate (110 mg, 0.22 mmol, 1.0 equiv) and TsOH (111 mg, 0.65 mmol, 3.0 equiv) in ACN (1.5 mL) was stirred for 2 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (S)—N—((S)-1-cyano-2-(4-(3-methyl-2-oxo-2,3-dihydrobenzo[d]oxazol-5-yl)phenyl)ethyl)-2-methoxy-3-(methylamino)propanamide (30 mg, 34%). LCMS (ES) $[M+1]^+$ m/z: 409.3

$^1H$ NMR (400 MHz, DMSO-$d_6$) δ 8.81 (brs, 1H), 7.70-7.63 (m, 2H), 7.57 (t, J=1.2 Hz, 1H), 7.45-7.36 (m, 4H), 5.11-5.02 (m, 1H), 3.73-3.63 (m, 1H), 3.41 (s, 3H), 3.27-3.11 (m, 5H), 2.51-2.49 (m, 2H), 2.23 (d, J=23.6 Hz, 3H).

Example 3. Synthesis of Compound 110: Synthesis of (2S)-3-amino-N-[(1S)-1-cyano-2-[4-(3-methyl-2-oxo-1,3-benzoxazol-5-yl)phenyl]ethyl]-2-hydroxypropanamide compound 110

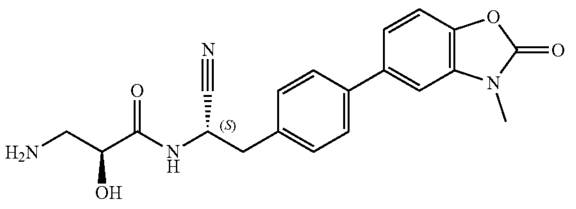

Synthesis of (2S)-3-amino-N-[(1S)-1-cyano-2-[4-(3-methyl-2-oxo-1,3-benzoxazol-5-yl)phenyl]ethyl]-2-hydroxypropanamide

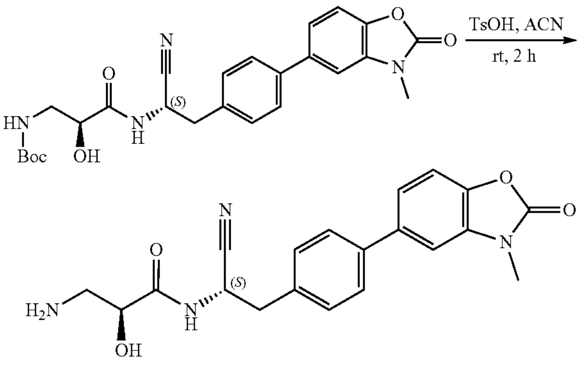

compound 110

Into a 25 mL round-bottom flask were added tert-butyl N-[(2S)-2-{[(1S)-1-cyano-2-[4-(3-methyl-2-oxo-1,3-benzoxazol-5-yl)phenyl]ethyl]carbamoyl}-2-hydroxyethyl]carbamate (120 mg, 0.25 mmol, 1.0 equiv), $TsOH \cdot H_2O$ (142 mg, 0.75 mmol, 3.0 equiv) and ACN (3 mL) at room temperature. The resulting mixture was stirred for 2 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. The fraction of the target was freezing dried, this resulted in (2S)-3-amino-N-[(1S)-1-cyano-2-[4-(3-methyl-2-oxo-1,3-benzoxazol-5-yl)phenyl]ethyl]-2-hydroxypropanamide (18 mg, 19%).

LCMS (ES, m z): $[M+H]^+$: 381.1

$^1H$ NMR (400 MHz, DMSO-$d_6$): δ 7.69-7.62 (m, 2H), 7.58 (d, J=1.5 Hz, 1H), 7.45-7.36 (m, 4H), 5.74 (brs, 1H), 5.07 (t, J=7.9 Hz, 1H), 3.84 (dd, J=6.5, 3.9 Hz, 1H), 3.41 (s, 3H), 3.24-3.13 (m, 2H), 2.61 (dd, J=13.2, 4.0 Hz, 1H), 2.49-2.43 (m, 1H).

Example 4. Synthesis of Compound 111: (2S)—N-[(1S)-1-cyano-2-[4-(3-methyl-2-oxo-1,3-benzoxazol-5-yl)phenyl]ethyl]-2-hydroxy-3-(methylamino)propanamide

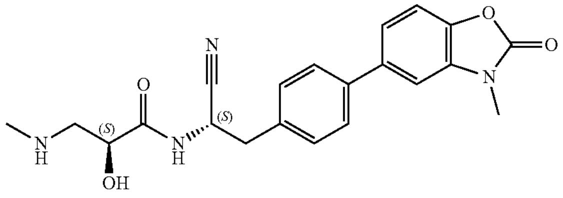

compound 111

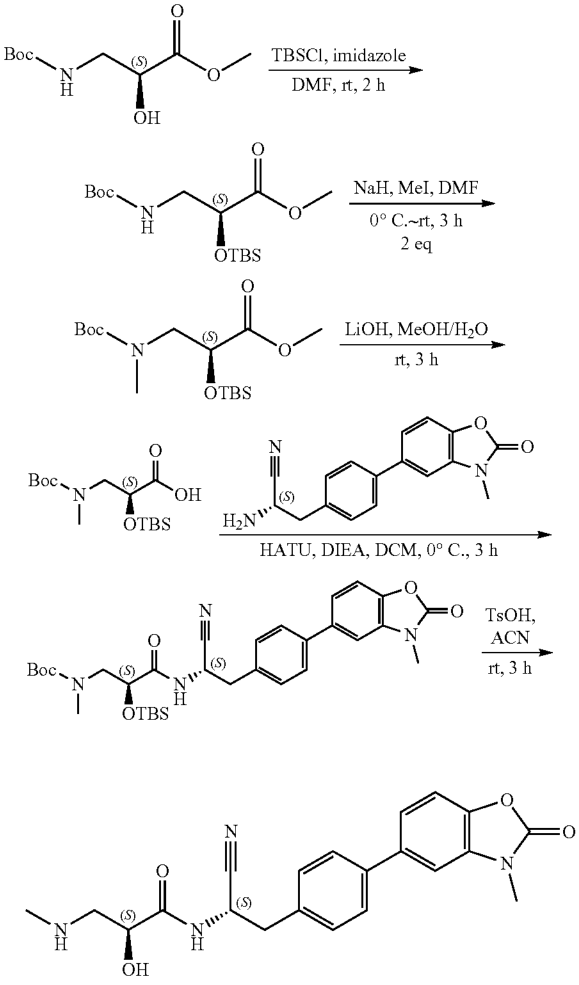

Synthesis of (2S)-3-[(tert-butoxycarbonyl)amino]-2-[(tert-butyldimethylsilyl)oxy]propanoate

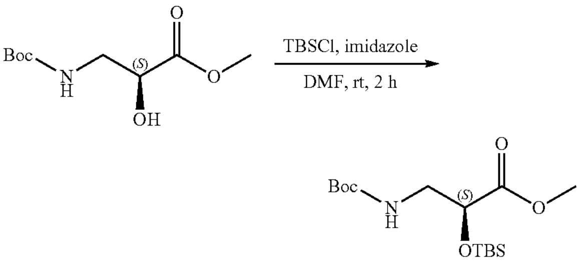

To a stirred solution of methyl (2S)-3-[(tert-butoxycarbonyl)amino]-2-hydroxypropanoate (2.2 g, 10.04 mmol, 1 equiv) and Imidazole (1.37 g, 20.07 mmol, 2 equiv) in DMF (22 mL) was added TBSCI (2.27 g, 15.05 mmol, 1.5 equiv) in portions at 0° C. The resulting mixture was stirred for 16 h at room temperature. The resulting mixture was extracted with EtOAc (3×20 mL). The combined organic layers were washed with water (3×20 mL), dried over anhydrous $Na_2SO_4$. After filtration, the filtrate was concentrated under reduced pressure. This resulted in methyl (2S)-3-[(tert-butoxycarbonyl)amino]-2-[(tert-butyldimethylsilyl)oxy]propanoate (2.7 g, 80.68%). LCMS (ES, m z): $[M+H]^+$: 334.

Synthesis of methyl (2S)-3-[(tert-butoxycarbonyl)(methyl)amino]-2-[(tert-butyldimethylsilyl)oxy]propanoate

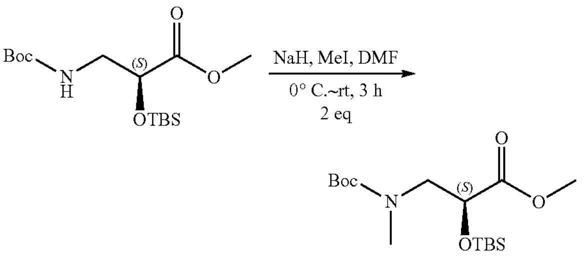

To a stirred solution of methyl (2S)-3-[(tert-butoxycarbonyl)amino]-2-[(tert-butyldimethylsilyl)oxy]propanoate (2.7 g, 8.10 mmol, 1 equiv) and NaH (0.39 g, 16.19 mmol, 2 equiv) in DMF (27 mL) was added NaH (0.39 g, 16.19 mmol, 2 equiv) at 0° C. The resulting mixture was stirred for 30 min at 0° C. To the above mixture was added Mel (1.38 g, 9.72 mmol, 1.2 equiv) dropwiseat 0° C. The resulting mixture was stirred for additional 3 h at room temperature. The resulting mixture was diluted with water (20 mL). The resulting mixture was extracted with EtOAc (3×40 mL). The combined organic layers were washed with water (3×20 mL), dried over anhydrous $Na_2SO_4$. After filtration, the filtrate was concentrated under reduced pressure. The residue was purified by silica gel column chromatography, eluted with PE/EA (5:1) to afford methyl (2S)-3-[(tert-butoxycarbonyl)(methyl)amino]-2-[(tert-butyldimethylsilyl)oxy]propanoate (1.7 g, 60.42%). LCMS (ES, m z): $[M+H]^+$: 348.

Synthesis of (2S)-3-[(tert-butoxycarbonyl)(methyl)amino]-2-[(tert-butyldimethylsilyl)oxy]propanoic acid

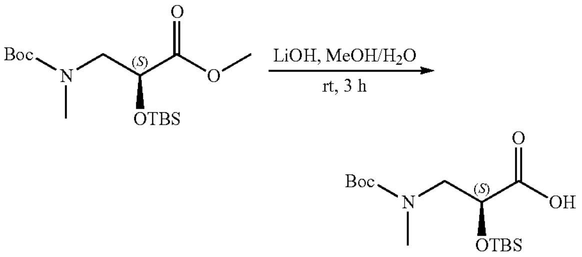

To a stirred solution/mixture of methyl (2S)-3-[(tert-butoxycarbonyl)(methyl)amino]-2-[(tert-butyldimethylsilyl)oxy]propanoate (600 mg, 1.73 mmol, 1 equiv) and MeOH (9 mL) was added LiOH (83 mg, 3.45 mmol, 2 equiv) in $H_2O$ (3 mL) dropwise at room temperature. The resulting mixture was stirred for 3 h at room temperature. The resulting mixture was concentrated under reduced pressure. The mixture was acidified to pH 4 with conc. HCl. The resulting mixture was extracted with EtOAc (3×30 mL). The combined organic layers were dried over anhydrous $Na_2SO_4$. After filtration, the filtrate was concentrated under reduced pressure. This resulted in (2S)-3-[(tert-butoxycarbonyl)(methyl)amino]-2-[(tert-butyldimethylsilyl)oxy]propanoic acid (500 mg, 86.84%). LCMS (ES, m z): $[M+H]^+$: 334.

Synthesis of tert-butyl N-[(2S)-2-{[(1S)-1-cyano-2-[4-(3-methyl-2-oxo-1,3-benzoxazol-5-yl)phenyl]ethyl]carbamoyl}-2-hydroxyethyl]—N-methylcarbamate

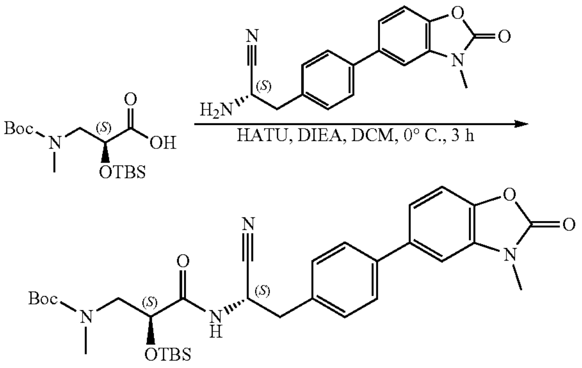

To a stirred mixture of (2S)-3-[(tert-butoxycarbonyl)(methyl)amino]-2-[(tert-butyldimethylsilyl)oxy]propanoic acid (182 mg, 0.55 mmol, 2 equiv), (2S)-2-amino-3-[4-(3-methyl-2-oxo-1,3-benzoxazol-5-yl)phenyl]propanenitrile (80 mg, 0.27 mmol, 1.00 equiv) and DIEA (106 mg, 0.82 mmol, 3 equiv) in DCM (5 mL) were added HATU (124 mg, 0.33 mmol, 1.2 equiv) in portions at 0° C. The resulting mixture was stirred for additional 3 h at 0° C. The residue was purified by silica gel column chromatography, eluted with PE/THE (1:1) to afford tert-butyl N-[(2S)-2-[(tert-butyldimethylsilyl)oxy]-2-{[(1S)-1-cyano-2-[4-(3-methyl-2-oxo-1,3-benzoxazol-5-yl)phenyl]ethyl]carbamoyl}ethyl]—N-methylcarbamate (120 mg, 72.27%). LCMS (ES, m z): $[M+H]^+$: 609.

Synthesis of (2S)—N-[(1S)-1-cyano-2-[4-(3-methyl-2-oxo-1,3-benzoxazol-5-yl)phenyl]ethyl]-2-hydroxy-3-(methylamino)propanamide

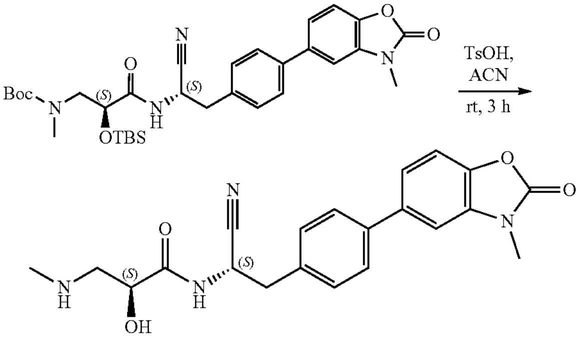

Into a 50 mL round-bottom flask were added tert-butyl N-[(2S)-2-[(tert-butyldimethylsilyl)oxy]-2-{[(1S)-1-cyano-2-[4-(3-methyl-2-oxo-1,3-benzoxazol-5-yl)phenyl]ethyl]carbamoyl}ethyl]—N-methylcarbamate (120 mg, 0.20 mmol, 1 equiv), TsOH (102 mg, 0.60 mmol, 3 equiv) and ACN (3 mL) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2S)—N-[(1S)-1-cyano-2-[4-(3-methyl-2-oxo-1,3-benzoxazol-5-yl)phenyl]ethyl]-2-hydroxy-3-(methylamino)propanamide (20 mg, 25.73%).

LCMS (ES, m z): $[M+H]^+$: 395.

$^1H$ NMR (400 MHz, DMSO-$d_6$) δ 8.70 (brs, 1H), 7.70-7.63 (m, 2H), 7.58 (d, J=1.9 Hz, 1H), 7.47-7.36 (m, 4H), 5.73 (brs, 1H), 5.05 (t, J=7.9 Hz, 1H), 4.00 (dd, J=7.4, 4.0 Hz, 1H), 3.41 (s, 3H), 3.27-3.13 (m, 2H), 2.57-2.51 (m, 1H), 2.43 (dd, J=12.2, 7.4 Hz, 1H), 2.20 (s, 3H).

Example 5. Synthesis of Compound 112: (2R)—N-[(1S)-1-cyano-2-[4-(3-methyl-2-oxo-1,3-benzoxazol-5-yl)phenyl]ethyl]-3-(dimethylamino)-2-methoxypropanamide

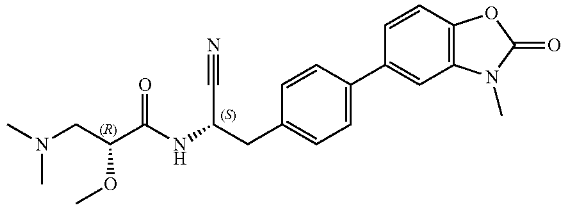

compound 112

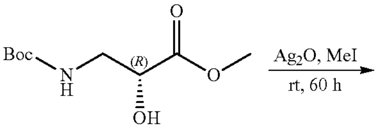

-continued

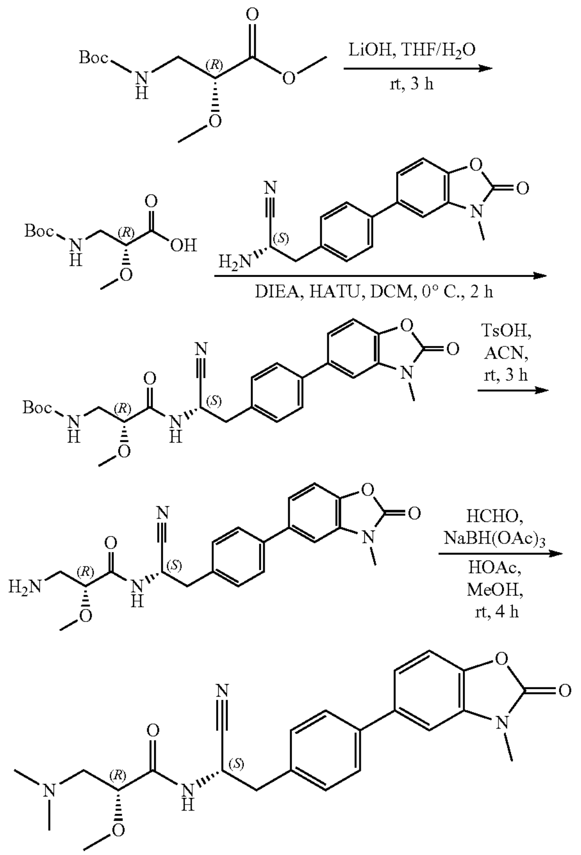

Synthesis of methyl (2R)-3-[(tert-butoxycarbonyl) amino]-2-methoxypropanoate

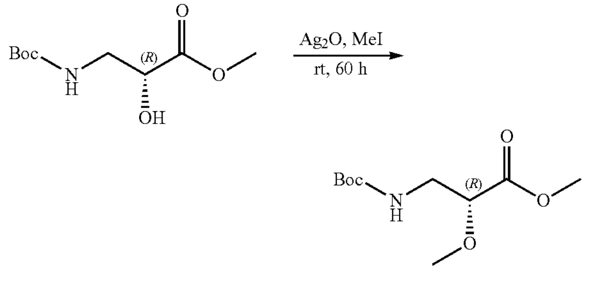

To a stirred solution of methyl (2R)-3-[(tert-butoxycarbonyl)amino]-2-hydroxypropanoate (550 mg, 2.509 mmol, 1.0 equiv) and $Ag_2O$ (1162 mg, 5.018 mmol, 2.0 equiv) in DCM (10 mL) were added MeI (712 mg, 5.018 mmol, 2.0 equiv) dropwise at 0° C. under nitrogen atmosphere. The resulting mixture was stirred for 60 h at room temperature. The resulting mixture was filtered, the filter cake was washed with DCM (3x10 mL). The filtrate was concentrated under reduced pressure. The residue was purified by silica gel column chromatography, eluted with PE/THF (9:1) to afford methyl (2R)-3-[(tert-butoxycarbonyl)amino]-2-methoxypropanoate (500 mg, 85.4%). LCMS (ES) $[M+1]^+$ m/z:234.

Synthesis of (2R)-3-[(tert-butoxycarbonyl)amino]-2-methoxypropanoic acid

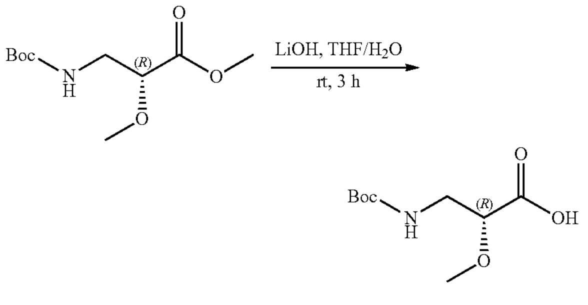

To a stirred solution of methyl (2R)-3-[(tert-butoxycarbonyl)amino]-2-methoxypropanoate (500 mg, 2.143 mmol, 1.0 equiv) in THE (9 mL) and $H_2O$ (3 mL) were added LiOH (154 mg, 6.429 mmol, 3.0 equiv). The resulting mixture was stirred for 3 h at room temperature. The resulting mixture was diluted with water (20 mL). The mixture was acidified to pH 5 with HCl (0.5 mol/L)(aq.). The resulting mixture was extracted with $CH_2Cl_2$ (5x20 mL). The combined organic layers were washed with brine (10 mL), dried over anhydrous $Na_2SO_4$. After filtration, the filtrate was concentrated under reduced pressure. This resulted in (2R)-3-[(tert-butoxycarbonyl)amino]-2-methoxypropanoic acid (400 mg, 85.1%). LCMS (ES) $[M+1]^+$ m/z: 220.

Synthesis of tert-butyl N-[(2R)-2-{[(1S)-1-cyano-2-[4-(3-methyl-2-oxo-1,3-benzoxazol-5-yl)phenyl] ethyl]carbamoyl}-2-methoxyethyl]carbamate

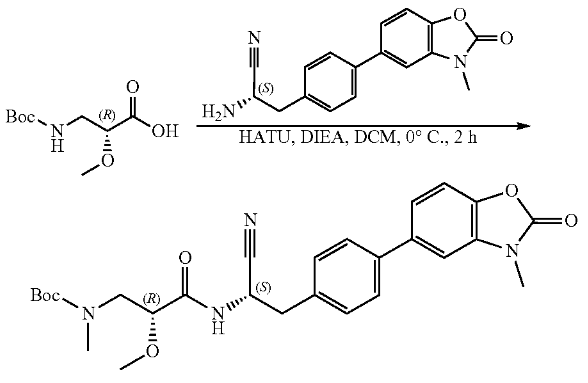

To a stirred solution of (2R)-3-[(tert-butoxycarbonyl) amino]-2-methoxypropanoic acid (200 mg, 0.912 mmol, 1.0 equiv) and (2S)-2-amino-3-[4-(3-methyl-2-oxo-1,3-benzoxazol-5-yl)phenyl]propanenitrile (294 mg, 1.003 mmol, 1.1 equiv) in DCM (3 mL) were added DIEA (353 mg, 2.736 mmol, 3.0 equiv) and HATU (416 mg, 1.094 mmol, 1.2 equiv) in portions at 0° C. under nitrogen atmosphere. The resulting mixture was stirred for 2 h at 0° C. under nitrogen atmosphere. The resulting mixture was concentrated under reduced pressure. The crude product was purified by Prep-HPLC with the following conditions (Column, XBridge Prep C18 OBD Column, 19*150 mm Sum; mobile phase, Water (0.1% $NH_3H_2O$) and ACN (10% PhaseB up to 80% in 20 min); Detector, UV 254 nm. This resulted in tert-butyl N-[(2R)-2-{[(1S)-1-cyano-2-[4-(3-methyl-2-oxo-1,3-benzoxazol-5-yl)phenyl]ethyl]carbamoyl}-2-methoxyethyl] carbamate (350 mg, 77.5%). LCMS (ES) $[M+1]^+$ m/z: 495.

Synthesis of (2R)-3-amino-N-[(1S)-1-cyano-2-[4-(3-methyl-2-oxo-1,3-benzoxazol-5-yl)phenyl]ethyl]-2-methoxypropanamide

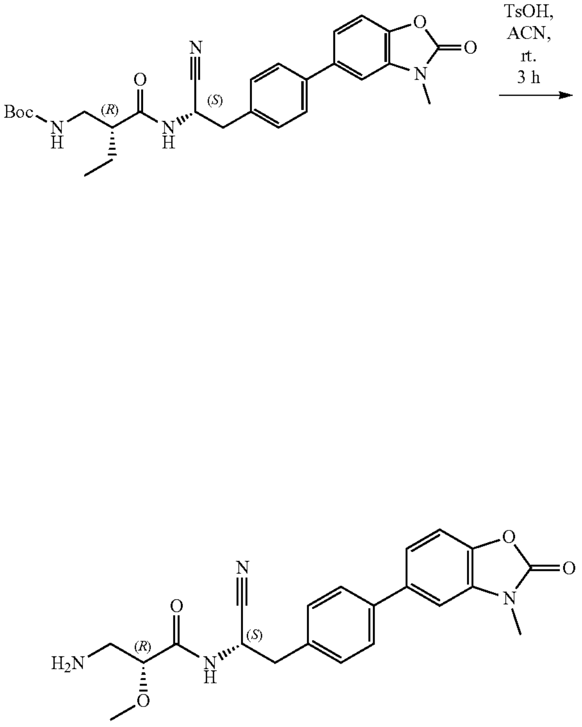

To a stirred solution of tert-butyl N-[(2R)-2-{[(1S)-1-cyano-2-[4-(3-methyl-2-oxo-1,3-benzoxazol-5-yl)phenyl] ethyl]carbamoyl}-2-methoxyethyl]carbamate (300 mg, 0.607 mmol, 1.0 equiv) in ACN (6 mL) was added TsOH (313 mg, 1.821 mmol, 3.0 equiv). The resulting mixture was stirred for 3 h at room temperature. The crude product was purified by Prep-HPLC with the following conditions (Column, XBridge Prep C18 OBD Column, 19*150 mm Sum; mobile phase, Water (0.1% $NH_3H_2O$) and ACN (10% PhaseB up to 80% in 20 min); Detector, UV 254 nm. This resulted in (2R)-3-amino-N-[(1S)-1-cyano-2-[4-(3-methyl-2-oxo-1,3-benzoxazol-5-yl)phenyl]ethyl]-2-methoxypropanamide (180 mg, 75.2%). LCMS (ES) $[M+1]^+$ m/z: 395.

Synthesis of (2R)—N-[(1S)-1-cyano-2-[4-(3-methyl-2-oxo-1,3-benzoxazol-5-yl)phenyl]ethyl]-3-(dimethylamino)-2-methoxypropanamide

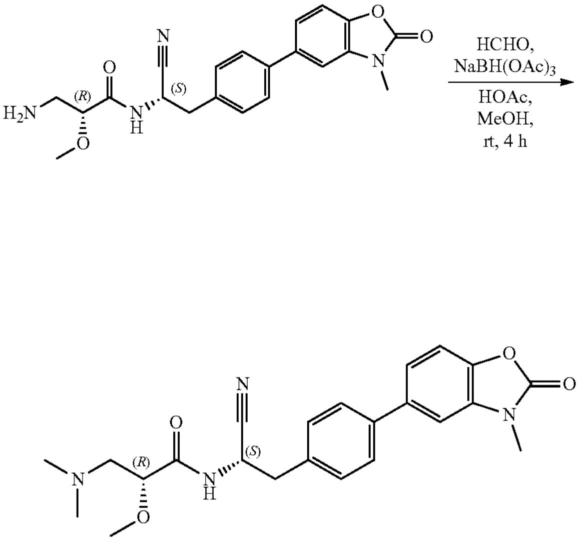

To a stirred solution of (2R)-3-amino-N-[(1S)-1-cyano-2-[4-(3-methyl-2-oxo-1,3-benzoxazol-5-yl)phenyl]ethyl]-2-methoxypropanamide (100 mg, 0.254 mmol, 1.0 equiv) and HCHO (114 mg, 3.810 mmol, 15.0 equiv) in MeOH (2 mL) were added HOAc (1 mg, 0.025 mmol, 0.1 equiv). The resulting mixture was stirred for 2 h at room temperature. To the above mixture was added $NaBH(OAc)_3$ (214 mg, 1.016 mmol, 4.0 equiv) in portions at 0° C. The resulting mixture was stirred for additional 2 h at room temperature. The crude product was purified by Prep-HPLC with the following conditions (Column, XBridge Prep C18 OBD Column, 19*150 mm Sum; mobile phase, Water (0.1% $NH_3H_2O$) and ACN (10% PhaseB up to 80% in 20 min); Detector, UV 254 nm. This resulted in (2R)—N-[(1S)-1-cyano-2-[4-(3-methyl-2-oxo-1,3-benzoxazol-5-yl)phenyl]ethyl]-3-(dimethylamino)-2-methoxypropanamide (70 mg, 65.3%). LCMS (ES) $[M+1]^+$ m/z: 423.2.

$^1H$ NMR (300 MHz, DMSO-d6) δ 8.86 (d, J=8.2 Hz, 1H), 7.71-7.62 (m, 2H), 7.58 (t, J=1.2 Hz, 1H), 7.47-7.35 (m, 4H), 5.04 (td, J=8.5, 7.0 Hz, 1H), 3.68 (dd, J=6.1, 5.2 Hz, 1H), 3.41 (s, 3H), 3.30-3.14 (m, 2H), 3.14 (s, 3H), 2.45-2.35 (m, 2H), 2.15 (s, 6H).

Example 6. Synthesis of Compound 118: (3R)—N-[(1S)-1-cyano-2-[4-(3-methyl-2-oxo-1,3-benzoxazol-5-yl)phenyl]ethyl]-4-(dimethylamino)-3-hydroxybutanamide

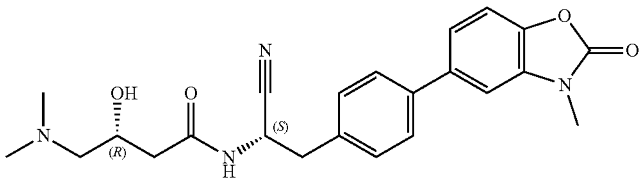

-continued

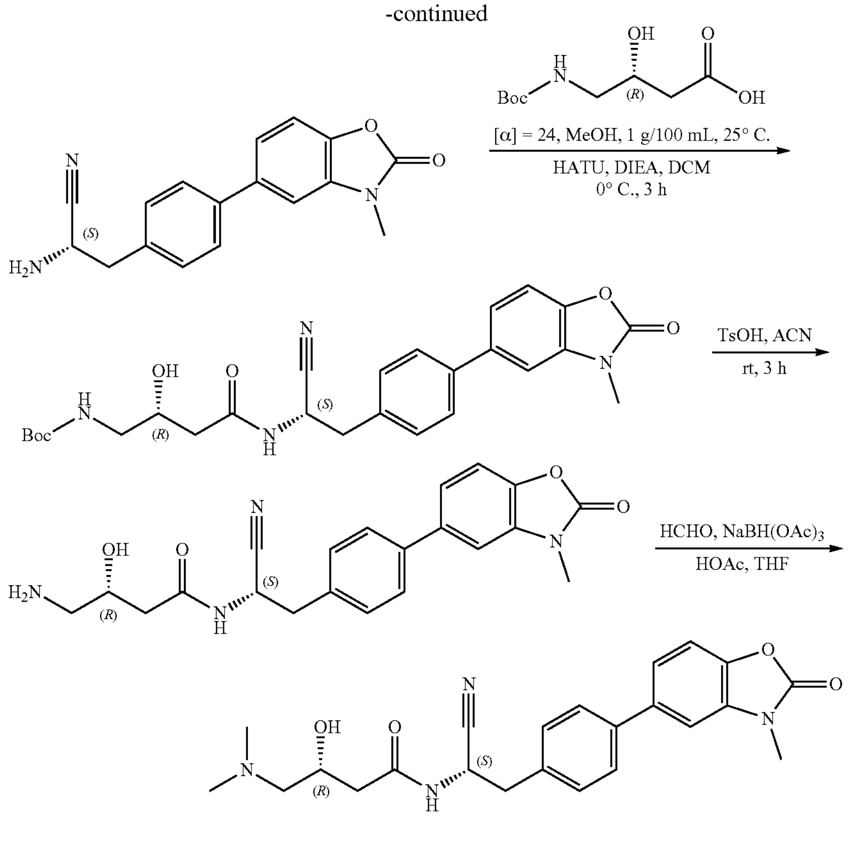

Synthesis of tert-butyl N-[(2R)-3-{[(1S)-1-cyano-2-[4-(3-methyl-2-oxo-1,3-benzoxazol-5-yl)phenyl]ethyl]carbamoyl}-2-hydroxypropyl]carbamate

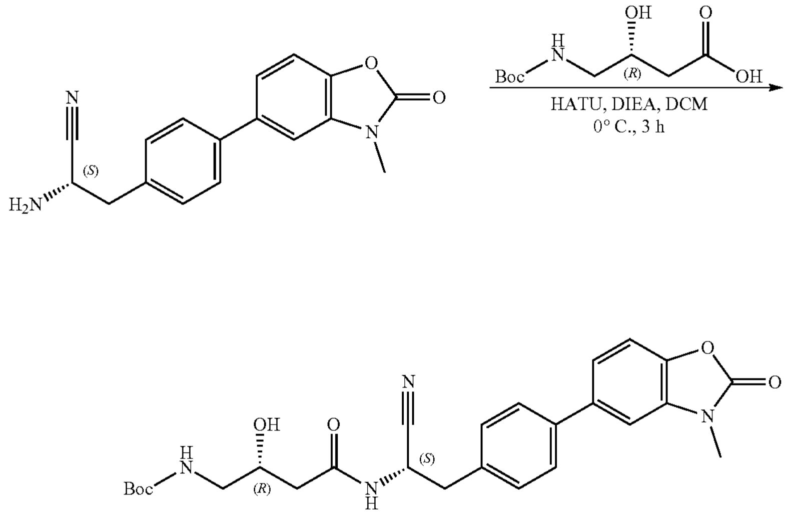

A solution of (2S)-2-amino-3-[4-(3-methyl-2-oxo-1,3-benzoxazol-5-yl)phenyl]propanenitrile (120 mg, 0.40 mmol, 1.0 equiv) in DCM (5 mL) was treated with (3R)-4-[(tert-butoxycarbonyl)amino]-3-hydroxybutanoic acid (89 mg, 0.409 mmol, 1.0 equiv), DIEA (159 mg, 1.22 mmol, 3.0 equiv). This was followed by the addition of HATU (187 mg, 0.49 mmol, 1.2 equiv) dropwise at 0° C. The resulting mixture was stirred for 3 h at 0° C. Concentrated under reduced pressure to remove the solvent, the residue was purified by silica gel column chromatography, eluted with PE/THE (1:1) to afford tert-butyl N-[(2R)-3-{[(1S)-1-cyano-2-[4-(3-methyl-2-oxo-1,3-benzoxazol-5-yl)phenyl]ethyl]carbamoyl}-2-hydroxypropyl]carbamate (150 mg, 74%). LCMS (ES, m/z): $[M+H]^+$: 495.

Synthesis of (3R)-4-amino-N-[(1S)-1-cyano-2-[4-(3-methyl-2-oxo-1,3-benzoxazol-5-yl)phenyl]ethyl]-3-hydroxybutanamide

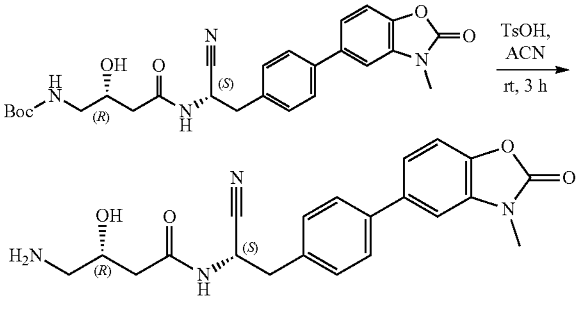

A solution of tert-butyl N-[(2R)-3-{[(1S)-1-cyano-2-[4-(3-methyl-2-oxo-1,3-benzoxazol-5-yl)phenyl]ethyl]carbamoyl}-2-hydroxypropyl]carbamate (150 mg, 0.30 mmol, 1.0 equiv) and TsOH (157 mg, 0.90 mmol, 3.0 equiv) in ACN (4.5 mL) was stirred for 3 h at room temperature. The resulting mixture was concentrated under reduced pressure. This resulted in (3R)-4-amino-N-[(1S)-1-cyano-2-[4-(3-methyl-2-oxo-1,3-benzoxazol-5-yl)phenyl]ethyl]-3-hydroxybutanamide (100 mg, 83.5%). LCMS (ES, m/z): $[M+H]^+$: 395. (After concentrated, epimerization at cyan group chiral center).

Synthesis of (3R)—N-[(1S)-1-cyano-2-[4-(3-methyl-2-oxo-1,3-benzoxazol-5-yl)phenyl]ethyl]-4-(dimethylamino)-3-hydroxybutanamide

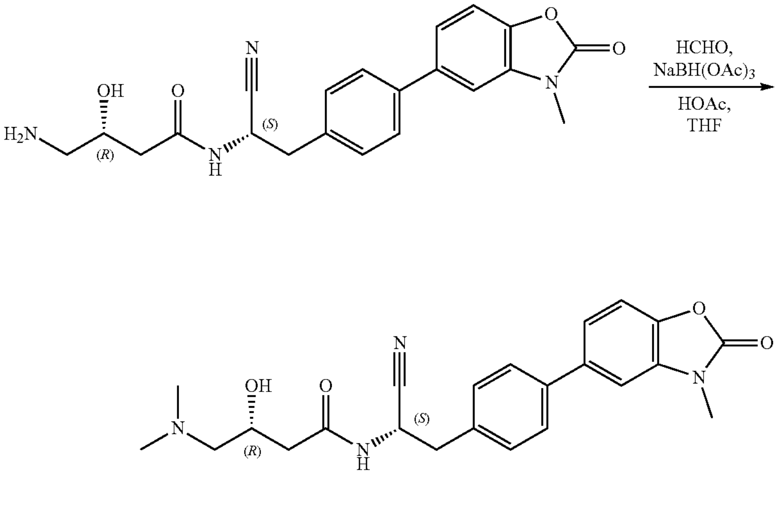

A solution of (3R)-4-amino-N-[(1S)-1-cyano-2-[4-(3-methyl-2-oxo-1,3-benzoxazol-5-yl)phenyl]ethyl]-3-hydroxybutanamide (100 mg, 0.25 mmol, 1.0 equiv) in THE (3 mL) was treated with HCHO (76 mg, 2.54 mmol, 10.0 equiv), HOAc (0.1 mL) and stirred for 0.5 h at room temperature. This was followed by the addition of NaBH $(OAc)_3$ (107 mg, 0.50 mmol, 2.0 equiv) in portions at room temperature. The resulting mixture was stirred for additional 1 h at room temperature. The residue was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (3R)—N-[(1S)-1-cyano-2-[4-(3-methyl-2-oxo-1,3-benzoxazol-5-yl)phenyl]ethyl]-4-(dimethylamino)-3-hydroxybutanamide (17.3 mg, 16.1%).

LCMS (ES, m/z): $[M+H]^+$: 423.4

$^1$H NMR (400 MHz, DMSO-$d_6$) δ 8.73 (dd, J=7.8, 5.8 Hz, 1H), 7.71-7.64 (m, 2H), 7.59 (t, J=1.9 Hz, 1H), 7.47-7.37 (m, 4H), 5.04-4.91 (m, 1H), 4.63 (brs, 1H), 3.94 (brs, 1H), 3.41 (s, 3H), 3.19-3.04 (m, 2H), 2.37-2.05 (m, 10H).

Example 7. Synthesis of Compound 137: (S)—N—((S)-1-cyano-2-(4-(1-methyl-3'-oxo-3'H-spiro[azetidine-3,1'-isobenzofuran]-6'-yl)phenyl)ethyl)-3-(dimethylamino)-2-hydroxypropanamide

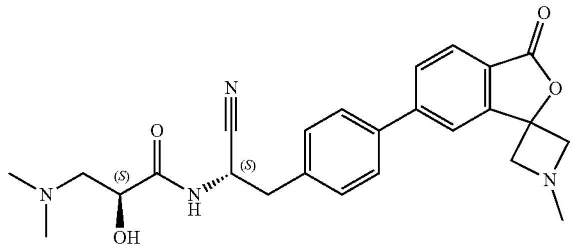

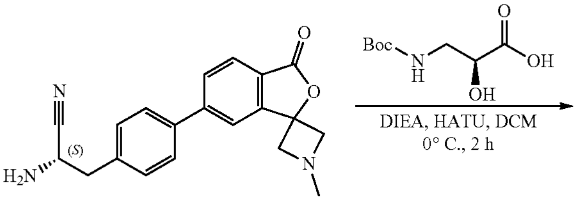

-continued

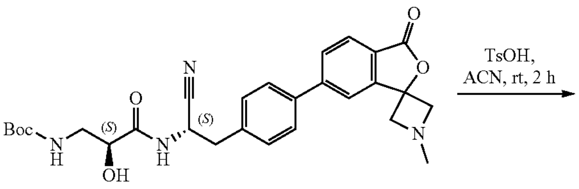

-continued

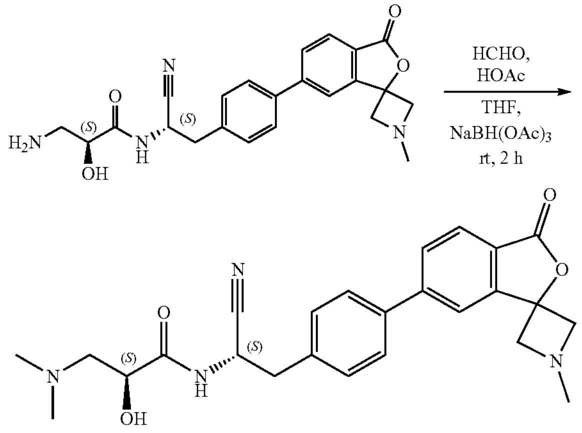

Synthesis of tert-butyl N-[(2S)-2-{[(1S)-1-cyano-2-(4-{1-methyl-3'-oxospiro [azetidine-3,1'-[2]benzofuran]-6'-yl}phenyl) ethyl]carbamoyl}-2-hydroxyethyl]carbamate

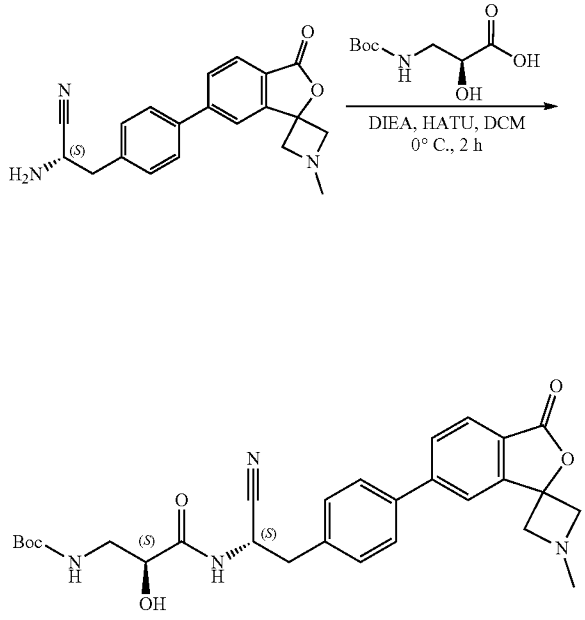

To a stirred solution of (2S)-2-amino-3-(4-{1-methyl-3'-oxospiro [azetidine-3,1'-[2]benzofuran]-6'-yl}phenyl) propanenitrile (450 mg, 1.35 mmol, 1.0 equiv), (2S)-3-[(tert-butoxycarbonyl) amino]-2-hydroxypropanoic acid (553 mg, 2.70 mmol, 2.0 equiv) and DIEA (523 mg, 4.05 mmol, 3.0 equiv) in DCM (5 mL) was added HATU (615 mg, 1.62 mmol, 1.2 equiv) in portions at 0° C. The resulting mixture was stirred for 2 h at 0° C. Concentrated under reduced pressure. The residue was purified by silica gel column chromatography, eluted with PE/EA (1:1) to afford tert-butyl N-[(2S)-2-{[(1S)-1-cyano-2-(4-{1-methyl-3'-oxospiro [azetidine-3,1'-[2]benzofuran]-6'-yl}phenyl) ethyl]carbamoyl}-2-hydroxyethyl]carbamate (180 mg, 25.6%). LCMS (ES) [M+H]m/z: 521.

Synthesis of (2S)-3-Amino-N-[(1S)-1-cyano-2-(4-{1-methyl-3'-oxospiro [azetidine-3,1'-[2]benzofuran]-6'-yl}phenyl) ethyl]-2-hydroxypropanamide

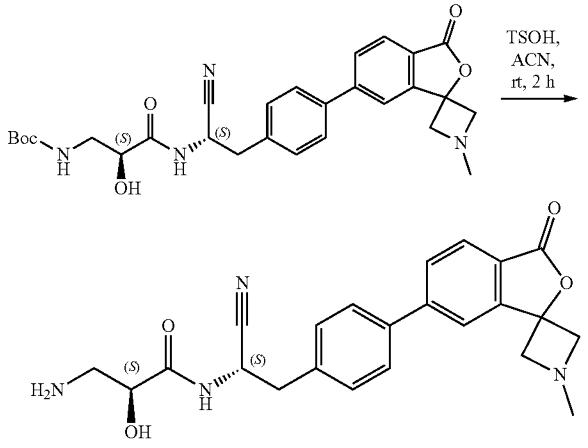

A solution of tert-butyl N-[(2S)-2-{[(1S)-1-cyano-2-(4-{1-methyl-3'-oxospiro [azetidine-3,1'-[2]benzofuran]-6'-yl}phenyl) ethyl]carbamoyl}-2-hydroxyethyl]carbamate (180 mg, 0.35 mmol, 1.0 equiv) and TsOH (178 mg, 1.04 mmol, 3.0 equiv) in ACN (2 mL) was stirred for 2 h at room temperature. The mixture was neutralized to pH 8 with saturated $NaHCO_3$ (aq.), extracted with EtOAc (3×10 mL). The combined organic layer was washed with water (2×20 mL), dried over anhydrous $Na_2SO_4$. After filtration, the filtrate was concentrated under reduced pressure. This resulted in (2S)-3-amino-N-[(1S)-1-cyano-2-(4-{1-methyl-3'-oxospiro[azetidine-3,1'-[2]benzofuran]-6'-yl}phenyl) ethyl]-2-hydroxypropanamide (110 mg, 75.7%). LCMS (ES) $[M+H]^+$ m/z: 421.

Synthesis of (S)—N—((S)-1-cyano-2-(4-(1-methyl-3'-oxo-3'H-spiro[azetidine-3,1'-isobenzofuran]-6'-yl) phenyl)ethyl)-3-(dimethylamino)-2-hydroxypropanamide

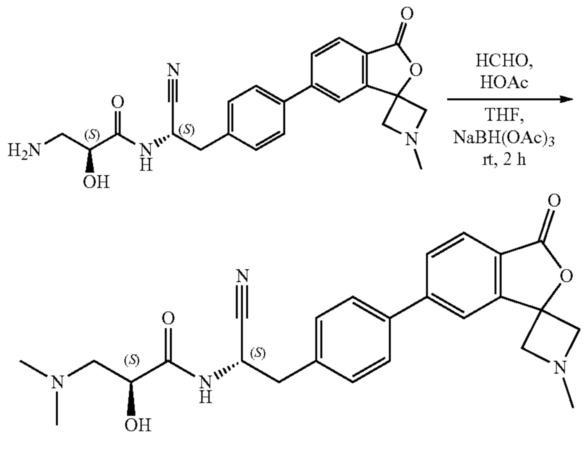

To a stirred solution of (2S)-3-Amino-N-[(1S)-1-cyano-2-(4-{1-methyl-3'-oxospiro [azetidine-3,1'-[2]benzofuran]-6'-yl}phenyl) ethyl]-2-hydroxypropanamide (100 mg, 0.24 mmol, 1.0 equiv) and HOAc (0.05 mL) in MeOH (2 mL) was added HCHO (220 mg, 2.38 mmol, 10.0 equiv, 30% in $H_2O$) in portions at room temperature. The resulting mixture was stirred for 1 h at room temperature. To the above mixture was added $NaBH(OAc)_3$ (151 mg, 0.72 mmol, 3.0 equiv) in portions over 2 min at 0° C. The resulting mixture was stirred for additional 2 h at room temperature. The reaction solution was purified by reversed-phase flash chromatography with the following conditions: column, C18 silica gel-120 g; mobile phase, MeCN in Water (10 mmol/L $NH_4HCO_3$), 10% to 60% gradient in 12 min; detector, UV 254 nm. This resulted in (S)—N—((S)-1-cyano-2-(4-(1-methyl-3'-oxo-3'H-spiro[azetidine-3,1'-isobenzofuran]-6'-yl)phenyl)ethyl)-3-(dimethylamino)-2-hydroxypropanamide (20 mg, 18.8%). LCMS (ES) $[M+H]^+$ m/z: 449.3

$^1H$ NMR (400 MHz, DMSO-$d_6$) δ 8.73 (d, J=8.6 Hz, 1H), 8.15 (d, J=1.4 Hz, 1H), 7.94-7.84 (m, 2H), 7.82-7.75 (m, 2H), 7.51-7.44 (m, 2H), 5.55 (d, J=4.8 Hz, 1H), 5.14-5.04 (m, 1H), 3.98 (dd, J=7.6, 3.8 Hz, 1H), 3.73-3.69 (m, 2H), 3.64 (d, J=8.2 Hz, 2H), 3.31-3.17 (m, 2H), 2.44 (s, 3H), 2.24 (dd, J=12.7, 4.0 Hz, 1H), 2.17 (dd, J=12.7, 7.8 Hz, 1H), 2.10 (s, 6H).

Example 8. Synthesis of Compound 199: 2-amino-N-[(1S)-1-cyano-2-[4-(3-methyl-2-oxo-1,3-benzoxazol-5-yl)phenyl]ethyl]-3-(2-hydroxypyridin-3-yl)propanamide compound 199

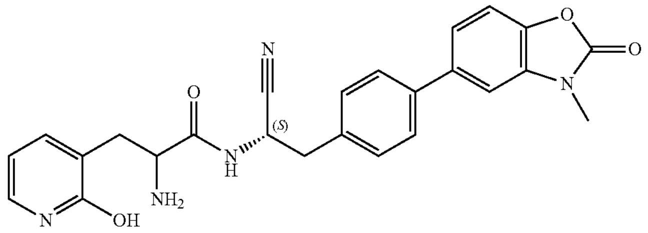

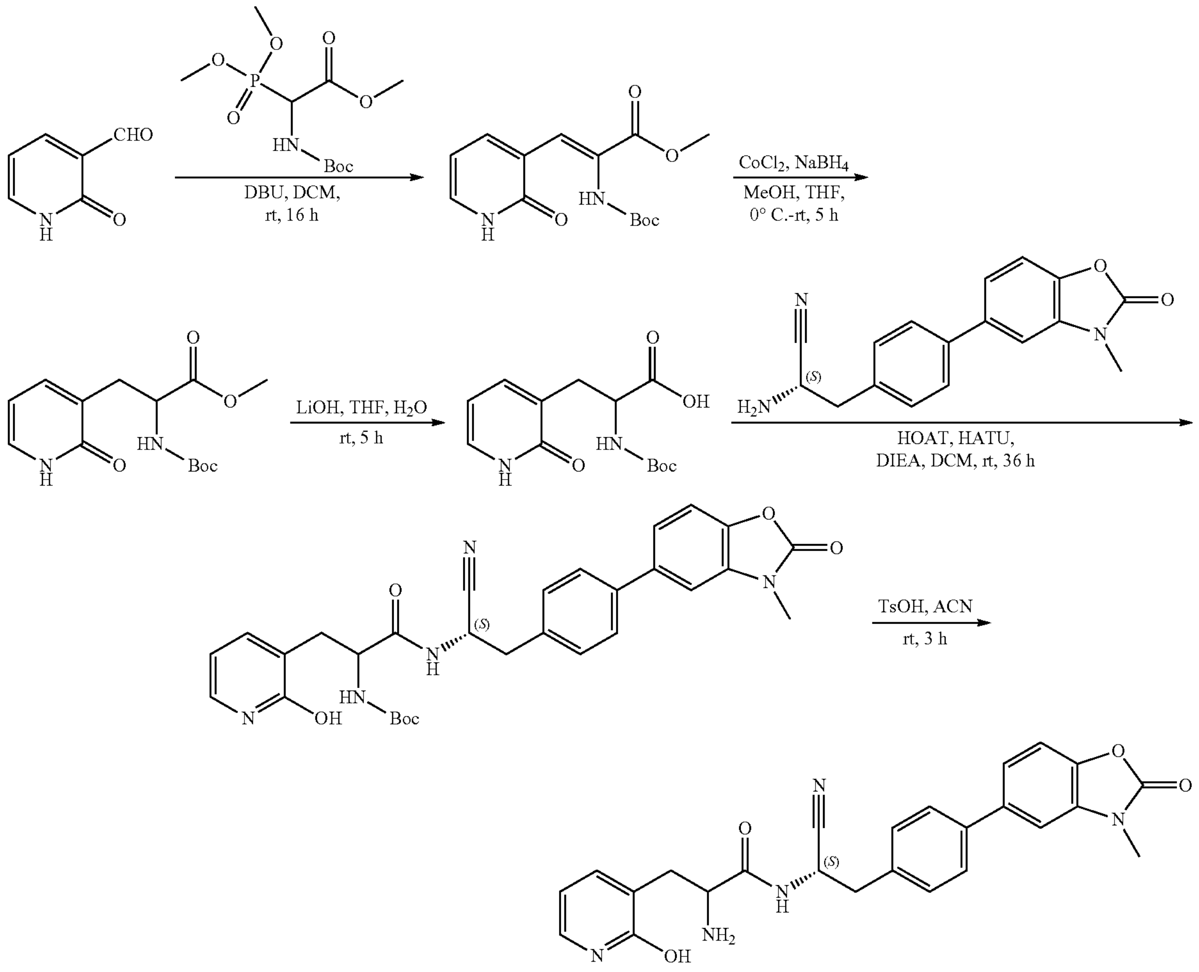

Synthesis of methyl 2-[(tert-butoxycarbonyl) amino]-3-(2-oxo-1H-pyridin-3-yl)prop-2-enoate

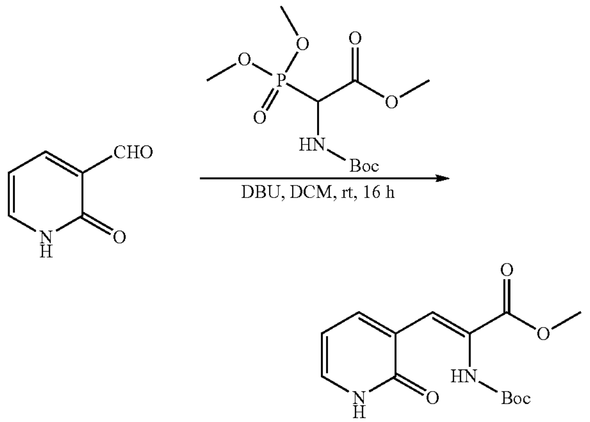

A solution of methyl 2-[(tert-butoxycarbonyl)amino]-2-(dimethoxyphosphoryl)acetate (3.6 g, 12.18 mmol, 1.0 equiv) in DCM (15 mL) was treated with DBU (1.9 g, 12.18 mmol, 1.0 equiv) for 30 min at 0° C. under nitrogen atmosphere. This was followed by the addition of 2-oxo-1H-pyridine-3-carbaldehyde (1.5 g, 12.18 mmol, 1.0 equiv) dropwise at 0° C. The resulting mixture was stirred for additional 16 h at room temperature. Concentrated under reduced pressure, the residue was purified by silica gel column chromatography, eluted with EA to afford methyl 2-[(tert-butoxycarbonyl)amino]-3-(2-oxo-1H-pyridin-3-yl) prop-2-enoate (1.0 g, 28%). LCMS (ES, m z): $[M+H]^+$: 295.

Synthesis of 2-[(tert-butoxycarbonyl)amino]-3-(2-oxo-1H-pyridin-3-yl)propanoate

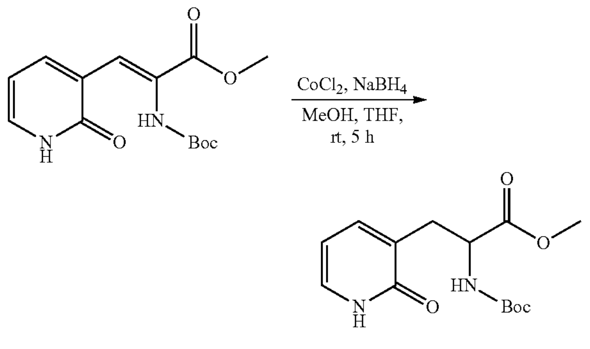

To a stirred mixture of methyl 2-[(tert-butoxycarbonyl) amino]-3-(2-oxo-1H-pyridin-3-yl)prop-2-enoate (1.0 g, 3.39 mmol, 1.0 equiv) and $CoCl_2$ (0.9 g, 6.79 mmol, 2.0 equiv) in MeOH (8 mL) and THE (1 mL) was added $NaBH_4$ (0.6 g, 16.99 mmol, 5.0 equiv) in portions at 0° C. The reaction was stirred for 5 h at room temperature. The reaction was quenched with water (20 mL), extracted with $CH_2Cl_2$ (3×30 mL). The combined organic layer was washed with brine (3×30 mL), dried over anhydrous $Na_2SO_4$. After filtration, the filtrate was concentrated under reduced pressure. This resulted in methyl 2-[(tert-butoxy-carbonyl)amino]-3-(2-oxo-1H-pyridin-3-yl)propanoate (350 mg, 34.7%). LCMS (ES, m/z): $[M+H]^+$: 297.

Synthesis of 2-[(tert-butoxycarbonyl)amino]-3-(2-oxo-1H-pyridin-3-yl)propanoic acid

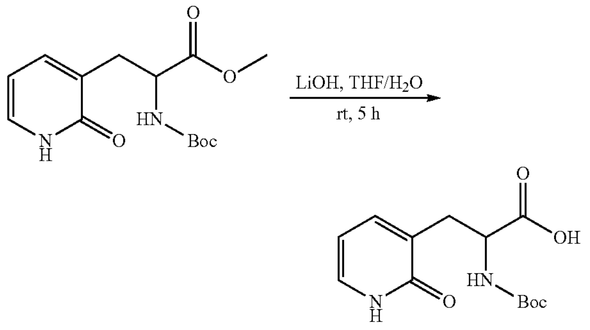

A solution of methyl 2-[(tert-butoxycarbonyl)amino]-3-(2-oxo-1H-pyridin-3-yl)propanoate (350 mg, 1.18 mmol, 1.0 equiv) in THE (3 mL) and LiOH (85 mg, 3.54 mmol, 3.0 equiv) in $H_2O$ (1 mL) was stirred for 5 h at room temperature. The mixture was acidified to pH 5 with HCl (1 M). The resulting mixture was extracted with EtOAc (3×30 mL). The combined organic layer was washed with brine (3×30 mL), dried over anhydrous $Na_2SO_4$. After filtration, the filtrate was concentrated under reduced pressure. This resulted in 2-[(tert-butoxycarbonyl)amino]-3-(2-oxo-1H-pyridin-3-yl) propanoic acid (300 mg, 90%). LCMS (ES, m/z): $[M+H]^+$: 283.

Synthesis of tert-butyl N-(1-{[(1S)-1-cyano-2-[4-(3-methyl-2-oxo-1,3-benzoxazol-5-yl)phenyl]ethyl] carbamoyl}-2-(2-hydroxypyridin-3-yl)ethyl)carbamate

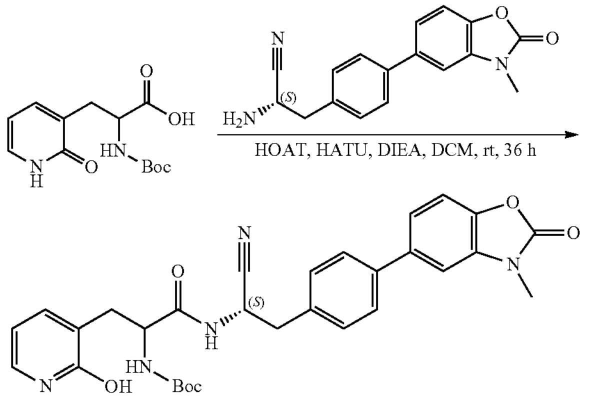

A solution of 2-[(tert-butoxycarbonyl)amino]-3-(2-oxo-1H-pyridin-3-yl)propanoic acid (110 mg, 0.39 mmol, 1.0 equiv) in DMF (5 mL) was treated with (2S)-2-amino-3-[4-(3-methyl-2-oxo-1,3-benzoxazol-5-yl)phenyl]propanenitrile (114 mg, 0.39 mmol, 1.0 equiv), DIEA (151 mg, 1.17 mmol, 3.0 equiv) followed by the addition of HOAt (80 mg, 0.58 mmol, 1.5 equiv), HATU (222 mg, 0.58 mmol, 1.5 equiv) dropwise at 0° C. The resulting mixture was stirred for 36 h at room temperature. The reaction was quenched with water (15 mL), extracted with ethyl acetate (20 mL×3). The combined organic phase was washed with brine (30 mL×2), dried over anhydrous sodium sulfate. Filtered and the filtrate was concentrated under reduced pressure. The residue was purified by silica gel column chromatography, eluted with PE/THE (1:2) to afford tert-butyl N-(1-{[(1S)-1-cyano-2-[4-(3-methyl-2-oxo-1,3-benzoxazol-5-yl)phenyl]ethyl]carbamoyl}-2-(2-hydroxypyridin-3-yl)ethyl)carbamate (70 mg, 32.2%). LCMS (ES, m/z): $[M+H]^+$: 558.

Synthesis of 2-amino-N-[(1S)-1-cyano-2-[4-(3-methyl-2-oxo-1,3-benzoxazol-5-yl)phenyl]ethyl]-3-(2-hydroxypyridin-3-yl)propanamide

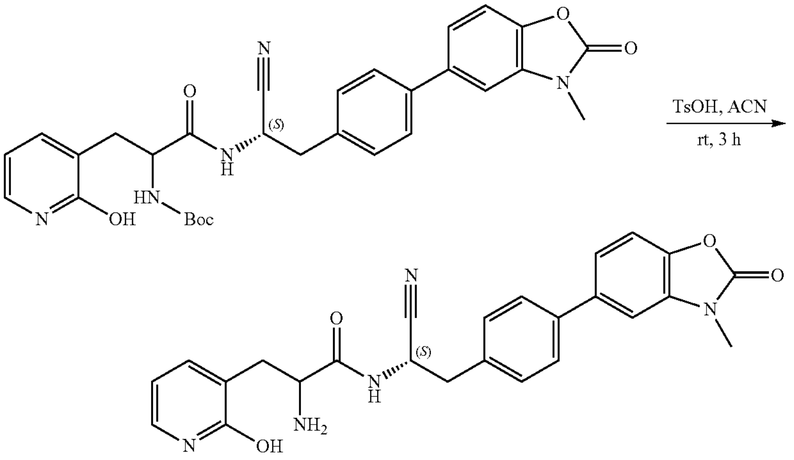

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-2-(2-hydroxypyridin-3-yl)ethyl)carbamate (70 mg, 0.12 mmol, 1.0 equiv) in ACN (3 mL) and TsOH (65 mg, 0.37 mmol, 3.0 equiv) at room temperature. The resulting mixture was stirred for 3 h at room temperature. The residue was purified by reversed-phase flash chromatography with the following conditions: column, C18 silica gel-120 g; mobile phase, MeCN in Water ($0.1\%\ NH_3 \cdot H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-3-(2-hydroxypyridin-3-yl)propanamide (17.3 mg, 30%).

LCMS (ES, m z): $[M+H]^+$: 458.2

$^1H$ NMR (400 MHz, DMSO-$d_6$) δ 11.53 (brs, 1H), 7.67 (dd, J=8.2, 3.4 Hz, 2H), 7.59 (d, J=1.7 Hz, 1H), 7.46-7.36 (m, 4H), 7.27-7.09 (m, 2H), 6.10-6.04 (m, 1H), 4.97 (td, J=7.7, 2.1 Hz, 1H), 3.50-3.45 (m, 1H), 3.41 (d, J=1.5 Hz, 3H), 3.21-3.06 (m, 2H), 2.76-2.62 (m, 1H), 2.45-2.37 (m, 1H).

Example 9. Synthesis of Compound 168: 2-amino-N-[(1S)-1-cyano-2-[4-(3-methyl-2-oxo-1,3-benzoxazol-5-yl)phenyl]ethyl]-5-hydroxy-4-methylpentanamide compound 168

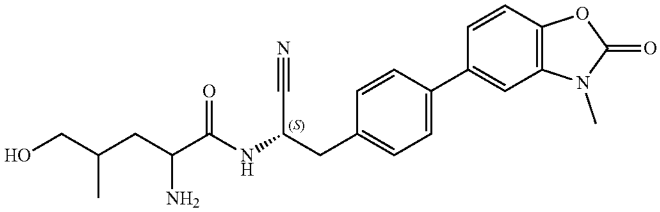

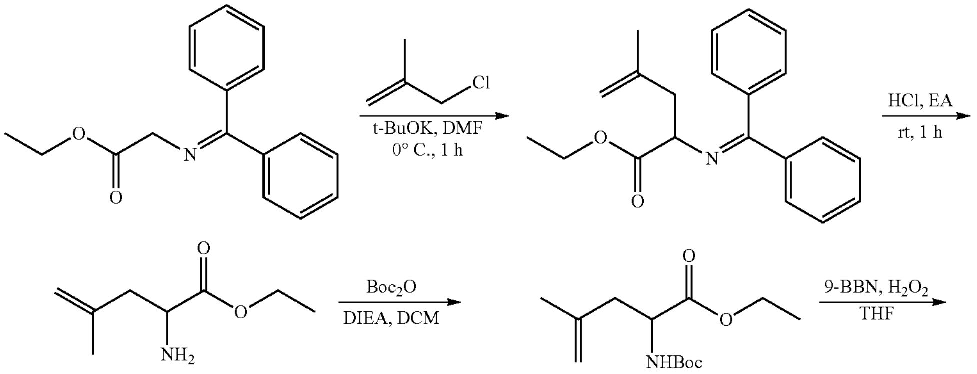

-continued

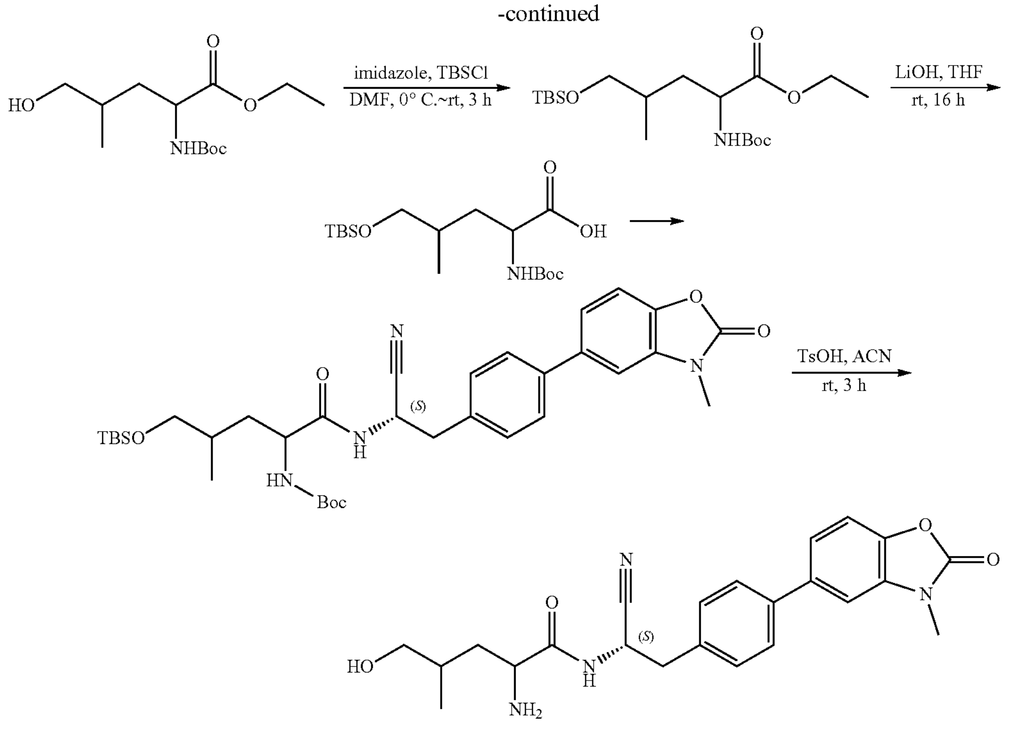

compound 168

Synthesis of ethyl 2-[(diphenylmethylidene)amino]-4-methylpent-4-enoate

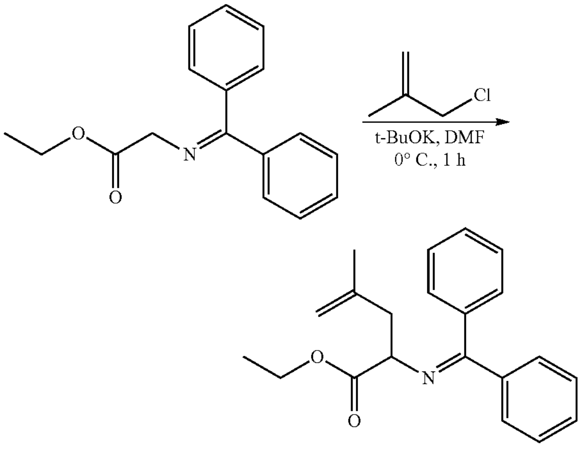

Ethyl N-(diphenylmethylidene)carbamate vanadium (15 g, 49.30 mmol, 1.0 equiv) was dissolved in 60 mL of DMF, after cooled to 0° C., sodium 2-methylpropan-2-olate (5.5 g, 57.23 mmol, 1.16 equiv) was added. The mixture was stirred for 30 minutes, followed by the addition of 3-chloro-2-methylpropene (4.5 g, 49.70 mmol, 1.01 equiv) at the same temperature. Stirring was continued for until the reaction was completed (0.5 h), and the reaction mixture was poured into ice water and stirred for 1 h, the solid was filtered, and the filter cake was washed with water and dried under infrared lamp for 4 h to afford ethyl 2-[(diphenylmethylidene)amino]-4-methylpent-4-enoate (5.1 g, 32%). LCMS (ES, m z): $[M+H]^+$: 322.

$^1H$ NMR (400 MHz, DMSO-$d_6$) δ 7.60-7.34 (m, 8H), 7.19-7.12 (m, 2H), 4.73-4.71 (m, 1H), 4.67-4.61 (m, 1H), 4.13-4.05 (m, 3H), 2.57 (ddd, J=13.5, 5.4, 1.0 Hz, 1H), 2.46 (ddd, J=13.6, 8.0, 0.9 Hz, 1H), 1.45 (s, 3H), 1.17 (t, J=7.1 Hz, 3H).

Synthesis of ethyl 2-amino-4-methylpent-4-enoate

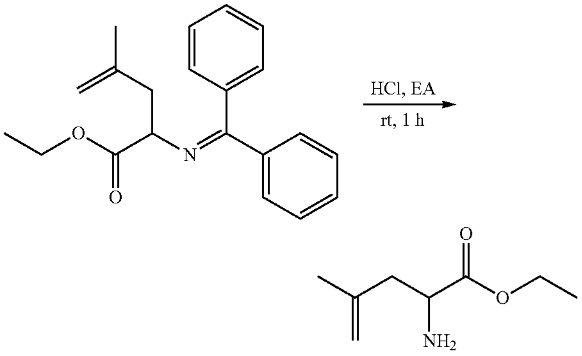

A solution of ethyl 2-[(diphenylmethylidene)amino]-4-methylpent-4-enoate (4 g, 12.45 mmol, 1.0 equiv) in ethyl acetate (30 mL) was treated with hydrochloric acid (1 N)(10 mL). The reaction was stirred for 1 hour at room temperature. The resulting mixture was quenched with $NaHCO_3$ (aq)(30 mL), extracted with ethyl acetate (3×30 mL). The combined organic layer was dried over anhydrous $Na_2SO_4$. After filtration, the filtrate was concentrated under reduced pressure to afford ethyl 2-amino-4-methylpent-4-enoate (1.5 g, 76.7%) and used to the next step directly without further purification. LCMS (ES, m z): $[M+H]^+$: 158.

Synthesis of ethyl 2-[(tert-butoxycarbonyl)amino]-4-methylpent-4-enoate

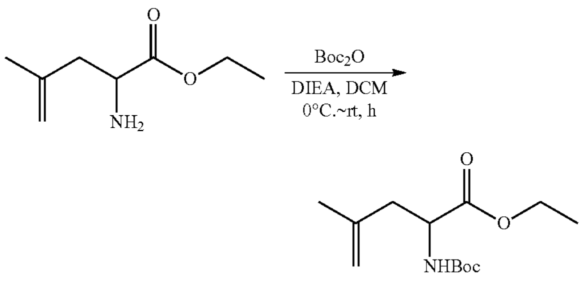

A solution of ethyl 2-amino-4-methylpent-4-enoate (1.5 g, 9.54 mmol, 1.0 equiv) in DCM (15 mL) was treated with DIEA (1.6 g, 12.4 mmol, 1.3 equiv) at room temperature under nitrogen atmosphere. This was followed by the addition of di-tert-butyl dicarbonate (2.43 g, 11.13 mmol, 1.2 equiv) at 0° C. After addition, the resulting mixture was quenched with water (30 mL), extracted with DCM (2×30 ml). The combined organic layer was washed with brine (30 ml), dried over anhydrous $Na_2SO_4$. After filtration, the filtrate was concentrated under reduced pressure, the residue was purified by silica gel column eluted with ethyl acetate/petroleum ether from 0% to 5% to afford ethyl 2-[(tert-butoxycarbonyl)amino]-4-methylpent-4-enoate (1.78 g, 72.5%). LCMS (ES, m z): $[M+H]^+$: 258.

Synthesis of ethyl 2-[(tert-butoxycarbonyl)amino]-5-hydroxy-4-methylpentanoate

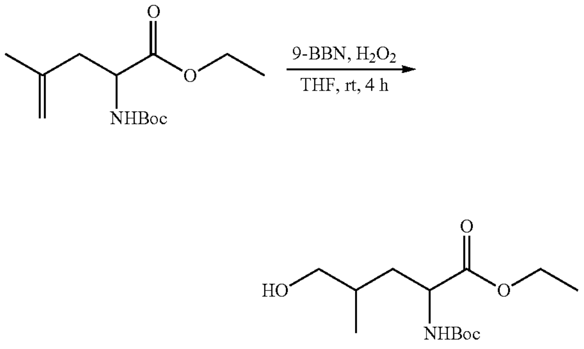

To a solution of ethyl 2-[(tert-butoxycarbonyl)amino]-4-methylpent-4-enoate (1 g, 3.89 mmol, 1.0 equiv) in THF (20 ml), 9-BBN-solution (0.5 M in THF)(9.3 mL, 4.67 mmol, 1.2 equiv) was added dropwise at rt. After stirred for 2 h, 30% $H_2O_2$(30%) and phosphate buffer (PH=7, 4 mL) were added. The mixture was stirred for 4 h, after TLC showed complete conversion, diluted with sat.aq. $Na_2S_2O_3$ solution and extracted with ethyl acetate (3×20 mL). The combined organic layer was dried over anhydrous $Na_2SO_4$. The residue was purified by silica gel column chromatography, eluted with petroleum ether, ethyl acetate (1:1) to afford ethyl 2-[(tert-butoxycarbonyl)amino]-5-hydroxy-4-methylpentanoate (0.77 g, 72%). LCMS (ES, m z): $[M+H]^+$: 276.

Synthesis of ethyl 2-[(tert-butoxycarbonyl)amino]-5-[(tert-butyldimethylsilyl)oxy]-4-methylpentanoate

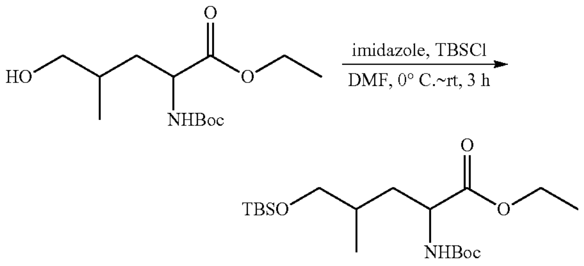

To a solution of ethyl 2-[(tert-butoxycarbonyl)amino]-5-hydroxy-4-methylpentanoate (450 mg, 1.63 mmol, 1.0 equiv) in DMF (9 mL) was added imidazole (278 mg, 4.08 mmol, 2.5 equiv) at room temperature under nitrogen atmosphere. This was followed by the addition of t-butyldimethylchlorosilane (308 mg, 2.04 mmol, 1.2 equiv). The reaction was stirred for 3 h at room temperature. The reaction was quenched with water (20 mL), extracted with EA (30 ml×2). The combined organic layer was washed with brine (30 ml×2), dried over anhydrous $Na_2SO_4$. After filtration, the filtrate was concentrated under reduced pressure. The residue was purified by chromatography (3-4% ethyl acetate in petroleum ether) to yield ethyl 2-[(tert-butoxycarbonyl)amino]-5-[(tert-butyldimethylsilyl)oxy]-4-methylpentanoate (360 mg, 56.5%). LCMS (ES, m z): $[M+H]^+$: 390.

Synthesis of 2-[(tert-butoxycarbonyl)amino]-5-[(tert-butyldimethylsilyl)oxy]-4-methylpentanoic acid

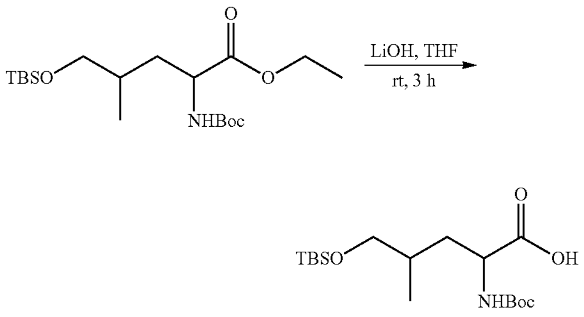

To a solution of ethyl 2-[(tert-butoxycarbonyl)amino]-5-[(tert-butyldimethylsilyl)oxy]-4-methylpentanoate (360 mg, 0.92 mmol, 1.0 equiv) in THF (7 mL), LiOH (33 mg, 1.39 mmol, 1.5 equiv) in $H_2O$ (10 mL) was added at room temperature. The reaction was stirred for 3 h. The mixture was acidified to pH 4 with 30% HCl (in $H_2O$). The resulting mixture was extracted with ethyl acetate (20 ml×2). The combined organic layer was washed with brine (20 ml), dried over anhydrous $Na_2SO_4$. After filtration, the filtrate was concentrated under reduced pressure, 2-[(tert-butoxycarbonyl)amino]-5-[(tert-butyldimethylsilyl)oxy]-4-methylpentanoic acid (220 mg, 65.9%) and used to the next step without further purification. LCMS (ES, m z): $[M+H]^+$: 362.

Synthesis of tert-butyl N-{4-[(tert-butyldimethylsilyl)oxy]-1-{[(1S)-1-cyano-2-[4-(3-methyl-2-oxo-1,3-benzoxazol-5-yl)phenyl]ethyl]carbamoyl}-3-methylbutyl}carbamate

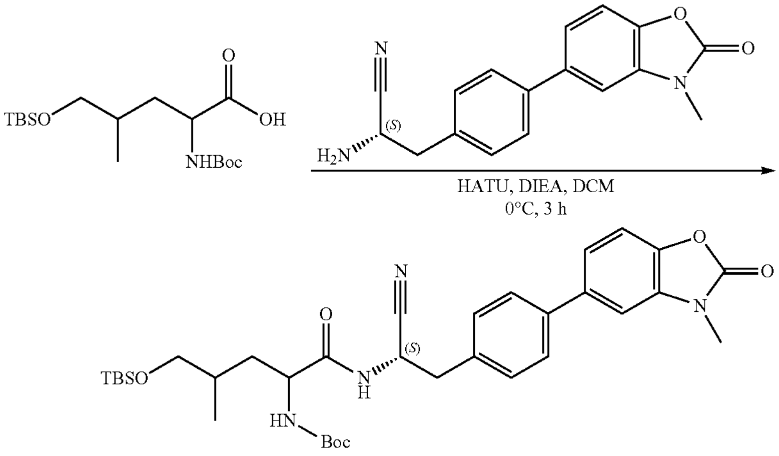

A solution of (2S)-2-amino-3-[4-(3-methyl-2-oxo-1,3-benzoxazol-5-yl)phenyl]propanenitrile (100 mg, 0.34 mmol, 1.0 equiv), 2-[(tert-butoxycarbonyl)amino]-5-[(tert-butyldimethylsilyl)oxy]-4-methylpentanoic acid (148 mg, 0.41 mmol, 1.20 equiv) in DCM (2 mL) was treated with DIEA (132 mg, 1.02 mmol, 3.0 equiv). This was followed by the addition of HATU (168 mg, 0.44 mmol, 1.3 equiv) in portions at 0° C. The reaction was stirred for 3 hours. The reaction was diluted with water (10 mL) and extracted with DCM (10 ml×2). The combined organic layer was dried over magnesium sulfate, filtered, the filtrate was concentrated in vacuo, and purified by silica gel chromatography (10% to 45% ethyl acetate in petroleum ether) to provide tert-butyl N-{4-[(tert-butyldimethylsilyl)oxy]-1-{[(1S)-1-cyano-2-[4-(3-methyl-2-oxo-1,3-benzoxazol-5-yl)phenyl]ethyl]carbamoyl}-3-methylbutyl}carbamate (180 mg, 82.9%). LCMS (ES, m z): $[M+H]^+$: 637.

Synthesis of 2-amino-N-[(1S)-1-cyano-2-[4-(3-methyl-2-oxo-1,3-benzoxazol-5-yl)phenyl]ethyl]-5-hydroxy-4-methylpentanamide

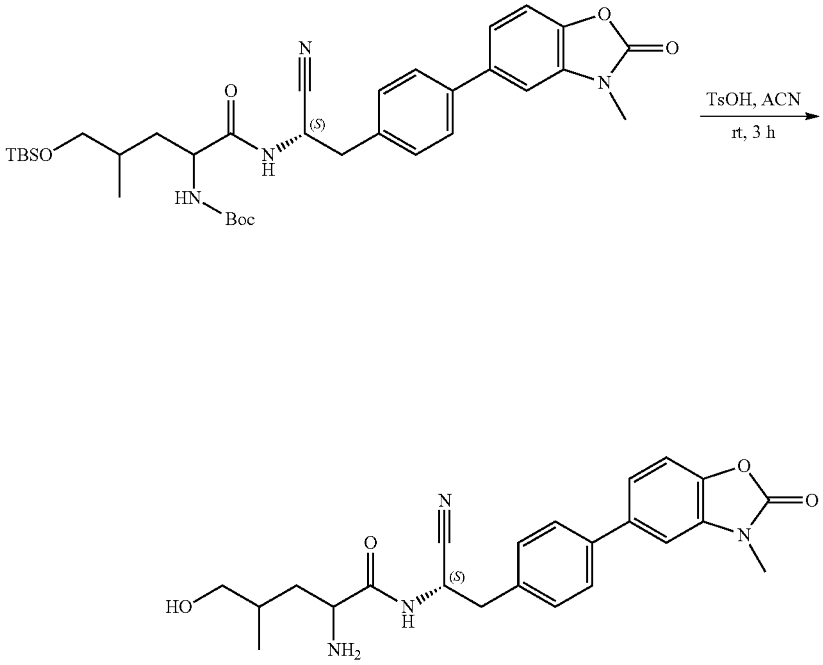

Into a 25 mL round-bottom flask were added tert-butyl N-{4-[(tert-butyldimethylsilyl)oxy]-1-{[(1S)-1-cyano-2-[4-(3-methyl-2-oxo-1,3-benzoxazol-5-yl)phenyl]ethyl]carbamoyl}-3-methylbutyl}carbamate (260 mg, 0.41 mmol, 1.0 equiv) in ACN (3 mL) and TsOH-$H_2O$ (211 mg, 1.22 mmol, 3.0 equiv) at 0° C. The resulting mixture was stirred for 3 h at room temperature. The reaction was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-5-hydroxy-4-methylpentanamide (8.5 mg, 5%).

LCMS (ES, m z): $[M+H]^+$: 423.3

$^1H$ NMR (400 MHz, DMSO-$d_6$) δ 7.68-7.63 (m, 2H), 7.58 (s, 1H), 7.43-7.38 (m, 4H), 5.02-4.98 (m, 1H), 4.70 (br, 1H), 3.41 (s, 3H), 3.22-3.13 (m, 5H), 1.62-1.48 (m, 1H), 1.30-1.09 (m, 2H), 0.83-0.75 (m, 3H).

Example 10. Synthesis of Compound 201: 2-amino-N-[(1S)-1-cyano-2-[4-(3-methyl-2-oxo-1,3-benzoxazol-5-yl)phenyl]ethyl]-3-(1,3-thiazol-5-yl) propanamide compound 201

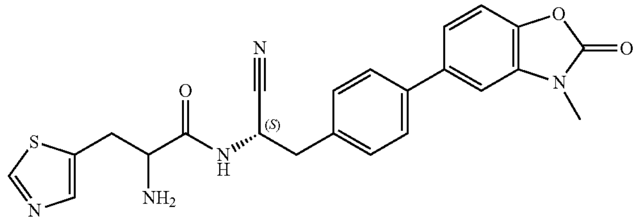

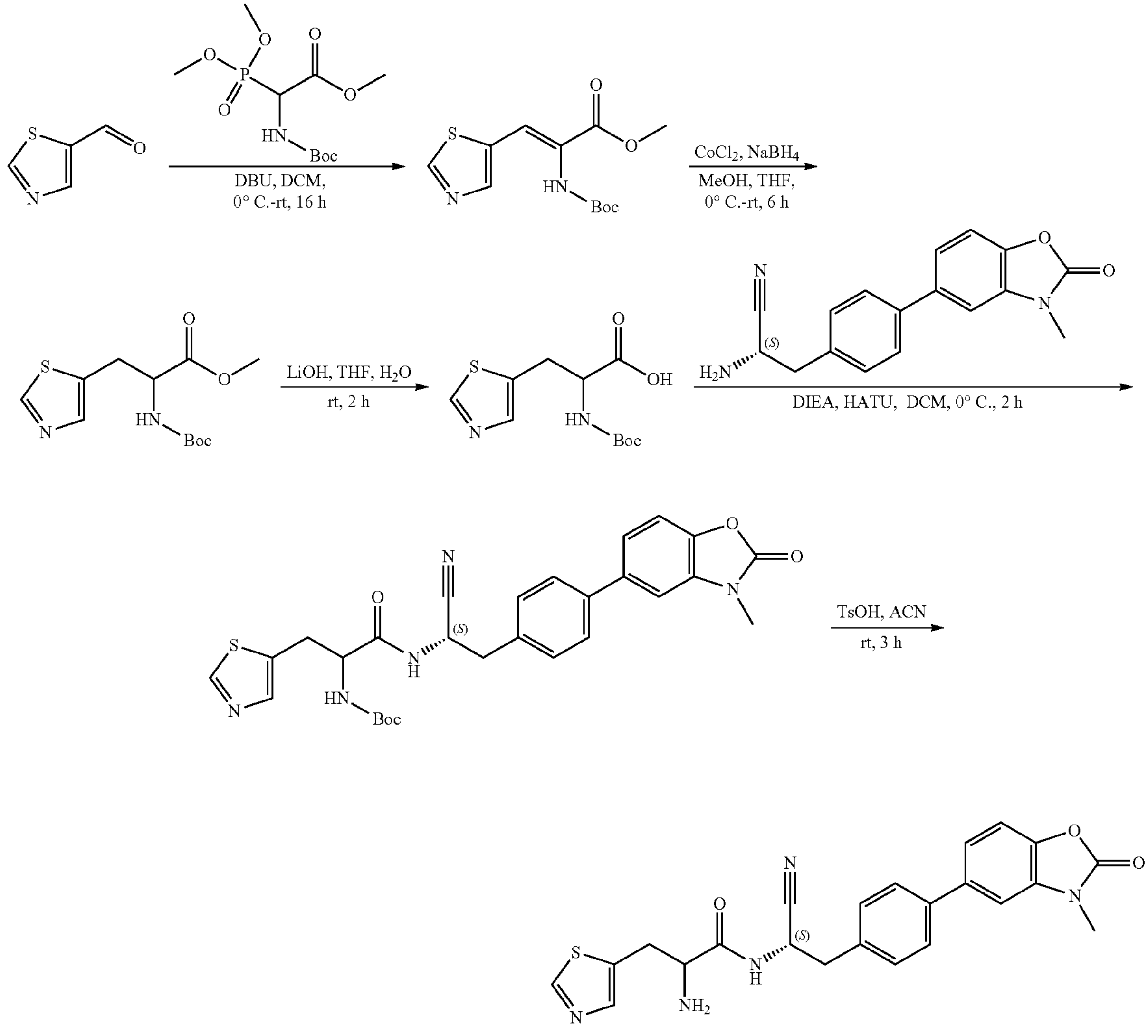

11Synthesis of methyl 2-[(tert-butoxycarbonyl) amino]-3-(1,3-thiazol-5-yl)prop-2-enoate

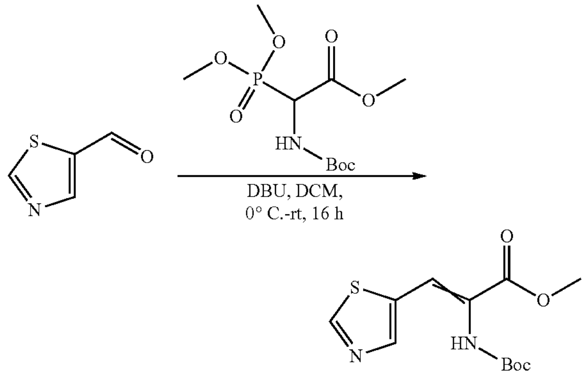

To a stirred solution of 1,3-thiazole-5-carbaldehyde (900 mg, 7.955 mmol, 1.0 equiv) and methyl 2-[(tert-butoxycarbonyl)amino]-2-(dimethoxyphosphoryl)acetate (2.36 g, 7.955 mmol, 1.0 equiv) in DCM (30 mL) was added DBU (1.21 g, 7.955 mmol, 1.0 equiv) dropwise at 0° C. under nitrogen atmosphere. The resulting mixture was stirred for 16 h at room temperature. The resulting mixture was diluted with water (30 mL). The resulting mixture was extracted with $CH_2Cl_2$ (3×30 mL). The combined organic layers were washed with brine (30 mL), dried over anhydrous $Na_2SO_4$. After filtration, the filtrate was concentrated under reduced pressure. The residue was purified by silica gel column chromatography, eluted with PE/EA (2:1) to afford methyl 2-[(tert-butoxycarbonyl)amino]-3-(1,3-thiazol-5-yl)prop-2-enoate (1.8 g, 79.5%). LCMS (ES) $[M+1]^+$ m/z:285.

Synthesis of methyl 2-[(tert-butoxycarbonyl) amino]-3-(1,3-thiazol-5-yl)propanoate

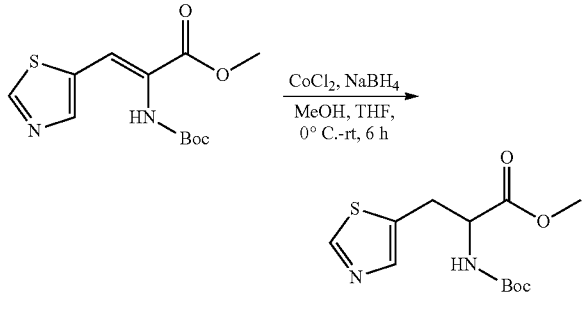

To a stirred solution of methyl 2-[(tert-butoxycarbonyl) amino]-3-(1,3-thiazol-5-yl)prop-2-enoate (1.6 g, 5.627 mmol, 1.0 equiv) and $CoCl_2$ (1.46 g, 11.254 mmol, 2.0 equiv) in MeOH (24 mL) and THF (3 mL) were added $NaBH_4$ (1.06 g, 28.135 mmol, 5.0 equiv) in portions at 0° C. under nitrogen atmosphere. The resulting mixture was stirred for 6 h at room temperature. The reaction was quenched with Water/Ice at 0° C. The resulting mixture was filtered, the filter cake was washed with DCM (3×20 mL). The filtrate was extracted with $CH_2Cl_2$ (3×40 mL). The combined organic layers were washed with brine (30 mL), dried over anhydrous $Na_2SO_4$. After filtration, the filtrate was concentrated under reduced pressure. The residue was purified by silica gel column chromatography, eluted with PE/THF (3:1) to afford methyl 2-[(tert-butoxycarbonyl) amino]-3-(1,3-thiazol-5-yl)propanoate (0.6 g, 37.2%). LCMS (ES) $[M+1]^+$ m/z: 287.

Synthesis of 2-[(tert-butoxycarbonyl)amino]-3-(1,3-thiazol-5-yl)propanoic acid

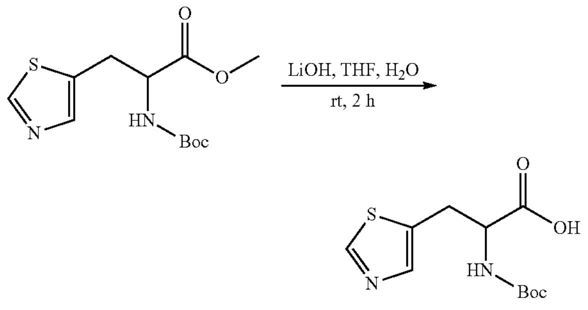

To a stirred solution of methyl 2-[(tert-butoxycarbonyl) amino]-3-(1,3-thiazol-5-yl)propanoate (500 mg, 1.746 mmol, 1.0 equiv) in THF (12 mL) and $H_2O$ (4 mL) were added LiOH (125 mg, 5.238 mmol, 3.0 equiv). The resulting mixture was stirred for 2 h at room temperature. The resulting mixture was diluted with water (20 mL). The mixture was acidified to pH 5 with HCl (aq.)(1 Mol/L). The resulting mixture was extracted with $CH_2Cl_2$ (3×20 mL). The combined organic layers were washed with brine (20 mL), dried over anhydrous $Na_2SO_4$. After filtration, the filtrate was concentrated under reduced pressure. This resulted in 2-[(tert-butoxycarbonyl)amino]-3-(1,3-thiazol-5-yl)propanoic acid (400 mg, 84.1%). LCMS (ES) $[M+1]^+$ m/z: 273.

Synthesis of tert-butyl N-(1-{[(1S)-1-cyano-2-[4-(3-methyl-2-oxo-1,3-benzoxazol-5-yl)phenyl]ethyl] carbamoyl}-2-(1,3-thiazol-5-yl)ethyl)carbamate

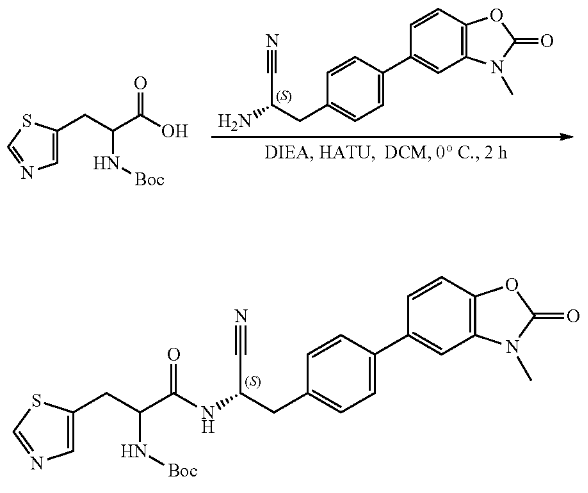

To a stirred solution of 2-[(tert-butoxycarbonyl)amino]-3-(1,3-thiazol-5-yl)propanoic acid (60 mg, 0.220 mmol, 1.0 equiv) and (2S)-2-amino-3-[4-(3-methyl-2-oxo-1,3-benzoxazol-5-yl)phenyl]propanenitrile (71 mg, 0.242 mmol, 1.1 equiv) in DCM (1 mL) were added DIEA (85 mg, 0.660 mmol, 3.0 equiv) and HATU (100 mg, 0.264 mmol, 1.2 equiv) in portions at 0° C. under nitrogen atmosphere. The resulting mixture was stirred for 2 h at 0° C. under nitrogen atmosphere. The residue was purified by silica gel column chromatography, eluted with PE/EA (1:1) to afford tert-butyl N-(1-{[(1S)-1-cyano-2-[4-(3-methyl-2-oxo-1,3-benzoxazol-5-yl)phenyl]ethyl]carbamoyl}-2-(1,3-thiazol-5-yl)ethyl) carbamate (100 mg, 82.8%). LCMS (ES) $[M+1]^+$ m/z: 548.

Synthesis of 2-amino-N-[(1S)-1-cyano-2-[4-(3-methyl-2-oxo-1,3-benzoxazol-5-yl)phenyl]ethyl]-3-(1,3-thiazol-5-yl)propanamide

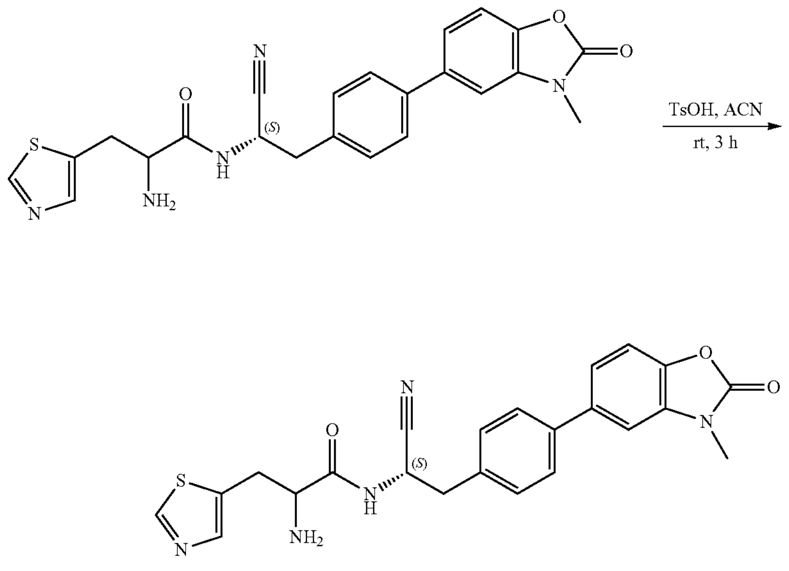

To a stirred solution of tert-butyl N-(1-{[(1S)-1-cyano-2-[4-(3-methyl-2-oxo-1,3-benzoxazol-5-yl)phenyl]ethyl]carbamoyl}-2-(1,3-thiazol-5-yl)ethyl)carbamate (100 mg, 0.183 mmol, 1.0 equiv) in ACN (3 mL) was added TsOH (94 mg, 0.549 mmol, 3.0 equiv). The resulting mixture was stirred for 3 h at room temperature. The crude product was purified by Prep-HPLC with the following conditions (Column, XBridge Prep C18 OBD Column, 19*150 mm 5um; mobile phase, Water (0.1% $NH_3H_2O$) and ACN (10% PhaseB up to 80% in 20 min); Detector, UV 254 nm. This resulted in 2-amino-N-[(1S)-1-cyano-2-[4-(3-methyl-2-oxo-1,3-benzoxazol-5-yl)phenyl]ethyl]-3-(1,3-thiazol-5-yl)propanamide (25 mg, 30.5%). LCMS (ES) $[M+1]^+$ m/z: 448.1. $^1H$ NMR (300 MHz, DMSO-d6) δ 8.88 (s, 1H), 7.72-7.64 (m, 2H), 7.64-7.53 (m, 2H), 7.48-7.35 (m, 4H), 5.00 (t, J=7.6 Hz, 1H), 3.41 (s, 3H), 3.34-3.29 (m, 1H), 3.24-2.98 (m, 3H), 2.90 (td, J=16.0, 15.1, 7.4 Hz, 1H).

Example 11. Synthesis of Compound 204: 2-amino-N-[(1S)-1-cyano-2-[4-(3-methyl-2-oxo-1,3-benzoxazol-5-yl)phenyl]ethyl]-3-(1,3-oxazol-4-yl)propanamide

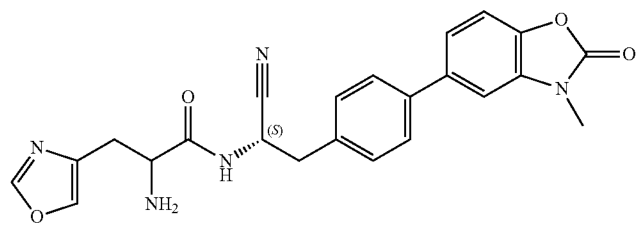

-continued

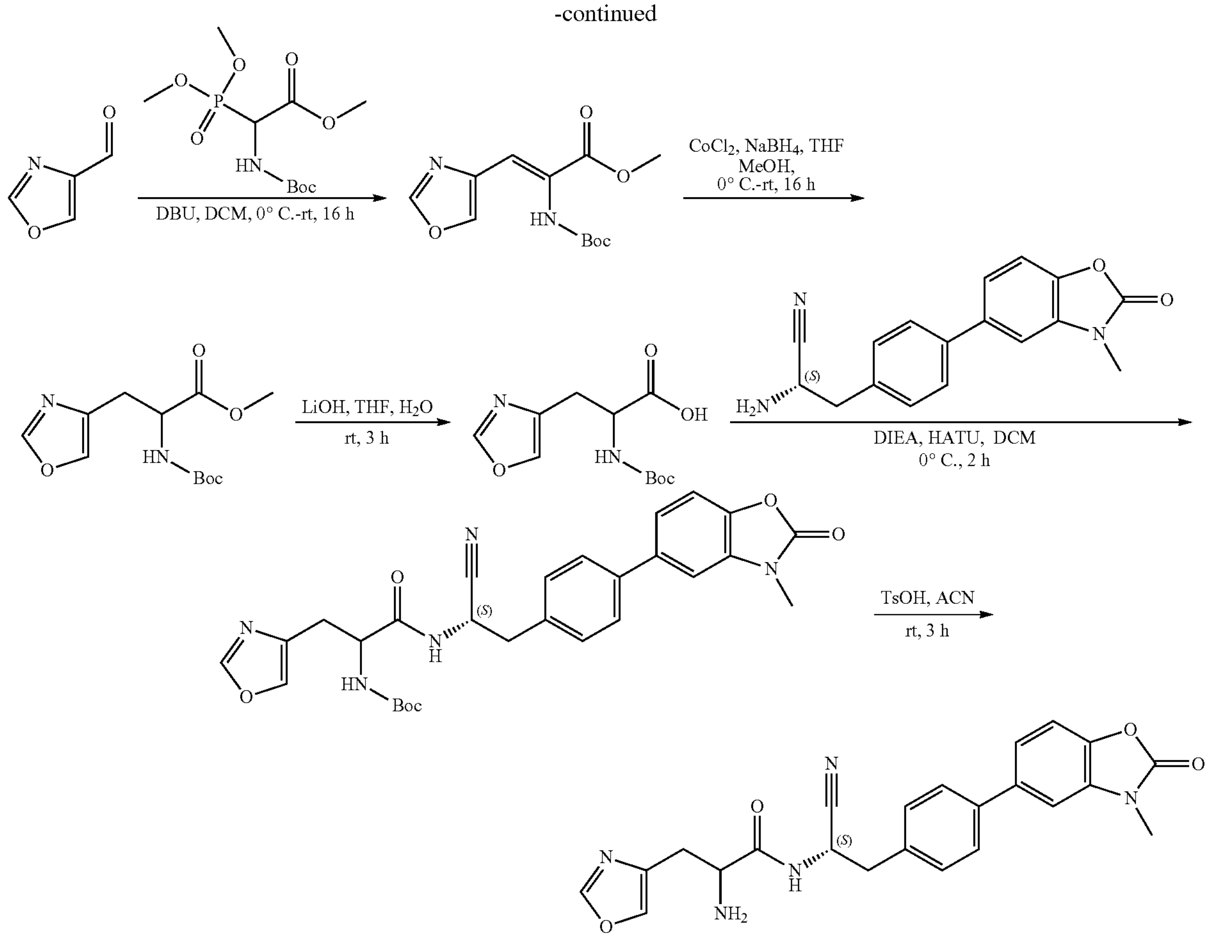

Synthesis of methyl 2-[(tert-butoxycarbonyl)amino]-3-(1,3-oxazol-4-yl)prop-2-enoate

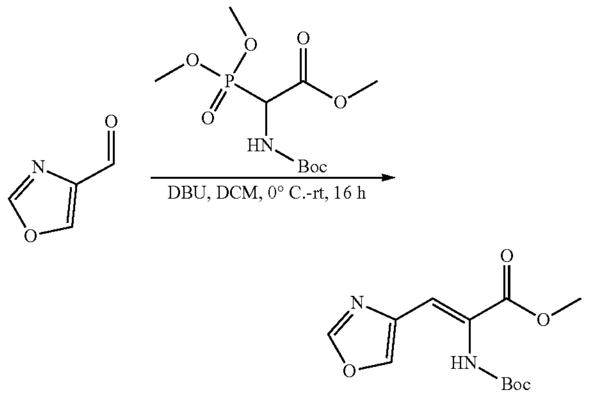

To a stirred solution of 1,3-oxazole-4-carbaldehyde (0.9 g, 9.27 mmol, 1.0 equiv) and methyl 2-[(tert-butoxycarbonyl)amino]-2-(dimethoxyphosphoryl)acetate (2.76 g, 9.27 mmol, 1.0 equiv) in DCM (20 mL) were added DBU (1.41 g, 9.27 mmol, 1.0 equiv) dropwise at 0° C. under nitrogen atmosphere. The resulting mixture was stirred for 16 h at room temperature. The resulting mixture was diluted with water (30 mL), extracted with $CH_2Cl_2$ (3×20 mL). The combined organic layer was washed with brine (20 mL), dried over anhydrous $Na_2SO_4$. After filtration, the filtrate was concentrated under reduced pressure. The residue was purified by silica gel column chromatography, eluted with PE/EA (6:1) to afford methyl 2-[(tert-butoxycarbonyl)amino]-3-(1,3-oxazol-4-yl)prop-2-enoate (1.9 g, 76.3%). LCMS (ES) $[M+1]^+$ m/z: 269.

Synthesis of methyl 2-[(tert-butoxycarbonyl)amino]-3-(1,3-oxazol-4-yl)propanoate

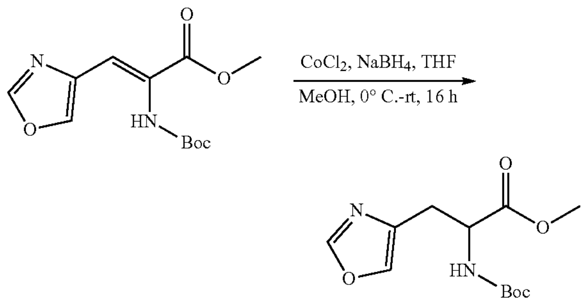

To a stirred mixture of methyl 2-[(tert-butoxycarbonyl)amino]-3-(1,3-oxazol-4-yl)prop-2-enoate (1.7 g, 6.34 mmol, 1.0 equiv) and $CoCl_2$ (1.65 g, 12.67 mmol, 2.0 equiv) in MeOH (32 mL) and THF (4 mL) were added $NaBH_4$ (1.92 g, 50.70 mmol, 8.0 equiv) in portions at 0° C. under nitrogen atmosphere. The resulting mixture was stirred for 16 h at room temperature. The reaction was quenched by the addition of water (50 mL) at 0° C. The resulting mixture was filtered, the filter cake was washed with $CH_2Cl_2$ (3×20 mL). The filtrate was extracted with $CH_2Cl_2$ (3×50 mL). The combined organic layer was washed with brine (50 mL), dried over anhydrous $Na_2SO_4$. After filtration, the filtrate was concentrated under reduced pressure. The residue was purified by silica gel column chromatography, eluted with PE/EA (4:1) to afford methyl 2-[(tert-butoxycarbonyl)amino]-3-(1,3-oxazol-4-yl)propanoate (1 g, 58.3%). LCMS (ES) $[M+1]^+$ m/z: 271.

Synthesis of 2-[(tert-butoxycarbonyl)amino]-3-(1,3-oxazol-4-yl)propanoic acid

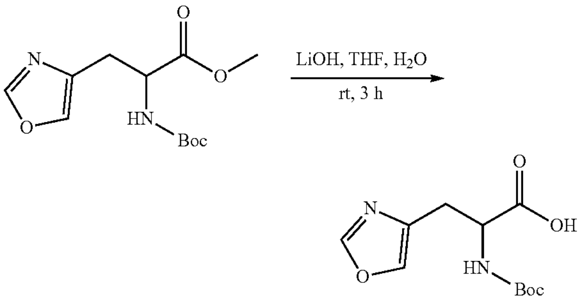

To a stirred solution of methyl 2-[(tert-butoxycarbonyl)amino]-3-(1,3-oxazol-4-yl)propanoate (900 mg, 3.33 mmol, 1.0 equiv) in THF (15 mL) and $H_2O$ (5 mL) was added LiOH (239 mg, 9.99 mmol, 3.0 equiv). The resulting mixture was stirred for 3 h at room temperature. The resulting mixture was diluted with water (30 mL), acidified to pH 5 with citric acid. The resulting mixture was extracted with $CH_2Cl_2$ (3×30 mL). The combined organic layer was washed with water (20 mL), dried over anhydrous $Na_2SO_4$. After filtration, the filtrate was concentrated under reduced pressure. This resulted in 2-[(tert-butoxycarbonyl)amino]-3-(1,3-oxazol-4-yl)propanoic acid (700 mg, 82.0%). LCMS (ES) $[M+1]^+$ m/z: 257.

Synthesis of tert-butyl N-(1-{[(1S)-1-cyano-2-[4-(3-methyl-2-oxo-1,3-benzoxazol-5-yl)phenyl]ethyl]carbamoyl}-2-(1,3-oxazol-4-yl)ethyl)carbamate

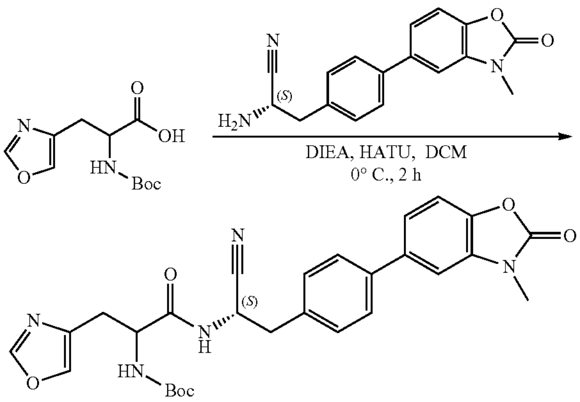

To a stirred solution of 2-[(tert-butoxycarbonyl)amino]-3-(1,3-oxazol-4-yl)propanoic acid (63 mg, 0.25 mmol, 1.1 equiv) and (2S)-2-amino-3-[4-(3-methyl-2-oxo-1,3-benzoxazol-5-yl)phenyl]propanenitrile (66 mg, 0.22 mmol, 1.0 equiv) in DCM (1 mL) were added DIEA (87 mg, 0.68 mmol, 3.0 equiv) and HATU (102 mg, 0.27 mmol, 1.2 equiv) in portions at 0° C. under nitrogen atmosphere. The resulting mixture was stirred for 2 h at 0° C. Concentrated to remove the solvent, the residue was purified by silica gel column chromatography, eluted with PE/THE (2:1) to afford tert-butyl N-(1-{[(1S)-1-cyano-2-[4-(3-methyl-2-oxo-1,3-benzoxazol-5-yl)phenyl]ethyl]carbamoyl}-2-(1,3-oxazol-4-yl)ethyl)carbamate (100 mg, 83.6%). LCMS (ES) $[M+1]^+$ m/z: 532.

Synthesis of 2-amino-N-[(1S)-1-cyano-2-[4-(3-methyl-2-oxo-1,3-benzoxazol-5-yl)phenyl]ethyl]-3-(1,3-oxazol-4-yl)propanamide

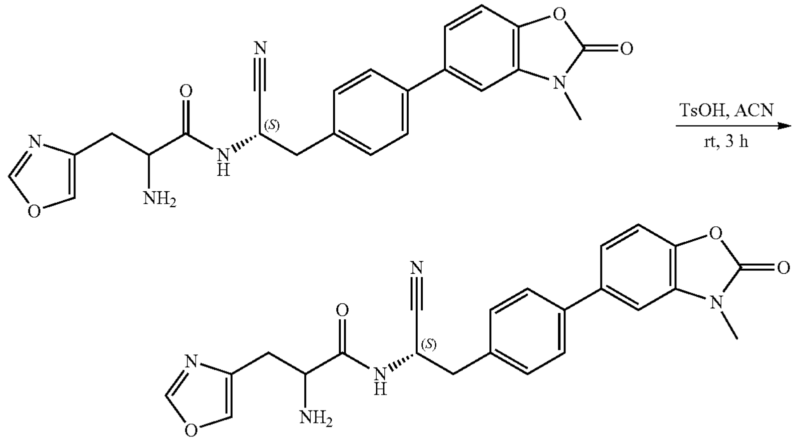

To a stirred solution of tert-butyl N-(1-{[(1S)-1-cyano-2-[4-(3-methyl-2-oxo-1,3-benzoxazol-5-yl)phenyl]ethyl]carbamoyl}-2-(1,3-oxazol-4-yl)ethyl)carbamate (100 mg, 0.19 mmol, 1.0 equiv) in ACN (3 mL) was added TsOH (97 mg, 0.56 mmol, 3.0 equiv). The resulting mixture was stirred for 3 h at room temperature. The reaction solution was purified by Prep-HPLC with the following conditions (Column, XBridge Prep C18 OBD Column, 19*150 mm, 5 um; mobile phase, Water (0.1% $NH_3H_2O$) and ACN (10% Phase B up to 80% in 20 min); Detector, UV 254 nm. This resulted in 2-amino-N-[(1S)-1-cyano-2-[4-(3-methyl-2-oxo-1,3-benzoxazol-5-yl)phenyl]ethyl]-3-(1,3-oxazol-4-yl)propenamide (30 mg, 36.9%). LCMS (ES) $[M+1]^+$ m/z: 432.3

$^1H$ NMR (300 MHz, DMSO-$d_6$) δ 8.27 (s, 1H), 7.75 (d, J=5.2 Hz, 1H), 7.67 (d, J=7.8 Hz, 2H), 7.59 (d, J=1.5 Hz, 1H), 7.43-7.38 (m, 4H), 5.00 (t, J=7.7 Hz, 1H), 3.49-3.40 (m, 4H), 3.20-3.09 (m, 2H), 2.82-2.67 (m, 1H), 2.58-2.54 (m, 1H).

Example 12. Synthesis of Compound 206 and 207: (S)-2-amino-N—((S)-1-cyano-2-(4-(3-methyl-2-oxo-2,3-dihydrobenzo[d]oxazol-5-yl)phenyl)ethyl)-2-((R)-2,3-dihydro-1H-inden-1-yl)acetamide & (S)-2-amino-N—((S)-1-cyano-2-(4-(3-methyl-2-oxo-2,3-dihydrobenzo[d]oxazol-5-yl)phenyl)ethyl)-2-((S)-2,3-dihydro-1H-inden-1-yl)acetamide

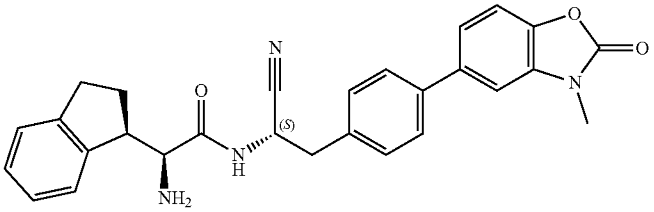

compound 206
(assumed)

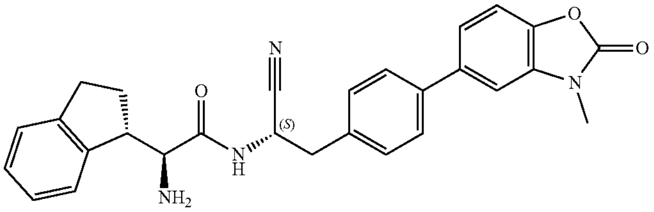

compound 207
(assumed)

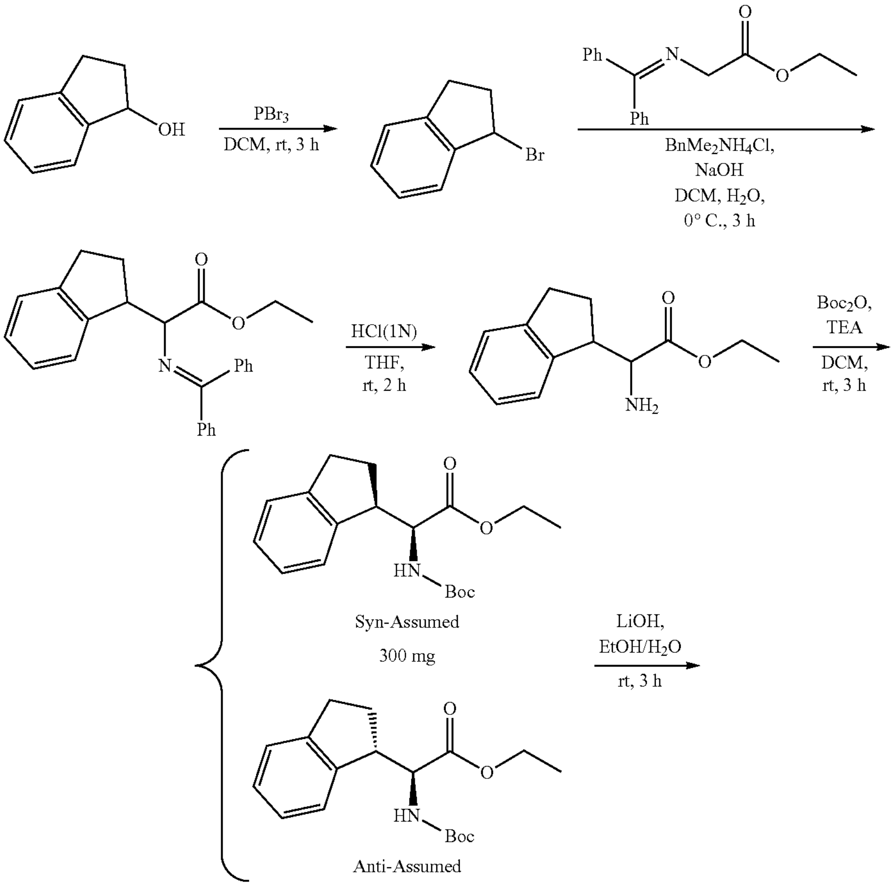

-continued
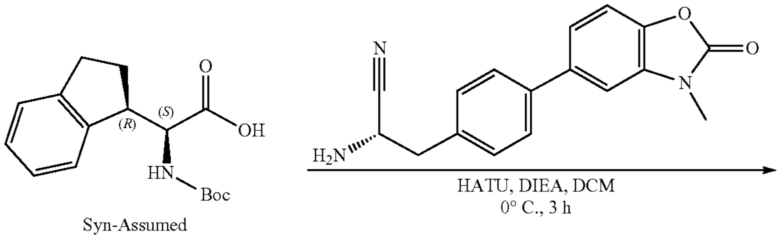
Syn-Assumed
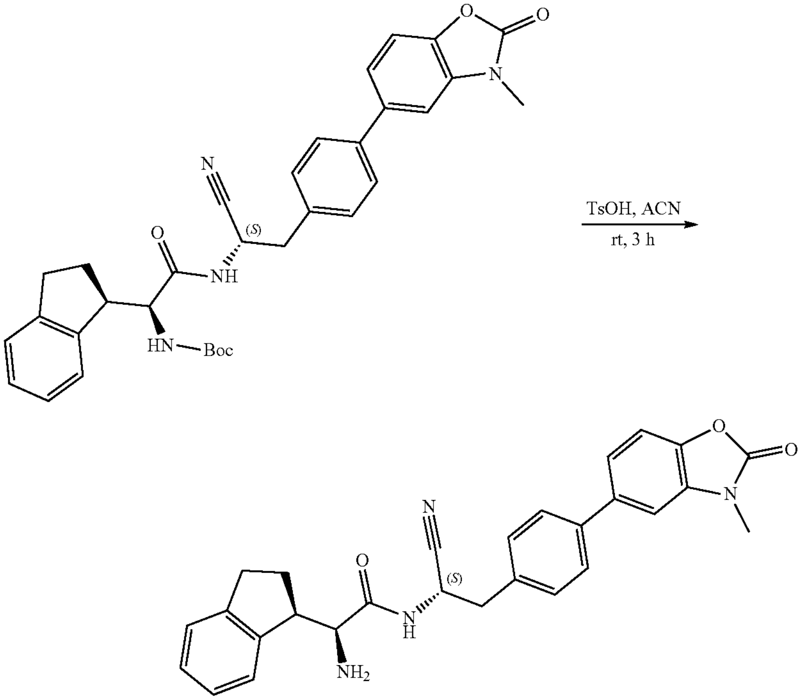
compound 206
(assumed)
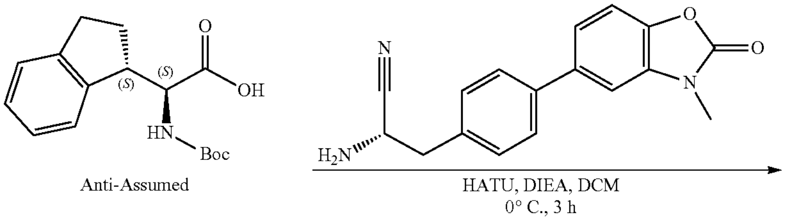
Anti-Assumed
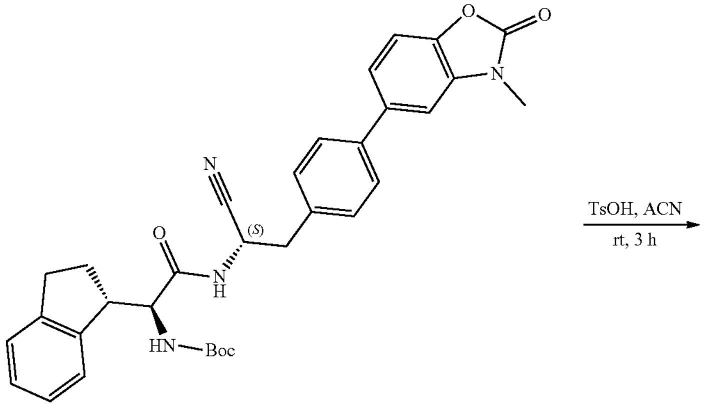

-continued

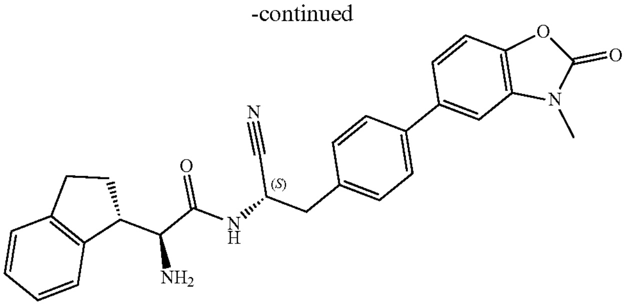

compound 207
(assumed)

Synthesis of 1-bromo-2,3-dihydro-1H-indene

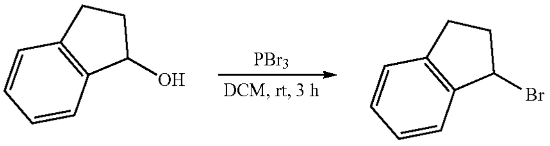 [SMILES: OC1CCc2ccccc21 ; "PBr3" ; BrC1CCc2ccccc21]

To a stirred solution of indanol (3 g, 22.35 mmol, 1.0 equiv) in DCM (30 mL) was added phosphorus tribromide (6.1 g, 22.35 mmol, 1.0 equiv) in portions at 0° C. The resulting mixture was stirred for additional 3 h at room temperature. The resulting mixture was extracted with $CH_2Cl_2$ (3x30 mL). The combined organic layers were washed with brine (3x30 mL), dried over anhydrous $Na_2SO_4$. After filtration, the filtrate was concentrated under reduced pressure. This resulted in 1-bromo-2,3-dihydro-1H-indene (2.8 g, 63.5%). 1H NMR (400 MHz, $CDCl_3$) δ 7.43-7.41 (m, 1H), 7.26-7.20 (m, 3H), 5.58 (dd, J=6.2, 2.4 Hz, 1H), 3.22-3.14 (m, 1H), 2.91-2.84 (m, 1H), 2.63-2.48 (m, 2H).

Synthesis of ethyl 2-(2,3-dihydro-1H-inden-1-yl)-2-[(diphenylmethylidene)amino]acetate

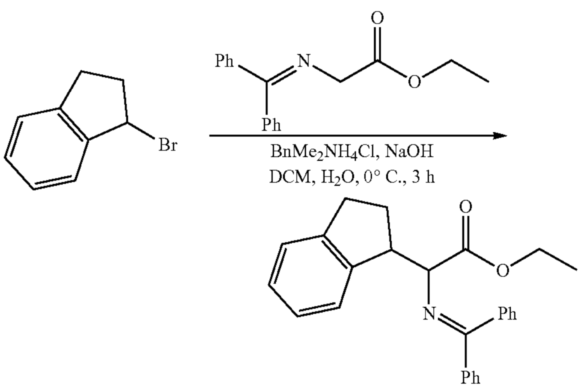

To a solution of 1-bromo-2,3-dihydro-1H-indene (500 mg, 2.54 mmol, 1.0 equiv) in DCM (5 mL) were added ethyl 2-[(diphenylmethylidene)amino]acetate (678 mg, 2.53 mmol, 1.0 equiv), benzyltrimethylazanium chloride (0.2 g, 0.75 mmol, 0.1 equiv), NaOH (203 mg, 5.07 mmol, 2.0 equiv) in $H_2O$ (0.5 mL) at 0° C. The reaction was stirred for 3 h at 0° C. The reaction was quenched with water (20 mL), extracted with $CH_2Cl_2$ (2x100 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/THF (5:1) to afford ethyl 2-(2,3-dihydro-1H-inden-1-yl)-2-[(diphenylmethylidene)amino]acetate (1 g, crude) and used to the next step without further purification. LCMS (ES, m/z): $[M+H]^+$: 384.

Synthesis of ethyl 2-amino-2-(2,3-dihydro-1H-inden-1-yl)acetate

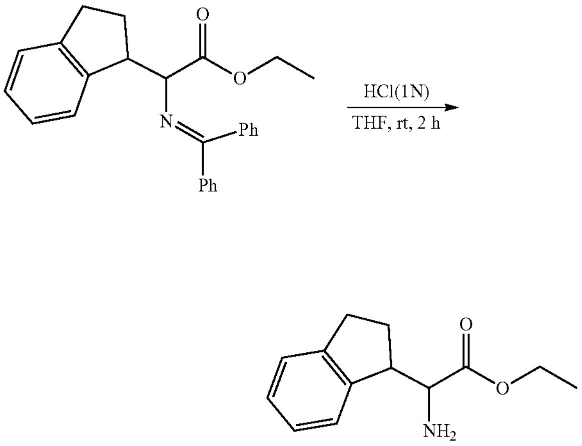

Into a 100 mL round-bottom flask were added ethyl 2-(2,3-dihydro-1H-inden-1-yl)-2-[(diphenylmethylidene) amino]acetate (1.0 g, 2.60 mmol, 1.0 equiv) and HCl (1 M)(2.5 mL), THF (50 mL), $H_2O$ (5 mL) at room temperature. The resulting mixture was stirred for 2 h at room temperature. The resulting mixture was extracted with $Et_2O$ (1x50 mL). The aqueous layer was basified to pH 5 with NaOH, extracted with $CH_2Cl_2$ (3x50 mL). The combined organic layer was washed with brine (3x50 mL), dried over anhydrous $Na_2SO_4$. After filtration, the filtrate was concentrated under reduced pressure. This resulted in ethyl 2-amino-2-(2,3-dihydro-1H-inden-1-yl)acetate (800 mg, crude) and used to the next step without further purification. LCMS (ES, m/z): $[M+H]^+$: 220.

Synthesis of (2S)-2-[(tert-butoxycarbonyl)amino]-2-[(1R)-2,3-dihydro-1H-inden-1-yl]acetate and ethyl (2S)-2-[(tert-butoxycarbonyl)amino]-2-[(1S)-2,3-dihydro-1H-inden-1-yl]acetate

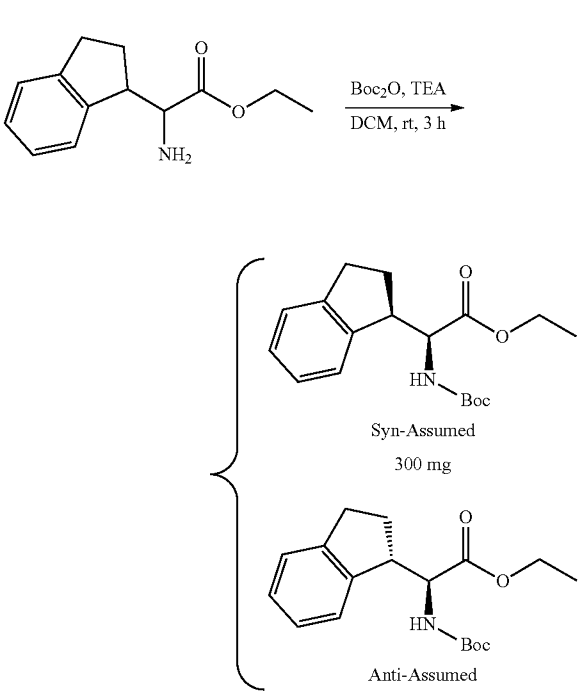 [SMILES: CCOC(=O)C(N)C1CCc2ccccc21 ; CCOC(=O)[C@@H](NC(=O)OC(C)(C)C)[C@@H]1CCc2ccccc21 ; CCOC(=O)[C@@H](NC(=O)OC(C)(C)C)[C@H]1CCc2ccccc21]

To a solution of ethyl 2-amino-2-(2,3-dihydro-1H-inden-1-yl)acetate (800 mg, 3.64 mmol, 1.0 equiv) in DCM (10 mL), triethyl amine (735 mg, 7.28 mmol, 2.0 equiv) and $Boc_2O$ (955 mg, 4.38 mmol, 1.2 equiv) was added in sequence. The mixture was stirred for 16 h at room temperature. Concentrated under reduced pressure, the residue was purified by silica gel column chromatography, eluted with PE/THF (5:1) to afford ethyl (2S)-2-[(tert-butoxycarbonyl)amino]-2-[(1R)-2,3-dihydro-1H-inden-1-yl]acetate (280 mg, 24.0%) and ethyl (2S)-2-[(tert-butoxycarbonyl)amino]-2-[(1S)-2,3-dihydro-1H-inden-1-yl]acetate (130 mg, 11.1%). LCMS (ES, m/z): $[M+H]^+$: 320.

Synthesis of (S)-[(tert-butoxycarbonyl)amino]((1S)-2,3-dihydro-1H-inden-1-yl)acetic acid

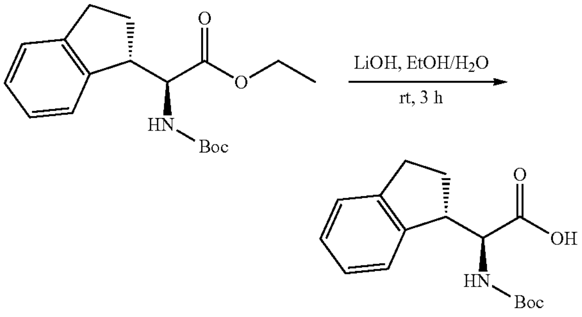

Into a 25 mL round-bottom flask were added ethyl (2S)-2-[(tert-butoxycarbonyl)amino]-2-[(1S)-2,3-dihydro-1H-inden-1-yl]acetate (280 mg, 0.87 mmol, 1.0 equiv) in EtOH (3 mL) and LiOH (63 mg, 2.63 mmol, 3.0 equiv) in $H_2O$ (1 mL) at room temperature. The resulting mixture was stirred for 3 h at room temperature. The mixture was acidified to pH 5 with HCl (1 M). The resulting mixture was extracted with EtOAc (3x30 mL). The combined organic layer was washed with brine (3x20 mL), dried over anhydrous $Na_2SO_4$. After filtration, the filtrate was concentrated under reduced pressure. This resulted in (S)-[(tert-butoxycarbonyl)amino]((1S)-2,3-dihydro-1H-inden-1-yl)acetic acid (240 mg, crude). LCMS (ES, m/z): $[M+H]^+$: 292.

Synthesis of tert-butyl N—[(S)-{[(1S)-1-cyano-2-[4-(3-methyl-2-oxo-1,3-benzoxazol-5-yl)phenyl]ethyl]carbamoyl}((1S)-2,3-dihydro-1H-inden-1-yl)methyl]carbamate

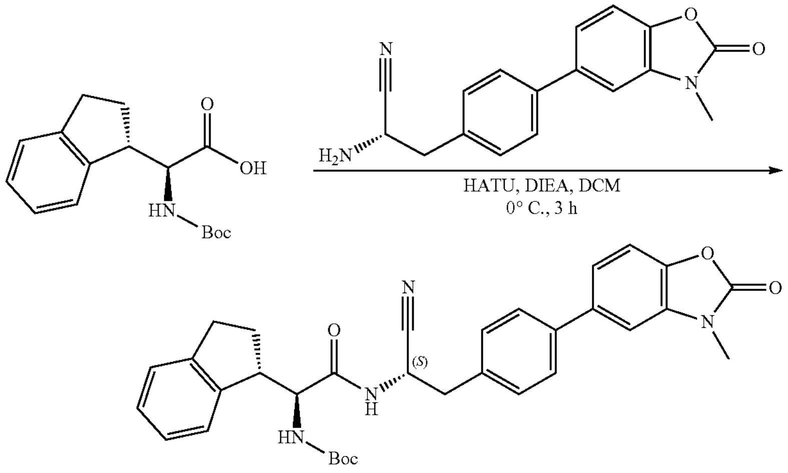

A solution of (S)-[(tert-butoxycarbonyl)amino]((1R)-2,3-dihydro-1H-inden-1-yl)acetic acid (120 mg, 0.41 mmol, 1.2 equiv) in DCM (3 mL) was treated with (S)-[(tert-butoxycarbonyl)amino]((1S)-2,3-dihydro-1H-inden-1-yl)acetic acid (120 mg, 0.41 mmol, 1.2 equiv), DIEA (133 mg, 1.03 mmol, 3.0 equiv). This was followed by the addition of HATU (157 mg, 0.41 mmol, 1.2 equiv) in portions at 0° C. The resulting mixture was stirred for 3 h at 0° C. Concentrated to remove the solvent, the residue was purified by silica gel column chromatography, eluted with PE/THE (2:1) to afford tert-butyl N—[(S)-{[(1S)-1-cyano-2-[4-(3-methyl-2-oxo-1,3-benzoxazol-5-yl)phenyl]ethyl]carbamoyl}((1 S)-2,3-dihydro-1H-inden-1-yl)methyl]carbamate (110 mg, 56.5%). LCMS (ES, m/z): $[M+H]^+$: 567.

Synthesis of (S)-2-amino-N—((S)-1-cyano-2-(4-(3-methyl-2-oxo-2,3-dihydrobenzo[d]oxazol-5-yl)phenyl)ethyl)-2-((R)-2,3-dihydro-1H-inden-1-yl)acetamide

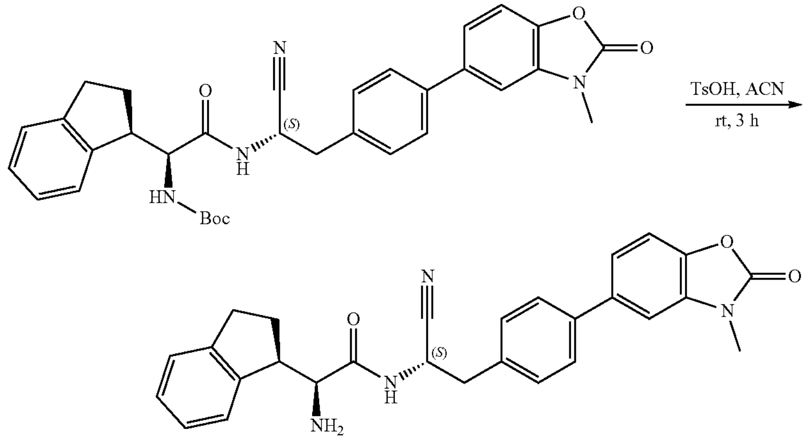

Into a 25 mL round-bottom flask were added tert-butyl N—[(S)-{[(1S)-1-cyano-2-[4-(3-methyl-2-oxo-1,3-benzoxazol-5-yl)phenyl]ethyl]carbamoyl}((1S)-2,3-dihydro-1H-inden-1-yl)methyl]carbamate (110 mg, 0.19 mmol, 1.0 equiv), ACN (3 mL) and $TsOH{\cdot}H_2O$ (110 mg, 0.58 mmol, 3.0 equiv) at room temperature. The resulting mixture was stirred for 3 h at room temperature. The reaction was purified by reversed-phase flash chromatography with the following conditions: column, C18 silica gel-120 g; mobile phase, MeCN in Water (0.1% $NH_3.H_2O$), 10% to 50% gradient in 10 min; detector, UV 254 nm. This resulted in (2S)-2-amino-N-[(1S)-1-cyano-2-[4-(3-methyl-2-oxo-1,3-benzoxazol-5-yl)phenyl]ethyl]-2-[(1S)-2,3-dihydro-1H-inden-1-yl]acetamide (20.5 mg, 22.6%).

LCMS (ES, m/z): $[M+H]^+$: 467.2

$^1H$ NMR (400 MHz, DMSO-$d_6$) δ 8.77 (br, 1H), 7.68 (d, J=7.7 Hz, 2H), 7.58 (d, J=3.0 Hz, 1H), 7.47-7.37 (m, 4H), 7.20-7.08 (m, 4H), 5.09 (q, J=8.3 Hz, 1H), 3.65 (dd, J=16.9, 4.8 Hz, 1H), 3.43-3.36 (m, 4H), 3.24-3.06 (m, 2H), 2.82-2.57 (m, 2H), 1.91-1.34 (m, 3H).

Synthesis of (2S)-2-amino-N-[(1S)-1-cyano-2-[4-(3-methyl-2-oxo-1,3-benzoxazol-5-yl)phenyl]ethyl]-2-[(1S)-2,3-dihydro-1H-inden-1-yl]acetamide

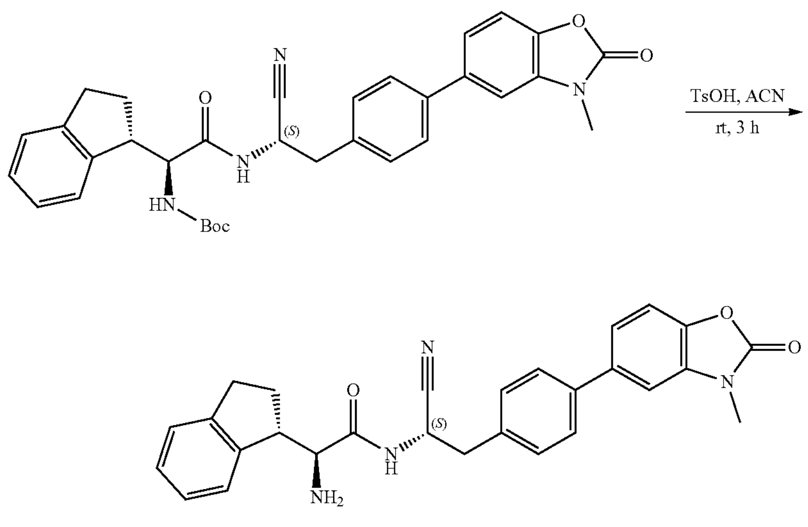

(2S)-2-amino-N-[(1S)-1-cyano-2-[4-(3-methyl-2-oxo-1,3-benzoxazol-5-yl)phenyl]ethyl]-2-[(1S)-2,3-dihydro-1H-inden-1-yl]acetamide (20.5 mg, 22.6%) was synthesized with the same procedure as compound 206.

LCMS (ES, m/z): $[M+H]^+$: 467.2

$^1H$ NMR (400 MHz, DMSO-$d_6$) δ 9.01-8.41 (br, 1H), 7.72-7.62 (m, 2H), 7.61-7.50 (m, 1H), 7.48-7.34 (m, 4H), 7.21-6.92 (m, 4H), 5.10 (q, J=7.9 Hz, 1H), 3.47-3.39 (m, 4H), 3.31-3.07 (m, 3H), 2.92-2.77 (m, 1H), 2.77-2.59 (m, 1H), 2.10-1.63 (m, 3H).

Example 13. Synthesis of Compound 210 and 212: (2S)-2-amino-N-[(1S)-1-cyano-2-[4-(3-methyl-2-oxo-1,3-benzoxazol-5-yl)phenyl]ethyl]-2-[(2S)-oxolan-2-yl]acetamide and (2S)-2-amino-N-[(1S)-1-cyano-2-[4-(3-methyl-2-oxo-1,3-benzoxazol-5-yl)phenyl]ethyl]-2-[(2R)-oxolan-2-yl]acetamide

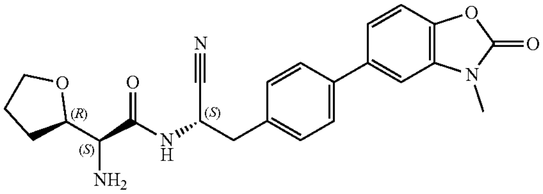

+ compound 210
Assumed

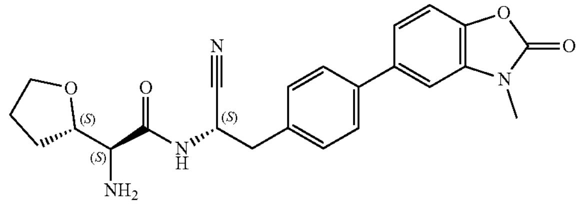

compound 212
Assumed

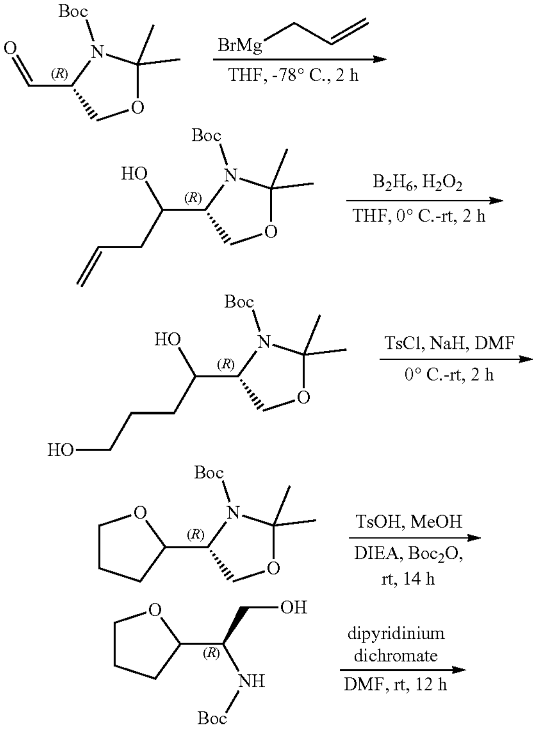

-continued

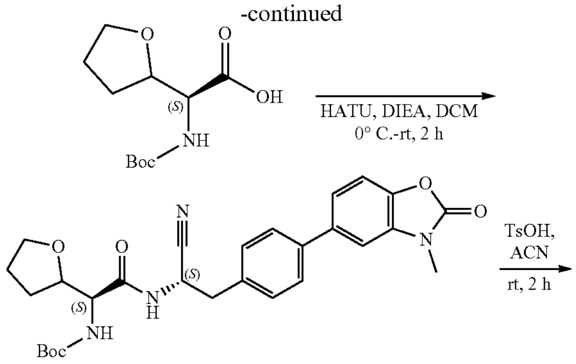

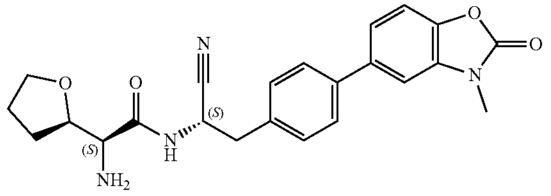

+ compound 210
Assumed

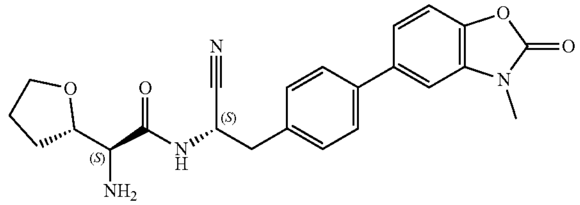

compound 212
Assumed

Synthesis of tert-butyl (4R)-4-(1-hydroxybut-3-en-1-yl)-2,2-dimethyloxazolidine-3-carboxylate

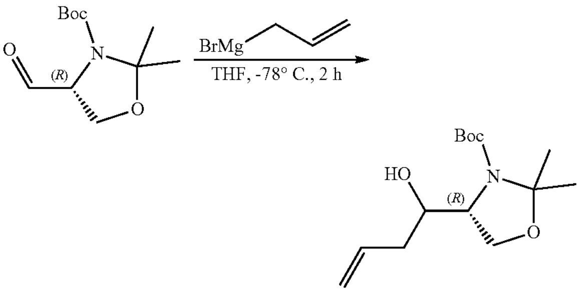

To a stirred solution of tert-butyl (4R)-4-formyl-2,2-dimethyl-1,3-oxazolidine-3-carboxylate (5.0 g, 21.81 mmol, 1.0 equiv) in THF (50.0 mL) were added allylmagnesium bromide (26 mL, 26.17 mmol, 1.2 equiv) allylmagnesium bromide (26 mL, 26.17 mmol, 1.2 equiv) dropwise at −78° C. under nitrogen atmosphere. The resulting mixture was stirred for additional 2 h at −78° C. to room temperature. The reaction was quenched by the addition of sat. $NH_4Cl$ (aq.) (20 mL) at 0° C. The resulting mixture was diluted with water (20 mL). The resulting mixture was extracted with EtOAc (3×30 mL). The combined organic layers were washed with brine (2×100 mL), dried over anhydrous $Na_2SO_4$. After filtration, the filtrate was concentrated under reduced pressure. This resulted in tert-butyl 4-[(1R)-1-hydroxybut-3-en-1-yl]-2,2-dimethyl-1,3-oxazolidine-3-carboxylate (4.2 g, 70.97%). The crude product was used in the next step directly without further purification. LCMS (ES, m z): $[M+H]^+$: 272.

Synthesis of tert-butyl (4R)-4-(1,4-dihydroxybutyl)-2,2-dimethyloxazolidine-3-carboxylate

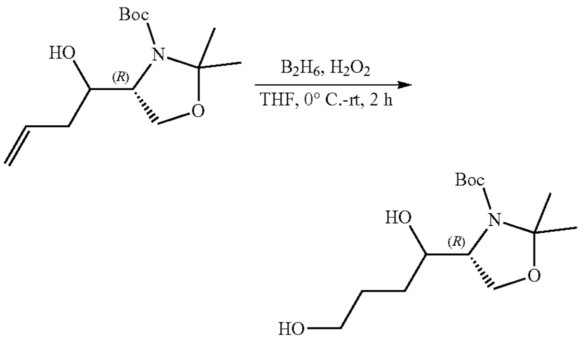

To a stirred solution of tert-butyl 4-[(1R)-1-hydroxybut-3-en-1-yl]-2,2-dimethyl-1,3-oxazolidine-3-carboxylate (4.7 g, 17.32 mmol, 1.0 equiv) in THF (75 mL) were added $BH_3$-THF (75 mL) dropwise at 0° C. under nitrogen atmosphere. The resulting mixture was stirred for additional 1 h at 0° C. To the above mixture was added NaOH (5.54 g, 138.56 mmol, 8.0 equiv) in $H_2O$ (75 mL) dropwise at 0° C. To the above mixture was added $H_2O_2$(30%)(75 mL) dropwise at room temperature. The resulting mixture was stirred for additional 30 min at room temperature. The resulting mixture was diluted with water (300 mL). The resulting mixture was extracted with DCM (3×150 mL). The combined organic layers were washed with brine (2×200 mL), dried over anhydrous $Na_2SO_4$. After filtration, the filtrate was concentrated under reduced pressure. This resulted in tert-butyl 4-[(1R)-1,4-dihydroxybutyl]-2,2-dimethyl-1,3-oxazolidine-3-carboxylate (3.8 g, 75.82%). The crude product was used in the next step directly without further purification. LCMS (ES, m z): $[M+H]^+$: 290.

Synthesis of tert-butyl (4R)-2,2-dimethyl-4-(oxolan-2-yl)-1,3-oxazolidine-3-carboxylate

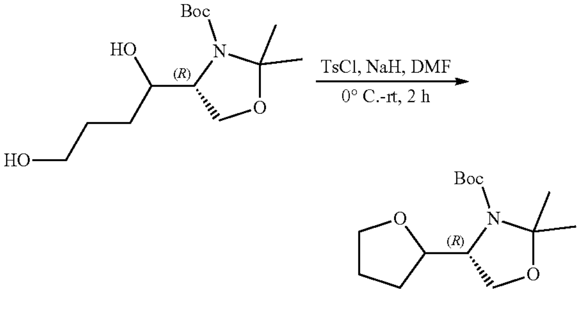

To a stirred solution of tert-butyl (4R)-4-(1,4-dihydroxybutyl)-2,2-dimethyl-1,3-oxazolidine-3-carboxylate (2.0 g, 6.91 mmol, 1.0 equiv) in DMF (40 mL) were added NaH (0.50 g, 20.74 mmol, 3.0 equiv) in portions at 0° C. under nitrogen atmosphere. The resulting mixture was stirred for additional 30 min at 0° C. To the above mixture was added TsCl (1.32 g, 6.91 mmol, 1.0 equiv) in portions at 0° C. The resulting mixture was stirred for additional 2 h at room temperature. The reaction was quenched with water at 0° C. The resulting mixture was extracted with EtOAc (3×20 mL). The combined organic layers were washed with brine (2×40 mL), dried over anhydrous $Na_2SO_4$. After filtration, the filtrate was concentrated under reduced pressure. This resulted in tert-butyl (4R)-2,2-dimethyl-4-(oxolan-2-yl)-1,3-oxazolidine-3-carboxylate (1.1 g, 58.65%). LCMS (ES, m/z): $[M+H]^+$: 272.

Synthesis of tert-butyl N-[(1R)-2-hydroxy-1-(oxolan-2-yl)ethyl]carbamate

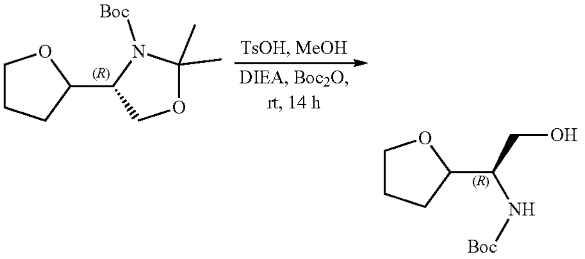

To a stirred solution of tert-butyl (4R)-2,2-dimethyl-4-(oxolan-2-yl)-1,3-oxazolidine-3-carboxylate (1.1 g, 4.05 mmol, 1.0 equiv) in MeOH (18 mL) was added TsOH (0.70 g, 4.05 mmol, 1.0 equiv) in portions at room temperature. The resulting mixture was stirred for additional overnight at room temperature. To the above mixture was added DIEA (1.57 g, 12.16 mmol, 3.0 equiv) and $Boc_2O$ (1.06 g, 4.87 mmol, 1.2 equiv) in portions at 0° C. The resulting mixture was stirred for additional 2 h at room temperature. The resulting mixture was concentrated under reduced pressure. The resulting mixture was diluted with water (20 mL). The resulting mixture was extracted with EtOAc (3×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (1:1) to afford tert-butyl N-[(1R)-2-hydroxy-1-(oxolan-2-yl)ethyl]carbamate (500 mg, 53.33%). LCMS (ES, m/z): $[M+H]^+$: 232.

Synthesis of (S)-[(tert-butoxycarbonyl) amino](oxolan-2-yl)acetic acid

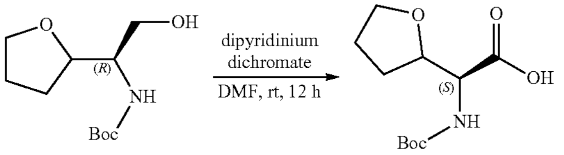

To a stirred solution of tert-butyl N-[(1R)-2-hydroxy-1-(oxolan-2-yl)ethyl]carbamate (500 mg, 2.16 mmol, 1.0 equiv) in DMF (8 mL) were added PDC (6.51 g, 17.30 mmol, 8.0 equiv) in portions at room temperature. The resulting mixture was stirred for additional overnight at room temperature. The resulting mixture was diluted with water (20 mL), and sat. $NaHSO_3$(aq)(60 mL). The resulting mixture was extracted with EtOAc (3×20 mL). The combined organic layers were washed with sat. $NaHCO_3$(aq)(15 mL), The aqueous layer was acidified to pH=4 with HCl (aq. 1 M). The resulting mixture was extracted with EtOAc (3×20 mL). The combined organic layers were washed with brine (2×40 mL), dried over anhydrous $Na_2SO_4$. After filtration, the filtrate was concentrated under reduced pressure. This resulted in (S)-[(tert-butoxycarbonyl) amino](oxolan-2-yl)acetic acid (190 mg, 35.83%). LCMS (ES, m/z): $[M+H]^+$: 246.

Synthesis of tert-butyl N—[(S)-{[(1S)-1-cyano-2-[4-(3-methyl-2-oxo-1,3-benzoxazol-5-yl) phenyl] ethyl]carbamoyl}(oxolan-2-yl)methyl]carbamate

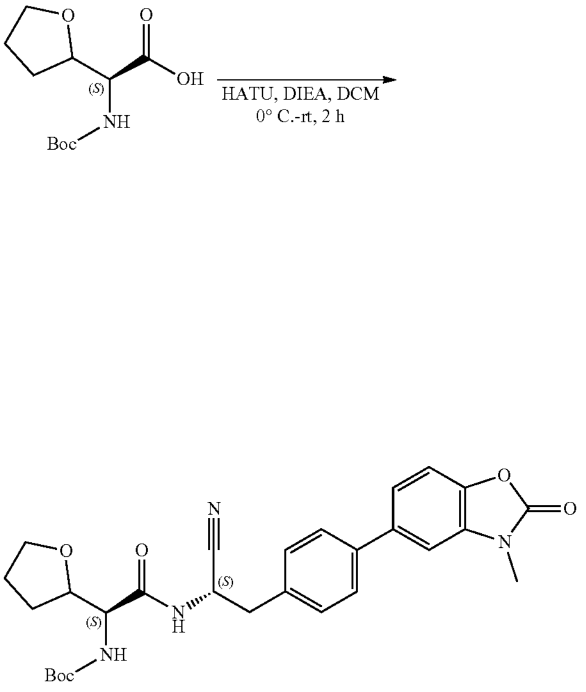

To a stirred mixture of (S)-[(tert-butoxycarbonyl) amino](oxolan-2-yl)acetic acid (160 mg, 0.65 mmol, 1.0 equiv) in DCM (4 mL) was added DIEA (168.62 mg, 1.30 mmol, 2.0 equiv) and HATU (297.65 mg, 0.78 mmol, 1.2 equiv) in portion at 0° C. To the above mixture was added (2S)-2-amino-3-[4-(3-methyl-2-oxo-1,3-benzoxazol-5-yl)phenyl] propanenitrile (191.35 mg, 0.65 mmol, 1.0 equiv) in portions at 0° C. The resulting mixture was stirred for additional 2 h at room temperature. The resulting mixture was diluted with water (15 mL). The resulting mixture was extracted with EtOAc (2×15 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (1:1) to afford tert-butyl N—[(S)-{[(1S)-1-cyano-2-[4-(3-methyl-2-oxo-1,3-benzoxazol-5-yl)phenyl]ethyl]carbamoyl}(oxolan-2-yl) methyl]carbamate (200 mg, 58.89%). LCMS (ES, m/z): $[M+H]^+$: 521.

Synthesis of (2S)-2-amino-N-[(1S)-1-cyano-2-[4-(3-methyl-2-oxo-1,3-benzoxazol-5-yl)phenyl]ethyl]-2-[(2S)-oxolan-2-yl]acetamide and (2S)-2-amino-N-[(1S)-1-cyano-2-[4-(3-methyl-2-oxo-1,3-benzoxazol-5-yl)phenyl]ethyl]-2-[(2R)-oxolan-2-yl] acetamide

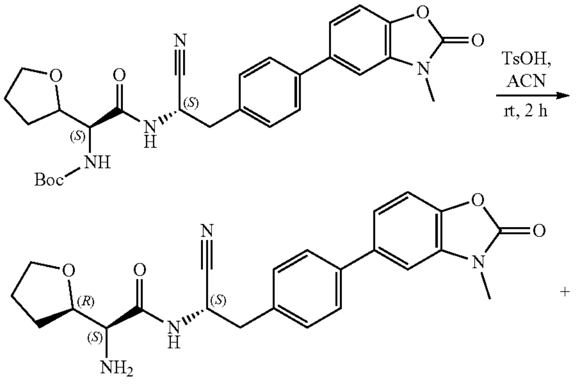

compound 210

Assumed

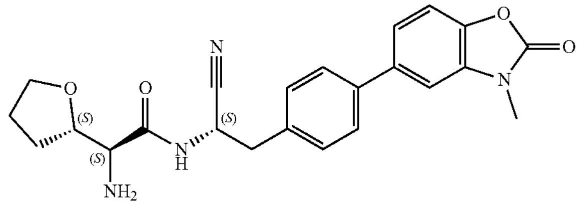

compound 212

Assumed

To a stirred solution of tert-butyl N—[(S)-{[(1S)-1-cyano-2-[4-(3-methyl-2-oxo-1,3-benzoxazol-5-yl) phenyl] ethyl]carbamoyl}((2S)-oxolan-2-yl)methyl]carbamate (160 mg, 0.31 mmol, 1.0 equiv) in ACN (3.0 mL) were added TsOH·$H_2O$ (175.38 mg, 0.92 mmol, 3.0 equiv) in portions at room temperature. The resulting mixture was stirred for additional 2 h at room temperature. The crude product was purified by Prep-HPLC with the following conditions (column, C18 silica gel; mobile phase, MeCN in Water (0.1% $NH_3$·$H_2O$), 20% to 40% gradient in 10 min; detector, UV 254 nm.) to afford (2S)-2-amino-N-[(1S)-1-cyano-2-[4-(3-methyl-2-oxo-1,3-benzoxazol-5-yl) phenyl]ethyl]-2-[(2S)-oxolan-2-yl]acetamide (20 mg, 15.48%) and (2S)-2-amino-N-[(1S)-1-cyano-2-[4-(3-methyl-2-oxo-1,3-benzoxazol-5-yl)phenyl]ethyl]-2-[(2R)-oxolan-2-yl]acetamide (18 mg, 13.93%).

LCMS (ES, m z): $[M+H]^+$: 421.1.

$^1$H NMR (300 MHz, DMSO-$d_6$) δ 7.67 (d, J=7.9 Hz, 2H), 7.58 (s, 1H), 7.45-7.38 (m, 4H), 5.01 (t, J=7.7 Hz, 1H), 3.90-3.66 (m, 2H), 3.59 (q, J=7.1 Hz, 1H), 3.41 (s, 3H), 3.26 (d, J=6.0 Hz, 1H), 3.17 (d, J=7.7 Hz, 2H), 1.78-1.65 (m, 3H), 1.60-1.53 (m, 2H).

LCMS (ES, m z): $[M+H]^+$: 421.1.

$^1$H NMR (300 MHz, DMSO-$d_6$) δ 7.67 (d, J=7.9 Hz, 2H), 7.59 (s, 1H), 7.45-7.39 (m, 4H), 5.01 (t, J=7.6 Hz, 1H), 3.89-3.81 (m, 1H), 3.74-3.67 (m, 1H), 3.63-3.55 (m, 1H), 3.41 (s, 3H), 3.23-3.04 (m, 3H), 1.87-1.55 (m, 5H).

Example 14. Synthesis of Compound 211 and 213: (2R)-2-amino-N-[(1S)-1-cyano-2-[4-(3-methyl-2-oxo-1,3-benzoxazol-5-yl)phenyl]ethyl]-2-[(2R)-oxolan-2-yl]acetamide and (2R)-2-amino-N-[(1S)-1-cyano-2-[4-(3-methyl-2-oxo-1,3-benzoxazol-5-yl)phenyl]ethyl]-2-[(2S)-oxolan-2-yl]acetamide

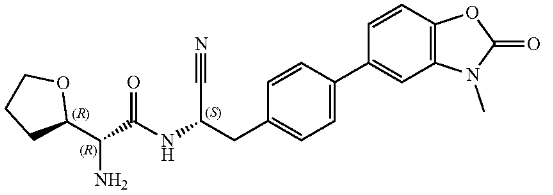

+ compound 211

Assumed

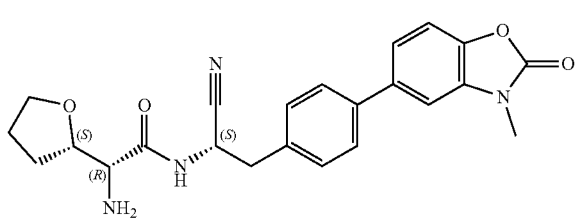

compound 213

Assumed

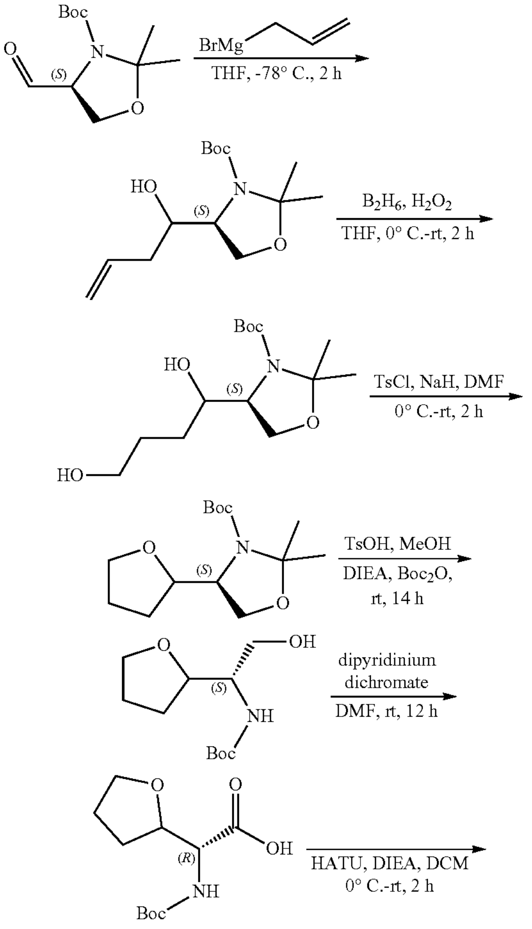

-continued

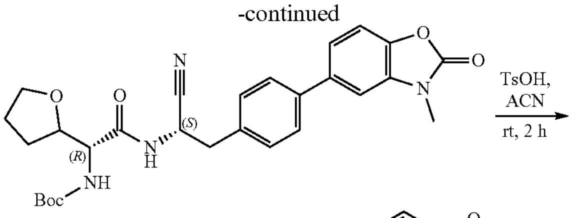

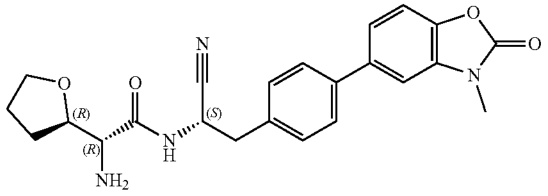

+ compound 211

Assumed

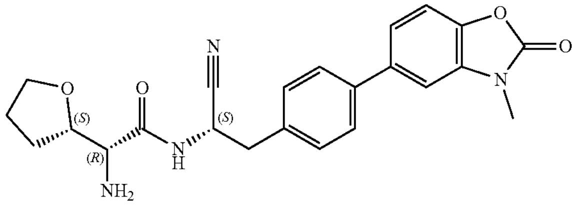

compound 213

Assumed

Synthesis of tert-butyl (4S)-4-(1-hydroxybut-3-en-1-yl)-2,2-dimethyloxazolidine-3-carboxylate

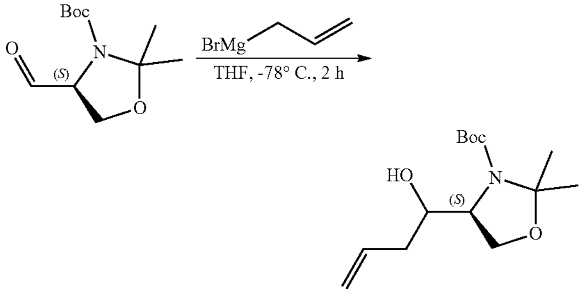

To a stirred solution of tert-butyl (4S)-4-formyl-2,2-dimethyl-1,3-oxazolidine-3-carboxylate (5.0 g, 21.81 mmol, 1.0 equiv) in THF (50.0 mL) were added allylmagnesium bromide (26 mL, 26.17 mmol, 1.2 equiv) allylmagnesium bromide (26 mL, 26.17 mmol, 1.2 equiv) dropwise at −78° C. under nitrogen atmosphere. The resulting mixture was stirred for additional 2 h at −78° C. to room temperature. The reaction was quenched by the addition of sat. $NH_4Cl$ (aq.) (20 mL) at 0° C. The resulting mixture was diluted with water (20 mL). The resulting mixture was extracted with EtOAc (3×30 mL). The combined organic layers were washed with brine (2×100 mL), dried over anhydrous $Na_2SO_4$. After filtration, the filtrate was concentrated under reduced pressure. This resulted in tert-butyl 4-[(1S)-1-hydroxybut-3-en-1-yl]-2,2-dimethyl-1,3-oxazolidine-3-carboxylate (3.8 g, 64.21%). The crude product was used in the next step directly without further purification. LCMS (ES, m z): $[M+H]^+$: 272.

Synthesis of tert-butyl (4S)-4-(1,4-dihydroxybutyl)-2,2-dimethyloxazolidine-3-carboxylate

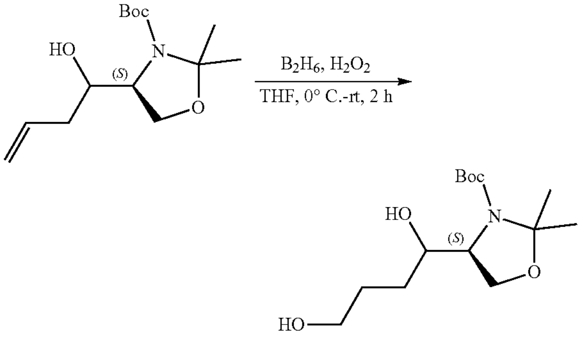

To a stirred solution of tert-butyl 4-[(1S)-1-hydroxybut-3-en-1-yl]-2,2-dimethyl-1,3-oxazolidine-3-carboxylate (3.8 g, 14.00 mmol, 1.0 equiv) in THF (61 mL) were added $BH_3$-THF (61 mL) dropwise at 0° C. under nitrogen atmosphere. The resulting mixture was stirred for additional 1 h at 0° C. To the above mixture was added NaOH (4.48 g, 112.03 mmol, 8.0 equiv) in $H_2O$ (61 mL) dropwise at 0° C. To the above mixture was added $H_2O_2$(30%)(61 mL) dropwise at room temperature. The resulting mixture was stirred for additional 30 min at room temperature. The resulting mixture was diluted with water (300 mL). The resulting mixture was extracted with DCM (3×150 mL). The combined organic layers were washed with brine (2×200 mL), dried over anhydrous $Na_2SO_4$. After filtration, the filtrate was concentrated under reduced pressure. This resulted in tert-butyl 4-[(1S)-1,4-dihydroxybutyl]-2,2-dimethyl-1,3-oxazolidine-3-carboxylate (3.6 g, 88.84%). The crude product was used in the next step directly without further purification. LCMS (ES, m z): $[M+H]^+$: 290.

Synthesis of tert-butyl (4S)-2,2-dimethyl-4-(oxolan-2-yl)-1,3-oxazolidine-3-carboxylate

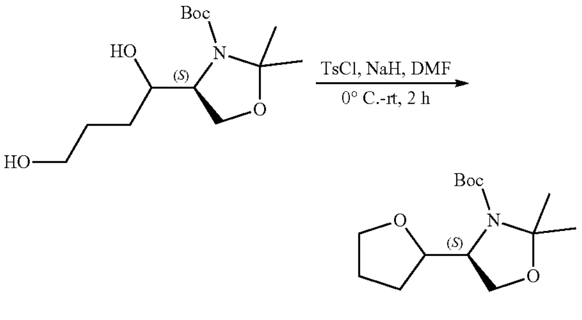

To a stirred solution of tert-butyl (4S)-4-(1,4-dihydroxybutyl)-2,2-dimethyl-1,3-oxazolidine-3-carboxylate (1.0 g, 3.46 mmol, 1.0 equiv) in DMF (20 mL) were added NaH (0.25 g, 10.37 mmol, 3.0 equiv) in portions at 0° C. under nitrogen atmosphere. The resulting mixture was stirred for additional 30 min at 0° C. To the above mixture was added TsCl (0.66 g, 3.46 mmol, 1.0 equiv) in portions at 0° C. The resulting mixture was stirred for additional 2 h at room temperature. The reaction was quenched with water at 0° C. The resulting mixture was extracted with EtOAc (3×20 mL).

The combined organic layers were washed with brine (2×40 mL), dried over anhydrous $Na_2SO_4$. After filtration, the filtrate was concentrated under reduced pressure. This resulted in tert-butyl (4S)-2,2-dimethyl-4-(oxolan-2-yl)-1,3-oxazolidine-3-carboxylate (0.8 g, 85.31%). LCMS (ES, m/z): $[M+H]^+$: 272.

Synthesis of tert-butyl N-[(1S)-2-hydroxy-1-(oxolan-2-yl)ethyl]carbamate

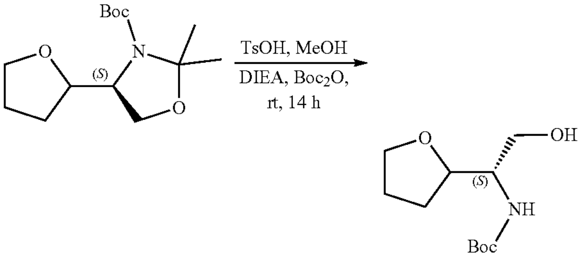

To a stirred solution of tert-butyl (4S)-2,2-dimethyl-4-(oxolan-2-yl)-1,3-oxazolidine-3-carboxylate (0.8 g, 2.95 mmol, 1.0 equiv) in MeOH (10 mL) was added TsOH (0.51 g, 2.96 mmol, 1.0 equiv) in portions at room temperature. The resulting mixture was stirred for additional overnight at room temperature. To the above mixture was added DIEA (1.14 g, 8.84 mmol, 3.0 equiv) and $Boc_2O$ (0.77 g, 3.54 mmol, 1.2 equiv) in portions at 0° C. The resulting mixture was stirred for additional 2 h at room temperature. The resulting mixture was concentrated under reduced pressure. The resulting mixture was diluted with water (20 mL). The resulting mixture was extracted with EtOAc (3×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (1:1) to afford tert-butyl N-[(1S)-2-hydroxy-1-(oxolan-2-yl)ethyl]carbamate (360 mg, 52.80%). LCMS (ES, m/z): $[M+H]^+$: 232.

Synthesis of (R)-[(tert-butoxycarbonyl) amino](oxolan-2-yl)acetic acid

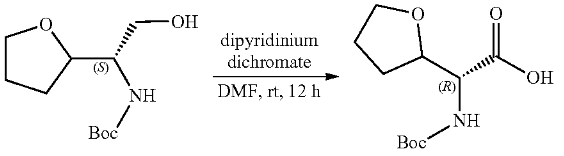

To a stirred solution of tert-butyl N-[(1S)-2-hydroxy-1-(oxolan-2-yl)ethyl]carbamate (360 mg, 1.56 mmol, 1.0 equiv) in DMF (6 mL) were added PDC (4.68 g, 12.45 mmol, 8.0 equiv) in portions at room temperature. The resulting mixture was stirred for additional overnight at room temperature. The resulting mixture was diluted with water (20 mL), and sat. $NaHSO_3$(aq)(60 mL). The resulting mixture was extracted with EtOAc (3×20 mL). The combined organic layers were washed with sat. $NaHCO_3$(aq)(15 mL), The aqueous layer was acidified to pH=4 with HCl (aq. 1 M). The resulting mixture was extracted with EtOAc (3×20 mL). The combined organic layers were washed with brine (2×40 mL), dried over anhydrous $Na_2SO_4$. After filtration, the filtrate was concentrated under reduced pressure. This resulted in (R)-[(tert-butoxycarbonyl) amino](oxolan-2-yl)acetic acid (140 mg, 36.67%). LCMS (ES, m/z): $[M+H]^+$: 246.

Synthesis of tert-butyl N—[(R)-{[(1S)-1-cyano-2-[4-(3-methyl-2-oxo-1,3-benzoxazol-5-yl) phenyl] ethyl]carbamoyl}(oxolan-2-yl)methyl]carbamate

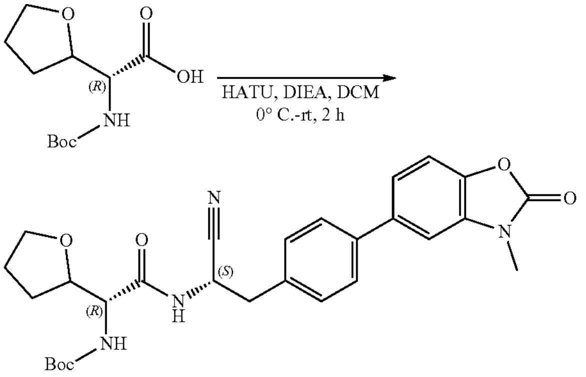

To a stirred mixture of (R)-[(tert-butoxycarbonyl) amino](oxolan-2-yl)acetic acid (120 mg, 0.49 mmol, 1.0 equiv) in DCM (3 mL) was added DIEA (126.47 mg, 0.98 mmol, 2.0 equiv) and HATU (223.23 mg, 0.59 mmol, 1.2 equiv) in portion at 0° C. To the above mixture was added (2S)-2-amino-3-[4-(3-methyl-2-oxo-1,3-benzoxazol-5-yl)phenyl]propanenitrile (143.51 mg, 0.49 mmol, 1.0 equiv) in portions at 0° C. The resulting mixture was stirred for additional 2 h at room temperature. The resulting mixture was diluted with water (15 mL). The resulting mixture was extracted with EtOAc (2×15 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/THF (3:2) to afford tert-butyl N—[(R)-{[(1S)-1-cyano-2-[4-(3-methyl-2-oxo-1,3-benzoxazol-5-yl)phenyl]ethyl]carbamoyl}(oxolan-2-yl)methyl]carbamate (150 mg, 58.89%). LCMS (ES, m/z): $[M+H]^+$: 521.

Synthesis of (2R)-2-amino-N-[(1S)-1-cyano-2-[4-(3-methyl-2-oxo-1,3-benzoxazol-5-yl)phenyl]ethyl]-2-[(2R)-oxolan-2-yl]acetamide (assumed) and (2R)-2-amino-N-[(1S)-1-cyano-2-[4-(3-methyl-2-oxo-1,3-benzoxazol-5-yl)phenyl]ethyl]-2-[(2S)-oxolan-2-yl]acetamide (assumed)

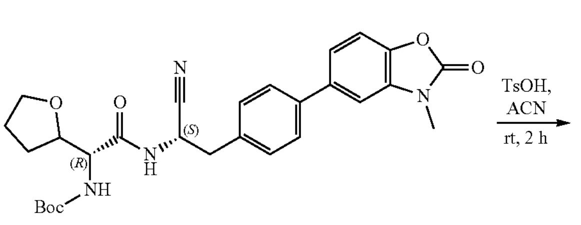

-continued

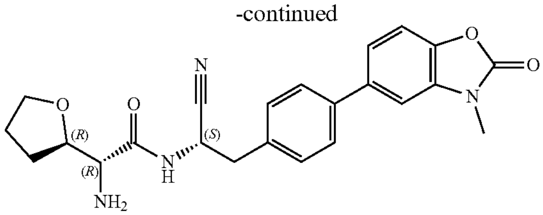

+ compupond 211

Assumed

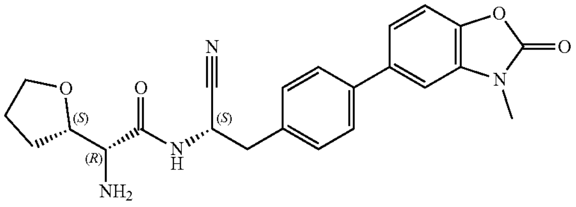

compound 213

Assumed

To a stirred solution of tert-butyl N—[(R)-{[(1S)-1-cyano-2-[4-(3-methyl-2-oxo-1,3-benzoxazol-5-yl) phenyl] ethyl]carbamoyl}((2S)-oxolan-2-yl)methyl]carbamate (120 mg, 0.23 mmol, 1.0 equiv) in ACN (3.0 mL) were added $TsOH{\cdot}H_2O$ (131.54 mg, 0.69 mmol, 3.0 equiv) in portions at room temperature. The resulting mixture was stirred for additional 2 h at room temperature. The crude product was purified by Prep-HPLC with the following conditions (column, C18 silica gel; mobile phase, MeCN in Water (0.1% $NH_3{\cdot}H_2O$), 20% to 40% gradient in 10 min; detector, UV 254 nm.) to afford (2R)-2-amino-N-[(1S)-1-cyano-2-[4-(3-methyl-2-oxo-1,3-benzoxazol-5-yl) phenyl]ethyl]-2-[(2S)-oxolan-2-yl]acetamide (19 mg, 19.60%) and (2R)-2-amino-N-[(1S)-1-cyano-2-[4-(3-methyl-2-oxo-1,3-benzoxazol-5-yl)phenyl]ethyl]-2-[(2R)-oxolan-2-yl]acetamide (17 mg, 17.54%).

LCMS (ES, m z): $[M+H]^+$: 421.1.

$^1H$ NMR (300 MHz, DMSO-$d_6$) δ 7.67 (d, J=7.9 Hz, 2H), 7.58 (s, 1H), 7.48-7.36 (m, 4H), 5.03 (t, J=7.6 Hz, 1H), 3.76-3.69 (m, 2H), 3.59 (q, J=7.4, 7.0 Hz, 1H), 3.41 (s, 3H), 3.27 (d, J=5.8 Hz, 1H), 3.21-3.05 (m, 2H), 1.77-1.41 (m, 5H).

LCMS (ES, m z): $[M+H]^+$: 421.1.

$^1H$ NMR (300 MHz, DMSO-$d_6$) δ 7.67 (d, J=7.9 Hz, 2H), 7.59 (s, 1H), 7.44-7.33 (m, 4H), 5.00 (t, J=7.7 Hz, 1H), 3.93 (q, J=6.2, 5.7 Hz, 1H), 3.72-3.65 (m, 1H), 3.61-3.53 (m, 1H), 3.41 (s, 3H), 3.25-3.03 (m, 3H), 1.86-1.56 (m, 4H).

Example 15. Synthesis of Compound 219: 2-amino-N-[(1S)-1-cyano-2-[4-(3-methyl-2-oxo-1,3-benzoxazol-5-yl)phenyl]ethyl]-2-cyclopentylpropanamide

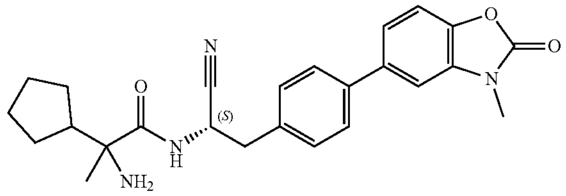

compound 219

-continued

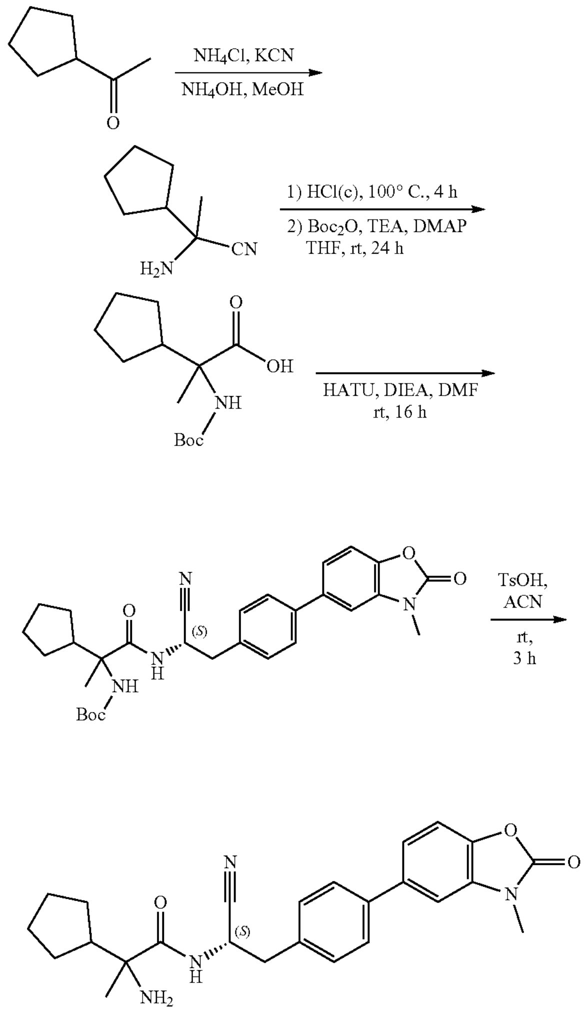

Synthesis of 2-amino-2-cyclopentylpropanenitrile

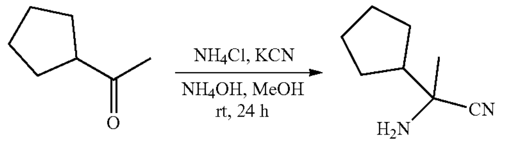

To a solution of $NH_4Cl$ (1.9 g, 35.66 mmol, 2.0 equiv) in $NH_3{\cdot}H_2O$ (20 mL), NaCN (2.2 g, 44.57 mmol, 2.5 equiv) was added at room temperature. This was followed by the addition of 1-cyclopentylethan-1-one (2.0 g, 17.83 mmol, 1.0 equiv) in MeOH (20 mL). The mixture was stirred for 24 h at room temperature. Concentrated to remove the solvent, the residue was diluted with water (30 mL), extracted with ethyl acetate (40 mL×2). The combined organic phase was washed with brine (50 mL), dried over anhydrous sodium sulfate. Filtered and the filtrate was concentrated under reduced pressure, 2-amino-2-cyclopentylpropanenitrile (1.8 g, 73.0%) was obtained which was used to the next step without further purification. LCMS (ES, m/z): $[M+H]^+$: 139.

Synthesis of 2-((tert-butoxycarbonyl)amino)-2-cyclopentylpropanoic acid

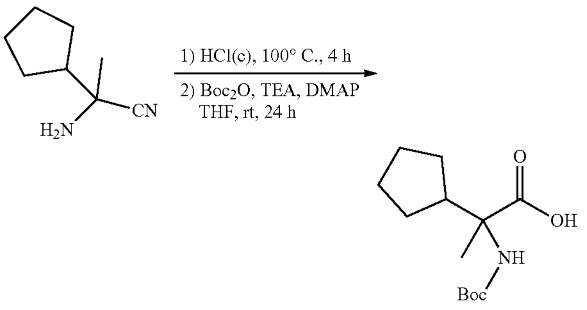

2-amino-2-cyclopentylpropanenitrile (1.8 g, 13.02 mmol, 1.0 equiv) was dissolved in conc. HCl (18 mL), the mixture was heated to 100° C. and stirred for 4 h. The reaction was cooled to room temperature, diluted with water (20 mL), adjust PH with $K_2CO_3$ solid to PH 7-8. To the mixture, THF (20 mL), TEA (3.95 g, 39.07 mmol, 3.0 equiv), DMAP (0.16 g, 1.30 mmol, 0.1 equiv) and $Boc_2O$ (3.65 g, 15.63 mmol, 1.2 equiv) were added in sequence at room temperature. The reaction was stirred for 12 h. The reaction was adjusted PH to 5-6 with HCl(1N), extracted with dichloromethane (50 mL×3). The combined organic phase was dried over anhydrous sodium sulfate. Filtered and the filtrate was concentrated under reduced pressure, this result in 2-((tert-butoxycarbonyl)amino)-2-cyclopentylpropanoic acid (1.1 g, 32.8%) and used to the next step without further purification. LCMS (ES, m/z): $[M+H]^+$: 258.

Synthesis of tert-butyl N-(1-{[(1S)-1-cyano-2-[4-(3-methyl-2-oxo-1,3-benzoxazol-5-yl)phenyl]ethyl]carbamoyl}-1-cyclopentylethyl)carbamate

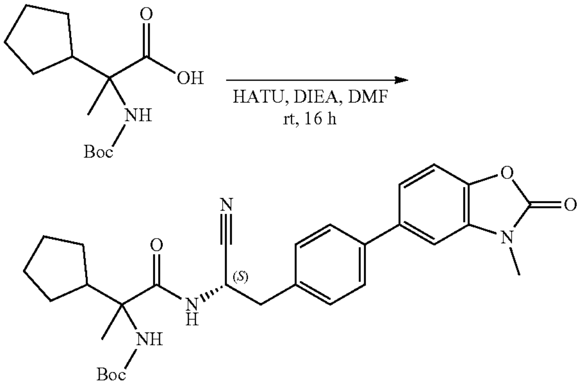

A solution of (2S)-2-amino-3-[4-(3-methyl-2-oxo-1,3-benzoxazol-5-yl)phenyl]propanenitrile (80 mg, 0.27 mmol, 1.0 equiv) in DMF (3 mL) was treated with 2-((tert-butoxycarbonyl)amino)-2-cyclopentylpropanoic acid (140 mg, 0.54 mmol, 2.0 equiv), DIEA (105 mg, 0.81 mmol, 3.0 equiv). This was followed by the addition of HATU (124 mg, 0.32 mmol, 1.2 equiv) in portions at 0° C. The resulting mixture was stirred for additional 2 h at 0° C. The reaction was quenched with water (10 mL), extracted with EtOAc (3×20 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-[4-(3-methyl-2-oxo-1,3-benzoxazol-5-yl)phenyl]ethyl]carbamoyl}-1-cyclopentylethyl)carbamate (140 mg, 80.0%). LCMS (ES, m/z): $[M+H]^+$: 533.

Synthesis of 2-amino-N-[(1S)-1-cyano-2-[4-(3-methyl-2-oxo-1,3-benzoxazol-5-yl)phenyl]ethyl]-2-cyclopentylpropanamide

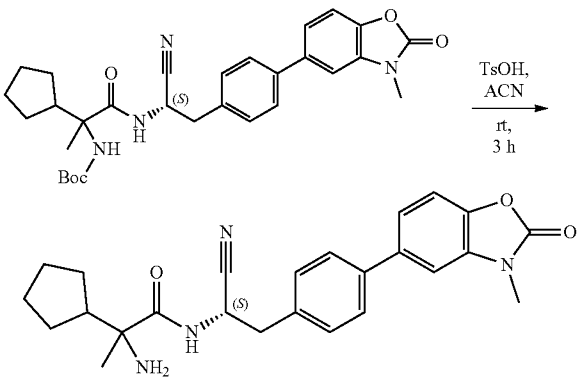

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-1-cyclopentylethyl)carbamate (140 mg, 0.26 mmol, 1.0 equiv) in ACN (4 mL) and $TsOH \cdot H_2O$ (149 mg, 0.78 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-2-cyclopentylpropanamide (17.3 mg, 15%).

LCMS (ES, m/z): $[M+H]^+$: 433.4

$^1H$ NMR (400 MHz, DMSO-$d_6$) δ 7.68-7.63 (m, 2H), 7.57 (dt, J=9.8, 1.2 Hz, 1H), 7.45-7.37 (m, 4H), 5.03-4.96 (m, 1H), 3.41 (d, J=1.8 Hz, 3H), 3.22-3.17 (m, 2H), 2.13-2.02 (m, 1H), 1.59-1.13 (m, 5H), 1.10-0.93 (m, 6H).

Example 16. Synthesis of Compound 220: 2-amino-N-[(1S)-1-cyano-2-[4-(3-methyl-2-oxo-1,3-benzoxazol-5-yl)phenyl]ethyl]-2-cyclobutylpropanamide compound 220

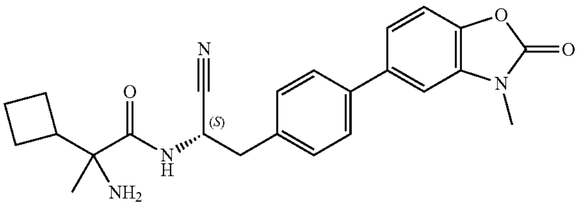

-continued

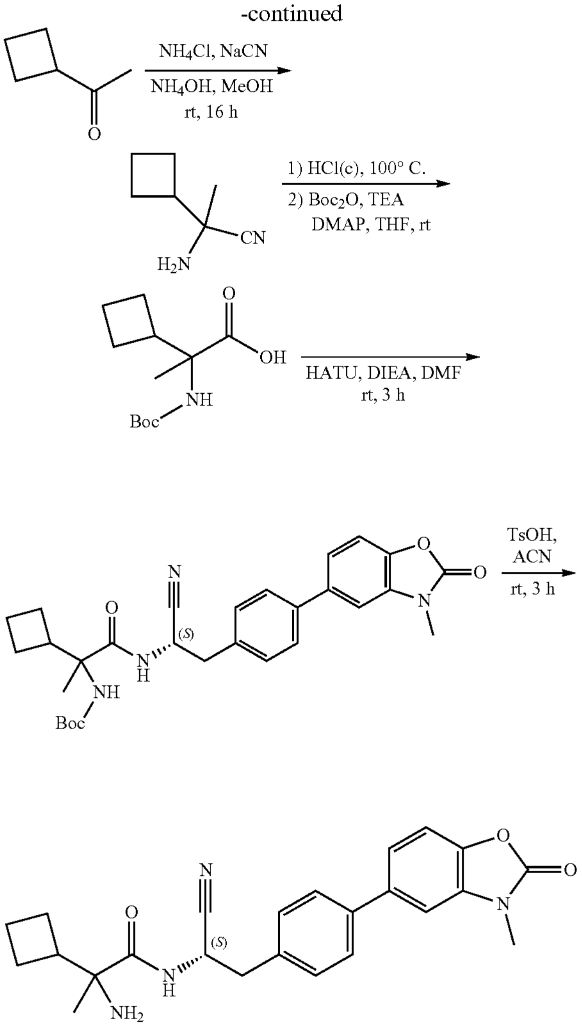

Synthesis of 2-amino-2-cyclobutylpropanenitrile

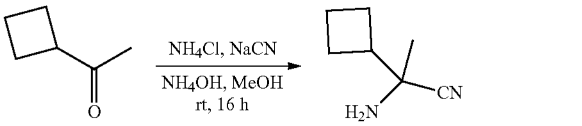

To a solution of $NH_4Cl$ (2.2 g, 40.75 mmol, 2.0 equiv) in $NH_4OH$ (30% in $H_2O$)(20 mL) was added NaCN (2.5 g, 50.94 mmol, 2.5 equiv) at room temperature. This was followed by the addition of 1-cyclobutylethan-1-one (2.0 g, 20.37 mmol, 1.0 equiv) in MeOH (20 mL) at room temperature. The reaction was stirred for 16 h. The mixture was concentrated to remove the solvent, the residue was diluted with water (30 mL), extracted with ethyl acetate (40 mL×2). The combined organic phase was washed with brine (50 mL), dried over anhydrous sodium sulfate. Filtered out the solid, the filtrate was concentrated under reduced pressure, this result in 2-amino-2-cyclobutylpropanenitrile (1.8 g, 71.1%), which used to the next step without further purification. LCMS (ES, m/z): $[M+H]^+$: 125.

Synthesis of 2-[(tert-butoxycarbonyl)amino]-2-cyclobutylpropanoic acid

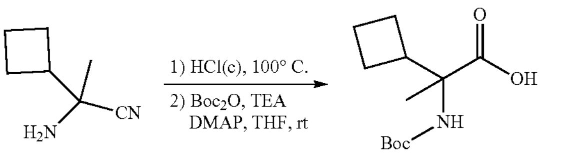

A solution of 2-amino-2-cyclobutylpropanenitrile (1.8 g, 14.49 mmol, 1.0 equiv) in conc. HCl (20 mL) was heated to 100° C. and stirred for 3 h. The reaction was cooled to room temperature, diluted with water (30 mL), adjust PH to 6-7 with $K_2CO_3$ solid. Concentrated to remove the solvent, the residue was dissolved in MeOH (30 mL), filtered out the solid, the filtrate was concentrated, the residue was added to a 100 mL round bottom flask, this was followed by the addition of THF (30 mL), $Boc_2O$ (4.8 g, 21.74 mmol, 1.5 equiv), TEA (2.9 g, 28.98 mmol, 2.0 equiv), DMAP (0.2 g, 1.44 mmol, 0.1 equiv) in sequence. The mixture was stirred for 48 h, diluted with water (20 mL), adjust PH to 5 with HCl (1 N), extracted with dichloromethane (50 mL×2). The combined organic phase was dried over anhydrous sodium sulfate. After filtration, the filtrate was concentrated under reduced pressure. This result in 2-[(tert-butoxycarbonyl) amino]-2-cyclobutylpropanoic acid (0.4 g, 11%) which was used to the next step directly without further purification. LCMS (ES, m/z): $[M+H]^+$: 244.

Synthesis of tert-butyl N-(1-{[(1S)-1-cyano-2-[4-(3-methyl-2-oxo-1,3-benzoxazol-5-yl)phenyl]ethyl]carbamoyl}-1-cyclobutylethyl)carbamate

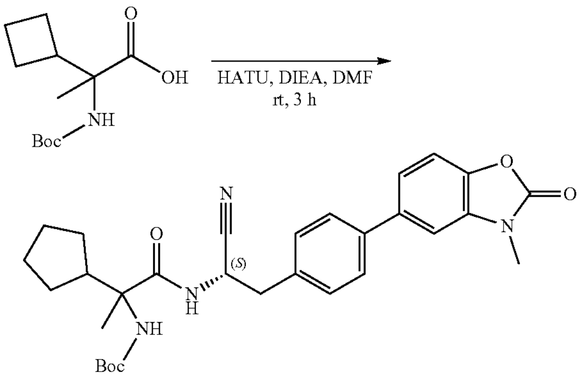

A solution of (2S)-2-amino-3-[4-(3-methyl-2-oxo-1,3-benzoxazol-5-yl)phenyl]propanenitrile (100 mg, 0.34 mmol, 1.0 equiv) in DMF (3 mL) was treated with 2-[(tert-butoxycarbonyl)amino]-2-cyclobutylpropanoic acid (124 mg, 0.51 mmol, 1.5 equiv), DIEA (132 mg, 1.02 mmol, 3.0 equiv). This was followed by the addition of HATU (155 mg, 0.40 mmol, 1.2 equiv) in portions at 0° C. The resulting mixture was stirred for additional 2 h at room temperature. The resulting mixture was extracted with EtOAc (3×20 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (2:1) to afford tert-butyl N-(1-{[(1S)-1-cyano-2-[4-(3-methyl-2-oxo-1,3-benzoxazol-5-yl)phenyl]ethyl]carbamoyl}-1-cyclobutylethyl)carbamate (120 mg, 67.8%). LCMS (ES, m/z): $[M+H]^+$: 519.

Synthesis of 2-amino-N-[(1S)-1-cyano-2-[4-(3-methyl-2-oxo-1,3-benzoxazol-5-yl)phenyl]ethyl]-2-cyclobutylpropanamide

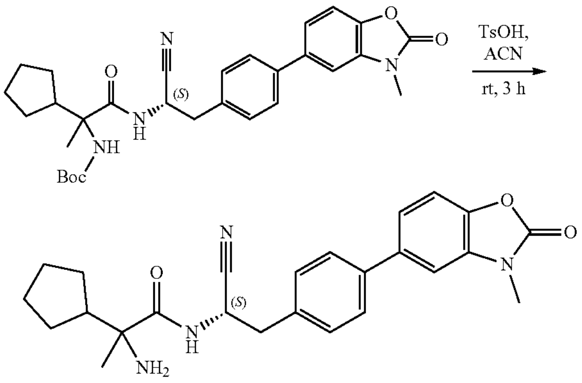

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-1-cyclobutylethyl)carbamate (120 mg, 0.23 mmol, 1.0 equiv), ACN (3 mL) and $TsOH \cdot H_2O$ (132 mg, 0.69 mmol, 3.0 equiv) at room temperature. The resulting mixture was stirred for additional 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-2-cyclobutylpropanamide (17.3 mg, 17.8%).

LCMS (ES, m/z): $[M+H]^+$: 419.4

$^1H$ NMR (400 MHz, DMSO-$d_6$) δ 7.68-7.64 (m, 2H), 7.58-7.55 (m, 1H), 7.45-7.36 (m, 4H), 4.98 (q, J=7.3 Hz, 1H), 3.40 (d, J=1.7 Hz, 3H), 3.24-3.14 (m, 2H), 2.50-2.41 (m, 1H), 1.94-1.34 (m, 6H), 0.98 (d, J=23.5 Hz, 3H).

Example 17. Synthesis of Compound 221: 2-amino-N-[(1S)-1-cyano-2-[4-(3-methyl-2-oxo-1,3-benzoxazol-5-yl)phenyl]ethyl]-3-(1H-pyrazol-3-yl)propanamide

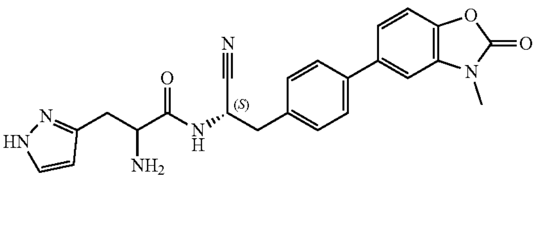

-continued

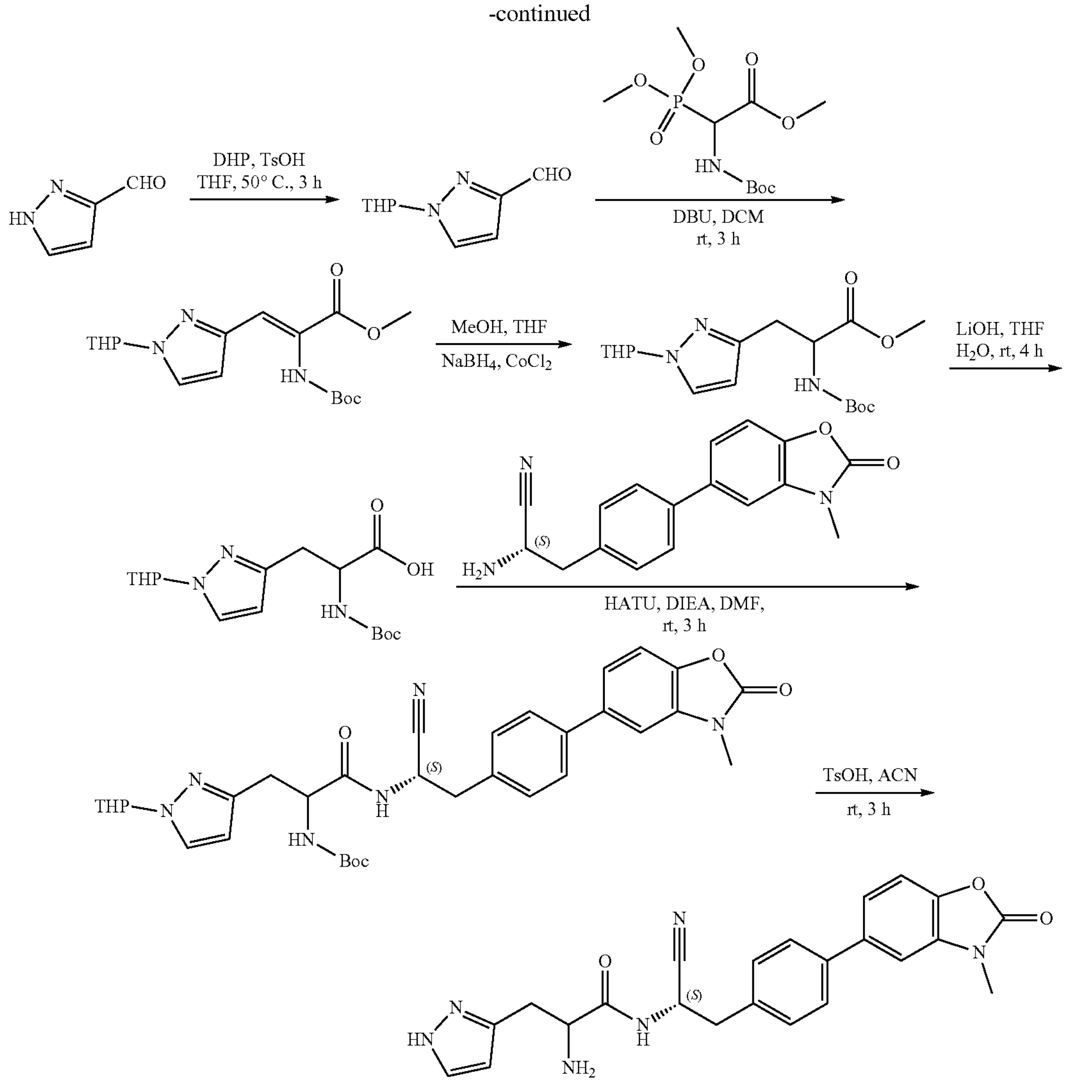

Synthesis of 1-(tetrahydro-2H-pyran-2-yl)-1H-pyrazole-3-carbaldehyde

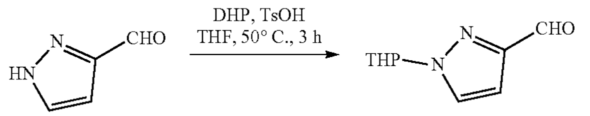

To a stirred solution of 1H-pyrazole-3-carbaldehyde (1 g, 10.41 mmol, 1.0 equiv) and DHP (0.88 g, 10.41 mmol, 1.0 equiv) in THF (20 mL) was added TsOH-$H_2O$ (0.20 g, 1.04 mmol, 0.1 equiv) at room temperature. The resulting mixture was stirred for 3 h at 50° C. The resulting mixture was concentrated under reduced pressure. The residue was purified by silica gel column chromatography, eluted with PE/EA (10:1) to afford 1-(oxan-2-yl)pyrazole-3-carbaldehyde (1.8 g, 96%). $^1H$ NMR (400 MHz, DMSO-$d_6$) δ 9.91 (s, 1H), 8.09 (d, J=2.6 Hz, 1H), 6.82 (d, J=2.6 Hz, 1H), 5.57 (dd, J=9.8, 2.6 Hz, 1H), 3.98-3.92 (m, 1H), 3.72-3.62 (m, 1H), 2.20-2.05 (m, 1H), 2.03-1.89 (m, 2H), 1.78-1.63 (m, 1H), 1.59-1.53 (m, 2H).

Synthesis of methyl 2-((tert-butoxycarbonyl)amino)-3-(1-(tetrahydro-2H-pyran-2-yl)-1H-pyrazol-3-yl)acrylate

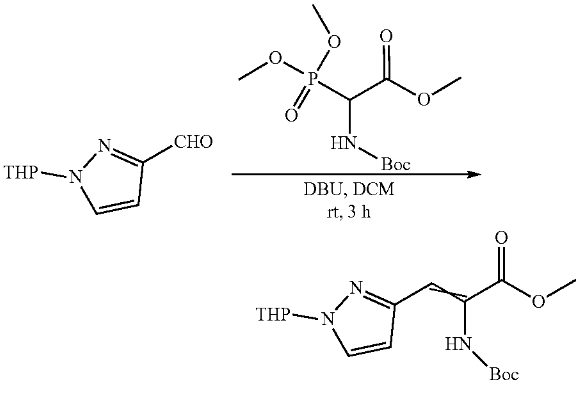

To a stirred solution of methyl 2-[(tert-butoxycarbonyl)amino]-2-(dimethoxyphosphoryl)acetate (2.97 g, 9.98 mmol, 1.0 equiv) in DCM (30 mL) was added DBU (1.52 g, 9.99 mmol, 1.0 equiv) dropwise at 0° C. The resulting mixture was stirred for 30 min at room temperature. To the above mixture was added 1-(oxan-2-yl)pyrazole-3-carbaldehyde (1.8 g, 9.99 mmol, 1.0 equiv) dropwise at room temperature. The resulting mixture was stirred for additional 3 h at room temperature. The resulting mixture was concentrated under reduced pressure. The residue was purified by silica gel column chromatography, eluted with PE/EA (5:1) to afford methyl 2-[(tert-butoxycarbonyl)amino]-3-[1-(oxan-2-yl)pyrazol-3-yl]prop-2-enoate (2.4 g, 68.4%). LCMS (ES, m/z): $[M+H]^+$: 352.

Synthesis of methyl 2-[(tert-butoxycarbonyl) amino]-3-[1-(oxan-2-yl)pyrazol-3-yl]propanoate

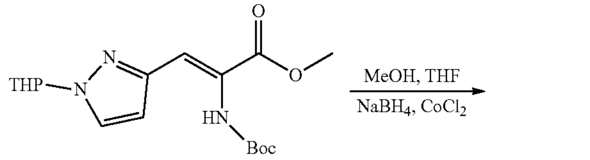

To a stirred solution of methyl 2-[(tert-butoxycarbonyl) amino]-3-[1-(oxan-2-yl)pyrazol-3-yl]prop-2-enoate (2.3 g, 6.54 mmol, 1.0 equiv) and $CoCl_2$ (1.7 g, 13.09 mmol, 2.0 equiv) in MeOH (24 mL) and THE (3 mL) was added $NaBH_4$ (1.2 g, 32.72 mmol, 5.0 equiv) in portions at 0° C. The resulting mixture was stirred for additional 16 h at room temperature. The resulting mixture was filtered, the filter cake was washed with THE (3x20 mL). The filtrate was concentrated under reduced pressure. The resulting mixture was extracted with EtOAc (3x30 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/EA (1:1) to afford methyl 2-[(tert-butoxycarbonyl)amino]-3-[1-(oxan-2-yl)pyrazol-3-yl]propanoate (1.5 g, 64.8%). LCMS (ES, m/z): $[M+H]^+$: 354.

Synthesis of 2-[(tert-butoxycarbonyl)amino]-3-[1-(oxan-2-yl)pyrazol-3-yl]propanoic acid

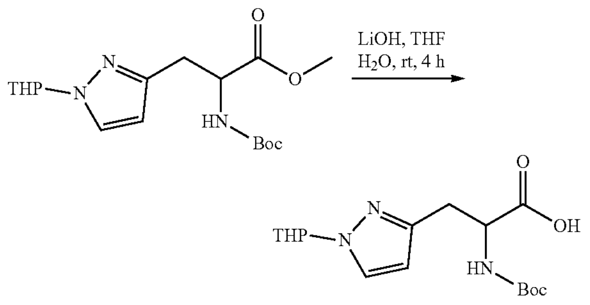

A solution of methyl 2-[(tert-butoxycarbonyl)amino]-3-[1-(oxan-2-yl)pyrazol-3-yl]propanoate (1.5 g, 4.24 mmol, 1.0 equiv) in THE (15 mL) and LiOH (0.3 g, 12.73 mmol, 3.0 equiv) in $H_2O$ (5 mL) was stirred for 4 h at room temperature. The mixture was acidified to pH 3 with HCl (1 M.). The resulting mixture was extracted with EtOAc (3x50 mL). The combined organic layer was washed with brine (3x50 mL), dried over anhydrous $Na_2SO_4$. After filtration, the filtrate was concentrated under reduced pressure. This resulted in 2-[(tert-butoxycarbonyl)amino]-3-[1-(oxan-2-yl) pyrazol-3-yl]propanoic acid (1.1 g, 76.3%). LCMS (ES, m/z): $[M+H]^+$: 340.

Synthesis of tert-butyl N-(1-{[(1S)-1-cyano-2-[4-(3-methyl-2-oxo-1,3-benzoxazol-5-yl)phenyl]ethyl]carbamoyl}-2-[1-(oxan-2-yl)pyrazol-3-yl]ethyl)carbamate

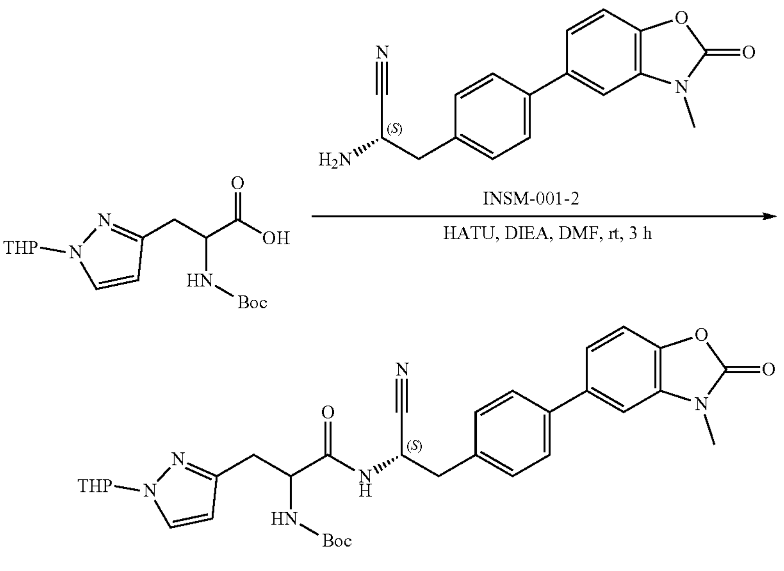

A solution of (2S)-2-amino-3-[4-(3-methyl-2-oxo-1,3-benzoxazol-5-yl)phenyl]propanenitrile (86 mg, 0.29 mmol, 1.0 equiv) in DMF (2 mL) was treated with 2-[(tert-butoxycarbonyl)amino]-3-[1-(oxan-2-yl)pyrazol-3-yl]propanoic acid (100 mg, 0.29 mmol, 1.0 equiv), DIEA (114 mg, 0.88 mmol, 3.0 equiv). This was followed by the addition of HATU (134 mg, 0.35 mmol, 1.2 equiv) in portions at 0° C. The resulting mixture was stirred for 3 h at room temperature. The resulting mixture was extracted with EtOAc (3×10 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-[4-(3-methyl-2-oxo-1,3-benzoxazol-5-yl)phenyl]ethyl]carbamoyl}-2-[1-(oxan-2-yl)pyrazol-3-yl]ethyl)carbamate (100 mg, 55.2%). LCMS (ES, m/z): $[M+H]^+$: 615.

Synthesis of 2-amino-N-[(1S)-1-cyano-2-[4-(3-methyl-2-oxo-1,3-benzoxazol-5-yl)phenyl]ethyl]-3-(1H-pyrazol-3-yl)propanamide

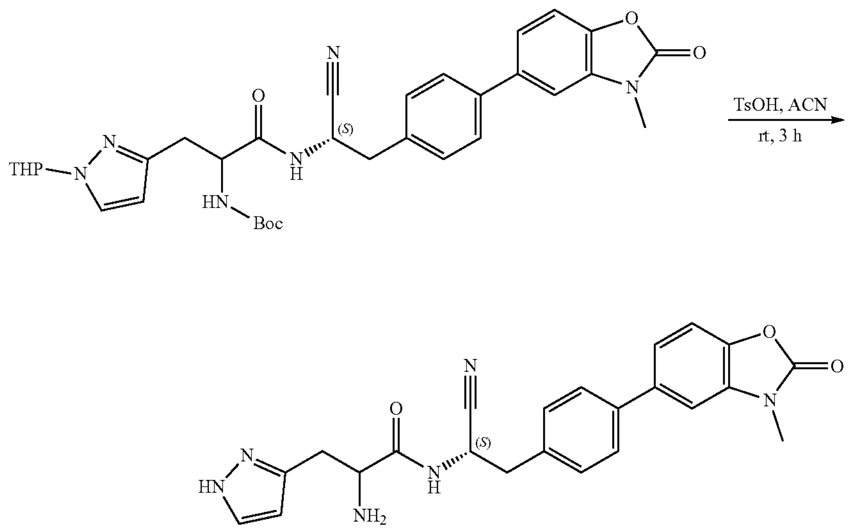

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-2-[1-(oxan-2-yl)pyrazol-3-yl]ethyl)carbamate (100 mg, 0.16 mmol, 1.0 equiv), ACN (3 mL) and $TsOH \cdot H_2O$ (93 mg, 0.48 mmol, 3.0 equiv) at room temperature. The resulting mixture was stirred for 3 h at room temperature. The residue was purified by reversed-phase flash chromatography with the following conditions: column, C18 silica gel-120 g; mobile phase, MeCN in Water (0.1% $NH_3.H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-3-(1H-pyrazol-3-yl)propanamide (20.5 mg, 29%).

LCMS (ES, m/z): $[M+H]^+$: 431.2

$^1$H NMR (400 MHz, DMSO-$d_6$) δ 12.50 (s, 1H), 7.67 (dd, J=8.3, 1.9 Hz, 2H), 7.62-7.27 (m, 6H), 5.99 (s, 1H), 5.01 (q, J=8.1 Hz, 1H), 3.45-3.40 (m, 4H), 3.22-3.06 (m, 2H), 2.90-2.80 (m, 1H), 2.70-2.59 (m, 1H).

Example 18. Synthesis of Compound 222: 4-amino-N-[(1S)-1-cyano-2-[4-(3-methyl-2-oxo-1,3-benzoxazol-5-yl)phenyl]ethyl]spiro[2.4]heptane-4-carboxamide

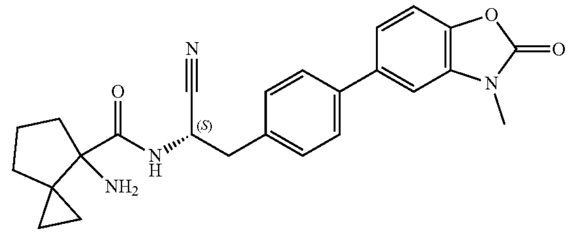

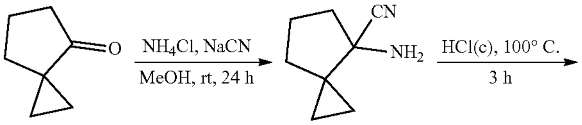

-continued

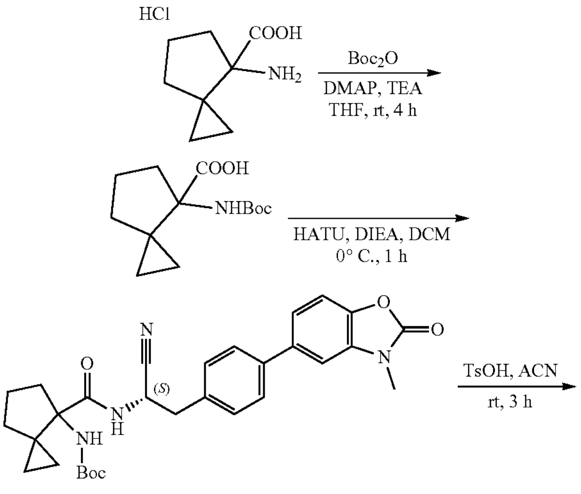

-continued

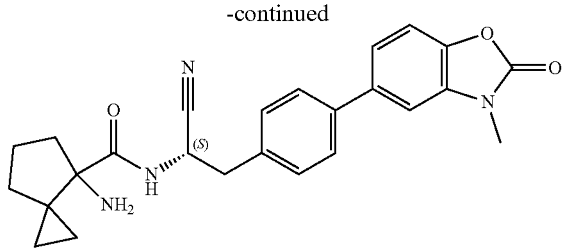

Synthesis of 4-aminospiro[2.4]heptane-4-carbonitrile

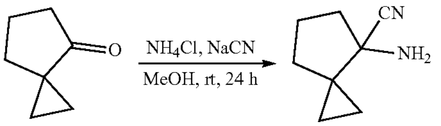 [SMILES: O=C1CCCC12CC2 ; N#CC1(N)CCCC12CC2]

To a solution of $NH_4Cl$ (1.94 g, 36.31 mmol, 2.0 equiv) in $NH_3 \cdot H_2O$ (20 mL) was added NaCN (2.22 g, 45.39 mmol, 2.5 equiv) at room temperature. This was followed by the addition of spiro[2.4]heptan-4-one (2 g, 18.16 mmol, 1.0 equiv) in MeOH (20 mL). The reaction was stirred for 24 h. Concentrated to remove the solvent, the residue was diluted with water (30 mL), extracted with ethyl acetate (40 mL×2). The combined organic phase was washed with brine (30 mL), dried over anhydrous sodium sulfate. After filtration, the filtrate was concentrated under reduced pressure, 4-aminospiro[2.4]heptane-4-carbonitrile (1.4 g, 56.6%) was obtained and used to the next step without further purification. LCMS (ES) $[M+H]^+$ m/z: 137.

Synthesis of 4-aminospiro[2.4]heptane-4-carboxylic acid hydrochloride

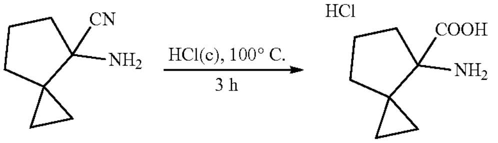 [SMILES: Cl ; N#CC1(N)CCCC12CC2 ; NC1(C(=O)O)CCCC12CC2]

A solution of 4-aminospiro[2.4]heptane-4-carbonitrile (1.2 g, 8.81 mmol, 1.0 equiv) in conc. HCl (15 mL) was stirred for 3 h at 100° C. The mixture was allowed to cool down to room temperature. The precipitated solid was collected by filtration and washed with conc. HCl (1 mL). This resulted in 4-aminospiro[2.4]heptane-4-carboxylic acid hydrochloride (600 mg, 36%). LCMS (ES) $[M-HCl+H]^+$ m/z: 156.

Synthesis of 4-[(tert-butoxycarbonyl)amino]spiro[2.4]heptane-4-carboxylic acid

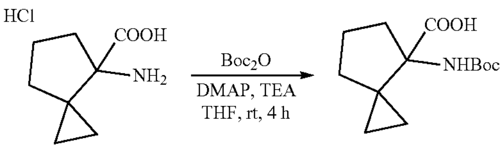 [SMILES: "Boc2O" ; Cl ; NC1(C(=O)O)CCCC12CC2 ; CC(C)(C)OC(=O)NC1(C(=O)O)CCCC12CC2]

To a stirred solution of 4-aminospiro[2.4]heptane-4-carboxylic acid hydrochloride (600 mg, 3.13 mmol, 1.0 equiv) in THF (10 mL) were added DMAP (38 mg, 0.31 mmol, 0.1 equiv) and TEA (950 mg, 9.39 mmol, 3.0 equiv) and di-tert-butyl dicarbonate (1366 mg, 6.26 mmol, 2.0 equiv). The resulting mixture was stirred for 4 h at room temperature. The reaction was diluted with water (30 mL), extracted with EtOAc (2×10 mL). The aqueous layer was acidified to pH 6 with citric acid, $CH_2Cl_2$ (5×20 mL). The combined organic layer were washed with brine (10 mL), dried over anhydrous $Na_2SO_4$. After filtration, the filtrate was concentrated under reduced pressure. This resulted in 4-[(tert-butoxycarbonyl)amino]spiro[2.4]heptane-4-carboxylic acid (300 mg, 37.5%) and used to the next step without further purification. LCMS (ES) $[M+H]^+$ m/z: 256.

Synthesis of tert-butyl N-(4-{[(1S)-1-cyano-2-[4-(3-methyl-2-oxo-1,3-benzoxazol-5-yl)phenyl]ethyl]carbamoyl}spiro[2.4]heptan-4-yl)carbamate

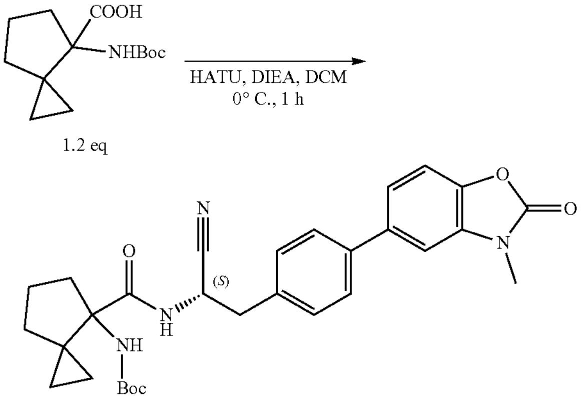

To a stirred solution of 4-[(tert-butoxycarbonyl)amino]spiro[2.4]heptane-4-carboxylic acid (125 mg, 0.49 mmol, 1.2 equiv) and (2S)-2-amino-3-[4-(3-methyl-2-oxo-1,3-benzoxazol-5-yl)phenyl]propanenitrile (120 mg, 0.41 mmol, 1.0 equiv) in DCM (2 mL) was added DIEA (158 mg, 1.23 mmol, 3.0 equiv) and HATU (186 mg, 0.49 mmol, 1.2 equiv) in portions at 0° C. under nitrogen atmosphere. The resulting mixture was stirred for 1 h at 0° C. The resulting mixture was concentrated under reduced pressure. The residue was purified by silica gel column chromatography, eluted with PE/THE (2:1) to afford tert-butyl N-(4-{[(1S)-1-cyano-2-[4-(3-methyl-2-oxo-1,3-benzoxazol-5-yl)phenyl]ethyl]carbamoyl}spiro[2.4]heptan-4-yl)carbamate (120 mg, 55.3%). LCMS (ES) $[M+H]^+$ m/z: 531.

Synthesis of 4-amino-N-[(1S)-1-cyano-2-[4-(3-methyl-2-oxo-1,3-benzoxazol-5-yl)phenyl]ethyl]spiro[2.4]heptane-4-carboxamide

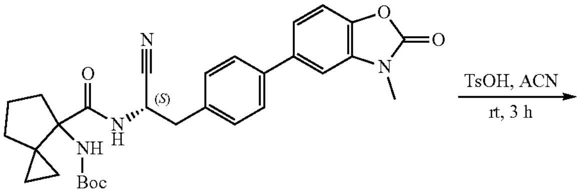

-continued

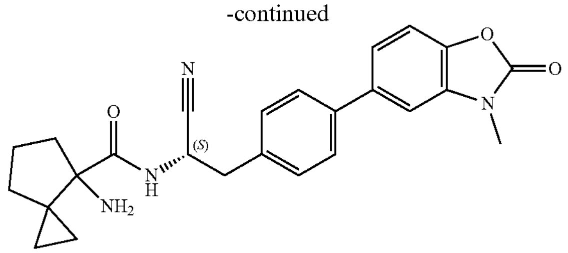

To a stirred solution of tert-butyl N-(4-{[(1S)-1-cyano-2-[4-(3-methyl-2-oxo-1,3-benzoxazol-5-yl)phenyl]ethyl] carbamoyl}spiro[2.4]heptan-4-yl)carbamate (100 mg, 0.19 mmol, 1.0 equiv) in ACN (2 mL) was added TsOH (97 mg, 0.56 mmol, 3.0 equiv). The resulting mixture was stirred for 3 h at room temperature. The mixture was purified by reversed-phase flash chromatography with the following conditions: column, C18 silica gel-120 g; mobile phase, MeCN in Water (10 mmol/L $NH_4HCO_3$), 10% to 60% gradient in 15 min; detector, UV 254 nm. This resulted in 4-amino-N-[(1S)-1-cyano-2-[4-(3-methyl-2-oxo-1,3-benzoxazol-5-yl)phenyl]ethyl]spiro[2.4]heptane-4-carboxamide (30 mg, 37%). LCMS (ES) $[M+H]^+$ m/z: 431.1

$^1$H NMR (300 MHz, DMSO-$d_6$) δ 7.66 (t, J=7.7 Hz, 2H), 7.58 (d, J=8.6 Hz, 1H), 7.47-7.34 (m, 4H), 5.01-4.90 (m, 1H), 3.41 (s, 3H), 3.25-3.10 (m, 2H), 2.42-2.28 (m, 1H), 1.77-1.56 (m, 5H), 0.44-0.28 (m, 2H), 0.22--0.11 (m, 2H).

Example 19. Synthesis of Compound 172: of 2-amino-N-[(1S)-1-cyano-2-[4-(3-methyl-2-oxo-1,3-benzoxazol-5-yl)phenyl]ethyl]-2,3-dimethylbutanamide

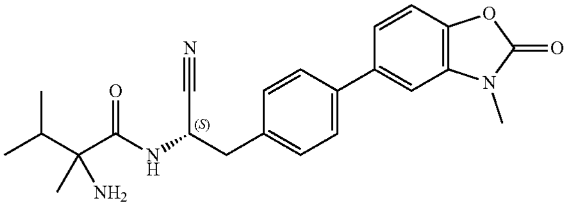

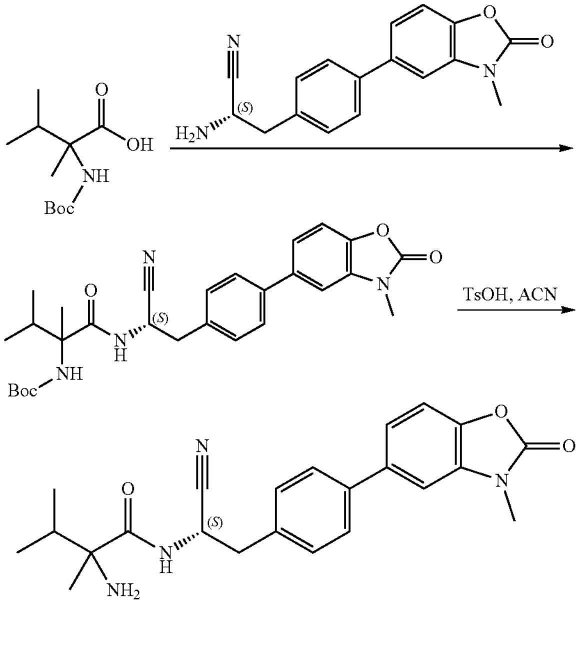

Synthesis of tert-butyl N-(1-{[(1S)-1-cyano-2-[4-(3-methyl-2-oxo-1,3-benzoxazol-5-yl)phenyl]ethyl] carbamoyl}-1,2-dimethylpropyl)carbamate

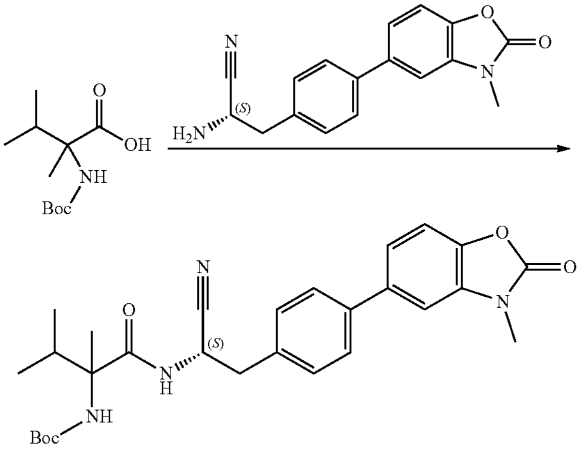

Into a 20 mL vial were added 2-[(tert-butoxycarbonyl) amino]-2,3-dimethylbutanoic acid (78.85 mg, 0.34 mmol, 2.00 equiv), (2S)-2-amino-3-[4-(3-methyl-2-oxo-1,3-benzoxazol-5-yl)phenyl]propanenitrile (50.00 mg, 0.17 mmol, 1.00 equiv), DIEA (66.09 mg, 0.51 mmol, 3.00 equiv) and DMF (5.00 mL) at room temperature. To the above mixture was added HATU (77.78 mg, 0.20 mmol, 1.20 equiv) in portions at 0° C. The resulting mixture was stirred for additional overnight at room temperature. The residue was purified by reversed-phase flash chromatography with the following conditions: column, C18 silica gel; mobile phase, MeCN in Water (0.1% FA), 15% to 85% gradient in 15 min; detector, UV 254 nm. This resulted in tert-butyl N-(1-{[(1S)-1-cyano-2-[4-(3-methyl-2-oxo-1,3-benzoxazol-5-yl)phenyl] ethyl]carbamoyl}-1,2-dimethylpropyl)carbamate (80.00 mg, 92.64%). LCMS (ES, m z): $[M+H]^+$: 507.

Synthesis of 2-amino-N-[(1S)-1-cyano-2-[4-(3-methyl-2-oxo-1,3-benzoxazol-5-yl)phenyl]ethyl]-2,3-dimethylbutanamide

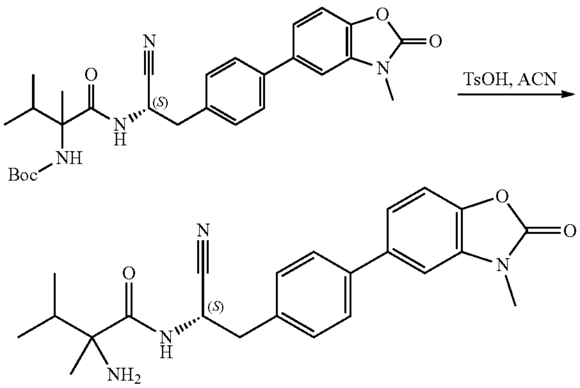

Into a 20 mL vial were added tert-butyl N-(1-{[(1S)-1-cyano-2-[4-(3-methyl-2-oxo-1,3-benzoxazol-5-yl)phenyl] ethyl]carbamoyl}-1,2-dimethylpropyl)carbamate (70.00 mg, 0.13 mmol, 1.00 equiv) and ACN (4.00 mL) at room temperature. To the above mixture was added TsOH (71.38 mg, 0.41 mmol, 3.00 equiv) in portions at °0 C. The resulting mixture was stirred for additional 2 h at room temperature. The reaction solution was purified by Prep-HPLC with the following conditions XBridge Prep C18 OBD Column, 19*150 mm, 5 um; mobile phase, Water (10 mmol/L $NH_4HCO_3$+0.05%$NH_3 \cdot H_2O$) and ACN (35% Phase B up to 55% in 8.8 min); Detector, UV 254 nm. This resulted in 2-amino-N-[(1S)-1-cyano-2-[4-(3-methyl-2-oxo-1,3-benzoxazol-5-yl)phenyl]ethyl]-2,3-dimethylbutanamide (17.80 mg, 31.69%).

LCMS (ES, m z): $[M+H]^+$: 407.2

$^1$H NMR (400 MHz, DMSO-$d_6$) δ 7.66 (dd, J=8.2, 6.7 Hz, 2H), 7.57 (d, J=7.1 Hz, 1H), 7.46-7.35 (m, 4H), 4.99 (t, J=7.8 Hz, 1H), 3.41 (s, 3H), 3.20 (dd, J=7.7, 4.3 Hz, 2H), 1.98-1.77 (m, 1H), 1.03 (d, J=16.8 Hz, 3H), 0.79-0.50 (m, 6H).

Example 20. Synthesis of Compound 174: N—((S)-1-cyano-2-(4-(3-methyl-2-oxo-2,3-dihydrobenzo[d]oxazol-5-yl)phenyl)ethyl)-2-((2-hydroxypropyl)amino)acetamide

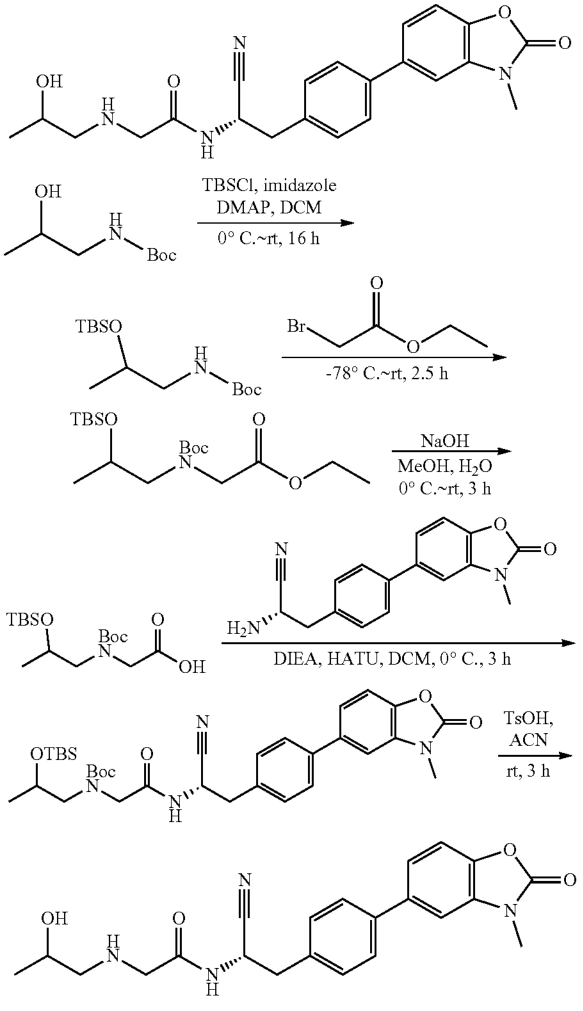

Synthesis of tert-butyl (2-((tert-butyldimethylsilyl)oxy)propyl)carbamate

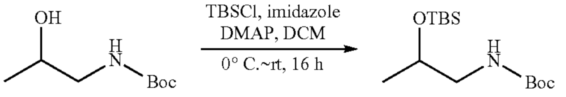 [SMILES: CC(O)CNC(=O)OC(C)(C)C ; CC(CNC(=O)OC(C)(C)C)O[Si](C)(C)C(C)(C)C]

To a stirred solution of tert-butyl N-(2-hydroxypropyl) carbamate (500 mg, 2.85 mmol, 1.0 equiv) and imidazole (388 mg, 5.70 mmol, 2.0 equiv) in DCM (6 mL) were added DMAP (35 mg, 0.28 mmol, 0.1 equiv) and TBSCI (645 mg, 4.28 mmol, 1.5 equiv) in portions at 0° C. under nitrogen atmosphere. The resulting mixture was stirred for 16 h at room temperature. The reaction was quenched with water (20 mL), extracted with $CH_2Cl_2$ (3×20 mL). The combined organic layer was washed with brine (50 mL), dried over anhydrous $Na_2SO_4$. After filtration, the filtrate was concentrated under reduced pressure. The residue was purified by silica gel column chromatography, eluted with PE/EA (3:1) to afford tert-butyl (2-((tert-butyldimethylsilyl)oxy)propyl) carbamate (800 mg, 96%). LCMS (ES, m/z): $[M+H]^+$: 290.

Synthesis of ethyl N-(tert-butoxycarbonyl)-N-(2-((tert-butyldimethylsilyl)oxy)propyl)glycinate

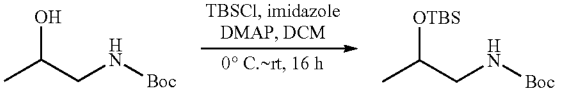 [SMILES: CC(O)CNC(=O)OC(C)(C)C ; CC(CNC(=O)OC(C)(C)C)O[Si](C)(C)C(C)(C)C]

To a stirred solution of tert-butyl (2-((tert-butyldimethylsilyl)oxy)propyl)carbamate (500 mg, 1.73 mmol, 1.0 equiv) in THE (6 mL) was added n-BuLi (2.5 M in THF)(0.83 mL, 2.07 mmol, 1.2 equiv) dropwise at −78° C. under nitrogen atmosphere. The resulting mixture was stirred for 30 min at −78° C. To the above mixture was added ethyl bromoacetate (346 mg, 2.07 mmol, 1.2 equiv) dropwise at −78° C. The resulting mixture was stirred for additional 2 h at room temperature. The reaction was quenched by the addition of sat. $NH_4Cl$ (aq.)(10 mL) at 0° C., extracted with EtOAc (3×20 mL). The combined organic layer was washed with brine (20 mL), dried over anhydrous $Na_2SO_4$. After filtration, the filtrate was concentrated under reduced pressure. The residue was purified by silica gel column chromatography, eluted with PE/EA (3:1) to afford ethyl N-(tert-butoxycarbonyl)-N-(2-((tert-butyldimethylsilyl)oxy)propyl) glycinate (300 mg, 46%). LCMS (ES, m/z): $[M+H]^+$: 376.

Synthesis of N-(tert-butoxycarbonyl)-N-(2-((tert-butyldimethylsilyl)oxy)propyl)glycine

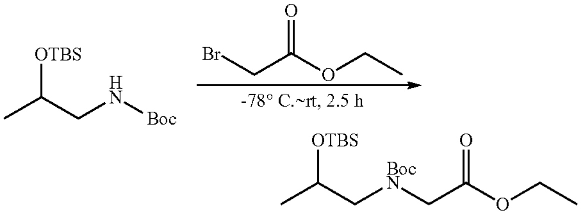

To a stirred solution of ethyl N-(tert-butoxycarbonyl)-N-(2-((tert-butyldimethylsilyl)oxy)propyl)glycinate (300 mg, 0.80 mmol, 1.0 equiv) in MeOH (3 mL) and $H_2O$ (1 mL) was added NaOH (64 mg, 1.60 mmol, 2.0 equiv) at 0° C. The resulting mixture was stirred for 3 h at room temperature. Concentrated under reduced pressure to remove the solvent, diluted with water (10 mL), extracted with EtOAc (2×10 mL). The aqueous layer was acidified to pH 6 with citric acid. The resulting mixture was extracted with $CH_2Cl_2$ (4×10 mL). The combined organic layer was washed with brine (10 mL), dried over anhydrous $Na_2SO_4$. After filtration, the filtrate was concentrated under reduced pressure. This resulted in N-(tert-butoxycarbonyl)-N-(2-((tert-butyldimethylsilyl)oxy)propyl)glycine (180 mg, 65%). LCMS (ES, m/z): $[M+H]^+$: 348.

Synthesis of tert-butyl N-{2-[(tert-butyldimethylsilyl)oxy]propyl}—N-({[(1S)-1-cyano-2-[4-(3-methyl-2-oxo-1,3-benzoxazol-5-yl)phenyl]ethyl]carbamoyl}methyl)carbamate

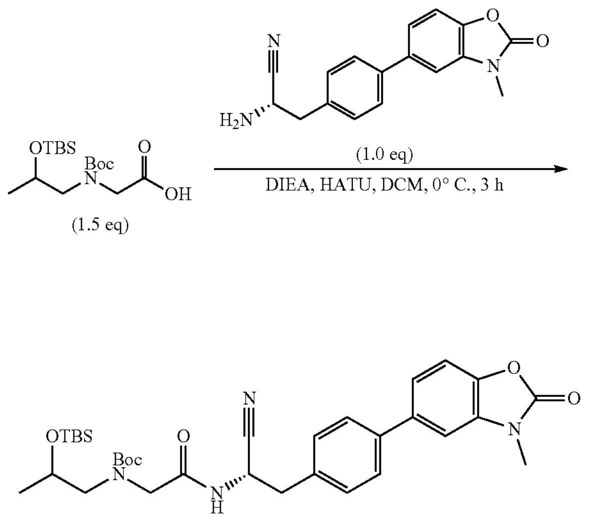

A solution of N-(tert-butoxycarbonyl)-N-(2-((tert-butyldimethylsilyl)oxy)propyl)glycine (196 mg, 0.56 mmol, 1.5 equiv) in DCM (3 mL) was treated with (2S)-2-amino-3-[4-(3-methyl-2-oxo-1,3-benzoxazol-5-yl)phenyl]propanenitrile (110 mg, 0.37 mmol, 1.0 equiv), DIEA (145 mg, 1.12 mmol, 3.0 equiv). This was followed by the addition of HATU (171 mg, 0.45 mmol, 1.2 equiv) in portions at 0° C. The resulting mixture was stirred for 3 h at 0° C. Concentrated to remove the solvent, the residue was purified by silica gel column chromatography, eluted with PE/THE (1:1) to afford tert-butyl N-{2-[(tert-butyldimethylsilyl)oxy]propyl}—N-({[(1S)-1-cyano-2-[4-(3-methyl-2-oxo-1,3-benzoxazol-5-yl)phenyl]ethyl]carbamoyl}methyl)carbamate (200 mg, 85.6%). LCMS (ES, m/z): $[M+H]^+$: 623.

Synthesis of 2-({2-[(tert-butyldimethylsilyl)oxy]propyl}amino)-N-[(1S)-1-cyano-2-[4-(3-methyl-2-oxo-1,3-benzoxazol-5-yl)phenyl]ethyl]acetamide

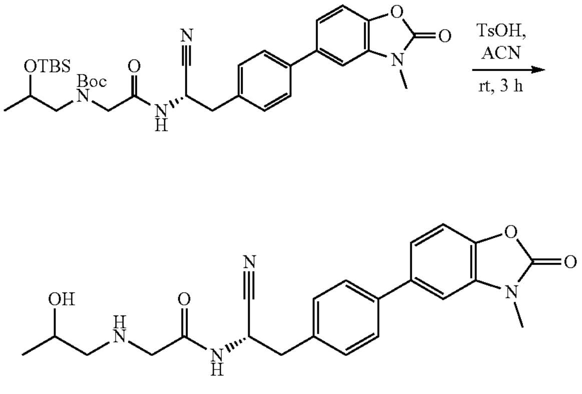

Into a 25 mL round-bottom flask were added tert-butyl N-{2-[(tert-butyldimethylsilyl)oxy]propyl}—N-({[(1S)-1-cyano-2-[4-(3-methyl-2-oxo-1,3-benzoxazol-5-yl)phenyl]ethyl]carbamoyl}methyl)carbamate (100 mg, 0.16 mmol, 1.0 equiv) ACN (3 mL) and $TsOH \cdot H_2O$ (92 mg, 0.48 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in 2-({2-[(tert-butyldimethylsilyl)oxy]propyl}amino)-N-[(1S)-1-cyano-2-[4-(3-methyl-2-oxo-1,3-benzoxazol-5-yl)phenyl]ethyl]acetamide (24.8 mg, 30%).

LCMS (ES, m/z): $[M+H]^+$: 409.1

$^1H$ NMR (300 MHz, DMSO-$d_6$) δ 8.68 (br, 1H), 7.67 (d, J=8.2 Hz, 2H), 7.59 (d, J=1.6 Hz, 1H), 7.46-7.36 (m, 4H), 5.03 (t, J=8.0 Hz, 1H), 4.54 (dd, J=8.7, 4.3 Hz, 1H), 3.66-3.60 (m, 1H), 3.41 (s, 3H), 3.20-3.15 (m, 3H), 3.09 (dd, J=16.4, 1.9 Hz, 1H), 2.34-2.23 (m, 2H), 0.99 (dd, J=6.2, 2.7 Hz, 3H).

Example 21. Synthesis of Compound 254: 2-amino-N-[(1S)-1-cyano-2-[4-(3-methyl-2-oxo-1,3-benzoxazol-5-yl)phenyl]ethyl]-3-(1-methylpyrrol-3-yl)propanamide

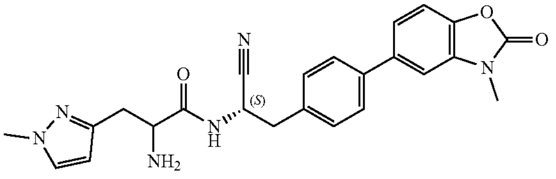

-continued

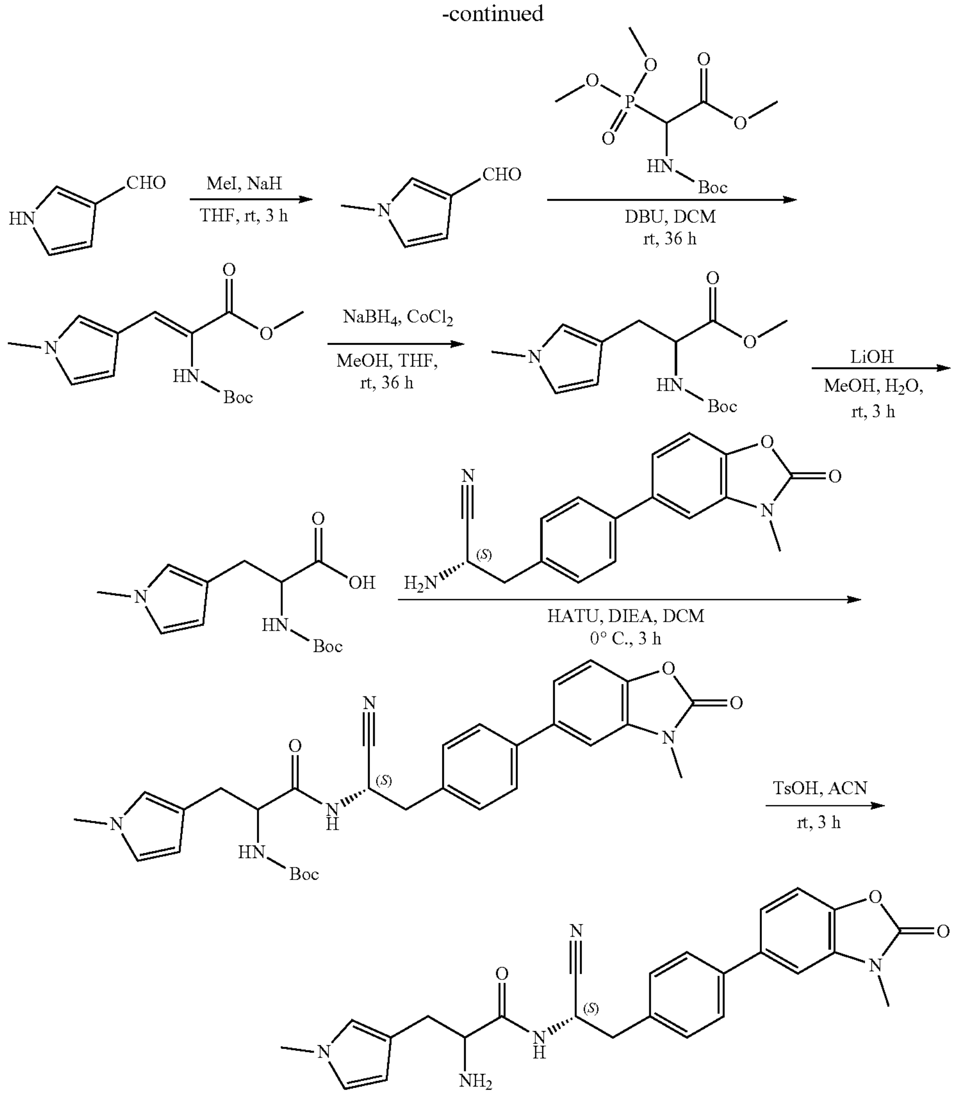

Synthesis of 1-methylpyrrole-3-carbaldehyde

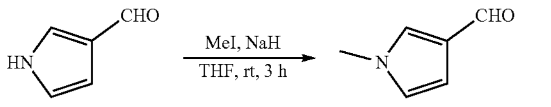

A solution of 1H-pyrrole-3-carbaldehyde (4.0 g, 42.06 mmol, 1.0 equiv) in THF (40 mL) was treated with NaH (2.5 g, 63.09 mmol, 1.5 equiv, 60% in mineral oil) for 30 min at 0° C. under nitrogen atmosphere followed by the addition of MeI (8.9 g, 63.09 mmol, 1.5 equiv) dropwise at 0° C. The resulting mixture was stirred for 3 h at room temperature. The resulting mixture was extracted with EtOAc (3×50 mL). The combined organic layer was washed with brine (3×50 mL), dried over anhydrous $Na_2SO_4$. After filtration, the filtrate was concentrated under reduced pressure. The residue was purified by silica gel column chromatography, eluted with PE/THF (1:1) to afford 1-methylpyrrole-3-carbaldehyde (2.8 g, 61%). LCMS (ES, m/z): $[M+H]^+$:110.

Synthesis of 2-[(tert-butoxycarbonyl)amino]-3-(1-methylpyrrol-3-yl)prop-2-enoate

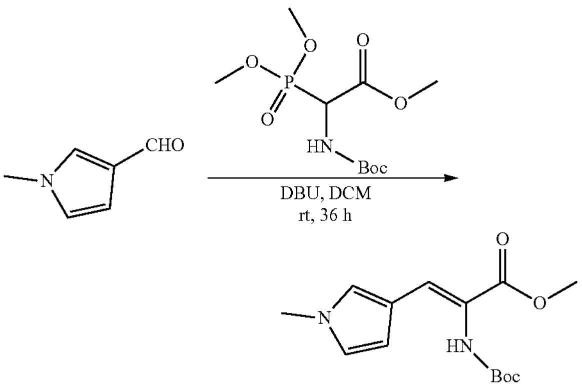

A solution of methyl 2-[(tert-butoxycarbonyl)amino]-2-(dimethoxyphosphoryl)acetate (7.6 g, 25.65 mmol, 1.0 equiv) in DCM (30 mL) was treated with DBU (3.9 g, 25.65 mmol, 1.0 equiv) for 30 min at 0° C. under nitrogen atmosphere followed by the addition of 1-methylpyrrole-3-carbaldehyde (2.8 g, 25.65 mmol, 1.0 equiv) dropwise at 0° C. The resulting mixture was stirred for additional 32 h at room temperature. The residue was purified by silica gel column chromatography, eluted with PE/THF (2:1) to afford methyl 2-[(tert-butoxycarbonyl)amino]-3-(1-methylpyrrol-3-yl)prop-2-enoate (6.8 g, 94.5%). LCMS (ES, m/z): $[M+H]^+$: 281.

Synthesis of methyl 2-[(tert-butoxycarbonyl) amino]-3-(1-methylpyrrol-3-yl)propanoate

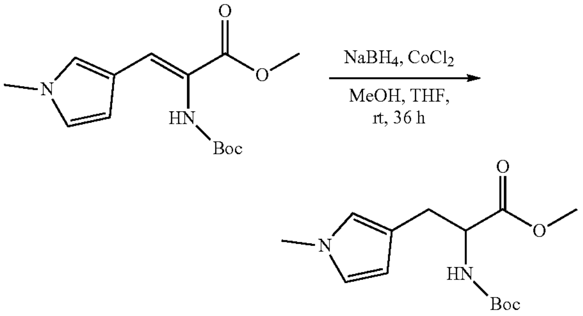

To a stirred solution of methyl 2-[(tert-butoxycarbonyl) amino]-3-(1-methylpyrrol-3-yl)prop-2-enoate (1.0 g, 3.56 mmol, 1.0 equiv) and $CoCl_2$ (0.9 g, 7.13 mmol, 2.0 equiv) in MeOH (8 mL) and THF (1 mL) was added $NaBH_4$ (0.7 g, 17.83 mmol, 5.0 equiv) at 0° C. The resulting mixture was stirred for 36 h at room temperature. After filtration, the filtrate was concentrated under reduced pressure. The resulting mixture was filtered, the filter cake was washed with THE (3×30 mL). The filtrate was concentrated under reduced pressure. The resulting mixture was extracted with $CH_2Cl_2$ (3×50 mL). The combined organic layer was washed with brine (3×30 mL), dried over anhydrous $Na_2SO_4$. After filtration, the filtrate was concentrated under reduced pressure. The residue was purified by silica gel column chromatography, eluted with PE/THF (3:1) to afford methyl 2-[(tert-butoxycarbonyl)amino]-3-(1-methylpyrrol-3-yl)propanoate (500 mg, 50%). LCMS (ES, m/z): $[M+H]^+$: 283.

Synthesis of 2-[(tert-butoxycarbonyl)amino]-3-(1-methylpyrrol-3-yl)propanoic acid

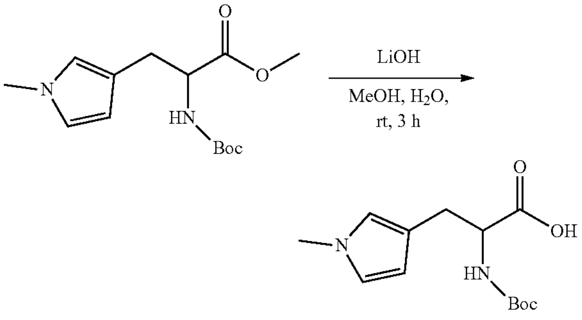

A solution of methyl 2-[(tert-butoxycarbonyl)amino]-3-(1-methylpyrrol-3-yl)propanoate (500 mg, 1.77 mmol, 1.0 equiv) in MeOH (6 mL) was treated with lithium hydroxide (127 mg, 5.31 mmol, 3.0 equiv) in $H_2O$ (2 mL) at room temperature. The resulting mixture was stirred for 3 h at room temperature. The resulting mixture was concentrated under reduced pressure. The mixture was acidified to pH 4 with HCl (1 M). The resulting mixture was extracted with EtOAc (3×30 mL). The combined organic layer was washed with brine (3×30 mL), dried over anhydrous $Na_2SO_4$. After filtration, the filtrate was concentrated under reduced pressure. This resulted in 2-[(tert-butoxycarbonyl)amino]-3-(1-methylpyrrol-3-yl)propanoic acid (300 mg, 63%). The crude product mixture was used in the next step directly without further purification. LCMS (ES, m/z): $[M+H]^+$: 269.

Synthesis of tert-butyl N-(1-{[(1S)-1-cyano-2-[4-(3-methyl-2-oxo-1,3-benzoxazol-5-yl)phenyl]ethyl] carbamoyl}-2-(1-methylpyrrol-3-yl)ethyl)carbamate

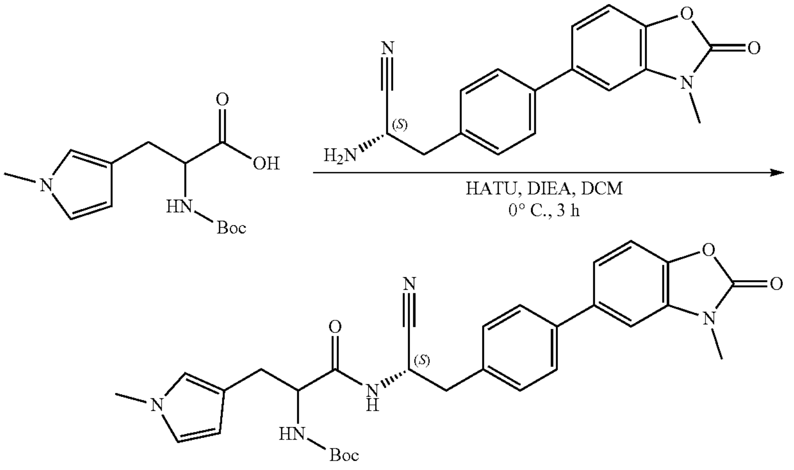

A solution of (2S)-2-amino-3-[4-(3-methyl-2-oxo-1,3-benzoxazol-5-yl)phenyl]propanenitrile (100 mg, 0.34 mmol, 1.0 equiv) in DCM (3 mL) was treated with 2-[(tert-butoxycarbonyl)amino]-3-(1-methylpyrrol-3-yl)propanoic acid (100 mg, 0.37 mmol, 1.1 equiv), DIEA (132 mg, 1.02 mmol, 3.0 equiv). This was followed by the addition of HATU (155 mg, 0.40 mmol, 1.2 equiv) in portions at 0° C. The resulting mixture was stirred for additional 3 h at 0° C. Concentrated under reduced pressure to remove the solvent, the residue was purified by silica gel column chromatography, eluted with PE/THE (2:1) to afford tert-butyl N-(1-{[(1S)-1-cyano-2-[4-(3-methyl-2-oxo-1,3-benzoxazol-5-yl)phenyl]ethyl]carbamoyl}-2-(1-methylpyrrol-3-yl)ethyl) carbamate (100 mg, 53.9%). LCMS (ES, m/z): [M+H]$^+$: 544.

Synthesis of 2-amino-N-[(1S)-1-cyano-2-[4-(3-methyl-2-oxo-1,3-benzoxazol-5-yl)phenyl]ethyl]-3-(1-methylpyrrol-3-yl)propanamide

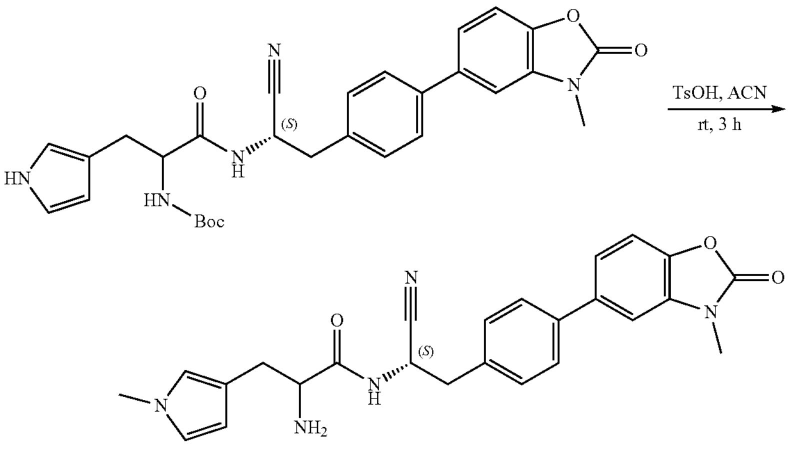

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-2-(1-methylpyrrol-3-yl)ethyl)carbamate (100 mg, 0.18 mmol, 1.0 equiv) in ACN (3 mL) and TsOH·$H_2O$ (105 mg, 0.55 mmol, 3.0 equiv) at room temperature. The resulting mixture was stirred for additional 3 h at room temperature. The reaction solution was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-3-(1-methylpyrrol-3-yl)propanamide (20.5 mg, 25%).

LCMS (ES, m/z): [M+H]$^+$: 444.1

$^1$H NMR (300 MHz, DMSO-$d_6$) δ 7.65 (d, J=7.9 Hz, 2H), 7.56 (s, 1H), 7.45-7.33 (m, 4H), 6.52 (t, J=2.4 Hz, 1H), 6.41 (dt, J=15.3, 2.0 Hz, 1H), 5.77-5.75 (m, 1H), 4.97 (q, J=7.6 Hz, 1H), 3.48 (d, J=3.1 Hz, 3H), 3.38 (s, 3H), 3.27-3.23 (m, 1H), 3.22-3.02 (m, 2H), 2.58 (dd, J=13.7, 5.0 Hz, 1H), 2.46-2.34 (m, 1H).

Example 22. Synthesis of Compound 253: N-[(1S)-1-cyano-2-[4-(3-methyl-2-oxo-1,3-benzoxazol-5-yl)phenyl]ethyl]-2-(4-methylpiperazin-2-yl)acetamide

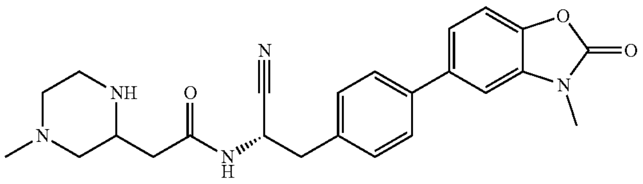

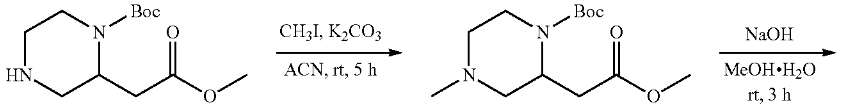

-continued

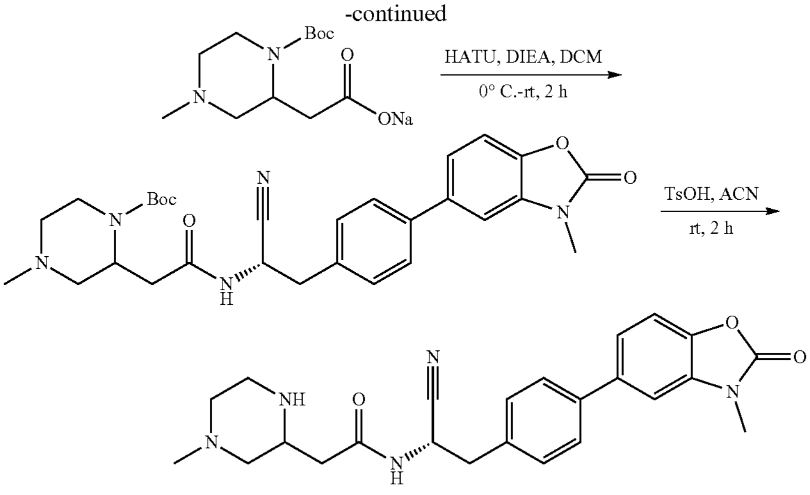

Synthesis of tert-butyl 2-(2-methoxy-2-oxoethyl)-4-methylpiperazine-1-carboxylate

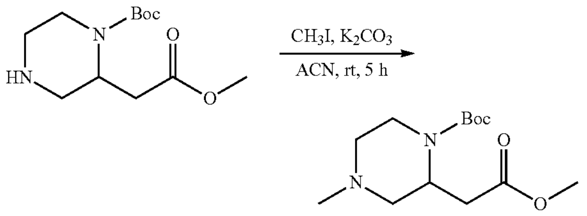

To a stirred mixture of tert-butyl 2-(2-methoxy-2-oxoethyl)piperazine-1-carboxylate (500 mg, 1.94 mmol, 1.0 equiv) and $K_2CO_3$ (802.53 mg, 5.81 mmol, 3.0 equiv) in ACN (8 mL) were added $CH_3I$ (412.11 mg, 2.90 mmol, 1.5 equiv) in portion at room temperature under nitrogen atmosphere. The resulting mixture was stirred for additional 5 h at room temperature. The resulting mixture was diluted with water (50 mL). The resulting mixture was extracted with EtOAc (3×15 mL). The combined organic layers were washed with brine (2×20 mL), dried over anhydrous $Na_2SO_4$. After filtration, the filtrate was concentrated under reduced pressure. This resulted in tert-butyl 2-(2-methoxy-2-oxoethyl)-4-methylpiperazine-1-carboxylate (280 mg, 53.12%). LCMS (ES, m z): $[M+H]^+$: 273.

Synthesis of sodium 2-(1-(tert-butoxycarbonyl)-4-methylpiperazin-2-yl)acetate

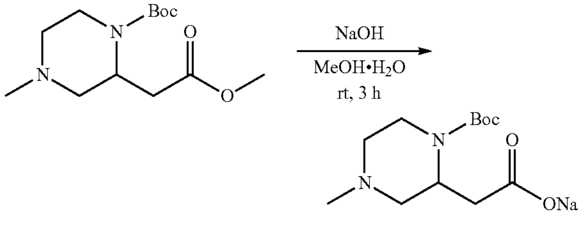

To a stirred solution of tert-butyl 2-(2-methoxy-2-oxoethyl)-4-methylpiperazine-1-carboxylate (270 mg, 0.99 mmol, 1.0 equiv) in MeOH (3 mL) were added NaOH (79.31 mg, 1.98 mmol, 2.0 equiv) in $H_2O$ (0.3 mL) dropwise at room temperature. The resulting mixture was stirred for additional 3 h at room temperature. The resulting mixture was concentrated under reduced pressure. The resulting mixture was diluted with water (3 mL). The resulting mixture was extracted with EtOAc (2×10 mL). The residue was acidified to pH=3 with 1N HCl (aq.). The resulting mixture was concentrated under reduced pressure. This resulted in tert-butyl 4-methyl-2-[2-oxo-2-(sodiooxy) ethyl] piperazine-1-carboxylate (300 mg, 107.96%). LCMS (ES, m z): $[M-Na+H+H]^+$: 259.

Synthesis of tert-butyl (2S)-2-({[(1S)-1-cyano-2-[4-(3-methyl-2-oxo-1,3-benzoxazol-5-yl)phenyl]ethyl] carbamoyl}methyl)-4-methylpiperazine-1-carboxylate

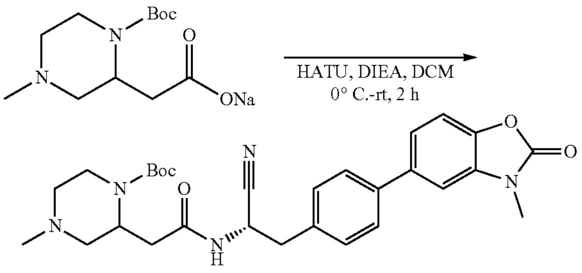

To a stirred mixture of tert-butyl 4-methyl-2-[2-oxo-2-(sodiooxy) ethyl]piperazine-1-carboxylate (300 mg, 1.07 mmol, 1.0 equiv) in DCM (6 mL) was added DIEA (276.66 mg, 2.14 mmol, 2.0 equiv) and HATU (488.35 mg, 1.28 mmol, 1.2 equiv) in portion at 0° C. To the above mixture was added (2S)-2-amino-3-[4-(3-methyl-2-oxo-1,3-benzoxazol-5-yl)phenyl]propanenitrile (156.97 mg, 0.54 mmol, 0.5 equiv) in portions at 0° C. The resulting mixture was stirred for additional 2 h at room temperature. The resulting mixture was diluted with water (15 mL). The resulting mixture was extracted with EtOAc (2×15 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (2:3) to afford tert-butyl (2S)-2-({[(1S)-1-cyano-2-[4-(3-methyl-2-oxo-1,3-benzoxazol-5-yl)phenyl]ethyl] carbamoyl}methyl)-4-methylpiperazine-1-carboxylate (130 mg, 22.76%). LCMS (ES, m/z): $[M+H]^+$: 534.

Synthesis of N-[(1S)-1-cyano-2-[4-(3-methyl-2-oxo-1,3-benzoxazol-5-yl) phenyl]ethyl]-2-(4-methylpiperazin-2-yl)acetamide

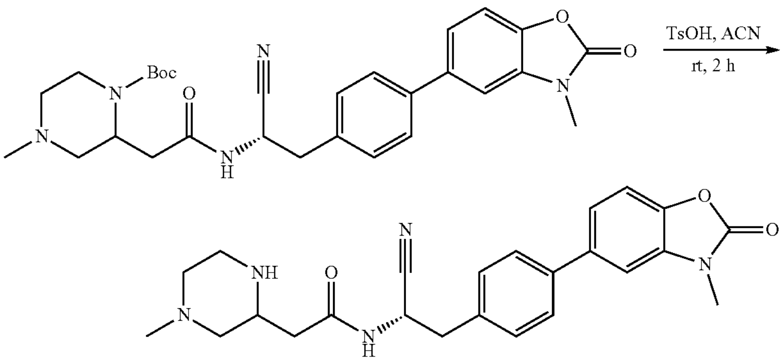

To a stirred solution of tert-butyl 2-({[(1S)-1-cyano-2-[4-(3-methyl-2-oxo-1,3-benzoxazol-5-yl)phenyl]ethyl] carbamoyl}methyl)-4-methylpiperazine-1-carboxylate (120 mg, 0.23 mmol, 1.0 equiv) in ACN (3.0 mL) were added $TsOH{\cdot}H_2O$ (128.32 mg, 0.66 mmol, 3.0 equiv) in portions at room temperature. The resulting mixture was stirred for additional 2 h at room temperature. The crude product was purified by Prep-HPLC with the following conditions (column, C18 silica gel; mobile phase, MeCN in Water (0.1% $NH_3{\cdot}H_2O$), 20% to 40% gradient in 10 min; detector, UV 254 nm.) to afford N-[(1S)-1-cyano-2-[4-(3-methyl-2-oxo-1,3-benzoxazol-5-yl)phenyl]ethyl]-2-(4-methylpiperazin-2-yl)acetamide (25 mg, 25.64%). LCMS (ES, m z): $[M+H]^+$: 434.1

$^1H$ NMR (300 MHz, DMSO-$d_6$) δ 8.88 (dd, J=16.3, 7.7 Hz, 1H), 7.68 (d, J=8.0 Hz, 2H), 7.59 (s, 1H), 7.50-7.36 (m, 4H), 5.01 (q, J=7.6 Hz, 1H), 3.41 (s, 3H), 3.11 (d, J=9.6 Hz, 2H), 2.88-2.82 (m, 1H), 2.74 (d, J=11.0 Hz, 1H), 2.61 (d, J=10.8 Hz, 1H), 2.51-2.41 (m, 2H), 2.13 (t, J=5.9 Hz, 2H), 2.04 (d, J=15.8 Hz, 3H), 1.83-1.71 (m, 1H), 1.48 (dt, J=20.2, 10.0 Hz, 1H).

Example 23. Synthesis of Compound 232: (2R)—N-[(1S)-1-cyano-2-[4-(3-methyl-2-oxo-1,3-benzoxazol-5-yl)phenyl]ethyl]-2-[(thiophen-2-ylmethyl) amino]propanamide

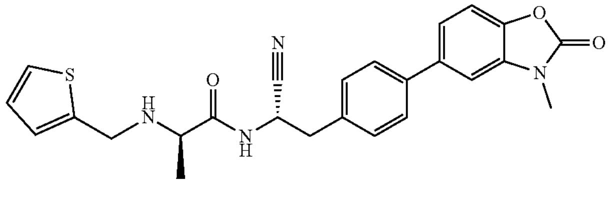

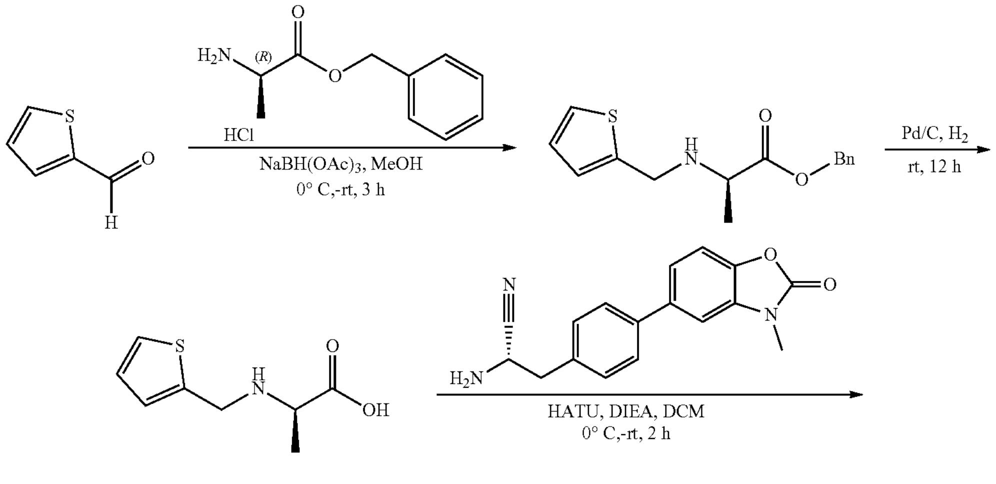

-continued

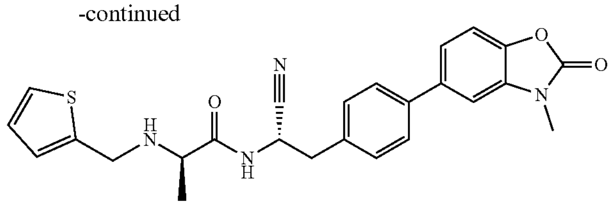

Synthesis of benzyl (2R)-2-[(thiophen-2-ylmethyl) amino]propanoate

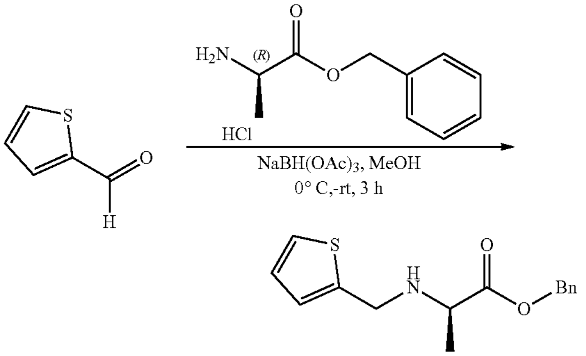

To a stirred mixture of benzyl (2R)-2-aminopropanoate hydrochloride (1.92 g, 8.92 mmol, 1.0 equiv) and DIEA (1.15 g, 8.92 mmol, 1.0 equiv) in MeOH (20.00 mL) were added thiophene-2-carboxaldehyde (1.0 g, 8.92 mmol, 1.0 equiv) in portion at 0° C. The resulting mixture was stirred for additional 3 min at room temperature. To the above mixture was added $NaBH(OAc)_3$ (5.67 g, 26.75 mmol, 3.0 equiv) in portions at 0° C. The resulting mixture was stirred for additional 2 h at room temperature. The resulting mixture was concentrated under reduced pressure. The resulting mixture was diluted with water (50 mL). The resulting mixture was extracted with EtOAc (3×20 mL). The combined organic layers were washed with brine (2×30 mL), dried over anhydrous $Na_2SO_4$. After filtration, the filtrate was concentrated under reduced pressure. This resulted in benzyl (2R)-2-[(thiophen-2-ylmethyl)amino]propanoate (1.9 g, 77.38%). LCMS (ES, m z): $[M+H]^+$: 276.

Synthesis of (2R)-2-[(thiophen-2-ylmethyl)amino] propanoic acid

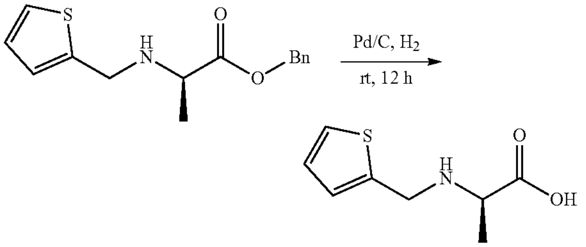

To a solution of benzyl (2R)-2-[(thiophen-2-ylmethyl) amino]propanoate (500 mg, 1.82 mmol, 1.0 equiv) in MeOH (10 mL) was added Pd/C (19.32 mg, 0.182 mmol, 0.1 equiv) under nitrogen atmosphere in a 100 mL round-bottom flask. The mixture was hydrogenated at room temperature for overnight under hydrogen atmosphere using a hydrogen balloon, filtered through a Celite pad and concentrated under reduced pressure. This resulted in (2R)-2-[(thiophen-2-ylmethyl)amino]propanoic acid (150 mg, 44.60%). LCMS (ES, m z): $[M+H]^+$: 186.

Synthesis of (2R)—N-[(1S)-1-cyano-2-[4-(3-methyl-2-oxo-1,3-benzoxazol-5-_yl)phenyl]ethyl]-2-[(thiophen-2-ylmethyl)amino]propanamide

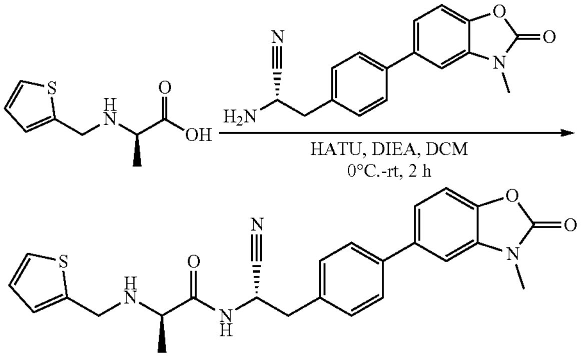

To a stirred mixture of (2R)-2-[(thiophen-2-ylmethyl) amino]propanoic acid (100 mg, 0.54 mmol, 1.0 equiv) in DCM (3 mL) was added DIEA (139.55 mg, 1.08 mmol, 2.0 equiv) and HATU (246.32 mg, 0.65 mmol, 1.2 equiv) in portion at 0° C. To the above mixture was added (2S)-2-amino-3-[4-(3-methyl-2-oxo-1,3-benzoxazol-5-yl)phenyl] propanenitrile (158.35 mg, 0.54 mmol, 1.0 equiv) in portions at 0° C. The resulting mixture was stirred for additional 2 h at room temperature. The resulting mixture was diluted with water (15 mL). The resulting mixture was extracted with EtOAc (2×15 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/THE (1:1) to afford (2R)—N-[(1S)-1-cyano-2-[4-(3-methyl-2-oxo-1,3-benzoxazol-5-yl)phenyl]ethyl]-2-[(thiophen-2-ylmethyl)amino] propanamide (90 mg, 36.25%). The product was purified by Prep-HPLC with the following conditions (column, C18 silica gel; mobile phase, MeCN in Water (0.1% $NH_3 \cdot H_2O$), 20% to 45% gradient in 10 min; detector, UV 254 nm.) to afford (2R)—N-[(1S)-1-cyano-2-[4-(3-methyl-2-oxo-1,3-benzoxazol-5-yl)phenyl]ethyl]-2-[(thiophen-2-ylmethyl) amino]propanamide (26 mg, 10.46%). LCMS (ES, m z): $[M+H]^+$: 461.4

$^1H$ NMR (300 MHz, DMSO-$d_6$) δ 8.66 (d, J=8.1 Hz, 1H), 7.62 (d, J=7.9 Hz, 2H), 7.52 (s, 1H), 7.42-7.33 (m, 5H), 6.92 (dd, J=5.1, 3.4 Hz, 1H), 6.84 (d, J=3.4 Hz, 1H), 5.05 (q,

J=7.8 Hz, 1H), 3.81-3.63 (m, 1H), 3.57 (dd, J=14.3, 5.2 Hz, 1H), 3.38 (s, 3H), 3.23-3.12 (m, 2H), 3.11-3.01 (m, 1H), 2.60-2.54 (m, 1H), 1.04 (d, J=6.9 Hz, 3H).

Example 24. Synthesis of Compound 226: (3R)-3-amino-N—((S)-1-cyano-2-(4-(3-methyl-2-oxo-2,3-dihydrobenzo[d]oxazol-5-yl)phenyl)ethyl)-3-(tetrahydrofuran-2-yl)propanamide

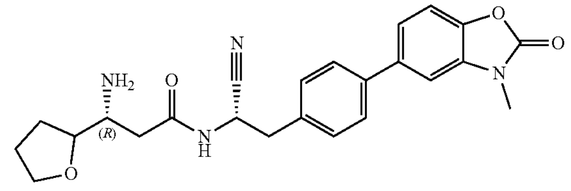

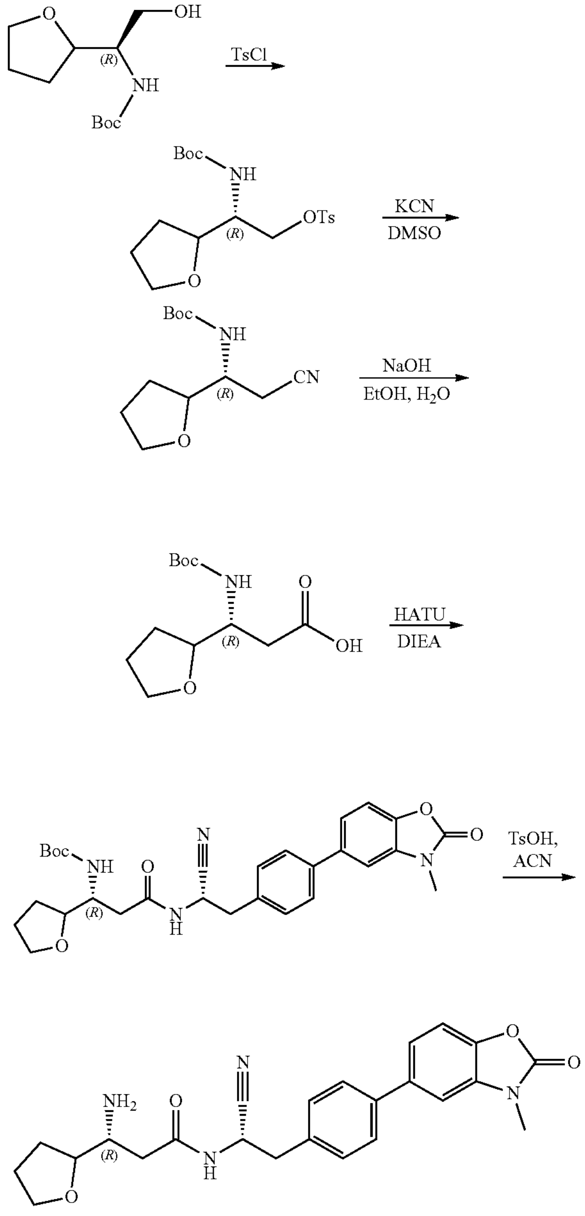

Synthesis of (2R)-2-((tert-butoxycarbonyl)amino)-2-(tetrahydrofuran-2-yl)ethyl 4-methylbenzene-sulfonate

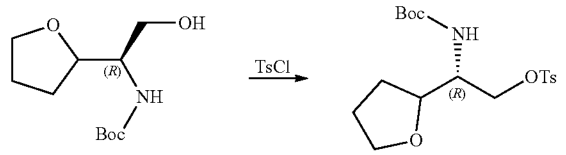

A solution of tert-butyl N-[(1R)-2-hydroxy-1-(oxolan-2-yl)ethyl]carbamate (3.1 g, 13.403 mmol, 1 equiv) in CH2Cl2 (50 mL) was treated with DIEA (3.46 g, 26.806 mmol, 2 equiv) at room temperature followed by the addition of P-toluenesulfonyl chloride (2.56 g, 13.403 mmol, 1 equiv) in portions at 0° C. The resulting mixture was stirred for 48 h at room temperature. The resulting mixture was diluted with CH2Cl2 (100 mL).The resulting mixture was washed with water (1×50 mL), dried over anhydrous Na2SO4. After filtration, the filtrate was concentrated under reduced pressure. The residue was purified by silica gel column chromatography, eluted with PE/EA (3:1) to afford tert-butyl N-[(1R)-2-[(4-methylbenzenesulfonyl)oxy]-1-(oxolan-2-yl) ethyl]carbamate (1.7 g, 32.90%). LCMS (ES, m/z): $[M+H]^+$: 386.

Synthesis of tert-butyl ((1R)-2-cyano-1-(tetrahydro-furan-2-yl)ethyl)carbamate

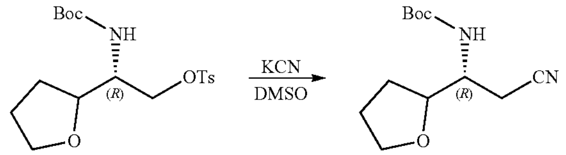

Into a 50 mL 3-necked round-bottom flask were added tert-butyl N-[(1R)-2-[(4-methylbenzenesulfonyl)oxy]-1-(oxolan-2-yl)ethyl]carbamate (1.7 g, 4.410 mmol, 1 equiv) and NaCN (0.26 g, 5.292 mmol, 1.2 equiv) at room temperature. The resulting mixture was stirred for 24 h at 90° C. The mixture was allowed to cool down to room temperature. The resulting mixture was diluted with water (50 mL).The resulting mixture was extracted with EtOAc (3×50 mL). The combined organic layers were washed with water (3×50 mL), dried over anhydrous $Na_2SO_4$. After filtration, the filtrate was concentrated under reduced pressure. The crude product tert-butyl N-[(1R)-2-cyano-1-(oxolan-2-yl)ethyl] carbamate (0.8 g, 75.49%) was used in the next step directly without further purification. LCMS (ES, m/z): $[M+H]^+$: 241.

Synthesis of (3R)-3-((tert-butoxycarbonyl)amino)-3-(tetrahydrofuran-2-yl)propanoic acid

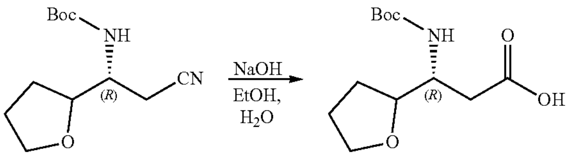

Into a 50 mL 3-necked round-bottom flask were added tert-butyl N-[(1R)-2-cyano-1-(oxolan-2-yl)ethyl]carbamate (0.8 g, 3.329 mmol, 1 equiv) and NaOH (8.32 mL, 16.645 mmol, 5 equiv) at room temperature. The resulting mixture was stirred for 12 h at 70° C. The mixture was allowed to cool down to room temperature. The resulting mixture was concentrated under reduced pressure. The resulting mixture was diluted with water (10 mL). The aqueous layer was extracted with EtOAc (2×20 mL).The aqueous layer was acidified to pH 3 with HCl (aq.). The resulting mixture was extracted with EtOAc (3×20 mL). The combined organic layers were washed with water (2×30 mL), dried over anhydrous $Na_2SO_4$. After filtration, the filtrate was concentrated under reduced pressure. This resulted in (3R)-3-[(tert-butoxycarbonyl)amino]-3-(oxolan-2-yl)propanoic acid (50 mg, 5.79%). LCMS (ES, m/z): $[M+H]^+$: 260.

Synthesis of tert-butyl ((1R)-3-(((S)-1-cyano-2-(4-(3-methyl-2-oxo-2,3-dihydrobenzo[d]oxazol-5-yl) phenyl)ethyl)amino)-3-oxo-1-(tetrahydrofuran-2-yl) propyl)carbamate

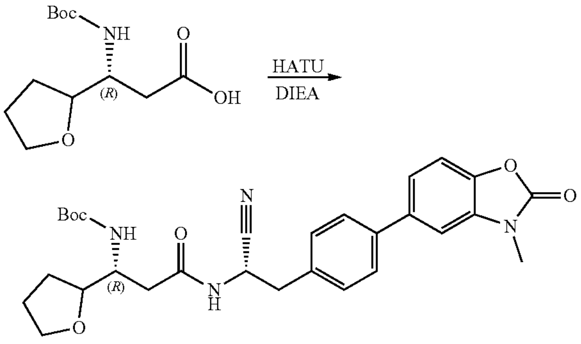

A solution of (3R)-3-[(tert-butoxycarbonyl)amino]-3-(oxolan-2-yl)propanoic acid (50 mg, 0.193 mmol, 1 equiv) in $CH_2Cl2$ (3 mL) was treated with DIEA (74.77 mg, 0.579 mmol, 3 equiv) at 0° C. followed by the addition of HATU (87.98 mg, 0.232 mmol, 1.2 equiv) in portions at 0° C. The resulting mixture was stirred for 12 h at room temperature. The resulting mixture was concentrated under reduced pressure. The residue was purified by silica gel column chromatography, eluted with PE/EA (5:1) to afford tert-butyl N-[(1R)-2-{[(1S)-1-cyano-2-[4-(3-methyl-2-oxo-1,3-benzoxazol-5-yl)phenyl]ethyl]carbamoyl}-1-(oxolan-2-yl) ethyl]carbamate (50 mg, 48.50%). LCMS (ES, m/z): $[M+H]^+$: 535.

Synthesis of (3R)-3-amino-N—((S)-1-cyano-2-(4-(3-methyl-2-oxo-2,3-dihydrobenzo[d]oxazol-5-yl) phenyl)ethyl)-3-(tetrahydrofuran-2-yl)propanamide

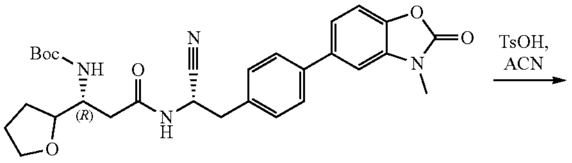

-continued

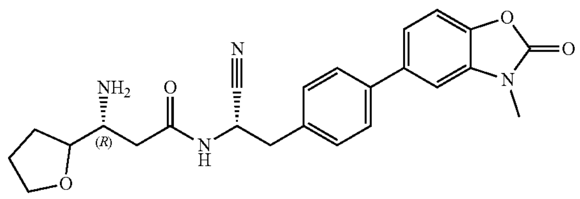

A solution of tert-butyl N-[(1R)-2-{[(1S)-1-cyano-2-[4-(3-methyl-2-oxo-1,3-benzoxazol-5-yl) phenyl]ethyl]carbamoyl}-1-(oxolan-2-yl) ethyl]carbamate (50 mg, 0.094 mmol, 1 equiv) and TsOH (48.32 mg, 0.282 mmol, 3 equiv) in ACN (3 mL) was stirred for 3 h at room temperature. The mixture was purified by Prep-HPLC to afford (3R)-3-amino-N-[(1S)-1-cyano-2-[4-(3-methyl-2-oxo-1,3-benzoxazol-5-yl) phenyl]ethyl]-3-(oxolan-2-yl) propanamide (10 mg, 24.61%). LCMS (ES, m z): $[M+H]^+$: 435.1

$^1H$ NMR (300 MHz, DMSO-$d_6$) δ 8.84 (brs, 1H), 7.65 (d, J=7.9 Hz, 2H), 7.57 (d, J=1.7 Hz, 1H), 7.45-7.32 (m, 4H), 5.08-4.98 (m, 1H), 3.70-3.62 (m, 1H), 3.59-3.50 (m, 1H), 3.47-3.38 (m, 1H), 3.39 (s, 3H), 3.17-3.01 (m, 2H), 2.98-2.77 (m, 1H), 2.34-2.17 (m, 1H), 2.02 (d, J=25.7 Hz, 1H), 1.80-1.49 (m, 5H).

Example 25. Synthesis of Compound 229: 3-amino-N-[(1S)-1-cyano-2-[4-(3-methyl-2-oxo-1,3-benzoxazol-5-yl)phenyl]ethyl]-3-(1,3-oxazol-4-yl) propanamide

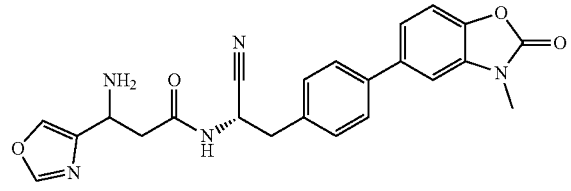

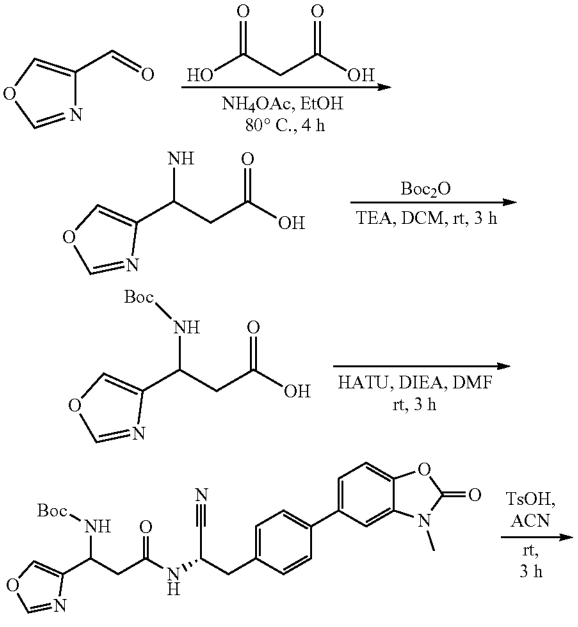

-continued

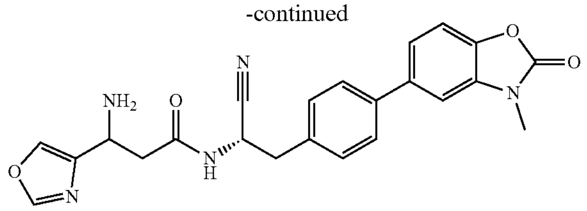

Synthesis of 3-amino-3-(1,3-oxazol-4-yl)propanoic acid

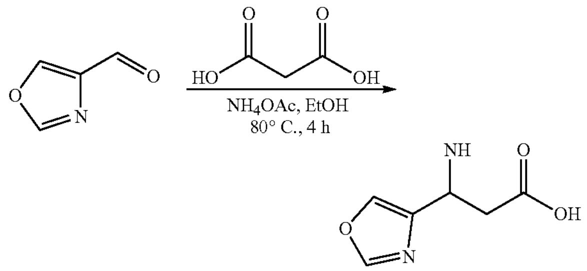

A solution of 1,3-oxazole-4-carbaldehyde (1.0 g, 10.30 mmol, 1.0 equiv), malonic acid (1.1 g, 10.30 mmol, 1.0 equiv) and NH$_{40}$Ac (1.6 g, 20.60 mmol, 2.0 equiv) in EtOH (10 mL) was stirred for 4 h at 80° C. The reaction was cooled to room temperature, concentrated to remove the solvent, the residue was purified by reversed-phase flash chromatography with the following conditions: column, C18 silica gel-120 g; mobile phase, MeCN in Water (0.1% FA), 0% to 10% gradient in 10 min; detector, UV 254 nm. This resulted in 3-amino-3-(1,3-oxazol-4-yl)propanoic acid (300 mg, 18.6%). LCMS (ES, m/z): [M+H]$^+$: 157.

Synthesis of 3-[(tert-butoxycarbonyl)amino]-3-(1,3-oxazol-4-yl)propanoic acid

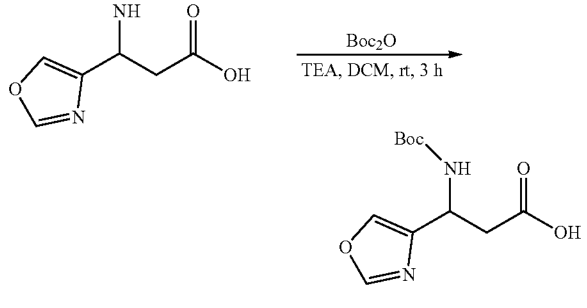

A solution of 3-amino-3-(1,3-oxazol-4-yl)propanoic acid (300 mg, 1.92 mmol, 1.0 equiv) and di-tert-butyl dicarbonate (503 mg, 2.30 mmol, 1.2 equiv), TEA (583 mg, 5.76 mmol, 3.0 equiv) in DCM (5 mL) was stirred for 3 h at room temperature. The reaction was diluted with water (20 mL), extracted with $CH_2Cl_2$ (1×10 mL). The aqueous layer was acidified to pH 4 with HCl (1 M), extracted with EtOAc (3×30 mL). The combined organic layer was washed with brine (3×20 mL), dried over anhydrous $Na_2SO_4$. After filtration, the filtrate was concentrated under reduced pressure. This resulted in 3-[(tert-butoxycarbonyl)amino]-3-(1,3-oxazol-4-yl)propanoic acid (120 mg, 24.3%). LCMS (ES, m/z): [M+H]$^+$: 257.

Synthesis of tert-butyl N-(2-{[(1S)-1-cyano-2-[4-(3-methyl-2-oxo-1,3-benzoxazol-5-yl)phenyl]ethyl]carbamoyl}-1-(1,3-oxazol-4-yl)ethyl)carbamate

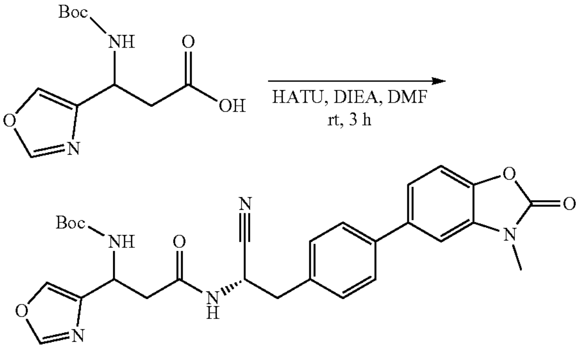

A solution of (2S)-2-amino-3-[4-(3-methyl-2-oxo-1,3-benzoxazol-5-yl)phenyl]propanenitrile (91 mg, 0.31 mmol, 0.67 equiv) in DMF (3 mL) was treated with 3-[(tert-butoxycarbonyl)amino]-3-(1,3-oxazol-4-yl)propanoic acid (120 mg, 0.46 mmol, 1.5 equiv), DIEA (121 mg, 0.93 mmol, 3.0 equiv). This was followed by the addition of HATU (142 mg, 0.37 mmol, 1.2 equiv) in portions at 0° C. The resulting mixture was stirred for 3 h at room temperature. The reaction was quenched with water (10 mL), extracted with EtOAc (3×20 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (2:1) to afford tert-butyl N-(2-{[(1S)-1-cyano-2-[4-(3-methyl-2-oxo-1,3-benzoxazol-5-yl)phenyl]ethyl]carbamoyl}-1-(1,3-oxazol-4-yl)ethyl) carbamate (90 mg, 54.2%). LCMS (ES, m/z): [M+H]$^+$: 532.

Synthesis of 3-amino-N-[(1S)-1-cyano-2-[4-(3-methyl-2-oxo-1,3-benzoxazol-5-yl)phenyl]ethyl]-3-(1,3-oxazol-4-yl)propanamide

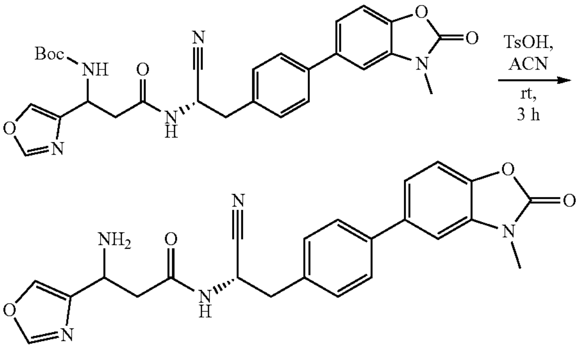

Into a 25 mL round-bottom flask were added tert-butyl N-(2-{[(1S)-1-cyano-2-[4-(3-methyl-2-oxo-1,3-benzoxazol-5-yl)phenyl]ethyl]carbamoyl}-1-(1,3-oxazol-4-yl)ethyl) carbamate (90 mg, 0.16 mmol, 1.0 equiv), ACN (3 mL) and TsOH·$H_2O$ (96 mg, 0.50 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 3-amino-N-[(1S)-1-cyano-2-[4-(3-methyl-2-oxo-1,3-benzoxazol-5-yl)phenyl]ethyl]-3-(1,3-oxazol-4-yl)propanamide (17.3 mg, 23.7%).

LCMS (ES, m/z): $[M+H]^+$: 432.3

$^1$H NMR (400 MHz, DMSO-$d_6$) δ 9.09-8.83 (m, 1H), 8.28 (dd, J=3.7, 1.0 Hz, 1H), 7.81 (dt, J=7.5, 1.1 Hz, 1H), 7.71-7.64 (m, 2H), 7.60 (d, J=1.7 Hz, 1H), 7.47-7.37 (m, 4H), 5.03-4.97 (m, 1H), 4.11 (dd, J=8.8, 4.8 Hz, 1H), 3.41 (s, 3H), 3.19-3.04 (m, 2H), 2.60-2.53 (m, 1H), 2.43-2.30 (m, 1H), 1.88 (br, 2H).

Example 26. Synthesis of Compound 193 and 194: (2R)-3-amino-N-[(1S)-1-cyano-2-[4-(3-methyl-2-oxo-1,3-benzoxazol-5-yl)phenyl]ethyl]-2-[(2-methylphenyl)methyl]propenamide; (2S)-3-amino-N-[(1S)-1-cyano-2-[4-(3-methyl-2-oxo-1,3-benzoxazol-5-yl)phenyl]ethyl]-2-[(2-methylphenyl)methyl]propanamide

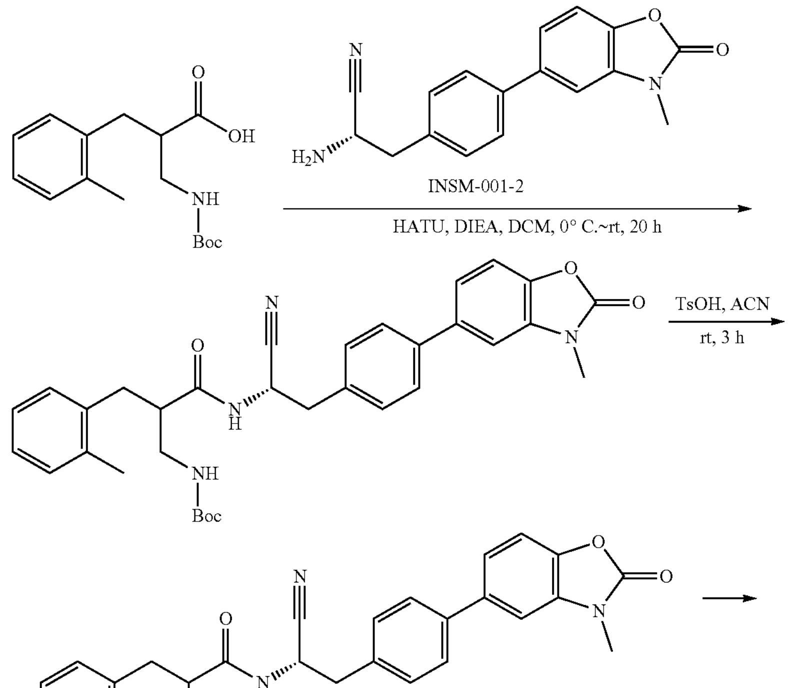

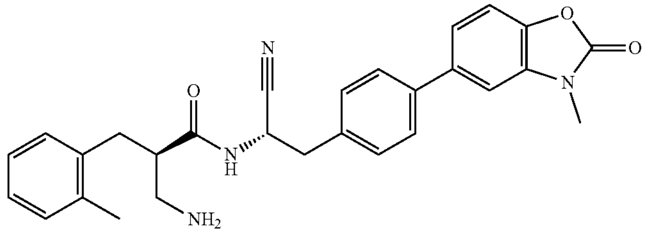

+ compound 193
assumed as anti

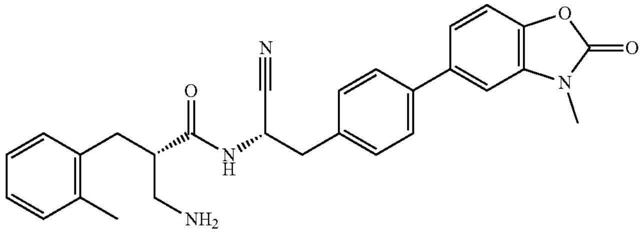

compound 194
assumed as syn

Synthesis of tert-butyl N-(2-{[(1S)-1-cyano-2-[4-(3-methyl-2-oxo-1,3-benzoxazol-5-yl)phenyl]ethyl]carbamoyl}-2-{(2-methylphenyl)methyl}ethyl)carbamate

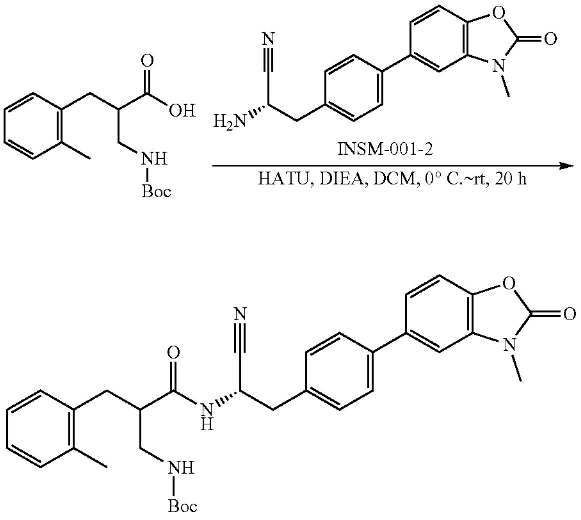

To a stirred solution of 3-[(tert-butoxycarbonyl)amino]-2-[(2-methylphenyl)methyl]propanoic acid (110 mg, 0.37 mmol, 1.0 equiv), (2S)-2-amino-3-[4-(3-methyl-2-oxo-1,3-benzoxazol-5-yl)phenyl]propanenitrile (121 mg, 0.413 mmol, 1.1 equiv) and DIEA (145 mg, 1.12 mmol, 3.0 equiv) in DCM (5 mL) was added HATU (171 mg, 0.45 mmol, 1.2 equiv) in portions at 0° C. The resulting mixture was stirred for additional 3 h at 0° C. The residue was purified by silica gel column chromatography, eluted with PE/THE (1:1) to afford tert-butyl N-(2-{[(1S)-1-cyano-2-[4-(3-methyl-2-oxo-1,3-benzoxazol-5-yl)phenyl]ethyl]carbamoyl}-2-[(2-methylphenyl)methyl]ethyl)carbamate (120 mg, 56.2%). LCMS (ES, m/z): $[M+H]^+$: 569.

Synthesis of (2R)-3-amino-N-[(1S)-1-cyano-2-[4-(3-methyl-2-oxo-1,3-benzoxazol-5-yl)phenyl]ethyl]-2-[(2-methylphenyl)methyl]propanamide; (2S)-3-amino-N-[(1S)-1-cyano-2-[4-(3-methyl-2-oxo-1,3-benzoxazol-5-yl)phenyl]ethyl]-2-[(2-methylphenyl)methyl]propanamide

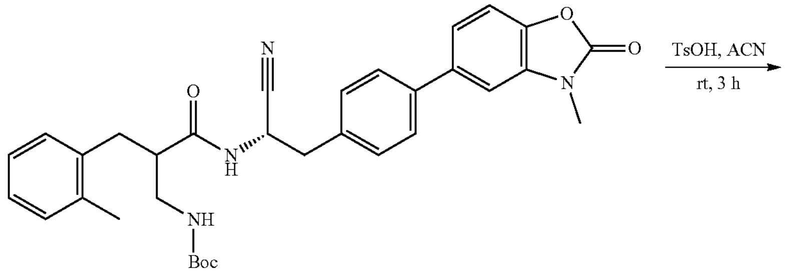

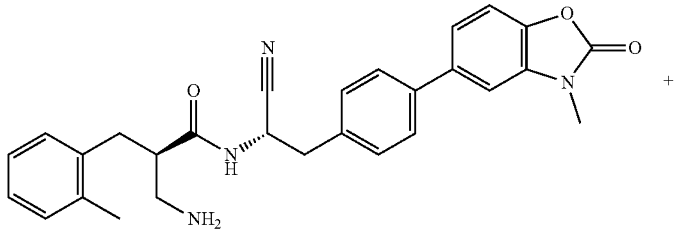

compound 194
assumed as Anti

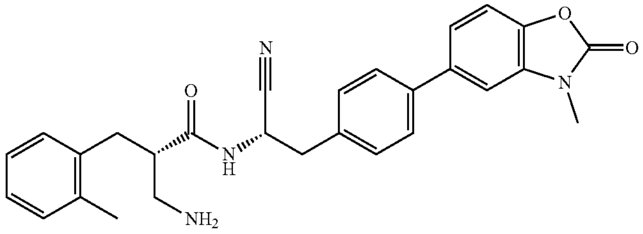

compound 193
assumed as Syn

Into a 50 mL round-bottom flask were added tert-butyl N-(2-{[(1S)-1-cyano-2-[4-(3-methyl-2-oxo-1,3-benzoxazol-5-yl)phenyl]ethyl]carbamoyl}-2-[(2-methylphenyl)methyl]ethyl)carbamate (120 mg, 0.21 mmol, 1.0 equiv) and TsOH (109 mg, 0.63 mmol, 3.0 equiv) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 80% gradient in 10 min; detector, UV 254 nm. This resulted in (2R)-3-amino-N-[(1S)-1-cyano-2-[4-(3-methyl-2-oxo-1,3-benzoxazol-5-yl)phenyl]ethyl]-2-[(2-methylphenyl)methyl]propanamide(16.33 mg6.67%); (2S)-3-amino-N-[(1S)-1-cyano-2-[4-(3-methyl-2-oxo-1,3-benzoxazol-5-yl)phenyl]ethyl]-2-[(2-methylphenyl)methyl]propanamide (17.0 mg, 6.67%).

LCMS (ES, m z): $[M+H]^+$: 469.2

$^1H$ NMR (400 MHz, DMSO-$d_6$) δ 7.68-7.61 (m, 2H), 7.57 (d, J=1.2 Hz, 1H), 7.45-7.34 (m, 4H), 7.16-7.02 (m, 4H), 4.99 (t, J=7.8 Hz, 1H), 3.40 (s, 3H), 3.17-2.99 (m, 2H), 2.78-2.55 (m, 4H), 2.43 (d, J=6.0 Hz, 1H), 2.27 (s, 3H).

LCMS (ES, m z): $[M+H]^+$: 469.2

$^1H$ NMR (400 MHz, DMSO-$d_6$) δ 7.66-7.60 (m, 2H), 7.56 (d, J=1.3 Hz, 1H), 7.41 (d, J=1.2 Hz, 2H), 7.32-7.25 (m, 2H), 7.12 (d, J=6.0 Hz, 1H), 7.10-7.01 (m, 3H), 4.98 (t, J=7.5 Hz, 1H), 3.40 (s, 3H), 3.04-2.89 (m, 2H), 2.74 (dd, J=12.4, 8.0 Hz, 1H), 2.66 (d, J=7.6 Hz, 2H), 2.60-2.50 (m, 2H), 2.25 (s, 3H).

Example 27. Synthesis of Compound 200: 2-amino-N-[(1S)-1-cyano-2-[4-(3-methyl-2-oxo-1,3-benzoxazol-5-yl)phenyl]ethyl]-2-(4-hydroxyphenyl)propanamide

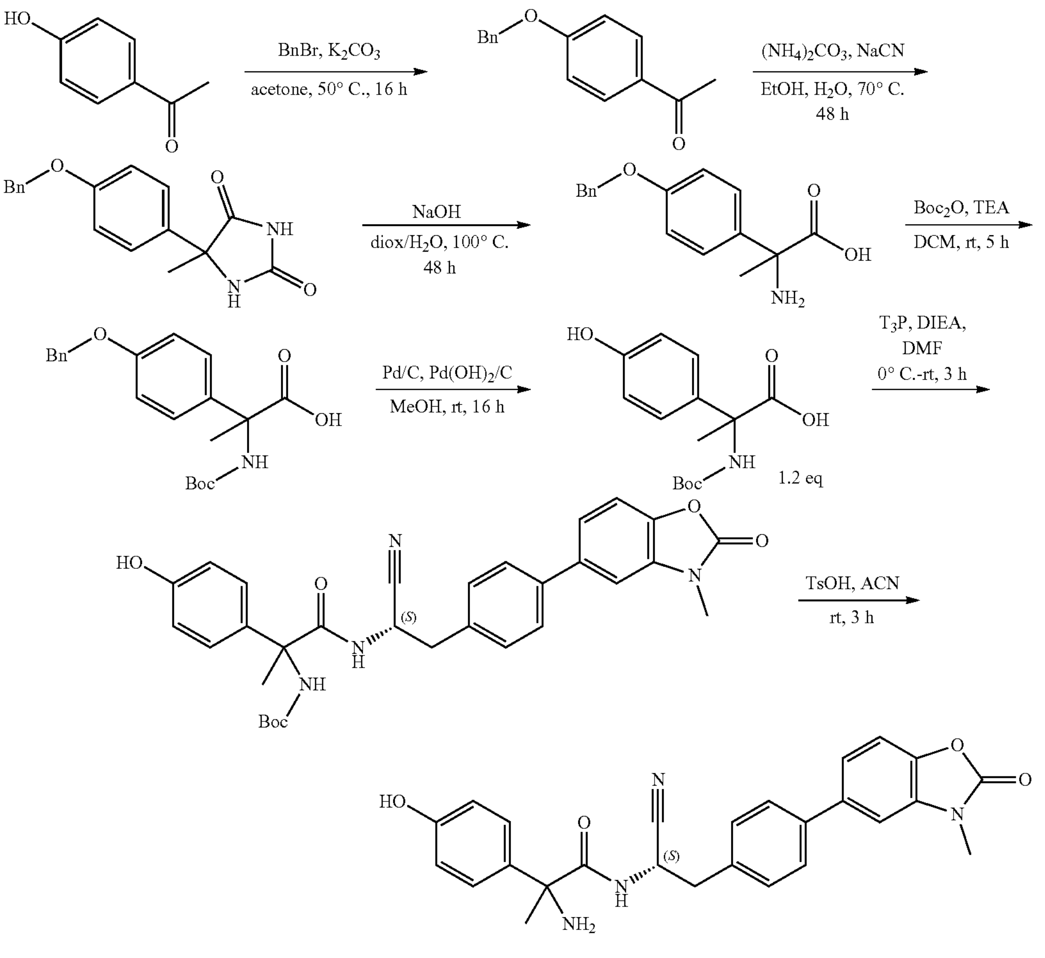

compound 200

Synthesis of 1-[4-benzyloxy)phenyl]ethanone

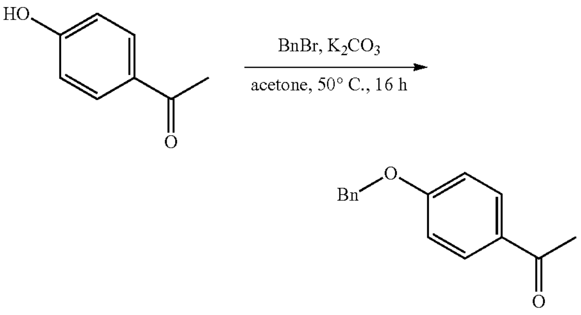

To a stirred solution of hydroxyacetophenone (8 g, 58.759 mmol, 1.0 equiv) and K2CO3 (12.18 g, 88.138 mmol, 1.5 equiv) in acetone (100 mL) was added BnBr (12.06 g, 70.511 mmol, 1.2 equiv) dropwise at room temperature. The resulting mixture was stirred for 16 h at 50° C. under nitrogen atmosphere. The mixture was allowed to cool down to room temperature. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by trituration with PE/EA=5/1 (100 mL). This resulted in 1-[4-(benzyloxy)phenyl]ethanone (11 g, 82.73%).

$^1H$ NMR (400 MHz, DMSO-d6) δ 7.97-7.90 (m, 2H), 7.51-7.30 (m, 5H), 7.16-7.09 (m, 2H), 5.21 (s, 2H), 2.52 (s, 3H).

Synthesis of 5-[4-(benzyloxy)phenyl]-5-methylimidazolidine-2,4-dione

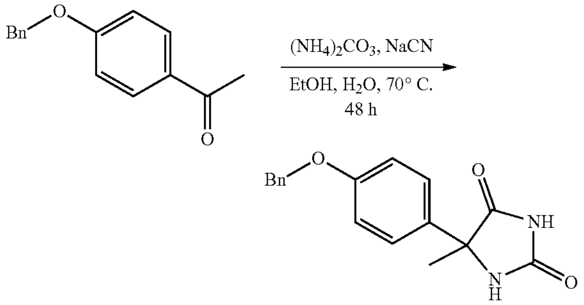

To a stirred solution of 1-[4-(benzyloxy)phenyl]ethanone (3.0 g, 13.258 mmol, 1.0 equiv) and $(NH_4)_2CO_3$ (6.37 g, 66.290 mmol, 5.0 equiv) in EtOH (30 mL) and $H_2O$ (10 mL) was added NaCN (1.62 g, 33.145 mmol, 2.5 equiv). The resulting mixture was stirred for 48 h at 70° C. under nitrogen atmosphere. The mixture was allowed to cool down to room temperature. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3{\cdot}H_2O$), 20% to 100% gradient in 15 min; detector, UV 254 nm. This resulted in 5-[4-(benzyloxy)phenyl]-5-methylimidazolidine-2,4-dione (1.0 g, 25.45%). LCMS (ES) $[M+H]^+$ m/z:297.

Synthesis of 2-amino-2-[4-(benzyloxy)phenyl]propanoic acid

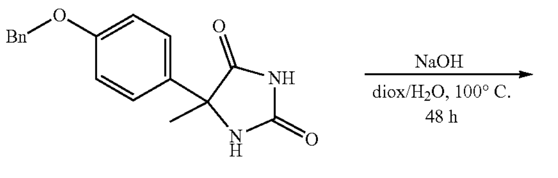

-continued

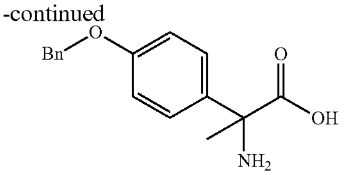

To a stirred solution of 5-[4-(benzyloxy)phenyl]-5-methylimidazolidine-2,4-dione (1.0 g, 3.375 mmol, 1.0 equiv) in dioxane (8 mL) and $H_2O$ (8 mL) was added caustic soda (404 mg, 10.125 mmol, 3.0 equiv). The resulting mixture was stirred for 48 h at 100° C. The mixture was allowed to cool down to room temperature. The mixture was purified by reversed-phase flash chromatography with the following conditions: column, C18 silica gel; mobile phase, MeCN in Water (0.1% FA), 10% to 50% gradient in 10 min; detector, UV 254 nm. This resulted in 2-amino-2-[4-(benzyloxy)phenyl]propanoic acid (400 mg, 43.69%). LCMS (ES) $[M-H]^-$m/z:270

Synthesis of 2-[4-(benzyloxy)phenyl]-2-[(tert-butoxycarbonyl)amino]propanoic acid

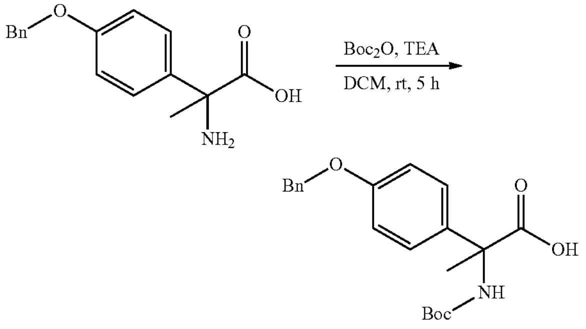

To a stirred solution of 2-amino-2-[4-(benzyloxy)phenyl]propanoic acid (400 mg, 1.474 mmol, 1.0 equiv) in DCM (8 mL) were added TEA (447 mg, 4.422 mmol, 3.0 equiv) and DMAP (9 mg, 0.074 mmol, 0.05 equiv) and $Boc_2O$ (482 mg, 2.211 mmol, 1.5 equiv). The resulting mixture was stirred for 5 h at room temperature. The resulting mixture was concentrated under reduced pressure. The resulting mixture was extracted with EtOAc (3×20 mL). The combined organic layers were washed with brine (10 mL), dried over anhydrous $Na_2SO_4$. After filtration, the filtrate was concentrated under reduced pressure. The crude product 2-[4-(benzyloxy)phenyl]-2-[(tert-butoxycarbonyl)amino]propanoic acid (350 mg) mixture was used in the next step directly without further purification. LCMS (ES) [M−H]-m/z:370.

Synthesis of 2-[(tert-butoxycarbonyl)amino]-2-(4-hydroxyphenyl)propanoic acid

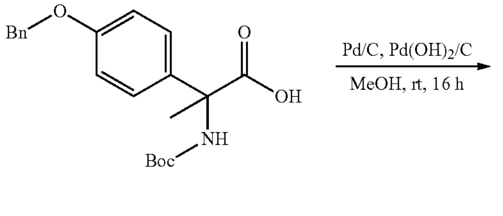

-continued

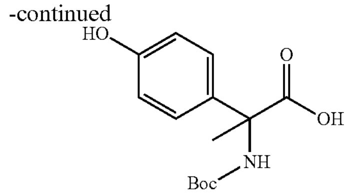

To a stirred solution of 2-[4-(benzyloxy)phenyl]-2-[(tert-butoxycarbonyl)amino]propanoic acid (350 mg, 0.942 mmol, 1.0 equiv) in MeOH (10 mL) was added Pd/C (50 mg) and $Pd(OH)_2/C$ (50 mg). The resulting mixture was stirred for 16 h at room temperature under hydrogen atmosphere (10 atm). The resulting mixture was filtered, the filter cake was washed with MeOH (20 mL). The filtrate was concentrated under reduced pressure. The residue was dissolved in NaOH (10 mL, 5%). The resulting mixture was extracted with EtOAc (2×10 mL). The aqueous layer was acidified to pH 6 with citric acid. The resulting mixture was extracted with $CH_2Cl_2$ (5×20 mL). The combined organic layers were washed with $H_2O$ (10 mL), dried over anhydrous $Na_2SO_4$. After filtration, the filtrate was concentrated under reduced pressure. This resulted in 2-[(tert-butoxycarbonyl)amino]-2-(4-hydroxyphenyl)propanoic acid (100 mg, 37.73%). LCMS (ES) [M−H]—m/z:280

Synthesis of tert-butyl N-(1-{[(1S)-1-cyano-2-[4-(3-methyl-2-oxo-1,3-benzoxazol-5-yl)phenyl]ethyl]carbamoyl}-1-(4-hydroxyphenyl)ethyl)carbamate

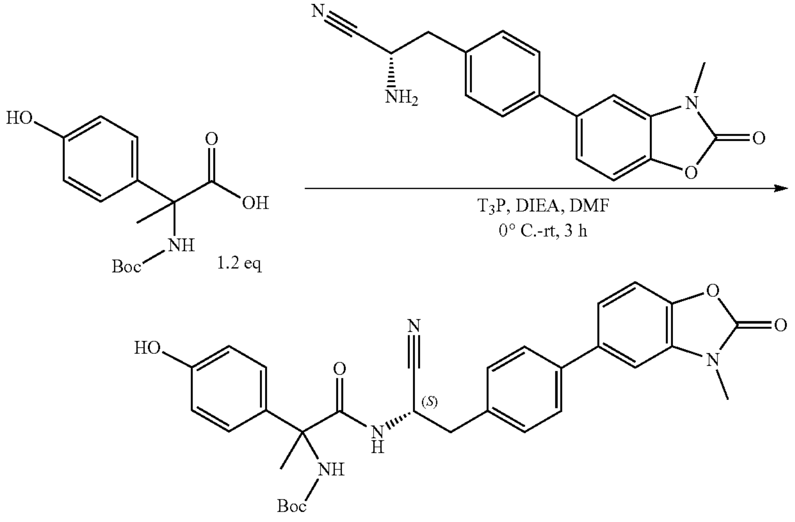

To a stirred solution of 2-[(tert-butoxycarbonyl)amino]-2-(4-hydroxyphenyl)propanoic acid (100 mg, 0.355 mmol, 1.0 equiv) and (2S)-2-amino-3-[4-(3-methyl-2-oxo-1,3-benzoxazol-5-yl)phenyl]propanenitrile (104 mg, 0.355 mmol, 1.0 equiv) in DMF (2 mL) was added DIEA (137 mg, 1.065 mmol, 3.0 equiv) and T3P (226 mg, 0.710 mmol, 2.0 equiv) dropwise at 0° C. The resulting mixture was stirred for 3 h at room temperature. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/THE (2:1) to afford tert-butyl N-(1-{[(1S)-1-cyano-2-[4-(3-methyl-2-oxo-1,3-benzoxazol-5-yl)phenyl]ethyl]carbamoyl}-1-(4-hydroxyphenyl)ethyl)carbamate (50 mg, 25.27%). LCMS (ES) $[M+H]^+$ m/z:557.

Synthesis of 2-amino-N-[(1S)-1-cyano-2-[4-(3-methyl-2-oxo-1,3-benzoxazol-5-yl)phenyl]ethyl]-2-(4-hydroxyphenyl)propanamide

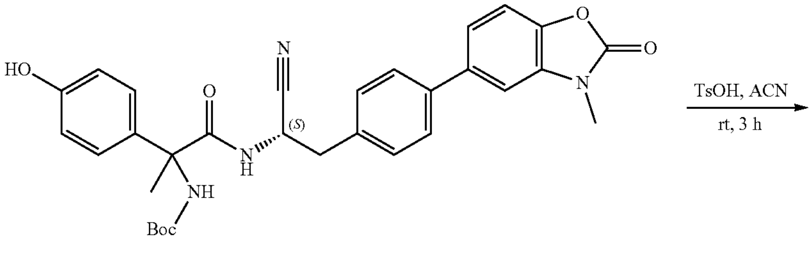

-continued

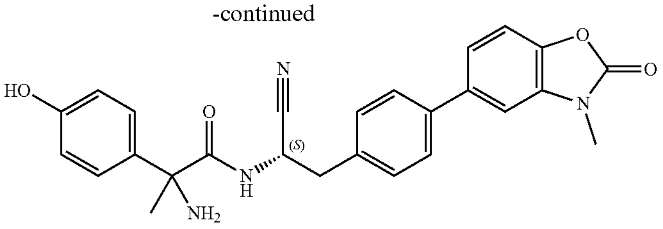

compound 200

To a stirred solution of tert-butyl N-(1-{[(1S)-1-cyano-2-[4-(3-methyl-2-oxo-1,3-benzoxazol-5-yl)phenyl]ethyl]carbamoyl}-1-(4-hydroxyphenyl)ethyl)carbamate (50 mg, 0.090 mmol, 1.0 equiv) in ACN (1 mL) was added TsOH (46 mg, 0.270 mmol, 3.0 equiv). The resulting mixture was stirred for 3 h at room temperature. The mixture was purified by reversed-phase flash chromatography with the following conditions: column, C18 silica gel; mobile phase, MeCN in Water (10 mmol/L $NH_4HCO_3$), 10% to 60% gradient in 15 min; detector, UV 254 nm. This resulted in 2-amino-N-[(1S)-1-cyano-2-[4-(3-methyl-2-oxo-1,3-benzoxazol-5-yl)phenyl]ethyl]-2-(4-hydroxyphenyl)propanamide. LCMS (ES) $[M+H]^+$ m/z:457.1.

$^1H$ NMR (400 MHz, DMSO-$d_6$) δ 9.27 (br, 1H), 7.75-7.51 (m, 3H), 7.44-7.40 (m, 2H), 7.39-7.27 (m, 2H), 7.24-7.02 (m, 2H), 6.73-6.58 (m, 2H), 5.02-4.91 (m, 1H), 3.42 (d, J=1.4 Hz, 3H), 3.22-3.11 (m, 2H), 1.49-1.44 (m, 3H).

Example 28. Synthesis of Compound 215: (2R)-2-amino-N-[(1S)-1-cyano-2-[4-(3-methyl-2-oxo-1,3-benzoxazol-5-yl)phenyl]ethyl]-3-(1H-imidazol-4-yl)propanamide

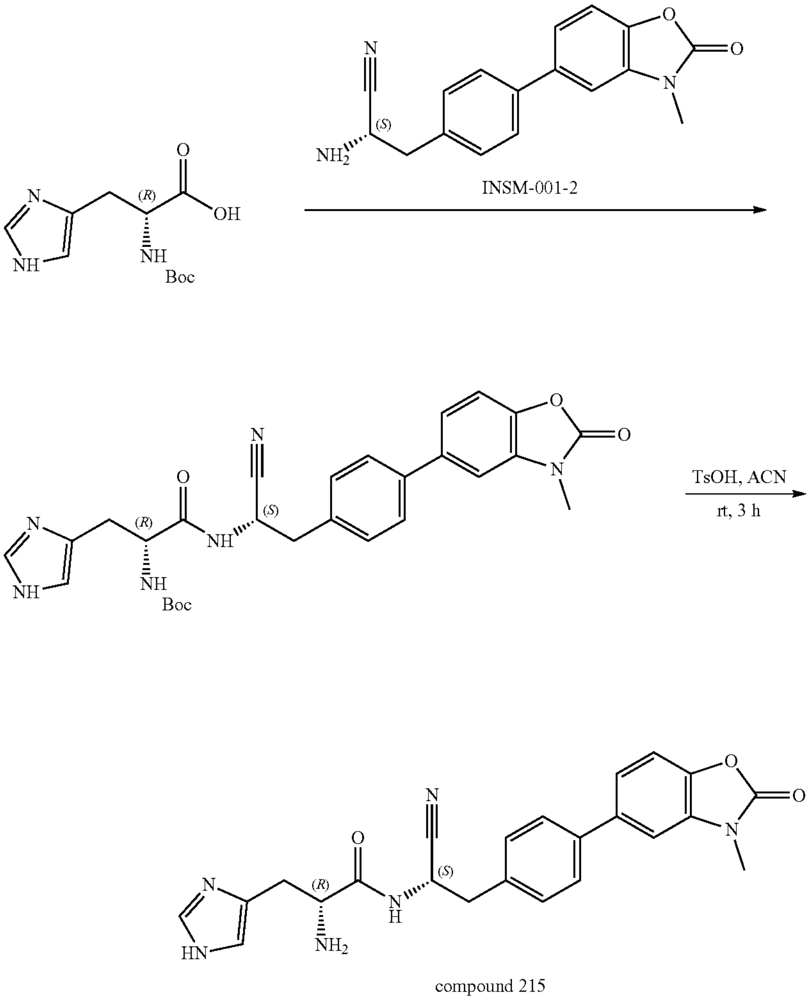

compound 215

Synthesis of tert-butyl N-[(1R)-1-{[(1S)-1-cyano-2-[4-(3-methyl-2-oxo-1,3-benzoxazol-5-yl)phenyl]ethyl]carbamoyl}-2-(1H-imidazol-4-yl)ethyl]carbamate

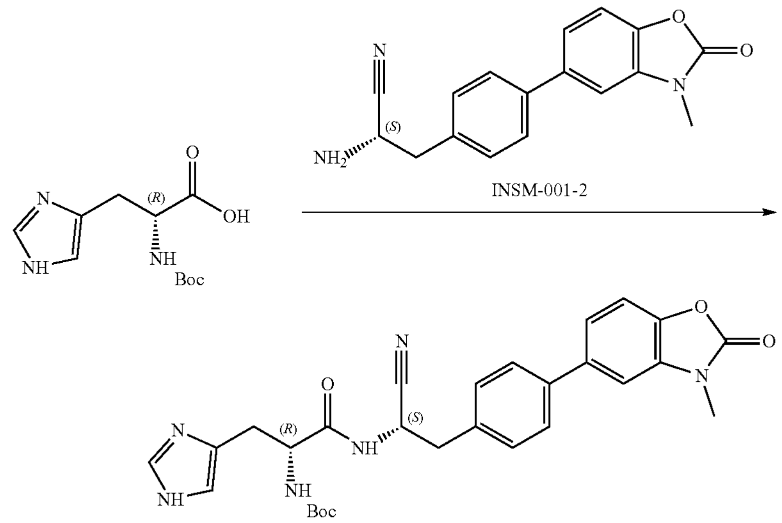

Into a 20 mL vial were added (2R)-2-[(tert-butoxycarbonyl)amino]-3-(1H-imidazol-4-yl)propanoic acid (70.00 mg, 0.27 mmol, 1.00 equiv), HOBt (37.05 mg, 0.27 mmol, 1.00 equiv), DIEA (97.46 mg, 0.75 mmol, 2.75 equiv), TBTU (88.05 mg, 0.27 mmol, 1.00 equiv) and DMF (4.00 mL) at room temperature. The resulting mixture was stirred for additional 15 min at room temperature. To the above mixture was added (2S)-2-amino-3-[4-(3-methyl-2-oxo-1,3-benzoxazol-5-yl)phenyl]propanenitrile (56.30 mg, 0.19 mmol, 0.70 equiv) in portions at room temperature. The resulting mixture was stirred for additional 24 h at room temperature. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in tert-butyl N-[(1R)-1-{[(1S)-1-cyano-2-[4-(3-methyl-2-oxo-1,3-benzoxazol-5-yl)phenyl]ethyl]carbamoyl}-2-(1H-imidazol-4-yl)ethyl]carbamate (90 mg, 61.86%). LCMS (ES) $[M+1]^+$ m/z: 531.

Synthesis of (2R)-2-amino-N-[(1S)-1-cyano-2-[4-(3-methyl-2-oxo-1,3-benzoxazol-5-yl)phenyl]ethyl]-3-(1H-imidazol-4-yl)propanamide

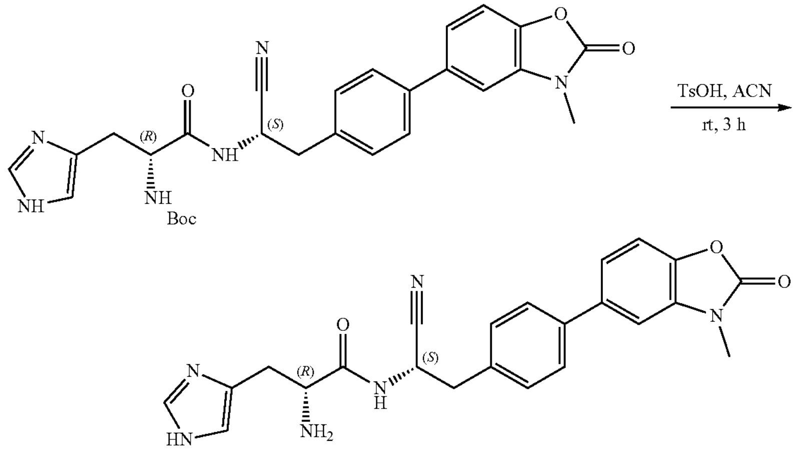

compound 215

Into a 20 mL vial were added tert-butyl N-[(1R)-1-{[(1S)-1-cyano-2-[4-(3-methyl-2-oxo-1,3-benzoxazol-5-yl)phenyl]ethyl]carbamoyl}-2-(1H-imidazol-4-yl)ethyl]carbamate (80.00 mg, 0.15 mmol, 1.00 equiv), TsOH (77.60 mg, 0.45 mmol, 3.00 equiv) and ACN (4.00 mL) at room temperature. The resulting mixture was stirred for additional 2 h at room temperature. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2R)-2-amino-N-[(1S)-1-cyano-2-[4-(3-methyl-2-oxo-1,3-benzoxazol-5-yl)phenyl]ethyl]-3-(1H-imidazol-4-yl)propanamide (18 mg, 27.71%).

)H NMR (300 MHz, DMSO-d6) δ 11.82 (s, 1H), 7.67 (d, J=7.9 Hz, 2H), 7.59 (s, 1H), 7.54 (s, 1H), 7.48-7.35 (m, 4H), 6.82-6.72 (m, 1H), 4.98 (t, J=7.8 Hz, 1H), 3.41 (s, 3H), 3.41-3.38 (m, 2H), 3.15 (d, J=7.3 Hz, 2H), 2.77 (d, J=16.6 Hz, 1H). LCMS (ES) $[M+1]^+$ m/z: 431.

Example 29. Synthesis of Compound 169: (2R)-2-amino-N-[(1S)-1-cyano-2-[4-(3-methyl-2-oxo-1,3-benzoxazol-5-yl)phenyl]ethyl]-4-hydroxybutanamide

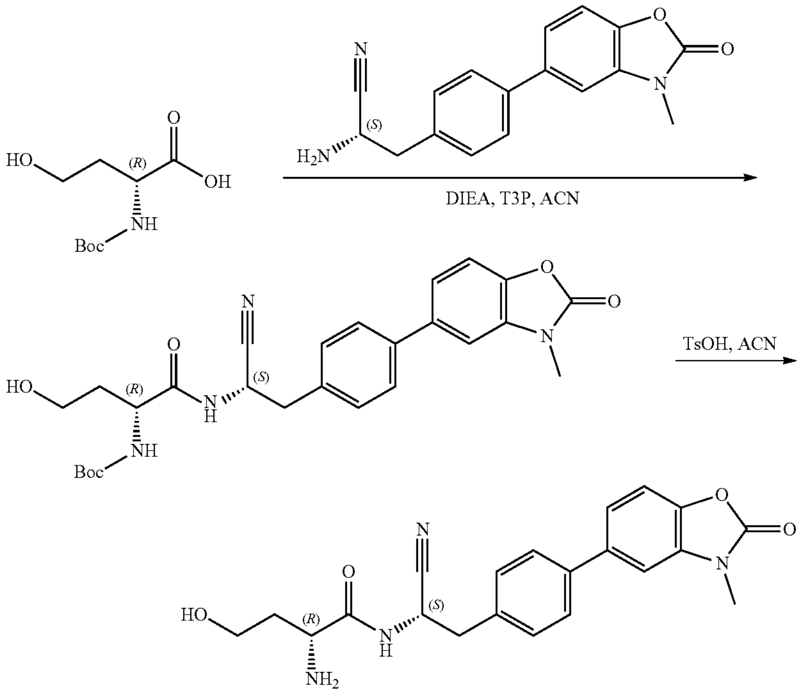

compound 169

Synthesis of tert-butyl N-[(1R)-1-{[(1S)-1-cyano-2-[4-(3-methyl-2-oxo-1,3-benzoxazol-5-yl)phenyl]ethyl]carbamoyl}-3-hydroxypropyl]carbamate

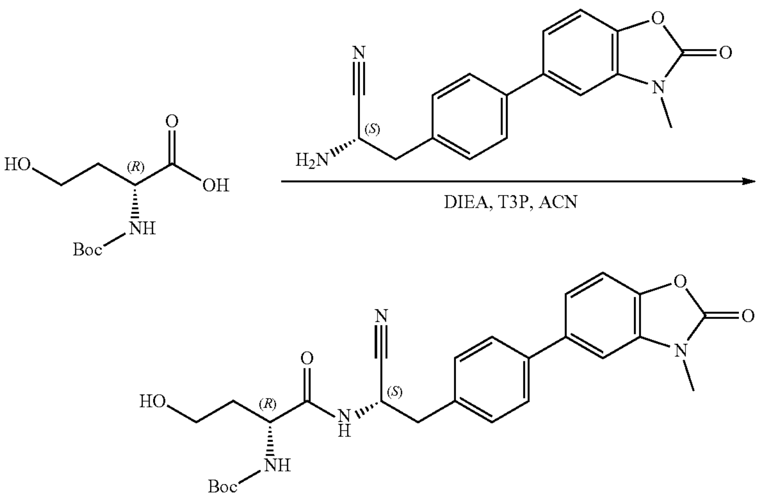

Into a 20 mL vial were added (2R)-2-[(tert-butoxycarbonyl)amino]-4-hydroxybutanoic acid (149.48 mg, 0.68 mmol, 2.00 equiv), (2S)-2-amino-3-[4-(3-methyl-2-oxo-1,3-benzoxazol-5-yl)phenyl]propanenitrile (100.00 mg, 0.34 mmol, 1.00 equiv), ACN (5.00 mL) and DIEA (176.25 mg, 1.36 mmol, 4.00 equiv) at room temperature. To the above mixture was added T3P (325.42 mg, 1.02 mmol, 3.00 equiv) dropwise at 0° C. The resulting mixture was stirred for additional overnight at room temperature. The residue was purified by reversed-phase flash chromatography with the following conditions: column, C18 silica gel; mobile phase, MeCN in Water (0.1% FA), 30% to 70% gradient in 10 min; detector, UV 254 nm. This resulted in tert-butyl N-[(1R)-1-{[(1S)-1-cyano-2-[4-(3-methyl-2-oxo-1,3-benzoxazol-5-yl)phenyl]ethyl]carbamoyl}-3-hydroxypropyl]carbamate (70.00 mg, 41.52%). LCMS (ES, m z): $[M+H]^+$: 495.

Synthesis of (2R)-2-amino-N-[(1S)-1-cyano-2-[4-(3-methyl-2-oxo-1,3-benzoxazol-5-yl)phenyl]ethyl]-4-hydroxybutanamide

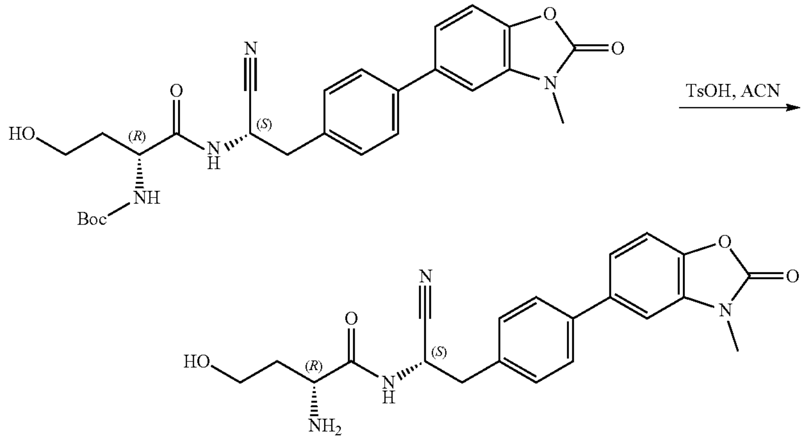

Into a 8 mL vial were added tert-butyl N-[(1R)-1-{[(1S)-1-cyano-2-[4-(3-methyl-2-oxo-1,3-benzoxazol-5-yl)phenyl]ethyl]carbamoyl}-3-hydroxypropyl]carbamate (50.00 mg, 0.10 mmol, 1.00 equiv) and ACN (3.00 mL) at room temperature. To the above mixture was added TsOH (52.23 mg, 0.30 mmol, 3.00 equiv) in portions at 0° C. The resulting mixture was stirred for additional 2 h at room temperature. The reaction solution was purified by Prep-HPLC with the following conditions XBridge Prep C18 OBD Column, 19*150 mm, 5 um; mobile phase, Water (10 mmol/L $NH_3$—$H_2O$) and ACN (30% Phase B up to 40% in 7 min); Detector, UV 254 nm. This resulted in (2R)-2-amino-N-[(1S)-1-cyano-2-[4-(3-methyl-2-oxo-1,3-benzoxazol-5-yl)phenyl]ethyl]-4-hydroxybutanamide (14.4 mg, 36.11%).

LCMS (ES, m z): $[M+H]^+$: 395

$^1$H NMR (400 MHz, DMSO-d6) δ 7.67 (d, J=8.1 Hz, 2H), 7.59 (d, J=1.6 Hz, 1H), 7.48-7.35 (m, 4H), 5.00 (t, J=7.7 Hz, 1H), 4.48 (brs, 1H), 3.50-3.37 (m, 5H), 3.26 (dd, J=8.8, 4.5 Hz, 1H), 3.24-3.07 (m, 2H), 1.69 (ddd, J=13.7, 11.5, 6.8 Hz, 1H), 1.49-1.31 (m, 1H).

Example 30. Synthesis of Compound 217: 2-amino-N-[(1S)-1-cyano-2-[4-(3-methyl-2-oxo-1,3-benzoxazol-5-yl)phenyl]ethyl]-3-(5-hydroxypyridin-3-yl)propanamide

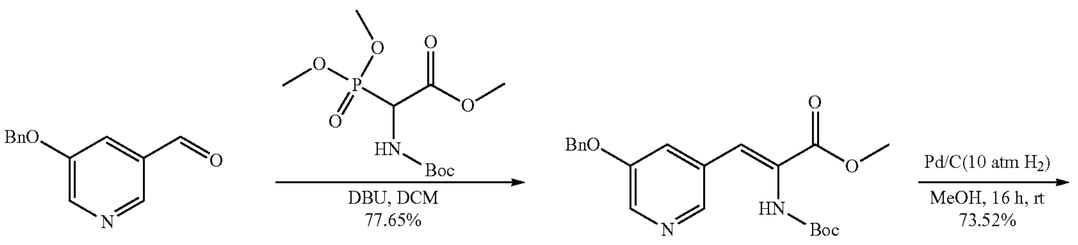

-continued

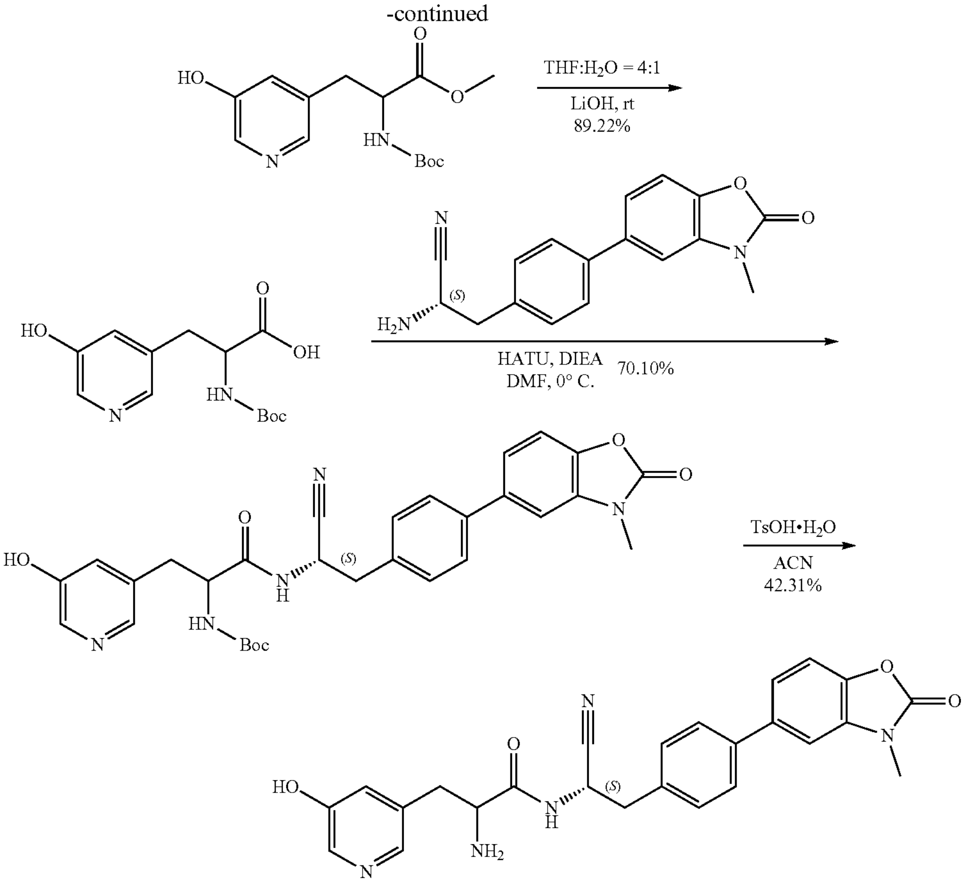

compound 217

Synthesis of methyl 3-[5-(benzyloxy)pyridin-3-yl]-2-[(tert-butoxycarbonyl)amino]prop-2-enoate

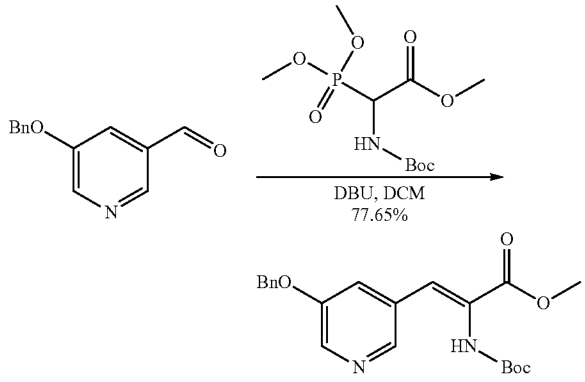

Into a 100 mL 3-necked round-bottom flask were added 5-(benzyloxy)pyridine-3-carbaldehyde (1.40 g, 6.57 mmol, 1.00 equiv), DCM (30.00 mL) and methyl 2-[(tert-butoxycarbonyl)amino]-2-(dimethoxyphosphoryl)acetate (1.95 g, 6.57 mmol, 1.00 equiv). To the above mixture was added DBU (1.00 g, 6.57 mmol, 1.00 equiv) dropwise at 0° C. The resulting mixture was stirred for additional 1 h at room temperature. The reaction was quenched with Water/Ice. The resulting mixture was extracted with DCM (3×40 mL). The combined organic layers were dried over anhydrous $Na_2SO_4$. After filtration, the filtrate was concentrated under reduced pressure. The residue was purified by silica gel column chromatography, eluted with THE/PE (18%) to afford methyl 3-[5-(benzyloxy)pyridin-3-yl]-2-[(tert-butoxycarbonyl)amino]prop-2-enoate (1.96 g, 77.65%). LCMS (ES, m z): $[M+H]^+$: 385.

Synthesis of methyl 2-[(tert-butoxycarbonyl)amino]-3-(5-hydroxypyridin-3-yl)propanoate

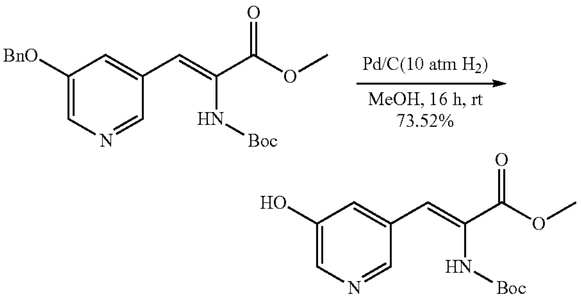

Into a 50 mL pressure tank reactor were added methyl 3-[5-(benzyloxy)pyridin-3-yl]-2-[(tert-butoxycarbonyl)amino]prop-2-enoate (210.00 mg, 0.55 mmol, 1.00 equiv), MeOH (20.00 mL) and Pd/C (5.81 mg, 0.06 mmol, 0.10 equiv). The resulting mixture was stirred for overnight at room temperature under carbon monoxide (10 atm) atmosphere. The resulting mixture was filtered, the filter cake was washed with MeOH (3×5 mL). The filtrate was concentrated under reduced pressure. This resulted in methyl 2-[(tert-butoxycarbonyl)amino]-3-(5-hydroxypyridin-3-yl)propanoate (119.00 mg, 73.52%). LCMS (ES, m z): $[M+H]^+$: 297.

Synthesis of 2-[(tert-butoxycarbonyl)amino]-3-(5-hydroxypyridin-3-yl)propanoic acid

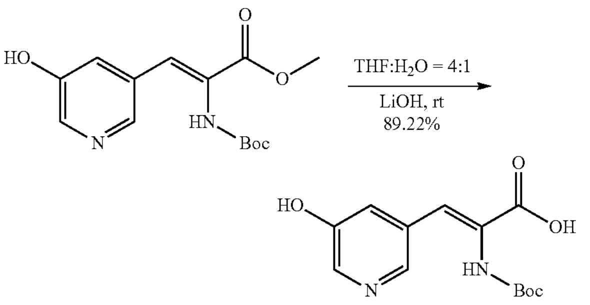

Into a 40 mL vial were added methyl 2-[(tert-butoxycarbonyl)amino]-3-(5-hydroxypyridin-3-yl)propanoate (100.00 mg, 0.34 mmol, 1.00 equiv), THE (8.00 mL) and $H_2O$ (2.00 mL). To the above mixture was added LiOH (16.16 mg, 0.67 mmol, 2.00 equiv) in portions at 0° C. The resulting mixture was stirred for additional 1 h at room temperature. The reaction solution was purified by Prep-HPLC with the following conditions: XBridge Prep C18 OBD Column, 19*150 mm, 5 um; mobile phase, Water (0.1% FA) and ACN (5% Phase B up to 50% in 6 min); Detector, UV 254 nm. This resulted in 2-[(tert-butoxycarbonyl)amino]-3-(5-hydroxypyridin-3-yl)propanoic acid (85.00 mg, 89.22%). LCMS (ES, m z): $[M+H]^+$: 283.

Synthesis of tert-butyl N-(1-{[(1S)-1-cyano-2-[4-(3-methyl-2-oxo-1,3-benzoxazol-5-yl)phenyl]ethyl]carbamoyl}-2-(5-hydroxypyridin-3-yl)ethyl)carbamate

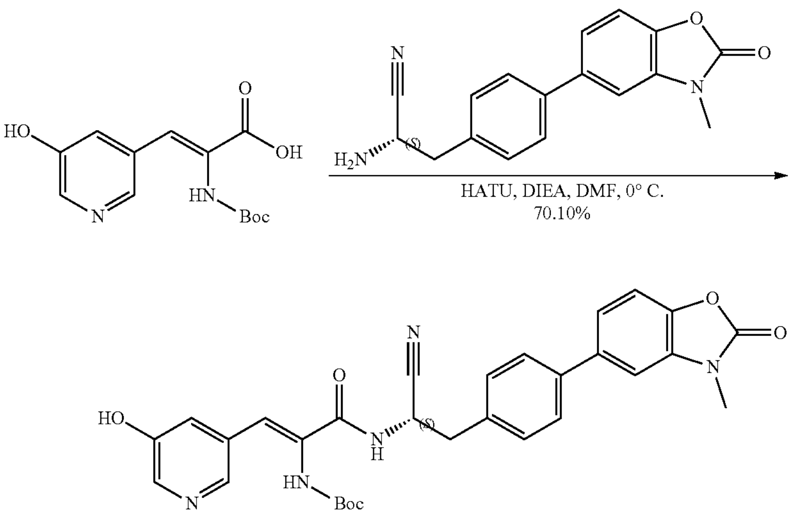

Into a 8 mL vial were added (2S)-2-amino-3-[4-(3-methyl-2-oxo-1,3-benzoxazol-5-yl)phenyl]propanenitrile (64.84 mg, 0.22 mmol, 1.20 equiv), DMF (3.00 mL) and DIEA (71.42 mg, 0.55 mmol, 3.00 equiv). To the above mixture was added HATU (84.05 mg, 0.22 mmol, 1.20 equiv) and 2-[(tert-butoxycarbonyl)amino]-3-(5-hydroxypyridin-3-yl)propanoic acid (52.00 mg, 0.18 mmol, 1.00 equiv) in portions at 0° C. The resulting mixture was stirred for additional 1 h at 0° C. The reaction solution was purified by Prep-HPLC with the following conditions: XBridge Prep C18 OBD Column, 19*150 mm, 5 um; mobile phase, Water (0.1% FA) and ACN (10% Phase B up to 60% in 7 min); Detector, UV 254 nm. This resulted in tert-butyl N-(1-{[(1S)-1-cyano-2-[4-(3-methyl-2-oxo-1,3-benzoxazol-5-yl)phenyl]ethyl]carbamoyl}-2-(5-hydroxypyridin-3-yl)ethyl)carbamate (72.00 mg, 70.10%). LCMS (ES, m z): $[M+H]^+$: 558.

Synthesis of 2-amino-N-[(1S)-1-cyano-2-[4-(3-methyl-2-oxo-1,3-benzoxazol-5-yl)phenyl]ethyl]-3-(5-hydroxypyridin-3-yl)propanamide

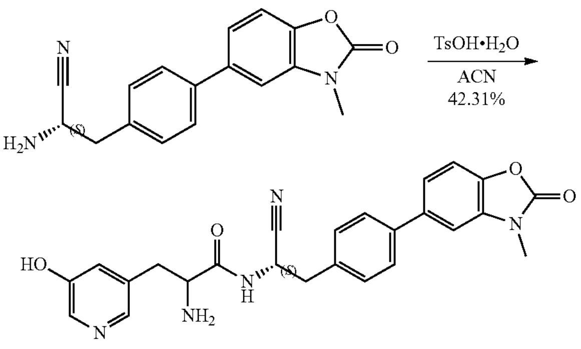

compound 217

Into a 8 mL vial were added tert-butyl N-(1-{[(1S)-1-cyano-2-[4-(3-methyl-2-oxo-1,3-benzoxazol-5-yl)phenyl]ethyl]carbamoyl}-2-(5-hydroxypyridin-3-yl)ethyl)carbamate (70.00 mg, 0.13 mmol, 1.00 equiv), ACN (5.00 mL) and TsOH-$H_2O$ (47.76 mg, 0.25 mmol, 2.00 equiv). The resulting mixture was stirred for 1 h at room temperature. The reaction solution was purified by Prep-HPLC with the following conditions: XBridge Prep C18 OBD Column, 19*150 mm, 5 um; mobile phase, Water (0.05% $NH_3$—$H_2O$) and ACN (25% Phase B up to 50% in 7 min); Detector, UV 254 nm. This resulted in 2-amino-N-[(1S)-1-cyano-2-[4-(3-methyl-2-oxo-1,3-benzoxazol-5-yl)phenyl]ethyl]-3-(5-hydroxypyridin-3-yl)propanamide (24.30 mg, 42.31%).

LCMS (ES, m z): $[M+H]^+$: 458

$^1$H NMR (300 MHz, DMSO-$d_6$) δ 9.78 (brs, 1H), 7.94 (d, J=2.6 Hz, 1H), 7.81 (dd, J=8.3, 1.8 Hz, 1H), 7.65 (dd, J=8.1, 3.5 Hz, 2H), 7.55 (d, J=5.2 Hz, 1H), 7.44-7.28 (m, 4H), 6.96 (dt, J=4.6, 2.2 Hz, 1H), 5.03-4.89 (m, 1H), 3.42-3.38 (m, 4H), 3.19-2.96 (m, 2H), 2.82-2.64 (m, 1H), 2.56-2.53 (m, 1H), 1.95 (brs, 2H).

Example 31. Synthesis of Compound 171A and 171C: (2S,3R)-2-amino-N-[(1S)-1-cyano-2-[4-(3-methyl-2-oxo-1,3-benzoxazol-5-yl)phenyl]ethyl]-3-hydroxy-2-methylbutanamide and (2R,3R)-2-amino-N-[(1S)-1-cyano-2-[4-(3-methyl-2-oxo-1,3-benzoxazol-5-yl)phenyl]ethyl]-3-hydroxy-2-methylbutanamide compound 171A

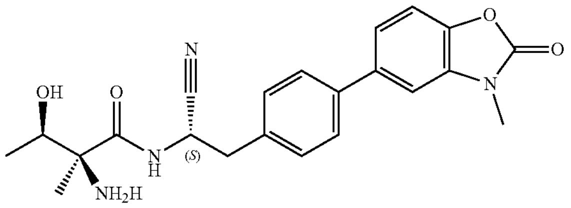

Assumed compound 171C

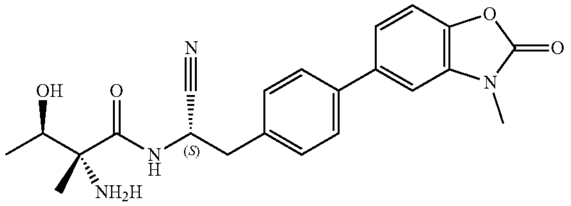

Assumed

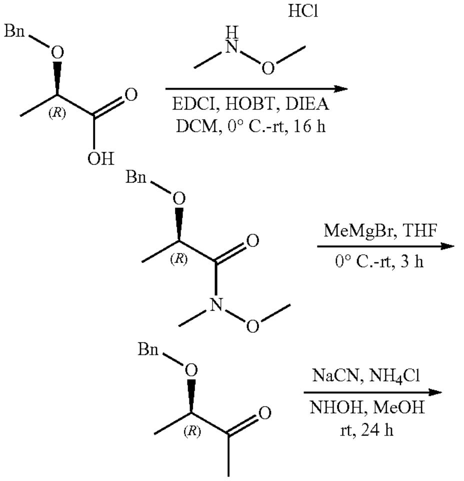

-continued

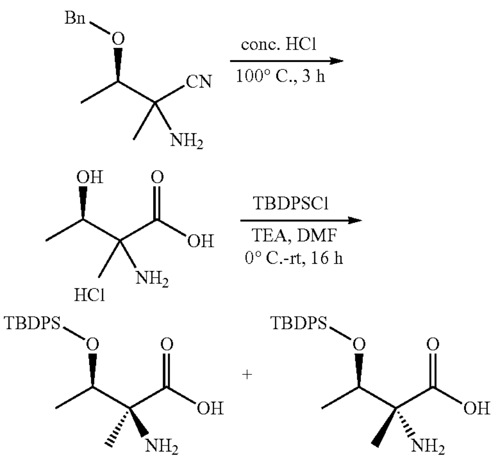

Assumed Assumed

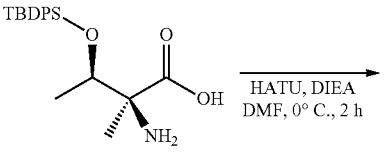

Assumed

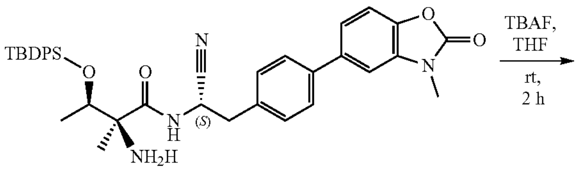

Assumed

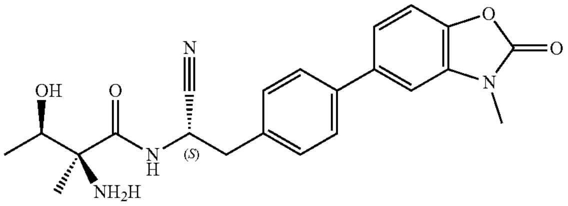

Assumed compound 171A

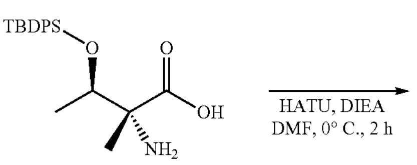

Assumed

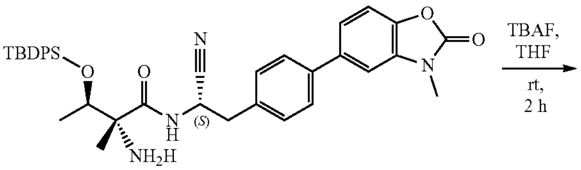

Assumed

-continued

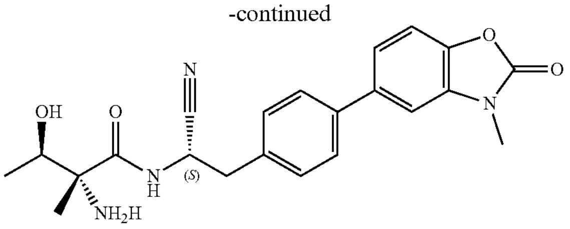

Assumed compound 171C

Synthesis of (2R)-2-(benzyloxy)-N-methoxy-N-methylpropanamide

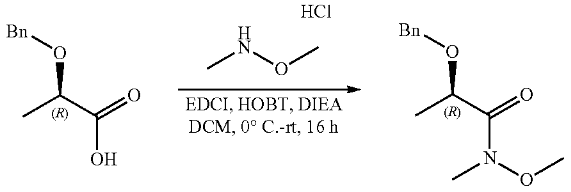

To a stirred solution of (2R)-2-(benzyloxy)propanoic acid (10 g, 55.493 mmol, 1.0 equiv) and N,O-dimethylhydroxylamine (5.08 g, 83.240 mmol, 1.5 equiv) in DCM (100 mL) were added DIEA (28.69 g, 221.972 mmol, 4.0 equiv) and HOBT (9.00 g, 66.592 mmol, 1.2 equiv) and EDCI (15.96 g, 83.240 mmol, 1.5 equiv) in portions at 0° C. under nitrogen atmosphere. The resulting mixture was stirred for 16 h at room temperature. The resulting mixture was extracted with $CH_2Cl_2$ (3x100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (3:1) to afford (2R)-2-(benzyloxy)-N-methoxy-N-methylpropanamide (12 g, 96.85%). LCMS (ES) $[M+H]^+$ m/z:224.

Synthesis of (3R)-3-(benzyloxy)butan-2-one

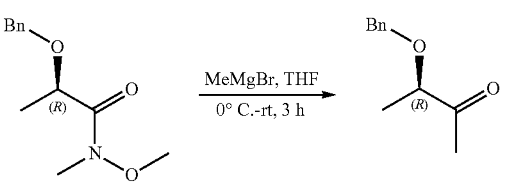

To a stirred solution of (2R)-2-(benzyloxy)-N-methoxy-N-methylpropanamide (10 g, 44.788 mmol, 1.0 equiv) in THE (100 mL) was added bromo(methyl)magnesium (33.59 mL, 67.182 mmol, 1.5 equiv) dropwise at 0° C. under nitrogen atmosphere. The resulting mixture was stirred for 3 h at room temperature. The reaction was quenched by the addition of sat. $NH_4Cl$ (aq.)(50 mL) at 0° C. The resulting mixture was extracted with EtOAc (3x100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (3:1) to afford (3R)-3-(benzyloxy)butan-2-one (6 g, 75.16%). LCMS (ES):no signal. $^1H$ NMR (300 MHz, DMSO-$d_6$) δ 7.43-7.24 (m, 5H), 4.53 (d, J=11.7 Hz, 1H), 4.46 (d, J=11.8 Hz, 1H), 3.97 (q, J=6.9 Hz, 1H), 2.15 (s, 3H), 1.24 (d, J=6.9 Hz, 3H).

Synthesis of (3R)-2-amino-3-(benzyloxy)-2-methylbutanenitrile

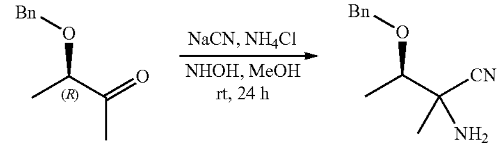

To a stirred solution of $NH_4Cl$ (1.20 g, 22.442 mmol, 2.0 equiv) in $NH_3H_2O$ (20 mL) were added NaCN (1.37 g, 28.053 mmol, 2.5 equiv) at room temperature. To the above mixture was added a solution of (3R)-3-(benzyloxy)butan-2-one (2.0 g, 11.221 mmol, 1.0 equiv) in MeOH (20 mL) dropwise at room temperature. The resulting mixture was stirred for additional 24 h at room temperature. The resulting mixture was concentrated under reduced pressure. The resulting mixture was extracted with EtOAc (3x30 mL). The combined organic layers were washed with brine (50 mL), dried over anhydrous $Na_2SO_4$. After filtration, the filtrate was concentrated under reduced pressure. This resulted in (3R)-2-amino-3-(benzyloxy)-2-methylbutanenitrile (2.1 g, 91.61%). LCMS (ES) $[M+H]^+$ m/z:205

Synthesis of (3R)-2-amino-3-hydroxy-2-methylbutanoic acid hydrochloride

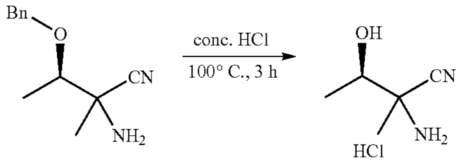

A solution of (3R)-2-amino-3-(benzyloxy)-2-methylbutanenitrile (1 g, 4.895 mmol, 1.0 equiv) in conc.HCl (10 mL) was stirred for 3 h at 100° C. The mixture was allowed to cool down to room temperature. The resulting mixture was extracted with EtOAc (2x20 mL). The aqueous layer was dried by lyophilization. This resulted in (3R)-2-amino-3-hydroxy-2-methylbutanoic acid hydrochloride (700 mg, 84.31%). LCMS (ES) $[M+H]^+$ m/z:134

Synthesis of (2R,3R)-2-amino-3-[(tert-butyldiphenylsilyl)oxy]-2-methylbutanoic acid and (2S,3R)-2-amino-3-[(tert-butyldiphenylsilyl)oxy]-2-methylbutanoic acid

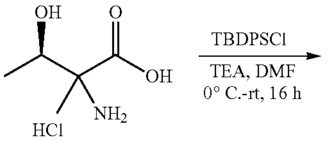

-continued

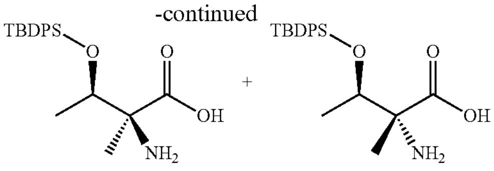

Assumed Assumed

To a stirred solution of (3R)-2-amino-3-hydroxy-2-methylbutanoic acid hydrochloride (600 mg, 3.538 mmol, 1.0 equiv) in DMF (10 mL) were added TEA (1.07 g, 10.614 mmol, 3.0 equiv) and tert-butyl(chloro)diphenylsilane (1.46 g, 5.307 mmol, 1.5 equiv) in portions at 0° C. under nitrogen atmosphere. The resulting mixture was stirred for 16 h at room temperature. The mixture was purified by reversed-phase flash chromatography with the following conditions: column, C18 silica gel; mobile phase, MeCN in Water (0.1% FA), 10% to 50% gradient in 15 min; detector, UV 254 nm. This resulted in (2R,3R)-2-amino-3-[(tert-butyldiphenylsilyl)oxy]-2-methylbutanoic acid (240 mg, 18.26%) and (2S, 3R)-2-amino-3-[(tert-butyldiphenylsilyl)oxy]-2-methylbutanoic acid (240 mg, 18.26%). LCMS (ES) $[M+H]^+$ m/z:372

$^1H$ NMR (300 MHz, DMSO-$d_6$) δ 7.79-7.66 (m, 4H), 7.51-7.35 (m, 6H), 4.26 (q, J=6.4 Hz, 1H), 1.13 (s, 3H), 0.95 (s, 9H), 0.86 (d, J=6.5 Hz, 3H).

$^1H$ NMR (300 MHz, DMSO-$d_6$) δ 7.73-7.62 (m, 4H), 7.52-7.38 (m, 6H), 3.91 (q, J=6.3 Hz, 1H), 1.31 (s, 3H), 1.01 (s, 9H), 0.90 (d, J=6.4 Hz, 3H).

Synthesis of (2S,3R)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide

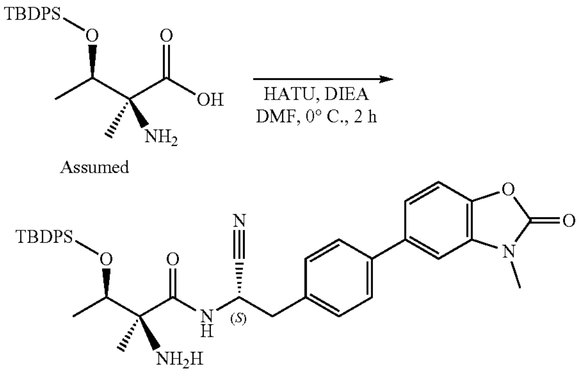

Assumed

Assumed

To a stirred solution of (2S,3R)-2-amino-3-[(tert-butyldiphenylsilyl)oxy]-2-methylbutanoic acid (240 mg, 0.646 mmol, 1.0 equiv) and (2S)-2-amino-3-[4-(3-methyl-2-oxo-1,3-benzoxazol-5-yl)phenyl]propanenitrile (189 mg, 0.646 mmol, 1.0 equiv) in DMF (3 mL) were added DIEA (250 mg, 1.938 mmol, 3.0 equiv) and HATU (319 mg, 0.840 mmol, 1.3 equiv) in portions at 0° C. under nitrogen atmosphere. The resulting mixture was stirred for 2 h at 0° C. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EA (1:1) to afford (2S,3R)-2-amino-3-[(tert-butyldiphenylsilyl)oxy]-N-[(1S)-1-cyano-2-[4-(3-methyl-2-oxo-1,3-benzoxazol-5-yl)phenyl]ethyl]-2-methylbutanamide (150 mg, 35.90%). LCMS (ES) $[M+H]^+$ m/z:647

Synthesis of (2S,3R)-2-amino-N-[(1S)-1-cyano-2-[4-(3-methyl-2-oxo-1,3-benzoxazol-5-yl)phenyl]ethyl]-3-hydroxy-2-methylbutanamide

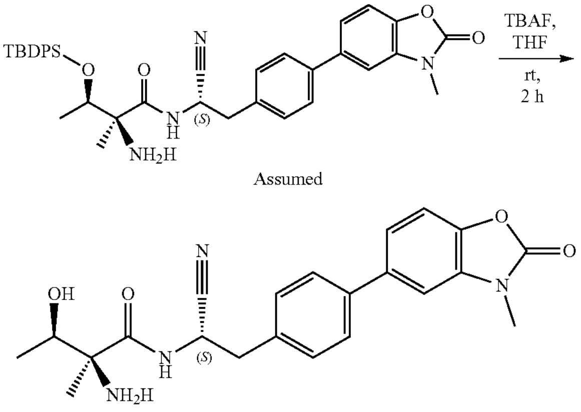

Assumed

Assumed
compound 171A

To a stirred solution of (2S,3R)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide (150 mg, 0.232 mmol, 1.0 equiv) in THE (2 mL) was added TBAF (60 mg, 0.232 mmol, 1.0 equiv). The resulting mixture was stirred for 2 h at room temperature. The resulting mixture was extracted with EtOAc (10×mL). The combined organic layers were washed with brine (20 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3 \cdot H_2O$), 10% to 50% gradient in 15 min; detector, UV 254 nm. This resulted in (2S,3R)-2-amino-N-[(1S)-1-cyano-2-[4-(3-methyl-2-oxo-1,3-benzoxazol-5-yl)phenyl]ethyl]-3-hydroxy-2-methylbutanamide (30 mg, 31.67%). LCMS (ES) $[M+H]^+$ m/z:409.

Chiral analysis data: (R,R) -WHELK-01 50*4.6 mm, 3.5 μm,

Method comment: Co-Solvent: MeOH/DCM=1/1(20 mM $NH_3$)

Gradient(B %): 10% to 50% in 2.0 min, hold 1.0 min at 50%.

Back Pressure(bar): 150

Column Temperature:35

Flow: 3.0 ml/min

Retention time=1.185 min (total: 3 min)

$^1H$ NMR (300 MHz, DMSO-$d_6$) δ 7.71-7.62 (m, 2H), 7.59 (dd, J=1.7, 0.8 Hz, 1H), 7.48-7.35 (m, 4H), 5.02-4.91 (m, 1H), 4.68 (s, 1H), 3.81 (d, J=6.5 Hz, 1H), 3.41 (s, 3H), 3.18 (d, J=7.5 Hz, 2H), 0.99 (s, 3H), 0.89 (d, J=6.3 Hz, 3H).

Synthesis of (2R,3R)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide

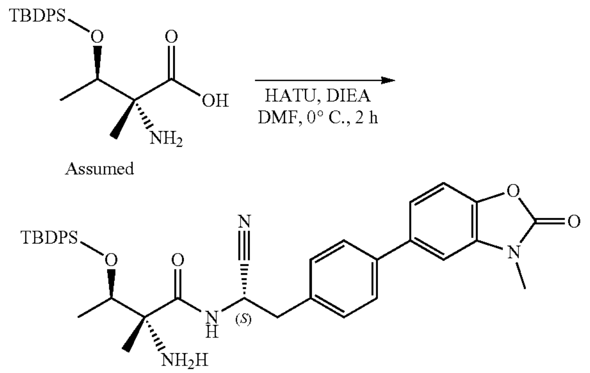

Assumed

Assumed

To a stirred solution of (2R,3R)-2-amino-3-[(tert-butyldiphenylsilyl)oxy]-2-methylbutanoic acid (240 mg, 0.646 mmol, 1.0 equiv) and (2S)-2-amino-3-[4-(3-methyl-2-oxo-1,3-benzoxazol-5-yl)phenyl]propanenitrile (189 mg, 0.646 mmol, 1.0 equiv) in DMF (3 mL) were added DIEA (250 mg, 1.938 mmol, 3.0 equiv) and HATU (319 mg, 0.840 mmol, 1.3 equiv) in portions at 0° C. under nitrogen atmosphere. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EA (1:1) to afford (2R,3R)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide (200 mg, 47.87%). LCMS (ES) [M−H]—m/z:647.

Synthesis of (2R,3R)-2-amino-N-[(1S)-1-cyano-2-[4-(3-methyl-2-oxo-1,3-benzoxazol-5-yl)phenyl]ethyl]-3-hydroxy-2-methylbutanamide

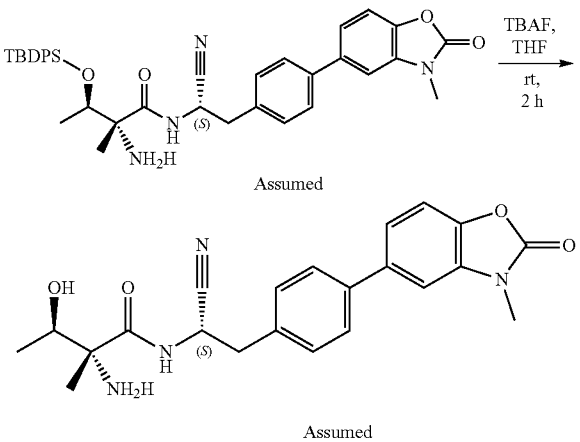

Assumed

Assumed
compound 171C

To a stirred solution of (2R,3R)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide (150 mg, 0.232 mmol, 1.0 equiv) in THE (2 mL) was added TBAF (60 mg, 0.232 mmol, 1.0 equiv). The resulting mixture was stirred for 2 h at room temperature. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3 \cdot H_2O$), 10% to 50% gradient in 15 min; detector, UV 254 nm. This resulted in (2R,3R)-2-amino-N-[(1S)-1-cyano-2-[4-(3-methyl-2-oxo-1,3-benzoxazol-5-yl)phenyl]ethyl]-3-hydroxy-2-methylbutanamide (30 mg, 31.67%). LCMS (ES) [M−H]*m/z:409

Chiral analysis data: (R,R) -WHELK-01 50*4.6 mm, 3.5 μm,

Method comment: Co-Solvent: MeOH/DCM=1/1(20 mM $NH_3$)

Gradient(B %): 10% to 50% in 2.0 min, hold 1.0 min at 50%.

Back Pressure(bar): 150

Column Temperature:35

Flow: 3.0 ml/min

Retention time=1.206 min (total: 3 min)

$^1$H NMR (300 MHz, DMSO-$d_6$) δ 7.72-7.63 (m, 2H), 7.62-7.55 (m, 1H), 7.47-7.35 (m, 4H), 5.03-4.92 (m, 1H), 4.75 (s, 1H), 3.64 (q, J=6.4 Hz, 1H), 3.41 (s, 3H), 3.30-3.11 (m, 2H), 1.07 (s, 3H), 0.89 (d, J=6.3 Hz, 3H).

Example 32. Synthesis of Compound 171B and 171D: (2S,3S)-2-amino-N-[(1S)-1-cyano-2-[4-(3-methyl-2-oxo-1,3-benzoxazol-5-yl)phenyl]ethyl]-3-hydroxy-2-methylbutanamide and (2R,3S)-2-amino-N-[(1S)-1-cyano-2-[4-(3-methyl-2-oxo-1,3-benzoxazol-5-yl)phenyl]ethyl]-3-hydroxy-2-methylbutanamide

171B

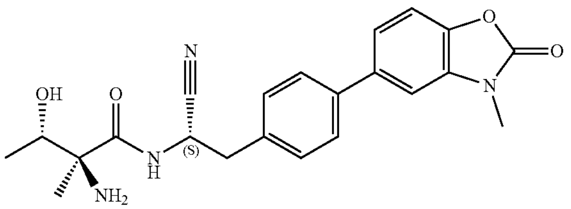

Assumed

171D

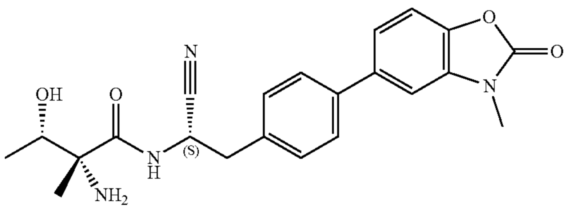

Assumed

-continued

Synthesis scheme:

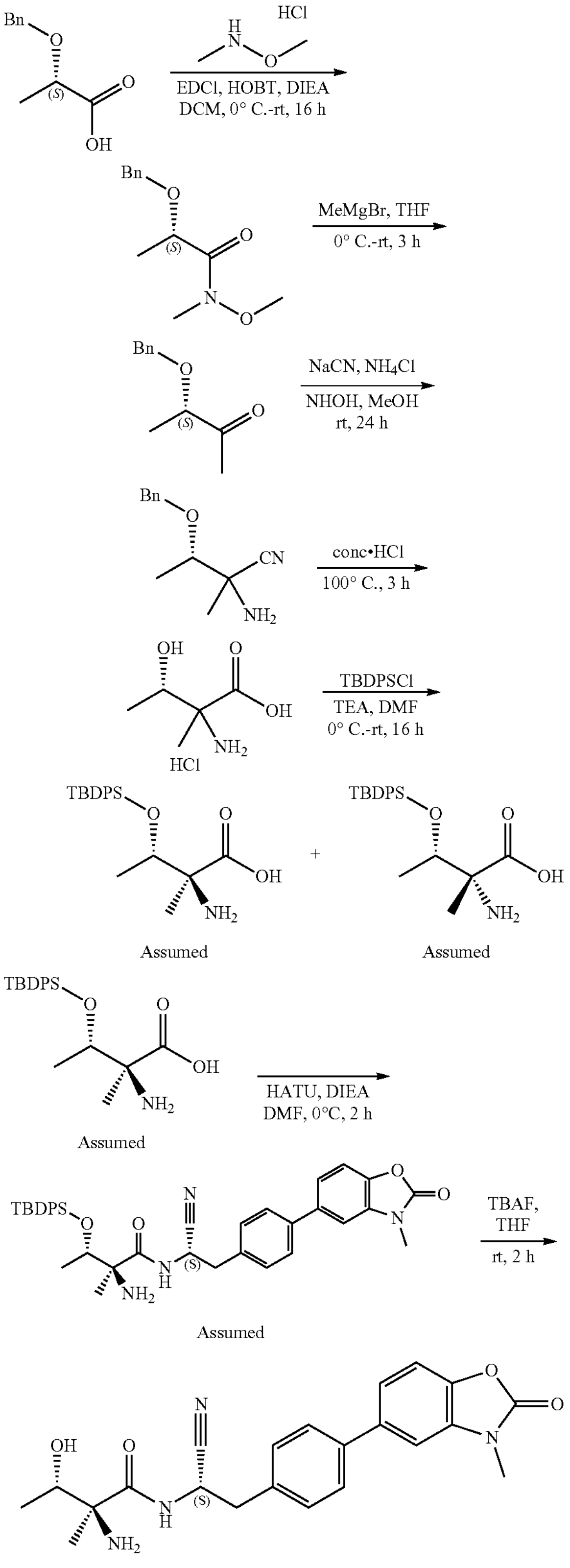

Assumed compound 171B

-continued

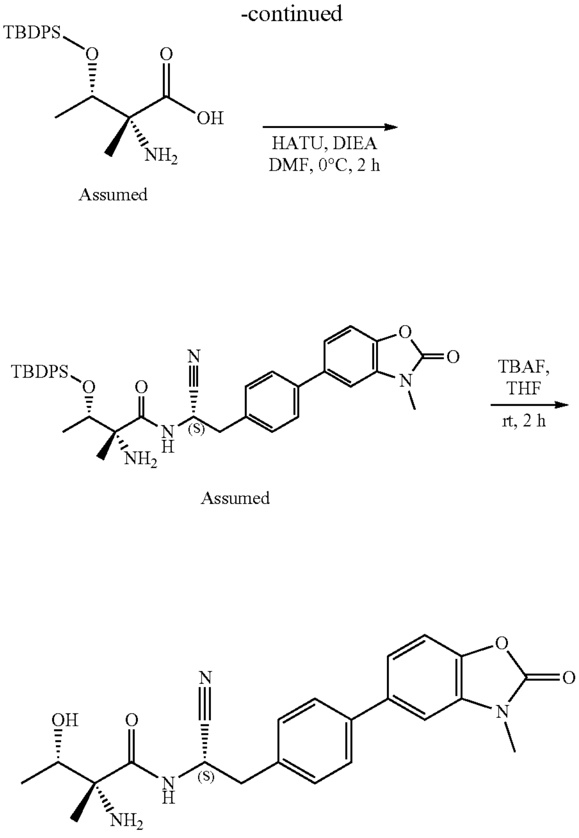

Assumed compound 171D

Synthesis of (2S)-2-(benzyloxy)-N-methoxy-N-methylpropanamide

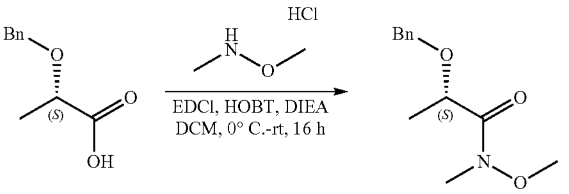

To a stirred solution of (2S)-2-(benzyloxy)propanoic acid (10 g, 55.493 mmol, 1.0 equiv) and N,O-dimethylhydroxylamine hydrochloride (8.12 g, 83.240 mmol, 1.5 equiv) in DCM (100 mL) were added DIEA (28.69 g, 221.972 mmol, 4.0 equiv) and HOBT (9.00 g, 66.592 mmol, 1.2 equiv) and EDCI (15.96 g, 83.240 mmol, 1.5 equiv) at 0° C. under nitrogen atmosphere. The resulting mixture was stirred for 16 h at room temperature. The resulting mixture was extracted with $CH_2Cl_2$ (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (3:1) to afford (2S)-2-(benzyloxy)-N-methoxy-N-methylpropanamide (12 g, 96.85%). LCMS (ES) $[M+H]^+$ m/z:224.

Synthesis of (3S)-3-(benzyloxy)butan-2-one

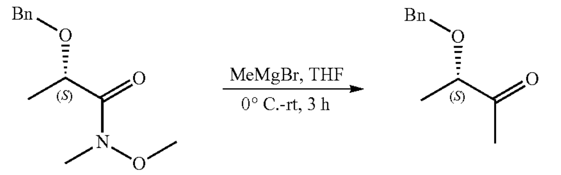

To a stirred solution of (2S)-2-(benzyloxy)-N-methoxy-N-methylpropanamide (5 g, 22.394 mmol, 1.0 equiv) in THE (60 mL) was added bromo(methyl)magnesium (33.5 mL, 33.591 mmol, 1.50 equiv) dropwise at 0° C. under nitrogen atmosphere. The resulting mixture was stirred for 3 h at room temperature under nitrogen atmosphere. The reaction was quenched by the addition of sat. $NH_4Cl$ (aq.) (20 mL) at 0° C. The resulting mixture was extracted with EtOAc (3×50 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (4:1) to afford (3S)-3-(benzyloxy)butan-2-one (3.5 g, 87.69%). LCMS (ES):no signal. $^1H$ NMR (300 MHz, DMSO-$d_6$) δ 7.43-7.24 (m, 5H), 4.53 (d, J=11.7 Hz, 1H), 4.46 (d, J=11.8 Hz, 1H), 3.97 (q, J=6.9 Hz, 1H), 2.15 (s, 3H), 1.24 (d, J=6.9 Hz, 3H).

Synthesis of (3S)-2-amino-3-(benzyloxy)-2-methylbutanenitrile

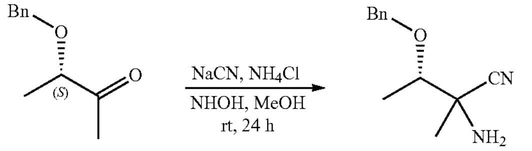

To a stirred solution of $NH_4Cl$ (1.20 g, 22.442 mmol, 2.0 equiv) in $NH_3H_2O$ (20 mL) was added NaCN (1.37 g, 28.053 mmol, 2.5 equiv) at room temperature. To the above mixture was added a solution of (3S)-3-(benzyloxy)butan-2-one (2 g, 11.221 mmol, 1.0 equiv) in MeOH (20 mL) dropwise at room temperature. The resulting mixture was stirred for additional 24 h at room temperature. The resulting mixture was concentrated under reduced pressure. The resulting mixture was extracted with EtOAc (3×50 mL). The combined organic layers were washed with brine (50 mL), dried over anhydrous $Na_2SO_4$. After filtration, the filtrate was concentrated under reduced pressure. This resulted in (3S)-2-amino-3-(benzyloxy)-2-methylbutanenitrile (2.0 g, 87.25%). LCMS (ES) $[M+H]^+$ m/z:205

Synthesis of (3S)-2-amino-3-hydroxy-2-methylbutanoic acid hydrochloride

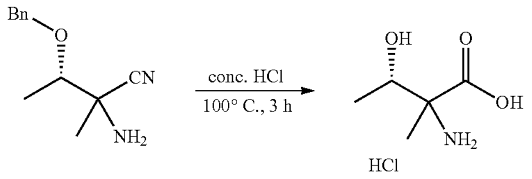

A solution of (3S)-2-amino-3-(benzyloxy)-2-methylbutanenitrile (1 g, 4.895 mmol, 1.0 equiv) in conc.HCl (10 mL) was stirred for 3 h at 100° C. The mixture was allowed to cool down to room temperature. The resulting mixture was extracted with EtOAc (2×20 mL). The aqueous layer was dried by lyophilization. This resulted in (3S)-2-amino-3-hydroxy-2-methylbutanoic acid hydrochloride (700 mg, 84.31%). LCMS (ES) $[M+H]^+$ m/z:134

Synthesis of (2R,3S)-2-amino-3-[(tert-butyldiphenylsilyl)oxy]-2-methylbutanoic acid and (2S,3S)-2-amino-3-[(tert-butyldiphenylsilyl)oxy]-2-methylbutanoic acid

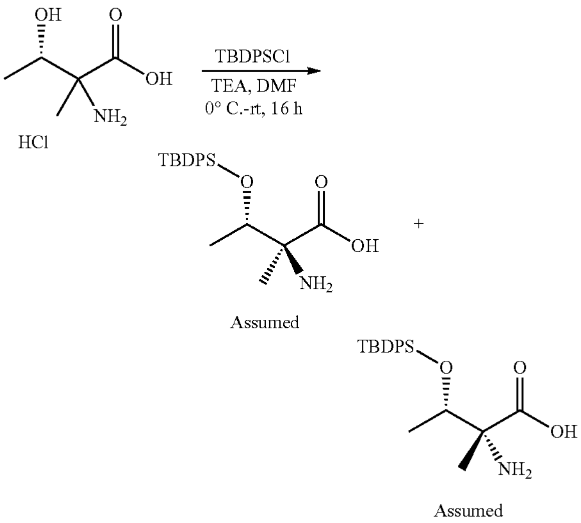

To a stirred solution of (3S)-2-amino-3-hydroxy-2-methylbutanoic acid hydrochloride (700 mg, 4.127 mmol, 1.0 equiv) in DMF (10 mL) were added TEA (1.25 g, 12.381 mmol, 3.0 equiv) and tert-butyl(chloro)diphenylsilane (1.70 g, 6.191 mmol, 1.5 equiv) dropwise at 0° C. under nitrogen atmosphere. The resulting mixture was stirred for 16 h at room temperature. The mixture was purified by reversed-phase flash chromatography with the following conditions: column, C18 silica gel; mobile phase, MeCN in Water (0.1% FA), 10% to 55% gradient in 15 min; detector, UV 254 nm. This resulted in (2R,3S)-2-amino-3-[(tert-butyldiphenylsilyl)oxy]-2-methylbutanoic acid (250 mg, 16.30%) and (2S,3S)-2-amino-3-[(tert-butyldiphenylsilyl)oxy]-2-methylbutanoic acid (250 mg, 16.30%). LCMS (ES) $[M+H]^+$ m/z:372

$^1H$ NMR (300 MHz, DMSO-$d_6$) δ 7.80-7.65 (m, 4H), 7.51-7.33 (m, 6H), 4.27 (q, J=6.5 Hz, 1H), 1.13 (s, 3H), 0.95 (s, 9H), 0.86 (d, J=6.5 Hz, 3H).

$^1$H NMR (300 MHz, DMSO-$d_6$) δ 7.73-7.62 (m, 4H), 7.55-7.37 (m, 6H), 3.92 (q, J=6.3 Hz, 1H), 1.31 (s, 3H), 1.01 (s, 9H), 0.90 (d, J=6.4 Hz, 3H).

Synthesis of (2S,3S)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide

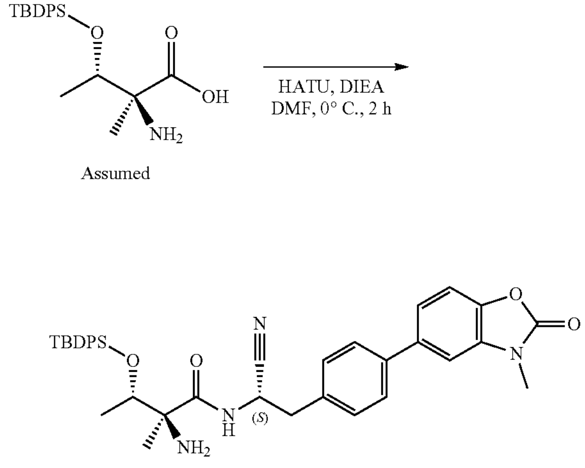

Assumed

Assumed

To a stirred solution of (2S,3S)-2-amino-3-[(tert-butyldiphenylsilyl)oxy]-2-methylbutanoic acid (250 mg, 0.673 mmol, 1.0 equiv) and (2S)-2-amino-3-[4-(3-methyl-2-oxo-1,3-benzoxazol-5-yl)phenyl]propanenitrile (197 mg, 0.673 mmol, 1.0 equiv) in DMF (3 mL) were added DIEA (260 mg, 2.019 mmol, 3.0 equiv) and HATU (332 mg, 0.875 mmol, 1.3 equiv) in portions at 0° C. under nitrogen atmosphere. The resulting mixture was stirred for 2 h at 0° C. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EA (1:1) to afford (2S,3S)-2-amino-3-[(tert-butyldiphenylsilyl)oxy]—N-[(1 S)-1-cyano-2-[4-(3-methyl-2-oxo-1,3-benzoxazol-5-yl)phenyl]ethyl]-2-methylbutanamide (150 mg, 34.46%). LCMS (ES) $[M+H]^+$ m/z:647

Synthesis of (2S,3S)-2-amino-N-[(1S)-1-cyano-2-[4-(3-methyl-2-oxo-1,3-benzoxazol-5-yl)phenyl]ethyl]-3-hydroxy-2-methylbutanamide

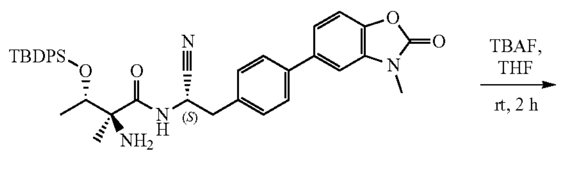

Assumed

-continued

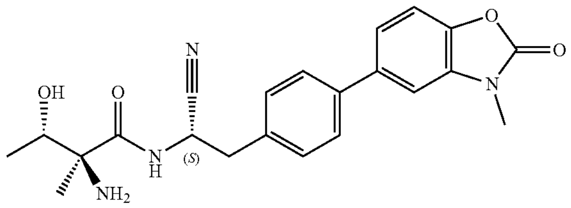

Assumed
compound 171A

To a stirred solution of (2S,3S)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide (150 mg, 0.232 mmol, 1.0 equiv) in THE (2 mL) was added TBAF (60 mg, 0.232 mmol, 1.0 equiv). The resulting mixture was stirred for 2 h at room temperature. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3 \cdot H_2O$), 10% to 50% gradient in 15 min; detector, UV 254 nm. This resulted in (2S,3S)-2-amino-N-[(1S)-1-cyano-2-[4-(3-methyl-2-oxo-1,3-benzoxazol-5-yl)phenyl]ethyl]-3-hydroxy-2-methylbutanamide (30 mg, 31.67%).

LCMS (ES) $[M+H]^+$ m/z:409

Chiral analysis data:(R,R) -WHELK-01 50*4.6 mm, 3.5 μm,

Method comment: Co-Solvent: MeOH/DCM=1/1(20 mM $NH_3$)

Gradient(B %): 10% to 50% in 2.0 min, hold 1.0 min at 50%.

Back Pressure(bar): 150

Column Temperature:35

Flow: 3.0 ml/min

Retention time=1.265 min (total: 3 min)

$^1$H NMR (300 MHz, DMSO-$d_6$) δ 7.71-7.62 (m, 2H), 7.67-7.55 (m, 1H), 7.47-7.35 (m, 4H), 5.04-4.93 (m, 1H), 4.73 (s, 1H), 3.90 (q, J=6.3 Hz, 1H), 3.41 (s, 3H), 3.24-3.15 (m, 2H), 0.95 (d, J=6.4 Hz, 3H), 0.84 (s, 3H).

Synthesis of (2R,3S)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide

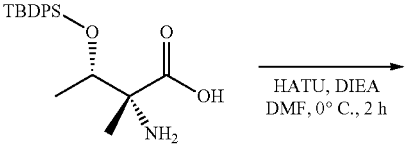

Assumed

-continued

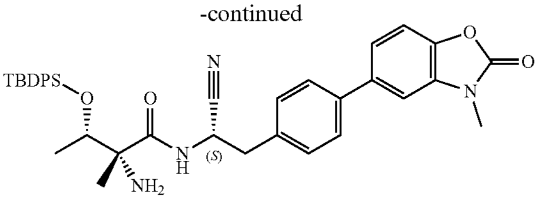

Assumed

To a stirred solution of (2R,3S)-2-amino-3-[(tert-butyldiphenylsilyl)oxy]-2-methylbutanoic acid (250 mg, 0.673 mmol, 1.0 equiv) and (2S)-2-amino-3-[4-(3-methyl-2-oxo-1,3-benzoxazol-5-yl)phenyl]propanenitrile (197 mg, 0.673 mmol, 1.0 equiv) in DMF (3 mL) were added DIEA (260 mg, 2.019 mmol, 3.0 equiv) and HATU (332 mg, 0.875 mmol, 1.3 equiv) in portions at 0° C. under nitrogen atmosphere. The resulting mixture was stirred for 2 h at 0° C. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EA (1:1) to afford (2R,3S)-2-amino-3-[(tert-butyldiphenylsilyl)oxy]-N-[(1S)-1-cyano-2-[4-(3-methyl-2-oxo-1,3-benzoxazol-5-yl)phenyl]ethyl]-2-methylbutanamide (150 mg, 34.46%). LCMS (ES) [M–H]—m/z:647

Synthesis of (2R,3S)-2-amino-N-[(1S)-1-cyano-2-[4-(3-methyl-2-oxo-1,3-benzoxazol-5-yl)phenyl]ethyl]-3-hydroxy-2-methylbutanamide

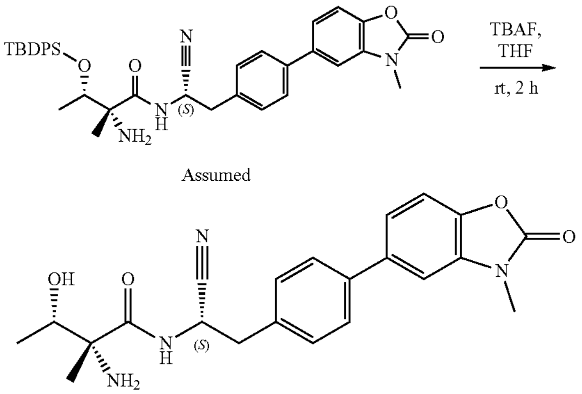

Assumed

Assumed
Compound 171D

To a stirred solution of (2R,3S)-2-amino-3-[(tert-butyldiphenylsilyl)oxy]—N-[(1S)-1-cyano-2-[4-(3-methyl-2-oxo-1,3-benzoxazol-5-yl)phenyl]ethyl]-2-methylbutanamide (150 mg, 0.232 mmol, 1.0 equiv) in THE (2 mL) was added TBAF (60 mg, 0.232 mmol, 1.0 equiv). The resulting mixture was stirred for 2 h at room temperature. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3 \cdot H_2O$), 10% to 50% gradient in 15 min; detector, UV 254 nm. This resulted in (2R,3S)-2-amino-N-[(1S)-1-cyano-2-[4-(3-methyl-2-oxo-1,3-benzoxazol-5-yl)phenyl]ethyl]-3-hydroxy-2-methylbutanamide (30 mg, 31.67%).

LCMS (ES) [M–H]*m/z:409

Chiral analysis data: (R,R) -WHELK-01 50*4.6 mm, 3.5 μm,

Method comment: Co-Solvent: MeOH/DCM=1/1(20 mM $NH_3$)

Gradient(B %): 10% to 50% in 2.0 min, hold 1.0 min at 50%.

Back Pressure(bar): 150

Column Temperature:35

Flow: 3.0 ml/min

Retention time=1.249 min (total: 3 min)

$^1$H NMR (300 MHz, DMSO-$d_6$) δ 7.70-7.61 (m, 2H), 7.57 (d, J=1.2 Hz, 1H), 7.44-7.36 (m, 4H), 4.98 (t, J=7.9 Hz, 1H), 4.66 (s, 1H), 3.61 (q, J=6.2 Hz, 1H), 3.41 (s, 3H), 3.21 (d, J=7.8 Hz, 2H), 1.15 (s, 3H), 0.68 (d, J=6.3 Hz, 3H).

Example 33. Synthesis of Compound 225: (3S)-3-amino-N-[(1S)-1-cyano-2-[4-(3-methyl-2-oxo-1,3-benzoxazol-5-yl)phenyl]ethyl]-4-(3-hydroxyphenyl)butanamide

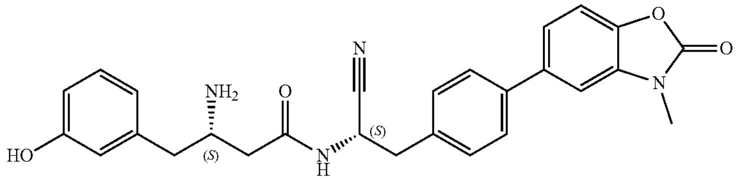

-continued

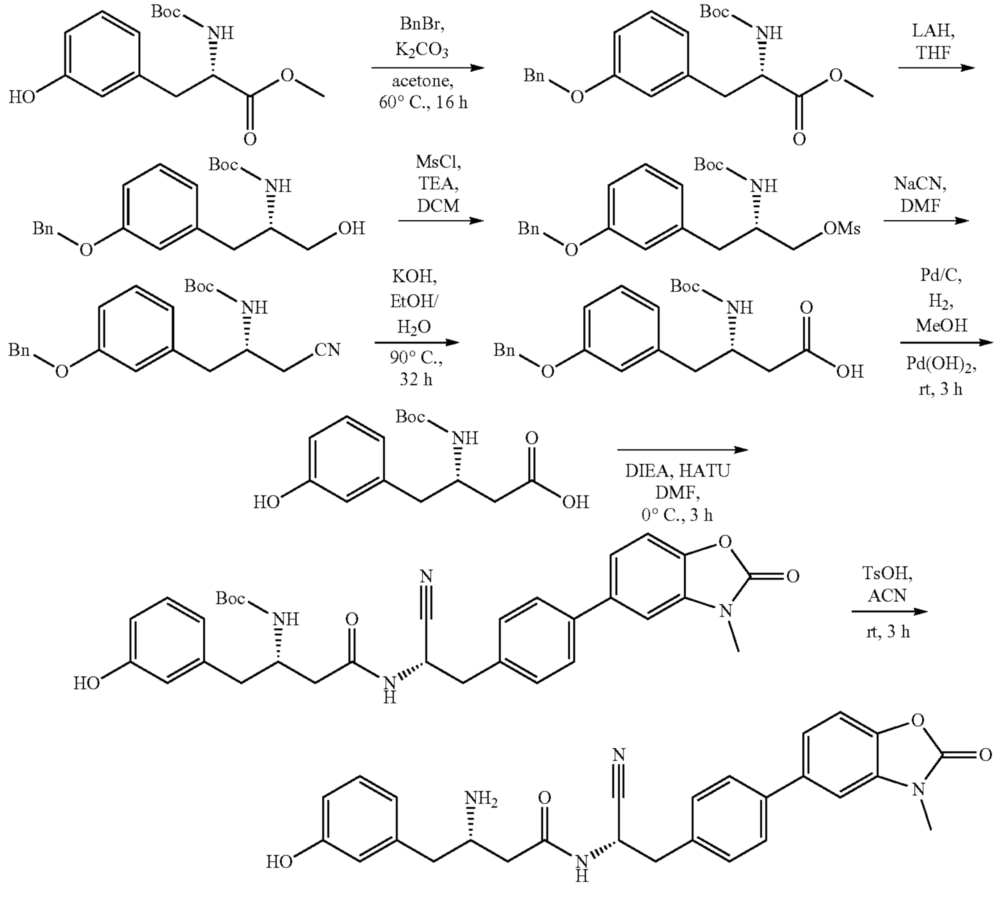

compound 225

Synthesis of methyl (2S)-3-[3-(benzyloxy)phenyl]-2-[(tert-butoxycarbonyl)amino]propanoate

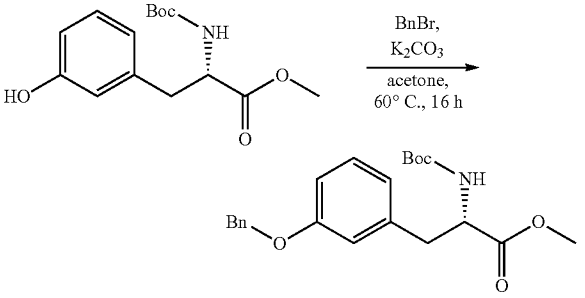

To a stirred solution of methyl (2S)-2-[(tert-butoxycarbonyl)amino]-3-(3-hydroxyphenyl)propanoate (5.0 g, 16.93 mmol, 1.0 equiv) in acetone (70 mL) were added $K_2CO_3$ (3.5 g, 25.39 mmol, 1.5 equiv) and BnBr (3.5 g, 20.31 mmol, 1.2 equiv). The resulting mixture was stirred for 16 h at 60° C. The mixture was allowed to cool down to room temperature. The resulting mixture was diluted with water (200 mL), extracted with EtOAc (3×100 mL). The combined organic layer was washed with brine (100 mL), dried over anhydrous $Na_2SO_4$. After filtration, the filtrate was concentrated under reduced pressure. The residue was purified by silica gel column chromatography, eluted with PE/EA (9:1) to afford methyl (2S)-3-[3-(benzyloxy)phenyl]-2-[(tert-butoxycarbonyl)amino]propanoate (5.8 g, 88.8%). LCMS (ES, m/z): $[M+H]^+$: 386.

Synthesis of tert-butyl N-[(2S)-1-[3-(benzyloxy)phenyl]-3-hydroxypropan-2-yl]carbamate

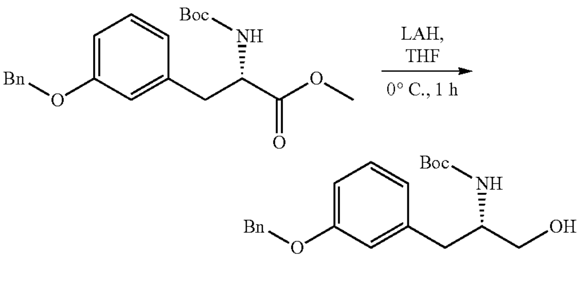

To a stirred solution of methyl (2S)-3-[3-(benzyloxy)phenyl]-2-[(tert-butoxycarbonyl)amino]propanoate (5.8 g, 15.04 mmol, 1.0 equiv) in THE (80 mL) were added LAH (1 M in THF)(9.0 mL, 18.06 mmol, 1.2 equiv) dropwise at 0° C. under nitrogen atmosphere. The resulting mixture was stirred for 1 h at 0° C. under nitrogen atmosphere. The reaction was quenched with $Na_2SO_4 \cdot 10H_2O$ at 0° C. The resulting mixture was filtered, the filter cake was washed with THE (3×50 mL). The filtrate was concentrated under reduced pressure. This resulted in tert-butyl N-[(2S)-1-[3-(benzyloxy)phenyl]-3-hydroxypropan-2-yl]carbamate (4.9 g, 91.1%). LCMS (ES, m/z): $[M+H]^+$: 358.

Synthesis of tert-butyl N-[(2S)-1-[3-(benzyloxy)phenyl]-3-(methanesulfonyloxy)propan-2-yl]carbamate

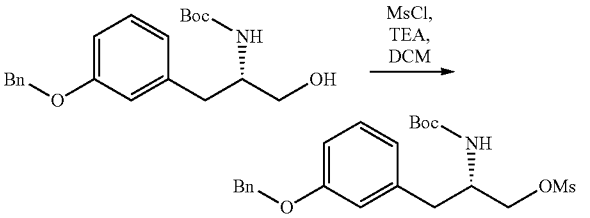

To a stirred solution of tert-butyl N-[(2S)-1-[3-(benzyloxy)phenyl]-3-hydroxypropan-2-yl]carbamate (4.8 g, 13.42 mmol, 1.0 equiv) and TEA (2.7 g, 26.85 mmol, 2.0 equiv) in DCM (70 mL) were added MsCl (1.8 g, 16.11 mmol, 1.2 equiv) dropwise at 0° C. under nitrogen atmosphere. The resulting mixture was stirred for 1 h at 0° C. under nitrogen atmosphere. The resulting mixture was quenched with water (100 mL), extracted with $CH_2Cl_2$ (3×100 mL). The combined organic layer was washed with brine (100 mL), dried over anhydrous $Na_2SO_4$. After filtration, the filtrate was concentrated under reduced pressure. This resulted in tert-butyl N-[(2S)-1-[3-(benzyloxy)phenyl]-3-(methanesulfonyloxy)propan-2-yl]carbamate (5.2 g, 88.9%). LCMS (ES, m/z): $[M+H]^+$: 436.

Synthesis of tert-butyl N-[(2S)-1-[3-(benzyloxy)phenyl]-3-cyanopropan-2-yl]carbamate

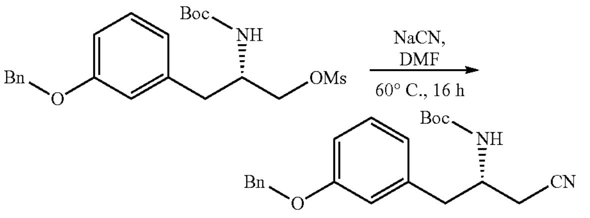

To a stirred solution of (2S)-3-[3-(benzyloxy)phenyl]-2-(methylamino)propyl methanesulfonate (5.0 g, 14.30 mmol, 1.0 equiv) in DMF (70 mL) was added NaCN (1.4 g, 28.61 mmol, 2.0 equiv). The resulting mixture was stirred for 16 h at 60° C. The mixture was allowed to cool down to room temperature, diluted with water (100 mL). The resulting mixture was extracted with EtOAc (3×100 mL). The combined organic layer was washed with brine (2×100 mL), dried over anhydrous $Na_2SO_4$. After filtration, the filtrate was concentrated under reduced pressure. The residue was purified by silica gel column chromatography, eluted with PE/EA (6:1) to afford tert-butyl N-[(2S)-1-[3-(benzyloxy)phenyl]-3-cyanopropan-2-yl]carbamate (3 g, 57.2%). LCMS (ES, m/z): $[M+H]^+$: 367.

Synthesis of (3S)-4-[3-(benzyloxy)phenyl]-3-[(tert-butoxycarbonyl)amino]butanoic acid

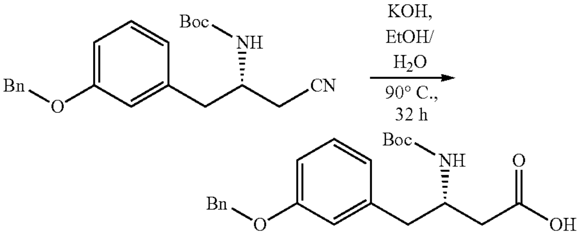

A solution of tert-butyl N-[(2S)-1-[3-(benzyloxy)phenyl]-3-cyanopropan-2-yl]carbamate (2.0 g, 5.45 mmol, 1.0 equiv) and KOH (0.6 g, 10.91 mmol, 2.0 equiv) in $H_2O$ (15 mL) was stirred for 32 h at 90° C. The resulting mixture was concentrated under reduced pressure. The mixture was acidified to pH 4 with HCl (1 M). The residue was purified by reversed-phase flash chromatography with the following conditions: column, C18 silica gel-120 g; mobile phase, MeCN in Water (0.1% TFA), 10% to 50% gradient in 10 min; detector, UV 254 nm. This resulted in (3S)-4-[3-(benzyloxy)phenyl]-3-[(tert-butoxycarbonyl)amino]butanoic acid (810 mg, 38.5%). LCMS (ES, m/z): $[M+H]^+$: 386.

Synthesis of (3S)-3-[(tert-butoxycarbonyl)amino]-4-(3-hydroxyphenyl)butanoic acid

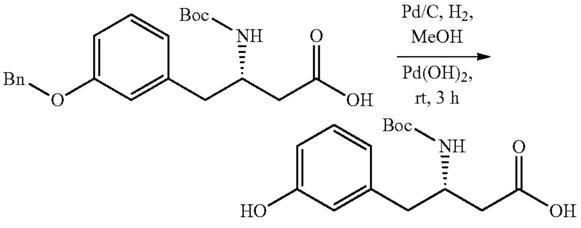

To a solution of (3S)-4-[3-(benzyloxy)phenyl]-3-[(tert-butoxycarbonyl)amino]butanoic acid (500 mg, 1.29 mmol, 1.0 equiv) in MeOH (10 mL) was added Pd/C (100 mg), $Pd(OH)_2/C$ (100 mg). The mixture was stirred for 3 h at room temperature under hydrogen atmosphere (10 atm). The resulting mixture was filtered, the filter cake was washed with MeOH (3×10 mL). The filtrate was concentrated under reduced pressure. This resulted in (3S)-3-[(tert-butoxycarbonyl)amino]-4-(3-hydroxyphenyl)butanoic acid. (400 mg, crude) and used to the next step without further purification. LCMS (ES, m/z): $[M+H]^+$: 296.

Synthesis of tert-butyl N-[(2S)-1-{[(1S)-1-cyano-2-[4-(3-methyl-2-oxo-1,3-benzoxazol-5-yl)phenyl]ethyl]carbamoyl}-3-(3-hydroxyphenyl)propan-2-yl]carbamate

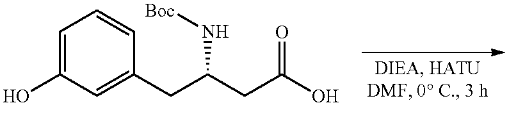

-continued

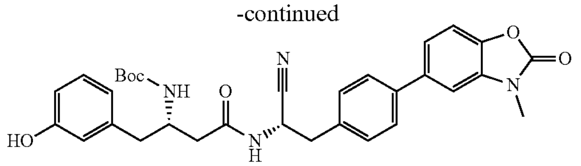

A solution of (2S)-2-amino-3-[4-(3-methyl-2-oxo-1,3-benzoxazol-5-yl)phenyl]propanenitrile (110 mg, 0.37 mmol, 1.0 equiv) in DMF (3 mL) was treated with (3S)-3-[(tert-butoxycarbonyl)amino]-4-(3-hydroxyphenyl)butanoic acid (166 mg, 0.56 mmol, 1.5 equiv), DIEA (145 mg, 1.12 mmol, 3.0 equiv). This was followed by the addition of HATU (171 mg, 0.45 mmol, 1.2 equiv) in portions at 0° C. The resulting mixture was stirred for 3 h at 0° C. The reaction was quenched with water (10 mL), extracted with ethyl acetate (30 mL×2). The combined organic phase was dried over anhydrous sodium sulfate. Filtered and the filtrate was concentrated under reduced pressure. The residue was purified by silica gel column chromatography, eluted with PE/THE (1:1) to afford tert-butyl N-[(2S)-1-{[(1S)-1-cyano-2-[4-(3-methyl-2-oxo-1,3-benzoxazol-5-yl)phenyl]ethyl]carbamoyl}-3-(3-hydroxyphenyl)propan-2-yl]carbamate (160 mg, 74.7%). LCMS (ES, m/z): $[M+H]^+$: 571.

Synthesis of (3S)-3-amino-N-[(1S)-1-cyano-2-[4-(3-methyl-2-oxo-1,3-benzoxazol-5-yl)phenyl]ethyl]-4-(3-hydroxyphenyl)butanamide $^1H$ NMR (400 MHz, DMSO-$d_6$) δ 9.24 (s, 1H), 8.91 (s, 1H), 7.69-7.61 (m, 2H), 7.52 (t, J=1.2 Hz, 1H), 7.45-7.32 (m, 4H), 7.04 (t, J=7.7 Hz, 1H), 6.56 (dtd, J=9.0, 7.0, 1.6 Hz, 3H), 5.01 (t, J=7.8 Hz, 1H), 3.39 (s, 3H), 3.22-3.01 (m, 3H), 2.46-2.33 (m, 2H), 2.15 (dd, J=14.5, 4.8 Hz, 1H), 2.06 (dd, J=14.6, 8.0 Hz, 1H), 1.50 (b rs, 2H).

Example 34. Synthesis of Compound 227A: (3S)-3-amino-N-[(1S)-1-cyano-2-[4-(3-methyl-2-oxo-1,3-benzoxazol-5-yl)phenyl]ethyl]-3-(2-hydroxyphenyl)propenamide

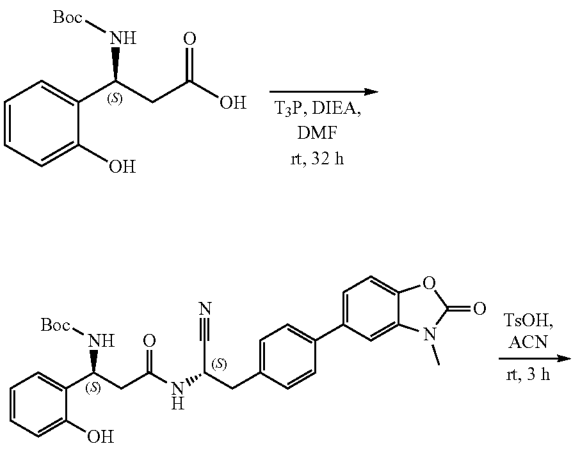

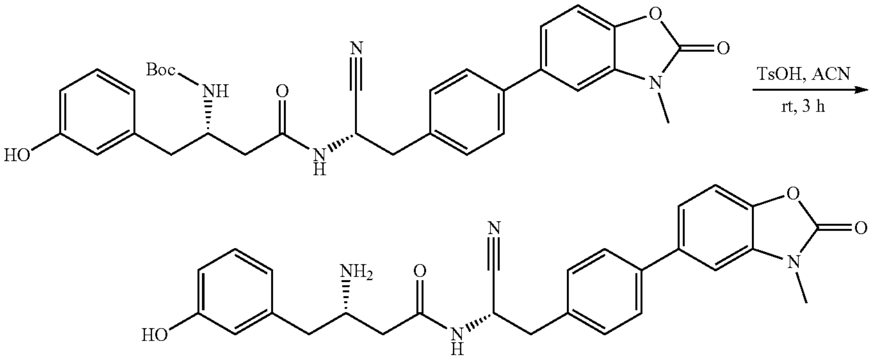

compound 225

Into a 25 mL round-bottom flask were added tert-butyl N-[(2S)-1-{[(1S)-1-cyano-2-[4-(3-methyl-2-oxo-1,3-benzoxazol-5-yl)phenyl]ethyl]carbamoyl}-3-(3-hydroxyphenyl)propan-2-yl]carbamate (150 mg, 0.26 mmol, 1.0 equiv) in ACN (3 mL) and $TsOH·H_2O$ (150 mg, 0.78 mmol, 3.0 equiv) a room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3·H_2O$), 10% to 50% gradient in 10 min; detector, UV 254 nm. This resulted in (3S)-3-amino-N-[(1S)-1-cyano-2-[4-(3-methyl-2-oxo-1,3-benzoxazol-5-yl)phenyl]ethyl]-4-(3-hydroxyphenyl)butanamide (20.3 mg, 16.4%).

LCMS (ES, m/z): $[M+H]^+$: 471.1.

-continued

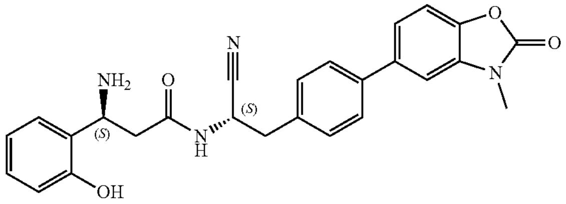

compound 227A

Synthesis of tert-butyl N-[(1S)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate

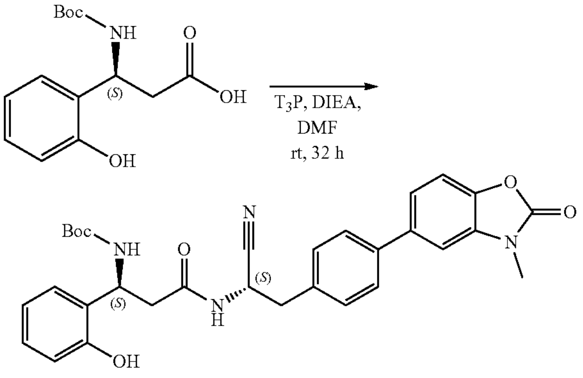

A solution of (2S)-2-amino-3-[4-(3-methyl-2-oxo-1,3-benzoxazol-5-yl)phenyl]propanenitrile (500 mg, 1.78 mmol, 1.0 equiv) in DMF (10 mL) was treated with (2S)-2-amino-3-[4-(3-methyl-2-oxo-1,3-benzoxazol-5-yl)phenyl]propanenitrile (523 mg, 1.78 mmol, 1.0 equiv), DIEA (661 mg, 5.11 mmol, 3.0 equiv). This was followed by the addition of $T_3P$ (50% in EA)(1.13 g, 1.78 mmol, 1.0 equiv) in portions at 0° C. The resulting mixture was stirred for 32 h at room temperature The reaction was quenched with water (20 mL), extracted with ethyl acetate (20 mL×2), dried over anhydrous sodium sulfate. After filtration, the filtrate was concentrated under reduced pressure. The residue was purified by silica gel column chromatography, eluted with PE/THE (1:1) to afford tert-butyl N-[(1S)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate (150 mg, 15.2%). LCMS (ES, m/z): $[M+H]^+$: 557.

Synthesis of (3S)-3-amino-N-[(1S)-1-cyano-2-[4-(3-methyl-2-oxo-1,3-benzoxazol-5-yl)phenyl]ethyl]-3-(2-hydroxyphenyl)propanamide

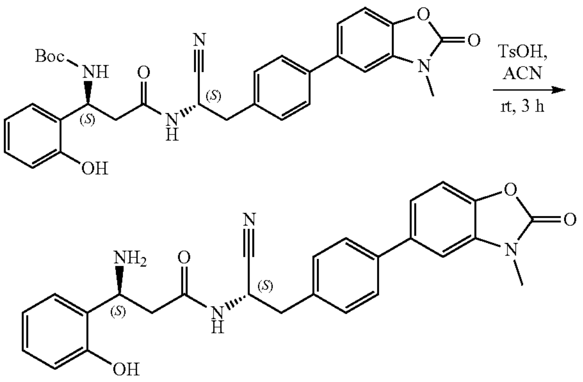

Into a 25 mL round-bottom flask were added tert-butyl N-[(1S)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate (130 mg, 0.23 mmol, 1.0 equiv) in ACN (3 mL) and TsOH-$H_2O$ (133 mg, 0.70 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (3S)-3-amino-N-[(1S)-1-cyano-2-[4-(3-methyl-2-oxo-1,3-benzoxazol-5-yl)phenyl]ethyl]-3-(2-hydroxyphenyl)propanamide (20.3 mg, 19.0%).

LCMS (ES, m/z): $[M+H]^+$: 457.4

$^1$H NMR (400 MHz, DMSO-d6) δ 8.93 (brs, 1H), 7.67 (d, J=8.1 Hz, 2H), 7.59 (d, J=1.6 Hz, 1H), 7.40 (dd, J=8.2, 4.0 Hz, 4H), 7.09-6.96 (m, 2H), 6.68 (t, J=7.6 Hz, 2H), 4.98 (t, J=7.8 Hz, 1H), 4.37 (t, J=6.9 Hz, 1H), 3.41 (s, 3H), 3.19-3.03 (m, 2H), 2.47 (d, J=6.9 Hz, 2H).

Example 35. Synthesis of Compound 227B: (3R)-3-amino-N-[(1S)-1-cyano-2-[4-(3-methyl-2-oxo-1,3-benzoxazol-5-yl)phenyl]ethyl]-3-(2-hydroxyphenyl)propanamide

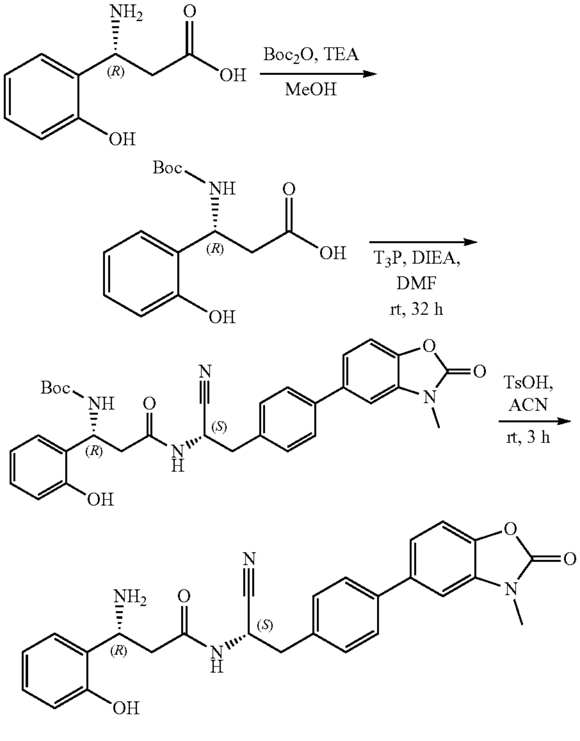

Synthesis of (2S)—N-[(1S)-1-cyano-4-(4-cyanophenyl)but-3-yn-1-yl]piperidine-2-carboxamide

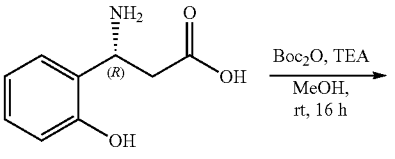

-continued

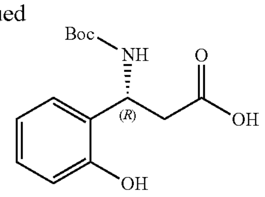

A solution of (3R)-3-amino-3-(2-hydroxyphenyl)propanoic acid (500 mg, 2.76 mmol, 1.0 equiv) and $Boc_2O$ (722 mg, 3.31 mmol, 1.2 equiv) in MeOH (10 mL) was stirred for 16 h at room temperature. The resulting mixture was concentrated under reduced pressure. The mixture was acidified to pH 4 with HCl (1 N). The resulting mixture was extracted with EtOAc (3×20 mL). The combined organic layer was washed with brine (3×10 mL), dried over anhydrous $Na_2SO_4$. After filtration, the filtrate was concentrated under reduced pressure. This resulted in (3R)-3-[(tert-butoxycarbonyl)amino]-3-(2-hydroxyphenyl)propanoic acid (610 mg, 78.5%). LCMS (ES, m/z): $[M+H]^+$: 282.

Synthesis of tert-butyl N-[(1R)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate

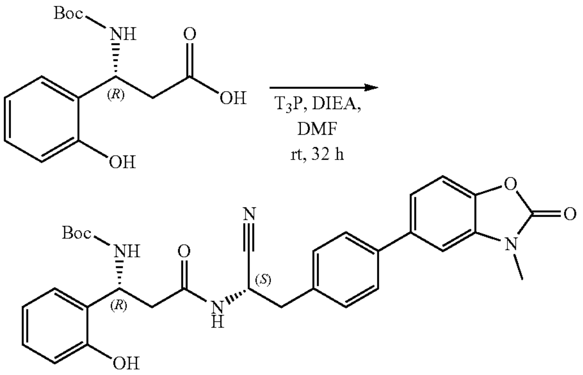

A solution of (2S)-2-amino-3-[4-(3-methyl-2-oxo-1,3-benzoxazol-5-yl)phenyl]propanenitrile (208 mg, 0.71 mmol, 1.0 equiv) in DMF (16 mL) was treated with (3R)-3-[(tert-butoxycarbonyl)amino]-3-(2-hydroxyphenyl)propanoic acid (400 mg, 1.42 mmol, 2.0 equiv), DIEA (276 mg, 2.13 mmol, 3.0 equiv). This was followed by the addition of $T_3P$ (452 mg, 0.71 mmol, 1.0 equiv, 50% in EA) in portions at 0° C. The resulting mixture was stirred for additional 32 h at room temperature. The reaction was quenched with water (20 mL), extracted with ethyl acetate (30 mL×2). The combined organic phase was washed with brine (20 mL×3), dried over anhydrous sodium sulfate. After filtration, the filtrate was concentrated under reduced pressure. The residue was purified by silica gel column chromatography, eluted with PE/THE (1:1) to afford tert-butyl N-[(1R)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate (150 mg, 37.9%). LCMS (ES, m/z): $[M+H]^+$: 557.

Synthesis of (3R)-3-amino-N-[(1S)-1-cyano-2-[4-(3-methyl-2-oxo-1,3-benzoxazol-5-yl)phenyl]ethyl]-3-(2-hydroxyphenyl)propanamide

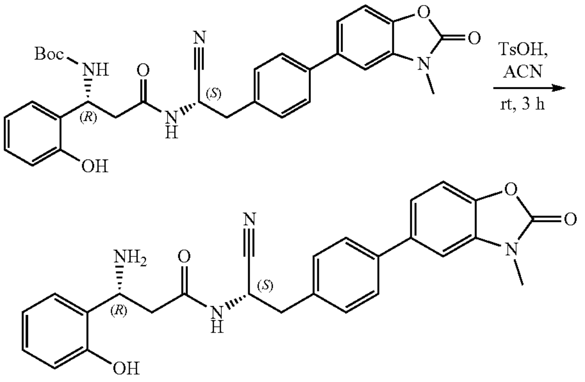

Into a 25 mL round-bottom flask were added tert-butyl N-[(1R)-2-{[(1S)-1-cyano-2-[4-(3-methyl-2-oxo-1,3-benzoxazol-5-yl)phenyl]ethyl]carbamoyl}-1-(2-hydroxyphenyl)ethyl]carbamate (150 mg, 0.26 mmol, 1.0 equiv) in ACN (4 mL) and $TsOH{\cdot}H_2O$ (91 mg, 0.53 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3{\cdot}H_2O$), 10% to 50% gradient in 10 min; detector, UV 254 nm. This resulted in (3R)-3-amino-N-[(1S)-1-cyano-2-[4-(3-methyl-2-oxo-1,3-benzoxazol-5-yl)phenyl]ethyl]-3-(2-hydroxyphenyl)propanamide (17.3 mg, 14%).

LCMS (ES, m/z): $[M+H]^+$: 457.1

$^1H$ NMR (400 MHz, DMSO-$d_6$) δ 8.91 (brs, 1H), 7.66 (d, J=8.1 Hz, 2H), 7.59 (d, J=1.6 Hz, 1H), 7.47-7.33 (m, 4H), 7.09-6.99 (m, 2H), 6.73-6.64 (m, 2H), 4.98 (t, J=7.8 Hz, 1H), 4.41-4.33 (m, 1H), 3.40 (s, 3H), 3.06 (dd, J=7.6, 4.3 Hz, 2H), 2.50-2.41 (m, 2H).

Example 36. Synthesis of Compound 228: 3-amino-N-[(1S)-1-cyano-2-[4-(3-methyl-2-oxo-1,3-benzoxazol-5-yl)phenyl]ethyl]-4-(2-hydroxyphenyl)butanamide

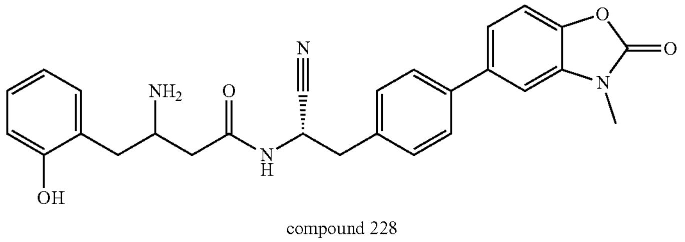

compound 228

-continued
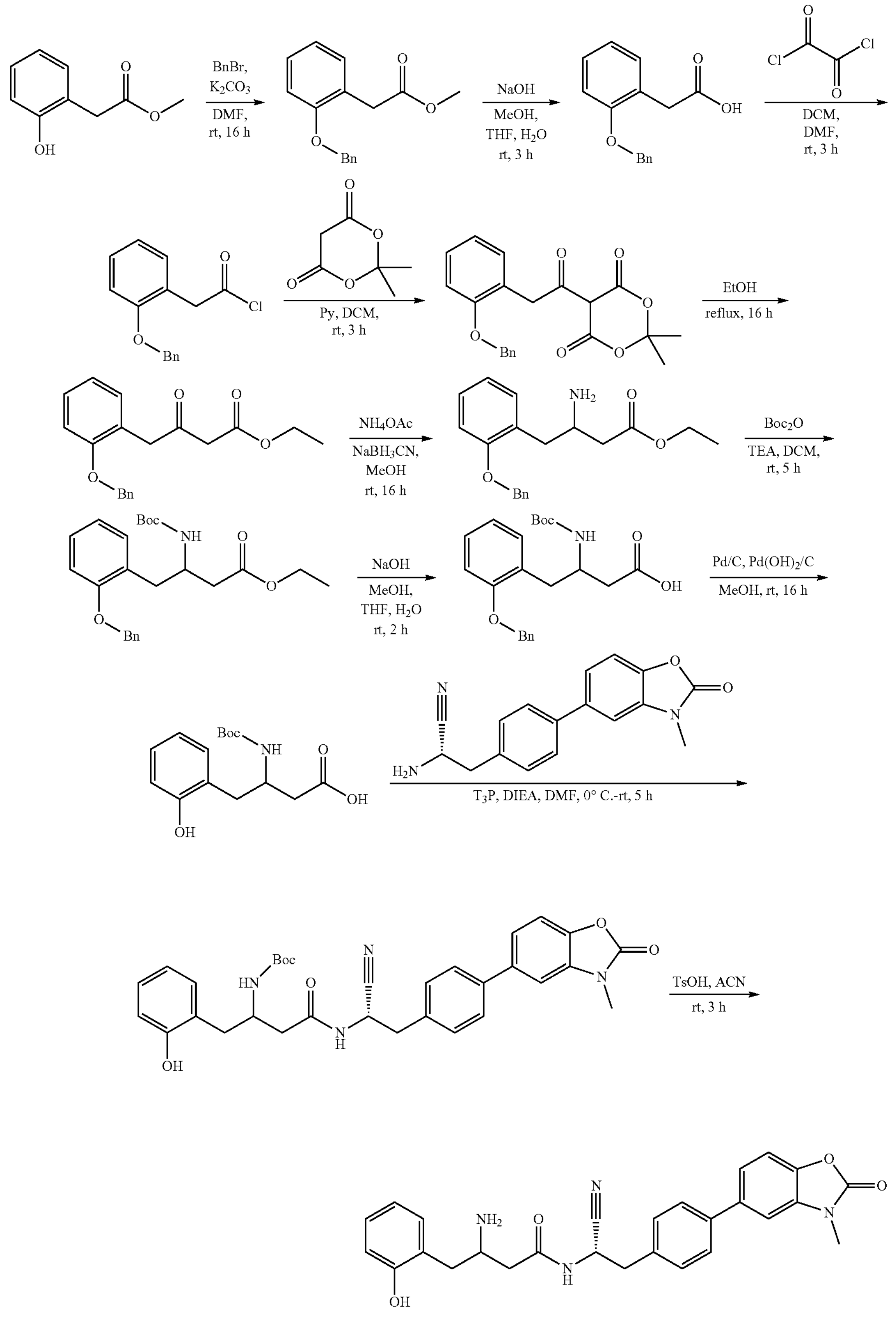

Synthesis of methyl 2-[2-(benzyloxy)phenyl]acetate

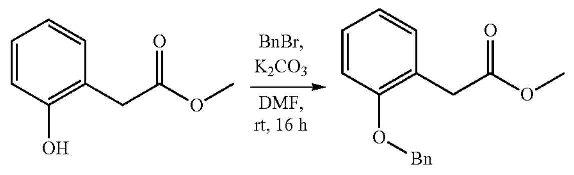 [SMILES: COC(=O)Cc1ccccc1O ; COC(=O)Cc1ccccc1OCc1ccccc1]

To a stirred solution of methyl 2-(2-hydroxyphenyl)acetate (6 g, 36.106 mmol, 1.0 equiv) in DMF (60 mL) was added $K_2CO_3$ (9.98 g, 72.212 mmol, 2.0 equiv) and benzyl bromide (8.03 g, 46.938 mmol, 1.3 equiv). The resulting mixture was stirred for 16 h at room temperature. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (8:1) to afford methyl 2-[2-(benzyloxy)phenyl]acetate (8 g, 86.45%). $^1H$ NMR (300 MHz, DMSO-d6) δ 7.47-7.34 (m, 4H), 7.40-7.27 (m, 1H), 7.32-7.18 (m, 2H), 7.06 (dd, J=8.3, 1.1 Hz, 1H), 6.92 (td, J=7.4, 1.1 Hz, 1H), 5.11 (s, 2H), 3.65 (s, 2H), 3.56 (s, 3H).

Synthesis of [2-(benzyloxy)phenyl]acetic acid

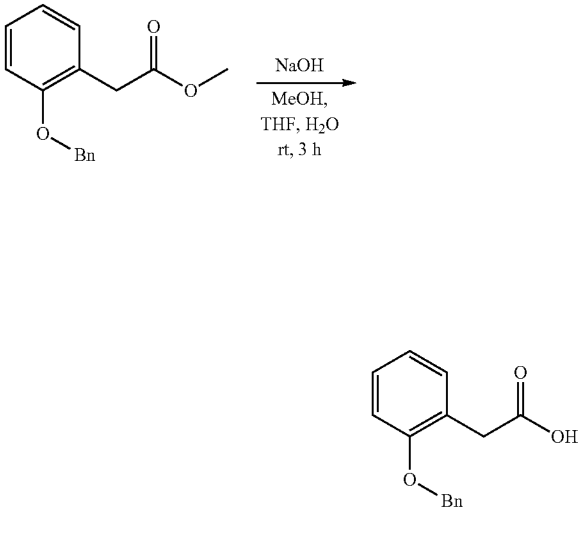

To a stirred solution of methyl 2-[2-(benzyloxy)phenyl]acetate (8 g, 31.213 mmol, 1.0 equiv) in MeOH (40 mL) and THF (40 mL) was added NaOH (2.50 g, 62.426 mmol, 2.0 equiv) in $H_2O$ (20 mL) dropwise. The resulting mixture was stirred for 3 h at room temperature. The resulting mixture was extracted with EtOAc (2×50 mL). The aqueous layer was acidified to pH 6 with citric acid. The resulting mixture was extracted with EtOAc (4×60 mL). The combined organic layers were dried over anhydrous $Na_2SO_4$. After filtration, the filtrate was concentrated under reduced pressure. This resulted in [2-(benzyloxy)phenyl]acetic acid (6.9 g, 91.24%). LCMS (ES) [M−H]—m/z:241.

Synthesis of [2-(benzyloxy)phenyl]acetyl chloride

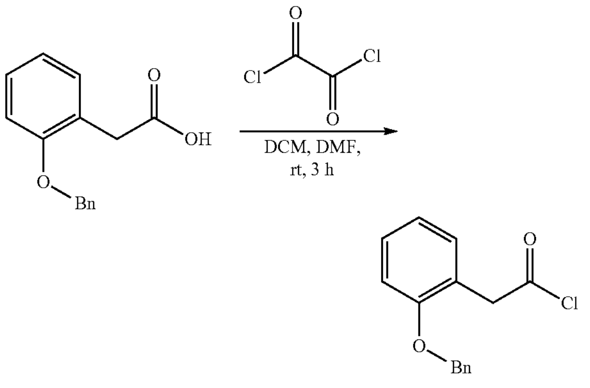

To a stirred solution of [2-(benzyloxy)phenyl]acetic acid (6.9 g, 28.480 mmol, 1.0 equiv) in DCM (80 mL) was added oxalyl chloride (5.42 g, 42.720 mmol, 1.5 equiv) and DMF (0.10 g, 1.424 mmol, 0.05 equiv) dropwise at 0° C. under nitrogen atmosphere. The resulting mixture was stirred for 3 h at room temperature. The resulting mixture was concentrated under reduced pressure. The crude product [2-(benzyloxy)phenyl]acetyl chloride (7 g, 94.27%) was used in the next step directly without further purification.

Synthesis of 5-{2-[2-(benzyloxy)phenyl]acetyl}-2,2-dimethyl-1,3-dioxane-4,6-dione

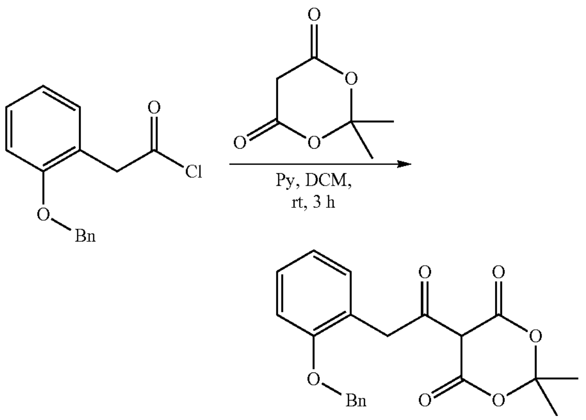

To a stirred solution of [2-(benzyloxy)phenyl]acetyl chloride (7.0 g, 26.849 mmol, 1.0 equiv) in DCM (80 mL) was added Pyridine (10.62 g, 134.245 mmol, 5.0 equiv) and 2,2-dimethyl-1,3-dioxane-4,6-dione (4.64 g, 32.219 mmol, 1.2 equiv) dropwise at 0° C. under nitrogen atmosphere. The resulting mixture was stirred for 3 h at room temperature under nitrogen atmosphere. The resulting mixture was extracted with $CH_2Cl_2$ (3×50 mL). The combined organic layers were washed with brine (100 mL), dried over anhydrous $Na_2SO_4$. After filtration, the filtrate was concentrated under reduced pressure. The residue was purified by silica gel column chromatography, eluted with PE/EA (5:1) to afford 5-{2-[2-(benzyloxy)phenyl]acetyl}-2,2-dimethyl-1,3-dioxane-4,6-dione (4.2 g, 42.46%). LCMS (ES) $[M+H]^+$ m/z:369

Synthesis of 2-[(tert-butoxycarbonyl)amino]-2-(4-hydroxyphenyl)propanoic acid

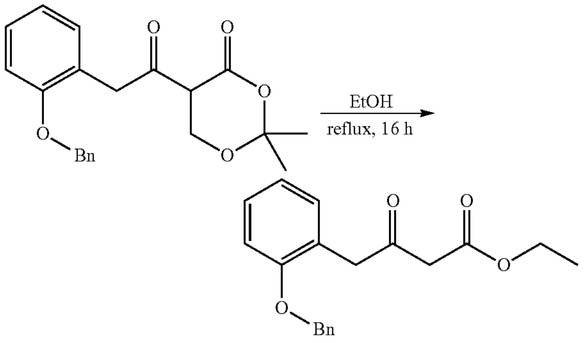

A solution of 5-{2-[2-(benzyloxy)phenyl]acetyl}-2,2-dimethyl-1,3-dioxane-4,6-dione (4.2 g, 11.401 mmol, 1.0 equiv) in ethyl alcohol (50 mL) was stirred for 16 h at 80° C. The mixture was allowed to cool down to room temperature. The resulting mixture was concentrated under reduced pressure. The residue was purified by silica gel column chromatography, eluted with PE/EA (4:1) to afford ethyl 4-[2-(benzyloxy)phenyl]-3-oxobutanoate (3.0 g, 84.24%). LCMS (ES) $[M+H]^+$ m/z:313

$^1$H NMR (300 MHz, DMSO-d6) δ 7.47-7.29 (m, 5H), 7.25 (td, J=7.8, 1.8 Hz, 1H), 7.17 (dd, J=7.5, 1.7 Hz, 1H), 7.05 (d, J=8.2 Hz, 1H), 6.92 (td, J=7.4, 1.1 Hz, 1H), 5.10 (s, 2H), 4.05 (q, J=7.1 Hz, 2H), 3.83 (s, 2H), 3.57 (s, 2H), 1.15 (t, J=7.1 Hz, 3H).

Synthesis of ethyl 3-amino-4-[2-(benzyloxy)phenyl]butanoate

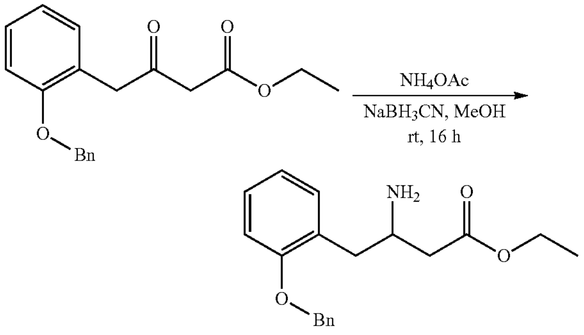

To a stirred solution of ethyl 4-[2-(benzyloxy)phenyl]-3-oxobutanoate (2.8 g, 8.964 mmol, 1.0 equiv) and $NH_{40}Ac$ (6.91 g, 89.640 mmol, 10 equiv) in MeOH (30 mL) was added $NaBH_3CN$ (1.69 g, 26.892 mmol, 3.0 equiv) in portions at 0° C. under nitrogen atmosphere. The resulting mixture was stirred for 16 h at room temperature. The mixture was acidified to pH 2 with conc. HCl. The resulting mixture was concentrated under reduced pressure. The residue was dissolved in $H_2O$ (20 mL). The mixture was basified to pH 10 with NaOH. The resulting mixture was extracted with EtOAc (3×30 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (2:1) to afford ethyl 3-amino-4-[2-(benzyloxy)phenyl]butanoate (1.8 g, 64.07%). LCMS (ES) $[M+H]^+$ m/z:314

Synthesis of ethyl 4-[2-(benzyloxy)phenyl]-3-[(tert-butoxycarbonyl)amino]butanoate

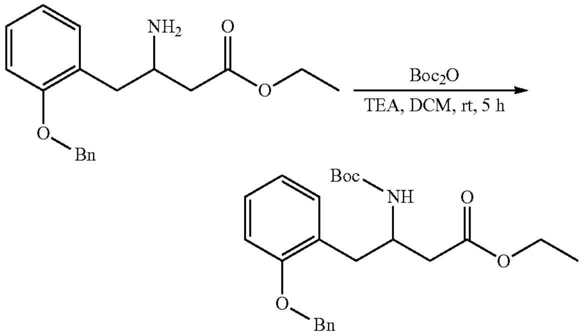

To a stirred solution of ethyl 3-amino-4-[2-(benzyloxy)phenyl]butanoate (1.8 g, 5.744 mmol, 1.0 equiv) and TEA (1.74 g, 17.232 mmol, 3.0 equiv) in DCM (20 mL) was added di-tert-butyl dicarbonate (1.50 g, 6.893 mmol, 1.2 equiv). The resulting mixture was stirred for 5 h at room temperature. The resulting mixture was extracted with $CH_2Cl_2$ (3×30 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (2:1) to afford ethyl 4-[2-(benzyloxy)phenyl]-3-[(tert-butoxycarbonyl)amino]butanoate (400 mg, 16.84%). LCMS (ES) $[M+H]^+$ m/z:414

Synthesis of 4-[2-(benzyloxy)phenyl]-3-[(tert-butoxycarbonyl)amino]butanoic acid

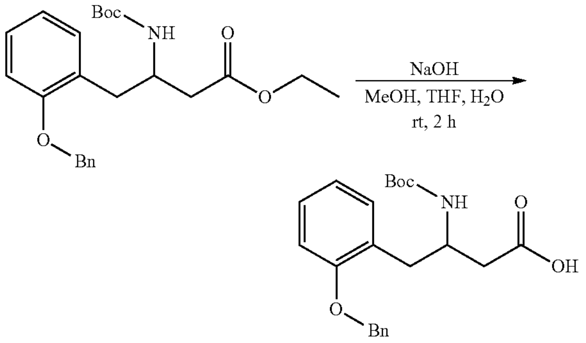

To a stirred solution of ethyl 4-[2-(benzyloxy)phenyl]-3-[(tert-butoxycarbonyl)amino]butanoate (400 mg, 0.967 mmol, 1.0 equiv) in MeOH (4 mL) and THE (4 mL) was added caustic soda (77.38 mg, 1.934 mmol, 2.0 equiv) in $H_2O$ (2 mL). The resulting mixture was stirred for 2 h at room temperature. The mixture was acidified to pH 6 with citric acid. The resulting mixture was extracted with EtOAc (3×20 mL). The combined organic layers were dried over anhydrous $Na_2SO_4$. After filtration, the filtrate was concentrated under reduced pressure. The crude product 4-[2-(benzyloxy)phenyl]-3-[(tert-butoxycarbonyl)amino]butanoic acid (280 mg, 75.09%) was used in the next step directly without further purification. LCMS (ES) [M–H]—m/z:384

Synthesis of 3-[(tert-butoxycarbonyl)amino]-4-(2-hydroxyphenyl)butanoic acid

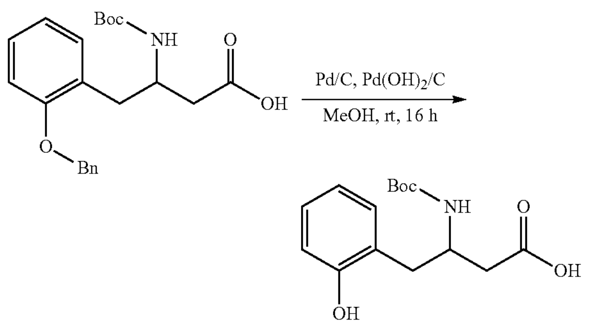

To a stirred solution of 4-[2-(benzyloxy)phenyl]-3-[(tert-butoxycarbonyl)amino]butanoic acid (280 mg, 0.726 mmol, 1.0 equiv) in methanol (5 mL) was added Pd/C (30 mg) and $Pd(OH)_2/C$ (30 mg). The resulting mixture was stirred for 16 h at room temperature under hydrogen atmosphere (3 atm). The resulting mixture was filtered, the filter cake was washed with MeOH (20 mL). The filtrate was concentrated under reduced pressure. The residue was purified by reversed-phase flash chromatography with the following conditions: column, C18 silica gel; mobile phase, MeCN in Water (0.1% FA), 10% to 60% gradient in 15 min; detector, UV 254 nm. This resulted in 3-[(tert-butoxycarbonyl) amino]-4-(2-hydroxyphenyl)butanoic acid (130 mg, 60.60%). LCMS (ES) [M–H]—m/z:294

Synthesis of tert-butyl N-(1-{[(1S)-1-cyano-2-[4-(3-methyl-2-oxo-1,3-benzoxazol-5-yl)phenyl]ethyl]carbamoyl}-3-(2-hydroxyphenyl)propan-2-yl)carbamate

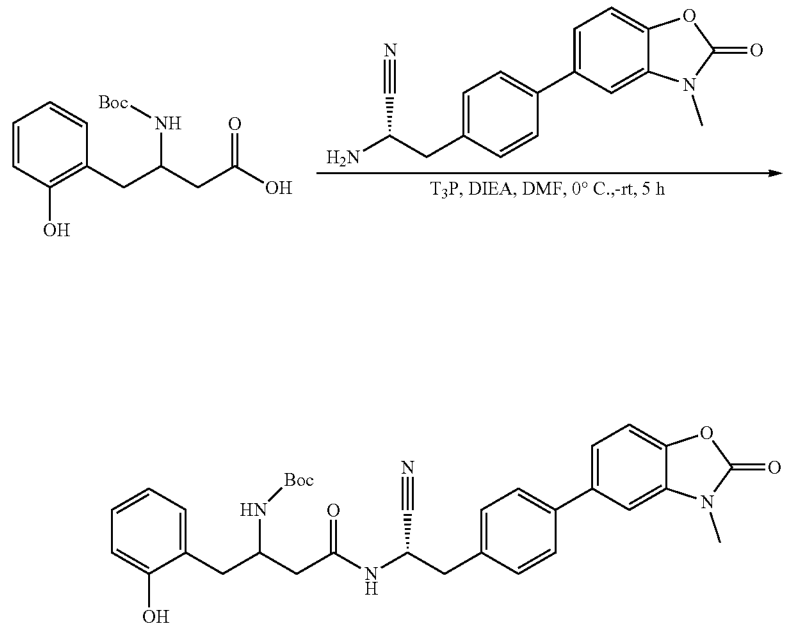

To a stirred solution of 3-[(tert-butoxycarbonyl)amino]-4-(2-hydroxyphenyl)butanoic acid (110 mg, 0.372 mmol, 1.0 equiv) and (2S)-2-amino-3-[4-(3-methyl-2-oxo-1,3-benzoxazol-5-yl)phenyl]propanenitrile (120 mg, 0.409 mmol, 1.1 equiv) in dimethylformamide (2 mL) were added DIEA (144 mg, 1.116 mmol, 3.0 equiv) and T3P (474 mg, 0.744 mmol, 2.0 equiv, 50%) dropwise at 0° C. under nitrogen atmosphere. The resulting mixture was stirred for 5 h at room temperature. The resulting mixture was extracted with EtOAc (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EA (2:1) to afford tert-butyl N-(1-{[(1S)-1-cyano-2-[4-(3-methyl-2-oxo-1,3-benzoxazol-5-yl)phenyl]ethyl]carbamoyl}-3-(2-hydroxyphenyl)propan-2-yl)carbamate (110 mg, 51.75%). LCMS (ES) $[M+H]^+$ m/z:571

Synthesis of 3-amino-N-[(1S)-1-cyano-2-[4-(3-methyl-2-oxo-1,3-benzoxazol-5-yl)phenyl]ethyl]-4-(2-hydroxyphenyl)butanamide

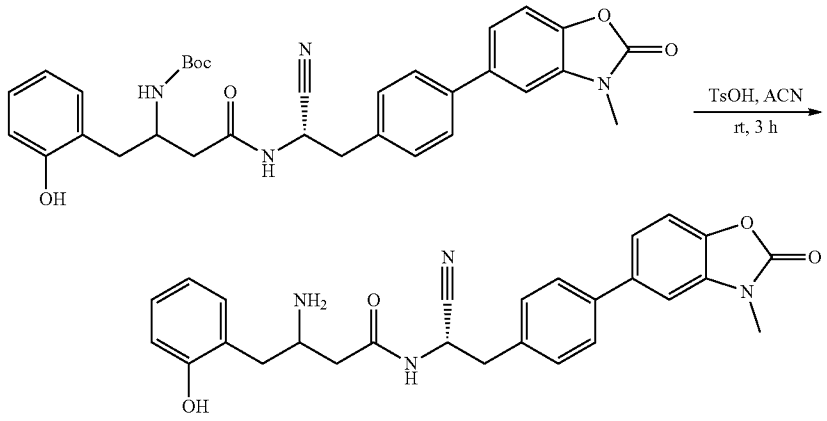

compound 228

To a stirred solution of tert-butyl N-(1-{[(1S)-1-cyano-2-[4-(3-methyl-2-oxo-1,3-benzoxazol-5-yl)phenyl]ethyl]carbamoyl}-3-(2-hydroxyphenyl)propan-2-yl)carbamate (110 mg, 0.193 mmol, 1.0 equiv) in ACN (2 mL) was added TsOH (99 mg, 0.579 mmol, 3.0 equiv). The resulting mixture was stirred for 3 h at room temperature. The mixture was purified by reversed-phase flash chromatography with the following conditions: column, C18 silica gel; mobile phase, MeCN in Water (0.1% $NH_3 \cdot H_2O$), 10% to 55% gradient in 15 min; detector, UV 254 nm. This resulted in 3-amino-N-[(1S)-1-cyano-2-[4-(3-methyl-2-oxo-1,3-benzoxazol-5-yl)phenyl]ethyl]-4-(2-hydroxyphenyl)butanamide (30 mg, 33.08%). LCMS (ES) $[M+H]^+$ m/z:471.2

$^1$H NMR (300 MHz, DMSO-$d_6$) δ 8.86 (brs, 1H), 7.71-7.62 (m, 2H), 7.56 (dt, J=4.1, 1.2 Hz, 1H), 7.46-7.36 (m, 4H), 7.07-6.93 (m, 1H), 6.96-6.78 (m, 1H), 6.75-6.64 (m, 1H), 6.69-6.53 (m, 1H), 5.09-4.95 (m, 1H), 3.40 (d, J=2.9 Hz, 3H), 3.30-3.19 (m, 3H), 3.20-3.02 (m, 2H), 2.62-2.52 (m, 2H), 2.29-2.03 (m, 2H).

Example 37. Synthesis of Compound 230: 3-amino-N-[(1S)-1-cyano-2-[4-(3-methyl-2-oxo-1,3-benzoxazol-5-yl)phenyl]ethyl]-4-(1,3-oxazol-4-yl)butanamide

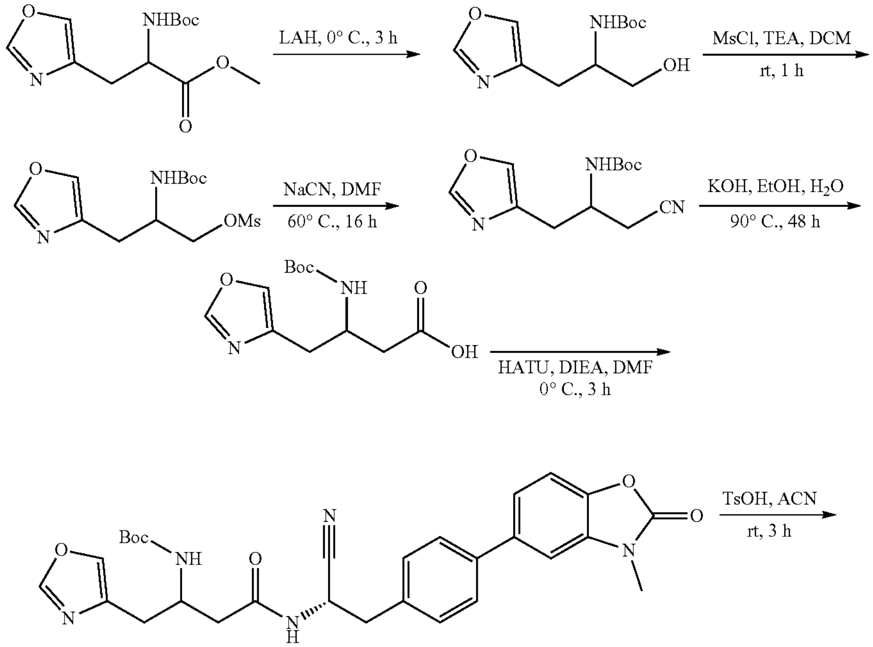

-continued

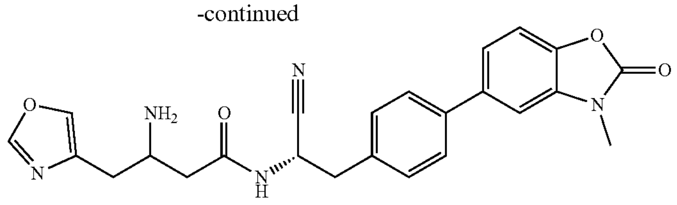

compound 230

Synthesis of tert-butyl N-[1-hydroxy-3-(1,3-oxazol-4-yl)propan-2-yl]carbamate

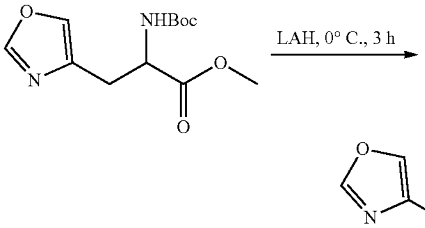

To a stirred solution of methyl 2-[(tert-butoxycarbonyl) amino]-3-(1,3-oxazol-4-yl)propanoate (3.6 g, 13.31 mmol, 1.0 equiv) in THE (40 mL) was added LAH (1.0 g, 26.64 mmol, 2.0 equiv) at 0° C. under nitrogen atmosphere. The resulting mixture was stirred for 3 h at 0° C. The reaction was quenched with $Na_2SO_4.10H_2O$ at 0° C. The resulting mixture was filtered, the filter cake was washed with THE (3x30 mL). The filtrate was concentrated under reduced pressure. The residue was purified by silica gel column chromatography, eluted with PE/THE (1:1) to afford tert-butyl N-[1-hydroxy-3-(1,3-oxazol-4-yl)propan-2-yl]carbamate (820 mg, 25.4%). LCMS (ES, m/z): $[M+H]^+$: 243.

Synthesis of tert-butyl N-[1-(methanesulfonyloxy)-3-(1,3-oxazol-4-yl)propan-2-yl]carbamate

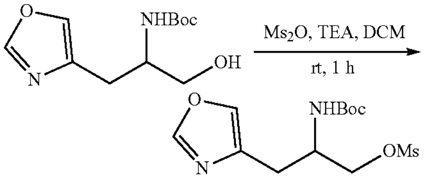

To a stirred solution of tert-butyl N-[1-hydroxy-3-(1,3-oxazol-4-yl)propan-2-yl]carbamate (820 mg, 3.38 mmol, 1.0 equiv) and TEA (1.37 g, 13.54 mmol, 4.0 equiv) in DCM (8 mL) were added $Ms_2O$ (1.2 g, 6.77 mmol, 2.0 equiv) dropwise at 0° C. The resulting mixture was stirred for 1 h at room temperature. The resulting mixture was quenched with water (10 mL), extracted with $CH_2Cl_2$(3x10 mL). The combined organic layer was washed with brine (30 mL), dried over anhydrous $Na_2SO_4$. After filtration, the filtrate was concentrated under reduced pressure. This resulted in tert-butyl N-[1-(methanesulfonyloxy)-3-(1,3-oxazol-4-yl) propan-2-yl]carbamate (930 mg, 85.7%). LCMS (ES, m/z): $[M+H]^+$: 307.

Synthesis of tert-butyl N-[1-cyano-3-(1,3-oxazol-4-yl)propan-2-yl]carbamate

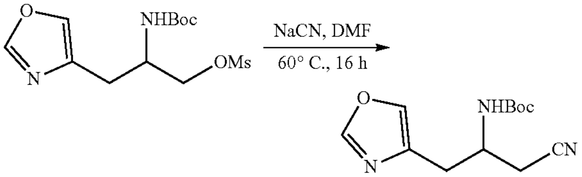

To a stirred solution of tert-butyl N-[1-(methanesulfonyloxy)-3-(1,3-oxazol-4-yl)propan-2-yl]carbamate (930 mg, 2.90 mmol, 1.0 equiv) in DMF (10 mL) was added NaCN (355 mg, 7.25 mmol, 2.5 equiv). The resulting mixture was stirred for 16 h at 60° C. The mixture was allowed to cool down to room temperature. The resulting mixture was diluted with water (20 mL). The resulting mixture was extracted with EtOAc (3x20 mL). The combined organic layer was washed with brine (2x20 mL), dried over anhydrous $Na_2SO_4$. After filtration, the filtrate was concentrated under reduced pressure. The residue was purified by silica gel column chromatography, eluted with PE/EA (2:1) to afford tert-butyl N-[1-cyano-3-(1,3-oxazol-4-yl)propan-2-yl]carbamate (430 mg, 58.9%). LCMS (ES, m/z): $[M+H]^+$: 252.

Synthesis of 3-[(tert-butoxycarbony)amino]-4-(1,3-oxazol-4-yl)butanoic acid

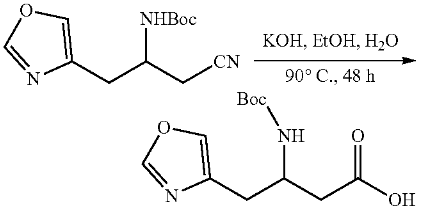

To a solution of tert-butyl N-[1-cyano-3-(1,3-oxazol-4-yl)propan-2-yl]carbamate (430 mg, 1.71 mmol, 1.0 equiv) in EtOH (4 mL), KOH (192 mg, 3.42 mmol, 2.0 equiv) in $H_2O$ (4 mL) was added dropwise at room temperature. The mixture was stirred for 48 h at 90° C. The reaction was cooled to room temperature, concentrated under reduced pressure to remove the solvent. The residue was acidified to pH 4 with HCl (1 M). The resulting mixture was extracted with EtOAc (3x10 mL). The combined organic layer was washed with brine (3x10 mL), dried over anhydrous $Na_2SO_4$. After filtration, the filtrate was concentrated under reduced pressure. This resulted in 3-[(tert-butoxycarbonyl)

amino]-4-(1,3-oxazol-4-yl)butanoic acid (160 mg, 34.6%). LCMS (ES, m/z): [M+H]$^+$: 271.

Synthesis of tert-butyl N-(1-{[(1S)-1-cyano-2-[4-(3-methyl-2-oxo-1,3-benzoxazol-5-yl)phenyl]ethyl]carbamoyl}-3-(1,3-oxazol-4-yl)propan-2-yl)carbamate

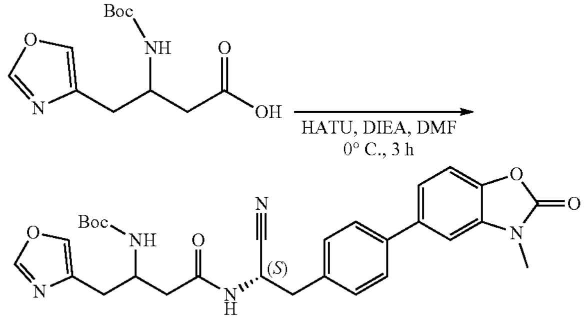

A solution of (2S)-2-amino-3-[4-(3-methyl-2-oxo-1,3-benzoxazol-5-yl)phenyl]propanenitrile (116 mg, 0.39 mmol, 1.0 equiv) in DMF (5 mL) was treated with 3-[(tert-butoxycarbonyl)amino]-4-(1,3-oxazol-4-yl)butanoic acid (160 mg, 0.59 mmol, 1.5 equiv), DIEA (153 mg, 1.18 mmol, 3.0 equiv). This was followed by the addition of HATU (180 mg, 0.47 mmol, 1.2 equiv) in portions at 0° C. The resulting mixture was stirred for 3 h at 0° C. The reaction was quenched with water (10 mL), extracted with ethyl acetate (30 mL×2). The combined organic phase was washed with brine (10 mL×3), dried over anhydrous sodium sulfate. After filtration, the filtrate was concentrated under reduced pressure. The residue was purified by silica gel column chromatography, eluted with PE/THE (1:1) to afford tert-butyl N-(1-{[(1S)-1-cyano-2-[4-(3-methyl-2-oxo-1,3-benzoxazol-5-yl)phenyl]ethyl]carbamoyl}-3-(1,3-oxazol-4-yl)propan-2-yl)carbamate (130 mg, 60.3%). LCMS (ES, m/z): [M+H]$^+$: 546.

Synthesis of 3-amino-N-[(1S)-1-cyano-2-[4-(3-methyl-2-oxo-1,3-benzoxazol-5-yl)phenyl]ethyl]-4-(1,3-oxazol-4-yl)butanamide

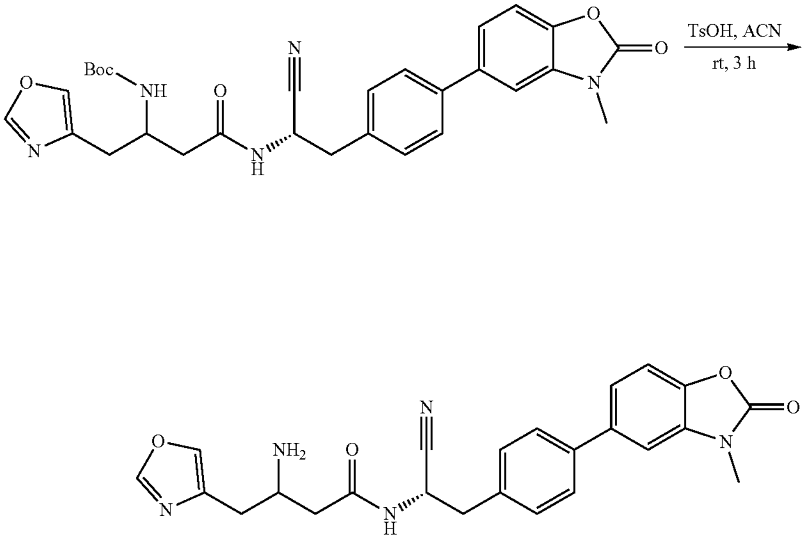

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-3-(1,3-oxazol-4-yl)propan-2-yl)carbamate (130 mg, 0.23 mmol, 1.0 equiv) in ACN (4 mL) and TsOH·$H_2O$ (136 mg, 0.71 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 3-amino-N-[(1S)-1-cyano-2-[4-(3-methyl-2-oxo-1,3-benzoxazol-5-yl)phenyl]ethyl]-4-(1,3-oxazol-4-yl)butanamide (20.5 mg, 19.3%). LCMS (ES, m/z): [M+H]$^+$: 446.0.

$^1$H NMR (400 MHz, DMSO-$d_6$) δ 8.91 (s, 1H), 8.27 (d, J=5.9 Hz, 1H), 7.82 (d, J=11.9 Hz, 1H), 7.70-7.62 (m, 2H), 7.60-7.53 (m, 1H), 7.46-7.37 (m, 4H), 5.01 (t, J=7.7 Hz, 1H), 3.24 (s, 1H), 3.18-3.05 (m, 2H), 2.51-2.33 (m, 3H), 2.23 (td, J=14.8, 4.7 Hz, 1H), 2.10 (dt, J=14.6, 9.2 Hz, 1H).

Example 38. Synthesis of Compound 231: 2-amino-N-[(1S)-1-cyano-2-[4-(3-methyl-2-oxo-1,3-benzoxazol-5-yl)phenyl]ethyl]-3-(1,2-oxazol-3-yl) propanamide

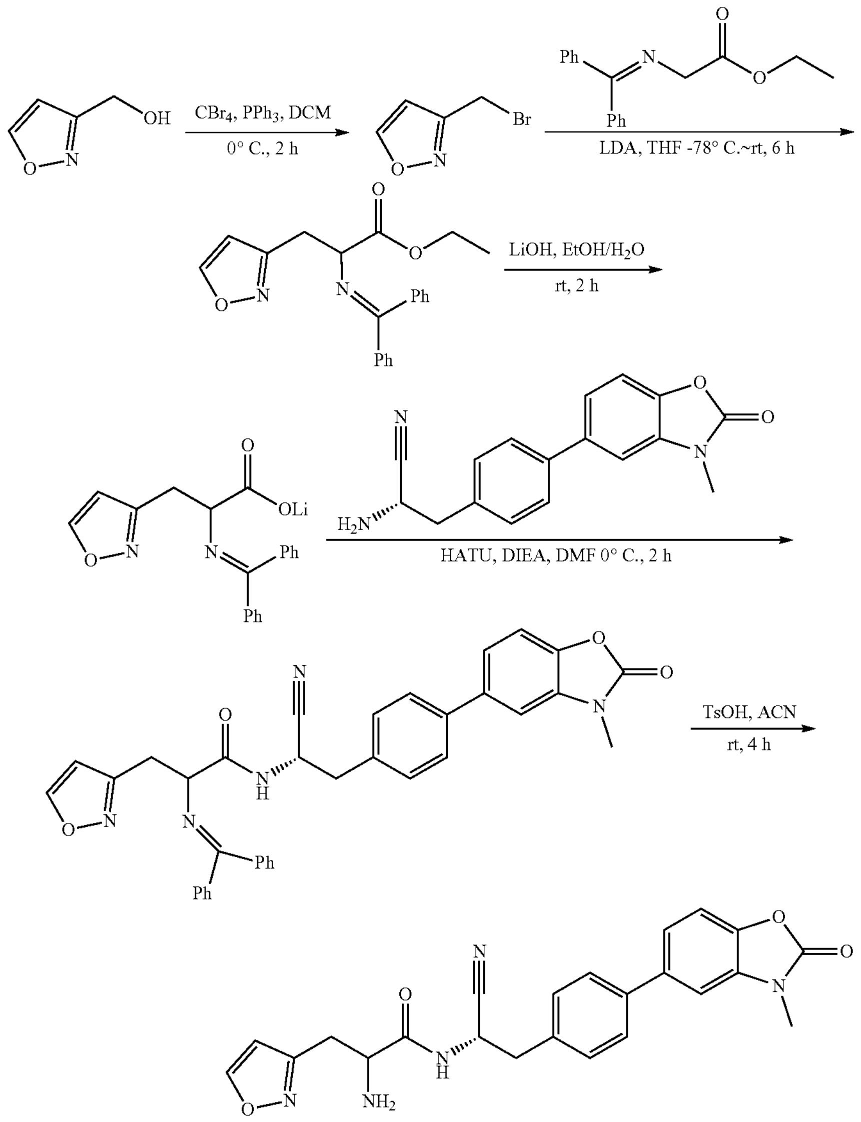

Synthesis of 3-(bromomethyl)-1,2-oxazole

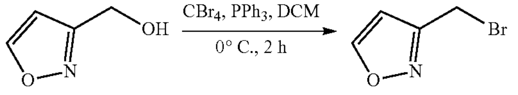 [SMILES: OCc1ccon1 ; BrCc1ccon1]

To a stirred solution of 1,2-oxazol-3-ylmethanol (2.7 g, 27.24 mmol, 1.0 equiv) and PPh$_3$ (10.72 g, 40.87 mmol, 1.5 equiv) in DCM (50 mL) was added CBr$_4$ (9.04 g, 27.24 mmol, 1.0 equiv) at 0° C. under nitrogen atmosphere. The resulting mixture was stirred for 2 h at 0° C. under nitrogen atmosphere. The resulting mixture was concentrated under reduced pressure. The residue was purified by silica gel column chromatography, eluted with PE/EA (10:1) to afford 3-(bromomethyl)-1,2-oxazole (1.6 g, 36%). LCMS (ES, m z): [M+H]$^+$: 162.

Synthesis of ethyl 2-[(diphenylmethylidene)amino]-3-(1,2-oxazol-3-yl)propanoate

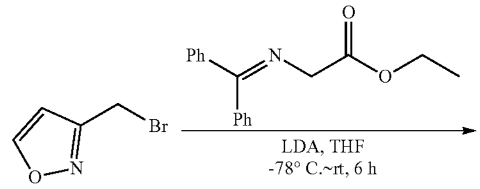

-continued

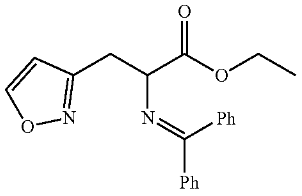

To a stirred solution of LDA (2 M in THF)(4.9 mL, 9.72 mmol, 1.05 equiv) in THE (20 mL) was added ethyl 2-[(di-phenylmethylidene)amino]acetate (2.60 g, 9.72 mmol, 1.05 equiv) in THE (40 mL) dropwise at −78° C. under nitrogen atmosphere. The resulting mixture was stirred for 30 min at −78° C. under nitrogen atmosphere. To the above mixture was added 3-(bromomethyl)-1,2-oxazole (1.5 g, 9.26 mmol, 1.0 equiv) in THF (20 mL) dropwise at −78° C. under nitrogen atmosphere. The resulting mixture was stirred for additional 1 h at −78° C. under nitrogen atmosphere. The resulting mixture was stirred for 3 h at room temperature under nitrogen atmosphere. The reaction was quenched with $NH_4Cl$ (aq.) at room temperature. The resulting mixture was extracted with EtOAc (3×50 mL). The combined organic layer were dried over anhydrous $Na_2SO_4$. After filtration, the filtrate was concentrated under reduced pressure. The residue was purified by silica gel column chromatography, eluted with PE/EA (8:1) to afford ethyl 2-[(diphenylmethylidene)amino]-3-(1,2-oxazol-3-yl)propanoate (1 g, 31%). LCMS (ES, m z): $[M+H]^+$: 349.

Synthesis of lithium 2-((diphenylmethylene)amino)-3-(isoxazol-3-yl)propanoate

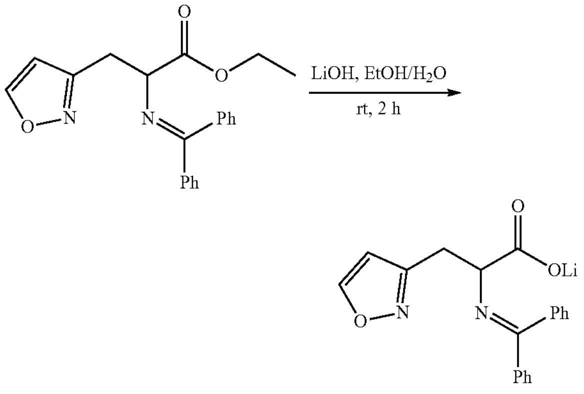

To a stirred solution of ethyl 2-[(diphenylmethylidene)amino]-3-(1,2-oxazol-3-yl)propanoate (500 mg, 1.43 mmol, 1.0 equiv) in EtOH (9 mL) was added $LiOH \cdot H_2O$ (180 mg, 4.30 mmol, 3.0 equiv) in $H_2O$ (3 mL) dropwise at room temperature. The resulting mixture was stirred for 2 h at room temperature. The resulting mixture was concentrated under reduced pressure. The crude product was used in the next step directly without further purification. This resulted in lithium 2-((diphenylmethylene)amino)-3-(isoxazol-3-yl)propanoate (450 mg, 96%). LCMS (ES, m z): $[M-Li+H]^+$: 321.

Synthesis of N-[(1S)-1-cyano-2-[4-(3-methyl-2-oxo-1,3-benzoxazol-5-yl)phenyl]ethyl]-2-[(diphenylmethylidene)amino]-3-(1,2-oxazol-3-yl)propanamide

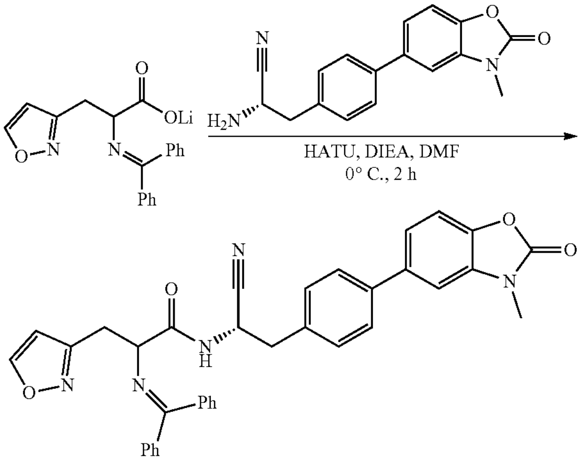

To a stirred mixture of lithium 2-((diphenylmethylene)amino)-3-(isoxazol-3-yl)propanoate e (166 mg, 0.51 mmol, 1.5 equiv), (2S)-2-amino-3-[4-(3-methyl-2-oxo-1,3-benzoxazol-5-yl)phenyl]propanenitrile (100 mg, 0.34 mmol, 1.0 equiv) and DIEA (132 mg, 1.02 mmol, 3.0 equiv) in DMF (5 mL) were added HATU (155 mg, 0.4 mmol, 1.2 equiv) in portions at 0° C. The resulting mixture was stirred for 2 h at 0° C. The reaction was quenched with water (10 mL), The resulting mixture was extracted with EtOAc (2×30 mL). The combined organic layer was washed with brine (3×30 mL), dried over anhydrous $Na_2SO_4$. After filtration, the filtrate was concentrated under reduced pressure. The residue was purified by silica gel column chromatography, eluted with PE/THE (1:1) to afford N-[(1S)-1-cyano-2-[4-(3-methyl-2-oxo-1,3-benzoxazol-5-yl)phenyl]ethyl]-2-[(diphenylmethylidene)amino]-3-(1,2-oxazol-3-yl)propanamide (150 mg, 73.9%). LCMS (ES, m z): $[M+H]^+$: 596.

Synthesis of 2-amino-N-[(1S)-1-cyano-2-[4-(3-methyl-2-oxo-1,3-benzoxazol-5-yl)phenyl]ethyl]-3-(1,2-oxazol-3-yl)propanamide

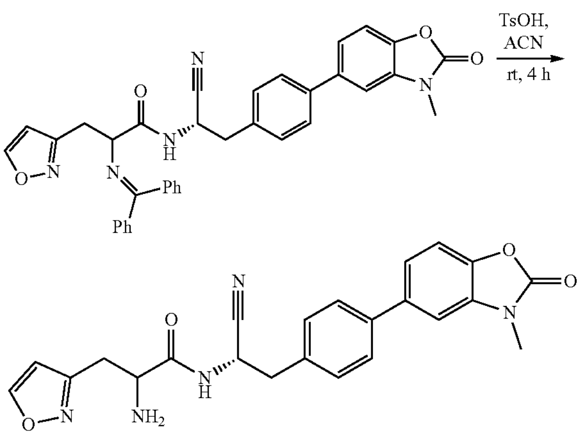

Into a 25 mL round-bottom flask were added N-[(1S)-1-cyano-2-[4-(3-methyl-2-oxo-1,3-benzoxazol-5-yl)phenyl]ethyl]-2-[(diphenylmethylidene)amino]-3-(1,2-oxazol-3-yl)propanamide (150 mg, 0.25 mmol, 1.0 equiv), TsOH·$H_2O$ (143 mg, 0.75 mmol, 3.0 equiv) and ACN (4 mL) at room temperature. The resulting mixture was stirred for 4 h at room temperature. The reaction solution was purified by reversed-phase flash chromatography with the following conditions: column, C18 silica gel-120 g; mobile phase, MeCN in Water (0.1% $NH_3.H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-3-(1,2-oxazol-3-yl)propanamide (30 mg, 27.6%).

LCMS (ES, m z): $[M+H]^+$: 432.5

$^1H$ NMR (400 MHz, DMSO-$d_6$): δ 8.76 (t, J=1.4 Hz, 1H), 7.67 (dd, J=8.3, 2.8 Hz, 2H), 7.58 (t, J=2.4 Hz, 1H), 7.49-7.34 (m, 4H), 6.38 (dd, J=11.4, 1.6 Hz, 1H), 5.06-4.97 (m, 1H), 3.57-3.47 (m, 1H), 3.41 (s, 3H), 3.23-3.06 (m, 2H), 2.96-2.86 (m, 1H), 2.78-2.67 (m, 1H), 1.92 (br, 1H).

Example 39: General Procedures

Procedure a (TBAF Deprotection)

To a solution of O-TBDMS protected alcohol (1 eq.) in anhydrous THF (6.0 mL/mmol of protected alcohol) was added a 1 M TBAF solution in THE (1.5 eq.) at 0° C. under argon atmosphere. The resulting mixture was allowed to warm to room temperature and stirred for 2 h. The reaction mixture was diluted with EtOAc (50 mL) and washed with brine (50 mL), dried over $Na_2SO_4$ and concentrated under reduced pressure. The crude was purified by flash chromatography over $SiO_2$ (see conditions for each compound) to afford the expected compound.

Procedure B (Peptide Coupling)

To a solution of amine derivative (1 eq.) in anhydrous DMF (7.14 mL/mmol of amine) and carboxylic acid derivative (1.05 eq.) were added DIPEA (2.5 eq.) and TBTU (1.5 eq.) at room temperature under argon atmosphere. The reaction mixture was stirred at room temperature for 18 h. The reaction mixture was diluted with EtOAc (10 mL) and water (10 mL). The aqueous layer was extracted with EtOAc (2×10 mL) and the combined organic layers were washed with brine (3×10 mL), dried over $Na_2SO_4$, filtered and concentrated under reduced pressure. The crude was purified by flash chromatography over $SiO_2$ (see conditions for each compound) to afford the expected compound.

Procedure C (N-Boc Deprotection)

To a preheated vial (50° C.) containing Boc protected amine derivative (1 eq.) was added formic acid (7.6 mL/mmol) also preheated at 50° C. The reaction mixture was stirred at 50° C. for 15 min. The reaction mixture was cooled back to room temperature and added dropwise into a cooled (0° C.) mixture of stirred aqueous solution of saturated $NaHCO_3$ (40 mL) and DCM (40 mL). The layers were separated, and the aqueous layer was extracted with DCM (2×40 mL). The combined organic layers were dried over $Na_2SO_4$, filtered and concentrated under reduced pressure. The crude was purified by flash chromatography over $SiO_2$ and/or preparative HPLC (see conditions for each compound) to afford the expected compound.

Procedure D (O-Bn Deprotection)

To an argon-purged solution of protected alcohol (1 eq.) in EtOH (4.78 mL/mmol of protected alcohol) was added 10% Pd/C (0.1 eq.) at room temperature. The resulting mixture was purged with argon (×3) and then with $H_2$ (3×). The reaction mixture was stirred under an atmospheric pressure of $H_2$ at room temperature for 18 h. The reaction mixture was purged with argon, filtered on a pad of celite and rinsed with EtOH (3×5 mL). The filtrate was concentrated under reduced pressure to afford the expected compound.

Procedure E (Alcohol Oxidation into Carboxylic Acid)

To a solution of alcohol derivative (1 eq.) in acetone (16.7 mL/mmol of alcohol) and sodium bromide (0.3 eq.) was added a saturated aqueous solution of $NaHCO_3$ (2.59 mL/mmol of alcohol) at room temperature. To the resulting mixture were added trichlorocyanuric acid (2.2 eq.) and 2,2,6,6-tetramethylpiperidine-1-oxyl (0.03 eq.) at 0° C. The reaction mixture was allowed to warm to room temperature and stirred for 18 h. Isopropanol (10 mL) was added at room temperature and the reaction mixture was stirred for 30 min. The reaction mixture was diluted with EtOAc (50 mL) and a saturated aqueous solution of $NaHCO_3$ (50 mL) was added. The two layers were separated, and the aqueous layer was washed with EtOAc (50 mL). The aqueous layer was then acidified with an aqueous solution of 3M HCl until pH ~1 and extracted with DCM (2×50 mL). The combined organic layers were dried over $Na_2SO_4$, filtered and concentrated under reduced pressure to afford the expected compound as a crude used as such without further purification.

Procedure F (O-Alkylation)

To a solution of alcohol derivative (1 eq.) in anhydrous DMF (5.49 mL/mmol of alcohol derivative) and halogenoalkyl (2 eq.) was added NaH 60% in oil (1.1 eq.) at 0° C. under argon atmosphere. The resulting mixture was allowed to warm to room temperature and stirred for 22 h. The reaction mixture was quenched with a saturated aqueous solution of $NH_4Cl$ (10 mL) at room temperature. EtOAc (50 mL) and water (50 mL) were then added and the two layers were separated. The aqueous layer was extracted with EtOAc (2×50 mL) and the combined organic layers were dried over $Na_2SO_4$, filtered and concentrated under reduced pressure. The crude residue was purified by silica gel flash chromatography (see conditions for each compound) to afford the expected compound.

Procedure G (N-Boc Protection)

To a solution of amine derivative (1 eq.) in DCM (4 mL/mmol of amine derivative) were added $Boc_2O$ (1.2 eq.) and $Et_3N$ (2 eq.) at room temperature. The resulting mixture was stirred at room temperature for 16 h. The reaction mixture was diluted with water (40 mL) and extracted with DCM (2×60 mL). The combined organic layers were washed with brine (30 mL), dried over $Na_2SO_4$, filtered and concentrated to dryness under reduced pressure. The crude residue was purified by silica gel flash chromatography (see conditions for each compound) to afford the expected compound.

Procedure H (Olefin Metathesis)

To a solution of diene (1 eq.) in DCM (63 mL/mmol) was added Benzylidene-bis(tricyclohexylphosphine)dichlororuthenium (0.1 eq.) at room temperature. The resulting mixture was stirred at 55° C. for 8 h. The reaction was concentrated to dryness under reduced pressure. The crude residue was purified by silica gel flash chromatography (see conditions for each compound) to afford the expected compound.

Procedure I (Hydroboration)

To an argon-purged solution of alkene derivative (1 eq.) in THE (2.5 mL/mmol) was added borane tetrahydrofuran complex solution 1 M in THF (1 eq.) at 0° C. The resulting mixture was stirred at 0° C. for 2.5 h. Then, NaOH 3M in water (1 eq.) and $H_2O_2$ 33% in water (1 eq.) were added sequentially and the resulting mixture was stirred at 0° C. for 3.5 h. The reaction mixture was diluted with water (100 mL) and extracted with EtOAc (3×100 mL). The combined organic layers were washed with brine (100 mL), dried over $Na_2SO_4$, filtered and concentrated to dryness under reduced pressure. The crude residue was purified by silica gel flash chromatography (see conditions for each compound) to afford the expected compound.

Example 40: Synthesis of Compound 182: (3S)-3-amino-N-[(1S)-1-cyano-2-[4-(3-methyl-2-oxo-2,3-dihydro-1,3-benzoxazol-5-yl)phenyl]ethyl]-4-(thiophen-2-yl)butanamide

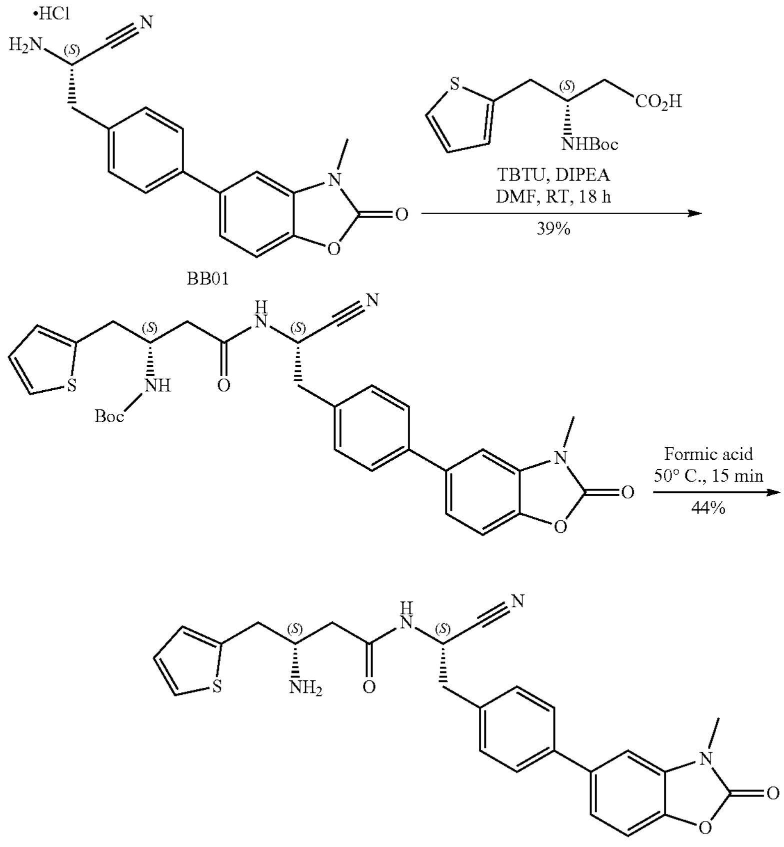

BB01 compound 182 tert-butyl N-[(2S)-1-{[(1S)-1-cyano-2-[4-(3-methyl-2-oxo-2,3-dihydro-1,3-benzoxazol-5-yl)phenyl]ethyl]carbamoyl}-3-(thiophen-2-yl)propan-2-yl]carbamate

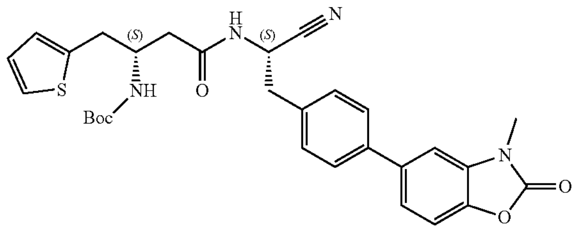

Starting from BB01 (1 eq., 110.063 mg, 0.33 mmol) and (3S)-3-{[(tert-butoxy)carbonyl]amino}-4-(thiophen-2-yl)butanoic acid (1.05 eq., 100 mg, 0.35 mmol), and using general procedure B, tert-butyl N-[(2S)-1-{[(1S)-1-cyano-2-[4-(3-methyl-2-oxo-2,3-dihydro-1,3-benzoxazol-5-yl)phenyl]ethyl]carbamoyl}-3-(thiophen-2-yl)propan-2-yl]carbamate was obtained (73.6 mg, 39%) after purifications by flash chromatographies over silica gel (1: irregular SiOH, 50 µm, 24 g Interchim, dry loading (silica), mobile phase gradient: cyclohexane/EtOAc from 100/0 to 40/60 over 40 min, 2: irregular SiOH, 50 µm, 24 g Interchim, dry loading (silica), mobile phase gradient: cyclohexane/EtOAc from 100/0 to 0/100 over 60 min, then DCM/MeOH 100/0 to 90/10 over 45 min).

LC/MS: Rt=2.57 min, 100%, $[M-Boc+H]^+$=461.2.

$^1$H NMR (400 MHz, DMSO) δ 8.78 (d, J=7.9 Hz, 1H), 7.65 (d, J=8.1 Hz, 2H), 7.51 (s, 1H), 7.41 (d, J=8.2 Hz, 2H), 7.38-7.31 (m, 2H), 7.28 (dd, J=5.1, 1.3 Hz, 1H), 6.87 (dd, J=5.1, 3.4 Hz, 1H), 6.79 (d, J=8.5 Hz, 1H), 6.71 (dd, J=3.4, 1.2 Hz, 1H), 5.03 (q, J=7.9 Hz, 1H), 3.94-3.84 (m, 1H), 3.39 (s, 3H), 3.19-3.04 (m, 2H), 2.83-2.69 (m, 2H), 2.35-2.21 (m, 2H), 1.34 (s, 9H).

(3S)-3-amino-N-[(1S)-1-cyano-2-[4-(3-methyl-2-oxo-2,3-dihydro-1,3-benzoxazol-5-yl)phenyl]ethyl]-4-(thiophen-2-yl)butanamide compound 182

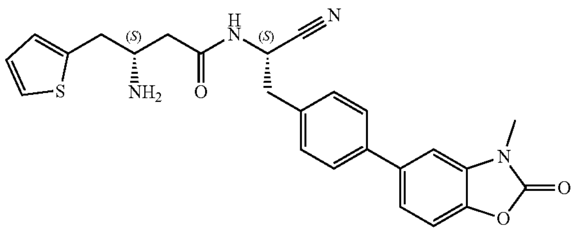

Starting from tert-butyl N-[(2S)-1-{[(1S)-1-cyano-2-[4-(3-methyl-2-oxo-2,3-dihydro-1,3-benzoxazol-5-yl)phenyl]ethyl]carbamoyl}-3-(thiophen-2-yl)propan-2-yl]carbamate (1 eq., 70 mg, 0.12 mmol) and using general procedure C, compound 182 was obtained (25.3 mg, 44%) after purification by flash chromatography over silica gel (15 μm, 12 g, DCM/MeOH 100:0 to 94:06 over 35 min).

LC/MS: Rt=7.47 min, 98.9%, $[M+H]^+$=461.3.

$^1$H NMR (400 MHz, DMSO) δ 8.87 (s, 1H), 7.71-7.62 (m, 2H), 7.54 (t, J=1.2 Hz, 1H), 7.46-7.35 (m, 4H), 7.31 (dd, J=5.1, 1.2 Hz, 1H), 6.92 (dd, J=5.1, 3.3 Hz, 1H), 6.79 (dd, J=3.3, 1.1 Hz, 1H), 5.01 (t, J=8.0 Hz, 1H), 3.40 (s, 3H), 3.20-3.06 (m, 3H), 2.78-2.64 (m, 2H), 2.20 (dd, J=14.6, 5.1 Hz, 1H), 2.10 (dd, J=14.6, 8.0 Hz, 1H), 1.57 (s, 2H).

Example 41: Synthesis of Compound 184: 3-amino-N-[(1S)-1-cyano-2-[4-(3-methyl-2-oxo-2,3-dihydro-1,3-benzoxazol-5-yl)phenyl]ethyl]-4-phenylbutanamide

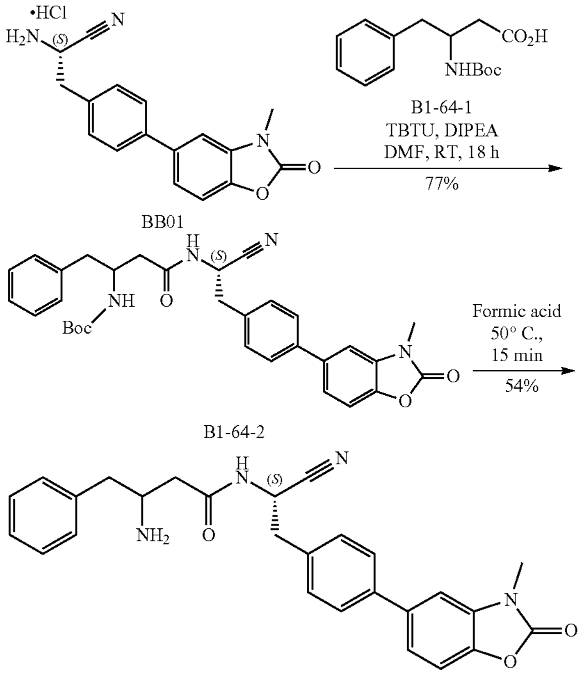

compound 184 tert-butyl N-(1-{[(1S)-1-cyano-2-[4-(3-methyl-2-oxo-2,3-dihydro-1,3-benzoxazol-5-yl)phenyl]ethyl]carbamoyl}-3-phenylpropan-2-yl)carbamate B1-64-2

B1-64-2

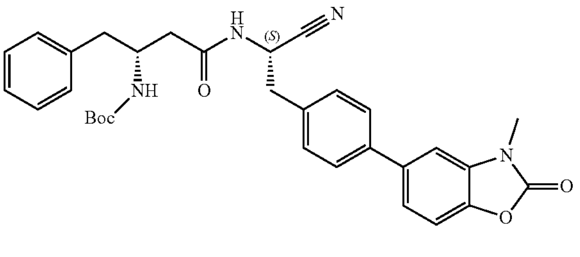

Starting from BB01 (1 eq., 150 mg, 0.45 mmol) and B1-64-1 (1.05 eq., 133.4 mg, 0.48 mmol), and using general procedure B, B1-64-2 was obtained (193 mg, 77%) after purification by flash chromatography over silica gel (50 μm, 25 g, cyclohexane/EtOAc from 100:0 to 50:50 over 50 min).

LC/MS: Rt=2.59 min, 100%, $[M-Boc+H]^+$=455.3.

$^1$H NMR (400 MHz, DMSO) δ 8.78 (dd, J=11.2, 7.8 Hz, 1H), 7.70-7.60 (m, 2H), 7.51 (d, J=32.7 Hz, 1H), 7.44-7.29 (m, 4H), 7.18 (ddt, J=22.5, 20.6, 7.5 Hz, 4H), 7.09-7.03 (m, 1H), 6.70 (dd, J=8.6, 4.6 Hz, 1H), 5.09-4.94 (m, 1H), 3.98-3.85 (m, 1H), 3.38 (d, J=8.0 Hz, 3H), 3.20-3.02 (m, 2H), 2.71-2.59 (m, 1H), 2.35-2.19 (m, 2H), 1.34-1.20 (m, 10H).

3-amino-N-[(1S)-1-cyano-2-[4-(3-methyl-2-oxo-2,3-dihydro-1,3-benzoxazol-5-yl)phenyl]ethyl]-4-phenylbutanamide compound 184 compound 184

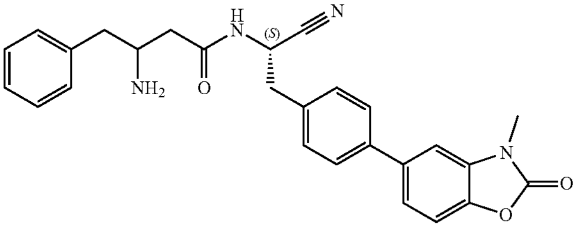

Starting from B1-64-2 (1 eq., 100 mg, 0.18 mmol) and using general procedure C, compound 184 was obtained (44 mg, 54%) after purification by flash chromatography over silica gel (15 μm, 4 g, DCM/MeOH from 100:0 to 93:07 over 30 min).

LC/MS: Rt=7.07 min, 99.0%, $[M+H]^+$=455.5.

$^1$H NMR (400 MHz, DMSO) δ 8.91 (s, 1H), 7.69-7.61 (m, 2H), 7.54 (d, J=16.8 Hz, 1H), 7.45-7.37 (m, 3H), 7.37-7.30 (m, 1H), 7.30-7.22 (m, 2H), 7.21-7.09 (m, 3H), 5.01 (t, J=7.8 Hz, 1H), 3.45-3.37 (m, 3H), 3.23-3.05 (m, 3H), 2.58 (dd, J=13.4, 6.2 Hz, 1H), 2.44 (dd, J=13.3, 7.6 Hz, 1H), 2.17 (ddd, J=14.3, 11.7, 4.8 Hz, 1H), 2.07 (dt, J=14.9, 7.7 Hz, 1H), 1.50 (s, 2H).

Example 42: Synthesis of Compound 164: 3-amino-N-[(1S)-1-cyano-2-[4-(3-methyl-2-oxo-2,3-dihydro-1,3-benzoxazol-5-yl)phenyl]ethyl]-4-methylpentanamide

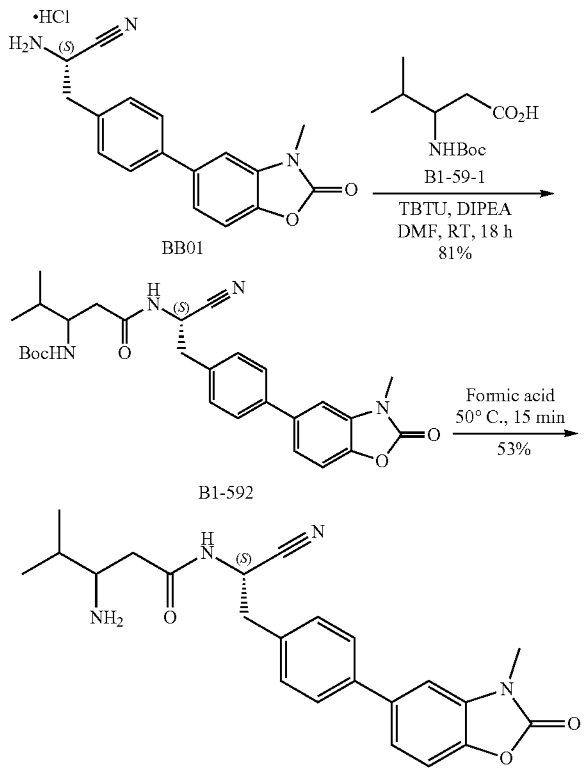

compound 164 tert-butyl N-(1-{[(1S)-1-cyano-2-[4-(3-methyl-2-oxo-2,3-dihydro-1,3-benzoxazol-5-yl)phenyl]ethyl]carbamoyl}-3-methylbutan-2-yl)carbamate B1-59-2

B1-59-2

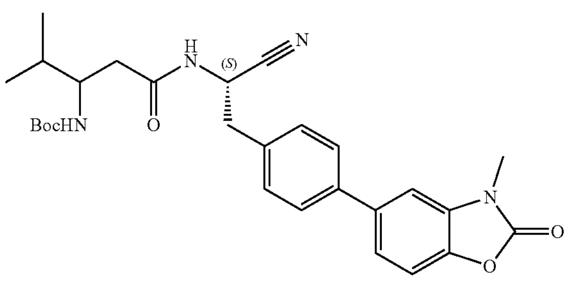

Starting from BB01 (1 eq., 150 mg, 0.45 mmol) and B1-59-1 (1.05 eq., 110.46 mg, 0.48 mmol) and using general procedure B, B1-59-2 was obtained (186 mg, 81%) after purification by flash chromatography over silica gel (50 μm, 25 g, cyclohexane/EtOAc from 100:0 to 50:50 over 45 min).

LC/MS: Rt=2.53 min, 100%, $[M-{}^{t}Bu+H]^+$=451.2.

$^1$H NMR (400 MHz, DMSO) δ 8.70 (dd, J=13.2, 7.8 Hz, 1H), 7.73-7.62 (m, 2H), 7.57 (t, J=2.1 Hz, 1H), 7.49-7.32 (m, 4H), 6.55 (dd, J=9.4, 4.4 Hz, 1H), 4.99 (dq, J=17.5, 7.8 Hz, 1H), 3.74-3.61 (m, 1H), 3.40 (s, 3H), 3.17-3.01 (m, 2H), 2.34-2.11 (m, 2H), 1.61-1.42 (m, 1H), 1.36 (s, 9H), 0.82-0.70 (m, 6H).

3-amino-N-[(1S)-1-cyano-2-[4-(3-methyl-2-oxo-2,3-dihydro-1,3-benzoxazol-5-yl)phenyl]ethyl]-4-methylpentanamide compound 164 compound 164

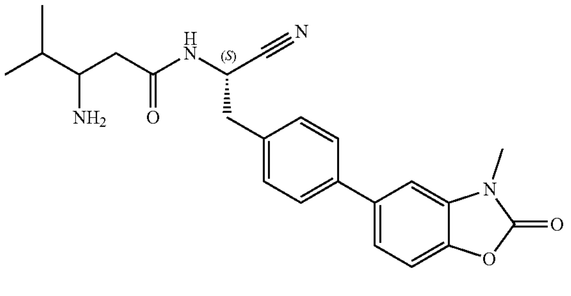

Starting from B1-59-2 (1 eq., 100 mg, 0.2 mmol) and using general procedure C, compound 164 was obtained (42.6 mg, 53%) after purification by flash chromatography over silica gel (15 μm, 4 g, DCM/MeOH from 100:0 to 90:10 over 60 min).

LC/MS: Rt=6.72 min, 99.0%, $[M+H]^+$=407.6.

$^1$H NMR (400 MHz, DMSO) δ 8.90 (s, 1H), 7.66 (dq, J=8.6, 2.2 Hz, 2H), 7.61-7.55 (m, 1H), 7.45-7.34 (m, 4H), 5.01 (t, J=7.7 Hz, 1H), 3.40 (s, 3H), 3.12 (qdd, J=13.5, 9.0, 5.5 Hz, 2H), 2.75 (dt, J=9.0, 4.5 Hz, 1H), 2.16 (td, J=13.9, 4.3 Hz, 1H), 1.99 (ddd, J=14.2, 9.0, 5.0 Hz, 1H), 1.66-1.32 (m, 3H), 0.85-0.72 (m, 6H).

Example 43: Synthesis of Compound 165: (3R)-3-amino-N-[(1S)-1-cyano-2-[4-(3-methyl-2-oxo-2,3-dihydro-1,3-benzoxazol-5-yl)phenyl]ethyl]hex-5-enamide tert-butyl N-[(2R)-1-{[(1S)-1-cyano-2-[4-(3-methyl-2-oxo-2,3-dihydro-1,3-benzoxazol-5-yl)phenyl]ethyl]carbamoyl}pent-4-en-2-yl]carbamate

B1-63-2

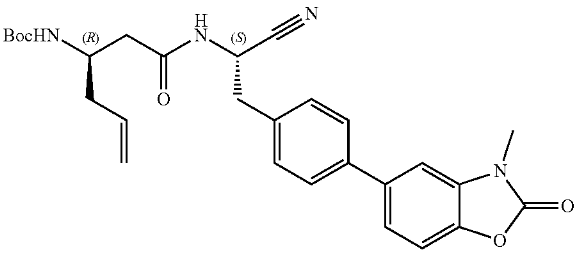

Starting from BB01 (1 eq., 0.14 g, 0.42 mmol) and B1-63-1 (1.05 eq., 0.1 g, 0.44 mmol) and using general procedure B, B1-63-2 was obtained (192 mg, 92%) after purification by flash chromatography over silica gel (irregular SiOH, 50 μm, 25 g Interchim, dry loading (silica), mobile phase gradient: DCM/MeOH from 100/0 to 95/5 over 30 min) and co-evaporation with DCM.

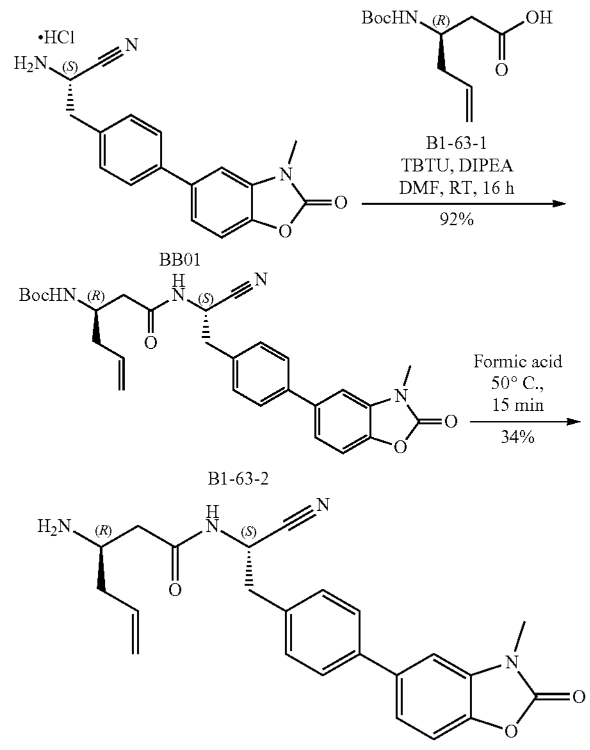

BB01

B1-63-2 compound 165

LC/MS: Rt=2.49 min, 100%, [M-Boc+H]$^+$=405.2.

$^1$H NMR (400 MHz, DMSO) δ 8.77 (d, J=7.8 Hz, 1H), 7.66 (d, J=8.1 Hz, 2H), 7.57 (d, J=1.6 Hz, 1H), 7.45-7.35 (m, 4H), 6.68 (d, J=8.7 Hz, 1H), 5.75-5.63 (m, 1H), 5.03-4.91 (m, 3H), 3.85-3.72 (m, 1H), 3.40 (s, 3H), 3.14-3.06 (m, 2H), 2.25 (d, J=7.0 Hz, 2H), 2.10-2.02 (m, 2H), 1.36 (s, 9H).

(3R)-3-amino-N-[(1S)-1-cyano-2-[4-(3-methyl-2-oxo-2,3-dihydro-1,3-benzoxazol-5-yl)phenyl]ethyl]hex-5-enamide: compound 165

Compound 165

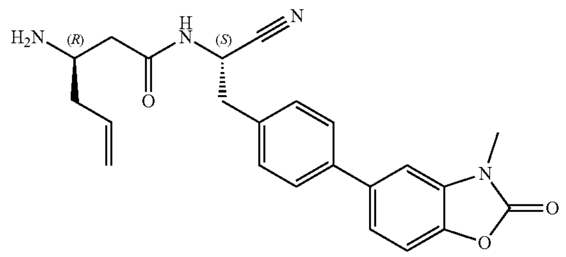

Starting from B1-63-2 (1 eq., 0.1 g, 0.2 mmol) and using general procedure C, Compound 165 was obtained (27.1 mg, 34%) after purification by flash chromatography over silica gel (regular SiOH, 15 μm, 12 g Interchim, dry loading (silica), mobile phase gradient: DCM/MeOH from 100/0 to 90/10 over 35 min), co-evaporation with DCM and freeze-drying using a mixture of ACN/water (1:10).

LC/MS: Rt=7.13 min, 98.9%, [M+H]$^+$=405.3.

$^1$H NMR (400 MHz, DMSO) δ 8.89 (s, 1H), 7.72-7.62 (m, 2H), 7.60-7.54 (m, 1H), 7.49-7.34 (m, 4H), 5.78 (ddt, J=18.9, 9.3, 7.1 Hz, 1H), 5.07-4.95 (m, 3H), 3.40 (s, 3H), 3.19-3.04 (m, 2H), 3.04-2.95 (m, 1H), 2.19 (dd, J=14.5, 4.9 Hz, 1H), 2.10-1.90 (m, 3H), 1.54 (s, 2H).

Example 44: Synthesis of Compound 167: 2-(aminomethyl)-N-[(1S)-1-cyano-2-[4-(3-methyl-2-oxo-2,3-dihydro-1,3-benzoxazol-5-yl)phenyl]ethyl]pent-4-enamide

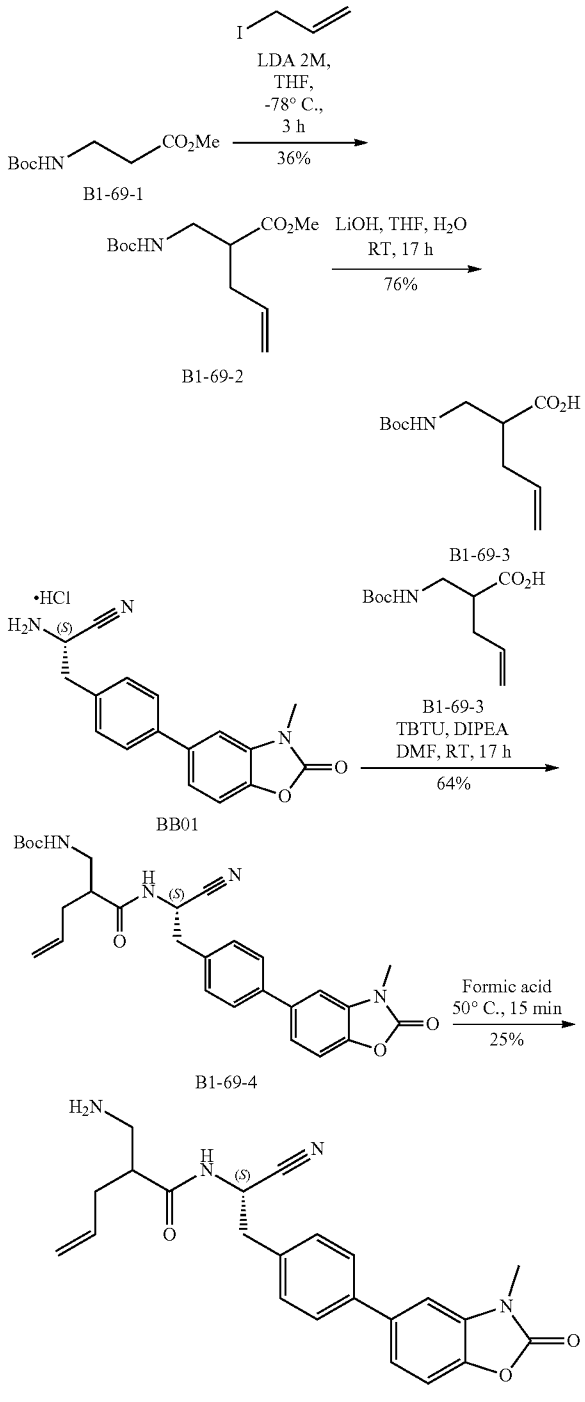

B1-69-1

B1-69-2

B1-69-3

BB01

B1-69-4

Compound 167

To methyl 2-({[(tert-butoxy)carbonyl]amino}methyl) pent-4-enoate B1-69-2

B1-69-2

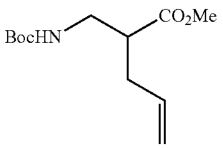

To an argon-purged solution of methyl B1-69-1 (1 eq., 500 mg, 2.46 mmol) in dried (on molecular sieves) THE (10.28 mL) was added dropwise LDA 2M in THF/Heptane/Ethyl benzene (1.2 eq., 1.48 mL, 2.95 mmol) at −78° C. The reaction mixture was stirred at −78° C. for 30 min. Then 3-iodopropene (1.2 eq., 495.902 mg, 0.27 mL, 2.95 mmol) was added at −78° C. The reaction mixture was stirred at −78° C. for 2 h. LDA 2M in THF/Heptane/Ethyl benzene (1.2 eq., 1.48 mL, 2.95 mmol) and 3-iodopropene (1.2 eq., 495.902 mg, 0.27 mL, 2.95 mmol) were added, the reaction mixture was stirred at −78° C. for 1 h. The reaction mixture was diluted with water (50 mL) and extracted with EtOAc (3×50 mL). The combined organic layers were washed with brine (50 mL), dried over $Na_2SO_4$, filtered and concentrated to dryness. The crude was purified by flash chromatography over silica gel (regular SiOH, 15 μm, 25 g, dry loading (silica), mobile phase gradient: Cyclohexane/EtOAc from 100/0 to 80/20 over 40 min) and co-evaporated with DCM affording B1-69-2 (213 mg, 36%).

LC/MS (AN01_001_012): Rt=2.35 min, 72.7%, $[M\text{-}Boc+H]^+$=144.0.

$^1$H NMR (400 MHz, DMSO) δ 6.93 (t, J=6.0 Hz, 1H), 5.78-5.64 (m, 1H), 5.04 (dq, J=17.2, 1.6 Hz, 1H), 4.99 (ddt, J=10.2, 2.2, 1.1 Hz, 1H), 3.57 (s, 3H), 3.20-2.98 (m, 2H), 2.63-2.51 (m, 1H), 2.29-2.08 (m, 2H), 1.37 (s, 9H).

2-({[(tert-butoxy)carbonyl]amino}methyl)pent-4-enoic acid B1-69-3

B1-69-3

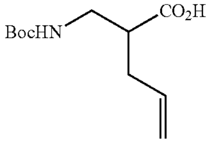

To an argon-purged solution of B1-69-2 (1 eq., 300 mg, 1.23 mmol) in THE (12.19 mL) was added a solution of LiOH (5 eq., 258.69 mg, 6.17 mmol) in water (5.85 mL) and the reaction mixture was stirred at room temperature for 17 h. The reaction was poured dropwise into a stirred aq. sol. of HCl 1 M (30 mL) and DCM (50 mL) cooled to 0° C. The mixture was stirred 1 h (pH ~1). The layers were separated, and the aqueous layer was extracted with DCM (2×30 mL). The combined organic layers were dried over $Na_2SO_4$, filtered and concentrated to dryness under reduced pressure affording B1-69-3 (216 mg, 76%).

LC/MS (AN01_001_012): Rt=2.10 min, 100%, [M−H]—= 228.0.

$^1$H NMR (400 MHz, DMSO) δ 12.16 (s, 1H), 6.79 (s, 1H), 5.81-5.66 (m, 1H), 5.06 (dq, J=17.2, 1.6 Hz, 1H), 5.00 (dd, J=10.2, 2.0 Hz, 1H), 3.17-2.93 (m, 2H), 2.57-2.42 (m, 1H), 2.28-2.11 (m, 2H), 1.37 (s, 9H).

tert-butyl N-(2-{[(1S)-1-cyano-2-[4-(3-methyl-2-oxo-2,3-dihydro-1,3-benzoxazol-5-yl)phenyl]ethyl]carbamoyl}-2-(prop-2-en-1-yl)ethyl)carbamate B1-69-4

B1-59-4

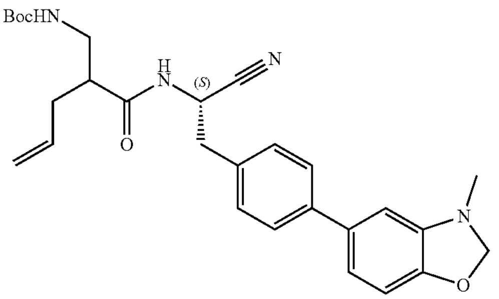

Starting from BB01 (1 eq., 0.2 g, 0.606 mmol) and B1-69-3 (1.05 eq., 0.17 g, 0.64 mmol) and using general procedure B, B1-69-4 was obtained (197 mg, 64%) after purification by flash chromatography over silica gel (regular SiOH, 50 μm, 25 g, dry loading (silica), mobile phase gradient: Cyclohexane/EtOAc from 100/0 to 30/70 over 45 min) and co-evaporation with DCM.

LC/MS: Rt=2.48 min, 100%, $[M\text{-}^tBu+H]^+$=449.1.

$^1$H NMR (400 MHz, DMSO) δ 8.79 (dd, J=15.2, 7.9 Hz, 1H), 7.70-7.62 (m, 2H), 7.60-7.52 (m, 1H), 7.45-7.35 (m, 4H), 6.77 (dt, J=19.9, 5.9 Hz, 1H), 5.74-5.29 (m, 1H), 5.07-4.92 (m, 2H), 4.88 (dd, J=38.6, 16.9 Hz, 1H), 3.40 (d, J=0.9 Hz, 3H), 3.18-2.88 (m, 4H), 2.47-2.41 (m, 1H), 2.15 (t, J=7.0 Hz, 1H), 2.04 (t, J=7.0 Hz, 1H), 1.42-1.34 (m, 9H).

2-(aminomethyl)-N-[(1S)-1-cyano-2-[4-(3-methyl-2-oxo-2,3-dihydro-1,3-benzoxazol-5-yl)phenyl]ethyl]pent-4-enamide: compound 167

Compound 167

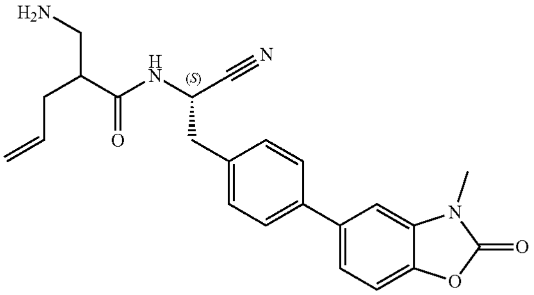

Starting from B1-69-4 (1 eq., 100 mg, 0.2 mmol) and using general procedure C, Compound 167 was obtained (20 mg, 25%) after purification by flash chromatography over silica gel (regular SiOH, 15 μm, 4 g, dry loading (silica), mobile phase gradient: DCM/MeOH from 100/0 to 80/20 over 60 min), co-evaporation with DCM and freeze-drying using a mixture of ACN/water (1:10).

LC/MS: Rt=7.23 min, 98.8%, $[M+H]^+$=405.4.

$^{1}$H NMR (400 MHz, DMSO) δ 8.81 (s, 1H), 7.70-7.62 (m, 2H), 7.57 (s, 1H), 7.45-7.31 (m, 4H), 5.58 (dddt, J=77.9, 17.0, 10.1, 6.9 Hz, 1H), 5.05-4.80 (m, 3H), 3.40 (s, 3H), 3.20-3.03 (m, 2H), 2.69-2.52 (m, 2H), 2.28-2.05 (m, 3H), 1.63 (s, 2H)

Example 45: Synthesis of Compound 189: 3-amino-N-[(1S)-1-cyano-2-[4-(3-methyl-2-oxo-2,3-dihydro-1,3-benzoxazol-5-yl)phenyl]ethyl]-3-phenylpropanamide

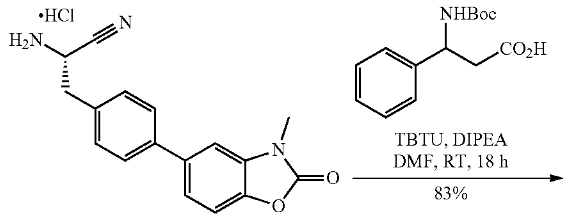

BB01

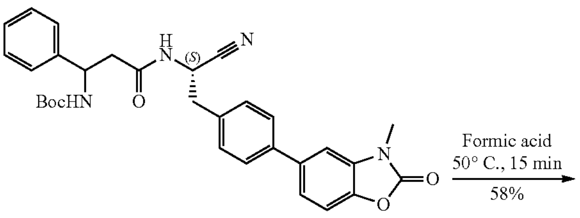

B1-95-2

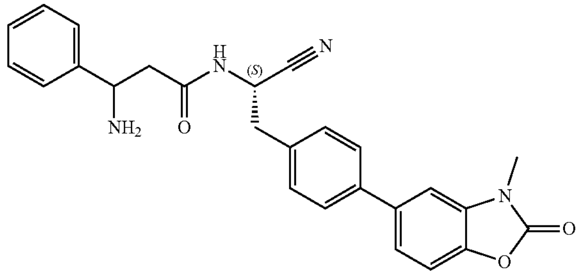

Compound 189 tert-butyl N-(2-{[(1S)-1-cyano-2-[4-(3-methyl-2-oxo-2,3-dihydro-1,3-benzoxazol-5-yl)phenyl]ethyl]carbamoyl}-1-phenylethyl)carbamate B1-95-2

B1-95-2

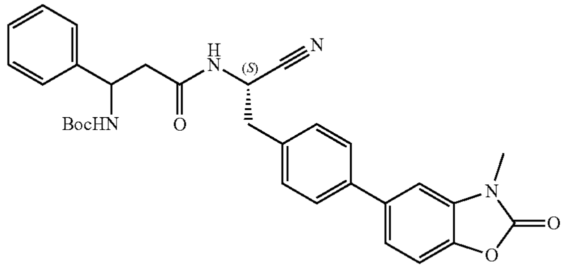

Starting from BB01 (1 eq., 150 mg, 0.45 mmol) and 3-{[(tert-butoxy)carbonyl]amino}-3-phenylpropanoic acid (1.05 eq., 130 mg, 0.48 mmol) and using general procedure B, B1-95-2 was obtained as an orange gum (205 mg, 83%) after purification by flash chromatography over silica gel (50 μm, 25 g, cyclohexane/EtOAc from 70:30 to 40:60 in 30 min).

LC/MS: Rt=1.70 min, 100%, $[M-Boc+H]^+$=441.4

3-amino-N-[(1S)-1-cyano-2-[4-(3-methyl-2-oxo-2,3-dihydro-1,3-benzoxazol-5-yl)phenyl]ethyl]-3-phenylpropanamide compound 189 compound 189

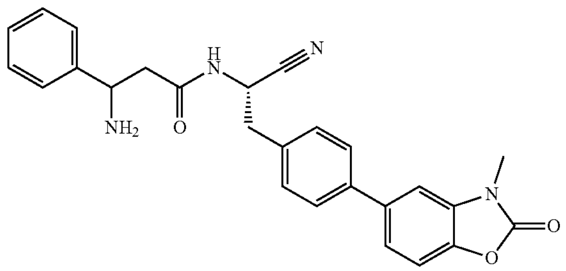

Starting from B1-95-2 (1 eq., 70.0 mg, 0.13 mmol) and using general procedure C, Compound 189 was obtained (26.0 mg, 58%) after purification by flash chromatography over silica gel (regular SiOH, 50 μm, 12 g Interchim, dry loading (silica), mobile phase gradient: DCM/MeOH from 100/0 to 90/10 over 35 min), then vacuum-dried at 40° C. for 18 h.

LC/MS: Rt=7.32 min, 96.55%, $[M+H]^+$=441.35

$^{1}$H NMR (400 MHz, DMSO) δ 8.89 (s, 1H), 7.71-7.53 (m, 3H), 7.47-7.11 (m, 9H), 5.03-4.91 (m, 1H), 4.23-4.11 (m, 1H), 3.40 (s, 3H), 3.16-2.97 (m, 2H), 2.46-2.34 (m, 2H), 2.20 (s, 2H).

Example 46. Synthesis of Compound 152: (R)—N—((S)-1-cyano-2-(4-(3-methyl-2-oxo-2,3-dihydrobenzo[d]oxazol-5-yl)phenyl)ethyl)-2-(methylamino)propanamide Compound 152 can be synthesized according to the schemes below.

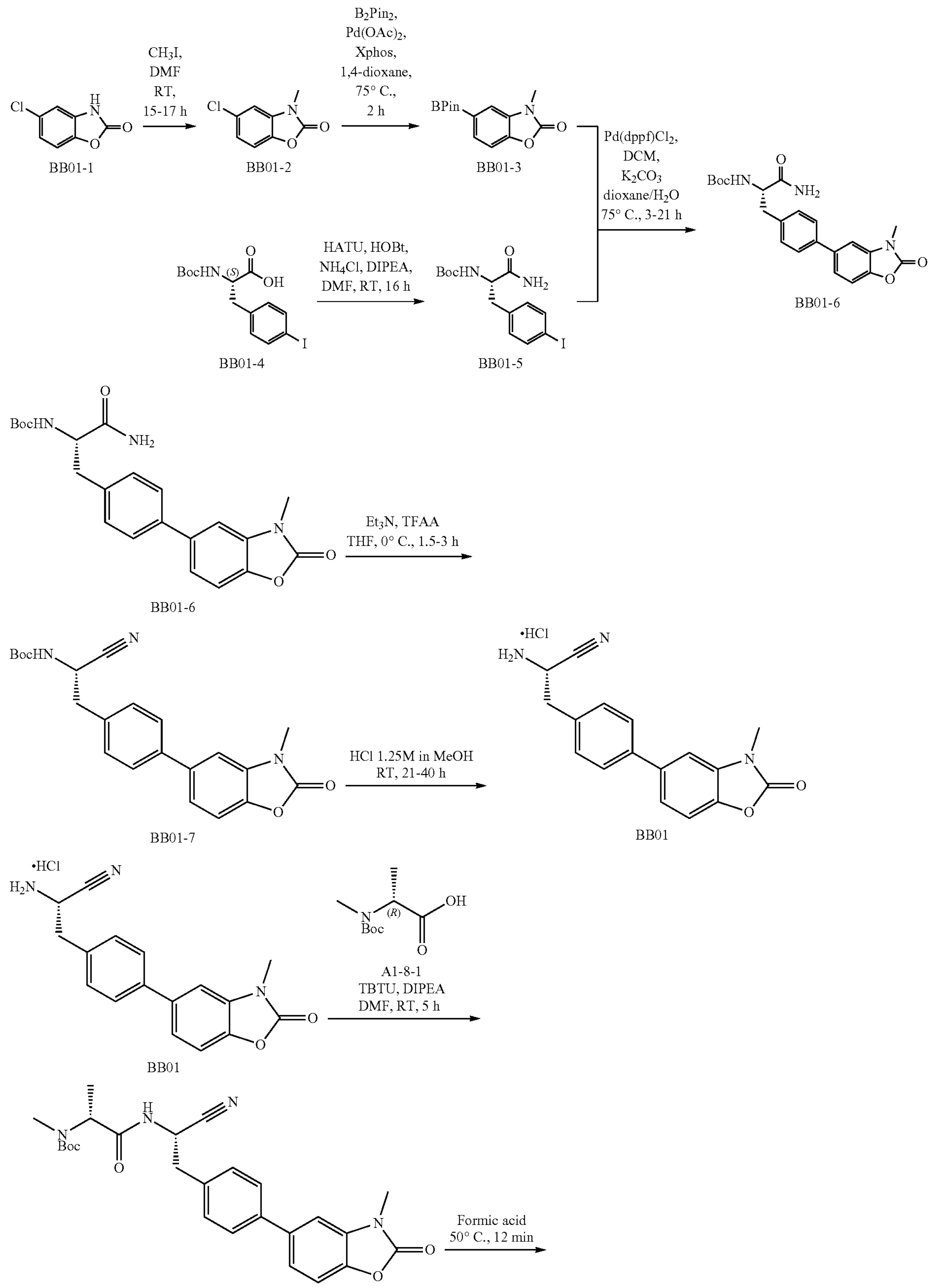
CH3I,
DMF
RT,
15-17 h
BB01-1
BB01-2
B2Pin2,
Pd(OAc)2,
Xphos,
1,4-dioxane,
75° C.,
2 h
BB01-3
Pd(dppf)Cl2,
DCM,
K2CO3
dioxane/H2O
75° C., 3-21 h
BB01-6
BB01-4
HATU, HOBt,
NH4Cl, DIPEA,
DMF, RT, 16 h
BB01-5
Et3N, TFAA
THF, 0° C., 1.5-3 h
BB01-6
HCl 1.25M in MeOH
RT, 21-40 h
BB01-7
BB01
A1-8-1
TBTU, DIPEA
DMF, RT, 5 h
BB01
Formic acid
50° C., 12 min -continued
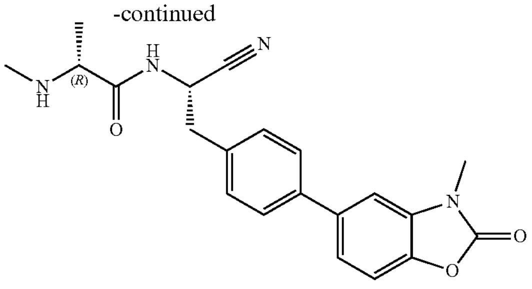
Compound 152
Example 47. Synthesis of Compound 153 and Compound 241
Compound 1241 can be synthesized according to the schemes below.
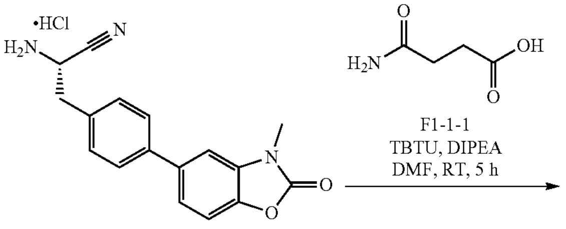
BB01
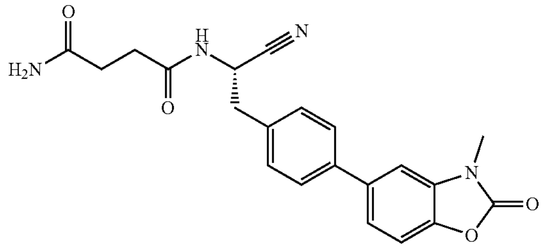
+
compound 153
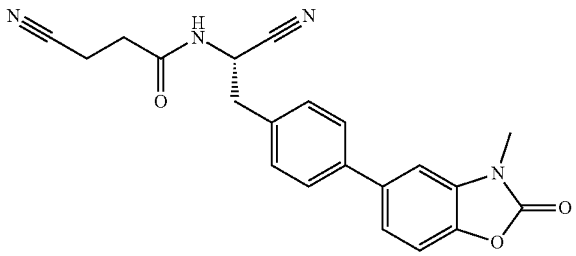
compound 241
Example 48. Synthesis of Compound 154
Compound 154 can be synthesized according to the schemes below.
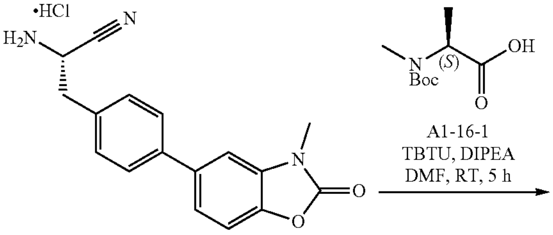
BB01
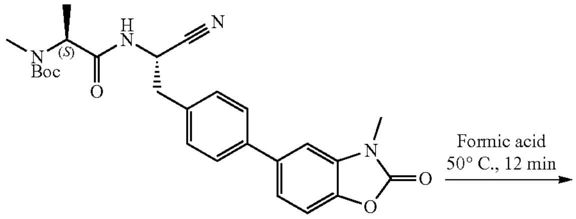
A1-16-2
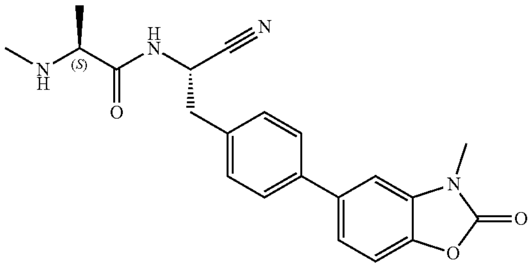
compound 154
Example 49. Synthesis of Compound 242
Compound 242 can be synthesized according to the schemes below.
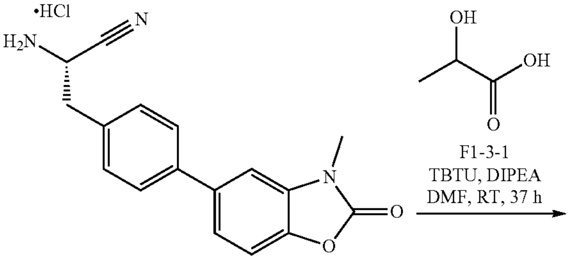
BB01

-continued
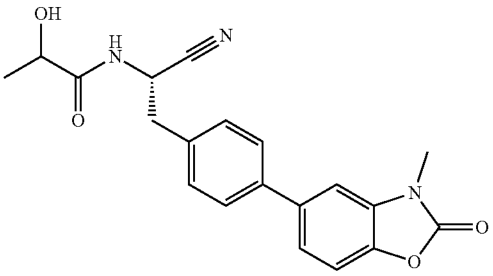
compound 242
Example 50. Synthesis of Compound 155
Compound 155 can be synthesized according to the schemes below.
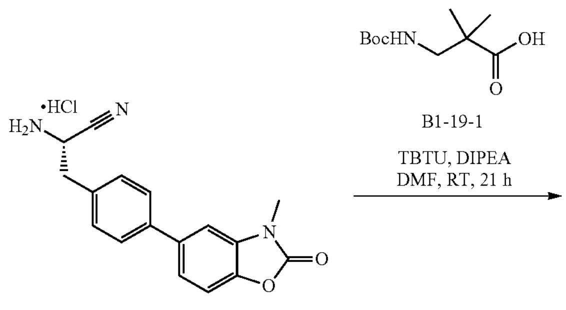
BB01
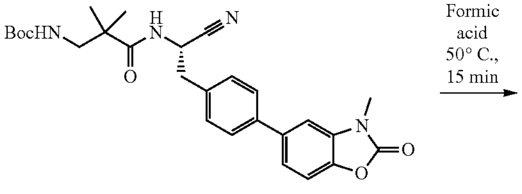
B1-19-2
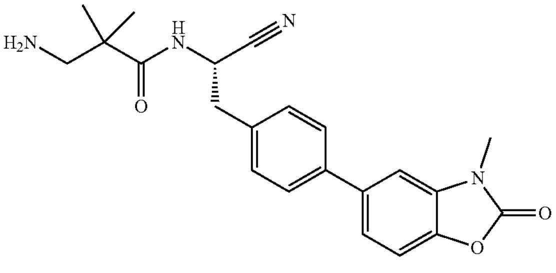
compound 155
Example 51. Synthesis of Compound 156
Compound 156 can be synthesized according to the schemes below.
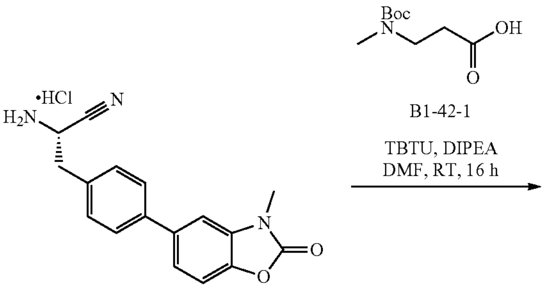
BB01
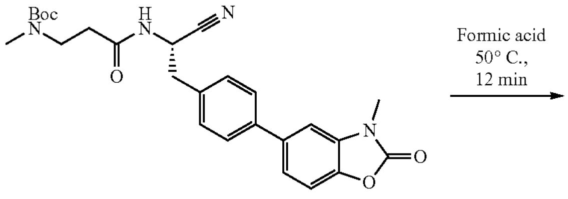
B1-42-2
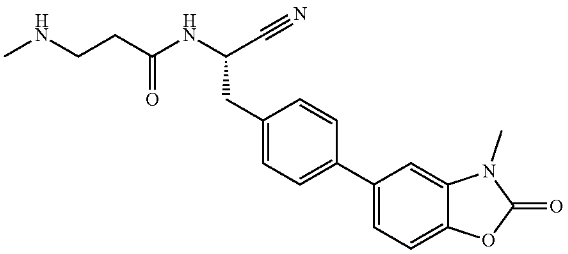
B1-42
Example 52. Synthesis of Compound 157
Compound 157 can be synthesized according to the schemes below.
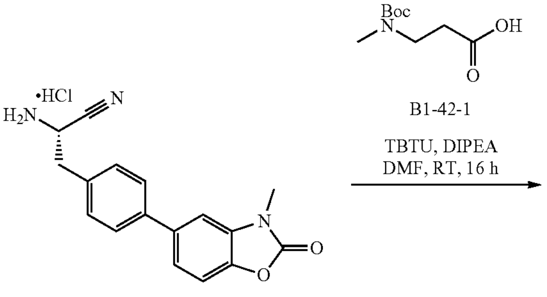
BB01
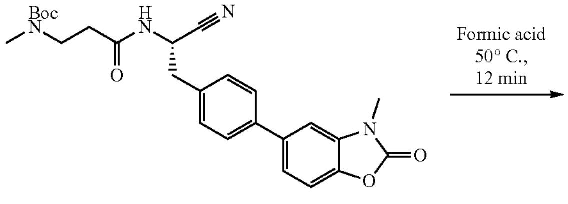
B1-42-2

-continued
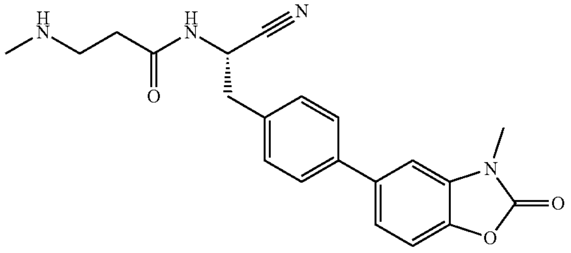
Compound 156
Example 53. Synthesis of Compound 158
Compound 158 can be synthesized according to the schemes below.
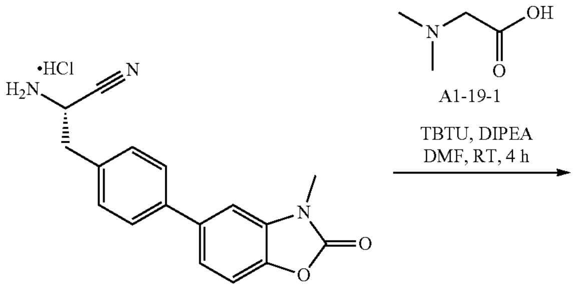
BB01
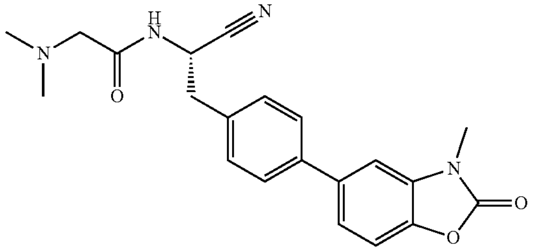
Compound 158
Example 54. Synthesis of Compound 181
Compound 181 can be synthesized according to the schemes below.
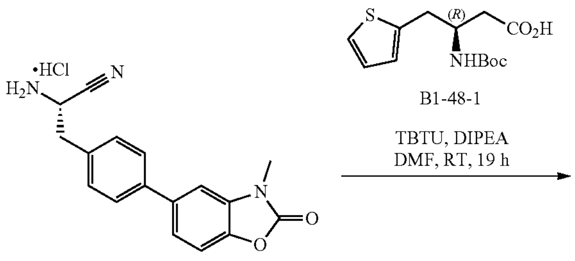
BB01
-continued
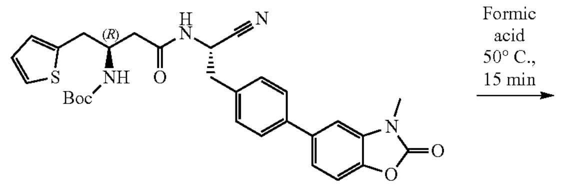
B1-48-2
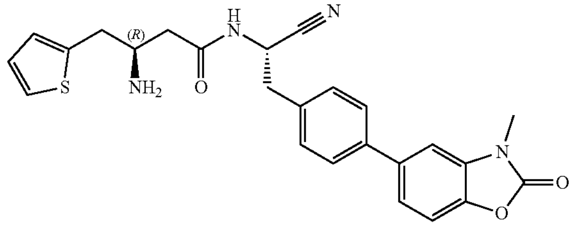
Compund 181
Example 55. Synthesis of Compound 159
Compound 159 can be synthesized according to the schemes below.
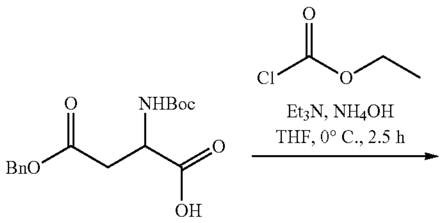
B1-29-1
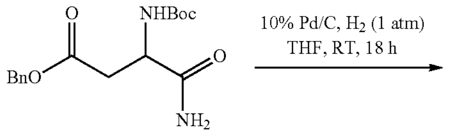
B1-29-2
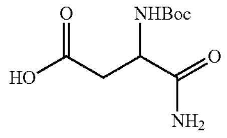
B1-29-3
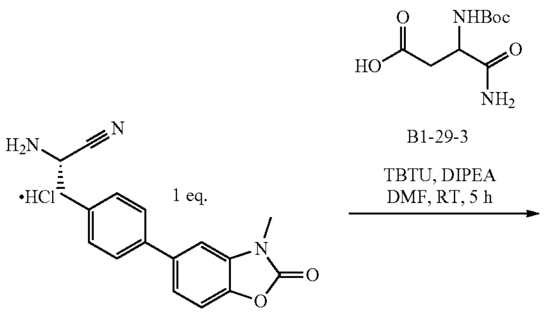
BB01

-continued
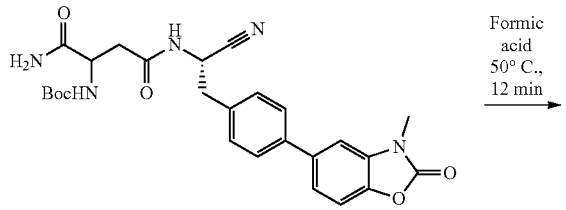
B1-29-4
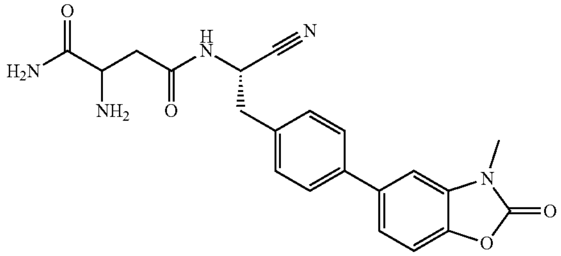
compound 159
Example 56. Synthesis of Compound 160
Compound 160 can be synthesized according to the schemes below.
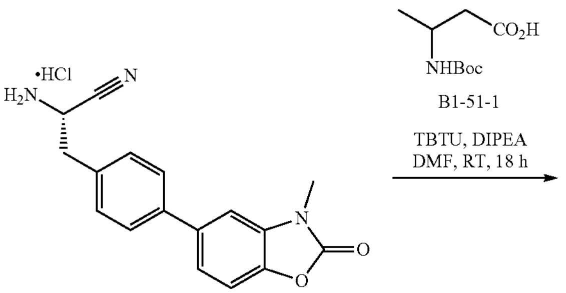
BB01
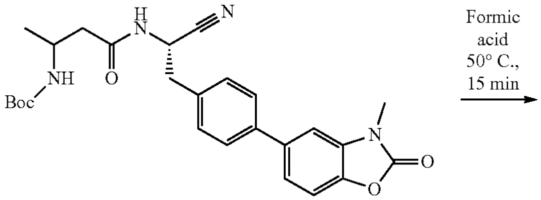
B1-51-2
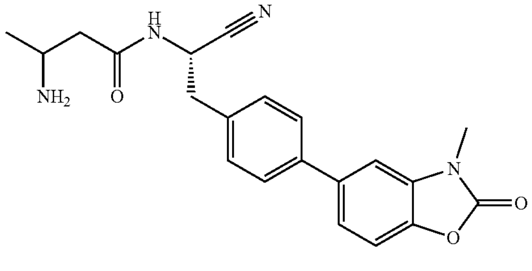
compound 160
Example 57. Synthesis of Compound 183
Compound 183 can be synthesized according to the schemes below.
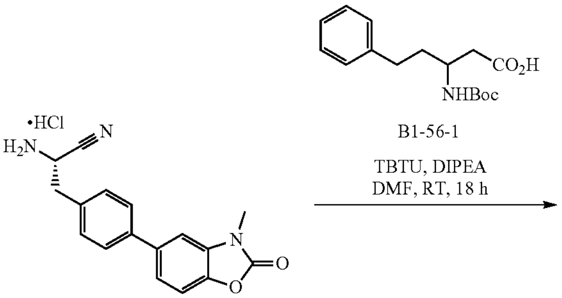
BB01
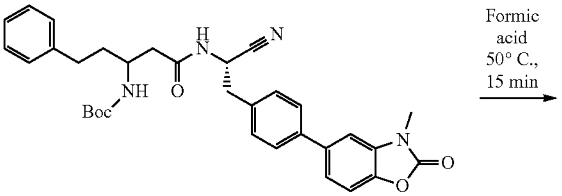
B1-56-2
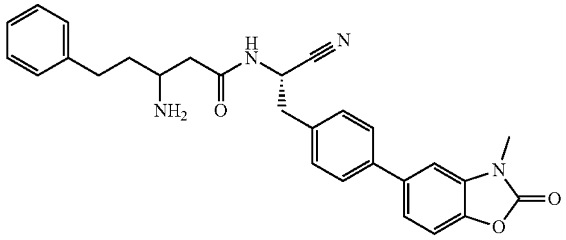
compound 183
Example 58. Synthesis of Compound 161
Compound 161 can be synthesized according to the schemes below.
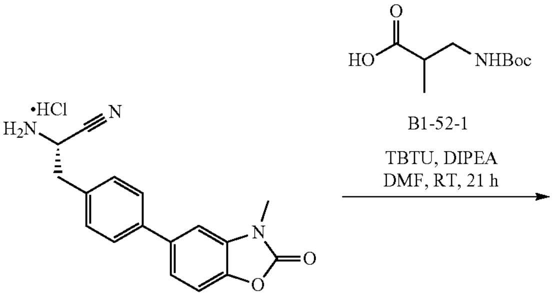
BB01

-continued
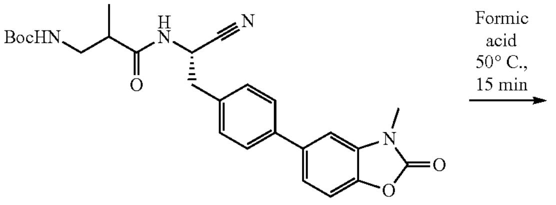
B1-52-2
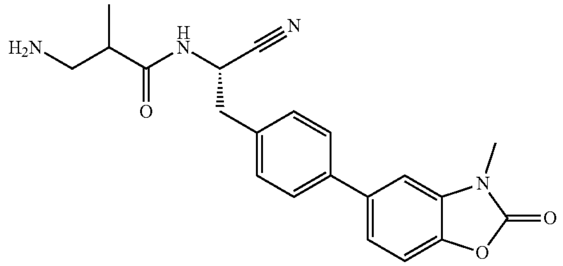
compound 161
Example 59. Synthesis of Compound 162
Compound 162 can be synthesized according to the schemes below.
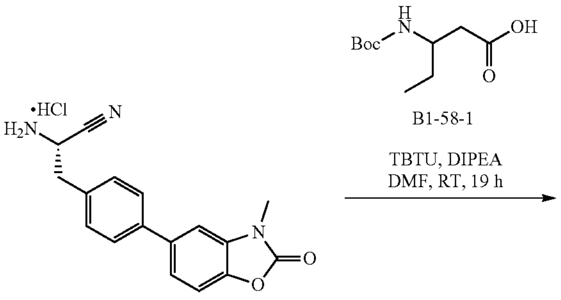
B1-58-1
BB01
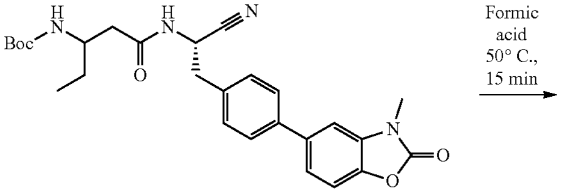
B1-58-2
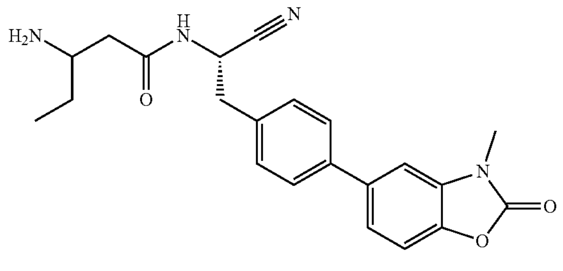
compound 162
Example 60. Synthesis of Compound 163
Compound 163 can be synthesized according to the schemes below.
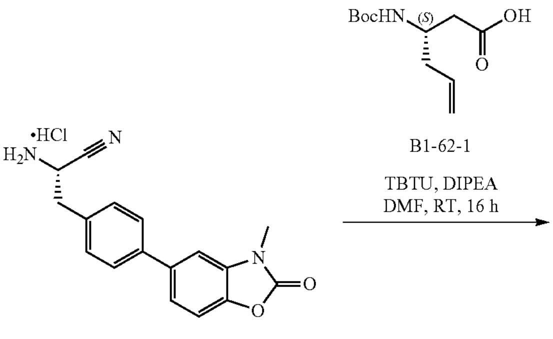
B1-62-1
BB01
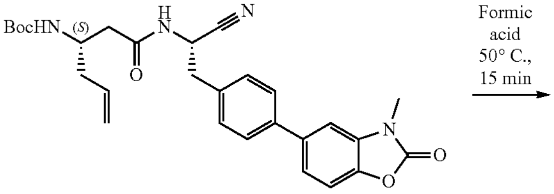
B1-62-2
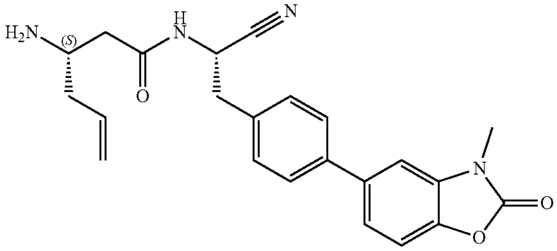
compound 163
Example 61. Synthesis of Compound 166
Compound 166 can be synthesized according to the schemes below.
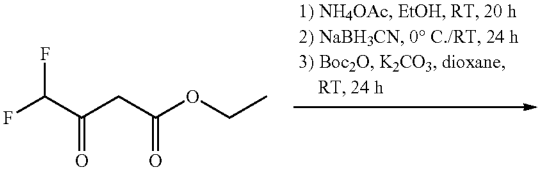
B1-60-1
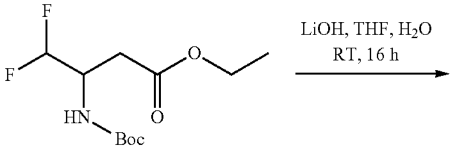
B1-60-2

-continued
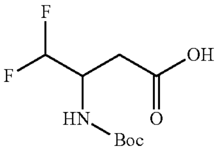
B1-60-3
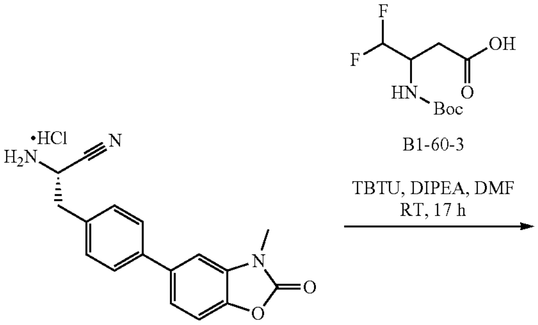
BB01
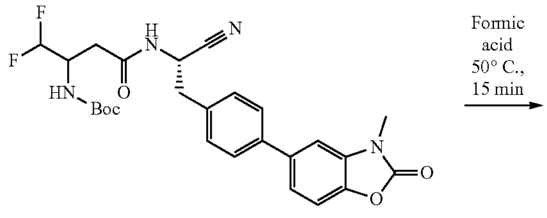
B1-60-4
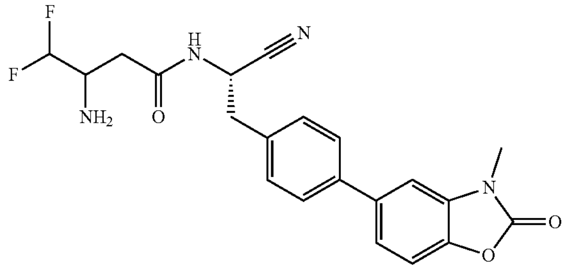
compound 166
Example 62. Synthesis of Compound 185
Compound 185 can be synthesized according to the schemes below.
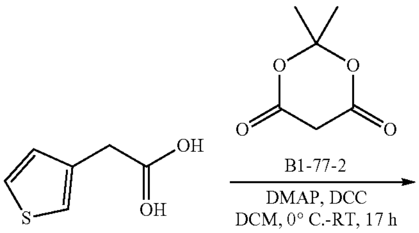
B1-77-1
-continued
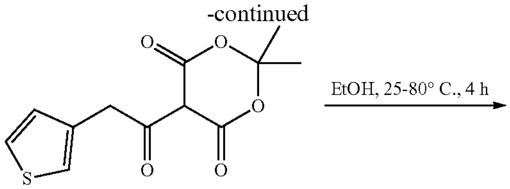
B1-77-3
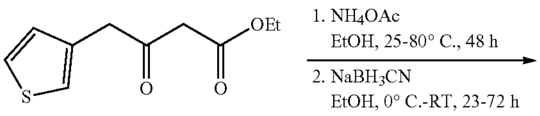
B1-77-4
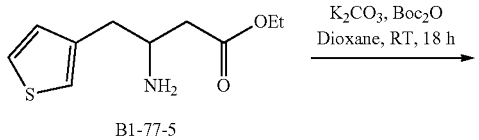
B1-77-5
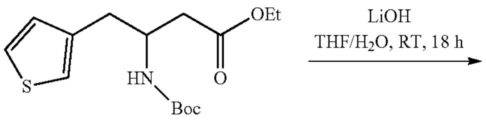
B1-77-6
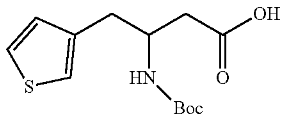
B1-77-7
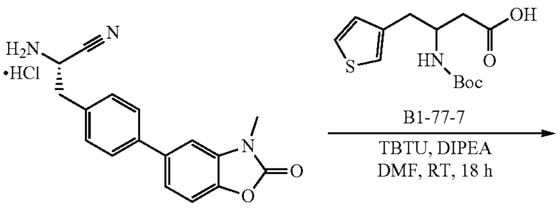
BB01
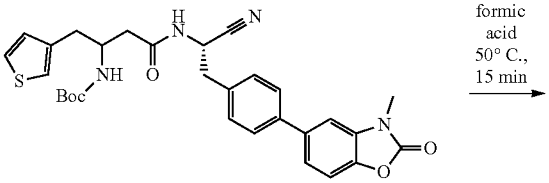
B1-77-8
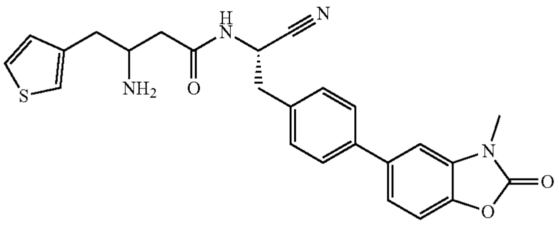
Compound 185
Example 63. Synthesis of Compound 186
Compound 186 can be synthesized according to the schemes below.

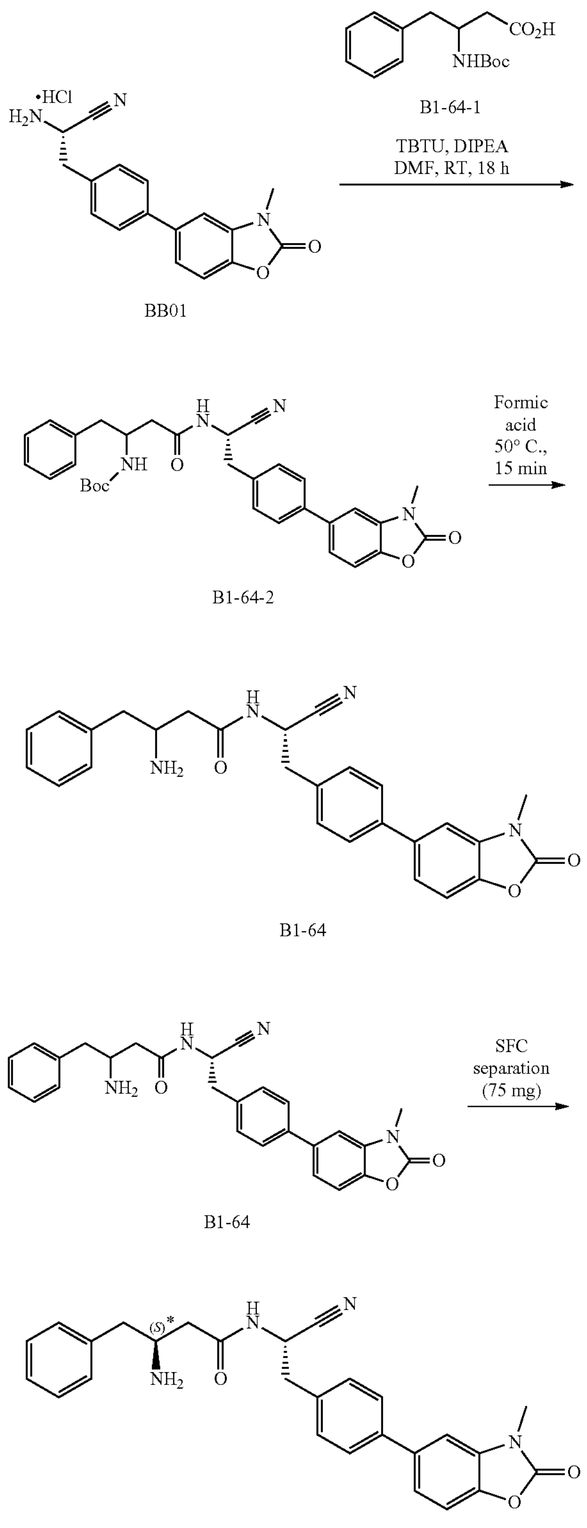
B1-64-1, BB01, B1-64-2, B1-64, B1-64, compuond 186
Example 64. Synthesis of Compound 187
Compound 187 can be synthesized according to the schemes below.
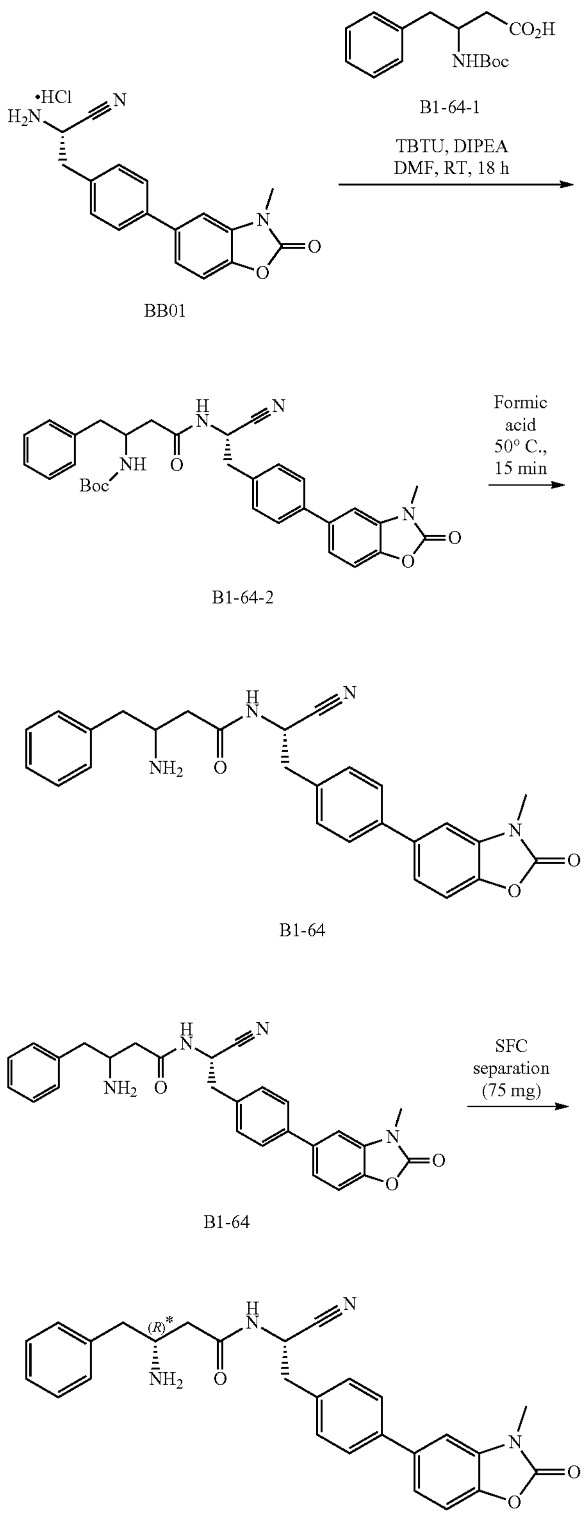
B1-64-1, BB01, B1-64-2, B1-64, B1-64, compound 187
Example 65. Synthesis of Compound 188
Compound 188 can be synthesized according to the schemes below.

-continued
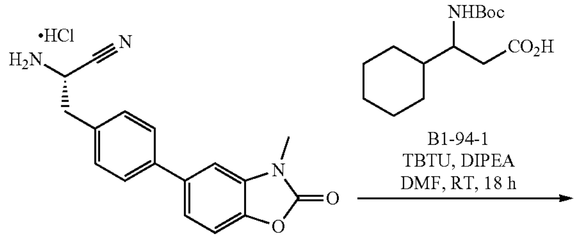
BB01
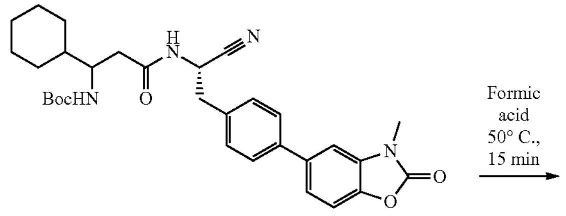
B1-94-2
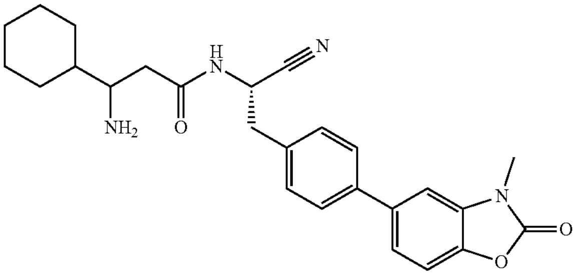
compound 188
Example 66. Synthesis of Compound 138
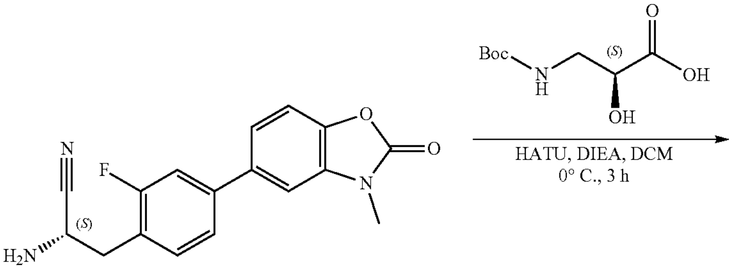
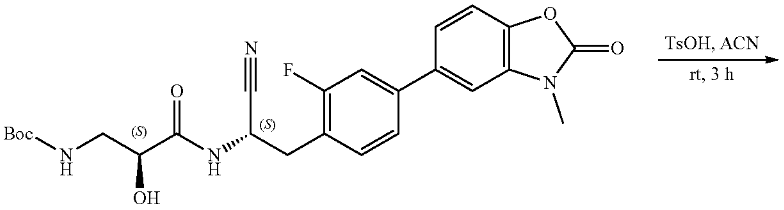
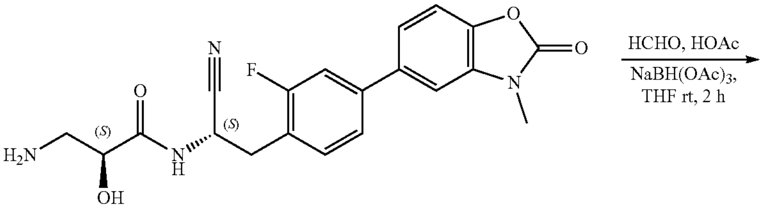
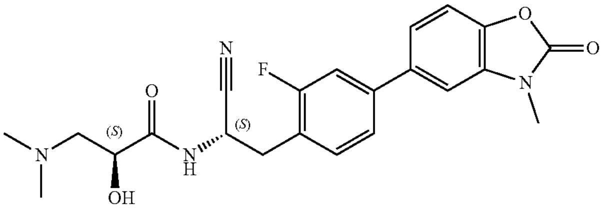
Compound 138

Synthesis of tert-butyl N-[(2S)-2-{1[(1S)-1-cyano-2-[2-fluoro-4-(3-methyl-2-oxo-1,3-benzoxazol-5-yl)phenyl]ethyl]carbamoyl}-2-hydroxyethyl]carbamate

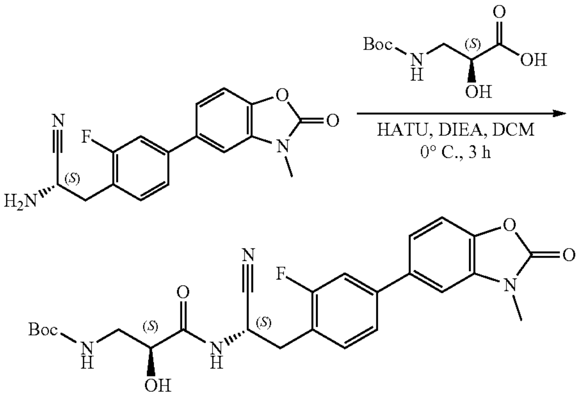

To a stirred solution of (2S)-2-amino-3-[2-fluoro-4-(3-methyl-2-oxo-1,3-benzoxazol-5-yl)phenyl]propanenitrile (100 mg, 0.32 mmol, 1.0 equiv), (2S)-3-[(tert-butoxycarbonyl)amino]-2-hydroxypropanoic acid (329 mg, 1.60 mmol, 5.0 equiv) and DIEA (124 mg, 0.96 mmol, 3.0 equiv) in DCM (5 mL) was added HATU (147 mg, 0.38 mmol, 1.2 equiv) in portions at 0° C. The resulting mixture was stirred for additional 3 h at 0° C. The residue was purified by silica gel column chromatography, eluted with PE/THE (1:1) to afford tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-hydroxyethyl]carbamate (130 mg, 81.1%). LCMS (ES, m/z): $[M+H]^+$: 499.

Synthesis of (2S)-3-amino-N-[(1S)-1-cyano-2-[2-fluoro-4-(3-methyl-2-oxo-1,3-benzoxazol-5-yl)phenyl]ethyl]-2-hydroxypropanamide

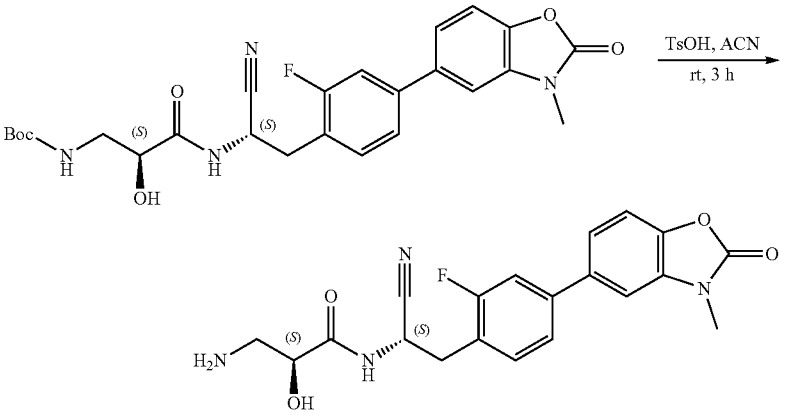

Into a 50 mL round-bottom flask were added tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-hydroxyethyl]carbamate (130 mg, 0.26 mmol, 1.0 equiv) in ACN (3 mL) and TsOH (135 mg, 0.78 mmol, 3.0 equiv) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 80% gradient in 10 min; detector, UV 254 nm. This resulted in (2S)-3-amino-N-[(1S)-1-cyano-2-[2-fluoro-4-(3-methyl-2-oxo-1,3-benzoxazol-5-yl)phenyl]ethyl]-2-hydroxypropanamide (150 mg, crude). LCMS (ES, m/z): $[M+H]^+$: 399.

Synthesis of (2S)—N-[(1S)-1-cyano-2-[2-fluoro-4-(3-methyl-2-oxo-1,3-benzoxazol-5-yl)phenyl]ethyl]-3-(dimethylamino)-2-hydroxypropanamide

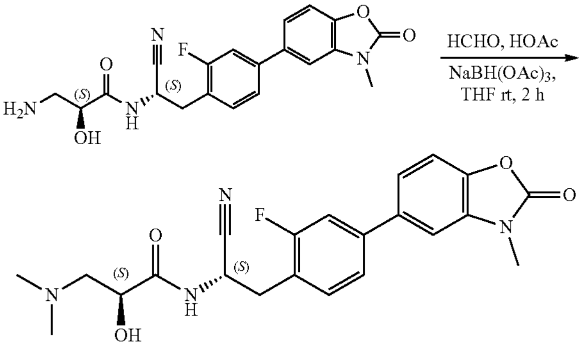

compound 138

A solution of (2S)-3-amino-N-[(1S)-1-cyano-2-[2-fluoro-4-(3-methyl-2-oxo-1,3-benzoxazol-5-yl)phenyl]ethyl]-2-hydroxypropanamide (130 mg, 0.32 mmol, 1.0 equiv) in THE (3 mL) was treated with HCHO (98 mg, 3.26 mmol, 10 equiv), HOAc (0.1 mL) for 1 h at room temperature followed by the addition of $NaBH(OAc)_3$ (138 mg, 0.65 mmol, 2.0 equiv) in portions at room temperature. The resulting mixture was stirred for additional 1 h at room temperature. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2S)—N-[(1S)-1-cyano-2-[2-fluoro-4-(3-methyl-2-oxo-1,3-benzoxazol-5-yl)phenyl]ethyl]-3-(dimethylamino)-2-hydroxypropanamide (17.3 mg, 12.43%). LCMS (ES, m/z): $[M+H]^+$: 427.2.

$^1$H NMR (400 MHz, DMSO-$d_6$) δ 8.81 (d, J=8.6 Hz, 1H), 7.66 (d, J=1.9 Hz, 1H), 7.64-7.52 (m, 2H), 7.52-7.43 (m, 2H), 7.41 (d, J=8.4 Hz, 1H), 5.58 (d, J=5.0 Hz, 1H), 5.08 (q, J=8.1 Hz, 1H), 4.01 (dt, J=8.6, 4.3 Hz, 1H), 3.40 (s, 3H), 3.32-3.25 (m, 1H), 3.20 (dd, J=13.8, 8.6 Hz, 1H), 2.35-2.15 (m, 2H), 2.11 (s, 6H).

Example 67: DPP1 IC50 Assay

Mouse DPP1 enzyme IC50 assay: Test articles were applied to active mouse DPP1 enzyme (R&D Systems; Minneapolis, MN) in Assay Buffer (50 mM MES pH 5.5, 50 mM NaCl, 5 mM DTT) in a total reaction volume of 125 μL. 25 μL of compound in Assay Buffer plus 5% DMSO was first added to 50 μL of active mouse DPP1 enzyme at a concentration of 62.5 pg/μL and allowed to pre-incubate for 10 minutes at 37° C. after which 50 μL of 1000 μM H-Gly-Arg-AMC substrate (Bachem; St. Torrance, CA) was added, giving final substrate concentration of 400 μM and a final DMSO concentration of 1%. Substrate cleavage was measured for 90 minutes at 37° C., with fluorescence at Excitation/Emission 350/450 nm measured every 5 minutes. DPP1 concentration was interpolated based on its activity relative to a standard curve of recombinant active mouse DPP1 enzyme. $IC_{50}$ values for each compound were calculated via the XLFit (IDBS Version 5.3.1.3) Add-On to Microsoft Excel using the four parameter fit equation y=(A+((B-A)/(1+((C/x)^D)))), which appears as equation number 205 (4 Parameter Logistic Model or Sigmoidal Dose-Response Model) in XLFit. Default constraints were used for each Parameter. $IC_{50}$ was defined as the compound concentration at which 50% of enzyme activity was inhibited when compared to the no-compound control. Results are provided in Table 1 below.

Human DPP1 enzyme $IC_{50}$ assay: Recombinant human DPP1 enzyme (R&D Systems; Minneapolis, MN) was first proteolytically processed into its mature form using recombinant human cathepsin L (R&D Systems) in a buffer consisting of 20 mM citric acid pH 4.5, 150 mM NaCl, 1 mM EDTA and 10 mM DTT. Test articles were applied to activated human DPP1 enzyme in Assay Buffer (25 mM MES pH 6.0, 50 mM NaCl, 5 mM DTT) in a total reaction volume of 125 μL. 25 μL of compound in Assay Buffer plus 5% DMSO was first added to 50 μL of activated human DPP1 enzyme at a concentration of 1 ng/μL and allowed to pre-incubate for 10 minutes at 37° C. after which 50 μL of 1000 μM H-Gly-Arg-AMC substrate (Bachem; St. Torrance, CA) was added, giving final substrate concentration of 400 μM and a final DMSO concentration of 1%. Substrate cleavage was measured for 90 minutes at 37° C., with fluorescence at Excitation/Emission 350/450 nm measured every 5 minutes. DPP1 concentration was interpolated based on its activity relative to a standard curve of activated human recombinant DPP1 enzyme. IC50 values for each compound were calculated via the XLFit (IDBS Version 5.3.1.3) Add-On to Microsoft Excel using the four parameter fit equation y={A+[(B-A)]/[1+((C/x)^D)]}, which appears as equation number 205 (4 Parameter Logistic Model or Sigmoidal Dose-Response Model) in XLFit. Default constraints were used for each Parameter. IC50 was defined as the compound concentration at which 50% of enzyme activity was inhibited when compared to the no-compound control. Results are provided in Table 1 below.

DPP1 Cell $IC_{50}$ assay: HL-60 cells (ATCC; Manassas, VA) were maintained in RPMI-1640 supplemented with 20% heat-inactivated FBS and 1× Antibiotic Antimycotic (Cytiva; Marlborough, MA). Media was changed every three to four days and cells were not allowed to exceed $1\times10^6$ cells per mL. Prior to assay, cells were collected by centrifugation at 500 rcf for 3 minutes, resuspended in PBS and counted. Cells were diluted in PBS to a concentration of $5\times10^5$ live cells per mL and transferred to black 96-well plates for assay, 60 μL per well. Test articles were diluted in PBS plus 0.5% DMSO, and 20 μL was added to each assay well. Compound was allowed to pre-incubate with cells with gentle shaking at 100 rpm for 60 minutes at 37° C. in a cell culture incubator maintained at 5% $CO_2$, after which 20 μL of 500 μM H-Gly-Phe-AFC substrate (MP Biomedicals; Solon, OH) was added to each well. Plates were returned to the incubator with shaking at 100 rpm for 30 minutes, after which fluorescence was measured at Excitation/Emission 400/505 nm. % Inhibition was calculated from RFU values compared to control cell wells that received only PBS plus 0.5% DMSO. $IC_{50}$ values for each compound were calculated via the XLFit (IDBS Version 5.3.1.3) Add-On to Microsoft Excel using the four parameter fit equation y=(A+((B-A)/(1+((C/x)^D)))), which appears as equation number 205 (4 Parameter Logistic Model or Sigmoidal Dose-Response Model) in XLFit. $IC_{50}$ was defined as the compound concentration at which 50% of enzyme activity was inhibited when compared to the no-compound control. Results are provided in Table 1 below.

TABLE 1

| DPP1 $IC_{50}$ values [1] | | | |
|---|---|---|---|
| compound No. | DPP1 IC50, nM; Human [2] | DPP1 IC50, nM; Mouse [2] | Cell Assay, nM [2] |
| 101 | * | ** | ** |
| 102 | N/A | N/A | N/A |
| 103 | * | N/A | * |
| 104 | * | N/A | N/A |
| 105 | * | N/A | ** |
| 106 | N/A | N/A | N/A |
| 107 | N/A | N/A | N/A |
| 108 | N/A | N/A | N/A |
| 109 | * | N/A | * |
| 110 | * | N/A | * |
| 111 | * | N/A | * |
| 112 | * | N/A | N/A |
| 113 | * | N/A | N/A |
| 114 | N/A | N/A | N/A |
| 115 | * | N/A | N/A |
| 116 | * | N/A | N/A |
| 117 | N/A | N/A | N/A |
| 118 | * | N/A | N/A |
| 119 | N/A | N/A | N/A |
| 120 | N/A | N/A | N/A |
| 121 | * | N/A | N/A |
| 137 | * | *** | * |
| 138 | ** | ** | *** |
| 139 | N/A | N/A | N/A |
| 140 | * | ** | * |
| 152 | * | * | N/A |
| 153 | * | * | N/A |
| 154 | * | * | N/A |
| 155 | * | * | N/A |
| 156 | * | * | N/A |
| 157 | * | * | N/A |
| 158 | * | * | N/A |
| 159 | * | * | N/A |
| 160 | * | * | N/A |
| 161 | * | * | N/A |
| 162 | * | * | N/A |
| 163 | * | * | N/A |
| 164 | * | * | * |
| 165 | * | * | * |
| 166 | * | * | N/A |
| 167 | * | * | * |
| 168 | * | N/A | N/A |

TABLE 1-continued

| DPP1 $IC_{50}$ values [1] | | | |
|---|---|---|---|
| 169 | * | N/A | * |
| 170 | N/A | N/A | N/A |
| 171 | N/A | N/A | N/A |
| 172 | ** | N/A | ** |
| 173 | N/A | N/A | N/A |
| 174 | * | N/A | N/A |
| 175 | * | ** | N/A |
| 181 | * | * | N/A |
| 182 | * | * | * |
| 183 | * | * | N/A |
| 184 | * | * | N/A |
| 185 | * | * | N/A |
| 186 | * | * | N/A |
| 187 | * | * | N/A |
| 188 | * | N/A | * |
| 189 | * | N/A | N/A |
| 190 | * | N/A | * |
| 191 | * | N/A | N/A |
| 192 | * | N/A | N/A |
| 196 | * | N/A | N/A |
| 197 | * | N/A | N/A |
| 198 | * | N/A | N/A |
| 199 | * | N/A | * |
| 200 | * | N/A | N/A |
| 201 | * | N/A | * |
| 202 | ** | N/A | * |
| 203 | ** | N/A | * |
| 204 | *** | N/A | ** |
| 205 | N/A | N/A | N/A |
| 206 | * | N/A | * |
| 207 | * | N/A | * |
| 208 | *** | N/A | * |
| 209 | N/A | N/A | N/A |
| 210 | ** | N/A | * |
| 211 | * | N/A | * |
| 212 | *** | N/A | ** |
| 213 | * | N/A | * |
| 214 | * | N/A | * |
| 215 | * | N/A | * |
| 216 | * | N/A | N/A |
| 217 | * | N/A | N/A |
| 218 | ** | N/A | * |
| 219 | *** | N/A | ** |
| 220 | *** | N/A | ** |
| 221 | *** | N/A | * |
| 222 | *** | N/A | ** |
| 229 | * | N/A | N/A |
| 238 | * | * | N/A |
| 239 | * | * | N/A |
| 240 | * | * | N/A |
| 241 | * | * | N/A |
| 242 | * | * | N/A |
| 243 | * | * | N/A |
| 244 | * | * | N/A |
| 245 | * | * | N/A |
| 248 | * | * | * |
| 249 | * | N/A | * |
| 254 | ** | N/A | * |
| 276 | * | N/A | * |
| 277A | * | N/A | * |
| 277B | * | N/A | N/A |
| 264A | * | N/A | * |
| 264B | *** | N/A | ** |
| 267 | *** | N/A | * |
| 268 | *** | N/A | ** |
| 269 | *** | N/A | * |
| 253 | * | N/A | N/A |
| 232 | * | N/A | * |
| 225 | * | N/A | N/A |
| 226 | * | N/A | N/A |
| 227 | #N/A | N/A | N/A |
| 228 | * | N/A | N/A |
| 230 | * | N/A | N/A |
| 231 | *** | N/A | * |
| 171A | * | N/A | * |
| 171B | * | N/A | * |
| 171C | * | N/A | N/A |
| 171D | ** | ** | * |

TABLE 1-continued

| DPP1 $IC_{50}$ values [1] | | | |
|---|---|---|---|
| 227A | * | N/A | N/A |
| 227B | * | N/A | N/A |
| 246 | ** | N/A | * |
| 195 | * | N/A | * |
| 120 | * | N/A | N/A |
| 130 | * | N/A | N/A |
| 141 | ** | N/A | ** |
| 142 | ** | N/A | * |
| 144 | * | N/A | * |
| 145 | * | N/A | ** |
| 146 | ** | N/A | * |
| 193 | * | N/A | N/A |
| 194 | * | N/A | N/A |
| 278 | * | N/A | * |
| 281 | * | N/A | * |
| 282 | * | N/A | * |
| 283 | ** | N/A | * |
| 284 | ** | N/A | * |
| 285 | ** | N/A | * |
| 286 | ** | N/A | * |
| 287 | ** | N/A | * |
| 288 | ** | N/A | ** |
| 102A | * | N/A | N/A |
| 102B | * | N/A | * |
| 102C | * | N/A | N/A |
| 258A | * | N/A | * |
| 258B | *** | N/A | ** |
| 259A | *** | N/A | ** |
| 259B | * | N/A | N/A |
| 272A | * | N/A | N/A |
| 272B | ** | N/A | ** |
| 270A | * | N/A | * |
| 270B | *** | N/A | ** |
| 273A | * | N/A | * |
| 273B | *** | N/A | *** |

[1] NA or N/A means the IC50 data for this entry is not available.

[2] The symbols correspond to ranges of IC50 according to the table below.

| symbol | DPP1 IC50, nM; Human | DPP1 IC50, nM; Mouse | Cell Assay, nM |
|---|---|---|---|
| *** | ≤5 | ≤5 | ≤1 |
| ** | 5-15 | 5-20 | 1-2.5 |
| * | ≥15 | ≥20 | ≥2.5 |

Example 68. Synthesis of Compound 269

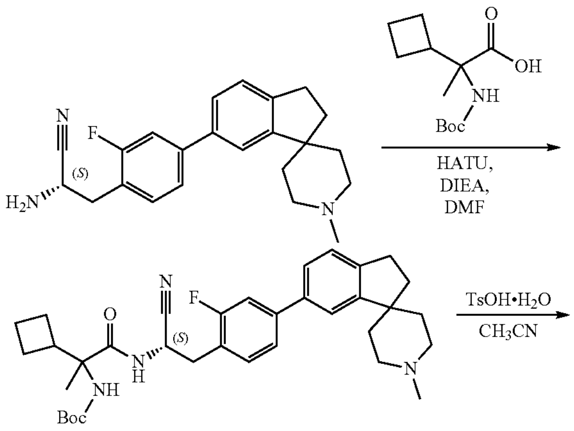

-continued

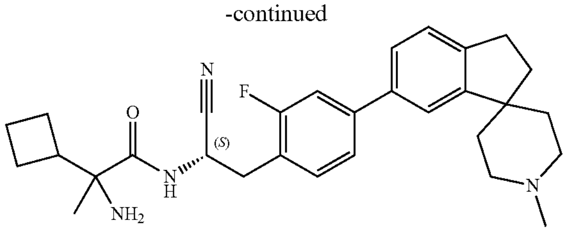

compound 269

Synthesis of tert-butyl (1-(((S)-1-cyano-2-(2-fluoro-4-(1'-methyl-2,3-dihydrospiro[indene-1,4'-piperidin]-6-yl)phenyl)ethyl)amino)-2-cyclobutyl-1-oxopropan-2-yl)carbamate

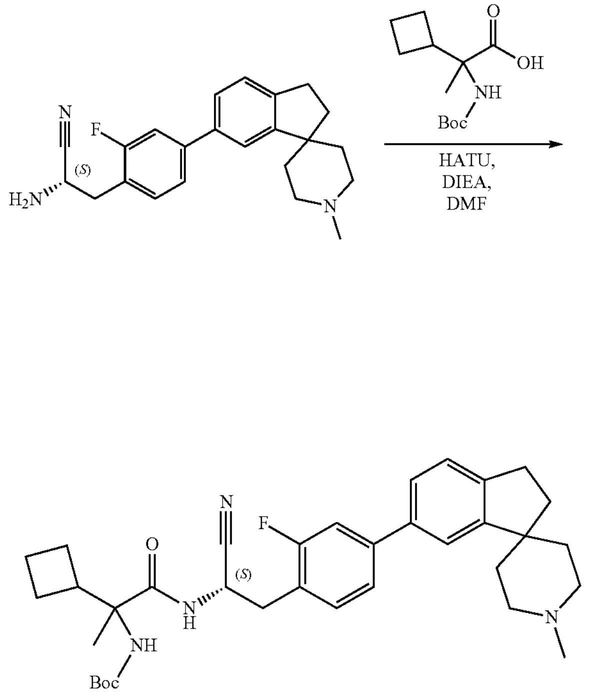

To a solution of 2-[(tert-butoxycarbonyl)amino]-2-cyclobutylpropanoic acid (161 mg, 0.66 mmol, 1.2 equiv), (2S)-2-amino-3-(2-fluoro-4-{1'-methyl-2,3-dihydrospiro[indene-1,4'-piperidin]-6-yl}phenyl)propanenitrile (200 mg, 0.55 mmol, 1.0 equiv), DIEA (214 mg, 1.66 mmol, 3.0 equiv) in DMF (4 mL) was added HATU (315 mg, 0.83 mmol, 1.5 equiv) in portions at 0° C. The reaction was quenched with water (15 mL) at room temperature. The resulting mixture was extracted with EtOAc (20 mL×2). The combined organic layer was washed with NaCl (aq.)(20 mL×2), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-(2-fluoro-4-{1'-methyl-2,3-dihydrospiro[indene-1,4'-piperidin]-6-yl}phenyl)ethyl]carbamoyl}-1-cyclobutylethyl)carbamate (160 mg, 49%). LCMS (ES) $[M+1]^+$ m/z: 589.

Synthesis of 2-amino-N-[(1S)-1-cyano-2-(2-fluoro-4-{1'-methyl-2,3-dihydrospiro[indene-1,4'-piperidin]-6-yl}phenyl)ethyl]-2-cyclobutylpropanamide

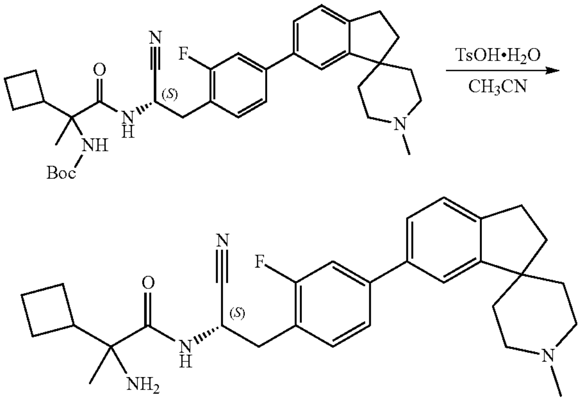

Into a 8 mL vial were added tert-butyl N-(1-{[(1S)-1-cyano-2-(2-fluoro-4-{1'-methyl-2,3-dihydrospiro[indene-1,4'-piperidin]-6-yl}phenyl)ethyl]carbamoyl}-1-cyclobutylethyl)carbamate (100 mg, 0.17 mmol, 1.0 equiv), ACN (3 mL) and $TsOH{\cdot}H_2O$ (97 mg, 0.51 mmol, 3.0 equiv) at room temperature. The resulting mixture was stirred for 3 h at room temperature. The residue product was purified by reverse phase flash with the following conditions: mobile phase, MeCN in water (0.1% $NH_3{\cdot}H_2O$), 10% to 70% gradient in 10 min. This resulted in 2-amino-N-[(1S)-1-cyano-2-(2-fluoro-4-{1'-methyl-2,3-dihydrospiro[indene-1,4'-piperidin]-6-yl}phenyl)ethyl]-2-cyclobutylpropanamide (17.9 mg, 21%). LCMS (ES) $[M+1]^+$ m/z: 489.

$^1H$ NMR (300 MHz, DMSO-$d_6$) δ 7.57-7.36 (m, 5H), 7.27 (d, J=7.7 Hz, 1H), 5.00 (td, J=8.2, 7.5, 3.3 Hz, 1H), 3.22 (ddt, J=21.2, 14.0, 7.1 Hz, 2H), 2.88 (t, J=7.3 Hz, 2H), 2.74 (d, J=10.8 Hz, 2H), 2.55-2.48 (m, 1H), 2.22 (s, 3H), 2.13-1.41 (m, 15H), 0.99 (d, J=17.4 Hz, 3H).

Example 69: Synthesis of Compound 244: 2-{[(1S)-1-cyano-2-[4-(3-methyl-2-oxo-1,3-benzoxazol-5-yl)phenyl]ethyl]carbamoyl}ethyl thiophene-2-carboxylate

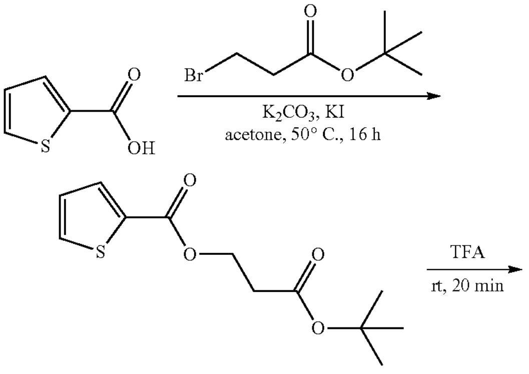

-continued

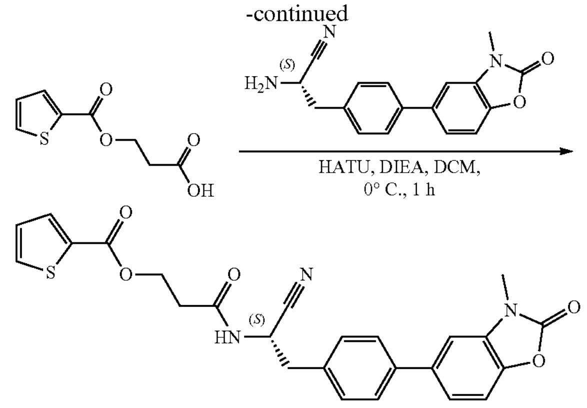

Synthesis of tert-butyl 3-(thiophene-2-carbonyloxy)propanoate

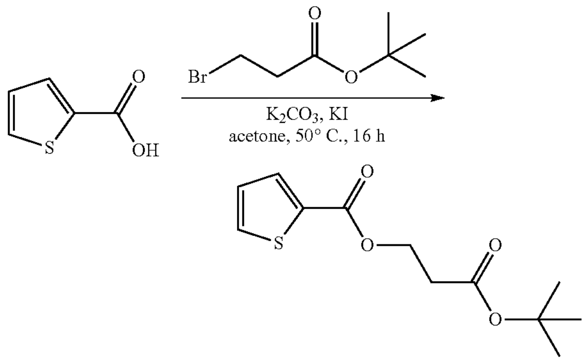

To a stirred solution of thiophene-2-carboxylic acid (2.5 g, 19.51 mmol, 1.0 equiv) and tert-butyl 3-bromopropanoate (4.89 g, 23.41 mmol, 1.2 equiv) in acetone (30 mL) was added $K_2CO_3$ (5.39 g, 39.02 mmol, 2.0 equiv) and KI (0.65 g, 3.90 mmol, 0.2 equiv) at room temperature. The resulting mixture was stirred for 16 h at 50° C. under nitrogen atmosphere. The reaction was cooled to room temperature, the resulting mixture was filtered, the filter cake was washed with DCM (10 mL). The filtrate was concentrated under reduced pressure. The residue was purified by silica gel column chromatography, eluted with PE/EA (10:1) to afford tert-butyl 3-(thiophene-2-carbonyloxy)propanoate (250 mg, 5.00%). LCMS (ES) $[M-56+H]^+$ m/z: 201.

Synthesis of 3-((thiophene-2-carbonyl)oxy)propanoic acid

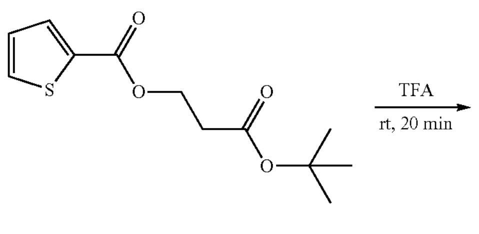

-continued

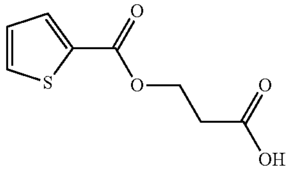

A solution of tert-butyl 3-(thiophene-2-carbonyloxy)propanoate (250 mg, 0.98 mmol, 1.0 equiv) in TFA (2 mL) was stirred for 20 min at room temperature. The resulting mixture was concentrated under reduced pressure. The residue as crude product 3-((thiophene-2-carbonyl)oxy)propanoic acid (100 mg) was used in the next step directly without purification. LCMS (ES) $[M-H]^+$ m/z: 199 (negative signal).

Synthesis of 2-{[(1S)-1-cyano-2-[4-(3-methyl-2-oxo-1,3-benzoxazol-5-yl)phenyl]ethyl]carbamoyl}ethyl thiophene-2-carboxylate

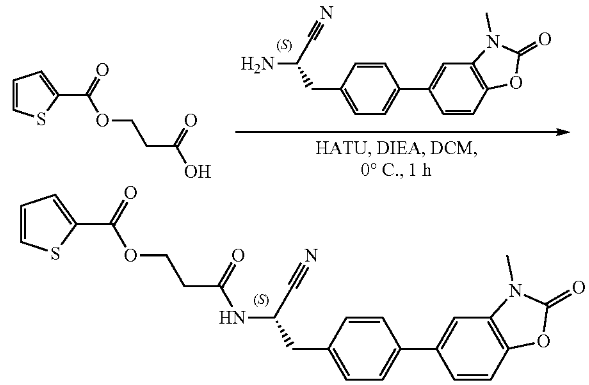

To a stirred solution of 3-(thiophene-2-carbonyloxy)propanoic acid (100 mg, 0.50 mmol, 1.0 equiv) and (2S)-2-amino-3-[4-(3-methyl-2-oxo-1,3-benzoxazol-5-yl)phenyl]propanenitrile (175 mg, 0.60 mmol, 1.2 equiv) in DCM (2.0 mL) was added DIEA (193 mg, 1.50 mmol, 3.0 equiv). To the above mixture was added HATU (227 mg, 0.60 mmol, 1.2 equiv) in portions at 0° C. The resulting mixture was stirred for 1 h at 0° C. The resulting mixture was concentrated under reduced pressure. The residue was purified by silica gel column chromatography, eluted with PE/EA (1:1) to afford crude product. The crude product was further purified by Prep-HPLC with the following conditions: Column, XBridge Prep C18 OBD Column, 19*150 mm, 5 um; mobile phase, Water (10 mmol/L $NH_4HCO_3$) and ACN (30% Phase B up to 40% in 7 min); Detector, UV, 220 nm. The fraction of the target was freezing dried to afford 2-{[(1S)-1-cyano-2-[4-(3-methyl-2-oxo-1,3-benzoxazol-5-yl)phenyl]ethyl]carbamoyl}ethyl thiophene-2-carboxylate (30 mg, 12.6%). LCMS (ES) $[M+1]^+$ m/z: 476

$^1H$ NMR (400 MHz, DMSO-$d_6$) δ 8.94 (d, J=7.7 Hz, 1H), 7.91 (dd, J=4.9, 1.3 Hz, 1H), 7.74 (dd, J=3.8, 1.3 Hz, 1H), 7.63 (d, J=8.2 Hz, 2H), 7.56 (s, 1H), 7.44-7.37 (m, 4H), 7.17 (dd, J=5.0, 3.7 Hz, 1H), 5.02 (q, J=7.6 Hz, 1H), 4.47-4.34 (m, 2H), 3.41 (s, 3H), 3.19-3.07 (m, 2H), 2.65-2.56 (m, 2H).

Example 70: Synthesis of Compound 245: (S)-2-((1-cyano-2-(4-(3-methyl-2-oxo-2,3-dihydrobenzo[d]oxazol-5-yl)phenyl)ethyl)amino)-2-oxoethyl thiophene-2-carboxylate

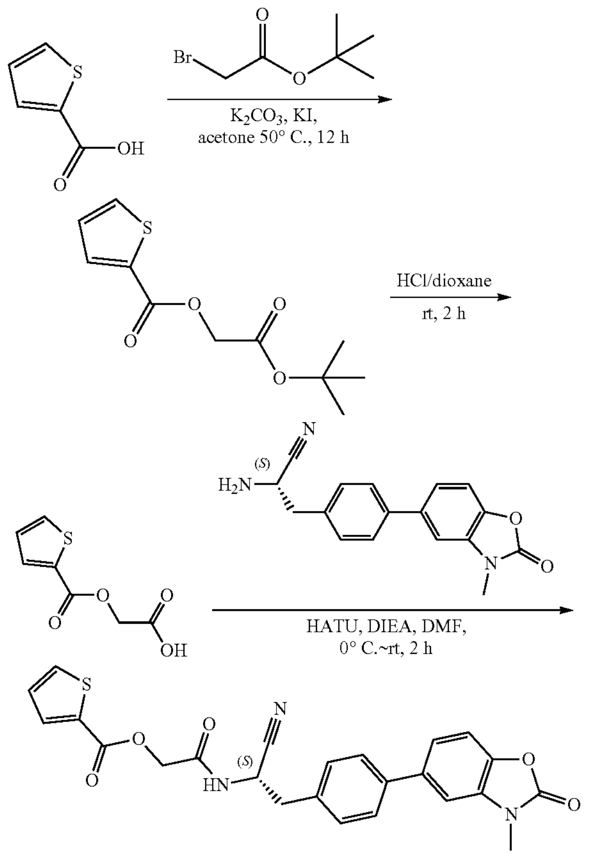

Synthesis of (S)-2-((1-cyano-2-(4-(3-methyl-2-oxo-2,3-dihydrobenzo[d]oxazol-5-y)phenyl)ethyl)amino-2-oxoethyl thiophene-2-carboxylate

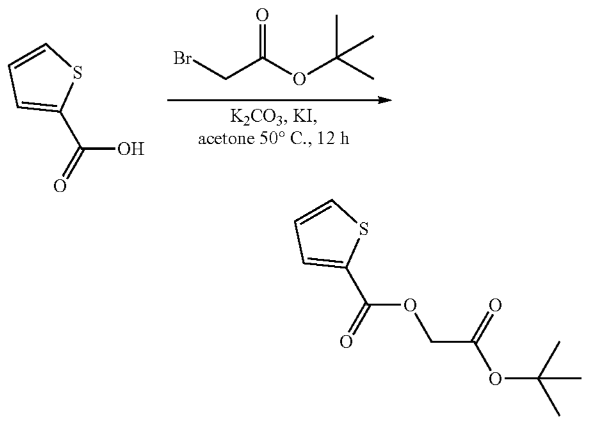

To a solution of thiophene-2-carboxylic acid (500 mg, 3.90 mmol, 1.0 equiv) in acetone (20 ml), $K_2CO_3$ (593 mg, 4.29 mmol, 1.1 equiv) was added, and mixture was stirred for 5 minutes, then KI (65 mg, 0.39 mmol, 0.1 equiv) was added, followed by dropwise addition of tert-butyl 2-bromoacetate (0.64 ml, 4.29 mmol, 1.1 equiv). The mixture was heated to 50° C. and stirred for 12 h. The reaction was cooled to room temperature, the solid was filtered out and washed with DCM (20 mL), the filtrate was evaporated and 900 mg 2-tert-butoxy-2-oxoethyl thiophene-2-carboxylate was obtained and used to the following reaction without further purification. LCMS (ES, m z): $[M+H]^+$: 243

Synthesis of (S)-2-((1-cyano-2-(4-(3-methyl-2-oxo-2,3-dihydrobenzo[d]oxazol-5-yl)phenyl)ethyl)amino)-2-oxoethyl thiophene-2-carboxylate

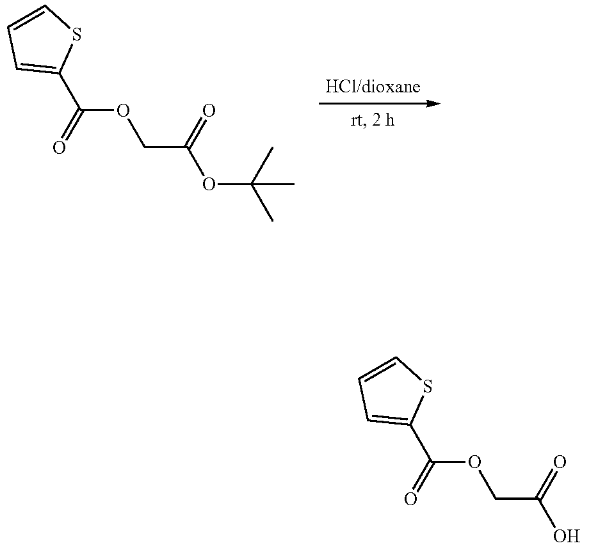

To a solution of 2-(tert-butoxy)-2-oxoethyl thiophene-2-carboxylate (900 mg, 3.72 mmol, 1.0 equiv) in DCM (10 ml), HCl (g)(2 mL)(4 M in dioxane) was added at room temperature. The mixture was stirred for 2 h. After concentrated in vacuo to remove the solvent, the residue was used to the next step without purification. LCMS (ES, m z): [M–H]f: 185.

Synthesis of (S)-2-((1-cyano-2-(4-(3-methyl-2-oxo-2,3-dihydrobenzo[d]oxazol-5-yl)phenyl)ethyl)amino)-2-oxoethyl thiophene-2-carboxylate

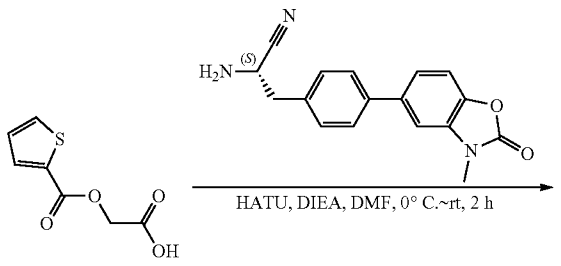

-continued

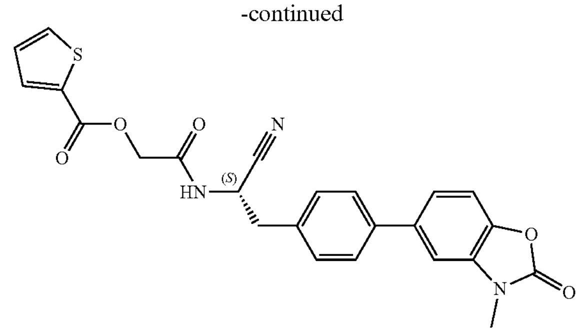

To a stirred solution of (thiophene-2-carbonyloxy)acetic acid (50 mg, 0.26 mmol, 1.0 equiv), (2S)-2-amino-3-[4-(3-methyl-2-oxo-1,3-benzoxazol-5-yl)phenyl]propanenitrile (94 mg, 0.32 mmol, 1.2 equiv) and DIEA (104 mg, 0.80 mmol, 3.0 equiv) in DMF (3 mL) was added HATU (122 mg, 0.32 mmol, 1.2 equiv) in portions at 0° C. The resulting mixture was stirred for additional 2 h at room temperature. The residue was purified by reversed-phase flash chromatography with the following conditions: column, C18 silica gel; mobile phase, MeCN in Water (0.1% $NH_3 \cdot H_2O$), 10% to 80% gradient in 10 min; detector, UV 254 nm. This resulted in (S)-2-((1-cyano-2-(4-(3-methyl-2-oxo-2,3-dihydrobenzo[d]oxazol-5-yl)phenyl)ethyl)amino)-2-oxoethyl thiophene-2-carboxylate (18.5 mg, 15%).

LCMS (ES, m z): $[M+H]^+$: 525.1

$^1$H NMR (400 MHz, DMSO-$d_6$) δ 9.05 (d, J=7.7 Hz, 1H), 8.02 (dd, J=5.0, 1.3 Hz, 1H), 7.91 (dd, J=3.8, 1.3 Hz, 1H), 7.70-7.64 (m, 2H), 7.59 (d, J=1.7 Hz, 1H), 7.46-7.37 (m, 4H), 7.26 (dd, J=5.0, 3.7 Hz, 1H), 5.03 (q, J=7.7 Hz, 1H), 4.75 (s, 2H), 3.41 (s, 3H), 3.16 (dd, J=7.6, 2.1 Hz, 2H).

Example 71: Synthesis of Compound 238: N-[(1S)-1-cyano-2-[4-(3-methyl-2-oxo-1,3-benzoxazol-5-yl)phenyl]ethyl]-3-(thiophen-2-ylformamido)propanamide

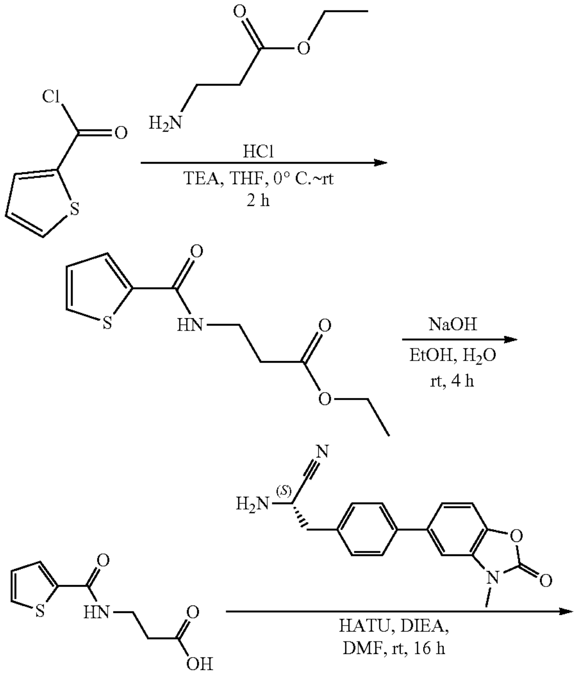

-continued

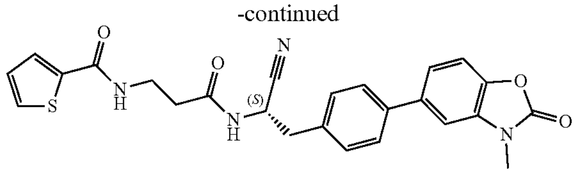

Synthesis of ethyl 3-(thiophene-2-carboxamido)propanoate

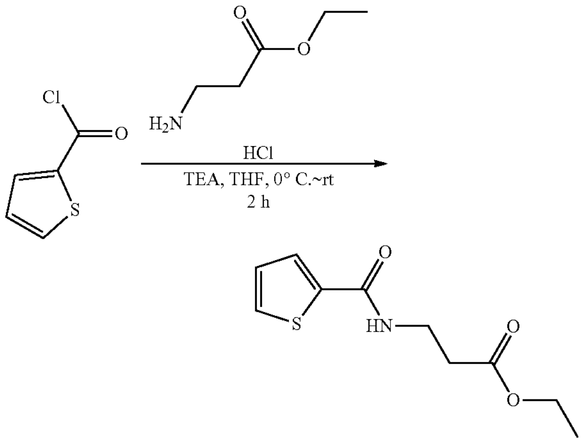

To a solution of ethyl 3-aminopropanoate hydrochloride (1.0 g, 6.53 mmol, 1.0 equiv) in THF (20 mL), TEA (1.3 g, 13.06 mmol, 2.0 equiv) was added at room temperature. The mixture was cooled to 0° C., this was followed by the addition of thiophene-2-carbonyl chloride (953 mg, 6.53 mmol, 1.0 equiv) in THF (2 mL) dropwise. After addition, the reaction was warmed to rt and stirred for 2 h. The reaction was quenched with water (30 mL), extracted with ethyl acetate (30 mL×2). The combined organic phase was washed with brine (20 mL), dried over anhydrous sodium sulfate. Filtered and the filtrate was concentrated, this result in ethyl 3-(thiophene-2-carboxamido)propanoate (1.3 g, 88%) and used to the next step without further purification. LCMS (ES, m z): $[M+H]^+$: 228.

Synthesis of N-[(1S)-1-cyano-2-[4-(3-methyl-2-oxo-1,3-benzoxazol-5-yl)phenyl]ethyl]-3-(thiophen-2-ylformamido)propanamide

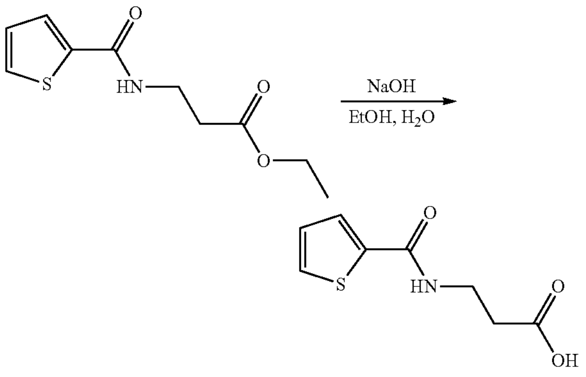

To a solution of ethyl 3-(thiophene-2-carboxamido)propanoate (1.3 g, 5.72 mmol, 1.0 equiv) in EtOH (15 mL), NaOH (458 mg, 11.44 mmol, 2.0 equiv) in $H_2O$ (10 mL) was added dropwise at room temperature, the mixture was stirred for 4 h. The reaction was diluted with water (30 mL), extracted with ethyl acetate (30 mL), the aqueous phase was adjust PH to 4 with HCl (3 N), extracted with ethyl acetate (50 mL×2). The combined organic phase was washed with brine, dried over anhydrous sodium sulfate. Filtered and the filtrate was concentrated under reduced pressure. This result in N-[(1S)-1-cyano-2-[4-(3-methyl-2-oxo-1,3-benzoxazol-5-yl)phenyl]ethyl]-3-(thiophen-2-ylformamido)propenamide (1.0 g, 88%) and used to the next step without further purification. LCMS (ES, m z): $[M+H]^+$: 200.

Synthesis of N-[(1S)-1-cyano-2-[4-(3-methyl-2-oxo-1,3-benzoxazol-5-yl)phenyl]ethyl]-3-(thiophen-2-ylformamido)propanamide

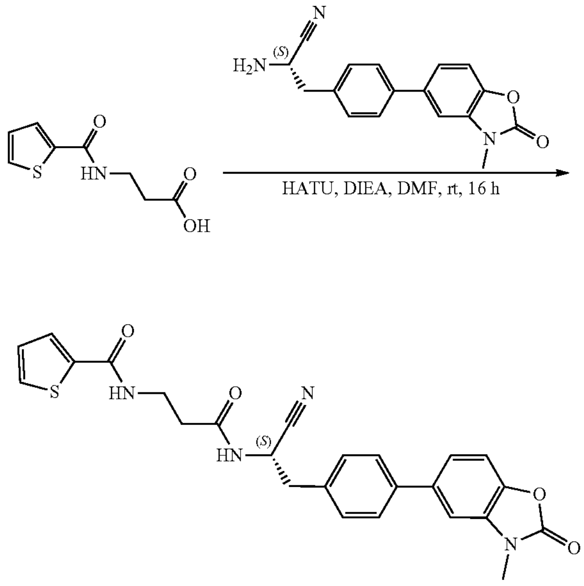

To a stirred mixture of 3-(thiophen-2-ylformamido)propanoic acid (40 mg, 0.20 mmol, 1.0 equiv), (2S)-2-amino-3-[4-(3-methyl-2-oxo-1,3-benzoxazol-5-yl)phenyl]propanenitrile (70 mg, 0.24 mmol, 1.2 equiv) and DIEA (78 mg, 0.60 mmol, 3.0 equiv) in DMF (3 mL) was added HATU (92 mg, 0.24 mmol, 1.2 equiv) in portions at 0° C. The resulting mixture was stirred for additional 2 h at room temperature. The reaction solution was purified by reversed-phase flash chromatography with the following conditions: column, C1-120 g, mobile phase, MeCN in Water (0.1% $NH_3 \cdot H_2O$), 10% to 80% gradient in 10 min; detector, UV 254 nm. The fraction of the target was freezing dried, N-[(1S)-1-cyano-2-[4-(3-methyl-2-oxo-1,3-benzoxazol-5-yl)phenyl]ethyl]-3-(thiophen-2-ylformamido)propanamide (20.9 mg, 22%) was obtained. LCMS (ES, m z): $[M+H]^+$: 475.1

$^1H$ NMR (400 MHz, DMSO-$d_6$) δ 8.83 (d, J=7.7 Hz, 1H), 8.58 (t, J=5.6 Hz, 1H), 7.74 (d, J=4.4 Hz, 2H), 7.60 (d, J=8.0 Hz, 2H), 7.55 (d, J=1.6 Hz, 1H), 7.39 (dd, J=5.3, 2.5 Hz, 4H), 7.13 (t, J=4.4 Hz, 1H), 4.97 (q, J=7.5 Hz, 1H), 3.41 (s, 5H), 3.12 (d, J=7.6 Hz, 2H), 2.47-2.39 (m, 2H).

Example 72: Synthesis of Compound 239:N-[(1S)-1-cyano-2-[4-(3-methyl-2-oxo-1,3-benzoxazol-5-yl)phenyl]ethyl]-2-(thiophen-2-ylformamido)acetamide

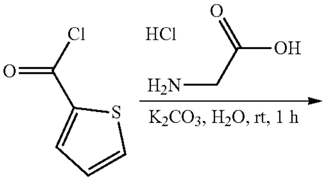

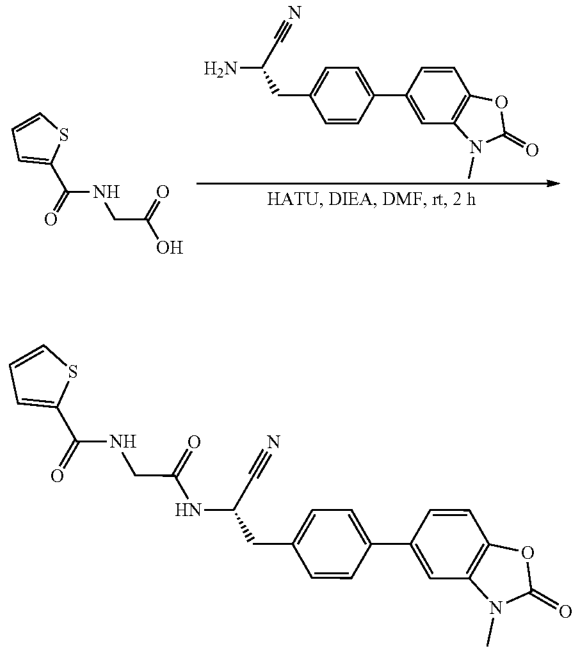

Synthesis of (thiophen-2-ylformamido)acetic acid

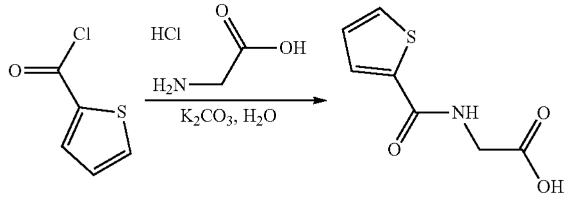 [SMILES: O=C(Cl)c1cccs1 ; Cl ; NCC(=O)O ; O=C(O)CNC(=O)c1cccs1]

To a solution of glycine chloride (6.67 g, 60 mmol, 1.2 equiv) and potassium carbonate (10.4 g, 75 mmol, 1.5 equiv) in water (100 ml), thiophene-2-carbonyl chloride (7.3 g, 50 mmol, 1.0 equiv) was added dropwise in 30 min with stirring. The resulting solution was stirred for 1 h, washed with diethyl ether (2×30 ml) and acidified with conc. HCl. After cooling for 1 h in an ice-bath, the precipitate was filtered out, washed with cold water, and dried in air to yield 7.0 g (76%) of (thiophene-2-carbonyl)glycine. LCMS (ES, m z): $[M+H]^*$: 186

Synthesis of N-[(1S)-1-cyano-2-[4-(3-methyl-2-oxo-1,3-benzoxazol-5-yl)phenyl]ethyl]-2-(thiophen-2-ylformamido)acetamide

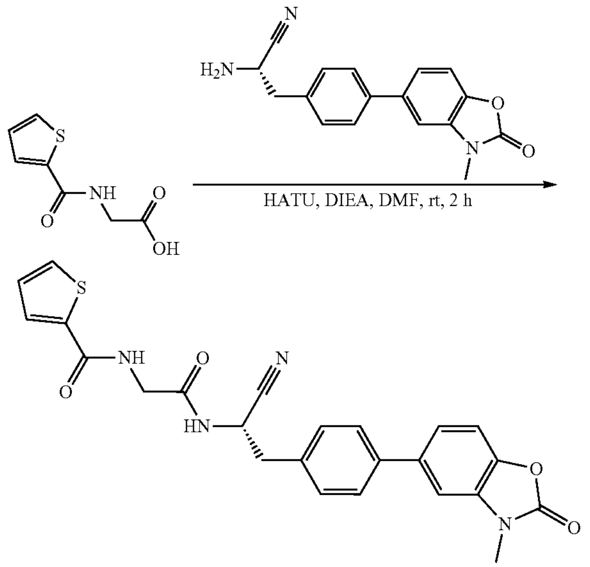

To a stirred solution of (thiophen-2-ylformamido)acetic acid (40 mg, 0.21 mmol, 1.0 equiv), (2S)-2-amino-3-[4-(3-methyl-2-oxo-1,3-benzoxazol-5-yl)phenyl]propanenitrile (76 mg, 0.25 mmol, 1.2 equiv) and DIEA (84 mg, 0.64 mmol, 3.0 equiv) in DMF (5 mL) was added HATU (99 mg, 0.25 mmol, 1.2 equiv) in portions at 0° C. The resulting mixture was stirred for 2 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 80% gradient in 10 min; detector, UV 254 nm. This resulted in N-[(1S)-1-cyano-2-[4-(3-methyl-2-oxo-1,3-benzoxazol-5-yl)phenyl]ethyl]-2-(thiophen-2-ylformamido)acetamide (20.9 mg, 21%).

LCMS (ES, m z): $[M+H]^+$: 461.1

$^1H$ NMR (400 MHz, DMSO-$d_6$) δ 8.87 (d, J=7.8 Hz, 1H), 8.81 (t, J=6.0 Hz, 1H), 7.80 (t, J=4.7 Hz, 2H), 7.66 (d, J=8.0 Hz, 2H), 7.58 (s, 1H), 7.46-7.36 (m, 4H), 7.18 (t, J=4.4 Hz, 1H), 5.00 (q, J=7.7 Hz, 1H), 3.91-3.84 (m, 2H), 3.41 (s, 3H), 3.21-3.07 (m, 2H).

Example 73: Synthesis of Compound 240: N-[(1S)-1-cyano-2-[4-(3-methyl-2-oxo-1,3-benzoxazol-5-yl)phenyl]ethyl]-2-(furan-2-ylformamido)acetamide

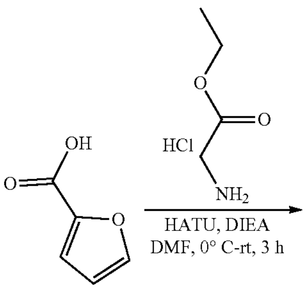

-continued

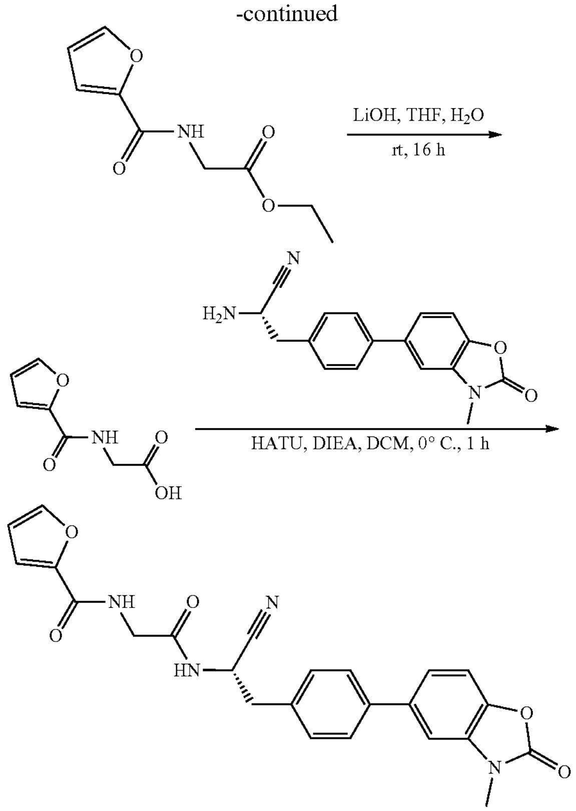

Synthesis of ethyl 2-(furan-2-ylformamido)acetate

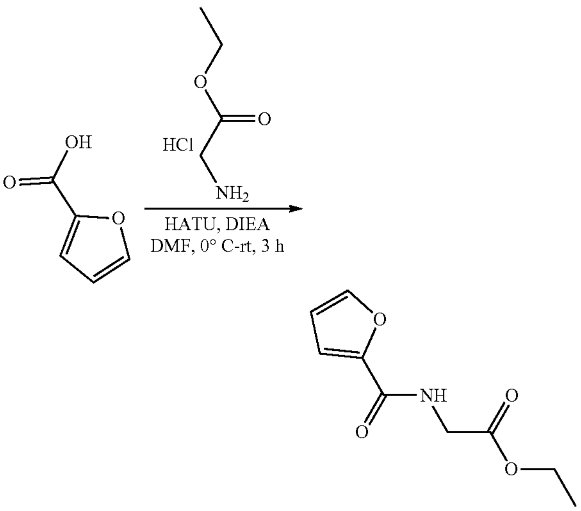

To a stirred solution of furoic acid (1.0 g, 8.922 mmol, 1.0 equiv) and amino-acetic acid ethyl ester (1.84 g, 17.844 mmol, 2.0 equiv) in DMF (10 mL) were added DIEA (3.46 g, 26.766 mmol, 3.0 equiv) and HATU (4.07 g, 10.706 mmol, 1.2 equiv) in portions at 0° C. under nitrogen atmosphere. The resulting mixture was stirred for 3 h at room temperature. The resulting mixture was extracted with EtOAc (3×30 mL). The combined organic layers were washed with brine (50 mL), dried over anhydrous $Na_2SO_4$.

After filtration, the filtrate was concentrated under reduced pressure. The residue was purified by silica gel column chromatography, eluted with PE/EA (1:1) to afford ethyl 2-(furan-2-ylformamido)acetate (1.1 g, 62.52%). LCMS (ES) $[M+H]^+$ m/z:198

Synthesis of (furan-2-carbonyl)glycine

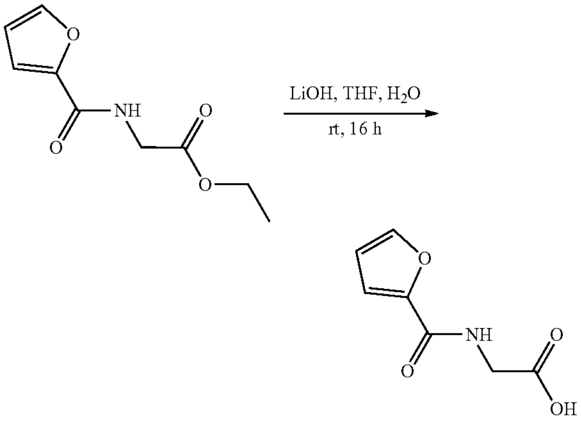

To a stirred solution of ethyl 2-(furan-2-ylformamido) acetate (1.0 g, 5.071 mmol, 1.0 equiv) in THF (10 mL) and $H_2O$ (5 mL) was added NaOH (0.41 g, 10.142 mmol, 2.0 equiv). The resulting mixture was stirred for 16 h at room temperature. The mixture was acidified to pH 7 with citric acid. The resulting mixture was extracted with EtOAc (5×20 mL). The combined organic layers were washed with brine (20 mL), dried over anhydrous $Na_2SO_4$. After filtration, the filtrate was concentrated under reduced pressure. The residue was purified by trituration with hexane (5 mL). This resulted in (furan-2-carbonyl)glycine (500 mg, 58.29%). LCMS (ES) $[M+H]^+$ m/z:170.

Synthesis of N-[(1S)-1-cyano-2-[4-(3-methyl-2-oxo-1,3-benzoxazol-5-yl)phenyl]ethyl]-2-(furan-2-ylformamido)acetamide

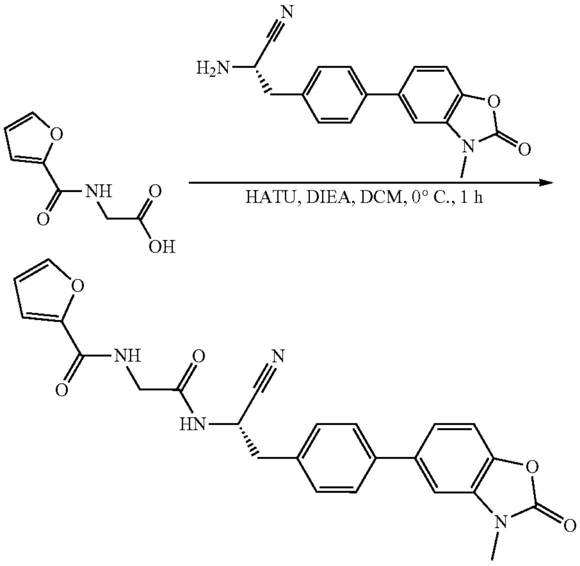

To a stirred solution of furoylglycine (40 mg, 0.236 mmol, 1.0 equiv) and (2S)-2-amino-3-[4-(3-methyl-2-oxo-1,3-benzoxazol-5-yl)phenyl]propanenitrile (83 mg, 0.283 mmol, 1.2 equiv) in DCM (2 mL) was added DIEA (91 mg, 0.708 mmol, 3.0 equiv). To the above mixture was added HATU (107 mg, 0.283 mmol, 1.2 equiv) in portions at 0° C. The resulting mixture was stirred for additional 1 h at ° C. The resulting mixture was extracted with $CH_2Cl_2$ (3×10 mL). The combined organic layers were washed with brine (20 mL), dried over anhydrous $Na_2SO_4$. After filtration, the filtrate was concentrated under reduced pressure. The crude product was purified by Prep-HPLC with the following conditions (Column, XBridge Prep C18 OBD Column, 19*150 mm Sum; mobile phase, Water (10 MMOL/L $NH_4 \cdot H_2O$) and ACN (30% PhaseB up to 40% in 7 min); Detector, UV, 220 nm.) to afford N-[(1S)-1-cyano-2-[4-(3-methyl-2-oxo-1,3-benzoxazol-5-yl)phenyl]ethyl]-2-(furan-2-ylformamido)acetamide (20 mg, 19.03%).

$^1H$ NMR (300 MHz, DMSO-$d_6$) δ 8.86 (d, J=7.7 Hz, 1H), 8.60 (t, J=6.1 Hz, 1H), 7.87 (dd, J=1.8, 0.8 Hz, 1H), 7.67 (d, J=8.1 Hz, 2H), 7.59 (d, J=1.5 Hz, 1H), 7.47-7.35 (m, 4H), 7.15 (dd, J=3.4, 0.8 Hz, 1H), 6.65 (dd, J=3.5, 1.8 Hz, 1H), 5.00 (q, J=7.6 Hz, 1H), 3.85 (d, J=6.1 Hz, 2H), 3.41 (s, 3H), 3.18-3.09 (m, 2H). LCMS (ES) $[M+H]^+$ m/z:445

Example 74: Synthesis of Compound 243: {[(1S)-1-cyano-2-[4-(3-methyl-2-oxo-1,3-benzoxazol-5-yl)phenyl]ethyl]carbamoyl}methyl furan-2-carboxylate

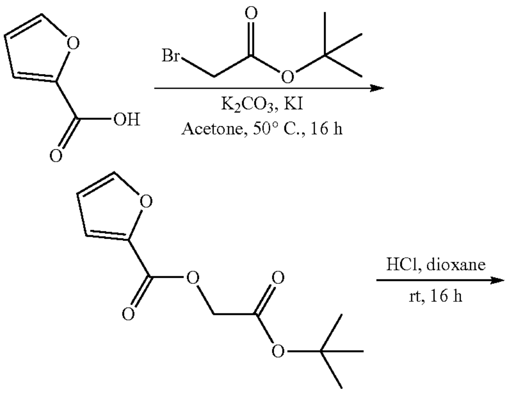

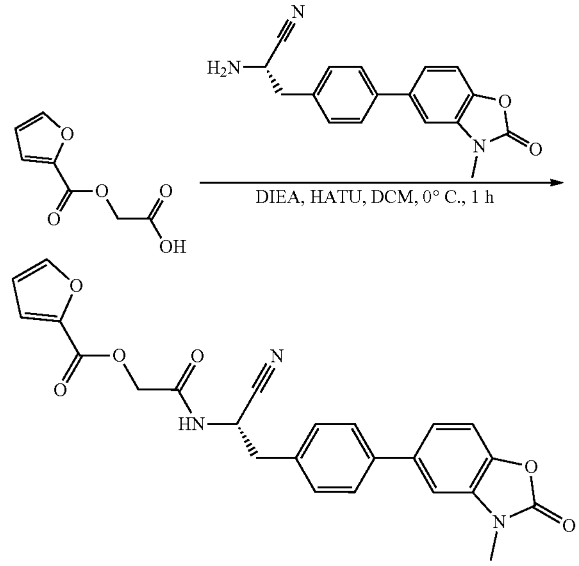

Synthesis of tert-butyl 2-(furan-2-carbonyloxy)acetate

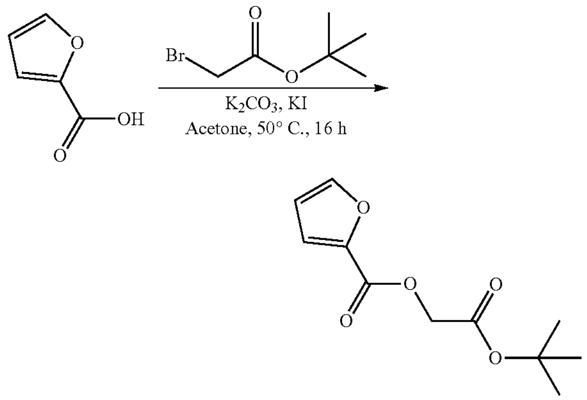

To a stirred solution of furoic acid (1 g, 8.92 mmol, 1.0 equiv) and tert-butyl 2-bromoacetate (2.09 g, 10.70 mmol, 1.2 equiv) in Acetone (15 mL) were added $K_2CO_3$ (2.47 g, 17.84 mmol, 2.0 equiv) and KI (0.74 g, 4.46 mmol, 0.5 equiv). The resulting mixture was stirred for 16 h at 50° C. The mixture was allowed to cool down to room temperature. The resulting mixture was concentrated under reduced pressure. The residue was purified by silica gel column chromatography, eluted with PE/EA (12:1) to afford tert-butyl 2-(furan-2-carbonyloxy)acetate (1.3 g, 64.4%). No MS signal.

Synthesis of (furan-2-carbonyloxy)acetic acid

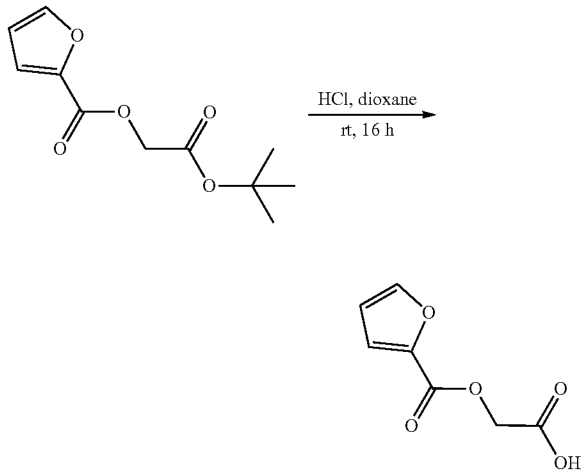

To a stirred solution of tert-butyl 2-(furan-2-carbonyloxy) acetate (200 mg, 0.88 mmol, 1.0 equiv) in dioxane (0.5 mL) were added HCl(gas) in 1,4-dioxane (3 mL). The resulting mixture was stirred for 16 h at room temperature. The resulting mixture was concentrated under reduced pressure. The crude product (furan-2-carbonyloxy)acetic acid (130 mg) was used in the next step directly without further purification. No MS signal.

Synthesis of {[(1S)-1-cyano-2-[4-(3-methyl-2-oxo-1,3-benzoxazol-5-yl)phenyl]ethyl]carbamoyl}methyl furan-2-carboxylate

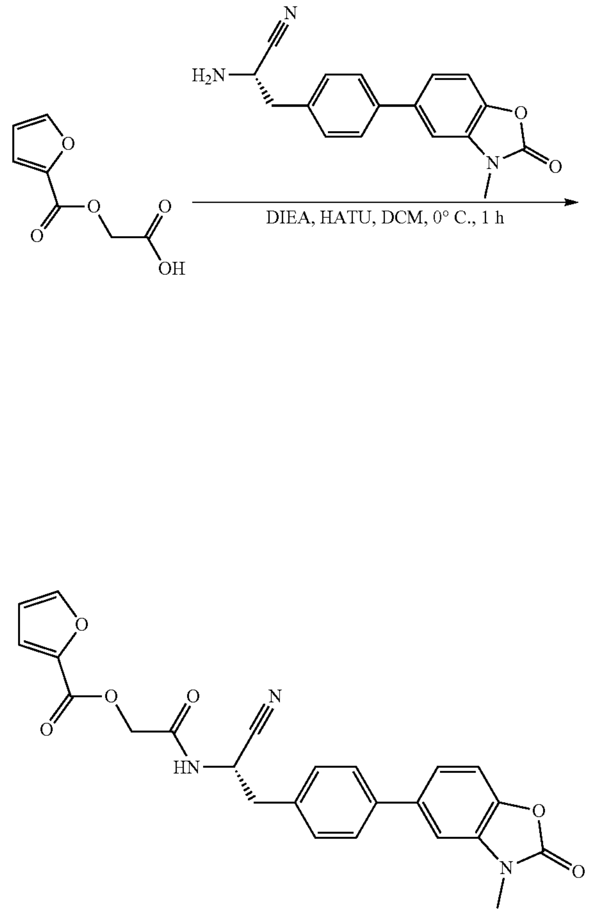

To a stirred solution of (furan-2-carbonyloxy)acetic acid (69 mg, 0.40 mmol, 1.2 equiv) and (2S)-2-amino-3-[4-(3-methyl-2-oxo-1,3-benzoxazol-5-yl)phenyl]propanenitrile (100 mg, 0.34 mmol, 1.0 equiv) in DCM (2 mL) were added DIEA (110 mg, 0.85 mmol, 2.50 equiv) and HATU (155 mg, 0.40 mmol, 1.2 equiv) in portions at 0° C. under nitrogen atmosphere. The resulting mixture was stirred for 1 h at 0° C. under nitrogen atmosphere. The residue was purified by silica gel column chromatography, eluted with PE/THE (1:1) to afford crude product. The crude product was purified by Prep-HPLC with the following conditions (Column, XBridge Prep C18 OBD Column, 19*150 mm Sum; mobile phase, Water(10 MMOL/L $NH_4HCO_3$) and ACN (30% PhaseB up to 40% in 7 min); Detector, UV. This resulted in {[(1S)-1-cyano-2-[4-(3-methyl-2-oxo-1,3-benzoxazol-5-yl) phenyl]ethyl]carbamoyl}methyl furan-2-carboxylate (40 mg, 26.3%). LCMS (ES) $[M+1]^+$ m/z: 446.

$^1H$ NMR (300 MHz, DMSO-$d_6$) δ 9.05 (d, J=7.7 Hz, 1H), 8.04 (d, J=1.7 Hz, 1H), 7.67 (d, J=8.1 Hz, 2H), 7.59 (d, J=1.5 Hz, 1H), 7.48-7.35 (m, 5H), 6.75 (dd, J=3.6, 1.7 Hz, 1H), 5.03 (q, J=7.6 Hz, 1H), 4.73 (s, 2H), 3.41 (s, 3H), 3.16 (d, J=7.7 Hz, 2H). LCMS (ES) $[M+1]^+$ m/z: 451.

Example 75: Synthesis of Compound 248 and 249: 4-amino-N-[(1S)-1-cyano-2-{4'-cyano-3-iodo-[1,1'-biphenyl]-4-yl}ethyl]oxane-4-carboxamide and 4-amino-N-[(1R)-1-cyano-2-{4'-cyano-3-iodo-[1,1'-biphenyl]-4-yl}ethyl]oxane-4-carboxamide

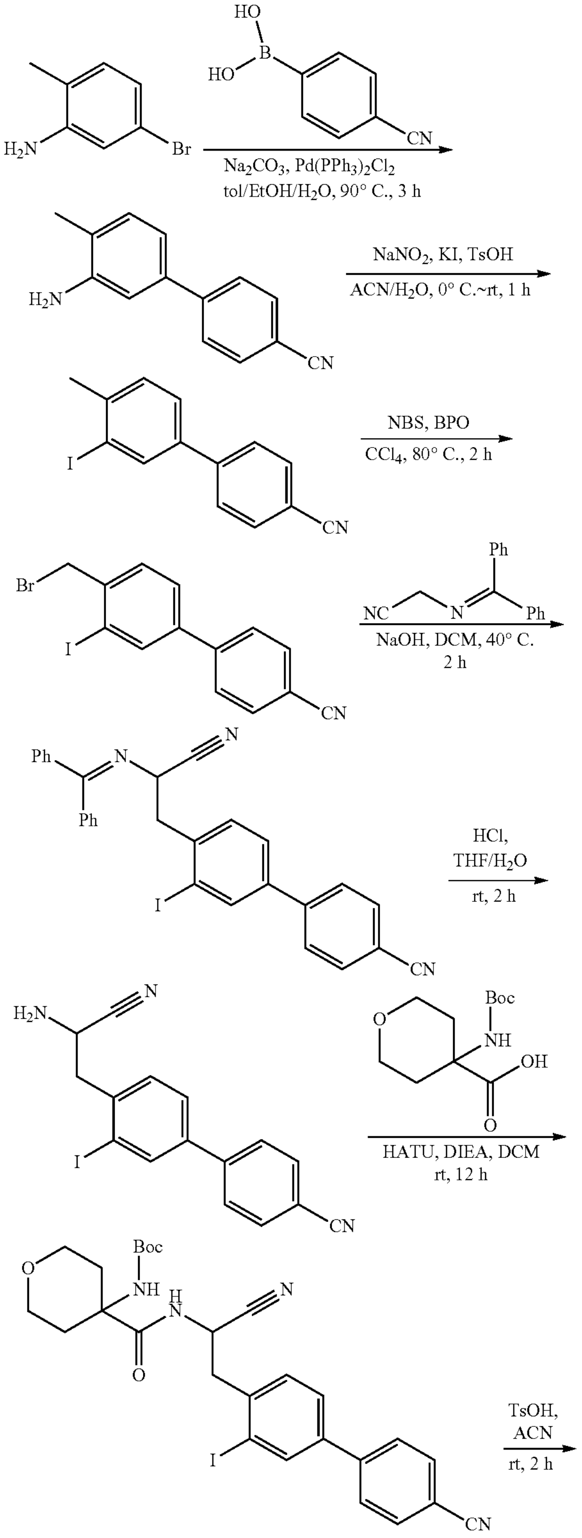

-continued

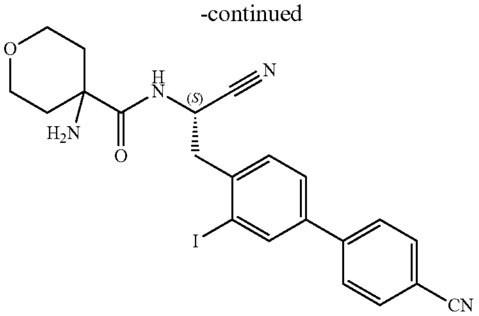

compound 248
(Assumed)

+

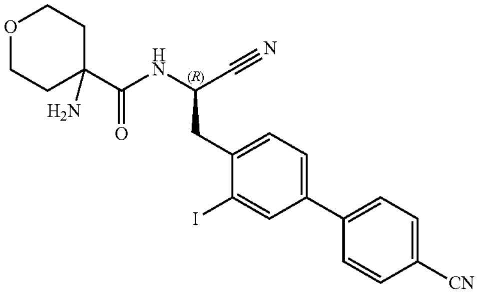

compound 249
(Assumed)

Synthesis of 3'-amino-4'-methyl-[1,1'-biphenyl]-4-carbonitrile

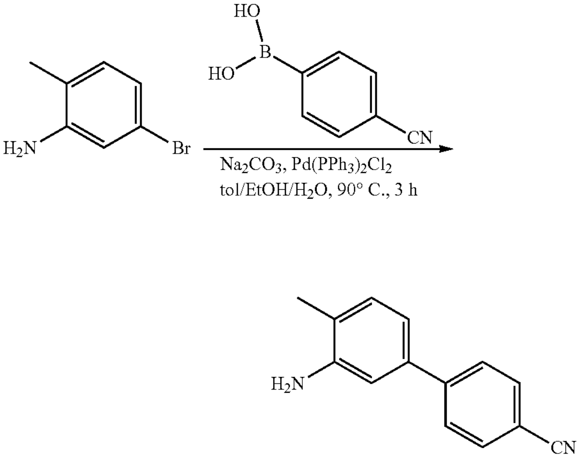

To a solution of 3-bromo-6-methylaniline (6 g, 32.25 mmol, 1.0 equiv) and 4-cyanophenylboronic acid (5.69 g, 38.70 mmol, 1.2 equiv) in toluene (60 mL), EtOH (15 mL) and $H_2O$ (30 mL) were added $Na_2CO_3$ (6.84 g, 64.50 mmol, 2.0 equiv) and $Pd(PPh_3)_2Cl_2$ (2.26 g, 3.22 mmol, 0.1 equiv). The mixture was heated to 90° C. and stirred for 3 h under nitrogen atmosphere. The reaction was cooled to room temperature, the resulting mixture was concentrated under reduced pressure. The residue was purified by silica gel column chromatography, eluted with PE/THE (1:1) to afford 3'-amino-4'-methyl-[1,1'-biphenyl]-4-carbonitrile (5.4 g, 80%). LCMS (ES, m z): $[M+H]^+$: 209.

Synthesis of 3'-iodo-4'-methyl-[1,1'-biphenyl]-4-carbonitrile

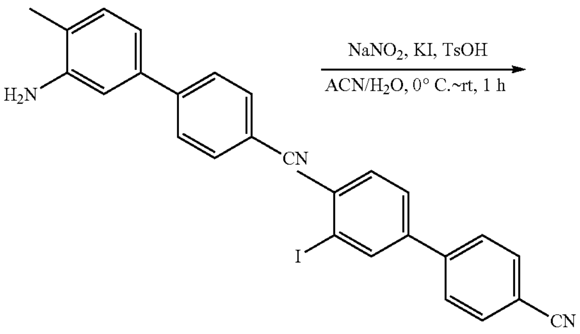

To a stirred mixture of 3'-amino-4'-methyl-[1,1'-biphenyl]-4-carbonitrile (5.4 g, 25.93 mmol, 1.0 equiv) in ACN (100 mL) was added TsOH (13.39 g, 77.79 mmol, 3.0 equiv) at room temperature under nitrogen atmosphere. To the above mixture was added $NaNO_2$ (3.58 g, 51.86 mmol, 2.0 equiv) in $H_2O$ (30 mL) dropwise at 0° C. To the above mixture was added KI (10.76 g, 64.82 mmol, 2.5 equiv) in $H_2O$ (30 mL) dropwise at 0° C. The resulting mixture was stirred for additional 1 h at room temperature. The resulting mixture was extracted with EtOAc (3×150 mL). The combined organic layer was washed with brine (2×100 mL), dried over anhydrous $Na_2SO_4$. After filtration, the filtrate was concentrated under reduced pressure. The residue was purified by silica gel column chromatography, eluted with PE/EA (5:1) to afford 3'-iodo-4'-methyl-[1,1'-biphenyl]-4-carbonitrile (6 g, 72%)(no MS signal).

Synthesis of 4'-(bromomethyl)-3'-iodo-[1,1'-biphenyl]-4-carbonitrile

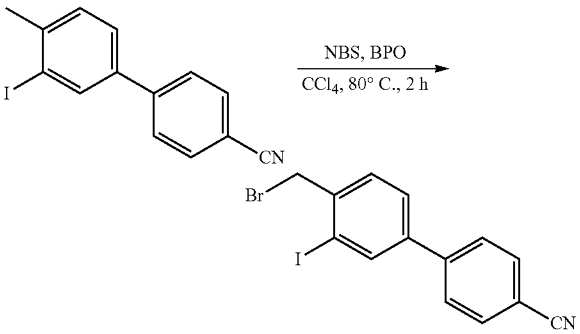

To a stirred solution of 3'-iodo-4'-methyl-[1,1'-biphenyl]-4-carbonitrile (3.5 g, 10.97 mmol, 1.0 equiv) and NBS (2.34 g, 13.16 mmol, 1.2 equiv) in $CCl_4$ (50 mL) was added BPO (0.28 g, 1.10 mmol, 0.1 equiv) at room temperature. The resulting mixture was stirred for 2 h at 80° C. under nitrogen atmosphere. The reaction was cooled to room temperature, the resulting mixture was concentrated under vacuum. The residue was purified by silica gel column chromatography, eluted with PE/THE (10:1) to afford 4'-(bromomethyl)-3'-iodo-[1,1'-biphenyl]-4-carbonitrile (2.8 g, 64%)(no MS signal).

Synthesis of 4'-{2-cyano-2-[(diphenylmethylidene)amino]ethyl}-3'-iodo-[1,1'-biphenyl]-4-carbonitrile

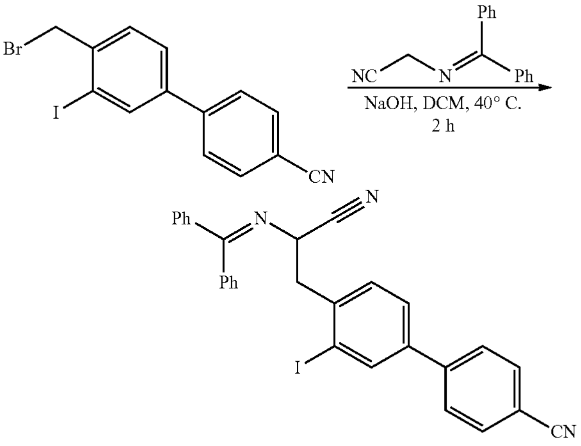

To a solution of 4'-(bromomethyl)-3'-iodo-[1,1'-biphenyl]-4-carbonitrile (1.5 g, 3.77 mmol, 1.0 equiv) in DCM (15 mL) were added 2-[(diphenylmethylidene)amino]acetonitrile (0.83 g, 3.77 mmol, 1.0 equiv), benzyltrimethylazanium chloride (0.07 g, 0.38 mmol, 0.1 equiv), NaOH (0.30 g, 7.54 mmol, 2.0 equiv) in $H_2O$ (1.5 mL) at room temperature. was stirred for 2 h at 40° C. The reaction was diluted with water (30 mL), extracted with $CH_2Cl_2$ (3×100 mL). The combined organic layer was washed with brine (3×30 mL), dried over anhydrous $Na_2SO_4$. After filtration, the filtrate was concentrated under reduced pressure. The residue was purified by silica gel column chromatography, eluted with PE/THE (5:1) to afford 4'-{2-cyano-2-[(diphenylmethylidene)amino]ethyl}-3'-iodo-[1,1'-biphenyl]-4-carbonitrile (2 g, 98%). LCMS (ES, m z): $[M+H]^+$: 538.

Synthesis of 4'-(2-amino-2-cyanoethyl)-3'-iodo-[1,1'-biphenyl]-4-carbonitrile

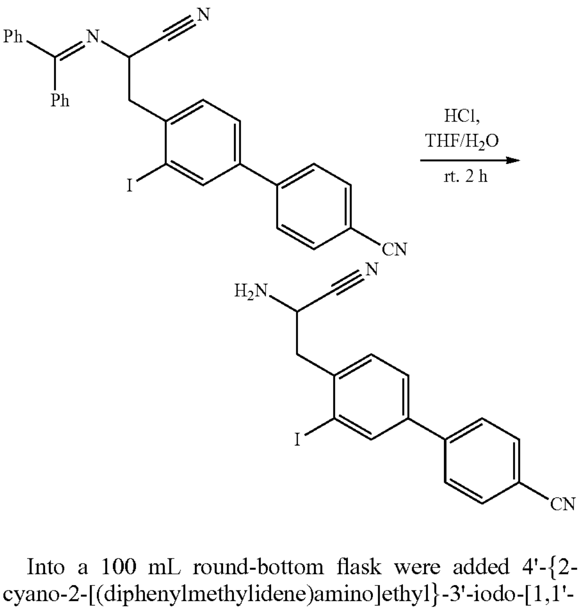

Into a 100 mL round-bottom flask were added 4'-{2-cyano-2-[(diphenylmethylidene)amino]ethyl}-3'-iodo-[1,1'- biphenyl]-4-carbonitrile (1 g, 1.86 mmol, 1.0 equiv), THE (30 mL) and HCl (2 M in $H_2O$)(2.0 mL, 4.00 mmol, 2.0 equiv) at room temperature. The resulting mixture was stirred for additional 2 h at room temperature. The resulting mixture was extracted with $Et_2O$ (1×50 mL). The aqueous phase was basified to pH 8 with $NaHCO_3$ (aq), extracted with $CH_2Cl_2$ (3×50 mL). The combined organic layer was washed with brine (3×50 mL), dried over anhydrous $Na_2SO_4$. After filtration, the filtrate was concentrated under reduced pressure. This resulted in 4'-(2-amino-2-cyano-ethyl)-3'-iodo-[1,1'-biphenyl]-4-carbonitrile (450 mg, 65%). LCMS (ES, m z): $[M+H]^+$: 374.

Synthesis of tert-butyl N-{4-[(1-cyano-2-{4'-cyano-3-iodo-[1,1'-biphenyl]-4-yl}ethyl)carbamoyl]oxan-4-yl}carbamate

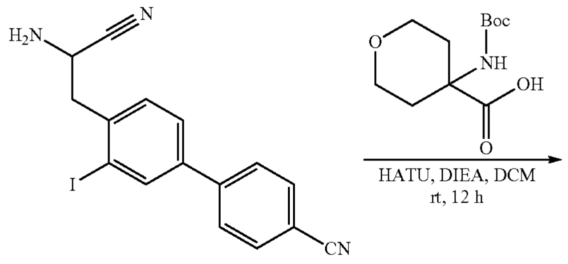

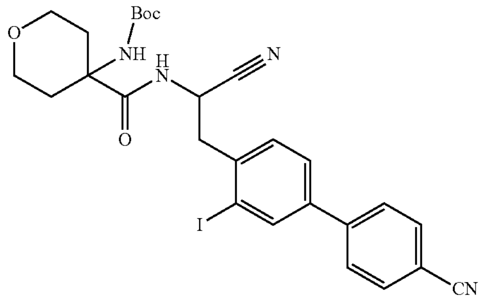

To a stirred solution of 4-[(tert-butoxycarbonyl)amino] oxane-4-carboxylic acid (197 mg, 0.80 mmol, 1.0 equiv) and 4'-(2-amino-2-cyanoethyl)-3'-iodo-[1,1'-biphenyl]-4-carbonitrile (300 mg, 0.80 mmol, 1.0 equiv), DIEA (125 mg, 0.97 mmol, 1.2 equiv) in DCM (5 mL) was added HATU (367 mg, 0.97 mmol, 1.2 equiv) at 0° C. The resulting mixture was stirred for 12 h at room temperature. The resulting mixture was concentrated under reduced pressure. The residue was purified by silica gel column chromatography, eluted with PE/THE (2:1) to afford tert-butyl N-{4-[(1-cyano-2-{4'-cyano-3-iodo-[1,1'-biphenyl]-4-yl}ethyl)carbamoyl]oxan-4-yl}carbamate (370 mg, 76%). LCMS (ES, m z): $[M+H]^+$: 601.

Synthesis of 4-amino-N-[(1S)-1-cyano-2-{4'-cyano-3-iodo-[1,1'-biphenyl]-4-yl}ethyl]oxane-4-carboxamide and 4-amino-N-[(1R)-1-cyano-2-{4'-cyano-3-iodo-[1,1'-biphenyl]-4-yl}ethyl]oxane-4-carboxamide

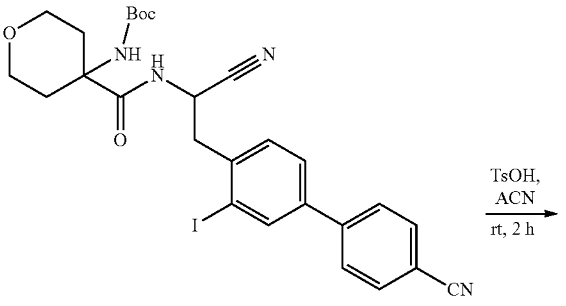

PH-INSM-113-116

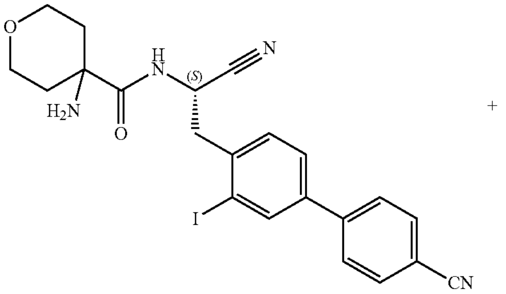

compound 248
(Assumed)

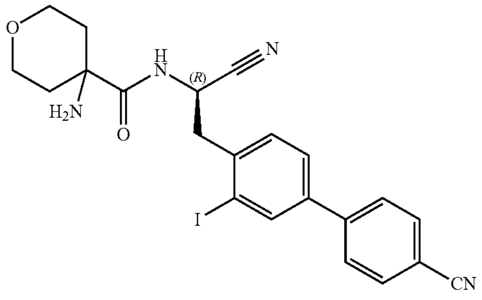

compound 249
(Assumed)

Into a 25 mL round-bottom flask were added tert-butyl N-{4-[(1-cyano-2-{4'-cyano-3-iodo-[1,1'-biphenyl]-4-yl}ethyl)carbamoyl]oxan-4-yl}carbamate (300 mg, 0.50 mmol, 1.0 equiv), ACN (10 mL) and TsOH·$H_2O$ (285 mg, 1.50 mmol, 3.0 equiv) at room temperature. The resulting mixture was stirred for 2 h at room temperature. The reaction solution was purified by Prep-HPLC with the following conditions: Column, Atlantis Prep T3 OBD Column, 19*150 mm, 5 m, mobile phase, Water (0.05% $NH_3H_2O$) and ACN (25% Phase B up to 50% in 10 min) to afford diastereomer mixture. The mixture was purified by Prep-HPLC with the following conditions: Column: CHIRALPAK IG, 3*25 cm, 5 m; Mobile Phase A: HEX: DCM=3: 1-HPLC, Mobile Phase B: EtOH(0.2% IPAmine)-HPLC; Flow rate: 35 mL/min; Gradient: isocratic 50; Wave Length: 254 nm. The fraction at 8.5 min was concentrated under reduced pressure to afford 4-amino-N-[(1S)-1-cyano-2-{4'-cyano-3-iodo-[1,1'-biphenyl]-4-yl}ethyl]oxane-4-carboxamide (31.8 mg, 25%) and the fraction at 14.1 min was concentrated to afford 4-amino-N-[(1R)-1-cyano-2-{4'-cyano-3-iodo-[1,1'-biphenyl]-4-yl}ethyl]oxane-4-carboxamide (29.4 mg, 23%).

LCMS (ES, m z): $[M+H]^+$: 501.

0:$^1$H NMR (400 MHz, DMSO-d6) δ 8.23 (d, J=2.0 Hz, 1H), 7.96-7.86 (m, 4H), 7.81-7.74 (m, 1H), 7.45 (d, J=8.0 Hz, 1H), 5.09 (t, J=8.0 Hz, 1H), 3.70-3.55 (m, 3H), 3.53-3.46 (m, 1H), 3.34 (d, J=8.1 Hz, 2H), 1.97-1.85 (m, 1H), 1.82-1.71 (m, 1H), 1.25-1.21 (m, 1H), 1.16 (d, J=13.3 Hz, 1H).

OA: $^1$H NMR (400 MHz, DMSO-d6) δ 8.23 (s, 1H), 7.96-7.86 (m, 4H), 7.81-7.74 (m, 1H), 7.45 (d, J=8.0 Hz, 1H), 5.09 (t, J=7.8 Hz, 1H), 3.66-3.58 (m, 3H), 3.53-3.47 (m, 1H), 3.34 (d, J=8.0 Hz, 2H), 1.97-1.85 (m, 1H), 1.82-1.70 (m, 1H), 1.26-1.22 (m, 1H), 1.16 (d, J=13.3 Hz, 1H).

Example 76: Synthesis of Compound 190: 3-amino-N-[(1S)-1-cyano-2-[4-(3-methyl-2-oxo-2,3-dihydro-1,3-benzoxazol-5-yl)phenyl]ethyl]-3-cyclohexylpropanamide

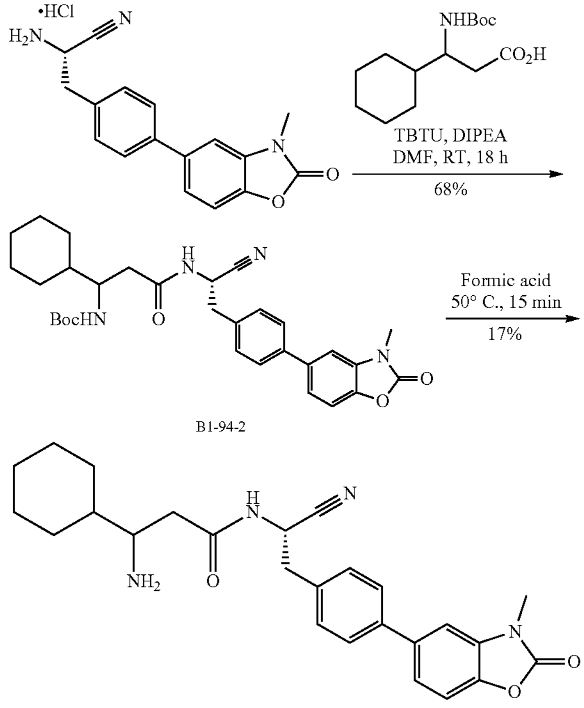

B1-94-2

Starting from B1-94-2 (1 eq., 70.0 mg, 0.13 mmol) and using general procedure C, compound 190 was obtained (10.0 mg, 17%) after purification by flash chromatography over silica gel (regular SiOH, 50 μm, 12 g Interchim, dry loading (silica), mobile phase gradient: DCM/MeOH from 100/0 to 80/20 over 35 min), then vacuum-dried at 40° C. for 18 h.

LC/MS (AN_01_001_021): Rt=7.62 min, 97.77%, $[M+H]^+$=447.42

$^1$H NMR (400 MHz, DMSO) δ 8.92 (s, 1H), 7.73-7.63 (m, 2H), 7.60-7.56 (m, 1H), 7.45-7.36 (m, 4H), 5.00 (td, J=7.6, 2.7 Hz, 1H), 3.40 (s, 3H), 3.20-3.01 (m, 2H), 2.73 (dq, J=8.8, 4.2 Hz, 1H), 2.20 (ddd, J=14.3, 7.7, 4.2 Hz, 1H), 2.01 (ddd, J=14.2, 9.0, 4.9 Hz, 1H), 1.73-1.50 (m, 6H), 1.21-0.98 (m, 5H), 0.98-0.82 (m, 2H).

Example 77: Synthesis of Compound 101: (2S)—N-[(1S)-1-cyano-2-[4-(3-methyl-2-oxo-1,3-benzoxazol-5-yl)phenyl]ethyl]-3-(dimethylamino)-2-hydroxypropanamide

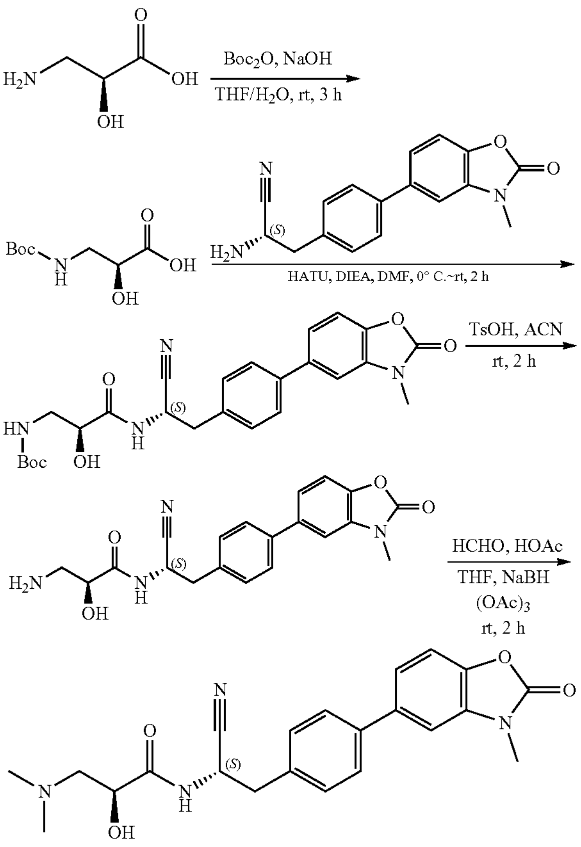

Synthesis of (2S)-3-[(tert-butoxycarbonyl)amino]-2-hydroxypropanoic acid

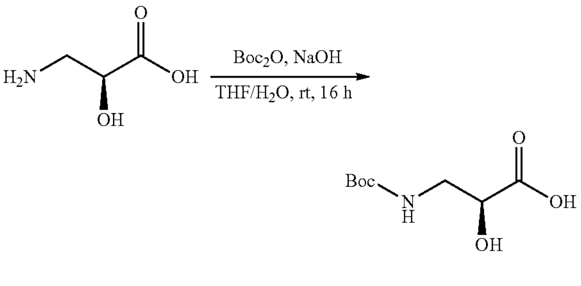

To a stirred solution of (2S)-3-amino-2-hydroxypropanoic acid (3 g, 28.55 mmol, 1.0 equiv) and THF (15 mL) was added NaOH (1.5 g, 37.50 mmol, 1.31 equiv) in $H_2O$ (15 mL) dropwise at room temperature. This was followed by the addition of $Boc_2O$ (6.85 g, 31.40 mmol, 1.1 equiv) in THE (15 mL) dropwise. The resulting mixture was stirred for 3 h at room temperature. The mixture was acidified to pH 4 with conc. HCl, extracted with EtOAc (3×100 mL). The combined organic layer was washed with brine (3×100 mL), dried over anhydrous $Na_2SO_4$. After filtration, the filtrate was concentrated under reduced pressure. This resulted in (2S)-3-[(tert-butoxycarbonyl)amino]-2-hydroxypropanoic acid (5 g, 85%). LCMS (ES, m z): $[M+H]^+$: 206.

Synthesis of tert-butyl N-[(2S)-2-{[(1S)-1-cyano-2-[4-(3-methyl-2-oxo-1,3-benzoxazol-5-yl)phenyl]ethyl]carbamoyl}-2-hydroxyethyl]carbamate

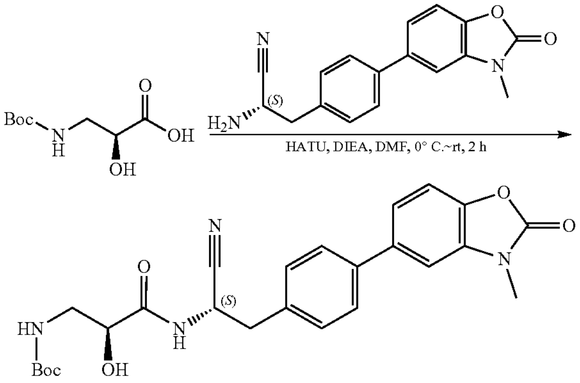

To a stirred mixture of (2S)-3-[(tert-butoxycarbonyl)amino]-2-hydroxypropanoic acid (2.62 g, 12.79 mmol, 2.5 equiv), (2S)-2-amino-3-[4-(3-methyl-2-oxo-1,3-benzoxazol-5-yl)phenyl]propanenitrile (1.5 g, 5.11 mmol, 1.0 equiv) and DIEA (1.98 g, 15.34 mmol, 3.0 equiv) in DCM (5 mL) were added HATU (2.33 g, 6.14 mmol, 1.2 equiv) in portions at 0° C. The resulting mixture was stirred for 2 h at 0° C. The residue was purified by silica gel column chromatography, eluted with PE/THF (1:1) to afford tert-butyl N-[(2S)-2-{[(1S)-1-cyano-2-[4-(3-methyl-2-oxo-1,3-benzoxazol-5-yl)phenyl]ethyl]carbamoyl}-2-hydroxyethyl]carbamate (2.2 g, 90%). LCMS (ES, m z): $[M+H]^+$: 481.

Synthesis of (2S)-3-amino-N-[(1S)-1-cyano-2-[4-(3-methyl-2-oxo-1,3-benzoxazol-5-yl)phenyl]ethyl]-2-hydroxypropanamide; para-toluene sulfonate p-toluenesulfonic acid salt

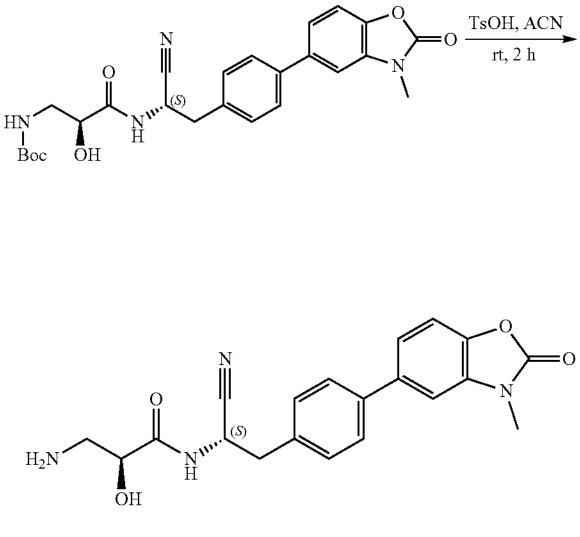

To a stirred solution of tert-butyl N-[(2S)-2-{[(1S)-1-cyano-2-[4-(3-methyl-2-oxo-1,3-benzoxazol-5-yl)phenyl]ethyl]carbamoyl}-2-hydroxyethyl]carbamate (1.2 g, 2.50 mmol, 1.0 equiv) in ACN (30 mL) was added $TsOH \cdot H_2O$ (1.43 g, 7.49 mmol, 3.0 equiv) at room temperature. The precipitated solid was collected by filtration and washed with acetonitrile (3×20 mL). This resulted in (2S)-3-amino-N-[(1S)-1-cyano-2-[4-(3-methyl-2-oxo-1,3-benzoxazol-5-yl)phenyl]ethyl]-2-hydroxypropanamide p-toluenesulfonic acid salt (1.2 g, 87%). LCMS (ES, m z): $[M+H]^+$: 381.

Synthesis of (2S)—N-[(1S)-1-cyano-2-[4-(3-methyl-2-oxo-1,3-benzoxazol-5-yl)phenyl]ethyl]-3-(dimethylamino)-2-hydroxypropanamide

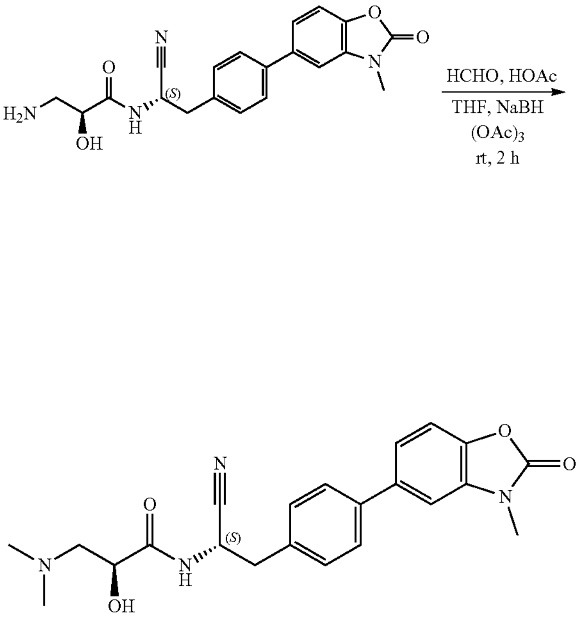

To a stirred solution of (2S)-3-amino-N-[(1S)-1-cyano-2-[4-(3-methyl-2-oxo-1,3-benzoxazol-5-yl)phenyl]ethyl]-2-hydroxypropanamide p-toluenesulfonic acid salt (1 g, 2.63 mmol, 1.0 equiv) and HCHO (2.08 g, 26.29 mmol, 10 equiv, 38% in water) in THF (20 mL) was added HOAc (16 mg, 0.26 mmol, 0.10 equiv) dropwise at room temperature. The resulting mixture was stirred for 2 h at room temperature. To the above mixture was added $NaBH(OAc)_3$ (1.67 g, 7.88 mmol, 3.0 equiv) at room temperature. The resulting mixture was stirred for additional 1 h at room temperature. The reaction solution was purified by Prep-HPLC with the following conditions: column, C18 silica gel-120 g; mobile phase, MeCN in Water (0.1% $NH_3 \cdot H_2O$), 10% to 50% gradient in 10 min; detector, UV 254 nm. The fraction of the target was freezing dried to afford (2S)—N-[(1S)-1-cyano-2-[4-(3-methyl-2-oxo-1,3-benzoxazol-5-yl)phenyl]ethyl]-3-(dimethylamino)-2-hydroxypropanamide (400 mg, 37%).

LCMS (ES, m z): $[M+H]^+$: 409.3

$^1H$ NMR (400 MHz, DMSO-$d_6$) δ 8.72 (d, J=8.5 Hz, 1H), 7.70-7.63 (m, 2H), 7.58 (t, J=1.1 Hz, 1H), 7.45-7.36 (m, 4H), 5.56 (brs, 1H), 5.08-5.02 (m, 1H), 4.00 (dd, J=7.7, 4.0 Hz, 1H), 3.40 (s, 3H), 3.27-3.13 (m, 2H), 2.30 (dd, J=12.8, 4.1 Hz, 1H), 2.22 (dd, J=12.7, 7.7 Hz, 1H), 2.11 (s, 6H).

Example 78: Synthesis of Compound 191: 3-Amino-N-[(1S)-1-cyano-2-[4-(3-methyl-2-oxo-1,3-benzoxazol-5-yl) phenyl]ethyl]-2-(pyridin-3-ylmethyl) propanamide

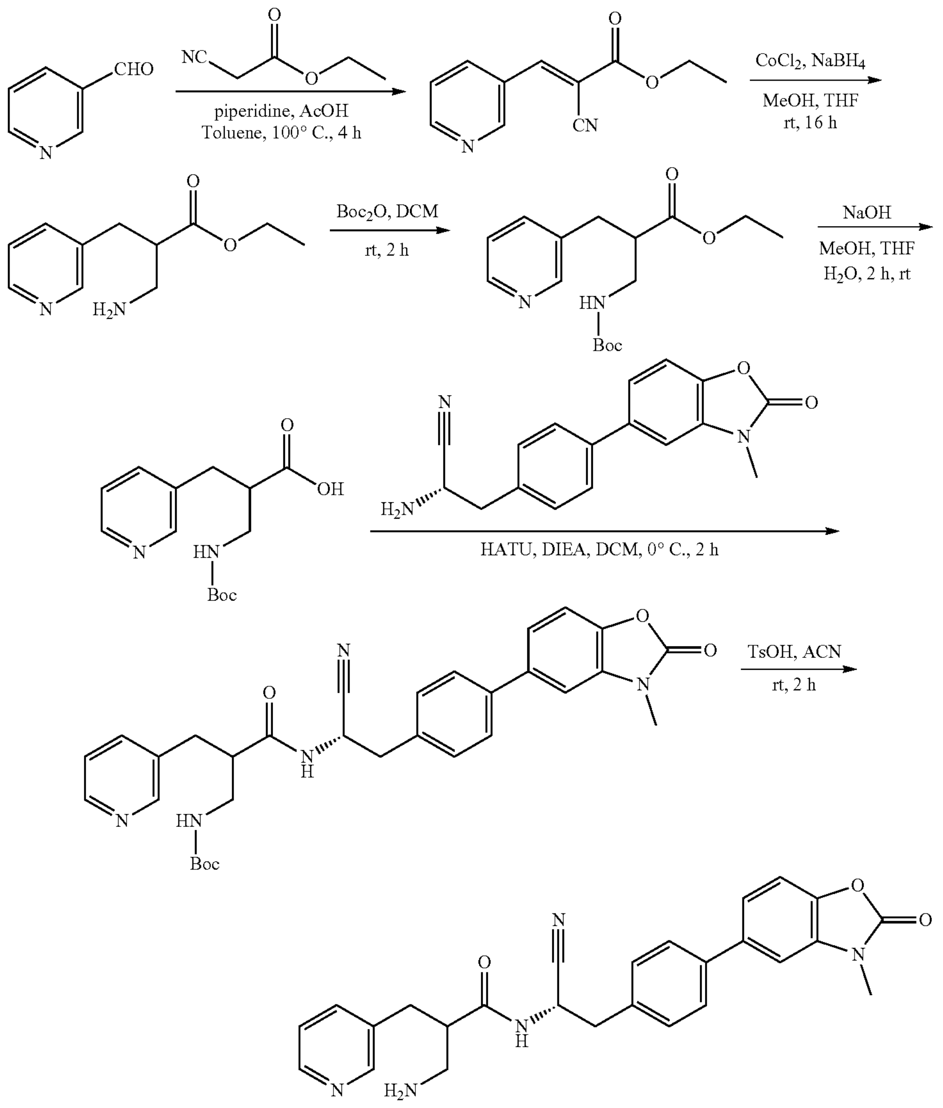

Synthesis of tert-butyl N-[(1S)-1-cyano-2-[4-(4,4,5,5-tetramethyl-1,3,2-dioxaborolan-2-yl) phenyl]ethyl] carbamate

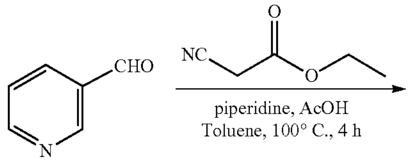

-continued

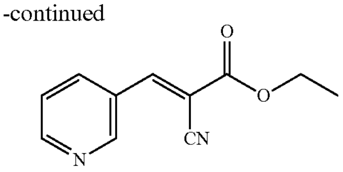

A solution of 3-pyridinecarboxaldehyde (2 g, 18.67 mmol, 1.0 equiv), piperdine (0.2 mL, 1.87 mmol, 0.1 equiv) and AcOH (0.08 mL, 1.40 mmol, 0.07 equiv) in toluene (10 mL) was stirred for 4 h at 100° C. under nitrogen atmosphere. The reaction was cooled to room temperature, diluted with water (20 mL). The resulting mixture was extracted with EtOAc (3×20 mL). The combined organic layer was washed with brine (2×20 mL), dried over anhydrous $Na_2SO_4$. After filtration, the filtrate was concentrated under reduced pressure. The residue was purified by silica gel column chromatography, eluted with PE/THE (1:1) to afford ethyl (2E)-2-cyano-3-(pyridin-3-yl)prop-2-enoate (3.4 g, 90%). LCMS (ES) [M+1]+ m/z: 203.

Synthesis of ethyl 3-amino-2-(pyridin-3-ylmethyl) propanoate

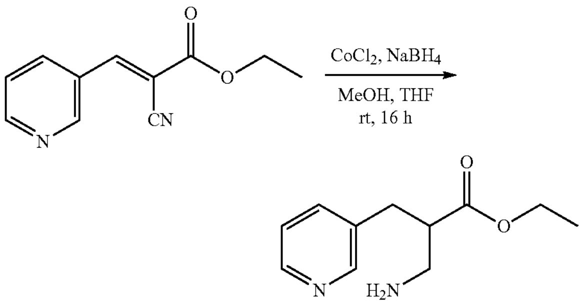

A solution of ethyl (2E)-2-cyano-3-(pyridin-3-yl) prop-2-enoate (3.4 g, 16.81 mmol, 1.0 equiv), $CoCl_2.6H_2O$ (12.0 g, 50.44 mmol, 3.0 equiv) and $NaBH_4$ (0.64 g, 16.814 mmol, 1.0 equiv) in THE (5 mL) and MeOH (40 mL) was stirred for 16 h at room temperature. The resulting mixture was filtered, the filter cake was washed with THE (3×20 mL). The filtrate was concentrated under reduced pressure. The resulting mixture was diluted with EtOAc (30 mL), washed with water (3×30 mL), dried over anhydrous $Na_2SO_4$. After filtration, the filtrate was concentrated under reduced pressure. This resulted in ethyl 3-amino-2-(pyridin-3-ylmethyl) propanoate (1.2 g, 34%). LCMS (ES) [M+1]+ m/z: 209.

Synthesis of ethyl 3-[(tert-butoxycarbonyl) amino]-2-(pyridin-3-ylmethyl) propanoate

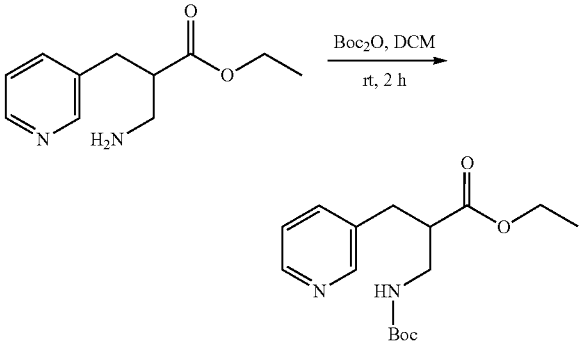

To a stirred solution of ethyl 3-amino-2-(pyridin-3-ylmethyl) propanoate (1.2 g, 5.76 mmol, 1.0 equiv) and NaOH (0.69 g, 17.29 mmol, 3.0 equiv) in DCM (12 mL) was added $Boc_2O$ (1.38 g, 6.34 mmol, 1.1 equiv) in portions at 0° C. The resulting mixture was stirred for 2 h at room temperature. The reaction was diluted with water, extracted with $CH_2Cl_2$ (3×30 mL). The combined organic layer was washed with water (2×30 mL), dried over anhydrous $Na_2SO_4$. After filtration, the filtrate was concentrated under reduced pressure. This resulted in ethyl 3-[(tert-butoxycarbonyl)amino]-2-(pyridin-3-ylmethyl)propanoate (750 mg, 42%). LCMS (ES) [M+1]+ m/z: 309.

Synthesis of 3-[(tert-butoxycarbonyl) amino]-2-(pyridin-3-ylmethyl) propanoic acid

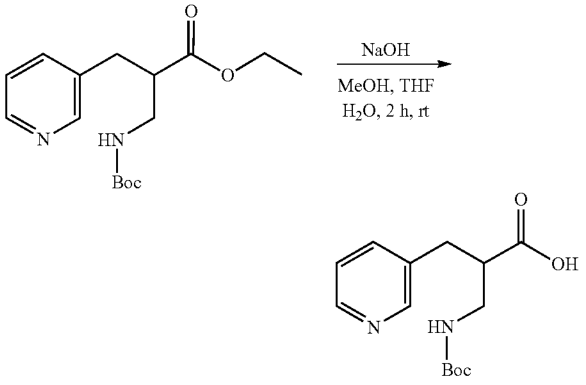

A solution of ethyl 3-[(tert-butoxycarbonyl) amino]-2-(pyridin-3-ylmethyl) propanoate (500 mg, 1.62 mmol, 1.0 equiv) and NaOH (129 mg, 3.24 mmol, 2.0 equiv) in MeOH (4 mL), THE (4 mL), $H_2O$ (2 mL) was stirred for 2 h at room temperature. The mixture was neutralized to pH 7 with citric acid. The resulting mixture was extracted with EtOAc (2×10 mL). The combined organic layer was washed with brine (2×5 mL), dried over anhydrous $Na_2SO_4$. After filtration, the filtrate was concentrated under reduced pressure. This resulted in 3-[(tert-butoxycarbonyl) amino]-2-(pyridin-3-ylmethyl) propanoic acid (400 mg, 88%). LCMS (ES) [M+1]+ m/z: 281.

Synthesis of (2S)—N-[(1S)-1-cyano-2-(4-{1-methyl-3'-oxospiro [azetidine-3,1'-[2]benzofuran]-6'-yl}phenyl) ethyl]-1,4-oxazocane-2-carboxamide

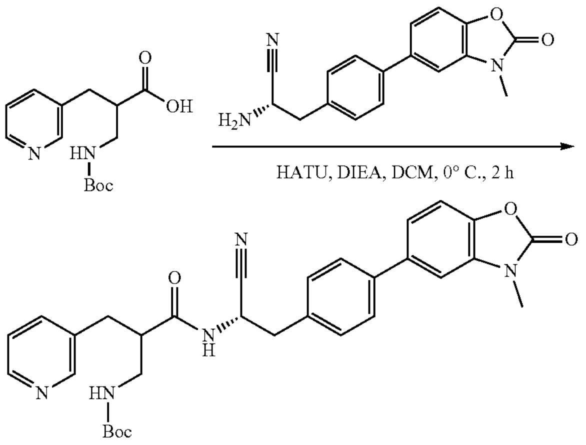

To a solution of 3-[(tert-butoxycarbonyl)amino]-2-(pyridin-3-ylmethyl)propanoic acid (100 mg, 0.36 mmol, 1.0 equiv) and (2S)-2-amino-3-[4-(3-methyl-2-oxo-1,3-benzoxazol-5-yl)phenyl]propanenitrile (104 mg, 0.36 mmol, 1.0 equiv) and DIEA (55 mg, 0.43 mmol, 1.2 equiv) in DCM (1 mL) was added HATU (203 mg, 0.54 mmol, 1.5 equiv). After addition, the reaction was stirred for 2 h at 0° C. Concentrated under reduced pressure to remove the solvent, the residue was purified by silica gel column chromatography, eluted with PE/THE (1:1) to afford tert-butyl N-(2-{[(1S)-1-cyano-2-[4-(3-methyl-2-oxo-1,3-benzoxazol-5-yl) phenyl]ethyl]carbamoyl}-2-(pyridin-3-ylmethyl)ethyl) carbamate. LCMS (ES) [M+1]+ m/z: 556.

Synthesis of 3-Amino-N-[(1S)-1-cyano-2-[4-(3-methyl-2-oxo-1,3-benzoxazol-5-yl) phenyl]ethyl]-2-(pyridin-3-ylmethyl) propanamide

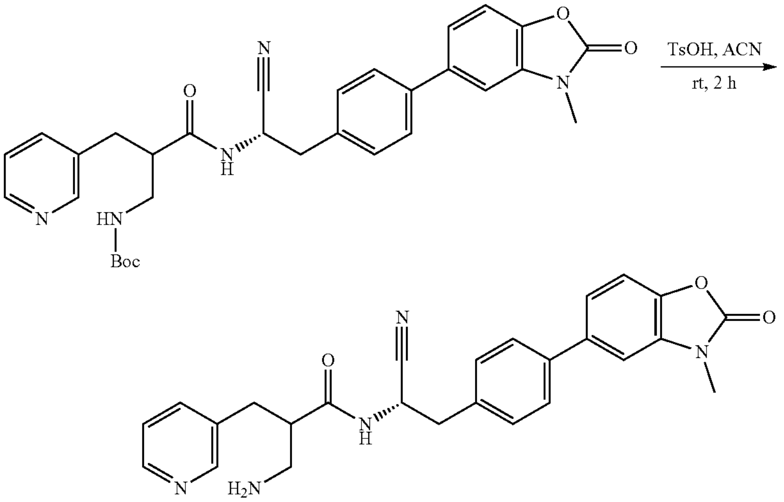

A solution of tert-butyl N-(2-{[(1S)-1-cyano-2-[4-(3-methyl-2-oxo-1,3-benzoxazol-5-yl) phenyl]ethyl]carbamoyl}-2-(pyridin-3-ylmethyl) ethyl) carbamate (130 mg, 0.23 mmol, 1.0 equiv) and TsOH (120 mg, 0.70 mmol, 3.0 equiv) in ACN (0.5 mL) was stirred for 2 h at room temperature. The reaction was purified by reversed-phase flash chromatography with the following conditions: column, C18 silica gel-120 g; mobile phase, MeCN in Water (0.1% $NH_3 \cdot H_2O$), 10% to 60% gradient in 10 min; detector, UV 254 nm. This resulted in 3-amino-N-[(1S)-1-cyano-2-[4-(3-methyl-2-oxo-1,3-benzoxazol-5-yl)phenyl]ethyl]-2-(pyridin-3-ylmethyl) propanamide (30 mg, 28%). LCMS (ES) $[M+1]^+$ m/z: 456. $^1H$ NMR (400 MHz, DMSO-$d_6$) δ 8.41-8.30 (m, 2H), 7.66-7.61 (m, 2H), 7.58-7.45 (m, 2H), 7.43-7.36 (m, 3H), 7.33-7.20 (m, 2H), 5.01-4.91 (m, 1H), 3.41 (s, 3H), 3.12-2.91 (m, 2H), 2.76-2.66 (m, 3H), 2.63-2.55 (m, 2H)

Example 79: Synthesis of Compound 193 and 194: (2R)-3-amino-N-[(1S)-1-cyano-2-[4-(3-methyl-2-oxo-1,3-benzoxazol-5-yl)phenyl]ethyl]-2-[(2-methylphenyl)methyl]propanamide; (2S)-3-amino-N-[(1S)-1-cyano-2-[4-(3-methyl-2-oxo-1,3-benzoxazol-5-yl)phenyl]ethyl]-2-[(2-methylphenyl)methyl]propanamide

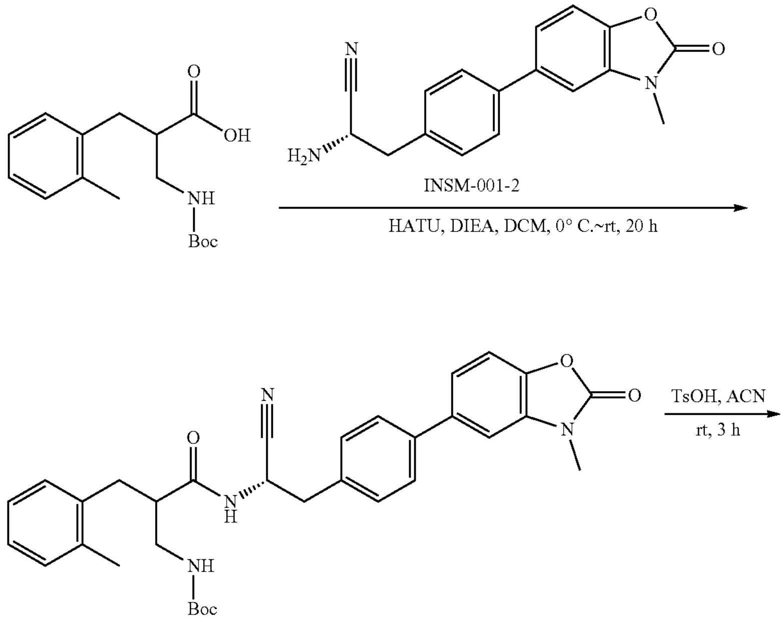

-continued

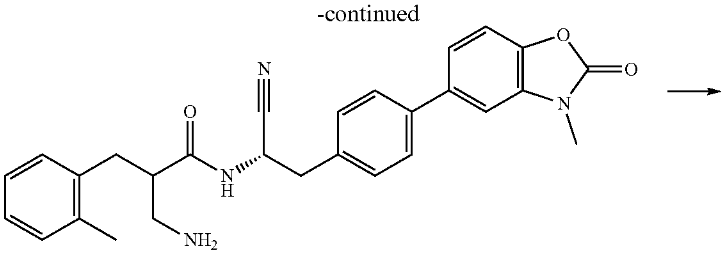

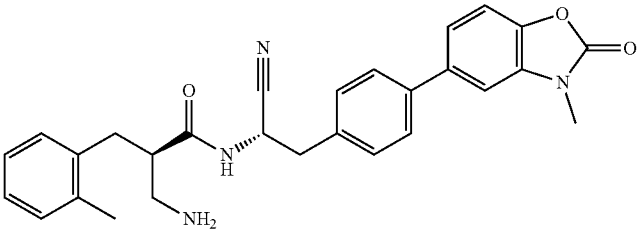

+

Compound 194
assumed as Anti

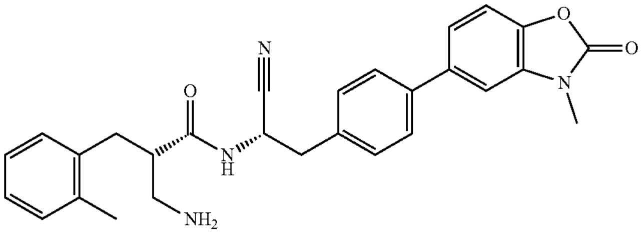

Compound 194
assumed as Syn

Synthesis of tert-butyl N-(2-{[(1S)-1-cyano-2-[4-(3-methyl-2-oxo-1,3-benzoxazol-5-yl)phenyl]ethyl]carbamoyl}-2-[(2-methylphenyl)methyl]ethyl)carbamate

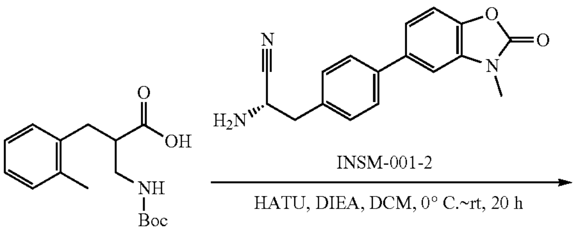

-continued

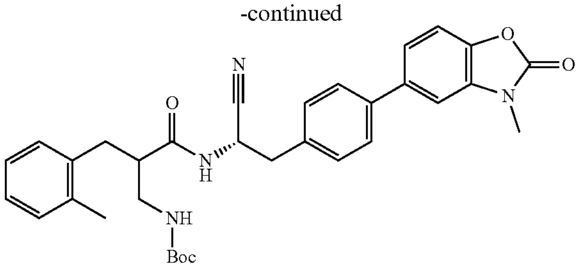

To a stirred solution of 3-[(tert-butoxycarbonyl)amino]-2-[(2-methylphenyl)methyl]propanoic acid (110 mg, 0.37 mmol, 1.0 equiv), (2S)-2-amino-3-[4-(3-methyl-2-oxo-1,3-benzoxazol-5-yl)phenyl]propanenitrile (121 mg, 0.413 mmol, 1.1 equiv) and DIEA (145 mg, 1.12 mmol, 3.0 equiv) in DCM (5 mL) was added HATU (171 mg, 0.45 mmol, 1.2 equiv) in portions at 0° C. The resulting mixture was stirred for additional 3 h at 0° C. The residue was purified by silica gel column chromatography, eluted with PE/THE (1:1) to afford tert-butyl N-(2-{[(1S)-1-cyano-2-[4-(3-methyl-2-oxo-1,3-benzoxazol-5-yl)phenyl]ethyl]carbamoyl}-2-[(2-methylphenyl)methyl]ethyl)carbamate (120 mg, 56.2%). LCMS (ES, m/z): $[M+H]^+$: 569.

Synthesis of (2R)-3-amino-N-[(1S)-1-cyano-2-[4-(3-methyl-2-oxo-1,3-benzoxazol-5-yl)phenyl]ethyl]-2-[(2-methylphenyl)methyl]propanamide; (2S)-3-amino-N-[(1S)-1-cyano-2-[4-(3-methyl-2-oxo-1,3-benzoxazol-5-yl)phenyl]ethyl]-2-[(2-methylphenyl)methyl]propanamide

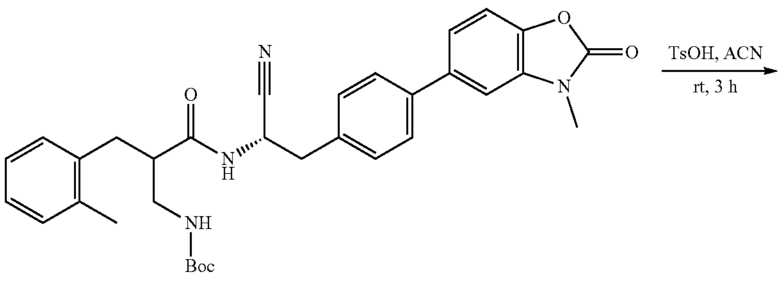

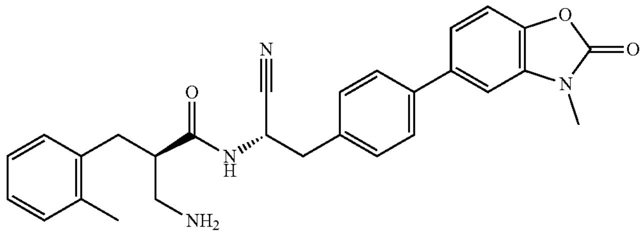

Compound 194
assumed as Anti

+

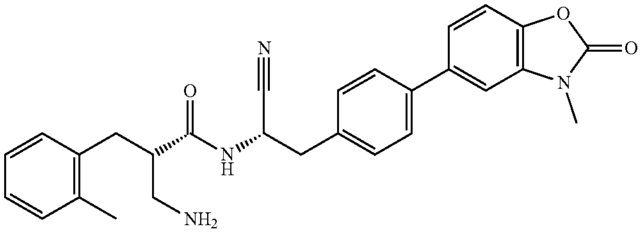

Compound 194
assumed as Syn

Into a 50 mL round-bottom flask were added tert-butyl N-(2-{[(1S)-1-cyano-2-[4-(3-methyl-2-oxo-1,3-benzoxazol-5-yl)phenyl]ethyl]carbamoyl}-2-[(2-methylphenyl)methyl]ethyl)carbamate (120 mg, 0.21 mmol, 1.0 equiv) and TsOH (109 mg, 0.63 mmol, 3.0 equiv) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 80% gradient in 10 min; detector, UV 254 nm. This resulted in (2R)-3-amino-N-[(1S)-1-cyano-2-[4-(3-methyl-2-oxo-1,3-benzoxazol-5-yl)phenyl]ethyl]-2-[(2-methylphenyl)methyl]propanamide(16.33 mg6.67%); (2S)-3-amino-N-[(1S)-1-cyano-2-[4-(3-methyl-2-oxo-1,3-benzoxazol-5-yl)phenyl]ethyl]-2-[(2-methylphenyl)methyl] propanamide (17.0 mg, 6.67%).

LCMS (ES, m z): $[M+H]^+$: 469.2

$^1H$ NMR (400 MHz, DMSO-$d_6$) δ 7.68-7.61 (m, 2H), 7.57 (d, J=1.2 Hz, 1H), 7.45-7.34 (m, 4H), 7.16-7.02 (m, 4H), 4.99 (t, J=7.8 Hz, 1H), 3.40 (s, 3H), 3.17-2.99 (m, 2H), 2.78-2.55 (m, 4H), 2.43 (d, J=6.0 Hz, 1H), 2.27 (s, 3H).

LCMS (ES, m z): $[M+H]^+$: 469.2

$^1H$ NMR (400 MHz, DMSO-$d_6$) δ 7.66-7.60 (m, 2H), 7.56 (d, J=1.3 Hz, 1H), 7.41 (d, J=1.2 Hz, 2H), 7.32-7.25 (m, 2H), 7.12 (d, J=6.0 Hz, 1H), 7.10-7.01 (m, 3H), 4.98 (t, J=7.5 Hz, 1H), 3.40 (s, 3H), 3.04-2.89 (m, 2H), 2.74 (dd, J=12.4, 8.0 Hz, 1H), 2.66 (d, J=7.6 Hz, 2H), 2.60-2.50 (m, 2H), 2.25 (s, 3H)

Example 80: Synthesis of COMPOUND 196: 3-Amino-N-[(1S)-1-cyano-2-[4-(3-methyl-2-oxo-1,3-benzoxazol-5-yl) phenyl]ethyl]-2-[(2-fluorophenyl) methyl]-2-methylpropanamide

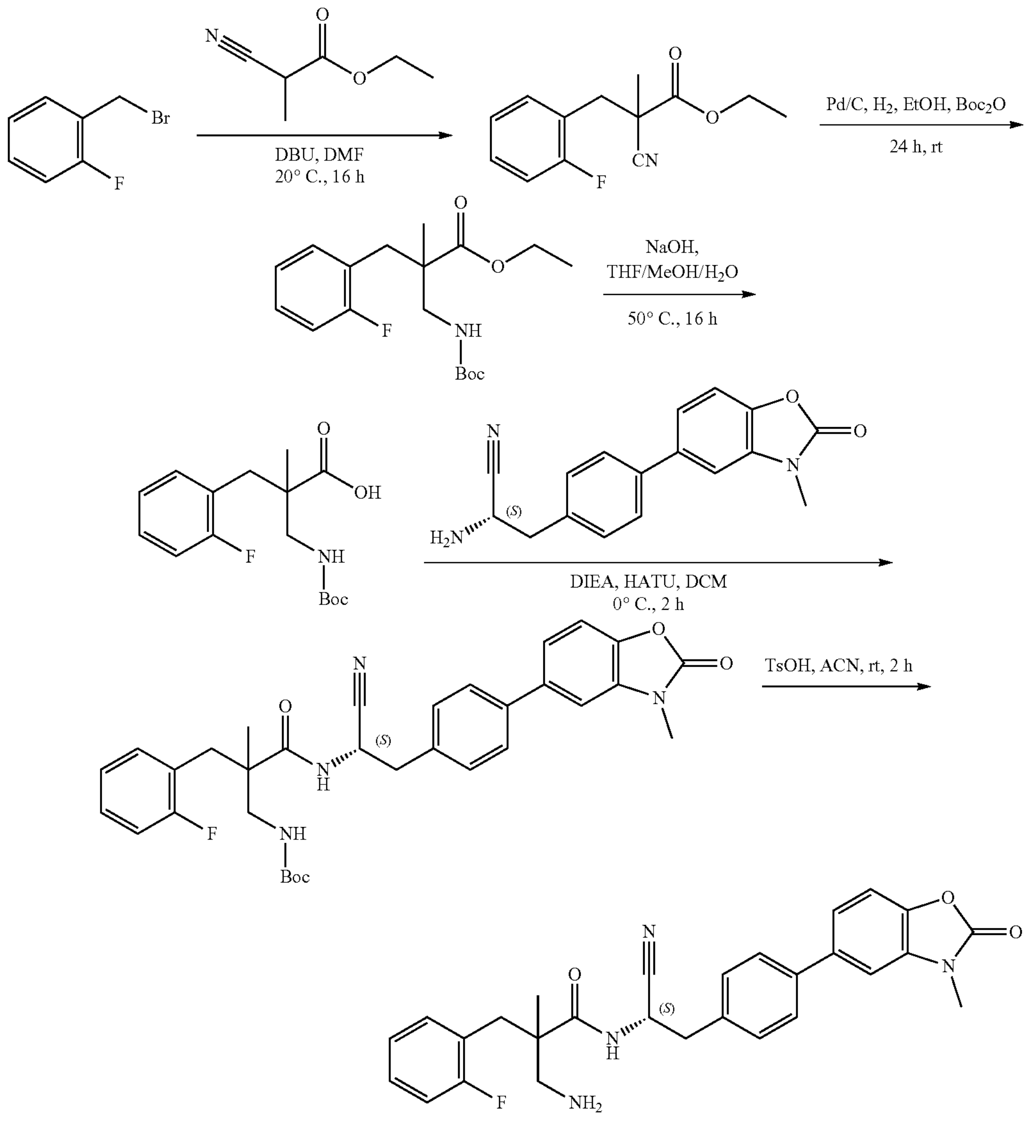

Synthesis of ethyl 2-cyano-3-(2-fluorophenyl)-2-methylpropanoat

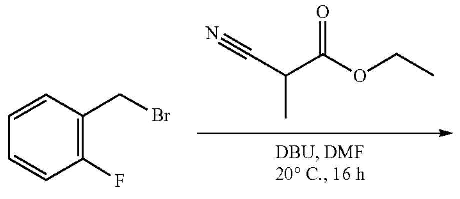

-continued

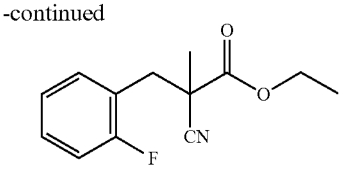

A solution of 1-(bromomethyl)-2-fluorobenzene (3.5 g, 18.52 mmol, 1.0 equiv), ethyl 2-cyanopropionate (2.35 g, 18.52 mmol, 1.0 equiv) and DBU (2.82 g, 18.52 mmol, 1.0 equiv) in DMF (35 mL) was stirred for 16 h at 20° C. The resulting mixture was diluted with water (35 mL), extracted with EtOAc (3×30 mL). The combined organic layer was washed with brine (2×30 mL), dried over anhydrous $Na_2SO_4$. After filtration, the filtrate was concentrated under reduced pressure. The residue was purified by silica gel column chromatography, eluted with PE/THE (5:1) to afford ethyl 2-cyano-3-(2-fluorophenyl)-2-methylpropanoate (2.7 g, 62%). $^1$H NMR (300 MHz, DMSO-$d_6$) δ 7.45-7.29 (m, 2H), 7.28-7.15 (m, 2H), 4.18 (q, J=7.1 Hz, 2H), 3.31-3.15 (m, 2H), 1.59 (s, 3H), 1.18 (t, J=7.1 Hz, 3H).

Synthesis of ethyl 3-[(tert-butoxycarbonyl) amino]-2-[(2-fluorophenyl) methyl]-2-methylpropanoate

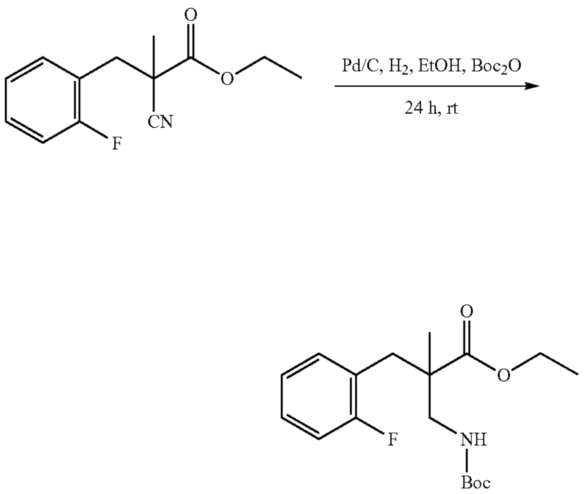

A mixture of ethyl 2-cyano-3-(2-fluorophenyl)-2-methylpropanoate (2.7 g, 11.48 mmol, 1.0 equiv), $Boc_2O$ (2.76 g, 12.62 mmol, 1.1 equiv) and Pd/C (0.85 g) in EtOH (30 mL) was stirred for 24 h at room temperature under hydrogen atmosphere (1-2 atm). The resulting mixture was filtered, the filter cake was washed with EtOAc (3×10 mL). The filtrate was concentrated under reduced pressure. This resulted in ethyl 3-[(tert-butoxycarbonyl) amino]-2-[(2-fluorophenyl) methyl]-2-methylpropanoate (2.1 g, 54%). LCMS (ES) $[M+1]^+$ m/z: 340.

Synthesis of 3-[(tert-butoxycarbonyl) amino]-2-[(2-fluorophenyl) methyl]-2-methylpropanoic acid

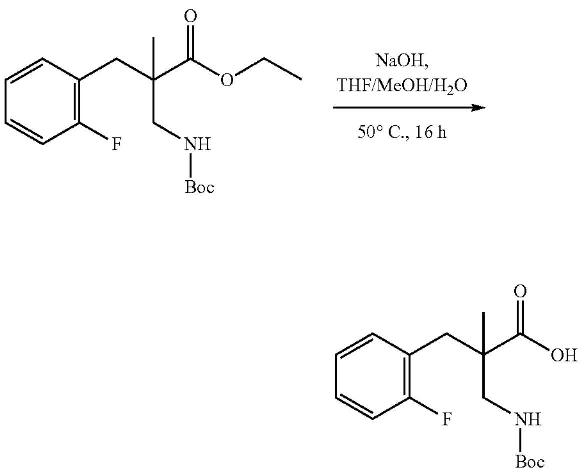

A mixture of ethyl 3-[(tert-butoxycarbonyl) amino]-2-[(2-fluorophenyl) methyl]-2-methylpropanoate (150 mg, 0.44 mmol, 1.0 equiv) and NaOH (35 mg, 0.88 mmol, 2.0 equiv) in THE (1 mL), MeOH (1 mL) and $H_2O$ (0.5 mL) was stirred for 16 h at 50° C. The resulting mixture was concentrated under reduced pressure. The residue was diluted with water (5 mL), extracted with EtOAc (2×3 mL). The aqueous layer was neutralized to pH 7 with citric acid. The resulting mixture was extracted with EtOAc (3×5 mL). The combined organic layer was washed with brine (2×3 mL), dried over anhydrous $Na_2SO_4$. After filtration, the filtrate was concentrated under reduced pressure. This resulted in 3-[(tert-butoxycarbonyl) amino]-2-[(2-fluorophenyl) methyl]-2-methylpropanoic acid (110 mg, 80%). LCMS (ES) $[M+1]^+$ m/z: 312.

Synthesis of tert-butyl N-(2-{[(1S)-1-cyano-2-[4-(3-methyl-2-oxo-1,3-benzoxazol-5-yl) phenyl]ethyl] carbamoyl}-2-[(2-fluorophenyl) methyl]-2-methylethyl) carbamate

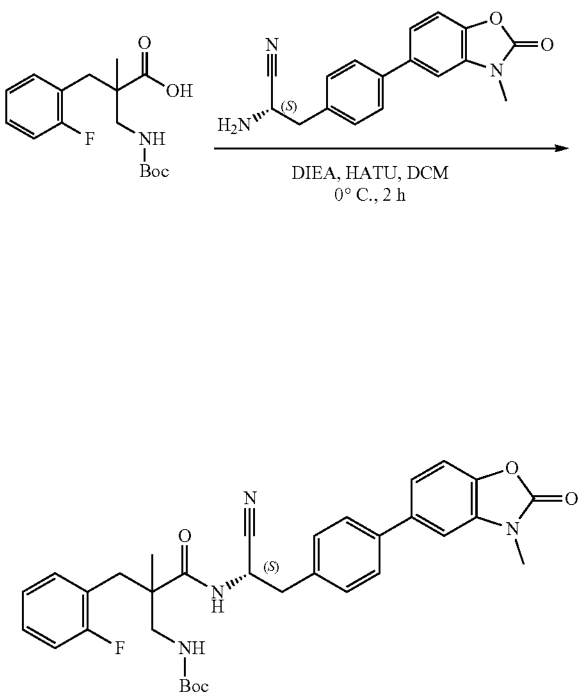

To a stirred solution of (2S)-2-amino-3-[4-(3-methyl-2-oxo-1,3-benzoxazol-5-yl) phenyl]propanenitrile (100 mg, 0.34 mmol, 1.0 equiv) and DIEA (132 mg, 1.02 mmol, 3.0 equiv) in DCM (1.5 mL) was added HATU (155 mg, 0.41 mmol, 1.2 equiv) in portions at 0° C. The resulting mixture was stirred for 2 h at 0° C. Concentrated under reduced pressure to remove the solvent, the residue was purified by silica gel column chromatography, eluted with PE/THE (3:1) to afford tert-butyl N-(2-{[(1S)-1-cyano-2-[4-(3-methyl-2-oxo-1,3-benzoxazol-5-yl) phenyl]ethyl]carbamoyl}-2-[(2-fluorophenyl) methyl]-2-methylethyl) carbamate (100 mg, 50%). LCMS (ES) $[M+1]^+$ m/z: 587.

Synthesis of 3-Amino-N-[(1S)-1-cyano-2-[4-(3-methyl-2-oxo-1,3-benzoxazol-5-yl) phenyl]ethyl]-2-[(2-fluorophenyl) methyl]-2-methylpropanamide

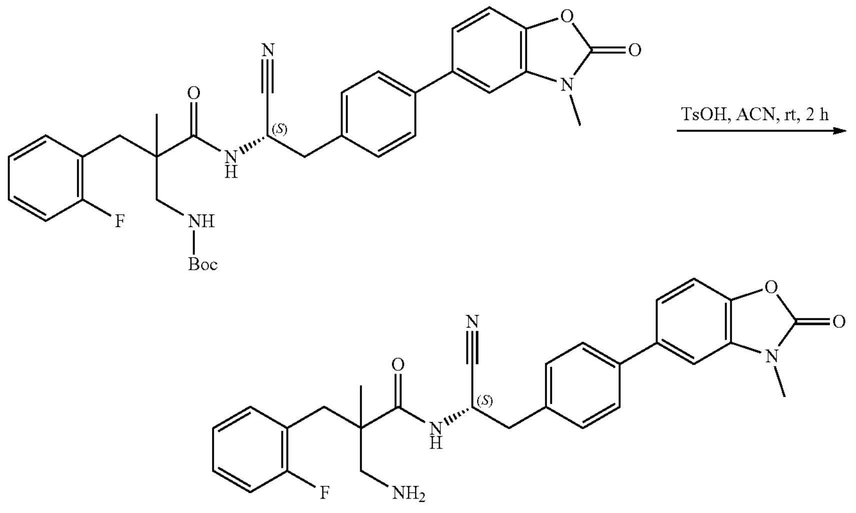

To a stirred solution of tert-butyl N-(2-{[(1S)-1-cyano-2-[4-(3-methyl-2-oxo-1,3-benzoxazol-5-yl) phenyl]ethyl]carbamoyl}-2-[(2-fluorophenyl) methyl]-2-methylethyl) carbamate (100 mg, 0.17 mmol, 1.0 equiv) in ACN (1.5 mL) was added TsOH (102 mg, 0.60 mmol, 3.5 equiv) in portions at room temperature. The resulting mixture was stirred for 2 h at room temperature. The reaction solution was purified by reversed-phase flash chromatography with the following conditions: column, C18 silica gel-120 g; mobile phase, MeCN in Water (0.1% $NH_3{\cdot}H_2O$), 10% to 55% gradient in 10 min; detector, UV 254 nm. This resulted in 3-Amino-N-[(1S)-1-cyano-2-[4-(3-methyl-2-oxo-1,3-benzoxazol-5-yl) phenyl]ethyl]-2-[(2-fluorophenyl) methyl]-2-methylpropanamide (20 mg, 24%). LCMS (ES) $[M+1]^+$ m/z: 487.5

$^1H$ NMR (400 MHz, DMSO-$d_6$) δ 7.68-7.65 (m, 2H), 7.61-7.53 (m, 1H), 7.46-7.37 (m, 4H), 7.23-7.18 (m, 1H), 7.17-6.91 (m, 3H), 5.07-5.01 (m, 1H), 3.41 (d, J=2.2 Hz, 3H), 3.24-3.11 (m, 2H), 2.87-2.71 (m, 2H), 2.69-2.66 (m, 1H), 2.49-2.45 (m, 1H), 0.91 (d, J=7.2 Hz, 3H).

Example 81: Synthesis of Compound 197: 3-amino-2-[(2-chloro-6-fluorophenyl)methyl]—N-[(1S)-1-cyano-2-[4-(3-methyl-2-oxo-1,3-benzoxazol-5-yl)phenyl]ethyl]-2-methylpropanamide

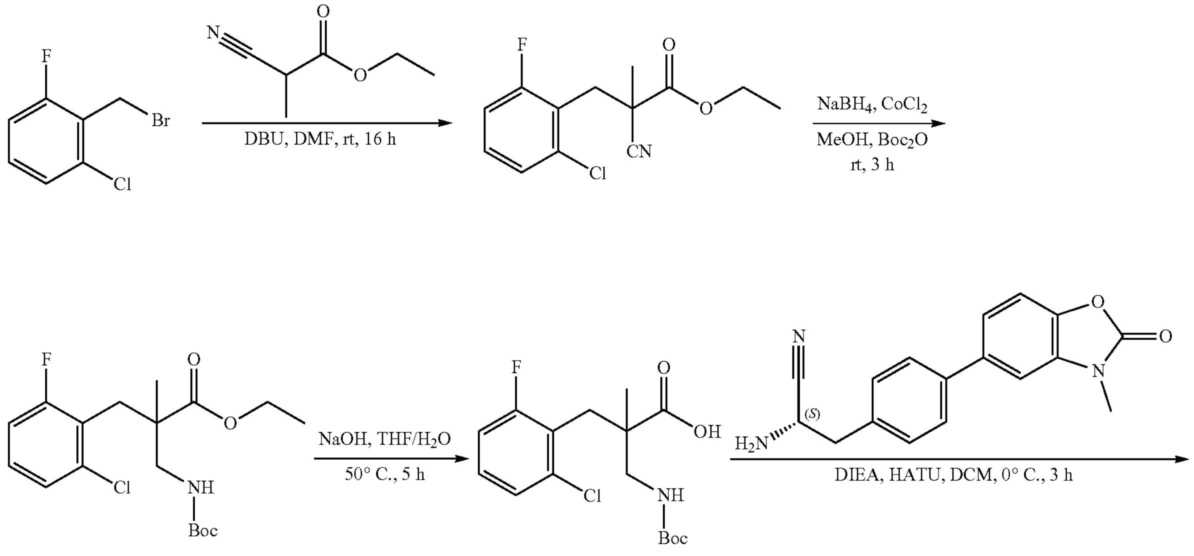

-continued

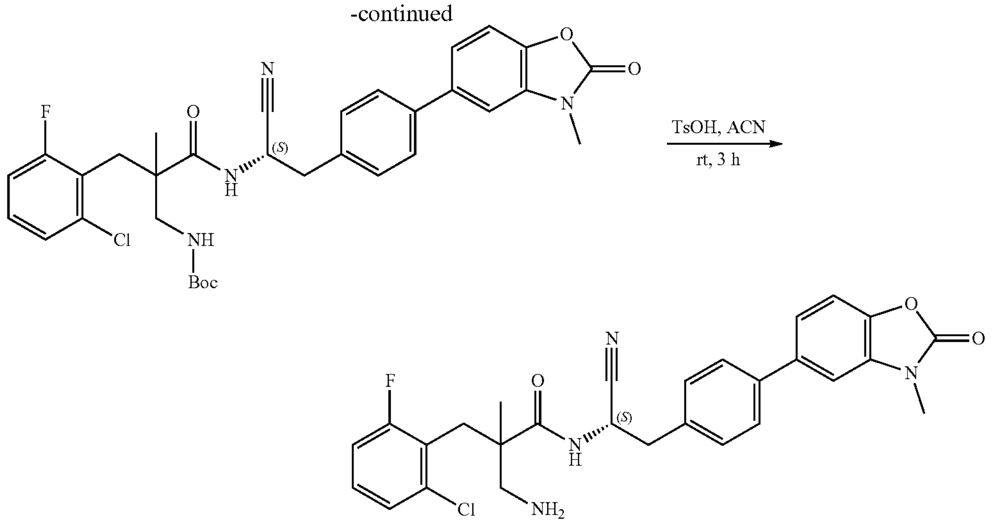

Synthesis of ethyl 3-(2-chloro-6-fluorophenyl)-2-cyano-2-methylpropanoate

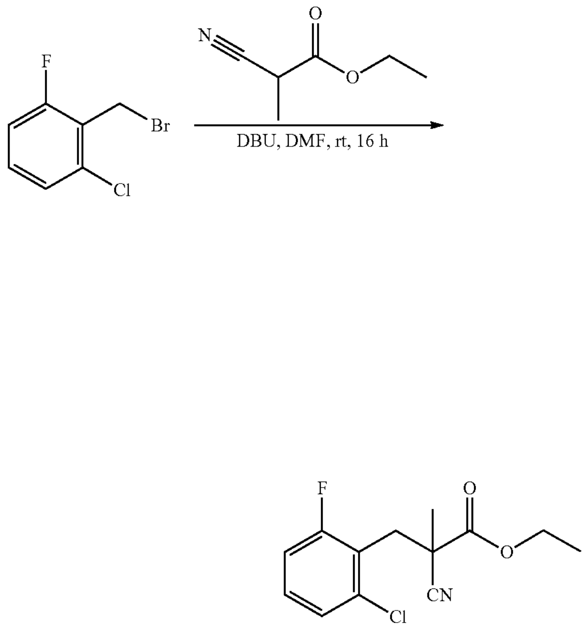

Into a 100 mL round-bottom flask were added 2-(bromomethyl)-1-chloro-3-fluorobenzene (4.0 g, 17.89 mmol, 1.0 equiv), ethyl 2-cyanopropionate (2.5 g, 19.68 mmol, 1.1 equiv) in DMF (40 mL) and DBU (2.7 g, 17.89 mmol, 1.0 equiv) at room temperature. The resulting mixture was stirred for additional 16 h at room temperature. The reaction was diluted with water (50 mL), extracted with EtOAc (3x50 mL). The combined organic layer was washed with brine (3x50 mL), dried over anhydrous $Na_2SO_4$. After filtration, the filtrate was concentrated under reduced pressure. The residue was purified by silica gel column chromatography, eluted with PE/EA (10:1) to afford ethyl 3-(2-chloro-6-fluorophenyl)-2-cyano-2-methylpropanoate (900 mg, 18.6%). LCMS (ES, m/z): $[M+H]^+$: 270.

Synthesis of ethyl 3-[(tert-butoxycarbonyl)amino]-2-[(2-chloro-6-fluorophenyl)methyl]-2-methylpropanoate

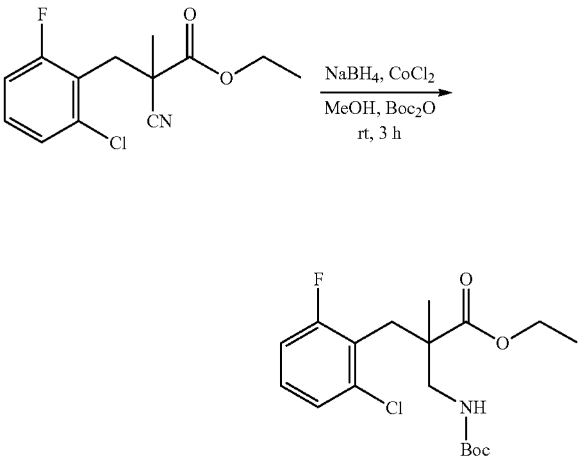

A solution of ethyl 3-(2-chloro-6-fluorophenyl)-2-cyano-2-methylpropanoate (900 mg, 3.33 mmol, 1.0 quiv) in MeOH (15 mL) was treated with $CoCl_2$ (866 mg, 6.67 mmol, 2.0 equiv) at room temperature under nitrogen atmosphere. This was followed by the addition of $NaBH_4$ (1.3 g, 33.37 mmol, 10.0 equiv) in portions at 0° C. The resulting mixture was stirred for additional 3 h at room temperature. To the above mixture was added $Boc_2O$ (2.2 g, 10.01 mmol, 3.0 equiv) dropwise at room temperature. The resulting mixture was stirred for additional 2 h at room temperature. The reaction was diluted with water (100 mL), the resulting mixture was extracted with $CH_2Cl_2$ (3x100 mL). The combined organic layer was washed with brine (3x50 mL), dried over anhydrous $Na_2SO_4$. After filtration, the filtrate was concentrated under reduced pressure. The residue was purified by silica gel column chromatography, eluted with PE/THE (4:1) to afford ethyl 3-[(tert-butoxycarbonyl)amino]-2-[(2-chloro-6-fluorophenyl)methyl]-2-methylpropanoate (420 mg, 33.6%). LCMS (ES, m/z): $[M+H]^+$: 374.

Synthesis of 3-[(tert-butoxycarbonyl)amino]-2-[(2-chloro-6-fluorophenyl)methyl]-2-methylpropanoic acid

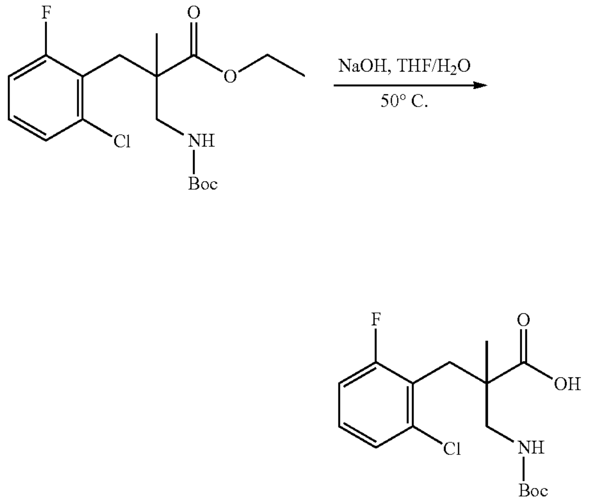

Into a 50 mL round-bottom flask were added ethyl 3-[(tert-butoxycarbonyl)amino]-2-[(2-chloro-6-fluorophenyl)methyl]-2-methylpropanoate (420 mg, 1.12 mmol, 1.0 equiv) THE (6 mL) and NaOH (89 mg, 2.24 mmol, 2.0 equiv) in $H_2O$ (3 mL) at room temperature. The resulting mixture was stirred for additional 5 h at 50° C. The resulting mixture was concentrated under reduced pressure to remove the solvent. The residue was diluted with water (20 mL), extracted with EtOAc (2x30 mL). The aqueous layer was acidified to pH 5 with citric acid. The resulting mixture was extracted with EtOAc (3x30 mL). The combined organic layer was washed with brine (3x30 mL), dried over anhydrous $Na_2SO_4$. After filtration, the filtrate was concentrated under reduced pressure. This resulted in 3-[(tert-butoxycarbonyl)amino]-2-[(2-chloro-6-fluorophenyl)methyl]-2-methylpropanoic acid (400 mg, crude). LCMS (ES, m/z): $[M+H]^+$: 346.

Synthesis of tert-butyl N-{2-[(2-chloro-6-fluorophenyl)methyl]-2-{1[(1S)-1-cyano-2-[4-(3-methyl-2-oxo-1,3-benzoxazol-5-yl)phenyl]ethyl]carbamoyl}-2-methylethyl}carbamate

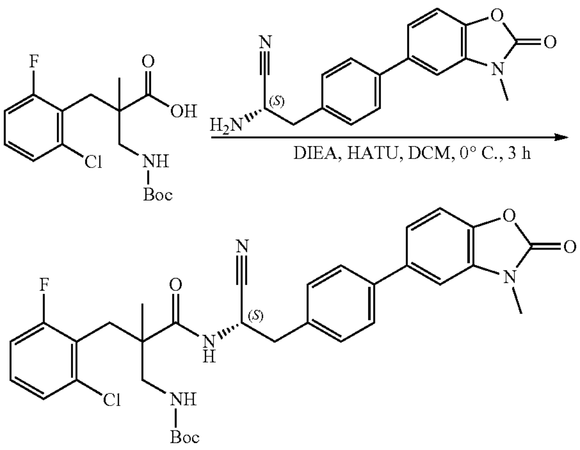

A solution of 3-[(tert-butoxycarbonyl)amino]-2-[(2-chloro-6-fluorophenyl)methyl]-2-methylpropanoic acid (200 mg, 0.57 mmol, 2.0 equiv) in DCM (8 mL) was treated with (2S)-2-amino-3-[4-(3-methyl-2-oxo-1,3-benzoxazol-5-yl)phenyl]propanenitrile (85 mg, 0.28 mmol, 1.0 equiv), DIEA (112 mg, 0.86 mmol, 3.0 equiv). This was followed by the addition of HATU (128 mg, 0.34 mmol, 1.2 equiv) at 0° C. The resulting mixture was stirred for additional 2 h at room temperature. The residue was purified by silica gel column chromatography, eluted with PE/THE (1:1) to afford tert-butyl N-{2-[(2-chloro-6-fluorophenyl)methyl]-2-{[(1S)-1-cyano-2-[4-(3-methyl-2-oxo-1,3-benzoxazol-5-yl)phenyl]ethyl]carbamoyl}-2-methylethyl}carbamate (100 mg, 55.6%). LCMS (ES, m/z): $[M+H]^+$: 621.

Synthesis of 3-amino-2-[(2-chloro-6-fluorophenyl)methyl]—N-[(1S)-1-cyano-2-[4-(3-methyl-2-oxo-1,3-benzoxazol-5-yl)phenyl]ethyl]-2-methylpropanamide

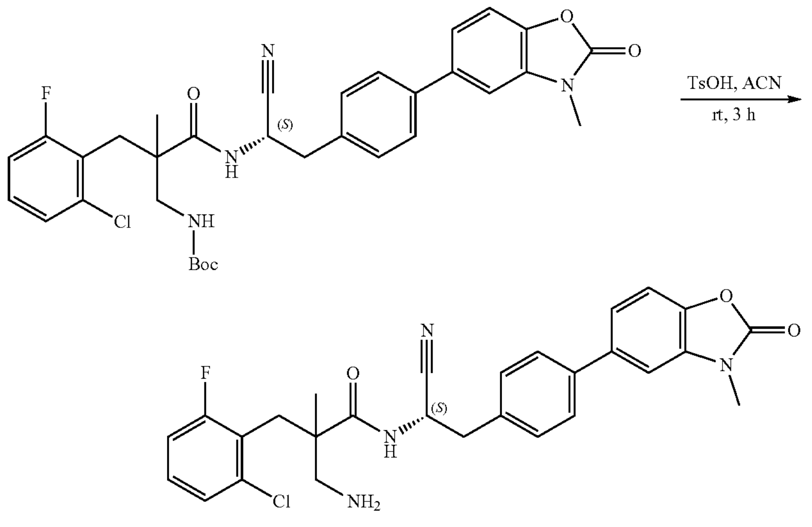

Into a 25 mL round-bottom flask were added tert-butyl N-{2-[(2-chloro-6-fluorophenyl)methyl]-2-{[(1S)-1-cyano-2-[4-(3-methyl-2-oxo-1,3-benzoxazol-5-yl)phenyl]ethyl] carbamoyl}-2-methylethyl}carbamate (100 mg, 0.16 mmol, 1.0 equiv) in ACN (3 mL) and TsOH (83 mg, 0.48 mmol, 3.0 equiv) at room temperature. The resulting mixture was stirred for additional 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in 3-amino-2-[(2-chloro-6-fluorophenyl)methyl]—N-[(1 S)-1-cyano-2-[4-(3-methyl-2-oxo-1,3-benzoxazol-5-yl)phenyl]ethyl]-2-methylpropanamide (17.3 mg, 20.6%).

LCMS (ES, m/z): $[M+H]^+$: 521.3.

$^1H$ NMR (400 MHz, DMSO-$d_6$) δ 7.69-7.65 (m, 2H), 7.61-7.55 (m, 1H), 7.46-7.38 (m, 4H), 7.32-7.28 (m, 2H), 7.21-7.14 (m, 1H), 5.09-5.04 (m, 1H), 3.41 (s, 3H), 3.20-3.09 (m, 2H), 3.07-2.96 (m, 1H), 2.91-2.77 (m, 2H), 2.46-2.41 (m, 1H), 0.98 (d, J=24.6 Hz, 3H).

Example 82: Synthesis of Compound 103: (2S)-3-amino-N-[(1S)-1-cyano-2-[4-(3-methyl-2-oxo-1,3-benzoxazol-5-yl)phenyl]ethyl]-2-methoxypropanamide

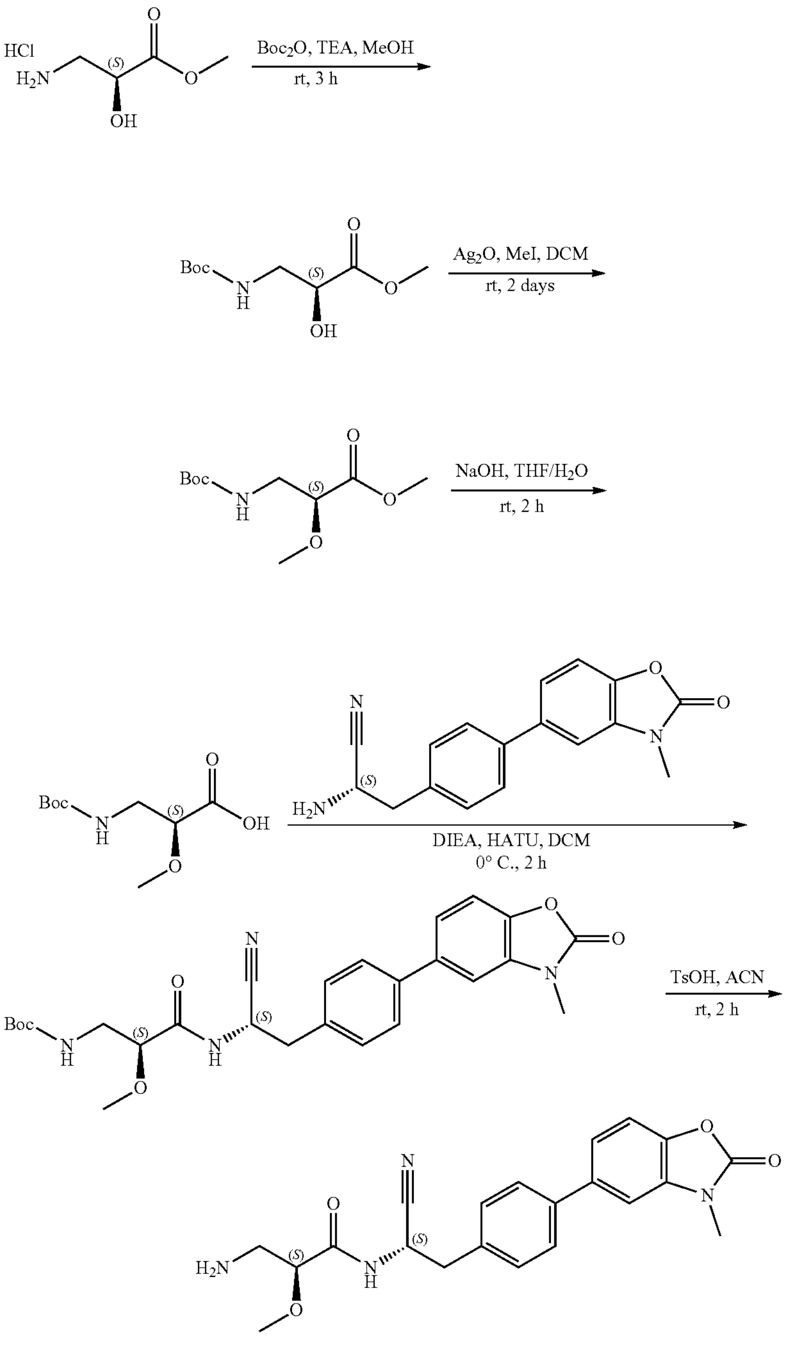

Synthesis of methyl (2S)-3-[(tert-butoxycarbonyl) amino]-2-hydroxypropanoate

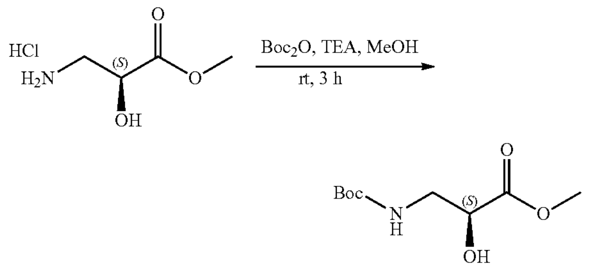

To a stirred mixture of methyl (2S)-3-amino-2-hydroxypropanoate hydrochloride (3.0 g, 19.28 mmol, 1.0 equiv) in MeOH (30 mL) was added TEA (5.85 g, 57.85 mmol, 3.0 equiv) dropwise at room temperature under nitrogen atmosphere. To the above mixture was added the solution of $Boc_2O$ (4.42 g, 20.24 mmol, 1.05 equiv) in MeOH (20 mL) dropwise at 0° C. The resulting mixture was stirred for 3 h at room temperature. The resulting mixture was concentrated under reduced pressure. The residue was diluted with water (60 mL), extracted with EtOAc (3×20 mL). The combined organic layer was washed with brine (50 mL), dried over anhydrous $Na_2SO_4$. After filtration, the filtrate was concentrated under reduced pressure. The crude product was used in the next step directly without further purification. LCMS (ES, m z): $[M+H]^+$: 220.

Synthesis of methyl (2S)-3-[(tert-butoxycarbonyl) amino]-2-methoxypropanoate

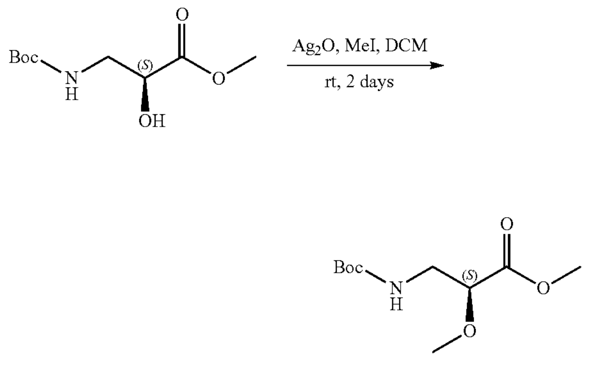

To a stirred mixture of methyl (2S)-3-[(tert-butoxycarbonyl)amino]-2-hydroxypropanoate (1.0 g, 4.56 mmol, 1.0 equiv) and $Ag_2O$ (2.11 g, 9.12 mmol, 2.0 equiv) in DCM (20 mL) was added MeI (1.29 g, 9.12 mmol, 2.0 equiv) dropwise at 0° C. under nitrogen atmosphere. The resulting mixture was stirred for 2 days at room temperature in dark place. The resulting mixture was filtered, the filter cake was washed with $CH_2Cl_2$ (3×10 mL). The filtrate was concentrated under reduced pressure. The residue was purified by silica gel column chromatography, eluted with PE/THF (3:1) to afford methyl (2S)-3-[(tert-butoxycarbonyl)amino]-2-methoxypropanoate (600 mg, 56.4%). LCMS (ES, m z): $[M+H]^+$: 234.

Synthesis of (2S)-3-[(tert-butoxycarbonyl)amino]-2-methoxypropanoic acid

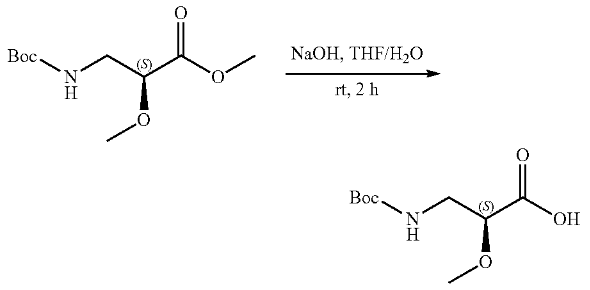

To a stirred mixture of methyl (2S)-3-[(tert-butoxycarbonyl)amino]-2-methoxypropanoate (600 mg, 2.57 mmol, 1.0 equiv) in THF (9.0 mL) was added the solution of NaOH (205 mg, 5.14 mmol, 2.0 equiv) in $H_2O$ (3 mL) dropwise at room temperature. The resulting mixture was stirred for 2 h at room temperature. The resulting mixture was diluted with water (30 mL), extracted with EtOAc (2×5 mL). The combined organic layer was washed with brine (20 mL). The residue was acidified to pH 5 with citric acid. The resulting mixture was extracted with $CH_2Cl_2$/MeOH=10/1 (3×10 mL). The combined organic layer was washed with brine (50 mL), dried over anhydrous $Na_2SO_4$. After filtration, the filtrate was concentrated under reduced pressure. The crude product was used in the next step directly without further purification. LCMS (ES, m/z): $[M+H]^+$: 220.

Synthesis of tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]carbamate

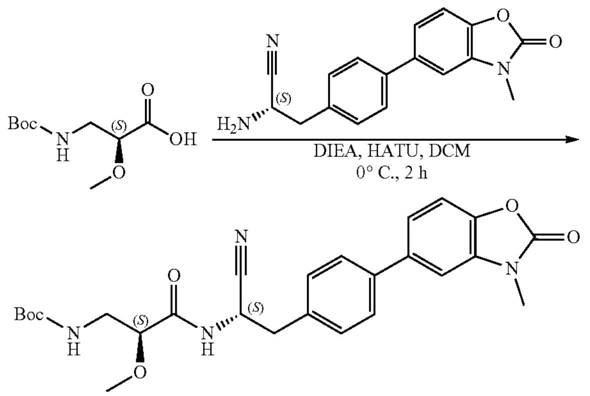

To a stirred mixture of (2S)-3-[(tert-butoxycarbonyl)amino]-2-methoxypropanoic acid (608 mg, 2.77 mmol, 1.1 equiv) and (2S)-2-amino-3-[4-(3-methyl-2-oxo-1,3-benzoxazol-5-yl)phenyl]propanenitrile (740 mg, 2.52 mmol, 1.0 equiv) in DCM (12.0 mL) were added DIEA (978 mg, 7.56 mmol, 3.0 equiv) and HATU (1.15 g, 3.02 mmol, 1.2 equiv) in portions at 0° C. under nitrogen atmosphere. The resulting mixture was stirred for 3 h at 0° C. under nitrogen atmosphere. The resulting mixture was concentrated under reduced pressure at room temperature. The residue was purified by trituration with PE/EA=3:1. This resulted in tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]carbamate (1.2 g, 96%). LCMS (ES, m/z): $[M+H]^+$: 495.

Synthesis of (2S)-3-amino-N-[(1S)-1-cyano-2-[4-(3-methyl-2-oxo-1,3-benzoxazol-5-yl)phenyl]ethyl]-2-methoxypropanamide

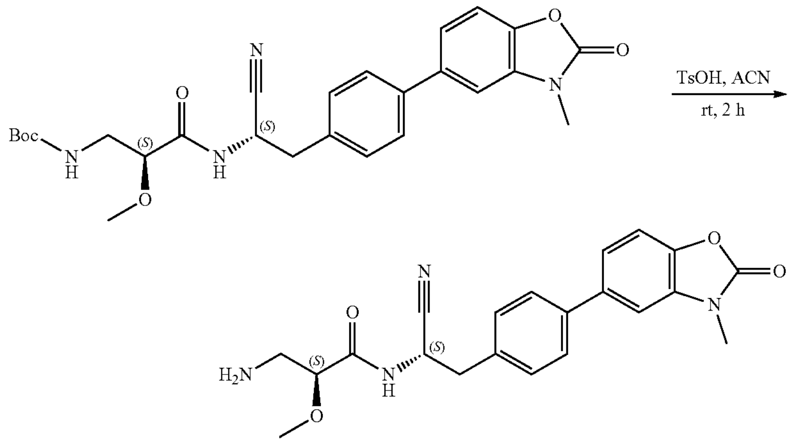

To a stirred solution of tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]carbamate (1.2 g, 2.42 mmol, 1.0 equiv) in ACN (12 mL) was added TsOH·$H_2O$ (1.38 g, 7.27 mmol, 3.0 equiv) in portions at room temperature. The resulting mixture was stirred for 2 h at room temperature. The resulting mixture was diluted with water (30 mL). The mixture was basified to pH 8 with saturated $NaHCO_3$ (aq.). The resulting mixture was extracted with EtOAc (3×20 mL). The combined organic layer was washed with brine (50 mL), dried over anhydrous $Na_2SO_4$. After filtration, the filtrate was concentrated under reduced pressure. The residue was purified by reversed-phase flash chromatography with the following conditions: column, C18 silica gel-120 g; mobile phase, MeCN in Water (0.1% $NH_3$·$H_2O$), 30% to 60% gradient in 10 min; detector, UV 254 nm. This resulted in (2S)-3-amino-N-[(1S)-1-cyano-2-[4-(3-methyl-2-oxo-1,3-benzoxazol-5-yl)phenyl]ethyl]-2-methoxypropanamide (400 mg, 41.8%).

LCMS (ES, m z): $[M+H]^+$: 395.2

$^1H$ NMR (300 MHz, DMSO-$d_6$) δ 8.74 (br, 1H), 7.71-7.61 (m, 2H), 7.57 (s, 1H), 7.48-7.34 (m, 4H), 5.12-5.03 (m, 1H), 3.54 (dd, J=6.2, 4.3 Hz, 1H), 3.41 (s, 3H), 3.30-3.10 (m, 5H), 2.68-2.53 (m, 2H).

Example 83: Synthesis of Compound 198: (3S)-3-amino-N-[(1S)-1-cyano-2-[4-(3-methyl-2-oxo-1,3-benzoxazol-5-yl)phenyl]ethyl]-3-(2-methylphenyl)propanamide

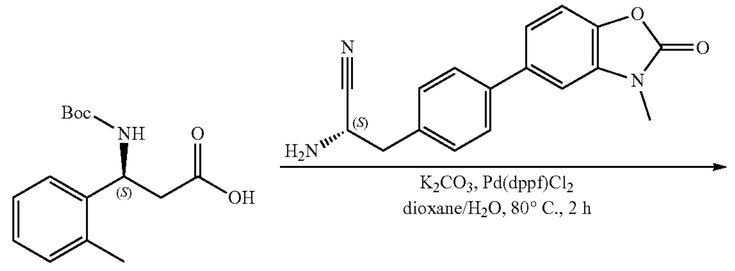

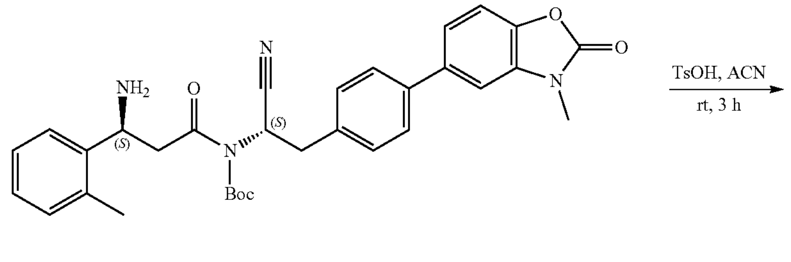

-continued

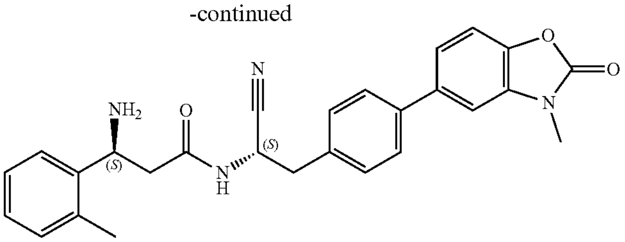

Synthesis of tert-butyl N-[(1S)-1-cyano-2-[4-(3-methyl-2-oxo-1,3-benzoxazol-5-yl)phenyl]ethyl]—N-[(3S)-3-(2-methylphenyl)butanoyl]carbamate

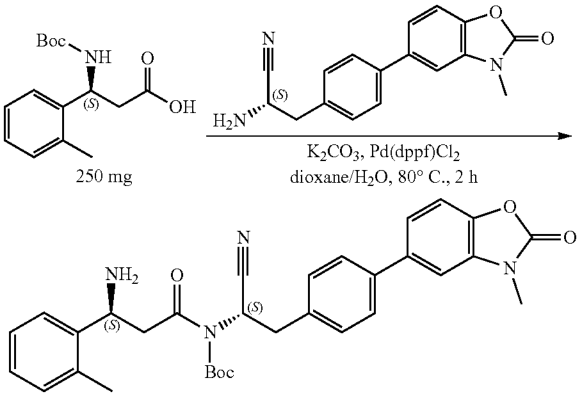

To a stirred mixture of (3S)-3-[(tert-butoxycarbonyl)amino]-3-(2-methylphenyl)propanoic acid (63 mg, 0.22 mmol, 1.1 equiv), (2S)-2-amino-3-[4-(3-methyl-2-oxo-1,3-benzoxazol-5-yl)phenyl]propanenitrile (60 mg, 0.20 mmol, 1.0 equiv) and DIEA (79 mg, 0.61 mmol, 3.0 equiv) in DCM (5 mL) was added HATU (93 mg, 0.24 mmol, 1.2 equiv) in portions at 0° C. The resulting mixture was stirred for additional 3 h at 0° C. The residue was purified by silica gel column chromatography, eluted with PE/THE (1:1) to afford tert-butyl N-[(1S)-1-cyano-2-[4-(3-methyl-2-oxo-1,3-benzoxazol-5-yl)phenyl]ethyl]-N-[(3S)-3-(2-methylphenyl)butanoyl]carbamate (80 mg, 70.6%). LCMS (ES, m/z): [M+H]*: 555.

Synthesis of (3S)-3-amino-N-[(1S)-1-cyano-2-[4-(3-methyl-2-oxo-1,3-benzoxazol-5-yl)phenyl]ethyl]-3-(2-methylphenyl)propanamide

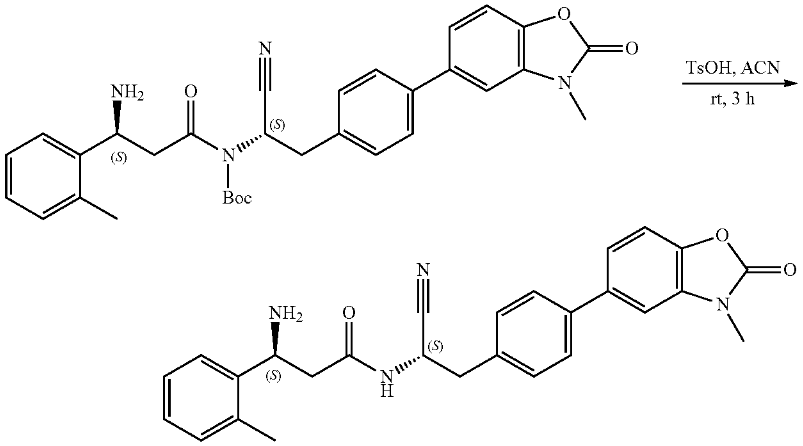

Into a 50 mL round-bottom flask were added tert-butyl N-[(1S)-1-cyano-2-[4-(3-methyl-2-oxo-1,3-benzoxazol-5-yl)phenyl]ethyl]—N-[(3S)-3-(2-methylphenyl)butanoyl]carbamate (80 mg, 0.14 mmol, 1.0 equiv) in ACN (3 mL) and TsOH (75 mg, 0.43 mmol, 3.0 equiv) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3{\cdot}H_2O$), 10% to 80% gradient in 10 min; detector, UV 254 nm. This resulted in (3S)-3-amino-N-[(1S)-1-cyano-2-[4-(3-methyl-2-oxo-1,3-benzoxazol-5-yl)phenyl]ethyl]-3-(2-methylphenyl)propanamide (20.7 mg, 31.52%).

LCMS (ES, m z): $[M+H]^+$: 455.4

$^1$H NMR (400 MHz, DMSO-$d_6$) δ 8.95 (s, 1H), 7.68 (d, J=8.2 Hz, 2H), 7.59 (d, J=1.7 Hz, 1H), 7.48-7.43 (m, 5H), 7.43-7.34 (m, 1H), 7.17 (dt, J=7.8, 4.3 Hz, 2H), 5.01 (s, 1H), 4.38 (dd, J=8.4, 5.1 Hz, 1H), 3.40 (s, 3H), 3.19-3.04 (m, 2H), 2.41-2.33 (m, 2H), 2.29 (s, 3H).

Example 84: Synthesis of Compound 104: (2R)—N-[(1S)-1-cyano-2-[4-(3-methyl-2-oxo-1,3-benzoxazol-5-yl)phenyl]ethyl]-3-(dimethylamino)-2-hydroxypropanamide

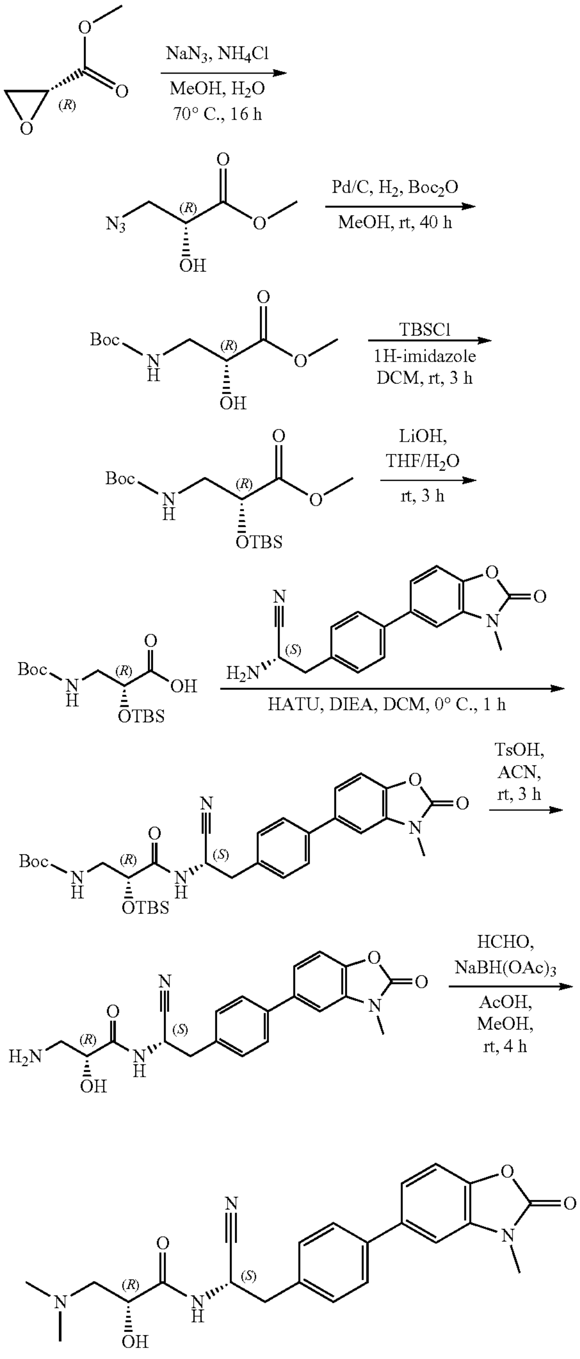

Synthesis of methyl (2R)-3-azido-2-hydroxypropanoate

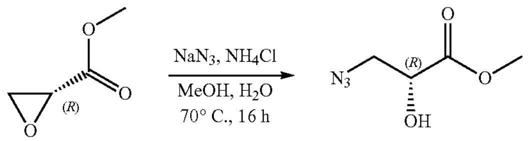

To a stirred solution of methyl (2R)-oxirane-2-carboxylate (11.7 g, 114.606 mmol, 1.0 equiv) and $NH_4Cl$ (9.20 g, 171.909 mmol, 1.5 equiv) in MeOH (200 mL) and $H_2O$ (10 mL) was added $NaN_3$ (22.35 g, 343.818 mmol, 3.0 equiv). The resulting mixture was stirred for 16 h at 70° C. The mixture was allowed to cool down to room temperature. The resulting mixture was extracted with $CH_2Cl_2$ (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/THE (10:1) to afford methyl (2R)-3-azido-2-hydroxypropanoate (10 g, 60.13%). LCMS (ES) $[M+1]^+$ m/z:146.

Synthesis of methyl (2R)-3-[(tert-butoxycarbonyl)amino]-2-hydroxypropanoate

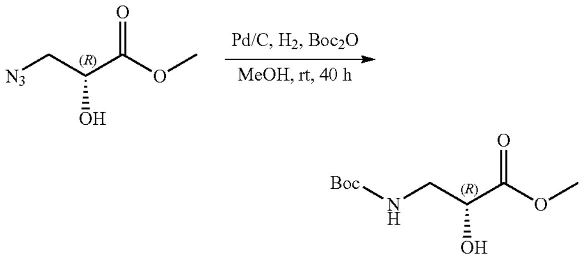

To a stirred solution of methyl (2R)-3-azido-2-hydroxypropanoate (10 g, 68.909 mmol, 1.0 equiv) and $Boc_2O$ (18.05 g, 82.691 mmol, 1.2 equiv) in methanol (150 mL) was added Pd/C (1.5 g). The resulting mixture was stirred for 40 h at room temperature under hydrogen atmosphere (3 atm). The resulting mixture was filtered, the filter cake was washed with MeOH (30 mL). The filtrate was concentrated under reduced pressure. The residue was purified by silica gel column chromatography, eluted with PE/EA (8:1) to afford methyl (2R)-3-[(tert-butoxycarbonyl)amino]-2-hydroxypropanoate (7 g, 46.33%). LCMS (ES) $[M+1]^+$ m/z: 220.

Synthesis of methyl (2R)-3-[(tert-butoxycarbonyl)amino]-2-[(tert-butyldimethylsilyl)oxy]propanoate

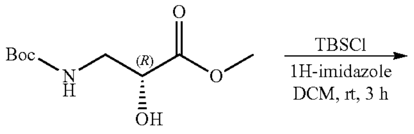

-continued

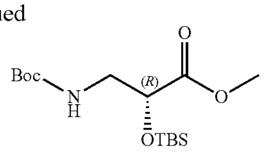

To a stirred solution of methyl (2R)-3-[(tert-butoxycarbonyl)amino]-2-hydroxypropanoate (500 mg, 2.281 mmol, 1.0 equiv) and 1H-imidazole (310 mg, 4.562 mmol, 2.0 equiv) in DCM (6 mL) was added t-butyldimethylchlorosilane (515 mg, 3.421 mmol, 1.5 equiv) in portions at 0° C. under nitrogen atmosphere. The resulting mixture was stirred for 3 h at room temperature. The resulting mixture was extracted with $CH_2Cl_2$ (3x20 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (2:1) to afford methyl (2R)-3-[(tert-butoxycarbonyl)amino]-2-[(tert-butyldimethylsilyl)oxy]propanoate (600 mg, 78.89%). LCMS (ES) $[M+1]^+$ m/z:334

Synthesis of (2R)-3-[(tert-butoxycarbonyl)amino]-2-[(tert-butyldimethylsilyl)oxy]propanoic acid

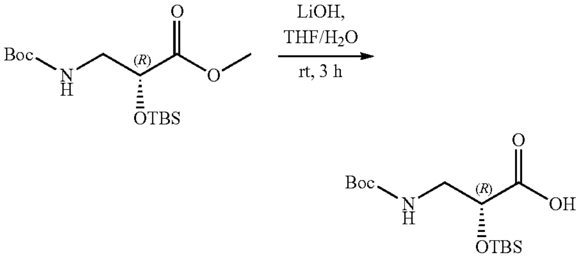

To a stirred solution of methyl (2R)-3-[(tert-butoxycarbonyl)amino]-2-[(tert-butyldimethylsilyl)oxy]propanoate (600 mg, 1.799 mmol, 1.0 equiv) in THE (6 mL) and $H_2O$ (2 mL) was added LiOH (129 mg, 5.397 mmol, 3.0 equiv). The resulting mixture was stirred for 3 h at room temperature. The resulting mixture was extracted with EtOAc (2x20 mL). The aqueous layer was acidified to pH 6 with citric acid. The resulting mixture was extracted with $CH_2Cl_2$ (4x20 mL). The combined organic layers were washed with brine (20 mL), dried over anhydrous $Na_2SO_4$. After filtration, the filtrate was concentrated under reduced pressure. This resulted in (2R)-3-[(tert-butoxycarbonyl)amino]-2-[(tert-butyldimethylsilyl)oxy]propanoic acid (300 mg, 52.20%). LCMS (ES) [M-1]-m/z:318

Synthesis of tert-butyl N-[(2R)-2-[(tert-butyldimethylsilyl)oxy]-2-{[(1S)-1-cyano-2-[4-(3-methyl-2-oxo-1,3-benzoxazol-5-yl)phenyl]ethyl]carbamoyl}ethyl] carbamate

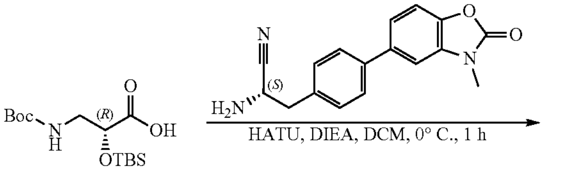

-continued

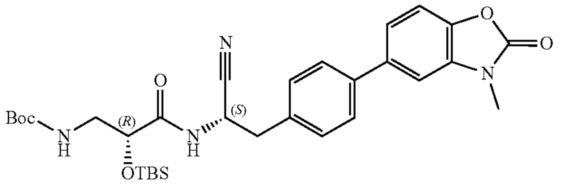

To a stirred solution of (2R)-3-[(tert-butoxycarbonyl)amino]-2-[(tert-butyldimethylsilyl)oxy]propanoic acid (450 mg, 1.409 mmol, 1.0 equiv) and (2S)-2-amino-3-[4-(3-methyl-2-oxo-1,3-benzoxazol-5-yl)phenyl]propanenitrile (413 mg, 1.409 mmol, 1.0 equiv) in DMF (6 mL) was added DIEA (364 mg, 2.818 mmol, 2.0 equiv). To the above mixture was added HATU (642 mg, 1.691 mmol, 1.2 equiv) in portions at 0° C. The resulting mixture was stirred for additional 1 h at 0° C. The resulting mixture was concentrated under reduced pressure. The residue was purified by silica gel column chromatography, eluted with PE/EA (2:1) to afford tert-butyl N-[(2R)-2-[(tert-butyldimethylsilyl)oxy]-2-{[(1S)-1-cyano-2-[4-(3-methyl-2-oxo-1,3-benzoxazol-5-yl)phenyl]ethyl]carbamoyl}ethyl]carbamate (600 mg, 71.62%). LCMS (ES) $[M+1]^+$ m/z:595

Synthesis of (2R)-3-amino-N-[(1S)-1-cyano-2-[4-(3-methyl-2-oxo-1,3-benzoxazol-5-yl)phenyl]ethyl]-2-hydroxypropanamide

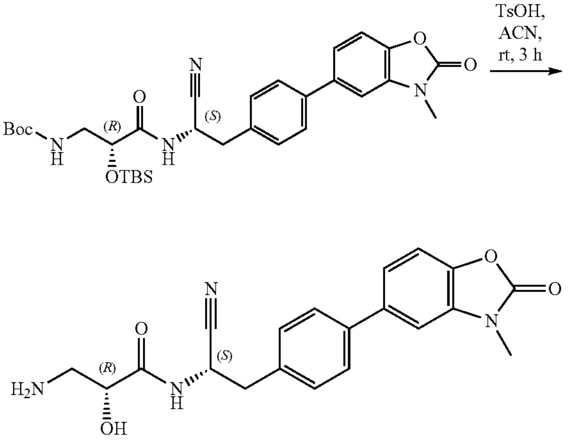

To a stirred solution of tert-butyl N-[(2R)-2-[(tert-butyldimethylsilyl)oxy]-2-{[(1S)-1-cyano-2-[4-(3-methyl-2-oxo-1,3-benzoxazol-5-yl)phenyl]ethyl]carbamoyl}ethyl]carbamate (600 mg, 1.009 mmol, 1.0 equiv) in ACN (8 mL) was added TsOH (521 mg, 3.027 mmol, 3.0 equiv). The resulting mixture was stirred for 3 h at room temperature. The mixture was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2R)-3-amino-N-[(1S)-1-cyano-2-[4-(3-methyl-2-oxo-1,3-benzoxazol-5-yl)phenyl]ethyl]-2-hydroxypropanamide (300 mg, 78.18%).

LCMS (ES) $[M+1]^+$ m/z:381

Synthesis of (2R)—N-[(1S)-1-cyano-2-[4-(3-methyl-2-oxo-1,3-benzoxazol-5-yl)phenyl]ethyl]-3-(dimethylamino)-2-hydroxypropanamide

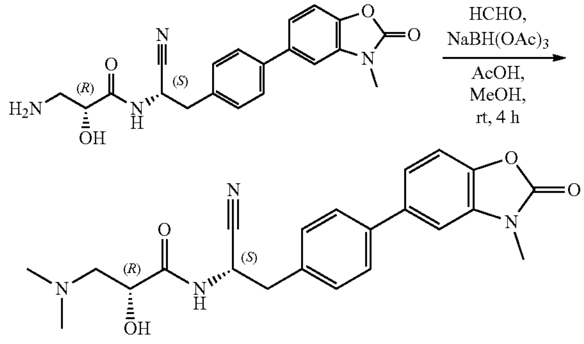

To a stirred solution of (2R)-3-amino-N-[(1S)-1-cyano-2-[4-(3-methyl-2-oxo-1,3-benzoxazol-5-yl)phenyl]ethyl]-2-hydroxypropanamide (100 mg, 0.263 mmol, 1.0 equiv) and HCHO (394 mg, 3.945 mmol, 15 equiv, 30% in $H_2O$) in MeOH (2 mL) was added AcOH (2 mg, 0.026 mmol, 0.1 equiv). The resulting mixture was stirred for 1 h at room temperature. To the above mixture was added $NaBH(OAc)_3$ (167 mg, 0.789 mmol, 3 equiv) in portions at room temperature. The resulting mixture was stirred for additional 3 h at room temperature. The mixture was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2R)—N-[(1S)-1-cyano-2-[4-(3-methyl-2-oxo-1,3-benzoxazol-5-yl)phenyl]ethyl]-3-(dimethylamino)-2-hydroxypropanamide (25 mg, 23.28%).

$^1$H NMR (300 MHz, DMSO-$d_6$) δ 8.73 (d, J=8.1 Hz, 1H), 7.67 (d, J=8.2 Hz, 2H), 7.59 (d, J=1.6 Hz, 1H), 7.47-7.35 (m, 4H), 5.52 (s, 1H), 4.99 (q, J=7.8 Hz, 1H), 3.97 (t, J=5.8 Hz, 1H), 3.41 (s, 3H), 3.20 (d, J=7.8 Hz, 2H), 2.51-2.30 (m, 2H), 2.17 (s, 6H). LCMS (ES) $[M+1]^+$ m/z:409

Example 85: Synthesis of Compound 113:(3S)—N-[(1S)-1-cyano-2-[4-(3-methyl-2-oxo-1,3-benzoxazol-5-yl)phenyl]ethyl]-4-(dimethylamino)-3-hydroxybutanamide

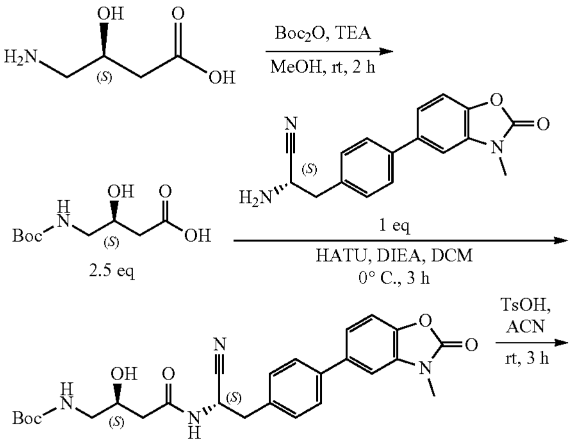

-continued

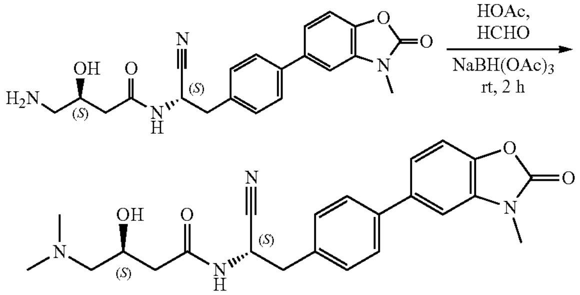

Synthesis of (2S)-3-[(tert-butoxycarbonyl)amino]-2-hydroxypropanoic acid

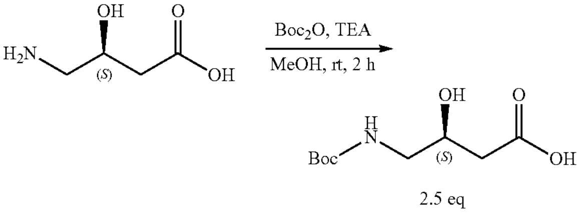

To a stirred solution of (2S)-3-amino-2-hydroxypropanoic acid (3 g, 28.54 mmol, 1.0 equiv) and THF (15 mL) was added NaOH (1.5 g, 37.50 mmol, 1.31 equiv) in $H_2O$ (15 mL) dropwise at room temperature. The resulting mixture was stirred for 3 h at room temperature. The mixture was acidified to pH 4 with conc. HCl. The resulting mixture was extracted with EtOAc (3×100 mL). The combined organic layers were washed with brine (3×100 mL), dried over anhydrous $Na_2SO_4$. After filtration, the filtrate was concentrated under reduced pressure. This resulted in (2S)-3-[(tert-butoxycarbonyl)amino]-2-hydroxypropanoic acid (5 g, 85.35%). LCMS (ES, m/z): $[M+H]^+$: 220.

Synthesis of tert-butyl (2S)-2-({1-cyano-2-[2,5-difluoro-4-(3-methyl-2-oxo-1,3-benzoxazol-5-yl)phenyl]ethyl}carbamoyl)-1,4-oxazepane-4-carboxylate

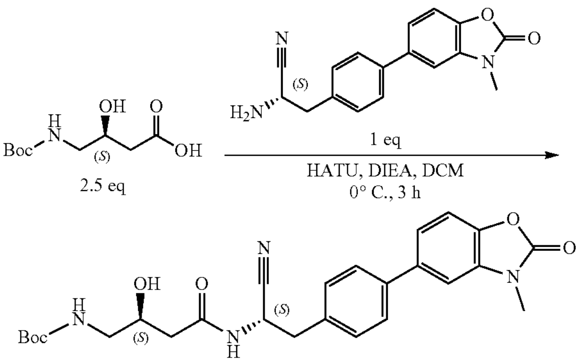

A solution of (3S)-4-[(tert-butoxycarbonyl)amino]-3-hydroxybutanoic acid (120 mg, 0.54 mmol, 1.0 equiv) in DCM (5 mL) was treated with (2S)-2-amino-3-[4-(3-methyl-2- oxo-1,3-benzoxazol-5-yl)phenyl]propanenitrile (401 mg, 1.36 mmol, 2.5 equiv), DIEA (212 mg, 1.64 mmol, 3.0 equiv) followed by the addition of HATU (249 mg, 0.65 mmol, 1.2 equiv) dropwise at 0° C. The resulting mixture was stirred for additional 2 h at room temperature. The residue was purified by silica gel column chromatography, eluted with PE/THE (1:1) to afford tert-butyl N-[(2S)-3-{[(1S)-1-cyano-2-[4-(3-methyl-2-oxo-1,3-benzoxazol-5-yl)phenyl]ethyl]carbamoyl}-2-hydroxypropyl]carbamate (190 mg, 70.1%). LCMS (ES, m/z): [M+H]$^+$: 495.

Synthesis of (3S)-4-amino-N-[(1S)-1-cyano-2-[4-(3-methyl-2-oxo-1,3-benzoxazol-5-yl)phenyl]ethyl]-3-hydroxybutanamide

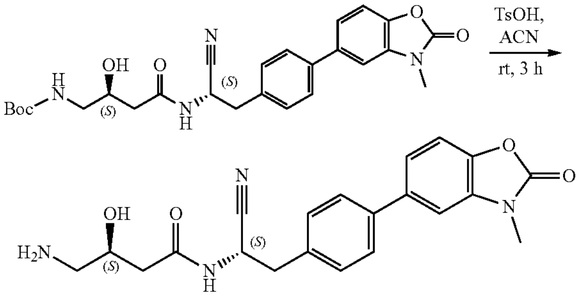

Into a 50 mL round-bottom flask were added tert-butyl N-[(2S)-3-{[(1S)-1-cyano-2-[4-(3-methyl-2-oxo-1,3-benzoxazol-5-yl)phenyl]ethyl]carbamoyl}-2-hydroxypropyl]carbamate (190 mg, 0.38 mmol, 1.0 equiv) in ACN (6 mL) and TsOH·$H_2O$ (219 mg, 1.15 mmol, 3.0 equiv) at room temperature. The resulting mixture was stirred for additional 3 h at room temperature. The precipitated solids were collected by filtration and washed with ACN (3×5 mL). This resulted in (3S)-4-amino-N-[(1S)-1-cyano-2-[4-(3-methyl-2-oxo-1,3-benzoxazol-5-yl)phenyl]ethyl]-3-hydroxybutanamide (260 mg, crude). LCMS (ES, m/z): [M+H]$^+$: 395

Synthesis of (3S)—N-[(1S)-1-cyano-2-[4-(3-methyl-2-oxo-1,3-benzoxazol-5-yl)phenyl]ethyl]-4-(dimethylamino)-3-hydroxybutanamide

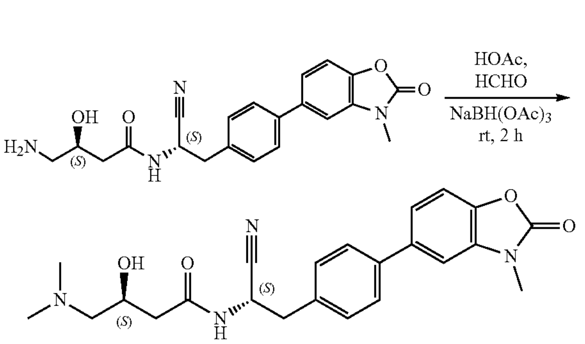

A solution of (3S)-4-amino-N-[(1S)-1-cyano-2-[4-(3-methyl-2-oxo-1,3-benzoxazol-5-yl)phenyl]ethyl]-3-hydroxybutanamide (140 mg, 0.3 mmol, 1.0 equiv) in THE (3 mL) was treated with HCHO (280 mg, 3.55 mmol, 10 equiv, 38%) for 1 h at room temperature followed by the addition of $NaBH(OAc)_3$ (150 mg, 0.71 mmol, 2.0 equiv) dropwise at room temperature. The resulting mixture was stirred for additional 1 h at room temperature. The residue was purified by reversed-phase flash chromatography with the following conditions: column, C18 silica gel; mobile phase, MeCN in Water (0.10% $NH_3$·$H_2O$), 10% to 80% gradient in 10 min; detector, UV 254 nm. This resulted in (3S)—N-[(1S)-1-cyano-2-[4-(3-methyl-2-oxo-1,3-benzoxazol-5-yl)phenyl]ethyl]-4-(dimethylamino)-3-hydroxybutanamide (17.3 mg, 11.54%).

LCMS (ES, m/z): [M+H]$^+$: 423.4.

$^1$H NMR (400 MHz, DMSO-$d_6$) δ 8.72 (d, J=7.7 Hz, 1H), 7.71-7.65 (m, 2H), 7.60 (d, J=1.7 Hz, 1H), 7.47-7.37 (m, 4H), 4.96 (q, J=7.7 Hz, 1H), 4.61 (s, 1H), 3.99-3.90 (m, 1H), 3.40 (s, 3H), 3.12 (d, J=7.7 Hz, 2H), 2.31 (d, J=4.9 Hz, 1H), 2.26-2.11 (m, 9H).

Example 86: Synthesis of Compound 115: (2S)—N-[(1S)-1-cyano-2-[4-(3-methyl-2-oxo-1,3-benzoxazol-5-yl)phenyl]ethyl]-3-(diethylamino)-2-hydroxypropanamide

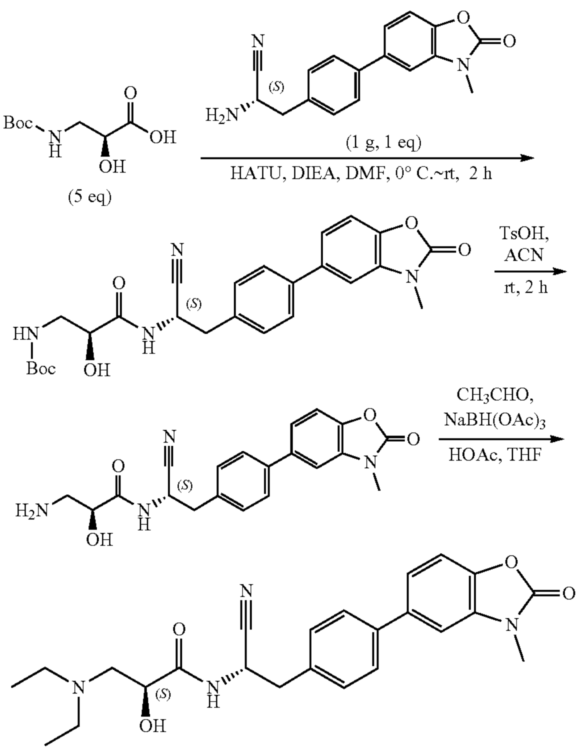

Synthesis of (2S)—N-[(1S)-1-cyano-2-[4-(3-methyl-2-oxo-1,3-benzoxazol-5-yl)phenyl]ethyl]-3-(diethylamino)-2-hydroxypropanamide

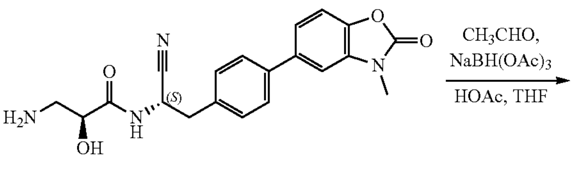

-continued

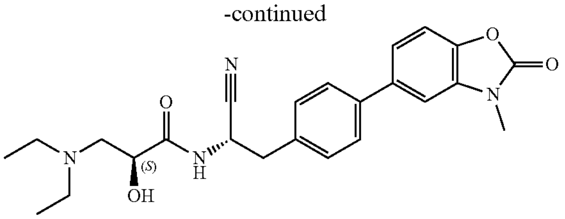

A solution of (2S)-3-amino-N-[(1S)-1-cyano-2-[4-(3-methyl-2-oxo-1,3-benzoxazol-5-yl)phenyl]ethyl]-2-hydroxypropanamide (100 mg, 0.26 mmol, 1.0 equiv) in THE (3 mL) was treated with $CH_3CHO$ (289 mg, 10.0 equiv, 40%), HOAc (0.1 mL) for 1 h at room temperature followed by the addition of $NaBH(OAc)_3$ (111 mg, 0.526 mmol, 2.0 equiv) in portions at room temperature. The resulting mixture was stirred for additional 1 h at room temperature. The residue was purified by reversed-phase flash chromatography with the following conditions: column, C18 silica gel; mobile phase, MeCN in Water (0.1% $NH_3{\cdot}H_2O$), 10% to 50% gradient in 10 min; detector, UV 254 nm. This resulted in (2S)—N-[(1S)-1-cyano-2-[4-(3-methyl-2-oxo-1,3-benzoxazol-5-yl)phenyl]ethyl]-3-(diethylamino)-2-hydroxypropanamide (17.3 mg, 15.08%).

LCMS (ES, m/z): $[M+H]^+$: 421.5.

$^1H$ NMR (400 MHz, DMSO-$d_6$) δ 8.70 (d, J=8.5 Hz, 1H), 7.66 (d, J=8.1 Hz, 2H), 7.57 (d, J=1.2 Hz, 1H), 7.43-7.37 (m, 4H), 5.38 (s, 1H), 5.06 (q, J=8.1 Hz, 1H), 3.95 (s, 1H), 3.25-3.13 (m, 2H), 2.51-2.35 (m, 11H), 2.31 (dd, J=13.4, 7.3 Hz, 1H), 0.87 (t, J=7.1 Hz, 6H).

Example 87: Synthesis of Compound 116: (2R)—N-[(1S)-1-cyano-2-[4-(3-methyl-2-oxo-1,3-benzoxazol-5-yl)phenyl]ethyl]-3-(diethylamino)-2-hydroxypropanamide

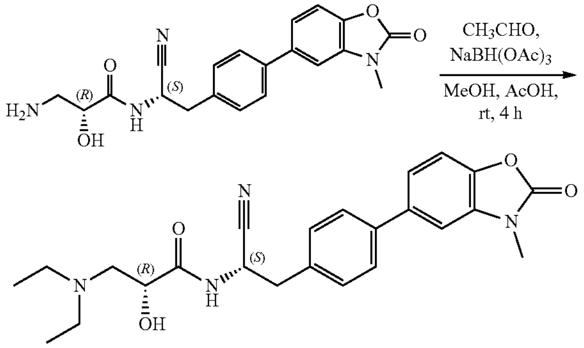

To a stirred solution of (2R)-3-amino-N-[(1S)-1-cyano-2-[4-(3-methyl-2-oxo-1,3-benzoxazol-5-yl)phenyl]ethyl]-2-hydroxypropanamide (100 mg, 0.263 mmol, 1.0 equiv) and acetaldehyde (434 mg, 3.945 mmol, 15 equiv, 40%) in MeOH (2 mL) was added AcOH (2 mg, 0.026 mmol, 0.1 equiv). The resulting mixture was stirred for 1 h at room temperature. To the above mixture was added $NaBH(OAc)_3$ (167 mg, 0.789 mmol, 3.0 equiv) in portions at room temperature. The resulting mixture was stirred for additional 3 h at room temperature. The mixture was purified by reversed-phase flash chromatography with the following conditions: column, C18 silica gel; mobile phase, MeCN in Water (0.1% $NH_3{\cdot}H_2O$), 10% to 50% gradient in 10 min; detector, UV 254 nm. This resulted in (2R)—N-[(1S)-1-cyano-2-[4-(3-methyl-2-oxo-1,3-benzoxazol-5-yl)phenyl]ethyl]-3-(diethylamino)-2-hydroxypropanamide (25 mg, 21.79%).

$^1H$ NMR (300 MHz, DMSO-$d_6$) δ 8.71 (d, J=8.2 Hz, 1H), 7.66 (d, J=8.1 Hz, 2H), 7.58 (s, 1H), 7.47-7.35 (m, 4H), 5.42 (brs, 1H), 5.00 (q, J=7.9 Hz, 1H), 3.94 (dd, J=7.0, 4.4 Hz, 1H), 3.41 (s, 3H), 3.24-3.15 (m, 2H), 2.64 (dd, J=13.4, 4.5 Hz, 1H), 2.58-2.51 (m, 3H), 2.51-2.38 (m, 2H), 0.92 (t, J=7.1 Hz, 6H). LCMS (ES) $[M+1]^+$ m/z:437

Example 88: Synthesis of Compound 121: (2S)—N-[(1S)-1-cyano-2-[4-(3-methyl-2-oxo-1,3-benzoxazol-5-yl)phenyl]ethyl]-2-hydroxy-3-(morpholin-4-yl)propanamide

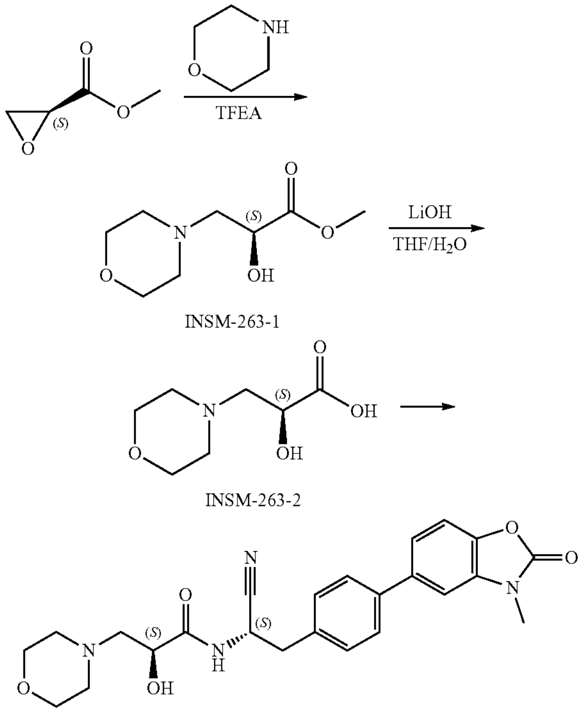

INSM-263-1

INSM-263-2

INSM-263

Synthesis of methyl (2S)-2-hydroxy-3-(morpholin-4-yl)propanoate (1.2 g, 64.75%) methyl (2S)-2-hydroxy-3-(morpholin-4-yl)propanoate

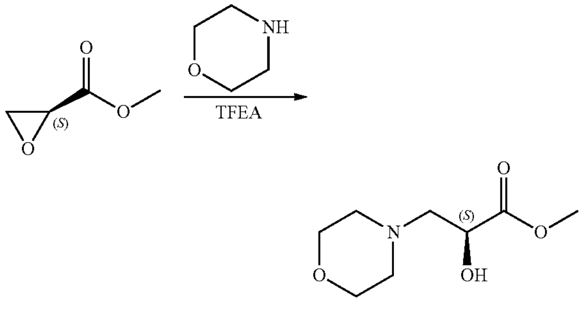

To a stirred mixture of morpholine (0.85 g, 9.79 mmol, 1.0 equiv) in TFEA (10 mL) was added methyl (2S)-oxirane-2-carboxylate (1 g, 9.79 mmol, 1.0 equiv) dropwise at 0° C. The resulting mixture was stirred for 2 h at 0° C. to room temperature. The reaction was concentrated. The residue was purified by silica gel column chromatography, eluted with PE/THE (2:1) to afford methyl (2S)-2-hydroxy-3-(morpholin-4-yl)propanoate (1.2 g, 64.75%). LCMS (ES, m z): $[M+H]^+$: 190.

Synthesis of (2S)-2-hydroxy-3-(morpholin-4-yl)propanoic acid

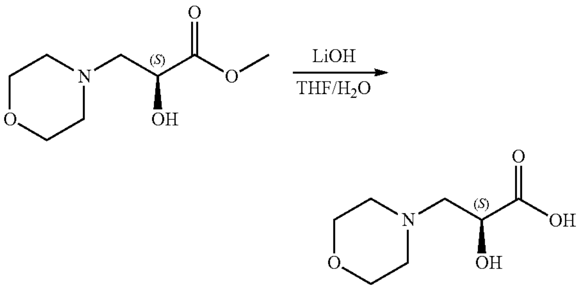

To a stirred mixture of methyl (2S)-2-hydroxy-3-(morpholin-4-yl)propanoate (300 mg, 1.58 mmol, 1.0 equiv) in THE (4 mL) was added LiOH·$H_2O$ (133 mg, 3.17 mmol, 2.0 equiv) in $H_2O$ (2 mL) at 0° C. The reaction stirred at 0° C. for 3 h. The reaction was adjusted pH to 5 with HCl (1 M) and concentrated. This resulted in (2S)-2-hydroxy-3-(morpholin-4-yl)propanoic acid (250 mg, 90.01%). LCMS (ES, m/z): $[M+H]^+$: 176

Synthesis of (2S)—N-[(1S)-1-cyano-2-[4-(3-methyl-2-oxo-1,3-benzoxazol-5-_yl)phenyl]ethyl]-2-hydroxy-3-(morpholin-4-yl)propanamide

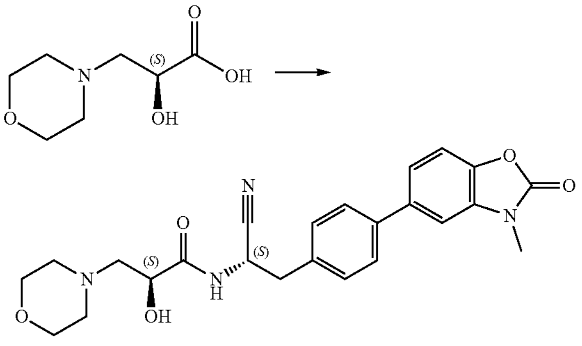

To a stirred mixture of (S)-2-hydroxy-3-morpholinopropanoic acid (67 mg, 0.37 mmol, 1.1 equiv), (2S)-2-amino-3-[4-(3-methyl-2-oxo-1,3-benzoxazol-5-yl)phenyl]propanenitrile (100 mg, 0.34 mmol, 1.0 equiv) and DIEA (110 mg, 0.85 mmol, 2.5 equiv) in DMF (5 mL) were added HATU (155 mg, 0.40 mmol, 1.2 equiv) in portions at 0° C. under nitrogen atmosphere. The resulting mixture was stirred for 3 h at 0° C. under nitrogen atmosphere. The reaction mixture was purified by Pre.HPLC with the following conditions: column, $C^{18}$; mobile phase, MeCN in Water (0.1% $NH_3.H_2O$), 10% to 50% gradient in 10 min; detector, UV 254 nm. This resulted in (2S)—N-[(1S)-1-cyano-2-[4-(3-methyl-2-oxo-1,3-benzoxazol-5-yl)phenyl]ethyl]-2-hydroxy-3-(morpholin-4-yl)propanamide (30 mg, 19.53%). LCMS (ES, m/z): $[M+H]^+$: 451

LCMS (ES, m z): $[M+H]^+$: 451.

1H NMR (300 MHz, DMSO-d6) δ 8.68 (d, J=8.5 Hz, 1H), 7.67 (d, J=8.1 Hz, 2H), 7.57 (d, J=1.3 Hz, 1H), 7.45-7.36 (m, 4H), 5.58 (d, J=5.2 Hz, 1H), 5.06 (q, J=8.2 Hz, 1H), 4.06 (dt, J=9.1, 4.6 Hz, 1H), 3.49 (t, J=4.67 Hz, 4H), 3.41 (s, 3H), 3.25-3.11 (m, 2H), 2.31-2.52 (m, 6H).

Example 89: Synthesis of Compound 138: (2S)—N-{1-cyano-2-[2,5-difluoro-4-(3-methyl-2-oxo-1,3-benzoxazol-5-yl)phenyl]ethyl}-1,4-oxazepane-2-carboxamide

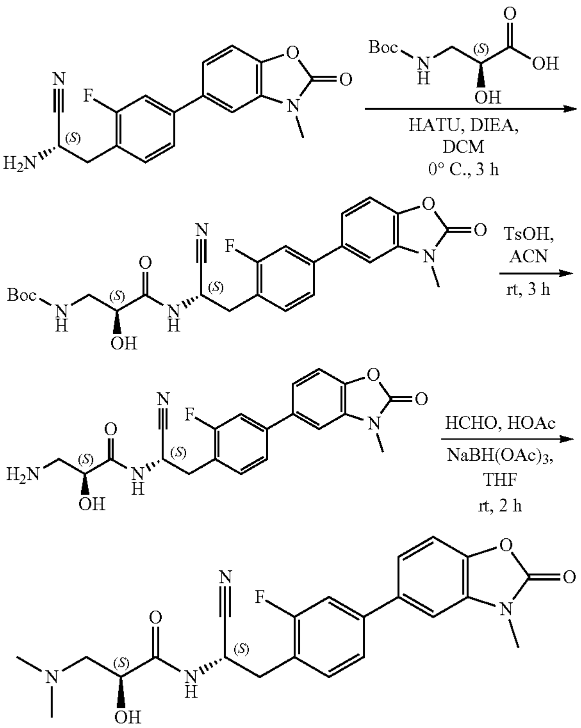

Synthesis of tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-hydroxyethyl]carbamate

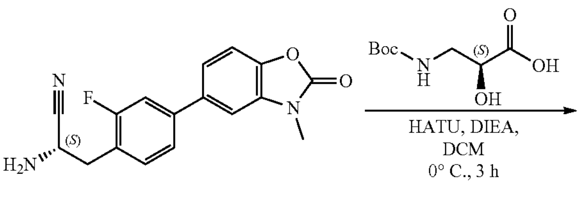

-continued

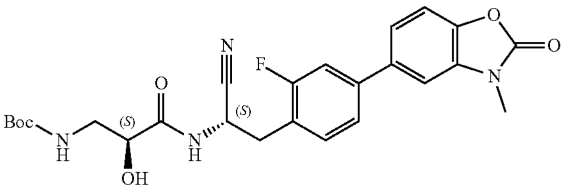

To a stirred solution of (2S)-2-amino-3-[2-fluoro-4-(3-methyl-2-oxo-1,3-benzoxazol-5-yl)phenyl]propanenitrile (100 mg, 0.32 mmol, 1.0 equiv), (2S)-3-[(tert-butoxycarbonyl)amino]-2-hydroxypropanoic acid (329 mg, 1.60 mmol, 5.0 equiv) and DIEA (124 mg, 0.96 mmol, 3.0 equiv) in DCM (5 mL) was added HATU (147 mg, 0.38 mmol, 1.2 equiv) in portions at 0° C. The resulting mixture was stirred for additional 3 h at 0° C. The residue was purified by silica gel column chromatography, eluted with PE/THE (1:1) to afford tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-hydroxyethyl]carbamate (130 mg, 81.1%). LCMS (ES, m/z): [M+H]+: 499.

Synthesis of (2S)-3-amino-N-[(1S)-1-cyano-2-[2-fluoro-4-(3-methyl-2-oxo-1,3-benzoxazol-5-yl)phenyl]ethyl]-2-hydroxypropanamide

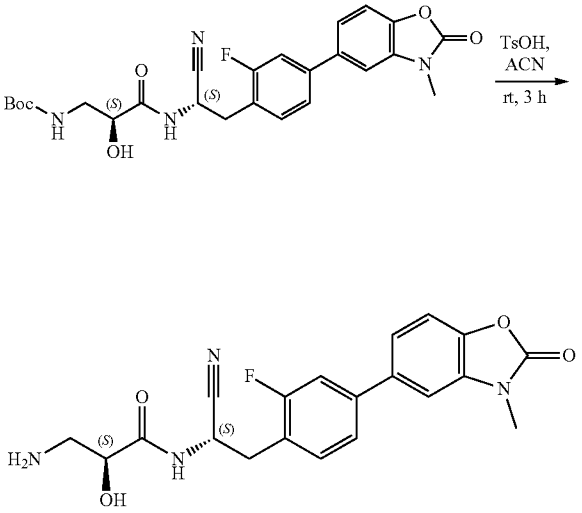

Into a 50 mL round-bottom flask were added tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-hydroxyethyl]carbamate (130 mg, 0.26 mmol, 1.0 equiv) in ACN (3 mL) and TsOH (135 mg, 0.78 mmol, 3.0 equiv) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 80% gradient in 10 min; detector, UV 254 nm. This resulted in (2S)-3-amino-N-[(1S)-1-cyano-2-[2-fluoro-4-(3-methyl-2-oxo-1,3-benzoxazol-5-yl)phenyl]ethyl]-2-hydroxypropanamide (150 mg, crude). LCMS (ES, m/z): [M+H]+: 399.

Synthesis of (2S)—N-[(1S)-1-cyano-2-[2-fluoro-4-(3-methyl-2-oxo-1,3-benzoxazol-5-yl)phenyl]ethyl]-3-(dimethylamino)-2-hydroxypropanamide

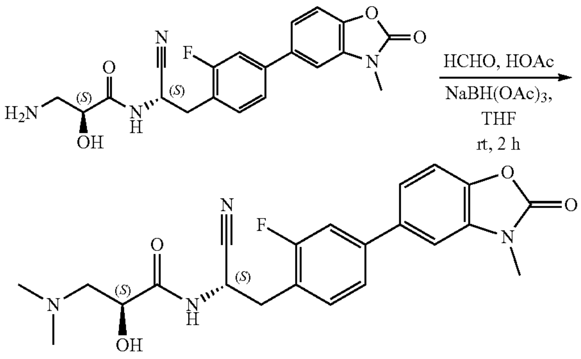

A solution of (2S)-3-amino-N-[(1S)-1-cyano-2-[2-fluoro-4-(3-methyl-2-oxo-1,3-benzoxazol-5-yl)phenyl]ethyl]-2-hydroxypropanamide (130 mg, 0.32 mmol, 1.0 equiv) in THE (3 mL) was treated with HCHO (98 mg, 3.26 mmol, 10 equiv), HOAc (0.1 mL) for 1 h at room temperature followed by the addition of $NaBH(OAc)_3$ (138 mg, 0.65 mmol, 2.0 equiv) in portions at room temperature. The resulting mixture was stirred for additional 1 h at room temperature. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2S)—N-[(1S)-1-cyano-2-[2-fluoro-4-(3-methyl-2-oxo-1,3-benzoxazol-5-yl)phenyl]ethyl]-3-(dimethylamino)-2-hydroxypropanamide (17.3 mg, 12.43%).

LCMS (ES, m/z): [M+H]+: 427.2.

$^1$H NMR (400 MHz, DMSO-$d_6$) δ 8.81 (d, J=8.6 Hz, 1H), 7.66 (d, J=1.9 Hz, 1H), 7.64-7.52 (m, 2H), 7.52-7.43 (m, 2H), 7.41 (d, J=8.4 Hz, 1H), 5.58 (d, J=5.0 Hz, 1H), 5.08 (q, J=8.1 Hz, 1H), 4.01 (dt, J=8.6, 4.3 Hz, 1H), 3.40 (s, 3H), 3.32-3.25 (m, 1H), 3.20 (dd, J=13.8, 8.6 Hz, 1H), 2.35-2.15 (m, 2H), 2.11 (s, 6H).

Example 90: Synthesis of Compound 140: (2S)—N-[(1S)-1-cyano-2-(4-{3-[2-(morpholin-4-yl)ethyl]-2-oxo-1,3-benzoxazol-5-yl}phenyl)ethyl]-3-(dimethylamino)-2-hydroxypropanamide

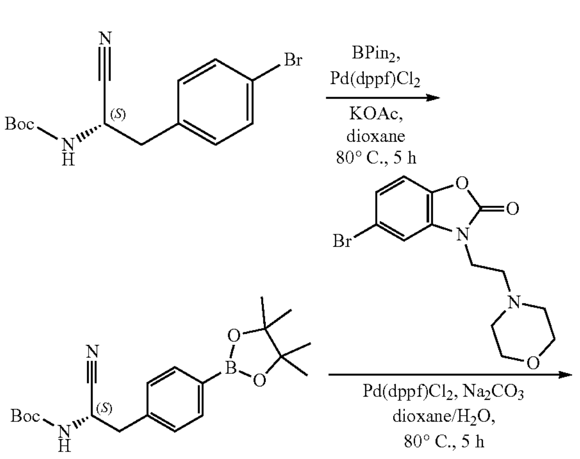

-continued

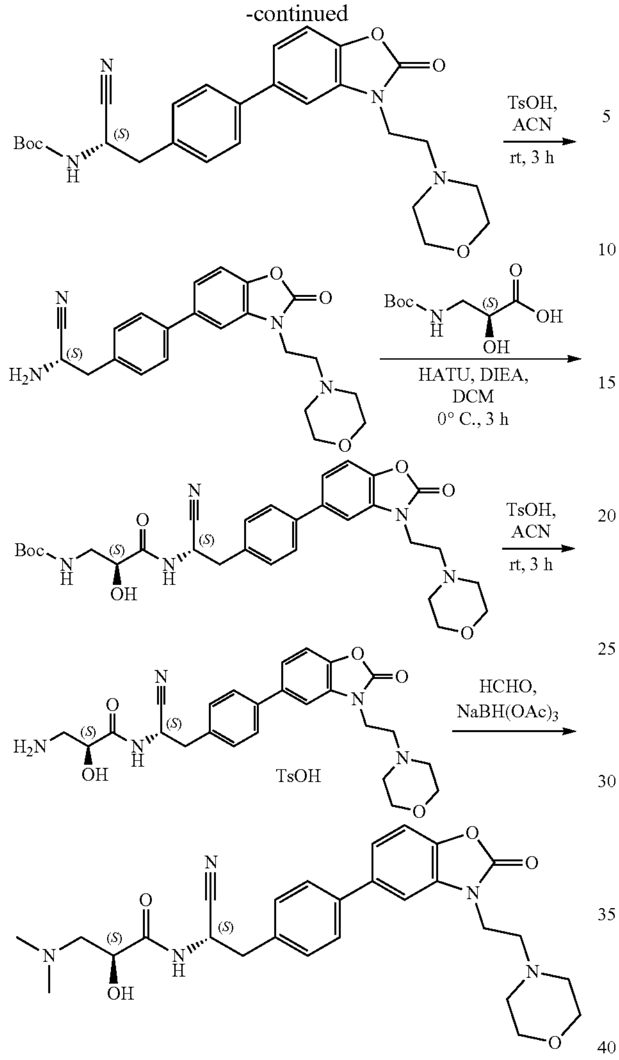

Synthesis of tert-butyl N-[(1S)-1-cyano-2-[4-(4,4,5,5-tetramethyl-1,3,2-dioxaborolan-2-yl)phenyl]ethyl]carbamate

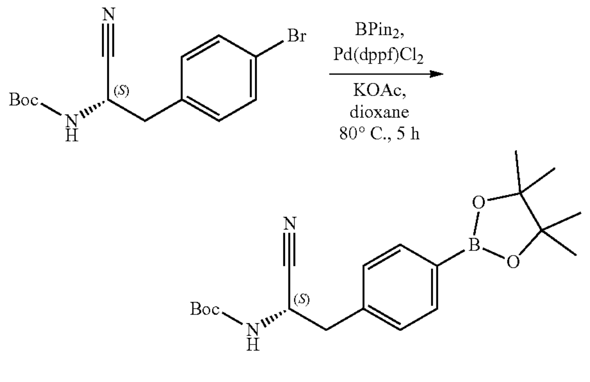

To a stirred solution of tert-butyl N-[(1S)-2-(4-bromophenyl)-1-cyanoethyl]carbamate (1.8 g, 5.54 mmol, 1 equiv) and bis(pinacolato)diboron (2.11 g, 8.30 mmol, 1.5 equiv) in dioxane (30 mL) were added KOAc (1.09 g, 11.07 mmol, 2 equiv) and Pd(dppf)$Cl_2CH_2Cl_2$ (0.45 g, 0.55 mmol, 0.1 equiv). The resulting mixture was stirred for 5 h at 80° C. under nitrogen atmosphere. The mixture was allowed to cool down to room temperature. The filtrate was concentrated under reduced pressure. The residue was purified by silica gel column chromatography, eluted with PE/THE (3:1) to afford tert-butyl N-[(1S)-1-cyano-2-[4-(4,4,5,5-tetramethyl-1,3,2-dioxaborolan-2-yl)phenyl]ethyl]carbamate (1.9 g, 92.21%). LCMS (ES, m/z): $[M+H]^+$: 373.

Synthesis of tert-butyl N-[(1S)-1-cyano-2-(4-{3-[2-(morpholin-4-yl)ethyl]-2-oxo-1,3-benzoxazol-5-yl}phenyl)ethyl]carbamate

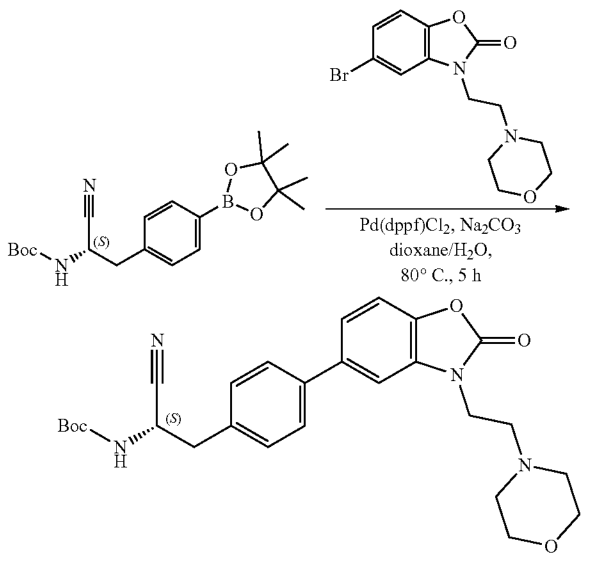

To a solution of tert-butyl N-[(1S)-1-cyano-2-[4-(4,4,5,5-tetramethyl-1,3,2-dioxaborolan-2-yl)phenyl]ethyl]carbamate (1.5 g, 4.03 mmol, 1 equiv) and 5-bromo-3-[2-(morpholin-4-yl)ethyl]-1,3-benzoxazol-2-one (1.32 g, 4.03 mmol, 1 equiv) in dioxane (30 mL) and $H_2O$ (3 mL) were added $Na_2CO_3$ (0.85 g, 8.06 mmol, 2 equiv) and Pd(dppf) $Cl_2CH_2Cl_2$ (0.33 g, 0.40 mmol, 0.1 equiv). After stirring for 5 h at 80° C. under a nitrogen atmosphere, the resulting mixture was concentrated under reduced pressure. The residue was purified by silica gel column chromatography, eluted with PE/THE (2:1) to afford tert-butyl N-[(1S)-1-cyano-2-(4-{3-[2-(morpholin-4-yl)ethyl]-2-oxo-1,3-benzoxazol-5-yl}phenyl)ethyl]carbamate (1.6 g, 80.61%). LCMS (ES, m z): $[M+H]^+$: 493.

Synthesis of (2S)-2-amino-3-(4-{3-[2-(morpholin-4-yl)ethyl]-2-oxo-1,3-benzoxazol-5-yl}phenyl)propanenitrile

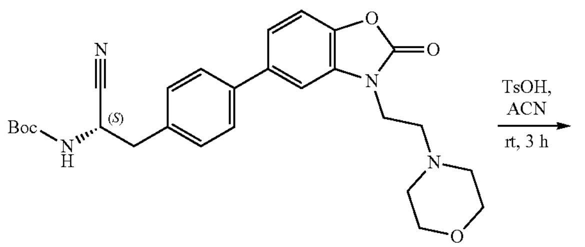

-continued

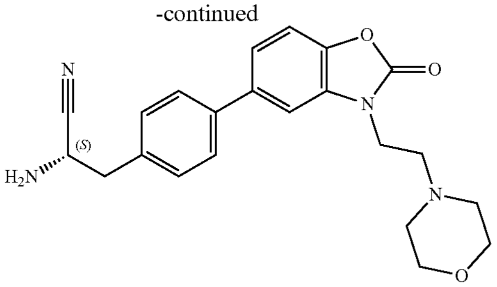

To a stirred solution of tert-butyl N-[(1S)-1-cyano-2-(4-{3-[2-(morpholin-4-yl)ethyl]-2-oxo-1,3-benzoxazol-5-yl}phenyl)ethyl]carbamate (1.6 g, 3.25 mmol, 1 equiv) and ACN (30 mL) was added TsOH·$H_2O$ (1.85 g, 9.74 mmol, 3 equiv) at room temperature. The resulting mixture was stirred for 3 h at room temperature. The mixture was acidified to pH 8 with saturated $NaHCO_3$ (aq.). The resulting mixture was extracted with EtOAc (3×50 mL). The combined organic layers were dried over anhydrous $Na_2SO_4$. After filtration, the filtrate was concentrated under reduced pressure. The residue was purified by silica gel column chromatography, eluted with PE/THE (1:2) to afford (2S)-2-amino-3-(4-{3-[2-(morpholin-4-yl)ethyl]-2-oxo-1,3-benzoxazol-5-yl}phenyl)propanenitrile (1.1 g, 86.29%). LCMS (ES, m z): $[M+H]^+$: 393.

Synthesis of tert-butyl N-[(2S)-2-{[(1S)-1-cyano-2-(4-{3-[2-(morpholin-4-yl)ethyl]-2-oxo-1,3-benzoxazol-5-yl}phenyl)ethyl]carbamoyl}-2-hydroxyethyl] carbamate

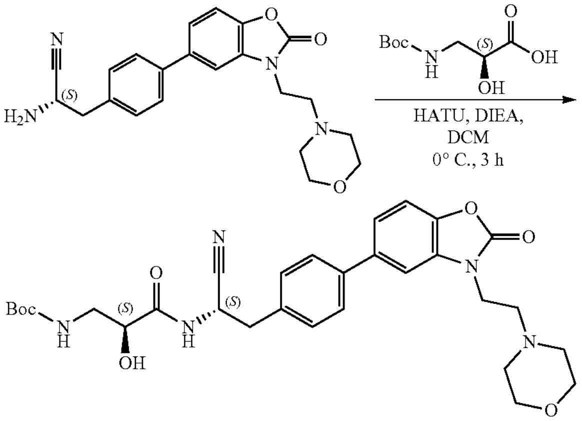

To a stirred mixture of (2S)-2-amino-3-(4-{3-[2-(morpholin-4-yl)ethyl]-2-oxo-1,3-benzoxazol-5-yl}phenyl)propanenitrile (1.1 g, 2.80 mmol, 1 equiv), ((2S)-3-[(tert-butoxycarbonyl)amino]-2-hydroxypropanoic acid (0.58 g, 2.80 mmol, 1 equiv) and DIEA (1.09 g, 8.41 mmol, 3 equiv) in DCM (20 mL) were added HATU (1.28 g, 3.36 mmol, 1.2 equiv) in portions at 0° C. The resulting mixture was stirred for additional 3 h at 0° C. The residue was purified by silica gel column chromatography, eluted with PE/THE (1:1) to afford tert-butyl N-[(2S)-2-{[(1S)-1-cyano-2-(4-{3-[2-(morpholin-4-yl)ethyl]-2-oxo-1,3-benzoxazol-5-yl}phenyl) ethyl]carbamoyl}-2-hydroxyethyl]carbamate (1.4 g, 86.17%). LCMS (ES, m z): $[M+H]^+$: 580.

Synthesis of (2S)-3-amino-N-[(1S)-1-cyano-2-(4-{3-[2-(morpholin-4-yl)ethyl]-2-oxo-1,3-benzoxazol-5-yl}phenyl)ethyl]-2-hydroxypropanamide; para-toluene sulfonate

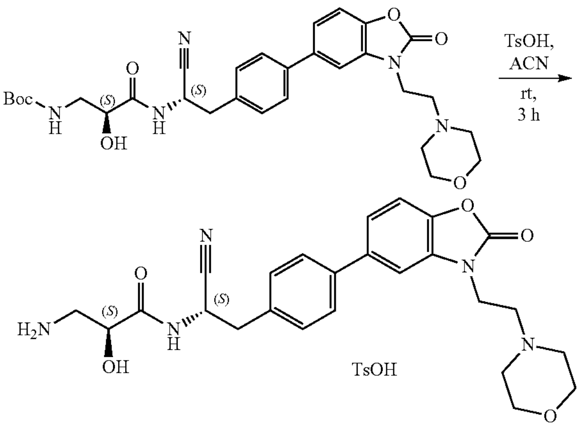

To a stirred solution of tert-butyl N-[(2S)-2-{[(1S)-1-cyano-2-(4-{3-[2-(morpholin-4-yl)ethyl]-2-oxo-1,3-benzoxazol-5-yl}phenyl)ethyl]carbamoyl}-2-hydroxyethyl]carbamate (1.4 g, 2.42 mmol, 1 equiv) and ACN (30 mL) was added TsOH·$H_2O$ (1.38 g, 7.25 mmol, 3 equiv) at room temperature. The resulting mixture was stirred for 3 h at room temperature. The precipitated solids were collected by filtration and washed with acetonitrile (3×10 mL). This resulted in (2S)-3-amino-N-[(1S)-1-cyano-2-(4-{3-[2-(morpholin-4-yl)ethyl]-2-oxo-1,3-benzoxazol-5-yl}phenyl) ethyl]-2-hydroxypropanamide; para-toluene sulfonate (1.2 g, 76.23%). LCMS (ES, m z): $[M+H]^+$: 480.

Synthesis of (2S)—N-[(1S)-1-cyano-2-(4-{3-[2-(morpholin-4-yl)ethyl]-2-oxo-1,3-benzoxazol-5-yl}phenyl)ethyl]-3-(dimethylamino)-2-hydroxypropanamide

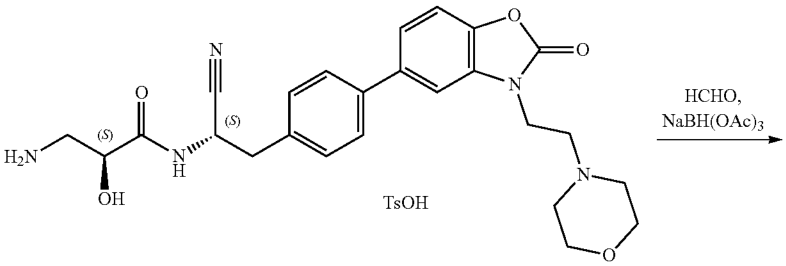

-continued

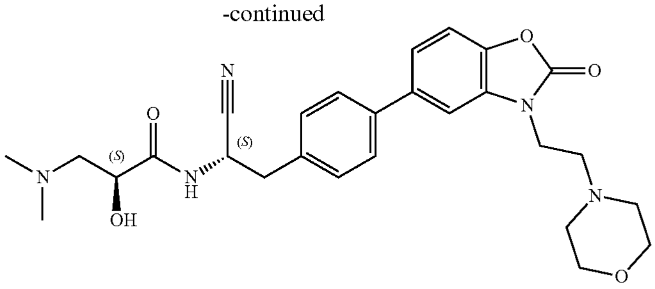

To a stirred solution of (2S)-3-amino-N-[(1S)-1-cyano-2-(4-{3-[2-(morpholin-4-yl)ethyl]-2-oxo-1,3-benzoxazol-5-yl}phenyl)ethyl]-2-hydroxypropanamide; para-toluene sulfonate (1.2 g, 1.84 mmol, 1 equiv) and HCHO (1.84 g, 18.41 mmol, 10 equiv, 30%) in THE (30 mL) was added HOAc (0.01 g, 0.17 mmol, 0.09 equiv) dropwise at room temperature. The resulting mixture was stirred for 1 h at room temperature. To the above mixture was added NaBH $(OAc)_3$ (1.17 g, 5.52 mmol, 3 equiv) at room temperature. The resulting mixture was stirred for additional 1 h at room temperature. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2S)—N-[(1S)-1-cyano-2-(4-{3-[2-(morpholin-4-yl)ethyl]-2-oxo-1,3-benzoxazol-5-yl}phenyl)ethyl]-3-(dimethylamino)-2-hydroxypropanamide (350 mg, 37.45%).

LCMS (ES, m z): $[M+H]^+$: 508.

$^1H$ NMR (400 MHz, DMSO-$d_6$) δ 8.72 (d, J=8.6 Hz, 1H), 7.70-7.61 (m, 3H), 7.43-7.37 (m, 4H), 5.57 (s, 1H), 5.10-5.00 (m, 1H), 4.02 (t, J=6.2 Hz, 3H), 3.49 (t, J=4.5 Hz, 4H), 3.25-3.13 (m, 2H), 2.66 (t, J=6.1 Hz, 2H), 2.48-2.42 (m, 4H), 2.35-2.27 (m, 1H), 2.27-2.18 (m, 1H), 2.12 (s, 6H).

Example 91: Synthesis of Compound 202: (S)-2-amino-N—((S)-1-cyano-2-(4-(3-methyl-2-oxo-2,3-dihydrobenzo[d]oxazol-5-yl)phenyl)ethyl)-3-(pyridin-3-yl)propanamide

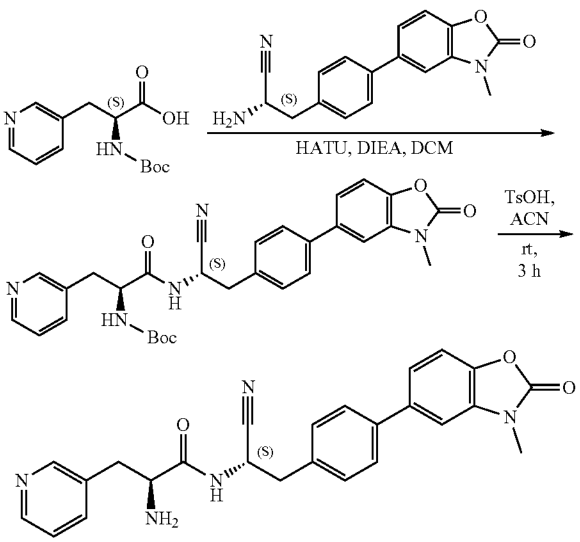

Synthesis of tert-butyl N-[(1S)-1-{[(1S)-1-cyano-2-[4-(3-methyl-2-oxo-1,3-benzoxazol-5-yl)phenyl]ethyl]carbamoyl}-2-(pyridin-3-yl)ethyl]carbamate

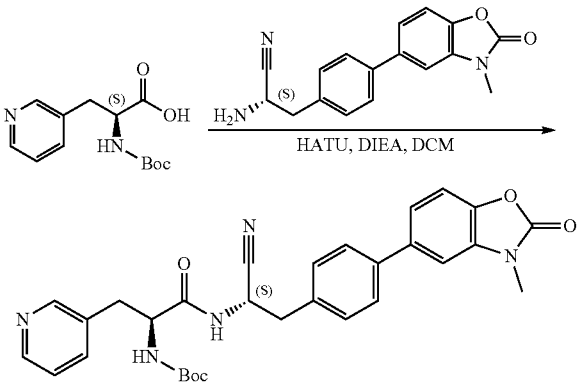

A solution of (2S)-2-[(tert-butoxycarbonyl)amino]-3-(pyridin-3-yl)propanoic acid (100 mg, 0.37 mmol, 1.0 equiv) in DCM (1 mL) was treated with (2S)-2-amino-3-[4-(3-methyl-2-oxo-1,3-benzoxazol-5-yl)phenyl]propanenitrile (110 mg, 0.37 mmol, 1.0 equiv) and DIEA (146 mg, 1.12 mmol, 3.0 equiv). This was followed by the addition of HATU (171 mg, 0.45 mmol, 1.2 equiv) dropwise at 0° C. The resulting mixture was stirred for 2 h at 0° C. Concentrated under reduced pressure to remove the solvent, the residue was purified by silica gel column chromatography, eluted with PE/THE (1:1) to afford tert-butyl N-[(1S)-1-{[(1S)-1-cyano-2-[4-(3-methyl-2-oxo-1,3-benzoxazol-5-yl)phenyl]ethyl]carbamoyl}-2-(pyridin-3-yl)ethyl]carbamate (100 mg, 49%). LCMS (ES, m/z): $[M+H]^+$: 542.

Synthesis of (S)-2-amino-N—((S)-1-cyano-2-(4-(3-methyl-2-oxo-2,3-dihydrobenzol[d]oxazol-5-yl)phenyl)ethyl)-3-(pyridin-3-yl)propanamide

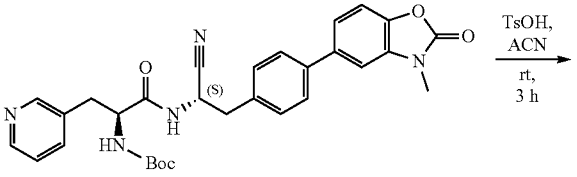

-continued

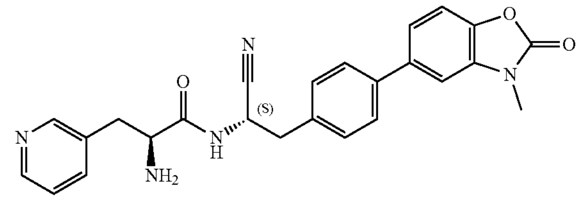

Into a 25 mL round-bottom flask were added tert-butyl N-[(1S)-1-{[(1S)-1-cyano-2-[4-(3-methyl-2-oxo-1,3-benzoxazol-5-yl)phenyl]ethyl]carbamoyl}-2-(pyridin-3-yl)ethyl] carbamate (100 mg, 0.18 mmol, 1.0 equiv) in ACN (3 mL) and TsOH (95 mg, 0.55 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (S)-2-amino-N—((S)-1-cyano-2-(4-(3-methyl-2-oxo-2,3-dihydrobenzo[d]oxazol-5-yl)phenyl)ethyl)-3-(pyridin-3-yl)propanamide (17.3 mg, 21%).

LCMS (ES, m/z): $[M+H]^+$: 442.2

$^1H$ NMR (400 MHz, DMSO-$d_6$) δ 8.43-8.32 (m, 2H), 7.68 (d, J=8.1 Hz, 2H), 7.58 (d, J=1.7 Hz, 1H), 7.55 (dt, J=7.9, 2.1 Hz, 1H), 7.45-7.37 (m, 4H), 7.26 (dd, J=7.7, 4.8 Hz, 1H), 4.99 (t, J=7.7 Hz, 1H), 3.44 (dd, J=7.9, 5.5 Hz, 1H), 3.41 (s, 3H), 3.21-3.06 (m, 2H), 2.84 (dd, J=13.6, 5.4 Hz, 1H), 2.64 (dd, J=13.6, 7.9 Hz, 1H).

Example 92: Synthesis of Compound 203: 2-amino-N-[(1S)-1-cyano-2-[4-(3-methyl-2-oxo-1,3-benzoxazol-5-yl)phenyl]ethyl]-3-(2-hydroxyphenyl) propanamide

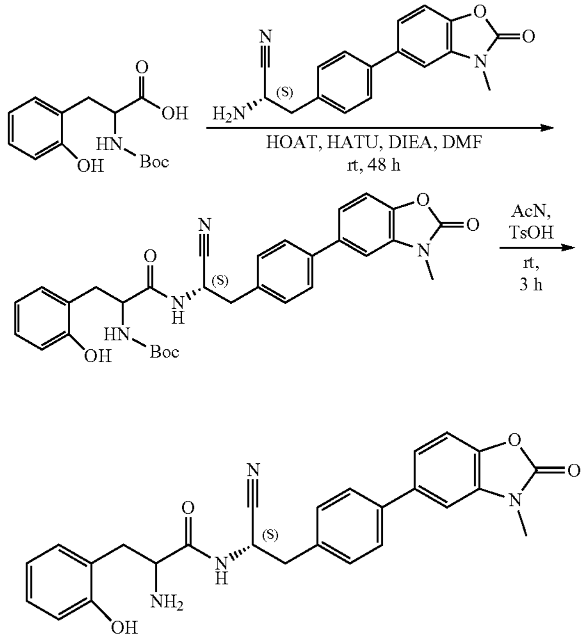

Synthesis of tert-butyl N-(1-{[(1S)-1-cyano-2-[4-(3-methyl-2-oxo-1,3-benzoxazol-5-yl)phenyl]ethyl] carbamoyl}-2-(2-hydroxyphenyl)ethyl)carbamate

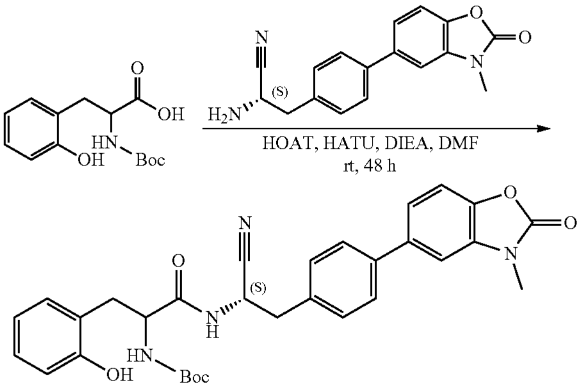

A solution of 2-[(tert-butoxycarbonyl)amino]-3-(2-hydroxyphenyl)propanoic acid (250 mg, 0.88 mmol, 1.0 equiv) in DMF (25 mL) was treated with HOAT (181 mg, 1.33 mmol, 1.5 equiv), HATU (506 mg, 1.33 mmol, 1.5 equiv) for 30 min at room temperature. This was followed by the addition of (2S)-2-amino-3-[4-(3-methyl-2-oxo-1,3-benzoxazol-5-yl)phenyl]propanenitrile (260 mg, 0.88 mmol, 1.0 equiv), DIEA (344 mg, 2.66 mmol, 3.0 equiv) at room temperature. The resulting mixture was stirred for additional 48 h at room temperature. The reaction was quenched with water (30 mL), extracted with EtOAc (30 mL×3). The combined organic layer was washed with brine (30 mL×3), dried over anhydrous $Na_2SO_4$. After filtration, the filtrate was concentrated under reduced pressure. The residue was purified by silica gel column chromatography, eluted with PE/THF (1:1) to afford tert-butyl N-(1-{[(1 S)-1-cyano-2-[4-(3-methyl-2-oxo-1,3-benzoxazol-5-yl)phenyl]ethyl]carbamoyl}-2-(2-hydroxyphenyl)ethyl)carbamate (90 mg, 18%). LCMS (ES, m/z): $[M+H]^+$: 557.

Synthesis of 2-amino-N-[(1S)-1-cyano-2-[4-(3-methyl-2-oxo-1,3-benzoxazol-5-yl)phenyl]ethyl]-3-(2-hydroxyphenyl)propanamide

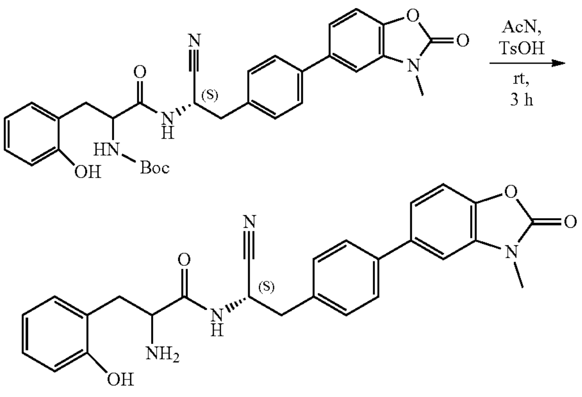

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-2-(2-hydroxyphenyl)

ethyl)carbamate (90 mg, 0.16 mmol, 1.0 equiv), ACN (3 mL) and TsOH·$H_2O$ (92 mg, 0.48 mmol, 3.0 equiv) at room temperature. The resulting mixture was stirred for 3 h at room temperature. The reaction was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-3-(2-hydroxyphenyl)propanamide (19.5 mg, 26%).

LCMS (ES, m/z): $[M+H]^+$: 457.2

$^1H$ NMR (400 MHz, DMSO-$d_6$) δ 7.73-7.65 (m, 2H), 7.58 (t, J=2.0 Hz, 1H), 7.47-7.36 (m, 4H), 7.06-6.82 (m, 2H), 6.78-6.59 (m, 2H), 5.01 (q, J=7.6 Hz, 1H), 3.49-3.44 (m, 1H), 3.40 (d, J=2.2 Hz, 3H), 3.25-3.04 (m, 2H), 2.80-2.54 (m, 2H).

Example 93: Synthesis of Compound 208: 2-amino-N-[(1S)-1-cyano-2-[4-(3-methyl-2-oxo-1,3-benzoxazol-5-yl)phenyl]ethyl]-3-(1H-pyrrol-3-yl)propanamide

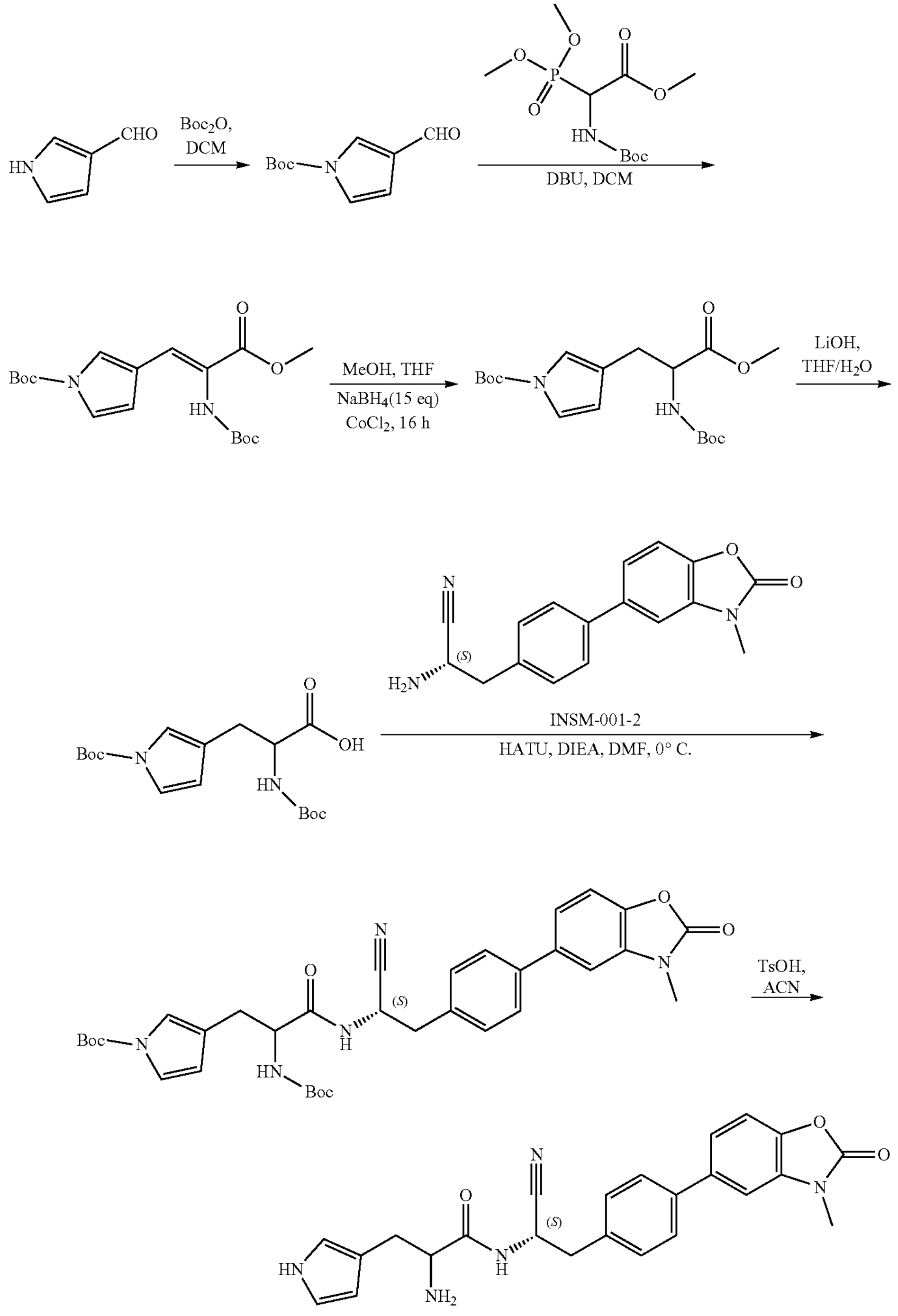

Synthesis of tert-butyl 3-formylpyrrole-1-carboxylate

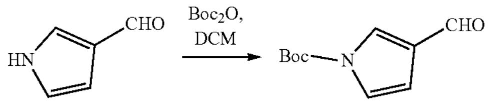 [SMILES: O=Cc1cc[nH]c1 ; CC(C)(C)OC(=O)n1ccc(C=O)c1]

Into a 250 mL 3-necked round-bottom flask were added 1H-pyrrole-3-carbaldehyde (1.50 g, 15.77 mmol, 1.00 equiv) and DCM (25.00 mL) at room temperature. To the above mixture was added di-tert-butyl dicarbonate (3.79 g, 17.35 mmol, 1.10 equiv) in portions at 0° C. The resulting mixture was stirred for additional 10 min at 0° C. To the above mixture was added DIEA (2.45 g, 18.92 mmol, 1.20 equiv) and DMAP (0.19 g, 1.57 mmol, 0.10 equiv) in DCM (10.00 mL) dropwise at 0° C. The resulting mixture was stirred for additional 1 h at room temperature. The reaction was quenched with Water/Ice at room temperature. The resulting mixture was extracted with $CH_2Cl_2$ (3x30 mL). The combined organic layers were dried over anhydrous $Na_2SO_4$. After filtration, the filtrate was concentrated under reduced pressure. The residue was purified by silica gel column chromatography, eluted with PE/EA (10:1) to afford tert-butyl 3-formylpyrrole-1-carboxylate (3 g, 97.43%). LCMS (ES) [M+1]$^+$ m/z: 196.

Synthesis of tert-butyl 3-{2-[(tert-butoxycarbonyl) amino]-3-methoxy-3-oxoprop-1-en-1-yl}pyrrole-1-carboxylate

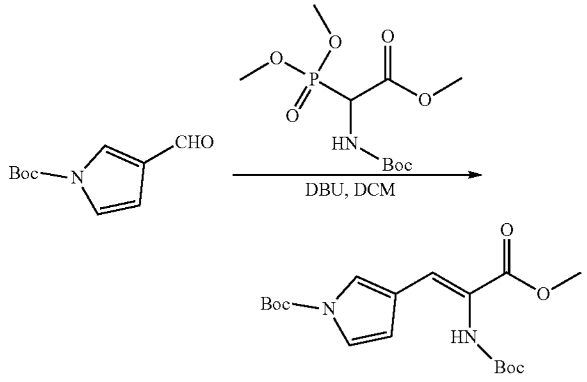

Into a 250 mL 3-necked round-bottom flask were added tert-butyl 3-formylpyrrole-1-carboxylate (3.00 g, 15.36 mmol, 1.00 equiv), DCM (50.00 mL) and methyl 2-[(tert-butoxycarbonyl)amino]-2-(dimethoxyphosphoryl)acetate (4.57 g, 15.36 mmol, 1.00 equiv) at room temperature. To the above mixture was added DBU (2.34 g, 15.36 mmol, 1.00 equiv) in portions at 0° C. The resulting mixture was stirred for additional 1 h at room temperature. The reaction was quenched with Water/Ice at room temperature. The resulting mixture was extracted with $CH_2Cl_2$ (3x30 mL). The combined organic layers were dried over anhydrous $Na_2SO_4$. After filtration, the filtrate was concentrated under reduced pressure. The residue was purified by silica gel column chromatography, eluted with PE/THE (5:1) to afford tert-butyl 3-{2-[(tert-butoxycarbonyl)amino]-3-methoxy-3-oxoprop-1-en-1-yl}pyrrole-1-carboxylate (5 g, 88.80%). LCMS (ES) [M+1]$^+$ m/z: 367.

Synthesis of tert-butyl 3-{2-[(tert-butoxycarbonyl) amino]-3-methoxy-3-oxopropyl}pyrrole-1-carboxylate

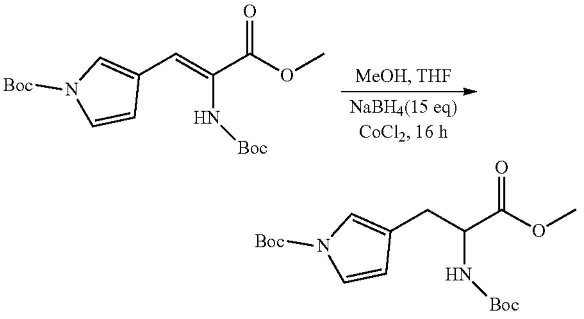

Into a 100 mL round-bottom flask were added tert-butyl 3-{2-[(tert-butoxycarbonyl)amino]-3-methoxy-3-oxoprop-1-en-1-yl}pyrrole-1-carboxylate (1.50 g, 4.09 mmol, 1.00 equiv), $CoCl_2$ (1.06 g, 8.18 mmol, 2.00 equiv) and MeOH (30.00 mL) at room temperature. To the above mixture was added $NaBH_4$ (2.32 g, 61.41 mmol, 15.00 equiv) in portions at 0° C. The resulting mixture was stirred for additional 16 h at room temperature. The reaction was quenched with Water/Ice at 0° C. The aqueous layer was extracted with EtOAc (3x30 mL). The resulting mixture was concentrated under reduced pressure. The residue was purified by silica gel column chromatography, eluted with PE/THE (3:1) to afford tert-butyl 3-{2-[(tert-butoxycarbonyl)amino]-3-methoxy-3-oxopropyl}pyrrole-1-carboxylate (800 mg, 53.04%). LCMS (ES) [M+1]$^+$ m/z: 369.

Synthesis of 2-[(tert-butoxycarbonyl)amino]-3-[1-(tert-butoxycarbonyl)pyrrol-3-y]propanoic acid

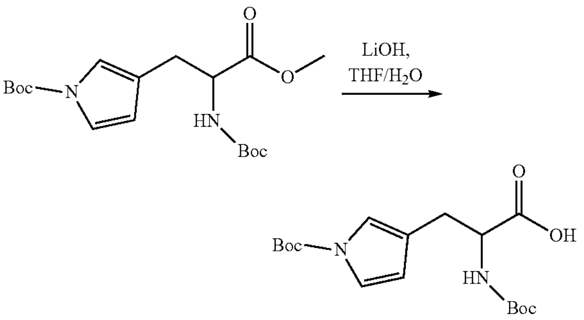

Into a 40 mL vial were added tert-butyl 3-{2-[(tert-butoxycarbonyl)amino]-3-methoxy-3-oxopropyl}pyrrole-1-carboxylate (500.00 mg, 1.35 mmol, 1.00 equiv) and MeOH (9.00 mL), $H_2O$ (3.00 mL) at room temperature. To the above mixture was added LiOH (97.51 mg, 4.07 mmol, 3.00 equiv) in portions at 0° C. The resulting mixture was stirred for additional 4 h at 50° C. The mixture was neutralized to pH 7 with citric acid. The aqueous layer was extracted with $CH_2Cl_2$ (3x30 mL). The resulting mixture was concentrated under reduced pressure. This resulted in 2-[(tert-butoxycarbonyl)amino]-3-[1-(tert-butoxycarbonyl)pyrrol-3-yl]propanoic acid (313 mg, 65.08%). LCMS (ES) [M+1]$^+$ m/z: 355.

Synthesis of tert-butyl 3-{2-[(tert-butoxycarbonyl)amino]-2-{[(1S)-1-cyano-2-[4-(3-methyl-2-oxo-1,3-benzoxazol-5-yl)phenyl]ethyl]carbamoyl}ethyl}pyrrole-1-carboxylate

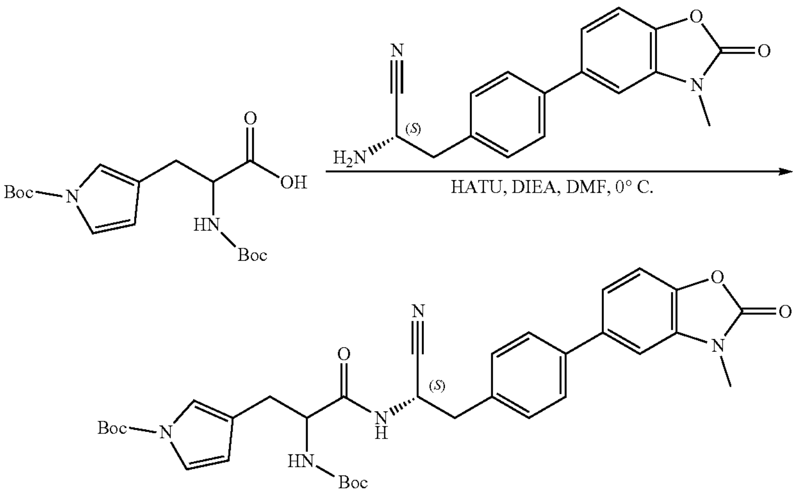

Into a 20 mL vial were added 2-[(tert-butoxycarbonyl)amino]-3-[1-(tert-butoxycarbonyl)pyrrol-3-yl]propanoic acid (123.24 mg, 0.34 mmol, 1.20 equiv), DCM (4.00 mL), (2S)-2-amino-3-[4-(3-methyl-2-oxo-1,3-benzoxazol-5-yl)phenyl]propanenitrile (85.00 mg, 0.29 mmol, 1.00 equiv) and DIEA (112.36 mg, 0.87 mmol, 3.00 equiv) at room temperature. To the above mixture was added HATU (132.22 mg, 0.34 mmol, 1.20 equiv) in portions at 0° C. The resulting mixture was stirred for additional 2 h at 0° C. The residue was purified by silica gel column chromatography, eluted with PE/THE (3:1) to afford tert-butyl 3-{2-[(tert-butoxycarbonyl)amino]-2-{[(1S)-1-cyano-2-[4-(3-methyl-2-oxo-1,3-benzoxazol-5-yl)phenyl]ethyl]carbamoyl}ethyl}pyrrole-1-carboxylate (190 mg, 69.76%). LCMS (ES) $[M+1]^+$ m/z: 630.

Synthesis of (S)—N—((S)-1-cyano-2-(2-fluoro-4-(3-(methyl-d3)-2-oxo-2,3-dihydrobenzo[d]oxazol-5-yl)phenyl)ethyl)-1,4-oxazepane-2-carboxamide

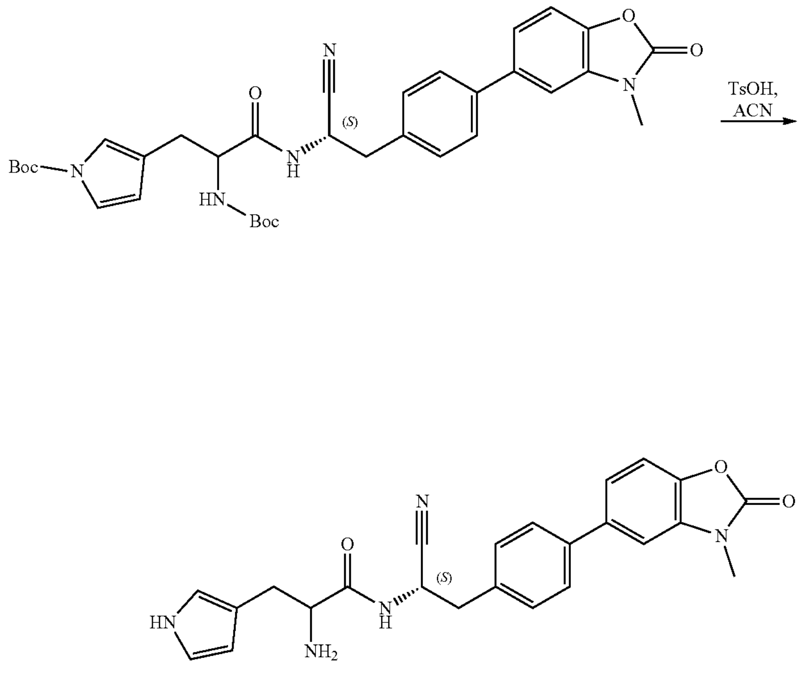

Into a 8 mL vial were added tert-butyl 3-{2-[(tert-butoxycarbonyl)amino]-2-{[(1S)-1-cyano-2-[4-(3-methyl-2-oxo-1,3-benzoxazol-5-yl)phenyl]ethyl]carbamoyl}ethyl}pyrrole-1-carboxylate (175.00 mg, 0.18 mmol, 1.00 equiv, 67%), ACN (5.00 mL) and TsOH (480.94 mg, 2.79 mmol, 15.00 equiv) at room temperature. The resulting mixture was stirred for additional 2 h at room temperature. The residue was purified by reversed-phase flash chromatography with the following conditions: column, C18 silica gel; mobile phase, MeCN in Water (0.1% $NH_3 \cdot H_2O$), 35% to 45% gradient in 8 min; detector, UV 254 nm. This resulted in 2-amino-N-[(1S)-1-cyano-2-[4-(3-methyl-2-oxo-1,3-benzoxazol-5-yl)phenyl]ethyl]-3-(1H-pyrrol-3-yl)propanamide (18.7 mg, 23.38%).

$^1H$ NMR (300 MHz, DMSO-d6) δ 10.52 (s, 1H), 7.72-7.63 (m, 2H), 7.59 (s, 1H), 7.45-7.35 (m, 4H), 6.62 (d, J=2.5 Hz, 1H), 6.52 (d, J=8.7 Hz, 1H), 5.84 (s, 1H), 5.00 (q, J=7.9 Hz, 1H), 3.40 (s, 3H), 3.30-3.25 (m, 1H), 3.13 (t, J=7.7 Hz, 2H), 2.66 (d, J=15.4 Hz, 1H), 2.46-2.29 (m, 1H).

LCMS (ES) $[M+1]^+$ m/z: 430.

Example 94: Synthesis of Compound 214: (2S)-2-amino-N-[(1S)-1-cyano-2-[4-(3-methyl-2-oxo-1,3-benzoxazol-5-yl)phenyl]ethyl]-3-(1H-pyrazol-4-yl)propanamide

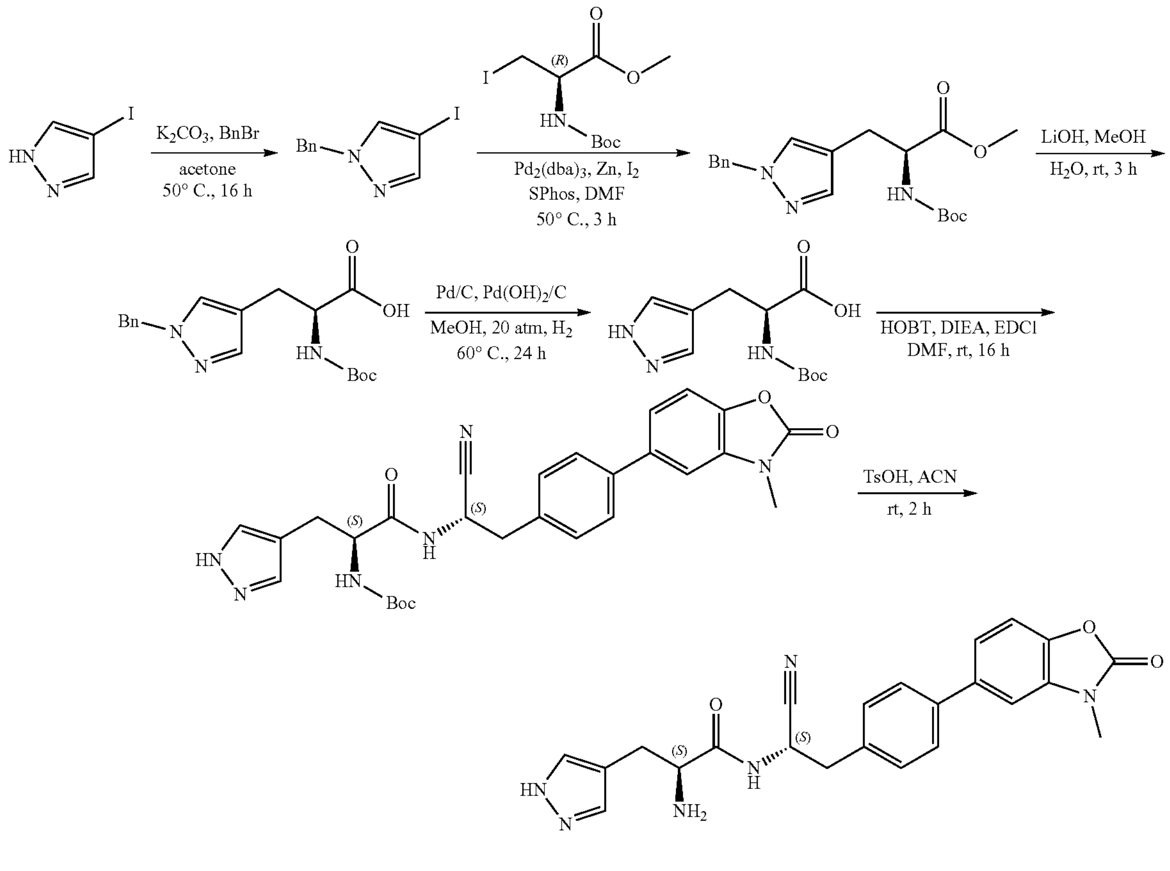

Synthesis of 1-benzyl-4-iodo-1H-pyrazole

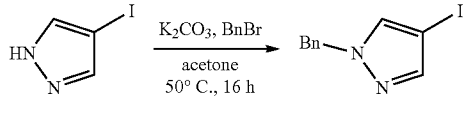 [SMILES: Ic1cn[nH]c1 ; Ic1cnn(Cc2ccccc2)c1]

To a stirred mixture of 4-iodopyrazole (2 g, 10.31 mmol, 1.0 equiv) and $K_2CO_3$ (4.27 g, 30.93 mmol, 3.0 equiv) in acetone (40 mL) was added BnBr (2.1 g, 12.37 mmol, 1.2 equiv) dropwise at room temperature. The resulting mixture was stirred for 16 h at 50° C. The reaction was cooled to room temperature, diluted with water (50 mL), with EtOAc (3×50 mL). The combined organic layer was dried over anhydrous $Na_2SO_4$. After filtration, the filtrate was concentrated under reduced pressure. The residue was purified by silica gel column chromatography, eluted with PE/EA (5:1) to afford 1-benzyl-4-iodopyrazole (2.8 g, 95%). LCMS (ES, m z): $[M+H]^+$: 285.

Synthesis of methyl (2S)-3-(1-benzylpyrazol-4-yl)-2-[(tert-butoxycarbonyl)amino]propanoate

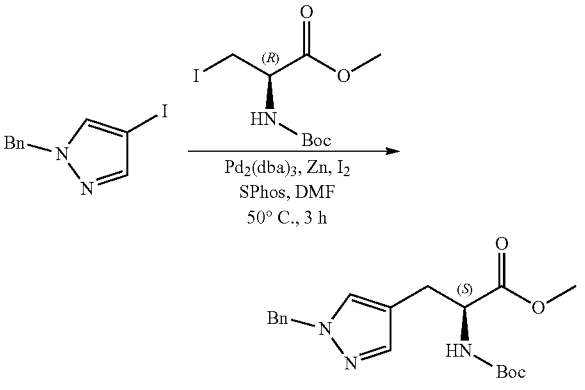

To a stirred mixture of Zn (1.9 g, 29.56 mmol, 3.0 equiv) and DMF (25 mL) was added $I_2$ (0.38 g, 1.47 mmol, 0.15 equiv) at room temperature under nitrogen atmosphere. To the above mixture was added methyl (2S)-2-[(tert-butoxycarbonyl)amino]-3-iodopropanoate (3.24 g, 9.85 mmol, 1 equiv) and 12 (0.38 g, 1.47 mmol, 0.15 equiv) at room temperature under nitrogen atmosphere. The resulting mixture was stirred for 10 min at room temperature under nitrogen atmosphere. To the above mixture was added 1-benzyl-4-iodopyrazole (2.8 g, 9.86 mmol, 1.0 equiv), $Pd_2(dba)_3CHCl_3$ (0.51 g, 0.49 mmol, 0.05 equiv) in DMF (25 mL) at room temperature under nitrogen atmosphere. The resulting mixture was stirred for additional 3 h at 50° C. under nitrogen atmosphere. The reaction was cooled to room temperature, diluted with water (30 mL), The resulting mixture was extracted with EtOAc (3×50 mL). The combined organic layer was washed with brine (3×100 mL), dried over anhydrous $Na_2SO_4$. After filtration, the filtrate was concentrated under reduced pressure. The residue was purified by silica gel column chromatography, eluted with PE/EA (3:1) to afford methyl (2S)-3-(1-benzylpyrazol-4-yl)-2-[(tert-butoxycarbonyl)amino]propanoate (1 g, 28%). LCMS (ES, m z): $[M+H]^+$: 360.

Synthesis of (2S)-3-(1-benzylpyrazol-4-yl)-2-[(tert-butoxycarbonyl)amino]propanoic acid

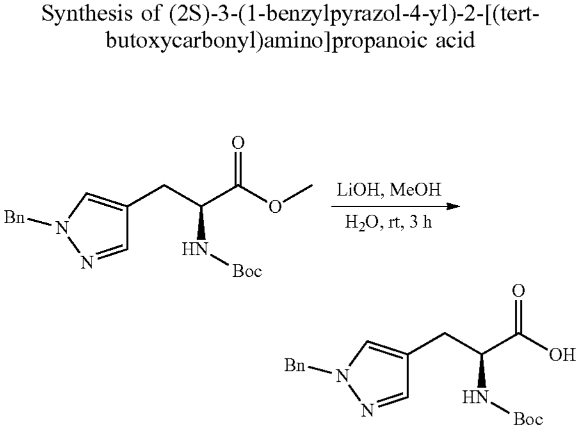

To a stirred solution of methyl (2S)-3-(1-benzylpyrazol-4-yl)-2-[(tert-butoxycarbonyl)amino]propanoate (1 g, 2.78 mmol, 1.0 equiv) in MeOH (15 mL) was added LiOH (0.13 g, 5.56 mmol, 2.0 equiv) in $H_2O$ (5 mL) dropwise at room temperature. The resulting mixture was concentrated under reduced pressure. The residue was acidified to pH 3 with HCl (1 M), extracted with EtOAc (3×50 mL). The combined organic layer was dried over anhydrous $Na_2SO_4$. After filtration, the filtrate was concentrated under reduced pressure. This resulted in (2S)-3-(1-benzylpyrazol-4-yl)-2-[(tert-butoxycarbonyl)amino]propanoic acid (800 mg, 83%). LCMS (ES, m z): $[M+H]^+$: 346.

Synthesis of (2S)-2-[(tert-butoxycarbonyl)amino]-3-(1H-pyrazol-4-yl)propanoic acid

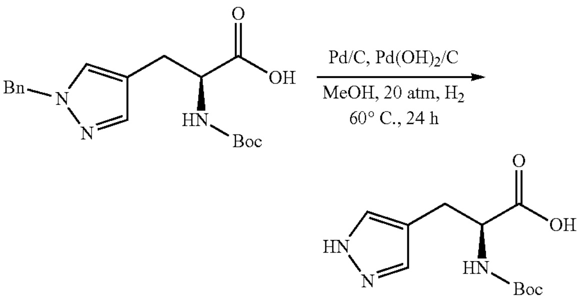

To a solution of (2S)-3-(1-benzylpyrazol-4-yl)-2-[(tert-butoxycarbonyl)amino]propanoic acid (400 mg, 1.15 mmol, 1.0 equiv) in MeOH (10 mL) was added Pd/C (50 mg) and $Pd(OH)_2/C$ (50 mg) in a pressure tank. The mixture was hydrogenated at 60° C. under 20 atm of hydrogen pressure for 24 h. The reaction was cooled to room temperature, filtered through a Celite pad and concentrated under reduced pressure. This resulted in (2S)-2-[(tert-butoxycarbonyl)amino]-3-(1H-pyrazol-4-yl)propanoic acid (130 mg, 44%). LCMS (ES, m z): $[M+H]^+$: 256.

Synthesis of tert-butyl N-[(1S)-1-{[(1S)-1-cyano-2-[4-(3-methyl-2-oxo-1,3-benzoxazol-5-yl)phenyl]ethyl]carbamoyl}-2-(1H-pyrazol-4-yl)ethyl]carbamate

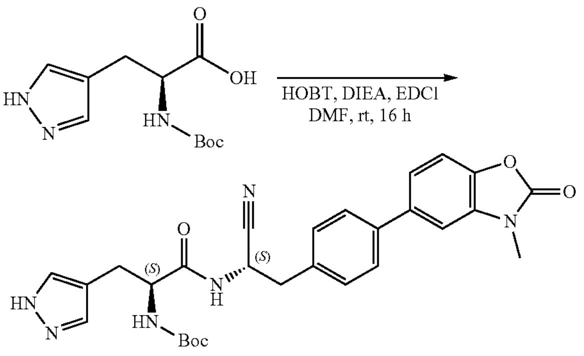

To a stirred mixture of (2S)-2-[(tert-butoxycarbonyl)amino]-3-(1H-pyrazol-4-yl)propanoic acid (104 mg, 0.40 mmol, 1.2 equiv), (2S)-2-amino-3-[4-(3-methyl-2-oxo-1,3-benzoxazol-5-yl)phenyl]propanenitrile (100 mg, 0.34 mmol, 1.0 equiv) and DIEA (132 mg, 1.02 mmol, 3.0 equiv) in DMF (5 mL) were added HOBT (55 mg, 0.40 mmol, 1.2 equiv) and EDCI (78 mg, 0.40 mmol, 1.2 equiv) in portions at 0° C. The resulting mixture was stirred for 16 h at room temperature. The reaction was quenched with water (20 mL), extracted with EtOAc (3×30 mL). The combined organic layer was washed with brine (3×50 mL), dried over anhydrous $Na_2SO_4$. After filtration, the filtrate was concentrated under reduced pressure. The residue was purified by silica gel column chromatography, eluted with PE/THE (1:1) to afford tert-butyl N-[(1S)-1-{[(1S)-1-cyano-2-[4-(3-methyl-2-oxo-1,3-benzoxazol-5-yl)phenyl]ethyl]carbamoyl}-2-(1H-pyrazol-4-yl)ethyl]carbamate (100 mg, 55%). LCMS (ES, m/z): $[M+H]^+$: 531.

Synthesis of (2S)-2-amino-N-[(1S)-1-cyano-2-[4-(3-methyl-2-oxo-1,3-benzoxazol-5-yl)phenyl]ethyl]-3-(1H-pyrazol-4-yl)propanamide

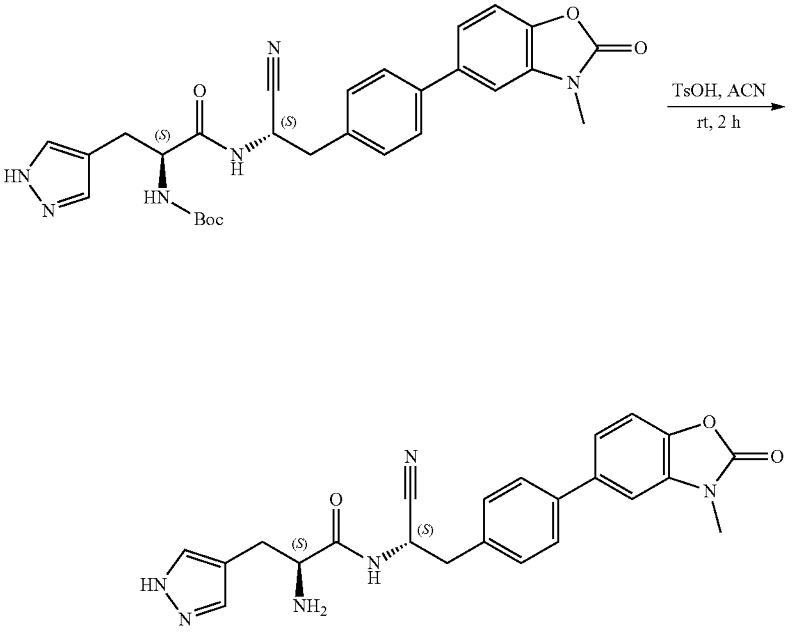

Into a 25 mL round-bottom flask were added tert-butyl N-[(1S)-1-{[(1S)-1-cyano-2-[4-(3-methyl-2-oxo-1,3-benzoxazol-5-yl)phenyl]ethyl]carbamoyl}-2-(1H-pyrazol-4-yl)ethyl]carbamate (100 mg, 0.18 mmol, 1.0 equiv), TsOH (97 mg, 0.56 mmol, 3.0 equiv) and ACN (3 mL) at room temperature. The resulting mixture was stirred for 2 h at room temperature. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (2S)-2-amino-N-[(1S)-1-cyano-2-[4-(3-methyl-2-oxo-1,3-benzoxazol-5-yl)phenyl]ethyl]-3-(1H-pyrazol-4-yl)propanamide (19 mg, 23%).

LCMS (ES, m z): $[M+H]^+$: 431.2

$^1H$ NMR (400 MHz, DMSO-$d_6$): δ 12.55 (s, 1H), 7.70-7.63 (m, 2H), 7.58 (d, J=1.6 Hz, 1H), 7.46-7.23 (m, 6H), 4.98 (t, J=7.7 Hz, 1H), 3.41 (s, 3H), 3.31-3.29 (m, 1H), 3.18-3.06 (m, 2H), 2.71-2.65 (m, 1H), 2.57-2.55 (m, 1H).

Example 95: Synthesis of Compound 216: 2-amino-N-[(1S)-1-cyano-2-[4-(3-methyl-2-oxo-1,3-benzoxazol-5-yl)phenyl]ethyl]-2-(pyridin-3-yl)propanamide

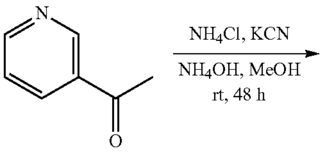

-continued

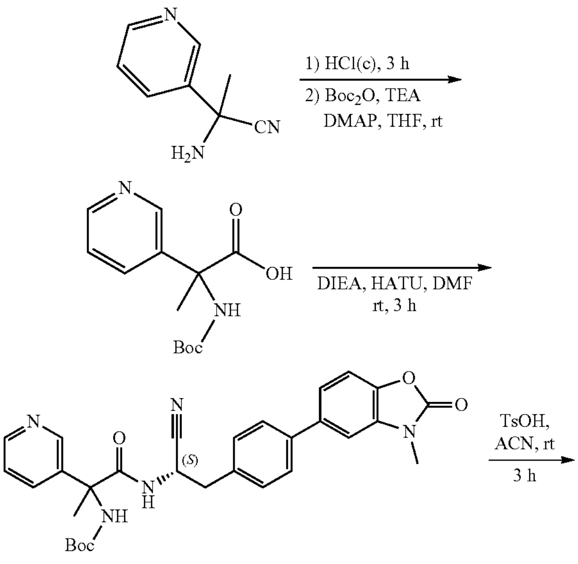

-continued

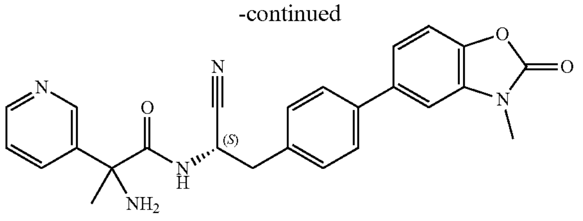

Synthesis of 2-amino-2-(pyridin-3-yl)propanenitrile

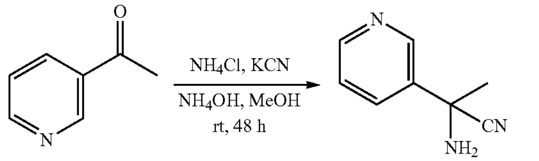

To a solution of $NH_4Cl$ (1.7 g, 33.02 mmol, 2.0 equiv) in $NH_4OH$ (30%)(20 mL), NaCN (2.0 g, 41.27 mmol, 2.5 equiv) was added at room temperature. This was followed by the addition of 3-acetylpyridine (2.0 g, 16.51 mmol, 1.0 equiv) in MeOH (20 mL) dropwise at room temperature. After addition, the reaction was stirred for 48 h at room temperature. Concentrated to remove the solvent, the residue was diluted with water (30 mL), extracted with ethyl acetate (40 mL×2). The combined organic phase was washed with brine (50 mL), dried over anhydrous sodium sulfate. After filtered out the solid, the filtrate was concentrated under reduced pressure. This result in 2-amino-2-(pyridin-3-yl) propanenitrile (1.7 g, 69.9%) and used to the next step without further purification. LCMS (ES, m/z): $[M+H]^+$: 148.

Synthesis of 2-[(tert-butoxycarbonyl)amino]-2-(pyridin-3-yl)propanoic acid

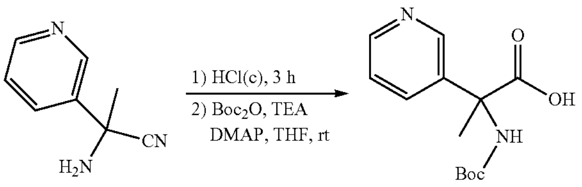 [SMILES: CC(N)(C#N)c1cccnc1 ; CC(C)(C)OC(=O)NC(C)(C(=O)O)c1cccnc1]

A solution of 2-amino-2-(pyridin-3-yl)propanenitrile (1.7 g, 11.55 mmol, 1.0 equiv) in conc. HCl (20 mL) was heated to 100° C. and stirred for 3 h. The reaction was cooled to room temperature, diluted with water (20 mL), adjust PH to 6-7 with $K_2CO_3$ solid, concentrated to remove the solvent. The residue was dissolved in MeOH (30 mL), filtered out the solid, the filtrate was concentrated. The residue was added to a 100 mL round bottom flask, this was followed by the addition of THF (30 mL), TEA (2.3 g, 23.10 mmol, 2.0 equiv), DMAP (0.1 g, 1.15 mmol, 0.1 equiv), and $Boc_2O$ (3.8 g, 17.32 mmol, 1.5 equiv) at room temperature in sequence. The mixture was stirred for 12 h. The mixture was diluted with water (20 mL), adjust PH to 4-5 with HCl (1 N). extracted with dichloromethane (50 mL×2). The combined organic phase was concentrated, the residue was further purified by HPLC with conditions: C18 silica-120 g, ACN/$H_2O$ (0.05% FA), gradient, 5% to 50%, within 10 min, flowrate, 70 mL/min. This result in 2-[(tert-butoxycarbonyl) amino]-2-(pyridin-3-yl)propanoic acid (310 mg, 10%). LCMS (ES, m/z): $[M+H]^+$: 267.

Synthesis of tert-butyl N-(1-{[(1S)-1-cyano-2-[4-(3-methyl-2-oxo-1,3-benzoxazol-5-yl)phenyl]ethyl] carbamoyl}-1-(pyridin-3-yl)ethyl)carbamate

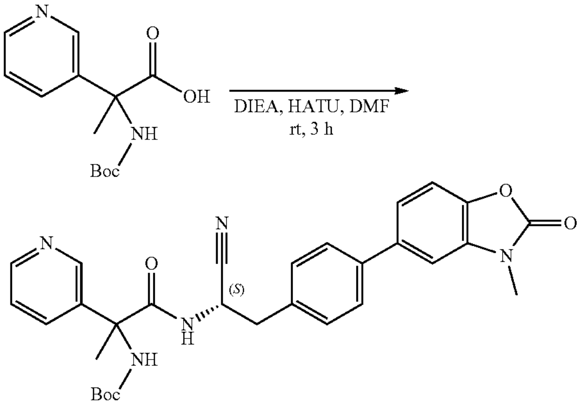

A solution of (2S)-2-amino-3-[4-(3-methyl-2-oxo-1,3-benzoxazol-5-yl)phenyl]propanenitrile (100 mg, 0.34 mmol, 1.0 equiv) in DMF (3 mL) was treated with 2-[(tert-butoxy-carbonyl)amino]-2-(pyridin-3-yl)propanoic acid (91 mg, 0.34 mmol, 1.0 equiv), DIEA (132 mg, 1.02 mmol, 3.0 equiv). This was followed by the addition of HATU (156 mg, 0.40 mmol, 1.2 equiv) in portions at 0° C. The resulting mixture was stirred for additional 3 h at room temperature. The residue was purified by silica gel column chromatography, eluted with PE/THE (1:1) to afford tert-butyl N-(1-{[(1S)-1-cyano-2-[4-(3-methyl-2-oxo-1,3-benzoxazol-5-yl) phenyl]ethyl]carbamoyl}-1-(pyridin-3-yl)ethyl)carbamate (100 mg, 54%). LCMS (ES, m/z): $[M+H]^+$: 542.

Synthesis of 2-amino-N-[(1S)-1-cyano-2-[4-(3-methyl-2-oxo-1,3-benzoxazol-5-yl)phenyl]ethyl]-2-(pyridin-3-yl)propanamide

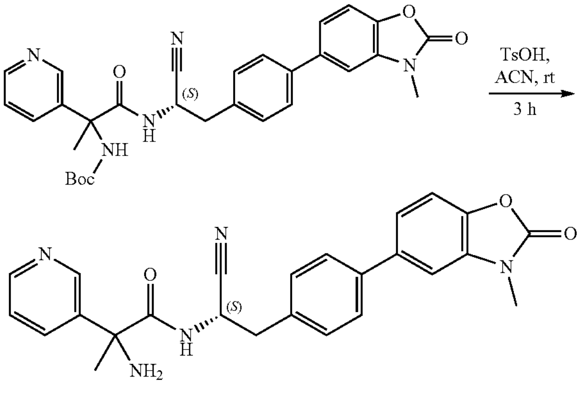

Into a 25 mL round-bottom flask were added tert-butyl N-(1-{[(1S)-1-cyano-2-[4-(3-methyl-2-oxo-1,3-benzoxazol-5-yl)phenyl]ethyl]carbamoyl}-1-(pyridin-3-yl)ethyl)

carbamate (100 mg, 0.18 mmol, 1.0 equiv), ACN (3 mL) and $TsOH{\cdot}H_2O$ (105 mg, 0.55 mmol, 3.0 equiv) at room temperature. The resulting mixture was stirred for additional 3 h at room temperature. The reaction solution was purified by reversed-phase flash chromatography with the following conditions: column, C18 silica gel-120 g; mobile phase, MeCN in Water (0.1% $NH_3{\cdot}H_2O$), 10% to 50% gradient in 10 min; detector, UV 254 nm. This resulted in 2-amino-N-[(1S)-1-cyano-2-[4-(3-methyl-2-oxo-1,3-benzoxazol-5-yl)phenyl]ethyl]-2-(pyridin-3-yl)propanamide (20.5 mg, 25%).

LCMS (ES, m/z): $[M+H]^+$: 442.1

$^1H$ NMR (400 MHz, DMSO-$d_6$) δ 8.62 (ddd, J=28.2, 2.5, 0.9 Hz, 1H), 8.42 (ddd, J=24.7, 4.7, 1.6 Hz, 1H), 7.80-7.53 (m, 4H), 7.44-7.38 (m, 2H), 7.37-7.16 (m, 3H), 4.99 (q, J=8.9 Hz, 1H), 3.42 (d, J=2.4 Hz, 3H), 3.20-3.15 (m, 2H), 1.53 (d, J=22.4 Hz, 3H).

Example 96: Synthesis of Compound 218: 2-amino-3-(5-chloro-1,3-thiazol-4-yl)-N-[(1S)-1-cyano-2-[4-(3-methyl-2-oxo-1,3-benzoxazol-5-yl)phenyl]ethyl]propanamide

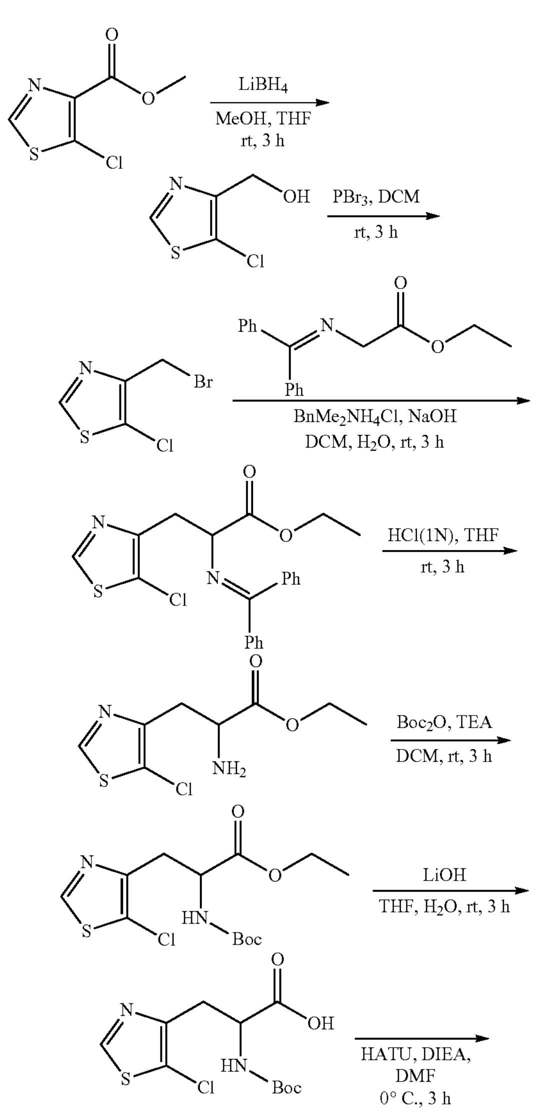

-continued

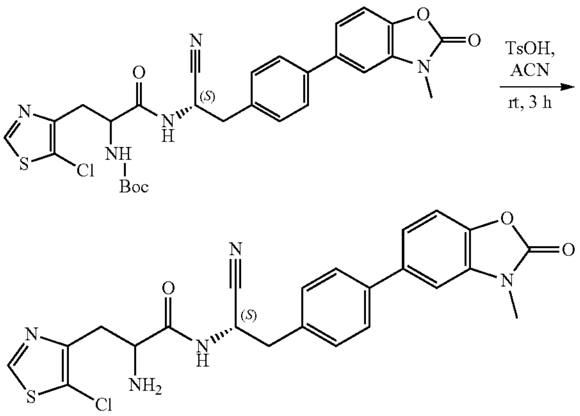

Synthesis of (5-chloro-1,3-thiazol-4-yl)methanol

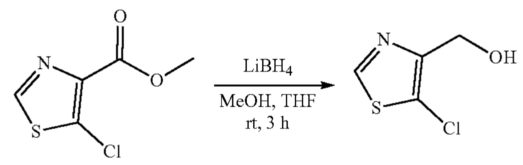

To a stirred solution of methyl 5-chloro-1,3-thiazole-4-carboxylate (3.0 g, 16.89 mmol, 1.0 equiv) in THF (30 mL) were added $LiBH_4$ (1 M in THF)(16.9 mL, 16.90 mmol, 1.0 equiv) and MeOH (1.1 g, 33.78 mmol, 2.0 equiv) in portions at 0° C. under nitrogen atmosphere. The resulting mixture was stirred for 3 h at room temperature. The reaction was quenched by the addition of sodium sulfate decahydrate solid at room temperature. The precipitated solid was filtered out and washed with THF (3×30 mL). After filtration, the filtrate was concentrated under reduced pressure. This resulted in (5-chloro-1,3-thiazol-4-yl)methanol (1.3 g, 51.4%) and used to the next step without further purification.

Synthesis of 4-(bromomethyl)-5-chloro-1,3-thiazole

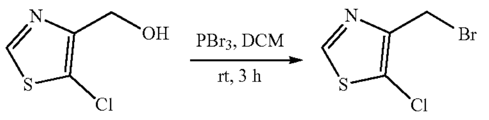

To a stirred solution of (5-chloro-1,3-thiazol-4-yl)methanol (1.0 g, 6.68 mmol, 1.0 equiv) in DCM (10 mL) was added $PBr_3$ (0.9 g, 3.34 mmol, 0.5 equiv) dropwise at 0° C. The resulting mixture was stirred for 3 h at room temperature. The reaction was quenched with water (20 mL), extracted with $CH_2Cl_2$ (2×50 mL). The combined organic layer was washed with brine (3×50 mL), dried over anhydrous $Na_2SO_4$. After filtration, the filtrate was concentrated under reduced pressure. This resulted in 4-(bromomethyl)-5-chloro-1,3-thiazole (1.0 g, 70.4%) and used to the next step without further purification.

Synthesis of ethyl 3-(5-chloro-1,3-thiazol-4-yl)-2-[(diphenylmethylidene)amino]propanoate

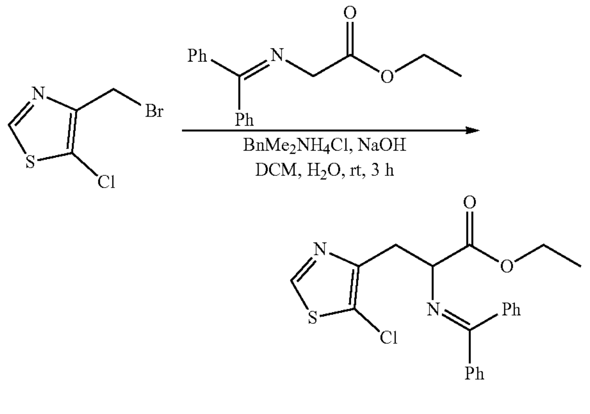

A solution of 4-(bromomethyl)-5-chloro-1,3-thiazole (1.0 g, 4.70 mmol, 1.0 equiv) in DCM (10 mL) was added ethyl 2-[(diphenylmethylidene)amino]acetate (1.3 g, 4.70 mmol, 1.0 equiv), benzyltrimethylazanium chloride (0.1 g, 0.47 mmol, 0.1 equiv), NaOH (0.4 g, 9.41 mmol, 2.0 equiv) in $H_2O$ (2 mL) was stirred for 3 h at room temperature. The resulting mixture was extracted with $CH_2Cl_2$ (3×100 mL). The combined organic layer was washed with brine (3×30 mL), dried over anhydrous $Na_2SO_4$. After filtration, the filtrate was concentrated under reduced pressure. The residue was purified by silica gel column chromatography, eluted with PE/THE (5:1) to afford ethyl 3-(5-chloro-1,3-thiazol-4-yl)-2-[(diphenylmethylidene)amino]propanoate (700 mg, crude). LCMS (ES, m/z): [M+H]$^+$: 399.

Synthesis of ethyl 2-amino-3-(5-chloro-1,3-thiazol-4-yl)propanoate

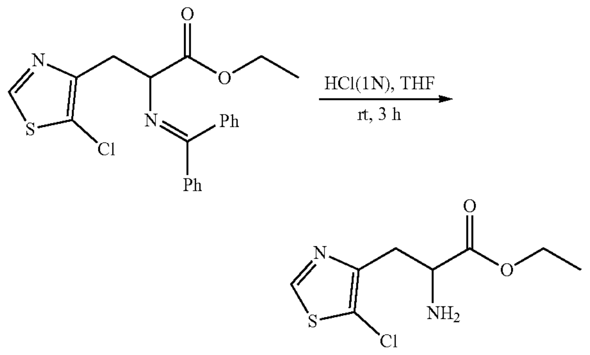

Into a 100 mL round-bottom flask were added ethyl 3-(5-chloro-1,3-thiazol-4-yl)-2-[(diphenylmethylidene)amino]propanoate (700 mg, 1.75 mmol, 1.0 equiv) and HCl(1 M)(1.5 mL), THE (35 mL) and $H_2O$ (3.5 mL) at room temperature. The resulting mixture was stirred for additional 3 h at room temperature. The resulting mixture was extracted with $Et_2O$ (50 mL). The aqueous layer was basified to pH 5 with $K_2CO_3$ solid, extracted with $CH_2Cl_2$ (3×50 mL). The combined organic layer was washed with brine (3×50 mL), dried over anhydrous $Na_2SO_4$. After filtration, the filtrate was concentrated under reduced pressure. This resulted in ethyl 2-amino-3-(5-chloro-1,3-thiazol-4-yl)propanoate (300 mg, 72.8%). LCMS (ES, m/z): [M+H]$^+$: 235.

Synthesis of 2-[(tert-butoxycarbonyl)amino]-3-(5-chloro-1,3-thiazol-4-yl)propanoic acid

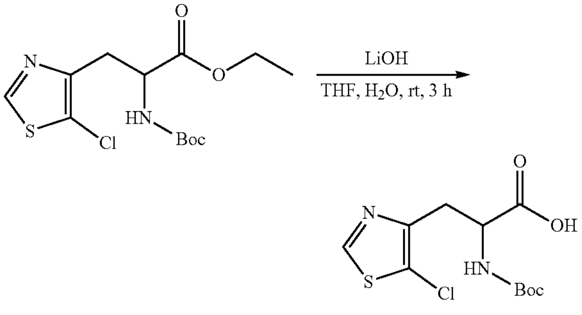

A solution of ethyl 2-[(tert-butoxycarbonyl)amino]-3-(5-chloro-1,3-thiazol-4-yl)propanoate (350 mg, 1.04 mmol, 1.0 equiv) in THF (3 mL) and LiOH (75 mg, 3.13 mmol, 3.0 equiv) in $H_2O$ (1 mL) was stirred for 3 h at room temperature. The mixture was acidified to pH 4 with HCl (1M.). The resulting mixture was extracted with EtOAc (3×30 mL). The combined organic layer was washed with brine (3×30 mL), dried over anhydrous $Na_2SO_4$. After filtration, the filtrate was concentrated under reduced pressure. This resulted in 2-[(tert-butoxycarbonyl)amino]-3-(5-chloro-1,3-thiazol-4-yl)propanoic acid (300 mg, 93.5%). LCMS (ES, m/z): [M+H]$^+$: 307.

Synthesis of tert-butyl N-[2-(5-chloro-1,3-thiazol-4-yl)-1-{1[(1S)-1-cyano-2-[4-(3-methyl-2-oxo-1,3-benzoxazol-5-yl)phenyl]ethyl]carbamoyl}ethyl]carbamate

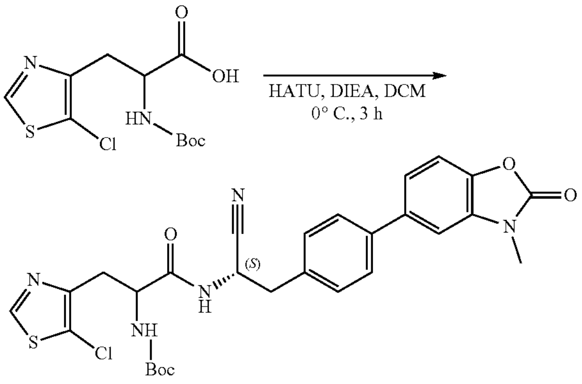

A solution of (2S)-2-amino-3-[4-(3-methyl-2-oxo-1,3-benzoxazol-5-yl)phenyl]propanenitrile (100 mg, 0.34 mmol, 1.0 equiv) in DCM (2 mL) was treated with 2-[(tert-butoxycarbonyl)amino]-3-(5-chloro-1,3-thiazol-4-yl)propanoic acid (104 mg, 0.34 mmol, 1.0 equiv), DIEA (132 mg, 1.02 mmol, 3.0 equiv). This was followed by the addition of HATU (156 mg, 0.40 mmol, 1.2 equiv) in portions at 0° C. The resulting mixture was stirred for 3 h at 0° C. Concentrated under reduced pressure to remove the solvent, the residue was purified by silica gel column chromatography, eluted with PE/THF (1:1) to afford tert-butyl N-[2-(5-chloro-1,3-thiazol-4-yl)-1-{[(1S)-1-cyano-2-[4-(3-methyl-2-oxo-1,3-benzoxazol-5-yl)phenyl]ethyl]carbamoyl}ethyl] carbamate (100 mg, 50.3%). LCMS (ES, m/z): [M+H]*: 582.

Synthesis of 2-amino-3-(5-chloro-1,3-thiazol-4-yl)-N-[(1S)-1-cyano-2-[4-(3-methyl-2-oxo-1,3-benzoxazol-5-yl)phenyl]ethyl]propanamide

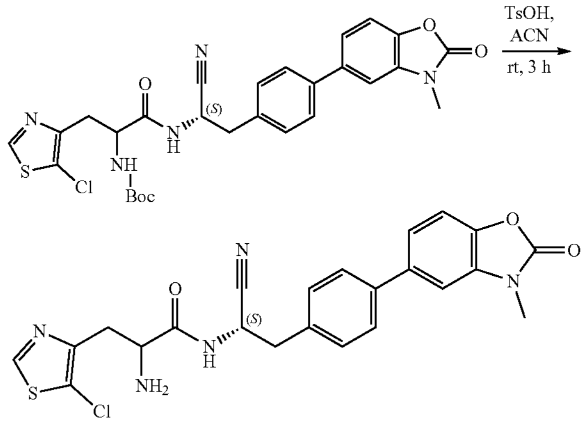

Into a 25 mL round-bottom flask were added tert-butyl N-[2-(5-chloro-1,3-thiazol-4-yl)-1-{[(1S)-1-cyano-2-[4-(3-methyl-2-oxo-1,3-benzoxazol-5-yl)phenyl]ethyl] carbamoyl}ethyl]carbamate (100 mg, 0.17 mmol, 1.0 equiv), ACN (3 mL) and TsOH·$H_2O$ (98 mg, 0.51 mmol, 3.0 equiv) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 2-amino-3-(5-chloro-1,3-thiazol-4-yl)-N-[(1S)-1-cyano-2-[4-(3-methyl-2-oxo-1,3-benzoxazol-5-yl)phenyl]ethyl] propanamide (20.5 mg, 24.8%).

LCMS (ES, m/z): [M+H]$^+$:482.0

$^1$H NMR (300 MHz, DMSO-$d_6$) δ 8.97 (s, 1H), 7.65 (dd, J=8.2, 2.2 Hz, 2H), 7.56 (d, J=1.6 Hz, 1H), 7.45-7.33 (m, 4H), 4.97 (t, J=7.6 Hz, 1H), 3.61-3.56 (m, 1H), 3.38 (s, 3H), 3.15-3.08 (m, 2H), 2.92-2.85 (m, 1H), 2.76-2.65 (m, 1H).

Example 97: Synthesis of Compound 120: (2S)—N-[(1S)-1-cyano-2-[4-(3-methyl-2-oxo-1,3-benzoxazol-5-yl)phenyl]ethyl]-2-hydroxy-3-(pyrrolidin-1-yl) propanamide

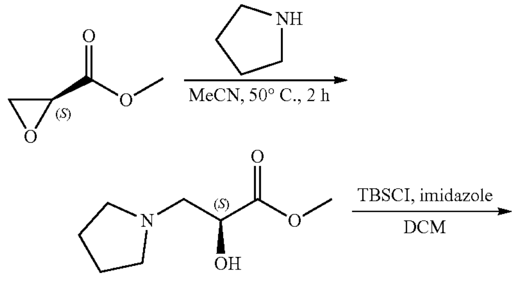

-continued

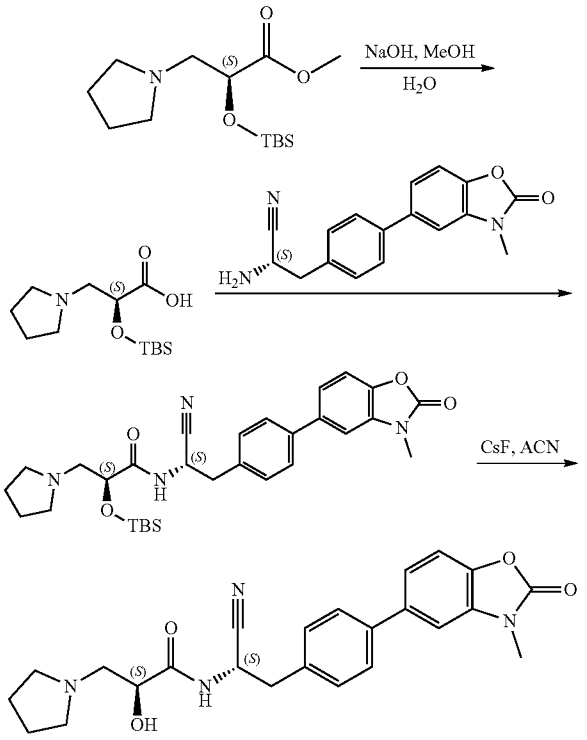

Compound 120

Synthesis of methyl (S)-2-hydroxy-3-(pyrrolidin-1-yl)propanoate

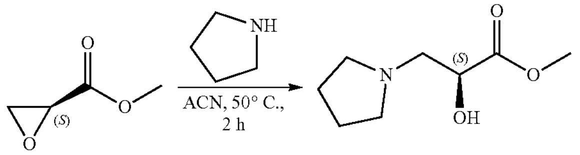

To a stirred mixture of methyl (2S)-oxirane-2-carboxylate (2 g, 19.61 mmol, 1.0 equiv) in ACN (30 mL) was added pyrrolidine (1.39 g, 19.61 mmol, 1.0 equiv) dropwise at room temperature. The resulting mixture was stirred for 2 h at 50° C. The reaction was concentrated to give crude methyl (S)-2-hydroxy-3-(pyrrolidin-1-yl)propanoate (2.2 g, crude) and used to the next step directly without further purification. LCMS (ES, m/z): [M+H]$^+$: 174.

Synthesis of methyl (S)-2-((tert-butyldimethylsilyl) oxy)-3-(pyrrolidin-1-yl)propanoate

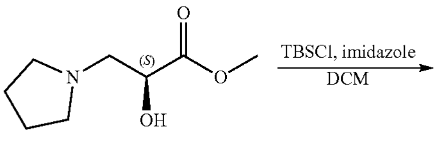

-continued

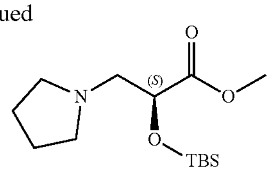

To a stirred solution of methyl (2S)-2-hydroxy-3-(pyrrolidin-1-yl)propanoate (2.2 g, 12.70 mmol, 1.0 equiv) in DCM (30 mL) was added imidazole (2.59 g, 38.10 mmol, 3.0 equiv) and TBSCI (2.87 g, 19.05 mmol, 1.5 equiv) in portions at 0° C. The resulting mixture was stirred at room temperature for 3 h. The resulting mixture was extracted with $CH_2Cl_2$ (3x50 mL). The combined organic layer was washed with brine (50 mL), dried over anhydrous $Na_2SO_4$. After filtration, the filtrate was concentrated under reduced pressure. The residue was purified by silica gel column chromatography, eluted with PE/EA (5:1) to afford methyl (2S)-2-[(tert-butyldimethylsilyl)oxy]-3-(pyrrolidin-1-yl) propanoate (3 g, 82% yield, 90% purity). LCMS (ES, m/z): $[M+H]^+$: 288.

Synthesis of (S)-2-((tert-butyldimethylsilyl)oxy)-3-(pyrrolidin-1-yl)propanoic acid

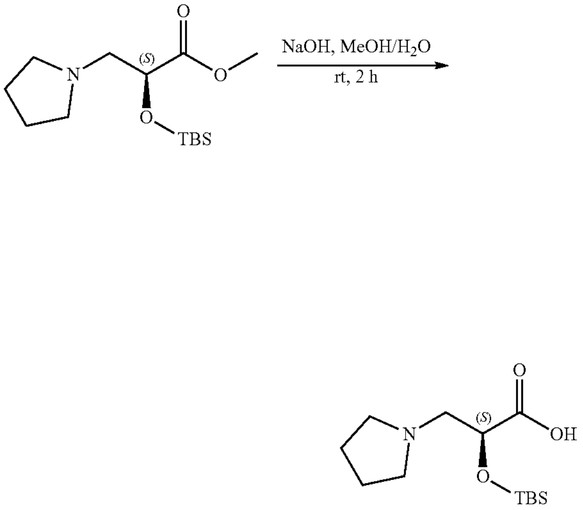

To a stirred solution of methyl (2S)-2-[(tert-butyldimethylsilyl)oxy]-3-(pyrrolidin-1-yl)propanoate (2.0 g, 6.96 mmol, 1.0 equiv) in MeOH (20 mL) and water (5 mL) was added NaOH (0.56 g, 13.91 mmol, 2.0 equiv). The resulting mixture was stirred at room temperature for 2 h. The resulting mixture was concentrated under reduced pressure. The residue was dissolved in $H_2O$ (30 mL), extracted with EtOAc (2x10 mL). The aqueous layer was acidified to pH 6 with citric acid. The resulting mixture was extracted with $CH_2Cl_2$ (5x20 mL). The combined organic layer was washed with brine (10 mL), dried over anhydrous $Na_2SO_4$. After filtration, the filtrate was concentrated under reduced pressure. This resulted in (2S)-2-[(tert-butyldimethylsilyl) oxy]-3-(pyrrolidin-1-yl)propanoic acid (1.0 g, 52% yield, 90% purity) and used to the next step directly without further purification. LCMS (ES, m/z): $[M+H]^+$: 274.

Synthesis of (2S)-2-[(tert-butyldimethylsilyl)oxy]—N-[(1S)-1-cyano-2-[4-(3-methyl-2-oxo-1,3-benzoxazol-5-yl)phenyl]ethyl]-3-(pyrrolidin-1-yl)propanamide

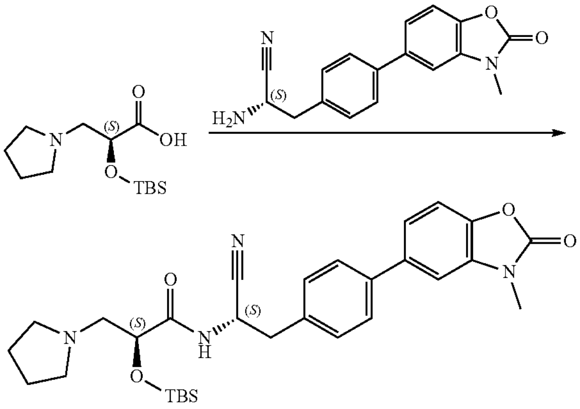

To a solution of (2S)-2-[(tert-butyldimethylsilyl)oxy]-3-(pyrrolidin-1-yl)propanoic acid (120 mg, 0.44 mmol, 2.0 equiv) in DMF (3 mL) was treated with (2S)-2-amino-3-[4-(3-methyl-2-oxo-1,3-benzoxazol-5-yl)phenyl]propanenitrile (64 mg, 0.22 mmol, 1.0 equiv), DIEA (85 mg, 0.66 mmol, 3.0 equiv). This was followed by the addition of HATU (108 mg, 0.29 mmol, 1.3 equiv) at 0° C. The mixture was stirred for 1.5 h at 0° C. The reaction was quenched by the addition of brine (20 mL) at room temperature. The resulting mixture was extracted with EtOAc (3x30 mL). The combined organic layer was washed with brine (3x20 mL), dried over anhydrous $Na_2SO_4$. After filtration, the filtrate was concentrated under reduced pressure. The residue was purified by silica gel column chromatography, eluted with PE/EA (5:1) to afford (2S)-2-[(tert-butyldimethylsilyl) oxy]—N-[(1S)-1-cyano-2-[4-(3-methyl-2-oxo-1,3-benzoxazol-5-yl)phenyl]ethyl]-3-(pyrrolidin-1-yl)propanamide (180 mg, 75%) LCMS (ES, m/z): $[M+H]^+$: 549.

Synthesis of (2S)—N-[(1S)-1-cyano-2-[4-(3-methyl-2-oxo-1,3-benzoxazol-5-yl)phenyl]ethyl]-2-hydroxy-3-(pyrrolidin-1-yl)propanamide

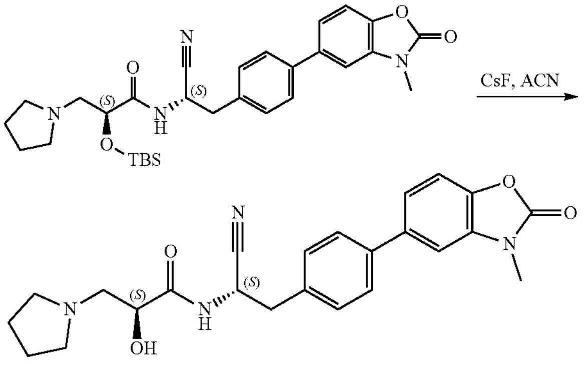

To a stirred solution of (2S)-2-[(tert-butyldimethylsilyl) oxy]—N-[(1S)-1-cyano-2-[4-(3-methyl-2-oxo-1,3-benzoxazol-5-yl)phenyl]ethyl]-3-(pyrrolidin-1-yl)propanamide (180 mg, 0.33 mmol, 1.0 equiv) in ACN (1.8 mL) was added CsF (150 mg, 0.98 mmol, 3.0 equiv). The resulting mixture was stirred for 1 h at room temperature. The reaction solution was filtered and the filtrate was purified by reversed-phase flash chromatography with conditions: C18 silica-120 g, $MeCN/H_2O$ ($NH_4HCO_3$, 0.05%)(10% to 80%), Flow rate, 70 mL/min, Detector, 220 nm. The fraction of the target was freezing dried to afford (2S)—N-[(1S)-1-cyano-2-[4-(3-methyl-2-oxo-1,3-benzoxazol-5-yl)phenyl]ethyl]-2-hydroxy-3-(pyrrolidin-1-yl)propanamide (25 mg, 18%). LCMS (ES) $[M+1]^+$ m/z: 435.2

$^1H$ NMR (400 MHz, DMSO-$d_6$) δ 8.70 (d, J=8.4 Hz, 1H), 7.69-7.64 (m, 2H), 7.57 (s, 1H), 7.45-7.36 (m, 4H), 5.55 (d, J=4.9 Hz, 1H), 5.05 (q, J=8.1 Hz, 1H), 4.01-3.97 (m, 1H), 3.40 (s, 3H), 3.24-3.12 (m, 2H), 2.49-2.36 (m 6H), 1.65-1.54 (m, 4H).

Example 98: Synthesis of Compound 130: (2S)—N-[(1S)-1-cyano-2-[4-(3-methyl-2-oxo-1,3-benzoxazol-5-yl)phenyl]ethyl]-3-[ethyl(methyl)amino]-2-methoxypropanamide

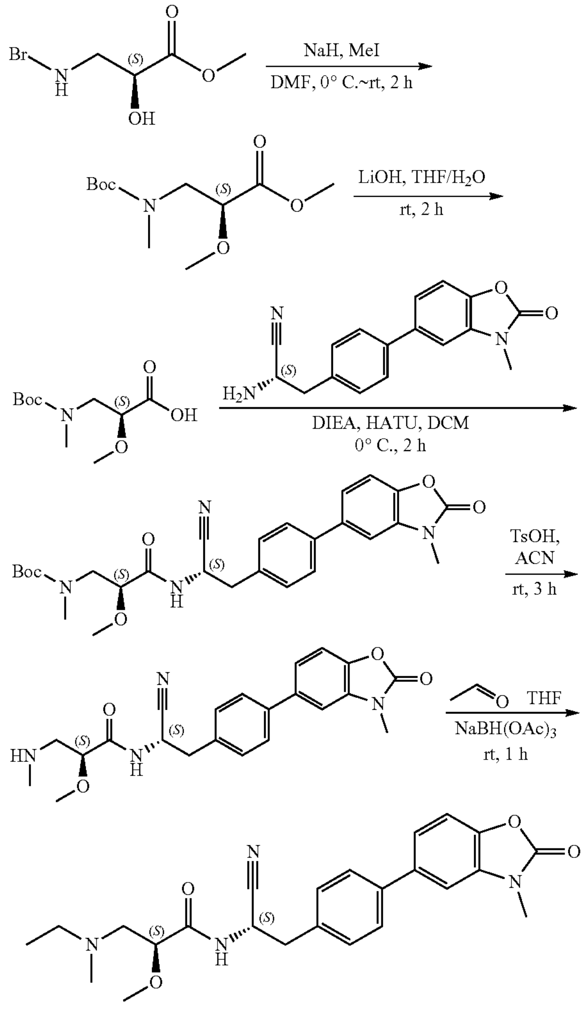

Compound 130

Synthesis of methyl (2S)-3-[(tert-butoxycarbonyl)(methyl)amino]-2-methoxypropanoate

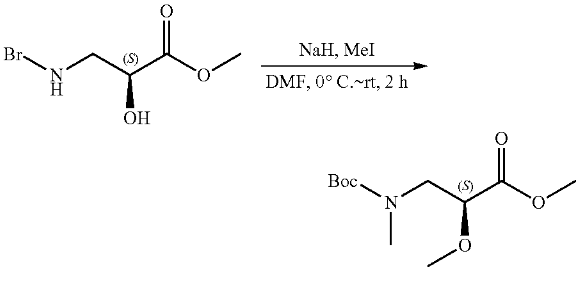

To a stirred solution of methyl (2S)-3-[(tert-butoxycarbonyl)amino]-2-hydroxypropanoate (1.1 g, 5.01 mmol, 1.0 equiv) in DMF (10 mL) was added NaH (802 mg, 20.04 mmol, 4.0 equiv)(60% in mineral oil) at 0° C. under nitrogen atmosphere. The resulting mixture was stirred at 0° C. for 1 h under nitrogen atmosphere. To the above mixture was added $CH_3I$ (2.85 g, 20.06 mmol, 4.0 equiv) dropwise at 0° C. The resulting mixture was stirred at room temperature for additional 2 h. The reaction was quenched by the addition of water (30 mL) at room temperature. The resulting mixture was extracted with EtOAc (3×50 mL). The combined organic layer was washed with brine (3×50 mL), dried over anhydrous $Na_2SO_4$. After filtration, the filtrate was concentrated under reduced pressure. The residue was purified by silica gel column chromatography, eluted with PE/THE (5:1) to afford methyl (2S)-3-[(tert-butoxycarbonyl)(methyl)amino]-2-methoxypropanoate (1.1 g, 88% yield, 90% purity). LCMS (ES, m z): $[M+H]^+$: 248.

Synthesis of (2S)-3-[(tert-butoxycarbonyl)(methyl)amino]-2-methoxypropanoic acid

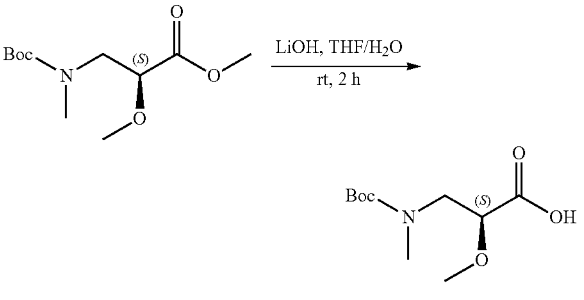

To a stirred solution of methyl (2S)-3-[(tert-butoxycarbonyl)(methyl)amino]-2-methoxypropanoate (1.1 g, 4.44 mmol, 1.0 equiv) in THE (12 mL) was added $LiOH·H_2O$ (0.56 g, 13.34 mmol, 3.0 equiv) in $H_2O$ (4 mL) dropwise at room temperature. The resulting mixture was stirred at room temperature for 2 h. The mixture was acidified to pH 3 with HCl (aq.). The resulting mixture was extracted with EtOAc (5×100 mL). The combined organic layer was dried over anhydrous $Na_2SO_4$. After filtration, the filtrate was concentrated under reduced pressure. The crude product was used in the next step directly without further purification. This resulted in (2S)-3-[(tert-butoxycarbonyl)(methyl)amino]-2-methoxypropanoic acid (400 mg). LCMS (ES, m z): $[M+H]^+$: 234.

Synthesis of tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]—N-methylcarbamate

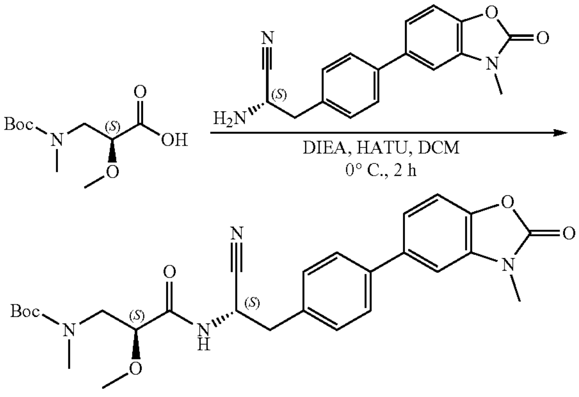

To a stirred solution of (2S)-3-[(tert-butoxycarbonyl)(methyl)amino]-2-methoxypropanoic acid (178 mg, 0.76 mmol, 1.5 equiv) and (2S)-2-amino-3-[4-(3-methyl-2-oxo-1,3-benzoxazol-5-yl)phenyl]propanenitrile (150 mg, 0.51 mmol, 1.0 equiv), and DIEA (198 mg, 1.53 mmol, 3.0 equiv) in DCM (10 mL) was added HATU (233 mg, 0.61 mmol, 1.2 equiv) at 0° C. The resulting mixture was stirred at 0° C. for 1 h. The reaction was concentrated under reduced pressure. The residue was purified by silica gel column chromatography, eluted with PE/THE (1:1) to afford tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]—N-methylcarbamate (160 mg, 61% yield, 90% purity). LCMS (ES, m z): $[M+H]^+$: 509.

Synthesis of (2S)—N-[(1S)-1-cyano-2-[4-(3-methyl-2-oxo-1,3-benzoxazol-5-yl)phenyl]ethyl]-2-methoxy-3-(methylamino)propanamide

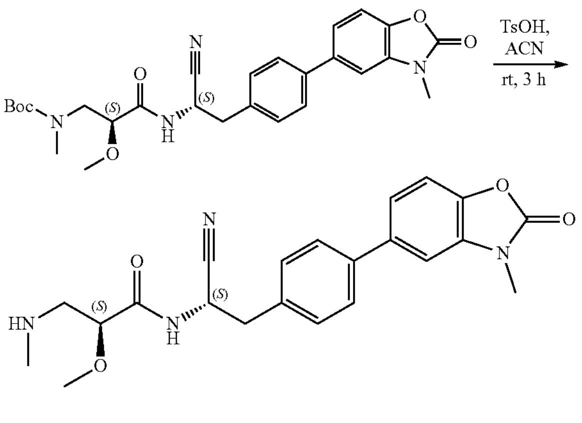

To a stirred solution of tert-butyl N-[(2S)-2-{[(1S)-1-cyano-2-[4-(3-methyl-2-oxo-1,3-benzoxazol-5-yl)phenyl]ethyl]carbamoyl}-2-methoxyethyl]—N-methylcarbamate (160 mg, 0.31 mmol, 1.0 equiv) in MeCN (5 mL) was added TsOH (162 mg, 0.94 mmol, 3.0 equiv) at room temperature. The resulting mixture was stirred at room temperature for 3 h. The mixture was acidified to pH 8 with saturated $NaHCO_3$ (aq.). The resulting mixture was extracted with EtOAc (3×30 mL). The combined organic layer was dried over anhydrous $Na_2SO_4$. After filtration, the filtrate was concentrated under reduced pressure. The crude product was used in the next step directly without further purification. This resulted in (2S)—N-[(1S)-1-cyano-2-[4-(3-methyl-2-oxo-1,3-benzoxazol-5-yl)phenyl]ethyl]-2-methoxy-3-(methylamino)propanamide (125 mg). LCMS (ES, m z): $[M+H]^+$: 409.

Synthesis of (2S)—N-[(1S)-1-cyano-2-[4-(3-methyl-2-oxo-1,3-benzoxazol-5-yl)phenyl]ethyl]-3-[ethyl(methyl)amino]-2-methoxypropanamide

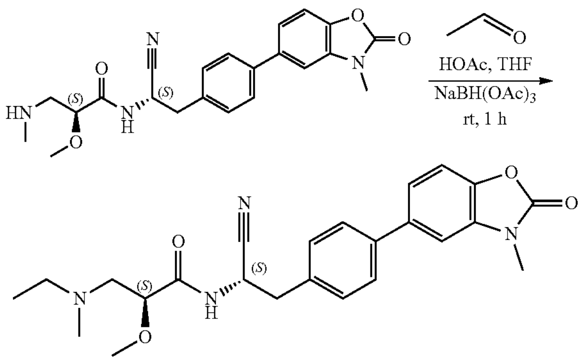

To a stirred solution of (2S)—N-[(1S)-1-cyano-2-[4-(3-methyl-2-oxo-1,3-benzoxazol-5-yl)phenyl]ethyl]-2-methoxy-3-(methylamino)propanamide (130 mg, 0.31 mmol, 1.0 equiv) and acetaldehyde (140 mg, 3.18 mmol, 10.0 equiv) in THF (5 mL) were added AcOH (4 mg, 0.06 mmol, 0.2 equiv) and sodium bis(acetyloxy)boranuidyl acetate (134 mg, 0.63 mmol, 2.0 equiv) at room temperature. The resulting mixture was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 15 min; detector, UV 254 nm. This resulted in (2S)—N-[(1S)-1-cyano-2-[4-(3-methyl-2-oxo-1,3-benzoxazol-5-yl)phenyl]ethyl]-3-[ethyl(methyl)amino]-2-methoxypropanamide (17 mg, 12% yield, 99.10% purity).

LCMS (ES, m z): $[M+H]^+$: 437.1

$^1$H NMR (400 MHz, DMSO-$d_6$): δ 8.81 (d, J=8.4 Hz, 1H), 7.69-7.62 (m, 2H), 7.56 (t, J=1.2 Hz, 1H), 7.44-7.37 (m, 4H), 5.12-5.09 (m, 1H), 3.70 (dd, J=6.6, 4.9 Hz, 1H), 3.41 (s, 3H), 3.28-3.11 (m, 5H), 2.42-2.24 (m, 4H), 2.11 (s, 3H), 0.87 (t, J=7.1 Hz, 3H).

Example 99: Synthesis of Compound 141: (2S)—N-[(1S)-1-cyano-2-[2-fluoro-4-(3-methyl-1,2,3-benzotriazol-5-yl)phenyl]ethyl]-3-(dimethylamino)-2-hydroxypropanamide

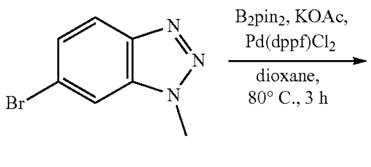

-continued

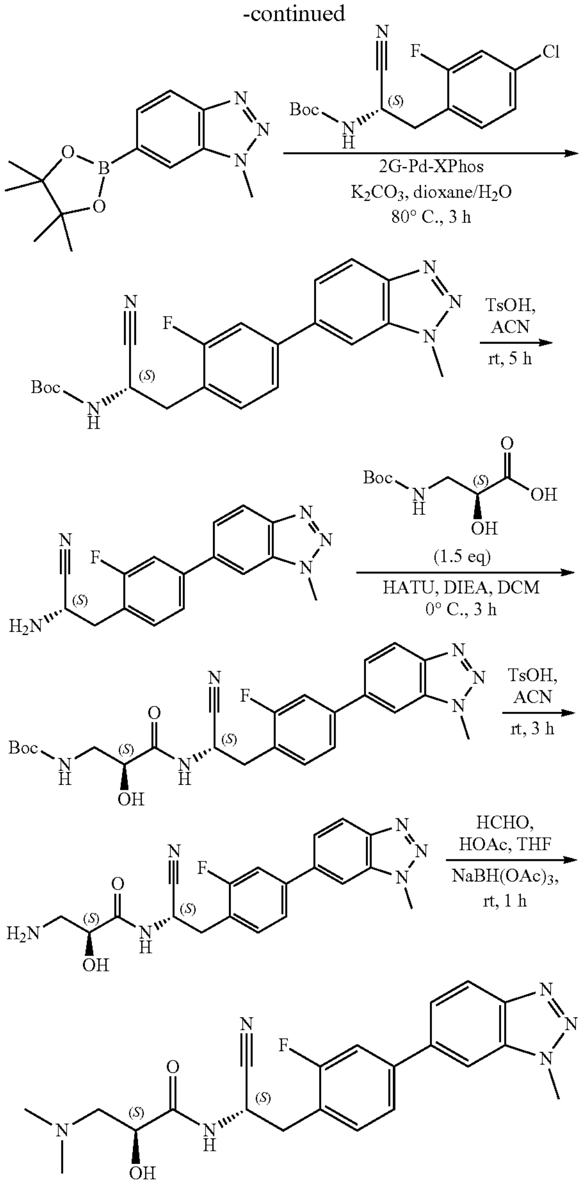

Compound 141

Synthesis of 1-methyl-6-(4,4,5,5-tetramethyl-1,3,2-dioxaborolan-2-yl)-1,2,3-benzotriazole

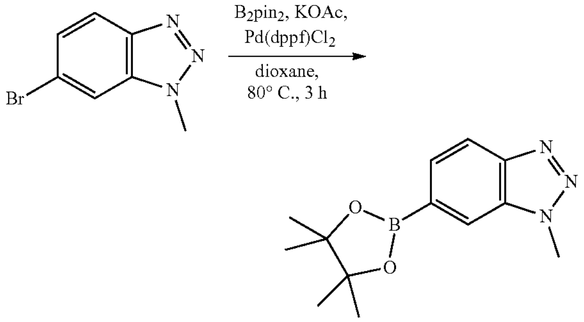

To a mixture of 6-bromo-1-methyl-1,2,3-benzotriazole (550 mg, 2.59 mmol, 1.0 equiv) and bis(pinacolato)diboron (790 mg, 3.11 mmol, 1.2 equiv), and AcOK (0.51 g, 5.18 mmol, 2.0 equiv) in 1,4-dioxane (10 mL) was added $Pd(dppf)Cl_2CH_2Cl_2$ (0.21 g, 0.25 mmol, 0.1 equiv). The reaction mixture was stirred at 80° C. for 3 h under nitrogen atmosphere. Concentrated under reduced pressure, the residue was purified by silica gel column chromatography, eluted with PE/THE (1:1) to afford 1-methyl-6-(4,4,5,5-tetramethyl-1,3,2-dioxaborolan-2-yl)-1,2,3-benzotriazole (600 mg, 89% yield, 90% purity). LCMS (ES, m z): $[M+H]^+$: 260.

Synthesis of tert-butyl N-[(1S)-1-cyano-2-(2-fluoro-4-{3-[2-(morpholin-4-yl)ethyl]-2-oxo-1,3-benzoxazol-5-yl}phenyl)ethyl]carbamate

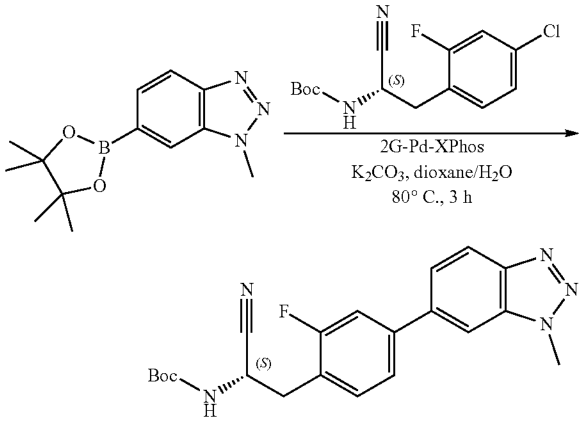

To a mixture of 3-[2-(morpholin-4-yl)ethyl]-5-(4,4,5,5-tetramethyl-1,3,2-dioxaborolan-2-yl)-1,3-benzoxazol-2-one (626 mg, 1.67 mmol, 1.0 equiv) and tert-butyl N-[(1S)-2-(4-chloro-2-fluorophenyl)-1-cyanoethyl]carbamate (576 mg, 1.93 mmol, 1.0 equiv) in 1,4-dioxane (11 mL) was added XPhos Pd G2 (151 mg, 0.19 mmol, 0.1 equiv). The reaction mixture was stirred at 80° C. for 3 h under nitrogen atmosphere. The reaction was cooled to room temperature, concentrated to remove the solvent. The residue was purified by silica gel column chromatography, eluted with PE/THE (1:1) to afford tert-butyl N-[(1S)-1-cyano-2-(2-fluoro-4-{3-[2-(morpholin-4-yl)ethyl]-2-oxo-1,3-benzoxazol-5-yl}phenyl)ethyl]carbamate (720 mg, 84% yield, 90% purity). LCMS (ES, m z): $[M+H]^+$: 396.

Synthesis of (2S)-2-amino-3-[2-fluoro-4-(3-methyl-1,2,3-benzotriazol-5-yl)phenyl]propanenitrile

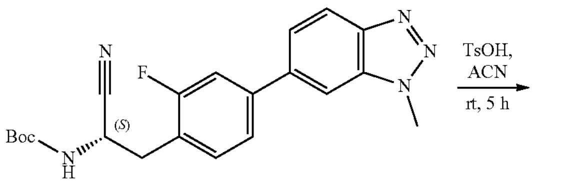

-continued

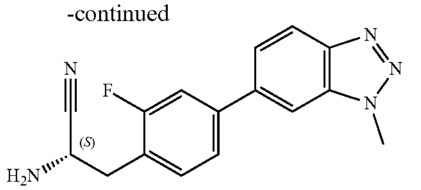

Into a mL round-bottom flask were added tert-butyl N-[(1S)-1-cyano-2-[2-fluoro-4-(3-methyl-1,2,3-benzotriazol-5-yl)phenyl]ethyl]carbamate (500 mg, 1.26 mmol, 1 equiv) in MeCN (21 mL) and TsOH (653 mg, 3.79 mmol, 3.0 equiv) at room temperature. The resulting mixture was stirred at room temperature for additional 6 h. The mixture was basified to pH 8 with saturated $NaHCO_3$ (aq.). The resulting mixture was extracted with EtOAc (3×50 mL). The combined organic layers were washed with brine (3×30 mL), dried over anhydrous $Na_2SO_4$. The residue was purified by silica gel column chromatography, eluted with PE/THE (1:2) to afford (2S)-2-amino-3-[2-fluoro-4-(3-methyl-1,2,3-benzotriazol-5-yl)phenyl]propanenitrile (300 mg, 80.34% yield, 90% purity). LCMS (ES, m z): $[M+H]^+$: 296.

Synthesis of tert-butyl N-[(2S)-2-{1[(1S)-1-cyano-2-[2-fluoro-4-(3-methyl-1,2,3-benzotriazol-5-yl) phenyl]ethyl]carbamoyl}-2-hydroxyethyl]carbamate

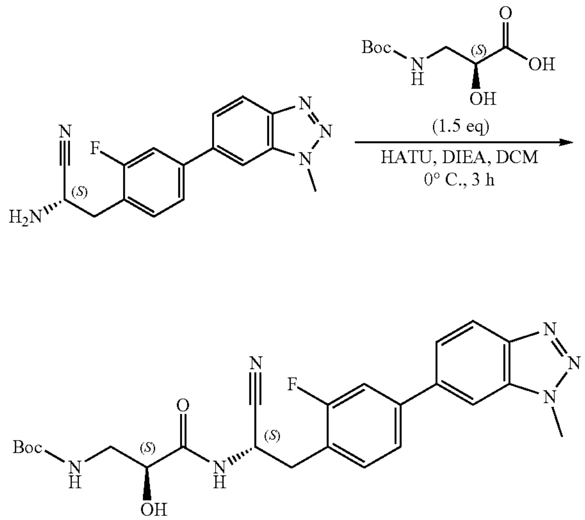

To a stirred solution of (2S)-2-amino-3-[2-fluoro-4-(3-methyl-1,2,3-benzotriazol-5-yl)phenyl]propanenitrile (200 mg, 0.67 mmol, 1.0 equiv) and (2S)-3-[(tert-butoxycarbonyl)amino]-2-hydroxypropanoic acid (208 mg, 1.01 mmol, 1.5 equiv) in DCM (10 mL) was added HATU (309 mg, 0.81 mmol, 1.2 equiv) at 0° C. The resulting mixture was stirred at 0° C. for 1 h. Concentrated to remove the solvent, the residue was purified by silica gel column chromatography, eluted with PE/THE (1:1) to afford tert-butyl N-[(2S)-2-{[(1S)-1-cyano-2-[2-fluoro-4-(3-methyl-1,2,3-benzotriazol-5-yl)phenyl]ethyl]carbamoyl}-2-hydroxyethyl]carbamate (150 mg, 46% yield, 90% purity). LCMS (ES, m z): $[M+H]^+$: 483.

Synthesis of (2S)-3-amino-N-[(1S)-1-cyano-2-[2-fluoro-4-(3-methyl-1,2,3-benzotriazol-5-yl)phenyl] ethyl]-2-hydroxypropanamide

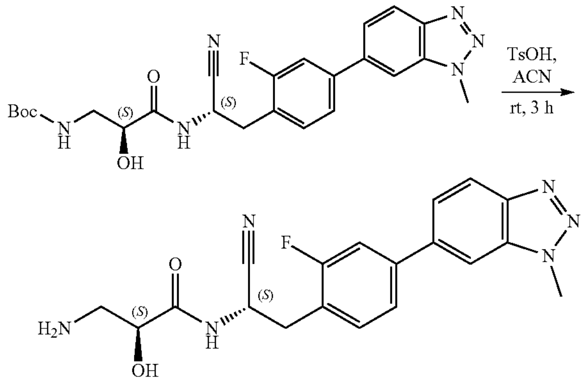

To a stirred solution of tert-butyl N-[(2S)-2-{[(1S)-1-cyano-2-[2-fluoro-4-(3-methyl-1,2,3-benzotriazol-5-yl)phenyl]ethyl]carbamoyl}-2-hydroxyethyl]carbamate (150 mg, 0.31 mmol, 1.0 equiv) in MeCN (5 mL) was added TsOH (160 mg, 0.93 mmol, 3.0 equiv) at room temperature. The resulting mixture was stirred at room temperature for 3 h. The mixture was acidified to pH 8 with saturated $NaHCO_3$ (aq.). The resulting mixture was extracted with EtOAc (3×30 mL). The combined organic layer was dried over anhydrous $Na_2SO_4$. After filtration, the filtrate was concentrated under reduced pressure. The crude product was used in the next step directly without further purification. This resulted in (2S)-3-amino-N-[(1S)-1-cyano-2-[2-fluoro-4-(3-methyl-1,2,3-benzotriazol-5-yl)phenyl]ethyl]-2-hydroxypropanamide (130 mg). LCMS (ES, m z): $[M+H]^+$: 383.

Synthesis of (2S)—N-[(1S)-1-cyano-2-[2-fluoro-4-(3-methyl-1,2,3-benzotriazol-5-yl)phenyl]ethyl]-3-(dimethylamino)-2-hydroxypropanamide

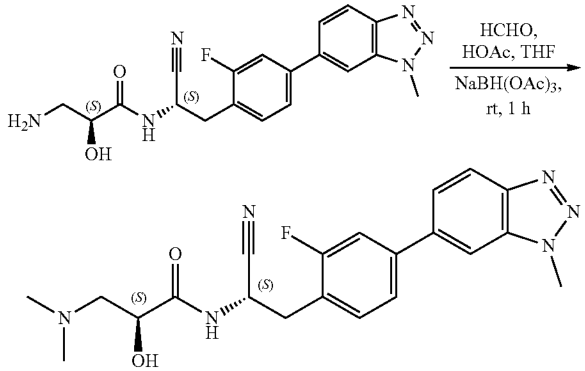

To a stirred solution of (2S)-3-amino-N-[(1S)-1-cyano-2-[2-fluoro-4-(3-methyl-1,2,3-benzotriazol-5-yl)phenyl] ethyl]-2-hydroxypropanamide (130 mg, 0.34 mmol, 1.0 equiv) and Formaldehyde solution (102 mg, 3.40 mmol, 10.0 equiv, 30% in water), Acetic acid (2.04 mg, 0.03 mmol, 0.1 equiv) in THF (5 mL) was added sodium bis(acetyloxy) boranuidyl acetate (144 mg, 0.68 mmol, 2.0 equiv) at room temperature. The resulting mixture was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 15 min; detector, UV 254 nm. This resulted in (2S)—N-[(1S)-1-cyano-2-[2-fluoro-4-(3-methyl-1,2,3-benzotriazol-5-yl)phenyl]ethyl]-3-(dimethylamino)-2-hydroxypropanamide (20 mg, 14% yield, 99% purity).

LCMS (ES, m z): $[M+H]^+$: 411.2

$^1$H NMR (400 MHz, DMSO-$d_6$): δ 8.83 (br, 1H), 8.24 (d, J=1.6 Hz, 1H), 8.10 (d, J=8.7 Hz, 1H), 7.77 (dd, J=8.8, 1.6 Hz, 1H), 7.73-7.61 (m, 2H), 7.52 (t, J=7.9 Hz, 1H), 5.68 (br, 1H), 5.10 (t, J=7.9 Hz, 1H), 4.36 (s, 3H), 4.01 (dd, J=7.7, 4.0 Hz, 1H), 3.31-3.18 (m, 2H), 2.41-2.24 (m, 2H), 2.12 (s, 6H).

Example 100: Synthesis of Compound 142: (2S)—N-[(1S)-1-cyano-2-(2-fluoro-4-{3-[2-(morpholin-4-yl)ethyl]-2-oxo-1,3-benzoxazol-5-yl}phenyl)ethyl]-3-(dimethylamino)-2-hydroxypropanamide

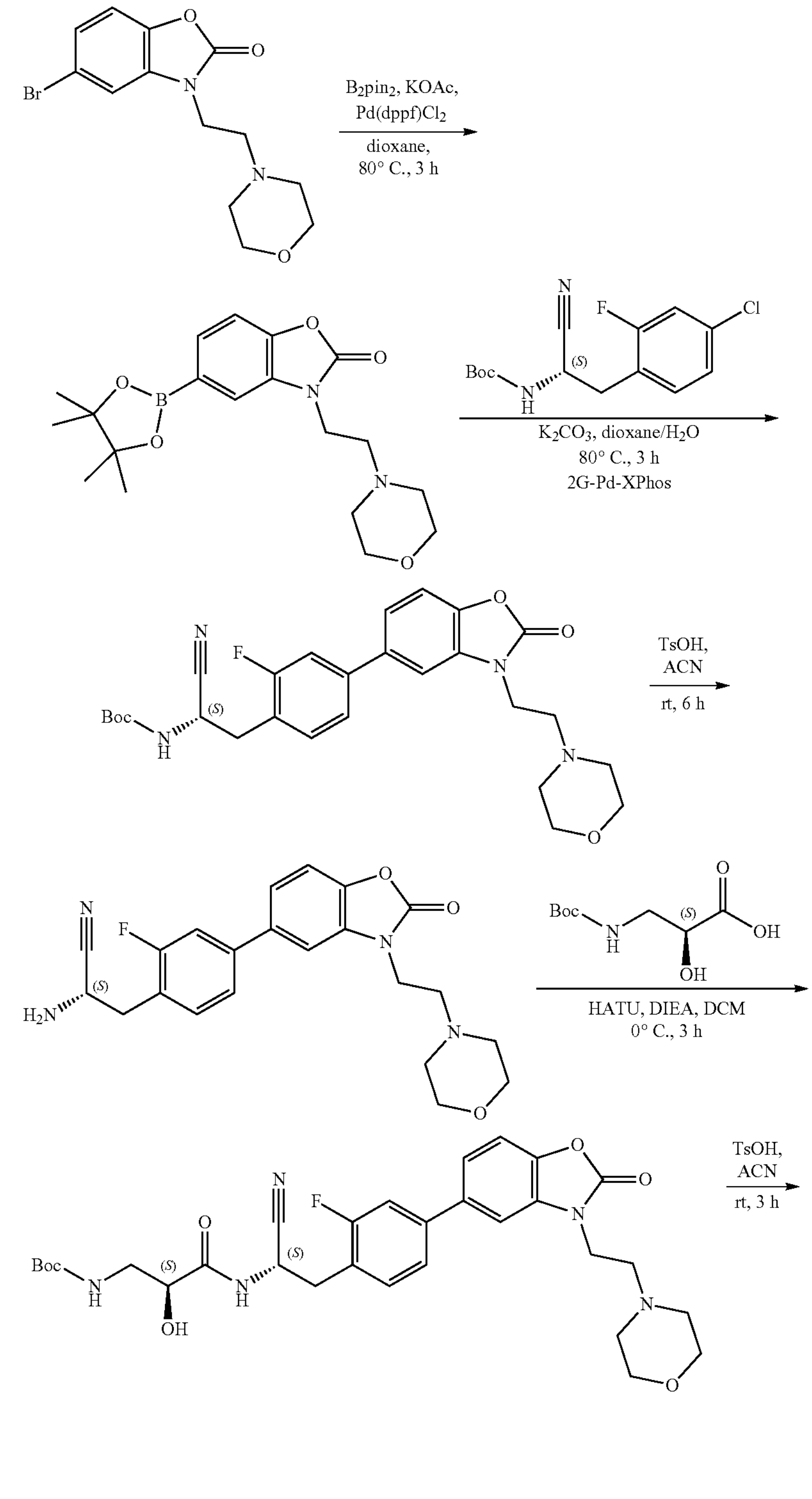

-continued

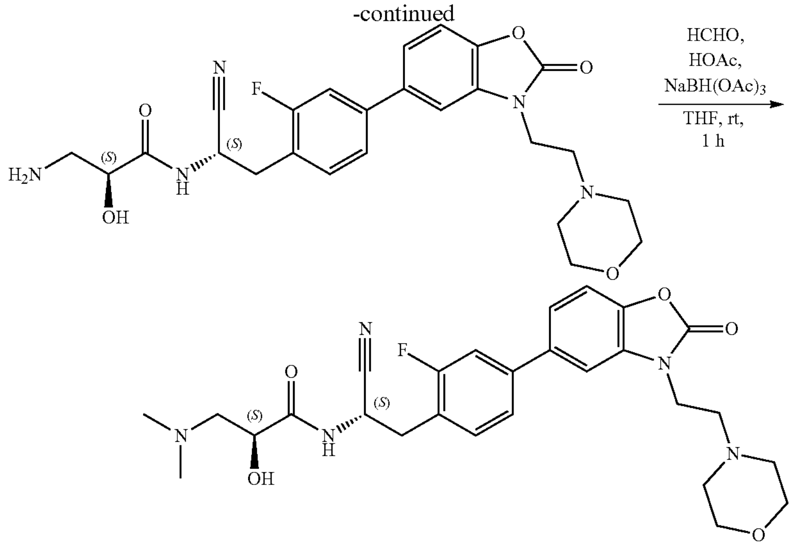

Compound 142

Synthesis of 3-[2-(morpholin-4-yl)ethyl]-5-(4,4,5,5-tetramethyl-1,3,2-dioxaborolan-2-yl)-1,3-benzoxazol-2-one

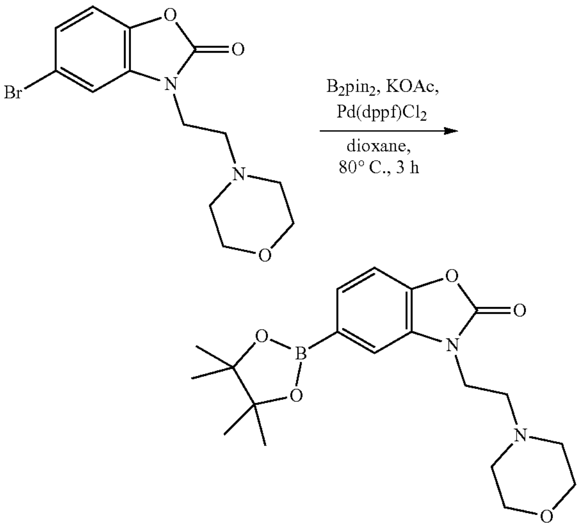

To a solution of 5-bromo-3-[2-(morpholin-4-yl)ethyl]-1,3-benzoxazol-2-one (1.0 g, 3.06 mmol, 1.0 equiv) and bis(pinacolato)diboron (0.93 g, 3.67 mmol, 1.2 equiv) in 1,4-dioxane (10 mL) were added $Pd(dppf)Cl_2CH_2Cl_2$ (0.25 g, 0.31 mmol, 0.1 equiv) and AcOK (0.60 g, 6.11 mmol, 2.0 equiv). The mixture was stirred at 80° C. for 3 h under nitrogen atmosphere. The reaction was cooled to room temperature, concentrated to remove the solvent. The residue was purified by silica gel column chromatography, eluted with PE/THF (1:1) to afford 3-[2-(morpholin-4-yl)ethyl]-5-(4,4,5,5-tetramethyl-1,3,2-dioxaborolan-2-yl)-1,3-benzoxazol-2-one (1.0 g, 87.4% yield, 95% purity). LCMS (ES, m/z): $[M+H]^+$: 375.

Synthesis of tert-butyl N-[(1S)-1-cyano-2-(2-fluoro-4-{3-[2-(morpholin-4-yl)ethyl]-2-oxo-1,3-benzoxazol-5-yl}phenyl)ethyl]carbamate

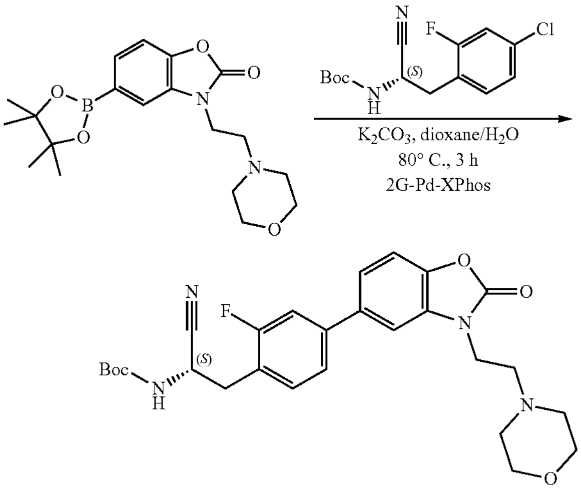

A mixture of 3-[2-(morpholin-4-yl)ethyl]-5-(4,4,5,5-tetramethyl-1,3,2-dioxaborolan-2-yl)-1,3-benzoxazol-2-one (626 mg, 1.67 mmol, 1.0 equiv) and tert-butyl N-[(1S)-2-(4-chloro-2-fluorophenyl)-1-cyanoethyl]carbamate (500 mg, 1.67 mmol, 1.00 equiv), XPhos Pd G2 (131 mg, 0.17 mmol, 0.1 equiv) in 1,4-dioxane (10 mL) was stirred at 80° C. for 3 h under nitrogen atmosphere. The reaction was cooled to room temperature, concentrated to remove the solvent. The residue was purified by silica gel column chromatography, eluted with PE/THE (1:1) to afford tert-butyl N-[(1S)-1-cyano-2-(2-fluoro-4-{3-[2-(morpholin-4-yl)ethyl]-2-oxo-1,3-benzoxazol-5-yl}phenyl)ethyl]carbamate (720 mg, 84% yield, 90% purity). LCMS (ES, m/z): $[M+H]^+$: 511.

Synthesis of (2S)-2-amino-3-(2-fluoro-4-{3-[2-(morpholin-4-yl)ethyl]-2-oxo-1,3-benzoxazol-5-yl}phenyl)propanenitrile

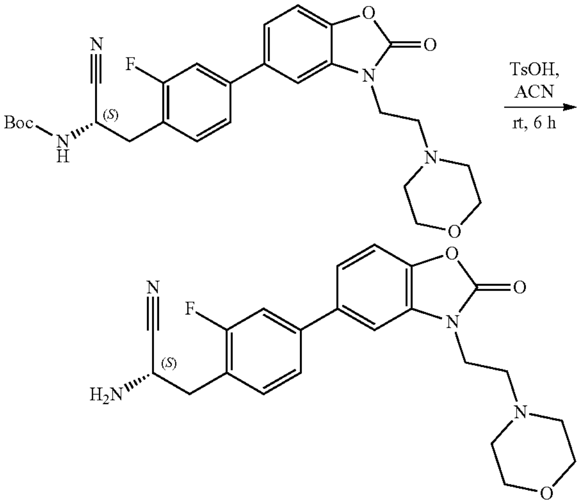

Into a 100 mL round-bottom flask were added tert-butyl N-[(1S)-1-cyano-2-(2-fluoro-4-{3-[2-(morpholin-4-yl) ethyl]-2-oxo-1,3-benzoxazol-5-yl}phenyl)ethyl]carbamate (720 mg, 1.41 mmol, 1.0 equiv), MeCN (21 mL) and TsOH (728 mg, 4.23 mmol, 3.0 equiv) at room temperature. The resulting mixture was stirred at room temperature for 6 h. The mixture was basified to pH 8 with saturated $NaHCO_3$ (aq.). The resulting mixture was extracted with EtOAc (3x50 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/THE (1:2) to afford (2S)-2-amino-3-(2-fluoro-4-{3-[2-(morpholin-4-yl)ethyl]-2-oxo-1, 3-benzoxazol-5-yl}phenyl)propanenitrile (450 mg, 77.8% yield, 95% purity). LCMS (ES, m/z): $[M+H]^+$: 411.

Synthesis of tert-butyl N-[(2S)-2-{[(1S)-1-cyano-2-(2-fluoro-4-{3-[2-(morpholin-4-yl)ethyl]-2-oxo-1,3-benzoxazol-5-yl}phenyl)ethyl]carbamoyl}-2-hydroxyethyl]carbamate

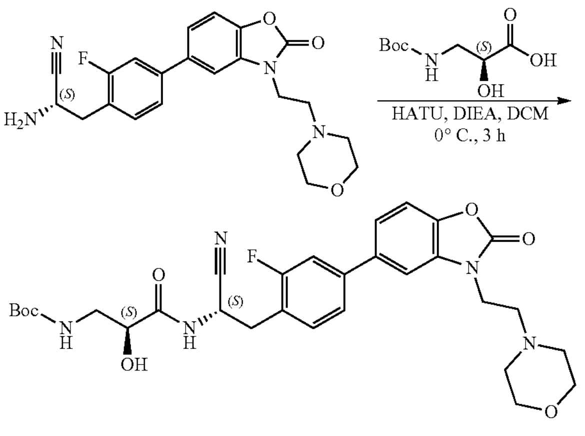

To a stirred solution of (2S)-2-amino-3-(2-fluoro-4-{3-[2-(morpholin-4-yl)ethyl]-2-oxo-1,3-benzoxazol-5-yl}phenyl) propanenitrile (200 mg, 0.48 mmol, 1.0 equiv) and (2S)-3-[(tert-butoxycarbonyl)amino]-2-hydroxypropanoic acid (149 mg, 0.73 mmol, 1.5 equiv), DIEA (188 mg, 1.46 mmol, 3.0 equiv) in DCM (5 mL) was added HATU (222 mg, 0.584 mmol, 1.2 equiv) in portions at 0° C. Concentrated to remove the solvent, the residue was purified by silica gel column chromatography, eluted with PE/EA (1:2) to afford tert-butyl N-[(2S)-2-{[(1S)-1-cyano-2-(2-fluoro-4-{3-[2-(morpholin-4-yl)ethyl]-2-oxo-1,3-benzoxazol-5-yl}phenyl) ethyl]carbamoyl}-2-hydroxyethyl]carbamate (160 mg, 55% yield, 92% purity). LCMS (ES, m/z): $[M+H]^+$: 598.

Synthesis of (2S)-3-amino-N-[(1S)-1-cyano-2-(2-fluoro-4-{3-[2-(morpholin-4-yl)ethyl]-2-oxo-1,3-benzoxazol-5-yl}phenyl)ethyl]-2-hydroxypropanamide

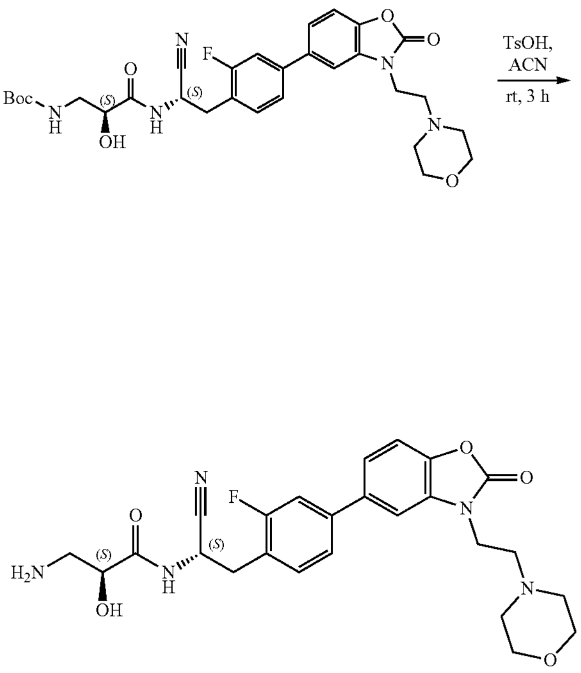

Into a 50 mL round-bottom flask were added tert-butyl N-[(2S)-2-{[(1S)-1-cyano-2-(2-fluoro-4-{3-[2-(morpholin-4-yl)ethyl]-2-oxo-1,3-benzoxazol-5-yl}phenyl)ethyl]carbamoyl}-2-hydroxyethyl]carbamate (160 mg, 0.27 mmol, 1.0 equiv), MeCN (4 mL) and TsOH (138 mg, 0.80 mmol, 3.0 equiv) at room temperature. The resulting mixture was stirred at room temperature for additional 3 h. The mixture was basified to pH 8 with saturated $NaHCO_3$ (aq.). The resulting mixture was extracted with EtOAc (3x20 mL). The combined organic layer was washed with brine (3x20 mL), dried over anhydrous $Na_2SO_4$. After filtration, the filtrate was concentrated under reduced pressure. This resulted in (2S)-3-amino-N-[(1S)-1-cyano-2-(2-fluoro-4-{3-[2-(morpholin-4-yl)ethyl]-2-oxo-1,3-benzoxazol-5-yl}phenyl) ethyl]-2-hydroxypropanamide (150 mg). The crude product was used in the next step directly without further purification. LCMS (ES, m/z): $[M+H]^+$: 498.

Synthesis of (2S)—N-[(1S)-1-cyano-2-(2-fluoro-4-{3-[2-(morpholin-4-yl)ethyl]-2-oxo-1,3-benzoxazol-5-yl}phenyl)ethyl]-3-(dimethylamino)-2-hydroxy-propanamide

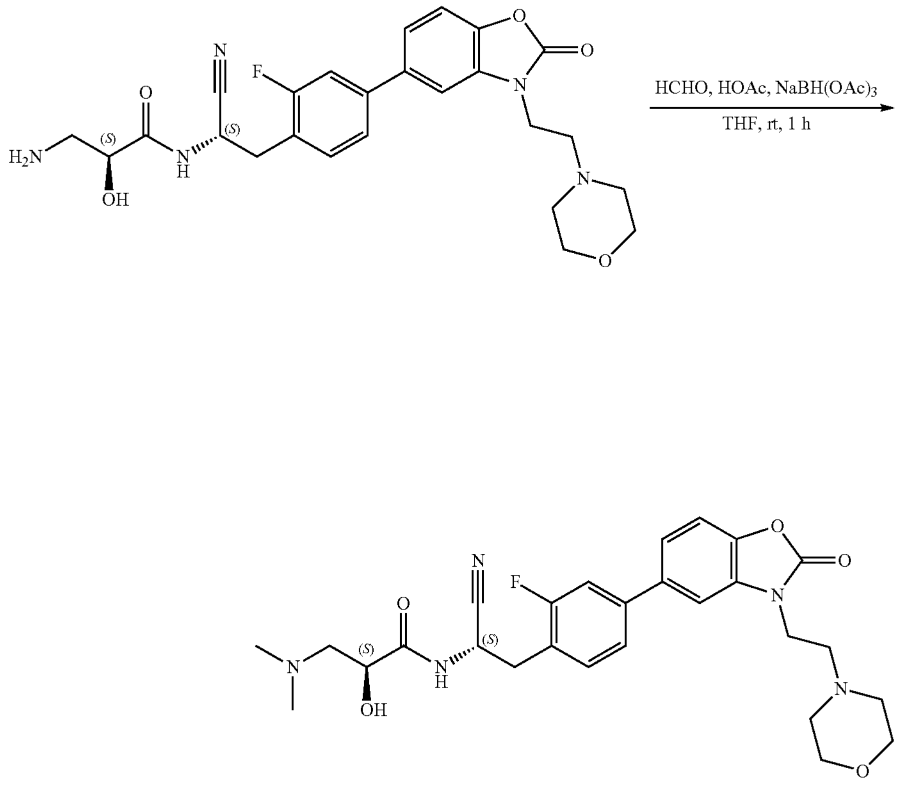

A solution of (2S)-3-amino-N-[(1S)-1-cyano-2-(2-fluoro-4-{3-[2-(morpholin-4-yl)ethyl]-2-oxo-1,3-benzoxazol-5-yl}phenyl)ethyl]-2-hydroxypropanamide (150 mg, 0.30 mmol, 1.0 equiv) and HOAc (0.1 mL), HCHO (238 mg, 3.01 mmol, 10 equiv, 38% in $H_2O$), $NaBH(OAc)_3$ (127 mg, 0.60 mmol, 2.0 equiv) in THF (3 mL) was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (2S)—N-[(1S)-1-cyano-2-(2-fluoro-4-{3-[2-(morpholin-4-yl)ethyl]-2-oxo-1,3-benzoxazol-5-yl}phenyl)ethyl]-3-(dimethyl-amino)-2-hydroxypropanamide (20.5 mg, 13% yield, 98% purity).

LCMS (ES, m/z): $[M+H]^+$: 526.2.

$^1H$ NMR (400 MHz, DMSO-$d_6$) δ 8.84 (brs, 1H), 7.71 (d, J=1.8 Hz, 1H), 7.60 (dd, J=11.6, 1.8 Hz, 1H), 7.55 (dd, J=8.0, 1.9 Hz, 1H), 7.51-7.38 (m, 3H), 5.67 (br, 1H), 5.11-5.04 (m, 1H), 4.13-3.93 (m, 3H), 3.49 (t, J=4.5 Hz, 4H), 3.29-3.15 (m, 2H), 2.67 (t, J=6.2 Hz, 2H), 2.45 (t, J=4.5 Hz, 4H), 2.34-2.20 (m, 2H), 2.11 (s, 6H).

Example 101: Synthesis of Compound 144: (2S)—N-[(1S)-1-cyano-2-{4-[1'-(oxetan-3-yl)-3H-spiro[2-benzofuran-1,4'-piperidin]-6-yl]phenyl}ethyl]-3-(dimethylamino)-2-hydroxypropanamide

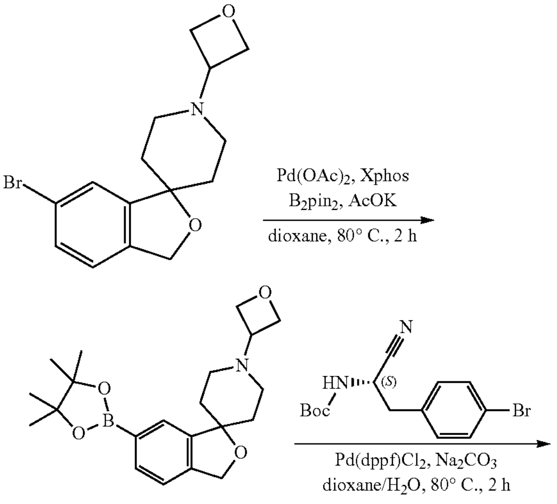

-continued

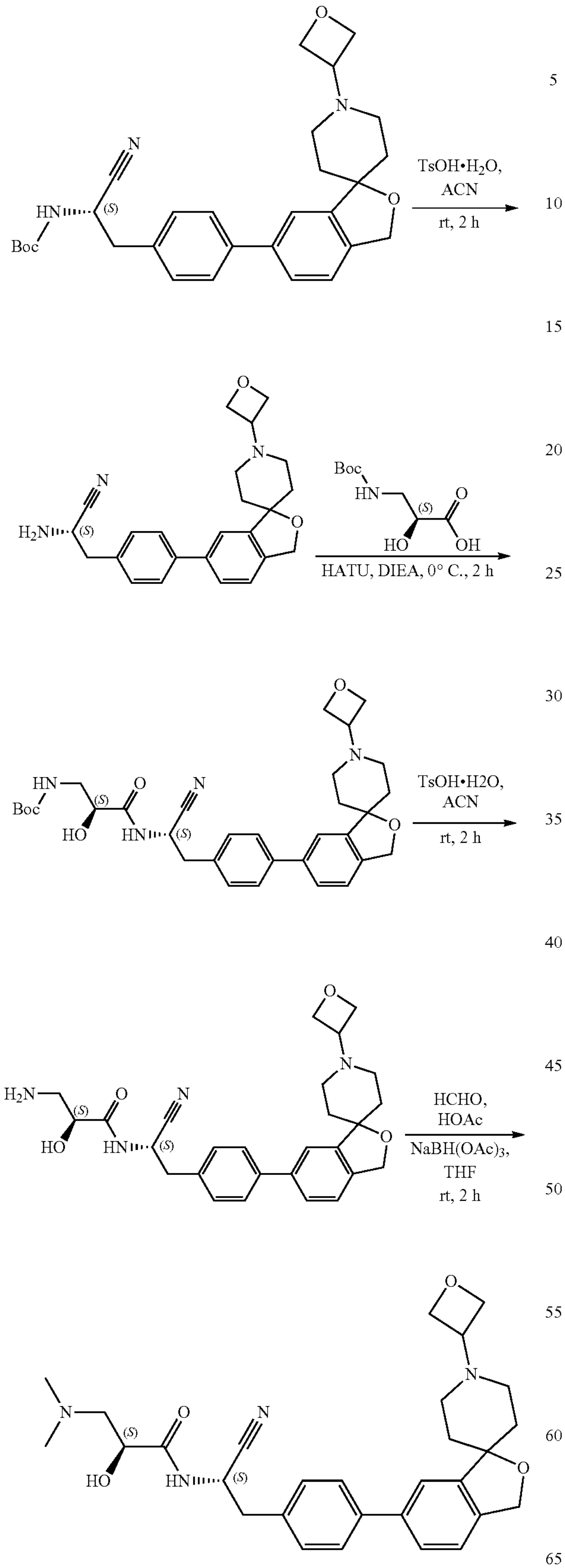

Synthesis of 1'-(oxetan-3-yl)-6-(4,4,5,5-tetramethyl-1,3,2-dioxaborolan-2-yl)-3H-spiro[2-benzofuran-1,4'-piperidine]

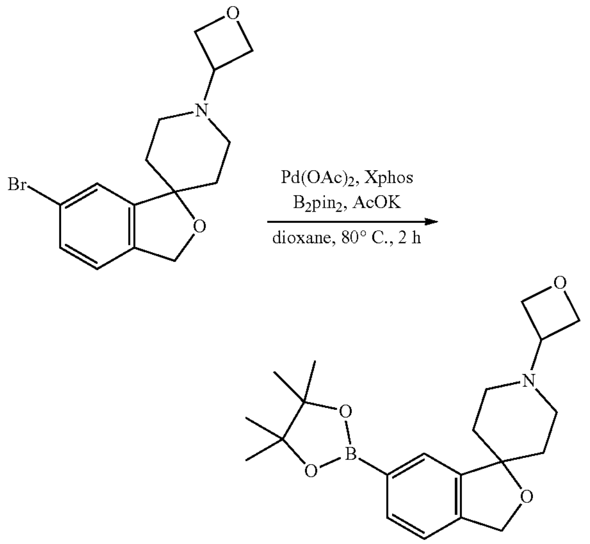

To a solution of 6-bromo-1'-(oxetan-3-yl)-3H-spiro[2-benzofuran-1,4'-piperidine](1.0 g, 3.08 mmol, 1.0 equiv), bis(pinacolato)diboron (939 mg, 3.70 mmol, 1.2 equiv) and AcOK (605 mg, 6.16 mmol, 2.0 equiv) in 1,4-dioxane (3 mL) was added $Pd(OAc)_2$ (69 mg, 0.31 mmol, 0.1 equiv) at room temperature. The resulting mixture stirred for 2 h at 80° C. under nitrogen atmosphere. The reaction was concentrated. The residue was purified by silica gel column chromatography, eluted with PE/THE (1:1) to afford 1'-(oxetan-3-yl)-6-(4,4,5,5-tetramethyl-1,3,2-dioxaborolan-2-yl)-3H-spiro[2-benzofuran-1,4'-piperidine](620 mg, 67.68% yield, 95% purity). LCMS (ES, m/z): $[M+H]^+$: 372.

Synthesis of N-[(1S)-1-cyano-2-{4-[1'-(oxetan-3-yl)-3H-spiro[2-benzofuran-1,4'-piperidin]-6-yl]phenyl}ethyl]carbamate

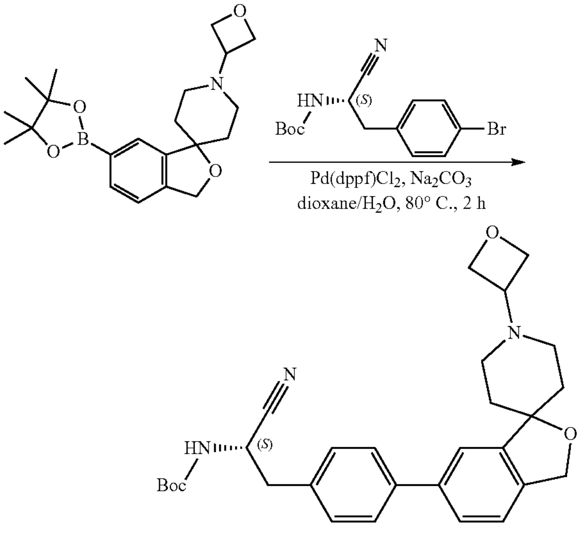

To a solution of 1'-(oxetan-3-yl)-6-(4,4,5,5-tetramethyl-1,3,2-dioxaborolan-2-yl)-3H-spiro[2-benzofuran-1,4'-piperidine](600 mg, 1.61 mmol, 1.0 equiv), tert-butyl N-[(1S)-2-(4-bromophenyl)-1-cyanoethyl]carbamate (525 mg, 1.61 mmol, 1.0 equiv) and $Na_2CO_3$ (342 mg, 3.23 mmol, 2.0 equiv) in 1,4-dioxane (12 mL) and $H_2O$ (1.2 mL) was added Pd(dppf)$Cl_2$ (118 mg, 0.16 mmol, 0.1 equiv) at room temperature. The resulting mixture stirred for 2 h at 80° C. under nitrogen atmosphere. The reaction was concentrated. The residue was purified by silica gel column chromatography, eluted with PE/THF (1:1) to afford tert-butyl N-[(1S)-1-cyano-2-{4-[1'-(oxetan-3-yl)-3H-spiro[2-benzofuran-1,4'-piperidin]-6-yl]phenyl}ethyl]carbamate (600 mg, 75.83% yield, 98% purity). LCMS (ES, m/z): $[M+H]^+$: 490.

Synthesis of (2S)-2-amino-3-{4-[1'-(oxetan-3-yl)-3H-spiro[2-benzofuran-1,4'-piperidin]-6-yl]phenyl}propanenitrile

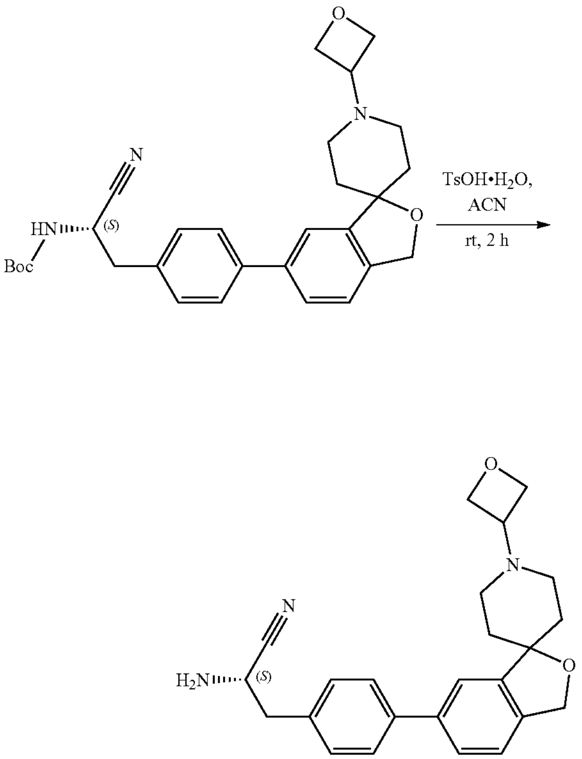

To a solution of tert-butyl N-[(1S)-1-cyano-2-{4-[1'-(oxetan-3-yl)-3H-spiro[2-benzofuran-1,4'-piperidin]-6-yl]phenyl}ethyl]carbamate (590 mg, 1.20 mmol, 1.0 equiv) in MeCN (6 mL, 114.14 mmol, 94.7 equiv) was added 4-methylbenzene-1-sulfonic acid hydrate (687 mg, 3.61 mmol, 3.0 equiv) at 0° C. The resulting mixture was stirred for 2 h at 0° C. to room temperature. The reaction mixture was adjusted pH to 8 with $NaHCO_3$ (5N), extracted with EtOAc (4x30 mL). The organic layer was concentrated. The residue was purified by silica gel column chromatography, eluted with PE/THE (10:1 to 1:2) to afford (2S)-2-amino-3-{4-[1'-(oxetan-3-yl)-3H-spiro[2-benzofuran-1,4'-piperidin]-6-yl]phenyl}propanenitrile (380 mg, 80.96% yield, 90% purity). LCMS (ES, m/z): $[M+H]^+$: 390.

Synthesis of tert-butyl N-[(2S)-2-{[(1S)-1-cyano-2-{4-[1'-(oxetan-3-yl)-3H-spiro[2-benzofuran-1,4'-piperidin]-6-yl]phenyl}ethyl]carbamoyl}-2-hydroxyethyl]carbamate

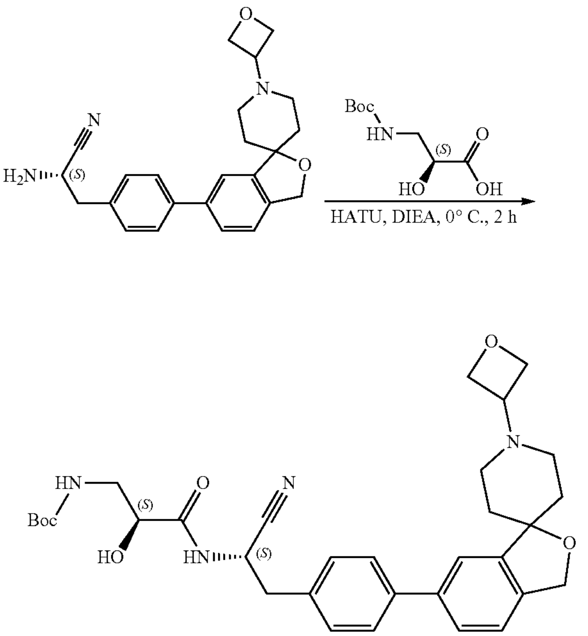

To a solution of (2S)-2-amino-3-{4-[1'-(oxetan-3-yl)-3H-spiro[2-benzofuran-1,4'-piperidin]-6-yl]phenyl}propanenitrile (200 mg, 0.51 mmol, 1.0 equiv), (2S)-3-[(tert-butoxycarbonyl)amino]-2-hydroxypropanoic acid (126 mg, 0.62 mmol, 1.2 equiv) and DIEA (199 mg, 1.54 mmol, 3.0 equiv) in DCM (4 mL) was added HATU (293 mg, 0.77 mmol, 1.5 equiv) at 0° C. The resulting mixture was stirred for 2 h at 0° C. The reaction was concentrated. The residue was purified by silica gel column chromatography, eluted with PE/THE (1:1) to afford tert-butyl N-[(2S)-2-{[(1S)-1-cyano-2-{4-[1'-(oxetan-3-yl)-3H-spiro[2-benzofuran-1,4'-piperidin]-6-yl]phenyl}ethyl]carbamoyl}-2-hydroxyethyl]carbamate (240 mg, 81.05% yield, 95% purity). LCMS (ES, m/z): $[M+H]^+$: 577.

Synthesis of (2S)-3-amino-N-[(1S)-1-cyano-2-{4-[1'-(oxetan-3-yl)-3H-spiro[2-benzofuran-1,4'-piperidin]-6-yl]phenyl}ethyl]-2-hydroxypropanamide

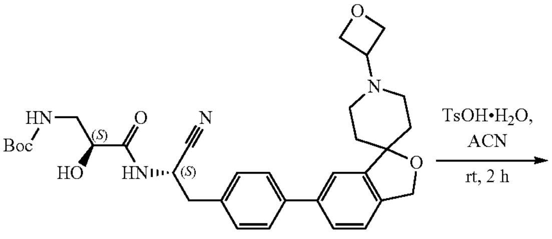

-continued

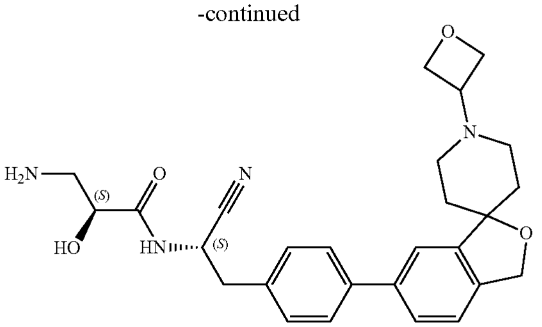

To a solution of tert-butyl N-[(2S)-2-{[(1S)-1-cyano-2-{4-[1'-(oxetan-3-yl)-3H-spiro[2-benzofuran-1,4'-piperidin]-6-yl]phenyl}ethyl]carbamoyl}-2-hydroxyethyl]carbamate (230 mg, 0.39 mmol, 1.0 equiv) in MeCN (4 mL) was added 4-methylbenzene-1-sulfonic acid hydrate (227 mg, 1.19 mmol, 3.0 equiv) at 0° C. The resulting mixture was stirred for 2 h at 0° C. to room temperature. The reaction mixture was adjusted pH to 8 with $NaHCO_3$ (5N), extracted with EtOAc (4×10 mL). The organic layer was concentrated. The residue was purified by silica gel column chromatography, eluted with PE/THE (10:1 to 1:2) to afford (2S)-3-amino-N-[(1S)-1-cyano-2-{4-[1'-(oxetan-3-yl)-3H-spiro[2-benzofuran-1,4'-piperidin]-6-yl]phenyl}ethyl]-2-hydroxypropanamide (120 mg, 63.13% yield, 98% purity). LCMS (ES, m/z): $[M+H]^+$: 477.

Synthesis of (2S)—N-[(1S)-1-cyano-2-{4-[1'-(oxetan-3-yl)-3H-spiro[2-benzofuran-1,4'-piperidin]-6-yl]phenyl}ethyl]-3-(dimethylamino)-2-hydroxypropanamide

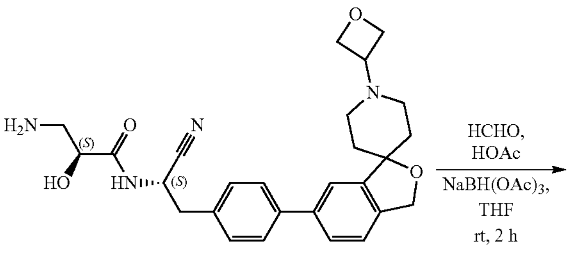

-continued

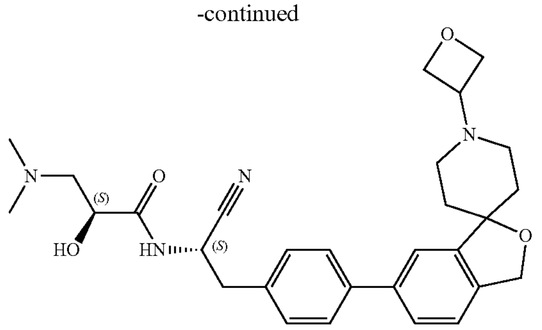

To a stirred solution of (2S)-3-amino-N-[(1S)-1-cyano-2-{4-[1'-(oxetan-3-yl)-3H-spiro[2-benzofuran-1,4'-piperidin]-6-yl]phenyl}ethyl]-2-hydroxypropanamide (110 mg, 0.23 mmol, 1.0 equiv) and Formaldehyde solution (182 mg, 2.30 mmol, 10.0 equiv, 38%) in THE (3 mL, 0.04 mmol, 0.2 equiv) were added AcOH (2 mg, 0.02 mmol, 0.1 equiv) and sodium bis(acetyloxy)boranuidyl acetate (97 mg, 0.46 mmol, 2.0 equiv) in portions at room temperature. The resulting mixture was stirred at room temperature for 2 h. The crude product was purified by Prep-HPLC with the following conditions (Column, XBridge Prep C18 OBD Column, 19*150 mm Sum; mobile phase, Water(0.1% $NH_3H_2O$) and ACN (10% PhaseB up to 80% in 20 min); Detector, UV 254 nm. This resulted in (2S)—N-[(1S)-1-cyano-2-{4-[1'-(oxetan-3-yl)-3H-spiro[2-benzofuran-1,4'-piperidin]-6-yl]phenyl}ethyl]-3-(dimethylamino)-2-hydroxypropanamide (33 mg, 28.33% yield, 99% purity).

LCMS (ES, m/z): $[M+H]^+$: 505.2

$^1H$ NMR (400 MHz, DMSO-$d_6$) δ 8.70 (d, J=8.6 Hz, 1H), 7.67 (d, J=8.1 Hz, 2H), 7.59-7.55 (m, 2H), 7.38-7.32 (m, 3H), 5.53 (s, 1H), 5.08-4.98 (m, 3H), 4.57 (t, J=6.4 Hz, 2H), 4.46 (t, J=6.1 Hz, 2H), 3.99 (dd, J=7.7, 4.1 Hz, 1H), 3.49-3.43 (m, 1H), 3.23-3.17 (m, 2H), 2.69-2.62 (m, 2H), 2.35-2.29 (m, 1H), 2.28-2.15 (m, 3H), 2.15-2.09 (m, 6H), 2.09-1.99 (m, 2H), 1.67 (d, J=12.8 Hz, 2H).

Example 102: Synthesis of Compound 145: (2S)—N-[(1S)-1-cyano-2-(4-{1,1'-dimethyl-2-oxospiro[indole-3,3'-piperidin]-5-yl}phenyl)ethyl]-3-(dimethylamino)-2-hydroxypropanamide

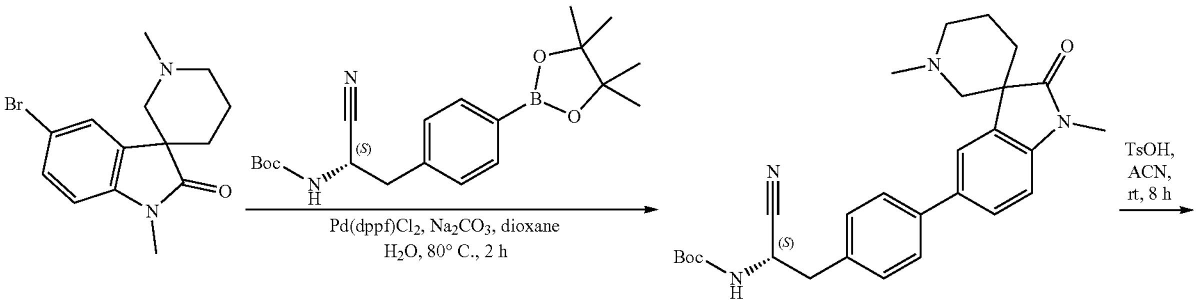

-continued

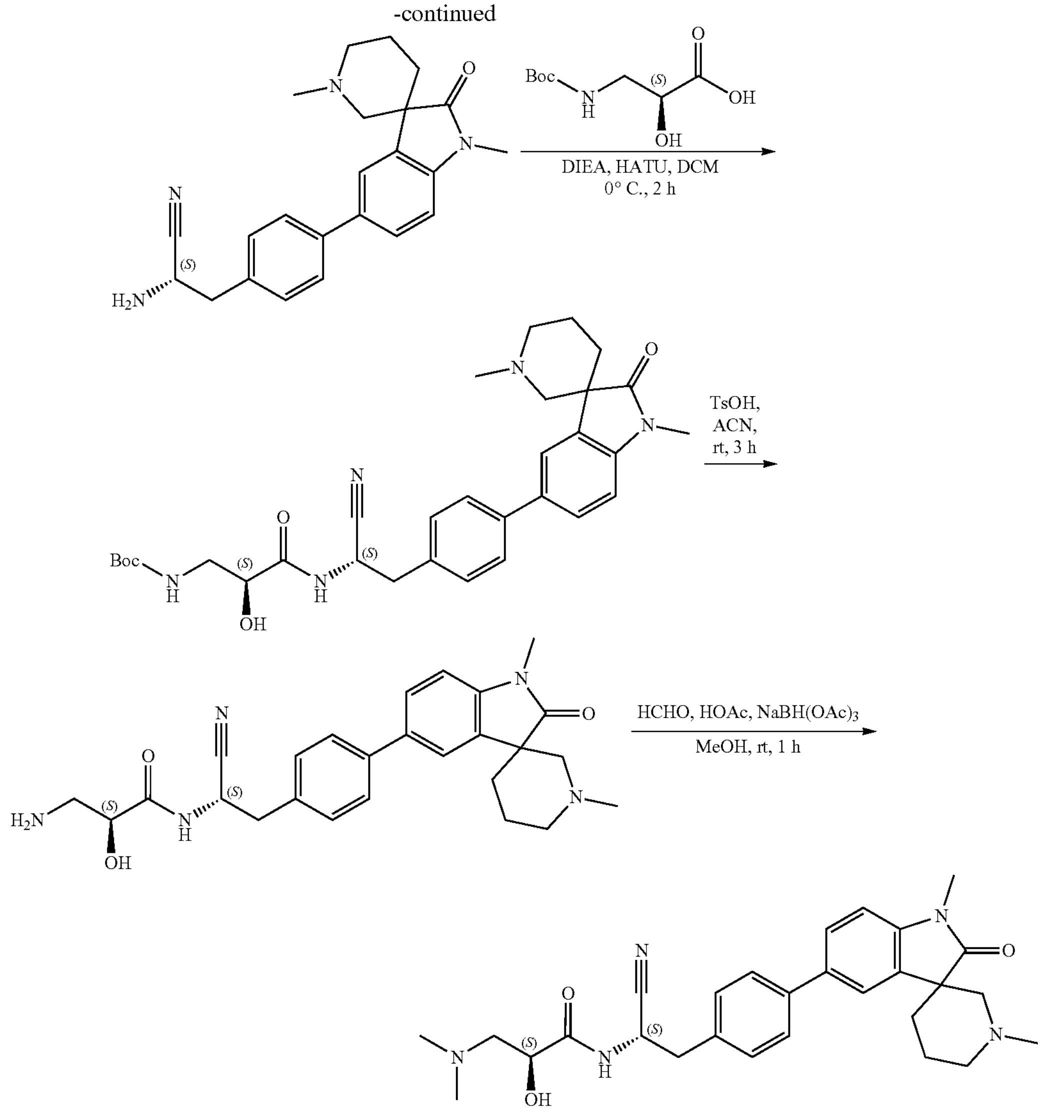

Compound 145

Synthesis of afford tert-butyl N-[(1S)-1-cyano-2-(4-{1,1'-dimethyl-2-oxospiro[indole-3,3'-piperidin]-5-yl}phenyl)ethyl]carbamate

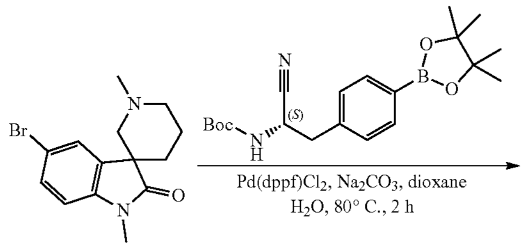

-continued

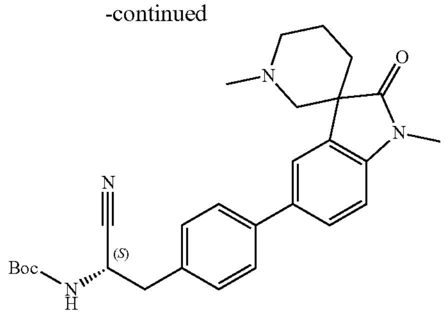

To a stirred solution of tert-butyl N-[(1S)-1-cyano-2-[4-(4,4,5,5-tetramethyl-1,3,2-dioxaborolan-2-yl)phenyl]ethyl]carbamate (400 mg, 1.07 mmol, 1.0 equiv) and 5-bromo-1,1'-dimethylspiro[indole-3,3'-piperidin]-2-one (365 mg, 1.18 mmol, 1.1 equiv) in dioxane (8 mL) and $H_2O$ (1 mL) were added Na2CO3 (227 mg, 2.15 mmol, 2.0 equiv) and $Pd(dppf)Cl_2$ (78 mg, 0.11 mmol, 0.1 equiv). The resulting mixture was stirred at 80° C. for 2 h under nitrogen atmosphere. The mixture was allowed to cool down to room temperature. The resulting mixture was concentrated under reduced pressure. The residue was purified by silica gel column chromatography, eluted with PE/THF (3:1) to afford tert-butyl N-[(1S)-1-cyano-2-(4-{1,1'-dimethyl-2-oxospiro[indole-3,3'-piperidin]-5-yl}phenyl)ethyl]carbamate (350 mg, 68.6% yield). LCMS (ES) [M+1]*m/z: 475.

Synthesis of (2S)-2-amino-3-(4-{1,1'-dimethyl-2-oxospiro[indole-3,3'-piperidin]-5-yl}phenyl)propanenitrile

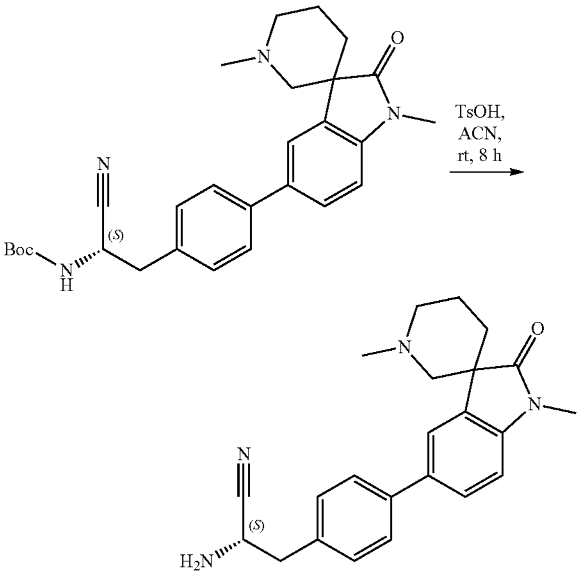

To a stirred solution of tert-butyl N-[(1S)-1-cyano-2-(4-{1,1'-dimethyl-2-oxospiro[indole-3,3'-piperidin]-5-yl}phenyl)ethyl]carbamate (310 mg, 0.65 mmol, 1.0 equiv) in ACN (6 mL) was added TsOH (337 mg, 1.96 mmol, 3.0 equiv). The resulting mixture was stirred at room temperature for 8 h. The mixture was basified to pH 8 with saturated $NaHCO_3$ (aq.). The resulting mixture was extracted with $CH_2Cl_2$ (3×10 mL). The combined organic layers were washed with brine (10 mL), dried over anhydrous $Na_2SO_4$. After filtration, the filtrate was concentrated under reduced pressure. This resulted in (2S)-2-amino-3-(4-{1,1'-dimethyl-2-oxospiro[indole-3,3'-piperidin]-5-yl}phenyl)propanenitrile (200 mg) and used to the next step without further purification. LCMS (ES) $[M+1]^+$ m/z: 375.

Synthesis of tert-butyl N-[(2S)-2-{[(1S)-1-cyano-2-(4-{1,1'-dimethyl-2-oxospiro[indole-3,3'-piperidin]-5-yl}phenyl)ethyl]carbamoyl}-2-hydroxyethyl]carbamate

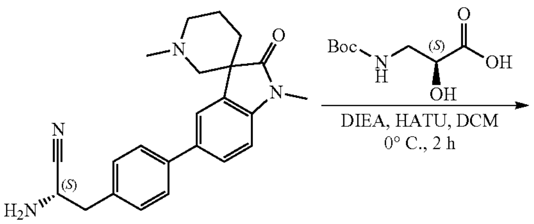

-continued

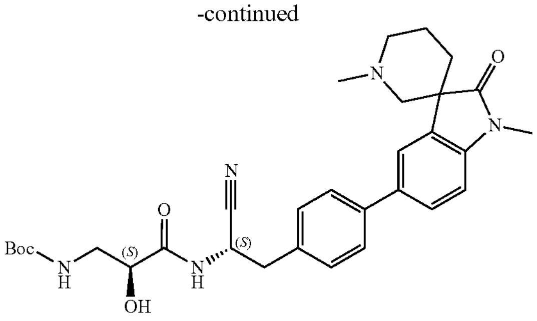

To a stirred solution of (2S)-3-[(tert-butoxycarbonyl)amino]-2-hydroxypropanoic acid (108 mg, 0.53 mmol, 1.1 equiv), (2S)-2-amino-3-(4-{1,1'-dimethyl-2-oxospiro[indole-3,3'-piperidin]-5-yl}phenyl)propanenitrile (180 mg, 0.48 mmol, 1.0 equiv), and DIEA (186 mg, 1.44 mmol, 3.0 equiv) in DCM (4 mL) was added and HATU (219 mg, 0.58 mmol, 1.2 equiv) in portions at 0° C. under nitrogen atmosphere. The resulting mixture was stirred at 0° C. for 2 h. The crude product was purified by Prep-HPLC with the following conditions Column, XBridge Prep C18 OBD Column, 19*150 mm, 5 um; mobile phase, Water (0.1% $NH_3H_2O$) and ACN (10% Phase B up to 80% in 20 min); Detector, UV 254 nm. This resulted in tert-butyl N-[(2S)-2-{[(1S)-1-cyano-2-(4-{1,1'-dimethyl-2-oxospiro[indole-3,3'-piperidin]-5-yl}phenyl)ethyl]carbamoyl}-2-hydroxyethyl]carbamate (170 mg, 62.9% yield). LCMS (ES) $[M+1]^+$ m/z: 562.

Synthesis of (2S)-3-amino-N-[(1S)-1-cyano-2-(4-{1,1'-dimethyl-2-oxospiro[indole-3,3'-piperidin]-5-yl}phenyl)ethyl]-2-hydroxypropanamide

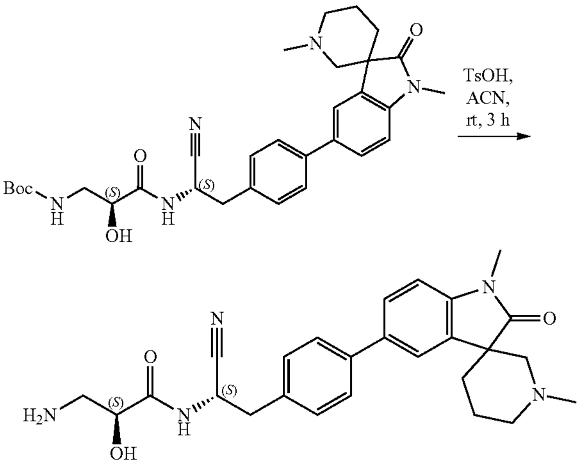

To a stirred solution of tert-butyl N-[(2S)-2-{[(1S)-1-cyano-2-(4-{1,1'-dimethyl-2-oxospiro[indole-3,3'-piperidin]-5-yl}phenyl)ethyl]carbamoyl}-2-hydroxyethyl]carbamate (160 mg, 0.28 mmol, 1.0 equiv) in ACN (3 mL) was added TsOH (147 mg, 0.85 mmol, 3.0 equiv). The resulting mixture was stirred at room temperature for 3 h. The mixture was basified to pH 8 with saturated $NaHCO_3$ (aq.). The resulting mixture was extracted with $CH_2Cl_2$ (3×10 mL). The combined organic layer was washed with brine (10 mL), dried over anhydrous $Na_2SO_4$. After filtration, the filtrate was concentrated under reduced pressure. This resulted in (2S)-3-amino-N-[(1S)-1-cyano-2-(4-{1,1'-dimethyl-2-oxospiro[indole-3,3'-piperidin]-5-yl}phenyl)ethyl]-2-hydroxypropanamide (80 mg, 60.8% yield). LCMS (ES) $[M+1]^+$ m/z: 462.

Synthesis of (2S)—N-[(1S)-1-cyano-2-(4-{1,1'-dimethyl-2-oxospiro[indole-3,3'-piperidin]-5-yl}phenyl) ethyl]-3-(dimethylamino)-2-hydroxypropanamide

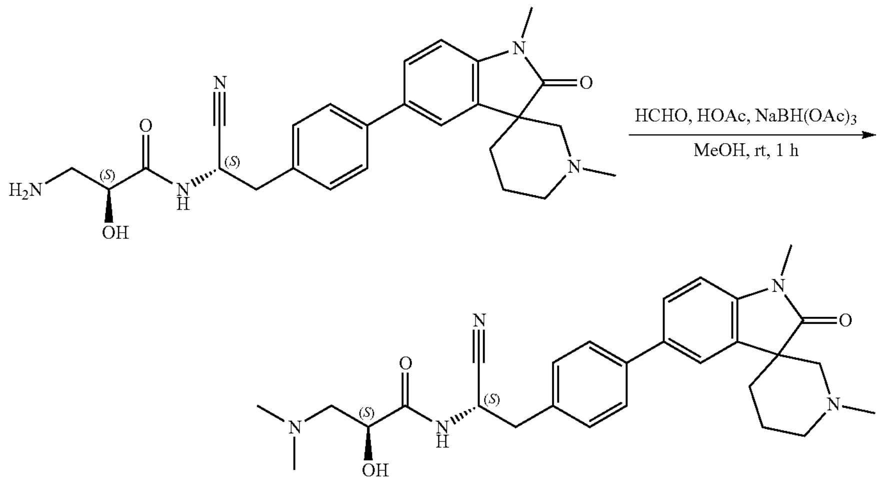

To a stirred solution of (2S)-3-amino-N-[(1S)-1-cyano-2-(4-{1,1'-dimethyl-2-oxospiro[indole-3,3'-piperidin]-5-yl}phenyl)ethyl]-2-hydroxypropanamide (70 mg, 0.15 mmol, 1.0 equiv) and Formaldehyde solution (45 mg, 1.52 mmol, 10.0 equiv) in methanol (2 mL) were added AcOH (2 mg, 0.03 mmol, 0.2 equiv) and sodium bis(acetyloxy)boranuidyl acetate (64 mg, 0.30 mmol, 2.0 equiv) in portions at room temperature. The resulting mixture was stirred at room temperature for 1 h. The reaction solution was purified by Prep-HPLC with the following conditions: Column, XBridge Prep C18 OBD Column, 19*150 mm, Sum; mobile phase, Water (0.1% $NH_3H_2O$) and ACN (10% Phase B up to 80% in 20 min); Detector, UV 254 nm. This resulted in (2S)—N-[(1S)-1-cyano-2-(4-{1,1'-dimethyl-2-oxospiro[indole-3,3'-piperidin]-5-yl}phenyl)ethyl]-3-(dimethylamino)-2-hydroxypropanamide (30 mg, 40.4% yield, 99% purity). LCMS (ES) $[M+1]^+$ m/z: 490.2

$^1$H NMR (300 MHz, DMSO-$d_6$) δ 8.72 (br, 1H), 7.94 (t, J=1.7 Hz, 1H), 7.62-7.49 (m, 3H), 7.37 (d, J=8.2 Hz, 2H), 7.12 (d, J=8.2 Hz, 1H), 5.60 (br, 1H), 5.08-5.00 (m, 1H), 3.99 (dd, J=7.5, 4.3 Hz, 1H), 3.22-(m, 5H), 2.99-2.92 (m, 1H), 2.49-2.44 (m, 1H), 2.33-2.13 (m, 6H), 2.09 (d, J=3.9 Hz, 8H), 1.80-1.66 (m, 2H), 1.50-1.43 (m, 1H).

Example 103: Synthesis of Compound 146: (2S)—N-[(1S)-2-{4-[3-(2-butoxyethyl)-2-oxo-1,3-benzoxazol-5-yl]-2-fluorophenyl}-1-cyanoethyl]-3-(dimethylamino)-2-hydroxypropanamide

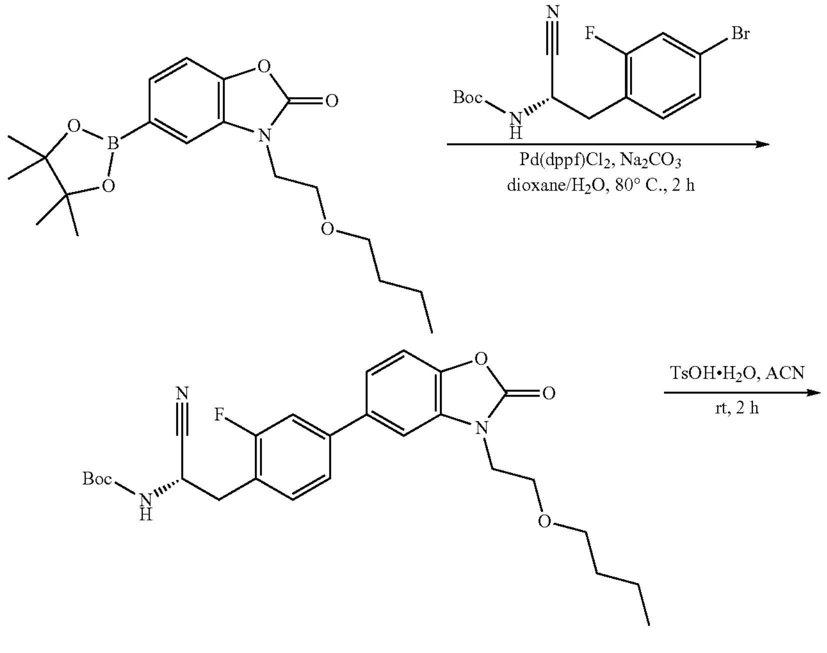

-continued
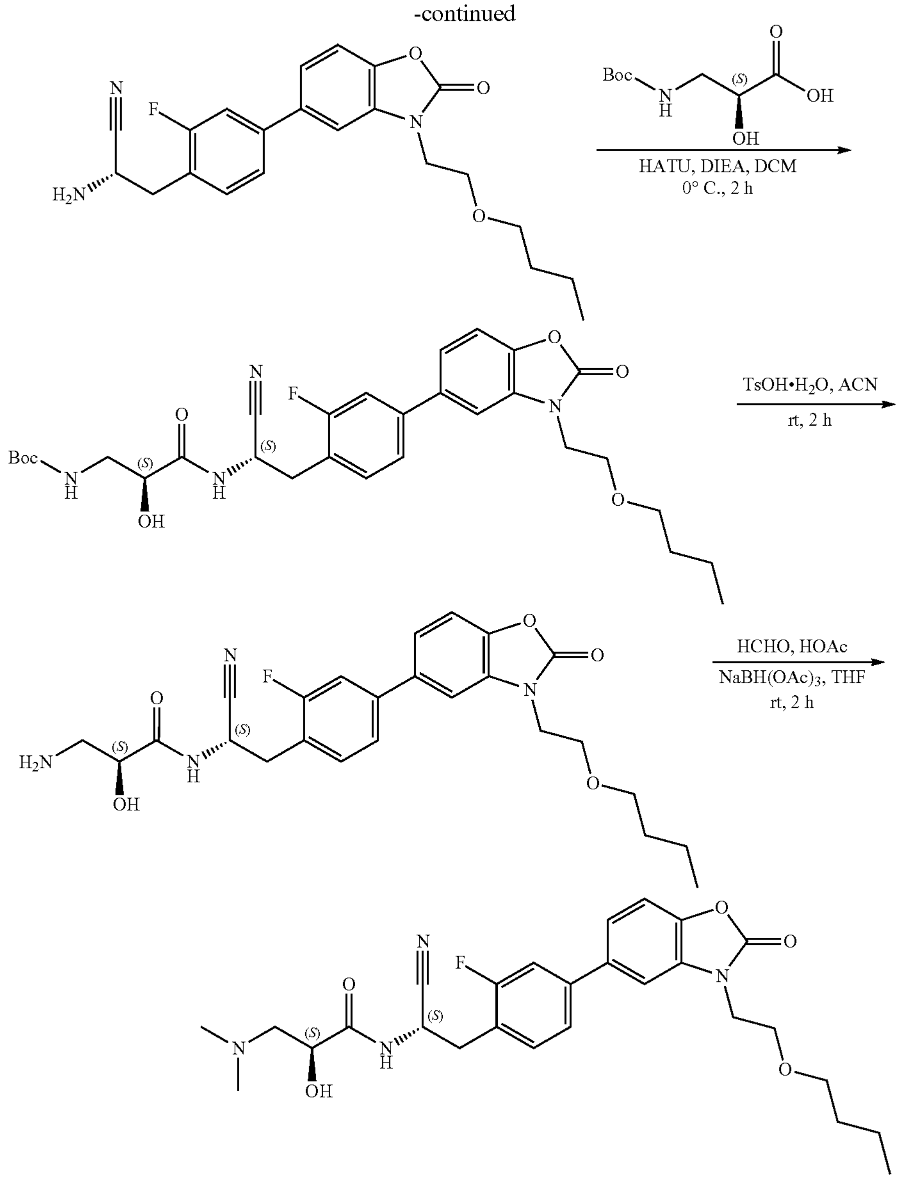
Compound 146
Synthesis of tert-butyl N-[(1S)-2-{4-[3-(2-butoxyethyl)-2-oxo-1,3-benzoxazol-5-yl]-2-fluorophenyl}-1-cyanoethyl]carbamate
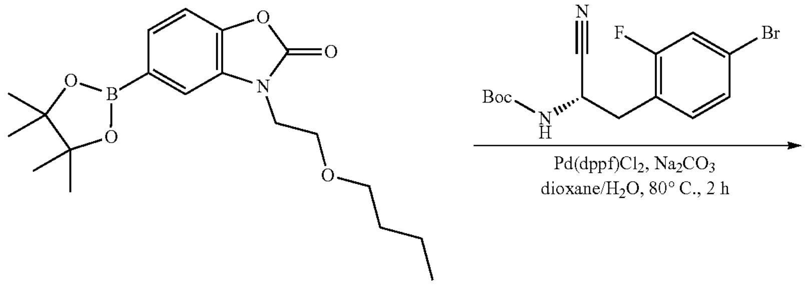

-continued

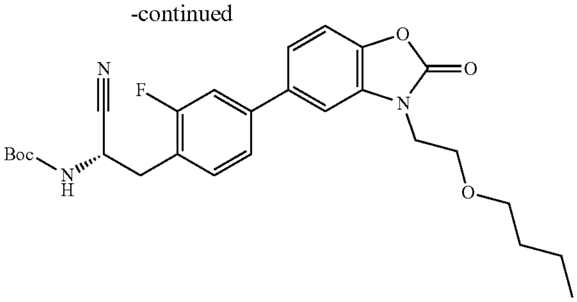

A solution of 3-(2-butoxyethyl)-5-(4,4,5,5-tetramethyl-1,3,2-dioxaborolan-2-yl)-1,3-benzoxazol-2-one (700 mg, 1.93 mmol, 1.2 equiv), tert-butyl N-[(1S)-2-(4-bromo-2-fluorophenyl)-1-cyanoethyl]carbamate (554 mg, 1.61 mmol, 1.0 equiv), $Na_2CO_3$ (342 mg, 3.23 mmol, 2.0 equiv) and Pd(dppf)$Cl_2$ (118 mg, 0.16 mmol, 0.1 equiv) in 1,4-dioxane (8 mL), $H_2O$ (1 mL) was stirred for 2 h at 80° C. under nitrogen atmosphere. The residue was purified by silica gel column chromatography, eluted with PE/THE (1:1) to afford tert-butyl N-[(1S)-2-{4-[3-(2-butoxyethyl)-2-oxo-1,3-benzoxazol-5-yl]-2-fluorophenyl}-1-cyanoethyl]carbamate (1.0 g, 99.68% yield, 79% purity). LCMS (ES, m/z): $[M+H]^+$: 498.

Synthesis of (2S)-2-amino-3-{4-[3-(2-butoxyethyl)-2-oxo-1,3-benzoxazol-5-yl]-2-fluorophenyl}propanenitrile

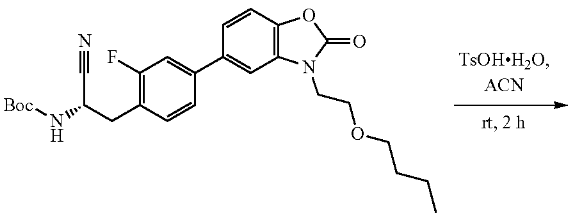

-continued

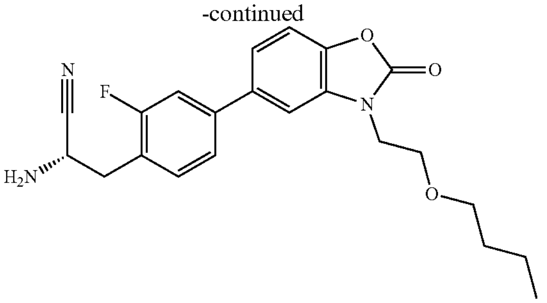

Into a 40 mL round-bottom flask were added tert-butyl N-[(1S)-2-{4-[3-(2-butoxyethyl)-2-oxo-1,3-benzoxazol-5-yl]-2-fluorophenyl}-1-cyanoethyl]carbamate (1.0 g, 2.01 mmol, 1.0 equiv), TSOH·$H_2O$ (1.04 g, 6.03 mmol, 3.0 equiv) and ACN (20 mL) at room temperature. The resulting mixture was stirred for additional 2 h at room temperature. The mixture was basified to pH 8 with saturated $NaHCO_3$ (aq.). The resulting mixture was extracted with EtOAc (3×50 mL). The combined organic layers were washed with brine (3×30 mL), dried over anhydrous $Na_2SO_4$. After filtration, the filtrate was concentrated under reduced pressure. The residue was purified by silica gel column chromatography, eluted with PE/EA (1:1) to afford (2S)-2-amino-3-{4-[3-(2-butoxyethyl)-2-oxo-1,3-benzoxazol-5-yl]-2-fluorophenyl}propanenitrile (750 mg, 95.90% yield, 98% purity). LCMS (ES, m/z): $[M+H]^+$: 398.

Synthesis of tert-butyl N-[(2S)-2-{[(1S)-2-{4-[3-(2-butoxyethyl)-2-oxo-1,3-benzoxazol-5-yl]-2-fluorophenyl}-1-cyanoethyl]carbamoyl}-2-hydroxyethyl] carbamate

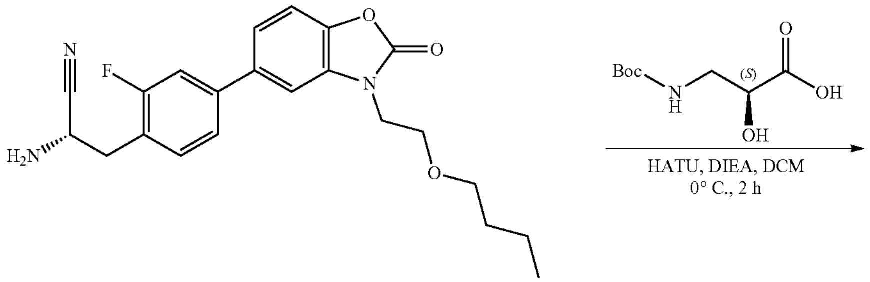

-continued

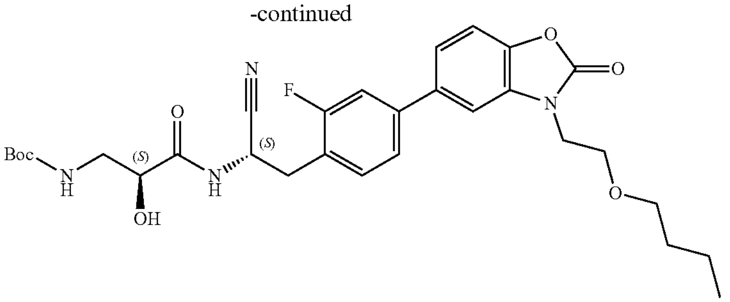

A solution of (2S)-2-amino-3-{4-[3-(2-butoxyethyl)-2-oxo-1,3-benzoxazol-5-yl]-2-fluorophenyl}propanenitrile (150 mg, 0.37 mmol, 1.0 equiv) in DCM (3 mL) was treated with (2S)-3-[(tert-butoxycarbonyl)amino]-2-hydroxypropanoic acid (92 mg, 0.45 mmol, 1.2 equiv), DIEA (146 mg, 1.13 mmol, 3.0 equiv) followed by the addition of HATU (215 mg, 0.56 mmol, 1.5 equiv) dropwise at 0° C. The resulting mixture was stirred for additional 2 h at room temperature. The residue was purified by silica gel column chromatography, eluted with PE/THE (1:1) to afford tert-butyl N-[(2S)-2-{[(1S)-2-{4-[3-(2-butoxyethyl)-2-oxo-1,3-benzoxazol-5-yl]-2-fluorophenyl}-1-cyanoethyl]carbamoyl}-2-hydroxyethyl]carbamate (160 mg, 73.46% yield, 99% purity). LCMS (ES, m/z): $[M+H]^+$: 585.

Synthesis of (2S)-3-amino-N-[(1S)-2-{4-[3-(2-butoxyethyl)-2-oxo-1,3-benzoxazol-5-yl]-2-fluorophenyl}-1-cyanoethyl]-2-hydroxypropanamide

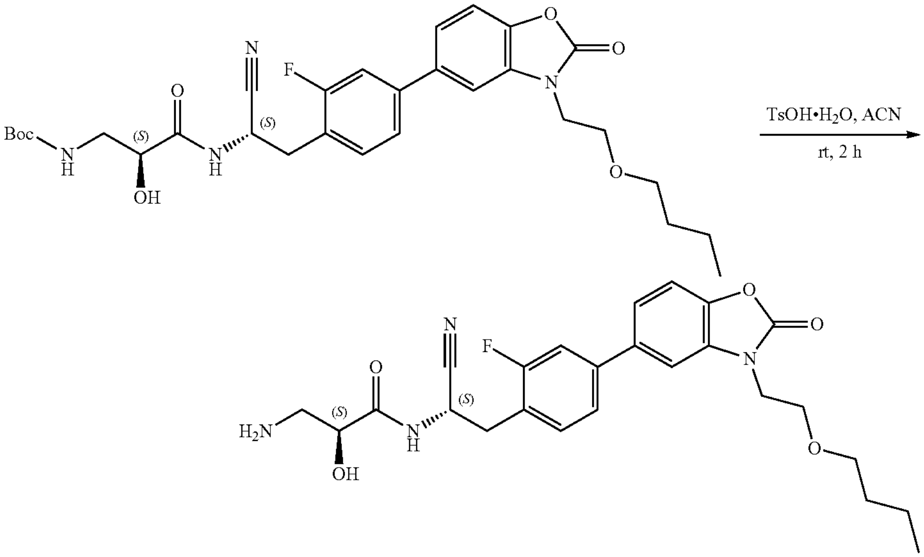

Into a 40 mL round-bottom flask were added tert-butyl N-[(2S)-2-{[(1S)-2-{4-[3-(2-butoxyethyl)-2-oxo-1,3-benzoxazol-5-yl]-2-fluorophenyl}-1-cyanoethyl]carbamoyl}-2-hydroxyethyl]carbamate (150 mg, 0.25 mmol, 1.0 equiv), $TSOH{\cdot}H_2O$ (132 mg, 0.77 mmol, 3.0 equiv) and ACN (3 mL) at room temperature. The resulting mixture was stirred for additional 2 h at room temperature. The mixture was basified to pH 8 with saturated $NaHCO_3$ (aq.). The resulting mixture was extracted with EtOAc (3×10 mL). The combined organic layers were washed with brine (3×5 mL), dried over anhydrous $Na_2SO_4$. After filtration, the filtrate was concentrated under reduced pressure. The residue was purified by silica gel column chromatography, eluted with PE/EA (1:1) to afford (2S)-3-amino-N-[(1S)-2-{4-[3-(2-butoxyethyl)-2-oxo-1,3-benzoxazol-5-yl]-2-fluorophenyl}-1-cyanoethyl]-2-hydroxypropanamide (100 mg, 82.29% yield, 98% purity). LCMS (ES, m/z): $[M+H]^+$: 485.

Synthesis of (2S)—N-[(1S)-2-{4-[3-(2-butoxyethyl)-2-oxo-1,3-benzoxazol-5-yl]-2-fluorophenyl}-1-cyanoethyl]-3-(dimethylamino)-2-hydroxypropanamide

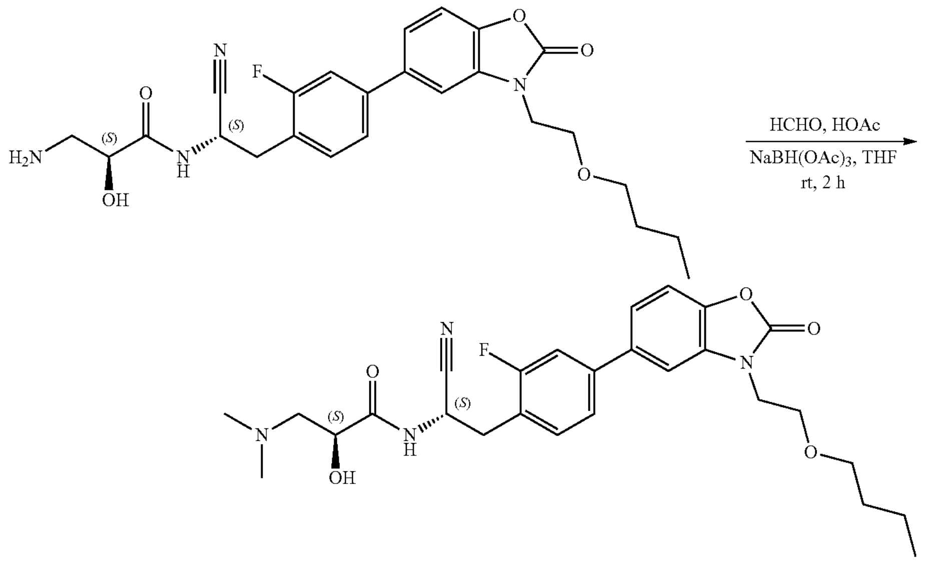

A solution of (2S)-3-amino-N-[(1S)-2-{4-[3-(2-butoxyethyl)-2-oxo-1,3-benzoxazol-5-yl]-2-fluorophenyl}-1-cyanoethyl]-2-hydroxypropanamide (90 mg, 0.18 mmol, 1.0 equiv) and AcOH (0.1 mL), HCHO (146 mg, 1.86 mmol, 10.0 equiv, 38%), NaBH(OAc)3 (78 mg, 0.37 mmol, 2.0 equiv) in THE (3 mL) was stirred at room temperature for 2 h. The residue was purified by reversed-phase flash chromatography with the following conditions: column, C18 silica gel; mobile phase, MeCN in Water (0.1% $NH_3 \cdot H_2O$), 10% to 50% gradient in 10 min; detector, UV 254 nm. This resulted in (2S)—N-[(1S)-2-{4-[3-(2-butoxyethyl)-2-oxo-1,3-benzoxazol-5-yl]-2-fluorophenyl}-1-cyanoethyl]-3-(dimethylamino)-2-hydroxypropanamide (20 mg, 21.43% yield, 98% purity).

LCMS (ES, m/z): $[M+H]^+$: 513.4

$^1H$ NMR (400 MHz, DMSO-$d_6$) δ 8.79 (d, J=8.6 Hz, 1H), 7.69 (d, J=1.8 Hz, 1H), 7.58-7.50 (m, 2H), 7.50-7.39 (m, 3H), 5.56 (s, 1H), 5.08 (q, J=8.2 Hz, 1H), 4.06 (t, J=5.3 Hz, 2H), 4.01 (s, 1H), 3.71 (t, J=5.2 Hz, 2H), 3.39 (t, J=12.8 Hz, 2H), 3.29-3.16 (m, 2H), 2.35-2.28 (m, 1H), 2.27-2.20 (m, 1H), 2.11 (s, 6H), 1.42-1.31 (m, 2H), 1.25-1.12 (m, 2H), 0.74 (t, J=7.4 Hz, 3H).

Example 104: Synthesis of Compound 258A and 258B: (2S)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide and (2R)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide

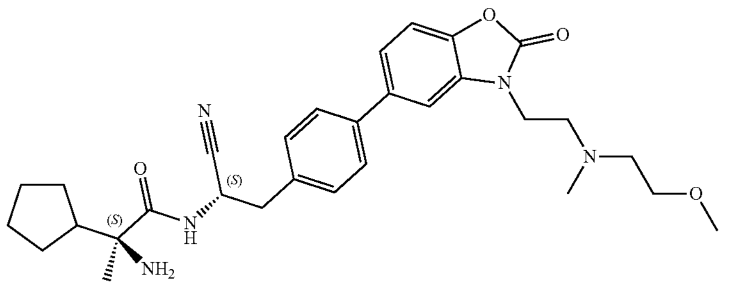

258A
Assumed

-continued
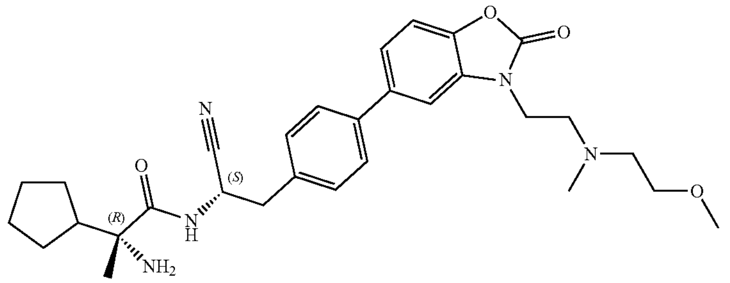
258B
Assumed
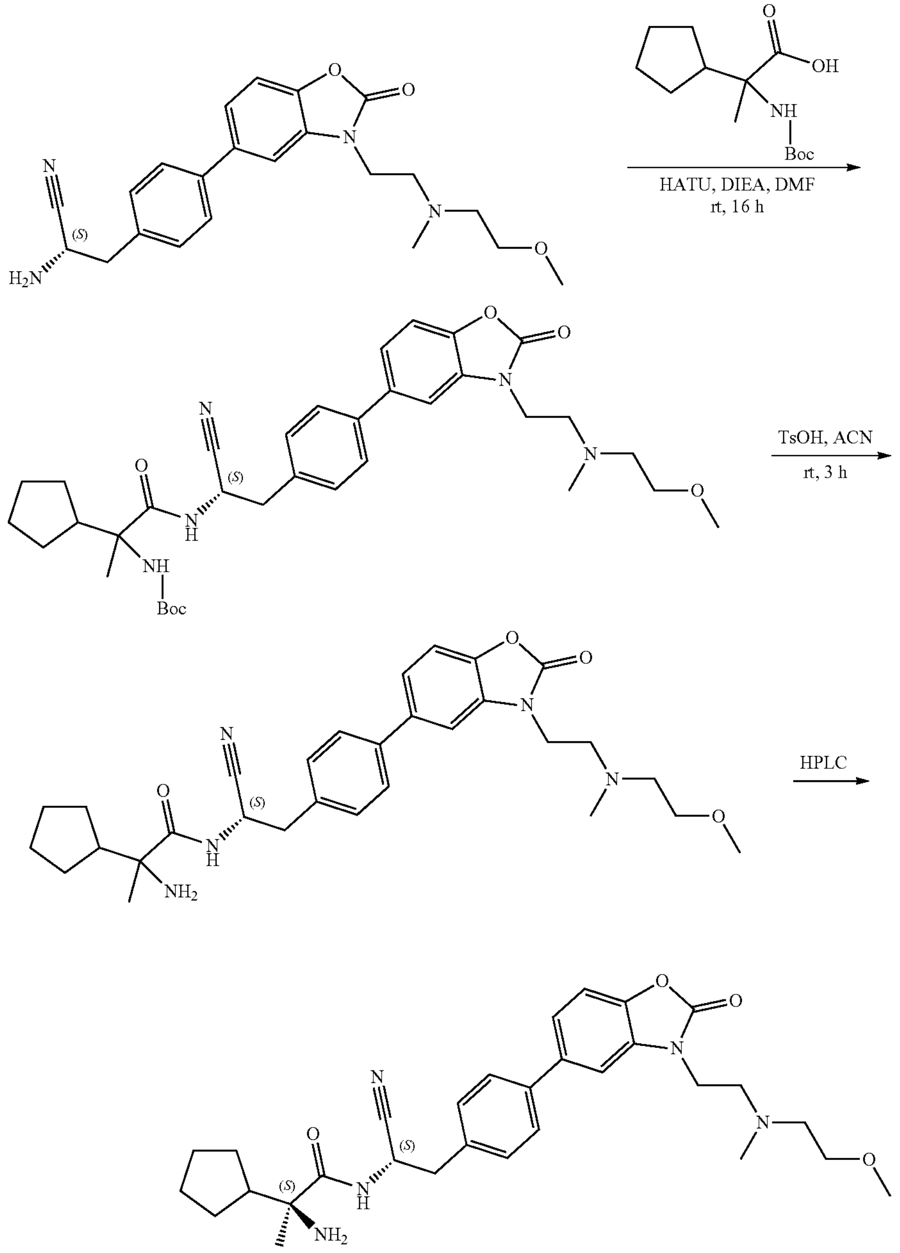
258A
Assumed

-continued

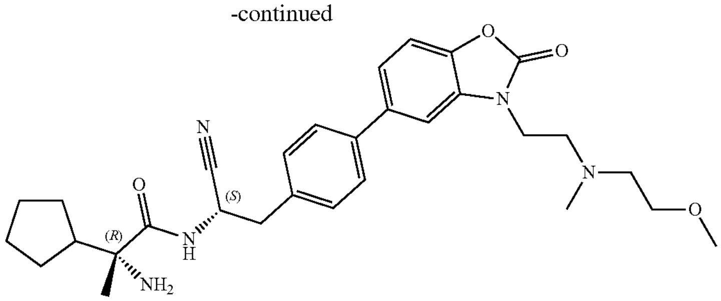

258B
Assumed

Synthesis of tert-butyl N-(1-{[(1S)-1-cyano-2-[4-(3-{2-[(2-methoxyethyl)(methyl) amino]ethyl}-2-oxo-1,3-benzoxazol-5-yl)phenyl]ethyl]carbamoyl}-1-cyclopentylethyl)carbamate

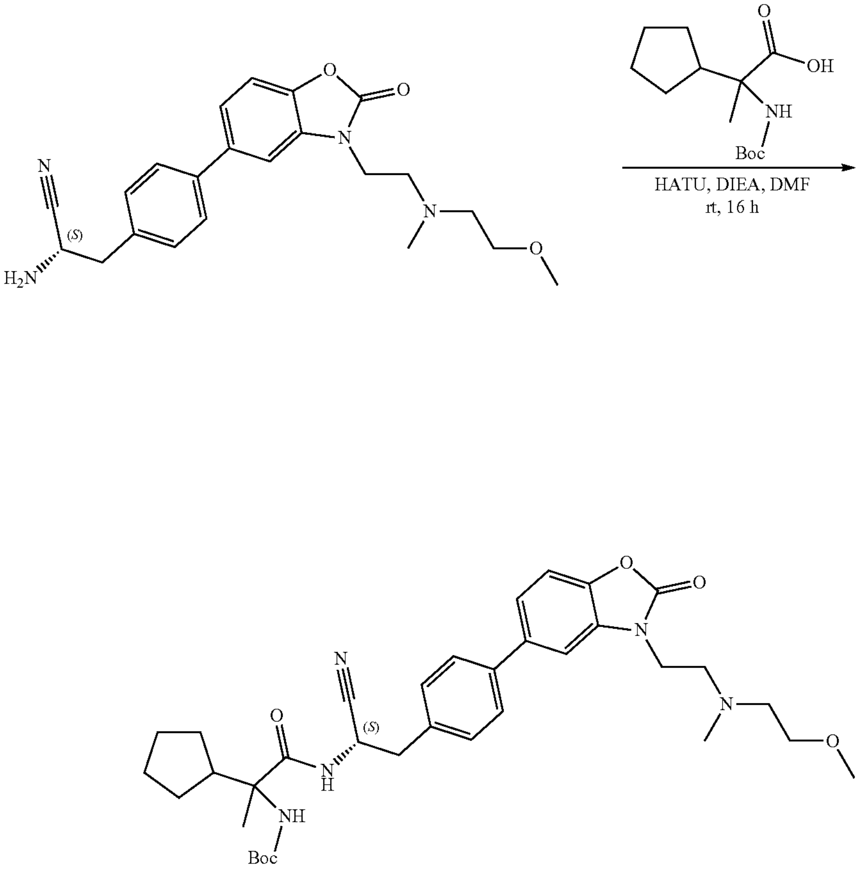

To a stirred solution of (2S)-2-amino-3-[4-(3-{2-[(2-methoxyethyl)(methyl)amino]ethyl}-2-oxo-1,3-benzoxazol-5-yl)phenyl]propanenitrile (250 mg, 0.63 mmol, 1.0 equiv) and 2-[(tert-butoxycarbonyl)amino]-2-cyclopentylpropanoic acid (261 mg, 1.01 mmol, 1.6 equiv), DIEA (245 mg, 1.90 mmol, 3.0 equiv) in DMF (4 mL) was added HATU (289 mg, 0.76 mmol, 1.2 equiv) in portions at 0° C. The resulting mixture was stirred for 16 h at room temperature. The reaction was quenched with water (10 mL), extracted with EtOAc (3x20 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-[4-(3-{2-[(2-methoxyethyl)(methyl)amino]ethyl}-2-oxo-1,3-benzoxazol-5-yl)phenyl]ethyl]carbamoyl}-1-cyclopentylethyl)carbamate (190 mg, 47.3%). LCMS (ES, m/z): $[M+H]^+$: 634.

Synthesis of 2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide

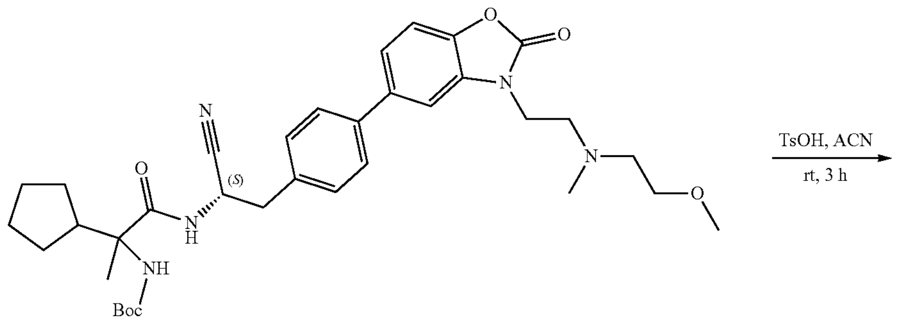

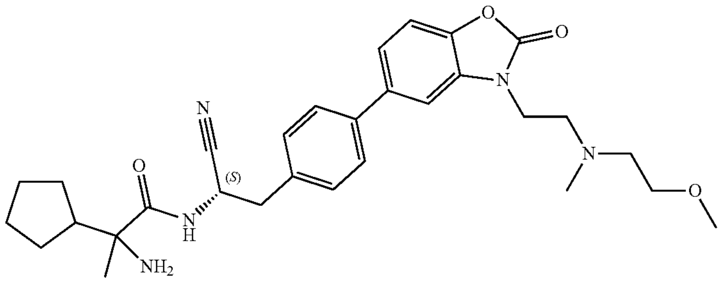

Into a 25 mL round-bottom flask were added tert-butyl N-(1-{[(1S)-1-cyano-2-[4-(3-{2-[(2-methoxyethyl)(methyl)amino]ethyl}-2-oxo-1,3-benzoxazol-5-yl)phenyl]ethyl]carbamoyl}-1-cyclopentylethyl)carbamate (200 mg, 0.32 mmol, 1.0 equiv), ACN (6 mL) and $TsOH{\cdot}H_2O$ (180 mg, 0.94 mmol, 3.0 equiv) at room temperature. The reaction solution was purified by reversed-phase flash chromatography with the following conditions: column, C18 silica gel-120 g; mobile phase, MeCN in Water (0.1% $NH_3{\cdot}H_2O$), 10% to 50% gradient in 10 min; detector, UV 254 nm. This resulted in 2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide (80 mg, 47.5%). LCMS (ES, m/z): $[M+H]^+$: 534.

Synthesis of (2S)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide; (2R)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide

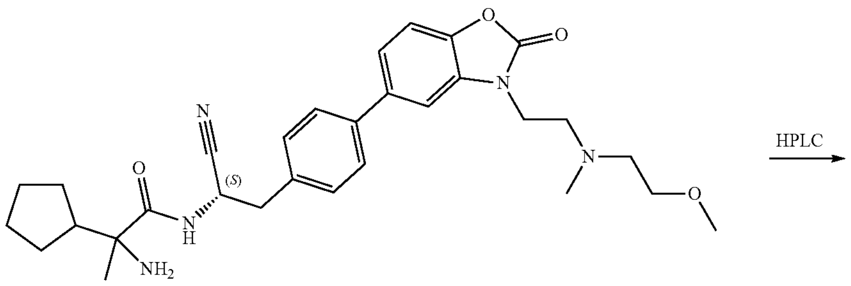

-continued

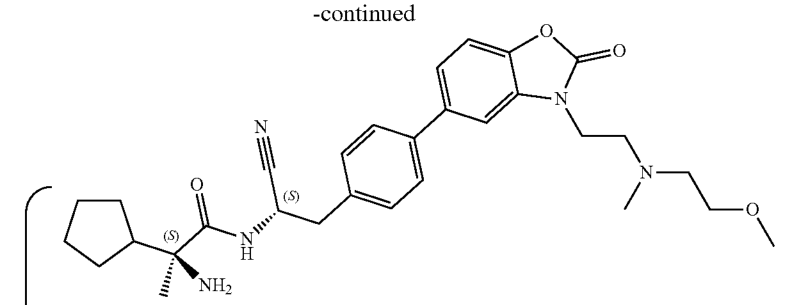

258A
Assumed

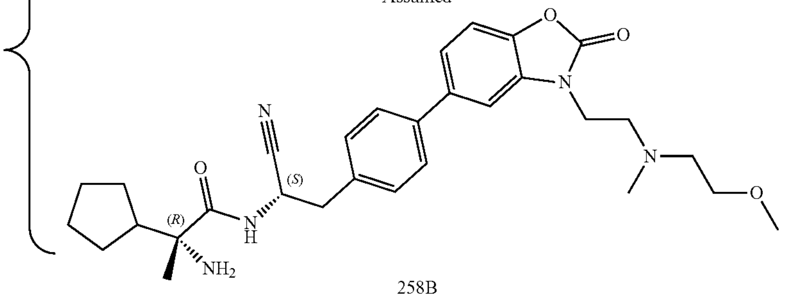

258B
Assumed 2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide (80 mg, 0.15 mmol, 1.0 equiv) was purified by Prep-HPLC with the following conditions Column: CHIRALPAK IF, 3*25 cm, 5 m; Mobile Phase A: Hex: DCM=5: 1-HPLC, Mobile Phase B: EtOH (0.1% 2M $NH_3$-MeOH); Flow rate: 35 mL/min; Gradient: isocratic 30; Wave Length: 254 nm; RT1(min): 9.3; RT2 (min): 12.1; Sample Solvent: EtOH: DCM=1: 1-HPLC; Injection Volume: 1 mL; Number Of Runs: 6. This resulted in (2S)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide (16.7 mg, 20.9%) and (2R)-2-amino-N-[(1S)-1-cyano-2-[4-(3-{2-[(2-methoxyethyl)(methyl)amino]ethyl}-2-oxo-1,3-benzoxazol-5-yl)phenyl]ethyl]-2-cyclopentylpropanamide (14.4 mg, 18.0%).

LCMS (ES, m/z): $[M+H]^+$: 534.3

Compound 258A: $^1H$ NMR (400 MHz, DMSO-$d_6$) δ 7.66 (d, J=7.8 Hz, 2H), 7.62 (s, 1H), 7.45-7.37 (m, 4H), 4.99 (t, J=7.8 Hz, 1H), 3.97 (t, J=6.1 Hz, 2H), 3.28-3.12 (m, 4H), 3.05 (s, 3H), 2.74 (t, J=6.1 Hz, 2H), 2.54-2.51 (m, 2H), 2.26 (s, 3H), 2.16-2.03 (m, 1H), 1.59-1.30 (m, 6H), 1.26-1.12 (m, 2H), 1.05 (s, 3H). Compound 258B: $^1H$ NMR (400 MHz, DMSO-$d_6$) δ 7.64 (d, J=7.9 Hz, 2H), 7.60 (s, 1H), 7.43-7.38 (m, 4H), 5.01 (t, J=7.8 Hz, 1H), 3.96 (t, J=6.1 Hz, 2H), 3.26-3.16 (m, 4H), 3.05 (s, 3H), 2.74 (t, J=6.1 Hz, 2H), 2.52-2.49 (m, 2H), 2.26 (s, 3H), 2.08-1.98 (m, 1H), 1.44-1.17 (m, 7H), 1.09-1.05 (m, 4H), 0.97-0.89 (m, 1H).

Example 105: Synthesis of Compound 259A and 259B (2S)-2-amino-N-[(1S)-1-cyano-2-[4-(1-ethyl-2-oxo-3H-indol-6-yl)phenyl]ethyl]-2-cyclopentylpropanamide and (2R)-2-amino-N-[(1S)-1-cyano-2-[4-(1-ethyl-2-oxo-3H-indol-6-yl)phenyl]ethyl]-2-cyclopentylpropanamid

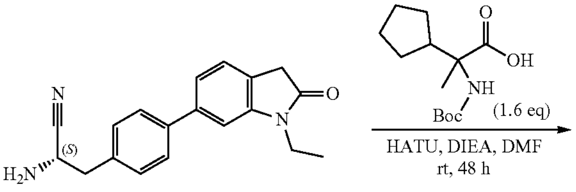

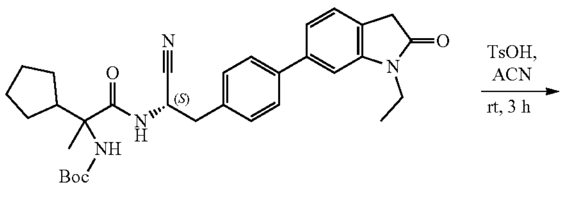

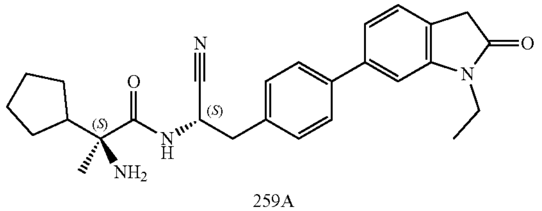

259A
Assumed

+

-continued

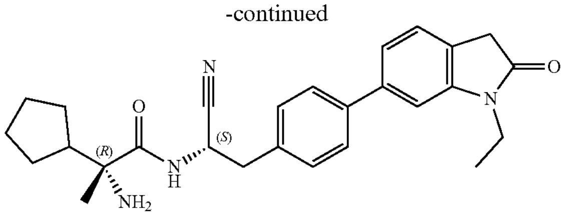

259B
Assumed

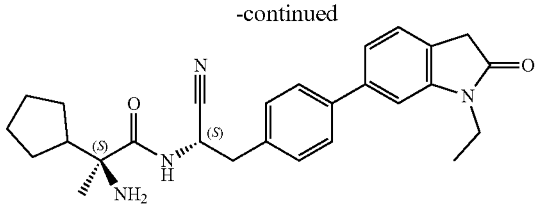

259A
Assumed

+

Synthesis of tert-butyl N-(1-{[(1S)-1-cyano-2-[4-(1-ethyl-2-oxo-3H-indol-6-yl)phenyl]ethyl]carbamoyl}-1-cyclopentylethyl)carbamate

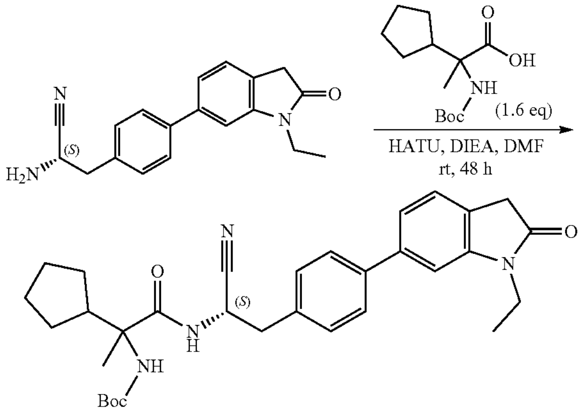

To a stirred mixture of (2S)-2-amino-3-[4-(1-ethyl-2-oxo-3H-indol-6-yl)phenyl]propanenitrile (150 mg, 0.49 mmol, 1 equiv), 2-[(tert-butoxycarbonyl)amino]-2-cyclopentylpropanoic acid (202 mg, 0.78 mmol, 1.6 equiv) and DIEA (126 mg, 0.98 mmol, 2 equiv) in DMF (5 mL) were added HATU (224 mg, 0.58 mmol, 1.2 equiv) in portions at 0° C. The resulting mixture was stirred for additional 48 h at room temperature. The residue was purified by silica gel column chromatography, eluted with PE/THE (1:1) to afford tert-butyl N-(1-{[(1S)-1-cyano-2-[4-(1-ethyl-2-oxo-3H-indol-6-yl)phenyl]ethyl]carbamoyl}-1-cyclopentylethyl)carbamate (150 mg, 56.06%). LCMS (ES, m z): $[M+H]^+$: 545.

Synthesis of (2S)-2-amino-N-[(1S)-1-cyano-2-[4-(1-ethyl-2-oxo-3H-indol-6-yl)phenyl]ethyl]-2-cyclopentylpropanamide and (2R)-2-amino-N-[(1S)-1-cyano-2-[4-(1-ethyl-2-oxo-3H-indol-6-yl)phenyl]ethyl]-2-cyclopentylpropanamide

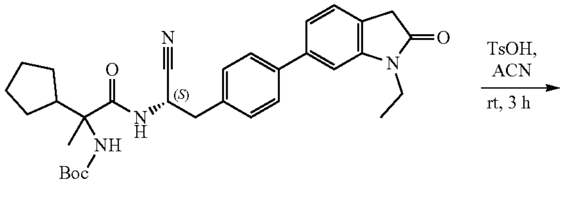

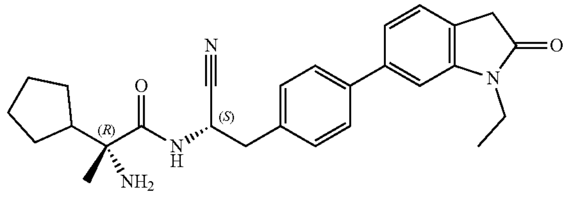

259B
Assumed

Into a 50 mL round-bottom flask were added tert-butyl N-(1-{[(1S)-1-cyano-2-[4-(1-ethyl-2-oxo-3H-indol-6-yl)phenyl]ethyl]carbamoyl}-1-cyclopentylethyl)carbamate (145 mg, 0.26 mmol, 1 equiv), $TsOH \cdot H_2O$ (151 mg, 0.79 mmol, 3 equiv) and ACN (5 mL) at room temperature. The resulting mixture was stirred for additional 3 h at room temperature. The residue was purified by reversed-phase flash chromatography with the following conditions: column, C18 silica gel; mobile phase, MeCN in Water (0.1% $NH_3 \cdot H_2O$), 10% to 60% gradient in 12 min; detector, UV 254 nm. The product was purified by Prep-CHIRAL-HPLC with the following conditions: Column: XA-CHIRALPAK IH, 3*25 cm, 5 m; Mobile Phase A: $CO_2$, Mobile Phase B: MEOH: DCM=2: 1(0.1% 2M $NH_3$-MeOH); Flow rate: 80 mL/min; Gradient: isocratic 40% B; Column Temperature(° C.): 35; Back Pressure(bar): 100; Wave Length: 220 nm; RT1(min): 3.4; RT2(min): 4.4; Sample Solvent: MEOH; Injection Volume: 1.5 mL. This resulted in (2S)-2-amino-N-[(1S)-1-cyano-2-[4-(1-ethyl-2-oxo-3H-indol-6-yl)phenyl]ethyl]-2-cyclopentylpropanamide (20 mg, 33.80%) and (2R)-2-amino-N-[(1S)-1-cyano-2-[4-(1-ethyl-2-oxo-3H-indol-6-yl)phenyl]ethyl]-2-cyclopentylpropanamide (20 mg, 33.80%).

LCMS (ES, m z): $[M+H]^+$: 445.

Compound 259A: $^1H$ NMR (300 MHz, DMSO-$d_6$) δ 7.65 (d, J=7.8 Hz, 2H), 7.39 (d, J=7.9 Hz, 2H), 7.33 (d, J=7.7 Hz, 1H), 7.26 (d, J=7.4 Hz, 2H), 5.01 (t, J=7.8 Hz, 1H), 3.78 (q, J=7.1 Hz, 2H), 3.57 (s, 2H), 3.26-3.17 (m, 2H), 2.07-1.96 (m, 1H), 1.43-1.29 (m, 6H), 1.17 (t, J=7.1 Hz, 3H), 1.09-1.00 (m, 4H), 0.92-0.73 (m, 1H).

Compound 259B: $^1H$ NMR (300 MHz, DMSO-$d_6$) δ 7.67 (d, J=7.9 Hz, 2H), 7.41 (d, J=7.9 Hz, 2H), 7.33 (d, J=7.9 Hz, 1H), 7.31-7.25 (m, 2H), 4.99 (t, J=7.8 Hz, 1H), 3.78 (q, J=7.1 Hz, 2H), 3.58 (s, 2H), 3.28-3.12 (m, 2H), 2.16-2.03 (m, 1H), 1.59-1.29 (m, 6H), 1.27-1.12 (m, 5H), 1.06 (s, 3H).

Example 106. Synthesis of Compound 264A and 264B: [0001](2S)-2-amino-N-[(1S)-1-cyano-2-[4-(1-ethyl-2-oxo-3H-indol-6-yl)-2-fluorophenyl]ethyl]-2-cyclopentylpropanamide and (2R)-2-amino-N-[(1S)-1-cyano-2-[4-(1-ethyl-2-oxo-3H-indol-6-yl)-2-fluorophenyl]ethyl]-2-cyclopentylpropanamide

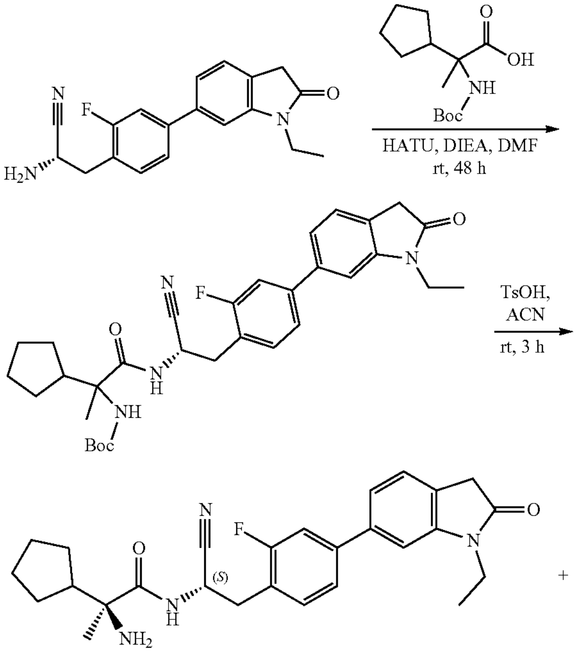

+

264A
Assumed

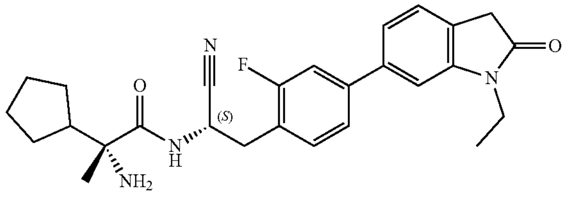

264B
Assumed

Synthesis of tert-butyl N-(1-{[(1S)-1-cyano-2-[4-(1-ethyl-2-oxo-3H-indol-6-yl)-2-fluorophenyl]ethyl] carbamoyl}-1-cyclopentylethyl)carbamate

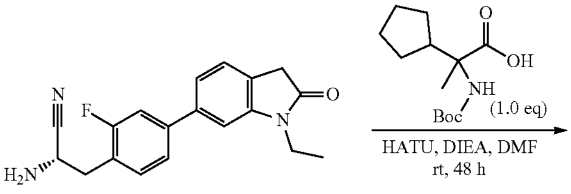

-continued

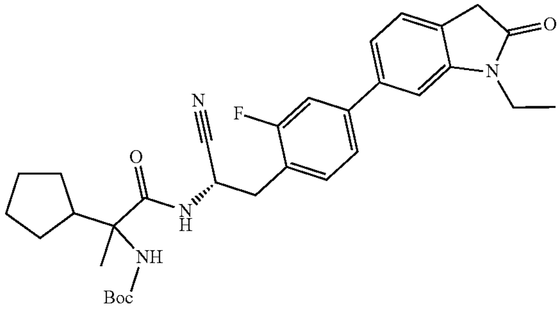

To a stirred mixture of (2S)-2-amino-3-[4-(1-ethyl-2-oxo-3H-indol-6-yl)-2-fluorophenyl]propanenitrile (160 mg, 0.50 mmol, 1.0 equiv), 2-[(tert-butoxycarbonyl)amino]-2-cyclopentylpropanoic acid (203 mg, 0.79 mmol, 1.6 equiv) and DIEA (127 mg, 0.99 mmol, 2.0 equiv) in DMF (5 mL) were added HATU (225 mg, 0.59 mmol, 1.2 equiv) in portions at 0° C. The resulting mixture was stirred for 48 h at room temperature. The reaction was quenched with water (20 mL), extracted with ethyl acetate (30 mL×2). The combined organic phase was washed with brine (15 mL×3), dried over anhydrous sodium sulfate. After filtered and the filtrate was concentrated under reduced pressure. The residue was purified by silica gel column chromatography, eluted with PE/THF (1:1) to afford tert-butyl N-(1-{[(1S)-1-cyano-2-[4-(1-ethyl-2-oxo-3H-indol-6-yl)-2-fluorophenyl]ethyl]carbamoyl}-1-cyclopentylethyl)carbamate (120 mg, 43%). LCMS (ES, m z): $[M+H]^+$: 563.

Synthesis of (2S)-2-amino-N-[(1S)-1-cyano-2-[4-(1-ethyl-2-oxo-3H-indol-6-yl)-2-fluorophenyl]ethyl]-2-cyclopentylpropanamide and (2R)-2-amino-N-[(1S)-1-cyano-2-[4-(1-ethyl-2-oxo-3H-indol-6-yl)-2-fluorophenyl]ethyl]-2-cyclopentylpropanamide

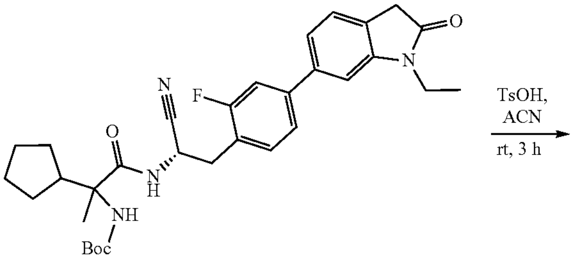

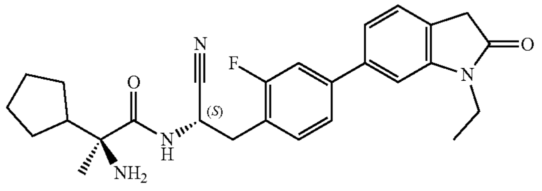

+

264A
Assumed

-continued

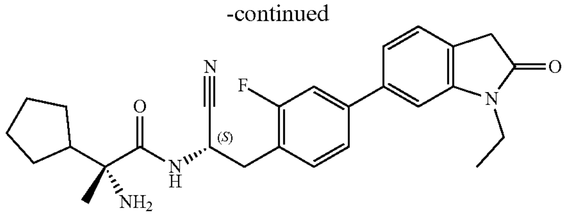

264B
Assumed

Into a 25 mL round-bottom flask were added tert-butyl N-(1-{[(1S)-1-cyano-2-[4-(1-ethyl-2-oxo-3H-indol-6-yl)-2-fluorophenyl]ethyl]carbamoyl}-1-cyclopentylethyl)carbamate (120 mg, 0.21 mmol, 1.0 equiv), $TsOH{\cdot}H_2O$ (121 mg, 0.63 mmol, 3.0 equiv) and ACN (5 mL) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3{\cdot}H_2O$), 10% to 60% gradient in 12 min; detector, UV 254 nm. The product was further purified by Prep-CHIRAL-HPLC with the following conditions: Column: CHIRALPAK IA, 2*25 cm, 5 m; Mobile Phase A: Hex-HPLC, Mobile Phase B: EtOH(0.1% 2M $NH_3$-MeOH); Flow rate: 25 mL/min; Gradient: isocratic 30; Wave Length: 254 nm; RT1(min): 7.7; RT2(min): 11.2; Sample Solvent: EtOH: DCM=1: 1. This resulted in (2S)-2-amino-N-[(1S)-1-cyano-2-[4-(1-ethyl-2-oxo-3H-indol-6-yl)-2-fluorophenyl]ethyl]-2-cyclopentylpropanamide (18 mg, 36.5%) and (2R)-2-amino-N-[(1S)-1-cyano-2-[4-(1-ethyl-2-oxo-3H-indol-6-yl)-2-fluorophenyl]ethyl]-2-cyclopentylpropanamide (13 mg, 26.4%).

LCMS (ES, m z): $[M+H]^+$: 463.1

Compound 264A: $^1$H NMR (300 MHz, DMSO-$d_6$) δ 7.64-7.50 (m, 2H), 7.45 (t, J=7.9 Hz, 1H), 7.34-7.30 (m, 3H), 5.00 (t, J=7.9 Hz, 1H), 3.77 (q, J=6.9 Hz, 2H), 3.56 (s, 2H), 3.28-3.11 (m, 2H), 2.15-2.03 (m, 1H), 1.61-1.20 (m, 8H), 1.16 (t, J=7.1 Hz, 3H), 1.04 (s, 3H).

Compound 264B: $^1$H NMR (300 MHz, DMSO-$d_6$) δ 7.62-7.48 (m, 2H), 7.44 (t, J=7.9 Hz, 1H), 7.34-7.27 (m, 3H), 5.01 (t, J=8.0 Hz, 1H), 3.77 (q, J=7.1 Hz, 2H), 3.56 (s, 2H), 3.23 (d, J=3.7 Hz, 2H), 2.09-1.97 (m, 1H), 1.52-1.20 (m, 6H), 1.15 (t, J=7.1 Hz, 3H), 1.08-0.89 (m, 5H).

Example 107: Synthesis of Compound 267: 2-amino-N-[(1S)-2-{4-[3-(2-butoxyethyl)-2-oxo-1,3-benzoxazol-5-yl]-2-fluorophenyl}-1-cyanoethyl]-2-cyclobutylpropanamide

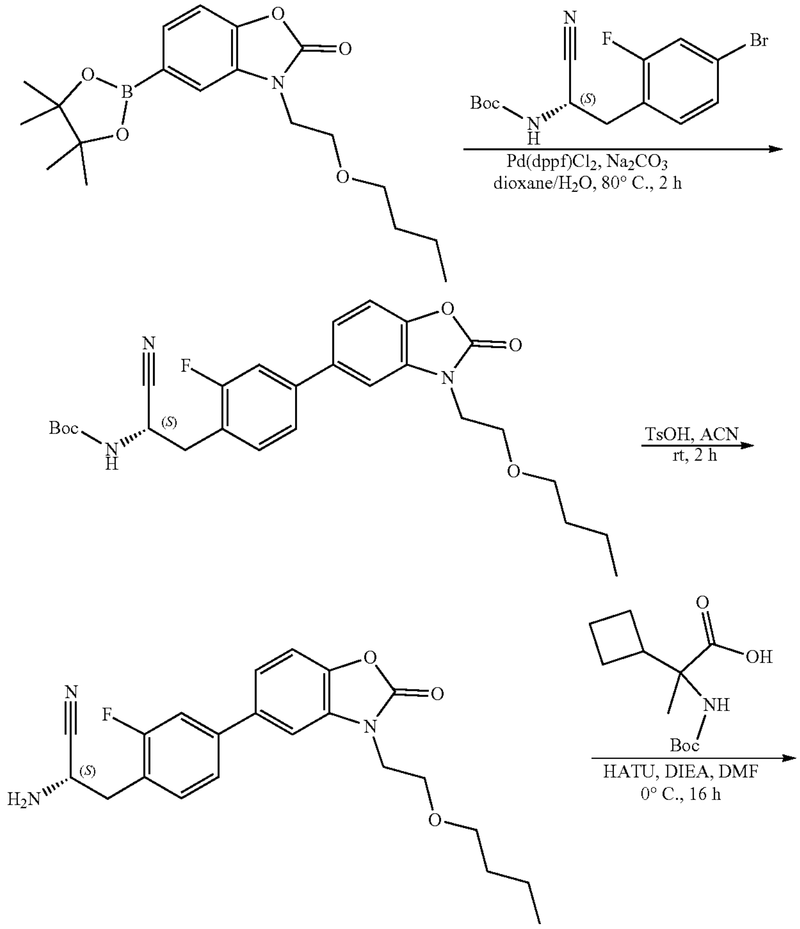

-continued

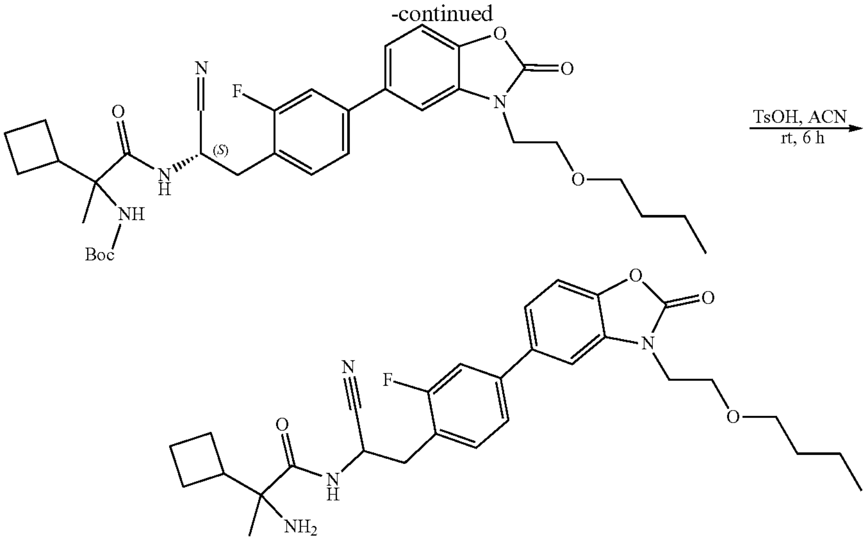

Compound 267

Synthesis of tert-butyl N-[(1S)-2-{4-[3-(2-butoxyethyl)-2-oxo-1,3-benzoxazol-5-yl]-2-fluorophenyl}-1-cyanoethyl]carbamate

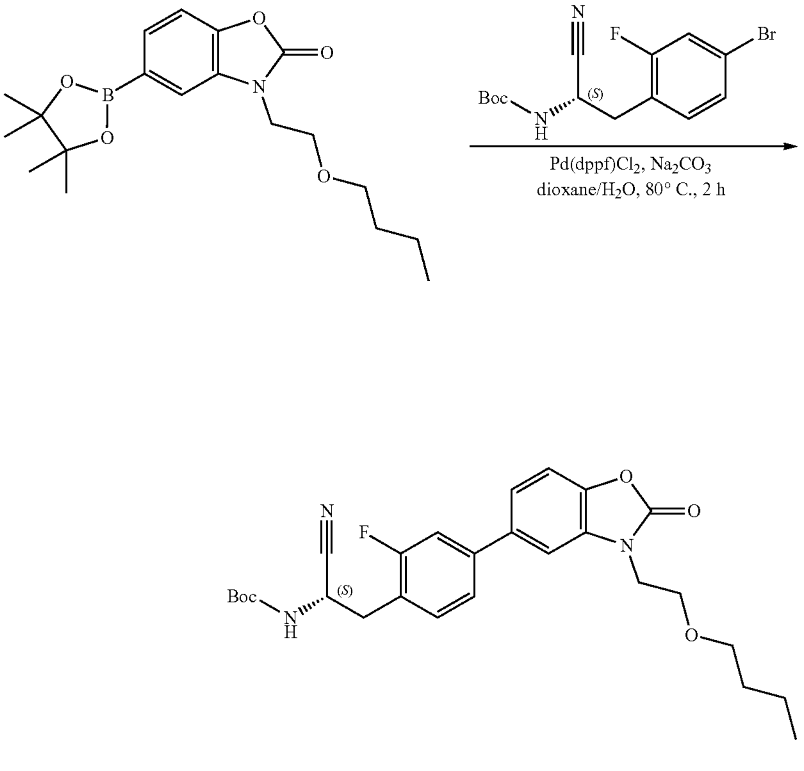

To a solution of 3-(2-butoxyethyl)-5-(4,4,5,5-tetramethyl-1,3,2-dioxaborolan-2-yl)-1,3-benzoxazol-2-one (800 mg, 2.21 mmol, 1.1 equiv), tert-butyl N-[(1S)-2-(4-bromo-2-fluorophenyl)-1-cyanoethyl]carbamate (690 mg, 2.01 mmol, 1.0 equiv) and $Na_2CO_3$ (426 mg, 4.02 mmol, 2.0 equiv) in dioxane (16 mL) and $H_2O$ (2 mL) was added Pd(dppf)$Cl_2$ (147 mg, 0.20 mmol, 0.1 equiv) at room temperature. The resulting mixture stirred for 2 h at 80° C. under nitrogen atmosphere. The reaction was concentrated. The residue was purified by silica gel column chromatography, eluted with PE/THE (1:1) to afford tert-butyl N-[(1S)-2-{4-[3-(2-butoxyethyl)-2-oxo-1,3-benzoxazol-5-yl]-2-fluorophenyl}-1-cyanoethyl]carbamate (1.1 g, 90% purity). LCMS (ES, m/z): $[M+H]^+$: 498.

Synthesis of (2S)-2-amino-3-{4-[3-(2-butoxyethyl)-2-oxo-1,3-benzoxazol-5-yl]-2-fluorophenyl}propanenitrile

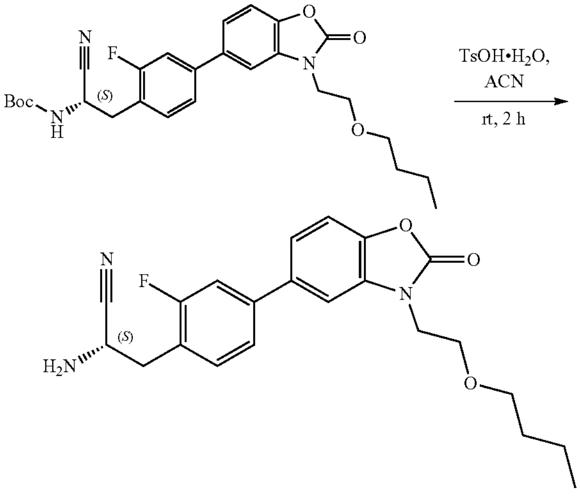

To a solution of tert-butyl N-[(1S)-2-{4-[3-(2-butoxyethyl)-2-oxo-1,3-benzoxazol-5-yl]-2-fluorophenyl}-1-cyanoethyl]carbamate (1.1 g, 2.21 mmol, 1.0 equiv) in ACN (20 mL) was added TsOH·$H_2O$(1.14 g, 6.63 mmol, 3.0 equiv) at 0° C. The resulting mixture was stirred for 2 h at 0° C. to room temperature. The reaction mixture was adjusted pH to 8 with $NaHCO_3$ (5N), extracted with EtOAc (4×20 mL). The organic layer was concentrated. The residue was purified by silica gel column chromatography, eluted with PE/THE (1:2) to afford (2S)-2-amino-3-{4-[3-(2-butoxyethyl)-2-oxo-1,3-benzoxazol-5-yl]-2-fluorophenyl}propanenitrile (750 mg, 96% purity). LCMS (ES, m/z): $[M+H]^+$: 398.

Synthesis of tert-butyl N-(1-{[(1S)-2-{4-[3-(2-butoxyethyl)-2-oxo-1,3-benzoxazol-5-yl]-2-fluorophenyl}-1-cyanoethyl]carbamoyl}-1-cyclobutylethyl) carbamate

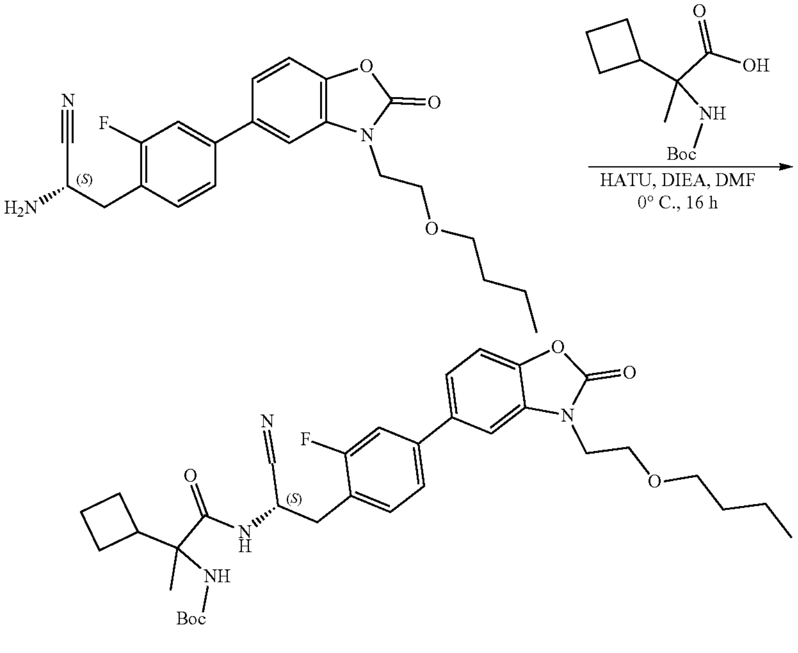

A solution of (2S)-2-amino-3-{4-[3-(2-butoxyethyl)-2-oxo-1,3-benzoxazol-5-yl]-2-fluorophenyl}propanenitrile (150 mg, 0.37 mmol, 1.0 equiv) in DMF (3 mL) was treated with 2-[(tert-butoxycarbonyl)amino]-2-cyclobutylpropanoic acid (147 mg, 0.603 mmol, 1.6 equiv), DIEA (146.34 mg, 1.13 mmol, 3.0 equiv) followed by the addition of HATU (215 mg, 0.56 mmol, 1.5 equiv) dropwise at 0° C. The resulting mixture was stirred for additional 16 h at room temperature. The residue was purified by silica gel column chromatography, eluted with PE/THE (1:1) to afford tert-butyl N-(1-{[(1S)-2-{4-[3-(2-butoxyethyl)-2-oxo-1,3-benzoxazol-5-yl]-2-fluorophenyl}-1-cyanoethyl]carbamoyl}-1-cyclobutylethyl)carbamate (185 mg, 78.72%). LCMS (ES, m/z): $[M+H]^+$: 623.

Synthesis of 2-amino-N-[(1S)-2-{4-[3-(2-butoxyethyl)-2-oxo-1,3-benzoxazol-5-yl]-2-fluorophenyl}-1-cyanoethyl]-2-cyclobutylpropanamide

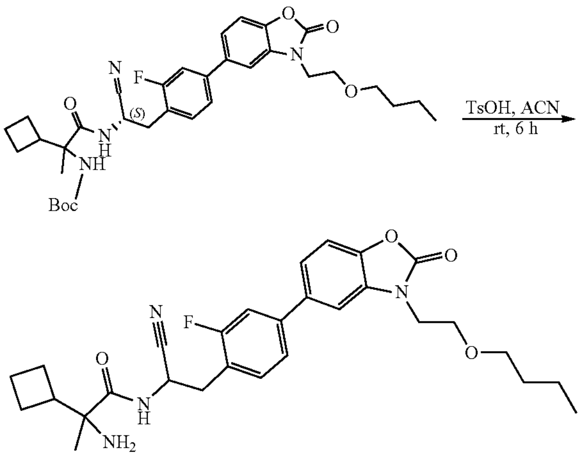

Compound 267

Into a 8 mL vial were added tert-butyl N-(1-{[(1S)-2-{4-[3-(2-butoxyethyl)-2-oxo-1,3-benzoxazol-5-yl]-2-fluorophenyl}-1-cyanoethyl]carbamoyl}-1-cyclobutylethyl)carbamate (170 mg, 0.27 mmol, 1.0 equiv), TsOH·$H_2O$ (141 mg, 0.82 mmol, 3.0 equiv) and ACN (3 mL) at room temperature. The resulting mixture was stirred for additional 6 h at room temperature. The residue was purified by reversed-phase flash chromatography with the following conditions: column, C18 silica gel; mobile phase, MeCN in Water (0.1% $NH_3.H_2O$), 10% to 80% gradient in 10 min; detector, UV 254 nm. This resulted in 2-amino-N-[(1S)-2-{4-[3-(2-butoxyethyl)-2-oxo-1,3-benzoxazol-5-yl]-2-fluorophenyl}-1-cyanoethyl]-2-cyclobutylpropanamide (75 mg, 52.57%).

LCMS (ES, m/z): $[M+H]^+$: 523.2

$^1$H NMR (400 MHz, DMSO-$d_6$) δ 7.66 (dd, J=7.4, 1.8 Hz, 1H), 7.57-7.48 (m, 2H), 7.48-7.42 (m, 2H), 7.39 (dd, J=8.4, 1.1 Hz, 1H), 5.07-4.91 (m, 1H), 4.12-3.99 (m, 2H), 3.69 (t, J=5.3 Hz, 2H), 3.37 (t, J=6.4 Hz, 2H), 3.28-[1394]3.14 (m, 2H), 2.51-2.46 (m, 1H), 1.91-1.41 (m, 6H), 1.39-1.30 (m, 2H), 1.22-1.10 (m, 2H), 0.97 (d, J=25.2 Hz, 3H), 0.75-0.68 (m, 3H).

Example 108: Synthesis of Compound 268: [0001] 2-amino-N-[(1S)-1-cyano-2-(4-{3-[2-(dimethylamino)ethyl]-2-oxo-1,3-benzoxazol-5-yl}-2-fluorophenyl)ethyl]-2-cyclobutylpropanamide

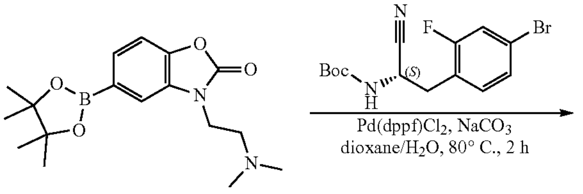

-continued

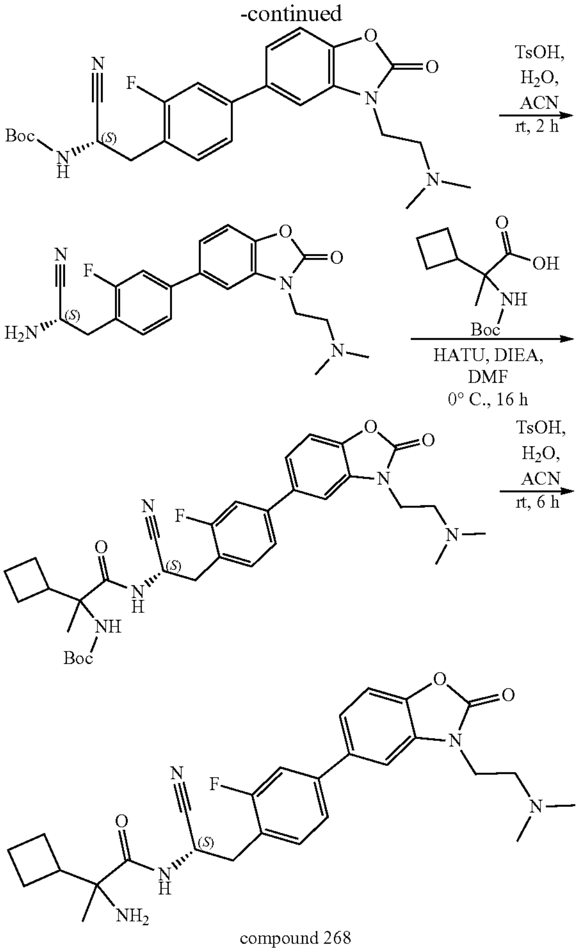

compound 268

Synthesis of tert-butyl N-[(1S)-1-cyano-2-(4-{3-[2-(dimethylamino)ethyl]-2-oxo-1,3-benzoxazol-5-yl}-2-fluorophenyl)ethyl]carbamate

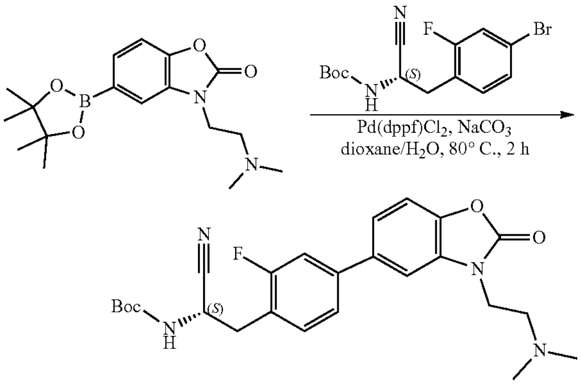

To a solution of 3-[2-(dimethylamino)ethyl]-5-(4,4,5,5-tetramethyl-1,3,2-dioxaborolan-2-yl)-1,3-benzoxazol-2-one (700 mg, 2.10 mmol, 1.2 equiv), tert-butyl N-[(1 S)-2-(4-bromo-2-fluorophenyl)-1-cyanoethyl]carbamate (602 mg, 1.76 mmol, 1.0 equiv) and $Na_2CO_3$ (372 mg, 3.51 mmol, 2.0 equiv) in dioxane (15 mL) and $H_2O$ (2 mL) was added $Pd(dppf)Cl_2$ (128 mg, 0.17 mmol, 0.1 equiv) at room temperature. The resulting mixture stirred for 2 h at 80° C. under nitrogen atmosphere. The reaction was concentrated. The residue was purified by silica gel column chromatography, eluted with PE/THE (1:1) to afford tert-butyl N-[(1S)-1-cyano-2-(4-{3-[2-(dimethylamino)ethyl]-2-oxo-1,3-benzoxazol-5-yl}-2-fluorophenyl)ethyl]carbamate (650 mg, 95% purity). LCMS (ES, m/z): $[M+H]^+$: 469.

Synthesis of (2S)-2-amino-3-(4-{3-[2-(dimethylamino)ethyl]-2-oxo-1,3-benzoxazol-5-yl}-2-fluorophenyl)propanenitrile

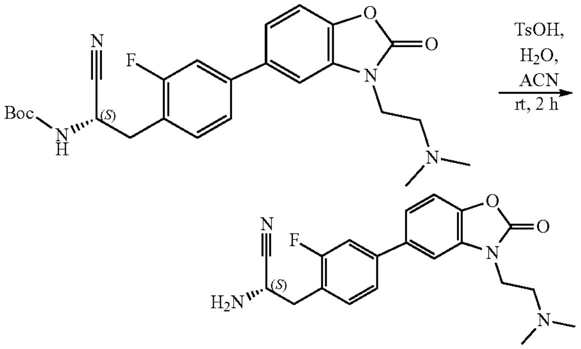

To a solution of tert-butyl N-[(1S)-1-cyano-2-(4-{3-[2-(dimethylamino)ethyl]-2-oxo-1,3-benzoxazol-5-yl}-2-fluorophenyl)ethyl]carbamate (650 mg, 1.38 mmol, 1.0 equiv) in ACN (20 mL) was added $TSOH{\cdot}H_2O$ (716 mg, 4.16 mmol, 3.0 equiv) at 0° C. The resulting mixture was stirred for 2 h at 0° C. to room temperature. The reaction mixture was adjusted pH to 8 with $NaHCO_3$ (5N), extracted with EtOAc (4×20 mL). The organic layer was concentrated. The residue was purified by silica gel column chromatography, eluted with PE/THE (1:2) to afford (2S)-2-amino-3-(4-{3-[2-(dimethylamino)ethyl]-2-oxo-1,3-benzoxazol-5-yl}-2-fluorophenyl)propanenitrile (420 mg, 95% purity). LCMS (ES, m/z): $[M+H]^+$: 369.

Synthesis of tert-butyl N-(1-{[(1S)-1-cyano-2-(4-{3-[2-(dimethylamino)ethyl]-2-oxo-1,3-benzoxazol-5-yl}-2-fluorophenyl)ethyl]carbamoyl}-1-cyclobutylethyl)carbamate

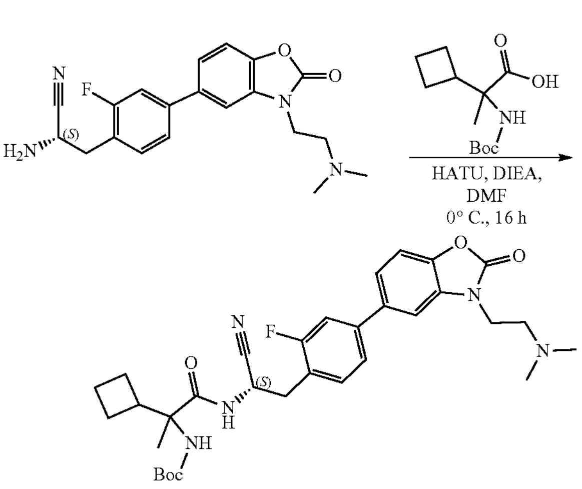

To a solution of (2S)-2-amino-3-(4-{3-[2-(dimethylamino)ethyl]-2-oxo-1,3-benzoxazol-5-yl}-2-fluorophenyl)propanenitrile (150 mg, 0.40 mmol, 1.0 equiv), 2-[(tert-butoxycarbonyl)amino]-2-cyclobutylpropanoic acid (148 mg, 0.61 mmol, 1.5 equiv) and DIEA (157 mg, 1.22 mmol, 3.0 equiv) in DMF (3 mL) was added HATU (232 mg, 0.61 mmol, 1.5 equiv) at 0° C. The resulting mixture was stirred for 16 h at 0° C. The reaction was concentrated. The residue was purified by silica gel column chromatography, eluted with PE/THE (1:1) to afford tert-butyl N-(1-{[(1S)-1-cyano-2-(4-{3-[2-(dimethylamino)ethyl]-2-oxo-1,3-benzoxazol-5-yl}-2-fluorophenyl)ethyl]carbamoyl}-1-cyclobutylethyl)carbamate (180 mg, 96% purity). LCMS (ES, m/z): $[M+H]^+$: 594.

Synthesis of 2-amino-N-[(1S)-1-cyano-2-(4-{3-[2-(dimethylamino)ethyl]-2-oxo-1,3-benzoxazol-5-yl}-2-fluorophenyl)ethyl]-2-cyclobutylpropanamide (70 mg, 99.1% purity)

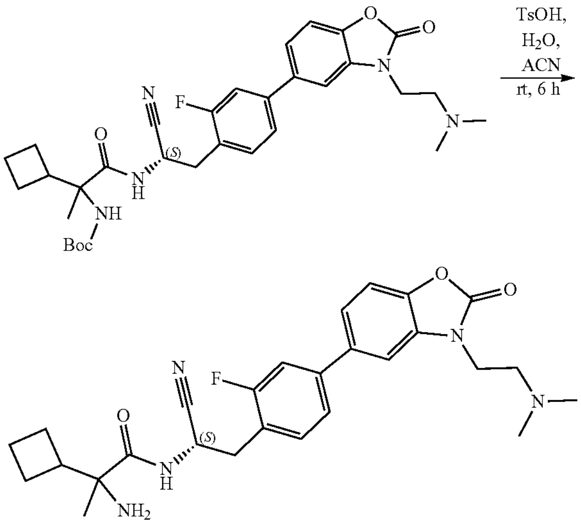

Into a 8 mL vial were added tert-butyl N-(1-{[(1S)-1-cyano-2-(4-{3-[2-(dimethylamino)ethyl]-2-oxo-1,3-benzoxazol-5-yl}-2-fluorophenyl)ethyl]carbamoyl}-1-cyclobutylethyl)carbamate (170 mg, 0.28 mmol, 1.0 equiv), $TSOH{\cdot}H_2O$(148 mg, 0.85 mmol, 3.0 equiv) and ACN (3 mL) at room temperature. The resulting mixture was stirred for additional 6 h at room temperature. The residue was purified by reversed-phase flash chromatography with the following conditions: column, C18 silica gel; mobile phase, MeCN in Water (0.1% $NH_3{\cdot}H_2O$), 10% to 80% gradient in 10 min; detector, UV 254 nm. This resulted in 2-amino-N-[(1S)-1-cyano-2-(4-{3-[2-(dimethylamino)ethyl]-2-oxo-1,3-benzoxazol-5-yl}-2-fluorophenyl)ethyl]-2-cyclobutylpropanamide (70 mg, 99.1% purity).

LCMS (ES, m/z): $[M+H]^+$: 494.2

$^1H$ NMR (400 MHz, DMSO-$d_6$) δ 7.68 (d, J=7.8 Hz, 1H), 7.62-7.51 (m, 2H), 7.49-7.38 (m, 3H), 5.01 (d, J=5.3 Hz, 1H), 3.98 (t, J=6.2 Hz, 2H), 3.29-3.12 (m, 2H), 2.61 (t, J=6.2 Hz, 2H), 2.49-2.40 (m, 1H), 2.18 (s, 6H), 1.91-1.35 (m, 6H), 0.98 (d, J=24.2 Hz, 3H).

Example 109: Synthesis of Compound 269: [0001] 2-amino-N—((S)-1-cyano-2-(2-fluoro-4-(1'-methyl-2,3-dihydrospiro[indene-1,4'-piperidin]-6-yl)phenyl)ethyl)-2-cyclobutylpropanamide

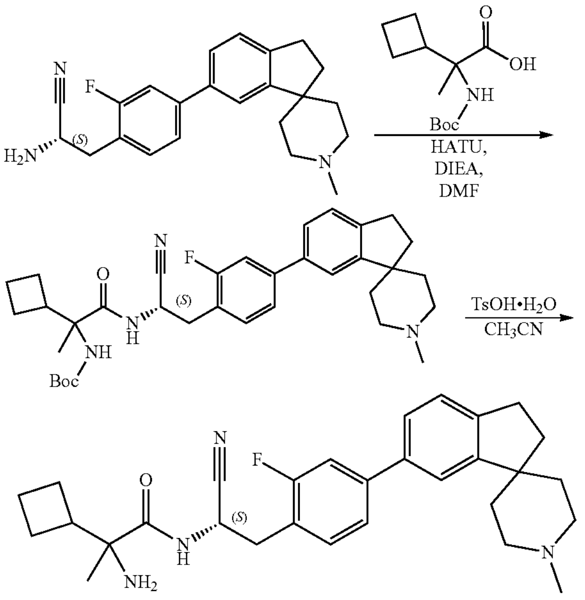

Compound 269

Synthesis of tert-butyl (1-(((S)-1-cyano-2-(2-fluoro-4-(1'-methyl-2,3-dihydrospiro[indene-1,4'-piperidin]-6-yl)phenyl)ethyl)amino)-2-cyclobutyl-1-oxopropan-2-yl)carbamate

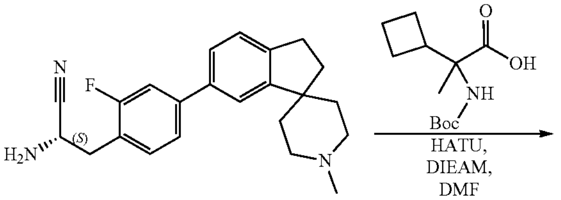

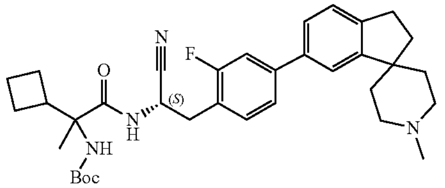

To a solution of 2-[(tert-butoxycarbonyl)amino]-2-cyclobutylpropanoic acid (161 mg, 0.66 mmol, 1.2 equiv), (2S)-2-amino-3-(2-fluoro-4-{1'-methyl-2,3-dihydrospiro[indene-1,4'-piperidin]-6-yl}phenyl)propanenitrile (200 mg, 0.55 mmol, 1.0 equiv), DIEA (214 mg, 1.66 mmol, 3.0 equiv) in DMF (4 mL) was added HATU (315 mg, 0.83 mmol, 1.5 equiv) in portions at 0° C. The reaction was quenched with water (15 mL) at room temperature. The resulting mixture was extracted with EtOAc (20 mL×2). The combined organic layer was washed with NaCl (aq.)(20 mL×2), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-(2-fluoro-4-{1'-methyl-2,3-dihydrospiro[indene-1,4'-piperidin]-6-yl}phenyl)ethyl]carbamoyl}-1-cyclobutylethyl)carbamate (160 mg, 49%). LCMS (ES) $[M+1]^+$ m/z: 589.

Synthesis of 2-amino-N-[(1S)-1-cyano-2-(2-fluoro-4-{1'-methyl-2,3-dihydrospiro[indene-1,4'-piperidin]-6-yl}phenyl)ethyl]-2-cyclobutylpropanamide

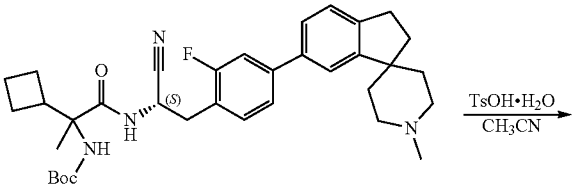

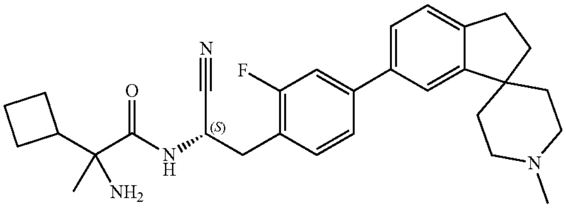

Compound 269

Into a 8 mL vial were added tert-butyl N-(1-{[(1S)-1-cyano-2-(2-fluoro-4-{1'-methyl-2,3-dihydrospiro[indene-1,4'-piperidin]-6-yl}phenyl)ethyl]carbamoyl}-1-cyclobutylethyl)carbamate (100 mg, 0.17 mmol, 1.0 equiv), ACN (3 mL) and $TsOH{\cdot}H_2O$ (97 mg, 0.51 mmol, 3.0 equiv) at room temperature. The resulting mixture was stirred for 3 h at room temperature. The residue product was purified by reverse phase flash with the following conditions: mobile phase, MeCN in water (0.1% $NH_3{\cdot}H_2O$), 10% to 70% gradient in 10 min. This resulted in 2-amino-N-[(1S)-1-cyano-2-(2-fluoro-4-{1'-methyl-2,3-dihydrospiro[indene-1,4'-piperidin]-6-yl}phenyl)ethyl]-2-cyclobutylpropanamide (17.9 mg, 21%). LCMS (ES) $[M+1]^+$ m/z: 489.

$^1H$ NMR (300 MHz, DMSO-$d_6$) δ 7.57-7.36 (m, 5H), 7.27 (d, J=7.7 Hz, 1H), 5.00 (td, J=8.2, 7.5, 3.3 Hz, 1H), 3.22 (ddt, J=21.2, 14.0, 7.1 Hz, 2H), 2.88 (t, J=7.3 Hz, 2H), 2.74 (d, J=10.8 Hz, 2H), 2.55-2.48 (m, 1H), 2.22 (s, 3H), 2.13-1.41 (m, 15H), 0.99 (d, J=17.4 Hz, 3H).

Example 110: Synthesis of Compound 272A and 272B: (R)-2-amino-N—((S)-1-cyano-2-(4-(1,3-dimethylpyrrolo[1,2-a]pyrazin-7-yl)-2-fluorophenyl)ethyl)-2-cyclobutylpropanamide and (S)-2-amino-N—((S)-1-cyano-2-(4-(1,3-dimethylpyrrolo[1,2-a]pyrazin-7-yl)-2-fluorophenyl)ethyl)-2-cyclobutylpropanamide

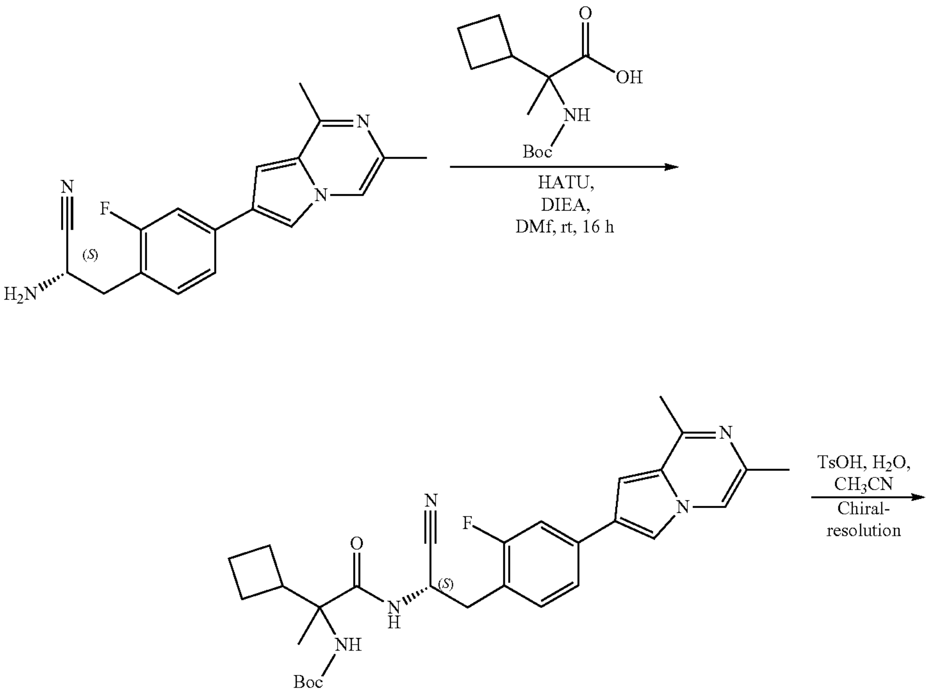

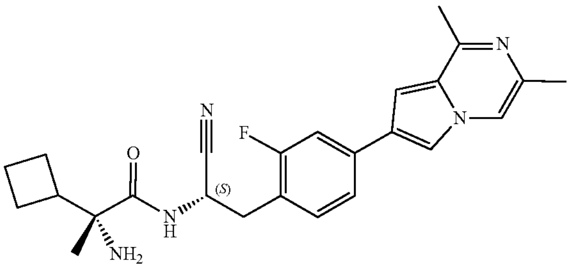

272A
Assumed

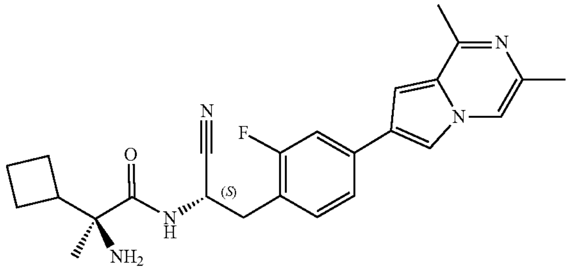

272B
Assumed

Synthesis of tert-butyl (1-(((S)-1-cyano-2-(4-(1,3-dimethylpyrrolo[1,2-a]pyrazin-7-yl)-2-fluorophenyl)ethyl)amino)-2-cyclobutyl-1-oxopropan-2-yl)carbamate Into a 40 mL vial were added (2S)-2-amino-3-(4-{1,3-dimethylpyrrolo[1,2-a]pyrazin-7-yl}-2-fluorophenyl)propanenitrile (150 mg, 0.49 mmol, 1.0 equiv), 2-[(tert-butoxycarbonyl)amino]-2-cyclobutylpropanoic acid (178 mg, 0.73 mmol, 1.5 equiv), DMF (5 mL), DIEA (189 mg, 1.46 mmol, 3.0 equiv). This was followed by the addition of HATU (277 mg, 0.73 mmol, 1.5 equiv) at 0° C. The resulting mixture was stirred for 16 h at room temperature. The reaction was quenched with water (15 mL) at room temperature. The aqueous layer was extracted with EtOAc (20 mL×2). The combined organic phase was washed with brine (15 mL×3), dried over anhydrous sodium sulfate. After filtration, the filtrate was concentrated under vacuum. The residue was purified by silica gel column chromatography, eluted with PE/EA (1:1) to afford tert-butyl N-(1-{[(1S)-1-cyano-2-(4-{1,3-dimethylpyrrolo[1,2-a]pyrazin-7-yl}-2-fluorophenyl)ethyl]carbamoyl}-1-cyclobutylethyl)carbamate (200 mg, 77%). LCMS (ES) $[M+1]^+$ m/z: 534.

Synthesis of (R)-2-amino-N—((S)-1-cyano-2-(4-(1,3-dimethylpyrrolo[1,2-a]pyrazin-7-yl)-2-fluorophenyl)ethyl)-2-cyclobutylpropanamide and (S)-2-amino-N—((S)-1-cyano-2-(4-(1,3-dimethylpyrrolo[1,2-a]pyrazin-7-yl)-2-fluorophenyl)ethyl)-2-cyclobutylpropanamide

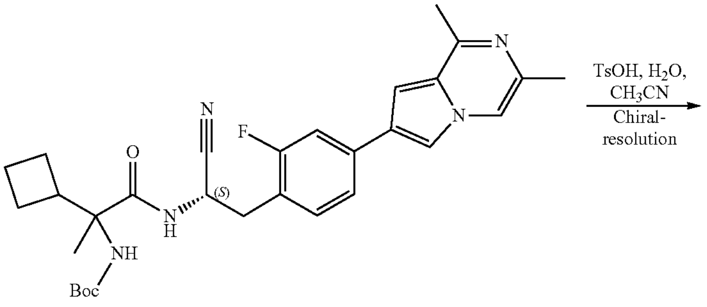

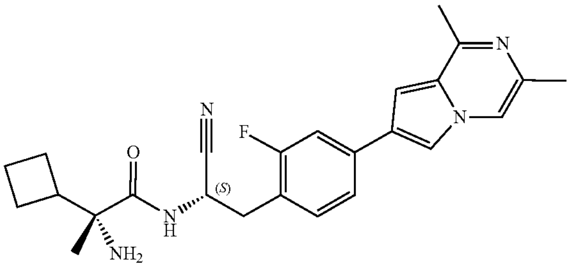
272A
Assumed

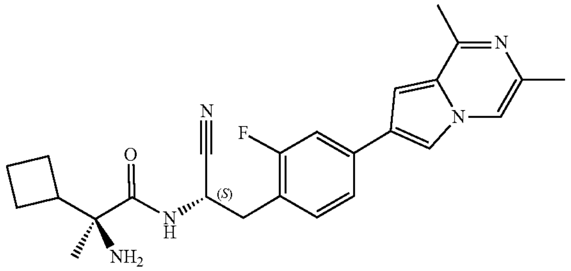
272B
Assumed

Into a 8 mL vial were added tert-butyl N-(1-{[(1S)-1-cyano-2-(4-{1,3-dimethylpyrrolo[1,2-a]pyrazin-7-yl}-2-fluorophenyl)ethyl]carbamoyl}-1-cyclobutylethyl)carbamate (180 mg, 0.34 mmol, 1.0 equiv), $CH_3CN$ (3 mL) and $TsOH{\cdot}H_2O$ (192 mg, 1.01 mmol, 3.0 equiv) at room temperature. The resulting mixture was stirred for 3 h at room temperature. The reaction solution was purified by reverse phase flash with the following conditions: column C18-120 g, mobile phase, MeCN in Water (0.1% $NH_3{\cdot}H_2O$), 10% to 70% gradient in 10 min; detector, UV 254 nm. This resulted in 2-amino-N-[(1S)-1-cyano-2-(4-{1,3-dimethylpyrrolo[1,2-a]pyrazin-7-yl}-2-fluorophenyl)ethyl]-2-cyclobutylpropanamide (100 mg, 68%) and separated by Chiral-HPLC Column: CHIRALPAK IF, 3*25 cm, 5 m; Mobile Phase A: Hex: DCM=5: 1-HPLC, Mobile Phase B: EtOH(0.1% 2 M $NH_3$-MeOH); Flow rate: 35 mL/min; Gradient: isocratic 25; Wave Length: 254 nm; RT1(min): 8; RT2(min): 14; Sample Solvent: EtOH: DCM=1: 1-HPLC; Injection Volume: 0.8 mL; Number Of Runs: 5 to afford (2R)-2-amino-N-[(1S)-1-cyano-2-(4-{1,3-dimethylpyrrolo[1,2-a]pyrazin-7-yl}-2-fluorophenyl)ethyl]-2-cyclobutylpropanamide (18.9 mg, 19%), (2S)-2-amino-N-[(1S)-1-cyano-2-(4-{1,3-dimethylpyrrolo[1,2-a]pyrazin-7-yl}-2-fluorophenyl)ethyl]-2-cyclobutylpropanamide (18.4 mg, 18%). LCMS (ES) $[M+1]^+$ m/z: 434.1

Compound 272A $^1H$ NMR (300 MHz, DMSO-$d_6$) δ 8.10 (s, 1H), 7.90 (s, 1H), 7.65-7.55 (m, 2H), 7.39 (t, J=8.0 Hz, 1H), 7.26 (s, 1H), 4.99 (t, J=7.8 Hz, 1H), 3.25 (dd, J=13.8, 7.3 Hz, 1H), 3.16 (dd, J=13.8, 8.4 Hz, 1H), 2.57-2.54 (m, 4H), 2.28 (s, 3H), 1.93-1.62 (m, 4H), 1.59-1.51 (m, 2H), 0.95 (s, 3H).

Compound 272B $^1H$ NMR (300 MHz, DMSO-$d_6$) δ 8.09 (s, 1H), 7.90 (s, 1H), 7.64-7.54 (m, 2H), 7.38 (t, J=7.9 Hz, 1H), 7.25 (s, 1H), 4.99 (t, J=7.8 Hz, 1H), 3.26-3.14 (m, 2H), 2.57 (s, 3H), 2.49-2.44 (m, 1H), 2.28 (s, 3H), 1.84-1.74 (m, 1H), 1.73-1.55 (m, 3H), 1.52-1.46 (m, 2H), 1.02 (s, 3H).

Example 111. Synthesis of Compound 270A and 270B:(2S)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide; (2R)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide
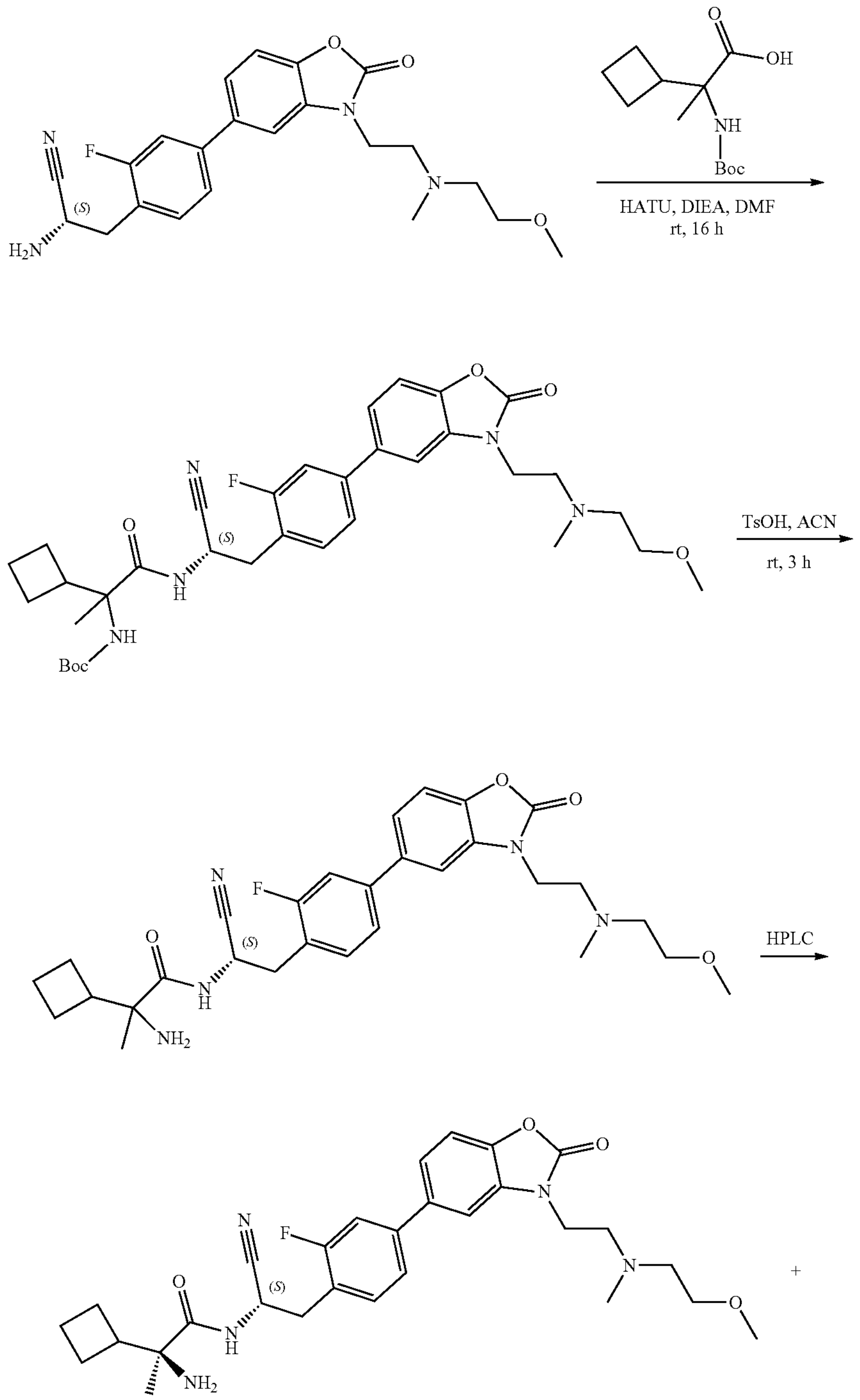
Compound 270A -continued

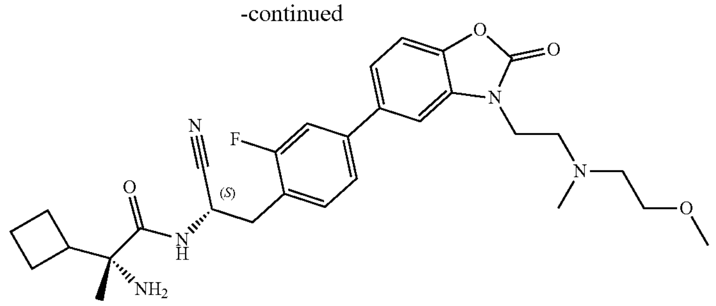

Compound 270B

Synthesis of tert-butyl N-(1-{[(1S)-1-cyano-2-[2-fluoro-4-(3-{2-[(2-methoxyethyl)(methyl)amino]ethyl}-2-oxo-1,3-benzoxazol-5-yl)phenyl]ethyl]carbamoyl}-1-cyclobutylethyl)carbamate

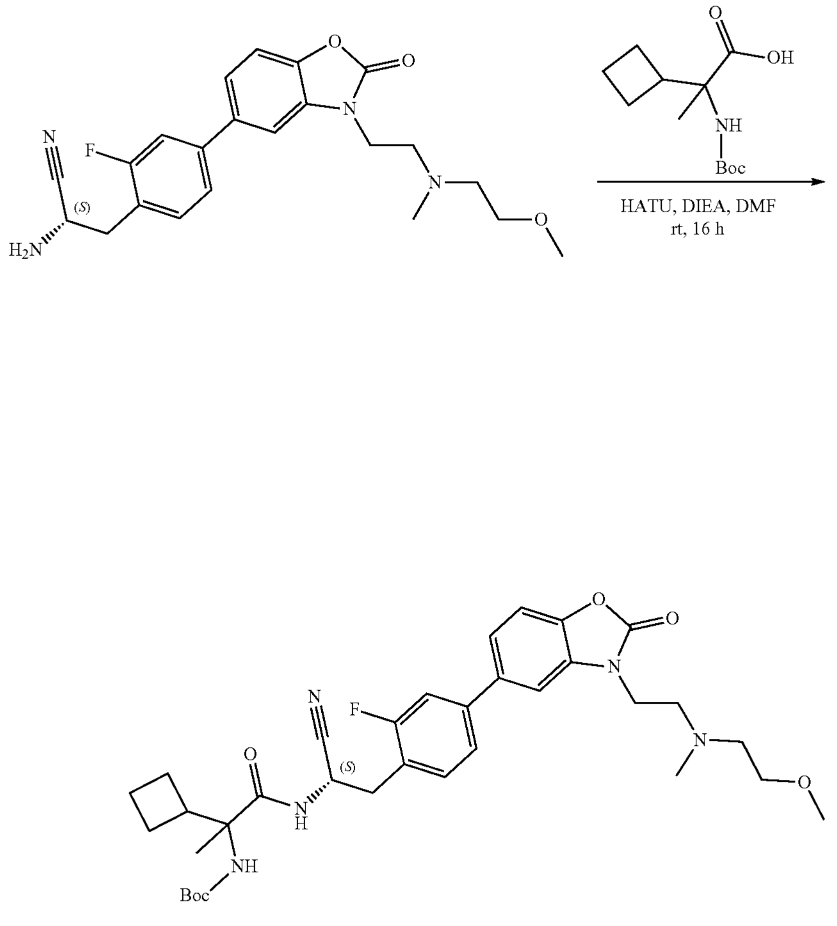

To a stirred solution of (2S)-2-amino-3-[2-fluoro-4-(3-{2-[(2-methoxyethyl)(methyl)amino]ethyl}-2-oxo-1,3-benzoxazol-5-yl)phenyl]propanenitrile (150 mg, 0.36 mmol, 1.0 equiv) and 2-[(tert-butoxycarbonyl)amino]-2-cyclobutylpropanoic acid (133 mg, 0.54 mmol, 1.5 equiv), DIEA (141 mg, 1.09 mmol, 3.0 equiv) in DMF (3 mL) was added HATU (166 mg, 0.43 mmol, 1.2 equiv) in portions at 0° C. The resulting mixture was stirred for 16 h at room temperature. The reaction was quenched with water (10 mL), extracted with EtOAc (3x20 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/THE (1:1) to afford tert-butyl N-(1-{[(1S)-1-cyano-2-[2-fluoro-4-(3-{2-[(2-methoxyethyl)(methyl)amino]ethyl}-2-oxo-1,3-benzoxazol-5-yl)phenyl]ethyl]carbamoyl}-1-cyclobutylethyl)carbamate (150 mg, 64.7%). LCMS (ES, m/z): $[M+H]^+$: 638.

Synthesis of 2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide

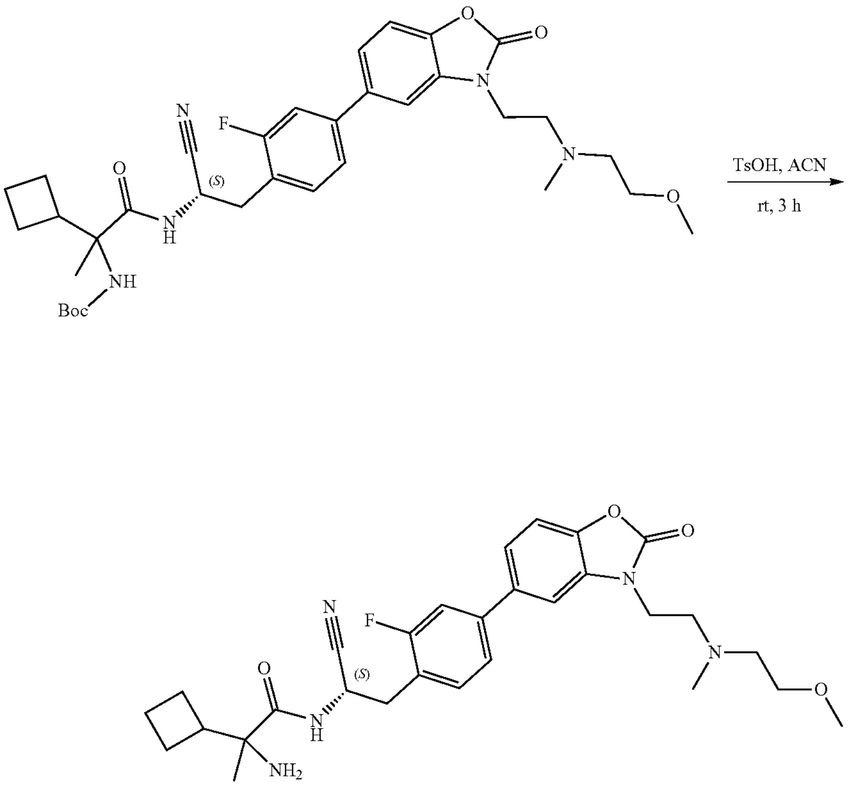

Into a 25 mL round-bottom flask were added tert-butyl N-(1-{[(1S)-1-cyano-2-[2-fluoro-4-(3-{2-[(2-methoxyethyl)(methyl)amino]ethyl}-2-oxo-1,3-benzoxazol-5-yl)phenyl]ethyl]carbamoyl}-1-cyclobutylethyl)carbamate (150 mg, 0.24 mmol, 1.0 equiv), ACN (4 mL) and TsOH·$H_2O$ (134 mg, 0.70 mmol, 3.0 equiv) at room temperature. The reaction solution was purified by reversed-phase flash chromatography with the following conditions: column, C18 silica gel-120 g; mobile phase, MeCN in Water (0.1% $NH_3$·$H_2O$), 10% to 50% gradient in 10 min; detector, UV 254 nm. This resulted in 2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide (60 mg, 47.4%). LCMS (ES, m/z): $[M+H]^+$: 538.

Synthesis of (2S)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide; (2R)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide

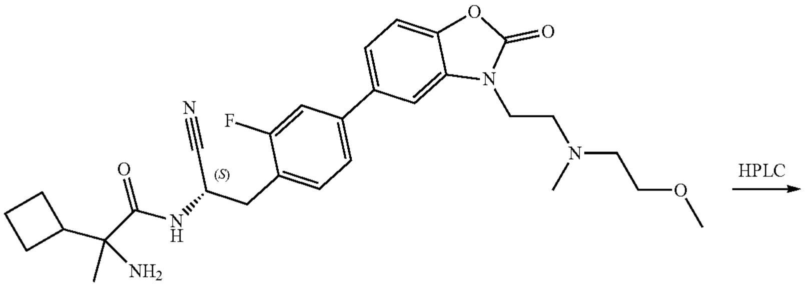

-continued

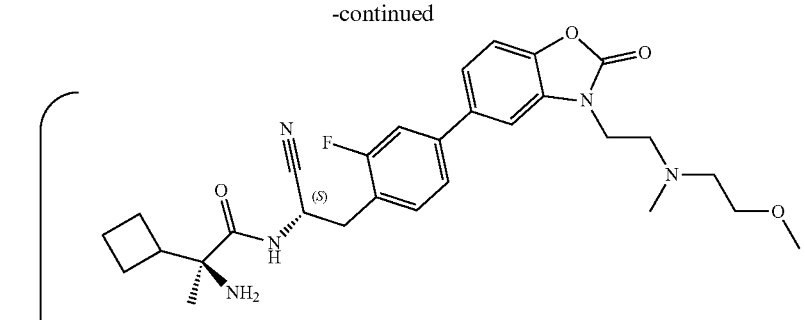

Compound 270A

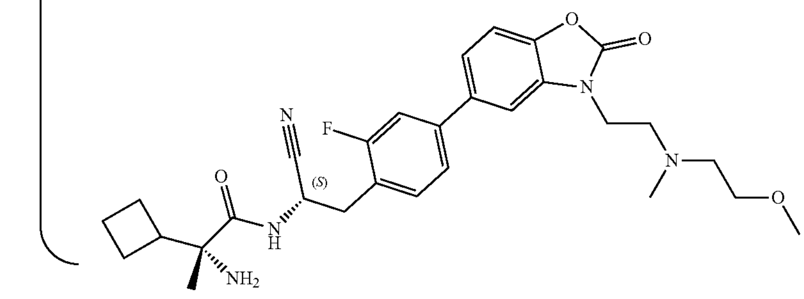

Compound 270B 2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide (60 mg, 0.12 mmol, 1.0 equiv) was purified by Prep-HPLC with the following conditions Column; XA-CHIRALPAK IF, 3*25 cm, 5 m; Mobile Phase A: Hex: DCM=3: 1-HPLC, Mobile Phase B: EtOH (0.1% 2M $NH_3$-MeOH); Flow rate: 35 mL/min; Gradient: isocratic 10; Wave Length: 254 nm; RT1(min): 10.3; RT2(min): 12.3; Sample Solvent: EtOH: DCM=1: 1-HPLC; Injection Volume: 0.8 mL; Number Of Runs: 6. This resulted in (2S)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide (13.3 mg, 22%) and (2R)-2-amino-N-[(1S)-1-cyano-2-[2-fluoro-4-(3-{2-[(2-methoxyethyl)(methyl)amino]ethyl}-2-oxo-1,3-benzoxazol-5-yl)phenyl]ethyl]-2-cyclobutylpropanamide (10.6 mg, 17%).

LCMS (ES, m/z): $[M+H]^+$: 538.5

Compound 270A: $^1H$ NMR (400 MHz, DMSO-$d_6$) δ 7.69 (s, 1H), 7.61-7.54 (m, 2H), 7.51-7.43 (m, 2H), 7.41 (d, J=8.4 Hz, 1H), 5.01 (t, J=7.8 Hz, 1H), 3.97 (t, J=6.0 Hz, 2H), 3.28-3.15 (m, 4H), 3.05 (s, 3H), 2.75 (t, J=6.0 Hz, 2H), 2.56-2.52 (m, 3H), 2.26 (s, 3H), 1.93-1.62 (m, 4H), 1.60-1.49 (m, 2H), 0.96 (s, 3H).

Compound 270B: $^1H$ NMR (400 MHz, DMSO-$d_6$) δ 7.67 (s, 1H), 7.60-7.53 (m, 2H), 7.48-7.39 (m, 3H), 5.02 (t, J=7.8 Hz, 1H), 3.97 (t, J=6.2 Hz, 2H), 3.27-3.22 (m, 4H), 3.05 (s, 3H), 2.74 (t, J=6.1 Hz, 2H), 2.54-2.45 (m, 3H), 2.26 (s, 3H), 1.84-1.55 (m, 4H), 1.53-1.37 (m, 2H), 1.02 (s, 3H).

Example 112: Synthesis of Compound 273A and 273B: (4S)-4-amino-N-[(1S)-1-cyano-2-[2-fluoro-4-(3-methyl-2-oxo-1,3-benzoxazol-5-yl)phenyl]ethyl]spiro[2.4]heptane-4-carboxamide and (4R)-4-amino-N-[(1S)-1-cyano-2-[2-fluoro-4-(3-methyl-2-oxo-1,3-benzoxazol-5-yl)phenyl]ethyl]spiro[2.4]heptane-4-carboxamide

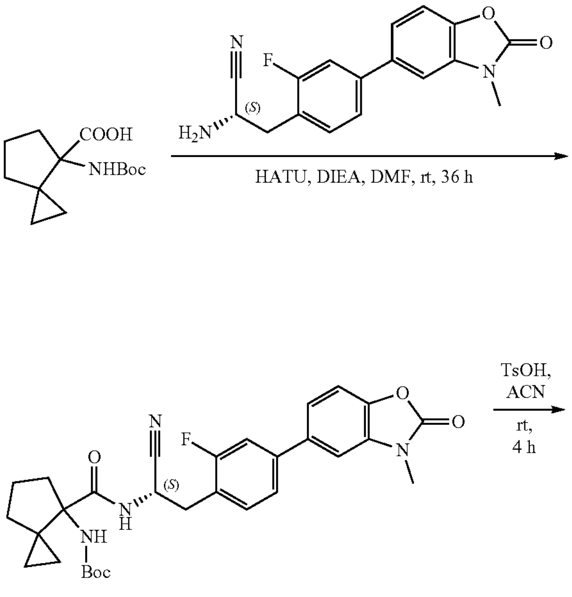

-continued

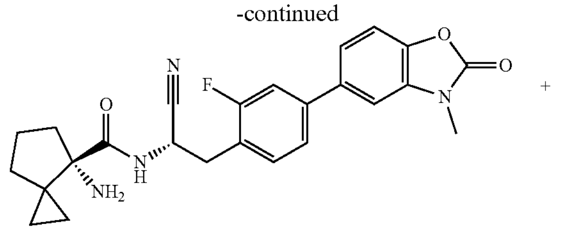

Compound 273A
Assumed

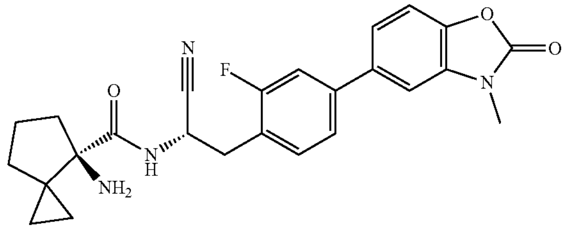

Compound 273B
Assumed

Synthesis of tert-butyl N-(4-{[(1S)-1-cyano-2-[2-fluoro-4-(3-methyl-2-oxo-1,3-benzoxazol-5-yl)phenyl]ethyl]carbamoyl}spiro[2.4]heptan-4-yl)carbamate

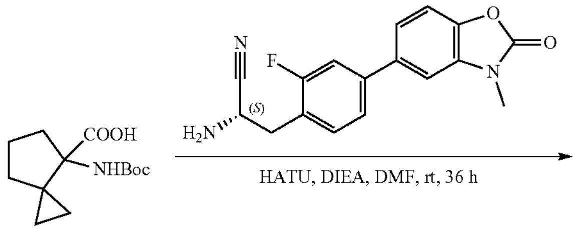

-continued

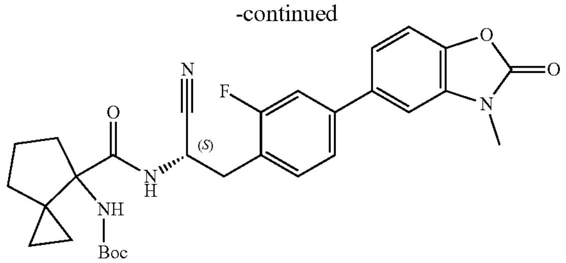

To a stirred mixture of 4-[(tert-butoxycarbonyl)amino]spiro[2.4]heptane-4-carboxylic acid (167 mg, 0.65 mmol, 1.2 equiv), (2S)-2-amino-3-[2-fluoro-4-(3-methyl-2-oxo-1,3-benzoxazol-5-yl)phenyl]propanenitrile (170 mg, 0.54 mmol, 1.0 equiv) and DIEA (141 mg, 1.09 mmol, 2.0 equiv) in DCM (5 mL) were added HATU (249 mg, 0.65 mmol, 1.2 equiv) at 0° C. The resulting mixture was stirred for 36 h at room temperature. Concentrated under reduced pressure to remove the solvent, the residue was purified by silica gel column chromatography, eluted with PE/THE (1:1) to afford tert-butyl N-(4-{[(1S)-1-cyano-2-[2-fluoro-4-(3-methyl-2-oxo-1,3-benzoxazol-5-yl)phenyl]ethyl]carbamoyl}spiro[2.4]heptan-4-yl)carbamate (200 mg, 66.8%). LCMS (ES, m z): $[M+H]^+$: 549.

Synthesis of (4S)-4-amino-N-[(1S)-1-cyano-2-[2-fluoro-4-(3-methyl-2-oxo-1,3-benzoxazol-5-yl)phenyl]ethyl]spiro[2.4]heptane-4-carboxamide and (4R)-4-amino-N—[(1S)-1-cyano-2-[2-fluoro-4-(3-methyl-2-oxo-1,3-benzoxazol-5-yl)phenyl]ethyl]spiro[2.4]heptane-4-carboxamide

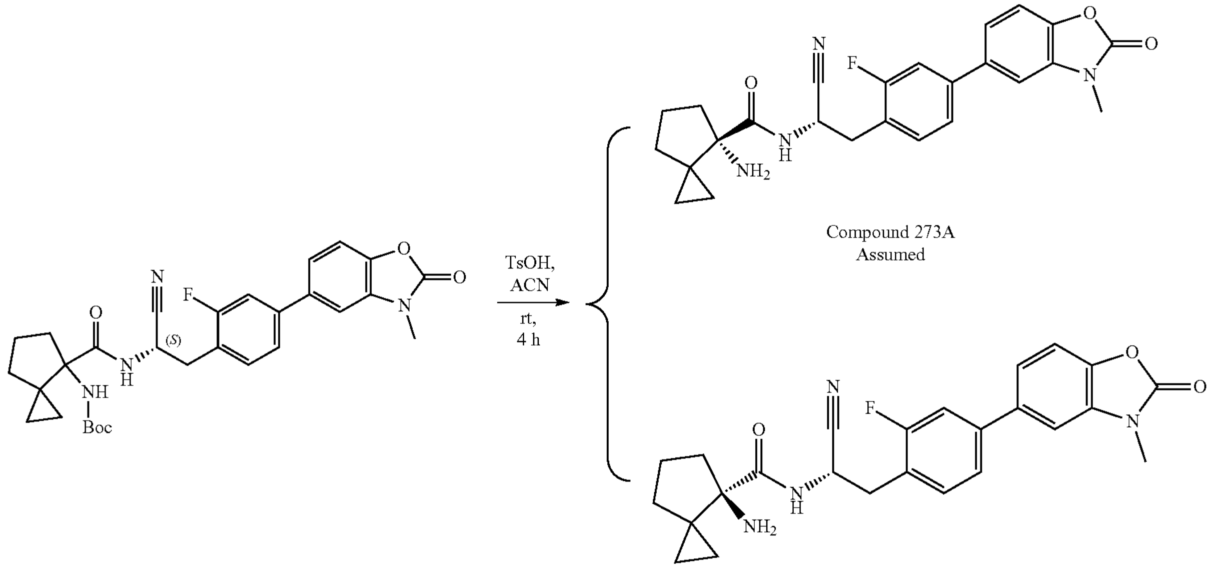

Compound 273A
Assumed

Compound 273B
Assumed

Into a 25 mL round-bottom flask were added tert-butyl N-(4-{[(1S)-1-cyano-2-[2-fluoro-4-(3-methyl-2-oxo-1,3-benzoxazol-5-yl)phenyl]ethyl]carbamoyl}spiro[2.4]heptan-4-yl)carbamate (190 mg, 0.34 mmol, 1.0 equiv), TsOH (178 mg, 1.03 mmol, 3.0 equiv) and ACN (5 mL) at room temperature. The resulting mixture was stirred for 3 h at room temperature. The reaction solution was purified by reversed-phase flash chromatography with the following conditions: column, C18 silica gel-120 g; mobile phase, MeCN in Water (0.1% $NH_3{\cdot}H_2O$), 10% to 60% gradient in 12 min; detector, UV 254 nm. The product was further purified by Prep-CHIRAL-HPLC with the following conditions: Column: CHIRALPAK IC, 2*25 cm, 5 m; Mobile Phase A: Hex: DCM=2: 1-HPLC, Mobile Phase B: EtOH (0.1% 2M $NH_3$-MEOH); Flow rate: 25 mL/min; Gradient: isocratic 20; Wave Length: 254 nm; RT1(min): 6.3; RT2 (min): 7.5; Sample Solvent: EtOH: DCM=1: 1. This resulted in (4S)-4-amino-N-[(1S)-1-cyano-2-[2-fluoro-4-(3-methyl-2-oxo-1,3-benzoxazol-5-yl)phenyl]ethyl]spiro[2.4]heptane-4-carboxamide (25 mg, 32%) and (4R)-4-amino-N-[(1S)-1-cyano-2-[2-fluoro-4-(3-methyl-2-oxo-1,3-benzoxazol-5-yl)phenyl]ethyl]spiro[2.4]heptane-4-carboxamide (25 mg, 32%).

LCMS (ES, m z): $[M+H]^+$: 449.1

Compound 273A: $^1H$ NMR (300 MHz, DMSO-$d_6$): δ 7.67 (s, 1H), 7.62-7.55 (m, 2H), 7.50-7.45 (m, 2H), 7.41 (d, J=8.3 Hz, 1H), 4.97 (t, J=7.9 Hz, 1H), 3.41 (s, 3H), 3.33-3.27 (m, 1H), 3.16 (dd, J=13.8, 7.8 Hz, 1H), 2.38-2.30 (m, 1H), 1.83-1.62 (m, 4H), 1.58-1.52 (m, 1H), 0.73-0.62 (m, 1H), 0.44-0.25 (m, 3H).

Compound 273B: $^1H$ NMR (300 MHz, DMSO-$d_6$): δ 7.64 (d, J=1.8 Hz, 1H), 7.63-7.52 (m, 2H), 7.52-7.43 (m, 2H), 7.40 (d, J=8.3 Hz, 1H), 5.01 (t, J=7.9 Hz, 1H), 3.41 (s, 3H), 3.29-3.14 (m, 2H), 2.43-2.35 (m, 1H), 1.84-1.53 (m, 5H), 0.49-0.44 (m, 1H), 0.24-0.18 (m, 2H), 0.01 −0.04 (m, 1H).

Example 113: Synthesis of Compound 276: (2S)—N-[(1S)-1-cyano-2-[2-fluoro-4-(5,6,7,8-tetrahydro-1,5-naphthyridin-2-yl)phenyl]ethyl]-3-(dimethylamino)-2-hydroxypropanamide

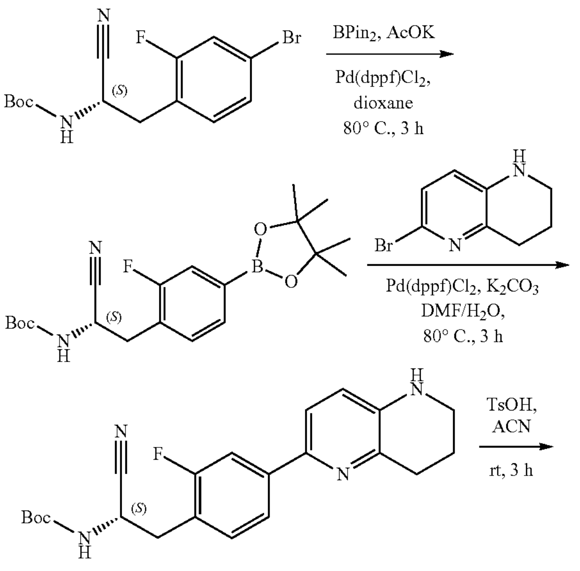

-continued

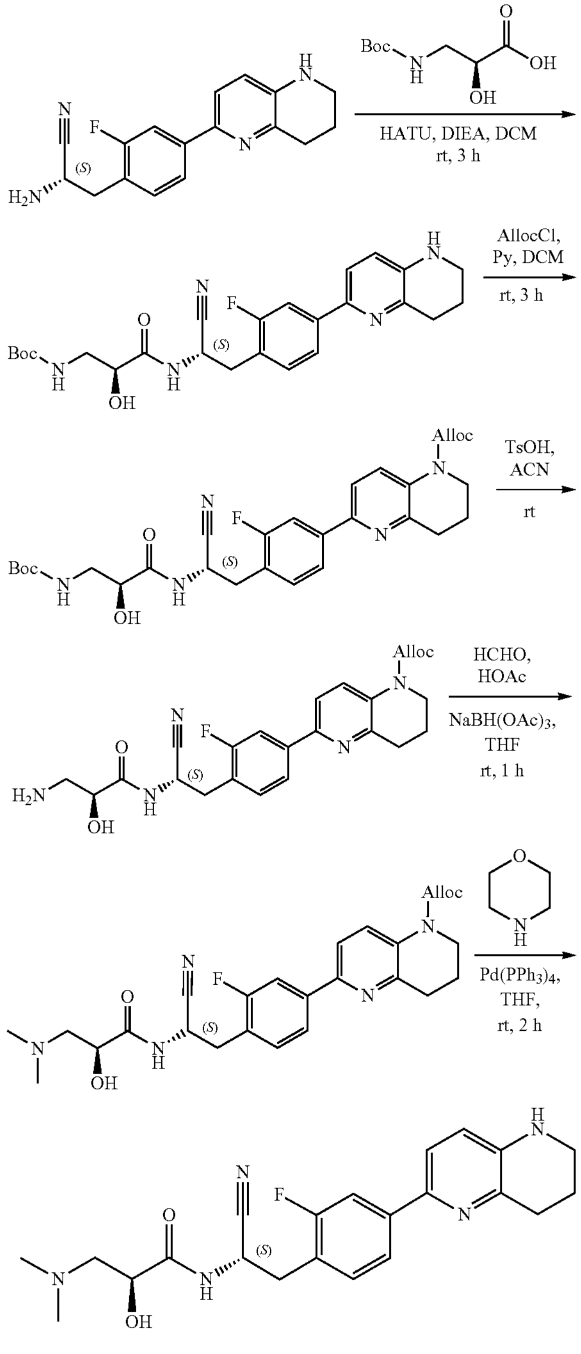

Synthesis of tert-butyl N-[(1S)-1-cyano-2-[2-fluoro-4-(4,4,5,5-tetramethyl-1,3,2-dioxaborolan-2-yl)phenyl]ethyl]carbamate

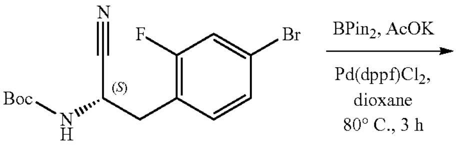

-continued

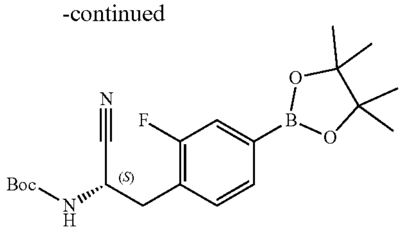

To a mixture of tert-butyl N-[(1S)-2-(4-bromo-2-fluorophenyl)-1-cyanoethyl]carbamate (1.2 g, 3.50 mmol, 1.0 equiv) and bis(pinacolato)diboron (1.1 g, 4.21 mmol, 1.20 equiv), AcOK (0.7 g, 6.99 mmol, 2.0 equiv) in 1,4-dioxane (12 mL) was added $Pd(dppf)Cl_2 \cdot CH_2Cl_2$ (0.3 g, 0.35 mmol, 0.1 equiv). The reaction mixture was stirred at 80° C. for 3 h under nitrogen atmosphere. The reaction was cooled to room temperature, concentrated to remove the solvent, the residue was purified by silica gel column chromatography, eluted with PE/THF (1:1) to afford tert-butyl N-[(1S)-1-cyano-2-[2-fluoro-4-(4,4,5,5-tetramethyl-1,3,2-dioxaborolan-2-yl)phenyl]ethyl]carbamate (1.2 g, 87.94% yield, 98% purity). LCMS (ES, m/z): $[M+H]^+$: 391.

Synthesis of tert-butyl N-[(1S)-1-cyano-2-[2-fluoro-4-(5,6,7,8-tetrahydro-1,5-naphthyridin-2-yl)phenyl]ethyl]carbamate

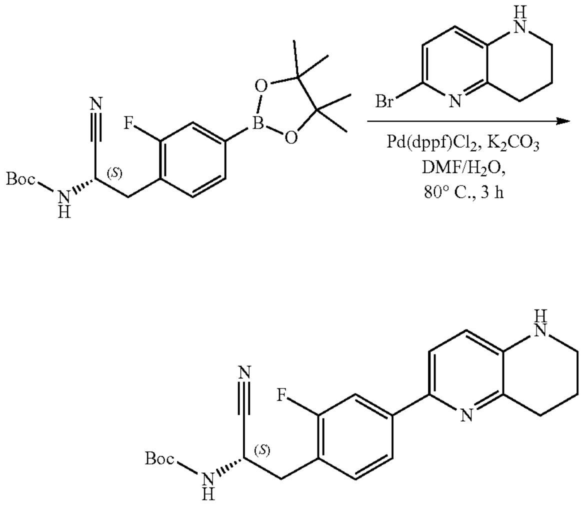

To a mixture of tert-butyl N-[(1S)-1-cyano-2-[2-fluoro-4-(4,4,5,5-tetramethyl-1,3,2-dioxaborolan-2-yl)phenyl]ethyl]carbamate (1.7 g, 4.52 mmol, 1.2 equiv) and 2-bromo-5,6,7,8-tetrahydro-1,5-naphthyridine (0.8 g, 3.77 mmol, 1.0 equiv) in DMF (20 mL) and $H_2O$ (2 mL) were added $Pd(dppf)Cl_2 \cdot CH_2Cl_2$ (0.3 g, 0.38 mmol, 0.1 equiv), $K_2CO_3$ (7.0 g, 7.54 mmol, 2.0 equiv). The mixture was stirred at 80° C. for 3 h under nitrogen atmosphere. The reaction was cooled to room temperature, concentrated to remove the solvent, the residue was purified by silica gel column chromatography, eluted with PE/THF (2:1) to afford tert-butyl N-[(1S)-1-cyano-2-[2-fluoro-4-(5,6,7,8-tetrahydro-1,5-naphthyridin-2-yl)phenyl]ethyl]carbamate (1 g, 67% yield, 97% purity). LCMS (ES, m/z): $[M+H]^+$: 397.

Synthesis of (2S)-2-amino-3-[2-fluoro-4-(5,6,7,8-tetrahydro-1,5-naphthyridin-2-yl)phenyl]propanenitrile

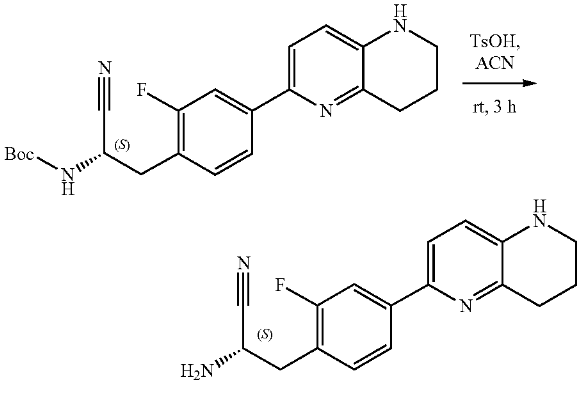

Into a 100 mL round-bottom flask were added tert-butyl N-[(1S)-1-cyano-2-[2-fluoro-4-(5,6,7,8-tetrahydro-1,5-naphthyridin-2-yl)phenyl]ethyl]carbamate (1.0 g, 2.52 mmol, 1.0 equiv) in acetonitrile (30 mL) and TsOH (1.30 g, 7.57 mmol, 3.0 equiv) at room temperature. The mixture was basified to pH 8 with saturated $NaHCO_3$ (aq.). The resulting mixture was extracted with EtOAc (3×50 mL). The combined organic layer was washed with brine (50 mL), dried over anhydrous $Na_2SO_4$. After filtration, the filtrate was concentrated under reduced pressure. The residue was purified by silica gel column chromatography, eluted with PE/THE (1:2) to afford (2S)-2-amino-3-[2-fluoro-4-(5,6,7,8-tetrahydro-1,5-naphthyridin-2-yl)phenyl]propanenitrile (700 mg, 93% yield, 95% purity). LCMS (ES, m/z): $[M+H]^+$: 297.

Synthesis of tert-butyl N-[(2S)-2-{[(1S)-1-cyano-2-[2-fluoro-4-(5,6,7,8-tetrahydro-1,5-naphthyridin-2-yl)phenyl]ethyl]carbamoyl}-2-hydroxyethyl]carbamate

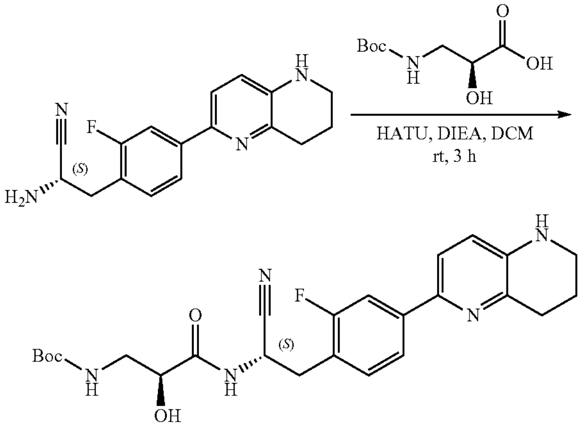

To a stirred solution of (2S)-2-amino-3-[2-fluoro-4-(5,6,7,8-tetrahydro-1,5-naphthyridin-2-yl)phenyl]propanenitrile (340 mg, 1.15 mmol, 1.0 equiv) and (2S)-3-[(tert-butoxycarbonyl)amino]-2-hydroxypropanoic acid (353 mg, 1.72 mmol, 1.5 equiv), DIEA (444 mg, 3.44 mmol, 3.0 equiv) in DCM (5 mL) was added HATU (523 mg, 1.376 mmol, 1.2 equiv) in portions at 0° C. under air atmosphere. Concentrated to remove the solvent, the residue was purified by silica gel column chromatography, eluted with PE/DCM/THE (1:1:1) to afford tert-butyl N-[(2S)-2-{[(1S)-1-cyano-2-[2-fluoro-4-(5,6,7,8-tetrahydro-1,5-naphthyridin-2-yl)phenyl]ethyl]carbamoyl}-2-hydroxyethyl]carbamate (500 mg, 90% yield, 87% purity). LCMS (ES, m/z): $[M+H]^+$: 484.

Synthesis of prop-2-en-1-yl 6-{4-[(2S)-2-[(2S)-3-[(tert-butoxycarbonyl)amino]-2-hydroxypropanamido]-2-cyanoethyl]-3-fluorophenyl}-3,4-dihydro-2H-1,5-naphthyridine-1-carboxylate

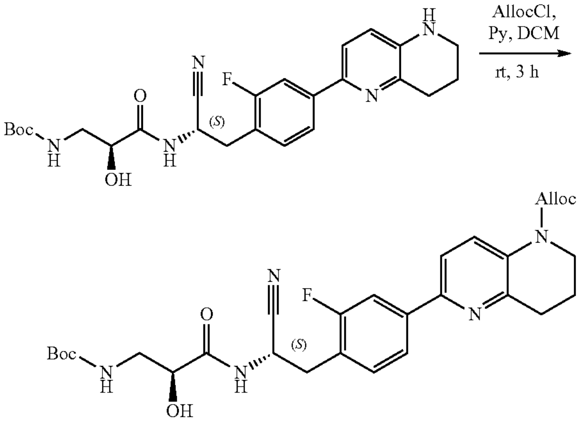

To a solution of tert-butyl N-[(2S)-2-{[(1S)-1-cyano-2-[2-fluoro-4-(5,6,7,8-tetrahydro-1,5-naphthyridin-2-yl)phenyl]ethyl]carbamoyl}-2-hydroxyethyl]carbamate (340 mg, 0.70 mmol, 1.0 equiv), pyridine (166 mg, 2.11 mmol, 3.0 equiv) in DCM (5 mL) was added and allyl chlorocarbonate (101 mg, 0.84 mmol, 1.20 equiv) dropwise at 0° C. After addition, the mixture was stirred at room temperature for 3 h. The reaction was quenched with water (20 mL), extracted with DCM (20 mL×1). The combined organic phase was dried over anhydrous sodium sulfate. After filtration, the filtrate was concentrated under reduced pressure. The residue was purified by silica gel column chromatography, eluted with PE/DCM/THF (1:1:1) to afford prop-2-en-1-yl 6-{4-[(2S)-2-[(2S)-3-[(tert-butoxycarbonyl)amino]-2-hydroxypropanamido]-2-cyanoethyl]-3-fluorophenyl}-3,4-dihydro-2H-1,5-naphthyridine-1-carboxylate (250 mg, 62% yield, 90% purity). LCMS (ES, m/z): $[M+H]^+$: 568.

Synthesis of (2S)—N-[(1S)-1-cyano-2-[2-fluoro-4-(5,6,7,8-tetrahydro-1,5-naphthyridin-2-yl)phenyl]ethyl]-3-(dimethylamino)-2-hydroxypropanamide

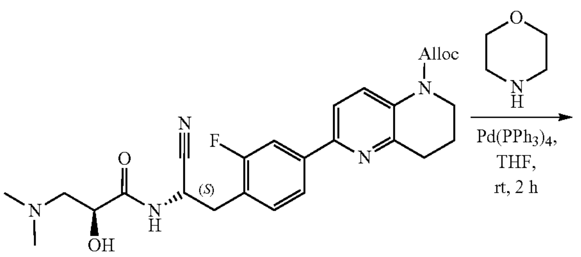

-continued

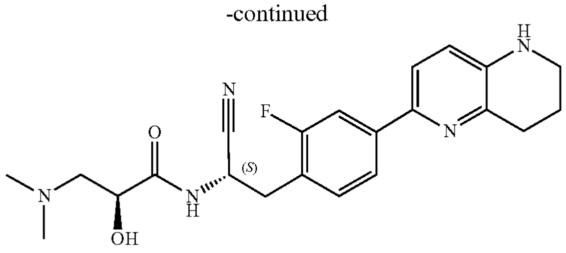

A solution of prop-2-en-1-yl 6-{4-[(2S)-2-cyano-2-[(2S)-3-(dimethylamino)-2-hydroxypropanamido]ethyl]-3-fluorophenyl}-3,4-dihydro-2H-1,5-naphthyridine-1-carboxylate (200 mg, 0.40 mmol, 1.0 equiv) and morpholine (70 mg, 0.81 mmol, 2.0 equiv), $Pd(PPh_3)_4$(18 mg, 0.016 mmol, 0.04 equiv) in THE (5 mL) was stirred at room temperature for 2 h under nitrogen atmosphere. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (2S)—N-[(1S)-1-cyano-2-[2-fluoro-4-(5,6,7,8-tetrahydro-1,5-naphthyridin-2-yl)phenyl]ethyl]-3-(dimethylamino)-2-hydroxypropanamide (20.5 mg, 12% yield, 99% purity).

LCMS (ES, m/z): $[M+H]^+$: 412.1

$^1H$ NMR (400 MHz, DMSO-$d_6$) δ 8.77 (d, J=8.5 Hz, 1H), 7.73-7.64 (m, 2H), 7.52 (d, J=8.4 Hz, 1H), 7.34 (t, J=8.1 Hz, 1H), 6.83 (d, J=8.4 Hz, 1H), 6.12 (t, J=2.4 Hz, 1H), 5.55 (br, 1H), 5.03 (q, J=8.2 Hz, 1H), 4.00 (dd, J=7.7, 4.1 Hz, 1H), 3.28-3.11 (m, 4H), 2.84 (t, J=6.4 Hz, 2H), 2.36-2.21 (m, 2H), 2.12 (s, 6H), 1.95-1.88 (m, 2H).

Example 114: Synthesis of Compound 277A and 277B: (2S)—N-[(1S)-1-cyano-2-{8-cyano-2-fluoro-6H-benzo[c]chromen-3-yl}ethyl]-3-(dimethylamino)-2-hydroxypropanamide; (2S)—N-[(1R)-1-cyano-2-{8-cyano-2-fluoro-6H-benzo[c]chromen-3-yl}ethyl]-3-(dimethylamino)-2-hydroxypropanamide

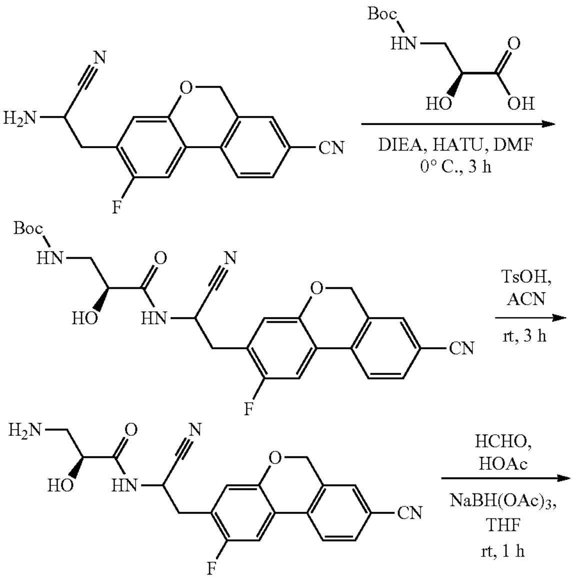

-continued

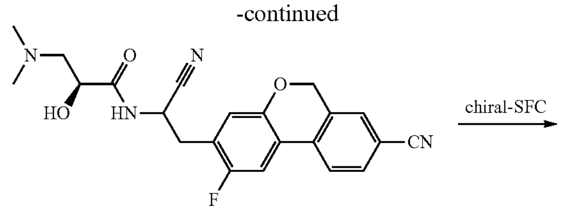

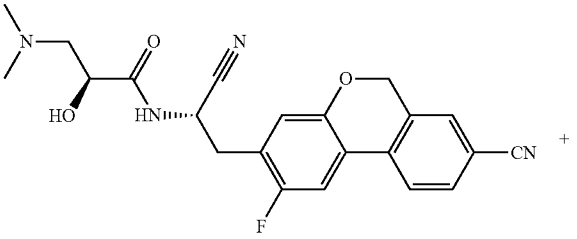

Compound 277A
(Assumed)

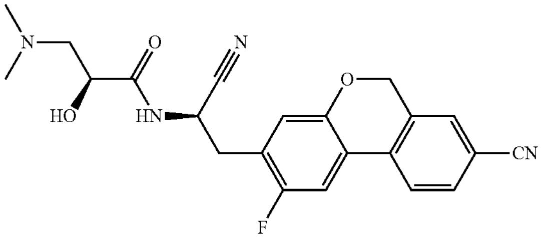

Compound 277B
(Assumed)

Synthesis of tert-butyl N-[(2S)-2-[(1-cyano-2-{8-cyano-2-fluoro-6H-benzo[c]chromen-3-yl}ethyl) carbamoyl]-2-hydroxyethyl]carbamate

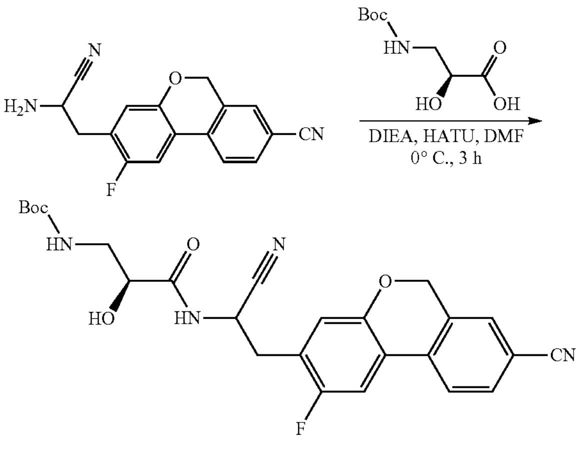

To a stirred solution of 3-(2-amino-2-cyanoethyl)-2-fluoro-6H-benzo[c]chromene-8-carbonitrile (150 mg, 0.51 mmol, 1.0 equiv) and (2S)-3-[(tert-butoxycarbonyl)amino]-2-hydroxypropanoic acid (157 mg, 0.77 mmol, 1.5 equiv), DIEA (198 mg, 1.53 mmol, 3.0 equiv) in DMF (3 mL) was added HATU (233 mg, 0.61 mmol, 1.2 equiv) in portions at 0° C. The resulting mixture was stirred at 0° C. for additional 3 h. The resulting mixture was extracted with EtOAc (3x30 mL). The combined organic layer ws washed with brine (3x30 mL), dried over anhydrous $Na_2SO_4$. After filtration, the filtrate was concentrated under reduced pressure. The residue was purified by silica gel column chromatography, eluted with PE/THE (1:1) to afford tert-butyl N-[(2S)-2-[(1-cyano-2-{8-cyano-2-fluoro-6H-benzo[c]chromen-3-yl}ethyl)carbamoyl]-2-hydroxyethyl]carbamate (140 mg, 57%). LCMS (ES, m/z): [M+H]*: 481.

Synthesis of (2S)-3-amino-N-[(1S)-1-cyano-2-{8-cyano-2-fluoro-6H-benzo[c]chromen-3-yl}ethyl]-2-hydroxypropanamide

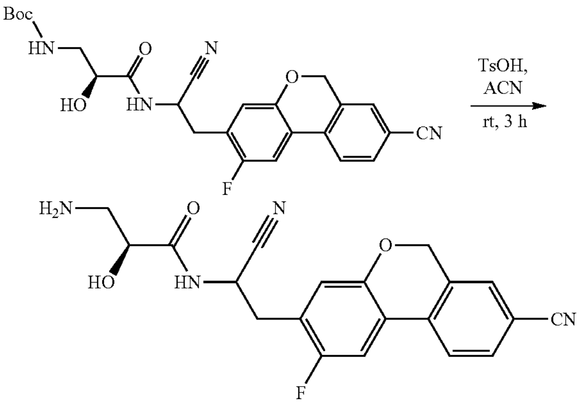

Into a 50 mL round-bottom flask were added tert-butyl N-[(2S)-2-{[(1S)-1-cyano-2-{8-cyano-2-fluoro-6H-benzo[c]chromen-3-yl}ethyl]carbamoyl}-2-hydroxyethyl]carbamate (140 mg, 0.29 mmol, 1.0 equiv), ACN (4 mL) and $TsOH·H_2O$ (150 mg, 0.87 mmol, 3.0 equiv) at room temperature. The resulting mixture was stirred at room temperature for additional 3 h. The precipitated solid was collected by filtration and washed with ACN (4 mL). This resulted in (2S)-3-amino-N-[(1S)-1-cyano-2-{8-cyano-2-fluoro-6H-benzo[c]chromen-3-yl}ethyl]-2-hydroxypropanamide (90 mg, 81%). The crude product mixture was used in the next step directly without further purification. LCMS (ES, m/z): $[M+H]^+$: 381.

Synthesis of (2S)—N-(1-cyano-2-{8-cyano-2-fluoro-6H-benzo[c]chromen-3-yl}ethyl)-3-(dimethylamino)-2-hydroxypropanamide

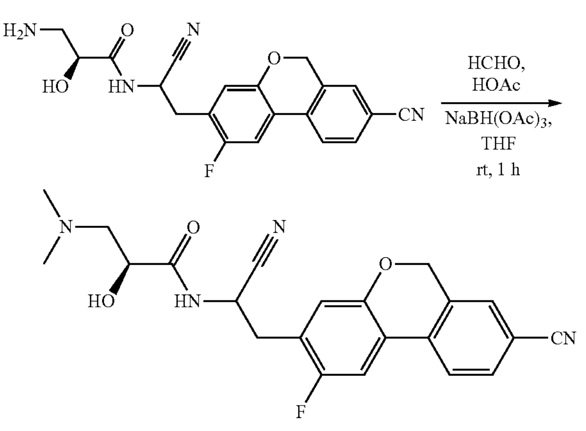

A solution of (2S)-3-amino-N-(1-cyano-2-{8-cyano-2-fluoro-6H-benzo[c]chromen-3-yl}ethyl)-2-hydroxypropanamide (90 mg, 0.24 mmol, 1.0 equiv) and HOAc (0.10 mL), HCHO (186 mg, 2.37 mmol, 10 equiv, 38% in $H_2O$), $NaBH(OAc)_3$ (100 mg, 0.47 mmol, 2.0 equiv) in THE (3.0 mL) was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 220 nm. This resulted in (2S)—N-(1-cyano-2-{8-cyano-2-fluoro-6H-benzo[c]chromen-3-yl}ethyl)-3-(dimethylamino)-2-hydroxypropanamide (40 mg, 41%). LCMS (ES, m/z): $[M+H]^+$: 409.

Synthesis of (2S)—N-[(1S)-1-cyano-2-{8-cyano-2-fluoro-6H-benzo[c]chromen-3-yl}ethyl]-3-(dimethylamino)-2-hydroxypropanamide; (2S)—N-[(1R)-1-cyano-2-{8-cyano-2-fluoro-6H-benzo[c]chromen-3-yl}ethyl]-3-(dimethylamino)-2-hydroxypropanamide

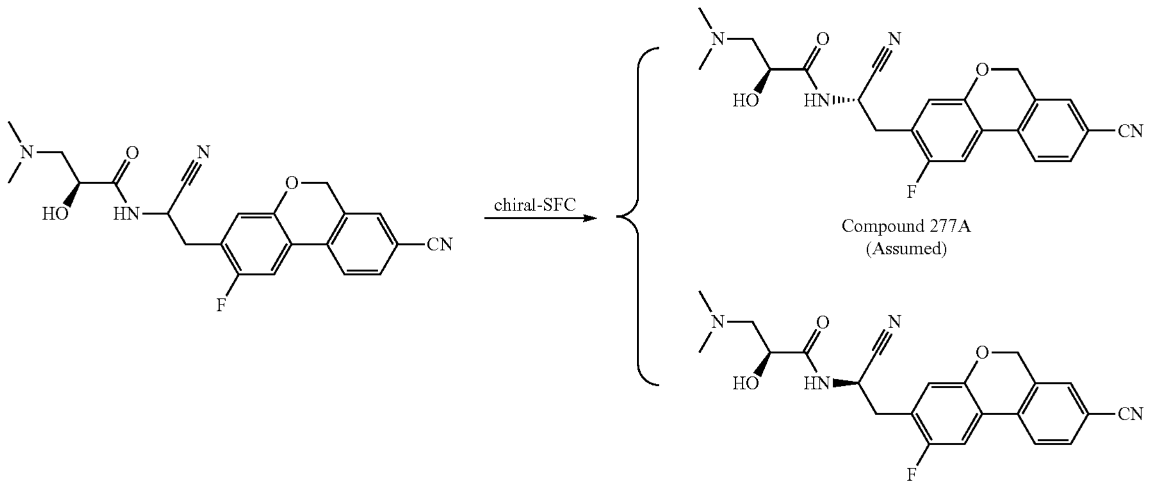

Compound 277A
(Assumed)

Compound 277B
(Assumed)

(2S)—N-(1-cyano-2-{8-cyano-2-fluoro-6H-benzo[c]chromen-3-yl}ethyl)-3-(dimethylamino)-2-hydroxypropanamide (40 mg) was separated by Chiral-SFC with the following conditions Column: CHIRALPAK IG, 3*25 cm, 5 m; Mobile Phase A: $CO_2$, Mobile Phase B: MeOH: DCM=2: 1(0.1% 2 M $NH_3$-MeOH); Flow rate: 80 mL/min; Gradient: isocratic 40% B; Column Temperature(° C.): 35; Back Pressure(bar): 100; Wave Length: 254 nm; $RT_1$(min): 5.95; $RT_2$(min): 7.6; Sample Solvent: MeOH; Injection Volume: 5 mL. This resulted in (2S)—N-[(1S)-1-cyano-2-{8-cyano-2-fluoro-6H-benzo[c]chromen-3-yl}ethyl]-3-(dimethylamino)-2-hydroxypropanamide (8.3 mg, 21%) and (2S)—N-[(1R)-1-cyano-2-{8-cyano-2-fluoro-6H-benzo[c]chromen-3-yl}ethyl]-3-(dimethylamino)-2-hydroxypropanamide (10.5 mg, 26%).

Compound 277A

LCMS (ES, m/z): $[M+H]^+$:409.1

$^1H$ NMR (400 MHz, DMSO-d6) δ 8.78 (d, J=8.6 Hz, 1H), 8.05 (d, J=8.1 Hz, 1H), 7.92-7.85 (m, 2H), 7.80 (d, J=1.7 Hz, 1H), 7.04 (d, J=6.4 Hz, 1H), 5.56 (d, J=4.8 Hz, 1H), 5.17 (s, 2H), 5.08 (q, J=8.3 Hz, 1H), 3.98 (dd, J=7.9, 4.0 Hz, 1H), 3.26-3.13 (m, 2H), 2.32-2.17 (m, 2H), 2.09 (s, 6H).

Compound 277B

LCMS (ES, m/z): $[M+H]^+$:409.1

$^1H$ NMR (400 MHz, DMSO-$d_6$) δ 8.76 (d, J=7.9 Hz, 1H), 8.06 (d, J=8.2 Hz, 1H), 7.93-7.85 (m, 2H), 7.80 (d, J=1.7 Hz, 1H), 7.05 (d, J=6.4 Hz, 1H), 5.50 (br, 1H), 5.18 (s, 2H), 5.01 (q, J=7.1 Hz, 1H), 3.98 (dd, J=7.6, 4.1 Hz, 1H), 3.27-3.16 (m, 2H), 2.45 (dd, J=12.7, 4.1 Hz, 1H), 2.35 (dd, J=12.7, 7.6 Hz, 1H), 2.16 (s, 6H).

Example 115: Synthesis of Compound 278: (2S)—N-[(1S)-1-cyano-2-[2-fluoro-4-(3-methyl-2-oxo-1,3-benzoxazol-5-yl)phenyl]ethyl]-3-(dimethylamino)-2-fluoropropanamide

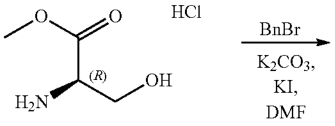

-continued

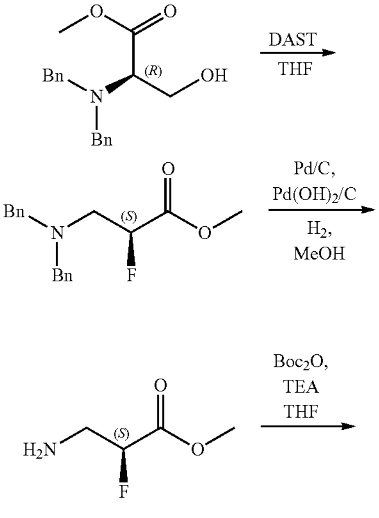

-continued

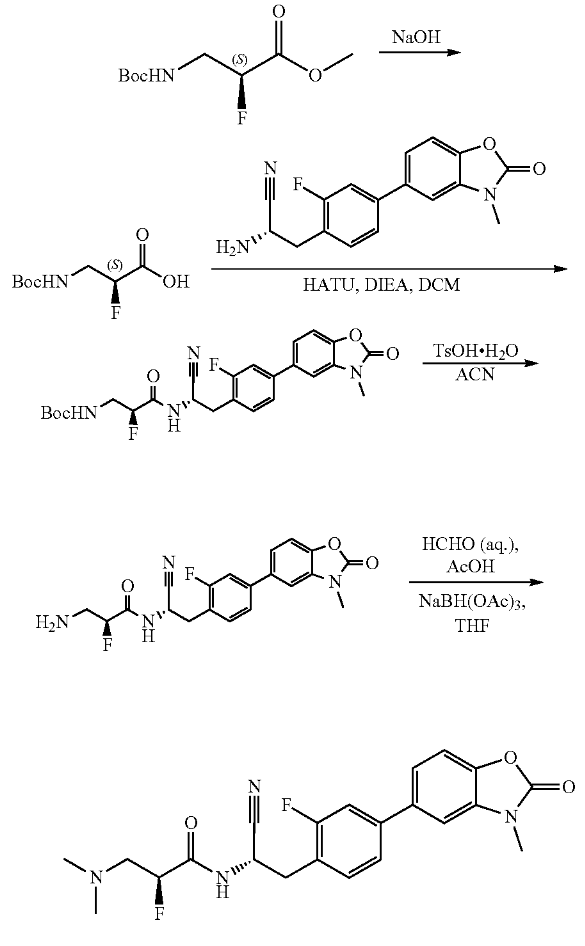

Compound 278

Synthesis of methyl (2R)-2-(dibenzylamino)-3-hydroxypropanoate

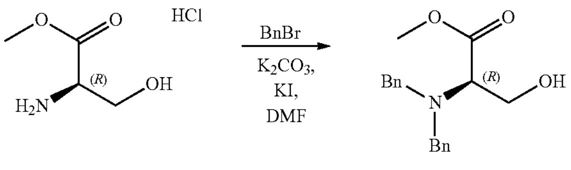

To a stirred mixture of methyl (2R)-2-amino-3-hydroxypropanoate hydrochloride (10.0 g, 64.27 mmol, 1.00 equiv) and KI (2.13 g, 12.85 mmol, 0.20 equiv) in DMF (100 mL) was added $K_2CO_3$ (26.6 g, 192.82 mmol, 3.00 equiv) and (bromomethyl)benzene (24.2 g, 141.40 mmol, 2.20 equiv) at 0° C. After the additional, the resulting mixture was stirred for 16 h at 0° C. to 25° C. The resulting mixture was diluted with EtOAc (500 mL), washed with $H_2O$ (4×100 mL), dried over $Na_2SO_4$ and concentrated under reduced pressure. The residue was purified by silica gel column chromatography, eluted with PE/EA (5:1) to afford methyl (2R)-2-(dibenzylamino)-3-hydroxypropanoate (15 g, 77.95% yield, 90% purity). LCMS (ES, m z): $[M+H]^+$: 300.

Synthesis of methyl (2S)-3-(dibenzylamino)-2-fluoropropanoate

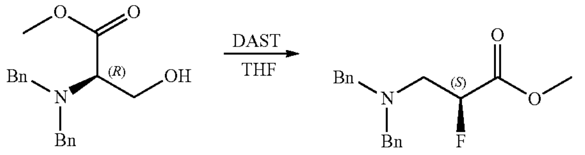

To a stirred mixture of methyl (2R)-2-(dibenzylamino)-3-hydroxypropanoate (3.00 g, 10.02 mmol, 1.00 equiv) in $CH_2Cl_2$ (30 mL) was added Diethylaminosulfur trifluoride (4.8 g, 30.06 mmol, 3.00 equiv) at 0° C. After the additional, the resulting mixture was stirred for 2 h at 0° C. to 25° C. The reaction mixture was poured into ice water (30 mL), adjusted pH to 8 with solid $NaHCO_3$. The resulting mixture extracted with DCM (3×100 mL), dried over $Na_2SO_4$ and concentrated under reduced pressure. The residue was purified by silica gel column chromatography, eluted with PE/EA (10:1) to afford methyl (2S)-3-(dibenzylamino)-2-fluoropropanoate (2.3 g, 76.16% yield, 90% purity). LCMS (ES, m z): $[M+H]^+$: 302.

Synthesis of methyl (2S)-3-amino-2-fluoropropanoate

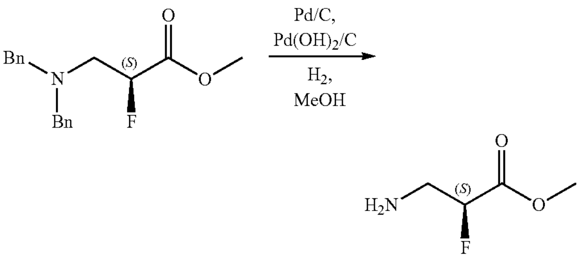

To a solution of methyl (2S)-3-(dibenzylamino)-2-fluoropropanoate (2.00 g, 6.63 mmol, 1.00 equiv) in methanol (20 mL) was added Pd/C (0.20 g, 1.88 mmol, 0.28 equiv) in a pressure tank. The mixture was hydrogenated at 20° C. at 10 psi of hydrogen pressure for 5 h. The reaction was filtered through a Celite pad and concentrated under reduced pressure to give methyl (2S)-3-amino-2-fluoropropanoate (0.8 g, 99.53% yield, 90% purity). LCMS (ES, m z): $[M+H]^+$: 122.

Synthesis of methyl (2S)-3-[(tert-butoxycarbonyl)amino]-2-fluoropropanoate

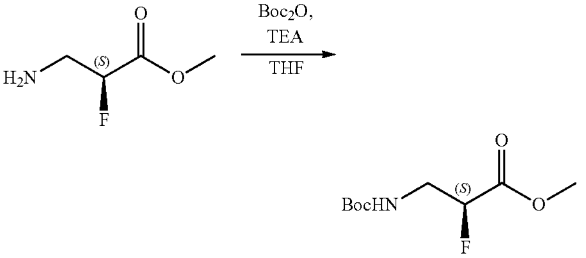

To a solution of methyl (2S)-3-amino-2-fluoropropanoate (700 mg, 5.78 mmol, 1.00 equiv) in THE (10 mL) ware added di-tert-butyl dicarbonate (1.51 g, 6.93 mmol, 1.20 equiv) and $Et_3N$ (2.92 g, 28.90 mmol, 5.00 equiv) at 20° C. The resulting mixture was stirred for 5 h at 20° C. The reaction was concentrated. The residue was purified by silica gel column chromatography, eluted with PE/EA (10:1) to afford methyl (2S)-3-[(tert-butoxycarbonyl)amino]-2-fluoropropanoate (850 mg, 66.48% yield, 90% purity). LCMS (ES, m z): $[M+H]^+$: 222.

Synthesis of (2S)-3-[(tert-butoxycarbonyl)amino]-2-fluoropropanoic acid

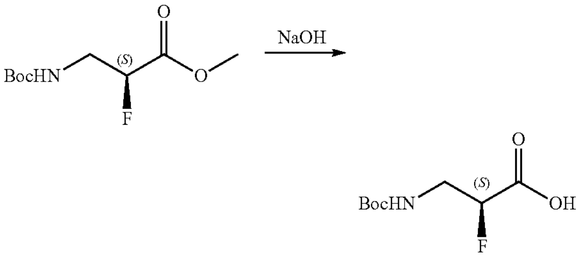

To a stirred solution of methyl (2S)-3-[(tert-butoxycarbonyl)amino]-2-fluoropropanoate (600 mg, 2.71 mmol, 1.00 equiv) in THE (5 mL) was added NaOH (216 mg, 5.42 mmol, 2.00 equiv) in $H_2O$ (5 mL) dropwise at 0° C. The resulting mixture was stirred for 2 h at 0° C. to 20° C. The resulting mixture was adjusted pH to 5 with HCl (2N). The resulting mixture was extracted with DCM (5×50 mL), the organic layer was washed with brine (10 mL), dried over $Na_2SO_4$ and concentrated under reduced pressure to afford (2S)-3-[(tert-butoxycarbonyl)amino]-2-fluoropropanoic acid (230 mg, 40.93% yield, 90% purity). LCMS (ES, m z): $[M+H]^+$: 208.

Synthesis of N-[(1S)-1-cyano-2-[2-fluoro-4-(3-methyl-2-oxo-1,3-benzoxazol-5-yl)phenyl]ethyl]-2-azabicyclo[2.2.2]octane-1-carboxamide

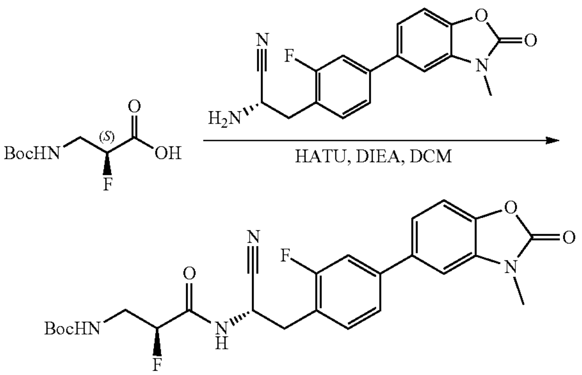

To a stirred solution of (2S)-3-[(tert-butoxycarbonyl)amino]-2-fluoropropanoic acid (150 mg, 0.72 mmol, 1.00 equiv) and DIEA (280 mg, 2.17 mmol, 3.00 equiv) in $CH_2Cl_2$ (10 mL) was added HATU (330 mg, 0.87 mmol, 1.20 equiv) in portions at 0° C. To the above mixture was added (2S)-2-amino-3-[2-fluoro-4-(3-methyl-2-oxo-1,3-benzoxazol-5-yl)phenyl]propanenitrile (225 mg, 0.72 mmol, 1.00 equiv). The resulting mixture was stirred for additional 2 h at 0° C. to 20° C. The reaction mixture was concentrated. The residue was purified by reversed-phase flash chromatography with the following conditions: column, C18 silica gel; mobile phase, MeCN in Water (0.1% $NH_3 \cdot H_2O$), 10% to 50% gradient in 15 min; detector, UV 254 nm. This resulted in N-[(1S)-1-cyano-2-[2-fluoro-4-(3-methyl-2-oxo-1,3-benzoxazol-5-yl)phenyl]ethyl]-2-azabicyclo[2.2.2]octane-1-carboxamide (320 mg). LCMS (ES, m/z): $[M+H]^+$: 501.

Synthesis of (2S)-3-amino-N-[(1S)-1-cyano-2-[2-fluoro-4-(3-methyl-2-oxo-1,3-benzoxazol-5-yl)phenyl]ethyl]-2-fluoropropanamide

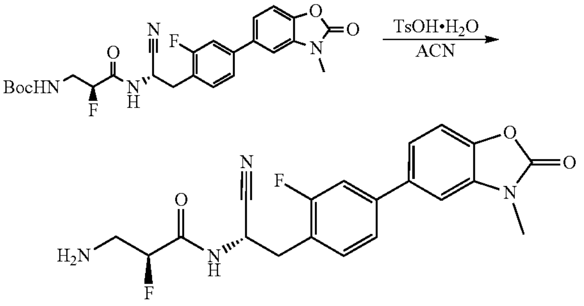

To a solution of tert-butyl N-[(2S)-2-{[(1S)-1-cyano-2-[2-fluoro-4-(3-methyl-2-oxo-1,3-benzoxazol-5-yl)phenyl]ethyl]carbamoyl}-2-fluoroethyl]carbamate (190 mg, 0.38 mmol, 1.00 equiv) in MeCN (5 mL) was added $TSOH \cdot H_2O$ (196 mg, 1.14 mmol, 3.00 equiv) at 0° C. The resulting mixture was stirred for 3 h at 0° C. to 25° C. The reaction mixture was adjust pH to 8 with $NaHCO_3$ (2N), extracted with DCM (3 25 mL), the organic layer was washed with brine (10 mL), dried over $Na_2SO_4$ and concentrated to give (2S)-3-amino-N-[(1S)-1-cyano-2-[2-fluoro-4-(3-methyl-2-oxo-1,3-benzoxazol-5-yl)phenyl]ethyl]-2-fluoropropanamide (110 mg, 72.37% yield, 90% purity). LCMS (ES, m z): $[M+H]^+$: 401.

Synthesis of (2S)—N-[(1S)-1-cyano-2-[2-fluoro-4-(3-methyl-2-oxo-1,3-benzoxazol-5-yl)phenyl]ethyl]-3-(dimethylamino)-2-fluoropropanamide

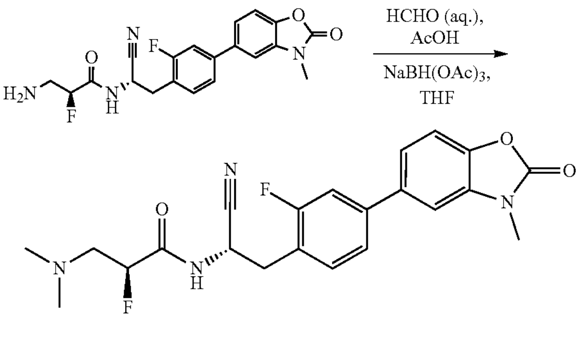

To a stirred solution of (2S)-3-amino-N-[(1S)-1-cyano-2-[2-fluoro-4-(3-methyl-2-oxo-1,3-benzoxazol-5-yl)phenyl]

ethyl]-2-fluoropropanamide (80 mg, 0.20 mmol, 1.00 equiv) and Formaldehyde solution (157 mg, 2.00 mmol, 10.00 equiv, 38%) in THE (10 mL) was added HOAc (1.2 mg, 0.02 mmol, 0.10 equiv) at 20° C. The reaction stirred at 20° C. to 25° C. for 2 h. To the above mixture was added $NaBH(OAc)_3$, (84 mg, 0.40 mmol, 2 equiv) in portions. The resulting mixture was stirred for additional 2 h at 20° C. to 25° C. The reaction mixture was purified by reversed-phase flash chromatography with the following conditions: column, C18 silica gel; mobile phase, MeCN in Water (0.10% $NH_3 \cdot H_2O$), 10% to 46% gradient in 17 min; detector, UV 254 nm. This resulted in (2S)—N-[(1S)-1-cyano-2-[2-fluoro-4-(3-methyl-2-oxo-1,3-benzoxazol-5-yl)phenyl]ethyl]-3-(dimethylamino)-2-fluoropropanamide (30 mg, 35.04% yield, 99.7% purity).

LCMS (ES, m z): $[M+H]^+$: 429.1

$^1H$ NMR (400 MHz, DMSO-$d_6$) δ 9.20 (dd, J=8.2, 1.4 Hz, 1H), 7.66 (d, J=1.8 Hz, 1H), 7.64-7.53 (m, 2H), 7.52-7.44 (m, 2H), 7.41 (d, J=8.4 Hz, 1H), 5.23-4.97 (m, 2H), 3.41 (s, 3H), 3.32-3.25 (m, 1H), 3.20-3.17 (m, 1H), 2.65-2.53 (m, 1H), 2.51-2.41 (m, 1H), 2.15 (s, 6H).

$^{19}F$ NMR (376 MHz, DMSO-$d_6$) δ-117.16, -190.14.

Example 116: Synthesis of Compound 281: (2S)—N-[(1S)-1-cyano-2-(4-{3-[1-(oxetan-3-yl)piperidin-4-yl]-1,3-dihydro-2-benzofuran-5-yl}phenyl)ethyl]-3-(dimethylamino)-2-hydroxypropanamide

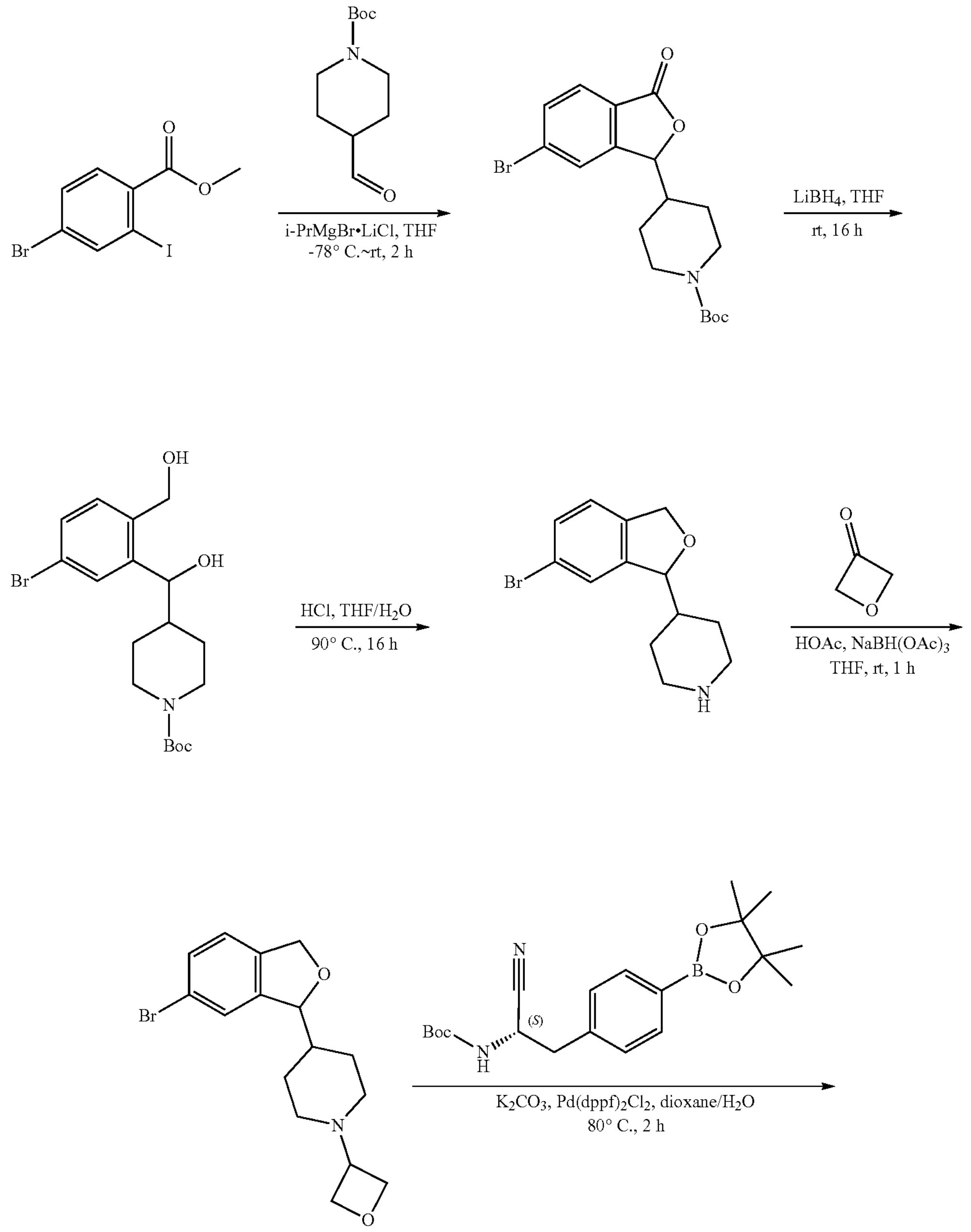

-continued
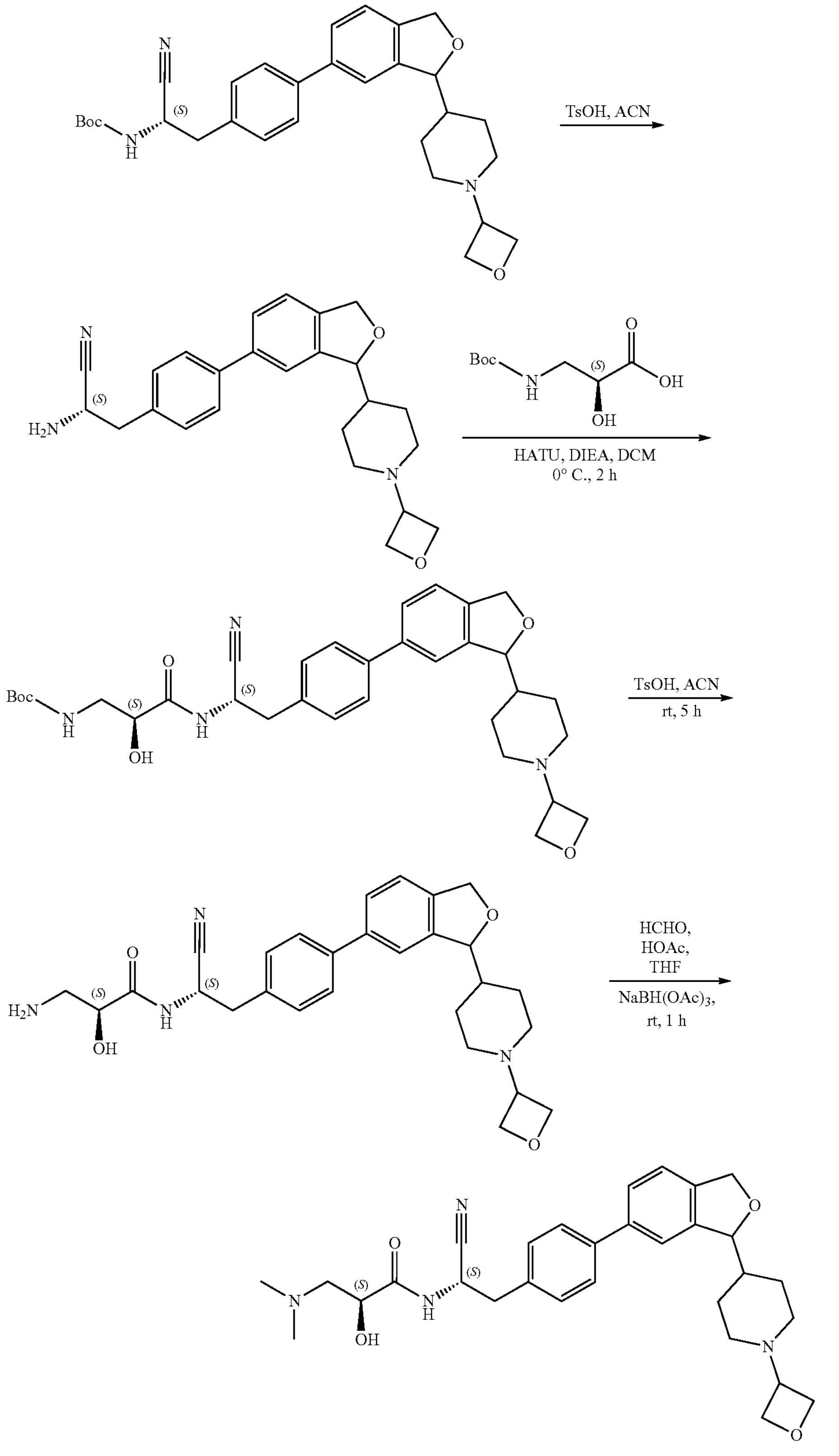
Compound 281

Synthesis of tert-butyl 4-(6-bromo-3-oxo-1H-2-benzofuran-1-yl)piperidine-1-carboxylate

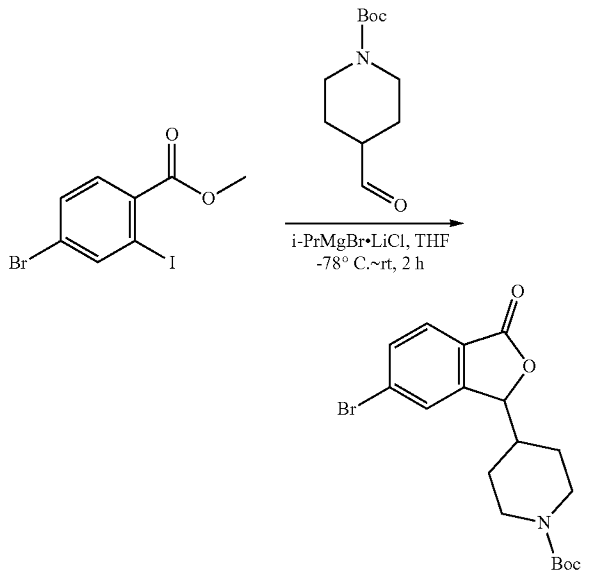

To a stirred solution of methyl 4-bromo-2-iodobenzoate (10 g, 29.33 mmol, 1.0 equiv) and tert-butyl 4-formylpiperidine-1-carboxylate (6.88 g, 32.26 mmol, 1.1 equiv) in THF (150 mL) was added i-PrMgBrLiC1 (1 M in THF)(32.3 mL, 32.26 mmol, 1.1 equiv) dropwise at −78° C. under nitrogen atmosphere. The resulting mixture was stirred for 20 min at −78° C. under nitrogen atmosphere. The resulting mixture was stirred for 1 h at room temperature under nitrogen atmosphere. The reaction was quenched by the addition of sat. $NH_4Cl$ (aq.)(100 mL) at room temperature. The resulting mixture was extracted with EtOAc (3×100 mL). The combined organic layer was dried over anhydrous $Na_2SO_4$. After filtration, the filtrate was concentrated under reduced pressure. The residue was purified by silica gel column chromatography, eluted with PE/EA (5:1) to afford tert-butyl 4-(6-bromo-3-oxo-1H-2-benzofuran-1-yl)piperidine-1-carboxylate (10 g, 86% yield, 90% purity). LCMS (ES, m z): $[M+H]^+$: 396.

Synthesis of tert-butyl 4-{[5-bromo-2-(hydroxymethyl)phenyl](hydroxy)methyl}piperidine-1-carboxylate

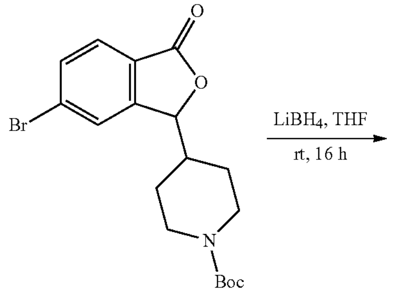

-continued

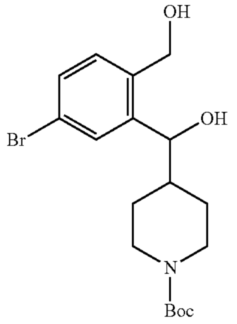

To a stirred solution of tert-butyl 4-(6-bromo-3-oxo-1H-2-benzofuran-1-yl)piperidine-1-carboxylate (10 g, 25.23 mmol, 1.0 equiv) and THE (100 mL) was added lithium borohydride (4.0 M in THF)(12.6 mL, 50.46 mmol, 2.0 equiv) at room temperature under nitrogen atmosphere. The resulting mixture was stirred for 16 h at room temperature under nitrogen atmosphere. The reaction was quenched with water (100 mL) at room temperature. The resulting mixture was extracted with EtOAc (3×100 mL). The combined organic layer was washed with brine (3×100 mL), dried over anhydrous $Na_2SO_4$. After filtration, the filtrate was concentrated under reduced pressure. The residue was purified by silica gel column chromatography, eluted with PE/THE (1:1) to afford tert-butyl 4-{[5-bromo-2-(hydroxymethyl)phenyl](hydroxy)methyl}piperidine-1-carboxylate (8 g, 79% yield, 90% purity). LCMS (ES, m z): $[M+H]^+$: 400.

Synthesis of 4-(6-bromo-1,3-dihydro-2-benzofuran-1-yl)piperidine

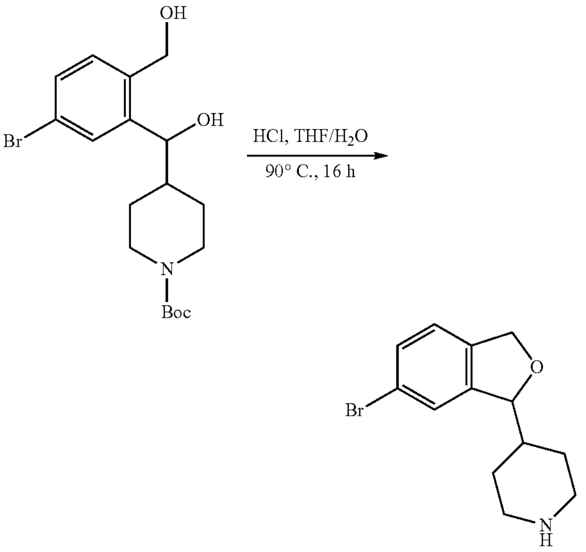

To a stirred solution of tert-butyl 4-{[5-bromo-2-(hydroxymethyl)phenyl](hydroxy)methyl}piperidine-1-carboxylate (2 g, 4.99 mmol, 1.0 equiv) in THE (5 mL) was added HCl (5 M)(5 mL) dropwise at room temperature. The resulting mixture was stirred for 16 h at 90° C. The reaction was cooled to room temperature, the mixture was acidified to pH 8 with saturated $NaHCO_3$ (aq.). The resulting mixture was extracted with EtOAc (3×50 mL). The combined organic layer was washed with brine (3×50 mL), dried over anhydrous $Na_2SO_4$. After filtration, the filtrate was concentrated under reduced pressure. This resulted in 4-(6-bromo-1,3-dihydro-2-benzofuran-1-yl)piperidine (1.4 g). LCMS (ES, m z): $[M+H]^+$: 282.

Synthesis of 4-(6-bromo-1,3-dihydro-2-benzofuran-1-yl)-1-(oxetan-3-yl)piperidine

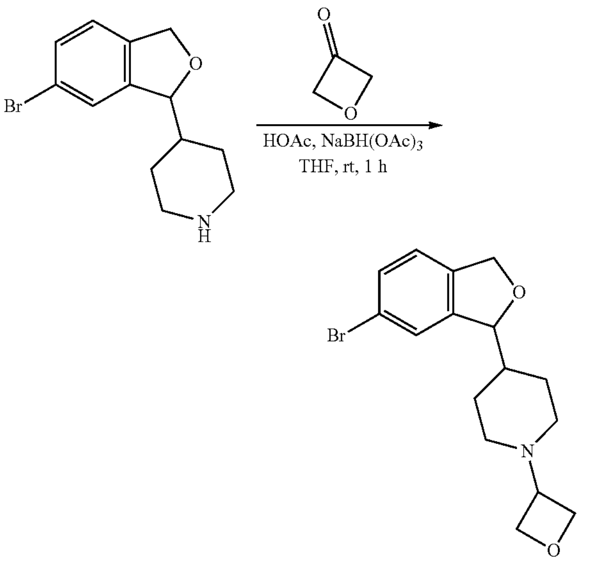

To a stirred solution of 4-(6-bromo-1,3-dihydro-2-benzofuran-1-yl)piperidine (1.4 g, 4.96 mmol, 1.0 equiv) and 3-oxetanone (1.07 g, 14.88 mmol, 3.0 equiv) in THF (20 mL) was added HOAc (29 mg, 0.49 mmol, 0.1 equiv) and $NaBH(OAc)_3$ (2.10 g, 9.92 mmol, 2.0 equiv) at room temperature. The resulting mixture was stirred at room temperature for 1 h. The resulting mixture was diluted with $NaHCO_3$ (aq)(30 mL), extracted with EtOAc (3×50 mL). The combined organic layer was dried over anhydrous $Na_2SO_4$. After filtration, the filtrate was concentrated under reduced pressure. The residue was purified by silica gel column chromatography, eluted with PE/EA (1:1) to afford 4-(6-bromo-1,3-dihydro-2-benzofuran-1-yl)-1-(oxetan-3-yl)piperidine (1.3 g, 77% yield, 90% purity). LCMS (ES, m z): $[M+H]^+$: 338.

Synthesis of tert-butyl N-[(1S)-1-cyano-2-(4-{3-[1-(oxetan-3-yl)piperidin-4-yl]-1,3-dihydro-2-benzofuran-5-yl}phenyl)ethyl]carbamate

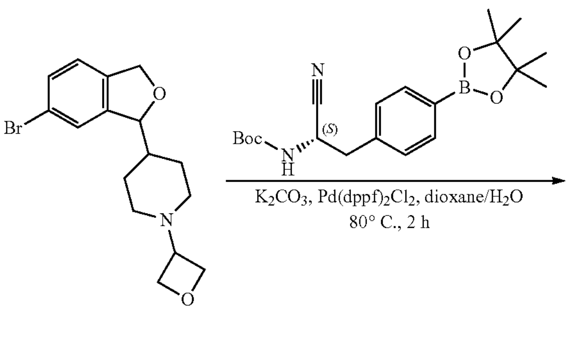

-continued

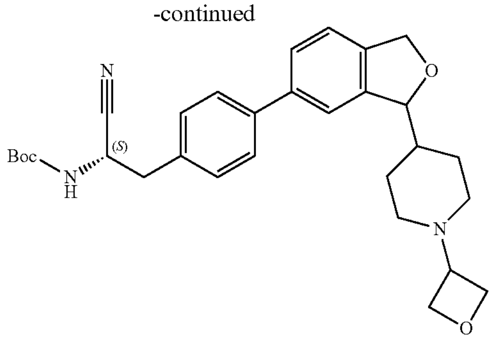

To a solution of 4-(6-bromo-1,3-dihydro-2-benzofuran-1-yl)-1-(oxetan-3-yl)piperidine (350 mg, 1.03 mmol, 1.0 equiv) and tert-butyl N-[(1S)-1-cyano-2-[4-(4,4,5,5-tetramethyl-1,3,2-dioxaborolan-2-yl)phenyl]ethyl]carbamate (462 mg, 1.24 mmol, 1.2 equiv) in 1,4-dioxane (10 mL) and $H_2O$ (1 mL) were added $K_2CO_3$ (429 mg, 3.10 mmol, 3.0 equiv) and $Pd(dppf)Cl_2CH_2Cl_2$ (84 mg, 0.10 mmol, 0.1 equiv). After stirring for 2 h at 80° C. under nitrogen atmosphere. The resulting mixture was concentrated under reduced pressure. The residue was purified by silica gel column chromatography, eluted with PE/EA (1:1) to afford tert-butyl N-[(1S)-1-cyano-2-(4-{3-[1-(oxetan-3-yl)piperidin-4-yl]-1,3-dihydro-2-benzofuran-5-yl}phenyl)ethyl]carbamate (350 mg, 67% yield, 90% purity). LCMS (ES, m z): $[M+H]^+$: 504.

Synthesis of (2S)-2-amino-3-(4-{3-[1-(oxetan-3-yl)piperidin-4-yl]-1,3-dihydro-2-benzofuran-5-yl}phenyl)propanenitrile

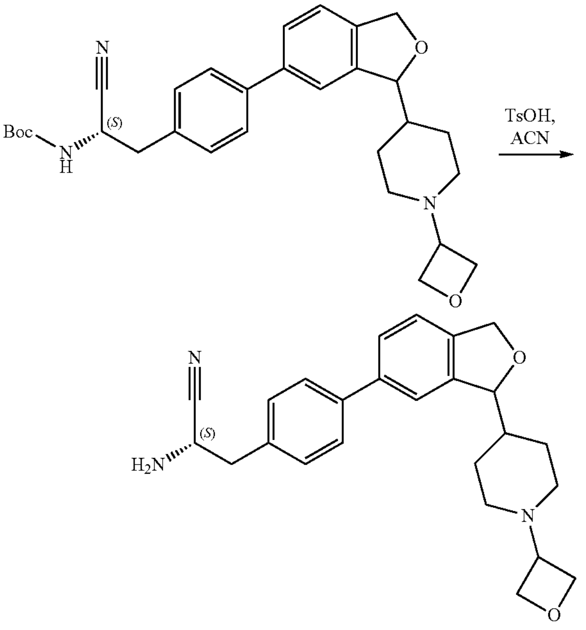

Into a 25 mL round-bottom flask were added tert-butyl N-[(1S)-1-cyano-2-(4-{3-[1-(oxetan-3-yl)piperidin-4-yl]-1,3-dihydro-2-benzofuran-5-yl}phenyl)ethyl]carbamate (350 mg, 0.69 mmol, 1.0 equiv), MeCN (3 mL) and TsOH (359 mg, 2.08 mmol, 3.0 equiv) at room temperature. The resulting mixture was stirred at room temperature for 6 h. The mixture was basified to pH 8 with saturated $NaHCO_3$ (aq.). The resulting mixture was extracted with EtOAc (3x30 mL). The combined organic layer was washed with brine (3x30 mL), dried over anhydrous $Na_2SO_4$. After filtration, the filtrate was concentrated under reduced pressure. The residue was purified by silica gel column chromatography, eluted with PE/THE (1:2) to afford (2S)-2-amino-3-(4-{3-[1-(oxetan-3-yl)piperidin-4-yl]-1,3-dihydro-2-benzofuran-5-yl}phenyl)propanenitrile (230 mg, 82% yield, 90% purity). LCMS (ES, m z): $[M+H]^+$: 404.

Synthesis of tert-butyl N-[(2S)-2-{[(1S)-1-cyano-2-(4-{3-[1-(oxetan-3-yl)piperidin-4-yl]-1,3-dihydro-2-benzofuran-5-yl}phenyl)ethyl]carbamoyl}-2-hydroxyethyl]carbamate

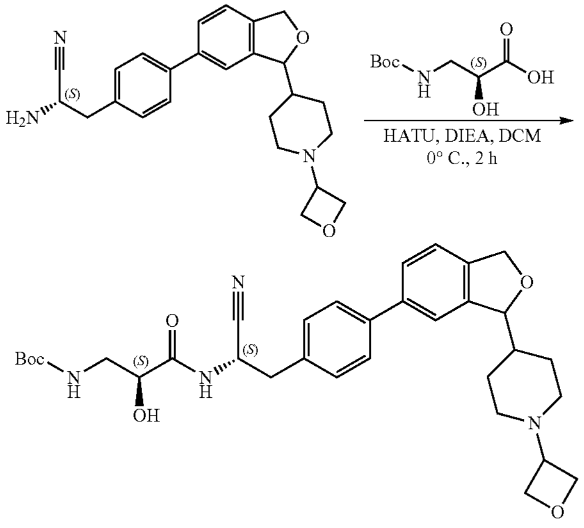

To a stirred solution of (2S)-2-amino-3-(4-{3-[1-(oxetan-3-yl)piperidin-4-yl]-1,3-dihydro-2-benzofuran-5-yl}phenyl) propanenitrile (110 mg, 0.27 mmol, 1.0 equiv) and (2S)-3-[(tert-butoxycarbonyl)amino]-2-hydroxypropanoic acid (83 mg, 0.41 mmol, 1.5 equiv), DIEA (105 mg, 0.81 mmol, 3.0 equiv) in DCM (10 mL) was added HATU (124 mg, 0.32 mmol, 1.2 equiv) at 0° C. The resulting mixture was stirred at 0° C. for 1 h. The residue was purified by silica gel column chromatography, eluted with PE/THE (1:1) to afford tert-butyl N-[(2S)-2-{[(1S)-1-cyano-2-(4-{3-[1-(oxetan-3-yl)piperidin-4-yl]-1,3-dihydro-2-benzofuran-5-yl}phenyl)ethyl] carbamoyl}-2-hydroxyethyl]carbamate (130 mg, 81% yield, 90% purity). LCMS (ES, m z): $[M+H]^+$: 591.

Synthesis of (2S)-3-amino-N-[(1S)-1-cyano-2-(4-{3-[1-(oxetan-3-yl)piperidin-4-yl]-1,3-dihydro-2-benzofuran-5-yl}phenyl)ethyl]-2-hydroxypropanamide

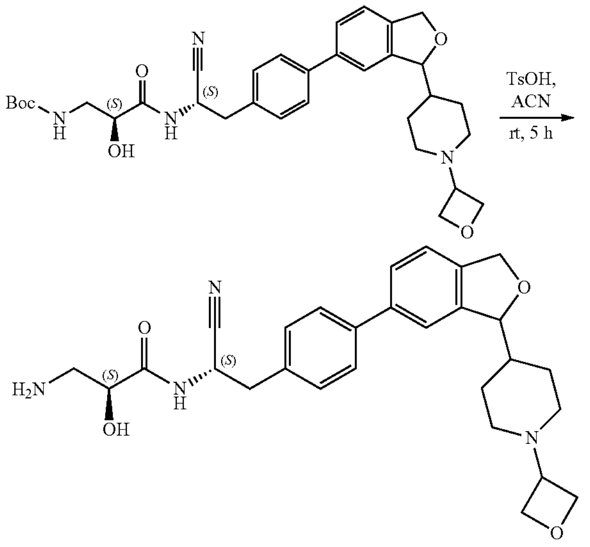

Into a 25 mL round-bottom flask were added tert-butyl N-[(2S)-2-{[(1S)-1-cyano-2-(4-{3-[1-(oxetan-3-yl)piperidin-4-yl]-1,3-dihydro-2-benzofuran-5-yl}phenyl)ethyl]carbamoyl}-2-hydroxyethyl]carbamate (130 mg, 0.22 mmol, 1.0 equiv), MeCN (3 mL) and TsOH (113 mg, 0.66 mmol, 3.0 equiv) at room temperature. The resulting mixture was stirred at room temperature for 5 h. The mixture was basified to pH 8 with saturated $NaHCO_3$ (aq.). The resulting mixture was extracted with EtOAc (3x30 mL). The combined organic layer was washed with brine (3x30 mL), dried over anhydrous $Na_2SO_4$. After filtration, the filtrate was concentrated under reduced pressure. This resulted in (2S)-3-amino-N-[(1S)-1-cyano-2-(4-{3-[1-(oxetan-3-yl)piperidin-4-yl]-1,3-dihydro-2-benzofuran-5-yl}phenyl)ethyl]-2-hydroxypropanamide (100 mg). The crude product was used in the next step directly without further purification. LCMS (ES, m z): $[M+H]^+$: 491.

Synthesis of (2S)—N-[(1S)-1-cyano-2-(4-{3-[1-(oxetan-3-yl)piperidin-4-yl]-1,3-dihydro-2-benzofuran-5-yl}phenyl)ethyl]-3-(dimethylamino)-2-hydroxypropanamide

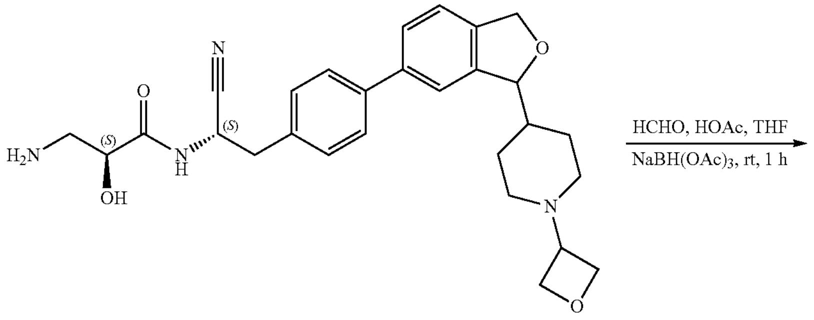

-continued

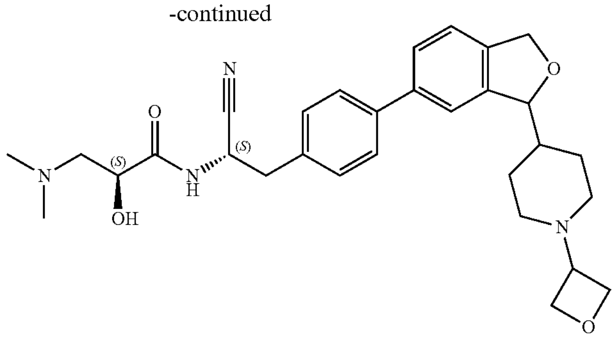

To a stirred solution of (2S)-3-amino-N-[(1S)-1-cyano-2-(4-{3-[1-(oxetan-3-yl)piperidin-4-yl]-1,3-dihydro-2-benzofuran-5-yl}phenyl)ethyl]-2-hydroxypropanamide (150 mg, 0.30 mmol, 1.0 equiv) and Formaldehyde solution (91 mg, 3.06 mmol, 10.0 equiv) in THE (5 mL) was added HOAc (1.84 mg, 0.03 mmol, 0.1 equiv) and $NaBH(OAc)_3$ (129 mg, 0.61 mmol, 2.0 equiv) at room temperature. The resulting mixture was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 45% gradient in 12 min; detector, UV 254 nm. This resulted in (2S)—N-[(1S)-1-cyano-2-(4-{3-[1-(oxetan-3-yl)piperidin-4-yl]-1,3-dihydro-2-benzofuran-5-yl}phenyl)ethyl]-3-(dimethylamino)-2-hydroxypropanamide (25 mg, 16% yield, 99.7% purity).

LCMS (ES, m z): $[M+H]^+$: 519.3

$^1H$ NMR (400 MHz, DMSO-$d_6$): δ 8.72 (brs, 1H), 7.64-7.61 (m, 2H), 7.60-7.54 (m, 1H), 7.51 (s, 1H), 7.39-7.36 (m, 3H), 5.67 (br, 1H), 5.15-4.93 (m, 4H), 4.49 (q, J=6.3 Hz, 2H), 4.38 (q, J=6.3 Hz, 2H), 3.98 (dd, J=7.7, 4.1 Hz, 1H), 3.31-3.27 (m, 1H), 3.24-3.12 (m, 2H), 2.74 (d, J=10.6 Hz, 1H), 2.65 (d, J=11.2 Hz, 1H), 2.28-2.11 (m, 2H), 2.08 (d, J=4.1 Hz, 6H), 1.86-1.45 (m, 5H), 1.43-1.21 (m, 2H).

Example 117: Synthesis of Compound 282: (2S)—N-[(1S)-1-cyano-2-(4-{1-[1-(oxetan-3-yl)piperidin-4-yl]indazol-6-yl}phenyl)ethyl]-3-(dimethylamino)-2-hydroxypropanamide

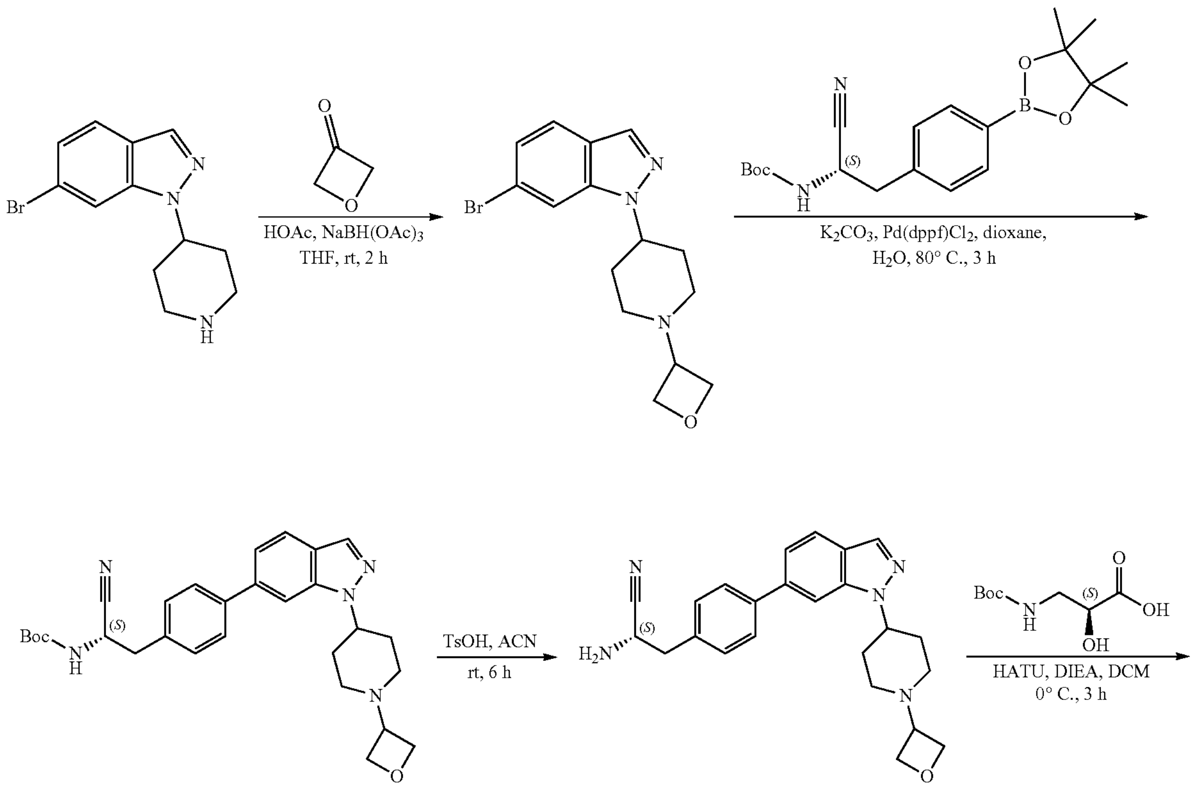

-continued
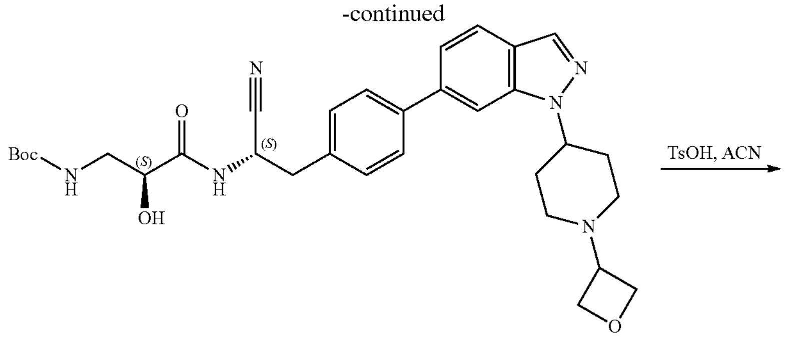
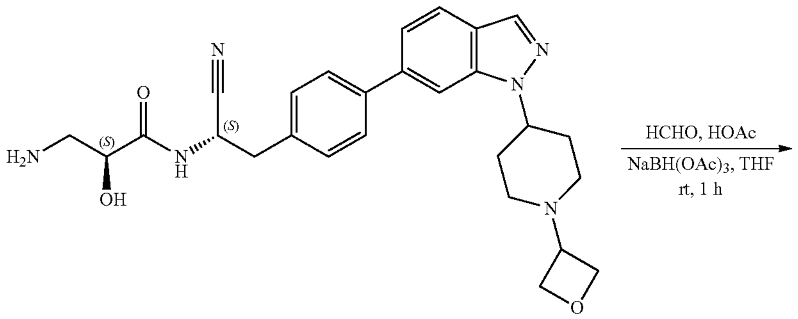
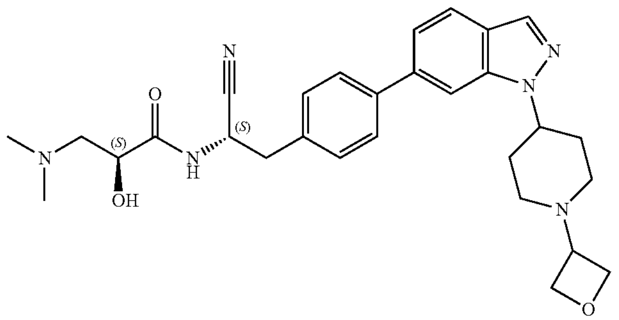
Compound 282
Synthesis of 6-bromo-1-[1-(oxetan-3-yl)piperidin-4-yl]indazole
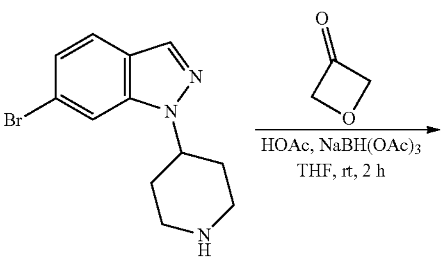
-continued
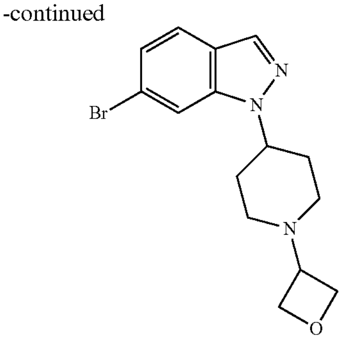
To a stirred solution of 6-bromo-1-(piperidin-4-yl)indazole (800 mg, 2.86 mmol, 1.0 equiv) and 3-oxetanone (247 mg, 3.43 mmol, 1.2 equiv), HOAc (0.1 mL) in THF (8 mL) was added $NaBH(OAc)_3$ (1210 mg, 5.71 mmol, 2.0 equiv) in portions at room temperature. The resulting mixture was stirred at room temperature for additional 2 h. The mixture was basified to pH 8 with saturated $NaHCO_3$ (aq.). The resulting mixture was extracted with EtOAc (3×50 mL). The combined organic layer was washed with brine (3×30 mL), dried over anhydrous $Na_2SO_4$. After filtration, the filtrate was concentrated under reduced pressure. The residue was purified by silica gel column chromatography, eluted with PE/THF (1:1) to afford 6-bromo-1-[1-(oxetan-3-yl)piperidin-4-yl]indazole (700 mg, 73% yield, 95% purity). LCMS (ES, m/z): $[M+H]^+$: 336.

Synthesis of tert-butyl N-[(1S)-1-cyano-2-(4-{1-[1-(oxetan-3-yl)piperidin-4-yl]indazol-6-yl}phenyl)ethyl]carbamate

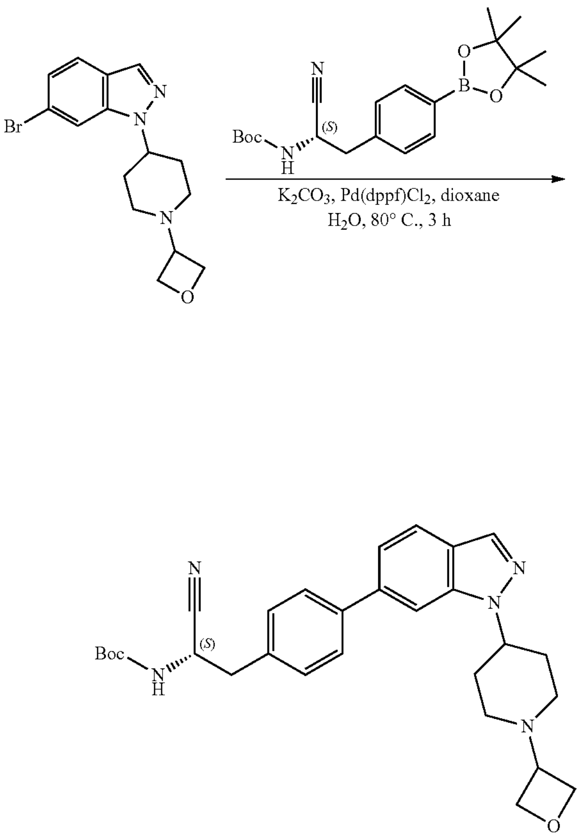

To a mixture of 6-bromo-1-[1-(oxetan-3-yl)piperidin-4-yl]indazole (200 mg, 0.60 mmol, 1.0 equiv) and tert-butyl N-[(1S)-1-cyano-2-[4-(4,4,5,5-tetramethyl-1,3,2-dioxaborolan-2-yl)phenyl]ethyl]carbamate (265 mg, 0.71 mmol, 1.2 equiv), $K_2CO_3$ (164 mg, 1.19 mmol, 2.0 equiv) in mixed solvent of 1,4-dioxane (14 mL) and $H_2O$ (1.4 mL) was added Pd(dppf)$Cl_2CH_2Cl_2$ (48 mg, 0.06 mmol, 0.1 equiv). The reaction was stirred at 80° C. for 3 h under nitrogen atmosphere. The reaction was cooled to room temperature, concentrated to remove the solvent, the residue was purified by silica gel column chromatography, eluted with PE/THF (2:1) to afford tert-butyl N-[(1S)-1-cyano-2-(4-{1-[1-(oxetan-3-yl)piperidin-4-yl]indazol-6-yl}phenyl)ethyl]carbamate (290 mg, 97% yield, 95% purity). LCMS (ES, m/z): $[M+H]^+$: 502.

Synthesis of (2S)-2-amino-3-(4-{1-[1-(oxetan-3-yl)piperidin-4-yl]indazol-6-yl}phenyl)propanenitrile

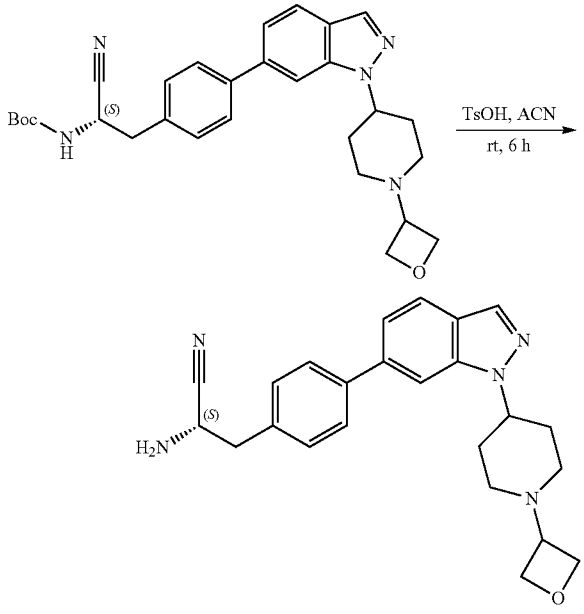

Into a 8-mL vial were added tert-butyl N-[(1S)-1-cyano-2-(4-{1-[1-(oxetan-3-yl)piperidin-4-yl]indazol-6-yl}phenyl)ethyl]carbamate (290 mg, 0.58 mmol, 1.0 equiv), acetonitrile (3 mL) and TsOH (298 mg, 1.73 mmol, 3.0 equiv) at room temperature. The resulting mixture was stirred at room temperature for additional 6 h. The mixture was basified to pH 8 with saturated $NaHCO_3$ (aq.). The resulting mixture was extracted with EtOAc (3×30 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (1:2) to afford (2S)-2-amino-3-(4-{1-[1-(oxetan-3-yl)piperidin-4-yl]indazol-6-yl}phenyl)propanenitrile (110 mg, 47% yield, 95% purity). LCMS (ES, m/z): $[M+H]^+$: 402.

Synthesis of tert-butyl N-[(2S)-2-{[(1S)-1-cyano-2-(4-{1-[1-(oxetan-3-yl)piperidin-4-yl]indazol-6-yl}phenyl)ethyl]carbamoyl}-2-hydroxyethyl]carbamate

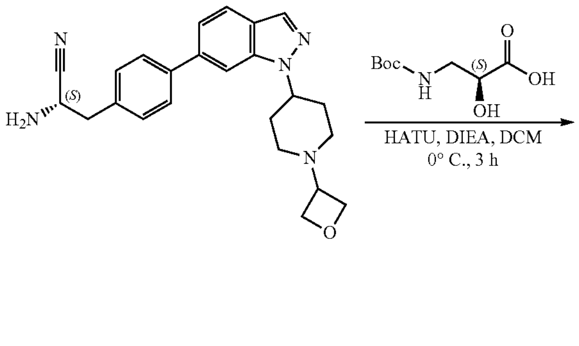

-continued

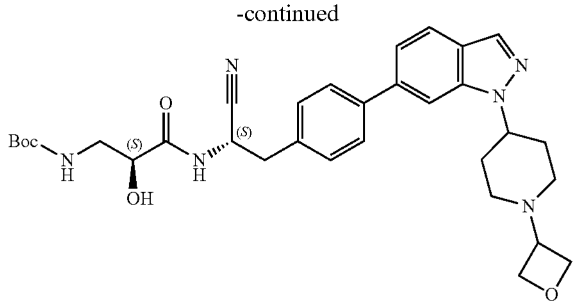

To a stirred solution of (2S)-2-amino-3-(4-{1-[1-(oxetan-3-yl)piperidin-4-yl]indazol-6-yl}phenyl)propanenitrile (110 mg, 0.27 mmol, 1.0 equiv) and (2S)-3-[(tert-butoxycarbonyl)amino]-2-hydroxypropanoic acid (67 mg, 0.33 mmol, 1.2 equiv), DIEA (106 mg, 0.82 mmol, 3.0 equiv) in DCM (3 mL) was added HATU (125 mg, 0.33 mmol, 1.2 equiv) in portions at 0° C. The resulting mixture was stirred at 0° C. for 3 h. Concentrated to remove the solvent, the residue was purified by silica gel column chromatography, eluted with PE/THE (1:1) to afford tert-butyl N-[(2S)-2-{[(1S)-1-cyano-2-(4-{1-[1-(oxetan-3-yl)piperidin-4-yl]indazol-6-yl}phenyl)ethyl]carbamoyl}-2-hydroxyethyl]carbamate (110 mg, 68% yield, 90% purity). LCMS (ES, m/z): $[M+H]^+$: 589.

Synthesis of (2S)-3-amino-N-[(1S)-1-cyano-2-(4-{1-[1-(oxetan-3-yl)piperidin-4-yl]indazol-6-yl}phenyl)ethyl]-2-hydroxypropanamide

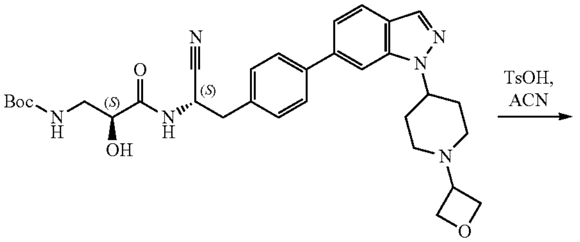

-continued

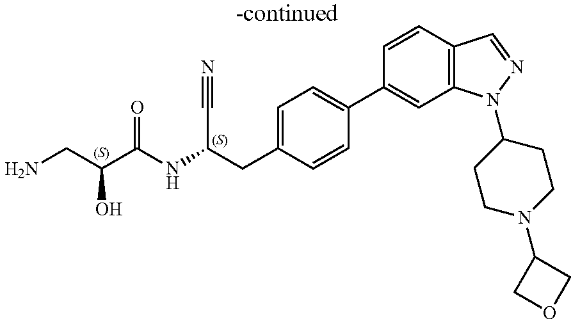

Into a 8 mL vial were added tert-butyl N-[(2S)-2-{[(1S)-1-cyano-2-(4-{1-[1-(oxetan-3-yl)piperidin-4-yl]indazol-6-yl}phenyl)ethyl]carbamoyl}-2-hydroxyethyl]carbamate (110 mg, 0.19 mmol, 1.0 equiv), acetonitrile (1.5 mL) and TsOH (96 mg, 0.56 mmol, 3.0 equiv) at room temperature. The resulting mixture was stirred at room temperature for 3 h. The mixture was basified to pH 8 with saturated $NaHCO_3$ (aq.). The resulting mixture was extracted with EtOAc (3×20 mL). The combined organic layer was washed with brine (20 mL), dried over anhydrous $Na_2SO_4$. After filtration, the filtrate was concentrated under reduced pressure. This resulted in (2S)-3-amino-N-[(1S)-1-cyano-2-(4-{1-[1-(oxetan-3-yl)piperidin-4-yl]indazol-6-yl}phenyl)ethyl]-2-hydroxypropanamide (90 mg). The crude product was used in the next step directly without further purification. LCMS (ES, m/z): $[M+H]^+$: 489.

Synthesis of (2S)—N-[(1S)-1-cyano-2-(4-{1-[1-(oxetan-3-yl)piperidin-4-yl]indazol-6-yl}phenyl)ethyl]-3-(dimethylamino)-2-hydroxypropanamide

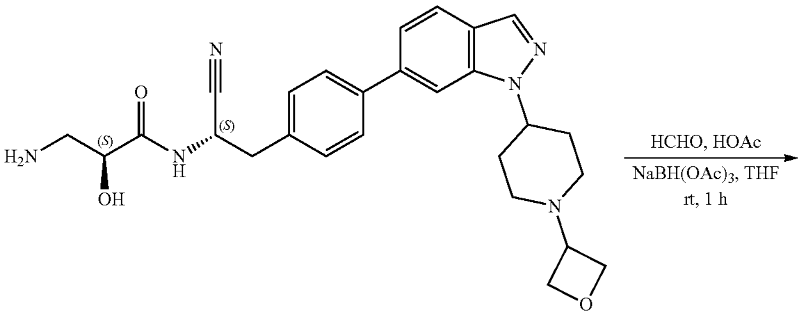

-continued

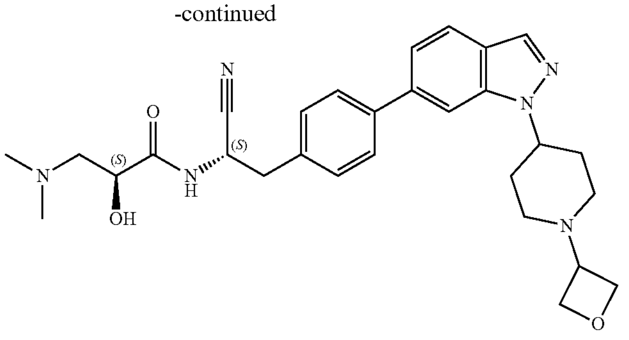

A solution of tert-butyl N-[(2S)-2-{[(1S)-1-cyano-2-(4-{1-[1-(oxetan-3-yl)piperidin-4-yl]indazol-6-yl}phenyl)ethyl]carbamoyl}-2-hydroxyethyl]carbamate (70 mg, 0.12 mmol, 1.0 equiv) and HOAc (0.04 mL), HCHO (93 mg, 1.20 mmol, 10 equiv, 38% in $H_2O$), $NaBH(OAc)_3$ (50 mg, 0.24 mmol, 2.0 equiv) in THF (3.0 mL) was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (2S)—N-[(1S)-1-cyano-2-(4-{1-[1-(oxetan-3-yl)piperidin-4-yl]indazol-6-yl}phenyl)ethyl]-3-(dimethylamino)-2-hydroxypropanamide (15.6 mg, 25% yield, 98% purity).

LCMS (ES, m/z): $[M+H]^+$: 517.3

$^1H$ NMR (400 MHz, DMSO-$d_6$) δ 8.72 (d, J=8.2 Hz, 1H), 8.10 (s, 1H), 7.98 (s, 1H), 7.81 (d, J=8.4 Hz, 1H), 7.79-7.72 (m, 2H), 7.46-7.40 (m, 3H), 5.59 (br, 1H), 5.06 (q, J=7.2 Hz, 1H), 4.84-4.74 (m, 1H), 4.58 (t, J=6.5 Hz, 2H), 4.48 (t, J=6.1 Hz, 2H), 3.99 (dd, J=7.8, 4.0 Hz, 1H), 3.52-3.46 (m, 1H), 3.25-3.19 (m, 2H), 2.86 (d, J=10.6 Hz, 2H), 2.31-2.02 (m, 12H), 1.95 (d, J=11.6 Hz, 2H).

Example 118: Synthesis of Compound 283: (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-hydroxypropanamide

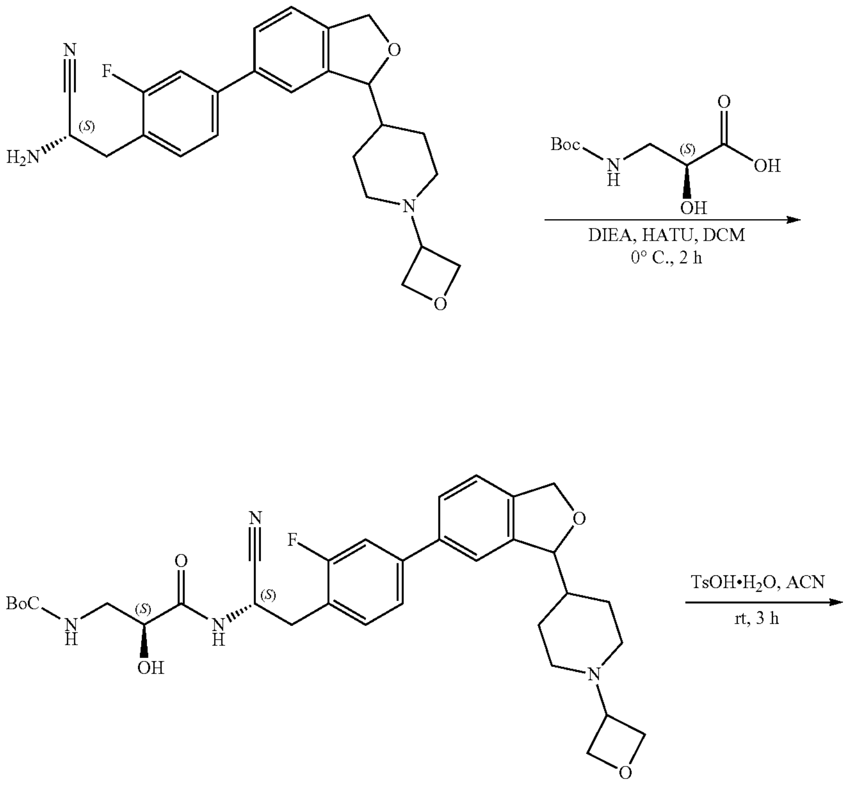

-continued

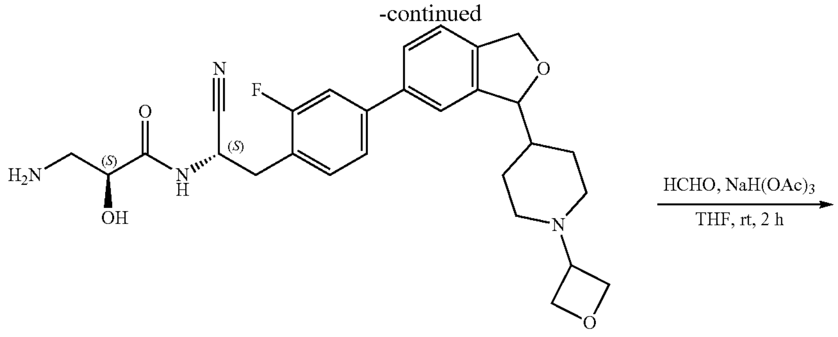

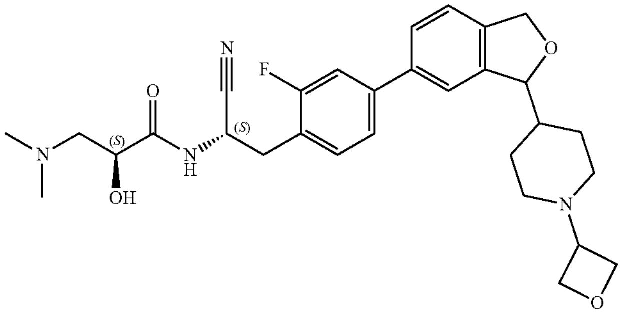

Compound 283

Synthesis of tert-butyl N-[(2S)-2-{[(1S)-1-cyano-2-{2-fluoro-4-[1'-(oxetan-3-yl)-3H-spiro[2-benzofuran-1,4'-piperidin]-6-yl]phenyl}ethyl]carbamoyl}-2-hydroxyethyl]carbamate

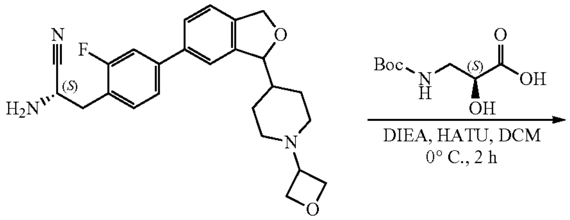

-continued

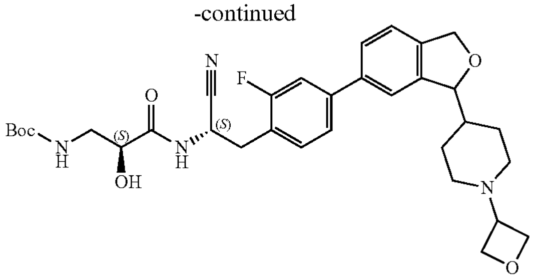

To a solution of (2S)-2-amino-3-{2-fluoro-4-[1'-(oxetan-3-yl)-3H-spiro[2-benzofuran-1,4'-piperidin]-6-yl] phenyl}propanenitrile (200 mg, 0.49 mmol, 1.0 equiv), (2S)-3-[(tert-butoxycarbonyl)amino]-2-hydroxypropanoic acid (201 mg, 0.98 mmol, 2.0 equiv) and DIEA (190 mg, 1.47 mmol, 3.0 equiv) in DCM (4 mL) was added HATU (279 mg, 0.73 mmol, 1.5 equiv) at 0° C. The resulting mixture was stirred for 2 h at 0° C. The reaction was concentrated. The residue was purified by silica gel column chromatography, eluted with PE/THF (1:1) to afford tert-butyl N-[(2S)-2-{[(1S)-1-cyano-2-{2-fluoro-4-[1'-(oxetan-3-yl)-3H-spiro[2-benzofuran-1,4'-piperidin]-6-yl]phenyl}ethyl]carbamoyl}-2-hydroxyethyl]carbamate (220 mg, 75.37% yield, 98% purity). LCMS (ES, m/z): $[M+H]^+$: 595.

Synthesis of (2S)-3-amino-N-[(1S)-1-cyano-2-{2-fluoro-4-[1'-(oxetan-3-yl)-3H-spiro[2-benzofuran-1,4'-piperidin]-6-yl]phenyl}ethyl]-2-hydroxypropanamide

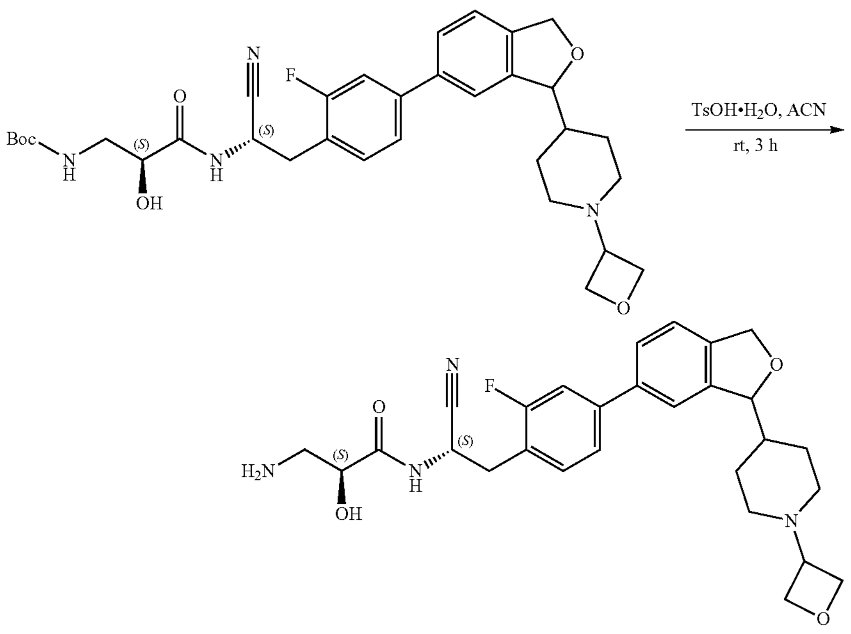

To a solution of tert-butyl N-[(2S)-2-{[(1S)-1-cyano-2-{2-fluoro-4-[1'-(oxetan-3-yl) 3H-spiro[2-benzofuran-1,4'-piperidin]-6-yl]phenyl}ethyl]carbamoyl}-2-hydroxyethyl]carbamate (210 mg, 0.35 mmol, 1.0 equiv) in MeCN (4 mL) was added 4-methylbenzene-1-sulfonic acid hydrate (201 mg, 1.05 mmol, 3.0 equiv) at 0° C. The resulting mixture was stirred for 3 h at 0° C. to room temperature. The reaction mixture was adjusted pH to 8 with $NaHCO_3$ (5N), extracted with EtOAc (4×10 mL). The organic layer was concentrated. The residue was purified by silica gel column chromatography, eluted with PE/THF (1:2) to afford (2S)-3-amino-N-[(1S)-1-cyano-2-{2-fluoro-4-[1'-(oxetan-3-yl)-3H-spiro[2-benzofuran-1,4'-piperidin]-6-yl]phenyl}ethyl]-2-hydroxypropanamide (140 mg, 80.16% yield, 95% purity). LCMS (ES, m/z): $[M+H]^+$: 495.

Synthesis of (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-hydroxypropanamide

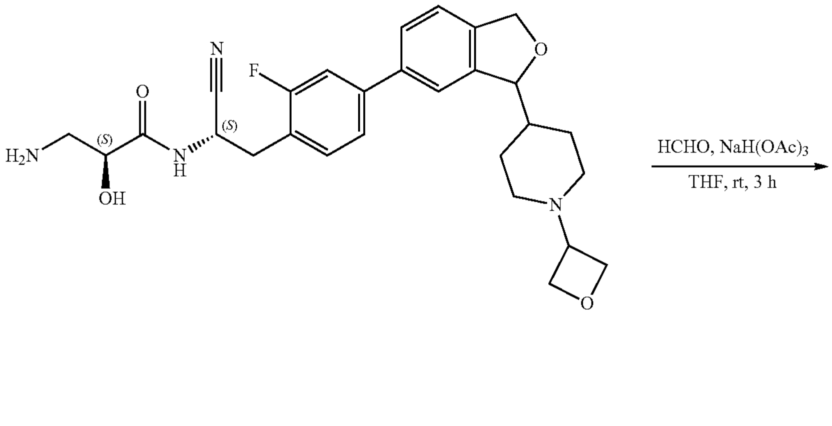

-continued

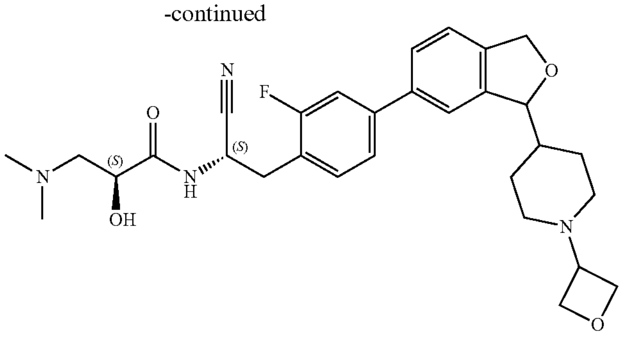

To a stirred solution of (2S)-3-amino-N-[(1S)-1-cyano-2-{2-fluoro-4-[1'-(oxetan-3-yl)-3H-spiro[2-benzofuran-1,4'-piperidin]-6-yl]phenyl}ethyl]-2-hydroxypropanamide (120 mg, 0.24 mmol, 1.0 equiv) and Formaldehyde solution (72 mg, 0.92 mmol, 3.8 equiv, 38%) in THF (3 mL) were added HOAc (2 mg, 0.02 mmol, 0.1 equiv) and sodium bis (acetyloxy)boranuidyl acetate (102 mg, 0.48 mmol, 2.0 equiv) in portions at room temperature. The resulting mixture was stirred at room temperature for 2 h. The crude product was purified by Prep-HPLC with the following conditions (Column, XBridge Prep C18 OBD Column, 19*150 mm Sum; mobile phase, Water(0.1% $NH_3H_2O$) and ACN (10% PhaseB up to 80% in 20 min); Detector, UV 254 nm. This resulted in (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-hydroxypropanamide (30 mg, 23.66% yield, 99.8% purity).

LCMS (ES, m/z): $[M+H]^+$: 523.2

$^1H$ NMR (400 MHz, DMSO-$d_6$) δ 8.88 (br, 1H), 7.67 (d, J=1.6 Hz, 1H), 7.65-7.54 (m, 3H), 7.44 (t, J=8.0 Hz, 1H), 7.36 (d, J=7.9 Hz, 1H), 5.61 (brs, 1H), 5.08 (t, J=7.9 Hz, 1H), 5.01 (s, 2H), 4.57 (t, J=6.4 Hz, 2H), 4.46 (t, J=6.1 Hz, 2H), 4.00 (dd, J=7.6, 4.0 Hz, 1H), 3.46 (p, J=6.4 Hz, 1H), 3.30-3.25 (m, 1H), 3.20 (dd, J=13.7, 8.5 Hz, 1H), 2.64 (d, J=10.3 Hz, 2H), 2.31 (dd, J=12.8, 4.1 Hz, 1H), 2.23 (dd, J=12.7, 7.7 Hz, 1H), 2.19-2.02 (m, 10H), 1.66 (d, J=12.5 Hz, 2H).

Example 119: Synthesis of Compound 284: (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-methoxypropanamide

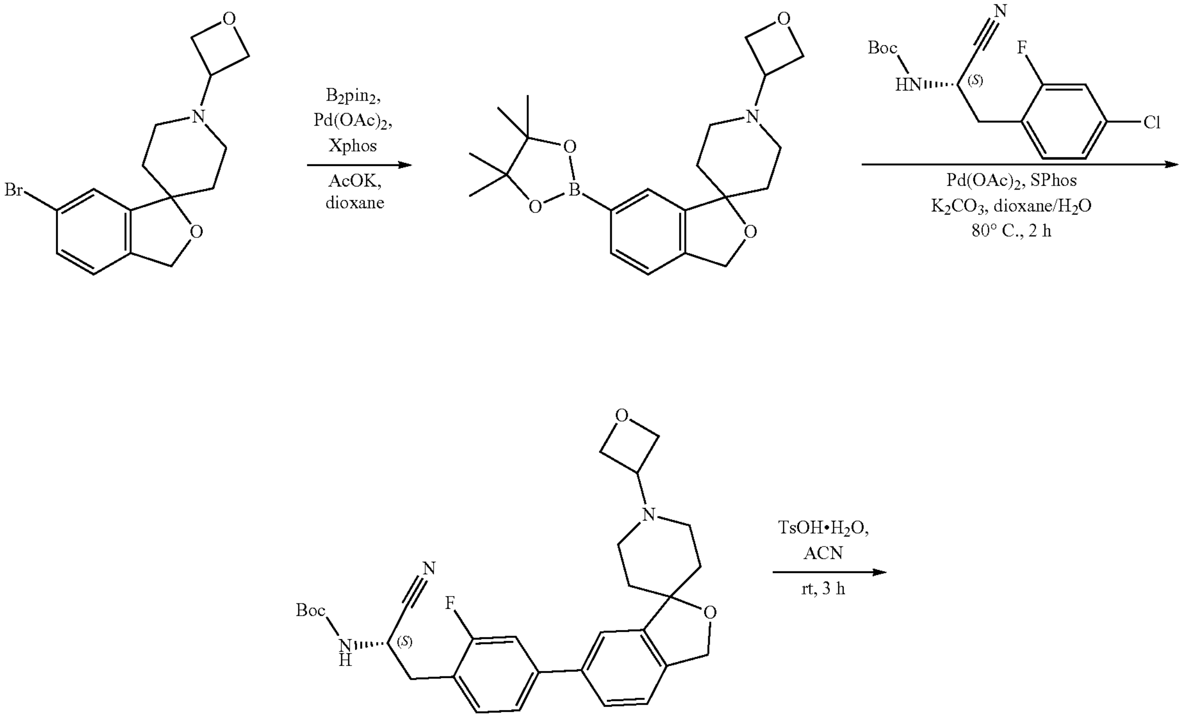

-continued

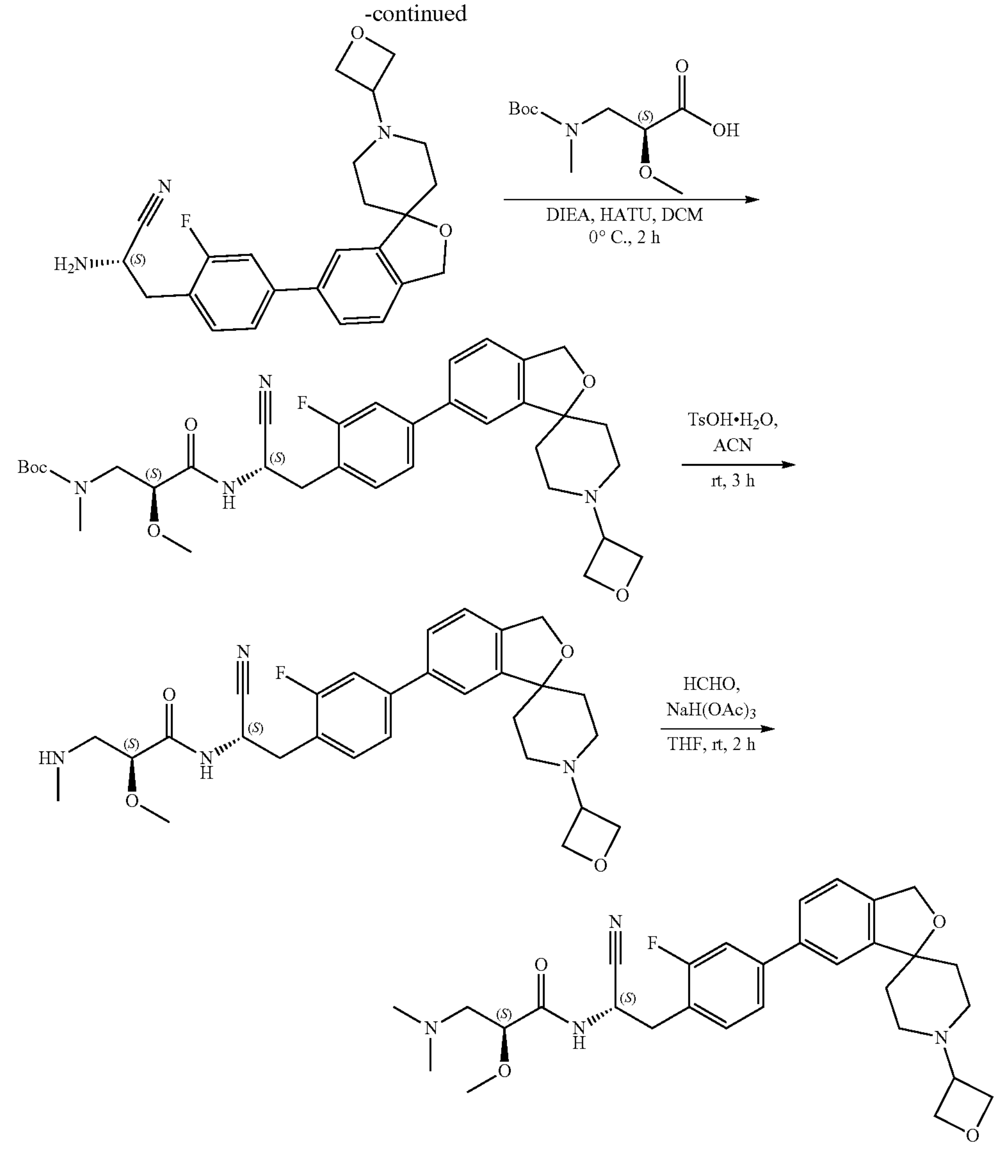

Compound 284

Synthesis of 1'-(oxetan-3-yl)-6-(4,4,5,5-tetramethyl-1,3,2-dioxaborolan-2-yl)-3H-spiro[2-benzofuran-1,4'-piperidine]

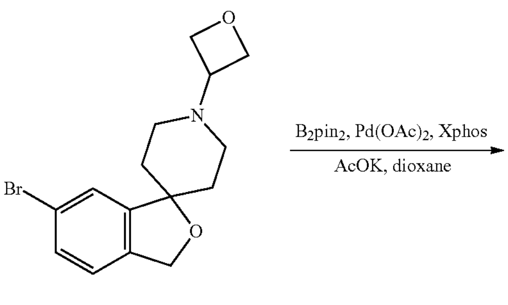

-continued

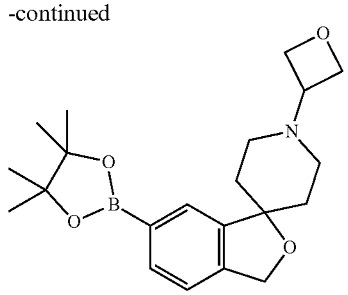

To a solution of 6-bromo-1'-(oxetan-3-yl)-3H-spiro[2-benzofuran-1,4'-piperidine](1.7 g, 5.24 mmol, 1.00 equiv), 4,4,5,5-tetramethyl-2-(tetramethyl-1,3,2-dioxaborolan-2-yl)-1,3,2-dioxaborolane (1.6 g, 6.29 mmol, 1.20 equiv) and AcOK (1.0 g, 10.48 mmol, 2.00 equiv) in 1,4-dioxane (30 mL) was added Pd(OAc)2 (0.1 g, 0.52 mmol, 0.10 equiv) and XPhos (0.5 g, 1.04 mmol, 0.20 equiv) at room temperature. The resulting mixture stirred for 2 h at 80° C. under nitrogen atmosphere. The reaction was concentrated. The residue was purified by silica gel column chromatography, eluted with PE/THE (1:1) to afford 1'-(oxetan-3-yl)-6-(4,4,5,5-tetramethyl-1,3,2-dioxaborolan-2-yl)-3H-spiro[2-benzofuran-1,4'-piperidine](1.1 g, 56.50% yield, 93% purity). LCMS (ES, m/z): $[M+H]^+$: 372.

Synthesis of tert-butyl N-[(1S)-1-cyano-2-{2-fluoro-4-[1'-(oxetan-3-yl)-3H-spiro[2-benzofuran-1,4'-piperidin]-6-yl]phenyl}ethyl]carbamate

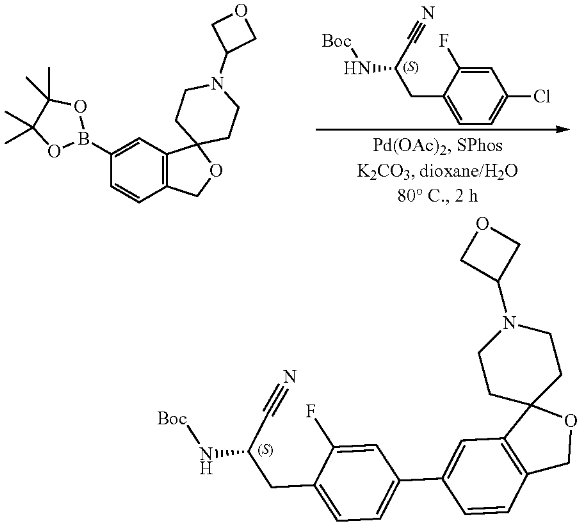

To a solution of 1'-(oxetan-3-yl)-6-(4,4,5,5-tetramethyl-1,3,2-dioxaborolan-2-yl)-3H-spiro[2-benzofuran-1,4'-piperidine](1.1 g, 2.96 mmol, 1.00 equiv), tert-butyl N-[(1S)-2-(4-chloro-2-fluorophenyl)-1-cyanoethyl]carbamate (0.9 g, 2.96 mmol, 1.00 equiv) and $K_2CO_3$ (0.8 g, 5.92 mmol, 2.00 equiv) in 1,4-dioxane (20 mL) and $H_2O$ (3 mL) was added Pd(OAc)2 (0.1 g, 0.29 mmol, 0.10 equiv) and SPhos Pd G2 (0.4 g, 0.59 mmol, 0.20 equiv) at room temperature. The resulting mixture stirred for 2 h at 80° C. under nitrogen atmosphere. The reaction was concentrated. The residue was purified by silica gel column chromatography, eluted with PE/THE (1:1) to afford tert-butyl N-[(1S)-1-cyano-2-{2-fluoro-4-[1'-(oxetan-3-yl)-3H-spiro[2-benzofuran-1,4'-piperidin]-6-yl]phenyl}ethyl]carbamate (850 mg, 56.52% yield, 95% purity). LCMS (ES, m/z): $[M+H]^+$: 508.

Synthesis of (2S)-2-amino-3-{2-fluoro-4-[1'-(oxetan-3-yl)-3H-spiro[2-benzofuran-1,4'-piperidin]-6-yl]phenyl}propanenitrile

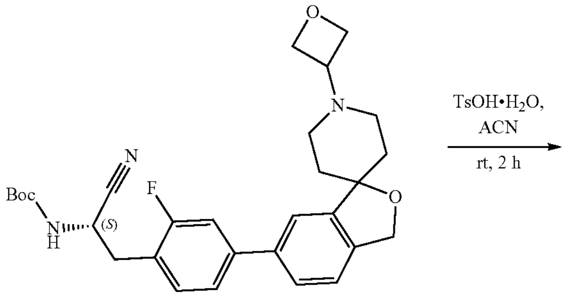

-continued

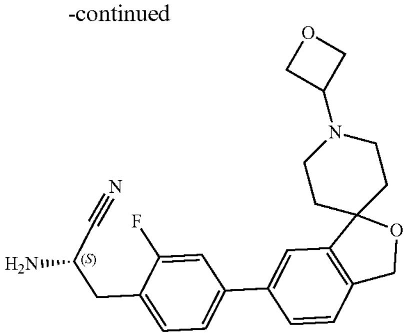

To a solution of tert-butyl N-[(1S)-1-cyano-2-{2-fluoro-4-[1'-(oxetan-3-yl)-3H-spiro[2-benzofuran-1,4'-piperidin]-6-yl]phenyl}ethyl]carbamate (850 mg, 1.67 mmol, 1.00 equiv) in MeCN (10 mL) was added 4-methylbenzene-1-sulfonic acid hydrate (955 mg, 5.02 mmol, 3.00 equiv) at 0° C. The resulting mixture was stirred for 2 h at 0° C. to room temperature. The reaction mixture was adjusted pH to 8 with $NaHCO_3$ (5N), extracted with EtOAc (4×20 mL). The organic layer was concentrated. The residue was purified by silica gel column chromatography, eluted with PE/THF (1:2) to afford (2S)-2-amino-3-{2-fluoro-4-[1'-(oxetan-3-yl)-3H-spiro[2-benzofuran-1,4'-piperidin]-6-yl] phenyl}propanenitrile (450 mg, 65.95% yield, 96% purity). LCMS (ES, m/z): $[M+H]^+$: 408.

Synthesis of tert-butyl N-[(2S)-2-{[(1S)-1-cyano-2-{2-fluoro-4-[1'-(oxetan-3-yl)-3H-spiro[2-benzofuran-1,4'-piperidin]-6-yl]phenyl}ethyl]carbamoyl}-2-methoxyethyl]-N-methylcarbamate

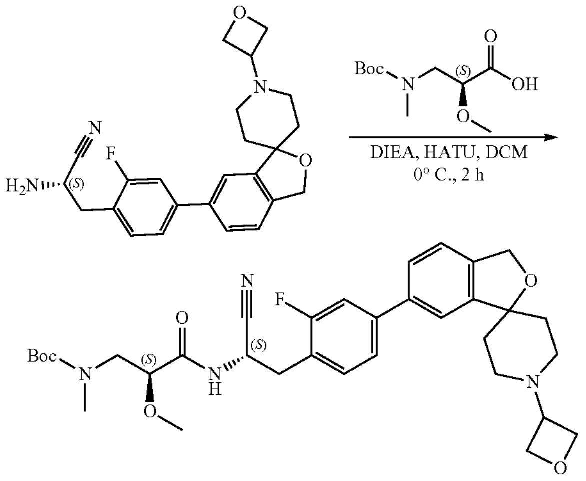

To a solution of (2S)-2-amino-3-{2-fluoro-4-[1'-(oxetan-3-yl)-3H-spiro[2-benzofuran-1,4'-piperidin]-6-yl] phenyl}propanenitrile (150 mg, 0.36 mmol, 1.00 equiv), (2S)-3-[(tert-butoxycarbonyl)(methyl)amino]-2-methoxypropanoic acid (128 mg, 0.55 mmol, 1.50 equiv) and DIEA (142 mg, 1.10 mmol, 3.00 equiv) in DCM (3 mL) was added HATU (210 mg, 0.55 mmol, 1.50 equiv) at 0° C. The resulting mixture was stirred for 2 h at 0° C. The reaction was concentrated. The residue was purified by silica gel column chromatography, eluted with PE/THF (1:1) to afford tert-butyl N-[(2S)-2-{[(1S)-1-cyano-2-{2-fluoro-4-[1'-

(oxetan-3-yl)-3H-spiro[2-benzofuran-1,4'-piperidin]-6-yl]phenyl}ethyl]carbamoyl}-2-methoxyethyl]—N-methylcarbamate (180 mg, 78.52% yield, 98% purity). LCMS (ES, m/z): $[M+H]^+$: 623.

Synthesis of (2S)—N-[(1S)-1-cyano-2-{2-fluoro-4-[1'-(oxetan-3-yl)-3H-spiro[2-benzofuran-1,4'-piperidin]-6-yl]phenyl}ethyl]-2-methoxy-3-(methylamino)propanamide

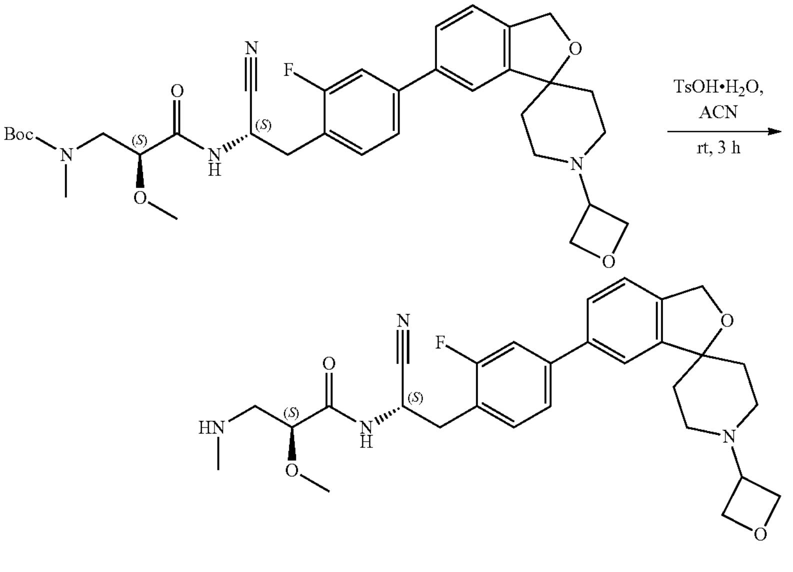

To a solution of tert-butyl N-[(2S)-2-{[(1S)-1-cyano-2-{2-fluoro-4-[1'-(oxetan-3-yl)-3H-spiro[2-benzofuran-1,4'-piperidin]-6-yl]phenyl}ethyl]carbamoyl}-2-methoxyethyl]-N-methylcarbamate (170 mg, 0.27 mmol, 1.00 equiv) in MeCN (3 mL) was added 4-methylbenzene-1-sulfonic acid hydrate (155 mg, 0.82 mmol, 3.00 equiv) at 0° C. The resulting mixture was stirred for 3 h at 0° C. to room temperature. The reaction mixture was adjusted pH to 8 with $NaHCO_3$ (5N), extracted with EtOAc (4×20 mL). The organic layer was concentrated. The residue was purified by silica gel column chromatography, eluted with PE/THF (1:2) to afford (2S)—N-[(1S)-1-cyano-2-{2-fluoro-4-[1'-(oxetan-3-yl)-3H-spiro[2-benzofuran-1,4'-piperidin]-6-yl]phenyl}ethyl]-2-methoxy-3-(methylamino)propanamide (110 mg, 77.10% yield, 95% purity). LCMS (ES, m/z): $[M+H]^+$: 523.

Synthesis of (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-methoxypropanamide

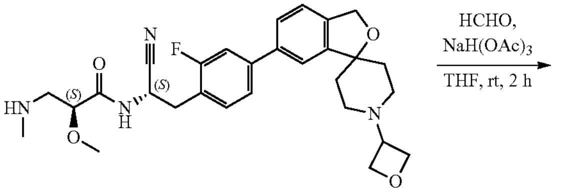

-continued

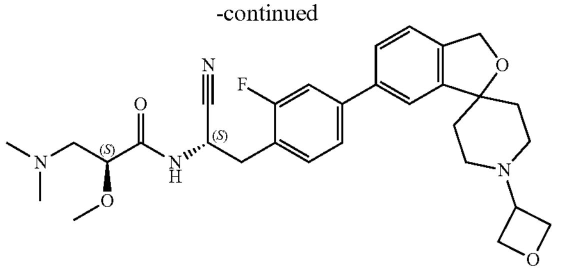

To a stirred solution of (2S)—N-[(1S)-1-cyano-2-{2-fluoro-4-[1'-(oxetan-3-yl)-3H-spiro[2-benzofuran-1,4'-piperidin]-6-yl]phenyl}ethyl]-2-methoxy-3-(methylamino)propanamide (100 mg, 0.19 mmol, 1.00 equiv) and Formaldehyde solution (151 mg, 1.91 mmol, 10.00 equiv, 38%) in THF (2 mL) were added HOAc (2 mg, 0.02 mmol, 0.10 equiv) and sodium bis(acetyloxy)boranuidyl acetate (81 mg, 0.38 mmol, 2.00 equiv) in portions at room temperature. The resulting mixture was stirred at room temperature for 2 h. The crude product was purified by Prep-HPLC with the following conditions (Column, XBridge Prep C18 OBD Column, 19*150 mm 5um; mobile phase, Water(0.1% $NH_3H_2O$) and ACN (10% PhaseB up to 80% in 20 min); Detector, UV 254 nm. This resulted in (2S)—N-[(1S)-1-cyano-2-{2-fluoro-4-[1'-(oxetan-3-yl)-3H-spiro[2-benzofuran-1,4'-piperidin]-6-yl]phenyl}ethyl]-3-(dimethylamino)-2-methoxypropanamide (30 mg, 29.22% yield, 98.4% purity).

LCMS (ES, m/z): $[M+H]^+$: 537.3.

$^1H$ NMR (400 MHz, DMSO-$d_6$) δ 8.91 (d, J=8.5 Hz, 1H), 7.67 (d, J=1.6 Hz, 1H), 7.65-7.54 (m, 3H), 7.45 (t, J=7.9 Hz,

1H), 7.35 (d, J=7.9 Hz, 1H), 5.16-5.08 (m, 1H), 5.00 (s, 2H), 4.57 (t, J=6.4 Hz, 2H), 4.46 (t, J=6.1 Hz, 2H), 3.73 (dd, J=7.0, 4.3 Hz, 1H), 3.50-3.41 (m, 1H), 3.30-3.24 (m, 1H), 3.24-3.16 (m, 4H), 2.64 (d, J=10.4 Hz, 2H), 2.37-2.24 (m, 2H), 2.13 (d, J=20.9 Hz, 10H), 1.66 (d, J=12.4 Hz, 2H).

Example 120: Synthesis of Compound 285: (S)—N—((S)-1-cyano-2-(2-fluoro-4-(1-(1-methylpiperidin-4-yl)-1H-indazol-6-yl)phenyl)ethyl)-3-(dimethylamino)-2-hydroxypropanamide

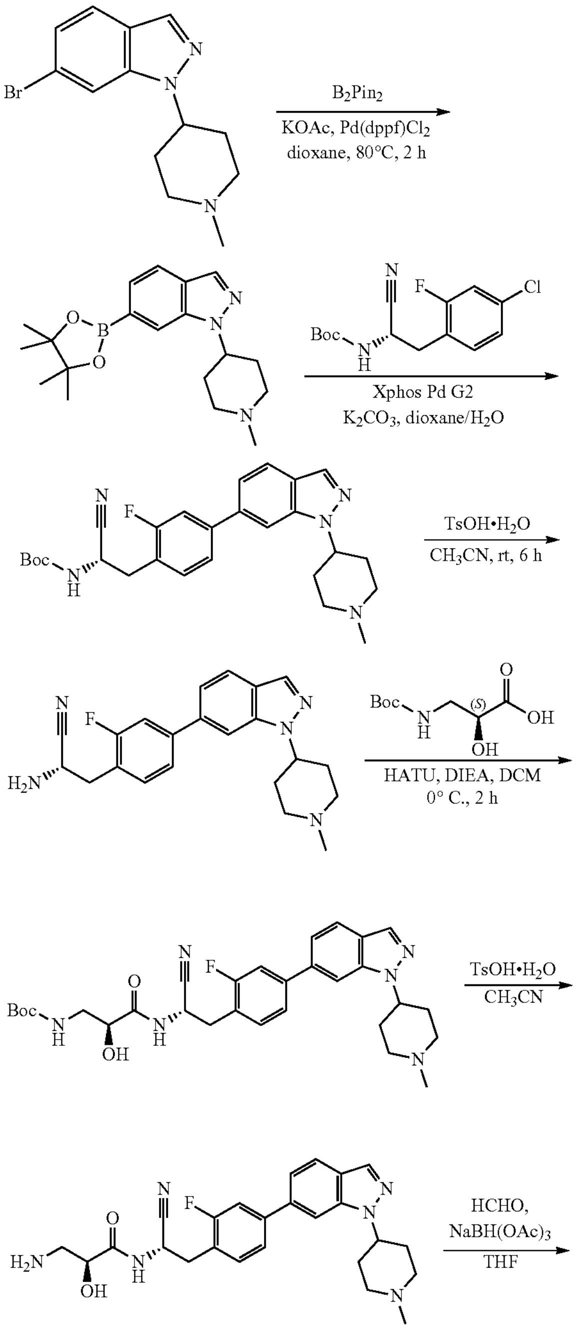

-continued

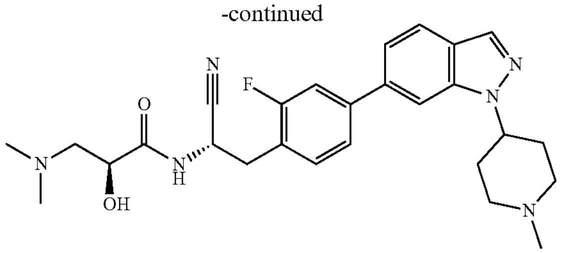

Compound 285

Synthesis of 1-(1-methylpiperidin-4-yl)-6-(4,4,5,5-tetramethyl-1,3,2-dioxaborolan-2-yl)-1H-indazole

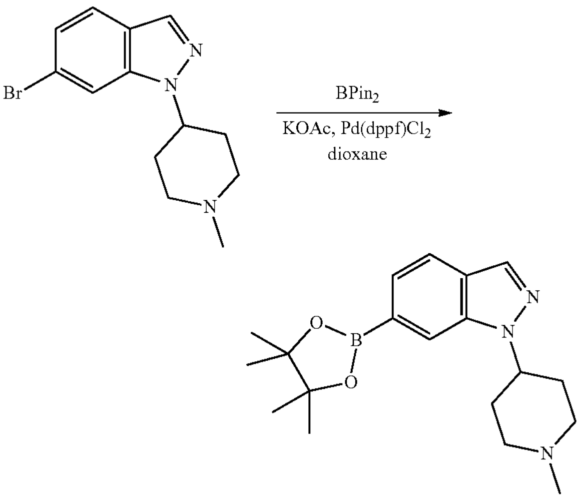

To a mixture of 6-bromo-1-(1-methylpiperidin-4-yl)indazole (2 g, 6.80 mmol, 1.0 equiv), bis(pinacolato)diboron (2.07 g, 8.16 mmol, 1.2 equiv) and AcOK (1.33 g, 13.60 mmol, 2.0 equiv) in dioxane (20 mL) was added Pd(dppf) $Cl_2CH_2Cl_2$ (0.56 g, 0.68 mmol, 0.1 equiv). The mixture was stirred at 80° C. for 2 h under nitrogen atmosphere. The resulting mixture was concentrated under reduced pressure. The residue was purified by silica gel column chromatography, eluted with PE/THE (0:100) to afford 1-(1-methylpiperidin-4-yl)-6-(4,4,5,5-tetramethyl-1,3,2-dioxaborolan-2-yl)indazole (1.7 g, 73.3% yield, 90% purity). LCMS (ES) $[M+H]^+$ m/z: 342.

Synthesis of tert-butyl (S)-(1-cyano-2-(2-fluoro-4-(1-(1-methylpiperidin-4-yl)-1H-indazol-6-yl)phenyl)ethyl)carbamate

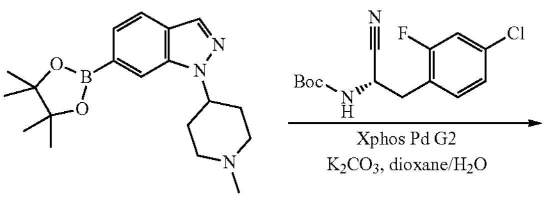

-continued

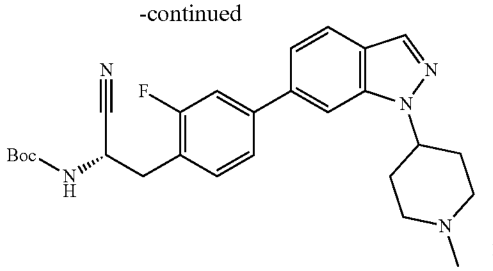

To a mixture of tert-butyl N-[(1S)-2-(4-chloro-2-fluoro-phenyl)-1-cyanoethyl]carbamate (1 g, 3.35 mmol, 1.0 equiv), 1-(1-methylpiperidin-4-yl)-6-(4,4,5,5-tetramethyl-1,3,2-dioxaborolan-2-yl)indazole (1.71 g, 5.02 mmol, 1.5 equiv), $K_2CO_3$ (0.93 g, 6.69 mmol, 2.0 equiv) in dioxane (20 mL), $H_2O$ (2 mL) was added 9-chloro-9-[dicyclohexyl({2',4',6'-triisopropyl-[1,1'-biphenyl]-2-yl})-lambda5-phosphanyl]-8-aza-9-palladatricyclo[8.4.0.0{2,7}]tetradeca-1(10),2(7),3,5,11,13-hexaene (0.26 g, 0.34 mmol, 0.1 equiv) at room temperature under nitrogen atmosphere. The resulting mixture was stirred at 80° C. for 2 h under nitrogen atmosphere. The resulting mixture was concentrated under reduced pressure. The residue was purified by silica gel column chromatography, eluted with PE/THE (1:3) to afford tert-butyl (S)-(1-cyano-2-(2-fluoro-4-(1-(1-methylpiperidin-4-yl)-1H-indazol-6-yl)phenyl)ethyl)carbamate (1.5 g, 93.8% yield, 90% purity). LCMS (ES) $[M+H]^+$ m/z: 478.

Synthesis of (S)-2-amino-3-(2-fluoro-4-(1-(1-methylpiperidin-4-yl)-1H-indazol-6-yl)phenyl)propanenitrile

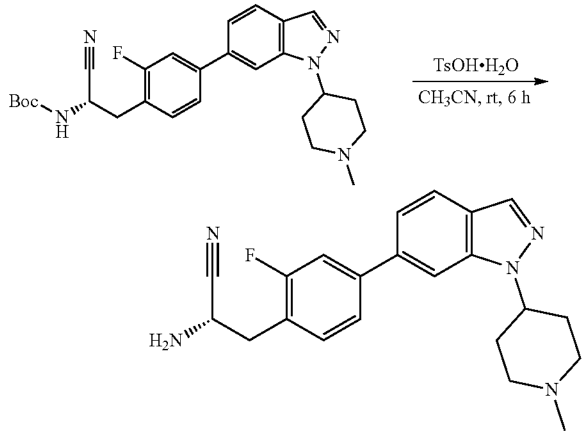

To a solution of tert-butyl N-[(1S)-1-cyano-2-{2-fluoro-4-[1-(1-methylpiperidin-4-yl)indazo-6-yl]phenyl}ethyl]carbamate (1.5 g, 3.14 mmol, 1.0 equiv) in Acetonitrile (25 mL) was added of TSOH (1.62 g, 9.42 mmol, 3.0 equiv) at room temperature. The resulting mixture was stirred at room temperature for 6 h. The mixture was basified to pH 8 with saturated $NaHCO_3$ (aq.). The aqueous layer was extracted with $CH_2Cl_2$ (30 mL×2). The combined organic phase was dried over anhydrous sodium sulfate. After filtration, the filtrate was concentrated under reduced pressure. The crude product was used in the next step directly without further purification. LCMS (ES) $[M+H]^+$ m/z: 378.

Synthesis of tert-butyl ((S)-3-(((S)-1-cyano-2-(2-fluoro-4-(1-(1-methylpiperidin-4-yl)-1H-indazol-6-yl)phenyl)ethyl)amino)-2-hydroxy-3-oxopropyl) carbamate

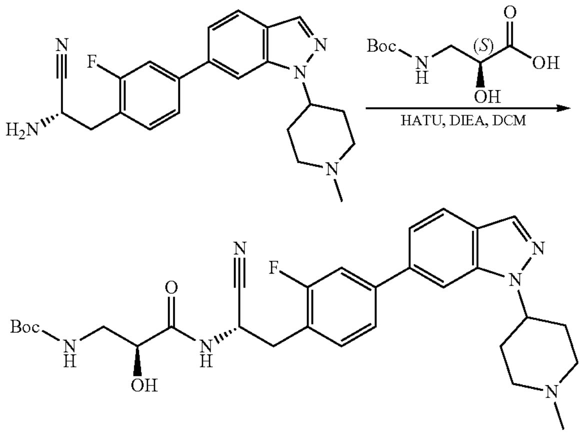

A solution of (2S)-2-amino-3-{2-fluoro-4-[1-(1-methylpiperidin-4-yl)indazo-6-yl]phenyl}propanenitrile (150 mg, 0.40 mmol, 1.0 equiv), DIEA (154 mg, 1.19 mmol, 3.0 equiv) in DCM (3 mL) was treated with HATU (181 mg, 0.48 mmol, 1.2 equiv) at 0° C. The resulting mixture was stirred at 0° C. for 2 h. The resulting mixture was concentrated under vacuum. The residue was purified by silica gel column chromatography, eluted with PE/THE to afford tert-butyl N-[(2S)-2-{[(1S)-1-cyano-2-{2-fluoro-4-[1-(1-methylpiperidin-4-yl)indazo-6-yl]phenyl}ethyl]carbamoyl}-2-hydroxyethyl]carbamate (120 mg, 53% yield, 90% purity). LCMS (ES) $[M+H]^+$ m/z: 565.

Synthesis of (S)-3-amino-N—((S)-1-cyano-2-(2-fluoro-4-(1-(1-methylpiperidin-4-yl)-1H-indazol-6-yl)phenyl)ethyl)-2-hydroxypropanamide

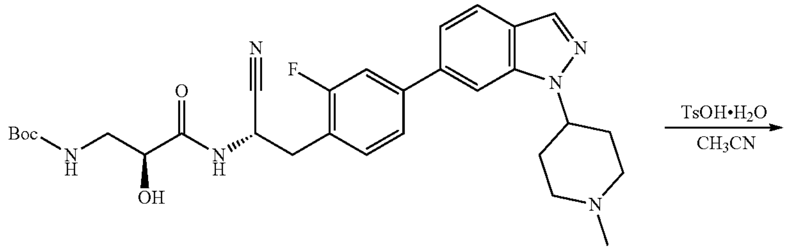

-continued

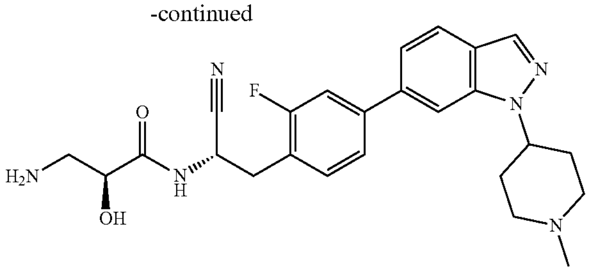

To a solution of tert-butyl N-[(2S)-2-{[(1S)-1-cyano-2-{2-fluoro-4-[1-(1-methylpiperidin-4-yl)indazo-6-yl]phenyl}ethyl]carbamoyl}-2-hydroxyethyl]carbamate (120 mg, 0.21 mmol, 1.0 equiv) in acetonitrile (3 mL) was added TsOH (110 mg, 0.64 mmol, 3.0 equiv) at room temperature. The mixture was basified to pH 8 with saturated $NaHCO_3$ (aq.). The aqueous layer was extracted with $CH_2Cl_2$ (20 mL×2). The combined organic phase was dried over anhydrous sodium sulfate. After filtration, the filtrate was concentrated under vacuum. The crude product was used in the next step directly without further purification. LCMS (ES) $[M+H]^+$ m/z: 465.

Synthesis of (S)—N—((S)-1-cyano-2-(2-fluoro-4-(1-(1-methylpiperidin-4-yl)-1H-indazol-6-yl)phenyl)ethyl)-3-(dimethylamino)-2-hydroxypropanamide

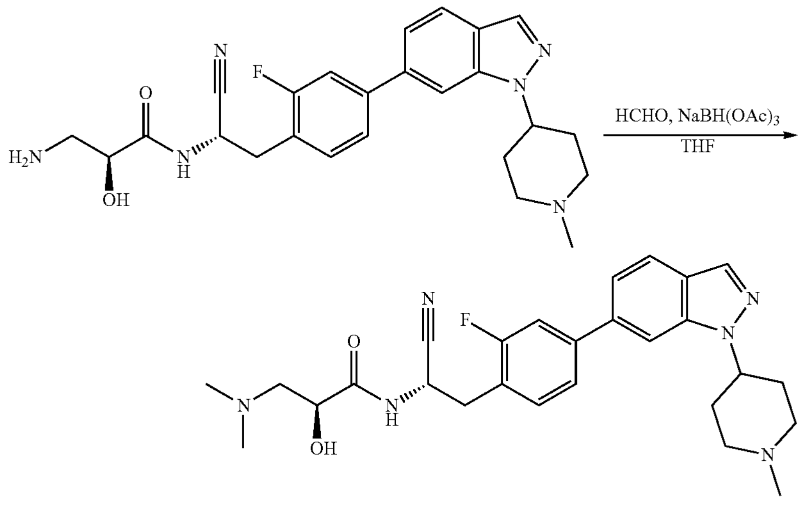

A solution of (2S)-3-amino-N-[(1S)-1-cyano-2-{2-fluoro-4-[1-(1-methylpiperidin-4-yl)indazol-6-yl]phenyl}ethyl]-2-hydroxypropanamide (90 mg, 0.20 mmol, 1.0 equiv), HCHO (194 mg, 1.94 mmol, 10 equiv, 30% in water) in THE (2 mL) was treated with sodium triacetoxyborohydride (82 mg, 0.39 mmol, 2.0 equiv) at room temperature. The resulting mixture was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 60% gradient in 10 min; detector, UV 254 nm. This resulted in (S)—N—((S)-1-cyano-2-(2-fluoro-4-(1-(1-methylpiperidin-4-yl)-1H-indazol-6-yl)phenyl)ethyl)-3-(dimethylamino)-2-hydroxypropanamide (16.3 mg, 17% yield, 95% purity). LCMS (ES) $[M+1]^+$ m/z: 493.5

$^1H$ NMR (300 MHz, DMSO-$d_6$) δ 8.81 (brs, 1H), 8.07 (s, 1H), 8.06 (s, 1H), 7.80 (d, J=8.5 Hz, 1H), 7.68 (dd, J=11.7, 1.8 Hz, 1H), 7.63 (dd, J=7.9, 1.8 Hz, 1H), 7.49-7.43 (m, 2H), 5.62 (br, 1H), 5.13-5.04 (m, 1H), 4.79-4.68 (m, 1H), 3.99 (dd, J=7.5, 4.1 Hz, 1H), 3.28-3.15 (m, 2H), 2.94-2.85 (m, 2H), 2.32-2.09 (m, 15H), 1.94-1.83 (m, 2H).

Example 121: Synthesis of Compound 286: (S)—N—((S)-1-cyano-2-(2-fluoro-4-(1-(1-methylpiperidin-4-yl)-1H-indazol-6-yl)phenyl)ethyl)-3-(dimethylamino)-2-methoxypropanamide

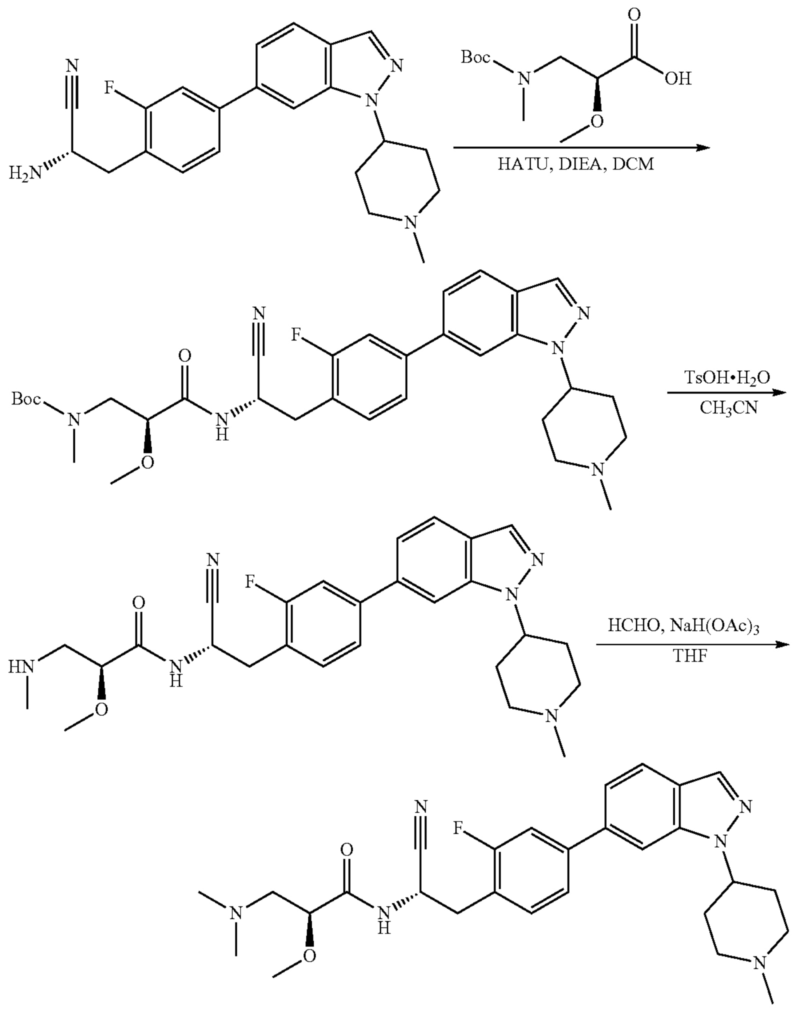

Compound 286

Synthesis of tert-butyl ((S)-3-(((S)-1-cyano-2-(2-fluoro-4-(1-(1-methylpiperidin-4-yl)-1H-indazol-6-yl)phenyl)ethyl)amino)-2-methoxy-3-oxopropyl)(methyl)carbamate

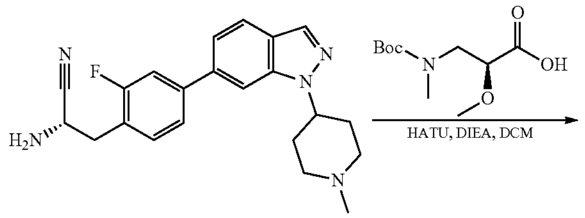

-continued

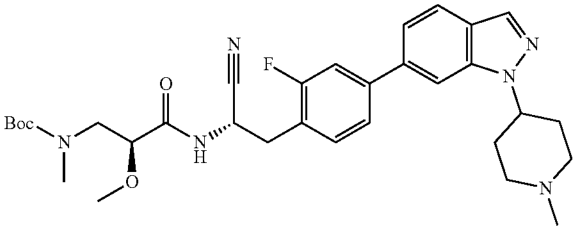

To a solution of (2S)-2-amino-3-{2-fluoro-4-[1-(1-methylpiperidin-4-yl)indazo-6-yl]phenyl}propanenitrile (150 mg, 0.40 mmol, 1.0 equiv), (2S)-3-[(tert-butoxycarbonyl)(methyl)amino]-2-methoxypropanoic acid (101.97 mg, 0.44 mmol, 1.1 equiv) and DIEA (154 mg, 1.19 mmol, 3.0 equiv) in DCM (3 mL) was added HATU (181 mg, 0.48 mmol, 1.2 equiv) in portions at 0° C. The resulting mixture was stirred at 0° C. for 2 h. The resulting mixture was concentrated under vacuum. The residue was purified by silica gel column chromatography, eluted with PE/THE to afford tert-butyl ((S)-3-(((S)-1-cyano-2-(2-fluoro-4-(1-(1-methylpiperidin-4-yl)-1H-indazol-6-yl)phenyl)ethyl)amino)-2-methoxy-3- oxopropyl)(methyl)carbamate (170 mg, 72% yield, 90% purity). LCMS (ES) $[M+H]^+$ m/z: 593.

Synthesis of (S)—N—((S)-1-cyano-2-(2-fluoro-4-(1-(1-methylpiperidin-4-yl)-1H-indazol-6-yl)phenyl)ethyl)-2-methoxy-3-(methylamino)propanamide

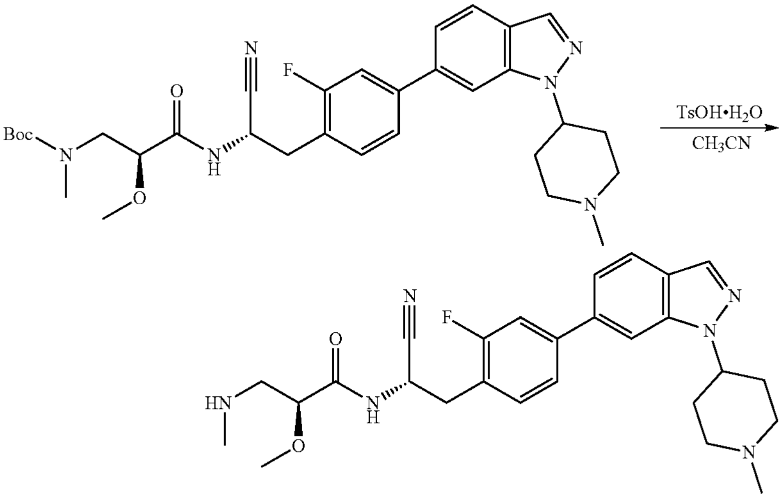

A solution of tert-butyl ((S)-3-(((S)-1-cyano-2-(2-fluoro-4-(1-(1-methylpiperidin-4-yl)-1H-indazol-6-yl)phenyl)ethyl)amino)-2-methoxy-3-oxopropyl)(methyl)carbamate (170 mg, 0.29 mmol, 1.0 equiv) in acetonitrile (3 mL) was treated with TsOH (256 mg, 0.86 mmol, 3.0 equiv) at room temperature. The resulting mixture was stirred at room temperature for 2 h. The mixture was basified to pH 8 with saturated $NaHCO_3$ (aq.). The aqueous layer was extracted with $CH_2Cl_2$ (30 mL×2). The combined organic phase was dried over anhydrous sodium sulfate. After filtration, the filtrate was concentrated under vacuum. The crude product was used in the next step directly without further purification. LCMS (ES) $[M+H]^+$ m/z: 493.

Synthesis of (S)—N—((S)-1-cyano-2-(2-fluoro-4-(1-(1-methylpiperidin-4-yl)-1H-indazol-6-yl)phenyl)ethyl)-3-(dimethylamino)-2-methoxypropanamide

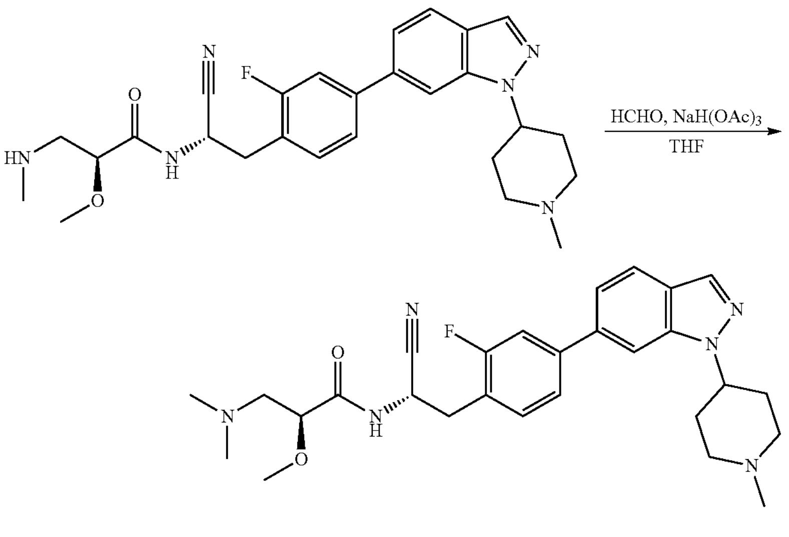

A solution of (S)—N—((S)-1-cyano-2-(2-fluoro-4-(1-(1-methylpiperidin-4-yl)-1H-indazol-6-yl)phenyl)ethyl)-2-methoxy-3-(methylamino)propanamide (140 mg, 0.28 mmol, 1.0 equiv) in THE (2 mL) was treated with sodium triacetoxyborohydride (120 mg, 0.57 mmol, 2.0 equiv) at room temperature. The mixture was stirred for 2 h. The reaction solution was purified by reversed-phase flash chromatography with the following conditions: column, C18 silica gel-120 g; mobile phase, MeCN in Water (0.1% $NH_3 \cdot H_2O$), 10% to 70% gradient in 10 min; detector, UV 254 nm. This resulted in (S)—N—((S)-1-cyano-2-(2-fluoro-4-(1-(1-methylpiperidin-4-yl)-1H-indazol-6-yl)phenyl)ethyl)-3-(dimethylamino)-2-methoxypropanamide (17.2 mg, 12% yield, 98.8% purity). LCMS (ES) $[M+1]^+$ m/z: 507.2

$^1H$ NMR (300 MHz, DMSO-$d_6$) δ 8.93 (d, J=8.7 Hz, 1H), 8.10-8.08 (m, 2H), 7.82 (d, J=8.4 Hz, 1H), 7.73-7.63 (m, 2H), 7.56-7.44 (m, 2H), 5.19-5.04 (m, 1H), 4.81-4.71 (m, 1H), 3.73 (dd, J=7.2, 4.0 Hz, 1H), 3.30-3.18 (m, 5H), 2.92 (d, J=6.8 Hz, 2H), 2.44-2.28 (m, 3H), 2.25 (s, 3H), 2.20-2.06 (m, 9H), 1.95-1.86 (m, 2H).

Example 122: Synthesis of Compound 287: (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-hydroxypropanamide

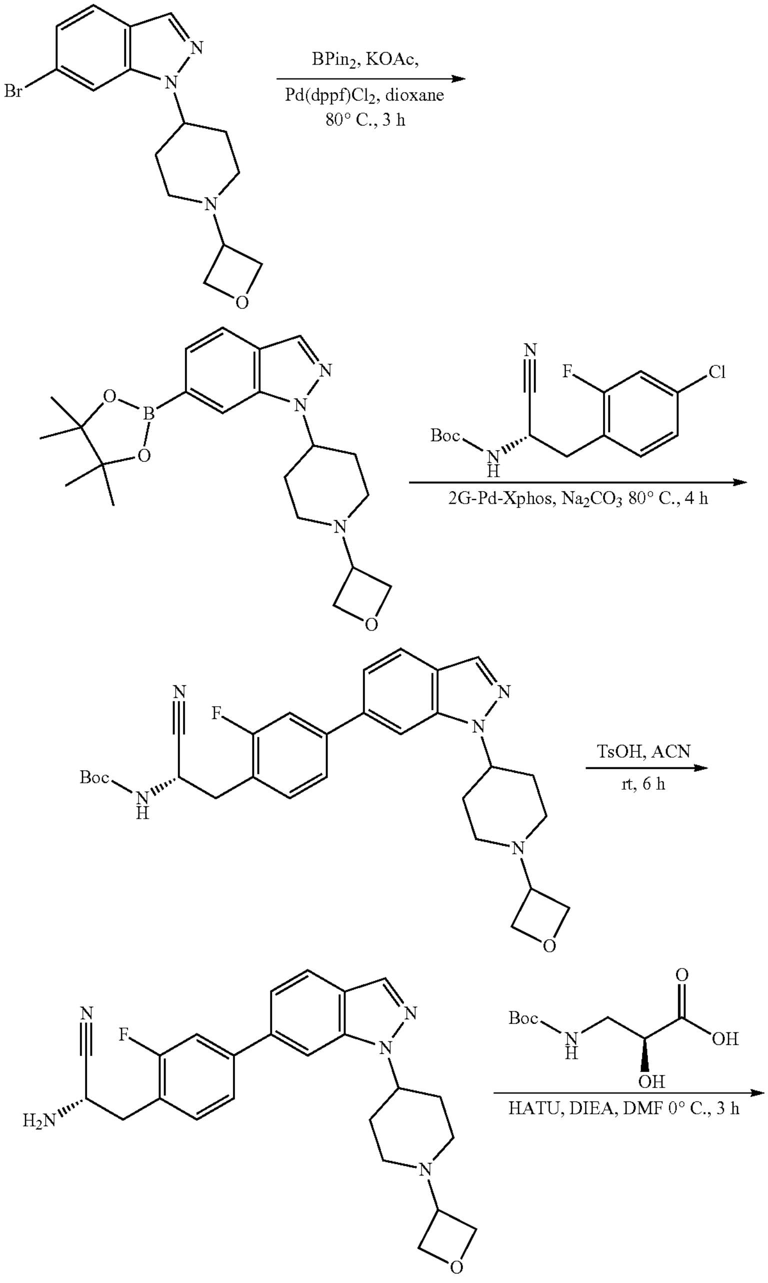

-continued
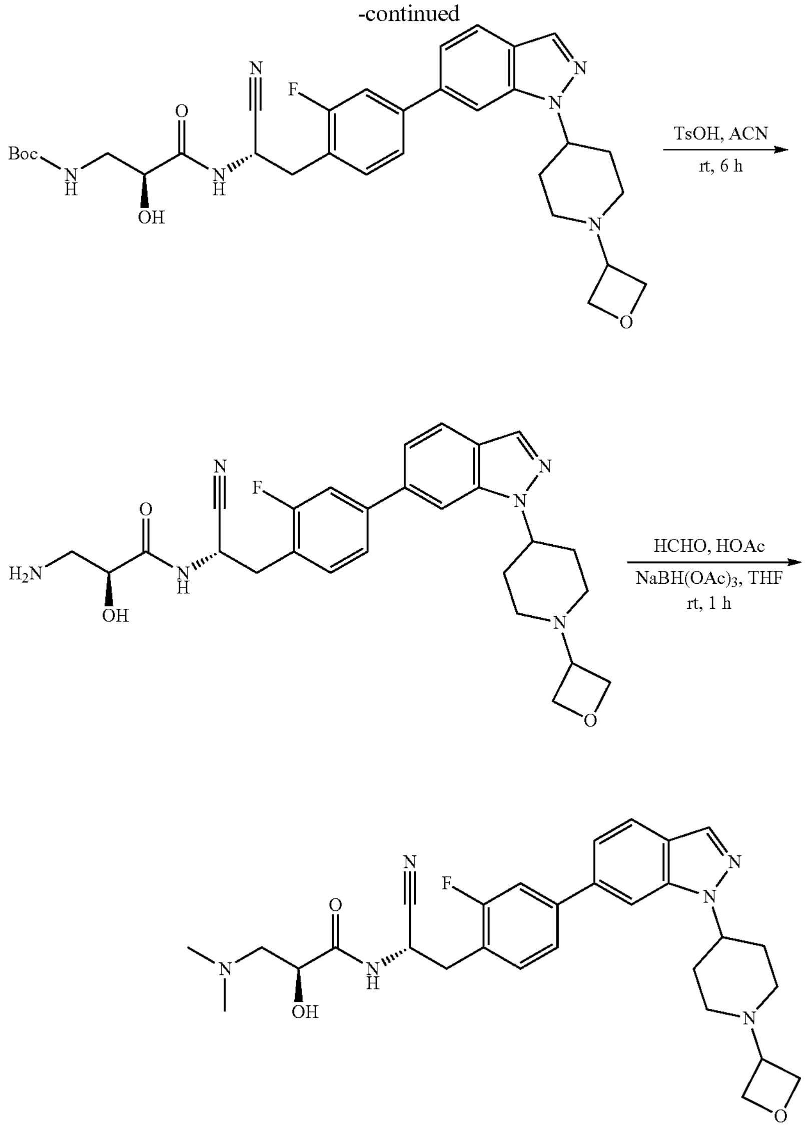
Compound 287
Synthesis of 1-[1-(oxetan-3-yl)piperidin-4-yl]-6-(4,4,5,5-tetramethyl-1,3,2-dioxaborolan-2-yl)indazole
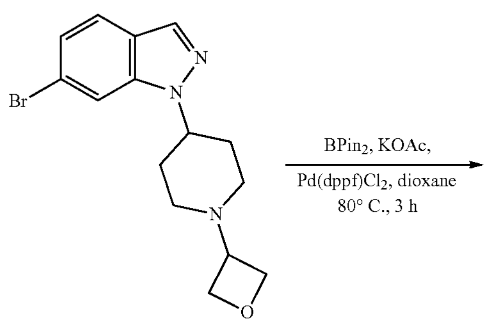
-continued
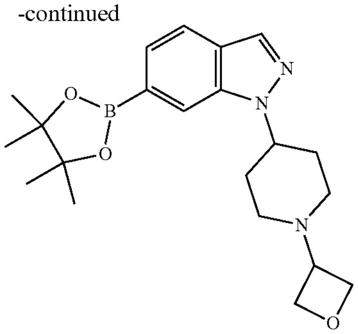
To a mixture of 6-bromo-1-[1-(oxetan-3-yl)piperidin-4-yl]indazole (500 mg, 1.49 mmol, 1.0 equiv) and bis(pinacolato)diboron (453 mg, 1.78 mmol, 1.2 equiv), AcOK (292 mg, 2.97 mmol, 2.0 equiv) in 1,4-dioxane (10 mL) was added $Pd(dppf)Cl_2CH_2Cl_2$ (121 mg, 0.15 mmol, 0.1 equiv). The mixture was stirred at 80° C. for 3 h under nitrogen atmosphere. The reaction was cooled to room temperature, concentrated to remove the solvent. The residue was purified by silica gel column chromatography, eluted with PE/THE (1:1) to afford 1-[1-(oxetan-3-yl)piperidin-4-yl]-6-(4,4,5,5-tetramethyl-1,3,2-dioxaborolan-2-yl)indazole (470 mg, 82% yield, 95% purity). LCMS (ES, m/z): $[M+H]^+$: 384.

Synthesis of tert-butyl N-[(1S)-1-cyano-2-(2-fluoro-4-{1-[1-(oxetan-3-yl)piperidin-4-yl]indazol-6-yl}phenyl)ethyl]carbamate

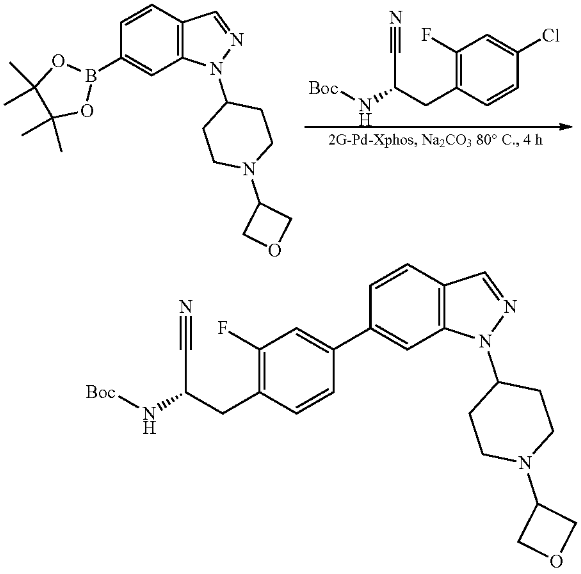

To a mixture of tert-butyl N-[(1S)-2-(4-chloro-2-fluorophenyl)-1-cyanoethyl]carbamate (450 mg, 1.51 mmol, 1.0 equiv) and 1-[1-(oxetan-3-yl)piperidin-4-yl]-6-(4,4,5,5-tetramethyl-1,3,2-dioxaborolan-2-yl)indazole (577 mg, 1.51 mmol, 1.0 equiv), $Na_2CO_3$ (319 mg, 3.01 mmol, 2.0 equiv) in 1,4-dioxane (10 mL)/$H_2O$ (1 mL) was added XPhos Pd G2 (118 mg, 0.15 mmol, 0.1 equiv). The reaction mixture was stirred at 80° C. for 4 h under nitrogen atmosphere. The reaction was cooled to room temperature, concentrated to remove the solvent. The residue was purified by silica gel column chromatography, eluted with PE/THE (1:2) to afford tert-butyl N-[(1S)-1-cyano-2-(2-fluoro-4-{1-[1-(oxetan-3-yl)piperidin-4-yl]indazol-6-yl}phenyl)ethyl]carbamate (400 mg, 51% yield, 98% purity). LCMS (ES, m/z): $[M+H]^+$: 520.

Synthesis of (2S)-2-amino-3-(2-fluoro-4-{1-[1-(oxetan-3-yl)piperidin-4-yl]indazol-6-yl}phenyl)propanenitrile

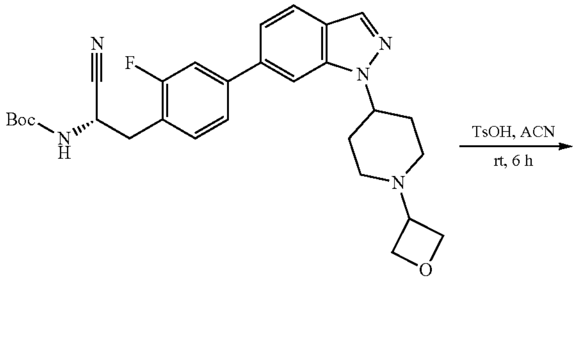

-continued

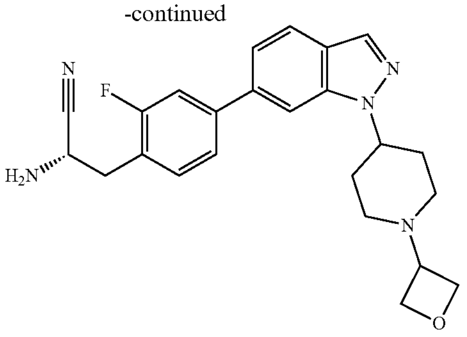

Into a 25 mL round-bottom flask were added tert-butyl N-[(1S)-1-cyano-2-(2-fluoro-4-{1-[1-(oxetan-3-yl)piperidin-4-yl]indazol-6-yl}phenyl)ethyl]carbamate (450 mg, 0.87 mmol, 1.0 equiv), MeCN (13 mL) and TsOH (447 mg, 2.60 mmol, 3.0 equiv) at room temperature. The resulting mixture was stirred at room temperature for additional 6 h. The mixture was neutralized to pH 8 with saturated $NaHCO_3$ (aq.). The resulting mixture was extracted with EtOAc (3x30 mL). The combined organic layer was washed with brine (30 mL), dried over anhydrous $Na_2SO_4$. After filtration, the filtrate was concentrated under reduced pressure. The residue was purified by silica gel column chromatography, eluted with PE/THE (1:2) to afford (2S)-2-amino-3-(2-fluoro-4-{1-[1-(oxetan-3-yl)piperidin-4-yl]indazol-6-yl}phenyl)propanenitrile (190 mg, 52% yield, 95% purity). LCMS (ES, m/z): $[M+H]^+$: 420.

Synthesis of tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-hydroxyethyl]carbamate

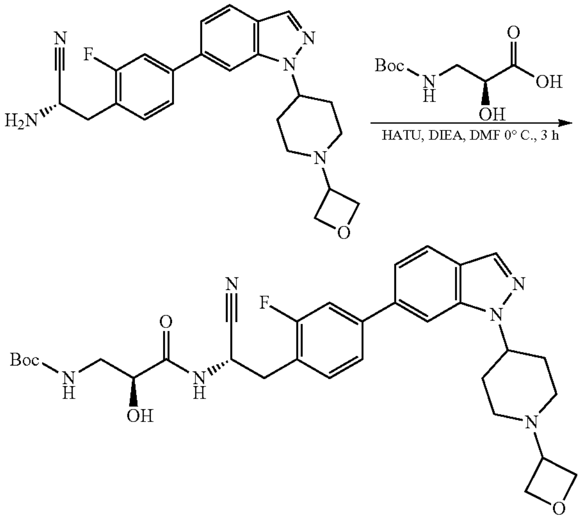

To a stirred solution of (2S)-2-amino-3-(2-fluoro-4-{1-[1-(oxetan-3-yl)piperidin-4-yl]indazol-6-yl}phenyl)propanenitrile (90 mg, 0.21 mmol, 1.0 equiv) and (2S)-3-[(tert-butoxycarbonyl)amino]-2-hydroxypropanoic acid (66 mg, 0.32 mmol, 1.5 equiv), DIEA (83 mg, 0.65 mmol, 3.0 equiv) in DMF (3 mL) was added HATU (97 mg, 0.26 mmol, 1.2 equiv) in portions at room temperature. The reaction was quenched with water (20 mL), the resulting mixture was extracted with EtOAc (3×20 mL). The combined organic layer was washed with brine (3×20 mL), dried over anhydrous $Na_2SO_4$. After filtration, the filtrate was concentrated under reduced pressure. The residue was purified by silica gel column chromatography, eluted with PE/THE (1:1) to afford tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-hydroxyethyl]carbamate (100 mg, 77% yield, 95% purity). LCMS (ES, m/z): $[M+H]^+$: 607.

Synthesis of (2S)-3-amino-N-[(1S)-1-cyano-2-(2-fluoro-4-{1-[1-(oxetan-3-yl)piperidin-4-yl]indazol-6-yl}phenyl)ethyl]-2-hydroxypropanamide

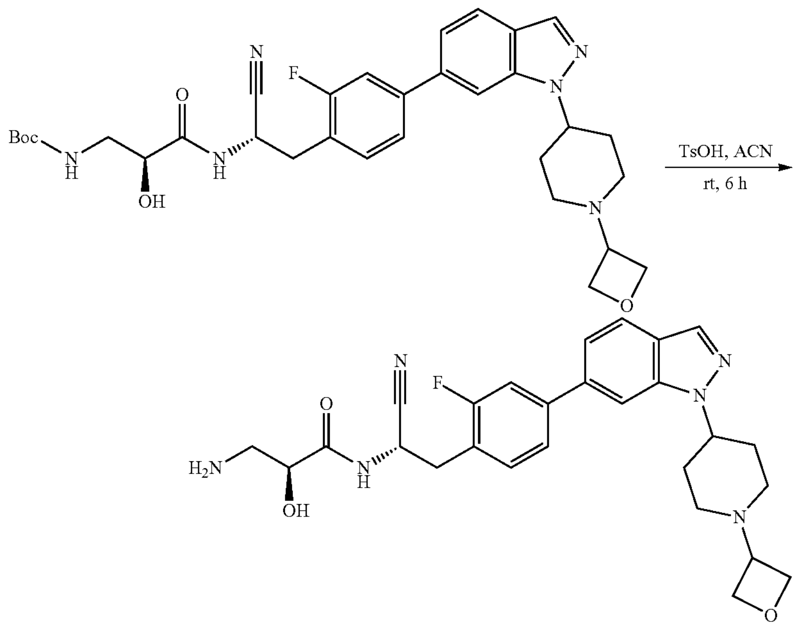

Into a 8 mL vial were added tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-hydroxyethyl]carbamate (100 mg, 0.16 mmol, 1.0 equiv) MeCN (3 mL) and TsOH (85 mg, 0.50 mmol, 3.0 equiv) at room temperature. The resulting mixture was stirred at room temperature for 6 h. The mixture was basified to pH 8 with saturated $NaHCO_3$ (aq.). The resulting mixture was extracted with EtOAc (3×20 mL). The combined organic layer was washed with brine (30 mL), dried over anhydrous $Na_2SO_4$. After filtration, the filtrate was concentrated under reduced pressure. This resulted in (2S)-3-amino-N-[(1S)-1-cyano-2-(2-fluoro-4-{1-[1-(oxetan-3-yl)piperidin-4-yl]indazol-6-yl}phenyl)ethyl]-2-hydroxypropanamide (80 mg). The crude product was used in the next step directly without further purification. LCMS (ES, m/z): $[M+H]^+$: 507.

Synthesis of (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-hydroxypropanamide

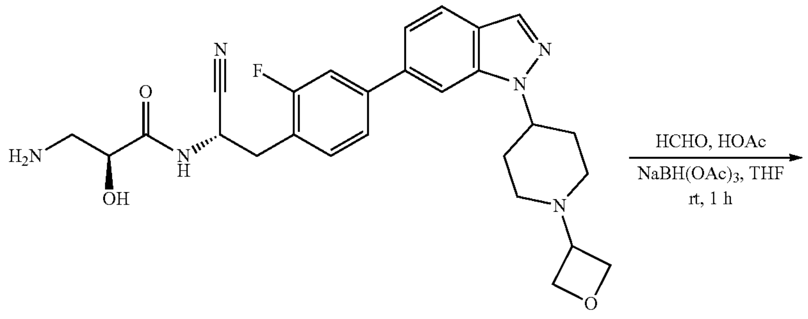

-continued

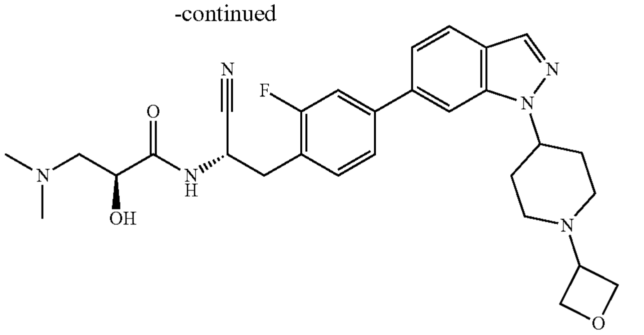

A solution of (2S)-3-amino-N-[(1S)-1-cyano-2-(2-fluoro-4-{1-[1-(oxetan-3-yl)piperidin-4-yl]indazol-6-yl}phenyl)ethyl]-2-hydroxypropanamide (80 mg, 0.16 mmol, 1.0 equiv) and HOAc (0.05 mL), HCHO (124 mg, 1.58 mmol, 10 equiv, 38% in $H_2O$), $NaBH(OAc)_3$ (66 mg, 0.32 mmol, 2.0 equiv) in THE (4.00 mL) was stirred at room temperature for 1 h. The reaction solution was purified by reversed-phase flash chromatography with the following conditions: column, C18 silica gel-120 g; mobile phase, MeCN in Water (0.1% $NH_3 \cdot H_2O$), 10% to 50% gradient in 10 min; detector, UV 254 nm. This resulted in (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-hydroxypropanamide (15.3 mg, 18% yield, 98% purity).

LCMS (ES, m/z): $[M+H]^+$: 535.2

$^1H$ NMR (400 MHz, DMSO-$d_6$) δ 8.82 (br, 1H), 8.10 (s, 1H), 8.07 (s, 1H), 7.82 (d, J=8.4 Hz, 1H), 7.69 (dd, J=11.6, 1.9 Hz, 1H), 7.64 (dd, J=7.9, 1.8 Hz, 1H), 7.50-7.45 (m, 2H), 5.63 (br, 1H), 5.09 (t, J=8.0 Hz, 1H), 4.86-4.76 (m, 1H), 4.58 (t, J=6.5 Hz, 2H), 4.48 (t, J=6.1 Hz, 2H), 4.00 (dd, J=7.7, 4.0 Hz, 1H), 3.51-3.46 (m, 1H), 3.29-3.16 (m, 2H), 2.86 (d, J=10.4 Hz, 2H), 2.35-2.22 (m, 2H), 2.18-2.03 (m, 10H), 1.94 (d, J=11.7 Hz, 2H).

Example 123: Synthesis of Compound 288: (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-methoxypropanamide

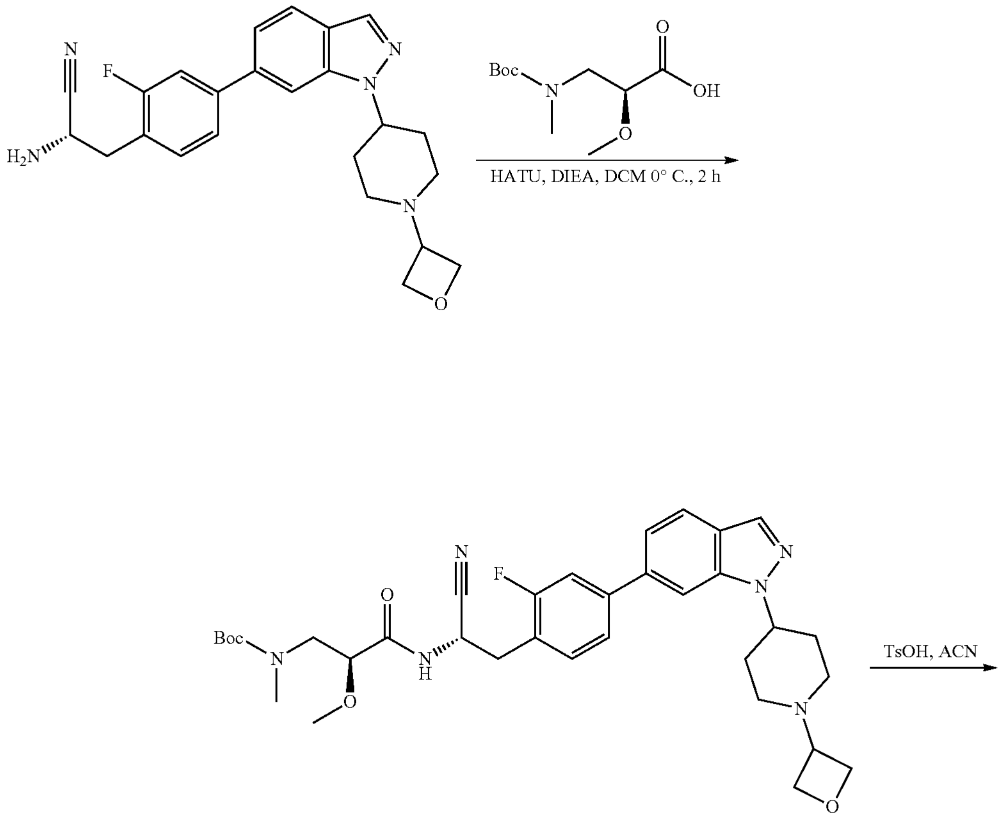

-continued

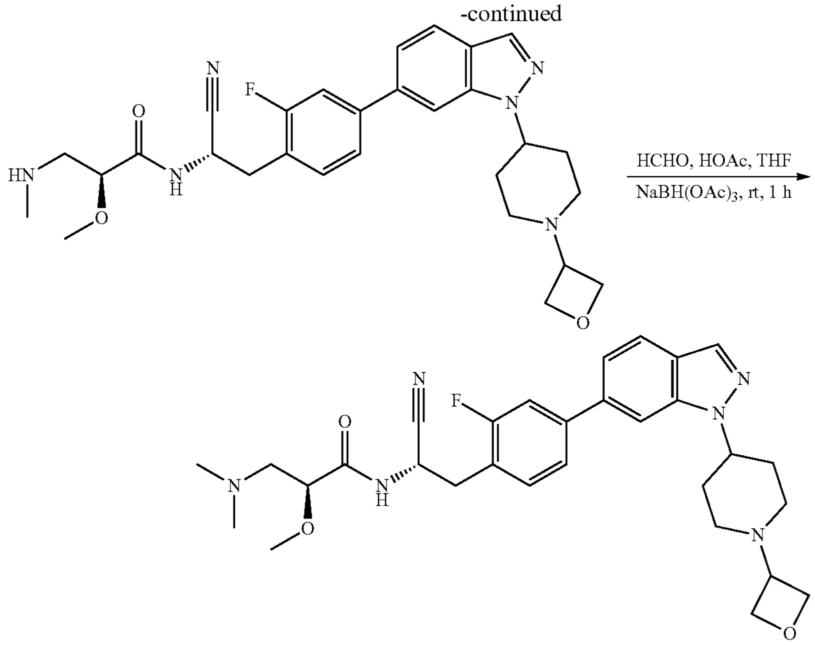

Compound 288

Synthesis of tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-methoxyethyl]-N-methylcarbamate

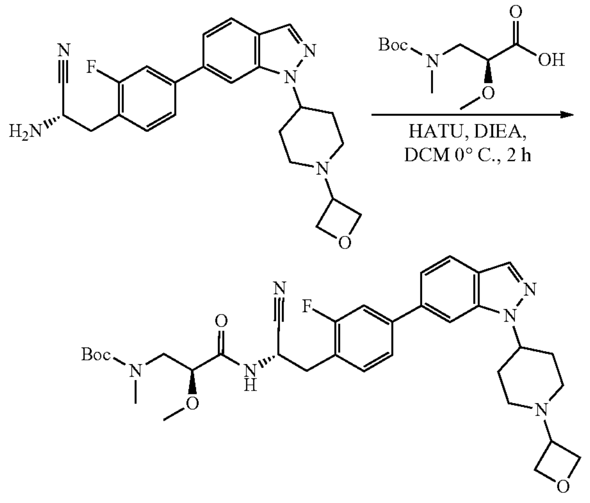

To a stirred solution of (2S)-2-amino-3-(2-fluoro-4-{1-[1-(oxetan-3-yl)piperidin-4-yl]indazol-6-yl}phenyl)propanenitrile (95 mg, 0.22 mmol, 1.0 equiv) and (2S)-3-[(tert-butoxycarbonyl)(methyl)amino]-2-methoxypropanoic acid (79 mg, 0.33 mmol, 1.5 equiv), DIEA (87 mg, 0.67 mmol, 3.0 equiv) in DCM (10 mL) was added HATU (103 mg, 0.27 mmol, 1.2 equiv) at 0° C. The resulting mixture was stirred at 0° C. for 2 h. The reaction was concentrated the residue was purified by silica gel column chromatography, eluted with PE/THE (1:1) to afford tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-methoxyethyl]-N-methylcarbamate (110 mg, 76% yield, 85% purity). LCMS (ES, m z): $[M+H]^+$: 635.

Synthesis of (2S)-3-amino-N-[(1S)-1-cyano-2-(2-fluoro-4-{1-[1-(oxetan-3-yl)piperidin-4-yl]indazol-6-yl}phenyl)ethyl]-2-methoxypropanamide

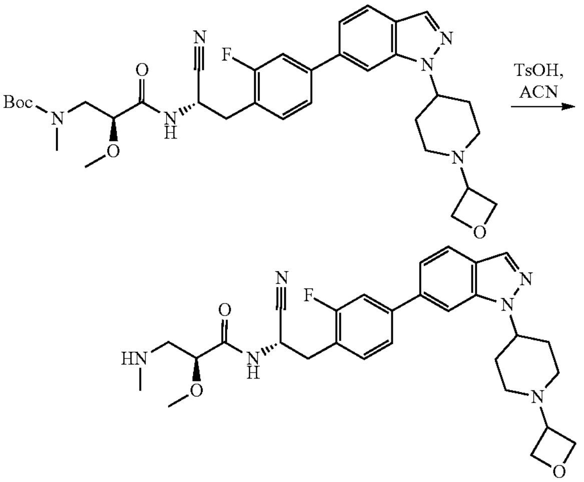

Into a 25 mL round-bottom flask were added tert-butyl N-[(2S)-2-{[(1S)-1-cyano-2-(2-fluoro-4-{1-[1-(oxetan-3-yl)piperidin-4-yl]indazol-6-yl}phenyl)ethyl]carbamoyl}-2-methoxyethyl]carbamate (110 mg, 0.17 mmol, 1.0 equiv), MeCN (3 mL) and TsOH (91 mg, 0.53 mmol, 3.0 equiv) at room temperature. The resulting mixture was stirred at room temperature for 6 h. The mixture was basified to pH 8 with saturated $NaHCO_3$ (aq.). The resulting mixture was extracted with EtOAc (3x30 mL). The combined organic layer was washed with brine (3×30 mL), dried over anhydrous $Na_2SO_4$. After filtration, the filtrate was concentrated under reduced pressure. This resulted in (2S)-3-amino-N-[(1S)-1-cyano-2-(2-fluoro-4-{1-[1-(oxetan-3-yl)piperidin-4-yl]indazol-6-yl}phenyl)ethyl]-2-methoxypropanamide (90 mg). The crude product was used in the next step directly without further purification. LCMS (ES, m z): [M+H]$^+$: 535.

Synthesis of (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-methoxypropanamide

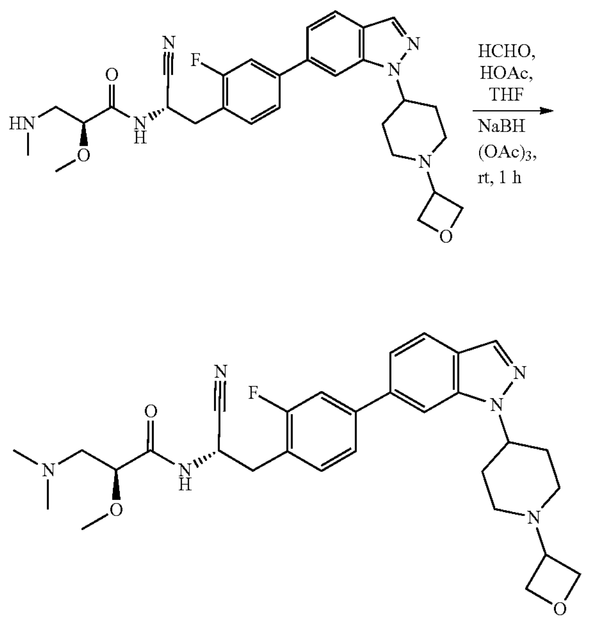

To a stirred solution of (2S)—N-[(1S)-1-cyano-2-(2-fluoro-4-{1-[1-(oxetan-3-yl)piperidin-4-yl]indazol-6-yl}phenyl)ethyl]-2-methoxy-3-(methylamino)propanamide (100 mg, 0.18 mmol, 1.0 equiv) and Formaldehyde solution (56 mg, 1.87 mmol, 10.0 equiv) in THE (5 mL) was added HOAc (1 mg, 0.01 mmol, 0.1 equiv) and $NaBH(OAc)_3$ (79 mg, 0.37 mmol, 2.0 equiv) at room temperature. The resulting mixture was stirred at room temperature for 1 h. The residue was purified by reversed-phase flash chromatography with the following conditions: column, C18 silica gel-120 g; mobile phase, MeCN in Water (0.1% $NH_3$·$H_2O$), 10% to 45% gradient in 12 min; detector, UV 254 nm. This resulted in (2S)—N-[(1S)-1-cyano-2-(2-fluoro-4-{1-[1-(oxetan-3-yl)piperidin-4-yl]indazol-6-yl}phenyl)ethyl]-3-(dimethylamino)-2-methoxypropanamide (20 mg, 20% yield, 99% purity).

LCMS (ES, m z): [M+H]$^+$: 549.3

$^1$H NMR (400 MHz, DMSO-$d_6$): δ 8.93 (d, J=7.8 Hz, 1H), 8.11 (s, 1H), 8.07 (s, 1H), 7.82 (d, J=8.4 Hz, 1H), 7.69 (dd, J=11.6, 1.8 Hz, 1H), 7.64 (dd, J=8.0, 1.9 Hz, 1H), 7.56-7.44 (m, 2H), 5.14 (q, J=7.8 Hz, 1H), 4.86-4.76 (m, 1H), 4.58 (t, J=6.5 Hz, 2H), 4.48 (t, J=6.1 Hz, 2H), 3.73 (dd, J=7.1, 4.2 Hz, 1H), 3.52-3.45 (m, 1H), 3.30-3.16 (m, 5H), 2.87 (d, J=10.5 Hz, 2H), 2.36-2.24 (m, 2H), 2.23-2.02 (m, 10H), 1.95 (d, J=11.3 Hz, 2H).

Example 124: Synthesis of Compound 291B and 291D: N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide and (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide

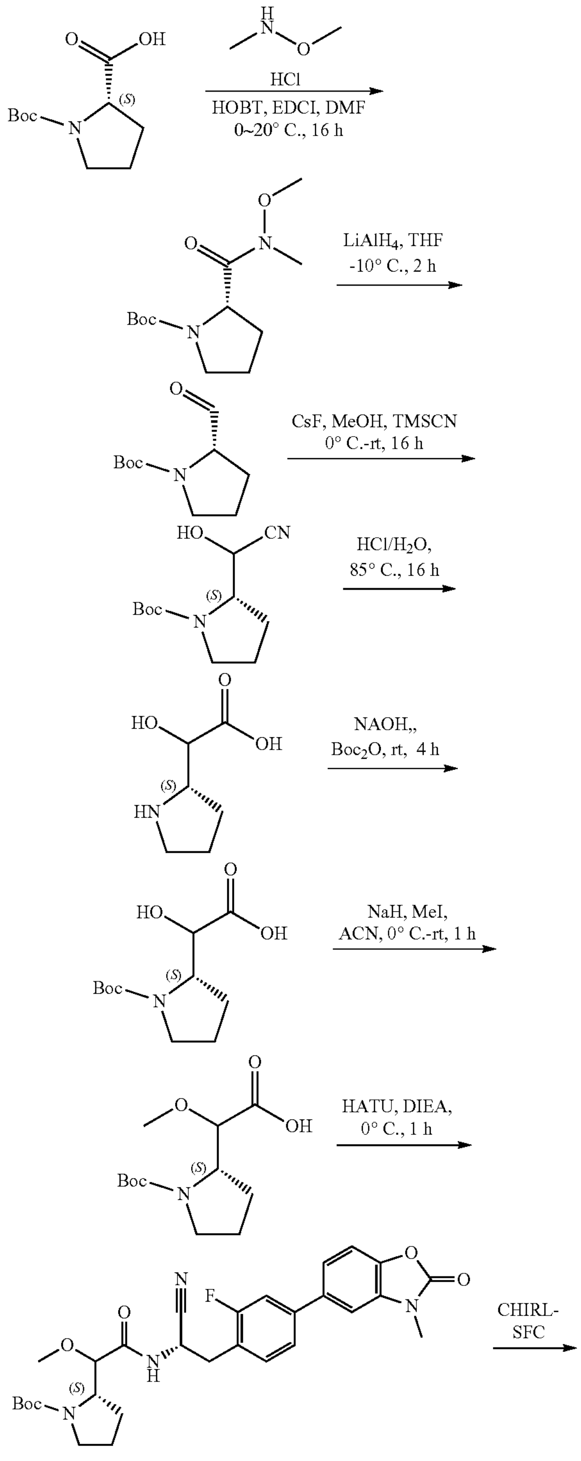

-continued
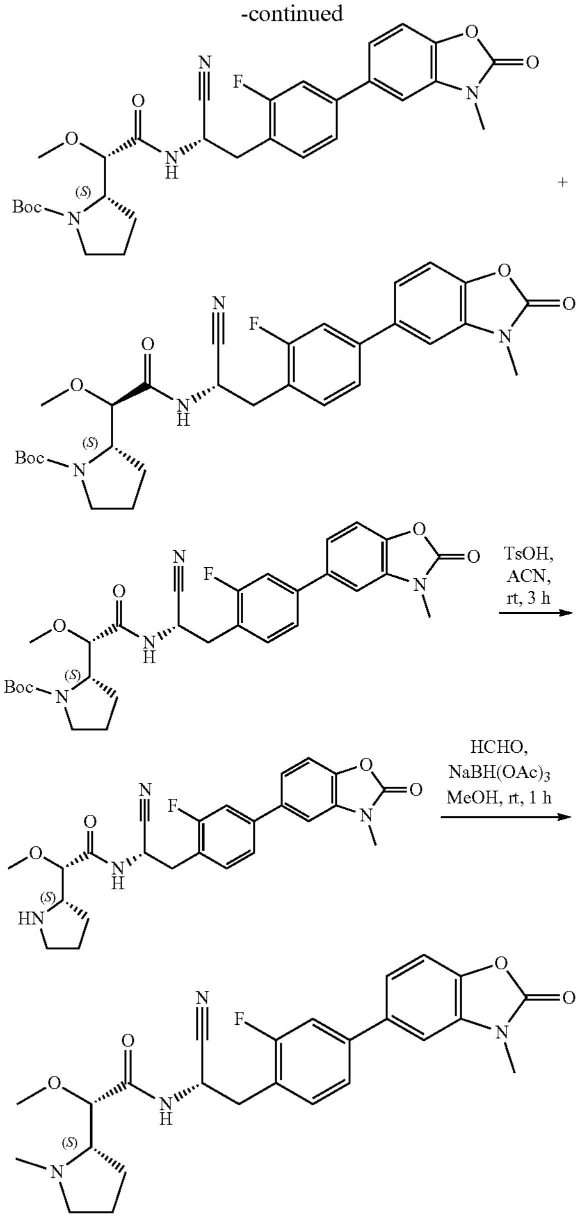
Assumed
Compound 291B
-continued
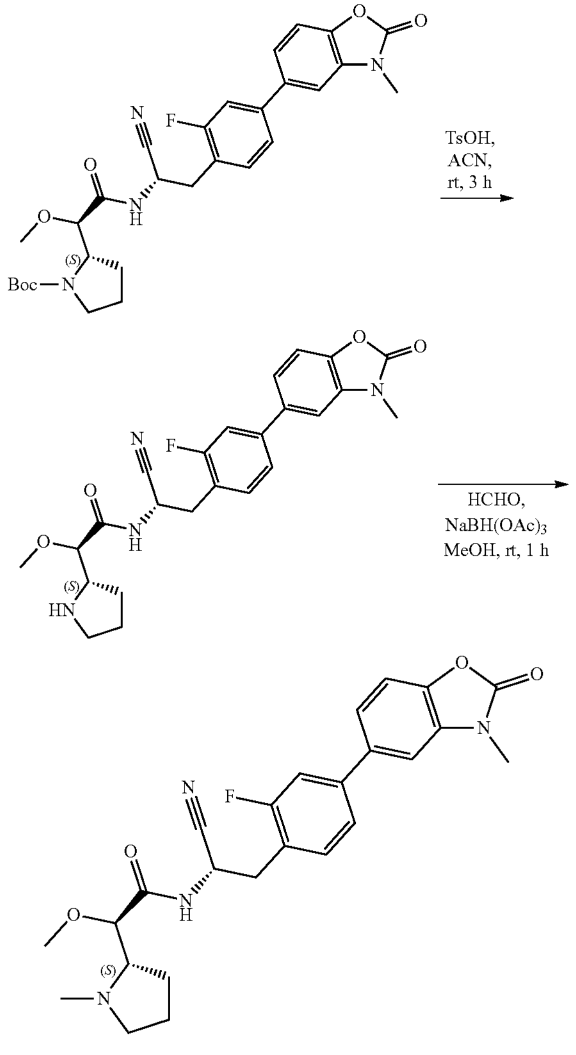
Assumed
Compound 291D
Synthesis of tert-butyl (S)-2-(methoxy(methyl)carbamoyl)pyrrolidine-1-carboxylate
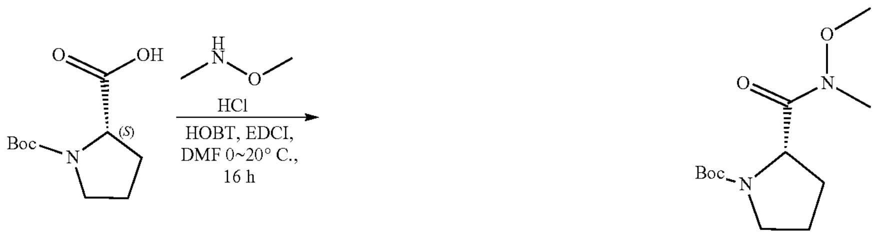

-continued

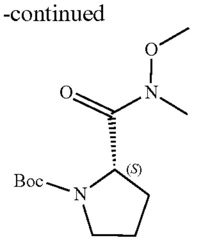

To a stirred solution of (2S)-1-(tert-butoxycarbonyl)pyrrolidine-2-carboxylic acid (15 g, 69.69 mmol, 1.0 equiv) and N,O-dimethylhydroxylamine hydrochloride (7.48 g, 76.65 mmol, 1.1 equiv), DIEA (45 g, 348.43 mmol, 5.0 equiv) in DMF (200 mL) was added HOBT (14.1 g, 104.53 mmol, 1.5 equiv) at 0° C. To the above mixture was added (3-[[(ethylimino)methylidene]amino]propyl)dimethylamine hydrochloride (20 g, 104.53 mmol, 1.5 equiv) in portions at 0° C. The resulting mixture was stirred at room temperature for 16 h. Desired product could be detected by LCMS. The resulting mixture was diluted with water (1000 mL), extracted with EtOAc (3x500 mL). The combined organic layer was washed with brine (3x200 mL), dried over anhydrous, $Na_2SO_4$. After filtration, the filtrate was concentrated under reduced pressure. The residue was purified by silica gel column chromatography, eluted with PE/EA (5:1) to afford tert-butyl (S)-2-(methoxy(methyl)carbamoyl)pyrrolidine-1-carboxylate (15 g, 83%) as colorless liquid. LCMS (ES) $[M+H]^+$ m/z: 259.

Synthesis of tert-butyl (S)-2-formylpyrrolidine-1-carboxylate

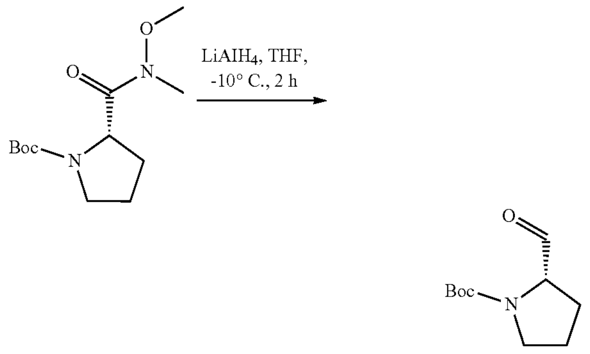

A solution of tert-butyl (S)-2-(methoxy(methyl)carbamoyl)pyrrolidine-1-carboxylate (9 g, 34.84 mmol, 1.0 equiv) in THF (100 mL) was stirred at room temperature under nitrogen atmosphere. To the above mixture was added Lithium aluminum hydride (2.0 M in TIF)(21 mL, 41.80 mmol, 1.2 equiv) dropwise at −10° C. The resulting mixture was stirred at −10° C. for additional 2 h. Desired product could be detected by LCMS. The resulting mixture was diluted with THF (200 mL). The reaction was quenched with $Na_2SO_4.10H_2O$ at 0° C. The resulting mixture was filtered, the filter cake was washed with THF (3x50 mL). The combined organic phase was dried over anhydrous $Na_2SO_4$, filtered and the filtrate was concentrated under reduced pressure to afford tert-butyl (S)-2-formylpyrrolidine-1-carboxylate (8 g, 92%) as a colorless liquid and used to the next step without further purification. LCMS (ES) $[M+1]^+$ m/z: 200.

Synthesis of tert-butyl (2S)-2-(cyano(hydroxy)methyl)pyrrolidine-1-carboxylate

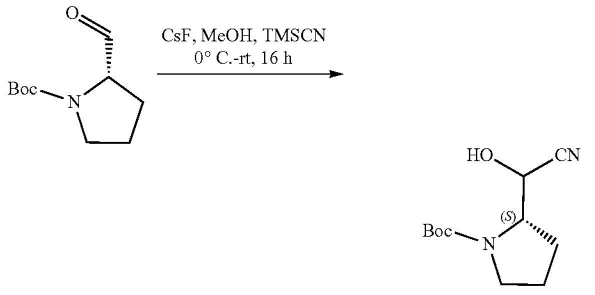

Into a 250 mL 3-necked round-bottom flask were added tert-butyl (S)-2-formylpyrrolidine-1-carboxylate (7 g, 35.13 mmol, 1.0 equiv), CsF (2.67 g, 17.56 mmol, 0.5 equiv) and MeOH (100 mL) at room temperature. To the above mixture was added trimethylsilanecarbonitrile (4.18 g, 42.15 mmol, 1.2 equiv) in portions at 0° C. under nitrogen atmosphere. The resulting mixture was stirred at room temperature for 16 h. Desired product could be detected by LCMS. The resulting mixture was diluted with water (500 mL), extracted with EtOAc (3x500 mL). The combined organic phase was dried over anhydrous $Na_2SO_4$. After filtration, the filtrate was concentrated under reduced pressure. The residue was purified by silica gel column chromatography, eluted with PE/EA (11:1) to afford tert-butyl (2S)-2-(cyano(hydroxy)methyl)pyrrolidine-1-carboxylate (5 g, 63%). LCMS (ES) $[M+H]^+$ m/z: 227.

Synthesis of 2-hydroxy-2-((S)-pyrrolidin-2-yl)acetic acidis

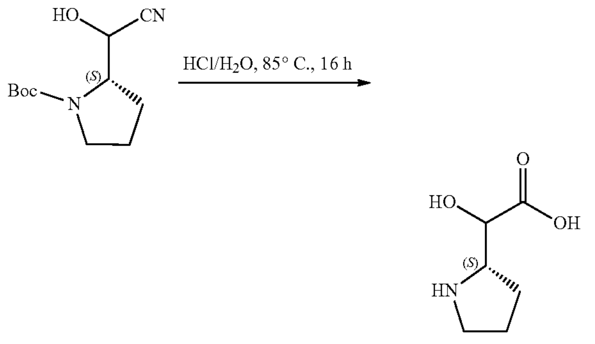

Into a 100 mL round-bottom flask were added tert-butyl (2S)-2-(cyano(hydroxy)methyl)pyrrolidine-1-carboxylate (3 g, 15.05 mmol, 1.0 equiv), $H_2O$ (15 mL) and HCl (c)(15 mL) at room temperature. The resulting mixture was stirred at 85° C. for 16 h. Desired product could be detected by LCMS. The reaction was cooled to room temperature, basified to pH 14 with NaOH. The mixture was used in the next step directly without purification. LCMS (ES) $[M+H]^+$ m/z: 146.

Synthesis of 2-((S)-1-(tert-butoxycarbonyl)pyrrolidin-2-yl)-2-hydroxyacetic acid

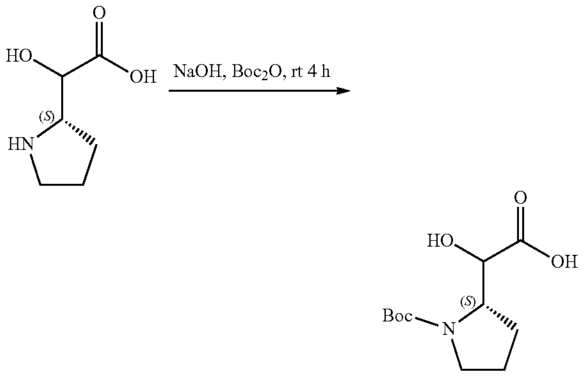

Into a 100 mL round-bottom flask were added THE (30 mL) and hydroxy((2S)-pyrrolidin-2-yl)acetic acid (reaction mixture of last step) at room temperature, this was followed by the addition of di-tert-butyl dicarbonate (9 g, 41.33 mmol, 2.0 equiv) in portions at 0° C. The resulting mixture was stirred at room temperature for 3 h. Desired product could be detected by LCMS. The resulting mixture was diluted with water (200 mL), extracted with EtOAc (3×100 mL). The aqueous phase was acidified to pH 2 with HCl (aq.1 M), extracted with $CH_2Cl_2$:MeOH=10:1 (5×100 mL). The combined organic layer was washed with DCM (3×50 mL), dried over anhydrous $Na_2SO_4$. After filtration, the filtrate was concentrated under reduced pressure. This resulted in 2-((S)-1-(tert-butoxycarbonyl)pyrrolidin-2-yl)-2-hydroxyacetic acid (1.2 g, 23% yield). LCMS (ES) $[M+H]^+$ m/z: 246.

Synthesis of 2-((S)-1-(tert-butoxycarbonyl)pyrrolidin-2-yl)-2-methoxyacetic acid

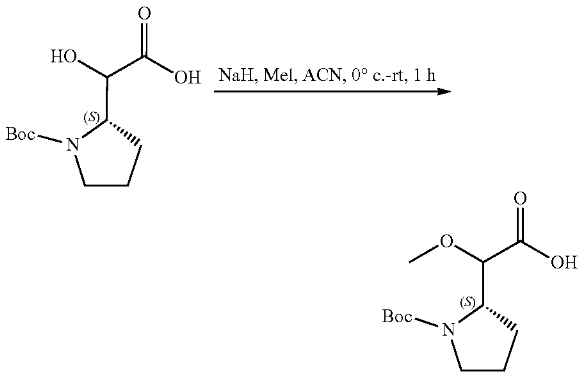

Into a 40 mL vial were added 2-((S)-1-(tert-butoxycarbonyl)pyrrolidin-2-yl)-2-hydroxyacetic acid (500 mg, 2.03 mmol, 1.0 equiv) and ACN (10 mL) at room temperature. To the above mixture was added NaH (60% in mineral oil)(204 mg, 5.09 mmol, 2.5 equiv) in portions at 0° C. The resulting mixture was stirred at 0° C. for 30 min. To the above mixture was added $CH_3I$ (0.87 g, 6.11 mmol, 3.0 equiv) dropwise at 0° C. The resulting mixture was stirred at room temperature for 2 h. Desired product could be detected by LCMS. The resulting mixture was quenched with water (100 mL). The aqueous layer was extracted with EtOAc (3×100 mL). The aqueous phase was acidified to pH 2 with citric acid, extracted with $CH_2Cl_2$ (3×100 mL). The combined organic layer was dried over anhydrous $Na_2SO_4$. After filtration, the filtrate was concentrated under reduced pressure. This resulted in 2-((S)-1-(tert-butoxycarbonyl)pyrrolidin-2-yl)-2-methoxyacetic acid (400 mg). LCMS (ES) $[M+H]^+$ m/z: 260.

Synthesis of tert-butyl (2S)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate

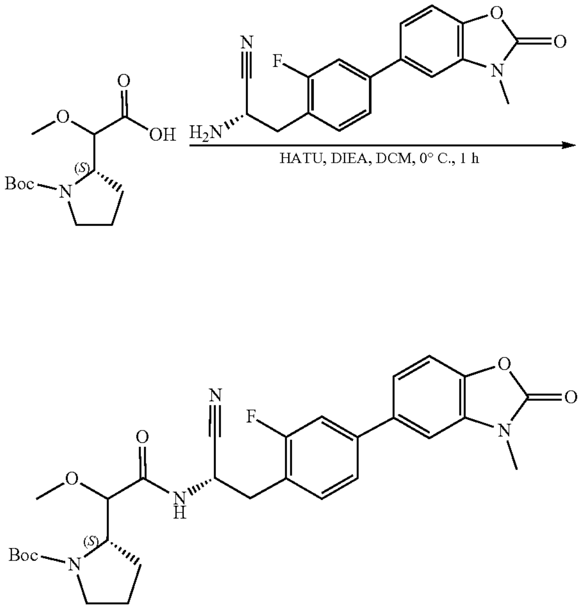

To a stirred solution of 2-((S)-1-(tert-butoxycarbonyl)pyrrolidin-2-yl)-2-methoxyacetic acid (300 mg, 1.15 mmol, 1.0 equiv), (2S)-2-amino-3-[2-fluoro-4-(3-methyl-2-oxo-1,3-benzoxazol-5-yl)phenyl]propanenitrile (360 mg, 1.15 mmol, 1.0 equiv) and DIEA (448 mg, 3.47 mmol, 3.0 equiv) in DCM (5 mL) was added HATU (530 mg, 1.38 mmol, 1.2 equiv) at 0° C. The resulting mixture was stirred at 0° C. for 1 h. Desired product could be detected by LCMS. Concentrated to remove the solvent, the residue was purified by silica gel column chromatography, eluted with PE/EA (1:1) to afford tert-butyl (2S)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (500 mg, 78% yield). LCMS (ES) $[M+H]^+$ m/z: 553.

Synthesis of tert-butyl (S)-2-((S)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate and tert-butyl (S)-2-((R)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate

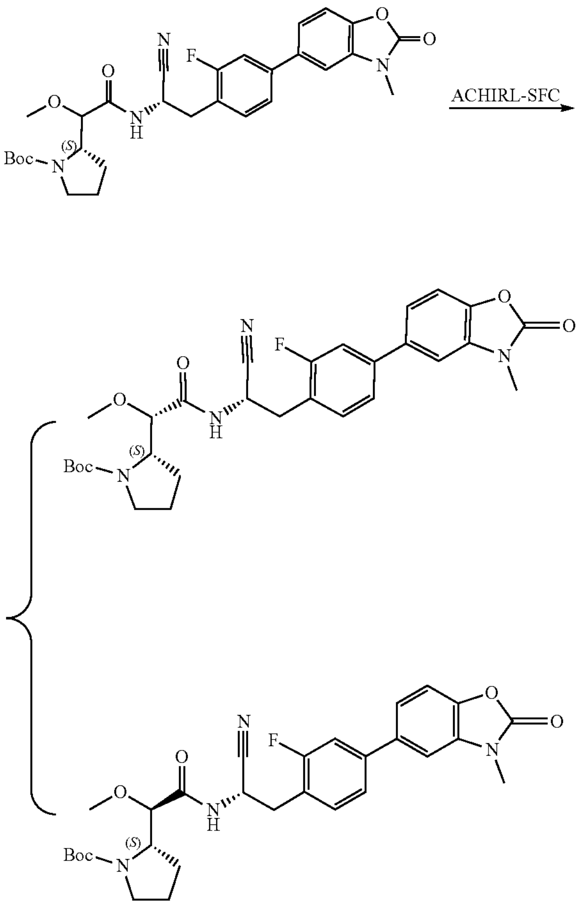

Tert-butyl (2S)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (500 mg) was purified by Achiral-SFC with the following conditions: Column: DAICEL DCpak P4VP, 3*25 cm, 5 m; Mobile Phase A: $CO_2$, Mobile Phase B: MeOH: EtOH: Hex=1: 1: 1(20 $mMNH_3$); Flow rate: 90 mL/min; Gradient: isocratic 30% B; Column Temperature(° C.): 35; Back Pressure(bar): 100; Wave Length: 220 nm; RT1(min): 4.89; RT2(min): 5.52; Sample Solvent: MeOH: DCM=1: 1-HPLC; Injection Volume: 0.6 mL; Number Of Runs: 16, to afford tert-butyl (S)-2-((S)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (120 mg, 26%) and tert-butyl (S)-2-((R)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (210 mg, 46% yield). LCMS (ES) $[M+H]^+$ m/z: 553.

Synthesis of (S)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide

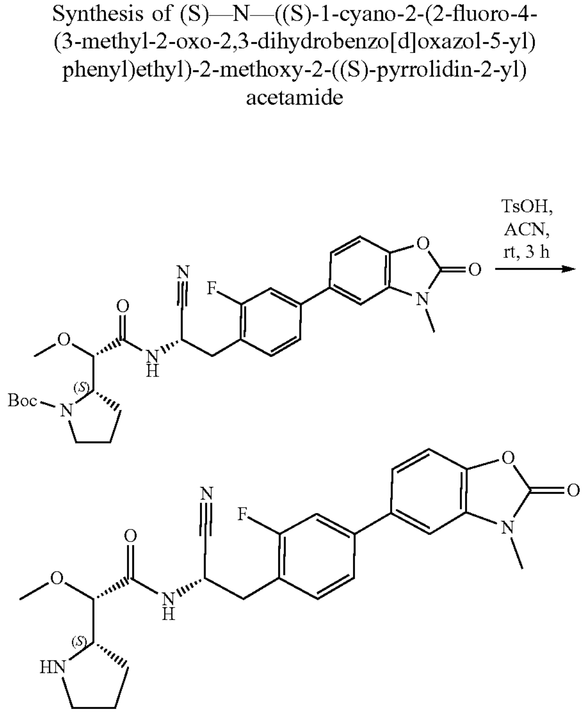

A mixture of tert-butyl (S)-2-((S)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (120 mg, 0.21 mmol, 1.0 equiv) and 4-methylbenzene-1-sulfonic acid hydrate (123 mg, 6.50 mmol, 3.0 equiv) in ACN (10 mL) was stirred at room temperature for 3 h. Desired product could be detected by LCMS. The mixture was basified to pH 9 with saturated $NaHCO_3$ (aq.). The aqueous layer was extracted with $CH_2Cl_2$ (3×50 mL). The combined organic layer was dried over anhydrous $Na_2SO_4$. After filtration, the filtrate was concentrated under reduced pressure. This resulted in (S)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide (100 mg crude). LCMS (ES) $[M+H]^+$ m/z: 453.

Synthesis of N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide

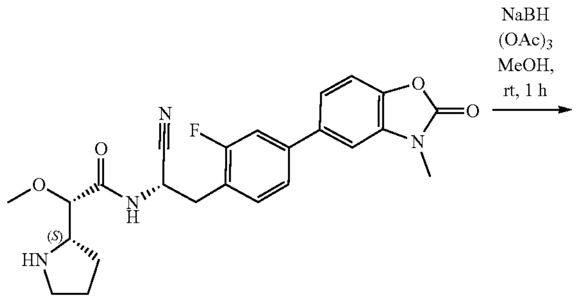

-continued

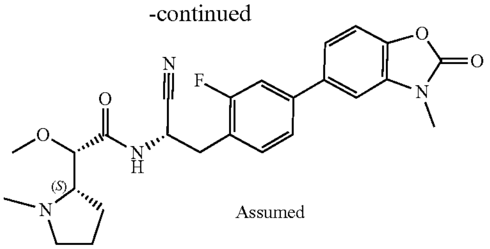

Assumed

Compound 291B

Into a 40 mL vial were added (S)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide (90 mg, 0.20 mmol, 1.0 equiv) and MeOH (3 mL) at room temperature. To the above mixture was added NaBH$(OAc)_3$ (126 mg, 0.59 mmol, 3.0 equiv), HCHO (60 mg, 1.99 mmol, 10.0 equiv, 30% in $H_2O$) in portions at room temperature. The resulting mixture was stirred at room temperature for 1 h. Desired product could be detected by LCMS. The reaction solution was purified by reversed-phase flash chromatography with the following conditions: column, C18 silica gel-120 g; mobile phase, MeCN in Water (0.1% $NH_3 \cdot H_2O$), 30% to 50% gradient in 12 min; detector, UV 220 nm. The fraction of the target was freezing dried to afford N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide (20 mg, 22% yield). LCMS (ES) $[M+H]^+$ m/z: 467.1

$^1H$ NMR (400 MHz, DMSO-$d_6$) δ 8.95 (d, J=8.3 Hz, 1H), 7.66 (s, 1H), 7.63-7.54 (m, 2H), 7.49 (dd, J=14.6, 7.9 Hz, 2H), 7.40 (d, J=8.3 Hz, 1H), 5.11 (q, J=8.0 Hz, 1H), 3.47 (d, J=5.3 Hz, 1H), 3.41 (s, 3H), 3.30-3.18 (m, 2H), 3.16 (s, 3H), 2.90-2.83 (m, 1H), 2.50-2.49 (m, 1H), 2.28 (s, 3H), 2.12 (q, J=8.3 Hz, 1H), 1.73-1.39 (m, 4H).

Synthesis of (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide

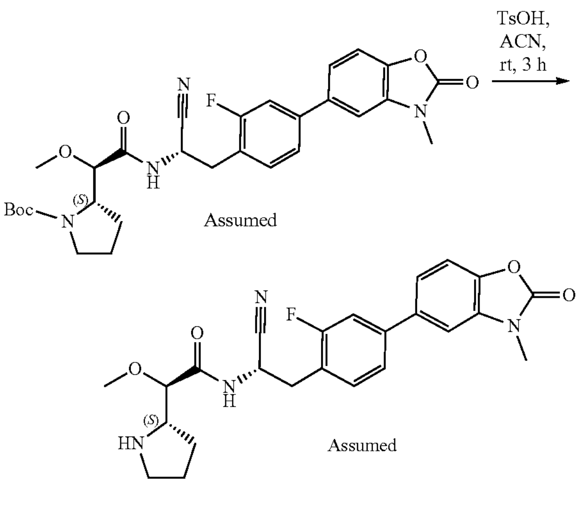

A mixture of tert-butyl (S)-2-((R)-2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (200 mg, 0.32 mmol, 1.0 equiv) and 4-methylbenzene-1-sulfonic acid hydrate (165 mg, 0.96 mmol, 3.0 equiv) in ACN (10 mL) was stirred at room temperature for 3 h. Desired product could be detected by LCMS. The mixture was basified to pH 9 with saturated $NaHCO_3$ (aq.). The aqueous layer was extracted with $CH_2Cl_2$ (3×50 mL). The combined organic layer was dried over anhydrous $Na_2SO_4$. After filtration, the filtrate was concentrated under reduced pressure. This resulted in (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide (150 mg, crude). LCMS (ES) $[M+H]^+$ m/z: 453.

Synthesis of (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide

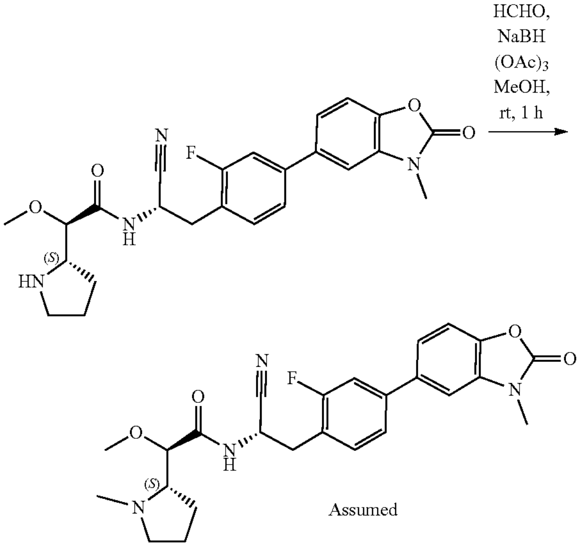

compound 291D

Into a 40 mL vial were added (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-pyrrolidin-2-yl)acetamide (130 mg, 0.28 mmol, 1.0 equiv, crude) and MeOH (5 mL) at room temperature. To the above mixture was added $NaBH(OAc)_3$ (181 mg, 0.86 mmol, 3.0 equiv), HCHO (286 mg, 2.80 mmol, 10 equiv, 30% in $H_2O$) in portions at room temperature. The resulting mixture was stirred at room temperature for additional 1 h. Desired product could be detected by LCMS. The reaction solution was purified by reversed-phase flash chromatography with the following conditions: column, C18 silica gel-120 g; mobile phase, MeCN in Water (0.1% $NH_3 \cdot H_2O$), 30% to 50% gradient in 12 min; detector, UV 220 nm. The fraction of the target was freezing dried to afford (R)—N—((S)-1-cyano-2-(2-fluoro-4-(3-methyl-2-oxo-2,3-dihydrobenzo[d]oxazol-5-yl)phenyl)ethyl)-2-methoxy-2-((S)-1-methylpyrrolidin-2-yl)acetamide (40 mg, 32% yield).

LCMS (ES) $[M+H]^+$ m/z: 467.1

$^1H$ NMR (400 MHz, DMSO-$d_6$) δ 8.84 (d, J=8.5 Hz, 1H), 7.64 (d, J=1.8 Hz, 1H), 7.61-7.51 (m, 2H), 7.51-7.44 (m, 2H), 7.40 (d, J=8.3 Hz, 1H), 5.13 (q, J=8.3 Hz, 1H), 3.64 (d,

J=3.5 Hz, 1H), 3.41 (s, 3H), 3.31-3.16 (m, 5H), 2.88-2.84 (m, 1H), 2.42-2.33 (m, 1H), 2.21 (s, 3H), 2.05 (q, J=8.6 Hz, 1H), 1.62-1.44 (m, 3H), 1.31 (t, J=9.6 Hz, 1H).

Example 125: Synthesis of Compound 291A and 291C: (R)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide and (S)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide

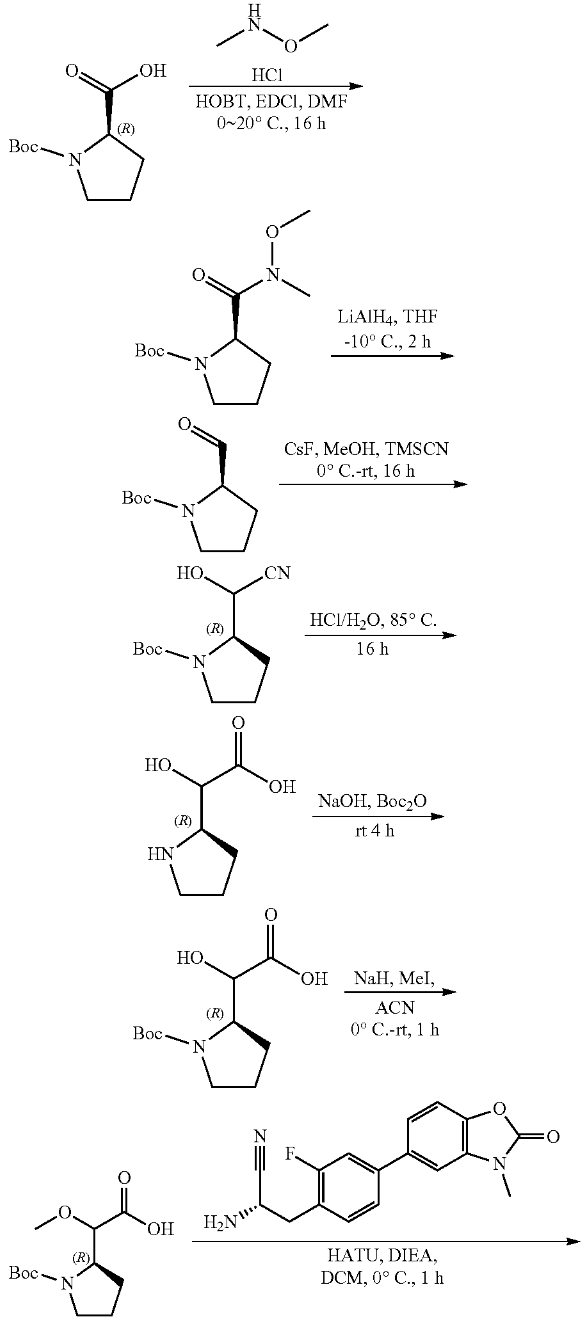

-continued

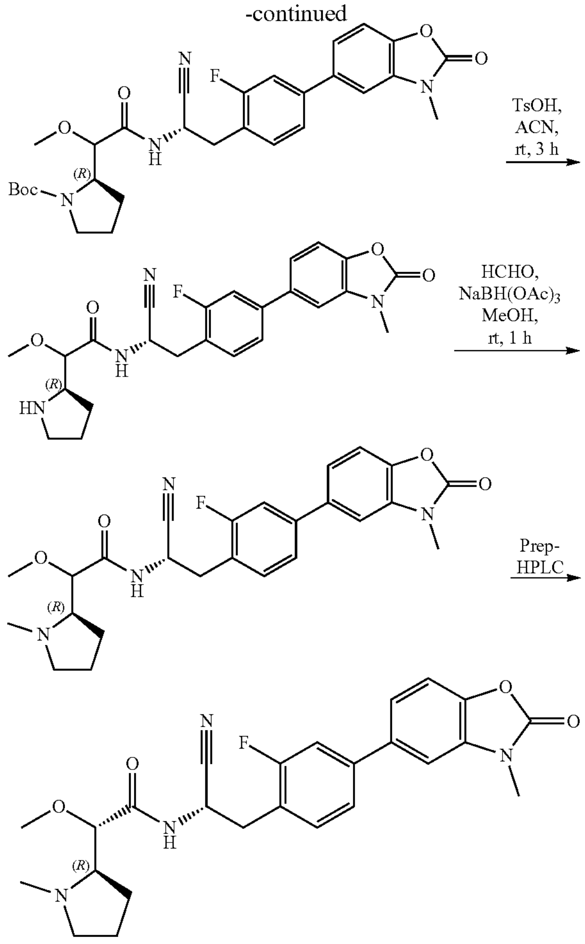

Assumed
Compound 291A

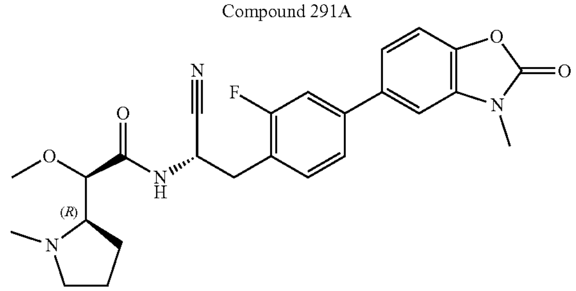

Assumed
Compound 291C

Synthesis of tert-butyl (R)-2-(methoxy(methyl)carbamoyl)pyrrolidine-1-carboxylate

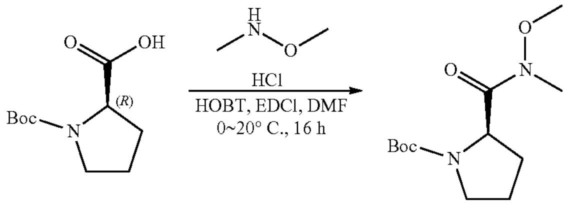

To a stirred solution of (tert-butoxycarbonyl)-D-proline (15 g, 69.69 mmol, 1.0 equiv) and N,O-dimethylhydroxylamine hydrochloride (7.48 g, 76.65 mmol, 1.1 equiv), DIEA (45 g, 348.43 mmol, 5.0 equiv) in DMF (200 mL) was added HOBT (14.1 g, 104.53 mmol, 1.5 equiv) at 0° C. To the above mixture was added (3-[[(ethylimino)methylidene] amino]propyl)dimethylamine hydrochloride (20 g, 104.53 mmol, 1.5 equiv) in portions at 0° C. The resulting mixture was stirred at room temperature for 16 h. Desired product could be detected by LCMS. The resulting mixture was diluted with water (1000 mL), extracted with EtOAc (3×500 mL). The combined organic layer was washed with brine (3×200 mL), dried over anhydrous, $Na_2SO_4$. After filtration, the filtrate was concentrated under reduced pressure. The residue was purified by silica gel column chromatography, eluted with PE/EA (5:1) to afford tert-butyl (R)-2-(methoxy (methyl)carbamoyl)pyrrolidine-1-carboxylate (15 g, 83%) as colorless liquid. LCMS (ES) $[M+H]^+$ m/z: 259.

Synthesis of tert-butyl (S)-2-formylpyrrolidine-1-carboxylate

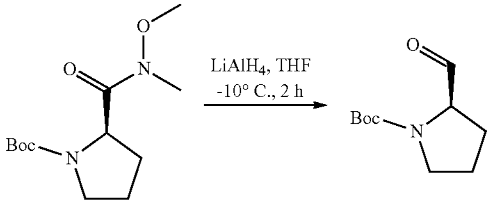 [SMILES: CON(C)C(=O)[C@H]1CCCN1C(=O)OC(C)(C)C ; "LiAlH4, THF-10° C., 2 h" ; CC(C)(C)OC(=O)N1CCC[C@@H]1C=O]

To a solution of tert-butyl (R)-2-(methoxy(methyl)carbamoyl)pyrrolidine-1-carboxylate (9 g, 34.84 mmol, 1.0 equiv) in THF (100 mL) was added Lithium aluminum hydride (2.0 M in THF)(21 mL, 41.80 mmol, 1.2 equiv) dropwise at −10° C. The resulting mixture was stirred at −10° C. for additional 2 h. Desired product could be detected by LCMS. The resulting mixture was diluted with THF (200 mL) and quenched with $Na_2SO_4.10H_2O$ at 0° C. The resulting mixture was filtered, the filter cake was washed with THF (3×20 mL). dried over anhydrous $Na_2SO_4$. Filtered and the filtrate was concentrated under reduced pressure, to afford tert-butyl (S)-2-formylpyrrolidine-1-carboxylate (8 g, 92%) as a colorless liquid. LCMS (ES) $[M+H]^+$ m/z: 200.

Synthesis of tert-butyl (2R)-2-(cyano(hydroxy) methyl)pyrrolidine-1-carboxylate

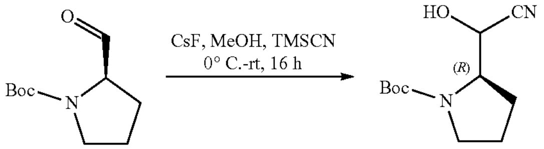

Into a 250 mL 3-necked round-bottom flask were added tert-butyl (S)-2-formylpyrrolidine-1-carboxylate (7 g, 35.13 mmol, 1.0 equiv), CsF (2.67 g, 17.56 mmol, 0.5 equiv) and MeOH (100 mL) at room temperature. To the above mixture was added trimethylsilanecarbonitrile (4.18 g, 42.15 mmol, 1.2 equiv) in portions at 0° C. under nitrogen atmosphere. The resulting mixture was stirred at room temperature for 16 h. Desired product could be detected by LCMS. The resulting mixture was diluted with water (500 mL), extracted with EtOAc (3×500 mL). The combined organic phase was dried over anhydrous $Na_2SO_4$. After filtration, the filtrate was concentrated under reduced pressure. The residue was purified by silica gel column chromatography, eluted with PE/EA (11:1) to afford tert-butyl (2R)-2-(cyano(hydroxy) methyl)pyrrolidine-1-carboxylate (4 g, 50%). LCMS (ES) $[M+H]^+$ m/z: 227.

Synthesis of 2-hydroxy-2-((R)-pyrrolidin-2-yl)acetic acid

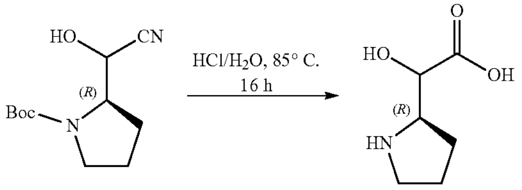

Into a 100 mL round-bottom flask were added tert-butyl (2R)-2-(cyano(hydroxy)methyl)pyrrolidine-1-carboxylate (2.5 g, 11.01 mmol, 1.0 equiv), $H_2O$ (15 mL) and HCl (c)(15 mL) at room temperature. The resulting mixture was stirred at 85° C. for 16 h. Desired product could be detected by LCMS. The reaction was cooled to room temperature, basified to pH 14 with NaOH and used in the next step directly without purification. LCMS (ES) $[M+H]^+$ m/z: 146.

Synthesis of 2-((R)-1-(tert-butoxycarbonyl)pyrrolidin-2-yl)-2-hydroxyacetic acid

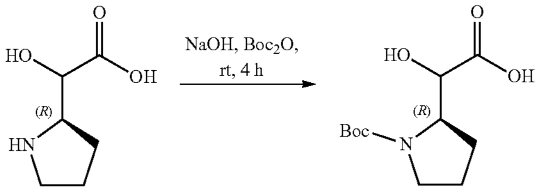

Into a 100 mL round-bottom flask were added THE (30 mL) and 2-hydroxy-2-((R)-pyrrolidin-2-yl)acetic acid (crude of last step) at room temperature. To the above mixture was added di-tert-butyl dicarbonate (7.4 g, 34.24 mmol, 2.0 equiv) in portions at 0° C. The resulting mixture was stirred at room temperature for 3 h. Desired product could be detected by LCMS. The resulting mixture was diluted with water (200 mL), extracted with EtOAc (3×100 mL). The aqueous layer was acidified to pH 2 with HCl (aq.1 M). extracted again with $CH_2Cl_2$:MeOH=10:1 (5×100 mL). The combined organic layer was washed with brine (50 mL), dried over anhydrous $Na_2SO_4$. After filtration, the filtrate was concentrated under reduced pressure. This resulted in 2-((R)-1-(tert-butoxycarbonyl)pyrrolidin-2-yl)-2-hydroxyacetic acid (800 mg, 19%). LCMS (ES) $[M+H]^+$ m/z: 246.

Synthesis of 2-((R)-1-(tert-butoxycarbonyl)pyrrolidin-2-yl)-2-methoxyacetic acid

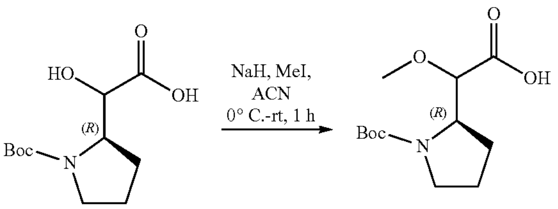

Into a 40 mL vial were added 2-((R)-1-(tert-butoxycarbonyl)pyrrolidin-2-yl)-2-hydroxyacetic acid (400 mg, 1.62 mmol, 1.0 equiv) and ACN (10 mL) at room temperature. To the above mixture was added NaH (97 mg, 4.06 mmol, 2.5 equiv)(60% in mineral oil) in portions at 0° C. The resulting mixture was stirred at 0° C. for 30 min. To the above mixture was added $CH_3I$ (0.68 g, 4.87 mmol, 3.0 equiv) dropwise at 0° C. The resulting mixture was stirred at room temperature for additional 2 h. Desired product could be detected by LCMS. The resulting mixture was quenched with water (100 mL), extracted with EtOAc (3×100 mL). The aqueous phase was acidified to pH 2 with citric acid, extracted with $CH_2Cl_2$ (3×100 mL). The combined organic layer was dried over anhydrous $Na_2SO_4$. After filtration, the filtrate was concentrated under reduced pressure. This resulted in 2-((R)-1-(tert-butoxycarbonyl)pyrrolidin-2-yl)-2-methoxyacetic acid (300 mg, 71%). LCMS (ES) $[M+H]^+$ m/z: 260.

Synthesis of tert-butyl (2R)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate

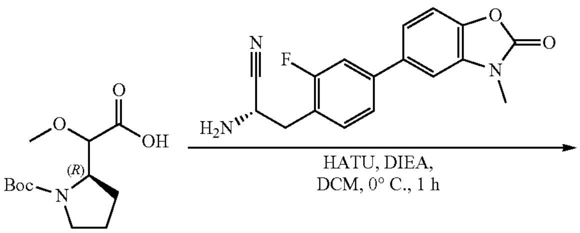

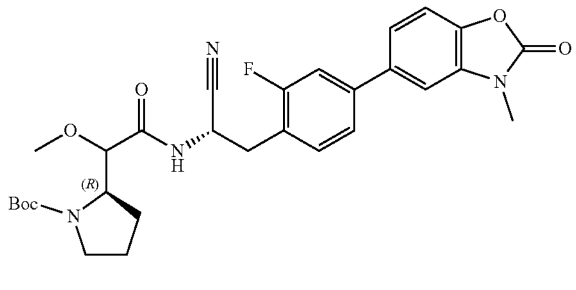

To a stirred solution of 2-((R)-1-(tert-butoxycarbonyl)pyrrolidin-2-yl)-2-methoxyacetic acid (300 mg, 1.15 mmol, 1.0 equiv), (2S)-2-amino-3-[2-fluoro-4-(3-methyl-2-oxo-1,3-benzoxazol-5-yl)phenyl]propanenitrile (360 mg, 1.15 mmol, 1.0 equiv) and DIEA (448 mg, 3.47 mmol, 3.0 equiv) in DCM (5 mL) was added HATU (530 mg, 1.38 mmol, 1.2 equiv) at 0° C. The resulting mixture was stirred at 0° C. for 1 h. Desired product could be detected by LCMS. Concentrated to remove the solvent, the crude was purified by silica gel column chromatography, eluted with PE/EA (1:1) to afford tert-butyl(2R)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (500 mg, 78% yield). LCMS (ES) $[M+1]^+$ m/z: 553.

Synthesis of N—((S)-1-cyano-2-(2-fluoro-4-(3-methyl-2-oxo-2,3-dihydrobenzo[d]oxazol-5-yl)phenyl)ethyl)-2-methoxy-2-((R)-pyrrolidin-2-yl)acetamide

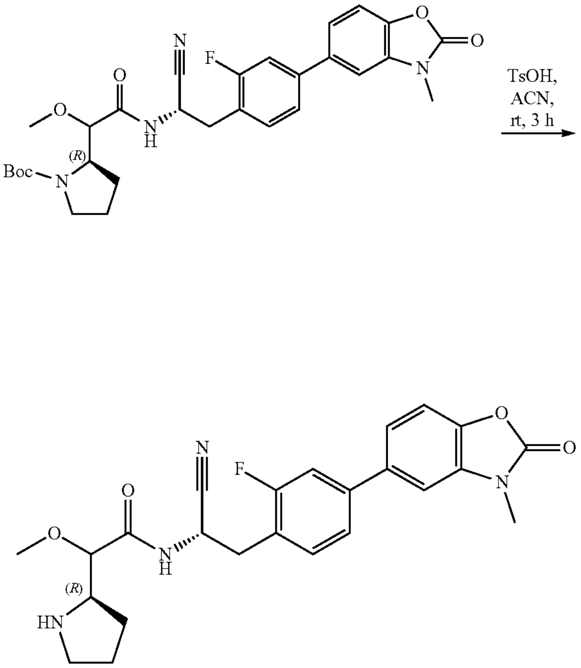

A mixture of tert-butyl(2R)-2-(2-(((S)-1-cyano-2-(2-fluoro-4-(3-methyl-2-oxo-2,3-dihydrobenzo[d]oxazol-5-yl)phenyl)ethyl)amino)-1-methoxy-2-oxoethyl)pyrrolidine-1-carboxylate (450 mg, 0.81 mmol, 1.0 equiv) and 4-methylbenzene-1-sulfonic acid hydrate (419 mg, 2.43 mmol, 3.0 equiv) in ACN (10 mL) was stirred at room temperature for 3 h. Desired product could be detected by LCMS. The mixture was basified to pH 9 with saturated $NaHCO_3$ (aq.). The aqueous layer was extracted with $CH_2Cl_2$ (3×50 mL). The combined organic layer was dried over anhydrous $Na_2SO_4$. After filtration, the filtrate was concentrated under reduced pressure. This resulted in N—((S)-1-cyano-2-(2-fluoro-4-(3-methyl-2-oxo-2,3-dihydrobenzo[d]oxazol-5-yl)phenyl)ethyl)-2-methoxy-2-((R)-pyrrolidin-2-yl)acetamide (400 mg, crude) and used to the next step without further purification. LCMS (ES) $[M+H]^+$ m/z: 453.

Synthesis of (S)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide and (R)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide

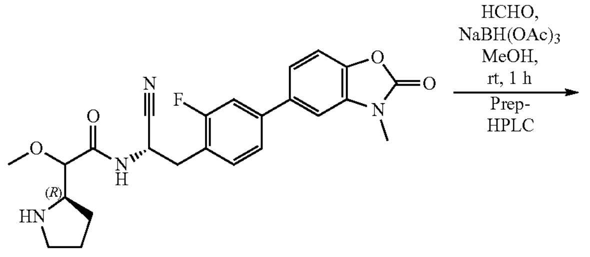

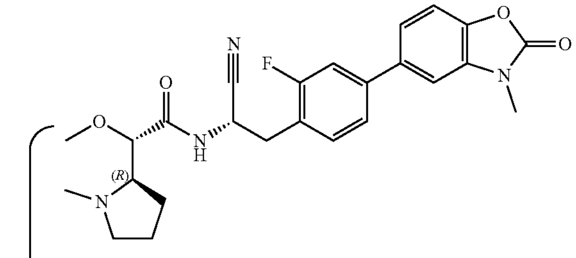

Assumed
Compound 291A

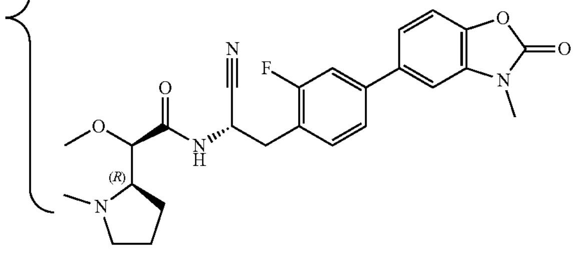

Assumed
Compound 291C

Into a 40 mL vial were added N—((S)-1-cyano-2-(2-fluoro-4-(3-methyl-2-oxo-2,3-dihydrobenzo[d]oxazol-5-yl)phenyl)ethyl)-2-methoxy-2-((R)-pyrrolidin-2-yl)acetamide (380 mg, 0.83 mmol, 1.0 equiv) and MeOH (5 mL) at room temperature. To the above mixture was added $NaBH(OAc)_3$ (530 mg, 2.51 mmol, 3.0 equiv), HCHO (265 mg, 8.30 mmol, 10 equiv) in portions at room temperature. The resulting mixture was stirred at room temperature for 1 h. Desired product could be detected by LCMS. Concentrated to remove the solvent, the residue was purified by Prep-HPLC with the following conditions: Column, XBridge Prep C18 OBD Column, 19*150 mm, 5 um; mobile phase, Water (0.1% $NH_3H_2O$) and ACN (30% Phase B up to 50% in 20 min); Detector, UV 254 nm. to afford (S)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide (60 mg, 15% yield) and (R)—N—((S)-1-cyano-2-(2-fluoro-4-(3-methyl-2-oxo-2,3-dihydrobenzo[d]oxazol-5-yl)phenyl)ethyl)-2-methoxy-2-((R)-1-methylpyrrolidin-2-yl)acetamide (40 mg, 10% yield).

Compound 291A

LCMS (ES) $[M+1]^+$ m/z: 467.1

$^1$H NMR (400 MHz, DMSO-$d_6$) δ 8.85 (d, J=8.5 Hz, 1H), 7.69-7.52 (m, 3H), 7.51-7.44 (m, 2H), 7.40 (d, J=8.3 Hz, 1H), 5.11-5.04 (m, 1H), 3.63 (d, J=3.4 Hz, 1H), 3.41 (s, 3H), 3.29-3.20 (m, 5H), 2.89-2.86 (m, 1H), 2.47-2.35 (m, 1H), 2.25 (s, 3H), 2.15-1.99 (m, 1H), 1.79-1.27 (m, 4H).

Compound 291C

LCMS (ES) $[M+1]^+$ m/z: 467.1

$^1$H NMR (400 MHz, DMSO-$d_6$) δ 8.94 (d, J=8.5 Hz, 1H), 7.64 (d, J=1.8 Hz, 1H), 7.62-7.53 (m, 2H), 7.53-7.44 (m, 2H), 7.40 (d, J=8.3 Hz, 1H), 5.10 (q, J=8.1 Hz, 1H), 3.49 (d, J=5.7 Hz, 1H), 3.41 (s, 3H), 3.29-3.17 (m, 5H), 2.89-2.77 (m, 1H), 2.41-2.35 (m, 1H), 2.28 (s, 3H), 2.14-2.05 (m, 1H), 1.64-1.49 (m, 4H).

Example 126: Synthesis of Compound 292: (2S)—N-[(1S)-1-cyano-2-[2-fluoro-4-(3-methyl-2-oxo-1,3-benzoxazol-5-yl)phenyl]ethyl]-3-(dimethylamino)-2-hydroxy-2-methylpropanamide

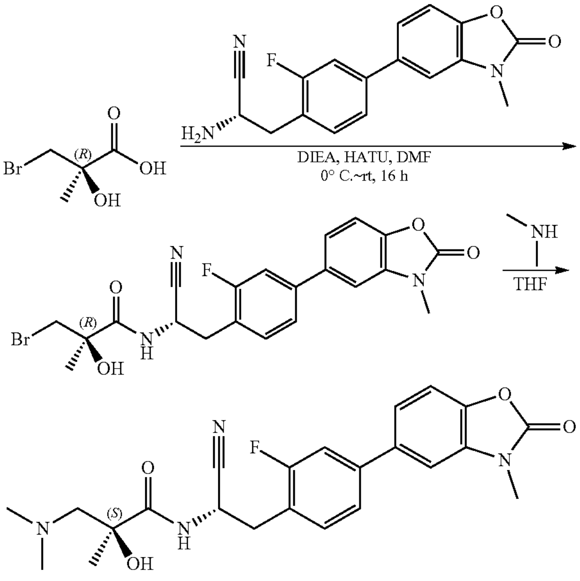

Compound 292

Synthesis of (2R)-3-bromo-N-[(1S)-1-cyano-2-[2-fluoro-4-(3-methyl-2-oxo-1,3-benzoxazol-5-yl)phenyl]ethyl]-2-hydroxy-2-methylpropanamide

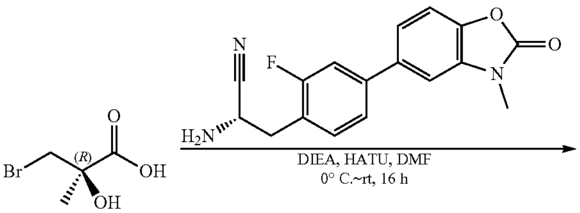

-continued

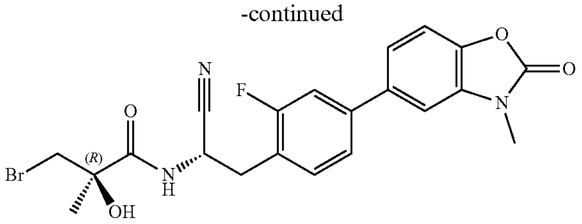

To a stirred solution of (2R)-3-bromo-2-hydroxy-2-methylpropanoic acid (200 mg, 1.09 mmol, 1.0 equiv) and (2S)-2-amino-3-[2-fluoro-4-(3-methyl-2-oxo-1,3-benzoxazol-5-yl)phenyl]propanenitrile (340 mg, 1.09 mmol, 1.0 equiv) in DMF (5 mL) was added DIEA (423 mg, 3.28 mmol, 3.0 equiv). To the above mixture was added HATU (498 mg, 1.31 mmol, 1.2 equiv) in portions at 0° C. The resulting mixture was stirred at room temperature for 16 h. The reaction was quenched with water (15 mL), extracted with EtOAc (3×10 mL). The combined organic layer was washed with brine (2×10 mL), dried over anhydrous $Na_2SO_4$. After filtration, the filtrate was concentrated under reduced pressure. The residue was purified by silica gel column chromatography, eluted with PE/EA (1:1) to afford (2R)-3-bromo-N—[(1S)-1-cyano-2-[2-fluoro-4-(3-methyl-2-oxo-1,3-benzoxazol-5-yl)phenyl]ethyl]-2-hydroxy-2-methylpropanamide (400 mg, 77% yield, 98% purity). LCMS (ES, m/z): $[M+H]^+$: 476.

Synthesis of (2S)—N-[(1S)-1-cyano-2-[2-fluoro-4-(3-methyl-2-oxo-1,3-benzoxazol-5-yl)phenyl]ethyl]-3-(dimethylamino)-2-hydroxy-2-methylpropanamide

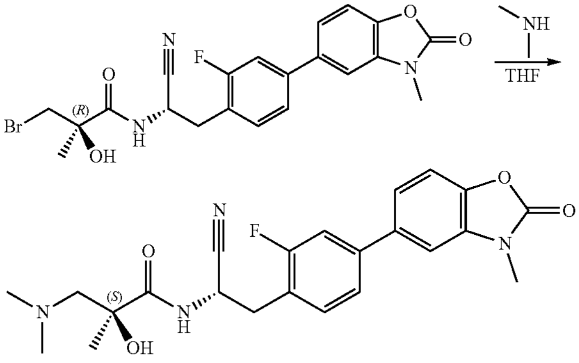

To a stirred solution of (2R)-3-bromo-N-[(1S)-1-cyano-2-[2-fluoro-4-(3-methyl-2-oxo-1,3-benzoxazol-5-yl)phenyl]ethyl]-2-hydroxy-2-methylpropanamide (150 mg, 0.32 mmol, 1.0 equiv) in tetrahydrofuran (2 mL) were added dimethylamine (0.3 mL, 0.63 mmol, 2.0 equiv)(2 M in THF) dropwise at 0° C. under nitrogen atmosphere. The resulting mixture was stirred at room temperature for 16 h. The reaction solution was purified by Prep-HPLC with the following conditions:column, C18 silica gel-120 g; mobile phase, MeCN in Water (0.1% $NH_3 \cdot H_2O$), 10% to 80% gradient in 10 min; detector, UV 254 nm to afford (2S)—N-[(1S)-1-cyano-2-[2-fluoro-4-(3-methyl-2-oxo-1,3-benzoxazol-5-yl)phenyl]ethyl]-3-(dimethylamino)-2-hydroxy-2-methylpropanamide (15 mg, 11% yield, 98.5% purity. LCMS (ES, m/z): $[M+H]^+$: 411.2

$^1H$ NMR (400 MHz, DMSO-$d_6$) δ 8.68 (d, J=8.4 Hz, 1H), 7.65 (d, J=1.9 Hz, 1H), 7.62-7.52 (m, 2H), 7.49-7.44 (m, 2H), 7.41 (d, J=8.4 Hz, 1H), 5.16 (brs, 1H), 5.01 (q, J=8.0 Hz, 1H), 3.41 (s, 3H), 3.29-3.24 (m, 2H), 2.50 (d, J=13.3 Hz, 1H)(mixed in DMSO), 2.21 (d, J=13.3 Hz, 1H), 2.07 (d, J=1.4 Hz, 6H), 1.18 (d, J=1.5 Hz, 3H).

Example 127: Synthesis of Various Compounds of the Present Disclosure

Some compounds of the present disclosure were synthesized according to the general scheme below.

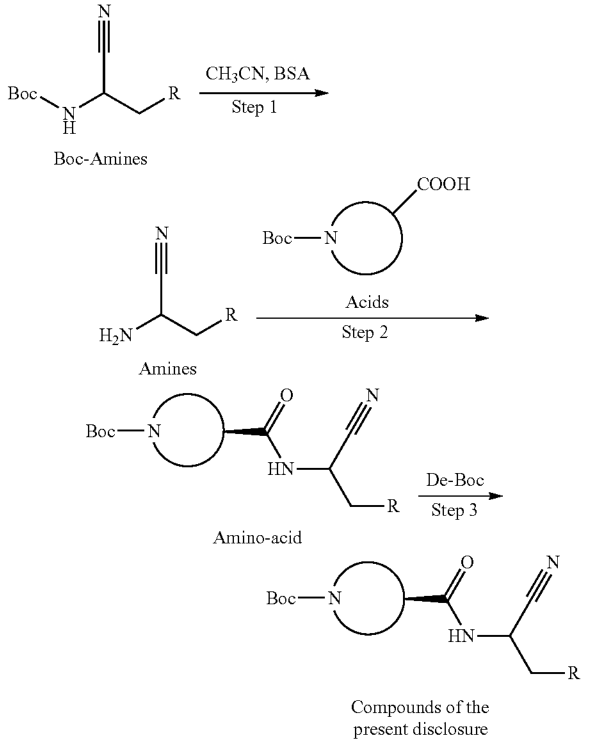

The list of Boc-Amines used in the synthesis of this example are included in the table below.

| | |
|---|---|
| Boc-Amine 1 | 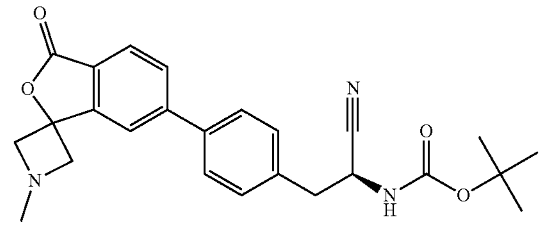 [SMILES: CN1CC2(C1)OC(=O)c1ccc(-c3ccc(C[C@@H](C#N)NC(=O)OC(C)(C)C)cc3)cc12] |

-continued
Boc-Amine 2
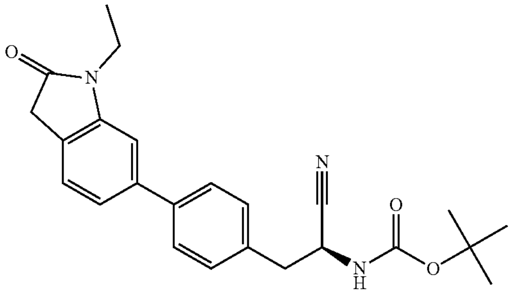 [SMILES: CCN1C(=O)Cc2ccc(-c3ccc(C[C@@H](C#N)NC(=O)OC(C)(C)C)cc3)cc21]
Boc-Amine 3
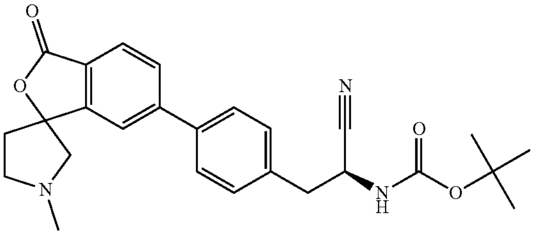 [SMILES: CN1CCC2(C1)OC(=O)c1ccc(-c3ccc(C[C@@H](C#N)NC(=O)OC(C)(C)C)cc3)cc12]
Boc-Amine 4
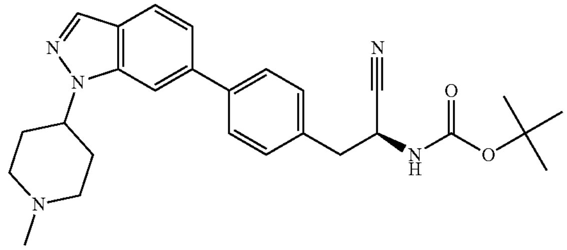 [SMILES: CN1CCC(n2ncc3ccc(-c4ccc(C[C@@H](C#N)NC(=O)OC(C)(C)C)cc4)cc32)CC1]
Boc-Amine 5
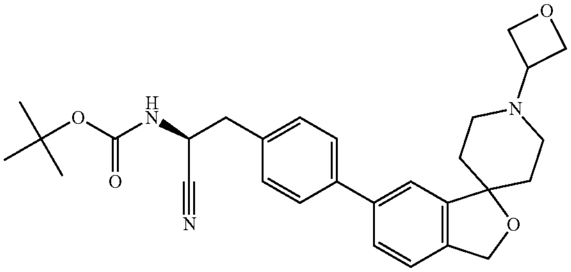 [SMILES: CC(C)(C)OC(=O)N[C@H](C#N)Cc1ccc(-c2ccc3c(c2)C2(CCN(C4COC4)CC2)OC3)cc1]
Boc-Amine 6
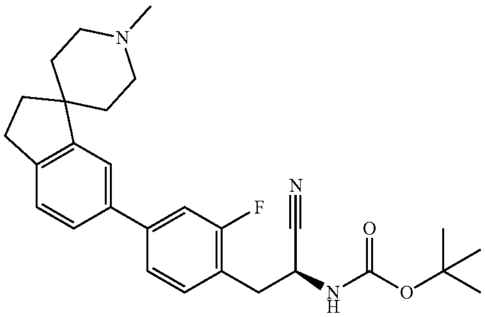 [SMILES: CN1CCC2(CCc3ccc(-c4ccc(C[C@@H](C#N)NC(=O)OC(C)(C)C)c(F)c4)cc32)CC1]

-continued
Boc-Amine 7
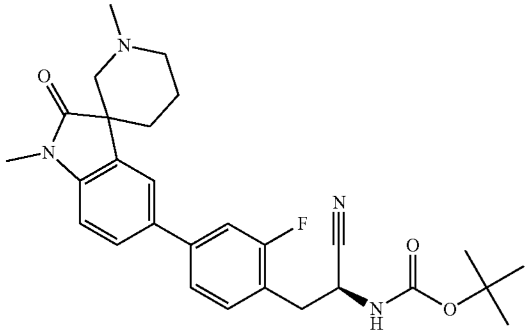 [SMILES: CN1CCCC2(C1)C(=O)N(C)c1ccc(-c3ccc(C[C@@H](C#N)NC(=O)OC(C)(C)C)c(F)c3)cc12]
Boc-Amine 8
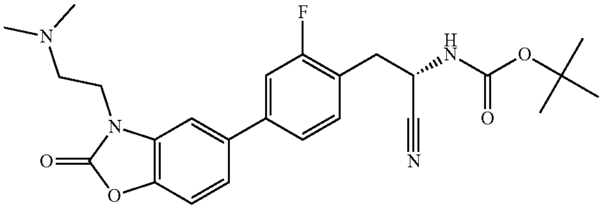 [SMILES: CN(C)CCn1c(=O)oc2ccc(-c3ccc(C[C@@H](C#N)NC(=O)OC(C)(C)C)c(F)c3)cc21]
Boc-Amine 9
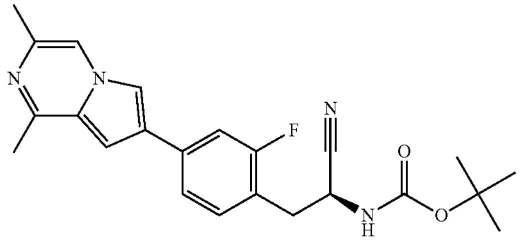 [SMILES: Cc1cn2cc(-c3ccc(C[C@@H](C#N)NC(=O)OC(C)(C)C)c(F)c3)cc2c(C)n1]
Boc-Amine 10
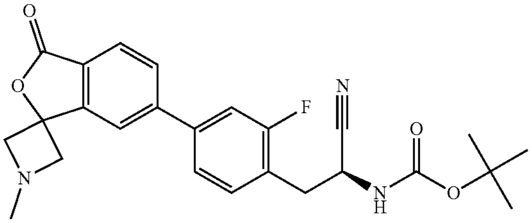 [SMILES: CN1CC2(C1)OC(=O)c1ccc(-c3ccc(C[C@@H](C#N)NC(=O)OC(C)(C)C)c(F)c3)cc12]
Boc-Amine 11
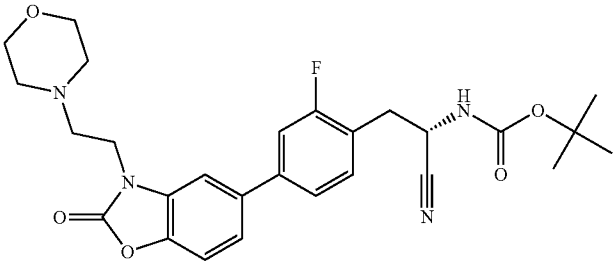 [SMILES: CC(C)(C)OC(=O)N[C@H](C#N)Cc1ccc(-c2ccc3oc(=O)n(CCN4CCOCC4)c3c2)cc1F]
Boc-Amine 12
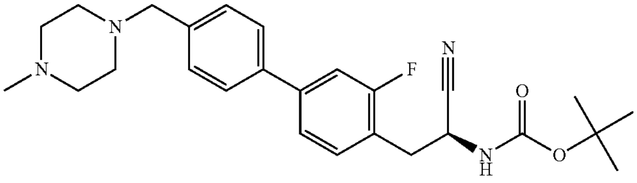 [SMILES: CN1CCN(Cc2ccc(-c3ccc(C[C@@H](C#N)NC(=O)OC(C)(C)C)c(F)c3)cc2)CC1]

-continued
Boc-Amine 13
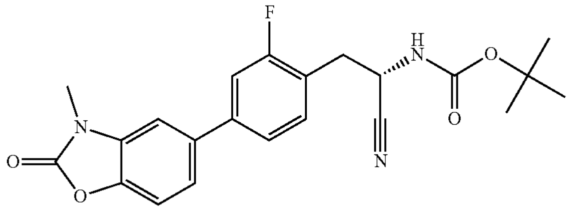 [SMILES: Cn1c(=O)oc2ccc(-c3ccc(C[C@@H](C#N)NC(=O)OC(C)(C)C)c(F)c3)cc21]
Boc-Amine 14
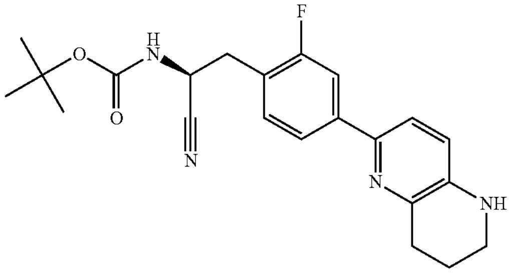 [SMILES: CC(C)(C)OC(=O)N[C@H](C#N)Cc1ccc(-c2ccc3c(n2)CCCN3)cc1F]
Boc-Amine 15
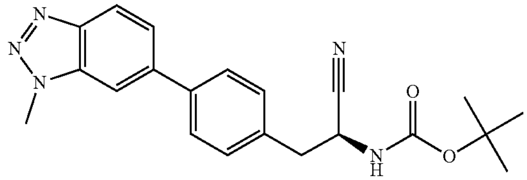
Boc-Amine 16
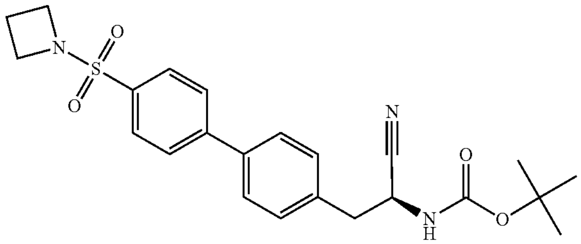 [SMILES: CC(C)(C)OC(=O)N[C@H](C#N)Cc1ccc(-c2ccc(S(=O)(=O)N3CCC3)cc2)cc1]
Boc-Amine 17
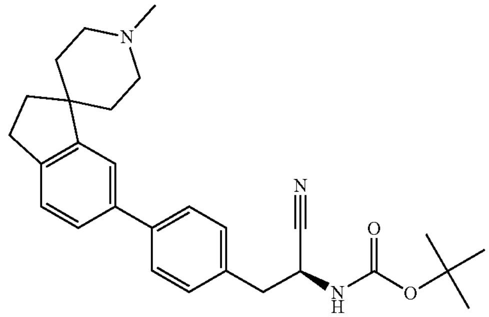 [SMILES: CN1CCC2(CCc3ccc(-c4ccc(C[C@@H](C#N)NC(=O)OC(C)(C)C)cc4)cc32)CC1]
Boc-Amine 18
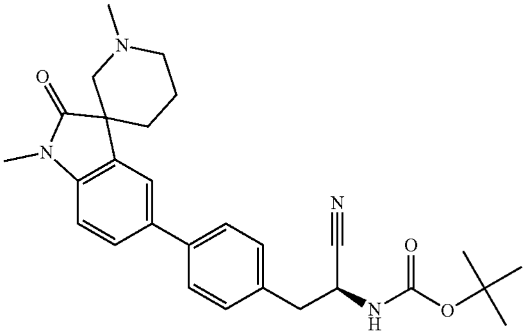 [SMILES: CN1CCCC2(C1)C(=O)N(C)c1ccc(-c3ccc(C[C@@H](C#N)NC(=O)OC(C)(C)C)cc3)cc12]

-continued
Boc-Amine 19
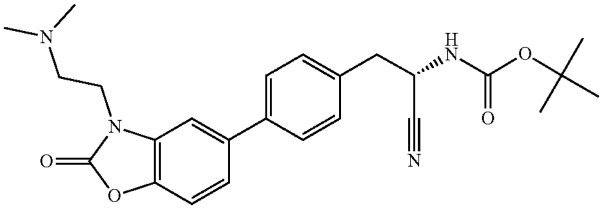 [SMILES: CN(C)CCn1c(=O)oc2ccc(-c3ccc(C[C@@H](C#N)NC(=O)OC(C)(C)C)cc3)cc21]
Boc-Amine 20
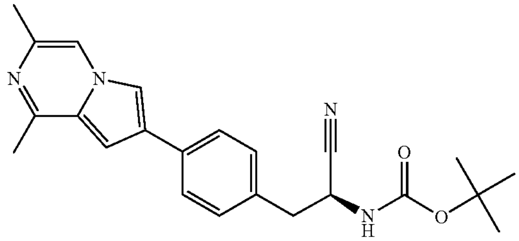 [SMILES: Cc1cn2cc(-c3ccc(C[C@@H](C#N)NC(=O)OC(C)(C)C)cc3)cc2c(C)n1]
Boc-Amine 21
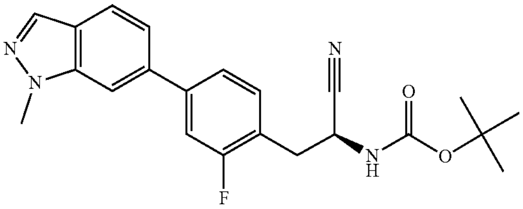 [SMILES: Cn1ncc2ccc(-c3ccc(C[C@@H](C#N)NC(=O)OC(C)(C)C)c(F)c3)cc21]
Boc-Amine 22
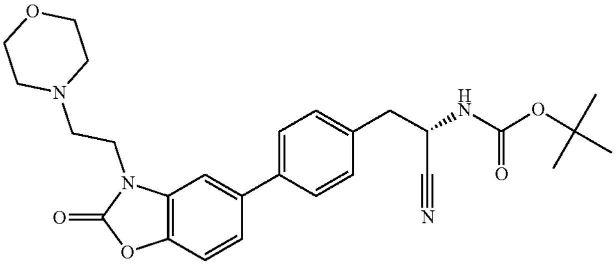 [SMILES: CC(C)(C)OC(=O)N[C@H](C#N)Cc1ccc(-c2ccc3oc(=O)n(CCN4CCOCC4)c3c2)cc1]
Boc-Amine 23
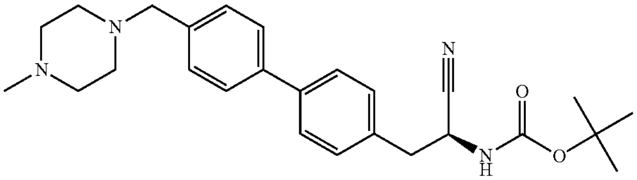 [SMILES: CN1CCN(Cc2ccc(-c3ccc(C[C@@H](C#N)NC(=O)OC(C)(C)C)cc3)cc2)CC1]
Boc-Amine 24
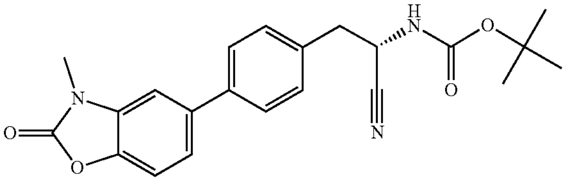 [SMILES: Cn1c(=O)oc2ccc(-c3ccc(C[C@@H](C#N)NC(=O)OC(C)(C)C)cc3)cc21]
Boc-Amine 25
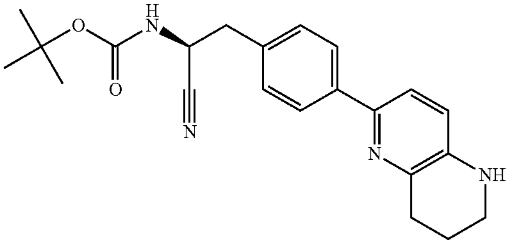 [SMILES: CC(C)(C)OC(=O)N[C@H](C#N)Cc1ccc(-c2ccc3c(n2)CCCN3)cc1]

-continued
Boc-Amine 26
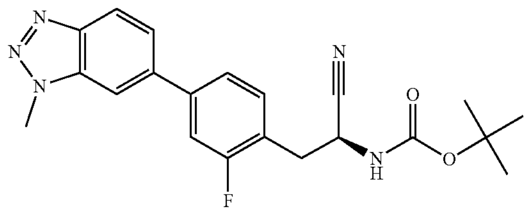 [SMILES: Cn1nnc2ccc(-c3ccc(C[C@@H](C#N)NC(=O)OC(C)(C)C)c(F)c3)cc21]
Boc-Amine 27
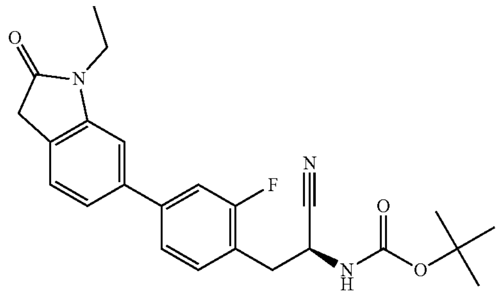 [SMILES: CCN1C(=O)Cc2ccc(-c3ccc(C[C@@H](C#N)NC(=O)OC(C)(C)C)c(F)c3)cc21]
Boc-Amine 28
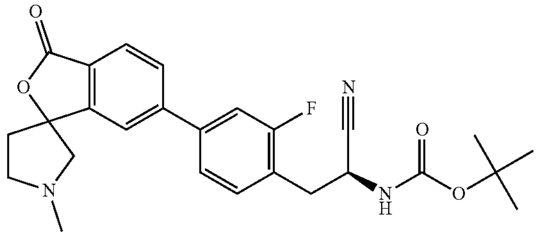 [SMILES: CN1CCC2(C1)OC(=O)c1ccc(-c3ccc(C[C@@H](C#N)NC(=O)OC(C)(C)C)c(F)c3)cc12]
Boc-Amine 29
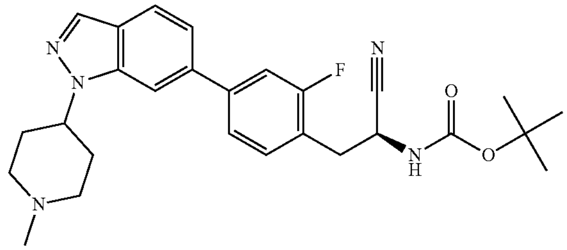 [SMILES: CN1CCC(n2ncc3ccc(-c4ccc(C[C@@H](C#N)NC(=O)OC(C)(C)C)c(F)c4)cc32)CC1]
Boc-Amine 30
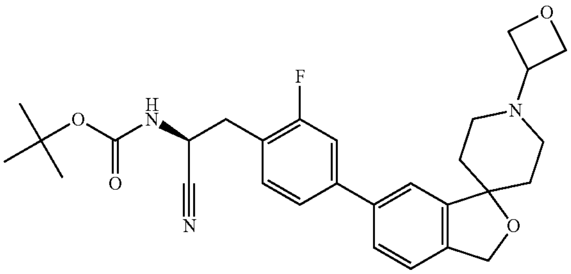 [SMILES: CC(C)(C)OC(=O)N[C@H](C#N)Cc1ccc(-c2ccc3c(c2)C2(CCN(C4COC4)CC2)OC3)cc1F]
Boc-Amine 31
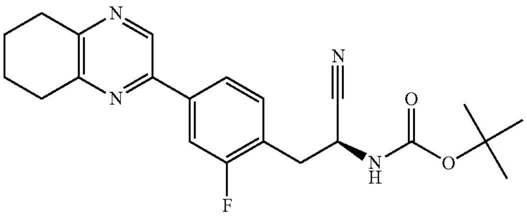 [SMILES: CC(C)(C)OC(=O)N[C@H](C#N)Cc1ccc(-c2cnc3c(n2)CCCC3)cc1F]

-continued
Boc-Amine 32
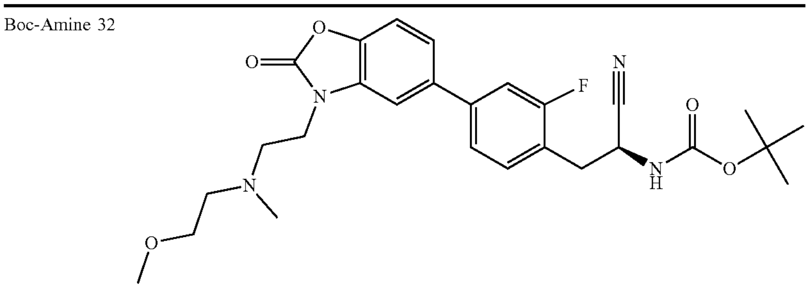
Boc-Amine 33
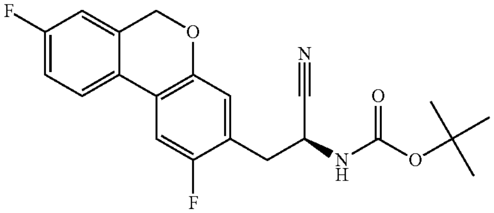 [SMILES: CC(C)(C)OC(=O)N[C@H](C#N)Cc1cc2c(cc1F)-c1ccc(F)cc1CO2]
Boc-Amine 34
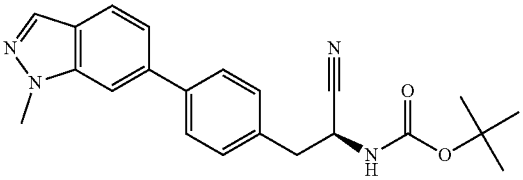 [SMILES: Cn1ncc2ccc(-c3ccc(C[C@@H](C#N)NC(=O)OC(C)(C)C)cc3)cc21]
Boc-Amine 35
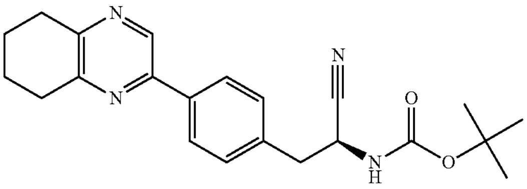 [SMILES: CC(C)(C)OC(=O)N[C@H](C#N)Cc1ccc(-c2cnc3c(n2)CCCC3)cc1]
Boc-Amine 36
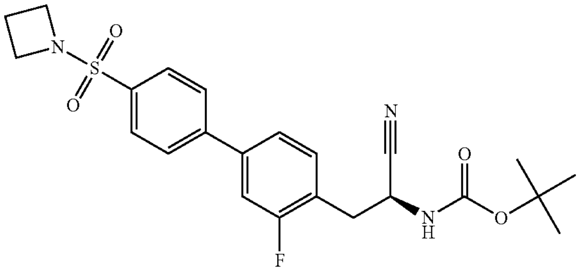 [SMILES: CC(C)(C)OC(=O)N[C@H](C#N)Cc1ccc(-c2ccc(S(=O)(=O)N3CCC3)cc2)cc1F]
The list of Amines used in the synthesis of this example are included in the table below.

Amine 1

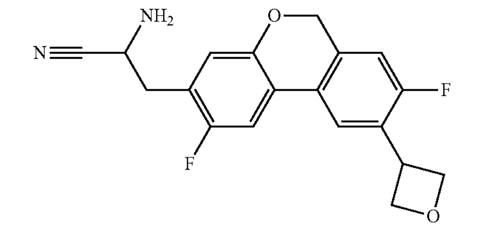 [SMILES: N#CC(N)Cc1cc2c(cc1F)-c1cc(C3COC3)c(F)cc1CO2]

Amine 2

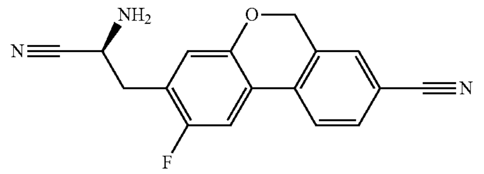 [SMILES: N#Cc1ccc2c(c1)COc1cc(C[C@H](N)C#N)c(F)cc1-2]

Amine 3

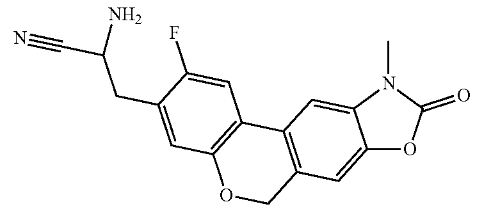 [SMILES: Cn1c(=O)oc2cc3c(cc21)-c1cc(F)c(CC(N)C#N)cc1OC3]

Amine 4

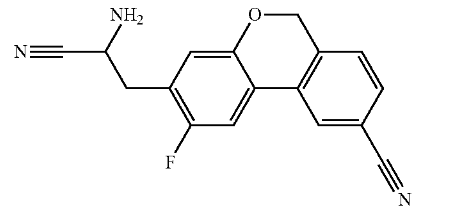 [SMILES: N#Cc1ccc2c(c1)-c1cc(F)c(CC(N)C#N)cc1OC2]

Amine 5

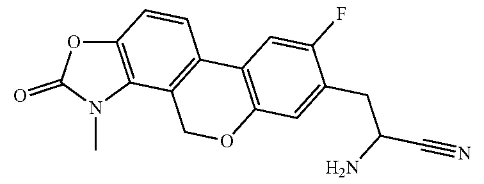 [SMILES: Cn1c(=O)oc2ccc3c(c21)COc1cc(CC(N)C#N)c(F)cc1-3]

The Acids used in the synthesis of this example include (Acid 1)

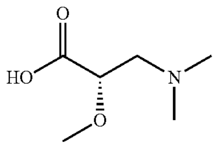

and (Acid 2)

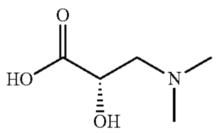

and (Acid 3)

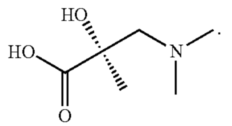

-continued

Step 1

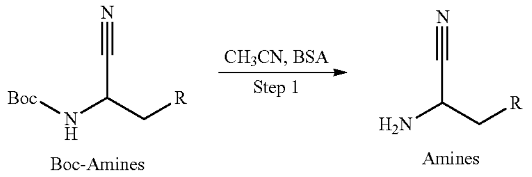

Into an 8-mL sealed tube, was placed Boc-Amine (25-30 mg, 1.00 equiv), $CH_3CN$ (2 mL) and N,O-bis(trimethylsilyl) acetamide BSA (1.20 equiv). The mixture was stirred for 4 h at 40° C. After cooled to room temperature. The reaction was used in the next step directly.

Step 2

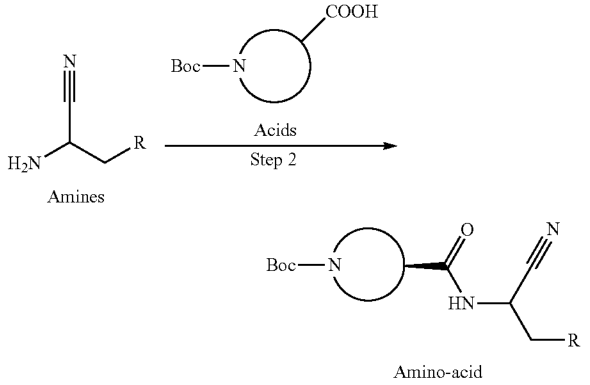

Step 2—Method A (for Acid 1 and Acid 2):

Into an 8-mL sealed tube, was placed Amine (25-30 mg, 1.00 equiv) in $CH_3CN$, or the mixture of the preceding step, this was followed by the addition DIEA (4.00 equiv), Acid (1.20 equiv), HATU (1.20 equiv) and $CH_3CN$ (2 mL). The mixture was stirred for 1 h at room temperature. The reaction was quenched with MeOH (1 mL). The mixture was purified by Prep-HPLC to give Amino-acid.

Step 2—Method B (for Acid 3):

Into an 8-mL sealed tube, was placed Amine (25-30 mg, 1.00 equiv) in $CH_3CN$, or the mixture of the preceding step. This was followed by the addition N-Methylmorpholine (NMM)(4.00 equiv), Acid 3 (1.20 equiv), 1-Ethyl-3-(3-dimethylaminopropyl)carbodiimide (EDCI)(1.20 equiv), 1-Hydroxybenzotriazole (HOBT)(0.30 equiv) and $CH_3CN$ (2 mL). The mixture was stirred for 1 h at room temperature. The reaction was quenched with MeOH (1 mL). The mixture was purified by Prep-HPLC to give the Amino acid.

Step 3

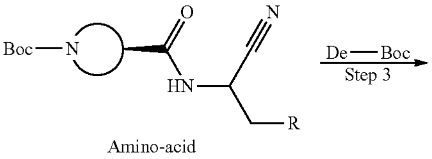

-continued

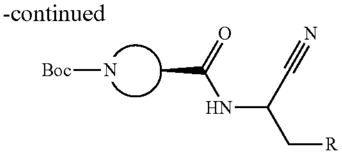

Compounds of the present disclosure

A mixture of Amino-acid (15-25 mg, 1.00 equiv), BSA (1.20 equiv) in $CH_3CN$ (3 mL) was stirred at room temperature for 4 h. The reaction was quenched with MeOH (1 mL). The mixture was purified by Prep-HPLC to give a compound of the present disclosure.

Purification Methods

Method 1:

Prep-HPLC: Column: Welch Xtimate C18 30*150 mm, 10 m; Mobile Phase A: Water (10 mmol $NH_4HCO_3$), Mobile Phase B: ACN; Flow rate: 35 mL/min; Wave Length: 254 nm, 220 nm.

Method 2:

Prep-HPLC: Column: Welch Xtimate C18 30*150 mm, 10 μm; Mobile phase A: 0.100 FA; Mobile phase B: ACN; Flow rate: 35 mL/min; Wave Length: 254 nm, 220 nm.

Method 3:

HP-Flash: YM C18 50*150 mm, 10 m; MobilePhase A: Water (10 mmol $NH_4HCO_3$), Mobile Phase B: ACN, Flow rate: 80 mL/min; Wave Length: 254 nm, 220 nm.

Compounds prepared according to this Example are listed in Table 2 below.

TABLE 2

Synthesized compounds

| Cmpd No. | MW (g/mol) | Yield (mg) | Yield (%); purity (%) | Mass (ES, m/z): [M + H]+ |
|---|---|---|---|---|
| 295 | 471.5 | 7.4 | 21.39%; 95.405% | calcd 472.2, found 472.2 |
| 296 | 422.46 | 16 | 53.18%; 98.279% | calcd 423.2, found 423.2 |
| 297 | 468.49 | 17.4 | 52.91%; 99.706% | calcd 469.2, found 469.2 |
| 298 | 422.46 | 14 | 47.01%; 99.268% | calcd 423.2, found 423.2 |
| 299 | 468.49 | 21.1 | 63.77%; 99.095% | calcd 469.2, found 469.2 |
| 300 | 474.65 | 4.3 | 14.75%; 91.363% | calcd 475.3, found 475.3 |
| 301 | 503.65 | 6.1 | 22.32%; 97.065% | calcd 504.3, found 504.3 |
| 302 | 479.58 | 8 | 29.8%; 99.142% | calcd 480.3, found 480.3 |
| 303 | 419.53 | 6.7 | 24.77%; 99.31% | calcd 420.2, found 420.2 |
| 304 | 462.55 | 8.9 | 33.06%; 99.078% | calcd 463.2, found 463.2 |
| 305 | 434.54 | 11.3 | 41.99%; 99.559% | calcd 435.2, found 435.2 |
| 306 | 476.58 | 8.1 | 29.81%; 97.961% | calcd 477.2, found 477.2 |
| 307 | 488.64 | 2.5 | 9.39%; 99.839% | calcd 489.3, found 489.3 |
| 308 | 518.66 | 10.9 | 40.16%; 97.57% | calcd 519.3, found 519.3 |
| 309 | 521.62 | 1.5 | 5.62%; 99.254% | calcd 522.3, found 522.3 |
| 310 | 463.63 | 4.9 | 18.23%; 99.253% | calcd 464.3, found 464.3 |
| 311 | 422.49 | 11 | 40.55%; 98.971% | calcd 423.2, found 423.2 |
| 312 | 407.52 | 6.2 | 22.26%; 96.666% | calcd 408.2, found 408.2 |
| 313 | 492.64 | 9.4 | 34.17%; 96.577% | calcd 493.3, found 493.3 |
| 314 | 521.64 | 12.5 | 47.02%; 99.59% | calcd 522.3, found 522.3 |
| 315 | 497.57 | 14 | 52.35%; 99.279% | calcd 498.2, found 498.2 |
| 316 | 437.52 | 12.6 | 46.72%; 99.288% | calcd 438.2, found 438.2 |
| 317 | 480.54 | 11.6 | 41.84%; 95.966% | calcd 481.2, found 481.2 |
| 318 | 452.53 | 11.2 | 41.83%; 99.785% | calcd 453.2, found 453.2 |
| 319 | 494.57 | 5.6 | 20.9%; 99.134% | calcd 495.2, found 495.2 |
| 320 | 506.63 | 6.8 | 22.56%; 87.99% | calcd 507.3, found 507.3 |
| 321 | 536.65 | 16.8 | 62.82%; 98.837% | calcd 537.3, found 537.3 |
| 322 | 539.61 | 11.8 | 44.47%; 99.58% | calcd 540.3, found 540.3 |
| 323 | 481.62 | 5.9 | 21.2%; 95.577% | calcd 482.3, found 482.3 |
| 324 | 440.48 | 8.7 | 31.55%; 97.068% | calcd 441.2, found 441.2 |
| 325 | 425.51 | 6.3 | 22.51%; 95.864% | calcd 426.2, found 426.2 |
| 326 | 541.62 | 9.1 | 34.27%; 99.494% | calcd 542.3, found 542.3 |
| 328 | 405.5 | 6.2 | 22.95%; 99.694% | calcd 406.2, found 406.2 |
| 329 | 406.49 | 9.5 | 34.68%; 98.278% | calcd 407.2, found 407.2 |
| 330 | 407.52 | 4.5 | 15.42%; 92.236% | calcd 408.2, found 408.2 |
| 331 | 470.59 | 4.8 | 16.94%; 94.041% | calcd 471.2, found 471.2 |

TABLE 2-continued

Synthesized compounds

| Cmpd No. | MW (g/mol) | Yield (mg) | Yield (%); purity (%) | Mass (ES, m/z): [M + H]+ |
|---|---|---|---|---|
| 332 | 423.49 | 8.6 | 30.86%; 96.321% | calcd 424.2, found 424.2 |
| 333 | 424.48 | 7.6 | 27.82%; 98.247% | calcd 425.2, found 425.2 |
| 334 | 425.51 | 5.7 | 20.82%; 98.006% | calcd 426.2, found 426.2 |
| 335 | 488.58 | 11.8 | 43.43%; 97.837% | calcd 489.2, found 489.2 |
| 336 | 415.44 | 4.4 | 15.59%; 95.218% | calcd 416.2, found 416.2 |
| 338 | 408.43 | 5 | 17.44%; 99.735% | calcd 409.2, found 409.2 |
| 339 | 454.46 | 10.1 | 31.44%; 99.014% | calcd 455.2, found 455.2 |
| 340 | 408.43 | 8.3 | 28.28%; 97.404% | calcd 409.2, found 409.2 |
| 341 | 454.46 | 5.6 | 16.83%; 95.577% | calcd 455.2, found 455.2 |
| 342 | 460.62 | 5 | 17.23%; 89.042% | calcd 461.3, found 461.3 |
| 343 | 489.62 | 0.6 | 2.22%; 95.24% | calcd 490.3, found 490.3 |
| 344 | 465.55 | 2.3 | 8.81%; 98.915% | calcd 466.2, found 466.2 |
| 345 | 405.5 | 6.1 | 23.37%; 99.453% | calcd 406.2, found 406.2 |
| 346 | 448.52 | 5 | 18.39%; 95.136% | calcd 449.2, found 449.2 |
| 347 | 420.51 | 5.8 | 22.29%; 99.62% | calcd 421.2, found 421.2 |
| 348 | 462.55 | 11 | 42.02%; 98.695% | calcd 463.2, found 463.2 |
| 349 | 474.61 | 6.1 | 23.21%; 98.228% | calcd 475.3, found 475.3 |
| 350 | 504.63 | 7.3 | 27.43%; 96.826% | calcd 505.3, found 505.3 |
| 351 | 507.59 | 2.5 | 8.97%; 92.403% | calcd 508.3, found 508.3 |
| 352 | 449.6 | 2.4 | 8.28%; 89.201% | calcd 450.3, found 450.3 |
| 353 | 408.46 | 3.8 | 14.39%; 98.28% | calcd 409.2, found 409.2 |
| 354 | 393.49 | 4.9 | 18.11%; 96.081% | calcd 394.2, found 394.2 |
| 355 | 478.61 | 3.6 | 13.32%; 95.523% | calcd 479.3, found 479.3 |
| 356 | 507.61 | 5.1 | 19.52%; 98.616% | calcd 508.3, found 508.3 |
| 357 | 483.54 | 2.3 | 8.69%; 97.442% | calcd 484.2, found 484.2 |
| 358 | 423.49 | 1.3 | 4.91%; 97.866% | calcd 424.2, found 424.2 |
| 359 | 466.51 | 2.1 | 7.59%; 93.356% | calcd 467.2, found 467.2 |
| 360 | 438.5 | 5 | 19.28%; 99.813% | calcd 439.2, found 439.2 |
| 361 | 480.54 | 4.5 | 17.2%; 98.621% | calcd 481.2, found 481.2 |
| 362 | 492.6 | 4.3 | 16.22%; 97.25% | calcd 493.3, found 493.3 |
| 363 | 522.62 | 2.1 | 7.77%; 95.238% | calcd 523.3, found 523.3 |
| 364 | 525.58 | 8.9 | 33.62%; 97.222% | calcd 526.2, found 526.2 |
| 365 | 467.59 | 5.4 | 19.87%; 95.036% | calcd 468.3, found 468.3 |
| 366 | 426.45 | 5.9 | 22.62%; 99.339% | calcd 427.2, found 427.2 |
| 367 | 411.48 | 5.5 | 20.28%; 95.657% | calcd 412.2, found 412.2 |
| 368 | 527.6 | 4 | 15.46%; 99.433% | calcd 528.3, found 528.3 |
| 370 | 391.48 | 4.9 | 18.02%; 95.587% | calcd 392.2, found 392.2 |
| 371 | 392.46 | 4.3 | 16.4%; 99.14% | calcd 393.2, found 393.2 |
| 372 | 393.49 | 5 | 18.7%; 97.234% | calcd 394.2, found 394.2 |
| 374 | 409.46 | 2.5 | 9.54%; 99.034% | calcd 410.2, found 410.2 |
| 375 | 410.45 | 2.3 | 8.58%; 96.755% | calcd 411.2, found 411.2 |
| 376 | 411.48 | 8.6 | 28.45%; 85.85% | calcd 412.2, found 412.2 |
| 377 | 474.55 | 11.4 | 43.71%; 98.978% | calcd 475.2, found 475.2 |
| 378 | 401.41 | 3.6 | 12.73%; 91.827% | calcd 402.2, found 402.2 |
| 379 | 471.5 | 19.9 | 59.65%; 98.92% | calcd 472.2, found 472.2 |
| 380 | 422.46 | 17.9 | 58.65%; 96.866% | calcd 423.2, found 423.2 |
| 381 | 468.49 | 17.8 | 53.42%; 98.398% | calcd 469.2, found 469.2 |
| 382 | 422.46 | 17.4 | 57.95%; 98.467% | calcd 423.2, found 423.2 |
| 383 | 468.49 | 20 | 60.08%; 98.491% | calcd 469.2, found 469.2 |
| 384 | 474.65 | 8.4 | 29.48%; 93.455% | calcd 475.3, found 475.3 |
| 385 | 503.65 | 2.1 | 7.8%; 98.593% | calcd 504.3, found 504.3 |
| 386 | 479.58 | 6.9 | 25%; 96.42% | calcd 480.3, found 480.3 |
| 387 | 419.53 | 11.9 | 44.3%; 100% | calcd 420.2, found 420.2 |
| 388 | 462.55 | 14.5 | 53.6%; 98.605% | calcd 463.2, found 463.2 |
| 389 | 434.54 | 17.3 | 63.41%; 98.195% | calcd 435.2, found 435.2 |
| 390 | 476.58 | 8.9 | 32.28%; 96.57% | calcd 477.2, found 477.2 |
| 391 | 488.64 | 8.3 | 26.74%; 85.619% | calcd 489.3, found 489.3 |
| 392 | 518.66 | 11.7 | 39.84%; 90.175% | calcd 519.3, found 519.3 |
| 393 | 521.62 | 14.7 | 54.56%; 98.268% | calcd 522.3, found 522.3 |
| 394 | 463.63 | 9.8 | 36.21%; 98.541% | calcd 464.3, found 464.3 |
| 395 | 422.49 | 11.2 | 41.25%; 98.875% | calcd 423.2, found 423.2 |
| 396 | 407.52 | 2.9 | 10.41%; 96.656% | calcd 408.2, found 408.2 |
| 397 | 492.64 | 7.8 | 27.9%; 95.014% | calcd 493.3, found 493.3 |
| 398 | 521.64 | 16.2 | 59.97%; 97.997% | calcd 522.3, found 522.3 |
| 399 | 497.57 | 13.5 | 49.54%; 97.433% | calcd 498.2, found 498.2 |
| 400 | 437.52 | 10.7 | 38.07%; 95.272% | calcd 438.2, found 438.2 |
| 401 | 480.54 | 10.2 | 37.51%; 97.852% | calcd 481.2, found 481.2 |
| 402 | 452.53 | 15.8 | 58.26%; 98.504% | calcd 453.2, found 453.2 |
| 403 | 494.57 | 17.3 | 61.69%; 94.714% | calcd 495.2, found 495.2 |
| 404 | 506.63 | 15.9 | 57.46%; 95.835% | calcd 507.3, found 507.3 |
| 405 | 536.65 | 15 | 55.24%; 97.341% | calcd 537.3, found 537.3 |
| 406 | 539.61 | 6 | 22.38%; 98.569% | calcd 540.3, found 540.3 |
| 407 | 481.62 | 14.3 | 45.73%; 85.073% | calcd 482.3, found 482.3 |
| 408 | 440.48 | 17.2 | 63.56%; 98.9% | calcd 441.2, found 441.2 |
| 409 | 425.51 | 12.5 | 42.72%; 91.697% | calcd 426.2, found 426.2 |

TABLE 2-continued

| Synthesized compounds | | | | |
|---|---|---|---|---|
| Cmpd No. | MW (g/mol) | Yield (mg) | Yield (%); purity (%) | Mass (ES, m/z): [M + H]+ |
| 410 | 541.62 | 7.2 | 26.37%; 96.747% | calcd 542.3, found 542.3 |
| 412 | 405.5 | 5 | 18.31%; 98.617% | calcd 406.2, found 406.2 |
| 413 | 406.49 | 13.1 | 46.24%; 95.044% | calcd 407.2, found 407.2 |
| 414 | 407.52 | 16.2 | 57.58%; 95.678% | calcd 408.2, found 408.2 |
| 415 | 470.59 | 5.7 | 19.3%; 90.231% | calcd 471.2, found 471.2 |
| 416 | 423.49 | 3.4 | 12.09%; 95.425% | calcd 424.2, found 424.2 |
| 417 | 424.48 | 16.5 | 59%; 95.954% | calcd 425.2, found 425.2 |
| 418 | 425.51 | 11.3 | 40.61%; 96.436% | calcd 426.2, found 426.2 |
| 419 | 488.58 | 13.9 | 50.91%; 97.346% | calcd 489.2, found 489.2 |
| 420 | 415.44 | 8.6 | 31.36%; 98.022% | calcd 416.2, found 416.2 |

Example 128. Human DPP1 Enzyme Single-Point Percent Inhibition Testing

A crude lysate of HL-60 cells (ATCC; Manassas, VA) was used as a source of human DPP1 enzyme in the assay. Lysate was prepared in 1% Triton X-100 in PBS at a concentration of 20,000 live cells per pL of lysis buffer and was centrifuged at 16,000 rcf for 10 minutes at 4° C., after which supernatant was collected and flash-frozen in liquid nitrogen. Test articles were applied to human DPP1 enzyme in Assay Buffer (25 mM MES pH 6.0, 50 mM NaCl, 5 mM DTT) in a total reaction volume of 125 μL. 25 μL of compound diluted to 50 nM in Assay Buffer plus 5% DMSO was first added to 50 μL of HL-60 lysate diluted to contain a DPP1 enzyme concentration of roughly 1 ng/μL and allowed to pre-incubate for 10 minutes at 37° C. after which 50 μL of 1000 μM H-Gly-Arg-AMC substrate (Bachem; St. Torrance, CA) was added, giving final compound concentration of 10 nM, a final substrate concentration of 400 μM and a final DMSO concentration of 1%. Substrate cleavage was measured for 90 minutes at 37° C., with fluorescence at Excitation/Emission 350/450 nm measured every 5 minutes. DPP1 concentration was interpolated based on its activity relative to a standard curve of activated human recombinant DPP1 enzyme. Percent inhibition at 10 nM was calculated for each test article based on remaining DPP1 activity compared to enzyme activity in wells that received only vehicle control.

Results are provided in Table 3 below. In Table 3, * * * represents percent inhibition of ≥66.7%, ** represents percent inhibition in the range of 40-66.7%, and * represents percent inhibition of ≤40%.

TABLE 3

| Human DPP1 Enzyme Single-Point Percent Inhibition | |
|---|---|
| Compound No. | human DPP1 enzyme % inhibition @ 10 nM |
| 295 | ** |
| 296 | * |
| 297 | * |
| 298 | * |
| 299 | * |
| 300 | ** |
| 301 | * |
| 302 | ** |
| 303 | * |
| 304 | * |
| 305 | * |
| 306 | * |
| 307 | ** |
| 308 | * |

TABLE 3-continued

| Human DPP1 Enzyme Single-Point Percent Inhibition | |
|---|---|
| Compound No. | human DPP1 enzyme % inhibition @ 10 nM |
| 309 | * |
| 310 | * |
| 311 | * |
| 312 | * |
| 313 | *** |
| 314 | ** |
| 315 | *** |
| 316 | * |
| 317 | ** |
| 318 | ** |
| 319 | *** |
| 320 | *** |
| 321 | ** |
| 322 | ** |
| 323 | * |
| 324 | ** |
| 325 | * |
| 326 | *** |
| 328 | * |
| 329 | * |
| 330 | * |
| 331 | * |
| 332 | * |
| 333 | ** |
| 334 | * |
| 335 | * |
| 336 | * |
| 338 | * |
| 339 | * |
| 340 | * |
| 341 | * |
| 342 | ** |
| 343 | * |
| 344 | ** |
| 345 | * |
| 346 | ** |
| 347 | * |
| 348 | ** |
| 349 | ** |
| 350 | * |
| 351 | * |
| 352 | * |
| 353 | ** |
| 354 | * |
| 355 | *** |
| 356 | ** |
| 357 | *** |
| 358 | * |
| 359 | ** |
| 360 | ** |
| 361 | ** |
| 362 | *** |
| 363 | ** |
| 364 | ** |
| 365 | * |
| 366 | ** |
| 368 | *** |
| 370 | * |
| 371 | * |
| 372 | * |
| 374 | * |
| 376 | * |
| 377 | * |
| 378 | * |
| 379 | * |
| 380 | * |
| 381 | ** |
| 382 | * |
| 383 | * |
| 384 | *** |
| 385 | *** |
| 386 | *** |
| 388 | *** |
| 389 | ** |
| 390 | *** |
| 391 | *** |

TABLE 3-continued

| Human DPP1 Enzyme Single-Point Percent Inhibition | |
|---|---|
| Compound No. | human DPP1 enzyme % inhibition @ 10 nM |
| 392 | *** |
| 393 | ** |
| 394 | * |
| 395 | *** |
| 396 | * |
| 397 | *** |
| 398 | *** |
| 399 | *** |
| 400 | ** |
| 401 | *** |
| 402 | *** |
| 403 | *** |
| 404 | *** |
| 405 | *** |
| 406 | *** |
| 407 | ** |
| 408 | *** |
| 409 | *** |
| 410 | *** |
| 413 | ** |
| 414 | * |
| 415 | * |
| 416 | ** |
| 417 | *** |
| 418 | ** |
| 419 | * |
| 420 | * |
| 375 | ** |

Example 129. DPP1 Cell Single-Point Percent Inhibition Testing

HL-60 cells (ATCC; Manassas, VA) were maintained in RPMI-1640 supplemented with 20% heat-inactivated FBS and 1× Antibiotic Antimycotic (Cytiva; Marlborough, MA). Media was changed every three to four days and cells were not allowed to exceed $1\times10^6$ cells per mL. Prior to assay, cells were collected by centrifugation at 500 rcf for 3 minutes, resuspended in RPMI (with no additional supplements) and counted. Cells were diluted in RPMI to a concentration of $5\times10^5$ live cells per mL and transferred to black 96-well plates for assay, 60 μL per well. Test articles were diluted to 25 nM in RPMI plus 0.5% DMSO, and 20 μL was added to each assay well. Compound was allowed to pre-incubate with cells with gentle shaking at 100 rpm for 60 minutes at 37° C. in a cell culture incubator maintained at 5% $CO_2$, after which 20 μL of 500 μM H-Gly-Phe-AFC cell-permeable substrate (MP Biomedicals; Solon, OH) in RPMI was added to each well, giving final compound concentration of 5 nM, a final substrate concentration of 100 μM and a final DMSO concentration of 0.1%. Plates were returned to the incubator with shaking at 100 rpm for 30 minutes, after which fluorescence was measured at Excitation/Emission 400/505 nm. Percent Inhibition was calculated from RFU values by first subtracting background values (wells in which RPMI was substituted for cells) from each well, and then subtracting background-subtracted RFU derived from wells that received a final concentration of 10 μM brensocatib. This value represents the non-specific substrate cleavage from the HL-60 cells, and the remaining RFU should theoretically be solely the contribution of DPP1 enzyme activity. The final percent inhibition value was calculated for each test article based on remaining RFU compared to RFU from wells that received only vehicle control.

Results are provided in Table 4 below. In Table 4, * * * represents percent inhibition of ≥93.900, * * represents percent inhibition in the range of 76.5-93.9%, and * represents percent inhibition of ≤76.5%.

TABLE 4

| DPP1 Cell Single-Point Percent Inhibition | |
|---|---|
| Compound No. | DPP1 cell % inhibition @ 5 nM |
| 295 | * |
| 296 | * |
| 297 | * |
| 298 | * |
| 299 | * |
| 300 | * |
| 301 | ** |
| 302 | * |
| 303 | * |
| 304 | * |
| 305 | * |
| 306 | * |
| 307 | * |
| 308 | * |
| 309 | * |
| 310 | ** |
| 311 | ** |
| 312 | * |
| 313 | * |
| 314 | *** |
| 315 | * |
| 316 | * |
| 317 | * |
| 318 | ** |
| 319 | * |
| 320 | * |
| 321 | * |
| 322 | * |
| 323 | ** |
| 324 | ** |
| 325 | * |
| 326 | * |
| 328 | * |
| 329 | * |
| 330 | * |
| 331 | * |
| 332 | * |
| 333 | ** |
| 334 | * |
| 335 | * |
| 336 | * |
| 338 | * |
| 339 | * |
| 341 | * |
| 342 | * |
| 343 | * |
| 344 | * |
| 345 | * |
| 346 | * |
| 347 | * |
| 348 | * |
| 349 | * |
| 350 | * |
| 351 | * |
| 352 | * |
| 353 | ** |
| 354 | * |
| 355 | * |
| 356 | ** |
| 357 | * |
| 358 | * |
| 359 | * |
| 360 | ** |
| 361 | * |
| 362 | * |
| 363 | * |
| 364 | * |
| 365 | * |
| 366 | ** |
| 368 | * |

TABLE 4-continued

| DPP1 Cell Single-Point Percent Inhibition | |
|---|---|
| Compound No. | DPP1 cell % inhibition @ 5 nM |
| 370 | * |
| 371 | * |
| 372 | * |
| 374 | * |
| 376 | * |
| 377 | * |
| 378 | * |
| 379 | * |
| 380 | * |
| 381 | ** |
| 382 | * |
| 383 | * |
| 384 | * |
| 385 | *** |
| 386 | ** |
| 388 | *** |
| 389 | ** |
| 390 | * |
| 391 | * |
| 392 | * |
| 393 | * |
| 394 | ** |
| 395 | ** |
| 396 | * |
| 397 | * |
| 398 | *** |
| 399 | *** |
| 400 | ** |
| 401 | *** |
| 402 | ** |
| 403 | ** |
| 404 | * |
| 405 | ** |
| 406 | ** |
| 407 | *** |
| 408 | *** |
| 409 | ** |
| 410 | *** |
| 413 | ** |
| 414 | * |
| 415 | * |
| 416 | ** |
| 417 | ** |
| 418 | * |
| 419 | * |
| 420 | * |
| 375 | ** |

NUMBER CLAUSES

Clauses—Set 1

1. A compound of Formula (I)

(I)

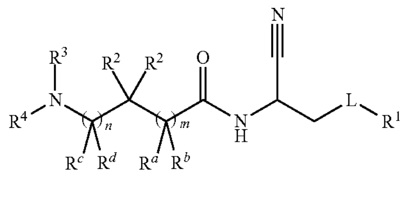

or a pharmaceutically acceptable salt, a stereoisomer or a deuterated form thereof, wherein $R^1$ is carbocyclyl, aryl, heterocyclyl, or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

each $R^2$ is independently H, OH, CN, $OC_{1-6}$ alkyl, $NH_2$, SH, C(═O)alkyl, C(═O)$NH_2$, $C_{1-6}$ alkyl, $C_{1-6}$ haloalkyl, $C_{2-6}$ alkenyl, carbocyclyl, heterocyclyl, aryl, heteroaryl, $C_{1-6}$ alkylene-aryl, $C_{1-6}$ alkylene-heteroaryl, or $C_{1-6}$ alkylene-carbocyclyl, each of aryl, heteroaryl, and carbocyclyl are optionally substituted with 1-4 groups independently selected from alkyl, halogen, OH, C(═O)OH, $NH_2$, NH(alkyl), $NH(alkyl)_2$, $OC_{1-6}$ alkyl;

or two $R^2$ together form (═O);

each of $R^3$ and $R^4$ is independently selected from H, alkyl, cycloalkyl, aryl, heterocyclyl, heteroaryl, alkylene-aryl, alkylene-heteroaryl, C(═O)alkyl, C(═O)cycloalkyl, C═(O)aryl, C(═O)heteroaryl, wherein the alkyl, cycloalkyl, aryl, heterocyclyl, heteroaryl, and alkylene is optionally substituted with 1-4 groups independently selected from alkyl, halogen, OH, $NH_2$, NH(alkyl), $NH(alkyl)_2$, $OC_{1-6}$ alkyl;

or $R^3$ and $R^4$ together with the nitrogen to which they are attached form a heterocyclyl, wherein the heterocyclyl is optionally substituted with 1-4 groups selected from alkyl, halogen, OH, $NH_2$, NH(alkyl), $NH(alkyl)_2$, or $OC_{1-6}$ alkyl;

each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, C(═O)$OC_{1-6}$ alkyl, $CONHC_{1-6}$ alkyl, $CON(C_{1-6}\ alkyl)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_2$-6alkynyl and $C_{3-6}$cycloalkyl; wherein the $C_{1-6}$ alkyl, $NH_2$, $N(C_{1-6}\ alkyl)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}\ alkyl)$, $N(C_{1-6}\ alkyl)_2$, cycloalkyl, aryl, heterocyclyl or heteroaryl and COOH;

each $R^7$ is independently H, ═O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH—$C_{1-6}$ alkyl, $N(C_{1-6}\ alkyl)_2$, COOH, $COC_{1-6}$ alkyl, C(═O)$OC_{1-6}$ alkyl, $CON_{1-6}$ alkyl, $CON(C_{1-6}\ alkyl)_2$, or $NHCOC_{1-6}$ alkyl;

or one $R^7$ and one $R^5$ together form a cycloalkyl, aryl, heterocyclyl or heteroaryl ring, wherein the cycloalkyl, aryl, heterocyclyl, heteroaryl is optionally substituted with 1-4 groups selected from alkyl, halogen, Oalkyl, haloalkyl, OH or CN;

each of $R^a$, $R^b$, $R^c$ and $R^d$ is independently selected from H, alkyl, halogen or haloalkyl;

each of n and m is independently 0, 1, 2, or 3;

provided that the compound is not

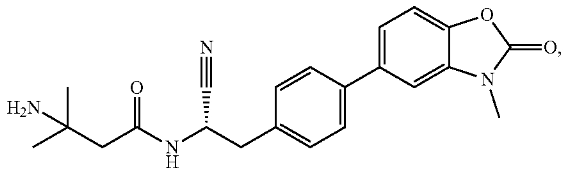

,

-continued

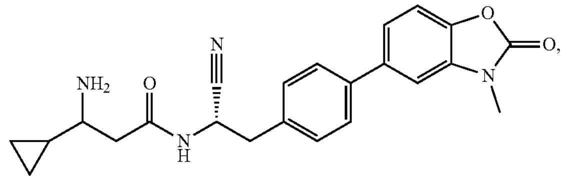

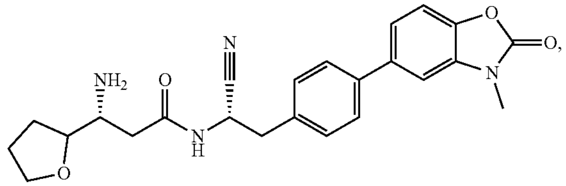

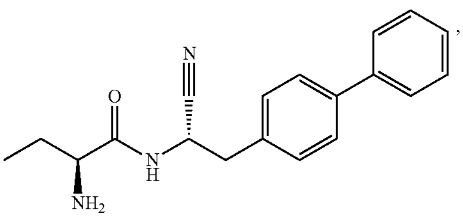

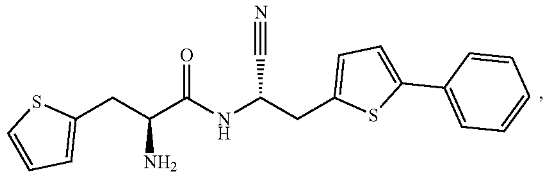

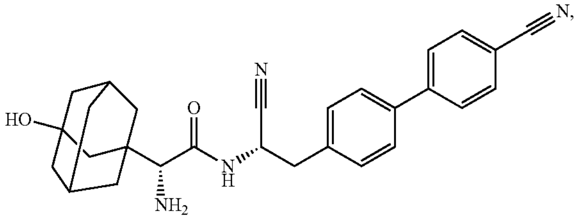

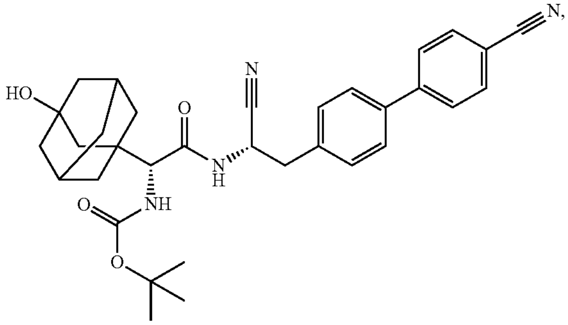

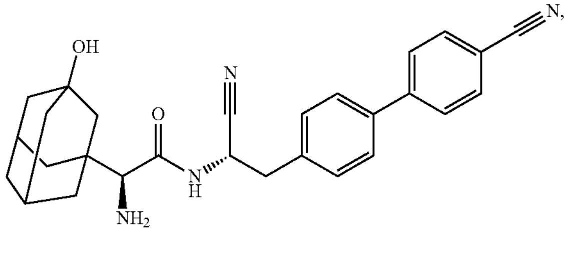

-continued

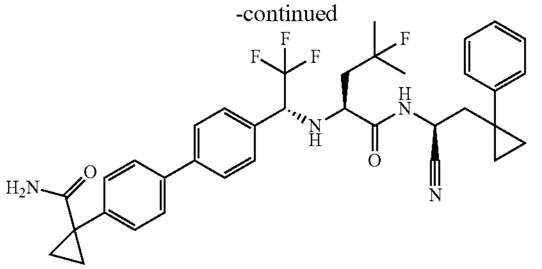

or

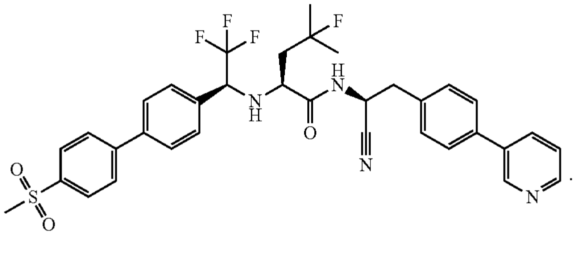

2. A compound of Formula (II)

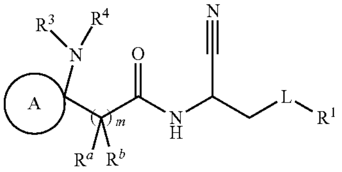

(II)

or a pharmaceutically acceptable salt, a stereoisomer or a deuterated form thereof, wherein $R^1$ is carbocyclyl, aryl, heterocyclyl, or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

Ring A is a carbocyclyl or heterocyclyl;

each of $R^3$ and $R^4$ is independently selected from H, alkyl, cycloalkyl, aryl, heterocyclyl, heteroaryl, alkylene-aryl, alkylene-heteroaryl, C(═O)alkyl, C(═O)cycloalkyl, C═(O)aryl, C(═O)heteroaryl, wherein the alkyl, cycloalkyl, aryl, heterocyclyl, heteroaryl, and alkylene is optionally substituted with 1-4 groups independently selected from alkyl, halogen, OH, $NH_2$, NH(alkyl), $NH(alkyl)_2$, $OC_{1-6}$alkyl; or $R^3$ and $R^4$ together with the nitrogen to which they are attached form a heterocyclyl, wherein the heterocyclyl is optionally substituted with 1-4 groups selected from alkyl, halogen, OH, $NH_2$, NH(alkyl), $NH(alkyl)_2$, or $OC_{1-6}$alkyl;

each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, $C({=}O)OC_{1-6}$ alkyl, $CONHC_{1-6}$ alkyl, $CON(C_{1-6}\ alkyl)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_2$-6alkynyl and $C_{3-6}$cycloalkyl;

wherein the alkyl, $NH_2$, $N(C_{1-6}$ alkyl$)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl or heteroaryl and COOH; each $R^7$ is independently H, =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH—$C_{1-6}$ alkyl, $N(C_{1-6}$ alkyl$)_2$, COOH, $COC_{1-6}$ alkyl, C(=O)$OC_{1-6}$ alkyl, $CON_{1-6}$ alkyl, $CON(C_{1-6}$ alkyl$)_2$, or $NHCOC_{1-6}$ alkyl;

each of $R^a$ and $R^b$ is independently selected from H, alkyl, halogen or haloalkyl;

m is independently 0, 1, 2, or 3;

provided that the compound is not

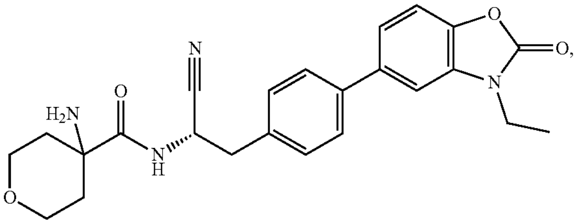

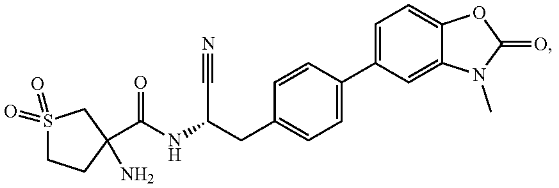

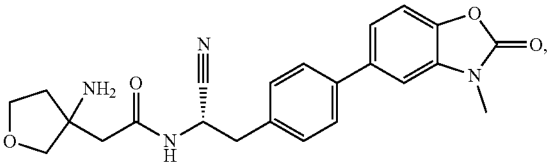

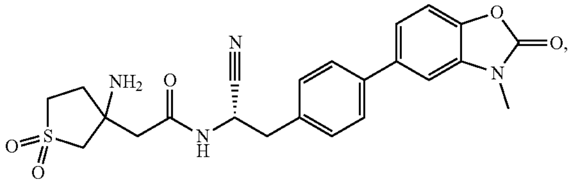

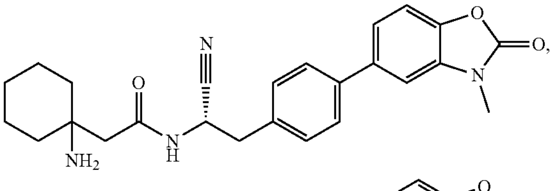

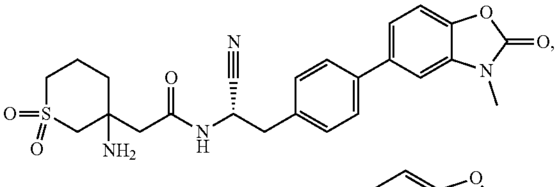

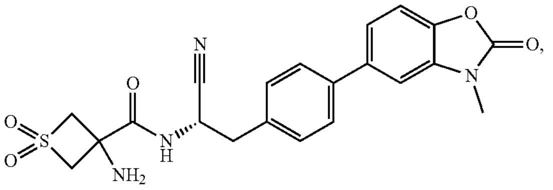

-continued

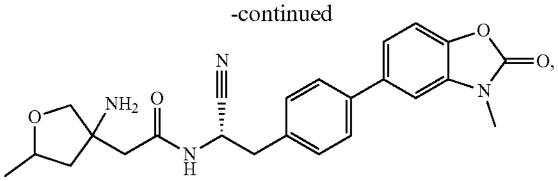

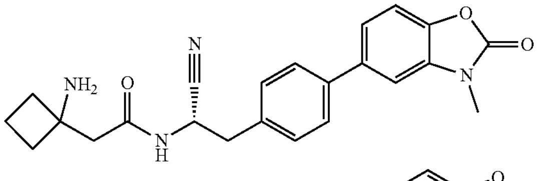

or

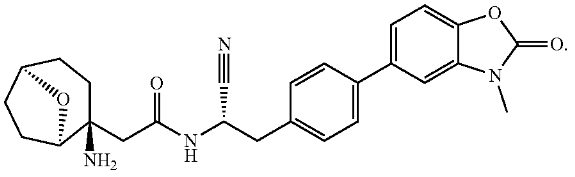

3. The compound of clause 1, or a pharmaceutically acceptable salt, a stereoisomer or a deuterated form thereof, wherein the compound is a compound of Formula (III)

(III)

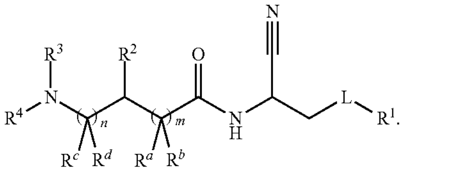

4. The compound of clause 1, or a pharmaceutically acceptable salt, a stereoisomer or a deuterated form thereof, wherein the compound is a compound of Formula (IV), (IV)

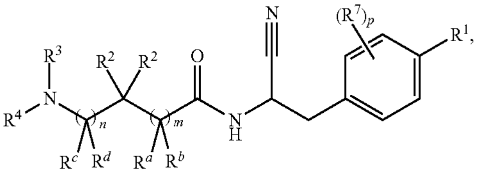

p is 0, 1, or 2, and $R^7$ is halogen, alkyl, Oalkyl or haloalkyl.

5. The compound of clause 1, or a pharmaceutically acceptable salt, a stereoisomer or a deuterated Form thereof, wherein the compound is a compound of Formula (V), (V)

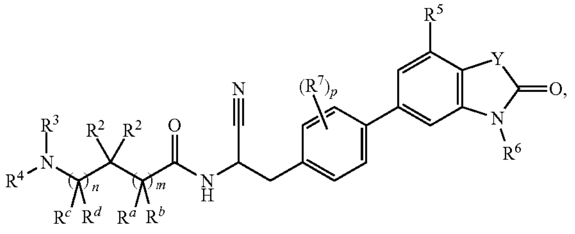

wherein each Y is independently $NR^6$, O, $CR^8R^9$, S, S(O) or $S(O)_2$, each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, $C(=O)OC_{1-6}$ alkyl, $CONHC_{1-6}$ alkyl, $CON(C_{1-6}\ alkyl)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_2$-6alkynyl and $C_{3-6}$cycloalkyl; wherein the alkyl, $NH_2$, $N(C_{1-6}\ alkyl)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}\ alkyl)$, $N(C_{1-6}\ alkyl)_2$, cycloalkyl, aryl, heterocyclyl or heteroaryl and COOH;

p is 0, 1, or 2,;

$R^7$ is halogen, alkyl, Oalkyl or haloalkyl;

$R^8$ and $R^9$ are each independently selected from H, halogen, $C_{1-6}$ alkyl, $C_{1-6}$alkoxy, $C_2$-6 alkenyl, $C_{2-6}$ alkynyl, $OC_{2-6}$alkenyl, $OC_{2-6}$ alkynyl, $C_{3-6}$ cycloalkyl, $OC_{3-6}$ cycloalkyl, CN, OH, $NH_2$, C(O)OH, —$S(O)C_{1-6}$alkyl, —$S(O)_2C_{1-6}$ alkyl, —$S(O)_2C_{3-6}$cycloalkyl, —$SO_2$-heterocyclyl, and heterocyclyl containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl and —COOH; and or $R^8$ and $R^9$ form =O.

6. The compound of clause 1, or a pharmaceutically acceptable salt, a stereoisomer or a deuterated form thereof, wherein the compound is a compound of Formula (VI), (VI)

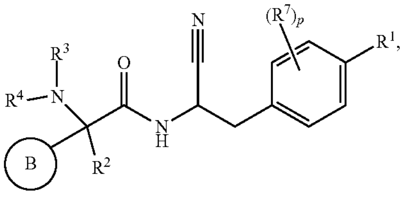

wherein Ring B is a 3-6 membered carbocyclyl or heterocyclyl.

7. The compound of clause 1, or a pharmaceutically acceptable salt, a stereoisomer or a deuterated form thereof, wherein the compound is a compound of Formula (VII), (VII)

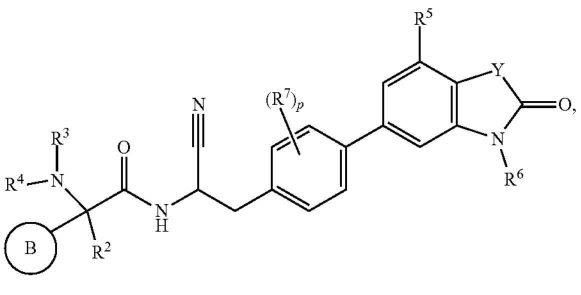

Ring B is a 3-6 membered carbocyclyl or heterocyclyl, each Y is independently $NR^6$, O, $CR^8R^9$, S, S(O) or $S(O)_2$, each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, $C(=O)OC_{1-6}$ alkyl, $CONHC_{1-6}$ alkyl, $CON(C_{1-6}\ alkyl)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_{2-6}$alkynyl and $C_{3-6}$cycloalkyl; wherein the alkyl, $NH_2$, $N(C_{1-6}\ alkyl)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}\ alkyl)$, $N(C_{1-6}\ alkyl)_2$, cycloalkyl, aryl, heterocyclyl or heteroaryl and COOH;

p is 0, 1, 2, 3 or 4;

$R^7$ is halogen, alkyl, Oalkyl or haloalkyl;

$R^8$ and $R^9$ are each independently selected from H, halogen, $C_{1-6}$ alkyl, $C_{1-6}$alkoxy, $C_2$-6 alkenyl, $C_{2-6}$ alkynyl, $OC_{2-6}$alkenyl, $OC_{2-6}$ alkynyl, $C_{3-6}$ cycloalkyl, $OC_{3-6}$ cycloalkyl, CN, OH, $NH_2$, C(O)OH, —$S(O)C_{1-6}$alkyl, —$S(O)_2C_{1-6}$ alkyl, —$S(O)_2C_{3-6}$cycloalkyl, —$SO_2$-heterocyclyl, and heterocyclyl containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl and —COOH; and or $R^8$ and $R^9$ form =O.

8. The compound of any one of clauses 1 and 3-7, wherein each $R^2$ is independently H, OH, CN, $OC_{1-6}$ alkyl, $NH_2$, SH, C(=O)alkyl, $C(=O)NH_2$, $C_{1-6}$ alkyl, $C_{1-6}$ haloalkyl, $C_{2-6}$ alkenyl, carbocyclyl, heterocyclyl, aryl, heteroaryl, $C_{1-6}$ alkylene-aryl, $C_{1-6}$ alkylene-heteroaryl, or $C_{1-6}$ alkylene-carbocyclyl, each of aryl, heteroaryl, and carbocyclyl are optionally substituted with 1-4 groups independently selected from alkyl, halogen, OH, C(=O)OH, $NH_2$, NH(alkyl), $NH(alkyl)_2$, $OC_{1-6}$ alkyl.

9. The compound of any one of clauses 1 and 3-8, wherein each $R^2$ is independently H, OH, CN, $OC_{1-6}$ alkyl, $NH_2$, SH, $C_{1-6}$ alkyl, $C_{2-6}$ alkenyl, $C_{1-6}$ haloalkyl, $C_{1-6}$ alkylene-aryl, $C_{1-6}$ alkylene-heteroaryl, $C_{1-6}$ alkylene-carbocyclyl, each of alkyl, alkylene, aryl, heteroaryl, and carbocyclyl are optionally substituted with 1-4 groups independently selected from alkyl, halogen, OH, $NH_2$, NH(alkyl), $NH(alkyl)_2$, $OC_{1-6}$ alkyl.

10. The compound of any one of clauses 1 and 3-9, or a pharmaceutically acceptable salt, a stereoisomer or a deuterated form thereof, wherein each $R^2$ is independently H, OH, CN, $OCH_3$, $OCH_2CH_3$, $OCH_2CH_2CH_3$, SH, $NH_2$, $CH_3$, $CH_2CH_3$, $CH_2(CH_3)_2$,

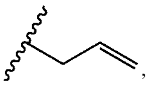

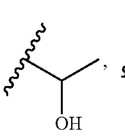

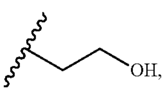

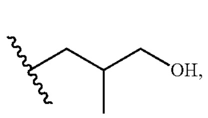

-continued
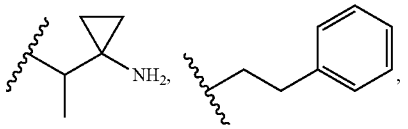
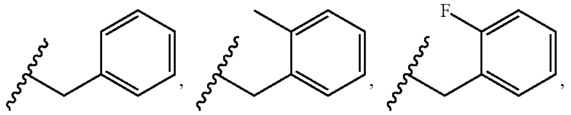
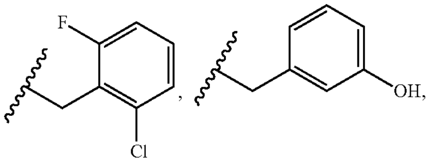
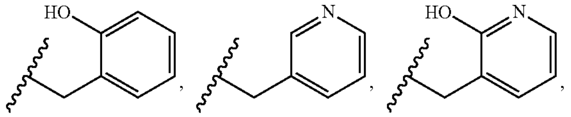
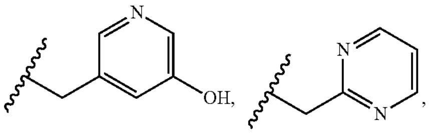
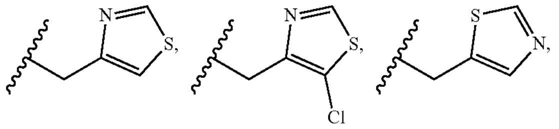
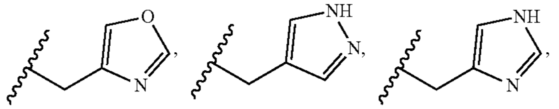
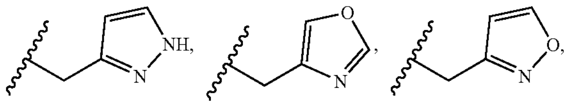
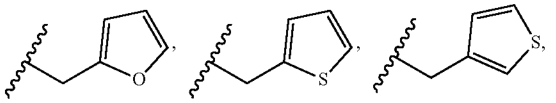
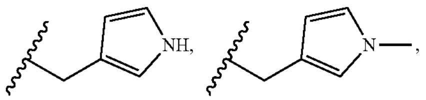
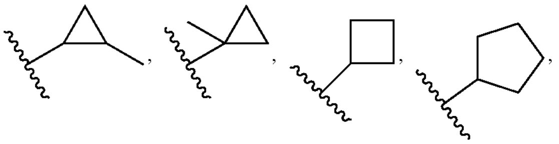
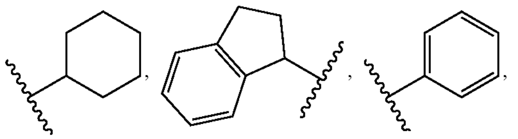
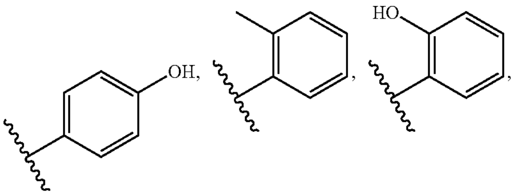
-continued
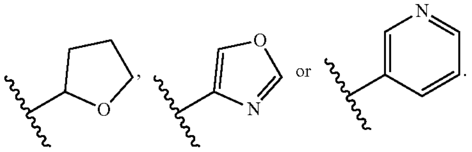
11. The compound of any one of clauses 1 and 4-5, or a pharmaceutically acceptable salt, a stereoisomer or a deuterated form thereof, wherein one of $R^2$ is H, and the other $R^2$ is H, OH, CN, $OCH_3$, $OCH_2CH_3$, $OCH_2CH_2CH_3$, SH, $NH_2$, $CH_3$, $CH_2CH_3$, $CH_2(CH_3)_2$,
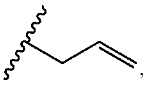 [SMILES: *CC=C]
$CHF_2$, $CH_2Cl$, —CH(COOH)$NH_2$, $CH_2CH_2CH_2F$,
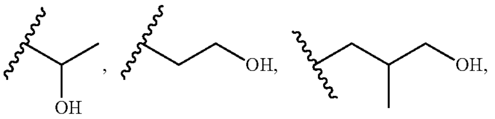
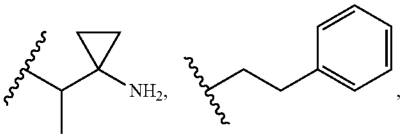
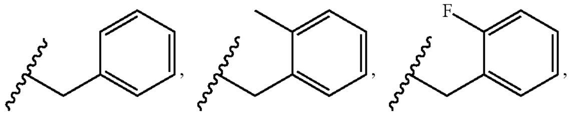
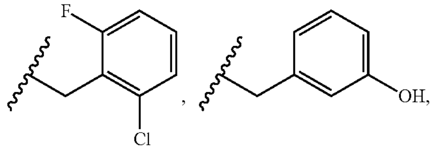
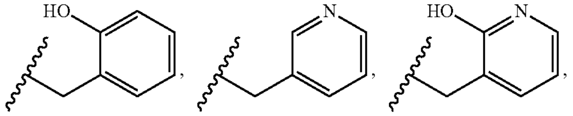
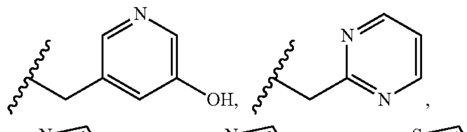
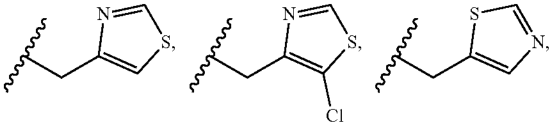
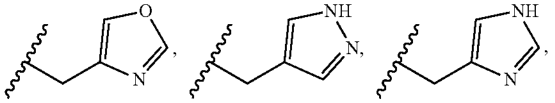
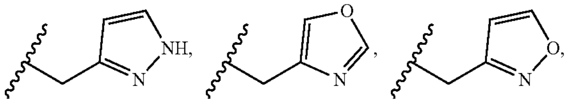

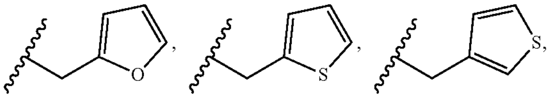

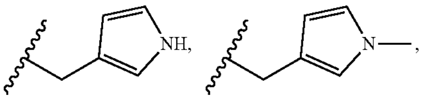

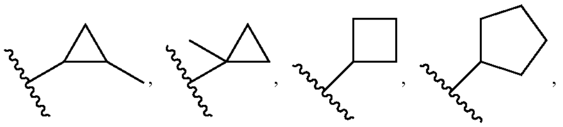

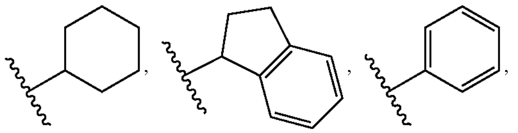

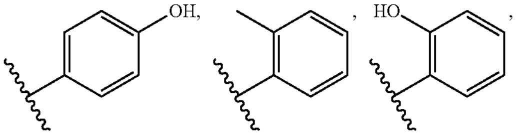

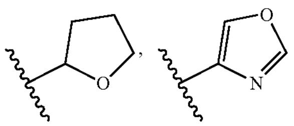

or

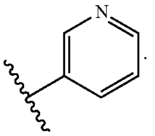

12. The compound of any one of clauses 1, 4-5 and 11, or a pharmaceutically acceptable salt, a stereoisomer or a deuterated form thereof, wherein one of $R^2$ is $CH_3$, and the other $R^2$ is H, OH, CN, $OCH_3$, $OCH_2CH_3$, $OCH_2CH_2CH_3$, SH, $NH_2$, $CH_3$, $CH_2CH_3$, $CH_2(CH_3)_2$,

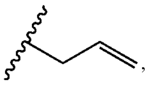

$CHF_2$, $CH_2Cl$, $—CH(COOH)NH_2$, $CH_2CH_2CH_2F$,

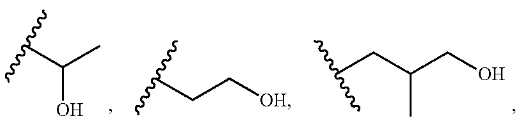

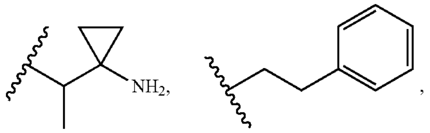

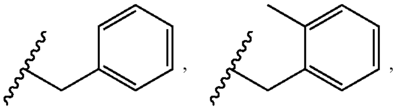

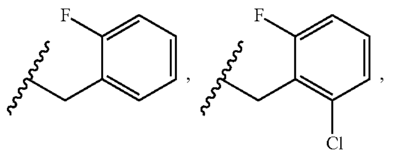

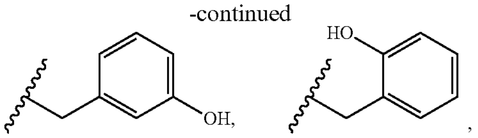

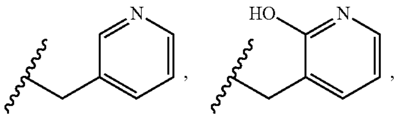

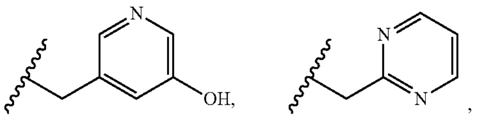

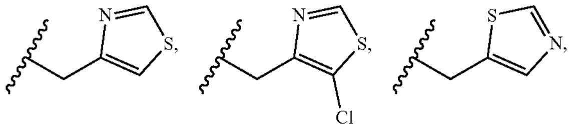

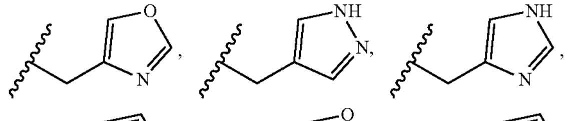

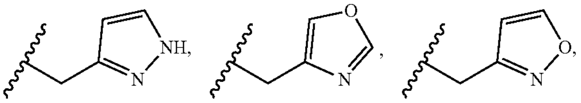

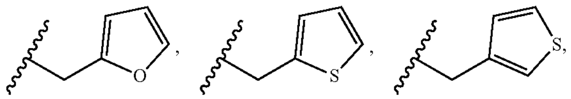

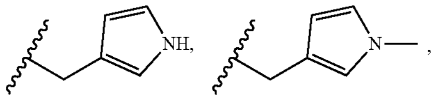

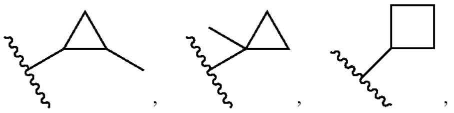

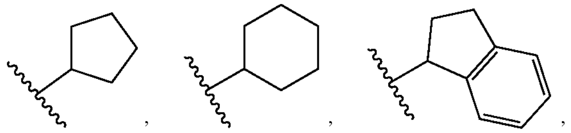

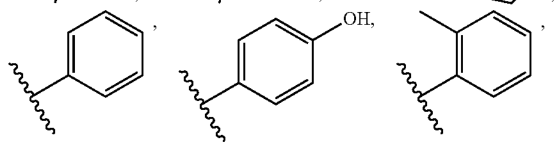

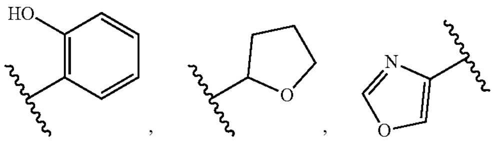

or

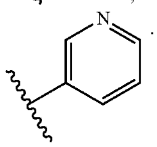

13. The compound of any one of clauses 1, 4-5 and 11-12, or a pharmaceutically acceptable salt, a stereoisomer or a deuterated form thereof, wherein one of $R^2$ is $C_{1-6}$ alkyl, and the other $R^2$ is cycloalkyl.

14. The compound of any one of clauses 1, 4-5 and 11-13, or a pharmaceutically acceptable salt, a stereoisomer or a deuterated form thereof, wherein one of $R^2$ is $C_{1-6}$ alkyl, and the other $R^2$ is $C_{3-6}$ cycloalkyl.

15. The compound of any one of clauses 1, 4-5 and 11-14, or a pharmaceutically acceptable salt, a stereoisomer or a deuterated form thereof, wherein one of $R^2$ is $CH_3$, and the other $R^2$ is

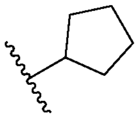

or

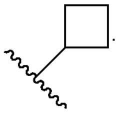

16. The compound of any one of clauses 1, 4-5 and 11-15, or a pharmaceutically acceptable salt or deuterated form thereof, wherein one of $R^2$ is $CH_3$, and the other $R^2$ is

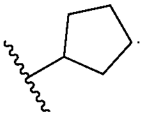

17. The compound of any one of clauses 1, 4-5 and 11-15, or a pharmaceutically acceptable salt or deuterated form thereof, wherein one of $R^2$ is $CH_3$, and the other $R^2$ is

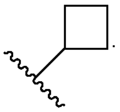

18. The compound of any one of clauses 1 and 4-5, or a pharmaceutically acceptable salt or deuterated form thereof, wherein one of $R^2$ is H, and the other $R^2$ is OH, $OCH_3$, $CH_3$, $CH_2CH_3$, $CH(CH_3)_2$,

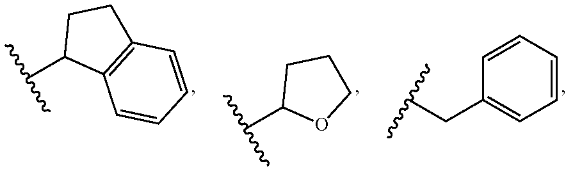

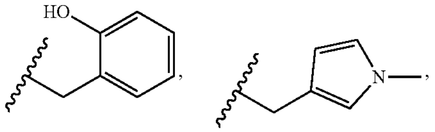

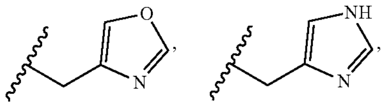

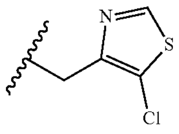

or

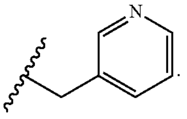

19. The compound of any one of clauses 1, 4-5 and 18, or a pharmaceutically acceptable salt or deuterated form thereof, wherein one of $R^2$ is H, and the other $R^2$ is OH or $OCH_3$.

20. The compound of any one of clauses 1, 3 and 6-7, or a pharmaceutically acceptable salt or deuterated form thereof, wherein $R^2$ is OH, $OCH_3$, $CH_3$, $CH_2CH_3$, $CH(CH_3)_2$,

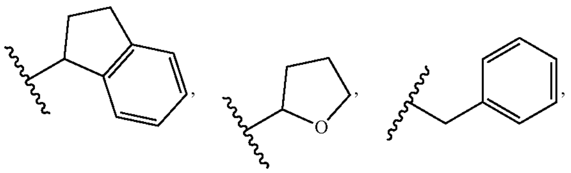

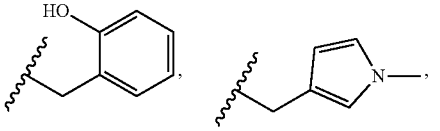

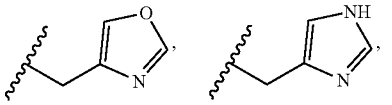

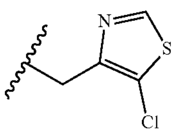

or

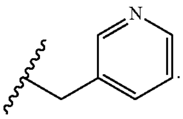

21. The compound of clause 1, 3, 6-7 and 20, or a pharmaceutically acceptable salt or deuterated form thereof, wherein $R^2$ is OH or $OCH_3$.

22. The compound of any clause 1 and 4-5, or a pharmaceutically acceptable salt or deuterated form thereof, wherein two $R^2$ together form (=O).

23. The compound of clause 2, or a pharmaceutically acceptable salt or deuterated form thereof, wherein the A ring is

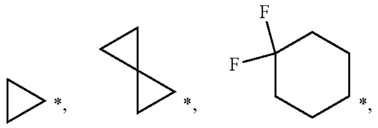

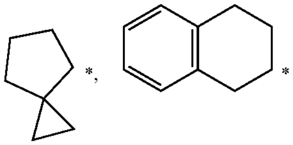

or

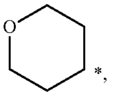

wherein the asterisk represents the site of attachment.

24. The compound of clause 2 or 23, or a pharmaceutically acceptable salt or deuterated form thereof, wherein the A ring is

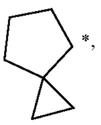

wherein the asterisk represents the site of attachment.

25. The compound of any one of clauses 1-24, or a pharmaceutically acceptable salt or deuterated form thereof, wherein each of $R^3$ and $R^4$ is independently selected from H, $C_{1-6}$ alkyl, cycloalkyl, aryl, heterocyclyl, heteroaryl, alkylene-aryl, or alkylene-heteroaryl, C(=O)aryl, C(=O) heteroaryl, wherein the alkyl, cycloalkyl, aryl, heterocyclyl, heteroaryl, and alkylene is optionally substituted with 1-4 groups selected from alkyl, halogen, OH, $NH_2$, $NH(C_{1-6}$ alkyl), $NH(C_{1-6}$ alkyl$)_2$, $OC_{1-6}$ alkyl.

26. The compound of any one of clauses 1-25, or a pharmaceutically acceptable salt or deuterated form thereof, wherein each of $R^3$ and $R^4$ is independently selected from H, $C_{1-6}$ alkyl, alkylene-heteroaryl, or C(=O)heteroaryl, wherein the $C_{1-6}$ alkyl, alkylene-heteroaryl, and C(=O) heteroaryl are optionally substituted with 1-4 groups selected from alkyl, halogen, OH, $OC_{1-6}$ alkyl.

27. The compound of any one of clauses 1-26, or a pharmaceutically acceptable salt or deuterated form thereof, wherein each of $R^3$ and $R^4$ is independently selected from H, $—CH_3$, $—CH_2CH_3$, $—CH_2CH_2CH_3$,

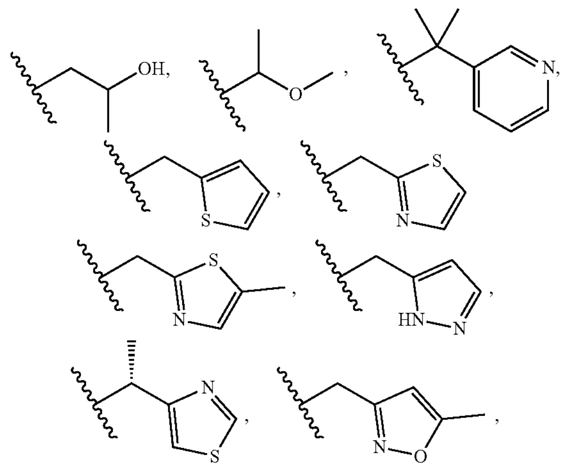

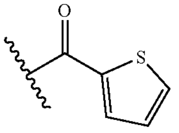

or

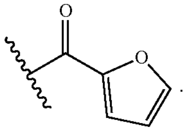

28. The compound of any one of clauses 1-27, or a pharmaceutically acceptable salt or deuterated form thereof, wherein $R^3$ and $R^4$ are each H.

29. The compound of any one of clauses 1-27, or a pharmaceutically acceptable salt or deuterated form thereof, wherein $R^3$ is H and $R^4$ is $—CH_3$, $—CH_2CH_3$, $—CH_2CH_2CH_3$,

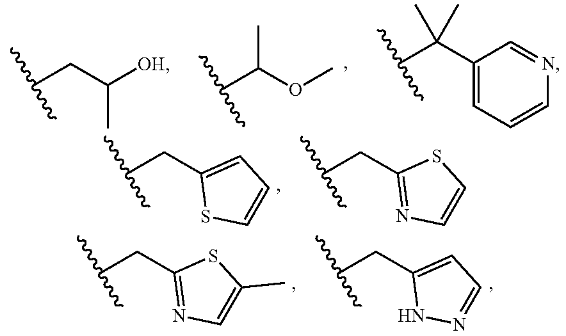

-continued

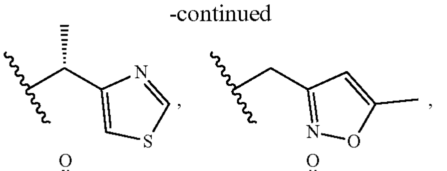

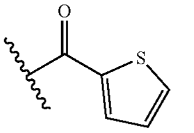

or

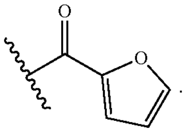

30. The compound of any one of clauses 1-27, or a pharmaceutically acceptable salt or deuterated form thereof, wherein $R^3$ and $R^4$ is independently selected from H or $C_{1-6}$ alkyl.

31. The compound of any one of clauses 1-27 and 30, or a pharmaceutically acceptable salt or deuterated form thereof, wherein each of $R^3$ and $R^4$ is independently selected from H, $—CH_3$, $—CH_2CH_3$ or $—CH_2CH_2CH_3$.

32. The compound of any one of clauses 1-27 and 30-31, or a pharmaceutically acceptable salt or deuterated form thereof, wherein $R^3$ is H and $R^4$ is $—CH_3$, $—CH_2CH_3$ or $—CH_2CH_2CH_3$.

33. The compound of any one of clauses 1-27 and 30-32, or a pharmaceutically acceptable salt or deuterated form thereof, wherein $R^3$ is H and $R^4$ is $—CH_3$.

34. The compound of any one of clauses 1-27 and 30-32, or a pharmaceutically acceptable salt or deuterated form thereof, wherein $R^3$ is H and $R^4$ is $—CH_2CH_3$.

35. The compound of any one of clauses 1-27 and 30-32, or a pharmaceutically acceptable salt or deuterated form thereof, wherein $R^3$ is H and $R^4$ is $—CH_2CH_2CH_3$.

36. The compound of any one of clauses 1-27, or a pharmaceutically acceptable salt or deuterated form thereof, wherein each of $R_3$ and $R^4$ is independently selected from $C_{1-6}$ alkyl optionally substituted with 1-4 groups selected from OH, halogen, $OC_{1-6}$ alkyl, cycloalkyl, aryl, heterocycle or heteroaryl.

37. The compound of any one of clauses 1-27 and 36, or a pharmaceutically acceptable salt or deuterated form thereof, wherein each of $R_3$ and $R^4$ is independently selected from $C_{1-6}$ alkyl.

38. The compound of any one of clauses 1-27 and 36-37, or a pharmaceutically acceptable salt or deuterated form thereof, wherein each of $R^3$ and $R^4$ is independently $—CH_3$, $—CH_2CH_3$ or $—CH_2CH_2CH_3$.

39. The compound of any one of clauses 1-27 and 36-38, or a pharmaceutically acceptable salt or deuterated form thereof, wherein each of $R^3$ and $R^4$ is $—CH_3$.

40. The compound of any one of clauses 1-27 and 36-38, or a pharmaceutically acceptable salt or deuterated form thereof, wherein each of $R^3$ and $R^4$ is $—CH_2CH_3$.

41. The compound of any one of clauses 1-27 and 36-38, or a pharmaceutically acceptable salt or deuterated form thereof, wherein $R^3$ is $—CH_3$ and $R^4$ is $—CH_2CH_3$.

42. The compound of any one of clauses 1-27 and 36-38, or a pharmaceutically acceptable salt or deuterated form thereof, wherein $R^3$ is $—CH_3$ and $R^4$ is $—CH_2CH_2CH_3$.

43. The compound of any one of clauses 1-26, or a pharmaceutically acceptable salt or deuterated form thereof, wherein $R^3$ and $R^4$ with the nitrogen they are connected to are taken together to form a heterocyclyl, wherein the heterocyclyl is optionally substituted with 1-4 groups selected from halogen, OH, $NH_2$, $NH(C_{1-6}$ alkyl), $NH(C_{1-6}$ alkyl$)_2$, $C_{1-6}$ alkyl, $OC_{1-6}$ alkyl.

44. The compound of any one of clauses 1-26 or 43, or a pharmaceutically acceptable salt or deuterated form thereof, wherein $R^3$ and $R^4$ with the nitrogen they are connected to are taken together to form a 3-8 membered heterocyclyl.

45. The compound of any one of clauses 1-26 and 43-44, or a pharmaceutically acceptable salt or deuterated form thereof, wherein $R^3$ and $R^4$ with the nitrogen they are connected to are taken together to form a heterocyclyl selected from,

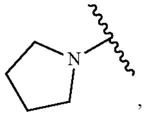
,
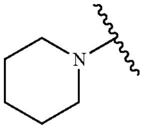
or
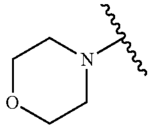
.

46. The compound of any one of clauses 1 and 3-45, or a pharmaceutically acceptable salt or deuterated form thereof, wherein each one of $R^a$, $R^b$, $R^c$ and $R^d$ is selected from H, $C_{1-6}$ alkyl, halogen or $C_{1-6}$ haloalkyl.

47. The compound of any one of clauses 1 and 3-46, or a pharmaceutically acceptable salt or deuterated form thereof, wherein each one of $R^a$, $R^b$, $R^c$ and $R^d$ is H.

48. The compound of any one of clauses 1 and 3-46, or a pharmaceutically acceptable salt or deuterated form thereof, wherein one of $R^a$, $R^b$, $R^c$ and $R^d$ is —$CH_3$ or —$CH_2CH_3$, $CH(CH_3)_2$, $CH_2Cl$, $CHF_2$, and all the remaining $R^a$, $R^b$, $R^c$ and $R^d$ is H.

49. The compound of any one of clauses 1, 3-46 and 48, or a pharmaceutically acceptable salt or deuterated form thereof, wherein $R^c$ is —$CH_3$ or —$CH_2CH_3$, $CH(CH_3)_2$, $CH_2Cl$, $CHF_2$, and each of $R^a$, $R^b$ and $R^d$ is H.

50. The compound of any one of clauses 1-49, or a pharmaceutically acceptable salt or deuterated form thereof, wherein m is 0, 1 or 2.

51. The compound of any one of clauses 1-50, or a pharmaceutically acceptable salt or deuterated form thereof, wherein m is 0.

52. The compound of any one of clauses 1-50, or a pharmaceutically acceptable salt or deuterated form thereof, wherein m is 1.

53. The compound of any one of clauses 1-50, or a pharmaceutically acceptable salt or deuterated form thereof, wherein m is 2.

54. The compound of any one of clauses 1 and 3-53, or a pharmaceutically acceptable salt or deuterated form thereof, wherein n is 0, 1 or 2.

55. The compound of any one of clauses 1 and 3-54, or a pharmaceutically acceptable salt or deuterated form thereof, wherein n is 0.

56. The compound of any one of clauses 1 and 3-54, or a pharmaceutically acceptable salt or deuterated form thereof, wherein n is 1.

57. The compound of any one of clauses 1 and 3-54, or a pharmaceutically acceptable salt or deuterated form thereof, wherein n is 2.

58. The compound of any one of clauses 1 and 3-50, or a pharmaceutically acceptable salt or deuterated form thereof, wherein m is 0 and n is 0, 1, or 2.

59. The compound of any one of clauses 1 and 3-50, or a pharmaceutically acceptable salt or deuterated form thereof, wherein m is 0 and n is 0.

60. The compound of any one of clauses 1 and 3-50, or a pharmaceutically acceptable salt or deuterated form thereof, wherein m is 0 and n is 1.

61. The compound of any one of clauses 1 and 3-50, or a pharmaceutically acceptable salt or deuterated form thereof, wherein m is 0 and n is 2.

62. The compound of any one of clauses 1 and 3-50, or a pharmaceutically acceptable salt or deuterated form thereof, wherein m is 1 and n is 0 or 1.

63. The compound of any one of clauses 1 and 3-50, or a pharmaceutically acceptable salt or deuterated form thereof, wherein m is 1 and n is 0.

64. The compound of any one of clauses 1 and 3-50, or a pharmaceutically acceptable salt or deuterated form thereof, wherein m is 1 and n is 1.

65. The compound of any one of clauses 1 and 3-50, or a pharmaceutically acceptable salt or deuterated form thereof, wherein m is 2 and n is 0.

66. The compound of any one of clauses 1-3 and 8-65, or a pharmaceutically acceptable salt or deuterated form thereof, wherein L is arylene, heterocyclylene or heteroarylene, wherein L is optionally substituted by 1-4 $R^7$.

67. The compound of any one of clauses 1-3 and 8-66, or a pharmaceutically acceptable salt or deuterated form thereof, wherein L is arylene optionally substituted by 1-4 $R^7$.

68. The compound of any one of clauses 1-3 and 8-67, or a pharmaceutically acceptable salt or deuterated form thereof, wherein L

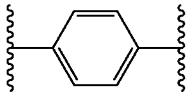

optionally substituted by 1-4 $R^7$.

69. The compound of any one of clauses 66-68, or a pharmaceutically acceptable salt or deuterated form thereof, wherein $R^7$ is halo.

70. The compound of any one of clauses 1-3 and 8-68, or a pharmaceutically acceptable salt or deuterated form thereof, wherein L is

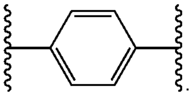 [SMILES: *c1ccc(*)cc1]
.

71. The compound of any one of clauses 1-3 and 8-68, or a pharmaceutically acceptable salt or deuterated form thereof, wherein L is

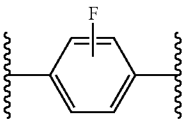
or
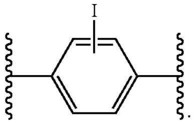
.

72. The compound of any one of clauses 1-3, 8-68 and 71, or a pharmaceutically acceptable salt or deuterated form thereof, wherein L is

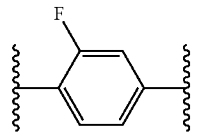
or
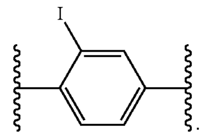.

73. The compound of any one of clauses 1-3, 8-68 and 72, or a pharmaceutically acceptable salt or deuterated form thereof, wherein L is

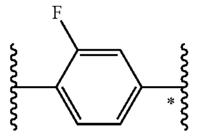
or
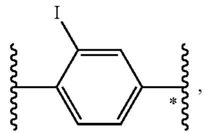, wherein the asterisk represents the point of attachment to $R^1$.

74. The compound of any one of clauses 4-7, or a pharmaceutically acceptable salt or deuterated form thereof, wherein p is 0.

75. The compound of any one of clauses 4-7, or a pharmaceutically acceptable salt or deuterated form thereof, wherein p is 1 and $R^7$ is halo.

76. The compound of any one of clauses 4-7 and 75, or a pharmaceutically acceptable salt or deuterated form thereof, wherein p is 1 and $R^7$ is F.

77. The compound of any one of clauses 1-4, 6 and 8-76, or a pharmaceutically acceptable salt or deuterated form thereof, wherein $R^1$ is 6-18 membered aryl optionally substituted with 1-3 groups independently selected from $R^5$ or $R^6$.

78. The compound of any one of clauses 1-4, 6, 8-77, or a pharmaceutically acceptable salt or deuterated form thereof, wherein $R^1$ is

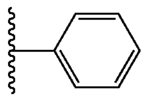
or
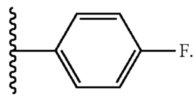.

79. The compound of any one of clauses 1-4, 6 and 8-76, or a pharmaceutically acceptable salt or deuterated form thereof, wherein $R^1$ is 5-20 membered heteroaryl containing 1-3 heteroatoms selected from N, S or O, wherein the heteroaryl is optionally substituted with 1-5 groups independently selected from $R^5$ or $R^6$.

80. The compound of any one of clauses 1-4, 6, 8-76 and 79, or a pharmaceutically acceptable salt or deuterated form thereof, wherein $R^1$ is selected from,

- 5-12 membered monocyclic heteroaryl containing 1-3 heteroatoms selected from N, S or O, wherein the monocyclic heteroaryl is optionally substituted with 1-3 groups independently selected from $R^5$ or $R^6$,
- 7-14 membered bicyclic heteroaryl containing 1-3 heteroatoms selected from N, S or O, wherein the bicyclic heteroaryl is optionally substituted with 1-4 groups independently selected from $R^5$ or $R^6$, or
- 7-20 membered tricyclic heteroaryl containing 1-3 heteroatoms selected from N, S or O, wherein the tricyclic heteroaryl is optionally substituted with 1-5 groups independently selected from $R^5$ or $R^6$.

81. The compound of any one of clauses 1-4, 6, 8-76 and 79-80, or a pharmaceutically acceptable salt or deuterated form thereof, wherein $R^1$ is 7-14 membered bicyclic heteroaryl containing 1-3 heteroatoms selected from N, S or O, wherein the heteroaryl is optionally substituted with 1-4 groups independently selected from $R^5$ or $R^6$.

82. The compound of any one of clauses 1-4, 6, 8-76 and 81, or a pharmaceutically acceptable salt or deuterated form thereof, wherein $R^1$ is

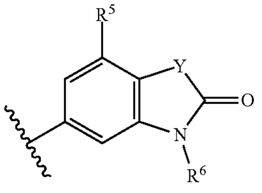
or

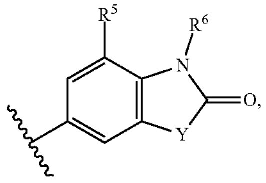, wherein

- each Y is independently $NR^6$, O, $CR^8R^9$, S, S(O) or $S(O)_2$,
- each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}$ alkyl$)_2$, COOH, $COC_{1-6}$ alkyl, C(=O)$OC_{1-6}$ alkyl, $CONHC_{1-6}$ alkyl, $CON(C_{1-6}$ alkyl$)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;
- each $R^6$ is independently selected from H, $C_{1-6}$ alkyl, $C_{1-6}$ alkylene-$NH_2$, $C_{1-6}$ alkylene-$N(C_{1-6}$ alkyl$)_2$, —$COC_{1-6}$ alkyl, $C_{2-6}$ alkenyl, $C_{2-6}$alkynyl and $C_{3-6}$cycloalkyl; wherein the alkyl, $NH_2$, $N(C_{1-6}$ alkyl$)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl or heteroaryl and COOH;
- $R^8$ and $R^9$ are each independently selected from H, halogen, $C_{1-6}$ alkyl, $C_{1-6}$alkoxy, $C_2$-6 alkenyl, $C_{2-6}$ alkynyl, $OC_{2-6}$alkenyl, OC 2-6 alkynyl, $C_{3-6}$ cycloalkyl, $OC_{3-6}$ cycloalkyl CN, OH, $NH_2$, COOH, —$S(O)C_{1-6}$alkyl, —$S(O)_2C_{1-6}$ alkyl, —$S(O)_2C_{3-6}$cycloalkyl, —$SO_2$-3-7 membered heterocyclyl, and a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl and —COOH;
- alternatively, $R^8$ and $R^9$ form =O.

83. The compound of any one of clauses 1-4, 6, 8-76 and 79-82, or a pharmaceutically acceptable salt or deuterated form thereof, wherein $R^1$ is

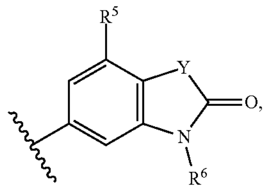

wherein each Y is independently $NR^6$, O, $CR^8R^9$, S, S(O) or $S(O)_2$, each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}$ alkyl$)_2$, COOH, $COC_{1-6}$ alkyl, C(=O)$OC_{1-6}$ alkyl, $CONHC_{1-6}$ alkyl, $CON(C_{1-6}$ alkyl$)_2$, $NHCOC_{1-6}$ alkyl, and a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl and COOH;

each $R^6$ is independently selected from H, $C_{1-6}$ alkyl, $C_{1-6}$ alkylene-$NH_2$, $C_{1-6}$ alkylene-$N(C_{1-6}$ alkyl$)_2$, —$COC_{1-6}$ alkyl, $C_{2-6}$ alkenyl, $C_{2-6}$alkynyl and $C_{3-6}$cycloalkyl; wherein the alkyl, $NH_2$, $N(C_{1-6}$ alkyl$)_2$, alkenyl, alkynyl and cycloalkyl is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl or heteroaryl and COOH;

$R^8$ and $R^9$ are each independently selected from H, halogen, $C_{1-6}$ alkyl, $C_{1-6}$alkoxy, $C_2$-6 alkenyl, $C_{2-6}$ alkynyl, $OC_{2-6}$alkenyl, OC 2-6 alkynyl, $C_{3-6}$ cycloalkyl, $OC_{3-6}$ cycloalkyl, CN, OH, $NH_2$, COOH, —$S(O)C_{1-6}$alkyl, —$S(O)_2C_{1-6}$ alkyl, —$S(O)_2C_{3-6}$cycloalkyl, —$SO_2$-3-7 membered heterocyclyl, and a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl and —COOH;

alternatively, $R^8$ and $R^9$ form =O.

84. The compound of any one of clauses 5 and 93-84, or a pharmaceutically acceptable salt or deuterated form thereof, wherein Y is O, S, $NR^6$ or $CR^8R^9$;

$R^5$ is H, halo or $C_{1-6}$ alkyl;

$R^6$ is $C_{1-6}$ alkyl, $C_{1-6}$ alkylene-$NH_2$ or $C_{1-6}$ alkylene-N$(C_{1-6}$ alkyl$)_2$ wherein $R^6$ is optionally substituted by 1-3 groups selected from halo, OH, $OC_{1-6}$ alkyl, $N(C_{1-6}$ alkyl$)_2$, cycloalkyl, aryl, heterocyclyl or heteroaryl;

$R^8$ and $R^9$ are independently H, halo or $C_{1-6}$ alkyl, or $R^8$ and $R^9$ form a (=O).

85. The compound of any one of clauses 5, 7 and 82-84, or a pharmaceutically acceptable salt or deuterated form thereof, wherein Y is NH, O, S, $CH_2$, CHF, or $CHF_2$.

86. The compound of any one of clauses 5, 7 and 82-85, or a pharmaceutically acceptable salt or deuterated form thereof, wherein Y is 0.

87. The compound of any one of clauses 5, 7 and 82-86, or a pharmaceutically acceptable salt or deuterated form thereof, wherein $R^6$ is $C_{1-6}$ alkyl.

88. The compound of any one of clauses 5, 7 and 82-87, or a pharmaceutically acceptable salt or deuterated form thereof, wherein $R^6$ is —$CH_3$.

89. The compound of any one of clauses 5, 7 and 82-86, or a pharmaceutically acceptable salt or deuterated form thereof, wherein $R^6$ is

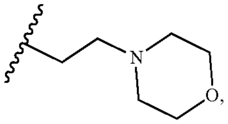

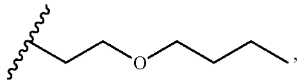

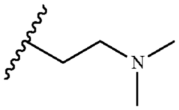

or

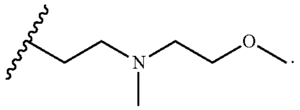

90. The compound of any one of clauses 5, 7 and 82-89, or a pharmaceutically acceptable salt or deuterated form thereof, wherein $R^5$ is H.

91. The compound of any one of clauses 5, 7 and 82-90, or a pharmaceutically acceptable salt or deuterated form thereof, wherein Y is O and $R^5$ is H.

92. The compound of any one of clauses 1-4 and 6-76, or a pharmaceutically acceptable salt or deuterated form thereof, wherein R is

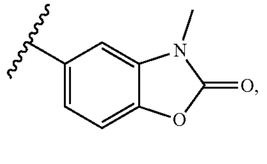

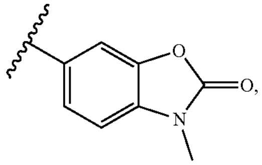

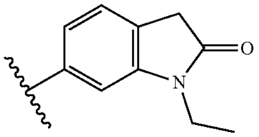

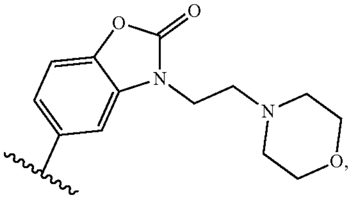

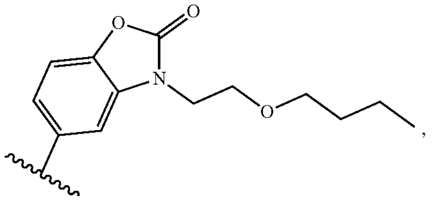

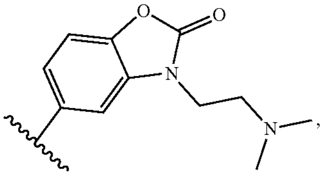

or

-continued

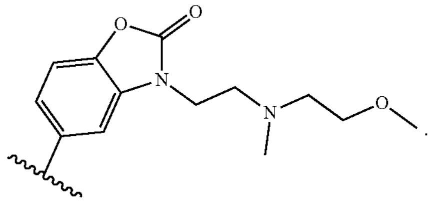

93. The compound of any one of clauses 1-4, 6 and 8-92, or a pharmaceutically acceptable salt or deuterated form thereof, wherein $R^1$ is

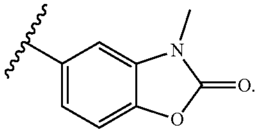 [SMILES: *c1ccc2oc(=O)n(C)c2c1]

94. The compound of any one of clauses 1-4, 6 and 8-92, or a pharmaceutically acceptable salt or deuterated form thereof, wherein $R^1$ is

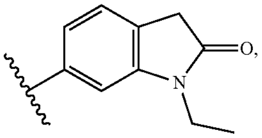

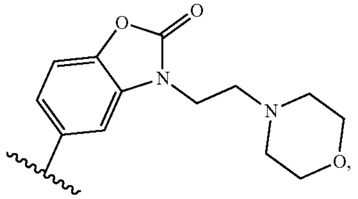

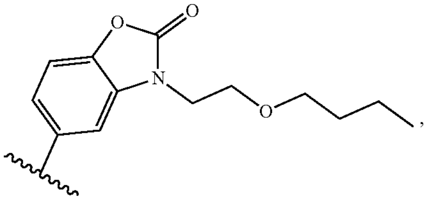

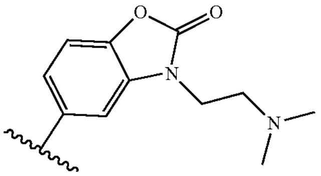

or

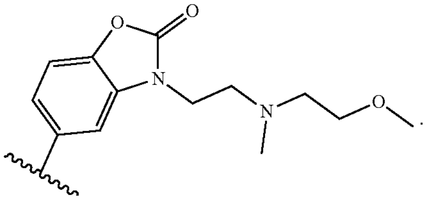

95. The compound of any one of clauses 1-4, 6 and 8-81, or a pharmaceutically acceptable salt or deuterated form thereof, wherein $R^1$ is

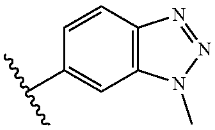

or

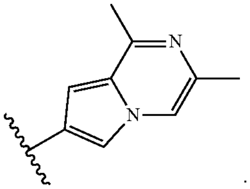

96. The compound of any one of clauses 1-4, 6 and 8-80, or a pharmaceutically acceptable salt or deuterated form thereof, wherein $R^1$ is 7-20 membered tricyclic heteroaryl containing heteroatoms selected from N, S or O, wherein the tricyclic heteroaryl is optionally substituted with 1-5 $R^6$ or $R^7$ groups.

97. The compound of any one of clauses 1-4, 6, 8-80 and 96, or a pharmaceutically acceptable salt or deuterated form thereof, wherein $R^1$ is 7-20 membered spiro tricyclic heteroaryl containing heteroatoms selected from N, S or O, wherein the tricyclic heteroaryl is optionally substituted with 1-5 $R^5$ or $R^6$ groups.

98. The compound of any one of clauses 1-4, 6, 8-80 and 96-97, or a pharmaceutically acceptable salt or deuterated form thereof, wherein $R^1$ is

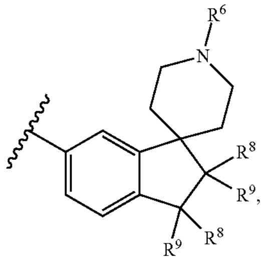

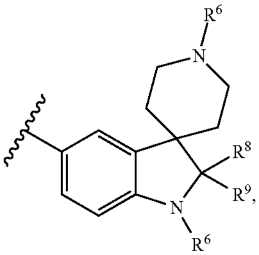

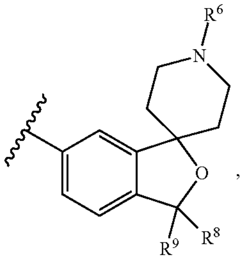

,

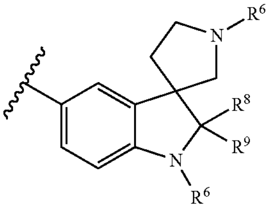

,

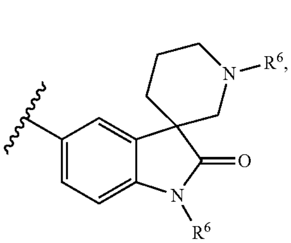

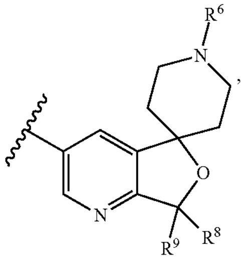

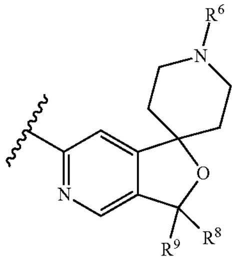

or

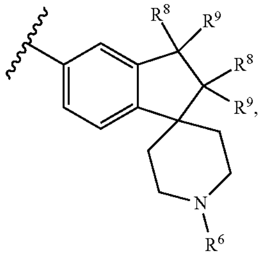

wherein each $R^6$ is independently selected from H, $C_{1-6}$ alkyl, —$COC_{1-6}$ alkyl, $C_{2-6}$ alkenyl, $C_{2-6}$ alkynyl, $C_{3-6}$ cycloalkyl, heterocyclyl or alkylene-O-alkyl; wherein the alkyl, alkenyl, alkynyl and cycloalkyl is optionally substituted with 1-3 groups selected from halogen, CN, OH, $NH_2$ or COOH; and, $R^8$ and $R^9$ are each independently selected from H, halogen, $C_{1-6}$ alkyl, $OC_{1-6}$ alkyl, $C_2$-6 alkenyl, $C_{2-6}$ alkynyl, $OC_{2-6}$alkenyl, OC 2-6 alkynyl, $C_{3-6}$ cycloalkyl, $OC_{3-6}$ cycloalkyl, CN, OH, $NH_2$, COOH, —$S(O)C_{1-6}$ alkyl, —$S(O)_2C_{1-6}$ alkyl, —$S(O)_2C_{3-6}$cycloalkyl, —$SO_2$-3-7 membered heterocyclyl or a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$ or —COOH; or alternatively, $R^8$ and $R^9$ form =O.

99. The compound of any one of clauses 1-4, 6, 8-80 and 96-98, or a pharmaceutically acceptable salt or deuterated form thereof, wherein $R^1$ is

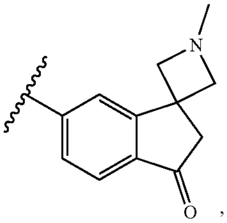,
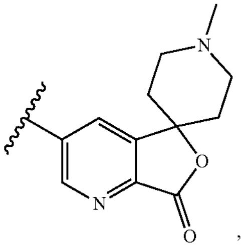,
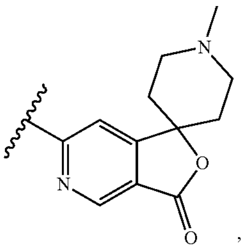,
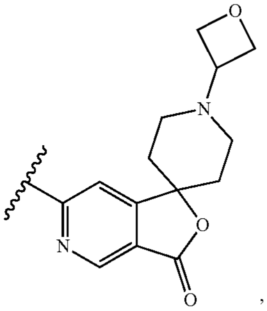,
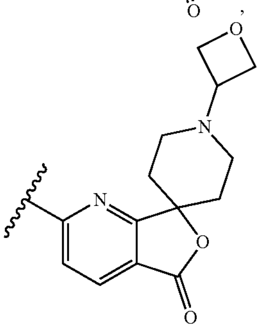,
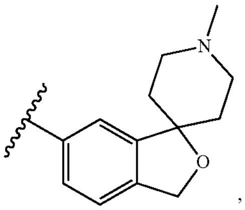,
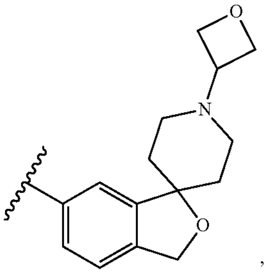,
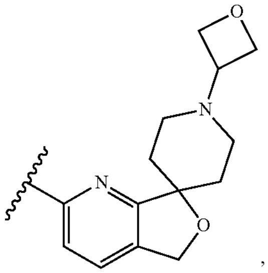, -continued

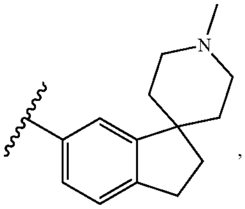,
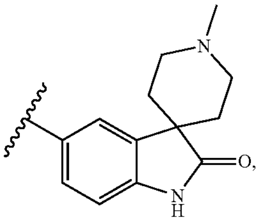,
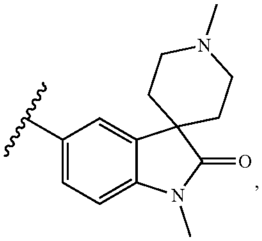,
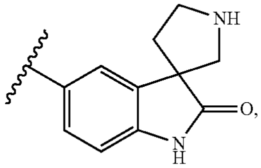,
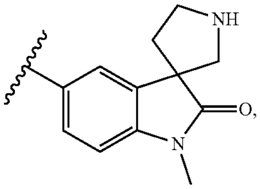,
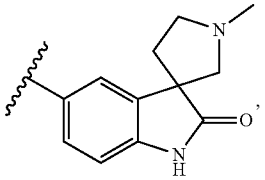,
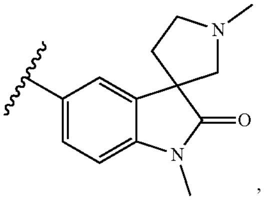,
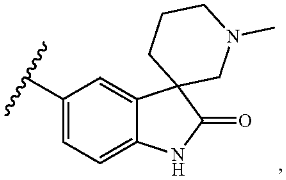,
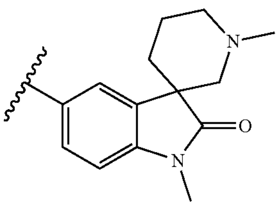
or
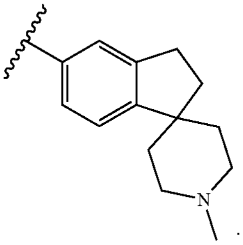.

100. The compound of any one of clauses 1-4, 6, 8-80 and 99, or a pharmaceutically acceptable salt or deuterated form thereof, wherein $R^1$ is

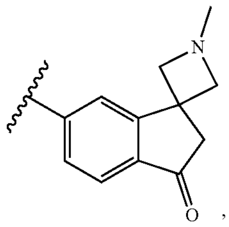,
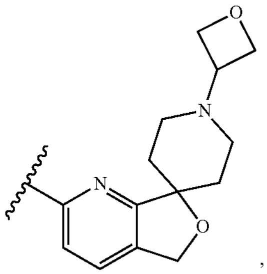,

-continued

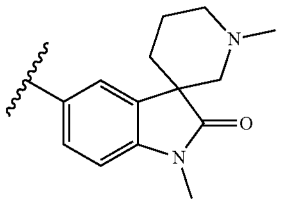

or

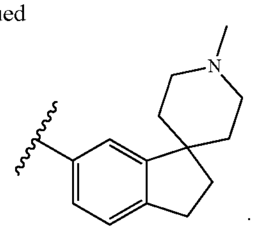

101. The compound of any one of clauses 1-4, 6 and 8-70, or a pharmaceutically acceptable salt or deuterated form thereof, wherein p is 1, 2, 3 or 4, and one $R^7$ and one $R^5$ together form a heterocyclyl ring.

102. The compound of any one of clauses 1-4, 6, 8-70 and 101, or a pharmaceutically acceptable salt or deuterated form thereof, wherein

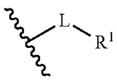

is

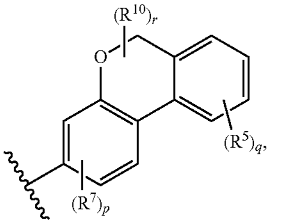

wherein p is 1, 2 or 3, q is 1, 2 or 3, r is 0 or 1, and $R^{10}$ is alkyl, halogen, Oalkyl, haloalkyl, OH or CN.

103. The compound of any one of clauses 1-4, 6, 8-70 and 101-102 or a pharmaceutically acceptable salt or deuterated form thereof, wherein

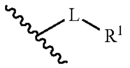

is

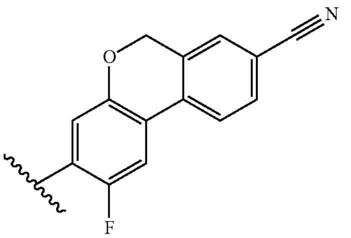

or

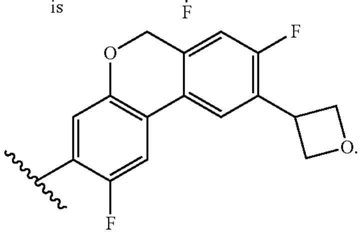

104. The compound of clause 1, or a pharmaceutically acceptable salt or deuterated form thereof, wherein the compound is selected from Table A.

105. A pharmaceutical composition comprising an effective amount of a compound of any one of clauses 1-104, or a pharmaceutically acceptable salt or deuterated form thereof and a pharmaceutically acceptable adjuvant, diluent or carrier.

106. A method for treating an obstructive disease of the airway in a patient in need thereof, comprising, administering to the patient an effective amount of a compound of any one of clauses 1-104, or the composition of clause 105.

107. The method of clause 106, wherein the obstructive disease of the airway is asthma, chronic obstructive pulmonary disease (COPD), bronchitis, emphysema, cystic fibrosis (CF), bronchiectasis, sarcoidosis, alpha-1 antitrypsin (A1AT) deficiency, farmer's lung and related diseases, hypersensitivity pneumonitis, lung fibrosis, complications of lung transplantation, vasculitic and thrombotic disorders of the lung vasculature, pulmonary hypertension, antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus, acute lung injury, or acute respiratory distress syndrome (ARDS).

108. The method of clause 107, wherein the obstructive disease of the airway is asthma.

109. The method of clause 107, wherein the obstructive disease of the airway is acute respiratory distress syndrome (ARDS).

110. The method of clause 107, wherein the obstructive disease of the airway is bronchitis.

111. The method of clause 107, wherein the obstructive disease of the airway is lung fibrosis.

112. The method of clause 107, wherein the obstructive disease of the airway is emphysema.

113. The method of clause 107, wherein the obstructive disease of the airway is cystic fibrosis (CF).

114. The method of clause 107, wherein the obstructive disease of the airway is bronchiectasis.

115. The method of clause 107, wherein the obstructive disease of the airway is sarcoidosis.

116. The method of clause 107, wherein the obstructive disease of the airway is alpha-1 antitrypsin (A1AT) deficiency.

117. The method of clause 107, wherein the obstructive disease of the airway is farmer's lung.

118. The method of clause 107, wherein the obstructive disease of the airway is hypersensitivity pneumonitis.

119. The method of clause 107, wherein the obstructive disease of the airway is a complication of lung transplantation.

120. The method of clause 107, wherein the obstructive disease of the airway is a vasculitic or thrombotic disorder of the lung vasulature.

121. The method of clause 107, wherein the obstructive disease of the airway is pulmonary hypertension.

122. The method of clause 107, wherein the obstructive disease of the airway is iatrogenic cough.

123. The method of clause 107, wherein the obstructive disease of the airway is acute rhinitis.

124. The method of clause 107, wherein the obstructive disease of the airway is chronic rhinitis.

125. The method of clause 107, wherein the obstructive disease of the airway is rhinitis medicamentosa or vasomotor rhinitis.

126. The method of clause 107, wherein the obstructive disease of the airway is nasal polyposis.

127. The method of clause 107, wherein the obstructive disease of the airway is COPD.

128. The method of clause 108, wherein the asthma is bronchial, allergic, intrinsic, extrinsic, exercise-induced or drug-induced asthma.

129. The method of clause 120, wherein the bronchitis is infectious bronchitis or eosinophilic bronchitis.

130. The method of clause 121, wherein the lung fibrosis is idiopathic pulmonary fibrosis, cryptogenic fibrosing alveolitis, idiopathic interstitial pneumonia, or fibrosis complicating anti-neoplastic therapy or chronic infection.

131. The method of clause 114, wherein the bronchiectasis is non-cystic fibrosis bronchiectasis (NCFBE).

132. The method of clause 114, wherein the bronchiectasis is associated with cystic fibrosis.

133. The method of clause 121, wherein the pulmonary hypertension is pulmonary arterial hypertension.

134. The method of clause 121, wherein the pulmonary hypertension is pulmonary hypertension due to left heart disease.

135. The method of clause 121, wherein the pulmonary hypertension is pulmonary hypertension associated with chronic lung disease.

136. A method for treating cystic fibrosis in a patient in need thereof, comprising, administering to the patient an effective amount of a compound of any one of clauses 1-104, or the composition of clause 105.

137. The method of clause 136, wherein the treating comprises improving the lung function of the patient, as compared to the lung function of the patient prior to treatment.

138. The method of clause 137, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior treatment.

139. The method of clause 137 or 138, wherein the lung function is measured by spirometry.

140. A method for treating bronchiectasis in a patient in need thereof, comprising, administering to the patient, an effective amount of a compound of any one of clauses 1-104, or the composition of clause 105.

141. The method of clause 140, wherein the bronchiectasis is non-cystic fibrosis bronchiectasis (NCFBE).

142. The method of clause 1408, wherein the bronchiectasis is associated with cystic fibrosis.

143. The method of any one of clauses 140-142, wherein treating comprises improving the lung function of the patient, as compared to the lung function of the patient prior to treatment.

144. The method of clause 143, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior to treatment.

145. The method of clause 143 or 144, wherein the lung function is measured by spirometry.

146. The method of any one of clauses 140-145, wherein treating comprises decreasing the rate of pulmonary exacerbation, as compared to the rate of pulmonary exacerbation of the patient prior to treatment.

147. The method of any one of clauses 140-146, wherein treating comprises increasing the time to first pulmonary exacerbation, as compared to an untreated patient.

148. The method of clause 146-147, wherein the pulmonary exacerbation is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis.

149. A method for treating chronic rhinosinusitis (CRS) in a patient in need thereof, comprising, administering to the patient, an effective amount of a compound of any one of clauses 1-104, or the composition of clause 105.

150. The method of clause 149, wherein the chronic rhinosinusitis is chronic rhinosinusitis without nasal polyps (CRSsNP).

151. The method of clause 149, wherein the chronic rhinosinusitis is chronic rhinosinusitis with nasal polyps (CRSwNP).

152. The method of any one of clauses 149-150, wherein the chronic rhinosinusitis is refractory chronic rhinosinusitis.

153. The method of any one of clauses 149-152, wherein treating comprises reducing, diminishing the severity of, delaying the onset of, or eliminating one or more symptoms of CRS.

154. The method of clause 153, wherein the one or more symptoms of CRS is nasal congestion; nasal obstruction; nasal discharge; post-nasal drip; facial pressure; facial pain; facial fullness; reduced smell; depression; mucosal edema; mucopurulent discharge; obstruction of the middle meatus; mucosal changes within the ostiomeatal complex and sinuses; or rhinorrhea.

155. A method for treating hidradenitis suppurativa (HS) in a patient in need thereof, comprising, administering to the patient, an effective amount of a compound of any one of clauses 1-104, or the composition of clause 105.

156. The method of clause 155, wherein the hidradenitis suppurativa (HS) is Hurley stage I.

157. The method of clause 155, wherein the hidradenitis suppurativa (HS) is Hurley stage II.

158. The method of clause 155, wherein the hidradenitis suppurativa (HS) is Hurley stage III.

159. A method for treating cancer in a patient in need thereof, comprising, administering to the patient, an effective amount of a compound of any one of clauses 1-104, or the composition of clause 105.

160. The method of clause 159, wherein the cancer is a metastatic cancer.

161. The method of clause 160, wherein the metastatic cancer is breast to lung metastatic cancer.

162. The method of clause 160, wherein the metastatic cancer comprises metastasis of breast cancer to the brain, bone, pancreas, lymph nodes or liver.

163. The method of clause 160, wherein the metastatic cancer comprises metastasis of bone cancer to the lung.

164. The method of clause 160, wherein the metastatic cancer comprises metastasis of colorectal cancer to the peritoneum, the pancreas, the stomach, the lung, the liver, the kidney, or the spleen.

165. The method of clause 160, wherein the metastatic cancer comprises metastasis of stomach cancer to the mesentery, the spleen, the pancreas, the lung, the liver, the adrenal gland, or the ovary.

166. The method of clause 160, wherein the metastatic cancer comprises metastasis of liver cancer to the intestine, spleen, pancreas, stomach, lung, or the kidney.

167. The method of clause 160, wherein the metastatic cancer comprises metastasis of lymphoma to the kidney, ovary, liver, bladder, or the spleen.

168. A method for treating lupus nephritis in a patient in need thereof, comprising, administering to the patient, an effective amount of a compound of any one of clauses 1-104, or the composition of clause 105.

169. A method for treating rheumatoid arthritis in a patient in need thereof, comprising, administering to the patient, an effective amount of a compound of any one of clauses 1-104, or the composition of clause 105.

170. A method for treating inflammatory bowel disease (IBD) in a patient in need thereof, comprising, administering to the patient, an effective amount of a compound of any one of clauses 1-104, or the composition of clause 105.

171. The method of clause 170, wherein the inflammatory bowel disease (IBD) is Crohn's disease.

172. The method of clause 170, wherein the inflammatory bowel disease (IBD) is ulcerative colitis.

173. A method for treating an anti-neutrophil cytoplasmic antibody (ANCA) associated vasculitis in a patient in need thereof, comprising, administering to the patient, an effective amount of a compound of any one of clauses 1-104, or the composition of clause 105.

174. The method of clause 173, wherein the ANCA associated disease is granulomatosis with polyangiitis (GPA).

175. The method of clause 1731, wherein the ANCA associated disease is microscopic polyangiitis (MPA).

176. A method for treating a disease in a patient in need thereof comprising, administering to the patient, an effective amount of a compound of any one of clauses 1-104, or the composition of clause 105, wherein the disease is giant cell arteritis, polyarteritis nodosa, anti-GBM disease (Goodpasture's), systemic scleroderma, diabetic nephropathy, diabetic neuropathy, diabetic retinopathy, diabetic ulcers, Duchenne muscular dystrophy, bronchiolitis obliterans, atopic dermatitis, pyoderma gangrenosum, sweet's syndrome, dermatomyositis/polymyositis, neutrophilic dermatoses, thrombosis, bronchopulmonary dysplasia, amyotrophic lateral sclerosis, sickle cell anemia, psoriasis, or a ventilator-induced lung injury.

177. A method for treating a heart failure in a patient in need thereof, comprising administering to the patient, an effective amount of a compound of any one of clauses 1-104, or the composition of clause 105.

178. The method of clause 177, wherein the heart failure is heart failure with reduced ejection fraction.

179. The method of clause 177, wherein the heart failure is heart failure with preserved ejection fraction.

180. A compound selected from Table A, or a pharmaceutically acceptable salt or deuterated form thereof.

Clauses—Set 2

1. A compound of Formula (I)

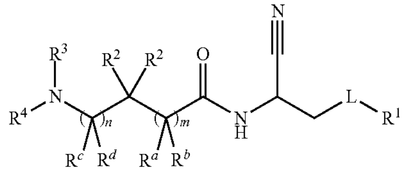

(I)

or a pharmaceutically acceptable salt or deuterated form thereof, wherein $R^1$ is carbocyclyl, aryl, heterocyclyl, or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

each $R^2$ is independently H, halogen, OH, CN, $OC_{1-6}$ alkyl, $NH_2$, SH, C(=O)alkyl, C(=O)$NH_2$, $C_{1-6}$ alkyl, $C_{1-6}$ haloalkyl, $C_{2-6}$ alkenyl, carbocyclyl, heterocyclyl, aryl, heteroaryl, $C_{1-6}$ alkylene-aryl, $C_{1-6}$ alkylene-heteroaryl, or $C_{1-6}$ alkylene-carbocyclyl, each of aryl, heteroaryl, and carbocyclyl are optionally substituted with 1-4 groups independently selected from alkyl, halogen, OH, C(=O)OH, $NH_2$, NH(alkyl), $NH(alkyl)_2$, $OC_{1-6}$ alkyl;

or two $R^2$ together form (=O);

each of $R^3$ and $R^4$ is independently selected from H, alkyl, cycloalkyl, aryl, heterocyclyl, heteroaryl, alkylene-aryl, alkylene-heteroaryl, C(=O)alkyl, C(=O)cycloalkyl, C=(O)aryl, or C(=O)heteroaryl, wherein the alkyl, cycloalkyl, aryl, heterocyclyl, heteroaryl, and alkylene is optionally substituted with 1-4 groups independently selected from alkyl, halogen, OH, $NH_2$, NH(alkyl), $NH(alkyl)_2$, $OC_{1-6}$ alkyl;

or $R^3$ and $R^4$ together with the nitrogen to which they are attached form a heterocyclyl, wherein the heterocyclyl is optionally substituted with 1-4 groups selected from alkyl, halogen, OH, $NH_2$, NH(alkyl), $NH(alkyl)_2$, or $OC_{1-6}$ alkyl;

each $R^5$ is independently selected from H, halogen, $C_{1-6}$ alkyl, $C_{1-6}$ alkoxy, $C_{2-6}$ alkenyl, $C_2$-6 alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, $COOC_{1-6}$ alkyl, $CONHC_{1-6}$ alkyl, $CON(C_{1-6}\ alkyl)_2$, $NHCOC_{1-6}$ alkyl, or a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_{2-6}$alkynyl, $C_{3-6}$cycloalkyl or 3-8 membered heterocyclyl containing 1-3 heteroatoms selected from N, S or O; wherein the $C_{1-6}$ alkyl, $NH_2$, $N(C_{1-6}\ alkyl)_2$, alkenyl, alkynyl, cycloalkyl and heterocyclyl within $R^6$ is optionally substituted with 1-3 groups selected from halogen, CN, OH, $C_{1-6}$ alkyl, $OC_{1-6}$ alkyl, $NH_2$, $NH(C_{1-6}\ alkyl)$, $N(C_{1-6}\ alkyl)_2$, cycloalkyl, aryl, heterocyclyl, heteroaryl or COOH;

each $R^7$ is independently H, =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH—$C_{1-6}$ alkyl, $N(C_{1-6}\ alkyl)_2$, COOH, $COC_{1-6}$ alkyl, $COOC_{1-6}$ alkyl, $CON_{1-6}$ alkyl, $CON(C_{1-6}\ alkyl)_2$, or $NHCOC_{1-6}$ alkyl;

or one $R^7$ and one $R^5$ together form a cycloalkyl, aryl, heterocyclyl or heteroaryl ring, wherein the cycloalkyl, aryl, heterocyclyl, heteroaryl is optionally substituted with 1-4 groups selected from alkyl, halogen, Oalkyl, haloalkyl, OH or CN;

each of $R^a$, $R^b$, $R^c$ and $R^d$ is independently selected from H, alkyl, halogen or haloalkyl;

each of n and m is independently 0, 1, 2, or 3;

provided that the compound is not

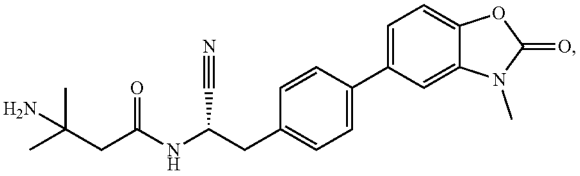

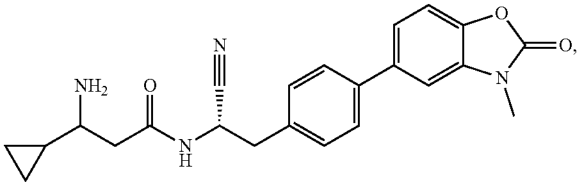

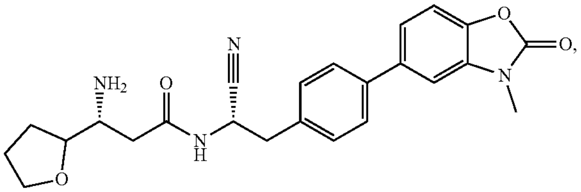

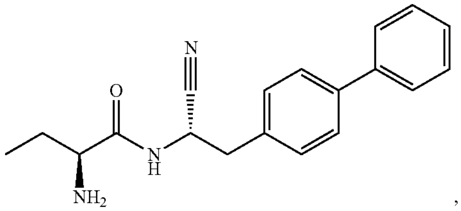

,

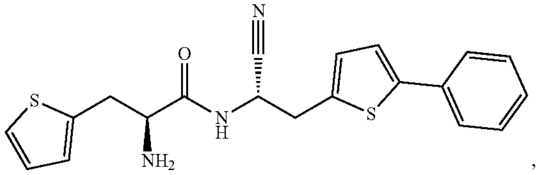

,

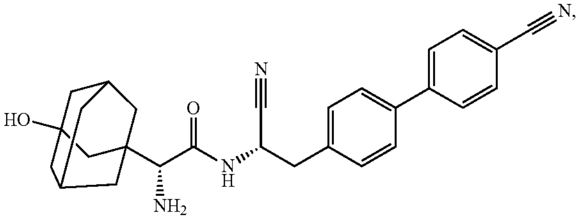

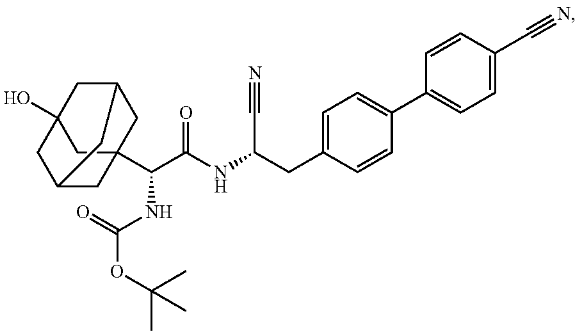

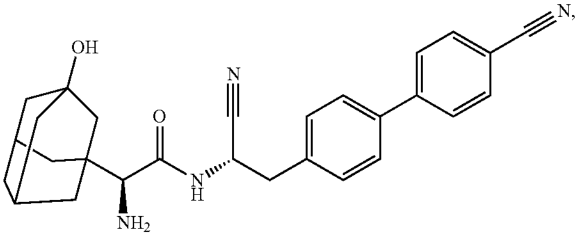

-continued

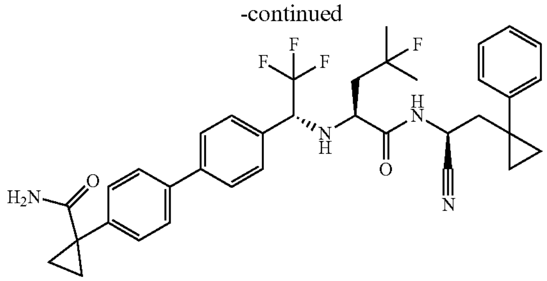

or

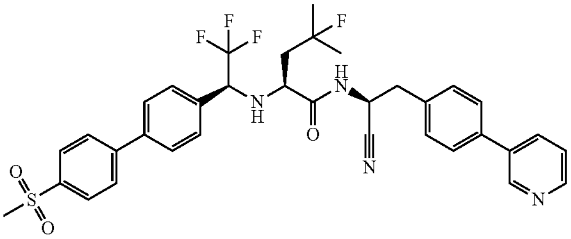

.

2. A compound of Formula (II)

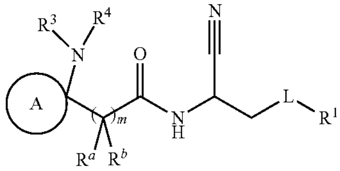

(II)

or a pharmaceutically acceptable salt or deuterated form thereof, wherein $R^1$ is carbocyclyl, aryl, heterocyclyl, or heteroaryl, wherein $R^1$ is optionally substituted with 1-5 groups independently selected from $R^5$ or $R^6$ L is arylene, heterocyclylene, heteroarylene or cycloalkylene, wherein L is optionally substituted by 1-4 $R^7$;

Ring A is a carbocyclyl or heterocyclyl;

each of $R^3$ and $R^4$ is independently selected from H, alkyl, cycloalkyl, aryl, heterocyclyl, heteroaryl, alkylene-aryl, alkylene-heteroaryl, C(═O)alkyl, C(═O)cycloalkyl, C═(O)aryl, or C(═O)heteroaryl, wherein the alkyl, cycloalkyl, aryl, heterocyclyl, heteroaryl, and alkylene is optionally substituted with 1-4 groups independently selected from alkyl, halogen, OH, $NH_2$, NH(alkyl), $NH(alkyl)_2$, $OC_{1-6}$alkyl; or $R^3$ and $R^4$ together with the nitrogen to which they are attached form a heterocyclyl, wherein the heterocyclyl is optionally substituted with 1-4 groups selected from alkyl, halogen, OH, $NH_2$, NH(alkyl), $NH(alkyl)_2$, or $OC_{1-6}$alkyl;

each $R^5$ is independently selected from H, halogen, $C_{1-6}$ alkyl, $C_{1-6}$ alkoxy, $C_{2-6}$ alkenyl, $C_2$-6 alkynyl, $C_{3-6}$cycloalkyl, CN, OH, $NH_2$, $NHC_{1-6}$ alkyl, $N(C_{1-6}\ alkyl)_2$, COOH, $COC_{1-6}$ alkyl, $COOC_{1-6}$ alkyl, $CONHC_{1-6}$ alkyl, $CON(C_{1-6}\ alkyl)_2$, $NHCOC_{1-6}$ alkyl, or a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl, COOH, cycloalkyl and heterocyclyl;

each $R^6$ is independently selected from H, $C_{1-6}$ alkyl, $C_{1-6}$ alkylene-$NH_2$, $C_{1-6}$ alkylene-$N(C_{1-6}\ alkyl)_2$, —$COC_{1-6}$ alkyl, $C_{2-6}$ alkenyl, $C_{2-6}$alkynyl, $C_{3-6}$cycloalkyl or 3-8 membered heterocyclyl containing 1-3 heteroatoms selected from N, S or O; wherein the $C_{1-6}$ alkyl, $NH_2$, $N(C_{1-6}\ alkyl)_2$, alkenyl, alkynyl, cycloalkyl and heterocyclyl within $R^6$ is optionally substituted with 1-3 groups selected from halogen, CN, OH, $C_{1-6}$ alkyl, $OC_{1-6}$ alkyl, $NH_2$, $NH(C_{1-6}\ alkyl)$, $N(C_{1-6}\ alkyl)_2$, cycloalkyl, aryl, heterocyclyl or heteroaryl and COOH;

each $R^7$ is independently H, =O, halogen, $C_{1-6}$ alkyl, $OC_{1-6}$ alkyl, S—$C_{1-6}$ alkyl, $C_{2-6}$ alkenyl, $C_{2-6}$ alkynyl, $C_{3-6}$ cycloalkyl, CN, OH, $NH_2$, NH—$C_{1-6}$ alkyl, $N(C_{1-6}\ alkyl)_2$, COOH, $COC_{1-6}$ alkyl, $COOC_{1-6}$ alkyl, $CON_{1-6}$ alkyl, $CON(C_{1-6}\ alkyl)_2$, or $NHCOC_{1-6}$ alkyl;

each of $R^a$ and $R^b$ is independently selected from H, alkyl, halogen or haloalkyl;

m is independently 0, 1, 2, or 3;

provided that the compound is not

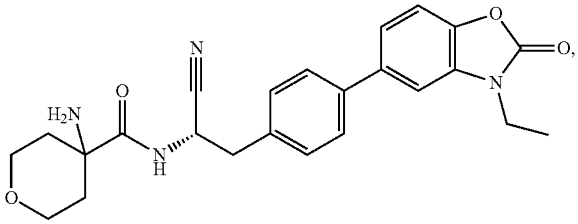

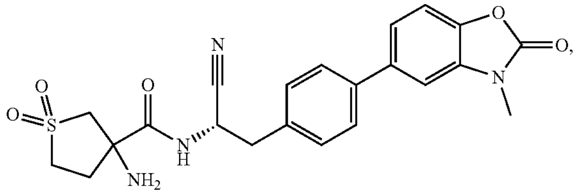

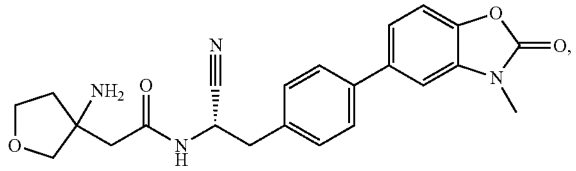

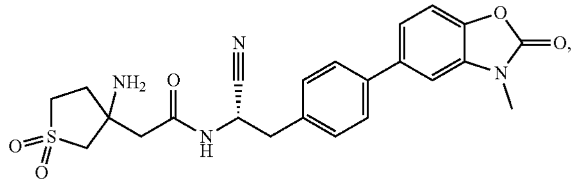

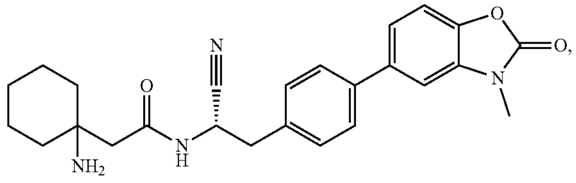

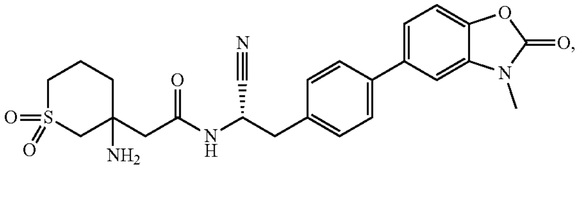

-continued

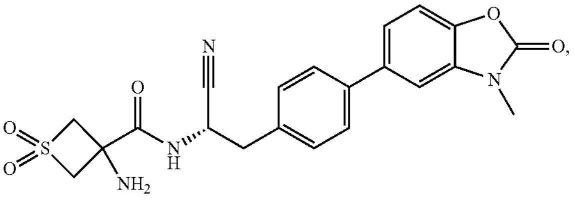

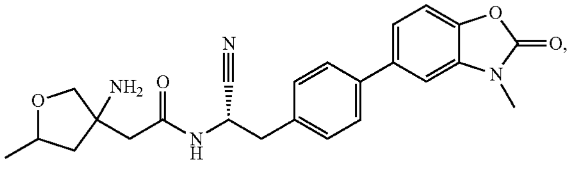

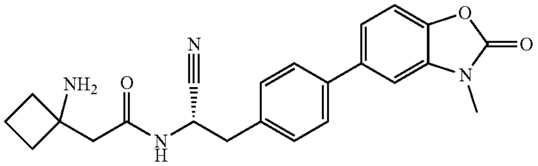

or

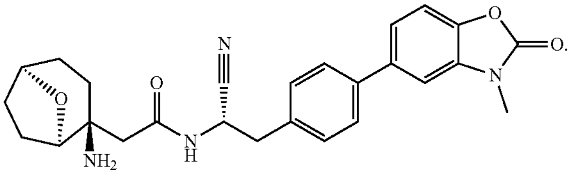

3. The compound of clause 1, or a pharmaceutically acceptable salt or deuterated form thereof, wherein the compound is a compound of Formula (III)

(III)

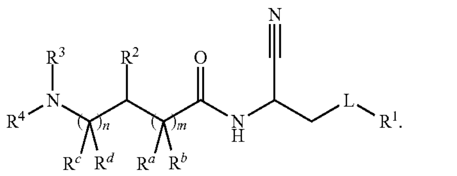

4. The compound of clause 1, or a pharmaceutically acceptable salt or deuterated form thereof, wherein the compound is a compound of Formula (IV), (IV)

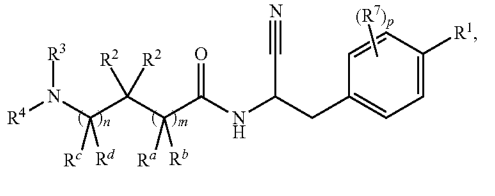

wherein p is 0, 1, or 2, and $R^7$ is halogen, alkyl, Oalkyl or haloalkyl.

5. The compound of clause 1, or a pharmaceutically acceptable salt or deuterated form thereof, wherein the compound is a compound of Formula (V), (V)

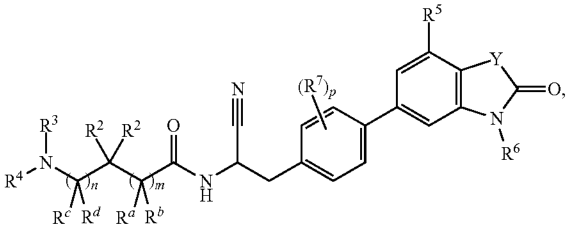

wherein each Y is independently $NR^6$, O, $CR^8R^9$, S, S(O) or $S(O)_2$, p is 0, 1, or 2;

$R^7$ is halogen, alkyl, Oalkyl or haloalkyl;

$R^8$ and $R^9$ are each independently selected from H, halogen, $C_{1-6}$ alkyl, $C_{1-6}$alkoxy, $C_{2-6}$ alkenyl, $C_{2-6}$ alkynyl, $OC_{2-6}$alkenyl, $OC_{2-6}$ alkynyl, $C_{3-6}$ cycloalkyl, $OC_{3-6}$ cycloalkyl, CN, OH, $NH_2$, C(O)OH, $S(O)C_{1-6}$alkyl, $S(O)_2C_{1-6}$ alkyl, $S(O)_2C_{3-6}$cycloalkyl, $SO_2$-heterocyclyl, or heterocyclyl containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl or —COOH; and or $R^8$ and $R^9$ form =O.

6. The compound of clause 1, or a pharmaceutically acceptable salt or deuterated form thereof, wherein the compound is a compound of Formula (VI), (VI)

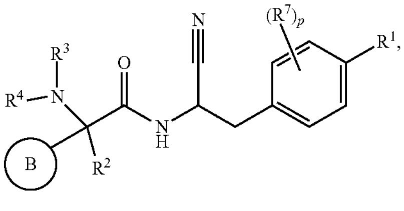

wherein Ring B is a 3-6 membered carbocyclyl or heterocyclyl.

7. The compound of clause 1, or a pharmaceutically acceptable salt or deuterated form thereof, wherein the compound is a compound of Formula (VII), (VII)

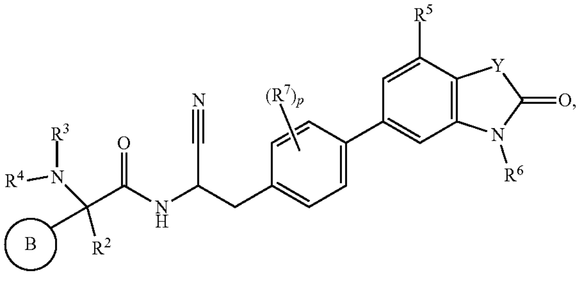

Ring B is a 3-6 membered carbocyclyl or heterocyclyl, each Y is independently $NR^6$, O, $CR^8R^9$, S, S(O) or $S(O)_2$, p is 0, 1, 2, 3 or 4;

$R^7$ is halogen, alkyl, Oalkyl or haloalkyl;

$R^8$ and $R^9$ are each independently selected from H, halogen, $C_{1-6}$ alkyl, $C_{1-6}$alkoxy, $C_{2-6}$ alkenyl, $C_{2-6}$ alkynyl, $OC_{2-6}$alkenyl, $OC_{2-6}$ alkynyl, $C_{3-6}$ cycloalkyl, $OC_{3-6}$ cycloalkyl, CN, OH, $NH_2$, C(O)OH, $S(O)C_{1-6}$alkyl, $S(O)_2C_{1-6}$ alkyl, $S(O)_2C_{3-6}$cycloalkyl, $SO_2$-heterocyclyl, or heterocyclyl containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl or COOH; and or $R^8$ and $R^9$ form =O.

8. The compound of any one of clauses 1 and 3-7, wherein each $R^2$ is independently H, halogen, OH, CN, $OC_{1-6}$ alkyl, $NH_2$, SH, C(=O)alkyl, C(=O)$NH_2$, $C_{1-6}$ alkyl, $C_{1-6}$ haloalkyl, $C_{2-6}$ alkenyl, carbocyclyl, heterocyclyl, aryl, heteroaryl, $C_{1-6}$ alkylene-aryl, $C_{1-6}$ alkylene-heteroaryl, or $C_{1-6}$ alkylene-carbocyclyl, each of aryl, heteroaryl, and carbocyclyl are optionally substituted with 1-4 groups independently selected from alkyl, halogen, OH, C(=O)OH, $NH_2$, NH(alkyl), $NH(alkyl)_2$, $OC_{1-6}$ alkyl.

9. The compound of any one of clauses 1 and 3-8, wherein each $R^2$ is independently H, halogen OH, CN, $OC_{1-6}$ alkyl, $NH_2$, SH, $C_{1-6}$ alkyl, $C_{2-6}$ alkenyl, $C_{1-6}$ haloalkyl, $C_{1-6}$ alkylene-aryl, $C_{1-6}$ alkylene-heteroaryl or $C_{1-6}$ alkylene-carbocyclyl, each of alkyl, alkylene, aryl, heteroaryl, and carbocyclyl are optionally substituted with 1-4 groups independently selected from alkyl, halogen, OH, $NH_2$, NH(alkyl), $NH(alkyl)_2$ or $OC_{1-6}$ alkyl.

10. The compound of any one of clauses 1 and 3-9, or a pharmaceutically acceptable salt or deuterated form thereof, wherein each $R^2$ is independently H, F, Cl, Br, OH, CN, $OCH_3$, $OCH_2CH_3$, $OCH_2CH_2CH_3$, SH, $NH_2$, $CH_3$, $CH_2CH_3$, $CH_2(CH_3)_2$,

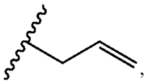 [SMILES: *CC=C], $CH_2F$, $CHF_2$, $CH_2Cl$, —CH(COOH)$NH_2$, $CH_2CH_2CH_2F$,

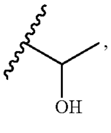, 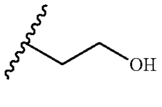, 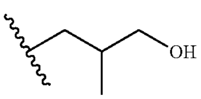,

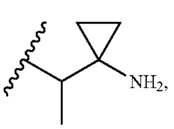, 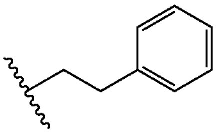,

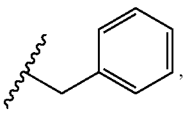, 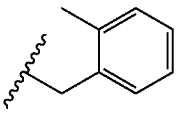, 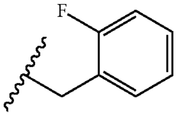,

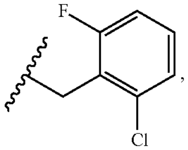, 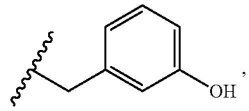,

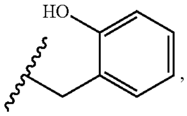, 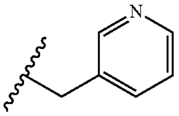, 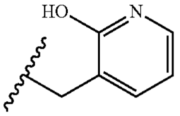,

-continued
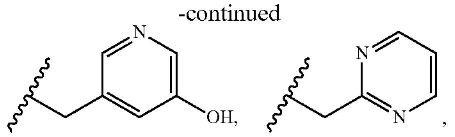
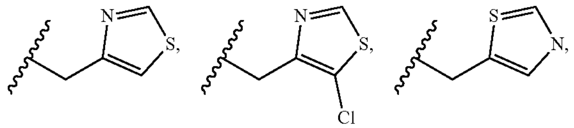
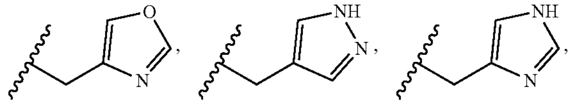
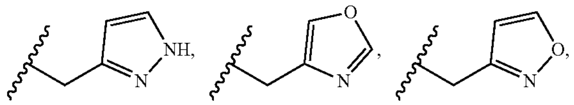
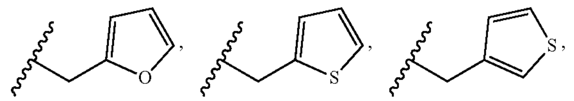
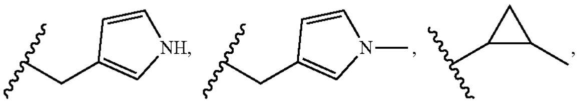
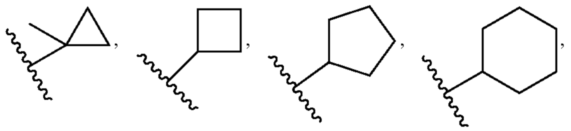
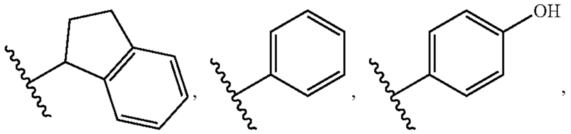
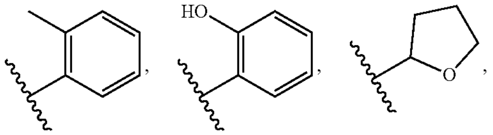
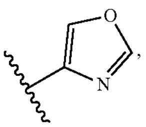 or 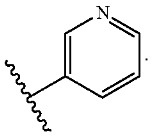.
11. The compound of any one of clauses 1 and 4-5, or a pharmaceutically acceptable salt or deuterated form thereof, wherein one of $R^2$ is H, and the other $R^2$ is H, F, OH, CN, $OCH_3$, $OCH_2CH_3$, $OCH_2CH_2CH_3$, SH, $NH_2$, $CH_3$, $CH_2CH_3$, $CH_2(CH_3)_2$,
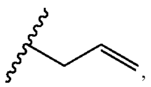 [SMILES: *CC=C]
$CH_2F$, $CHF_2$, $CH_2Cl$, —CH(COOH)$NH_2$, $CH_2CH_2CH_2F$,
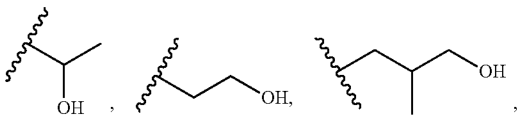
-continued
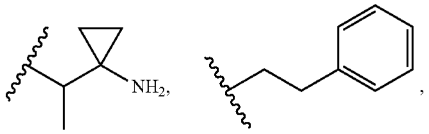
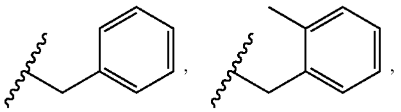
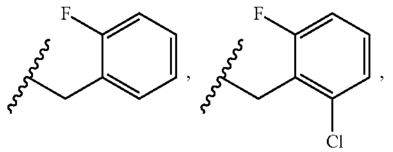
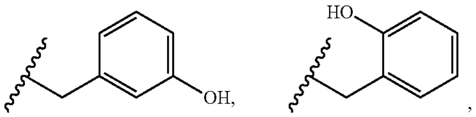
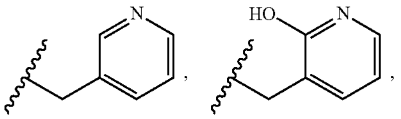
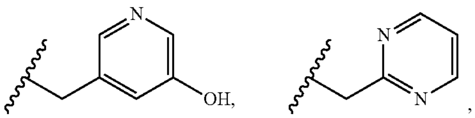
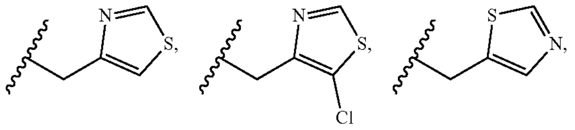
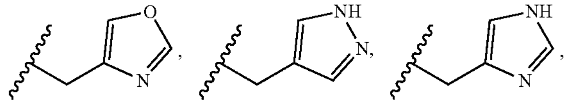
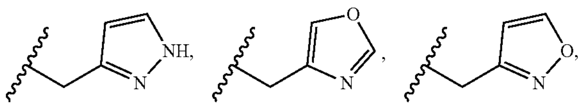
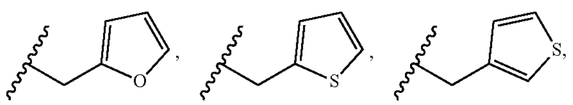
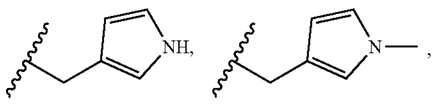
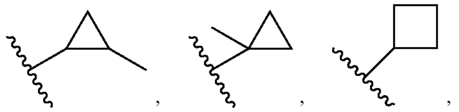
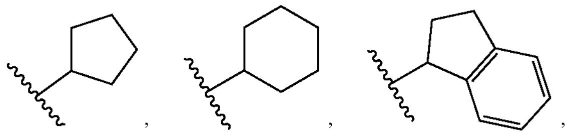
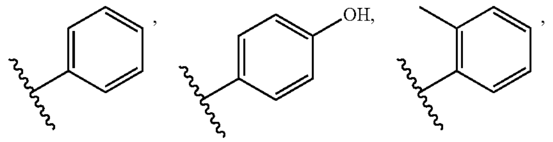

-continued

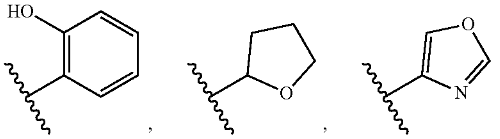 or

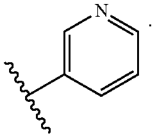.

12. The compound of any one of clauses 1, 4-5 and 11, or a pharmaceutically acceptable salt or deuterated form thereof, wherein one of $R^2$ is —$CH_3$, and the other $R^2$ is H, F, OH, CN, $OCH_3$, $OCH_2CH_3$, $OCH_2CH_2CH_3$, SH, $NH_2$, $CH_3$, $CH_2CH_3$, $CH_2(CH_3)_2$,

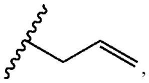 [SMILES: *CC=C], $CH_2F$, $CHF_2$, $CH_2Cl$, —$CH(COOH)NH_2$, $CH_2CH_2CH_2F$,

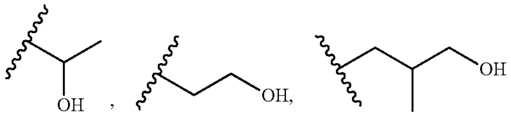,

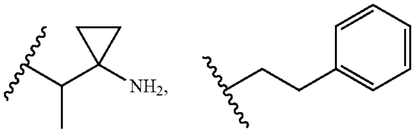,

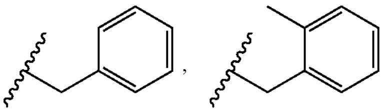,

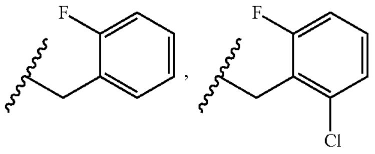,

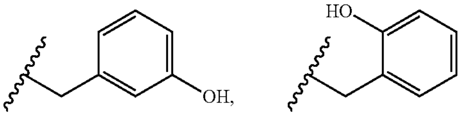,

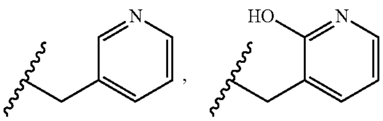,

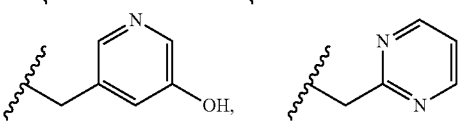,

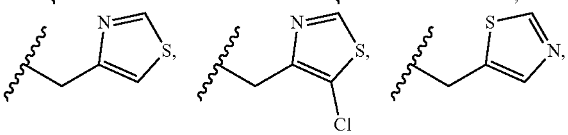

-continued

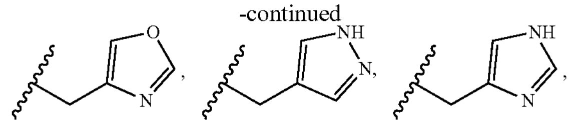

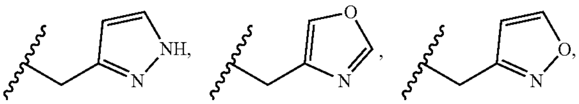

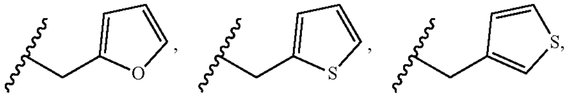

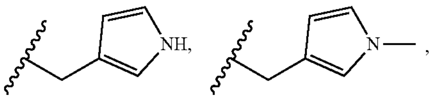,

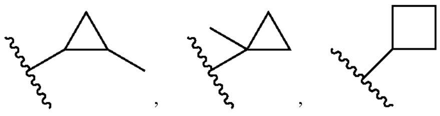,

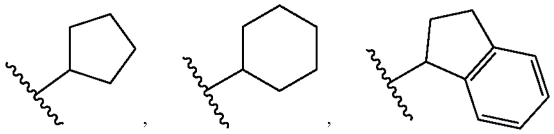,

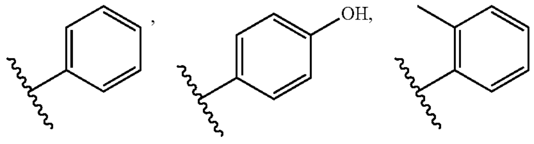,

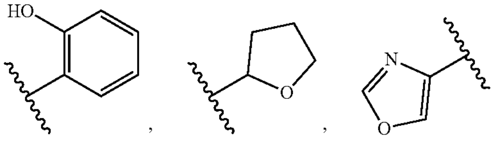 or

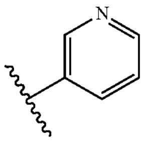.

13. The compound of any one of clauses 1, 4-5 and 11-12, or a pharmaceutically acceptable salt or deuterated form thereof, wherein one of $R^2$ is $C_{1-6}$ alkyl, and the other $R^2$ is cycloalkyl.

14. The compound of any one of clauses 1, 4-5 and 11-13, or a pharmaceutically acceptable salt or deuterated form thereof, wherein one of $R^2$ is $C_{1-6}$ alkyl, and the other $R^2$ is $C_{3-6}$ cycloalkyl.

15. The compound of any one of clauses 1, 4-5 and 11-14, or a pharmaceutically acceptable salt or deuterated form thereof, wherein one of $R^2$ is —$CH_3$, and the other $R^2$ is

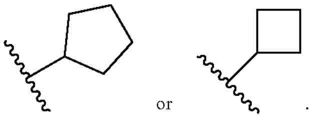.

16. The compound of any one of clauses 1, 4-5 and 11-15, or a pharmaceutically acceptable salt or deuterated form thereof, wherein one of $R^2$ is —$CH_3$, and the other $R^2$ is

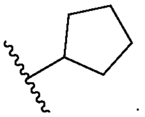 [SMILES: *C1CCCC1]

17. The compound of any one of clauses 1, 4-5 and 11-15, or a pharmaceutically acceptable salt or deuterated form thereof, wherein one of $R^2$ is —$CH_3$, and the other $R^2$ is

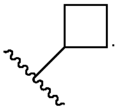

18. The compound of any one of clauses 1 and 4-5, or a pharmaceutically acceptable salt or deuterated form thereof, wherein one of $R^2$ is H, and the other $R^2$ is OH, $OCH_3$, $CH_3$, $CHCH_3$, $CH(CH_3)_2$,

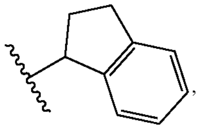, 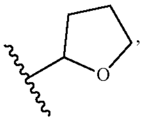, 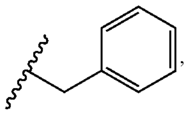,

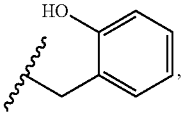, 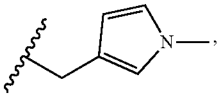,

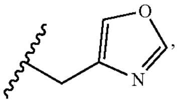, 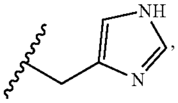,

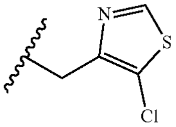 or 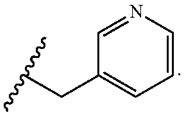.

19. The compound of any one of clauses 1, 4-5 and 18, or a pharmaceutically acceptable salt or deuterated form thereof, wherein one of $R^2$ is H, and the other $R^2$ is OH or $OCH_3$.

20. The compound of any one of clauses 1, 3 and 6-7, or a pharmaceutically acceptable salt or deuterated form thereof, wherein $R^2$ is OH, $OCH_3$, $CH_3$, $CHCH_3$, $CH(CH_3)_2$,

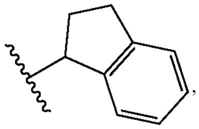, 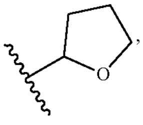, 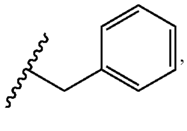,

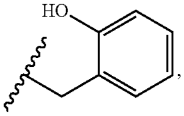, 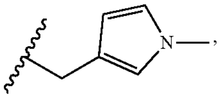,

-continued

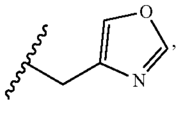, 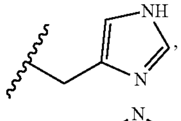,

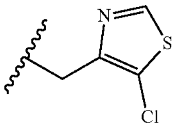 or 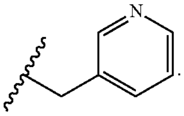.

21. The compound of clause 1, 3, 6-7 and 20, or a pharmaceutically acceptable salt or deuterated form thereof, wherein $R^2$ is OH or $OCH_3$.

22. The compound of any clause 1 and 4-5, or a pharmaceutically acceptable salt or deuterated form thereof, wherein two $R^2$ together form (═O).

23. The compound of clause 2, or a pharmaceutically acceptable salt or deuterated form thereof, wherein the A ring is

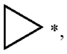, 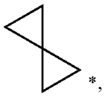, 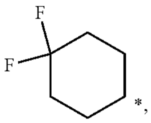,

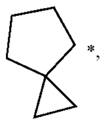, 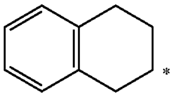 or 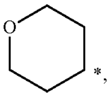, wherein the asterisk represents the site of attachment.

24. The compound of clause 2 or 23, or a pharmaceutically acceptable salt or deuterated form thereof, wherein the A ring is

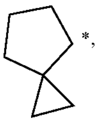, wherein the asterisk represents the site of attachment.

25. The compound of any one of clauses 1-24, or a pharmaceutically acceptable salt or deuterated form thereof, wherein each of $R^3$ and $R^4$ is independently selected from H, $C_{1-6}$ alkyl, cycloalkyl, aryl, heterocyclyl, heteroaryl, alkylene-aryl, alkylene-heteroaryl, C(═O)aryl or C(═O)heteroaryl, wherein the alkyl, cycloalkyl, aryl, heterocyclyl, heteroaryl, and alkylene is optionally substituted with 1-4 groups selected from alkyl, halogen, OH, $NH_2$, NH($C_{1-6}$ alkyl), NH($C_{1-6}$ alkyl)$_2$ or $OC_{1-6}$ alkyl.

26. The compound of any one of clauses 1-25, or a pharmaceutically acceptable salt or deuterated form thereof, wherein each of $R^3$ and $R^4$ is independently selected from H, $C_{1-6}$ alkyl, alkylene-heteroaryl, or C(═O)heteroaryl, wherein the $C_{1-6}$ alkyl, alkylene-heteroaryl, and C(═O)heteroaryl are optionally substituted with 1-4 groups selected from alkyl, halogen, OH, $OC_{1-6}$ alkyl.

27. The compound of any one of clauses 1-26, or a pharmaceutically acceptable salt or deuterated form thereof, wherein each of $R^3$ and $R^4$ is independently selected from H, $—CH_3$, $—CH_2CH_3$, $—CH_2CH_2CH_3$,

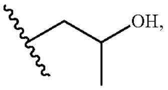, 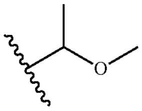, 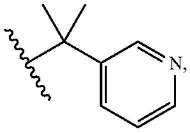, 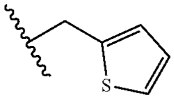, 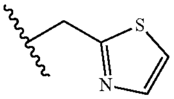, 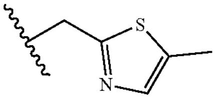, 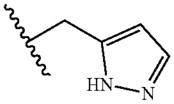, 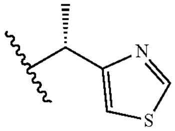, 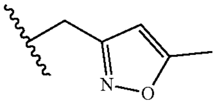, 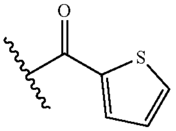 or 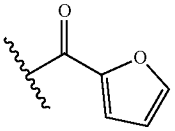.

28. The compound of any one of clauses 1-27, or a pharmaceutically acceptable salt or deuterated form thereof, wherein $R^3$ and $R^4$ are each H.

29. The compound of any one of clauses 1-27, or a pharmaceutically acceptable salt or deuterated form thereof, wherein $R^3$ is H and $R^4$ is $—CH_3$, $—CH_2CH_3$, $—CH_2CH_2CH_3$,

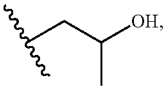, 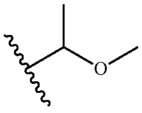, 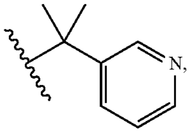, 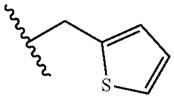, 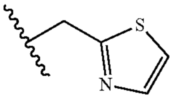, 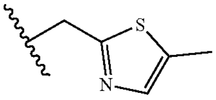, 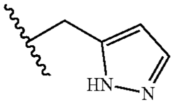, 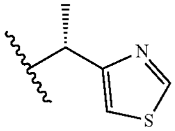, 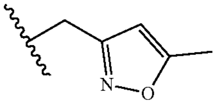, 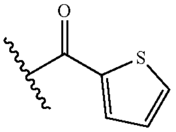 or 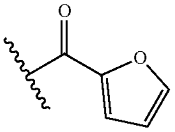.

30. The compound of any one of clauses 1-27, or a pharmaceutically acceptable salt or deuterated form thereof, wherein $R^3$ and $R^4$ is independently selected from H or $C_{1-6}$ alkyl.

31. The compound of any one of clauses 1-27 and 30, or a pharmaceutically acceptable salt or deuterated form thereof, wherein each of $R^3$ and $R^4$ is independently selected from H, $—CH_3$, $—CH_2CH_3$ or $—CH_2CH_2CH_3$.

32. The compound of any one of clauses 1-27 and 30-31, or a pharmaceutically acceptable salt or deuterated form thereof, wherein $R^3$ is H and $R^4$ is $—CH_3$, $—CH_2CH_3$ or $—CH_2CH_2CH_3$.

33. The compound of any one of clauses 1-27 and 30-32, or a pharmaceutically acceptable salt or deuterated form thereof, wherein $R^3$ is H and $R^4$ is $—CH_3$.

34. The compound of any one of clauses 1-27 and 30-32, or a pharmaceutically acceptable salt or deuterated form thereof, wherein $R^3$ is H and $R^4$ is $—CH_2CH_3$.

35. The compound of any one of clauses 1-27 and 30-32, or a pharmaceutically acceptable salt or deuterated form thereof, wherein $R^3$ is H and $R^4$ is $—CH_2CH_2CH_3$.

36. The compound of any one of clauses 1-27, or a pharmaceutically acceptable salt or deuterated form thereof, wherein each of $R^3$ and $R^4$ is independently selected from $C_{1-6}$ alkyl optionally substituted with 1-4 groups selected from OH, halogen, $OC_{1-6}$ alkyl, cycloalkyl, aryl, heterocycle or heteroaryl.

37. The compound of any one of clauses 1-27 and 36, or a pharmaceutically acceptable salt or deuterated form thereof, wherein each of $R^3$ and $R^4$ is independently selected from $C_{1-6}$ alkyl.

38. The compound of any one of clauses 1-27 and 36-37, or a pharmaceutically acceptable salt or deuterated form thereof, wherein each of $R^3$ and $R^4$ is independently $—CH_3$, $—CH_2CH_3$ or $—CH_2CH_2CH_3$.

39. The compound of any one of clauses 1-27 and 36-38, or a pharmaceutically acceptable salt or deuterated form thereof, wherein each of $R^3$ and $R^4$ is $—CH_3$.

40. The compound of any one of clauses 1-27 and 36-38, or a pharmaceutically acceptable salt or deuterated form thereof, wherein each of $R^3$ and $R^4$ is $—CH_2CH_3$.

41. The compound of any one of clauses 1-27 and 36-38, or a pharmaceutically acceptable salt or deuterated form thereof, wherein $R^3$ is $—CH_3$ and $R^4$ is $—CH_2CH_3$.

42. The compound of any one of clauses 1-27 and 36-38, or a pharmaceutically acceptable salt or deuterated form thereof, wherein $R^3$ is $—CH_3$ and $R^4$ is $—CH_2CH_2CH_3$.

43. The compound of any one of clauses 1-26, or a pharmaceutically acceptable salt or deuterated form thereof, wherein $R^3$ and $R^4$ with the nitrogen they are connected to are taken together to form a heterocyclyl, wherein the heterocyclyl is optionally substituted with 1-4 groups selected from halogen, OH, $NH_2$, $NH(C_{1-6}$ alkyl), $NH(C_{1-6}$ alkyl$)_2$, $C_{1-6}$ alkyl or $OC_{1-6}$ alkyl.

44. The compound of any one of clauses 1-26 or 43, or a pharmaceutically acceptable salt or deuterated form thereof, wherein $R^3$ and $R^4$ with the nitrogen they are connected to are taken together to form a 3-8 membered heterocyclyl.

45. The compound of any one of clauses 1-26 and 43-44, or a pharmaceutically acceptable salt or deuterated form thereof, wherein $R^3$ and $R^4$ with the nitrogen they are connected to are taken together to form a heterocyclyl selected from,

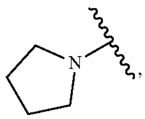, 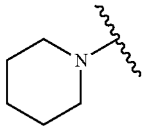 or 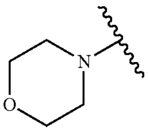.

46. The compound of any one of clauses 1 and 3-45, or a pharmaceutically acceptable salt or deuterated form thereof, wherein each one of $R^a$, $R^b$, $R^c$ and $R^d$ is selected from H, $C_{1-6}$ alkyl, halogen or $C_{1-6}$ haloalkyl.

47. The compound of any one of clauses 1 and 3-46, or a pharmaceutically acceptable salt or deuterated form thereof, wherein each one of $R^a$, $R^b$, $R^c$ and $R^d$ is H.

48. The compound of any one of clauses 1 and 3-46, or a pharmaceutically acceptable salt or deuterated form thereof, wherein one of $R^a$, $R^b$, $R^c$ and $R^d$ is $—CH_3$, $—CH_2CH_3$, $CH(CH_3)_2$, $CH_2C_1$ or $CHF_2$, and all the remaining $R^a$, $R^b$, $R^c$ and $R^d$ is H.

49. The compound of any one of clauses 1, 3-46 and 48, or a pharmaceutically acceptable salt or deuterated form thereof, wherein $R^c$ is $—CH_3$, $—CH_2CH_3$, $CH(CH_3)_2$, $CH_2Cl$, or $CHF_2$, and each of $R^a$, $R^b$ and $R^d$ is H.

50. The compound of any one of clauses 1-49, or a pharmaceutically acceptable salt or deuterated form thereof, wherein m is 0, 1 or 2.

51. The compound of any one of clauses 1-50, or a pharmaceutically acceptable salt or deuterated form thereof, wherein m is 0.

52. The compound of any one of clauses 1-50, or a pharmaceutically acceptable salt or deuterated form thereof, wherein m is 1.

53. The compound of any one of clauses 1-50, or a pharmaceutically acceptable salt or deuterated form thereof, wherein m is 2.

54. The compound of any one of clauses 1 and 3-53, or a pharmaceutically acceptable salt or deuterated form thereof, wherein n is 0, 1 or 2.

55. The compound of any one of clauses 1 and 3-54, or a pharmaceutically acceptable salt or deuterated form thereof, wherein n is 0.

56. The compound of any one of clauses 1 and 3-54, or a pharmaceutically acceptable salt or deuterated form thereof, wherein n is 1.

57. The compound of any one of clauses 1 and 3-54, or a pharmaceutically acceptable salt or deuterated form thereof, wherein n is 2.

58. The compound of any one of clauses 1 and 3-50, or a pharmaceutically acceptable salt or deuterated form thereof, wherein m is 0 and n is 0, 1, or 2.

59. The compound of any one of clauses 1 and 3-50, or a pharmaceutically acceptable salt or deuterated form thereof, wherein m is 0 and n is 0.

60. The compound of any one of clauses 1 and 3-50, or a pharmaceutically acceptable salt or deuterated form thereof, wherein m is 0 and n is 1.

61. The compound of any one of clauses 1 and 3-50, or a pharmaceutically acceptable salt or deuterated form thereof, wherein m is 0 and n is 2.

62. The compound of any one of clauses 1 and 3-50, or a pharmaceutically acceptable salt or deuterated form thereof, wherein m is 1 and n is 0 or 1.

63. The compound of any one of clauses 1 and 3-50, or a pharmaceutically acceptable salt or deuterated form thereof, wherein m is 1 and n is 0.

64. The compound of any one of clauses 1 and 3-50, or a pharmaceutically acceptable salt or deuterated form thereof, wherein m is 1 and n is 1.

65. The compound of any one of clauses 1 and 3-50, or a pharmaceutically acceptable salt or deuterated form thereof, wherein m is 2 and n is 0.

66. The compound of any one of clauses 1-3 and 8-65, or a pharmaceutically acceptable salt or deuterated form thereof, wherein L is arylene, heterocyclylene or heteroarylene, wherein L is optionally substituted by 1-4 $R^7$.

67. The compound of any one of clauses 1-3 and 8-66, or a pharmaceutically acceptable salt or deuterated form thereof, wherein L is arylene optionally substituted by 1-4 $R^7$.

68. The compound of any one of clauses 1-3 and 8-67, or a pharmaceutically acceptable salt or deuterated form thereof, wherein L is

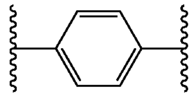 [SMILES: *c1ccc(*)cc1]

optionally substituted by 1-4 $R^7$.

69. The compound of any one of clauses 66-68, or a pharmaceutically acceptable salt or deuterated form thereof, wherein $R^7$ is halo.

70. The compound of any one of clauses 1-3 and 8-68, or a pharmaceutically acceptable salt or deuterated form thereof, wherein L is

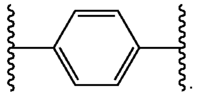

71. The compound of any one of clauses 1-3 and 8-68, or a pharmaceutically acceptable salt or deuterated form thereof, wherein L is

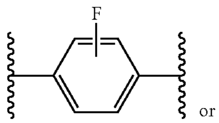 or 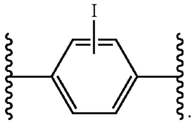

72. The compound of any one of clauses 1-3, 8-68 and 71, or a pharmaceutically acceptable salt or deuterated form thereof, wherein L is

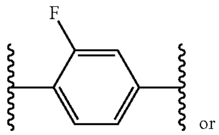 or 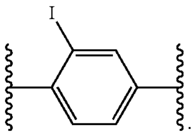

73. The compound of any one of clauses 1-3, 8-68 and 72, or a pharmaceutically acceptable salt or deuterated form thereof, wherein L is

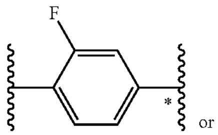 or 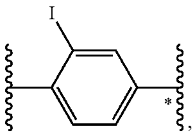, wherein the asterisk represents the point of attachment to $R^1$.

74. The compound of any one of clauses 4-7, or a pharmaceutically acceptable salt or deuterated form thereof, wherein p is 0.

75. The compound of any one of clauses 4-7, or a pharmaceutically acceptable salt or deuterated form thereof, wherein p is 1 and $R^7$ is halo.

76. The compound of any one of clauses 4-7 and 75, or a pharmaceutically acceptable salt or deuterated form thereof, wherein p is 1 and $R^7$ is F.

77. The compound of any one of clauses 1-4, 6 and 8-76, or a pharmaceutically acceptable salt or deuterated form thereof, wherein $R^1$ is 6-18 membered aryl optionally substituted with 1-3 groups independently selected from $R^5$ or $R^6$.

78. The compound of any one of clauses 1-4, 6, and 8-77, or a pharmaceutically acceptable salt or deuterated form thereof, wherein $R^1$ is

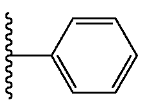
,
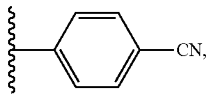

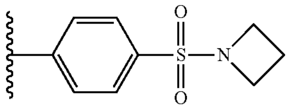
or
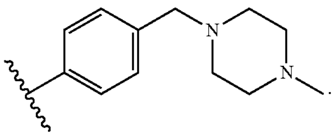

79. The compound of any one of clauses 1-4, 6 and 8-76, or a pharmaceutically acceptable salt or deuterated form thereof, wherein $R^1$ is 5-20 membered heteroaryl containing 1-3 heteroatoms selected from N, S or O, wherein the heteroaryl is optionally substituted with 1-5 groups independently selected from $R^5$ or $R^6$.

80. The compound of any one of clauses 1-4, 6, 8-76 and 79, or a pharmaceutically acceptable salt or deuterated form thereof, wherein $R^1$ is selected from:

5-12 membered monocyclic heteroaryl containing 1-3 heteroatoms selected from N, S or O, wherein the monocyclic heteroaryl is optionally substituted with 1-3 groups independently selected from $R^5$ or $R^6$, 7-14 membered bicyclic heteroaryl containing 1-3 heteroatoms selected from N, S or O, wherein the bicyclic heteroaryl is optionally substituted with 1-4 groups independently selected from $R^5$ or $R^6$, or 7-20 membered tricyclic heteroaryl containing 1-3 heteroatoms selected from N, S or O, wherein the tricyclic heteroaryl is optionally substituted with 1-5 groups independently selected from $R^5$ or $R^6$.

81. The compound of any one of clauses 1-4, 6, 8-76 and 79-80, or a pharmaceutically acceptable salt or deuterated form thereof, wherein $R^1$ is 7-14 membered bicyclic heteroaryl containing 1-3 heteroatoms selected from N, S or O, wherein the heteroaryl is optionally substituted with 1-4 groups independently selected from $R^5$ or $R^6$.

82. The compound of any one of clauses 1-4, 6, 8-76 and 81, or a pharmaceutically acceptable salt or deuterated form thereof, wherein $R^1$ is

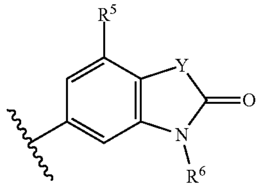
or
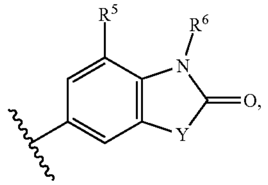

wherein each Y is independently $NR^6$, O, $CR^8R^9$, S, S(O) or $S(O)_2$, each $R^5$ is independently selected from H, halogen, $C_{1-6}$ alkyl, $C_{1-6}$ alkoxy, $C_{2-6}$ alkenyl, $C_{2-6}$ alkynyl, $C_{3-6}$cycloalkyl, CN, OH, $NH_2$, $NHC_{1-6}$ alkyl, $N(C_{1-6}$ alkyl$)_2$, COOH, $COC_{1-6}$ alkyl, $COOC_{1-6}$ alkyl, $CONHC_{1-6}$ alkyl, $CON(C_{1-6}$ alkyl$)_2$, $NHCOC_{1-6}$ alkyl, or a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-$N(C_{1-6}$ alkyl$)_2$, —$COC_{1-6}$ alkyl, $C_{2-6}$ alkenyl, $C_{2-6}$alkynyl, $C_{3-6}$cycloalkyl or 3-8 membered heterocyclyl containing 1-3 heteroatoms selected from N, S or O; wherein the $C_{1-6}$ alkyl, $NH_2$, $N(C_{1-6}$ alkyl$)_2$, alkenyl, alkynyl, cycloalkyl and heterocyclyl within $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

$R^8$ and $R^9$ are each independently selected from H, halogen, $C_{1-6}$ alkyl, $C_{1-6}$alkoxy, $C_{2-6}$ alkenyl, $C_{2-6}$ alkynyl, $OC_{2-6}$alkenyl, OC 2-6 alkynyl, $C_{3-6}$ cycloalkyl, $OC_{3-6}$ cycloalkyl, CN, OH, $NH_2$, COOH, $S(O)C_{1-6}$alkyl, $S(O)_2$ $C_{1-6}$ alkyl, $S(O)_2C_{3-6}$cycloalkyl, $SO_2$-3-7 membered heterocyclyl, or a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl or —COOH;

alternatively, $R^8$ and $R^9$ form =O.

83. The compound of any one of clauses 1-4, 6, 8-76 and 79-82, or a pharmaceutically acceptable salt or deuterated form thereof, wherein $R^1$ is

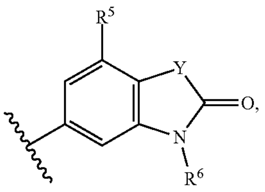

wherein each Y is independently $NR^6$, O, $CR^8R^9$, S, S(O) or $S(O)_2$, each $R^5$ is independently selected from H, halogen, $C_{1-6}$ alkyl, $C_{1-6}$ alkoxy, $C_{2-6}$ alkenyl, $C_2$-6 alkynyl, $C_{3-6}$cycloalkyl, CN, OH, $NH_2$, $NHC_{1-6}$ alkyl, $N(C_{1-6}$ alkyl$)_2$, COOH, $COC_{1-6}$ alkyl, $COOC_{1-6}$ alkyl, $CONHC_{1-6}$ alkyl, $CON(C_{1-6}$ alkyl$)_2$, $NHCOC_{1-6}$ alkyl, or a 4-7 membered heterocycle containing 1-3 heteroatoms selected from N, S or O; wherein the alkyl, alkenyl, alkynyl, cycloalkyl and heterocycle groups within $R^5$ are optionally substituted with 1-3 groups selected from halogen, CN, OH, $NH_2$, $OC_{1-6}$ alkyl, COOH, cycloalkyl or heterocyclyl;

each $R^6$ is independently selected from H, $C_{1-6}$ alkyl, $C_{1-6}$ alkylene-$NH_2$, $C_{1-6}$ alkylene-$N(C_{1-6}$ alkyl$)_2$, $-COC_{1-6}$ alkyl, $C_{2-6}$ alkenyl, $C_{2-6}$alkynyl, $C_{3-6}$cycloalkyl or 3-8 membered heterocyclyl containing 1-3 heteroatoms selected from N, S or O; wherein the $C_{1-6}$ alkyl, $NH_2$, $N(C_{1-6}$ alkyl$)_2$, alkenyl, alkynyl, cycloalkyl and heterocyclyl within $R^6$ is optionally substituted with 1-3 groups selected from halogen, CN, OH, $C_{1-6}$ alkyl, $OC_{1-6}$ alkyl, $NH_2$, $NH(C_{1-6}$ alkyl), $N(C_{1-6}$ alkyl$)_2$, cycloalkyl, aryl, heterocyclyl, heteroaryl or COOH;

$R^8$ and $R^9$ are each independently selected from H, halogen, $C_{1-6}$ alkyl, $C_{1-6}$alkoxy, $C_{2-6}$ alkenyl, $C_{2-6}$ alkynyl, $OC_{2-6}$alkenyl, OC 2-6 alkynyl, $C_{3-6}$ cycloalkyl, $OC_{3-6}$ cycloalkyl, CN, OH, $NH_2$, COOH, $S(O)C_{1-6}$alkyl, $S(O)_2$ $C_{1-6}$ alkyl, $S(O)_2C_{3-6}$cycloalkyl, $SO_2$-3-7 membered heterocyclyl, or a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$, $OC_{1-6}$ alkyl or COOH;

alternatively, $R^8$ and $R^9$ form =O.

84. The compound of any one of clauses 5 and 93-84, or a pharmaceutically acceptable salt or deuterated form thereof, wherein Y is O, S, $NR^6$ or $CR^8R^9$;

$R^5$ is H, halo or $C_{1-6}$ alkyl;

$R^6$ is $C_{1-6}$ alkyl, $C_{1-6}$ alkylene-$NH_2$ or $C_{1-6}$ alkylene-N $(C_{1-6}$ alkyl$)_2$ wherein $R^6$ is optionally substituted by 1-3 groups selected from halo, OH, $OC_{1-6}$ alkyl, $N(C_{1-6}$ alkyl$)_2$, cycloalkyl, aryl, heterocyclyl or heteroaryl;

$R^8$ and $R^9$ are independently H, halo or $C_{1-6}$ alkyl, or $R^8$ and $R^9$ form a (=O).

85. The compound of any one of clauses 5, 7 and 82-84, or a pharmaceutically acceptable salt or deuterated form thereof, wherein Y is NH, O, S, $CH_2$, CHF, or $CF_2$.

86. The compound of any one of clauses 5, 7 and 82-85, or a pharmaceutically acceptable salt or deuterated form thereof, wherein Y is 0.

87. The compound of any one of clauses 5, 7 and 82-86, or a pharmaceutically acceptable salt or deuterated form thereof, wherein $R^6$ is $C_{1-6}$ alkyl.

88. The compound of any one of clauses 5, 7 and 82-87, or a pharmaceutically acceptable salt or deuterated form thereof, wherein $R^6$ is $-CH_3$.

89. The compound of any one of clauses 5, 7 and 82-86, or a pharmaceutically acceptable salt or deuterated form thereof, wherein $R^6$ is

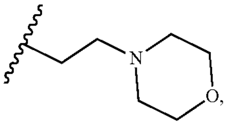

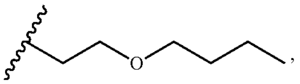

-continued

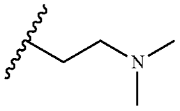

or

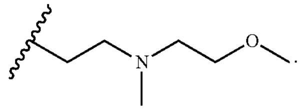

90. The compound of any one of clauses 5, 7 and 82-89, or a pharmaceutically acceptable salt or deuterated form thereof, wherein $R^5$ is H.

91. The compound of any one of clauses 5, 7 and 82-90, or a pharmaceutically acceptable salt or deuterated form thereof, wherein Y is O and $R^5$ is H.

92. The compound of any one of clauses 1-4 and 6-76, or a pharmaceutically acceptable salt or deuterated form thereof, wherein $R^1$ is

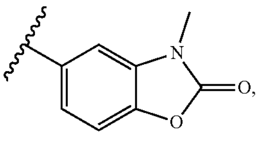

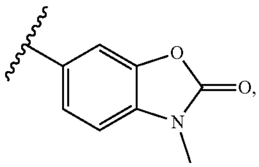

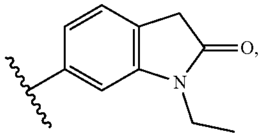

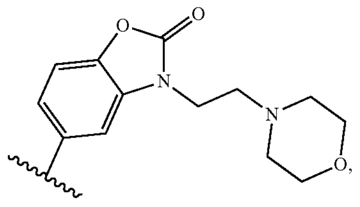

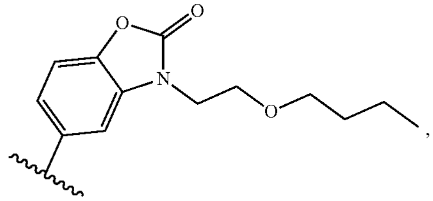

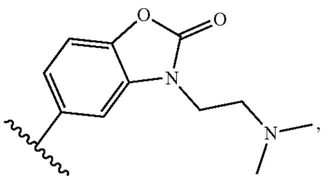

or

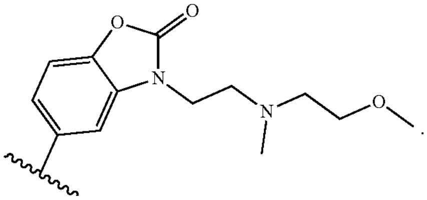

93. The compound of any one of clauses 1-4, 6 and 8-92, or a pharmaceutically acceptable salt or deuterated form thereof, wherein $R^1$ is

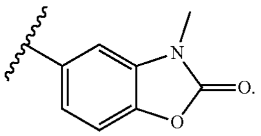 [SMILES: *c1ccc2oc(=O)n(C)c2c1]

94. The compound of any one of clauses 1-4, 6 and 8-92, or a pharmaceutically acceptable salt or deuterated form thereof, wherein $R^1$ is

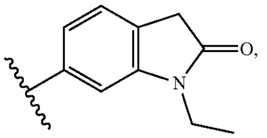

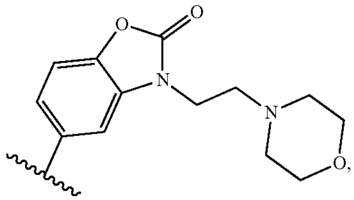

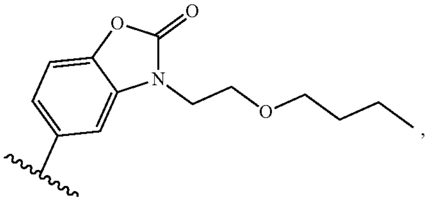

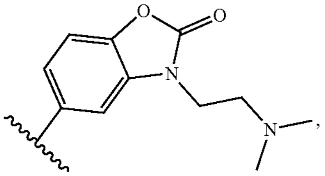

or

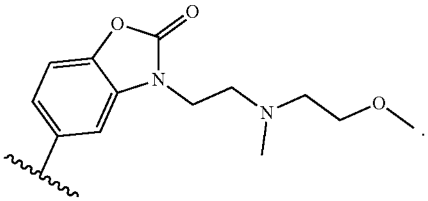

95. The compound of any one of clauses 1-4, 6 and 8-81, or a pharmaceutically acceptable salt or deuterated form thereof, wherein $R^1$ is

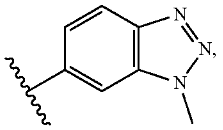

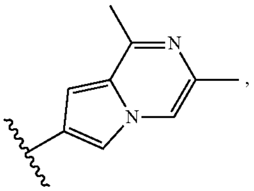

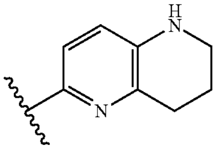

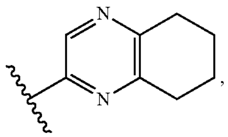

-continued

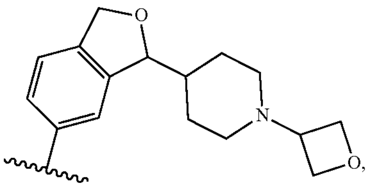

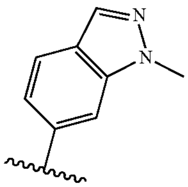

,

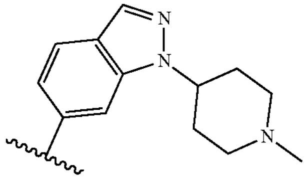

or

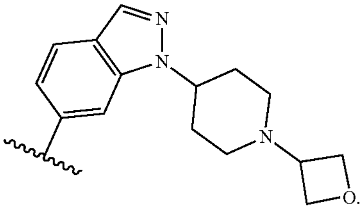

96. The compound of any one of clauses 1-4, 6 and 8-80, or a pharmaceutically acceptable salt or deuterated form thereof, wherein $R^1$ is 7-20 membered tricyclic heteroaryl containing heteroatoms selected from N, S or O, wherein the tricyclic heteroaryl is optionally substituted with 1-5 $R^6$ or $R^7$ groups.

97. The compound of any one of clauses 1-4, 6, 8-80 and 96, or a pharmaceutically acceptable salt or deuterated form thereof, wherein $R^1$ is 7-20 membered spiro tricyclic heteroaryl containing heteroatoms selected from N, S or O, wherein the tricyclic heteroaryl is optionally substituted with 1-5 $R^5$ or $R^6$ groups.

98. The compound of any one of clauses 1-4, 6, 8-80 and 96-97, or a pharmaceutically acceptable salt or deuterated form thereof, wherein $R^1$ is

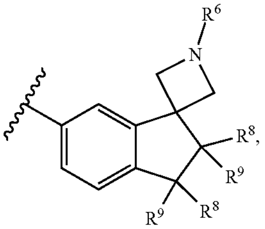

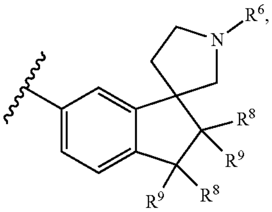

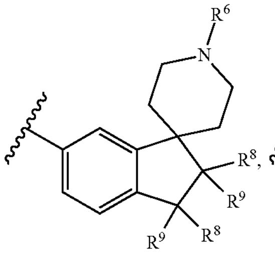

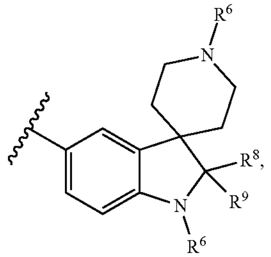

-continued

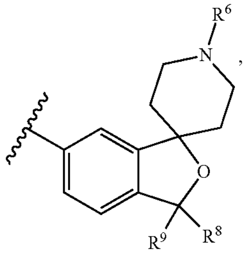,
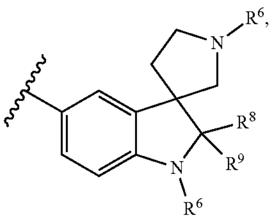
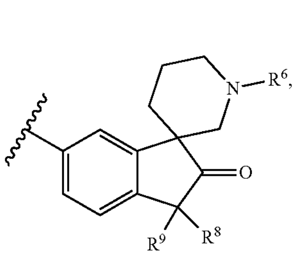
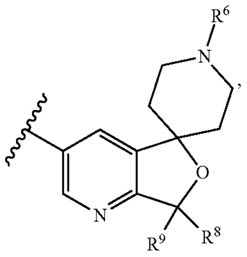
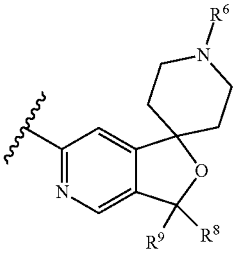
or
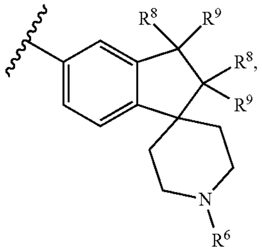

wherein each $R^6$ is independently selected from H, $C_{1-6}$ alkyl, $C_{1-6}$ alkylene-$NH_2$, $C_{1-6}$ alkylene-N($C_{1-6}$ alkyl)$_2$, —$COC_{1-6}$ alkyl, $C_{2-6}$ alkenyl, $C_{2-6}$alkynyl, $C_{3-6}$cycloalkyl and 3-8 membered heterocyclyl containing 1-3 heteroatoms selected from N, S or O; wherein the $C_{1-6}$ alkyl, $NH_2$, N($C_{1-6}$ alkyl)$_2$, alkenyl, alkynyl, cycloalkyl and heterocyclyl within $R^6$ is optionally substituted with 1-3 groups selected from halogen, CN, OH, $C_{1-6}$ alkyl, $OC_{1-6}$ alkyl, $NH_2$, NH($C_{1-6}$ alkyl), N($C_{1-6}$ alkyl)$_2$, cycloalkyl, aryl, heterocyclyl, heteroaryl or COOH;

$R^8$ and $R^9$, in each instance, are each independently selected from H, halogen, $C_{1-6}$ alkyl, $OC_{1-6}$ alkyl, $C_{2-6}$ alkenyl, $C_{2-6}$ alkynyl, $OC_{2-6}$alkenyl, OC 2-6 alkynyl, $C_{3-6}$ cycloalkyl, $OC_{3-6}$ cycloalkyl, CN, OH, $NH_2$, COOH, —S(O)$C_{1-6}$ alkyl, —S(O)$_2C_{1-6}$ alkyl, —S(O)$_2$ $C_{3-6}$cycloalkyl, —$SO_2$-3-7 membered heterocyclyl or a 4-7 membered heterocycle containing 1-3 heteroatoms selected from N, S or O, wherein the alkyl, alkoxy, alkenyl, alkynyl, cycloalkyl and heterocycle is optionally substituted with 1-3 groups selected from halogen, CN, OH, $NH_2$ or —COOH; or alternatively, $R^8$ and $R^9$ form =O.

99. The compound of any one of clauses 1-4, 6, 8-80 and 96-98, or a pharmaceutically acceptable salt or deuterated form thereof, wherein $R^1$ is

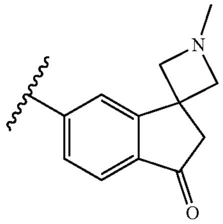,
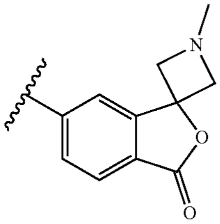,
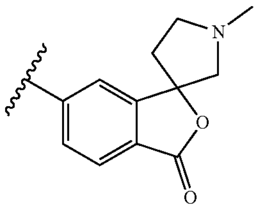,
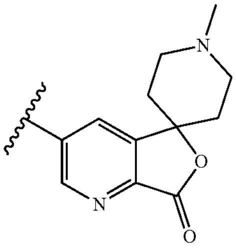,
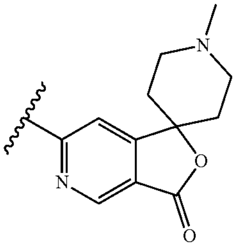,
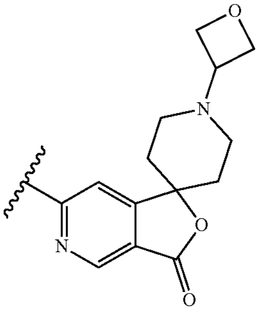,
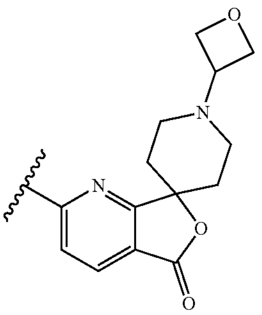,
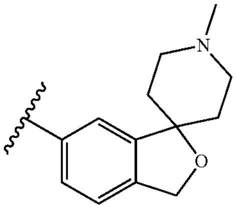,
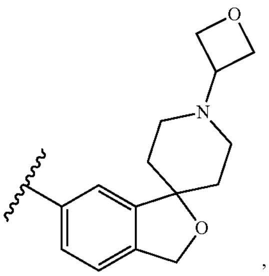,
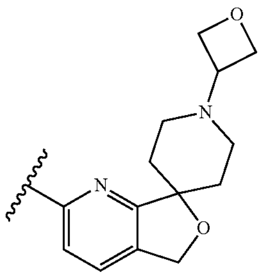,
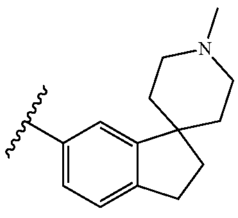,
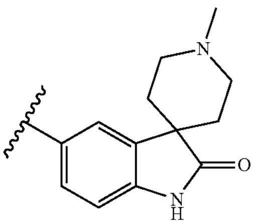, -continued

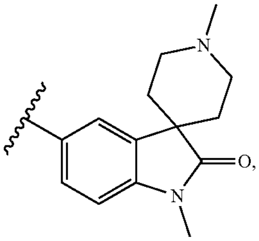,

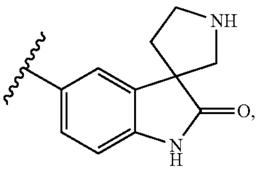,

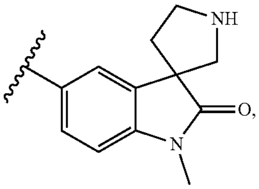,

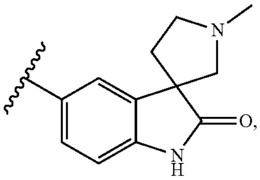,

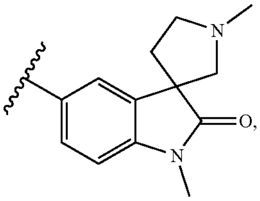,

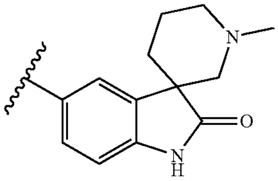,

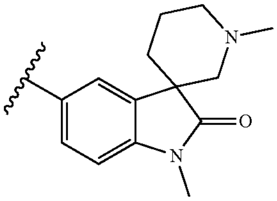

or

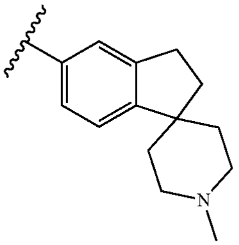.

100. The compound of any one of the clauses 1-4, 6, 8-80 and 99, or a pharmaceutically acceptable salt or deuterated form thereof, wherein $R^1$ is

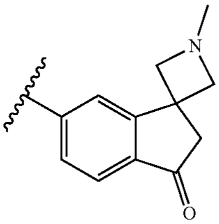,

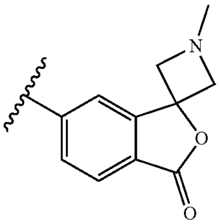,

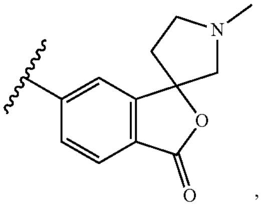,

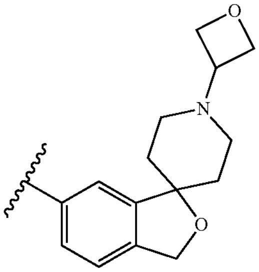,

-continued

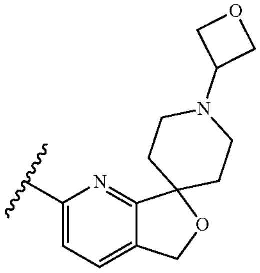,

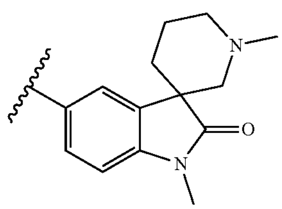

or

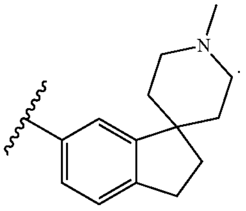.

101. The compound of any one of clauses 1-4, 6 and 8-70, or a pharmaceutically acceptable salt or deuterated form thereof, wherein p is 1, 2, 3 or 4, and one $R^7$ and one $R^5$ together form a cycloalkyl or heterocyclyl ring.

102. The compound of any one of clauses 1-4, 6 and 8-70, or a pharmaceutically acceptable salt or deuterated form thereof, wherein

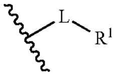

is

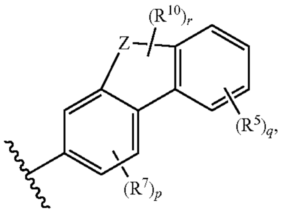,

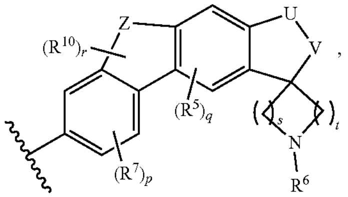,

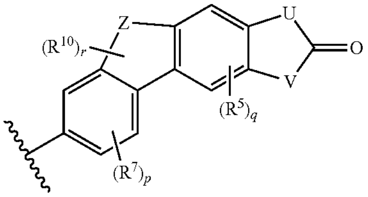

or

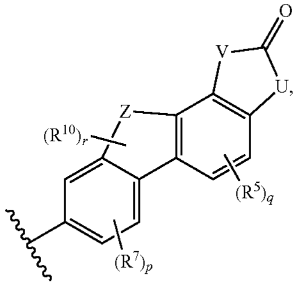, wherein p is 0, 1, 2 or 3, q is 0, 1, 2 or 3, r is 0 or 1, and each of s and t is 0, 1, 2 or 3, provided that s and t are not 0 at the same time, U and V are each independently $CH_2$, $C(=O)$, 0 or $NR^6$, Z is O, $CH_2O$, $OCH_2$, $CH_2$ or $CH_2CH_2$, and $R^{10}$ is alkyl, halogen, Oalkyl, haloalkyl, OH or CN.

103. The compound of clause 102, or a pharmaceutically acceptable salt or deuterated form thereof, wherein Z is $CH_2O$ or $OCH_2$.

104. The compound of clause 102 or 103, or a pharmaceutically acceptable salt or deuterated form thereof, wherein U and V are each independently O or $N(R^6)$.

105. The compound of any one of clauses 102-104, or a pharmaceutically acceptable salt or deuterated form thereof, wherein U and V are each independently O or $N(CH_3)$.

106. The compound of any one of clauses 102-105, or a pharmaceutically acceptable salt or deuterated form thereof, wherein U is O, and V is $N(CH_3)$.

107. The compound of any one of clauses 101-106, or a pharmaceutically acceptable salt or deuterated form thereof, wherein

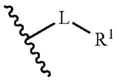

is

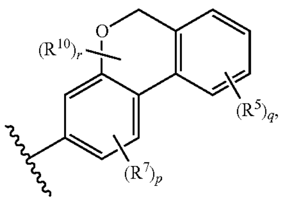

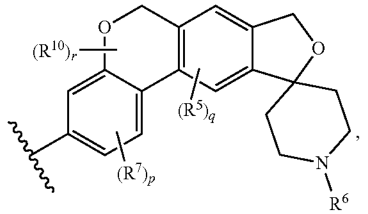

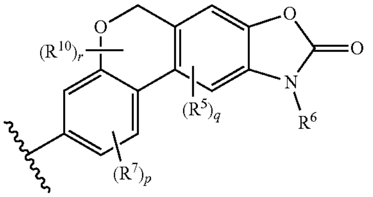

or

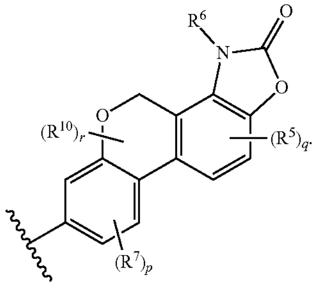

108. The compound of any one of clauses 1-4, 6, 8-70 and 101, or a pharmaceutically acceptable salt or deuterated form thereof, wherein

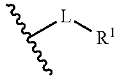

is

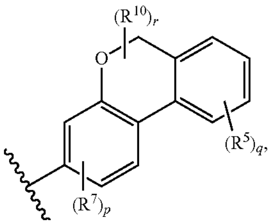

wherein p is 0, 1, 2 or 3, q is 0, 1, 2 or 3, r is 0 or 1, and $R^{10}$ is alkyl, halogen, Oalkyl, haloalkyl, OH or CN.

109. The compound of any one of clauses 1-4, 6, 8-70 and 101-107, or a pharmaceutically acceptable salt or deuterated form thereof, wherein

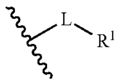

is

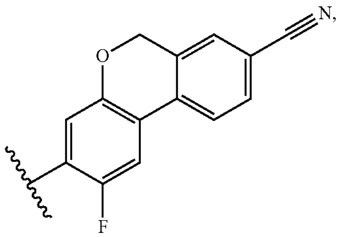

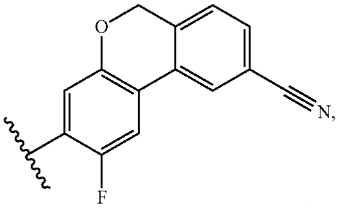

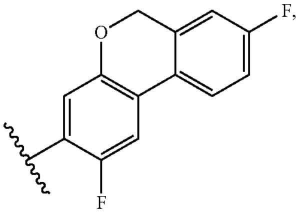

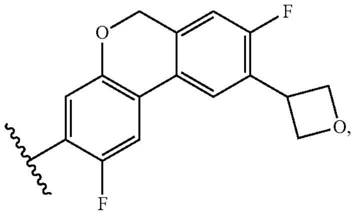

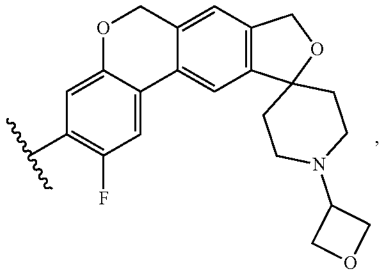

-continued

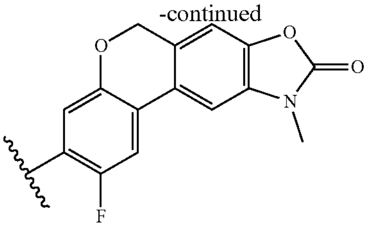

or

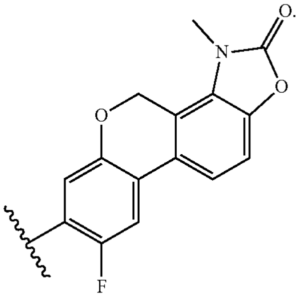

110. The compound of clause 1, or a pharmaceutically acceptable salt or deuterated form thereof, wherein the compound is selected from Table A.

111. A pharmaceutical composition comprising an effective amount of a compound of any one of clauses 1-110, or a pharmaceutically acceptable salt or deuterated form thereof and a pharmaceutically acceptable adjuvant, diluent or carrier.

112. A method for treating an obstructive disease of the airway in a patient in need thereof, comprising, administering to the patient an effective amount of a compound of any one of clauses 1-110, or the composition of clause 111.

113. The method of clause 106, wherein the obstructive disease of the airway is asthma, chronic obstructive pulmonary disease (COPD), bronchitis, emphysema, cystic fibrosis (CF), bronchiectasis, sarcoidosis, alpha-1 antitrypsin (A1AT) deficiency, farmer's lung and related diseases, hypersensitivity pneumonitis, pulmonary fibrosis, complications of lung transplantation, vasculitic and thrombotic disorders of the lung vasculature, pulmonary hypertension, antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus, acute lung injury, or acute respiratory distress syndrome (ARDS).

114. The method of clause 113, wherein the obstructive disease of the airway is asthma.

115. The method of clause 113, wherein the obstructive disease of the airway is acute respiratory distress syndrome (ARDS).

116. The method of clause 113, wherein the obstructive disease of the airway is bronchitis.

117. The method of clause 113, wherein the obstructive disease of the airway is pulmonary fibrosis.

118. The method of clause 113, wherein the obstructive disease of the airway is emphysema.

119. The method of clause 113, wherein the obstructive disease of the airway is cystic fibrosis (CF).

120. The method of clause 113, wherein the obstructive disease of the airway is bronchiectasis.

121. The method of clause 113, wherein the obstructive disease of the airway is sarcoidosis.

122. The method of clause 113, wherein the obstructive disease of the airway is alpha-1 antitrypsin (A1AT) deficiency.

123. The method of clause 113, wherein the obstructive disease of the airway is farmer's lung.

124. The method of clause 113, wherein the obstructive disease of the airway is hypersensitivity pneumonitis.

125. The method of clause 113, wherein the obstructive disease of the airway is a complication of lung transplantation.

126. The method of clause 113, wherein the obstructive disease of the airway is a vasculitic or thrombotic disorder of the lung vasulature.

127. The method of clause 113, wherein the obstructive disease of the airway is pulmonary hypertension.

128. The method of clause 113, wherein the obstructive disease of the airway is iatrogenic cough.

129. The method of clause 113, wherein the obstructive disease of the airway is acute rhinitis.

130. The method of clause 113, wherein the obstructive disease of the airway is chronic rhinitis.

131. The method of clause 113, wherein the obstructive disease of the airway is rhinitis medicamentosa or vasomotor rhinitis.

132. The method of clause 113, wherein the obstructive disease of the airway is nasal polyposis.

133. The method of clause 113, wherein the obstructive disease of the airway is COPD.

134. The method of clause 114, wherein the asthma is bronchial, allergic, intrinsic, extrinsic, exercise-induced or drug-induced asthma.

135. The method of clause 126, wherein the bronchitis is infectious bronchitis or eosinophilic bronchitis.

136. The method of clause 127, wherein the pulmonary fibrosis is idiopathic pulmonary fibrosis, cryptogenic fibrosing alveolitis, idiopathic interstitial pneumonia, or fibrosis complicating anti-neoplastic therapy or chronic infection.

137. The method of clause 120, wherein the bronchiectasis is non-cystic fibrosis bronchiectasis (NCFBE).

138. The method of clause 120, wherein the bronchiectasis is associated with cystic fibrosis.

139. The method of clause 127, wherein the pulmonary hypertension is pulmonary arterial hypertension.

140. The method of clause 127, wherein the pulmonary hypertension is pulmonary hypertension due to left heart disease.

141. The method of clause 127, wherein the pulmonary hypertension is pulmonary hypertension associated with chronic lung disease.

142. A method for treating cystic fibrosis in a patient in need thereof, comprising, administering to the patient an effective amount of a compound of any one of clauses 1-110, or the composition of clause 111.

143. The method of clause 142, wherein the treating comprises improving the lung function of the patient, as compared to the lung function of the patient prior to treatment.

144. The method of clause 143, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior treatment.

145. The method of clause 143 or 144, wherein the lung function is measured by spirometry.

146. A method for treating bronchiectasis in a patient in need thereof, comprising, administering to the patient, an effective amount of a compound of any one of clauses 1-110, or the composition of clause 111.

147. The method of clause 146, wherein the bronchiectasis is non-cystic fibrosis bronchiectasis (NCFBE).

148. The method of clause 146, wherein the bronchiectasis is associated with cystic fibrosis.

149. The method of any one of clauses 146-148, wherein treating comprises improving the lung function of the patient, as compared to the lung function of the patient prior to treatment.

150. The method of clause 149, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior to treatment.

151. The method of clause 149 or 150, wherein the lung function is measured by spirometry.

152. The method of any one of clauses 146-151, wherein treating comprises decreasing the rate of pulmonary exacerbation, as compared to the rate of pulmonary exacerbation of the patient prior to treatment.

153. The method of any one of clauses 146-152, wherein treating comprises increasing the time to first pulmonary exacerbation, as compared to an untreated patient.

154. The method of clause 152-153, wherein the pulmonary exacerbation is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis.

155. A method for treating chronic rhinosinusitis (CRS) in a patient in need thereof, comprising, administering to the patient, an effective amount of a compound of any one of clauses 1-110, or the composition of clause 111.

156. The method of clause 155, wherein the chronic rhinosinusitis is chronic rhinosinusitis without nasal polyps (CRSsNP).

157. The method of clause 155, wherein the chronic rhinosinusitis is chronic rhinosinusitis with nasal polyps (CRSwNP).

158. The method of any one of clauses 155-156, wherein the chronic rhinosinusitis is refractory chronic rhinosinusitis.

159. The method of any one of clauses 155-158, wherein treating comprises reducing, diminishing the severity of, delaying the onset of, or eliminating one or more symptoms of CRS.

160. The method of clause 159, wherein the one or more symptoms of CRS is nasal congestion; nasal obstruction; nasal discharge; post-nasal drip; facial pressure; facial pain; facial fullness; reduced smell; depression; mucosal edema; mucopurulent discharge; obstruction of the middle meatus; mucosal changes within the ostiomeatal complex and sinuses; or rhinorrhea.

161. A method for treating hidradenitis suppurativa (HS) in a patient in need thereof, comprising, administering to the patient, an effective amount of a compound of any one of clauses 1-110, or the composition of clause 111.

162. The method of clause 161, wherein the hidradenitis suppurativa (HS) is Hurley stage I.

163. The method of clause 161, wherein the hidradenitis suppurativa (HS) is Hurley stage II.

164. The method of clause 161, wherein the hidradenitis suppurativa (HS) is Hurley stage III.

165. A method for treating cancer in a patient in need thereof, comprising, administering to the patient, an effective amount of a compound of any one of clauses 1-110, or the composition of clause 111.

166. The method of clause 164, wherein the cancer is a metastatic cancer.

167. The method of clause 166, wherein the metastatic cancer is breast to lung metastatic cancer.

168. The method of clause 166, wherein the metastatic cancer comprises metastasis of breast cancer to the brain, bone, pancreas, lymph nodes or liver.

169. The method of clause 166, wherein the metastatic cancer comprises metastasis of bone cancer to the lung.

170. The method of clause 166, wherein the metastatic cancer comprises metastasis of colorectal cancer to the peritoneum, the pancreas, the stomach, the lung, the liver, the kidney, or the spleen.

171. The method of clause 166, wherein the metastatic cancer comprises metastasis of stomach cancer to the mesentery, the spleen, the pancreas, the lung, the liver, the adrenal gland, or the ovary.

172. The method of clause 166, wherein the metastatic cancer comprises metastasis of liver cancer to the intestine, spleen, pancreas, stomach, lung, or the kidney.

173. The method of clause 166, wherein the metastatic cancer comprises metastasis of lymphoma to the kidney, ovary, liver, bladder, or the spleen.

174. A method for treating lupus nephritis in a patient in need thereof, comprising, administering to the patient, an effective amount of a compound of any one of clauses 1-110, or the composition of clause 111.

175. A method for treating rheumatoid arthritis in a patient in need thereof, comprising, administering to the patient, an effective amount of a compound of any one of clauses 1-110, or the composition of clause 111.

176. A method for treating inflammatory bowel disease (IBD) in a patient in need thereof, comprising, administering to the patient, an effective amount of a compound of any one of clauses 1-110, or the composition of clause 111.

177. The method of clause 176, wherein the inflammatory bowel disease (IBD) is Crohn's disease.

178. The method of clause 176, wherein the inflammatory bowel disease (IBD) is ulcerative colitis.

179. A method for treating an anti-neutrophil cytoplasmic antibody (ANCA) associated vasculitis in a patient in need thereof, comprising, administering to the patient, an effective amount of a compound of any one of clauses 1-110, or the composition of clause 111.

180. The method of clause 179, wherein the ANCA associated disease is granulomatosis with polyangiitis (GPA).

181. The method of clause 179, wherein the ANCA associated disease is microscopic polyangiitis (MPA).

182. A method for treating a disease in a patient in need thereof comprising, administering to the patient, an effective amount of a compound of any one of clauses 1-110, or the composition of clause 111, wherein the disease is giant cell arteritis, polyarteritis nodosa, anti-GBM disease (Goodpasture's), systemic scleroderma, diabetic nephropathy, diabetic neuropathy, diabetic retinopathy, diabetic ulcers, Duchenne muscular dystrophy, bronchiolitis obliterans, atopic dermatitis, pyoderma gangrenosum, sweet's syndrome, dermatomyositis/polymyositis, neutrophilic dermatoses, thrombosis, bronchopulmonary dysplasia, amyotrophic lateral sclerosis, sickle cell anemia, psoriasis, or a ventilator-induced lung injury.

183. A method for treating a heart failure in a patient in need thereof, comprising administering to the patient, an effective amount of a compound of any one of clauses 1-110, or the composition of clause 111.

184. The method of clause 183, wherein the heart failure is heart failure with reduced ejection fraction.

185. The method of clause 183, wherein the heart failure is heart failure with preserved ejection fraction.

186. A compound selected from Table A, or a pharmaceutically acceptable salt or deuterated form thereof.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A compound of Formula (IX), (IX)

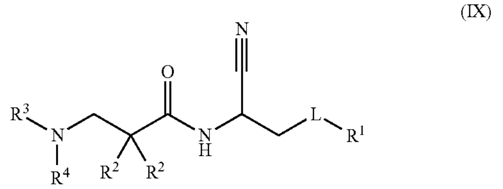

or a pharmaceutically acceptable salt, a stereoisomer or a deuterated form thereof, wherein:

$R^1$ is carbocyclyl, aryl, heterocyclyl or heteroaryl, wherein $R^1$ is optionally substituted with 1-5 groups independently selected from $R^5$ or $R^6$;

L is arylene, heterocyclylene, heteroarylene or cycloalkylene, wherein L is optionally substituted by 1-4 $R^7$;

each $R^2$ is independently H, halogen, —OH, —CN, —Oalkyl, -$NH_2$, —SH, —C(═O)alkyl, -C(═O)$NH_2$, alkyl, haloalkyl, -alkylene-OH, -alkylene-CH(COOH)($NH_2$), alkenyl, alkynyl, -S(alkyl), —S(═O)alkyl, —S(═O)$_2$alkyl, carbocyclyl, heterocyclyl, aryl, heteroaryl, alkylene-aryl, alkylene-heteroaryl, alkylene-heterocyclyl or alkylene-carbocyclyl, wherein $R^2$ is optionally substituted with 1-4 $R^{2a}$, provided that at least one $R^2$ is not H;

or two $R^2$ together form (═O);

$R^3$ is H, alkyl, cycloalkyl, aryl, heterocyclyl, heteroaryl, -alkylene-OH, -alkylene-O-alkyl, -alkylene-carbocyclyl, -alkylene-heterocyclyl, -alkylene-aryl, -alkylene-heteroaryl, —C(═O)alkyl, —C(═O)cycloalkyl, —C(═O)aryl or -C(═O) heteroaryl, wherein $R^3$ is optionally substituted with 1-4 $R^{3a}$;

$R^4$ is $C_{1-6}$ alkyl;

or $R^3$ and $R^4$ together with the nitrogen to which they are attached form a heterocyclyl, wherein the heterocyclyl is optionally substituted with 1-4 $R^{3a}$;

each of $R^{2a}$ and $R^{3a}$ is independently alkyl, halogen, haloalkyl, —Oalkyl, —OH, —CN, -C(═O)OH, —$NH_2$, —NH(alkyl), —NH(alkyl)$_2$, cycloalkyl or heterocyclyl;

each $R^5$ is independently halogen, $C_{1-6}$ alkyl, —O ($C_{1-6}$ alkyl), $C_{1-6}$ haloalkyl, $C_{2-6}$ alkenyl, $C_{2-6}$ alkynyl, $C_{3-6}$ cycloalkyl, —CN, oxo, —OH, —$NH_2$, —$NHC_{1-6}$ alkyl, —N($C_{1-6}$ alkyl)$_2$, -COOH, -C(═O)($C_{1-6}$ alkyl), —C(═O)O ($C_{1-6}$ alkyl), —C(═O)NH ($C_{1-6}$ alkyl), C(═O)N ($C_{1-6}$ alkyl)$_2$, NHC(═O)($C_{1-6}$ alkyl), —S(═O)$_2$($C_{1-6}$ alkyl), -($C_{1-6}$ alkylene)-cycloalkyl, —S(═O)$_2$-cycloalkyl, -($C_{1-6}$ alkylene)-heterocyclyl, —S(═O)$_2$-heterocyclyl, -heterocyclylene-heterocyclyl or heterocyclyl, wherein each $R^5$ is optionally substituted with 1-3 groups selected from halogen, —CN, —OH, —$NH_2$, $C_{1-6}$ alkyl, —O ($C_{1-6}$ alkyl), -COOH, cycloalkyl or heterocyclyl;

each $R^6$ is independently H, $C_{1-6}$ alkyl, -($C_{1-6}$ alkylene)-O-($C_{1-6}$ alkyl), -($C_{1-6}$ alkylene)-$NH_2$, -($C_{1-6}$ alkylene)-NH($C_{1-6}$ alkyl)$_2$, -$C_{1-6}$ alkylene-N ($C_{1-6}$ alkyl)$_2$, -$C_{1-6}$ alkylene-NH($C_{1-6}$ alkylene-O-$C_{1-6}$ alkyl), -$C_{1-6}$ alkylene-N($C_{1-6}$ alkylene-O-$C_{1-6}$ alkyl)($C_{1-6}$ alkyl), -$C_{1-6}$ alkylene-heterocyclyl, C(═O)($C_{1-6}$ alkyl), $C_{2-6}$ alkenyl, $C_{2-6}$ alkynyl, $C_{3-6}$ cycloalkyl, -heterocyclylene-heterocyclyl or heterocyclyl, wherein each $R^6$ is optionally substituted with 1-3 groups selected from halogen, —CN, —OH, $C_{1-6}$ alkyl, —O ($C_{1-6}$ alkyl), —$NH_2$, —NH($C_{1-6}$ alkyl), —N($C_{1-6}$ alkyl)$_2$, cycloalkyl, aryl, heterocyclyl, heteroaryl or -COOH; and each $R^7$ is independently ═O, halogen, $C_{1-6}$ alkyl, —O ($C_{1-6}$ alkyl), —S($C_{1-6}$ alkyl), $C_{2-6}$ alkenyl, $C_{2-6}$ alkynyl, $C_{3-6}$ cycloalkyl, —CN, —OH, —$NH_2$, —NH ($C_{1-6}$ alkyl), —N($C_{1-6}$ alkyl)$_2$, -COOH, -C(═O)($C_{1-6}$ alkyl), —C(═O)O ($C_{1-6}$ alkyl), —C(═O)N ($C_{1-6}$ alkyl)$_2$, or —NHC(═O)($C_{1-6}$ alkyl);

or one $R^7$ and one $R^5$ together form a carbocyclyl, aryl, heterocyclyl or heteroaryl ring, wherein the carbocyclyl, aryl, heterocyclyl, heteroaryl is optionally substituted with 1-4 groups selected from $C_{1-6}$ alkyl, halogen, —$OC_{1-6}$ alkyl, haloalkyl, —OH, —CN, or heterocyclyl.

2. The compound of claim 1, or a pharmaceutically acceptable salt, a stereoisomer or a deuterated form thereof, wherein $R^1$ is 8-10 membered fused bicyclic heteroaryl containing 1-3 heteroatoms selected from N, S or O, wherein the heteroaryl is optionally substituted with 1-4 groups independently selected from $R^5$ or $R^6$.

3. The compound of claim 1, or a pharmaceutically acceptable salt, a stereoisomer or a deuterated form thereof, wherein:

$R^1$ is

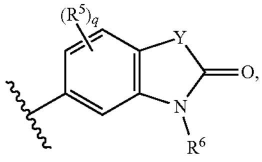,

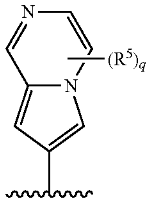,

-continued
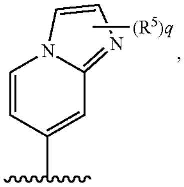
,
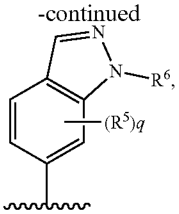
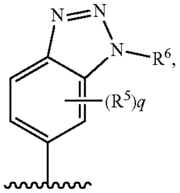
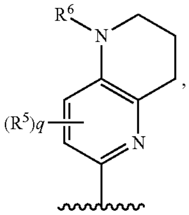
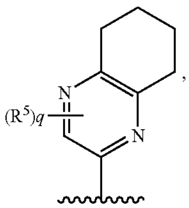
, or
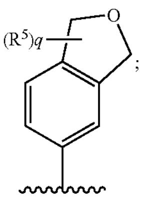
q is 0, 1, 2 or 3; and
Y is NH, O, S, $CH_2$, CHF, or $CF_2$.
4. The compound of claim 1, or a pharmaceutically acceptable salt, a stereoisomer or a deuterated form thereof, wherein $R^1$ is
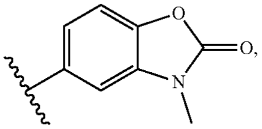
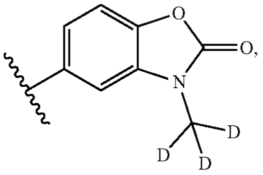
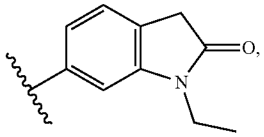
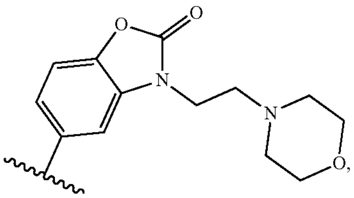
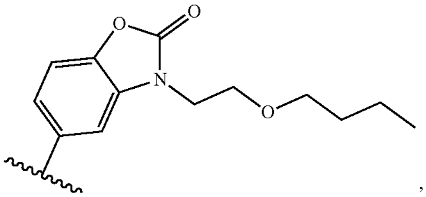
,
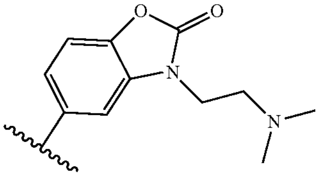
,
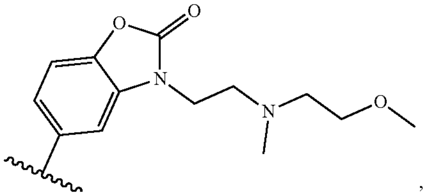
,
-continued
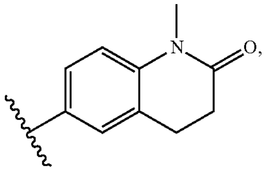
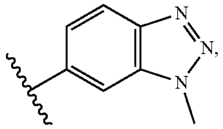
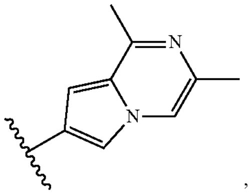
,
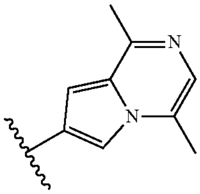
,
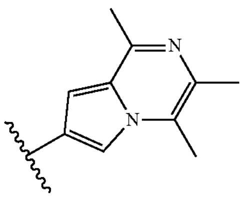
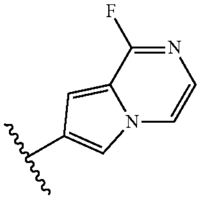
,
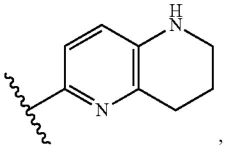
,
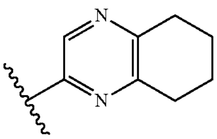
,
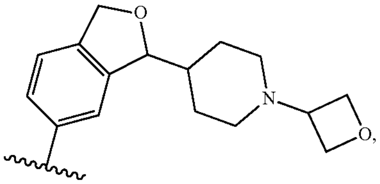
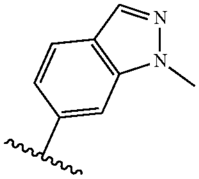
,
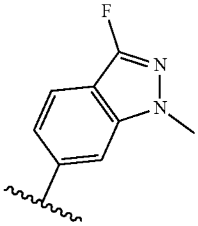
,
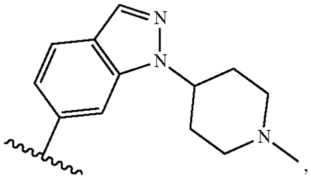
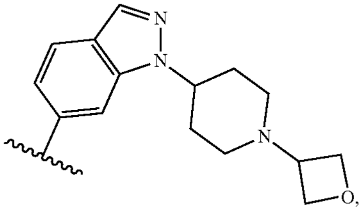
or
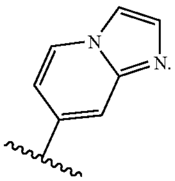

5. The compound of claim 1, or a pharmaceutically acceptable salt, a stereoisomer or a deuterated form thereof, wherein L is arylene optionally substituted by 1-4 $R^7$.

6. The compound of claim 1, or a pharmaceutically acceptable salt, a stereoisomer or a deuterated form thereof, wherein L is

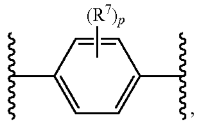

wherein p is 0, 1, 2, 3 or 4.

7. The compound of claim 1, or a pharmaceutically acceptable salt, a stereoisomer or a deuterated form thereof, wherein L is

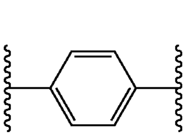 or 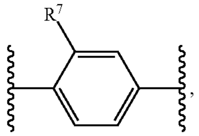, wherein $R^7$ is a halogen.

8. The compound of claim 1, or a pharmaceutically acceptable salt, a stereoisomer or a deuterated form thereof, wherein one of $R^2$ is H, and the other $R^2$ is —F, —Cl, —Br, —OH, —CN, —$OCH_3$, —$OCH_2CH_3$, —$OCH_2CH_2CH_3$, —SH, —$NH_2$, —$CH_3$, —$CH_2CH_3$, —$CH_2$ $(CH_3)_2$,

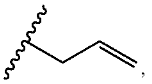,

—$CH_2F$, —$CHF_2$, —$CH_2Cl$, —CH $(COOH)NH_2$, —$CH_2CH_2CH_2F$,

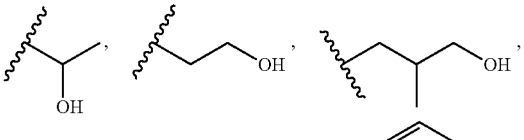

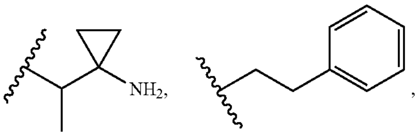

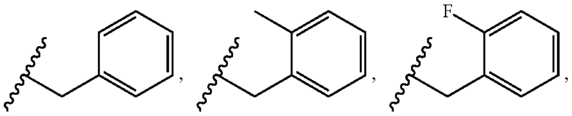

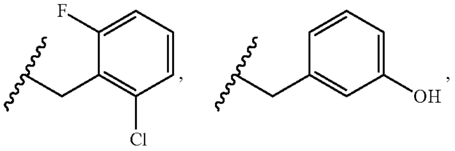

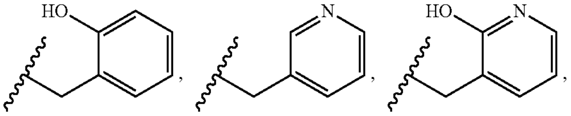

-continued

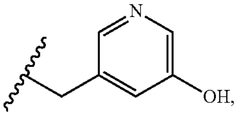 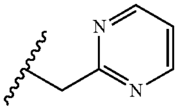,

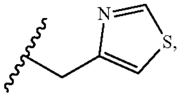 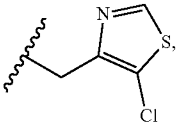 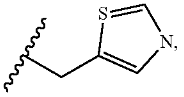

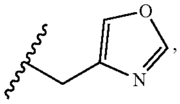, 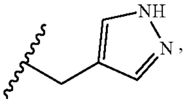, 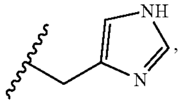,

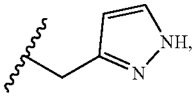 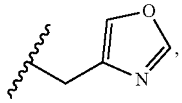, 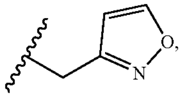

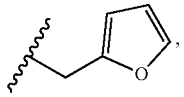, 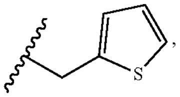, 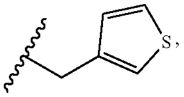

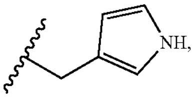 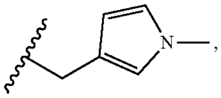, 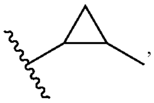,

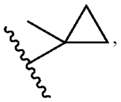, 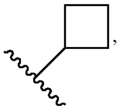, 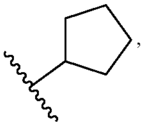, 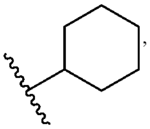,

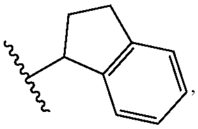, 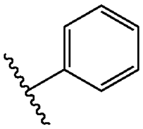, 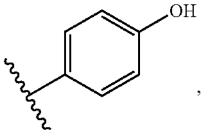,

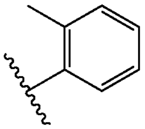, 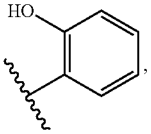, 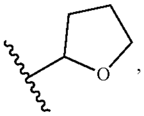,

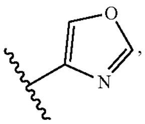, or 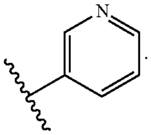.

9. The compound of claim 1, or a pharmaceutically acceptable salt, a stereoisomer or a deuterated form thereof, wherein one of $R^2$ is H, and the other $R^2$ is —F, —Cl, —Br, —OH, —CN, —$OCH_3$, —$OCH_2CH_3$, —$OCH_2CH_2CH_3$, —SH, —$NH_2$, —$CH_3$, —$CH_2CH_3$, —$CH_2$ $(CH_3)_2$,

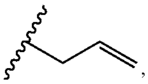 [SMILES: *CC=C],

—$CH_2F$, —$CHF_2$, —$CH_2Cl$, —CH $(COOH)NH_2$, —$CH_2CH_2CH_2F$,

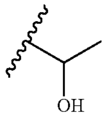
,
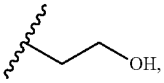
or
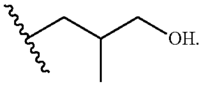

10. The compound of claim 1, or a pharmaceutically acceptable salt, a stereoisomer or a deuterated form thereof, wherein one of $R^2$ is H, and the other $R^2$ is —OH or —$OCH_3$.

11. The compound of claim 1, or a pharmaceutically acceptable salt, a stereoisomer or a deuterated form thereof, wherein $R^3$ is H or -$C_{1-6}$ alkyl.

12. The compound of claim 1, or a pharmaceutically acceptable salt, a stereoisomer or a deuterated form thereof, wherein the compound has the structure of Formula (IX-A), (IX-A)

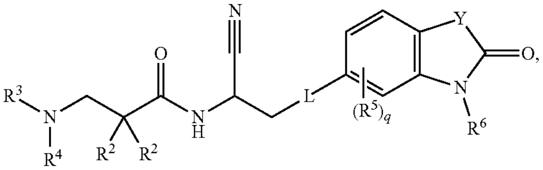

or a pharmaceutically acceptable salt, a stereoisomer or a deuterated form thereof, wherein:

q is 0, 1, 2 or 3;

Y is $NR^6$, O, $CR^8R^9$, S, S(O) or $S(O)_2$; and $R^8$ and $R^9$ are each independently H, halogen, $C_{1-6}$ alkyl, —O ($C_{1-6}$ alkyl), $C_{1-6}$ haloalkyl, $C_{3-6}$ cycloalkyl or heterocyclyl;

or $R^8$ and $R^9$ form-O.

13. The compound of claim 1, or a pharmaceutically acceptable salt, a stereoisomer or a deuterated form thereof, wherein the compound has the structure of Formula (IX-C), (IX-C)

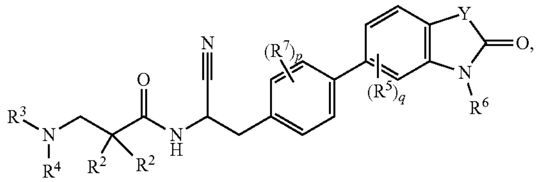

or a pharmaceutically acceptable salt, a stereoisomer or a deuterated form thereof, wherein:

p is 0, 1, 2, 3 or 4;

q is 0, 1, 2 or 3;

Y is $NR^6$, O, $CR^8R^9$, S, S(O) or $S(O)_2$; and $R^8$ and $R^{\circ}$ are each independently H, halogen, $C_{1-6}$ alkyl, —O ($C_{1-6}$ alkyl), $C_{1-6}$ haloalkyl, $C_{3-6}$ cycloalkyl or heterocyclyl;

or $R^8$ and $R^9$ form =O.

14. The compound of claim 1, or a pharmaceutically acceptable salt, a stereoisomer or a deuterated form thereof, wherein the compound has the structure of Formula (IX-B), (IX-B)

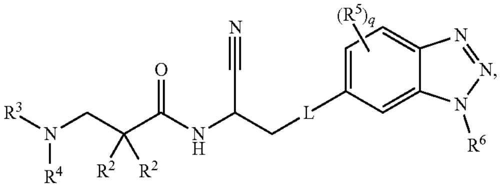

or a pharmaceutically acceptable salt, a stereoisomer or a deuterated form thereof, wherein q is 0, 1, 2 or 3.

15. The compound of claim 1, or a pharmaceutically acceptable salt, a stereoisomer or a deuterated form thereof, wherein the compound has the structure of Formula (IX-D), (IX-D)

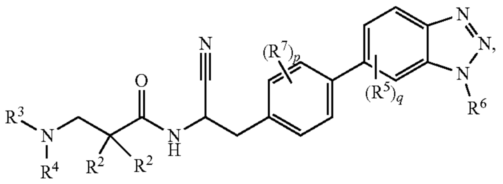

or a pharmaceutically acceptable salt, a stereoisomer or a deuterated form thereof, wherein:

p is 0, 1, 2, 3 or 4; and q is 0, 1, 2 or 3.

16. The compound of claim 1, or a pharmaceutically acceptable salt, a stereoisomer or a deuterated form thereof, wherein the compound has the structure of Formula (X), (X)

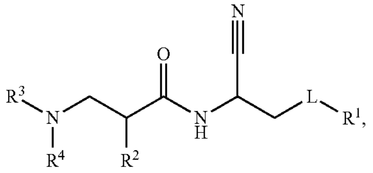

or a pharmaceutically acceptable salt, a stereoisomer or a deuterated form thereof.

17. The compound of claim 16, or a pharmaceutically acceptable salt, a stereoisomer or a deuterated form thereof, wherein $R^1$ is

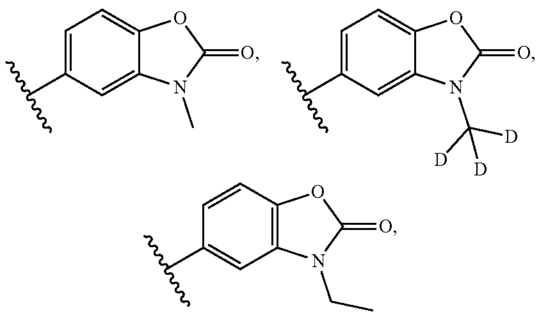

-continued

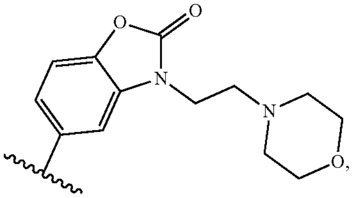

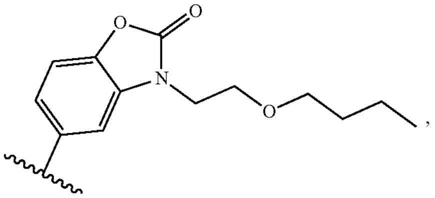

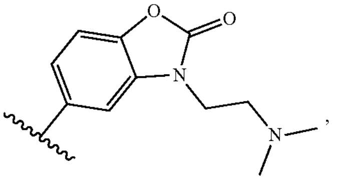

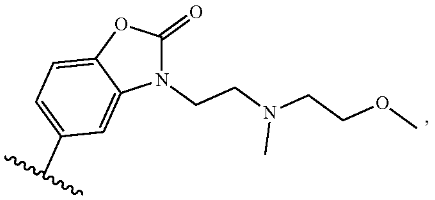

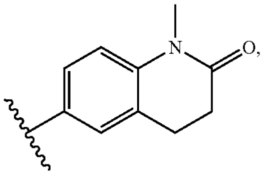

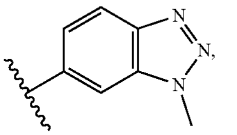

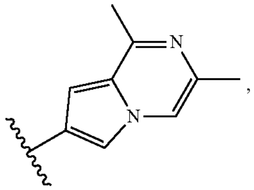

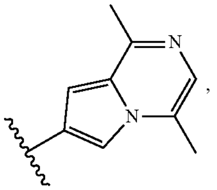

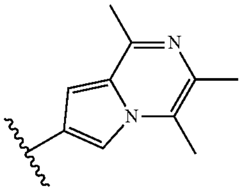

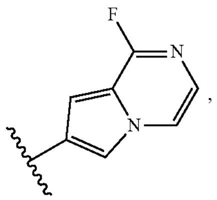

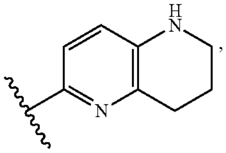

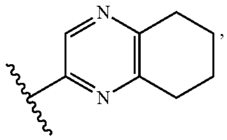

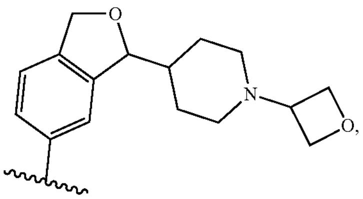

-continued

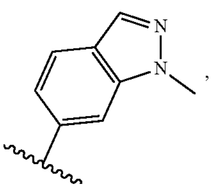

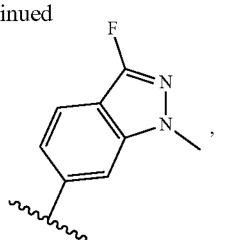

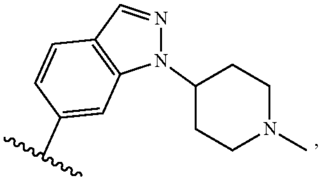

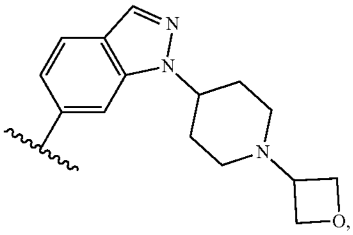

or

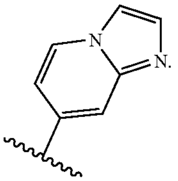

18. The compound of claim 16, or a pharmaceutically acceptable salt, a stereoisomer or a deuterated form thereof, wherein $R^1$ is

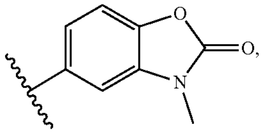

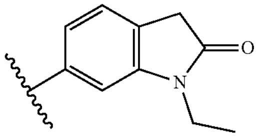

or

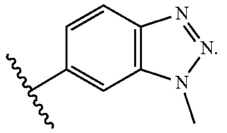

19. The compound of claim 16, or a pharmaceutically acceptable salt, a stereoisomer or a deuterated form thereof, wherein:

L is

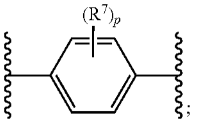

$R^7$ is a halogen; and p is 0 or 1.

20. The compound of claim 16, or a pharmaceutically acceptable salt, a stereoisomer or a deuterated form thereof, wherein $R^2$ is —F, —Cl, -Br, —OH, —CN, —$OCH_3$, -$OCH_2CH_3$, —$OCH_2CH_2CH_3$, —SH, —$NH_2$, —$CH_3$, —$CH_2CH_3$, —$CH_2$ $(CH_3)_2$,

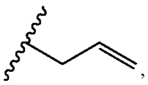 [SMILES: *CC=C],

—$CH_2F$, —$CHF_2$, —$CH_2Cl$, —CH(COOH)$NH_2$, —$CH_2CH_2CH_2F$,

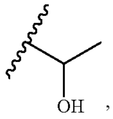, 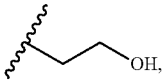, or 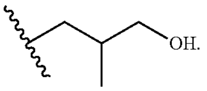

21. The compound of claim 16, or a pharmaceutically acceptable salt, a stereoisomer or a deuterated form thereof, wherein $R^2$ is —OH or —O($C_{1-6}$ alkyl).

22. The compound of claim 16, or a pharmaceutically acceptable salt, a stereoisomer or a deuterated form thereof, wherein $R^2$ is —OH or —$OCH_3$.

23. The compound of claim 16, or a pharmaceutically acceptable salt, a stereoisomer or a deuterated form thereof, wherein $R^3$ is H or —$C_{1-6}$ alkyl.

24. The compound of claim 16, or a pharmaceutically acceptable salt, a stereoisomer or a deuterated form thereof, wherein $R^3$ is H, $CH_3$, $CH_2CH_3$ or $CH_2CH_2CH_3$ and $R^4$ is $CH_3$, $CH_2CH_3$ or $CH_2CH_2CH_3$.

25. The compound of claim 16, or a pharmaceutically acceptable salt, a stereoisomer or a deuterated form thereof, wherein:

L is

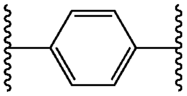 or 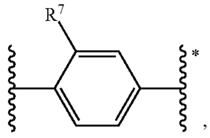, wherein the asterisk (*) represents the point of attachment to $R^1$;

$R^1$ is

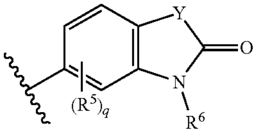 or 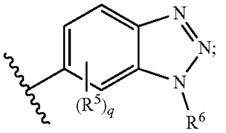

$R^5$ is halogen, —CN, $C_{1-6}$ alkyl, $C_{1-6}$ haloalkyl, or —O($C_{1-6}$ alkyl);

$R^6$ is H or $C_{1-6}$ alkyl;

$R^7$ is halogen;

Y is O or $CH_2$; and q is 0, 1, 2 or 3.

26. The compound of claim 16, or a pharmaceutically acceptable salt, a stereoisomer or a deuterated form thereof, wherein:

L is

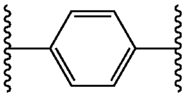 or 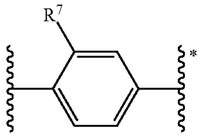, wherein the asterisk (*) represents the point of attachment to $R^1$;

$R^1$ is

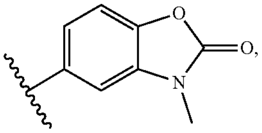, 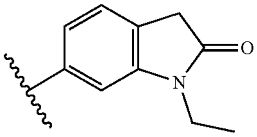 or 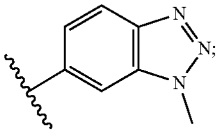;

$R^2$ is —OH or —$OCH_3$;

$R^3$ is H or $C_{1-6}$ alkyl; and $R^7$ is halogen.

27. The compound of claim 16, or a pharmaceutically acceptable salt, a stereoisomer or a deuterated form thereof, wherein the compound has the structure of Formula (X-A), (X-A)

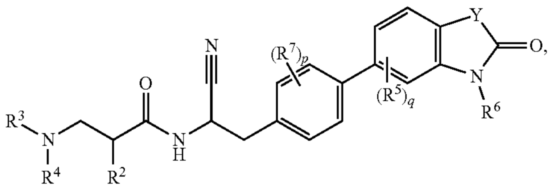

or a pharmaceutically acceptable salt, a stereoisomer or a deuterated form thereof, wherein:

Y is O or $CH_2$;

$R^2$ is —OH or —$OCH_3$;

$R^3$ is H or $C_{1-6}$ alkyl;

$R^5$ is halogen, —CN, $C_{1-6}$ alkyl, $C_{1-6}$ haloalkyl, or —O($C_{1-6}$ alkyl);

$R^6$ is H or $C_{1-6}$ alkyl;

$R^7$ is halogen;

p is 0 or 1; and q is 0 or 1.

28. A pharmaceutical composition comprising the compound of claim 1, or a pharmaceutically acceptable salt, a stereoisomer or a deuterated form thereof, and a pharmaceutically acceptable adjuvant, diluent or carrier.

29. A compound selected from:
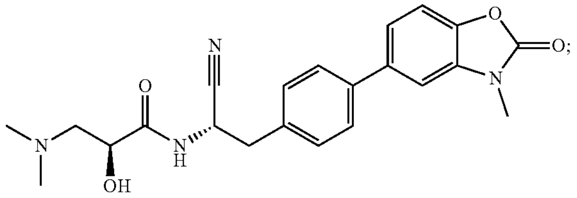
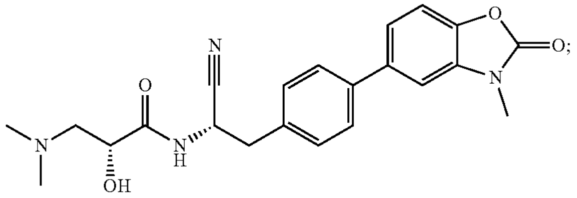
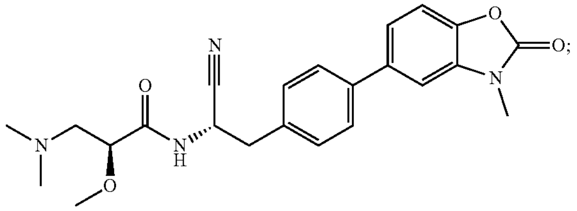
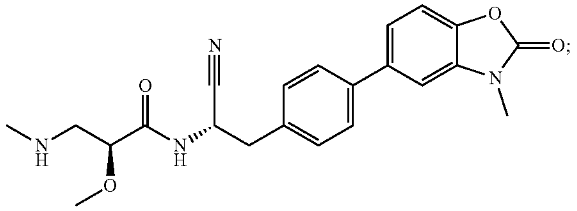
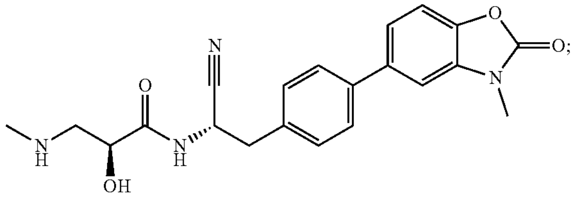
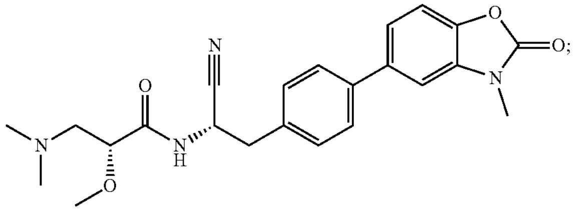
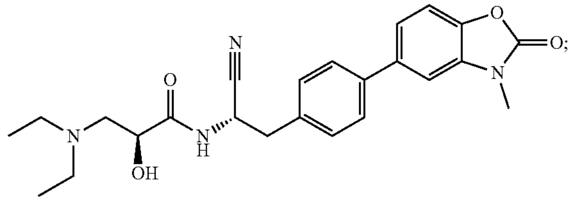
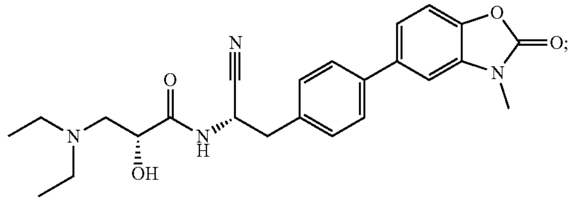
-continued
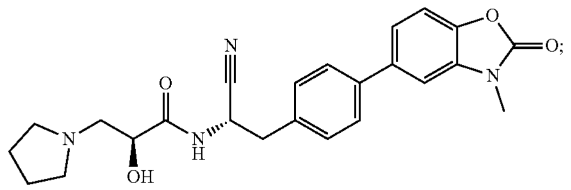
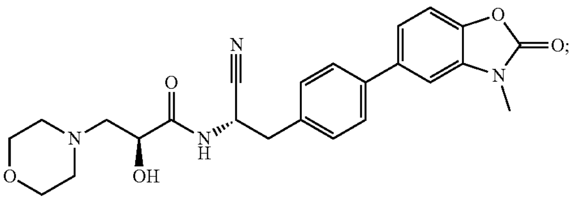
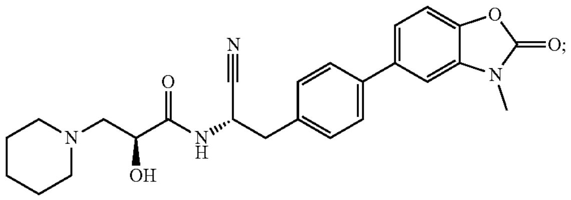
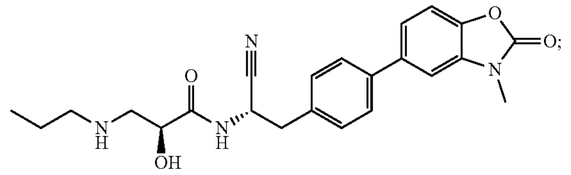
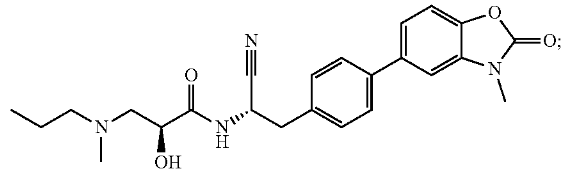
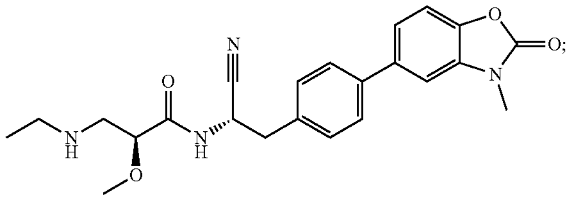
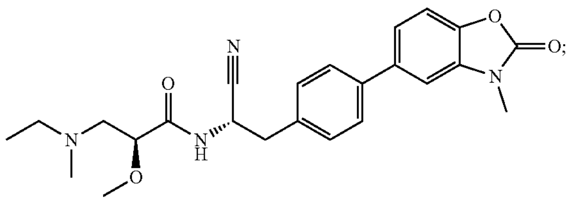
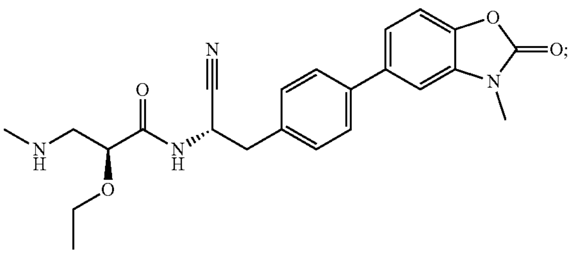

-continued
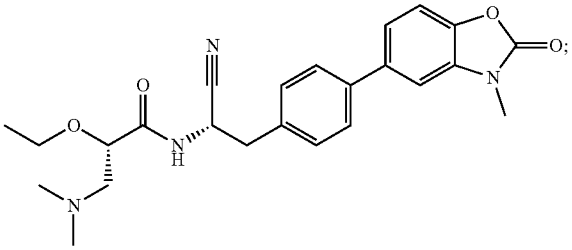
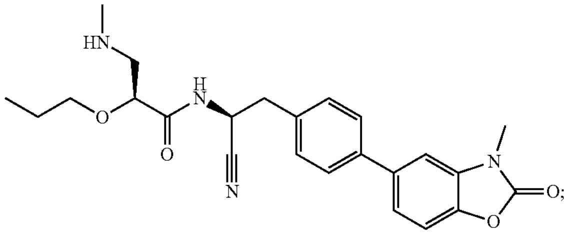
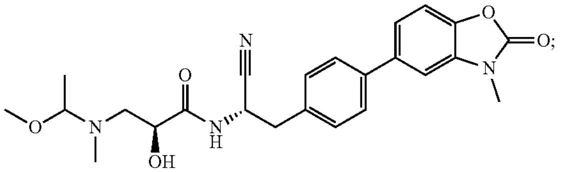
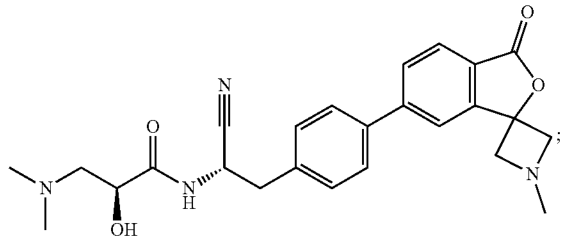
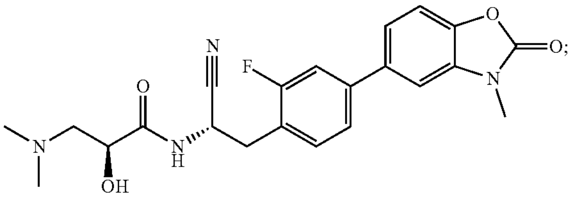
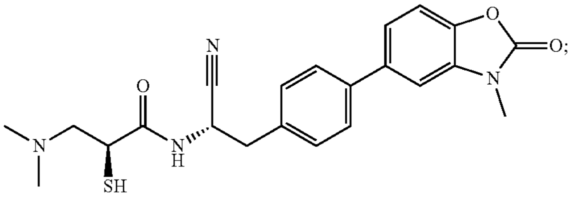
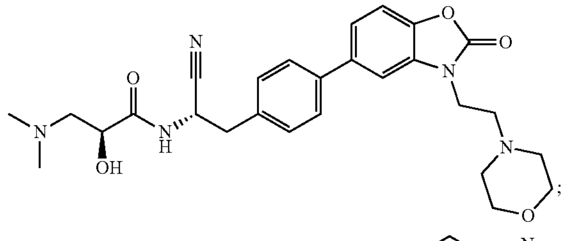
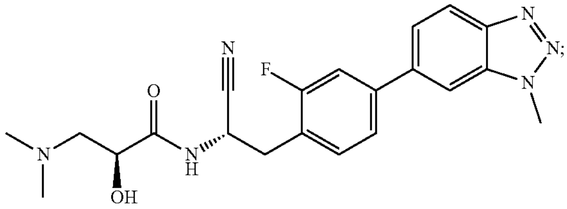
-continued
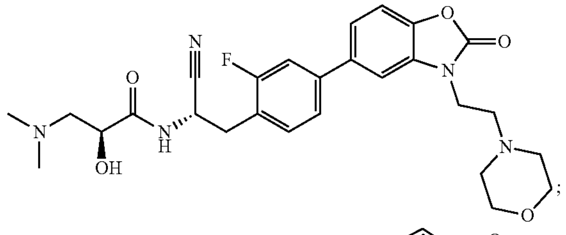
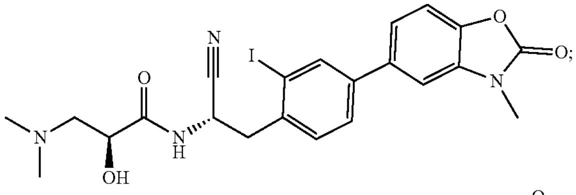
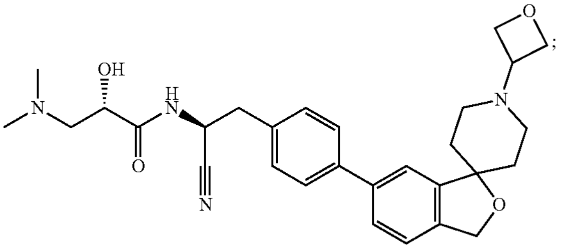
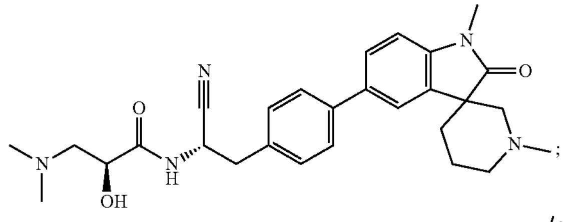
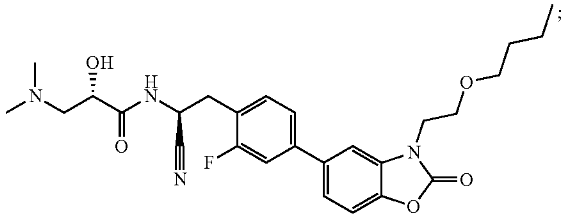
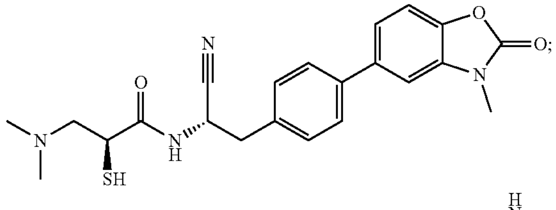
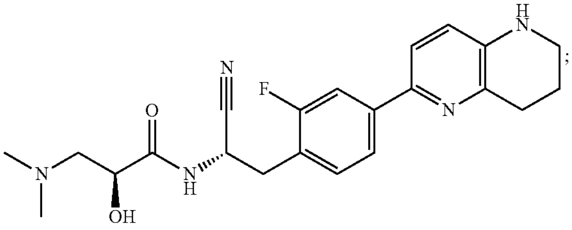
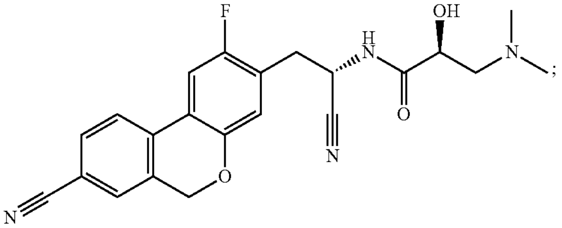

-continued
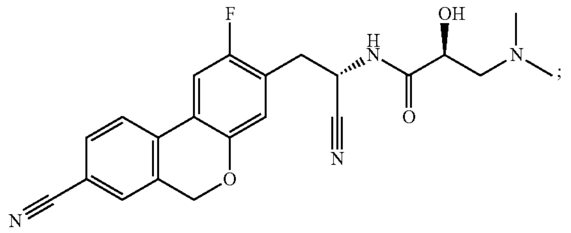
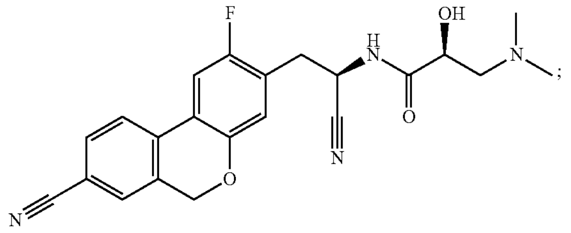
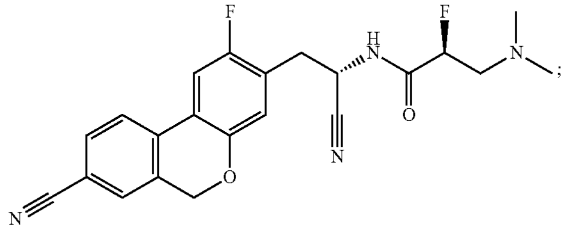
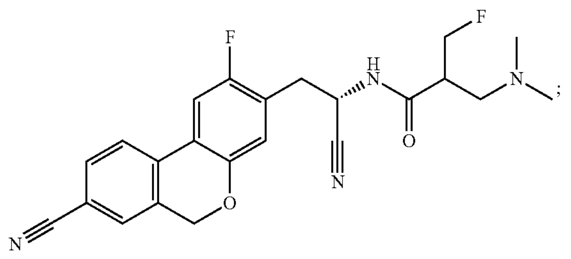
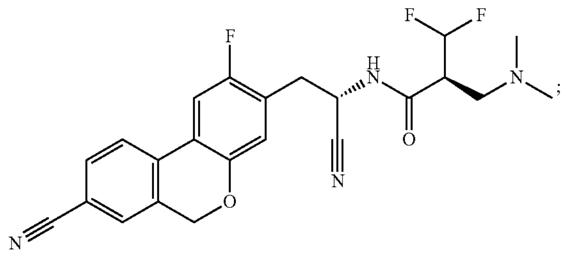
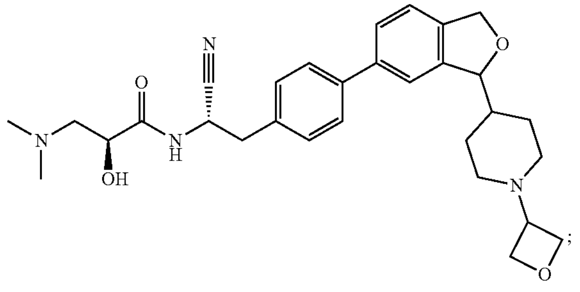
-continued
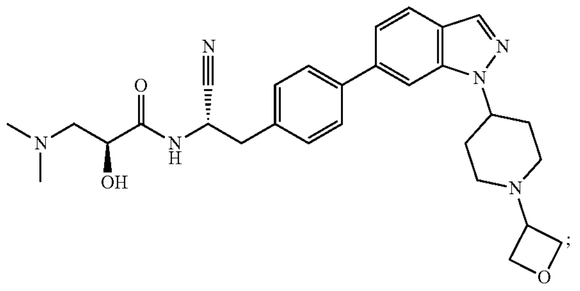
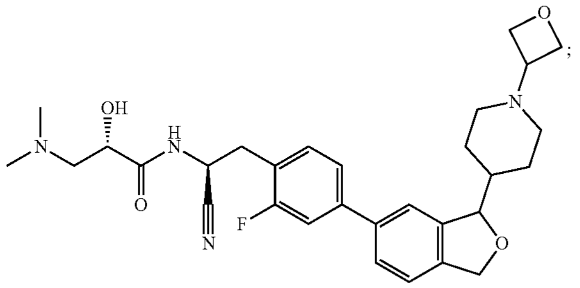
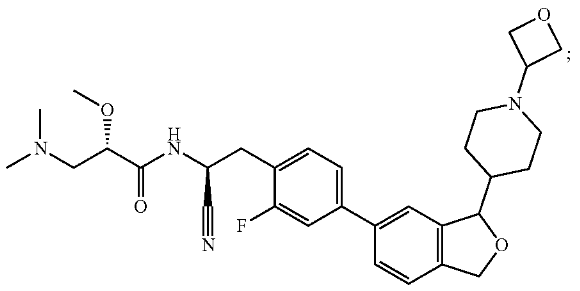
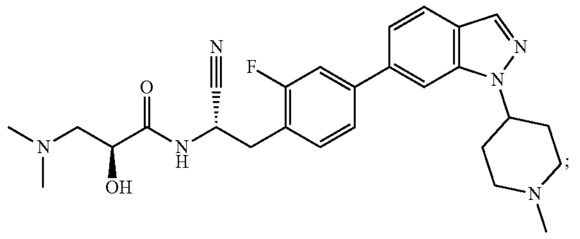
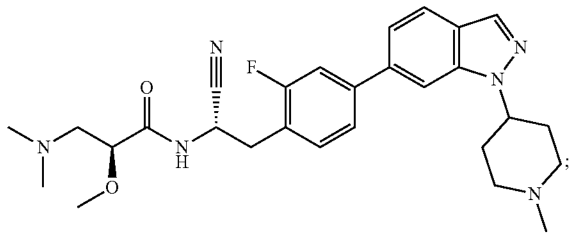
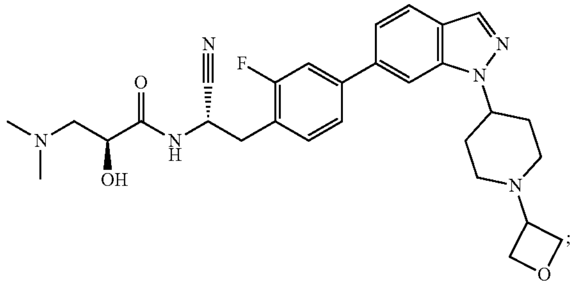

-continued
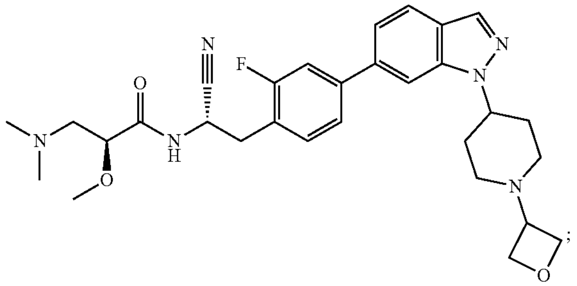
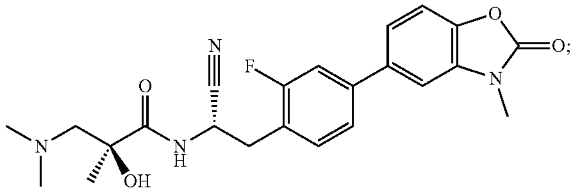
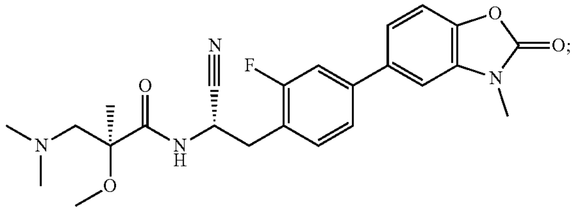
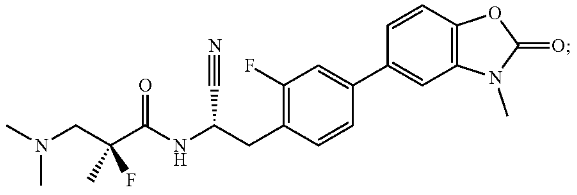
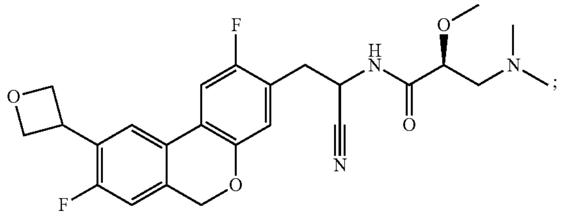
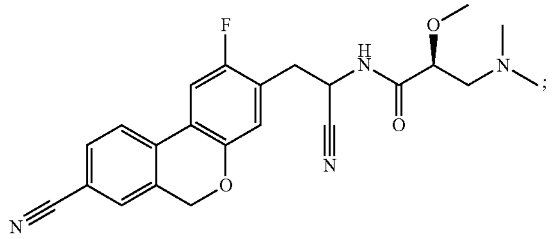
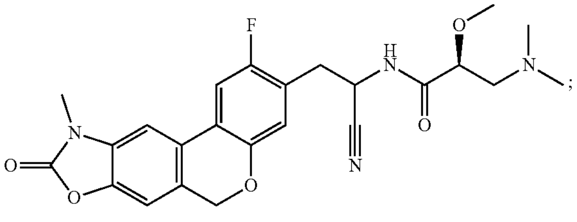
-continued
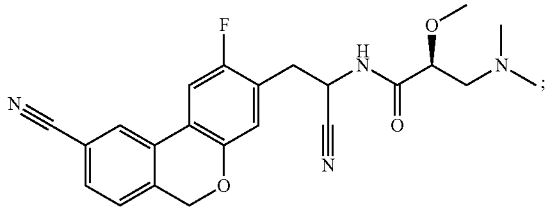
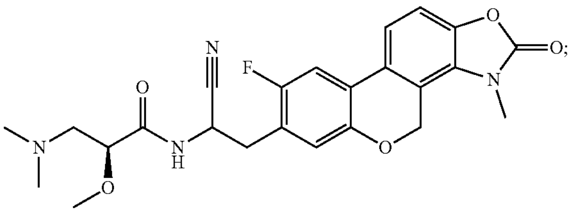
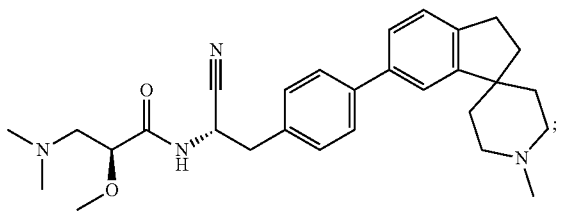
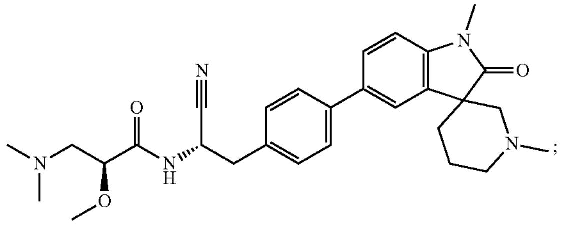
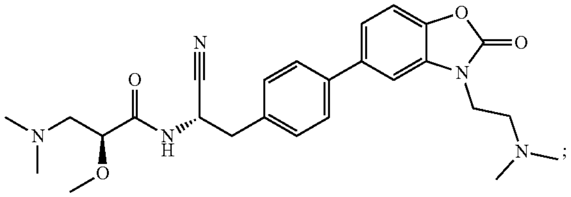
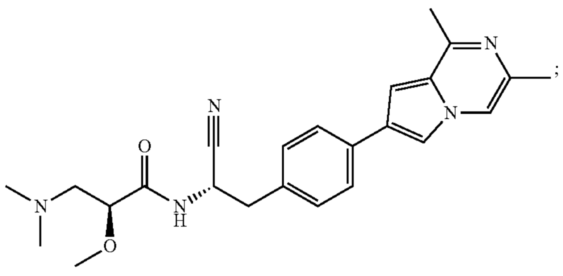
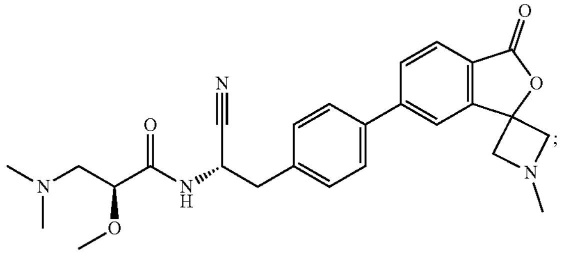

-continued
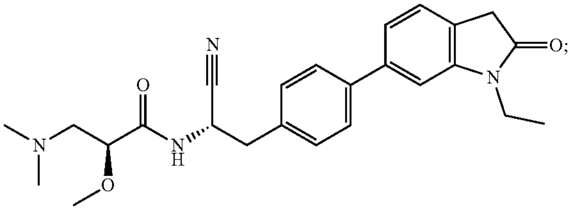
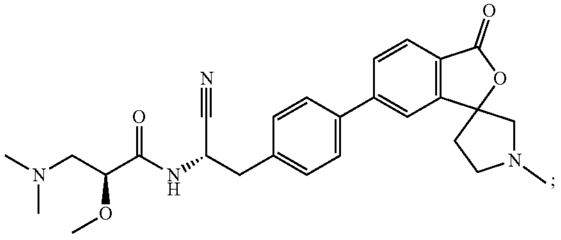
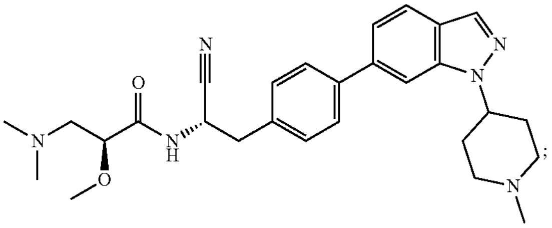
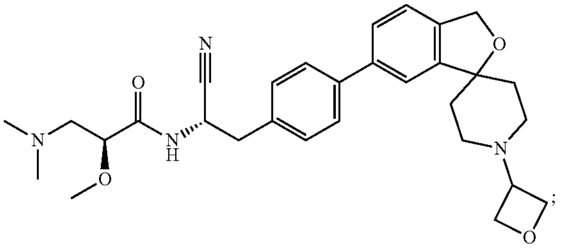
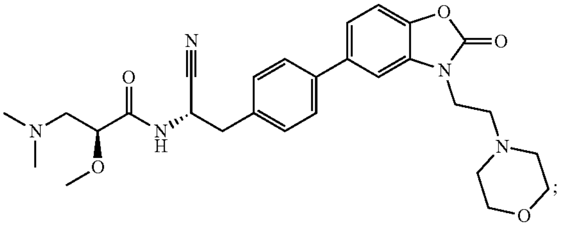
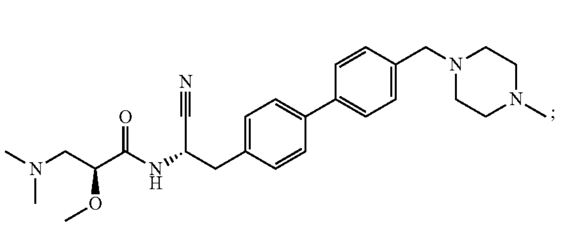
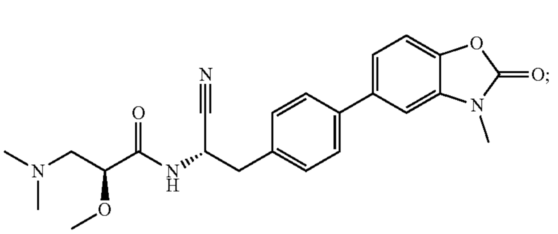
-continued
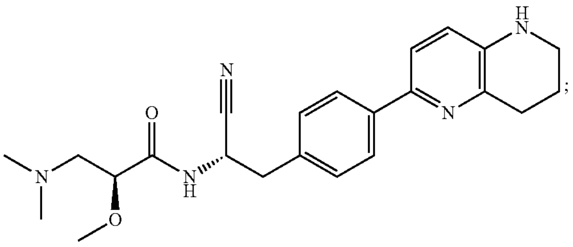 [SMILES: CO[C@@H](CN(C)C)C(=O)N[C@H](C#N)Cc1ccc(-c2ccc3c(n2)CCCN3)cc1]
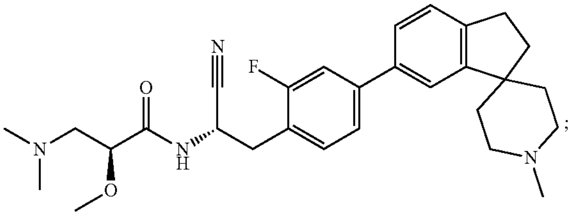
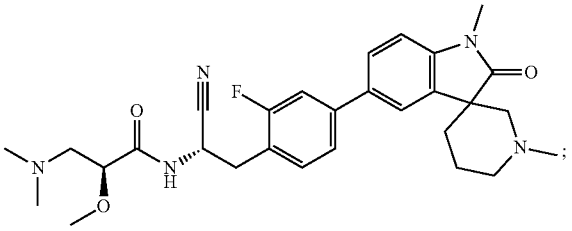
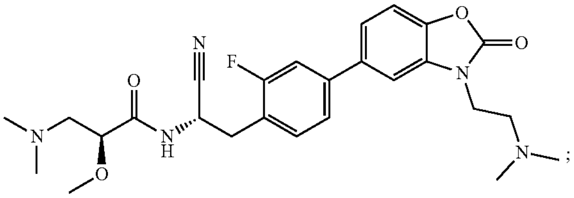
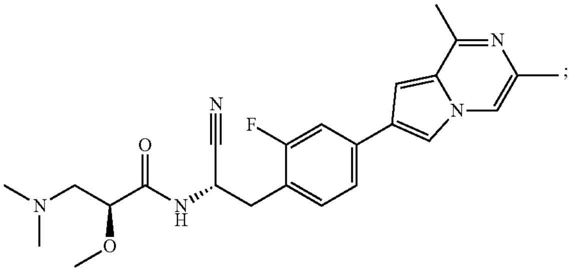
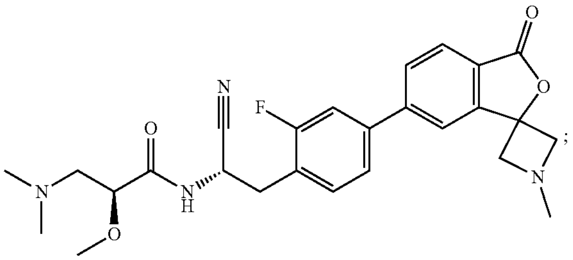
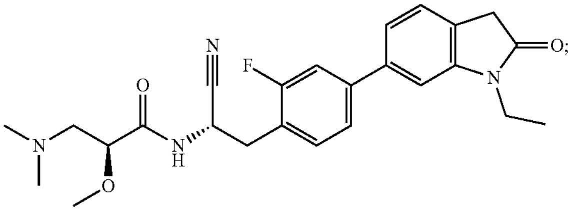

-continued
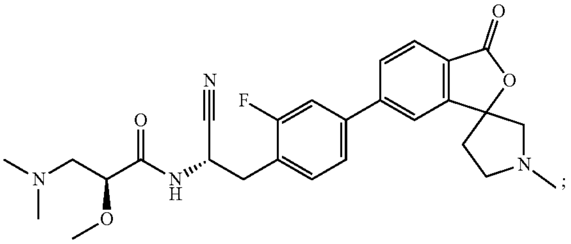
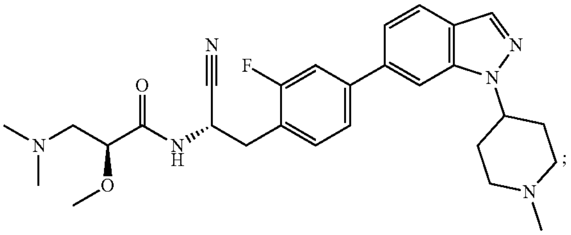
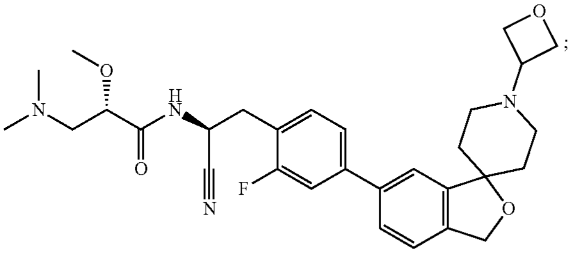
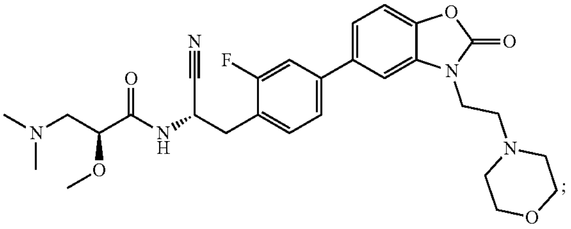
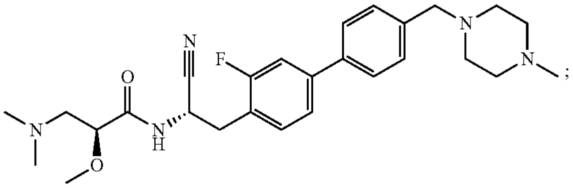
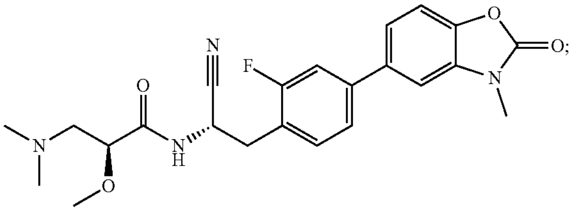
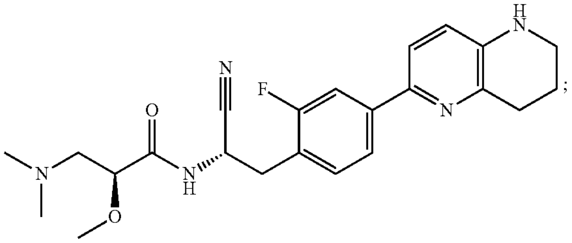
-continued
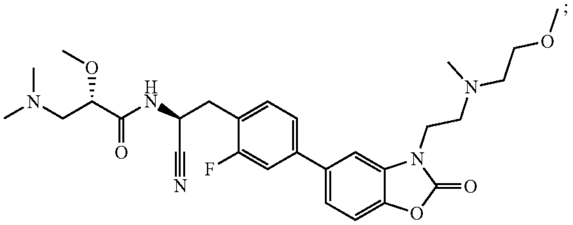
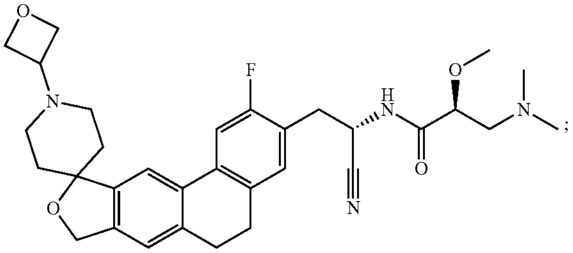
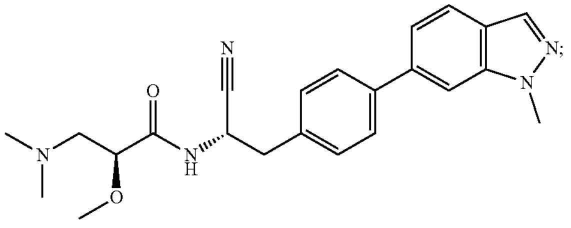
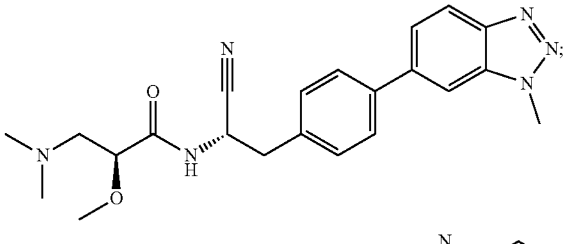
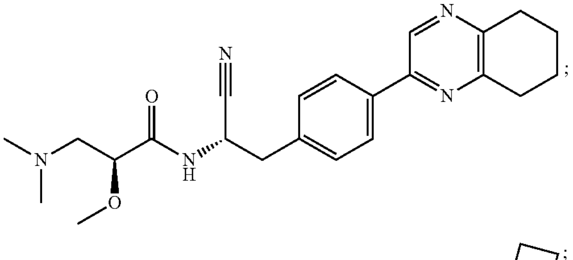
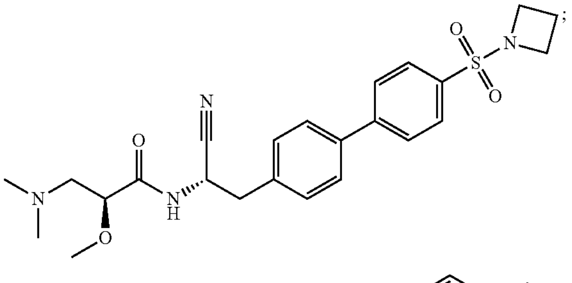
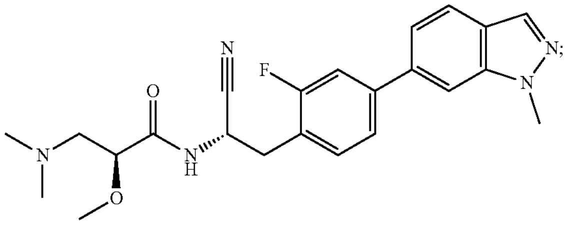

-continued
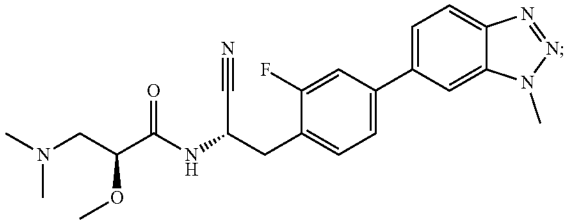
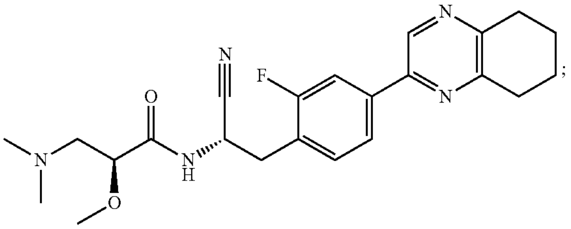
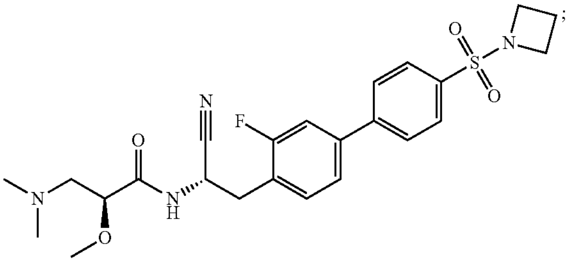
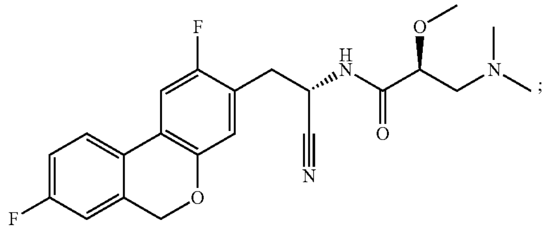
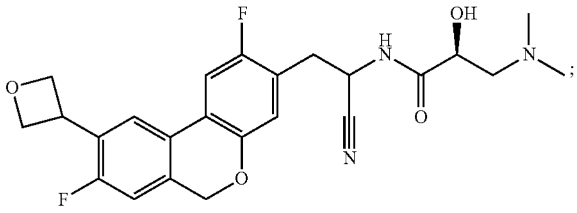
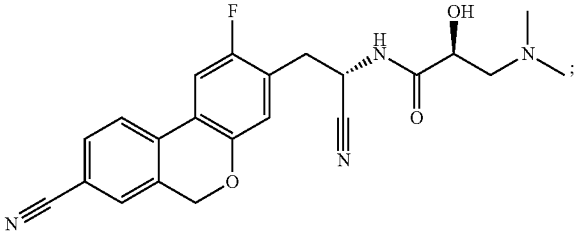
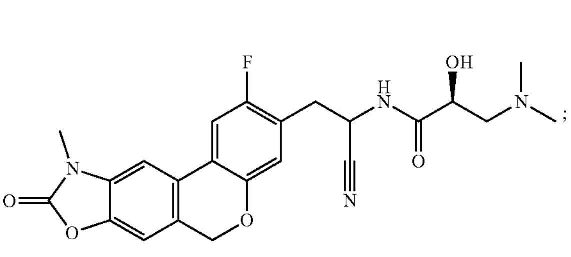
-continued
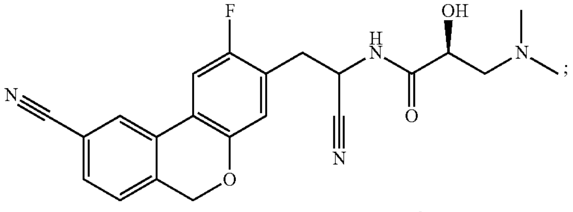
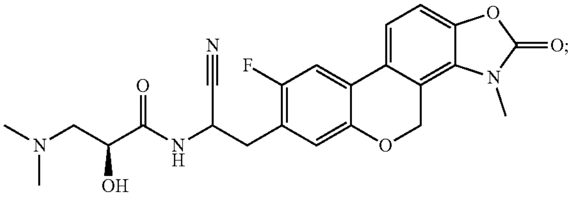
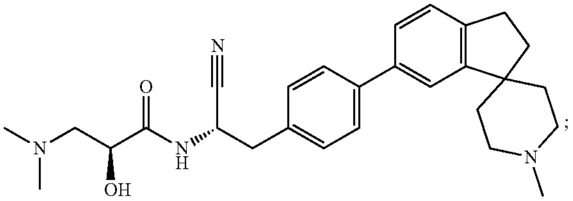
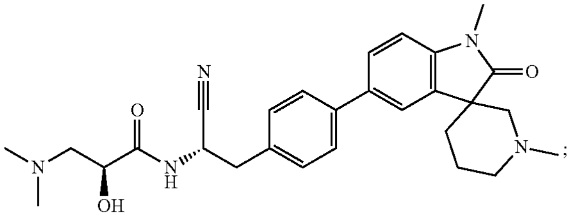
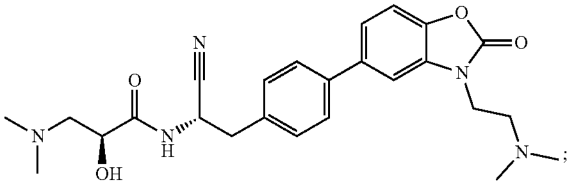
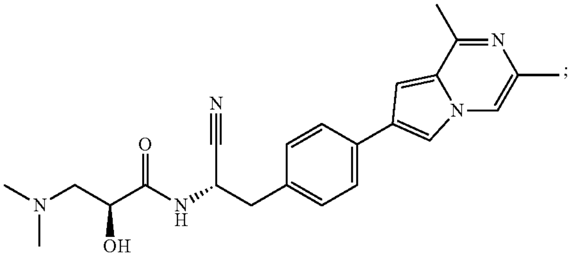
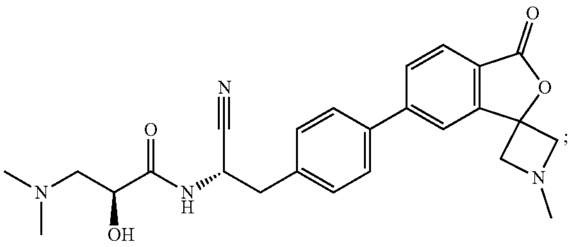
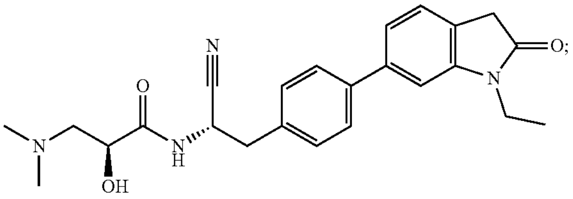

-continued
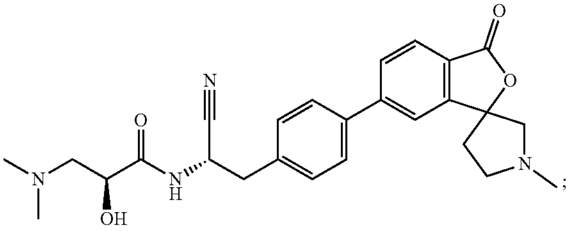
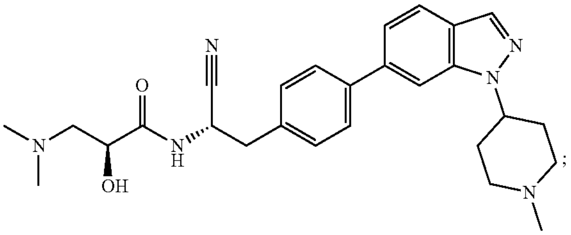
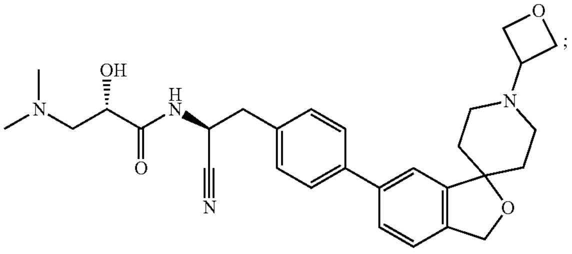
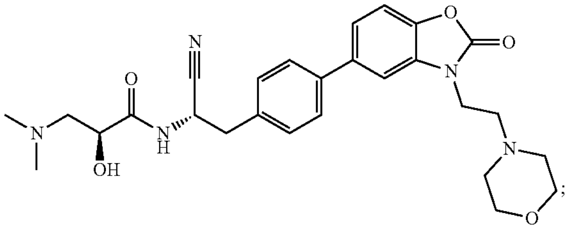
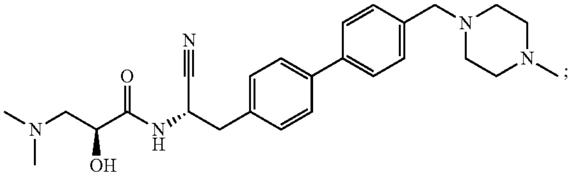
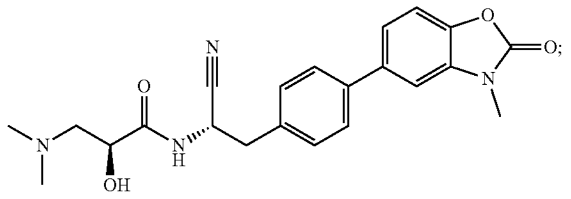
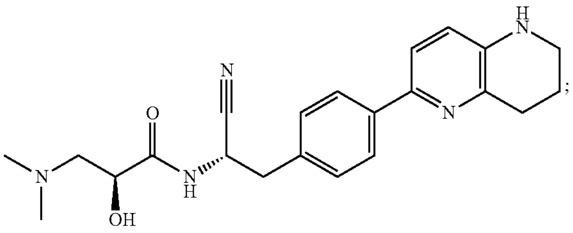
-continued
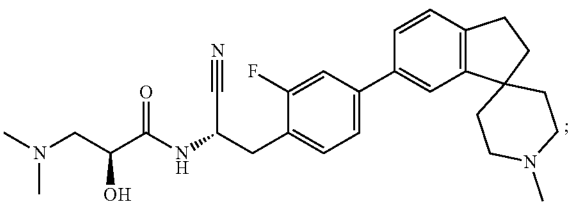
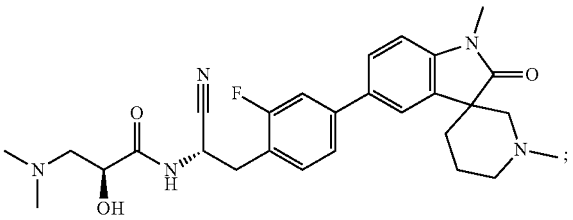
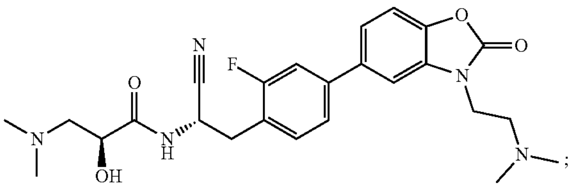
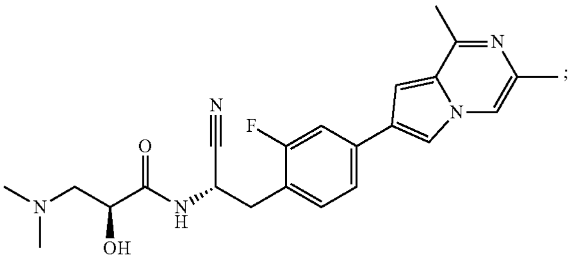
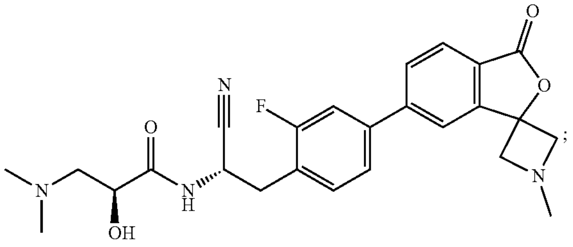
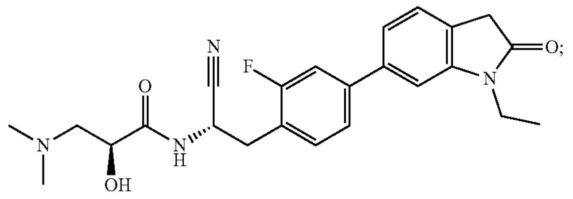
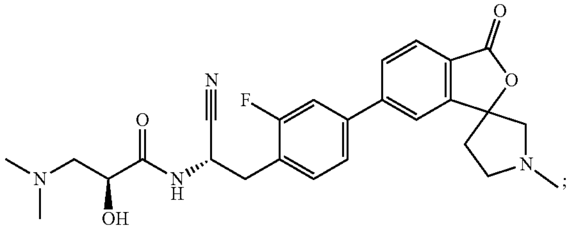

-continued
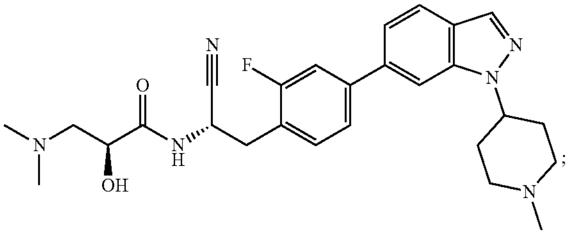
;
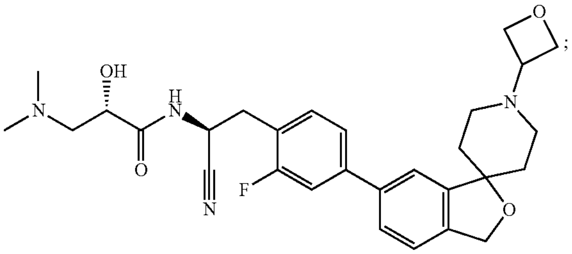
;
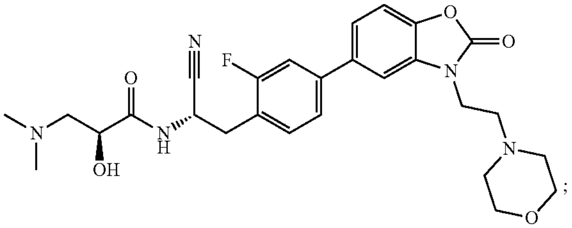
;
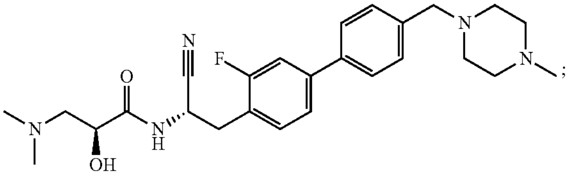
;
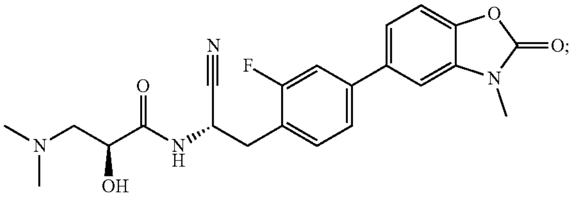
;
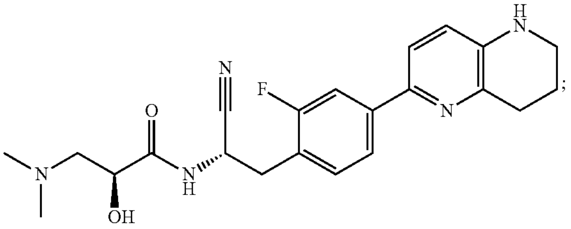
;
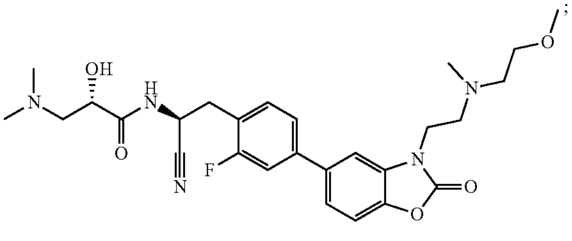
;
-continued
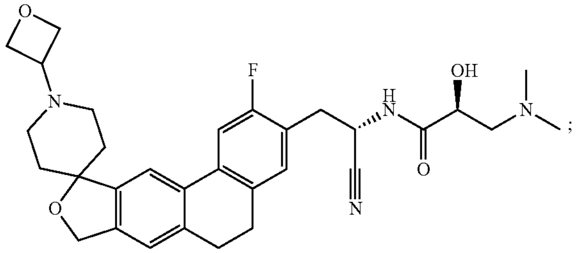
;
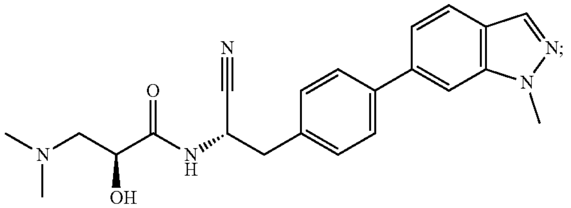
;
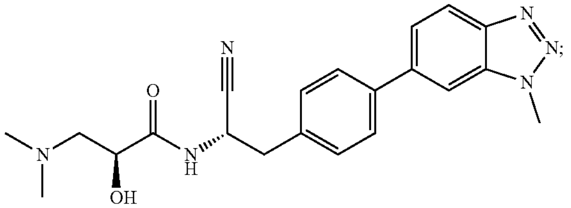
;
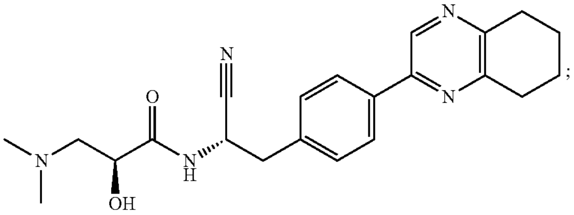
;
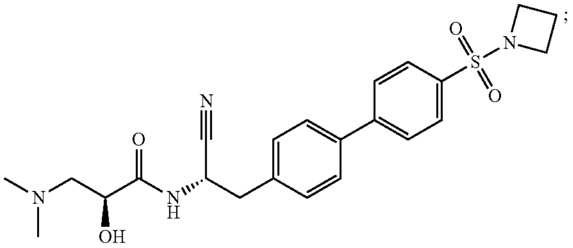
;
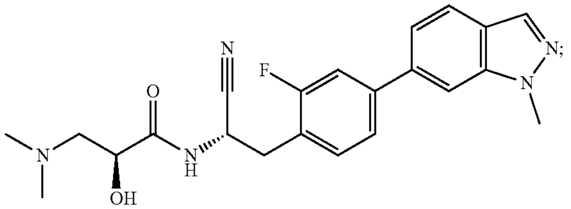
;
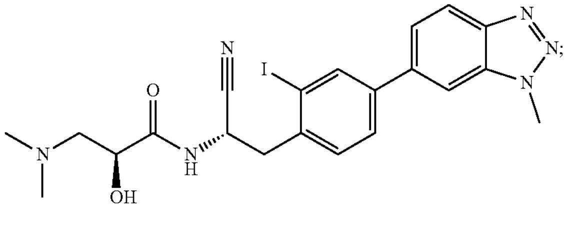
;

-continued
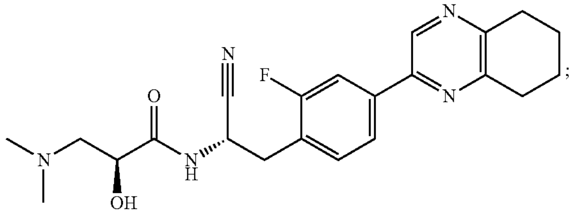
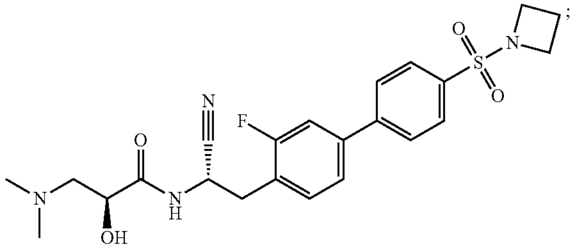
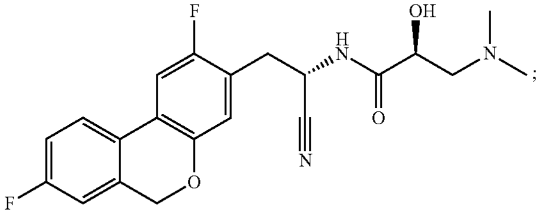
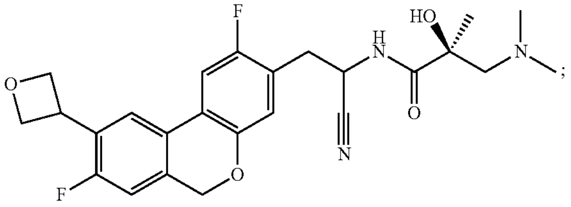
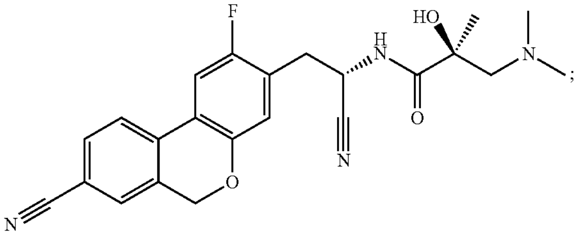
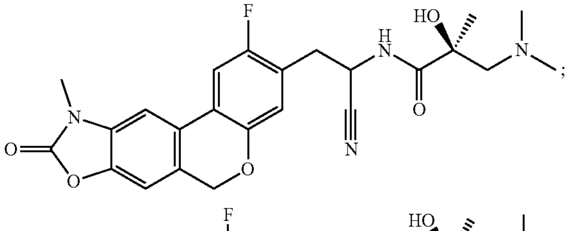
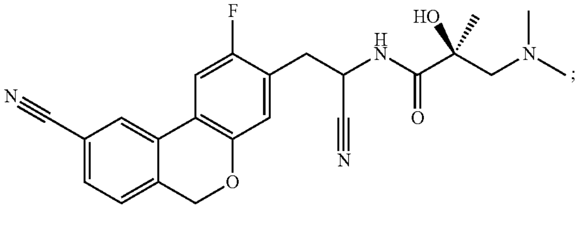
-continued
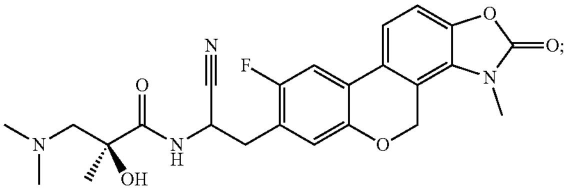
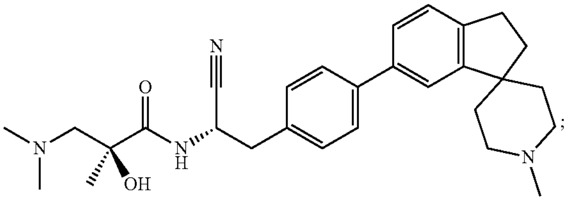
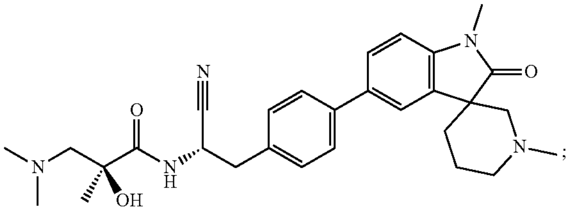
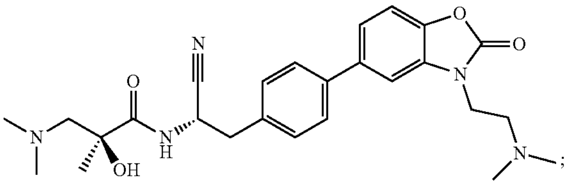
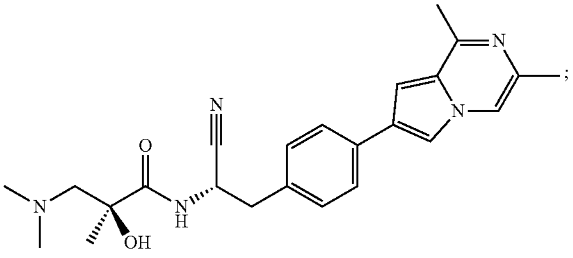
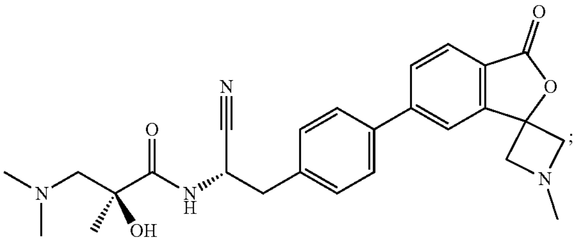
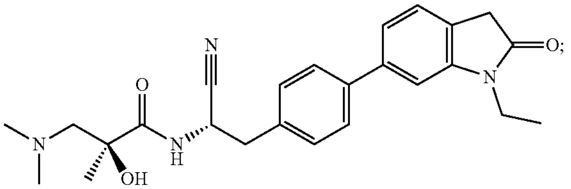
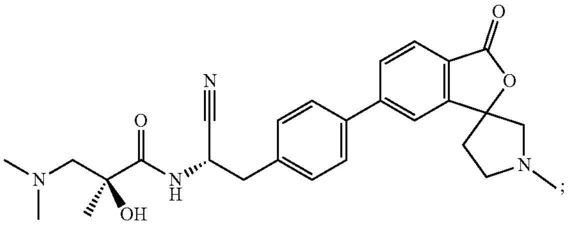

-continued
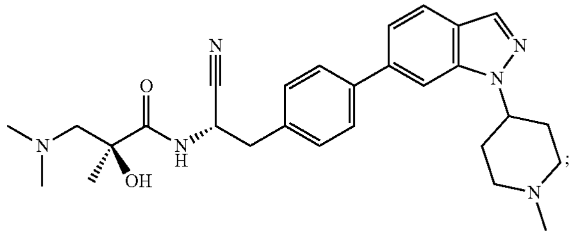
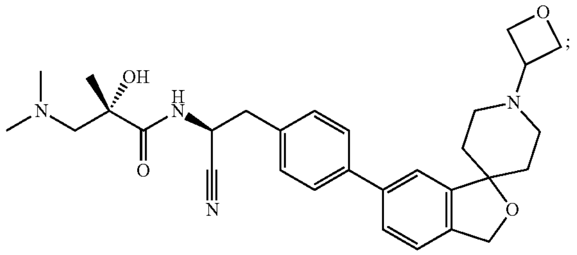
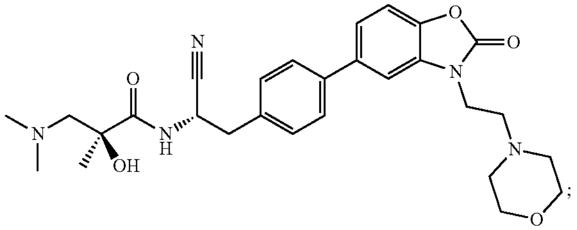
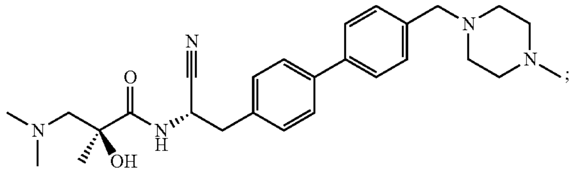
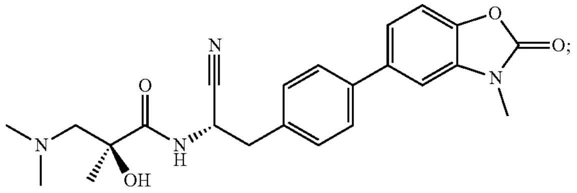
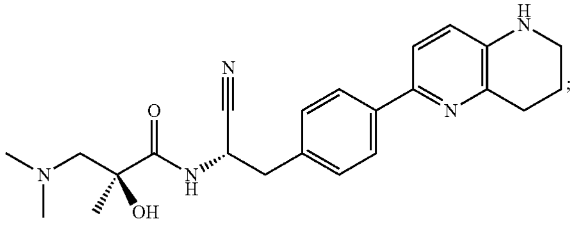
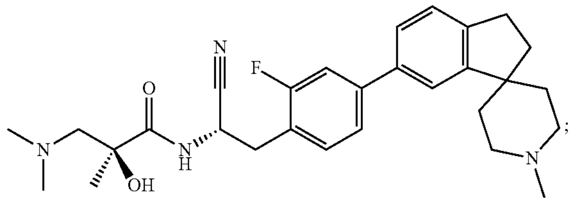
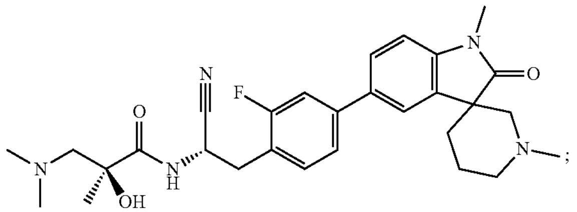
-continued
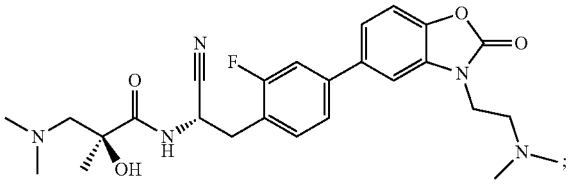
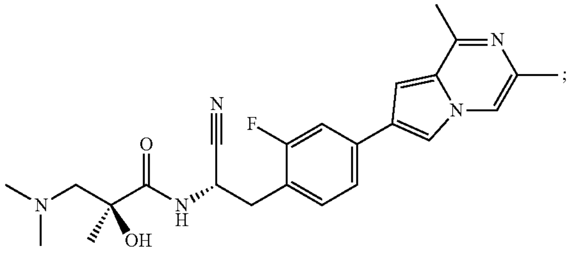
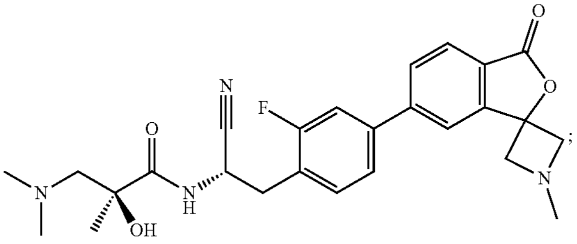
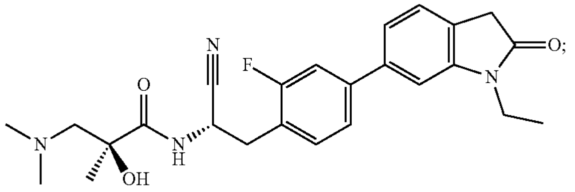
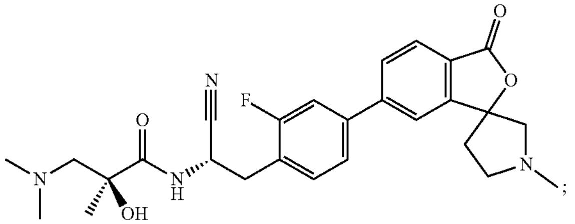
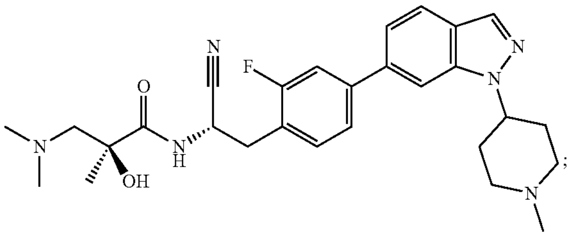
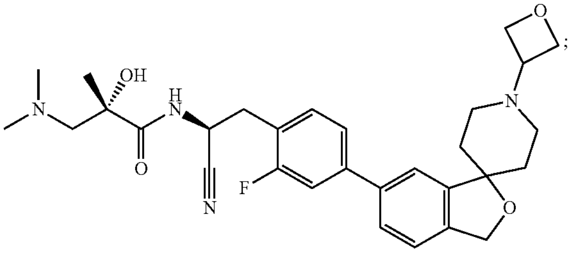

-continued
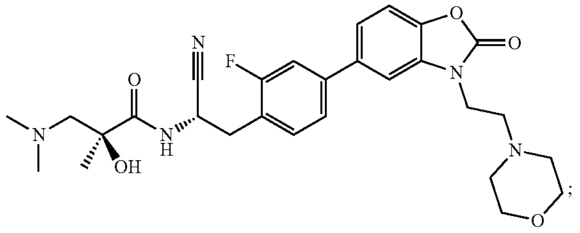
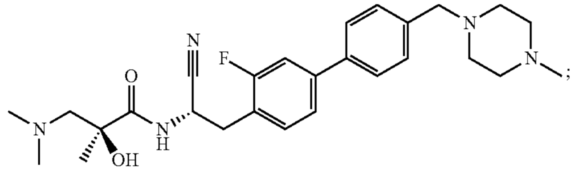
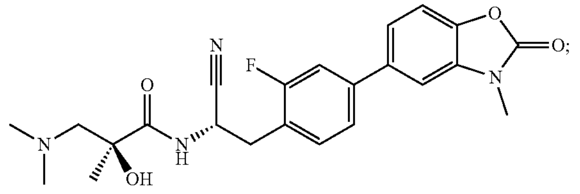
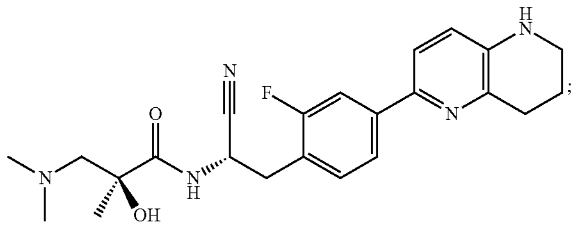
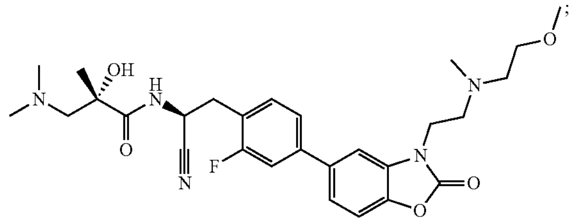
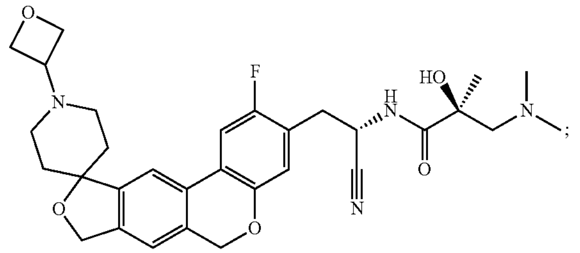
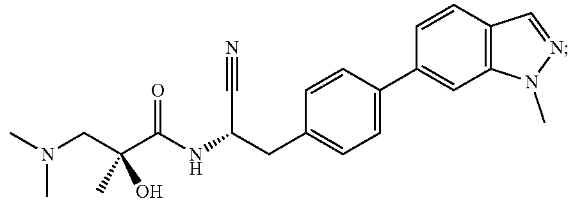
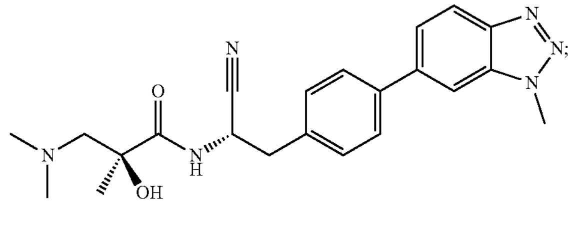
-continued
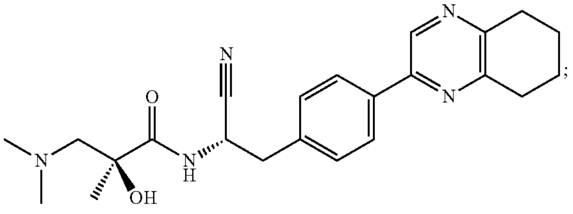
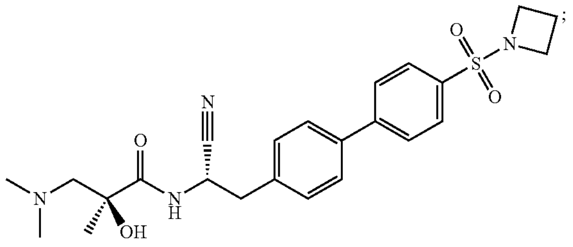
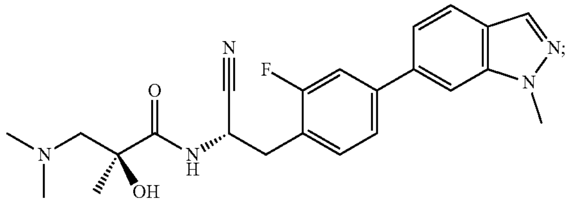
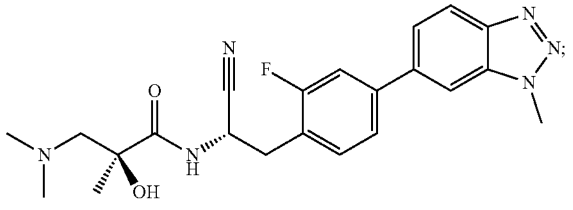
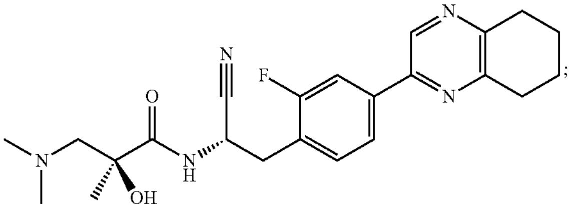
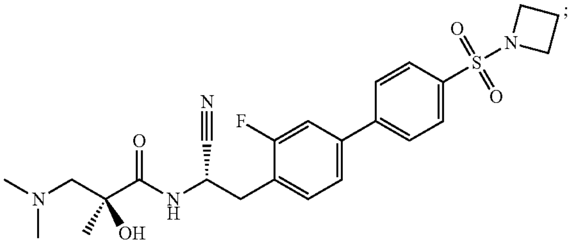
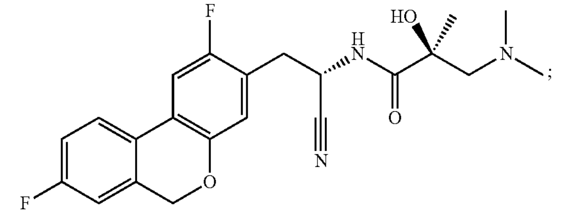

-continued
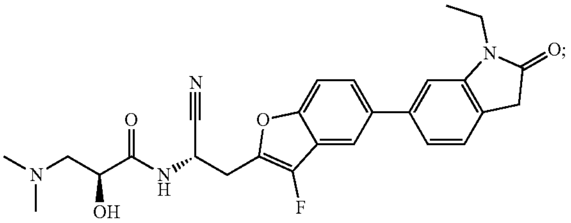
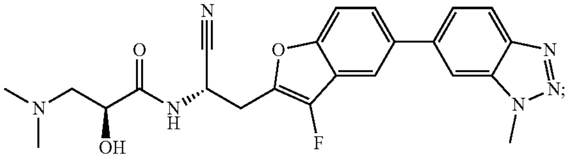
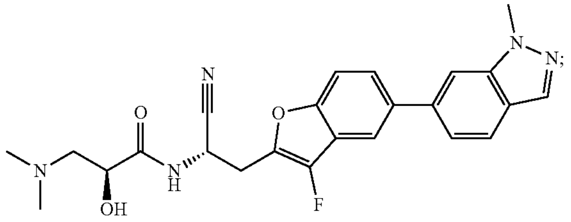
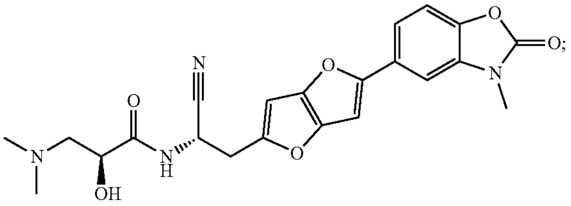
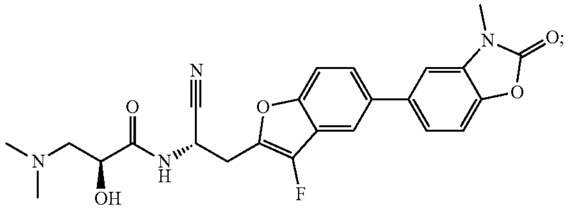
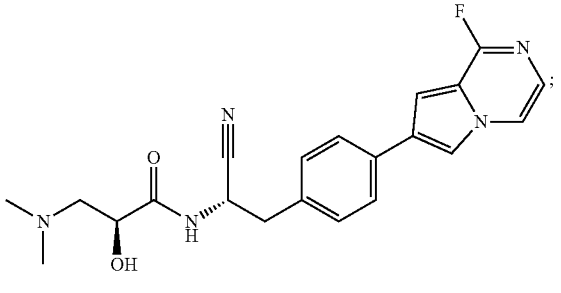
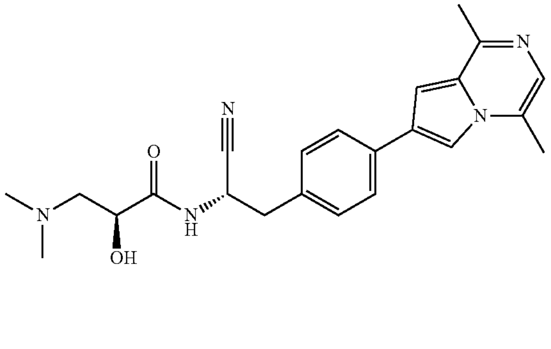
-continued
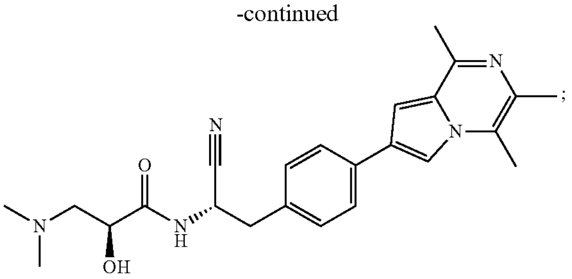
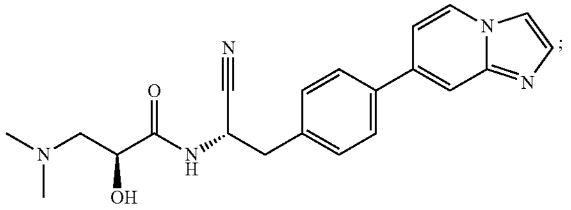
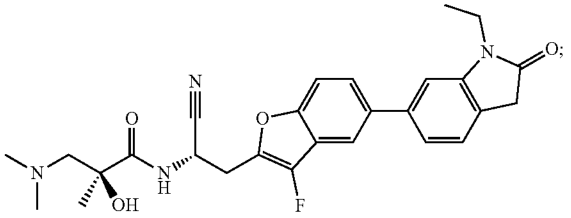
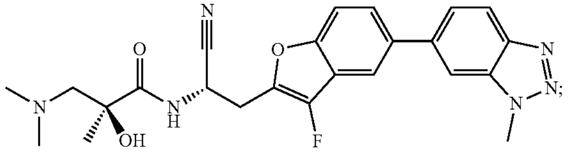
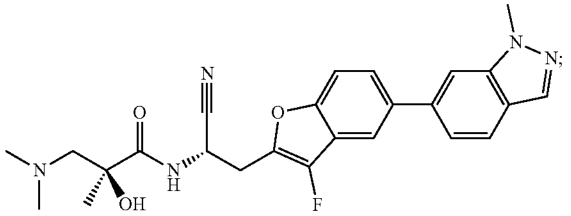
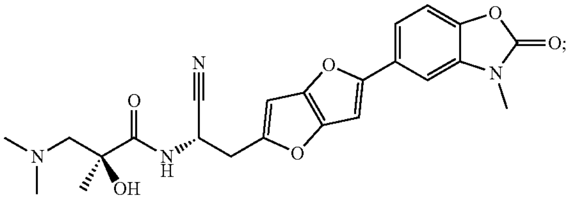
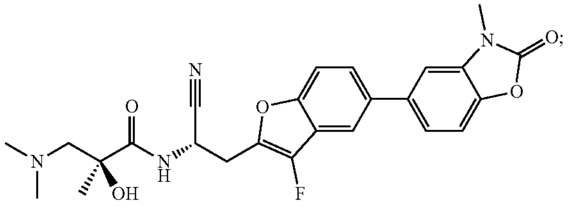
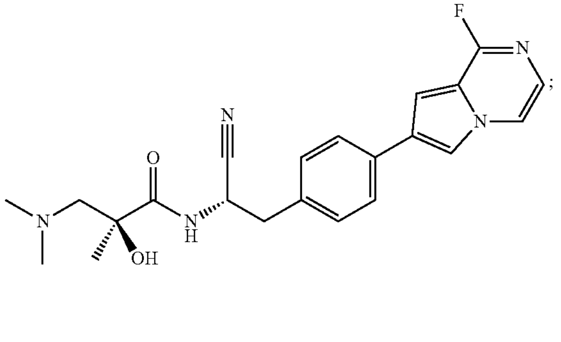

-continued
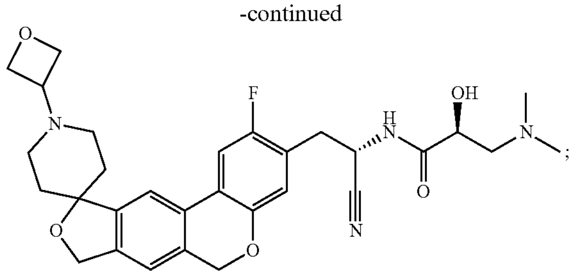
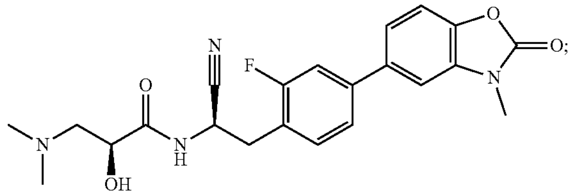
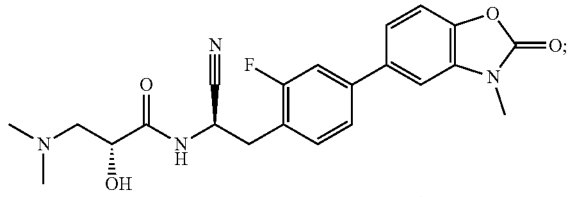
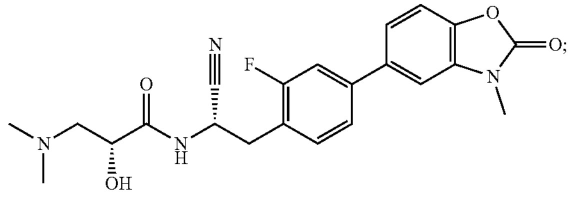
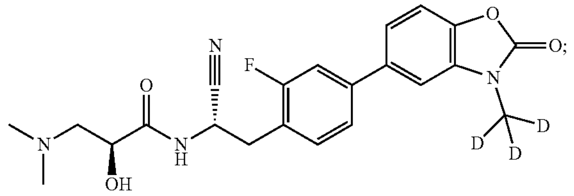
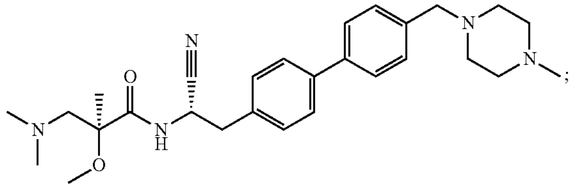
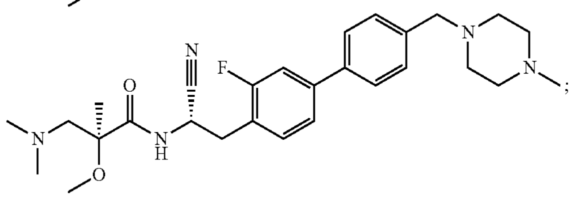
-continued
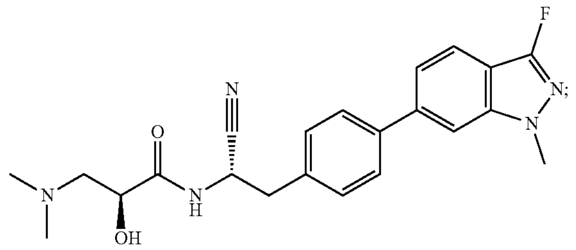
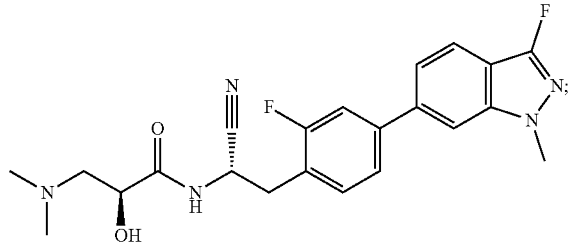
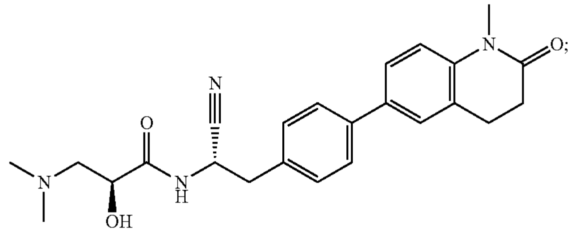
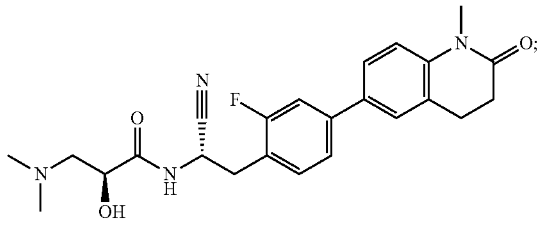
or
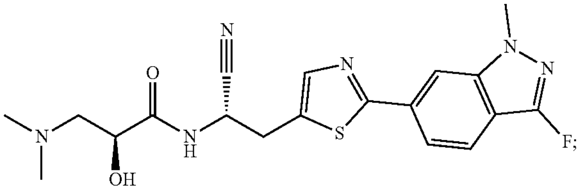
or a pharmaceutically acceptable salt, a stereoisomer, a racemic form, or a deuterated form thereof.
30. A pharmaceutical composition comprising the compound of claim 29, or a pharmaceutically acceptable salt, a stereoisomer or a deuterated form thereof, and a pharmaceutically acceptable adjuvant, diluent or carrier.
* * * * *